(12) United States Patent
Goldberg et al.

(10) Patent No.: US 12,024,524 B2
(45) Date of Patent: *Jul. 2, 2024

(54) IMIDAZOPYRIDAZINES AS MODULATORS OF IL-17

(71) Applicant: JANSSEN PHARMACEUTICA NV, Beerse (BE)

(72) Inventors: Steven Goldberg, San Diego, CA (US); David Kummer, San Diego, CA (US); John Keith, San Diego, CA (US); Craig Woods, San Diego, CA (US); Timothy Rhorer, San Diego, CA (US); Virginia M. Tanis, Vista, CA (US); Connor Martin, San Diego, CA (US); Steven Meduna, San Diego, CA (US); Stefan McCarver, San Diego, CA (US); Alexander Valdes, San Diego, CA (US); Steven Loskot, San Diego, CA (US); Douglas Behenna, San Juan Capistrano, CA (US); Alexander Rovira, San Diego, CA (US); Charlotte Deckhut, San Diego, CA (US); Xiaohua Xue, San Diego, CA (US)

(73) Assignee: JANSSEN PHARMACEUTICA NV, Beerse (BE)

(*) Notice: Subject to any disclaimer, the term of this patent is extended or adjusted under 35 U.S.C. 154(b) by 0 days.

This patent is subject to a terminal disclaimer.

(21) Appl. No.: 18/297,268

(22) Filed: Apr. 7, 2023

(65) Prior Publication Data
US 2023/0357254 A1   Nov. 9, 2023

Related U.S. Application Data

(63) Continuation of application No. 17/242,512, filed on Apr. 28, 2021, now Pat. No. 11,691,979.

(60) Provisional application No. 63/017,682, filed on Apr. 30, 2020.

(51) Int. Cl.
C07D 487/04 (2006.01)
(52) U.S. Cl.
CPC ............... C07D 487/04 (2013.01)
(58) Field of Classification Search
CPC .................................... C07D 487/04
USPC ...................................... 514/248
See application file for complete search history.

(56) References Cited

U.S. PATENT DOCUMENTS

| | | | |
|---|---|---|---|
| 9,284,283 B2 | 3/2016 | Taylor et al. | |
| 10,208,349 B2 | 2/2019 | Platt et al. | |
| 11,691,979 B2* | 7/2023 | Goldberg | C07D 487/04 |
| | | | 514/248 |
| 11,702,422 B2* | 7/2023 | Goldberg | C07D 487/04 |
| | | | 514/248 |
| 2015/0005319 A1 | 1/2015 | Taylor et al. | |
| 2020/0247785 A1 | 8/2020 | Fatheree et al. | |
| 2023/0167497 A1* | 6/2023 | Blain | C12Q 1/6883 |
| | | | 435/6.12 |

FOREIGN PATENT DOCUMENTS

| | | |
|---|---|---|
| CN | 112341429 A | 2/2021 |
| CN | 112341435 A | 2/2021 |
| CN | 112341439 A | 2/2021 |
| CN | 112341440 A | 2/2021 |
| CN | 112341441 A | 2/2021 |
| CN | 112341442 A | 2/2021 |
| CN | 112341446 A | 2/2021 |
| CN | 112341450 A | 2/2021 |
| CN | 112341451 A | 2/2021 |
| WO | WO 2013/116682 A1 | 8/2013 |
| WO | WO 2014/039595 A1 | 3/2014 |
| WO | WO 2014/066726 A2 | 5/2014 |
| WO | WO 2014/181287 A1 | 11/2014 |
| WO | WO 2016/022312 A1 | 2/2016 |
| WO | WO 2017/087590 A1 | 5/2017 |
| WO | WO 2018/229079 A1 | 12/2018 |
| WO | WO 2019/138017 A1 | 7/2019 |
| WO | WO 2019/223718 A1 | 11/2019 |
| WO | WO 2020/021103 A1 | 1/2020 |

(Continued)

OTHER PUBLICATIONS

U.S. Appl. No. 17/242,512 / 2022-0402922 A1, filed Apr. 28, 2021 / Dec. 22, 2022, Steven Goldberg.

(Continued)

*Primary Examiner* — Kristin A Vajda
(74) *Attorney, Agent, or Firm* — Brian C. Trinque; Lathrop GPM LLP

(57) ABSTRACT

The present application discloses compounds having the following formula:

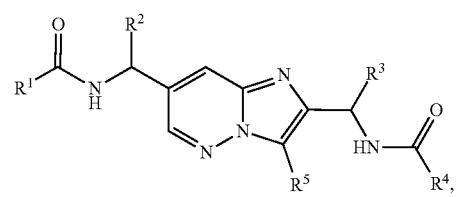

or pharmaceutically acceptable salts thereof, wherein $R^1$, $R^2$, $R^3$, $R^4$ and $R^5$ are defined in the specification, as well as methods of making and using the compounds disclosed herein for treating or ameliorating an IL-17 mediated syndrome, disorder and/or disease.

20 Claims, No Drawings

Specification includes a Sequence Listing.

(56) References Cited

FOREIGN PATENT DOCUMENTS

| WO | WO 2020/120140 A1 | 6/2020 |
| WO | WO 2020/120141 A1 | 6/2020 |
| WO | WO 2020/120978 A1 | 6/2020 |
| WO | WO 2020/127685 A1 | 6/2020 |
| WO | WO 2020/146194 A1 | 7/2020 |
| WO | WO 2020/182666 A1 | 9/2020 |
| WO | WO 2020/260425 A1 | 12/2020 |
| WO | WO 2020/260426 A1 | 12/2020 |
| WO | WO 2020/261141 A1 | 12/2020 |
| WO | WO 2021/170627 A1 | 9/2021 |
| WO | WO 2021/170631 A1 | 9/2021 |
| WO | WO 2021/204800 A1 | 10/2021 |
| WO | WO 2021/204801 A1 | 10/2021 |

OTHER PUBLICATIONS

U.S. Appl. No. 17/576,535 / 2023-0081548 A1, filed Jan. 14, 2022 / Mar. 16, 2023, Steven Goldberg.
U.S. Appl. No. 18/297,268, filed Apr. 7, 2023, Steven Goldberg.
Adamopoulos et al., "Alternative pathways of osteoclastogenesis in inflammatory arthritis", *Nature Reviews Rheumatology* 11:189-194, 2015.
Amatya et al., "IL-17 Signaling: The Yin and the Yang", *Trends in Immunology* 38:310-322, 2017.
Appel et al., "Analysis of IL-17(+) cells in facet joints of patients with spondyloarthritis suggests that the innate immune pathway might be of greater relevance than the Th17-mediated adaptive immune response", *Arthritis Research & Therapy* 13(3), R95, 2011.
Baeten et al., "Risankizumab, an IL-23 inhibitor, for ankylosing spondylitis: results of a randomised, double-blind, placebo-controlled, proof-of-concept, dose-finding phase 2 study", *Annals of the Rheumatic Diseases* 77(9):1295-1302, 2018.
Blauvelt et al., "The Immunologic Role of IL-17 in Psoriasis and Psoriatic Arthritis Pathogenesis", *Clinical Reviews in Allergy & Immunology* 55(3):379-390, 2018.
Camargo et al., "Effects of Anti-IL-17 on Inflammation, Remodeling, and Oxidative Stress in an Experimental Model of Asthma Exacerbated by LPS", *Frontiers in Immunology* 8:1835, 2018.
Chakievska et al., "IL-17A is functionally relevant and a potential therapeutic target in bullous pemphigoid", *Journal of Autoimmunity* 96:104-112, 2019.
Chakir et al., "Airway remodeling-associated mediators in moderate to severe asthma: effect of steroids on TGF-beta, IL-11, IL-17, and type I and type III collagen expression", *The Journal of Allergy and Clinical Immunology* 111(6):1293-1298, 2003.
Chen et al., "Plasma IL-17A is increased in new-onset SLE patients and associated with disease activity", *Journal of Clinical Immunology* 30(2):221-225, 2010.
Chen et al., "The Effects of Th17 Cytokines on the Inflammatory Mediator Production and Barrier Function of ARPE-19 Cells", *PLOS One* 6:e18139, 2011.
Christenson et al., "An airway epithelial IL-17A response signature identifies a steroid-unresponsive COPD patient subgroup", *Journal of Clinical Investigation* 129(1):169-181, 2019.
De Boer et al., "Diazomethane", *Organic Syntheses* 36:16-19, 1956.
Deodhar et al., "Three Multicenter, Randomized, Double-Blind, Placebo-Controlled Studies Evaluating the Efficacy and Safety of Ustekinumab in Axial Spondyloarthritis", *Arthritis & Rheumatology* 71(2):258-270, 2019.
Dick et al., "Secukinumab in the treatment of noninfectious uveitis: results of three randomized, controlled clinical trials", *Ophthalmology* 120(4):777-787, 2013.
Dolff et al., "Disturbed Th1, Th2, Th17 and T(reg) balance in patients with systemic lupus erythematosus", *Clinical Immunology* 141(2):197-204, 2011.
Dos Santos et al., "Effect of Anti-IL17 Antibody Treatment Alone and in Combination With Rho-Kinase Inhibitor in a Murine Model of Asthma", *Frontiers in Physiology* 9:1183, 2018.
Eby et al., "Immune Responses in a Mouse Model of Vitiligo with Spontaneous Epidermal De- and Repigmentation", *Pigment Cell & Melanoma Research* 27(6):1075-1085, 2014.
El-Asrar et al., "Cytokine profiles in aqueous humor of patients with different clinical entities of endogenous uveitis", *Clinical Immunology* 139(2):177-184, 2011.
Gaffen, "Structure and signaling in the IL-17 receptor family", *Nature Reviews Immunology* 9:556-567, 2009.
Havrdova et al., "Activity of secukinumab, an anti-IL-17A antibody, on brain lesions in RRMS: results from a randomized, proof-of-concept study", *Journal of Neurology* 263:1287-1295, 2016.
Hawkes et al., "Psoriasis Pathogenesis and the Development of Novel, Targeted Immune Therapies", *The Journal of Allergy and Clinical Immunology* 140(3):645-653, 2017.
HitGen, "HitGen presents new IL-17RA antagonists", BioWorld Science, Immunomodulatin Agents, Dec. 9, 2019.
International Search Report and Written Opinion for corresponding Application No. PCT/US2021/029641, dated Jul. 2, 2021.
Jansen et al., "IL-17-producing CD4+ T cells are increased in early, active axial spondyloarthritis including patients without imaging abnormalities", *Rheumatology* (Oxford), 54(4):728-735, 2014.
Jawad et al., "Elevated Serum Levels of Interleukin-17A in Uveitis Patients", *Ocular Immunology and Inflammation* 21(6):434-439, 2013.
Kelly et al., "Dysregulated cytokine expression in lesional and nonlesional skin in hidradenitis suppurativa", *British Journal of Dermatology* 173(6):1431-1439, 2015.
Khattri et al., "Efficacy and safety of ustekinumab treatment in adults with moderate-to-severe atopic dermatitis", *Experimental Dermatology* 26(1):28-35, 2016.
Koga et al., "Possible pathogenic role of Th17 cells for atopic dermatitis", *Journal of Investigative Dermatology* 128:2625-2630, 2008.
Koga et al., "The role of IL-17 in systemic lupus erythematosus and its potential as a therapeutic target", *Expert Review of Clinical Immunology* 15(6):629-637, 2019.
Kuiper et al., "Intraocular interleukin-17 and proinflammatory cytokines in HLA-A29-associated birdshot chorioretinopathy", *American Journal of Ophthalmology* 152(2):177-182, 2011.
Le Jan et al., "Innate immune cell-produced IL-17 sustains inflammation in bullous pemphigoid", *Journal of Investigative Dermatology* 134(12):2908-2917, 2014.
Lemancewicz et al., "The role of Interleukin-17A and Interleukin-17E in multiple myeloma patients", *Medical Science Monitor* 18(1):BR54-BR59, 2012.
Letko et al., "Efficacy and safety of intravenous secukinumab in noninfectious uveitis requiring steroid-sparing immunosuppressive therapy", *Ophthalmology* 122(5):939-948, 2015.
Lock et al., "Gene-microarray analysis of multiple sclerosis lesions yields new targets validated in autoimmune encephalomyelitis", *Nature Medicine* 8:500-508, 2002.
Ma et al., "The imbalance between regulatory and IL-17-secreting CD4+ T cells in lupus patients", *Clinical Rheumatology* 29(11):1251-1258, 2010.
Matusevicius et al., "Interleukin-17 mRNA expression in blood and CSF mononuclear cells is augmented in multiple sclerosis", *Multiple Sclerosis Journal* 5:101-104, 1999.
Mease et al., "Comparative effectiveness of secukinumab and etanercept in biologic-naïve patients with psoriatic arthritis assessed by matching-adjusted indirect comparison", *European Journal of Rheumatology* 6(3):113-121, 2019.
Mease et al., "A head-to-head comparison of the efficacy and safety of ixekizumab and adalimumab in biological-naïve patients with active psoriatic arthritis: 24-week results of a randomised, open-label, blinded-assessor trial", *Annals of Rheumatic Diseases* 79:123-131, 2020.
Menon et al., "Interleukin-17+CD8+ T cells are enriched in the joints of patients with psoriatic arthritis and correlate with disease activity and joint damage progression", *Arthritis & Rheumatology* 66:1272-1281, 2014.
Molet et al., "IL-17 is increased in asthmatic airways and induces human bronchial fibroblasts to produce cytokines", *Journal of Allergy and Clinical Immunology* 108(3):430-438, 2001.

(56) References Cited

OTHER PUBLICATIONS

Moran et al., "Hidradenitis Suppurativa Is Characterized by Dysregulation of the Th17: Treg Cell Axis, Which Is Corrected by Anti-TNF Therapy", *Journal of Investigative Dermatology* 137(11):2389-2395, 2017.

Mugheddu et al., "Successful ustekinumab treatment of noninfectious uveitis and concomitant severe psoriatic arthritis and plaque psoriasis", *Dermatologic Therapy* 30(5):e12527, 2017.

Nash et al., "Secukinumab Versus Adalimumab for Psoriatic Arthritis: Comparative Effectiveness up to 48 Weeks Using a Matching-Adjusted Indirect Comparison", *Rheumatology and Therapy* 5(1):99-122, 2018.

Mayo Clinic, "Ixekizumab in the Treatment of Bullous Pemphigoid", ClinicalTrials.gov. http://clinicaltrials.gov/show/NCT03099538, [Last Accessed on Jul. 2, 2021]. Apr. 2017.

Pollet et al., "Tetronic Acids and Derivatives; Part VI. A Convenient Synthesis of New 4-Oxo-2-phenyl-2H-4,6-dihydrofuro[3,4-d]triazole and 4-Oxo-4,6-dihydrofuro[3,4-c]furazan Systems", *Synthesis* 12:977-979, 1979.

Prabhala et al., "Targeting IL-17A in multiple myeloma: a potential novel therapeutic approach in myeloma", *Leukemia* 30(2):379-389, 2016.

Prussick et al., "Open-label, investigator-initiated, single-site exploratory trial evaluating secukinumab, an anti-interleukin-17A monoclonal antibody, for patients with moderate-to-severe hidradenitis suppurativa", *British Journal of Dermatology* 181(3):609-611, 2019.

Robert et al., "IL-17 in Rheumatoid Arthritis and Precision Medicine: From Synovitis Expression to Circulating Bioactive Levels", *Frontiers in Medicine* 5:364, 2019.

Schlapbach et al., "Expression of the IL-23/Th17 pathway in lesions of hidradenitis suppurativa", *Journal of the American Academy of Dermatology* 65(4):790-798, 2011.

Setiadi et al., "IL-17A is associated with the breakdown of the blood-brain barrier in relapsing-remitting multiple sclerosis", *Journal of Neuroimmunology* 332:147-154, 2019.

Shen et al., "Frequency and phenotype of peripheral blood Th17 cells in ankylosing spondylitis and rheumatoid arthritis", *Arthritis & Rheumatology* 60(6):1647-1656, 2009.

Singh et al., "The role of IL-17 in vitiligo: A review", *Autoimmunity Reviews* 15(4):397-404, 2016.

Stamp et al., "Interleukin-17: the missing link between T-cell accumulation and effector cell actions in rheumatoid arthritis?", *Immunology & Cell Biology* 82(1):1-9, 2004.

Strand et al., "Matching-adjusted indirect comparison: secukinumab versus infliximab in biologic-naive patients with psoriatic arthritis", *Journal of Comparative Effectiveness Research* 8(7):497-510, 2019.

Thomi et al., "Association of Hidradenitis Suppurativa With T Helper 1/T Helper 17 Phenotypes: A Semantic Map Analysis", *JAMA Dermatology* 154(5):592-595, 2018.

Tzartos et al., "Interleukin-17 production in central nervous system-infiltrating T cells and glial cells is associated with active disease in multiple sclerosis", *The American Journal of Pathology* 172:146-155, 2008.

Van Vollenhoven et al., "Efficacy and safety of ustekinumab, an IL-12 and IL-23 inhibitor, in patients with active systemic lupus erythematosus: results of a multicentre, double-blind, phase 2, randomised, controlled study", *Lancet* 392:1330-1339, 2018.

Vargas-Rojas et al., "Increase of Th17 cells in peripheral blood of patients with chronic obstructive pulmonary disease", *Respiratory Medicine* 105(11):1648-1654, 2011.

Wen et al., "Interleukin-17 Expression Positively Correlates with Disease Severity of Lupus Nephritis by Increasing Anti-Double-Stranded DNA Antibody Production in a Lupus Model Induced by Activated Lymphocyte Derived DNA", *PLOS One* 8:e58161, 2013.

Wendling et al., "Serum IL-17, BMP-7, and bone turnover markers in patients with ankylosing spondylitis", *Joint Bone Spine* 74:304-305, 2007.

Willing et al., "Production of IL-17 by MAIT Cells Is Increased in Multiple Sclerosis and Is Associated with IL-7 Receptor Expression", *Journal of Immunology* 200(3):974-982, 2018.

Wong et al., "Hyperproduction of IL-23 and IL-17 in patients with systemic lupus erythematosus: implications for Th17-mediated inflammation in auto-immunity", *Clinical Immunology* 127(3):385-393, 2008.

Wong et al., "Elevation of proinflammatory cytokine (IL-18, IL-17, IL-12) and Th2 cytokine (IL-4) concentrations in patients with systemic lupus erythematosus", *Lupus* 9(8):589-593, 2000.

Xing et al., "Elevated Th17 cells are accompanied by FoxP3+ Treg cells decrease in patients with lupus nephritis", *Rheumatology International* 32(4):949-958, 2012.

Zhang et al., "Increased Frequencies of Th22 Cells as well as Th17 Cells in the Peripheral Blood of Patients with Ankylosing Spondylitis and Rheumatoid Arthritis", *PLOS One* 7(4):e31000, 2012.

Zhang et al., "Suppression of experimental autoimmune uveoretinitis by Anti-IL-17 antibody", *Current Eye Research* 34(4):297-303, 2009.

Zhao et al., "Increased serum interleukin 17 in patients with systemic lupus erythematosus", *Molecular Biology Reports* 37(1):81-85, 2010.

\* cited by examiner

IMIDAZOPYRIDAZINES AS MODULATORS OF IL-17

CROSS-REFERENCE TO RELATED APPLICATIONS

This application is a continuation of U.S. patent application Ser. No. 17/242,512, filed on Apr. 28, 2021, which application claims the benefit under 35 U.S.C. § 119(e) of U.S. Provisional Application No. 63/017,682, filed Apr. 30, 2020, the contents of each of which are incorporated herein by reference in their entirety.

REFERENCE TO SEQUENCE LISTING SUBMITTED ELECTRONICALLY

This application contains a sequence listing, which is submitted electronically as an XML formatted sequence listing with a file name "740848_NTT-6306CON2_SL.xml", creation date of Apr. 6, 2023 and having a size of about 3.98 KB. The sequence listing submitted electronically is part of the specification and is herein incorporated by reference in its entirety.

FIELD

Disclosed herein are imidazopyridazine compounds, and pharmaceutical compositions thereof, which modulate Interleukin-17A. Also disclosed herein is the therapeutic use of such compounds, for example, in treating and/or ameliorating an IL-17A mediated inflammatory syndrome, disorder, or disease.

BACKGROUND

Interleukin-17 ("IL-17"), also known as IL-17A and CTLA-8, is produced mainly by CD4+ Th17 cells, and also by other immune cells such as CD8+ T cells, γδ T cells, NK cells, NKT cells, and innate lymphoid cells (ILCs). IL-17A exists as a homodimer (A/A) or as a heterodimer (A/F) with IL-17F and signals through binding to dimeric receptor complex IL-17RA and IL-17RC. IL-17RA is ubiquitously expressed at particularly high levels by haematopoietic cell types, whereas IL-17RC is preferentially expressed by non-haematopoietic cells (Gaffen, S. Structure and signaling in the IL-17 receptor family. Nat. Rev. Immunol. 2009, 9, 556-567). IL-17A/IL-17R signaling induces de novo gene transcription by triggering NF-kB, C/EBP and MAPK pathways through ACT1-TRAF6-TRAF4. It can also stabilize target mRNA transcripts through the ACT1-TRAF2-TRAF5 complex (Amatya N. et al., Trends in Immunology, 2017, 38, 310-322). IL-17A stimulates the release of inflammatory mediators including IL-6, IL-8, G-CSF, TNF-α, and IL-10 that recruit and activate lymphocytes to the site of injury or inflammation and maintain a proinflammatory state.

As discussed below, preclinical and clinical data have demonstrated the significant pathological role of IL-17A in multiple autoimmune and inflammatory diseases.

For psoriasis: IL-17A mRNA and/or protein levels are elevated in the lesional skin and blood of patients with psoriasis and correlate with disease severity. IL-17A acts directly in synergy with other cytokines (such as TNFα, IFNγ or IL-22) on keratinocytes triggering a self-amplifying inflammatory response in the skin and leading to the formation of psoriatic plaques. The blockade of IL-17A by means of antibodies to IL-17A or IL-23 results in complete reversal of the molecular and clinical disease features in majority of psoriasis patients, manifesting the significant role of IL-17A and IL-17-producing T-cells in the immunopathogenesis of psoriasis. (Hawkes et al., Psoriasis Pathogenesis and the Development of Novel, Targeted Immune Therapies. J Allergy Clin Immunol. 2017, 140(3): 645-653). The development and approval of IL-17 monoclonal antibodies such as secukinumab, ixekizumab, and brodalumab and their transformational efficacy for psoriasis have demonstrated IL-17A as a valid target for psoriasis treatments. (Blauvelt A. and Chiricozzi A. The Immunologic Role of IL-17 in Psoriasis and Psoriatic Arthritis Pathogenesis. Clin Rev Allergy Immunol. 2018, 55(3):379-390).

For psoriatic arthritis (PsA): IL-17A is mechanistically relevant to PsA through NFκB activation that triggers transcription of several PsA related genes including the receptor activator of nuclear factor κB ligand (RANKL). RANKL triggers the differentiation of osteoclast precursor cells into activated osteoclasts, resulting in bone resorption and subsequently joint deformity in PsA (Adamopoulos I. and Mellins E. Nature reviews Rheumatology 2015; 11:189-94). PsA joint is enriched for IL-17+CD8+ T cells, and the levels of this T cell subset are correlated with disease activity (Menon B. et al., Arthritis & Rheumatology 2014; 66: 1272-81). Synovial fibroblasts isolated from PsA patients also contain elevated IL-17R expression and secrete increased IL-6, CXCL8 and MMP3 ex vivo compared to osteoarthritis patients. Both secukinumab and ixekizumab are FDA approval drugs for PsA. In matching-adjusted indirect comparison analysis, secukinumab was associated with higher ACR 20/50/70 response rates in patients with active PsA than anti-TNFα antibodies (Mease P. et al., Eur. J. Rheumatol. 2019 Jul. 1; 6(3):113-121; Strand V. et al., J. Comp. Eff. Res. 2019, 8(7):497-510; Nash P. et al., Rheumatol. Ther. 2018, 5(1):99-122). In a recent head-to-head study, ixekizumab was superior to adalimumab in achieving simultaneous improvement of joint and skin disease (ACR50 and PASI100) in patients with PsA and inadequate response to conventional synthetic disease-modifying anti-rheumatic drug (Mease, P. et al. Ann Rheum Diss 2020; 79:123-131). By hitting the same target, IL-17A small molecule inhibitor compounds may exert similar or better efficacy than biologics considering that small molecules generally have better tissue penetration.

For rheumatoid arthritis (RA): IL-17A has been recognized as critical to the progression of rheumatoid arthritis. "The recognition of IL-17 as a pro-inflammatory T cell derived cytokine, and its abundance within rheumatoid joints, provides the strongest candidate mechanism to date through which T cells can capture and localize macrophage effector functions in rheumatoid arthritis" Stamp, L. et al., Immunol. Cell Biol. 2004, 82(1): 1-9. Moreover, in rheumatoid arthritis IL-17A acts locally on synoviocytes and osteoblasts contributing to synovitis and joint destruction. Robert and Miossec have proposed the use of synovial biopsies and/or biomarkers to precisely identify patients that would respond to IL-17A inhibition. Their work concludes that IL-17 inhibitors should now be considered in the development of precision medicine in RA. (Robert M. and Miossec P., Front. Med., 2019, 5:364)

For Ankylosing Spondylitis (AS): Various studies have reported elevated IL-17A and Th17 and other cells producing IL-17 in AS blood samples (Wendling D. et al., Joint Bone Spine. 2007; 74:304-305; Shen H. et al., Arthritis Rheum. 2009; 60(6):1647-56; Zhang L. et al., PLoS One. 2012; 7(4):e31000; Jansen D. et al., Rheumatology (Oxford). 2015 April; 54(4): 728-735). In situ analysis of AS spine has revealed increased IL-17A-producing cells in bone of facet (zygapophyseal) joints (Appel H. et al., Arthritis Res. Ther. 2011; 13(3):R95). Two advanced IL-17A neutralizing antibodies, secukinumab, approved by FDA for AS, and ixekizumab, have demonstrated efficacy over placebo even in anti-TNF inadequate responders. In contrast, anti-IL-23 p40 and p19 biologics failed to demonstrate beneficial effect (Deodhar A. et al., Arthritis Rheumatol. 2019, 71(2): 258-270; Baeten D. et al., Ann. Rheum. Dis. 2018, 77(9): 1295-1302), indicating the differential underling mechanism along IL-23/IL-17 pathway in AS and providing a strong evidence to support continuing developing IL-17A inhibitors.

For hidradenitis suppurativa (HS): Increased IL-17 and IL-17-producing T helper cells in the skin lesions of HS patients were reported and molecular proteomics and gene expression data indicate that the IL-23/Th17 pathway is upregulated in HS lesions (Schlapbach C. et al., J. Am. Acad. Dermatol. 2011; 65(4):790; Kelly G. et al., British J. Dermatol. 2015 December; 173(6):1431-9; Moran B. et al., J. Invest. Dermatol. 2017; 137(11):2389; Thomi R. et al., JAMA Dermatol. 2018; 154(5):592). Seven of nine (78%) patients with moderate-to-severe HS achieved HiSCR in an open-label pilot-trial with Secukinumab (Prussick L. et al., British J. Dermatol. 2019 September; 181(3):609-611), and more clinical trials with anti-IL-17 mAbs in HS are ongoing.

For bullous pemphigold (BP): IL-17 is elevated in the blister fluid and perilesional skin of BP patients. (Le Jan S. et al., J. Invest. Dermatol. 2014; 134 (12):2908-2917; Chakievska L. J Autoimmun. 2019, 96:104-112). Exome sequencing of BP patients revealed mutations in twelve IL-17-related genes in one third of patients, providing the genetic link between IL-17 pathway and BP (Chakievska L. J Autoimmun. 2019, 96:104-112). In experimental murine BP, IL-17A-/- mice are protected, and anti-IL-17A treatment significantly reduced skin lesions in wild type (Chakievska L. J Autoimmun. 2019, 96:104-112). Ixekizumab Phase 2 of treatment naive and refractory BP patients is on-going (NCT03099538).

For atopic dermatitis (AD): IL-17 was found to be elevated in peripheral blood and lesions in AD patients and Th17 cells infiltrated more markedly in acute than chronic lesions, suggesting its role in acute phase of AD (Koga C. et al., J. Invest. Dermatol. 2008, 128, 2625-2630). Molecular profile analysis from ustekinumab Phase II suggest likely contribution of IL-23/Th17/IL-17 pathway in AD (Khattri S. et al., Exp. Dermatol. 2017 January; 26(1):28-35).

For vitiligo: Many studies in vitiligo patients have demonstrated an increased frequency of Th17 cells and higher levels of IL-17 in both circulation and lesions that positively correlates with disease duration, extent, and activity (Singh R. et al., Autoimmun. Rev 2016, April; 15(4):397-404). Mouse studies demonstrated that depigmentation correlates with greater IL-17 expression/secretion, which modulates vitiligo development (Eby J. et al., Pigment Cell & Melanoma Res. 2014, November; 27(6):1075-85).

For multiple sclerosis (MS): IL-17 expression is increased in PBMCs, cerebrospinal fluid (CSF) as well as in brain lesions and cells from MS patients (Lock, C. et al., Nat. Med. 2002, 8: 500-508; Matusevicius, D. et al., Mult. Scler. 1999, 5: 101-104; Tzartos, J. et al., Am. J. Pathol. 2008, 172: 146-155). IL-17-producing T cells are enriched in active MS lesions (Tzartos, J. et al., Am. J. Pathol. 2008, 172: 146-155; Willing A. et al., J. Immunol. 2018, 200(3):974-982). IL-17A levels were elevated in the CSF of relapsing-remitting MS (RRMS) patients and correlated with the CSF/serum albumin quotient, a measure of blood-brain barrier (BBB) dysfunction, together with in vitro data that IL-17A in combination with IL-6 reduced the expression of tight junction—associated genes and disrupted monolayer integrity in a BBB cell line, highlighting the potential importance of targeting IL-17A in preserving BBB integrity in RRMS (Setiadi A F et al., J Neuroimmunol. 2019, 332:147-154). Secukinumab yielded promising first results in a proof-of-concept study in MS patients (Havrdovi, E. et al., J. Neurol. 2016, 263: 1287-1295).

For Asthma: IL-17 expression is increased in the lung, sputum, bronchoalveolar lavage fluid, and sera in patients with asthma, and the severity of airway hyperresponsiveness is positively correlated with IL-17 expression levels. (Chakir J. et al., J. Allergy Clin. Immunol. 2003,111(6):1293-8). IL-17 was reported to be increased in asthmatic airways and induce human bronchial fibroblasts to produce cytokines (Molet S. et al., J. Allergy Clin. Immunol. 2001, 108(3): 430-8). Anti-IL-17 antibody modulates airway responsiveness, inflammation, tissue remodeling, and oxidative stress in chronic mouse asthma models (Camargo LdN. et al., Front Immunol. 2018; 8:1835; dos Santos T. et al., Front. Physiol. 2018, 9:1183).

For Chronic Obstructive Pulmonary Disease (COPD): An increase in Th17 cells was observed in patients with COPD compared with current smokers without COPD and healthy subjects, and inverse correlations were found between Th17 cells with lung function (Vargas-Rojas M. et al., Respir. Med. 2011 November; 105(11):1648-54). In three recent human COPD studies, gene expression profile in bronchial epithelia showed that higher IL-17 signature expression is associated with a lack of response to inhaled corticosteroid, suggesting that there is a COPD subgroup that may benefit from IL-17 inhibitor therapy (Christenson S. et al., J. Clin. Invest. 2019; 129(1):169-181).

For Uveitis: IL-17 promotes the release of inflammatory mediators from retinal pigment epithelium cell line, disrupting the retinal pigment epithelium barrier function (Chen Y. et al., PLoS One. 2011; 6:e18139). IL-17 levels were elevated in the serum or aqueous humor of uveitis patients (El-Asrar A. et al., Clin. Immunol. 2011; 139(2):177-84; Jawad S. et al., Ocul. Immunol. Inflamm. 2013; 21(6):434-9; Kuiper J. et al., Am. J. Ophthalmol. 2011; 152(2):177-182.). Anti-IL-17 antibody delayed the onset of ocular inflammation and markedly inhibited the development of experimental autoimmune uveitis in rats (Zhang R. et al., Curr. Eye Res. 2009 April; 34(4):297-303). The analysis of secondary efficacy data from subcutaneous (sc) secukinumab phase 3 trials in uveitis suggested a beneficial effect of secukinumab in reducing the use of concomitant immunosuppressive medication (Dick A. et al., Ophthalmology 2013; 120(4): 777-87). Later study of intravenous secukinumab in uveitis demonstrated greater efficacy than sc dosing, suggesting requiring optimal exposure for efficacy and confirming the therapeutic potential of IL-17A inhibition (Letko E. et al., Ophthalmology 2015, 122(5), 939-948). Ustekinumab that blocks IL-23/IL-17 pathway was also reported to successfully treat a noninfectious uveitis patient who had severe concomitant psoriasis and PsA and failed to respond to conventional immune suppressants (Mugheddu C. et al., Dermatol. Ther. 2017 September; 30(5); e12527.).

For multiple myeloma (MM): IL-17A serum levels were significantly higher in MM patients and also in patients with advanced stage compared with healthy subjects (Lemancewicz D. et al., Med. Sci. Monit. 2012; 18(1): BR54-BR59). Administration of secukinumab in the SCIDhu model of human myeloma weekly for 4 weeks after the first detection of tumor in mice led to a significant inhibition of tumor growth and reduced bone damage compared to isotype control mice (Prabhala R. et al., Leukemia. 2016 February; 30(2): 379-389).

For systemic lupus erythematosus (SLE): Increased serum or plasma levels of IL-17, expansion of IL-17-producing T cells in the peripheral blood, and infiltration of Th17 cells in target organs like the kidneys was observed in SLE patients (Wong C. et al., Lupus. 2000; 9(8):589-593; Wong C. et al., Clinical Immunology. 2008; 127(3):385-393; Zhao X-F. et al., Mol. Biol. Rep. 2010 January; 37(1):81-5; Chen X. et al., J. Clin. Immunol. 2010 March; 30(2):221-5; Xing Q. et al., Rheumatol. Int. 2012 April; 32(4):949-58). Imbalance between Th17 cells and regulatory T (Treg) cells has been observed in SLE patients including quiescent stage (Ma J. et al., Clin. Rheumatol. 2010; 29(11):1251-1258; Dolff S. et al., Clin. Immunol. 2011, 141(2):197-204). Overexpression of IL-17A using adenovirus enhanced the severity of lupus nephritis, while blockade of IL-17A using neutralizing antibody resulted in decreased severity of lupus nephritis (Wen, Z. et al., PLoS One. 2013, 8: e58161). In a phase 2 study, ustekinumab, an anti-IL-12/23 p40 monoclonal antibody blocking IL-23/IL-17 pathway, has demonstrated efficacy in SLE patients (van Vollenhoven R. et al., Lancet 2018; 392: 1330-39). Human expression studies, animal models, and clinical trials indicate that IL-17 blockade may become a promising therapeutic strategy for SLE (Koga T. et al., Expert Rev. Clin. Immunol. 2019, 15 (6) 629-637).

In summary, animal and human studies have shown that IL-17A plays crucial role in pathogenesis of the multiple diseases and/or conditions discussed above. The significance of targeting IL-17A has been demonstrated by the transformational efficacy of IL-17A neutralizing antibodies in patients. While no oral small molecule IL-17A inhibitors have progressed into late stage clinical trials yet, they are in an attractive area for discovery as their development may broaden treatment options for many patients without access to biologics. In addition, a safe and efficacious small molecule IL-17A inhibitor may offer significant benefits to patients such as convenient dosing regimens and cost savings, which in turn may provide effective long-term disease management. Accordingly, there is a need for new small molecule IL-17A modulators (e.g., inhibitors).

SUMMARY

The present application discloses a compound of Formula I:

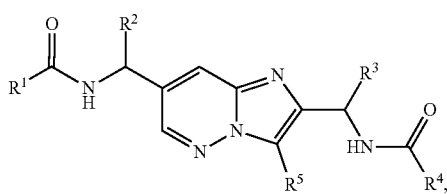

(I)

or a pharmaceutically acceptable salt thereof, wherein:
$R^1$ is —$C_{(1-6)}$alkyl, —$C_{(0-2)}$alkyl$C_{(3-6)}$cycloalkyl, or a 5- to 6-membered heterocyclyl having 1 to 2 nitrogen atoms;
  wherein the —$C_{(1-6)}$alkyl is unsubstituted or substituted with one to six $R^{1a}$ groups;
  wherein the —$C_{(0-2)}$alkyl$C_{(3-6)}$cycloalkyl is unsubstituted or substituted with one to six $R^{1b}$ groups; and
  wherein the 5- to 6-membered heterocyclyl is unsubstituted or substituted with one to three $R^{1c}$ groups;
$R^2$ is H, —$C_{(3-5)}$cycloalkyl, or —$C_{(1-4)}$alkyl; wherein the —$C_{(1-4)}$alkyl is unsubstituted or substituted with one to six $R^{2a}$ groups;
$R^{1a}$, $R^{1b}$ and $R^{2a}$ are each independently fluorine, —$C_{(3-5)}$cycloalkyl, —CN, —OH, —$OC_{(1-3)}$alkyl or —$OC_{(3-4)}$cycloalkyl, wherein the —$OC_{(1-3)}$alkyl and —$OC_{(3-4)}$cycloalkyl groups are unsubstituted or substituted with one to three fluorine atoms;
each $R^{1c}$ is independently —$OCH_3$, —$OCF_3$, —$OCHF_2$, or —$C_{(1-4)}$alkyl that is unsubstituted or substituted with one to six fluorine atoms;
$R^3$ is —$C_{(0-1)}$alkyl$C_{(3-6)}$cycloalkyl, —$C_{(3-6)}$alkyl or —$C_{(1-2)}$alkyl-O—$C_{(1-3)}$alkyl, wherein the —$C_{(0-1)}$alkyl$C_{(3-6)}$cycloalkyl, —$C_{(3-6)}$alkyl and —$C_{(1-2)}$alkyl-O—$C_{(1-3)}$alkyl are unsubstituted or substituted with one to five $R^{3a}$ groups each independently selected from fluorine, —$CH_3$—$CHF_2$, —$CF_3$, OH and =O;
$R^4$ is —$C_{(3-6)}$cycloalkyl, phenyl, or a 5- to 6-membered heteroaryl having 1 to 4 heteroatoms selected from N, O, and S;
  wherein the $C_{(3-6)}$cycloalkyl is unsubstituted or substituted with one to three $R^{4a}$ groups each independently selected from halogen, —$OC_{(1-3)}$alkyl, and —$C_{(1-4)}$alkyl wherein the —$OC_{(1-3)}$alkyl, and —$C_{(1-4)}$alkyl are unsubstituted or substituted with one to three fluorine atoms;
    alternatively, two $R^{4a}$ groups attached to the same ring atom can be combined with the atom to which they are attached to form a $C_{(3-6)}$cycloalkyl;
  wherein the phenyl is unsubstituted or substituted with one to three $R^{4b}$ groups each independently selected from halogen, —CN, —$C_{(0-2)}$alkyl-$C_{(3-4)}$cycloalkyl, —$OC_{(0-2)}$alkyl-$C_{(3-4)}$cycloalkyl, —$OC_{(1-3)}$alkyl, —$C_{(1-4)}$alkyl and a 3 to 6-membered heterocyclyl having 1 to 2 heteroatoms selected from N and O, wherein the —$OC_{(1-3)}$alkyl, —$C_{(0-2)}$alkyl-$C_{(3-4)}$cycloalkyl and —$C_{(1-4)}$alkyl are unsubstituted or substituted with one to three fluorine atoms, and wherein the heterocyclyl is unsubstituted or substituted with 1 oxo;
  wherein the 5- to 6-membered heteroaryl is unsubstituted or substituted with one or two $R^{4c}$ groups;
each $R^{4c}$ is independently halogen, —CN, —OH, —$N(R^{4c1})(R^{4c2})$, —$C_{(0-2)}$alkyl$C_{(3-6)}$cycloalkyl, —$OC_{(0-2)}$alkyl-$C_{(3-4)}$cycloalkyl, —$C_{(1-4)}$alkyl, —$OC_{(1-3)}$alkyl, or a 3 to 6-membered heterocyclyl having 1 to 2 heteroatoms selected from N and O, wherein the —$C_{(0-2)}$alkyl$C_{(3-6)}$cycloalkyl, —$C_{(1-4)}$alkyl, —$OC_{(1-3)}$alkyl and heterocyclyl groups are unsubstituted or substituted with one to six $R^{4d}$ groups;
  alternatively, two $R^{4c}$ groups attached to adjacent ring atoms can be combined to form a $C_{(4-6)}$cycloalkyl;
each $R^{4d}$ is independently fluorine, —CN, —OH, oxo, —$C_{(1-3)}$alkyl, —$OC_{(1-3)}$alkyl, —$OC_{(3-4)}$cycloalkyl, —$C_{(0-2)}$alkyl-$N(R^{4d1})(R^{4d2})$, —$C_{(0-2)}$alkyl-$N(C_{(1-4)}$alkyl)$C(O)(C_{(1-4)}$alkyl) or a 3 to 6-membered heterocyclyl having 1 to 2 heteroatoms selected from N and O, wherein the —$C_{(1-3)}$alkyl, —$OC_{(1-3)}$alkyl, —$OC_{(3-4)}$cycloalkyl and heterocyclyl groups are unsubstituted or substituted with one to three fluorine atoms;
$R^{4c1}$, $R^{4c2}$, $R^{4d1}$ and $R^{4d2}$ are each independently H or —$C_{(1-3)}$alkyl, wherein the —$C_{(1-3)}$alkyl is unsubstituted or substituted with one to six groups selected from fluorine and chlorine;

alternatively $R^{4d1}$ and $R^{4d2}$ can be combined with the atom to which they are attached to form a 3 to 6 membered heterocyclyl having 1 to 3 heteroatoms selected from N, O and S, wherein the heterocyclyl is unsubstituted or substituted with 1 to 4 fluorine atoms; and $R^5$ is hydrogen or halogen;

wherein when $R^4$ is 1,2,4-triazolyl, then $R^4$ is

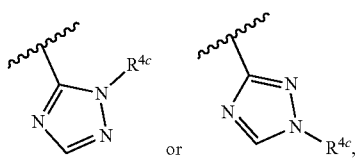

and when $R^4$ is a substituted 6-membered heteroaryl, the substituted heteroaryl is unsubstituted at the para-position.

The present application also discloses compounds of Formula I'. All compounds of Formula I are compounds of Formula I'. Some compounds of Formula I' are compounds of Formula I.

Accordingly disclosed herein is a compound of Formula I':

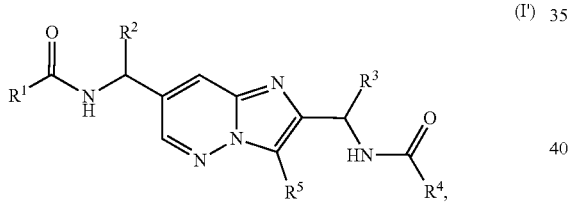
(I')

or a pharmaceutically acceptable salt thereof, wherein:

$R^1$ is —$C_{(1-6)}$alkyl, —$C_{(0-2)}$alkyl$C_{(3-6)}$cycloalkyl, —$C_{(0-2)}$alkyl-cyclopropyl-$C_{(1-3)}$perfluoroalkyl, or a 5- to 6-membered heterocyclyl having 1 to 2 nitrogen atoms;

wherein the —$C_{(1-6)}$alkyl is unsubstituted or substituted with one to six $R^{1a}$ groups;

wherein the —$C_{(0-2)}$alkyl$C_{(3-6)}$cycloalkyl is unsubstituted or substituted with one to six $R^{1b}$ groups; and wherein the 5- to 6-membered heterocyclyl is unsubstituted or substituted with one to three $R^{1c}$ groups;

$R^2$ is H, —$C_{(3-5)}$cycloalkyl, —$C_{(1-4)}$alkyl, or a 6-membered heterocycle having 1 to 2 oxygen atoms;

wherein the —$C_{(1-4)}$alkyl is unsubstituted or substituted with one to six $R^{2a}$ groups; and wherein the —$C_{(3-5)}$cycloalkyl is unsubstituted or substituted with —CN;

$R^{1a}$, $R^{1b}$ and $R^{2a}$ are each independently fluorine, —$C_{(3-5)}$cycloalkyl, —CN, —OH, —$OC_{(1-3)}$alkyl or —$OC_{(3-4)}$cycloalkyl, wherein the —$OC_{(1-3)}$alkyl and —$OC_{(3-4)}$cycloalkyl groups are unsubstituted or substituted with one to three fluorine atoms;

each $R^{1c}$ is independently —$OCH_3$, —$OCF_3$, —$OCHF_2$, or —$C_{(1-4)}$alkyl that is unsubstituted or substituted with one to six fluorine atoms;

$R^3$ is —$C_{(0-1)}$alkyl$C_{(3-6)}$cycloalkyl, —$C_{(3-6)}$alkyl or —$C_{(1-2)}$alkyl-O—$C_{(1-3)}$alkyl, wherein the —$C_{(0-1)}$alkyl$C_{(3-6)}$cycloalkyl, —$C_{(3-6)}$alkyl and —$C_{(1-2)}$alkyl-O—$C_{(1-3)}$alkyl are unsubstituted or substituted with one to five $R^{3a}$ groups each independently selected from fluorine, —$CH_3$—$CHF_2$, —$CF_3$, OH and =O;

$R^4$ is —$C_{(3-6)}$cycloalkyl, phenyl, or a 5 to 6-membered heteroaryl having 1 to 4 heteroatoms selected from N, O, and S;

wherein the $C_{(3-6)}$cycloalkyl is unsubstituted or substituted with one to three $R^{4a}$ groups each independently selected from halogen, —$OC_{(1-3)}$alkyl, and —$C_{(1-4)}$alkyl wherein the —$OC_{(1-3)}$alkyl, and —$C_{(1-4)}$alkyl are unsubstituted or substituted with one to three fluorine atoms;

alternatively, two $R^{4a}$ groups attached to the same ring atom can be combined with the atom to which they are attached to form a $C_{(3-6)}$cycloalkyl;

wherein the phenyl is unsubstituted or substituted with one to three $R^{4b}$ groups each independently selected from halogen, —CN, —$C_{(0-2)}$alkyl-$C_{(3-4)}$cycloalkyl, —$OC_{(0-2)}$alkyl-$C_{(3-4)}$cycloalkyl, —$OC_{(1-3)}$alkyl, —$C_{(1-4)}$alkyl and a 3 to 6-membered heterocyclyl having 1 to 2 heteroatoms selected from N and O, wherein the —$OC_{(1-3)}$alkyl, —$C_{(0-2)}$alkyl-$C_{(3-4)}$cycloalkyl and —$C_{(1-4)}$alkyl are unsubstituted or substituted with one to three fluorine atoms, and wherein the heterocyclyl is unsubstituted or substituted with 1 oxo;

wherein the 5- to 6-membered heteroaryl is unsubstituted or substituted with one or two $R^{4c}$ groups;

each $R^{4c}$ is independently halogen, —CN, —OH, —N($R^{4c1}$)($R^{4c2}$), —$C_{(0-2)}$alkyl$C_{(3-6)}$cycloalkyl, —$OC_{(0-2)}$alkyl-$C_{(3-4)}$cycloalkyl, —$C_{(1-4)}$alkyl, —$OC_{(1-3)}$alkyl, or a 3 to 6-membered heterocyclyl having 1 to 2 heteroatoms selected from N and O, wherein the —$C_{(0-2)}$alkyl$C_{(3-6)}$cycloalkyl, —$C_{(1-4)}$alkyl, —$OC_{(1-3)}$alkyl and heterocyclyl groups are unsubstituted or substituted with one to six $R^{4d}$ groups;

alternatively, two $R^{4c}$ groups attached to adjacent ring atoms can be combined to form a $C_{(4-6)}$cycloalkyl;

each $R^{4d}$ is independently fluorine, —CN, —OH, oxo, —$C_{(1-3)}$alkyl, —$OC_{(1-3)}$alkyl, —$OC_{(3-4)}$cycloalkyl, —$C_{(0-2)}$alkyl-N($R^{4d1}$)($R^{4d2}$), —$C_{(0-2)}$alkyl-N($C_{(1-4)}$alkyl)C(O)($C_{(1-4)}$alkyl) or a 3- to 6-membered heterocyclyl having 1 to 2 heteroatoms selected from N and O, wherein the —$C_{(1-3)}$alkyl, —$OC_{(1-3)}$alkyl, —$OC_{(3-4)}$cycloalkyl and heterocyclyl groups are unsubstituted or substituted with one to three fluorine atoms;

$R^{4c1}$, $R^{4c2}$, $R^{4d1}$ and $R^{4d2}$ are each independently H or —$C_{(1-3)}$alkyl, wherein the —$C_{(1-3)}$alkyl is unsubstituted or substituted with one to six groups selected from fluorine and chlorine;

alternatively $R^{4d1}$ and $R^{4d2}$ can be combined with the atom to which they are attached to form a 3- to 6-membered heterocyclyl having 1 to 3 heteroatoms selected from N, O and S, wherein the heterocyclyl is unsubstituted or substituted with 1 to 4 fluorine atoms; and R$^5$ is hydrogen or halogen;

wherein:

when R$^4$ is 1,2,4-triazolyl, then R$^4$ is

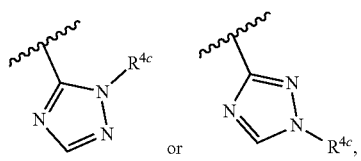

and when R$^4$ is a substituted 6-membered heteroaryl, the substituted heteroaryl is unsubstituted at the para-position.

In some embodiments, disclosed herein is a pharmaceutical composition comprising a compound of Formula I, or pharmaceutically acceptable salt thereof, and a pharmaceutically acceptable carrier.

Also described herein is a method for treating and/or ameliorating an IL-17A mediated inflammatory syndrome, disorder, or disease (e.g., psoriasis, psoriatic arthritis, rheumatoid arthritis, ankylosing spondylitis, etc.) comprising administering to a subject in need thereof a therapeutically effective amount of a compound of Formula I, or a pharmaceutically acceptable salt thereof.

In some embodiments, disclosed herein is the use of a therapeutically effective amount of compound of Formula I, or a pharmaceutically acceptable salt thereof, for treating and/or ameliorating an IL-17A mediated inflammatory syndrome, disorder, or disease (e.g., psoriasis, psoriatic arthritis, rheumatoid arthritis, ankylosing spondylitis, etc.).

In some embodiments, disclosed herein is the use of a compound of Formula I, or pharmaceutically acceptable salt thereof, in the manufacture of a medicament for treating and/or ameliorating an IL-17A mediated inflammatory syndrome, disorder, or disease (e.g., psoriasis, psoriatic arthritis, rheumatoid arthritis, ankylosing spondylitis, etc.).

In some embodiments, provided herein are processes and intermediates disclosed herein that are useful for preparing a compound of Formula I or pharmaceutically acceptable salts thereof.

In some embodiments, disclosed herein is a pharmaceutical composition comprising a compound of Formula I', or pharmaceutically acceptable salt thereof, and a pharmaceutically acceptable carrier.

Also described herein is a method for treating and/or ameliorating an IL-17A mediated inflammatory syndrome, disorder, or disease (e.g., psoriasis, psoriatic arthritis, rheumatoid arthritis, ankylosing spondylitis, etc.) comprising administering to a subject in need thereof a therapeutically effective amount of a compound of Formula I', or a pharmaceutically acceptable salt thereof.

In some embodiments, disclosed herein is the use of a therapeutically effective amount of compound of Formula I', or a pharmaceutically acceptable salt thereof, for treating and/or ameliorating an IL-17A mediated inflammatory syndrome, disorder, or disease (e.g., psoriasis, psoriatic arthritis, rheumatoid arthritis, ankylosing spondylitis, etc.).

In some embodiments, disclosed herein is the use of a compound of Formula I', or pharmaceutically acceptable salt thereof, in the manufacture of a medicament for treating and/or ameliorating an IL-17A mediated inflammatory syndrome, disorder, or disease (e.g., psoriasis, psoriatic arthritis, rheumatoid arthritis, ankylosing spondylitis, etc.).

In some embodiments, provided herein are processes and intermediates disclosed herein that are useful for preparing a compound of Formula I' or pharmaceutically acceptable salts thereof.

The disclosure also provides a compound or method as described herein.

DETAILED DESCRIPTION

Definitions

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains.

Otherwise, certain terms used herein have the meanings as set forth in the specification. All patents, published patent applications and publications cited herein are incorporated by reference as if set forth fully herein.

It must be noted that as used herein and in the appended claims, the singular forms "a," "an," and "the" include plural reference unless the context clearly dictates otherwise.

In an attempt to help the reader of the application, the description has been separated in various paragraphs or sections, or is directed to various embodiments of the application. These separations should not be considered as disconnecting the substance of a paragraph or section or embodiments from the substance of another paragraph or section or embodiments. To the contrary, one skilled in the art will understand that the description has broad application and encompasses all the combinations of the various sections, paragraphs and sentences that can be contemplated. The discussion of any embodiment is meant only to be exemplary and is not intended to suggest that the scope of the disclosure, including the claims, is limited to these examples.

The term "administering" with respect to the methods of the invention, means a method for therapeutically or prophylactically preventing, treating or ameliorating a syndrome, disorder or disease as described herein by using a compound of the disclosure, or pharmaceutically acceptable salt thereof, composition thereof, or medicament thereof. Such methods include administering a therapeutically effective amount of a compound of the disclosure, or pharmaceutically acceptable salt thereof, composition thereof, or medicament thereof, at different times during the course of a therapy or concurrently or sequentially as a combination therapy.

The term "subject" refers to a patient, which may be an animal, preferably a mammal, most preferably a human, whom will be or has been treated by a method according to an embodiment of the application. Examples of mammals include, but are not limited to, cows, horses, sheep, pigs, cats, dogs, mice, rats, rabbits, guinea pigs, non-human primates (NHPs) such as monkeys or apes, humans, etc., more preferably a human.

The term "therapeutically effective amount" or "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

As used herein, "IL-17" or "IL-17A" refers to interleukin 17A. It is also named IL17, CTLA8, CTLA-8. Interleukin 17A is a pro-inflammatory cytokine. This cytokine is produced by a group of immune cells in response to their stimulation. An exemplary amino acid sequence of human IL-17 is represented in GenBank Accession No. NP_002181.1, which can be encoded by a nucleic acid sequence such as that of GenBank Accession No. NM_002190.3.

The term "modulator" as used herein refers to any agents or molecules that can bind to IL-17, including small molecule compounds.

As used herein, the term "composition" is intended to encompass a product comprising the specified ingredients in the specified amounts, as well as any product which results, directly or indirectly, from combinations of the specified ingredients in the specified amounts.

As used herein, the term "treat", "treating", or "treatment" of any disease, condition, syndrome or disorder refers, in one embodiment, to ameliorating the disease, condition, syndrome or disorder (i.e., slowing or arresting or reducing the development of the disease or at least one of the clinical symptoms thereof). In another embodiment, "treat", "treating", or "treatment" refers to alleviating or ameliorating at least one physiological or biochemical parameter associated with or causative of the disease, condition, syndrome or disorder, including those which may not be discernible by the patient. In a further embodiment, "treat", "treating", or "treatment" refers to modulating the disease, condition, syndrome or disorder either physically (e.g. stabilization of a discernible symptom), physiologically, (e.g. stabilization of a physical parameter), or both. In yet another embodiment, "treat", "treating", or "treatment" refers to preventing or delaying the onset or development or progression of the disease, condition, syndrome or disorder.

As used herein, the term "QD" means once daily.

As used herein, the term "BID" means twice daily.

The term "alkyl" is a straight or branched saturated hydrocarbon. For example, an alkyl group can have 1 to 12 carbon atoms (i.e., $(C_1-C_{12})$alkyl) or 1 to 6 carbon atoms (i.e., $(C_1-C_6)$alkyl). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), isopropyl (i-Pr, i-propyl, —$CH(CH_3)_2$), 1-butyl (n-bu, n-butyl, —$CH_2CH_2CH_2CH_3$), 2-butyl (s-bu, s-butyl, —$CH(CH_3)CH_2CH_3$), tert-butyl (t-bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 1-hexyl (—$CH_2CH_2CH_2CH_2CH_2CH_3$), 2-hexyl (—$CH(CH_3)CH_2CH_2CH_2CH_3$), heptyl (—$(CH_2)_6CH_3$), octyl (—$(CH_2)_7CH_3$), 2,2,4-trimethylpentyl (—$CH_2C(CH_3)_2CH_2CH(CH_3)_2$), nonyl (—$(CH_2)_8CH_3$), decyl (—$(CH_2)_9CH_3$), undecyl (—$(CH_2)_{10}CH_3$), and dodecyl (—$(CH_2)_{11}CH_3$). Any alkyl group may be unsubstituted or substituted.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "perfluoroalkyl" refers to an alkyl group, as defined herein, wherein all carbon-hydrogen bonds have been replaced with carbon-fluorine bonds. For example, a perfluoroalkyl group can have 1 to 6 carbon atoms (i.e., $(C_{1-6})$perfluoroalkyl) or 1 to 3 carbon atoms (i.e., $(C_{1-3})$ perfluoroalkyl). Examples of perfluoroalkyl groups include, but are not limited to, trifluoromethyl (—$CF_3$), pentafluoroethyl (—$CF_2CF_3$), heptafluoropropyl (—$CF_2CF_2CF_3$), and heptafluoroisopropyl (—$CF(CF_3)_2$).

The term "heterocycle" or "heterocyclyl" refers to a single saturated or partially unsaturated ring that has at least one atom other than carbon in the ring, wherein the atom is selected from the group consisting of oxygen, nitrogen and sulfur. Exemplary heterocycles include, but are not limited to oxetanyl, aziridinyl, azetidinyl, pyrrolidinyl, piperidinyl, piperazinyl, morpholinyl, tetrahydropyranyl, tetrahydrofuranyl, and thiomorpholinyl.

The term "cycloalkyl" refers to a saturated or partially unsaturated all carbon ring system having 3 to 8 carbon atoms (i.e., $C_{(3-8)}$cycloalkyl), and preferably 3 to 6 carbon atoms (i.e., $C_{(3-6)}$cycloalkyl), wherein the cycloalkyl ring system has a single ring or multiple rings in a spirocyclic or bicyclic form. Exemplary cycloalkyls include, but are not limited to, cyclopropyl, cyclobutyl, cyclopentyl, cyclohexyl, cycloheptyl, and cyclooctyl. Unless otherwise stated specifically in the specification, a cycloalkyl group may be unsubstituted or substituted. Some cycloalkyl groups may exist as spirocycloalkyls, wherein two cycloalkyl rings are fused through a single carbon atom; for example and without limitation, an example of a spiropentyl group is

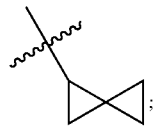 [SMILES: *C1CC12CC2]

for example and without limitation, examples of spirohexyl groups include

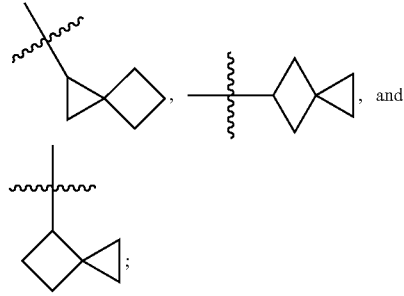

for example and without limitation examples of cycloheptyl groups include

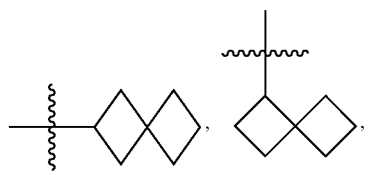

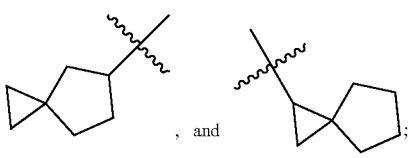, and ;

for example and without limitation examples of cyclooctyl groups include

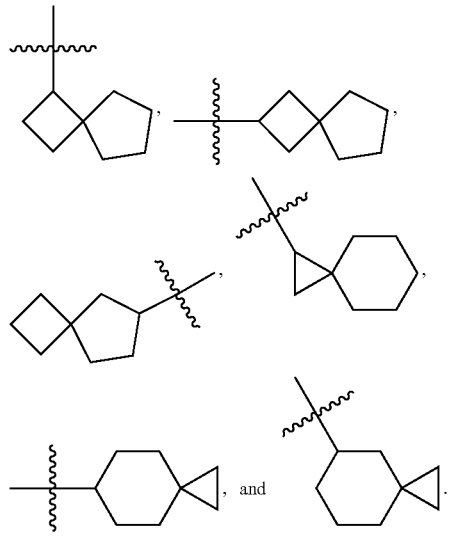

Unless otherwise stated specifically in the specification, a siprocycloalkyl group may be unsubstituted or substituted. Bicyclic cycloalkyl ring systems also include

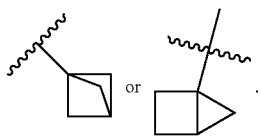

The term "heteroaryl" refers to a single aromatic ring that has at least one atom other than carbon in the ring, wherein the atom is selected from the group consisting of oxygen, nitrogen and sulfur. The term "heteroaryl" includes single aromatic rings of from 1 to 6 carbon atoms and 1 to 4 heteroatoms selected from the group consisting of oxygen, nitrogen and sulfur. Exemplary heteroaryl ring systems include but are not limited to pyridinyl, pyrimidinyl, pyrazinyl, pyridazinyl, pyrimidinyl, pyrazolyl, oxazolyl, oxadiazolyl, isoxazolyl, triazolyl, imidazolyl, tetrazolyl, thienyl, thiazolyl, isothiazolyl, thiadiazolyl, or furyl.

The terms "ortho," "meta," and "para" have the meanings as understood in the art and are used herein to indicate the position of a substituent on a phenyl or 6-membered heteroaryl ring relative to the point of attachment of the ring. For example, the structure below is described as 3-pyridinyl with the $X_1$ substituent in the ortho position, the $X_2$ substituent in the meta position, and the $X_3$ substituent in the para position:

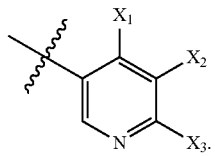

The term "halogen" refers to bromo (—Br), chloro (—Cl), fluoro (—F) or iodo (—I).

Where the compounds disclosed herein have at least one stereocenter, they may accordingly exist as enantiomers or diastereomers. It is to be understood that all such isomers and mixtures thereof are encompassed within the scope of the present invention.

"Diastereoisomers" are stereoisomers that have at least two asymmetric atoms, but which are not mirror images of each other.

"Enantiomers" are a pair of stereoisomers that are non-superimposable mirror images of each other. A "racemic" mixture is a 1:1 mixture of a pair of enantiomers. A "scalemic" mixture of enantiomers is mixture of enantiomers at a ratio other than 1:1.

Where the processes for the preparation of the compounds according to the invention give rise to mixture of stereoisomers, these isomers may be separated by conventional techniques such as preparative chromatography. The compounds may be prepared in racemic form, a scalemic mixture, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral column vial HPLC or SFC. In some instances rotamers of compounds may exist which are observable by $^1$H NMR leading to complex multiplets and peak integration in the $^1$H NMR spectrum.

The absolute stereochemistry is specified according to the Cahn-Ingold-Prelog R-S system. Chiral centers, of which the absolute configurations are known, are labelled by prefixes R and S, assigned by the standard sequence-rule procedure, and preceded when necessary by the appropriate locants (*Pure & Appl. Chem.* 45, 1976, 11-30). Certain examples contain chemical structures that are depicted or labelled as an (R*) or (S*). When (R*) or (S*) is used in the name of a compound or in the chemical representation of the compound, it is intended to convey that the compound is a pure single isomer at that stereocenter; however, absolute configuration of that stereocenter has not been established. Thus, a compound designated as (R*) refers to a compound that is a pure single isomer at that stereocenter with an absolute configuration of either (R) or (S), and a compound designated as (S*) refers to a compound that is a pure single isomer at that stereocenter with an absolute configuration of either (R) or (S). For example, N—((S)-(7-((S*)-Cyclopropyl(4,4,4-trifluorobutanamido)methyl)imidazo[1,2-b]pyridazin-2-yl)(4,4-difluorocyclohexyl)methyl)-1-(3,3,3-trifluoropropyl)-1H-pyrazole-4-carboxamide:

15

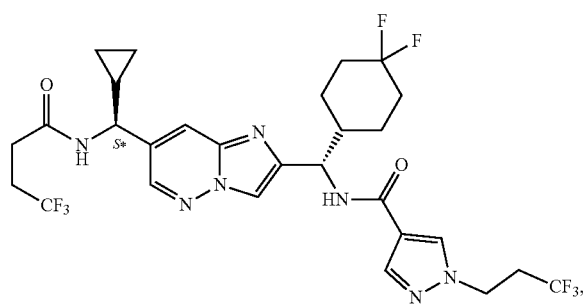 [SMILES: O=C(CCC(F)(F)F)N[C@H](c1cnn2cc([C@@H](NC(=O)c3cnn(CCC(F)(F)F)c3)C3CCC(F)(F)CC3)nc2c1)C1CC1]

refers to a compound that is either:

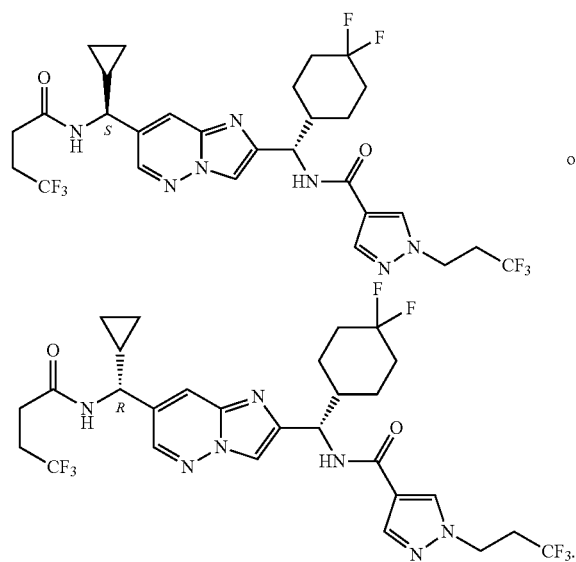

Pseudoasymmetric stereogenic centers are treated in the same way as chiral centers, but are given lower-case symbols, r or s (*Angew. Chem. Int. Ed. Engl.* 1982, 21, 567-583).

During any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Furthermore, it is intended that within the scope of the present invention, any element, in particular when mentioned in relation to a compound of the disclosure, or pharmaceutically acceptable salt thereof, shall comprise all isotopes and isotopic mixtures of said element, either naturally occurring or synthetically produced, either with natural abundance or in an isotopically enriched form. For example, a reference to hydrogen includes within its scope $^1$H, $^2$H (i.e., deuterium or D), and $^3$H (i.e., tritium or T). In some embodiments, the compounds described herein include a $^2$H (i.e., deuterium) isotope. By way of example, the group denoted —$C_{(1-6)}$alkyl includes not only —CH$_3$, but also CD$_3$; not only —CH$_2$CH$_3$, but also CD$_2$CD$_3$, etc. Similarly, references to carbon and oxygen include within their scope respectively $^{12}$C, $^{13}$C and $^{14}$C and $^{15}$O and $^{16}$O and $^{17}$O and $^{18}$O. The isotopes may be radioactive or non-radioactive. Radiolabelled compounds of the disclosure may include a radioactive isotope selected from the group comprising $^3$H, $^{11}$C, $^{18}$F, $^{35}$S, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

Compounds of the Disclosure

The present application discloses a compound of Formula I:

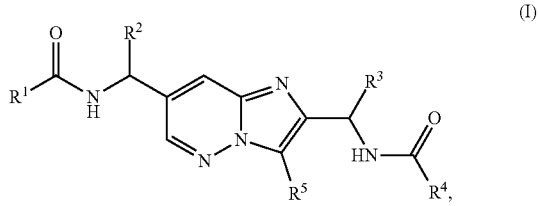

(I)

or a pharmaceutically acceptable salt thereof, wherein:
R$^1$ is —C$_{(1-6)}$alkyl, —C$_{(0-2)}$alkylC$_{(3-6)}$cycloalkyl, or a 5- to 6-membered heterocyclyl having 1 to 2 nitrogen atoms;
  wherein the —C$_{(1-6)}$alkyl is unsubstituted or substituted with one to six R$^{1a}$ groups;
  wherein the —C$_{(0-2)}$alkylC$_{(3-6)}$cycloalkyl is unsubstituted or substituted with one to six R$^{1b}$ groups; and
  wherein the 5- to 6-membered heterocyclyl is unsubstituted or substituted with one to three R$^{1c}$ groups;
R$^2$ is H, —C$_{(3-5)}$cycloalkyl, or —C$_{(1-4)}$alkyl; wherein the —C$_{(1-4)}$alkyl is unsubstituted or substituted with one to six R$^{2a}$ groups;
R$^{1a}$, R$^{1b}$ and R$^{2a}$ are each independently fluorine, —C$_{(3-5)}$cycloalkyl, —CN, —OH, —OC$_{(1-3)}$alkyl or —OC$_{(3-4)}$cycloalkyl, wherein the —OC$_{(1-3)}$alkyl and —OC$_{(3-4)}$cycloalkyl groups are unsubstituted or substituted with one to three fluorine atoms;
each R$^{1c}$ is independently —OCH$_3$, —OCF$_3$, —OCHF$_2$, or —C$_{(1-4)}$alkyl that is unsubstituted or substituted with one to six fluorine atoms;
R$^3$ is —C$_{(0-1)}$alkylC$_{(3-6)}$cycloalkyl, —C$_{(3-6)}$alkyl or —C$_{(1-2)}$alkyl-O—C$_{(1-3)}$alkyl, wherein the —C$_{(0-1)}$alkylC$_{(3-6)}$cycloalkyl, —C$_{(3-6)}$alkyl and —C$_{(1-2)}$alkyl-O—C$_{(1-3)}$alkyl are unsubstituted or substituted with one to five R$^{3a}$ groups each independently selected from fluorine, —CH$_3$—CHF$_2$, —CF$_3$, OH and =O;
R$^4$ is —C$_{(3-6)}$cycloalkyl, phenyl, or a 5 to 6-membered heteroaryl having 1 to 4 heteroatoms selected from N, O, and S;
  wherein the C$_{(3-6)}$cycloalkyl is unsubstituted or substituted with one to three R$^{4a}$ groups each independently selected from halogen, —OC$_{(1-3)}$alkyl, and —C$_{(1-4)}$alkyl wherein the —OC$_{(1-3)}$alkyl, and —C$_{(1-4)}$alkyl are unsubstituted or substituted with one to three fluorine atoms;
  alternatively, two R$^{4a}$ groups attached to the same ring atom can be combined with the atom to which they are attached to form a C$_{(3-6)}$cycloalkyl;
  wherein the phenyl is unsubstituted or substituted with one to three R$^{4b}$ groups each independently selected from halogen, —CN, —C$_{(0-2)}$alkyl-C$_{(3-4)}$cycloalkyl, —OC$_{(0-2)}$alkyl-C$_{(3-4)}$cycloalkyl, —OC$_{(1-3)}$alkyl, —C$_{(1-4)}$alkyl and a 3- to 6-membered heterocyclyl having 1 to 2 heteroatoms selected from N and O, wherein the —OC$_{(1-3)}$alkyl, —C$_{(0-2)}$alkyl-C$_{(3-4)}$cycloalkyl and —C$_{(1-4)}$alkyl are unsubstituted or substituted with one to three fluorine atoms, and wherein the heterocyclyl is unsubstituted or substituted with 1 oxo;

wherein the 5- to 6-membered heteroaryl is unsubstituted or substituted with one or two R$^{4c}$ groups;

each R$^{4c}$ is independently halogen, —CN, —OH, —N(R$^{4c1}$)(R$^{4c2}$), —C$_{(0-2)}$alkylC$_{(3-6)}$cycloalkyl, —OC$_{(0-2)}$alkyl-C$_{(3-4)}$cycloalkyl, —C$_{(1-4)}$alkyl, —OC$_{(1-3)}$alkyl, or a 3- to 6-membered heterocyclyl having 1 to 2 heteroatoms selected from N and O, wherein the —C$_{(0-2)}$alkylC$_{(3-6)}$cycloalkyl, —C$_{(1-4)}$alkyl, —OC$_{(1-3)}$alkyl and heterocyclyl groups are unsubstituted or substituted with one to six R$^{4d}$ groups;

alternatively, two R$^{4c}$ groups attached to adjacent ring atoms can be combined to form a C$_{(4-6)}$cycloalkyl;

each R$^{4d}$ is independently fluorine, —CN, —OH, oxo, —C$_{(1-3)}$alkyl, —OC$_{(1-3)}$alkyl, —OC$_{(3-4)}$cycloalkyl, —C$_{(0-2)}$alkyl-N(R$^{4d1}$)(R$^{4d2}$), —C$_{(0-2)}$alkyl-N(C$_{(1-4)}$alkyl)C(O)(C$_{(1-4)}$alkyl) or a 3 to 6 membered heterocyclyl having 1 to 2 heteroatoms selected from N and O, wherein the —C$_{(1-3)}$alkyl, —OC$_{(1-3)}$alkyl, —OC$_{(3-4)}$cycloalkyl and heterocyclyl groups are unsubstituted or substituted with one to three fluorine atoms;

R$^{4c1}$, R$^{4c2}$, R$^{4d1}$ and R$^{4d2}$ are each independently H or —C$_{(1-3)}$alkyl, wherein the —C$_{(1-3)}$alkyl is unsubstituted or substituted with one to six groups selected from fluorine and chlorine;

alternatively R$^{4d1}$ and R$^{4d2}$ can be combined with the atom to which they are attached to form a 3 to 6 membered heterocyclyl having 1 to 3 heteroatoms selected from N, O and S, wherein the heterocyclyl is unsubstituted or substituted with 1 to 4 fluorine atoms; and R$^5$ is hydrogen or halogen;

wherein when R$^4$ is 1,2,4-triazolyl, then R$^4$ is

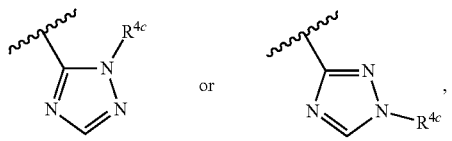

and when R$^4$ is a substituted 6-membered heteroaryl, the substituted heteroaryl is unsubstituted at the para-position.

In some embodiments, disclosed herein is a compound of Formula I, or a pharmaceutically acceptable salt thereof, wherein:

R$^1$ is —C$_{(1-6)}$alkyl, —C$_{(0-2)}$alkylC$_{(3-6)}$cycloalkyl, or piperidinyl;

wherein the —C$_{(1-6)}$alkyl is unsubstituted or substituted with one to six R$^{1a}$ groups;

wherein the —C$_{(0-2)}$alkylC$_{(3-6)}$cycloalkyl is unsubstituted or substituted with one to six R$^{1b}$ groups; and wherein the piperidinyl is unsubstituted or substituted with one to three R$^{1c}$ groups;

R$^{1a}$ and R$^{1b}$ are each independently —OH, —OCH$_3$, —OCF$_3$, —OCHF$_2$, or fluorine;

each R$^{1c}$ is independently —C$_{(1-2)}$alkyl that is unsubstituted or substituted with one to three fluorine atoms;

R$^2$ is H, —C$_{(3-5)}$cycloalkyl, or —C$_{(1-4)}$alkyl;

R$^3$ is —C$_{(5-6)}$cycloalkyl that is unsubstituted or substituted with one to two fluorine atoms;

R$^4$ is —C$_{(3-4)}$cycloalkyl, phenyl, or a 5-membered heteroaryl having 1 to 4 heteroatoms selected from N, O, and S;

wherein the C$_{(3-6)}$cycloalkyl is unsubstituted or substituted with one to three R$^{4a}$ groups each independently selected from halogen and C$_{(1-4)}$alkyl that is unsubstituted or substituted with one to three fluorine atoms;

alternatively, two R$^{4a}$ groups attached to the same ring atom can be combined with the atom to which they are attached to form a C$_{(3-6)}$cycloalkyl;

wherein the phenyl is unsubstituted or substituted with one or two R$^{4b}$ groups each independently selected from halogen, —CN, —C$_{(0-2)}$alkyl-C$_{(3-4)}$cycloalkyl, —OC$_{(0-2)}$alkyl-C$_{(3-4)}$cycloalkyl, —OC$_{(1-3)}$alkyl, C$_{(1-4)}$alkyl, and a 3 to 6-membered heterocyclyl having 1 to 2 heteroatoms selected from N and O, wherein the —OC$_{(1-3)}$alkyl, —C$_{(0-2)}$alkyl-C$_{(3-4)}$cycloalkyl and —C$_{(1-4)}$alkyl are unsubstituted or substituted with one to three fluorine atoms, and wherein the heterocyclyl is unsubstituted or substituted with 1 oxo;

wherein the 5-membered heteroaryl is unsubstituted or substituted with one or two R$^{4c}$ groups;

each R$^{4c}$ is independently halogen, —CN, —C$_{(0-2)}$alkylC$_{(3-6)}$cycloalkyl, —OC$_{(0-2)}$alkyl-C$_{(3-4)}$cycloalkyl, —C$_{(1-4)}$alkyl, —OC$_{(1-3)}$alkyl, or a 3 to 6-membered heterocyclyl having 1 to 2 heteroatoms selected from N and O, wherein the —C$_{(0-2)}$alkyl C$_{(3-6)}$cycloalkyl, —C$_{(1-4)}$alkyl, —OC$_{(1-3)}$alkyl and heterocyclyl groups are unsubstituted or substituted with one to six R$^{4d}$ groups;

each R$^{4d}$ is independently fluorine, —CN, oxo, —C$_{(1-3)}$alkyl, —OC$_{(1-3)}$alkyl, —OC$_{(3-4)}$cycloalkyl, —C$_{(0-2)}$alkyl-N(R$^{4d1}$)(R$^{4d2}$), or —C$_{(0-2)}$alkyl-N(C$_{(1-4)}$alkyl)C(O)(C$_{(1-4)}$alkyl), wherein the —C$_{(1-3)}$alkyl, —OC$_{(1-3)}$alkyl and —OC$_{(3-4)}$cycloalkyl groups are unsubstituted or substituted with one to three fluorine atoms;

R$^{4d1}$ and R$^{4d2}$ are each independently H or —C$_{(1-3)}$alkyl, wherein the —C$_{(1-3)}$alkyl is unsubstituted or substituted with one to six groups selected from fluorine and chlorine;

alternatively R$^{4d1}$ and R$^{4d2}$ can be combined with the atom to which they are attached to form a 3 to 6 membered heterocyclyl having 1 to 3 heteroatoms selected from N, O and S, wherein the heterocyclyl is unsubstituted or substituted with 1 to 4 fluorine atoms; and R$^5$ is hydrogen or fluorine;

wherein when R$^4$ is 1,2,4-triazolyl, then R$^4$ is

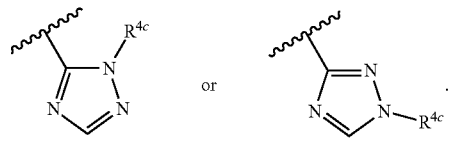

In some embodiments, disclosed herein is a compound of Formula I, or a pharmaceutically acceptable salt thereof, wherein:
- $R^1$ is $—C_{(1-6)}$alkyl, $—CH_2C_{(3-6)}$cycloalkyl, or piperidinyl wherein the $—C_{(1-6)}$alkyl is unsubstituted or substituted with one to six $R^{1a}$ groups;
  - wherein the $—CH_2C_{(3-6)}$cycloalkyl is unsubstituted or substituted with one to four fluorine atoms; and
  - wherein the piperidinyl is unsubstituted or substituted with $—C_{(1-2)}$alkyl that is unsubstituted or substituted with one to three fluorine atoms;
- each $R^{1a}$ is independently —OH, —OCH$_3$, —OCF$_3$, —OCHF$_2$, or fluorine;
- $R^2$ is H, $—C_{(3-5)}$cycloalkyl, or $—C_{(1-3)}$alkyl;
- $R^3$ is cyclohexyl that is unsubstituted or substituted with one to two fluorine atoms;
- $R^4$ is $—C_{(3-4)}$cycloalkyl, spiropentanyl, spirohexanyl, spiroheptanyl, spirooctanyl, phenyl, pyridinyl, pyrimidinyl, pyrazinyl, pyrrolyl, pyrazolyl, oxazolyl, oxadiazolyl, isoxazolyl, triazolyl, imidazolyl, or thiadiazolyl;
  - wherein the $—C_{(3-4)}$cycloalkyl is unsubstituted or substituted with one to three groups selected from halogen, and $C_{(1-2)}$alkyl that is unsubstituted or substituted with one to three fluorine atoms;
  - wherein the phenyl, pyridinyl, pyrimidinyl, and pyrazinyl are unsubstituted or substituted with one or two groups selected from halogen and $C_{(1-2)}$alkyl that is unsubstituted or substituted with one to three fluorine atoms;
  - wherein the pyrazolyl, oxazolyl, oxadiazolyl, isoxazolyl, triazolyl, imidazolyl, and thiadiazolyl are substituted with one or two $R^{4c}$ groups;
- each $R^{4c}$ is independently $—C_{(0-2)}$alkyl$C_{(3-6)}$cycloalkyl, or $—C_{(1-4)}$alkyl, wherein the $—C_{(0-2)}$alkyl$C_{(3-6)}$cycloalkyl and $—C_{(1-4)}$alkyl groups are unsubstituted or substituted with one to four $R^{4d}$ groups;
- each $R^{4d}$ is independently —OCH$_3$, —OCF$_3$, —OCHF$_2$, or fluorine; and
- $R^5$ is hydrogen or fluorine.

In some embodiments, disclosed herein is a compound of Formula I, or a pharmaceutically acceptable salt thereof, wherein:
- $R^1$ is $—C_{(3-5)}$alkyl,

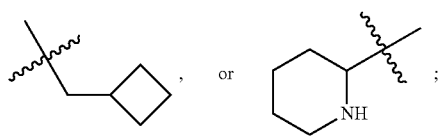 [SMILES: *CC1CCC1 ; *C1CCCCN1]

- wherein the $—C_{(3-5)}$alkyl is unsubstituted or substituted with one to six $R^{1a}$ groups;
  - wherein the

is unsubstituted or substituted with one to four fluorine atoms; and wherein the

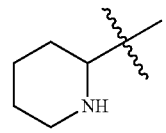 [SMILES: *C1CCCCN1]

is unsubstituted or substituted with $—C_{(1-2)}$alkyl that is unsubstituted or substituted with one to three fluorine atoms;
- each $R^{1a}$ is independently —OH or fluorine;
- $R^2$ is H, cyclopropyl, methyl, or isopropyl;
- $R^3$ is cyclohexyl, or

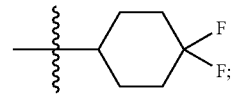 [SMILES: *C1CCC(F)(F)CC1]

- $R^4$ is cyclopropyl, spiropentanyl, spirohexanyl, phenyl, pyridinyl, pyrazolyl, oxazolyl, isoxazolyl, triazolyl, imidazolyl, or 1,2,3-thiadiazolyl;
  - wherein the cyclopropyl is unsubstituted or substituted with one to three groups selected from fluorine and $C_{(1-2)}$alkyl that is unsubstituted or substituted with one to three fluorine atoms;
  - wherein the phenyl and pyridinyl are unsubstituted or substituted with one to two groups selected from chlorine and $C_{(1-2)}$alkyl that is unsubstituted or substituted with one to three fluorine atoms;
  - wherein the 1,2,3-thiadiazolyl is unsubstituted or substituted with $C_{(1-3)}$alkyl, wherein the $C_{(1-3)}$alkyl is unsubstituted or substituted with one to three fluorine atoms;
  - wherein the pyrazolyl, oxazolyl, isoxazolyl, triazolyl, and imidazolyl are unsubstituted or substituted with one or two $R^{4c}$ groups;
- each $R^{4c}$ is independently $—C_{(0-1)}$alkyl$C_{(3-4)}$cycloalkyl, or $—C_{(1-4)}$alkyl, wherein the $—C_{(0-1)}$alkyl$C_{(3-4)}$cycloalkyl and $—C_{(1-4)}$alkyl groups are unsubstituted or substituted with one to four $R^{4d}$ groups;
- each $R^{4d}$ is independently —OCH$_3$, —OCF$_3$, —OCHF$_2$, or fluorine; and
- $R^5$ is hydrogen or fluorine.

In some embodiments, disclosed herein is a compound of Formula I, or a pharmaceutically acceptable salt thereof, wherein:
- $R^1$ is $—C_{(1-6)}$alkyl, $—CH_2C_{(3-6)}$cycloalkyl, or piperidinyl wherein the $—C_{(1-6)}$alkyl is unsubstituted or substituted with one to six $R^{1a}$ groups;
  - wherein the $—CH_2C_{(3-6)}$cycloalkyl is unsubstituted or substituted with one to four fluorine atoms; and
  - wherein the piperidinyl is unsubstituted or substituted with $—C_{(1-2)}$alkyl that is unsubstituted or substituted with one to three fluorine atoms;
- each $R^{1a}$ is independently —OH, —OCH$_3$, —OCF$_3$, —OCHF$_2$, or fluorine;
- $R^2$ is H, $—C_{(3-5)}$cycloalkyl, or $—C_{(1-3)}$alkyl;
- $R^3$ is cyclohexyl that is unsubstituted or substituted with one to two fluorine atoms;
- $R^4$ is $—C_{(3-4)}$cycloalkyl, spiropentanyl, spirohexanyl, spiroheptanyl, spirooctanyl, phenyl, pyrrolyl, pyrazolyl, oxazolyl, oxadiazolyl, isoxazolyl, triazolyl, tetrazolyl, imidazolyl, thienyl, thiazolyl, isothiazolyl or thiadiazolyl; wherein the $—C_{(3-4)}$cycloalkyl is unsubstituted or substituted with one to three groups selected from halogen, and $C_{(1-2)}$alkyl that is unsubstituted or substituted with one to three fluorine atoms;

wherein the phenyl is unsubstituted or substituted with one or two groups selected from halogen, —CN, —$C_{(0-2)}$alkyl-$C_{(3-4)}$cycloalkyl, —$OC_{(0-2)}$alkyl-$C_{(3-4)}$cycloalkyl, —$OC_{(1-3)}$alkyl, $C_{(1-4)}$alkyl, and a 3 to 6-membered heterocyclyl having 1 to 2 heteroatoms selected from N and O, wherein the —$OC_{(1-3)}$alkyl, —$C_{(0-2)}$alkyl-$C_{(3-4)}$cycloalkyl and —$C_{(1-4)}$alkyl are unsubstituted or substituted with one to three fluorine atoms, and wherein the heterocyclyl is unsubstituted or substituted with 1 oxo;

wherein the pyrazolyl, oxazolyl, oxadiazolyl, isoxazolyl, triazolyl, tetrazolyl, imidazolyl, thiazolyl, isothiazolyl and thiadiazolyl are substituted with one or two $R^{4c}$ groups;

each $R^{4c}$ is independently halogen, —CN, —$C_{(0-2)}$alkyl $C_{(3-6)}$cycloalkyl, —$OC_{(0-2)}$alkyl-$C_{(3-4)}$cycloalkyl, —$C_{(1-4)}$alkyl, —$OC_{(1-3)}$alkyl, or a 3 to 6-membered heterocyclyl having 1 to 2 heteroatoms selected from N and O, wherein the —$C_{(0-2)}$alkyl$C_{(3-6)}$cycloalkyl, —$C_{(1-4)}$alkyl, —$OC_{(1-3)}$alkyl and heterocyclyl groups are unsubstituted or substituted with one to four $R^{4d}$ groups;

each $R^{4d}$ is independently —$OCH_3$, —$OCF_3$, —$OCHF_2$, or fluorine; and $R^5$ is hydrogen or fluorine;

wherein when $R^4$ is 1,2,4-triazolyl, then $R^4$ is

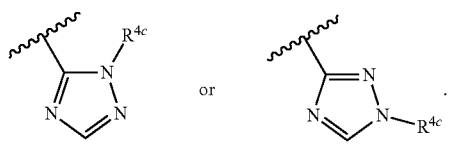

In some embodiments, disclosed herein is a compound of Formula I, or a pharmaceutically acceptable salt thereof, wherein:

$R^1$ is —$C_{(3-5)}$alkyl,

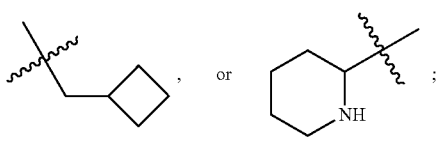 [SMILES: *CC1CCC1 ; *C1CCCCN1]

wherein the —$C_{(3-5)}$alkyl is substituted with one to six $R^{1a}$ groups;

wherein the

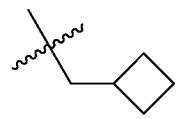 [SMILES: *CC1CCC1]

is substituted with two fluorine atoms; and
wherein the

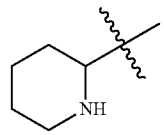 [SMILES: *C1CCCCN1]

is substituted with —$CF_3$;
each $R^{1a}$ is independently —OH or fluorine;
$R^2$ is H, cyclopropyl, methyl, or isopropyl;
$R^3$ is cyclohexyl, or

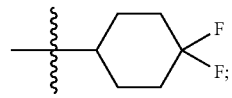

$R^4$ is cyclopropyl, spiropentanyl, spirohexanyl, phenyl, pyridinyl, pyrazolyl, oxazolyl, isoxazolyl, triazolyl, imidazolyl, or 1,2,3-thiadiazolyl;
  wherein the cyclopropyl is substituted with one to two groups selected from fluorine and $C_{(1)}$alkyl that is unsubstituted or substituted with three fluorine atoms;
  wherein the phenyl is unsubstituted or substituted with -chlorine, or —$C_{(1-2)}$alkyl;
  wherein the pyridyl is substituted with $C_{(1-2)}$alkyl that is unsubstituted or substituted with one to three fluorine atoms;
  wherein the 1,2,3-thiadiazolyl is substituted with $C_{(2-3)}$alkyl;
  wherein the pyrazolyl, oxazolyl, isoxazolyl, triazolyl, and imidazolyl are substituted with one or two $R^{4c}$ groups;
each $R^{4c}$ is independently —$C_{(0-1)}$alkyl$C_{(3-4)}$cycloalkyl, or —$C_{(1-3)}$alkyl, wherein the —$C_{(0-1)}$alkyl$C_{(3-4)}$cycloalkyl and —$C_{(1-3)}$alkyl groups are unsubstituted or substituted with one to four $R^{4d}$ groups;
each $R^{4d}$ is independently —$OCH_3$, —$OCF_3$, —$OCHF_2$, or fluorine; and
$R^5$ is hydrogen.

In some embodiments, disclosed herein is a compound of Formula I, or a pharmaceutically acceptable salt thereof, wherein:

$R^1$ is —$C_{(3-5)}$alkyl,

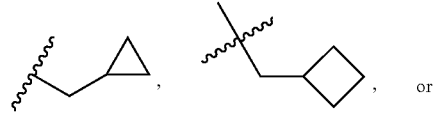

-continued

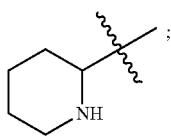

wherein the —C$_{(3-5)}$alkyl is unsubstituted or substituted with one to six R$^{1a}$ groups;
wherein the

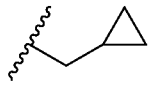

is unsubstituted or substituted with one to four fluorine atoms;
wherein the

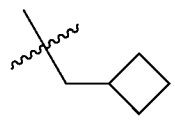 [SMILES: *CC1CCC1]

is unsubstituted or substituted with one to four fluorine atoms; and
wherein the

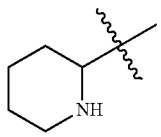 [SMILES: *C1CCCCN1]

is unsubstituted or substituted with —C$_{(1-2)}$alkyl that is unsubstituted or substituted with one to three fluorine atoms;
each R$^{1a}$ is independently —OH or fluorine;
R$^2$ is H, methyl, isopropyl or cyclopropyl;
R$^3$ is cyclohexyl or

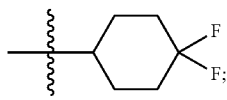

R$^4$ is cyclopropyl, spiropentanyl, spirohexanyl, phenyl, pyrazolyl, oxazolyl, isoxazolyl, 1,2,5-oxadiazolyl, triazolyl, tetrazolyl, imidazolyl, thienyl, thiazolyl, isothiazolyl, 1,2,3-thiadiazolyl or 1,2,5-thiadiazolyl;
wherein the cyclopropyl is unsubstituted or substituted with one to three groups selected from fluorine and C$_{(1-2)}$alkyl that is unsubstituted or substituted with one to three fluorine atoms;
wherein the phenyl is unsubstituted or substituted with one to two groups selected from chlorine and C$_{(1-2)}$alkyl that is unsubstituted or substituted with one to three fluorine atoms;
wherein the 1,2,3-thiadiazolyl is unsubstituted or substituted with C$_{(1-3)}$alkyl, wherein the C$_{(1-3)}$alkyl is unsubstituted or substituted with one to three fluorine atoms; wherein the pyrazolyl, oxazolyl, isoxazolyl, 1,2,5-oxadiazolyl, triazolyl, tetrazolyl, imidazolyl, thiazolyl, isothiazolyl, or 1,2,5-thiadiazolyl are unsubstituted or substituted with one or two R$^{4c}$ groups;

each R$^{4c}$ is independently —C$_{(0-1)}$alkylC$_{(3-4)}$cycloalkyl, or —C$_{(1-4)}$alkyl, wherein the —C$_{(0-1)}$alkylC$_{(3-4)}$cycloalkyl and —C$_{(1-4)}$alkyl groups are unsubstituted or substituted with one to four R$^{4d}$ groups;

each R$^{4d}$ is independently —OCH$_3$, —OCF$_3$, —OCHF$_2$, or fluorine; and

R$^5$ is hydrogen or fluorine;
wherein
when R$^4$ is 1,2,4-triazolyl, then R$^4$ is

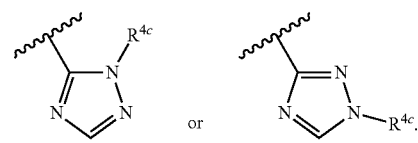

In some embodiments, disclosed herein is a compound of Formula I, or a pharmaceutically acceptable salt thereof, wherein:

R$^1$ is —C$_{(3-5)}$alkyl,

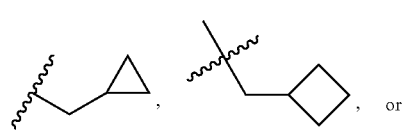

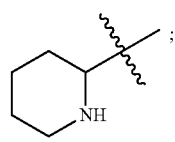

wherein the —C$_{(3-5)}$alkyl is substituted with one to six R$^{1a}$ groups;
wherein the

is unsubstituted or substituted with one to two fluorine atoms;

wherein the

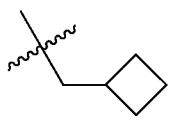 [SMILES: *CC1CCC1]

is substituted with two fluorine atoms; and
wherein the

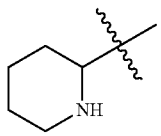 [SMILES: *C1CCCCN1]

is substituted with —CF$_3$;
each R$^{1a}$ is independently —OH or fluorine;
R$^2$ is H, methyl, isopropyl or cyclopropyl;
R$^3$ is cyclohexyl or

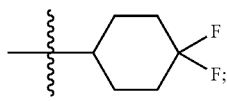 [SMILES: *C1CCC(F)(F)CC1]

R$^4$ is cyclopropyl, spiropentanyl, spirohexanyl, phenyl, pyrazolyl, oxazolyl, isoxazolyl, oxadiazolyl, triazolyl, tetrazolyl, imidazolyl, 1,2,3-thiadiazolyl or 1,2,5-thiadiazolyl;
  wherein the cyclopropyl is substituted with one to two groups selected from fluorine and C$_{(1)}$alkyl that is unsubstituted or substituted with three fluorine atoms;
  wherein the phenyl is unsubstituted or substituted with -chlorine, or —C$_{(1-2)}$alkyl;
  wherein the 1,2,3-thiadiazolyl and 1,2,5-thiadiazolyl are substituted with C$_{(2-3)}$alkyl;
  wherein the pyrazolyl, oxazolyl, isoxazolyl, oxadiazolyl, triazolyl, tetrazolyl and imidazolyl are substituted with one or two R$^{4c}$ groups;
each R$^{4c}$ is independently —C$_{(0-1)}$alkylC$_{(3-4)}$cycloalkyl, or —C$_{(1-3)}$alkyl, wherein the —C$_{(0-1)}$alkylC$_{(3-4)}$cycloalkyl and —C$_{(1-3)}$alkyl groups are unsubstituted or substituted with one to four R$^{4d}$ groups;
each R$^{4d}$ is independently —OCH$_3$, —OCF$_3$, —OCHF$_2$, or fluorine; and
R$^5$ is hydrogen;
wherein
  when R$^4$ is 1,2,4-triazolyl, then R$^4$ is

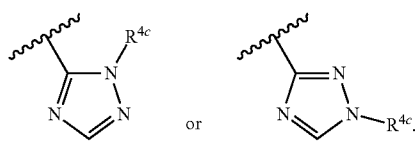

In some embodiments, disclosed herein is a compound of Formula I, or a pharmaceutically acceptable salt thereof, wherein:
  R$^1$ is —C$_{(3-6)}$alkyl, —C$_{(0-2)}$alkylC$_{(3-6)}$cycloalkyl, or a 6-membered heterocyclyl having 1 to 2 nitrogen atoms;

wherein the —C$_{(1-6)}$alkyl is unsubstituted or substituted with one to six R$^{1a}$ groups;
wherein the —C$_{(0-2)}$alkylC$_{(3-6)}$cycloalkyl is unsubstituted or substituted with one to three R$^{1b}$ groups; and
wherein the 6-membered heterocyclyl is substituted with one R$^{1c}$ group;
each R$^{1a}$ is independently fluorine or —OH;
each R$^{1b}$ is independently fluorine;
R$^{1c}$ is —C$_{(1-4)}$alkyl that is substituted with one to three fluorine atoms.

In some embodiments, disclosed herein is a compound of Formula I, or a pharmaceutically acceptable salt thereof, wherein R$^1$ is:

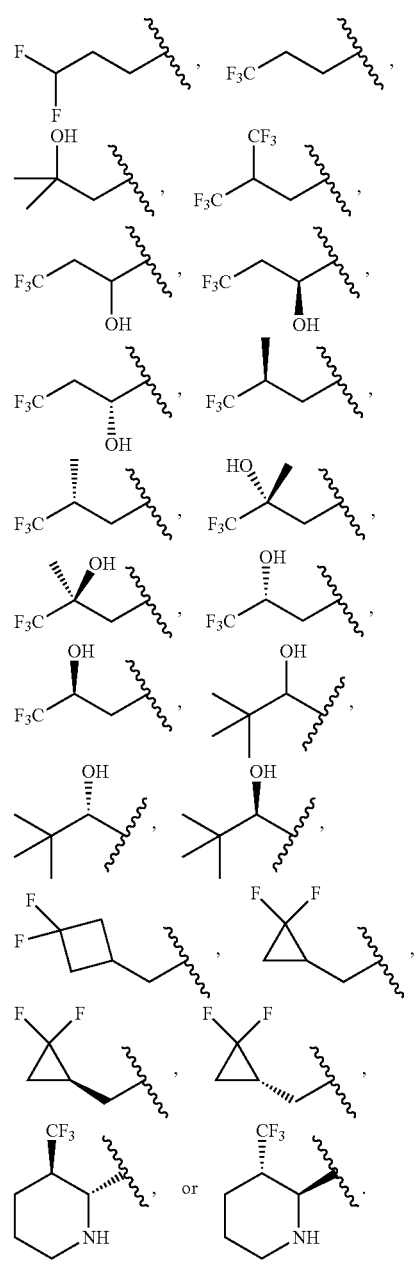

In some embodiments, disclosed herein is a compound of Formula I, or a pharmaceutically acceptable salt thereof, wherein R$^1$ is:

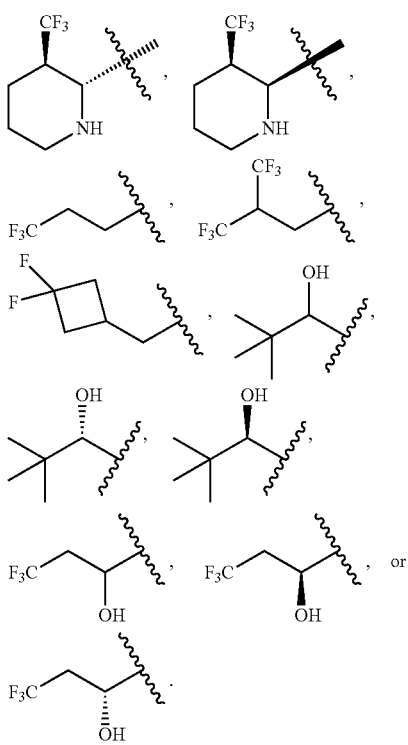

In some embodiments, disclosed herein is a compound of Formula I, or a pharmaceutically acceptable salt thereof, wherein R¹ is:

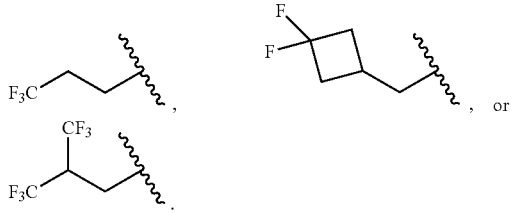

In some embodiments, disclosed herein is a compound of Formula I, or a pharmaceutically acceptable salt thereof, wherein R¹ is

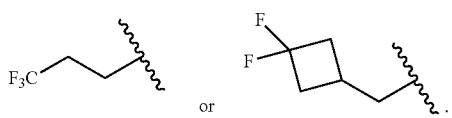 [SMILES: *CCC(F)(F)F ; *CC1CC(F)(F)C1]

In some embodiments, disclosed herein is a compound of Formula I, or a pharmaceutically acceptable salt thereof, wherein R¹ is

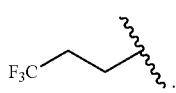

In some embodiments, disclosed herein is a compound of Formula I, or a pharmaceutically acceptable salt thereof, wherein R¹ is

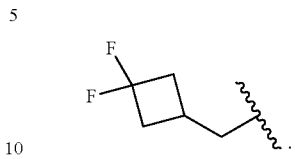

In some embodiments, disclosed herein is a compound of Formula I, or a pharmaceutically acceptable salt thereof, wherein R² is H, methyl, isopropyl or cyclopropyl.

In some embodiments, disclosed herein is a compound of Formula I, or a pharmaceutically acceptable salt thereof, wherein R² is H or cyclopropyl. In some embodiments, disclosed herein is a compound of Formula I, or a pharmaceutically acceptable salt thereof, wherein R² is H. In some embodiments, disclosed herein is a compound of Formula I, or a pharmaceutically acceptable salt thereof, wherein R² is cyclopropyl.

In some embodiments, disclosed herein is a compound of Formula I, or a pharmaceutically acceptable salt thereof, wherein R² is unsubstituted cyclopropyl.

In some embodiments, disclosed herein is a compound of Formula I, or a pharmaceutically acceptable salt thereof, which is a compound of formula Ia:

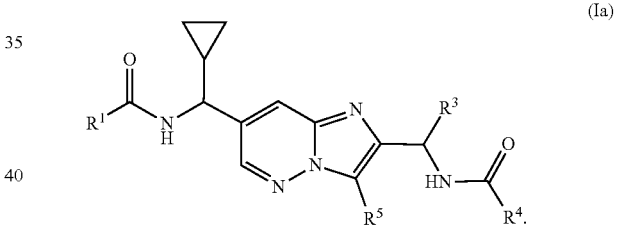

(Ia)

In some embodiments, disclosed herein is a compound of Formula I, or a pharmaceutically acceptable salt thereof, wherein R³ is —C$_{(0-1)}$alkylC$_{(3-6)}$cycloalkyl that is unsubstituted or substituted with one to two fluorine atoms. In some embodiments, disclosed herein is a compound of Formula I, or a pharmaceutically acceptable salt thereof, wherein R³ is cyclohexyl that is unsubstituted or substituted with one to two fluorine atoms.

In some embodiments, disclosed herein is a compound of Formula I, or a pharmaceutically acceptable salt thereof, wherein R³ is

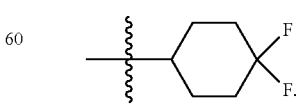

In some embodiments, disclosed herein is a compound of Formula I or Ia, or a pharmaceutically acceptable salt thereof, which is a compound of formula Ib:

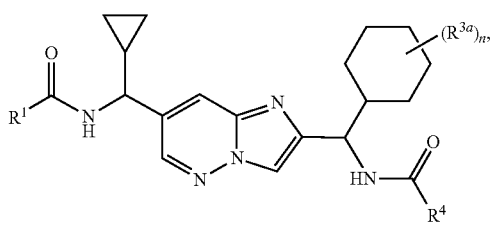

(Ib)

wherein R³ᵃ is fluorine and n is 0, 1, or 2.

In some embodiments, disclosed herein is a compound of Formula I, Ia or Ib, or a pharmaceutically acceptable salt thereof, which is a compound of formula Ib-1:

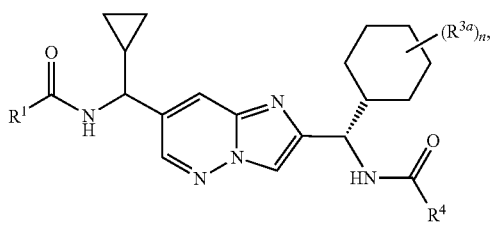

(Ib-1)

wherein R³ᵃ is fluorine and n is 2.

In some embodiments, disclosed herein is a compound of Formula I, Ia, Ib or Ib-1, or a pharmaceutically acceptable salt thereof, which is a compound of formula Ib-2a:

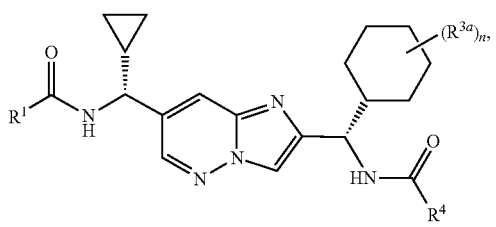

(Ib-2a)

wherein R³ᵃ is fluorine and n is 2.

In some embodiments, disclosed herein is a compound of Formula I, Ia, Ib or Ib-1, or a pharmaceutically acceptable salt thereof, which is a compound of formula Ib-2b:

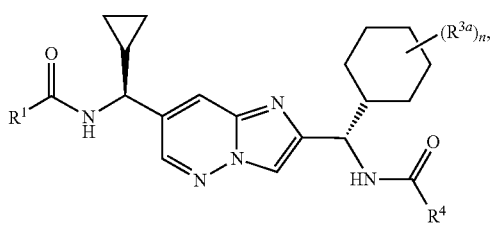

(Ib-2b)

wherein R³ᵃ is fluorine and n is 2.

In some embodiments, disclosed herein is a compound of Formula I, Ia, Ib, Ib-1, or Ib-2a, or a pharmaceutically acceptable salt thereof, which is a compound of formula Ib-3a:

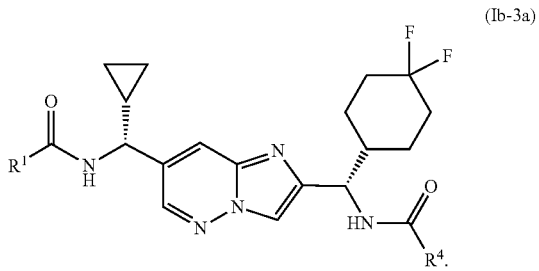

(Ib-3a)

In some embodiments, disclosed herein is a compound of Formula I, Ia, Ib, Ib-1, or Ib-2b, or a pharmaceutically acceptable salt thereof, which is a compound of formula Ib-3b:

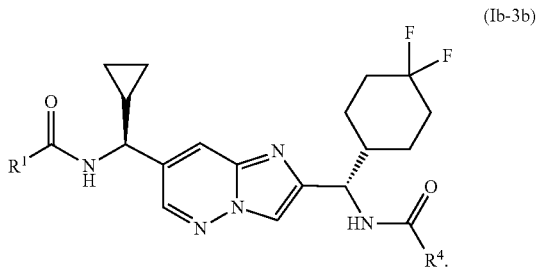

(Ib-3b)

In some embodiments, disclosed herein is a compound of Formula I, or a pharmaceutically acceptable salt thereof, wherein R³ is

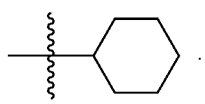 [SMILES: *C1CCCCC1]

.

In some embodiments, disclosed herein is a compound of Formula I, or a pharmaceutically acceptable salt thereof, wherein:
R⁴ is —C₍₃₋₆₎cycloalkyl that is unsubstituted or substituted with one to three R⁴ᵃ groups; and
each R⁴ᵃ is independently selected from halogen, —OC₍₁₋₃₎alkyl, and —C₍₁₋₄₎alkyl, wherein the —OC₍₁₋₃₎alkyl, and —C₍₁₋₄₎alkyl are unsubstituted or substituted with one to three fluorine atoms;
alternatively, two R⁴ᵃ groups attached to the same ring atom can be combined with the atom to which they are attached to form a C₍₃₋₆₎cycloalkyl.

In some embodiments, disclosed herein is a compound of Formula I, or a pharmaceutically acceptable salt thereof, wherein each R⁴ᵃ group is fluorine, methyl, or —CF₃, or two R⁴ᵃ groups attached to the same ring atom can be combined with the atom to which they are attached to form a cyclopropyl, cyclobutyl or cyclopentyl.

In some embodiments, disclosed herein is a compound of Formula I, or a pharmaceutically acceptable salt thereof, wherein R⁴ is cyclopropyl that is unsubstituted or substituted with one to three groups selected from fluorine, CH₃, and CF₃.

In some embodiments, disclosed herein is a compound of Formula I, or a pharmaceutically acceptable salt thereof, wherein R⁴ is cyclopropyl that is unsubstituted or substituted with one to two groups selected from fluorine, CH₃, and CF₃.

In some embodiments, disclosed herein is a compound of Formula I, or a pharmaceutically acceptable salt thereof, wherein R⁴ is

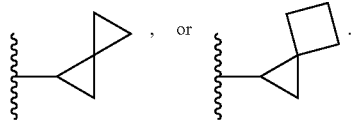 [SMILES: *C1CC12CC2 ; *C1CC12CCC2]

In some embodiments, disclosed herein is a compound of Formula I, or a pharmaceutically acceptable salt thereof, wherein R⁴ is a spirocycle. In some embodiments, disclosed herein is a compound of Formula I, or a pharmaceutically acceptable salt thereof, wherein R⁴ is spiropentanyl or spirohexanyl.

In some embodiments, disclosed herein is a compound of Formula I, or a pharmaceutically acceptable salt thereof, wherein R⁴ is:

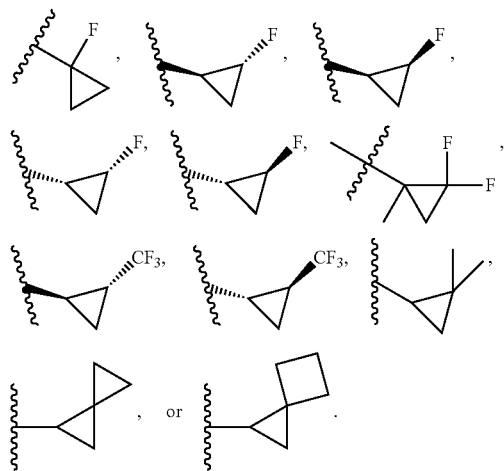

In some embodiments, disclosed herein is a compound of Formula I, or a pharmaceutically acceptable salt thereof, wherein R⁴ is:

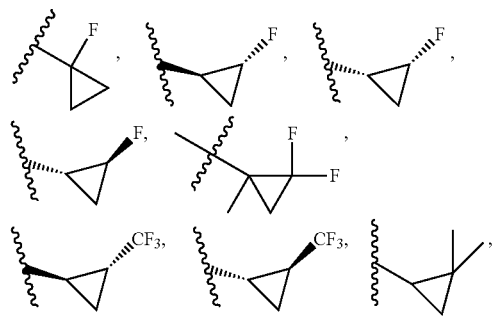

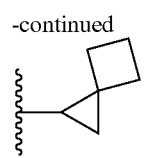

In some embodiments, disclosed herein is a compound of Formula I, or a pharmaceutically acceptable salt thereof, wherein:
R⁴ is phenyl that is unsubstituted or substituted with one to two R⁴ᵇ groups; and
each R⁴ᵇ is independently selected from chlorine, fluorine, —CN, cyclopropyl, —OCH₂— cyclopropyl, —OC₍₁₋₂₎alkyl, —C₍₁₋₂₎alkyl and pyrrolidin-2-one, wherein the cyclopropyl, —OC₍₁₋₂₎alkyl, and C₍₁₋₂₎alkyl are unsubstituted or substituted with one to three fluorine atoms.

In some embodiments, disclosed herein is a compound of Formula I, or a pharmaceutically acceptable salt thereof, wherein each R⁴ᵇ group is independently H, fluorine, chlorine, —CN, methyl, ethyl, —CHF₂, —CH₂CF₃, —OCHF₂, —OCH₂CHF₂, —OCH₂CF₃, cyclopropyl,

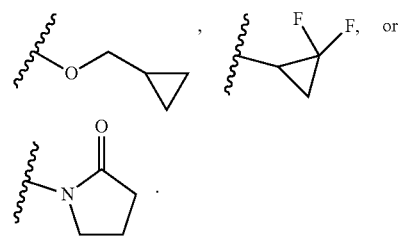

In some embodiments, disclosed herein is a compound of Formula I, or a pharmaceutically acceptable salt thereof, wherein R⁴ is phenyl that is unsubstituted or substituted with halogen (e.g., chlorine), —CH₃, or —CH₂CH₃.

In some embodiments, disclosed herein is a compound of Formula I, or a pharmaceutically acceptable salt thereof, wherein R⁴ is phenyl that is unsubstituted or substituted with chlorine, —CH₃, or —CH₂CH₃.

In some embodiments, disclosed herein is a compound of Formula I, or a pharmaceutically acceptable salt thereof, wherein R⁴ is:

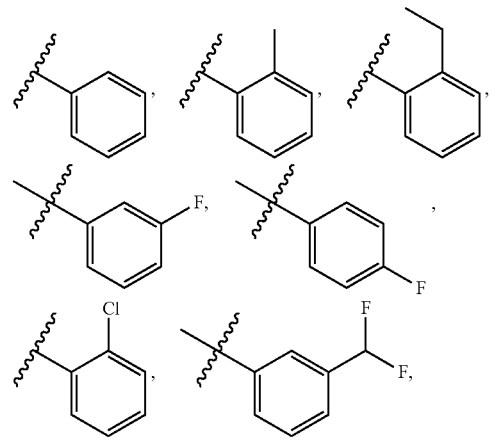

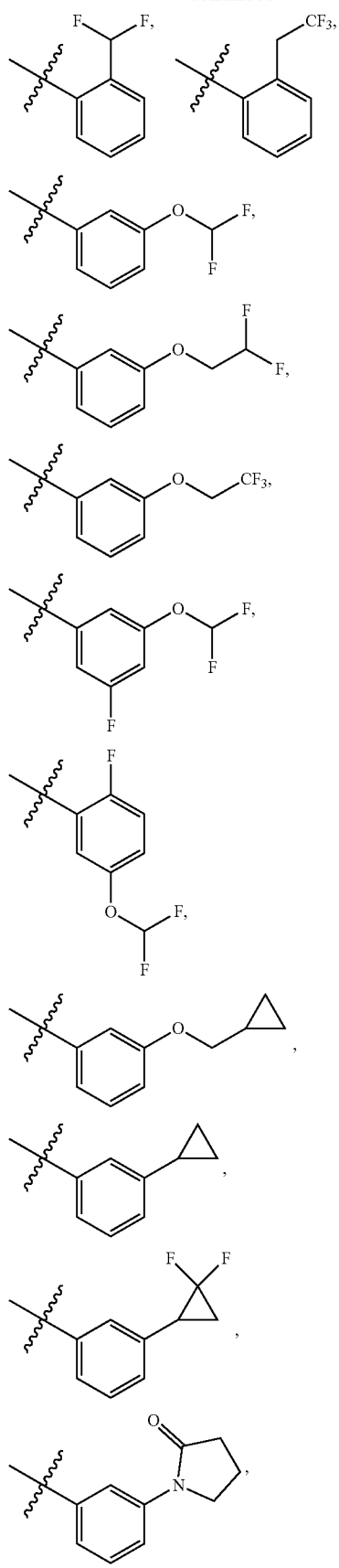
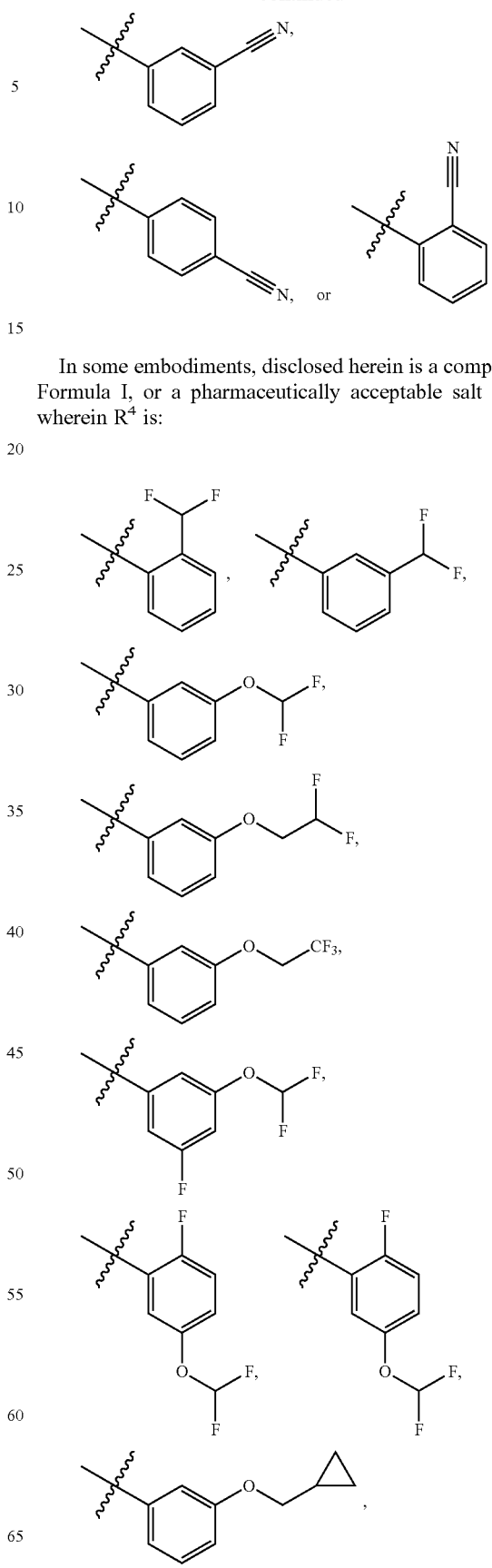
In some embodiments, disclosed herein is a compound of Formula I, or a pharmaceutically acceptable salt thereof, wherein R⁴ is:

-continued

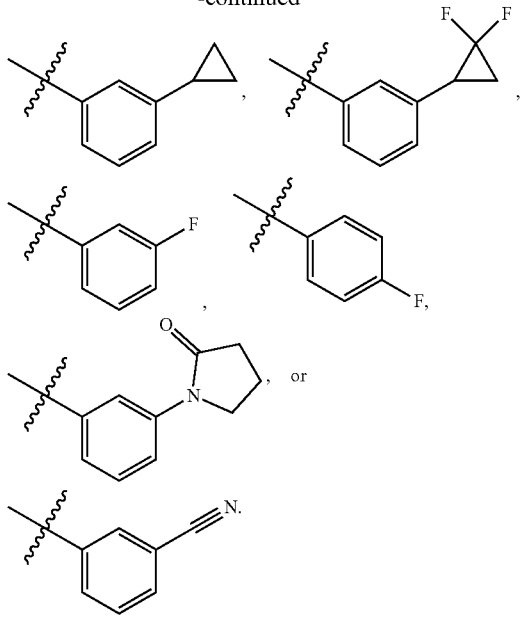

In some embodiments, disclosed herein is a compound of Formula I, or a pharmaceutically acceptable salt thereof, wherein R⁴ is:

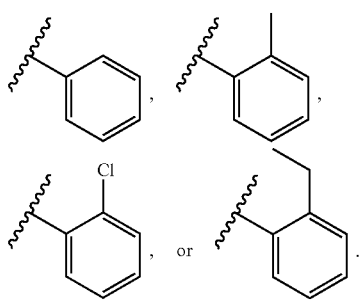

In some embodiments, disclosed herein is a compound of Formula I, or a pharmaceutically acceptable salt thereof, wherein:

R⁴ is a 5 to 6-membered heteroaryl having 1 to 4 heteroatoms selected from N, O, and S, that is substituted with one or two $R^{4c}$ groups;

each $R^{4c}$ is independently halogen, —CN, —C$_{(0-2)}$alkyl C$_{(3-6)}$cycloalkyl, —OC$_{(0-2)}$alkyl-C$_{(3-4)}$cycloalkyl, —C$_{(1-4)}$alkyl, —OC$_{(1-3)}$alkyl, or a 3 to 6-membered heterocyclyl having 1 to 2 heteroatoms selected from N and O, wherein the —C$_{(0-2)}$alkylC$_{(3-6)}$cycloalkyl, —C$_{(1-4)}$alkyl, —OC$_{(1-3)}$alkyl and heterocyclyl groups are unsubstituted or substituted with one to six $R^{4d}$ groups;

alternatively, two $R^{4c}$ groups attached to adjacent ring atoms can be combined to form a C$_{(4-6)}$cycloalkyl;

each $R^{4d}$ is independently fluorine, —CN, oxo, —C$_{(1-3)}$ alkyl, —OC$_{(1-3)}$alkyl, —OC$_{(3-4)}$cycloalkyl, —C$_{(0-2)}$alkyl-N(R$^{4d1}$)(R$^{4d2}$), or —C$_{(0-2)}$alkyl-N(C$_{(1-4)}$alkyl)C(O)(C$_{(1-4)}$alkyl), wherein the —C$_{(1-3)}$alkyl, —OC$_{(1-3)}$ alkyl and —OC$_{(3-4)}$cycloalkyl groups are unsubstituted or substituted with one to three fluorine atoms; and $R^{4d1}$ and $R^{4d2}$ are each independently H or —C$_{(1-3)}$alkyl, wherein the —C$_{(1-3)}$alkyl is unsubstituted or substituted with one to six groups selected from fluorine and chlorine;

alternatively $R^{4d1}$ and $R^{4d2}$ can be combined with the atom to which they are attached to form a 3 to 6 membered heterocyclyl having 1 to 3 heteroatoms selected from N, O and S, wherein the heterocyclyl is unsubstituted or substituted with 1 to 4 fluorine atoms;

wherein when R⁴ is 1,2,4-triazolyl, then R⁴ is 1H-1,2,4-triazolyl, and when R⁴ is a 6-membered heteroaryl, the heteroaryl is unsubstituted at the para-position.

In some embodiments, disclosed herein is a compound of Formula I, or a pharmaceutically acceptable salt thereof, wherein:

each $R^{4c}$ is independently fluorine, —CN, methyl, ethyl, isopropyl, —CD$_2$CD$_3$, —OCH$_3$, —OCH$_2$CH$_3$, —OCH(CH$_3$)$_2$, —CHF$_2$, —CF$_3$, —CH$_2$CH$_2$F, —CH$_2$CHF$_2$, —CH$_2$CF$_3$, —CF$_2$CH$_3$, —CH$_2$CH$_2$CH$_2$F, —CH$_2$CH$_2$CHF$_2$, —CH$_2$CH$_2$CF$_3$, —CH(CH$_3$)CF$_3$, —CH(CH$_2$F)$_2$, —CH$_2$OCH$_3$, —CH$_2$CH$_2$OCH$_3$, —CH$_2$CH$_2$OCHF$_2$, —CH$_2$CH$_2$OCF$_3$, —OCHF$_2$, —OCH$_2$CHF$_2$, —OCH$_2$CF$_3$, cyclopropyl, cyclobutyl, cyclopentyl, —CH$_2$-cyclopropyl, —O-cyclopropyl, —O-cyclobutyl,

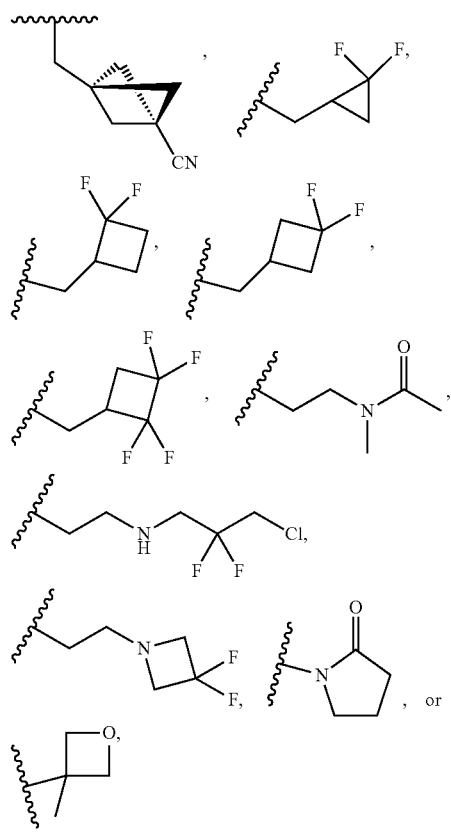

alternatively two R$^{4c}$ groups attached to adjacent ring atoms can be combined to form the group:

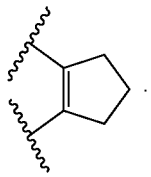

In some embodiments, disclosed herein is a compound of Formula I, or a pharmaceutically acceptable salt thereof, wherein:
R$^4$ is a 5 membered heteroaryl ring having from 1 to 4 heteroatoms selected from N, O and S, that is substituted with one or two R$^{4c}$ groups,
wherein when R$^4$ is 1,2,4-triazolyl, then R$^4$ is

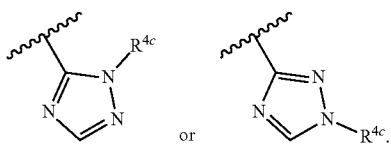

In some embodiments, disclosed herein is a compound of Formula I, or a pharmaceutically acceptable salt thereof, wherein:
R$^4$ is pyrrolyl, pyrazolyl, imidazolyl, triazolyl, tetrazolyl, furanyl, oxazolyl, isoxazolyl, oxadiazolyl, thienyl, thiazolyl, isothiazolyl or thiadiazolyl, that is substituted with one or two R$^{4c}$ groups,
wherein when R$^4$ is 1,2,4-triazolyl, then R$^4$ is

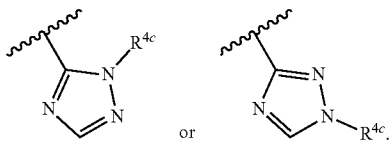

In some embodiments, disclosed herein is a compound of Formula I, or a pharmaceutically acceptable salt thereof, wherein R$^4$ is pyrrolyl, pyrazolyl, imidazolyl, 1H-1,2,3-triazolyl, 2H-1,2,3-triazolyl, 1H-1,2,4-triazolyl, tetrazolyl, furanyl, oxazolyl, isoxazolyl, 1,2,3-oxadiazolyl, 1,2,4-oxadiazolyl, 1,2,5-oxadiazolyl, 1,3,4-oxadiazolyl, thienyl, thiazolyl, isothiazolyl, 1,2,3-thiadiazolyl, 1,2,4-thiadiazolyl, 1,2,5-thiadiazolyl or 1,3,4-thiadiazolyl, that is substituted with one or two R$^4$, groups.

In some embodiments, disclosed herein is a compound of Formula I, or a pharmaceutically acceptable salt thereof, wherein R$^4$ is pyrazolyl, imidazolyl, 1H-1,2,3-triazolyl, 2H-1,2,3-triazolyl, 1H-1,2,4-triazolyl, tetrazolyl, oxazolyl, isoxazolyl, 1,2,5-oxadiazolyl, thienyl, thiazolyl, isothiazolyl, 1,2,3-thiadiazolyl, or 1,2,5-thiadiazolyl, that is substituted with one or two R$^{4c}$ groups.

In some embodiments, disclosed herein is a compound of Formula I, or a pharmaceutically acceptable salt thereof, wherein:
R$^4$ is oxazolyl, isoxazolyl or oxadiazolyl that is substituted with one or two R$^{4c}$ groups, wherein each R$^{4c}$ is independently C$_{(3-5)}$cycloalkyl, —C$_{(1-3)}$alkyl or

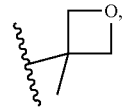

wherein the C$_{(3-5)}$cycloalkyl and —C$_{(1-3)}$alkyl groups are unsubstituted or substituted with —OCH$_3$, or one to three fluorine atoms.

In some embodiments, disclosed herein is a compound of Formula I, or a pharmaceutically acceptable salt thereof, wherein
R$^4$ is oxazolyl, isoxazolyl, or thiadiazolyl (e.g., 1,2,3-thiadiazolyl) that is or substituted with one or two R$^{4c}$ groups,
wherein each R$^{4c}$ is independently cyclopropyl or —C$_{(1-3)}$alkyl, wherein the cyclopropyl and —C$_{(1-3)}$alkyl groups are unsubstituted or substituted with one to three fluorine atoms.

In some embodiments, disclosed herein is a compound of Formula I, or a pharmaceutically acceptable salt thereof, wherein R$^4$ is
isoxazolyl substituted with one or two R$^{4c}$ groups each independently methyl, ethyl, isopropyl, —CF$_3$, —CH$_2$CH$_2$F, —CH$_2$CH$_2$CF$_3$, —CH$_2$—OCH$_3$, cyclopropyl, cyclopentyl, or

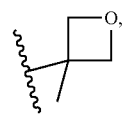

oxazolyl substituted with one isopropyl, or
oxadiazolyl substituted with one methyl or ethyl.

In some embodiments, disclosed herein is a compound of Formula I, or a pharmaceutically acceptable salt thereof, wherein R$^4$ is oxadiazolyl substituted with one —C$_{(1-3)}$alkyl.

In some embodiments, disclosed herein is a compound of Formula I, or a pharmaceutically acceptable salt thereof, wherein R$^4$ is:

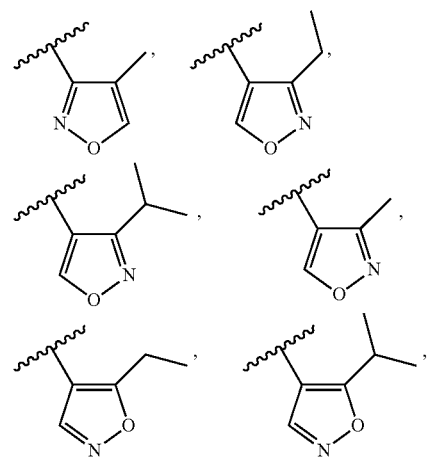

-continued

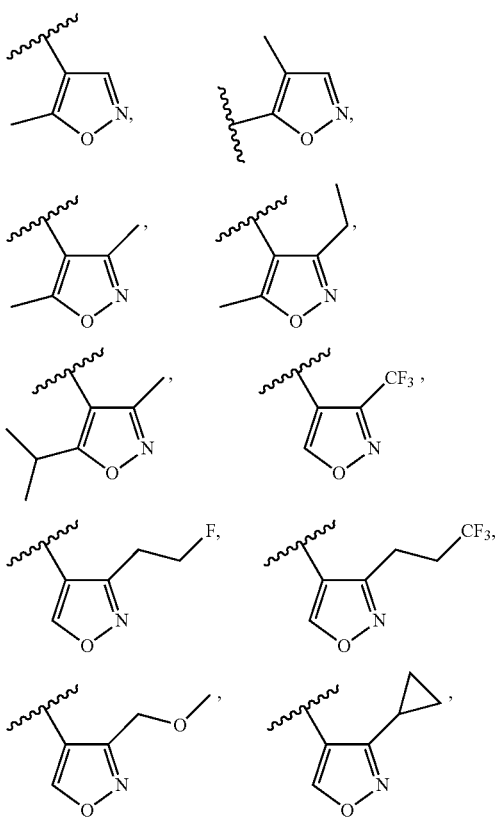

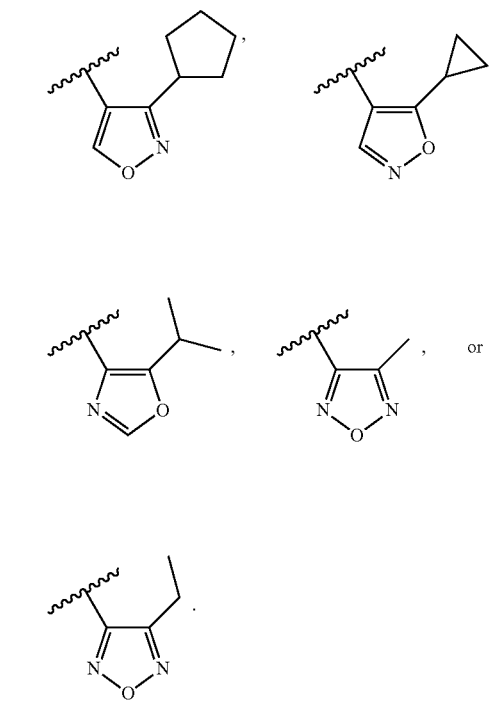

In some embodiments, disclosed herein is a compound of Formula I, or a pharmaceutically acceptable salt thereof, which is a compound of Formula Ic:

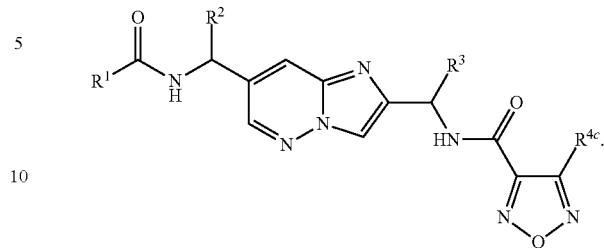

In some embodiments, disclosed herein is a compound of Formula I, or a pharmaceutically acceptable salt thereof, which is a compound of Formula Ic-1:

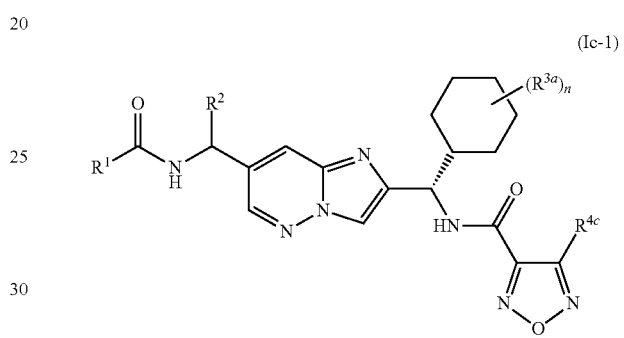

wherein $R^{3a}$ is fluorine and n is 2.

In some embodiments, disclosed herein is a compound of Formula I, or a pharmaceutically acceptable salt thereof, wherein $R^4$ is:

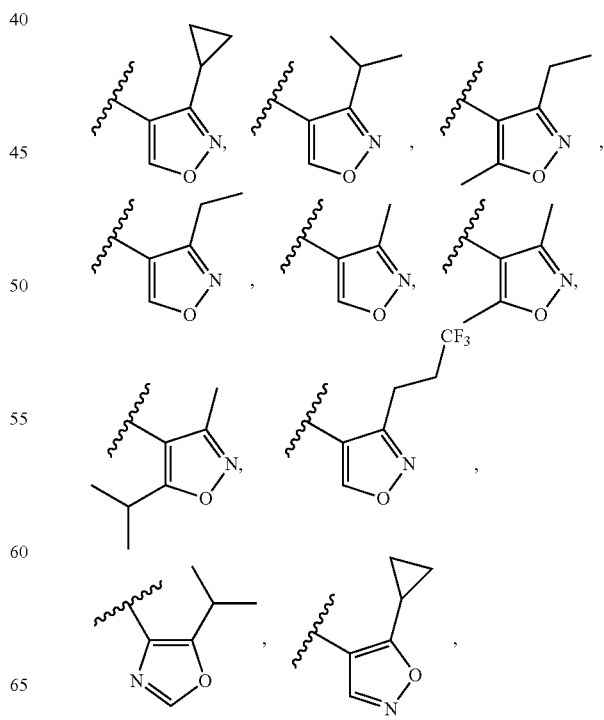

-continued

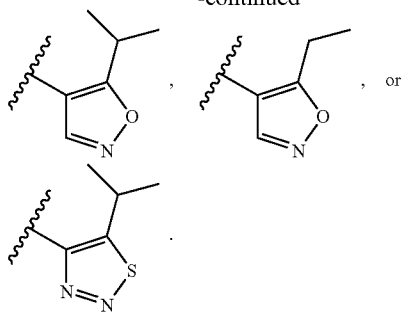

In some embodiments, disclosed herein is a compound of Formula I, or a pharmaceutically acceptable salt thereof, wherein $R^4$ is:

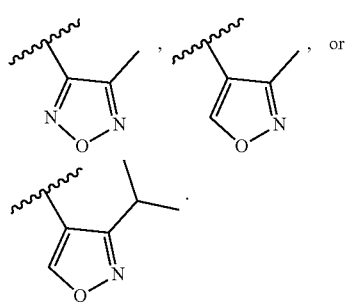

In some embodiments, disclosed herein is a compound of Formula I, or a pharmaceutically acceptable salt thereof, wherein:
  $R^4$ is pyrazolyl or imidazolyl that is unsubstituted or substituted with one or two $R^{4c}$ groups, wherein each $R^{4c}$ is independently fluorine or —$C_{(1-3)}$alkyl that is unsubstituted or substituted with one to three groups selected from —$CHF_2$, —$CF_3$, —$OCHF_2$, —$OCF_3$ and fluorine.

In some embodiments, disclosed herein is a compound of Formula I, or a pharmaceutically acceptable salt thereof, wherein $R^4$ is pyrazolyl or imidazolyl that is unsubstituted or substituted with one or two $R^{4c}$ groups, wherein each $R^{4c}$ is independently —$C_{(1-3)}$alkyl that is unsubstituted or substituted with one to three groups selected from —$CHF_2$, —$CF_3$, —$OCHF_2$, —$OCF_3$ and fluorine.

In some embodiments, disclosed herein is a compound of Formula I, or a pharmaceutically acceptable salt thereof, wherein $R^4$ is pyrazolyl or imidazolyl that is substituted with one or two $R^{4c}$ groups, wherein each $R^{4c}$ is independently —$C_{(1-3)}$alkyl that is unsubstituted or substituted with one to three groups selected from —$CHF_2$, —$CF_3$, —$OCHF_2$, —$OCF_3$ and fluorine.

In some embodiments, disclosed herein is a compound of Formula I, or a pharmaceutically acceptable salt thereof, wherein $R^4$ is
  pyrazolyl substituted with one or two $R^{4c}$ groups each independently methyl, ethyl, isopropyl, —$CD_2CD_3$, fluorine, —$CHF_2$, —$CF_3$, —$CH_2CHF_2$, —$CH_2CF_3$, —$CH(CH_3)CF_3$, —$CH(CH_2F)_2$, —$CH_2CH_2OCHF_2$, or —$CH_2CH_2OCF_3$, or
  imidazolyl substituted with one isopropyl.

In some embodiments, disclosed herein is a compound of Formula I, or a pharmaceutically acceptable salt thereof, wherein $R^4$ is pyrazolyl substituted with one —$C_{(1-3)}$alkyl.

In some embodiments, disclosed herein is a compound of Formula I, or a pharmaceutically acceptable salt thereof, wherein $R^4$ is:

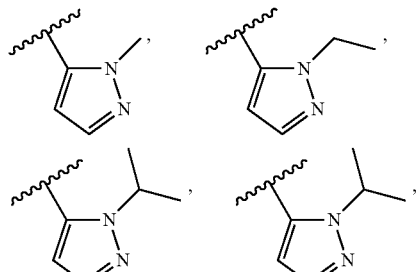
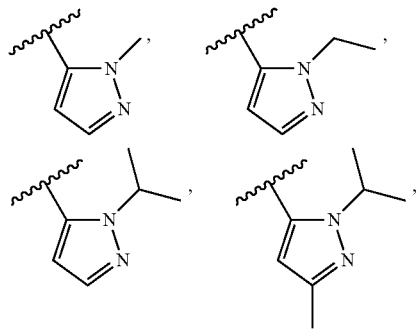
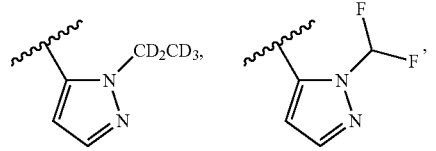
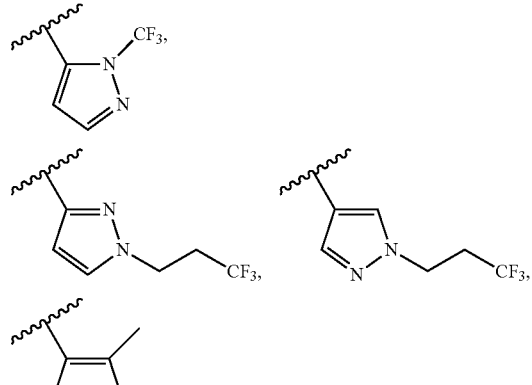
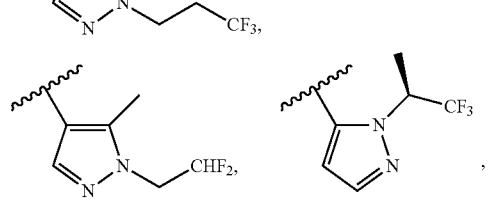
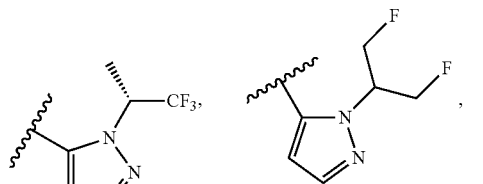
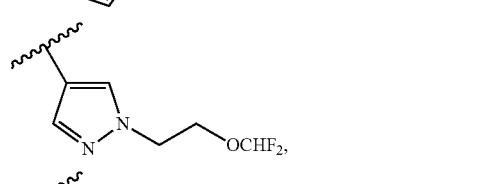
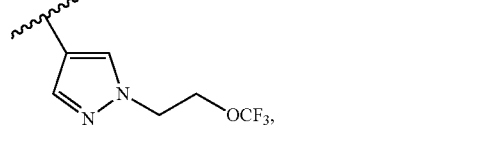

-continued

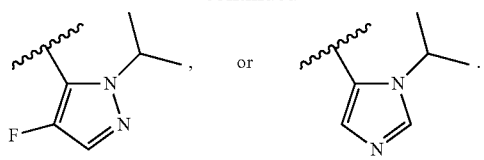

In some embodiments, disclosed herein is a compound of Formula I, or a pharmaceutically acceptable salt thereof, wherein $R^4$ is:

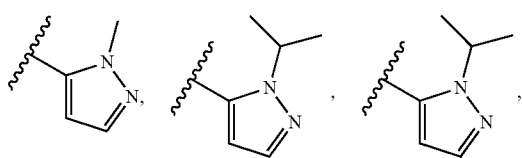

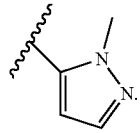 [SMILES: *c1ccnn1C]

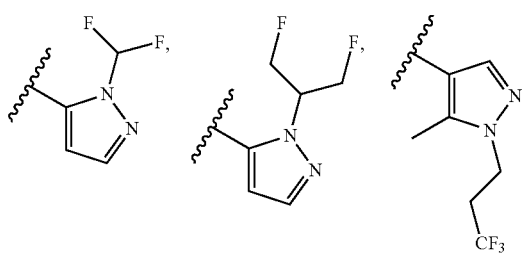

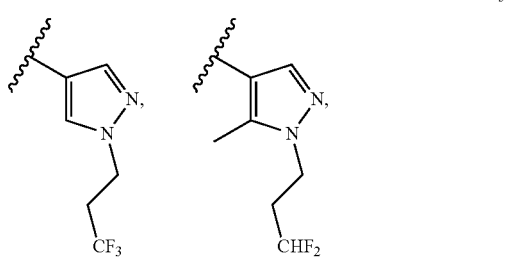

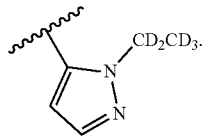

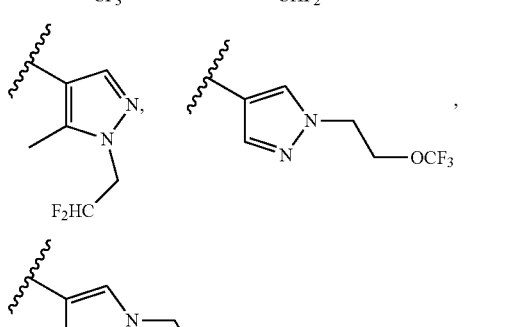

In some embodiments, disclosed herein is a compound of Formula I, or a pharmaceutically acceptable salt thereof, wherein $R^4$ is:

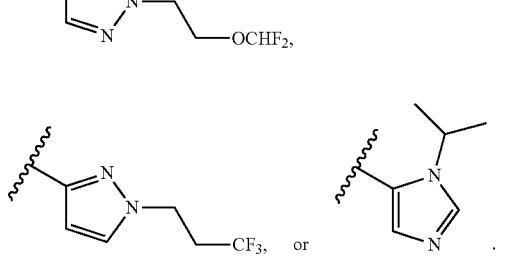

In some embodiments, disclosed herein is a compound of Formula I, or a pharmaceutically acceptable salt thereof, wherein $R^4$ is

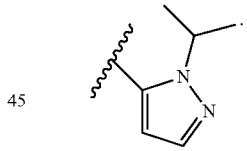

In some embodiments, disclosed herein is a compound of Formula I, or a pharmaceutically acceptable salt thereof, wherein $R^4$ is

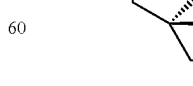

In some embodiments, disclosed herein is a compound of Formula I, or pharmaceutically acceptable salt thereof, wherein $R^4$ is In some embodiments, disclosed herein is a compound of Formula I, or a pharmaceutically acceptable salt thereof, wherein:
  $R^4$ is triazolyl that is unsubstituted or substituted with one or two $R^{4c}$ groups;
  each $R^{4c}$ is independently —$C_{(0-1)}$alkyl$C_{(3-4)}$cycloalkyl, —$C_{(1-3)}$alkyl, wherein the —$C_{(0-1)}$alkyl$C_{(3-4)}$cycloalkyl and —$C_{(1-3)}$alkyl groups are unsubstituted or substituted with one to four $R^{4d}$ groups; and each $R^{4d}$ is independently —OCH$_3$, —OCF$_3$, —OCHF$_2$, fluorine,

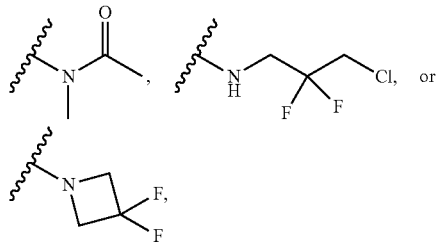

wherein when $R^4$ is 1,2,4-triazolyl, then $R^4$ is

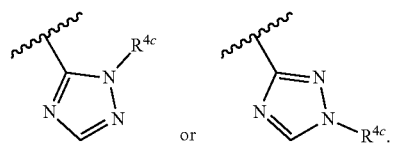

Alternatively, when $R^4$ is 1,2,4-triazolyl, then $R^4$ is 1H-1,2,4-triazolyl.

In some embodiments, disclosed herein is a compound of Formula I, or a pharmaceutically acceptable salt thereof, wherein
  $R^4$ is triazolyl that is unsubstituted or substituted with one or two $R^{4c}$ groups, wherein:
  each $R^{4c}$ is independently —C$_{(0-1)}$alkylC$_{(3-4)}$cycloalkyl, or —C$_{(1-3)}$alkyl, wherein the —C$_{(0-1)}$alkylC$_{(3-4)}$cycloalkyl and —C$_{(1-3)}$alkyl groups are unsubstituted or substituted with one to four $R^{4d}$ groups; and
  each $R^{4d}$ is independently —OCH$_3$, —OCF$_3$, or —OCHF$_2$, or fluorine.

In some embodiments, disclosed herein is a compound of Formula I, or a pharmaceutically acceptable salt thereof, wherein:
  $R^4$ is triazolyl that is unsubstituted or substituted with one or two $R^{4c}$ groups; and
  each $R^{4c}$ is independently methyl, ethyl, isopropyl, —CH$_2$CH$_2$OCH$_3$, —CHF$_2$, —CF$_3$, —CH$_2$CH$_2$F, —CH$_2$CHF$_2$, —CH$_2$CF$_3$, —CH$_2$CH$_2$CH$_2$F, —CH$_2$CH$_2$CHF$_2$, —CH$_2$CH$_2$CF$_3$, —CH$_2$CH$_2$OCHF$_2$, —CH$_2$CH$_2$OCF$_3$, cyclopropyl, —CH$_2$-cyclopropyl,

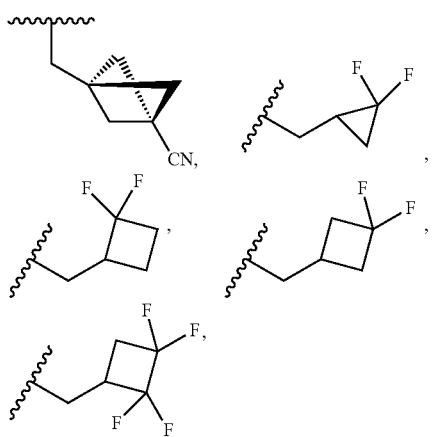

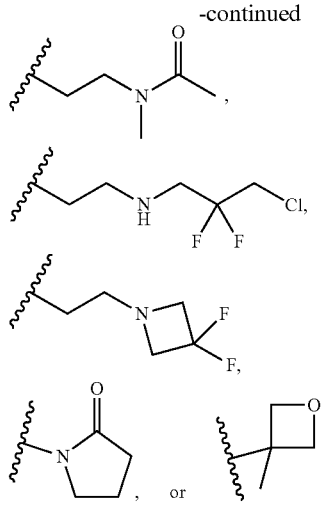

wherein when $R^4$ is 1,2,4-triazolyl, then $R^4$ is

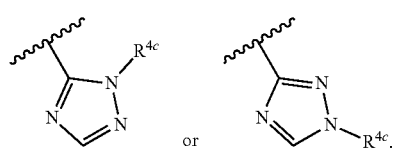

In some embodiments, disclosed herein is a compound of Formula I, or a pharmaceutically acceptable salt thereof, wherein $R^4$ is:

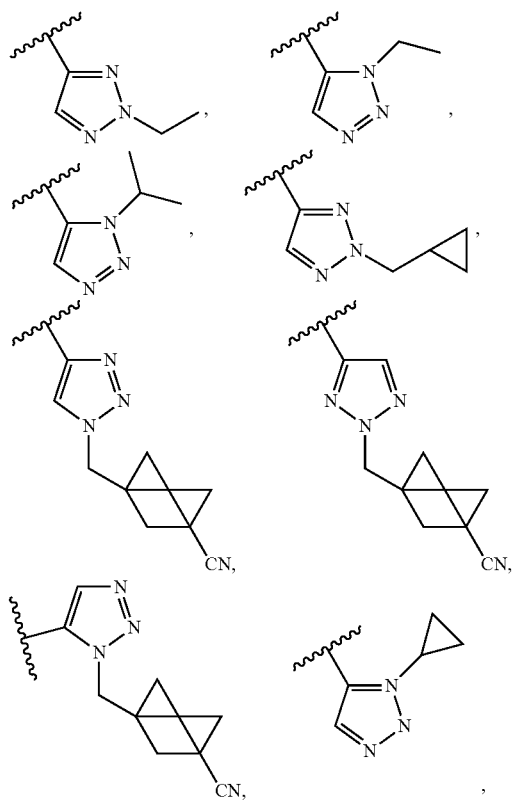

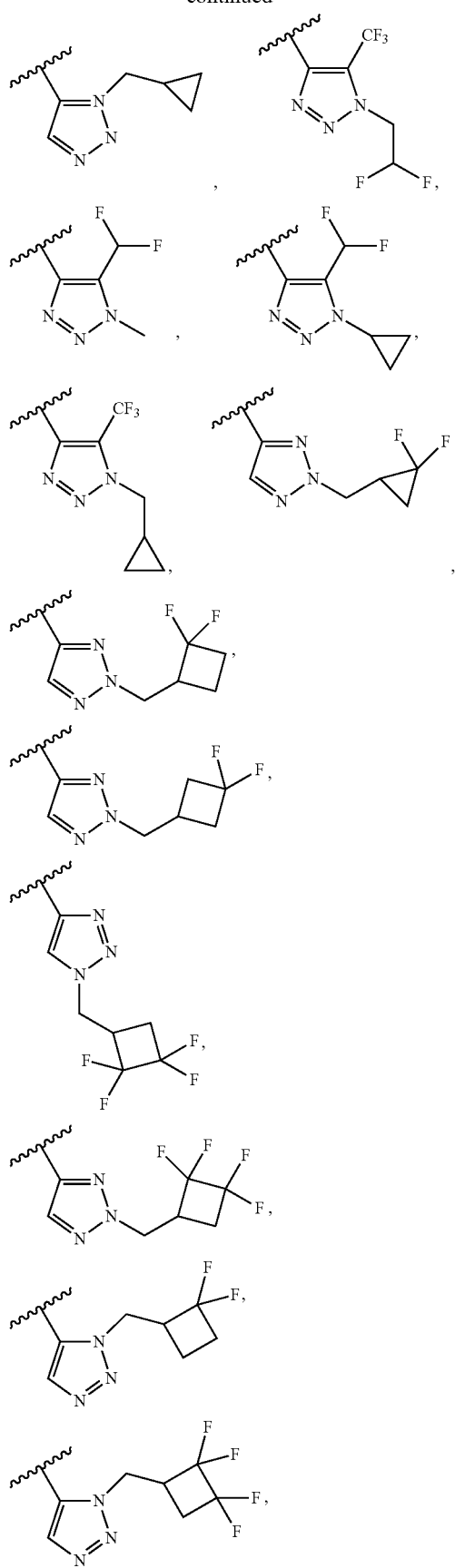
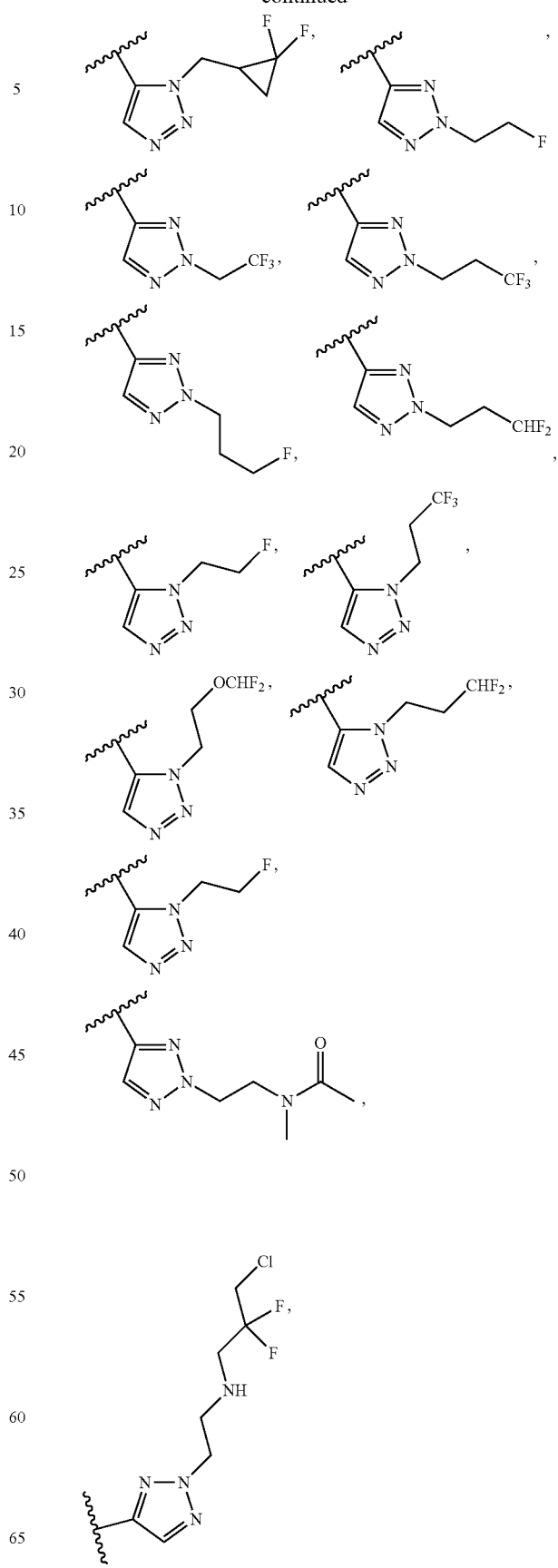

-continued
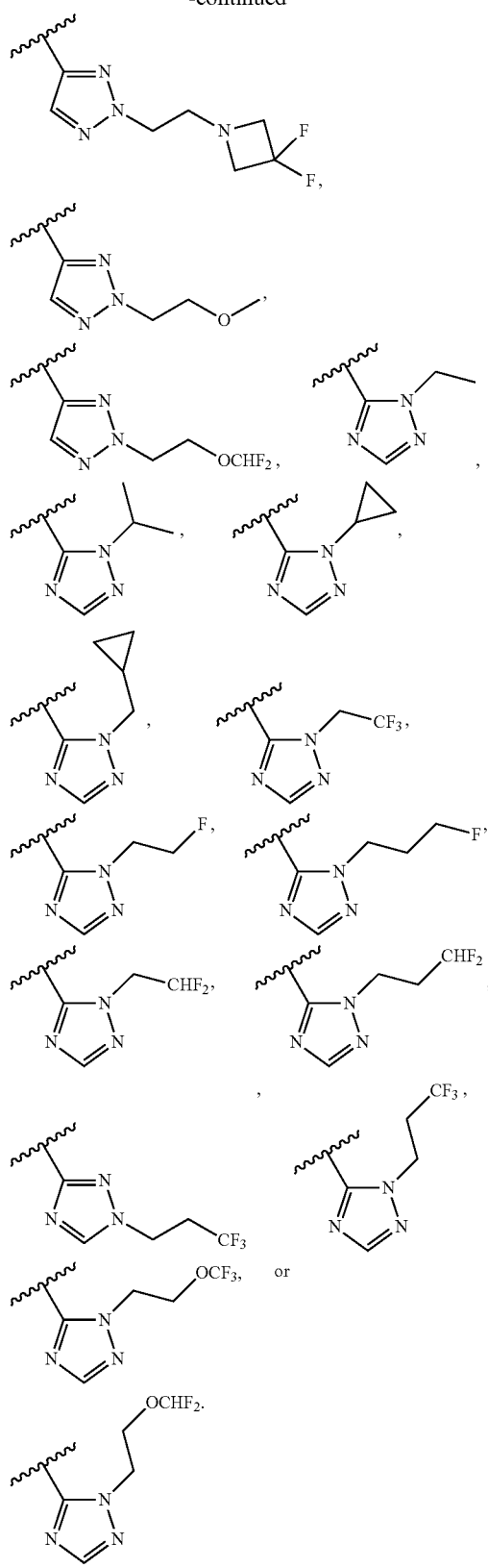
In some embodiments, disclosed herein is a compound of Formula I, or a pharmaceutically acceptable salt thereof, wherein R⁴ is:

-continued

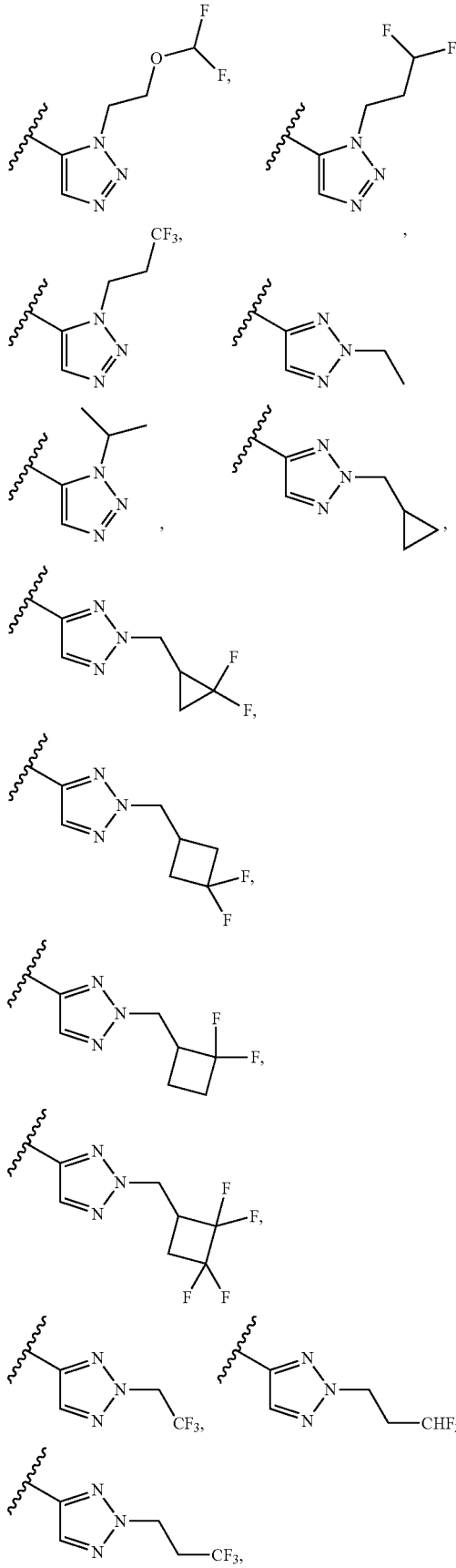

-continued

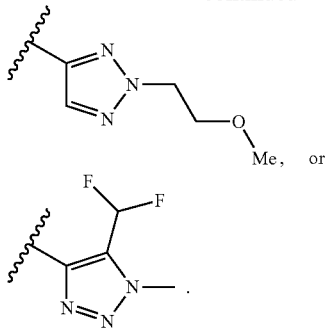

In some embodiments, disclosed herein is a compound of Formula I, or a pharmaceutically acceptable salt thereof, wherein $R^4$ is tetrazolyl substituted with $-C_{(1-4)}$alkyl.

In some embodiments, disclosed herein is a compound of Formula I, or a pharmaceutically acceptable salt thereof, wherein $R^4$ is tetrazolyl substituted with methyl or isopropyl.

In some embodiments, disclosed herein is a compound of Formula I, or a pharmaceutically acceptable salt thereof, wherein $R^4$ is:

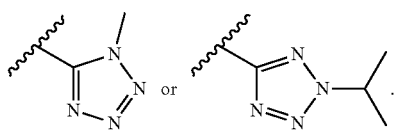

In some embodiments, disclosed herein is a compound of Formula I, or a pharmaceutically acceptable salt thereof, wherein $R^4$ is thienyl, thiazolyl, isothiazolyl or thiadiazolyl, each substituted with $-C_{(1-3)}$alkyl, or $-C_{(3-6)}$cycloalkyl.

In some embodiments, disclosed herein is a compound of Formula I, or a pharmaceutically acceptable salt thereof, wherein $R^4$ is thienyl, thiazolyl, isothiazolyl or thiadiazolyl, each substituted with methyl, isopropyl or cyclopropyl.

In some embodiments, disclosed herein is a compound of Formula I, or a pharmaceutically acceptable salt thereof, wherein $R^4$ is
  thienyl substituted with isopropyl,
  isothiazolyl substituted with methyl,
  thiazolyl substituted with isopropyl, or
  thiadiazolyl substituted with methyl, isopropyl or cyclopropyl.

In some embodiments, disclosed herein is a compound of Formula I, or a pharmaceutically acceptable salt thereof, wherein $R^4$ is:

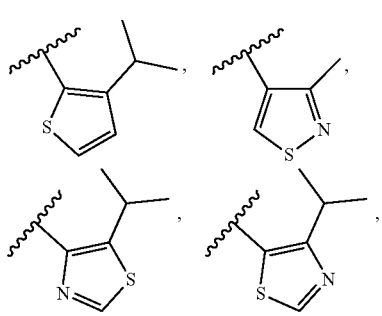

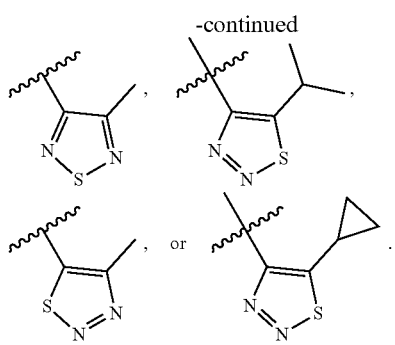

In some embodiments, disclosed herein is a compound of Formula I, or a pharmaceutically acceptable salt thereof, wherein:
  $R^4$ is a 6-membered heteroaryl having 1 to 2 heteroatoms selected from N, that is substituted with one or two $R^{4c}$ groups; and
  each $R^{4c}$ group is independently fluorine, —CN, pyrrolidin-2-one, $C_{(3-4)}$cycloalkyl, —$OC_{(3-4)}$cycloalkyl, —$OC_{(1-3)}$alkyl, or $C_{(1-3)}$alkyl wherein the —$OC_{(1-3)}$alkyl, and $C_{(1-3)}$alkyl are unsubstituted or substituted with —$OCH_3$, or one to three fluorine atoms,
    alternatively, two $R^{4c}$ groups attached to adjacent ring atoms can be combined to form a $C_{(4-6)}$cycloalkyl;
  wherein the heteroaryl is unsubstituted at the para-position.

In some embodiments, disclosed herein is a compound of Formula I, or a pharmaceutically acceptable salt thereof, wherein when $R^4$ is a substituted 6-membered heteroaryl, then $R^4$ is

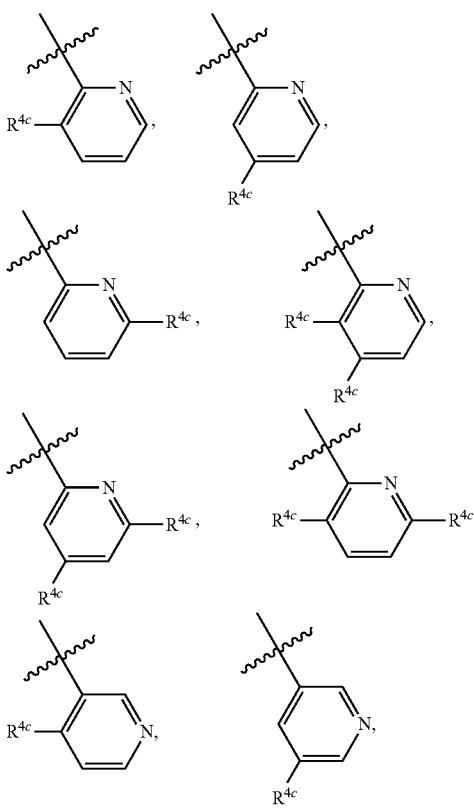

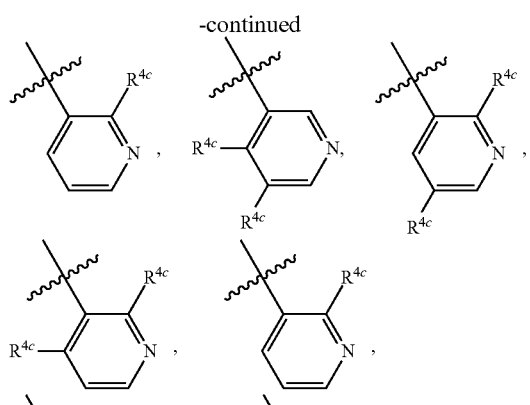

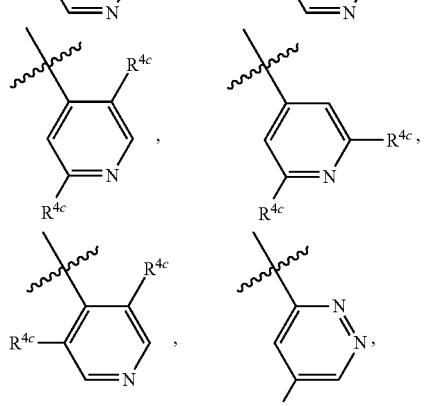

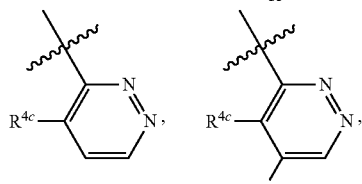

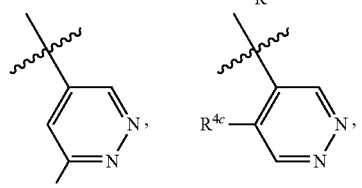

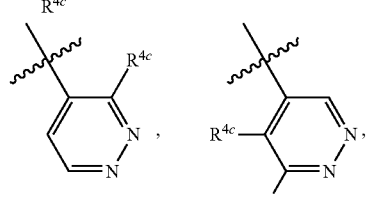

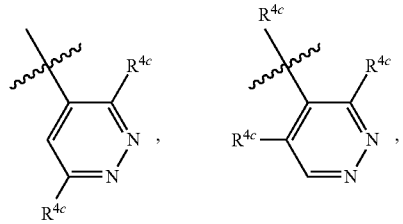

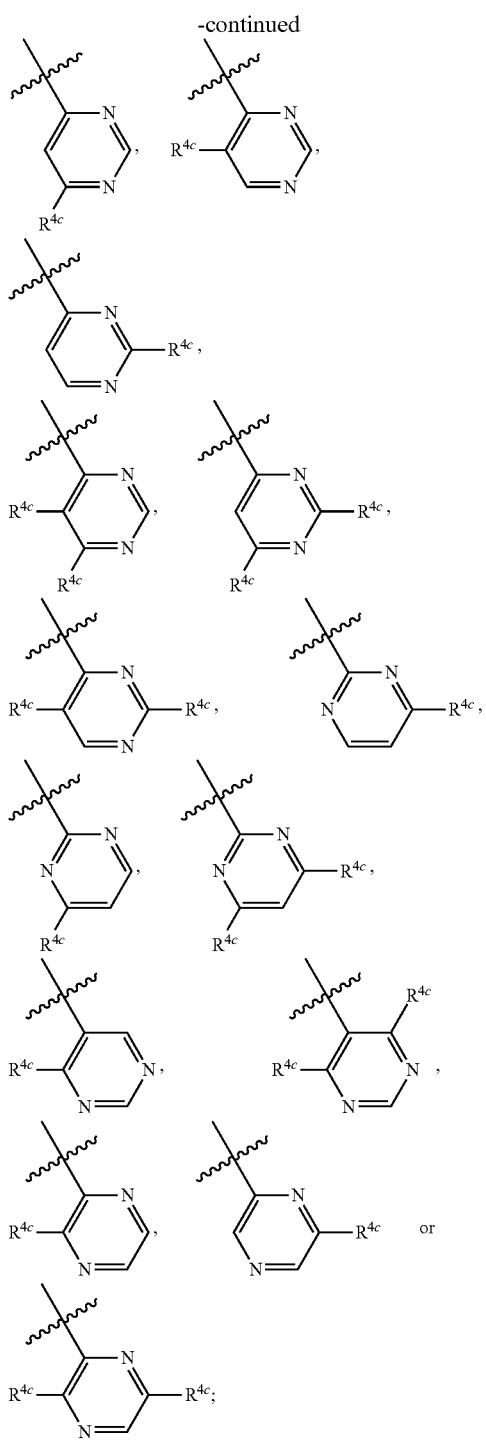

and
each $R^{4c}$ group is independently fluorine, —CN, pyrrolidin-2-one, $C_{(3-4)}$cycloalkyl, —$OC_{(3-4)}$cycloalkyl, —$OC_{(1-3)}$alkyl, or $C_{(1-3)}$alkyl wherein the —$OC_{(1-3)}$alkyl, and $C_{(1-3)}$alkyl are unsubstituted or substituted with —$OCH_3$, or one to three fluorine atoms;
alternatively, two $R^{4c}$ groups attached to adjacent ring atoms can be combined to form a $C_{(4-6)}$cycloalkyl.

In some embodiments, disclosed herein is a compound of Formula I, or a pharmaceutically acceptable salt thereof, wherein:

$R^4$ is a pyridinyl, pyridazinyl, pyrimidinyl, or pyrazinyl, that is substituted with one or two $R^{4c}$ groups; and
each $R^{4c}$ group is independently fluorine, —CN, pyrrolidin-2-one, $C_{(3-4)}$cycloalkyl, —$OC_{(3-4)}$cycloalkyl, —$OC_{(1-3)}$alkyl, or $C_{(1-3)}$alkyl wherein the —$OC_{(1-3)}$alkyl, and $C_{(1-3)}$alkyl are unsubstituted or substituted with —$OCH_3$, or one to three fluorine atoms;
alternatively, two $R^{4c}$ groups attached to adjacent ring atoms can be combined to form a $C_{(4-6)}$cycloalkyl;
wherein the heteroaryl is unsubstituted at the para-position.

In some embodiments, disclosed herein is a compound of Formula I, or a pharmaceutically acceptable salt thereof, wherein:

$R^4$ is pyridyl that is unsubstituted or substituted with 1 to 2 $R^{4c}$ groups; and
each $R^{4c}$ group is independently fluorine, —CN, pyrrolidin-2-one, $C_{(3-4)}$cycloalkyl, —$OC_{(3-4)}$cycloalkyl, —$OC_{(1-3)}$alkyl, or $C_{(1-3)}$alkyl wherein the —$OC_{(1-3)}$alkyl, and $C_{(1-3)}$alkyl are unsubstituted or substituted with —$OCH_3$, or one to three fluorine atoms;
alternatively, two $R^{4c}$ groups attached to adjacent ring atoms can be combined to form a $C_{(4-6)}$cycloalkyl;
wherein the pyridyl is unsubstituted at the para-position.

In some embodiments, disclosed herein is a compound of Formula I, or a pharmaceutically acceptable salt thereof, wherein $R^4$ is pyridyl unsubstituted or substituted with $C_{(1-2)}$alkyl unsubstituted or substituted with one to three fluorine atoms, wherein the pyridyl is unsubstituted at the para-position. In some embodiments, disclosed herein is a compound of Formula I, or a pharmaceutically acceptable salt thereof, wherein $R^4$ is pyridinyl that is unsubstituted or substituted with $C_{(1-2)}$alkyl that is unsubstituted or substituted with one to three fluorine atoms.

In some embodiments, disclosed herein is a compound of Formula I, or a pharmaceutically acceptable salt thereof, wherein:

$R^4$ is pyridyl that is unsubstituted or substituted with 1 to 2 $R^{4c}$ groups; and
each $R^{4c}$ group is independently fluorine, —CN, pyrrolidin-2-one, cyclopropyl, cyclobutyl, —O— cyclopropyl, —O-cyclobutyl, —OMe, —OEt, —O-isopropyl, —$OCHF_2$, —$OCH_2CHF_2$, —$OCH_2CF_3$, methyl, ethyl, isopropyl, —$CH_2$—$OCH_3$, —$CHF_2$, —$CF_3$, —$C(CH_3)F_2$, —$CH_2CHF_2$, —$CH_2CF_3$, or —$CH_2CH_2CHF_2$;
alternatively, two $R^{4c}$ groups attached to adjacent ring atoms can be combined to form a cyclopentyl,
wherein the pyridyl is unsubstituted at the para-position.

In some embodiments, disclosed herein is a compound of Formula I, or a pharmaceutically acceptable salt thereof, wherein when $R^4$ is a substituted 6-membered heteroaryl, then $R^4$ is:

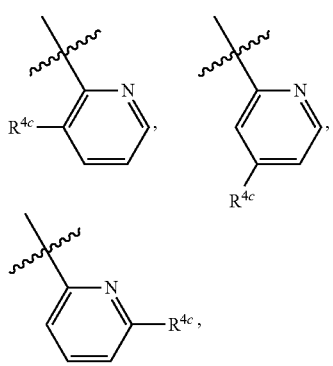

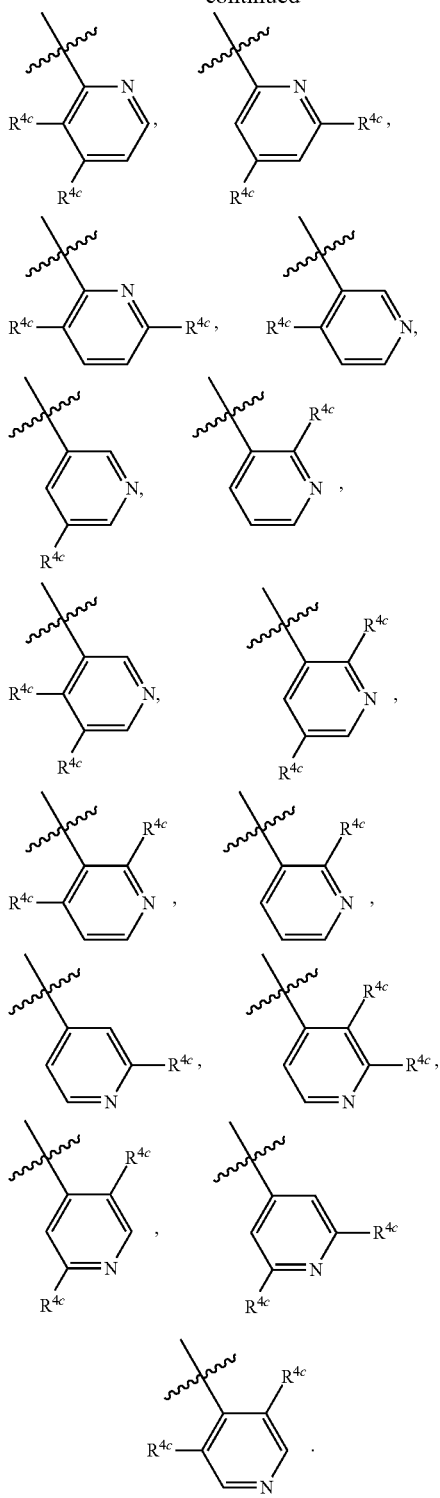
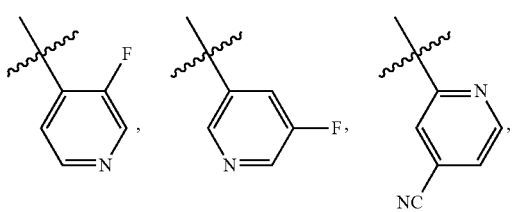
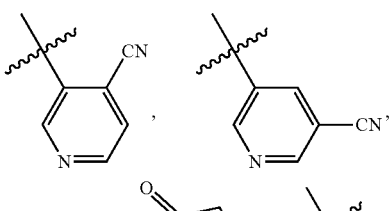
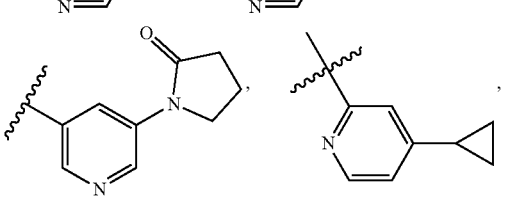
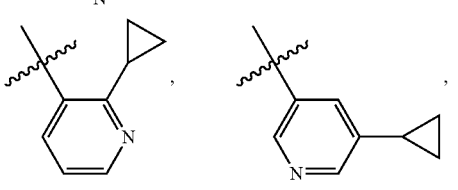
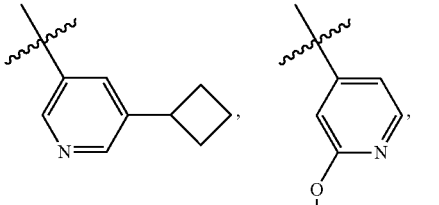
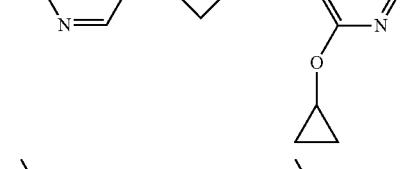
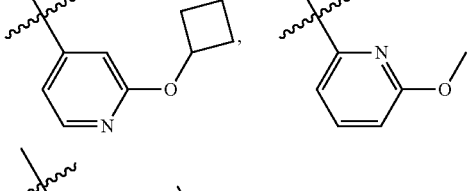
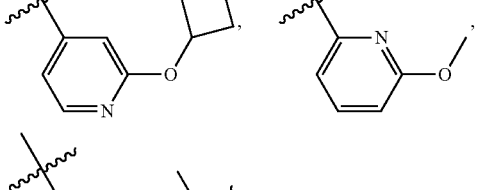
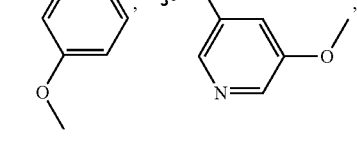
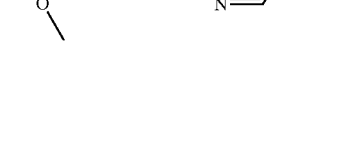
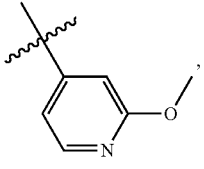
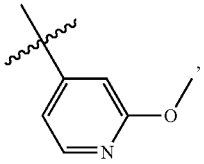
In some embodiments, disclosed herein is a compound of Formula I, or a pharmaceutically acceptable salt thereof, wherein $R^4$ is:

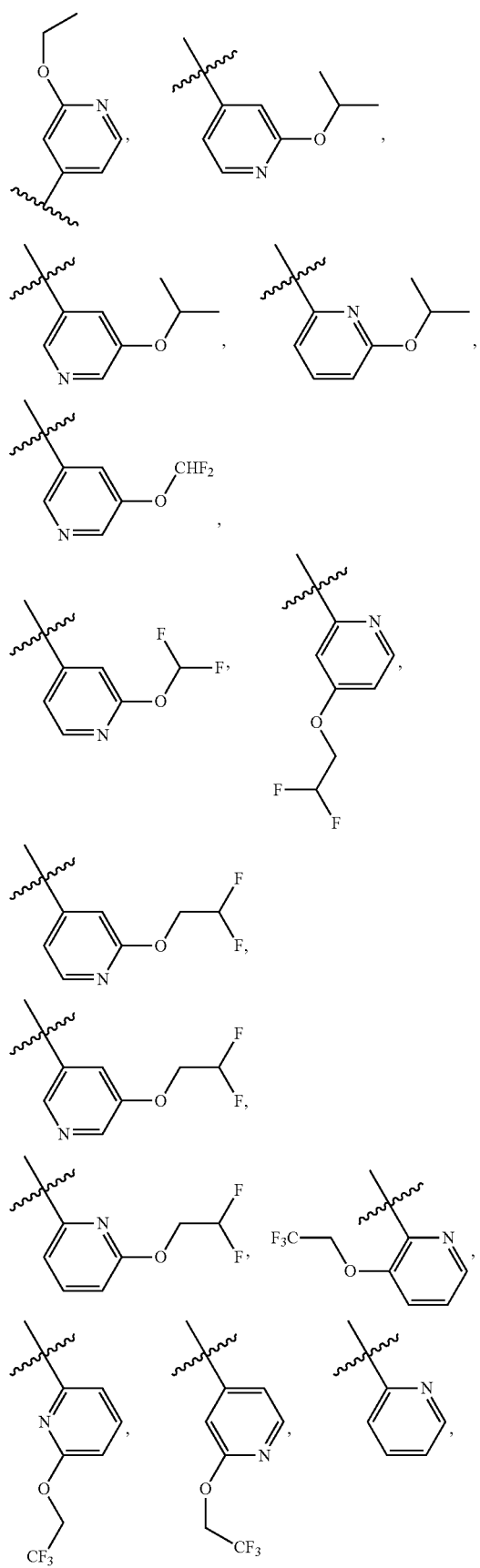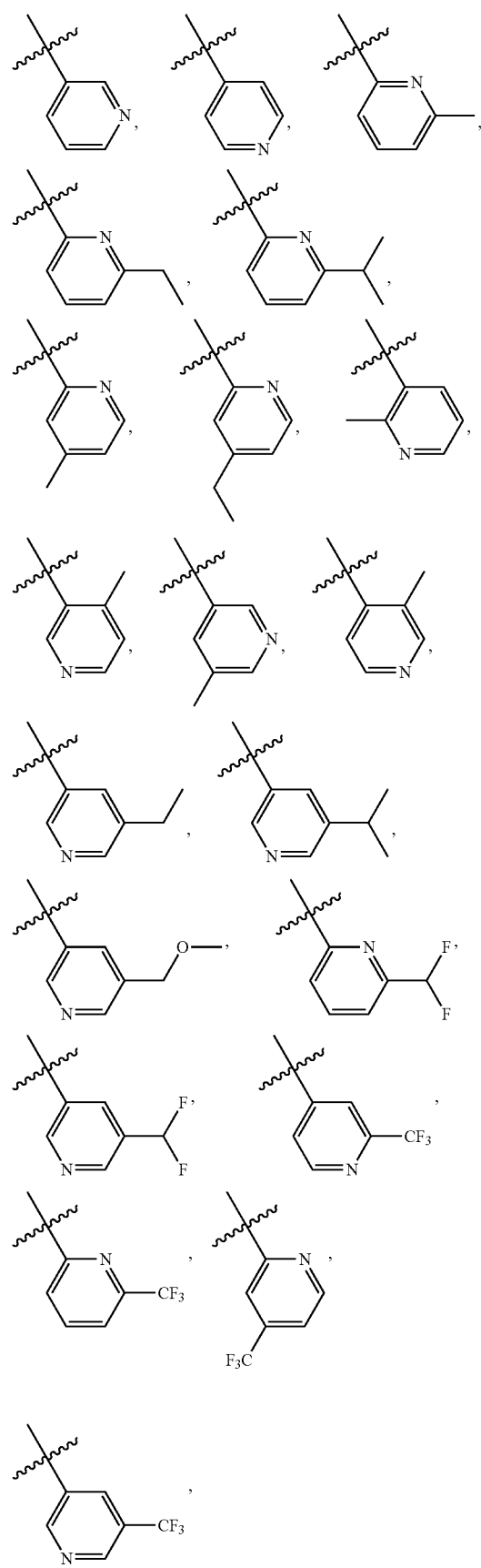

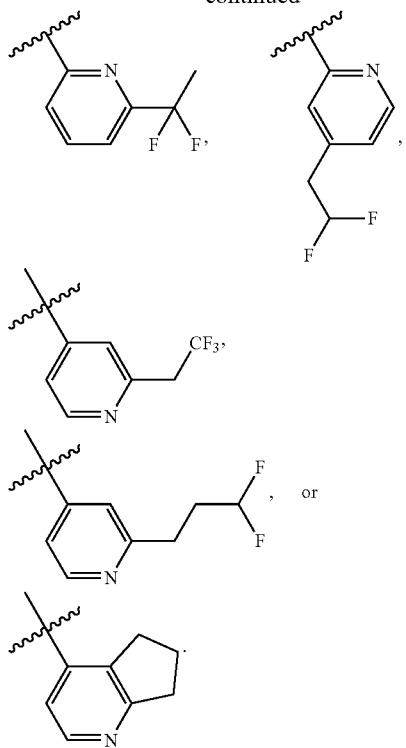

In some embodiments, disclosed herein is a compound of Formula I, or a pharmaceutically acceptable salt thereof, wherein:
- $R^4$ is pyridazinyl, pyrimidinyl, or pyrazinyl, wherein each is unsubstituted or substituted with one or two $R^{4c}$ groups;
- each $R^{4c}$ is independently selected from —$C_{(3-4)}$cycloalkyl, —$OC_{(1-3)}$alkyl and —$C_{(1-4)}$alkyl, wherein the —$C_{(1-4)}$alkyl groups are unsubstituted or substituted with one to three fluorine atoms, wherein the pyridazinyl, pyrimidinyl and pyrazinyl are unsubstituted at the para-position.

In some embodiments, disclosed herein is a compound of Formula I, or a pharmaceutically acceptable salt thereof, wherein:
- $R^4$ is pyridazinyl, pyrimidinyl, or pyrazinyl, wherein each is unsubstituted or substituted with one or two $R^{4c}$ groups; and
- each $R^{4c}$ is independently selected from methyl, isopropyl, —OMe, cyclopropyl, —$CHF_2$, and —$CF_3$,
- wherein the pyridazinyl, pyrimidinyl and pyrazinyl are unsubstituted at the para-position.

In some embodiments, disclosed herein is a compound of Formula I, or a pharmaceutically acceptable salt thereof, wherein when $R^4$ is a substituted 6-membered heteroaryl, then $R^4$ is:

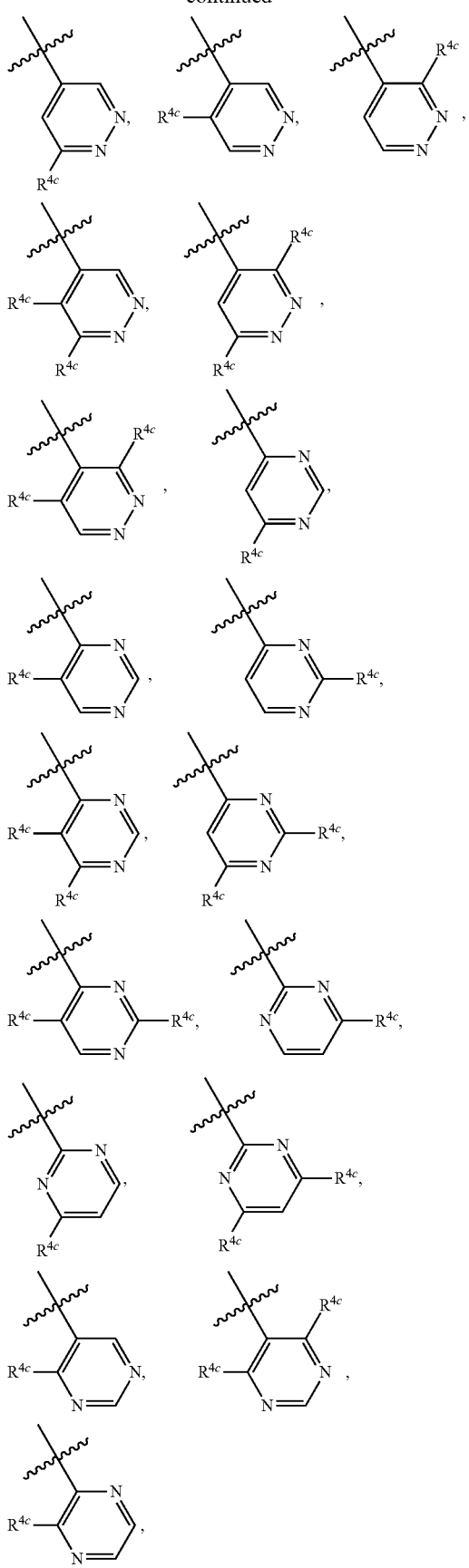

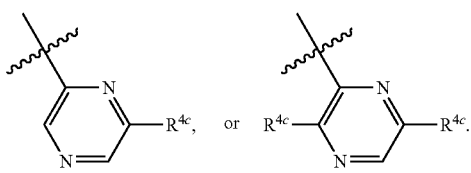

In some embodiments, disclosed herein is a compound of Formula I, or a pharmaceutically acceptable salt thereof, wherein $R^4$ is:
- pyridazinyl unsubstituted or substituted with —OCH$_3$ or —CH$_3$,
- pyrimidinyl unsubstituted or substituted with methyl, isopropyl, —OCH$_3$, or cyclopropyl, wherein the methyl is unsubstituted or substituted with one to three fluorine atoms, or
- pyrazinyl unsubstituted or substituted with —OCH$_3$, —CH$_3$, or —CF$_3$,
- wherein the pyridazinyl, pyrimidinyl and pyrazinyl are unsubstituted at the para-position.

In some embodiments, disclosed herein is a compound of Formula I, or a pharmaceutically acceptable salt thereof, wherein $R^4$ is:

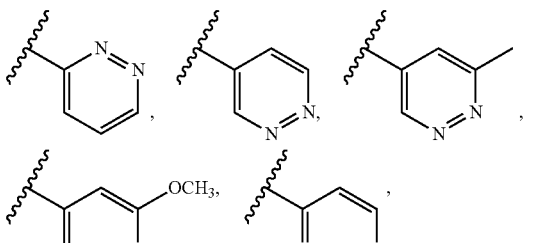

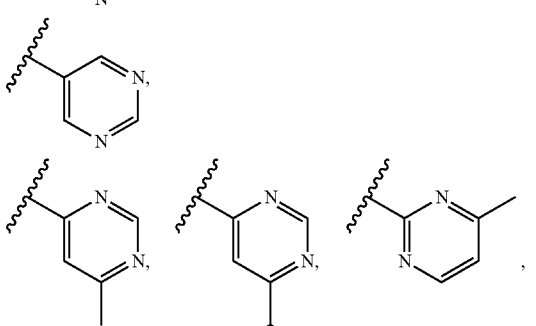

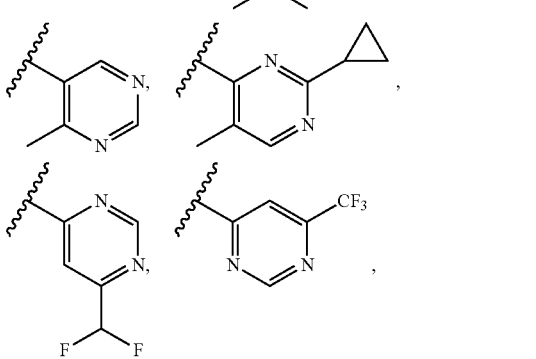

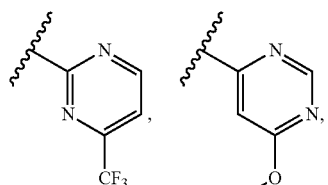

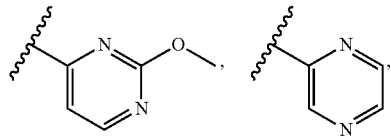

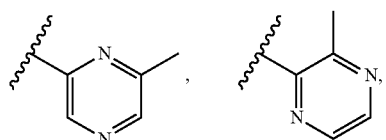

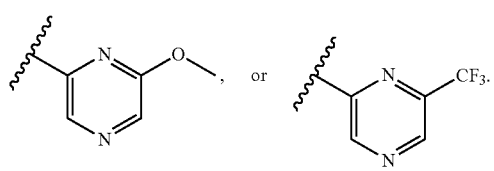

In some embodiments, disclosed herein is a compound of Formula I, or a pharmaceutically acceptable salt thereof, wherein $R^4$ is:

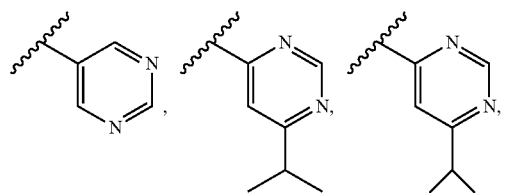

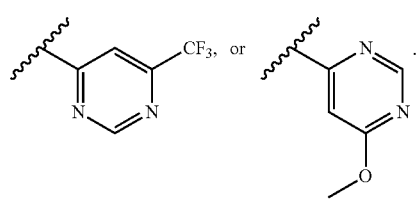

In some embodiments, disclosed herein is a compound of Formula I, or a pharmaceutically acceptable salt thereof, wherein: $R^5$ is hydrogen or halogen.

In some embodiments, disclosed herein is a compound of Formula I, or a pharmaceutically acceptable salt thereof, wherein: $R^5$ is hydrogen or fluorine.

In some embodiments, disclosed herein is a compound of Formula I, or a pharmaceutically acceptable salt thereof, wherein: $R^5$ is hydrogen.

In some embodiments, disclosed herein is a compound of Formula I, or a pharmaceutically acceptable salt thereof, wherein: $R^5$ is halogen. In some embodiments, disclosed herein is a compound of Formula I, or a pharmaceutically acceptable salt thereof, wherein: $R^5$ is fluorine.

TABLE 1A
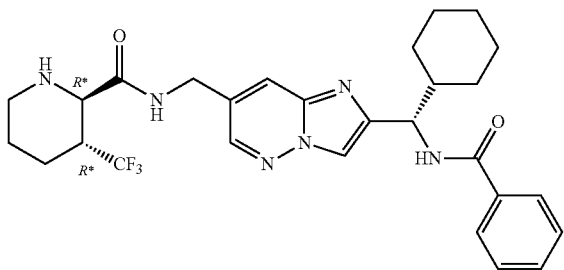 [SMILES: O=C(N[C@H](c1cn2ncc(CNC(=O)[C@@H]3NCCC[C@H]3C(F)(F)F)cc2n1)C1CCCCC1)c1ccccc1]
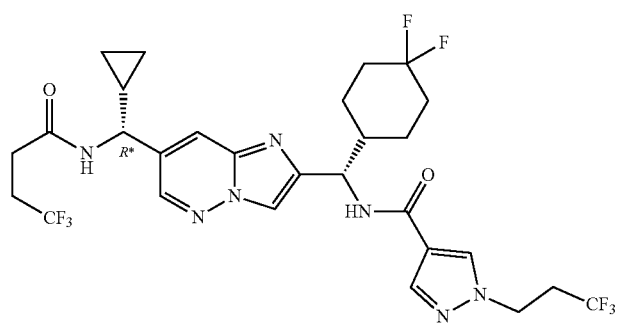 [SMILES: O=C(CCC(F)(F)F)N[C@@H](c1cnn2cc([C@@H](NC(=O)c3cnn(CCC(F)(F)F)c3)C3CCC(F)(F)CC3)nc2c1)C1CC1]
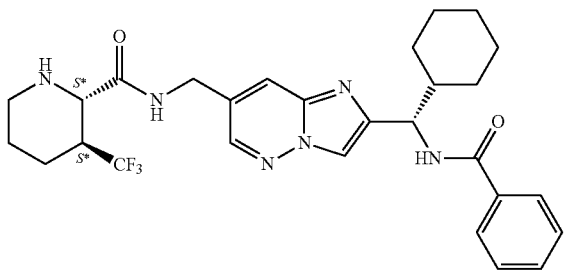 [SMILES: O=C(N[C@H](c1cn2ncc(CNC(=O)[C@H]3NCCC[C@@H]3C(F)(F)F)cc2n1)C1CCCCC1)c1ccccc1]
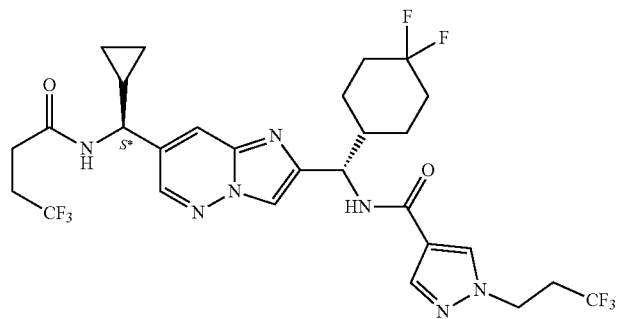 [SMILES: O=C(CCC(F)(F)F)N[C@H](c1cnn2cc([C@@H](NC(=O)c3cnn(CCC(F)(F)F)c3)C3CCC(F)(F)CC3)nc2c1)C1CC1]
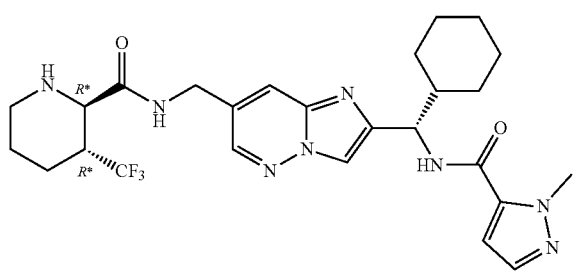 [SMILES: Cn1nccc1C(=O)N[C@H](c1cn2ncc(CNC(=O)[C@@H]3NCCC[C@H]3C(F)(F)F)cc2n1)C1CCCCC1]

TABLE 1A-continued
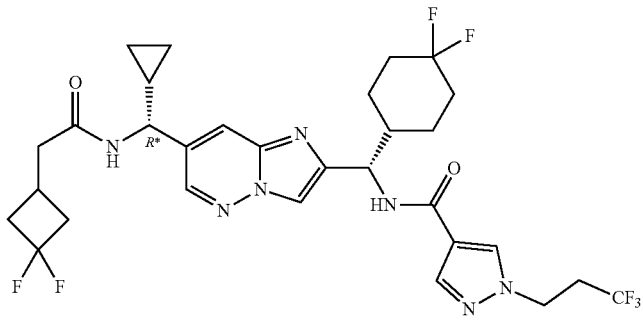 [SMILES: O=C(CC1CC(F)(F)C1)N[C@@H](c1cnn2cc([C@@H](NC(=O)c3cnn(CCC(F)(F)F)c3)C3CCC(F)(F)CC3)nc2c1)C1CC1]
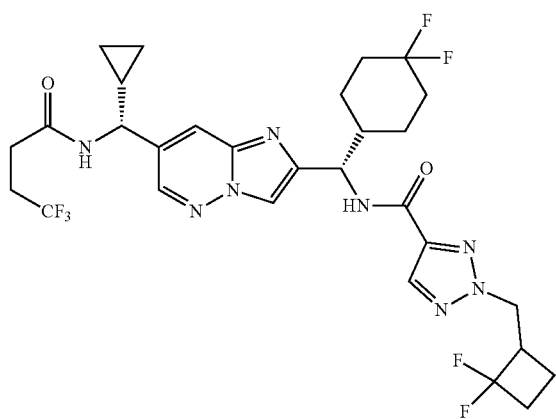 [SMILES: O=C(CCC(F)(F)F)N[C@@H](c1cnn2cc([C@@H](NC(=O)c3cnn(CC4CCC4(F)F)n3)C3CCC(F)(F)CC3)nc2c1)C1CC1]
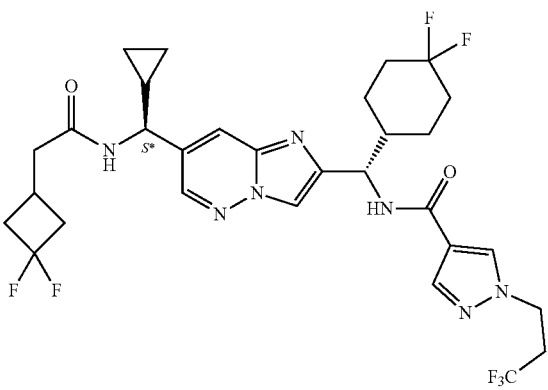 [SMILES: O=C(CC1CC(F)(F)C1)N[C@H](c1cnn2cc([C@@H](NC(=O)c3cnn(CCC(F)(F)F)c3)C3CCC(F)(F)CC3)nc2c1)C1CC1]
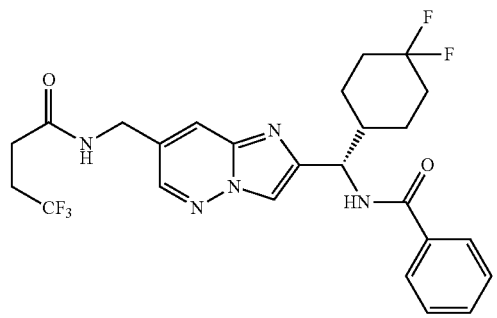 [SMILES: O=C(CCC(F)(F)F)NCc1cnn2cc([C@@H](NC(=O)c3ccccc3)C3CCC(F)(F)CC3)nc2c1]

TABLE 1A-continued
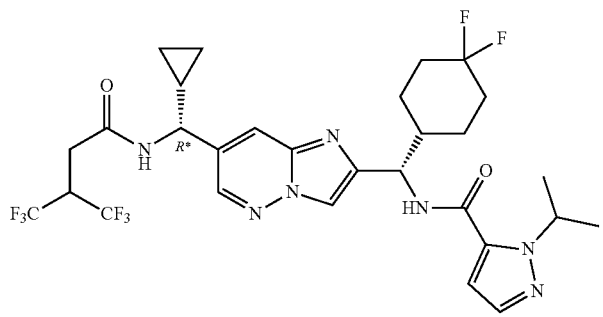 [SMILES: CC(C)n1nccc1C(=O)N[C@H](c1cn2ncc([C@H](NC(=O)CC(C(F)(F)F)C(F)(F)F)C3CC3)cc2n1)C1CCC(F)(F)CC1]
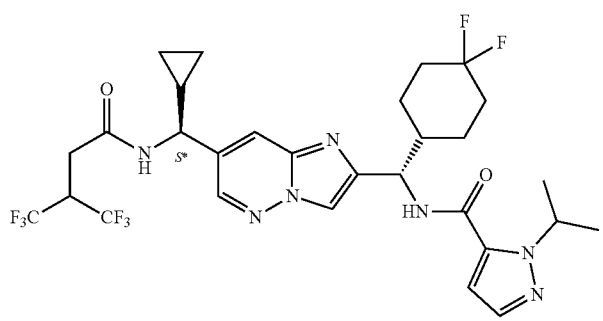
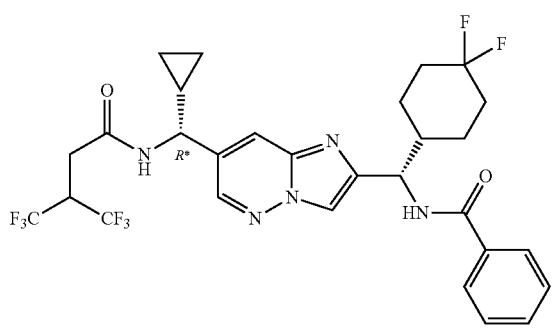 [SMILES: O=C(CC(C(F)(F)F)C(F)(F)F)N[C@@H](c1cnn2cc([C@@H](NC(=O)c3ccccc3)C3CCC(F)(F)CC3)nc2c1)C1CC1]
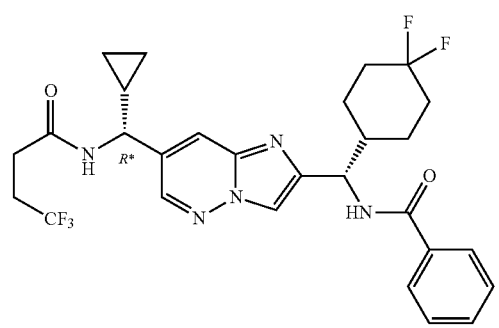 [SMILES: O=C(CCC(F)(F)F)N[C@@H](c1cnn2cc([C@@H](NC(=O)c3ccccc3)C3CCC(F)(F)CC3)nc2c1)C1CC1]
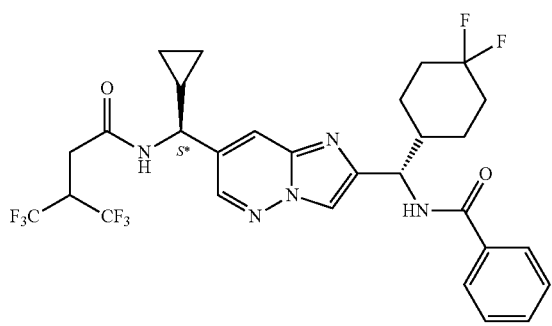 [SMILES: O=C(CC(C(F)(F)F)C(F)(F)F)N[C@H](c1cnn2cc([C@@H](NC(=O)c3ccccc3)C3CCC(F)(F)CC3)nc2c1)C1CC1]

TABLE 1A-continued
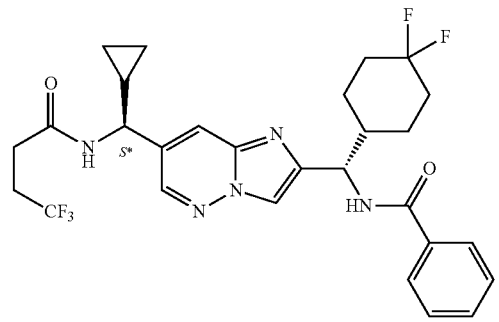 [SMILES: O=C(CCC(F)(F)F)N[C@H](c1cnn2cc([C@@H](NC(=O)c3ccccc3)C3CCC(F)(F)CC3)nc2c1)C1CC1]
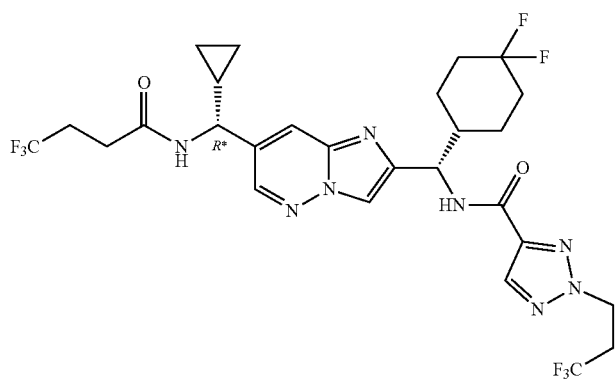 [SMILES: O=C(CCC(F)(F)F)N[C@@H](c1cnn2cc([C@@H](NC(=O)c3cnn(CCC(F)(F)F)n3)C3CCC(F)(F)CC3)nc2c1)C1CC1]
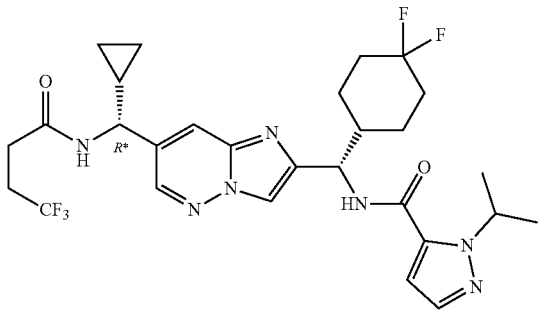 [SMILES: CC(C)n1nccc1C(=O)N[C@H](c1cn2ncc([C@H](NC(=O)CCC(F)(F)F)C3CC3)cc2n1)C1CCC(F)(F)CC1]
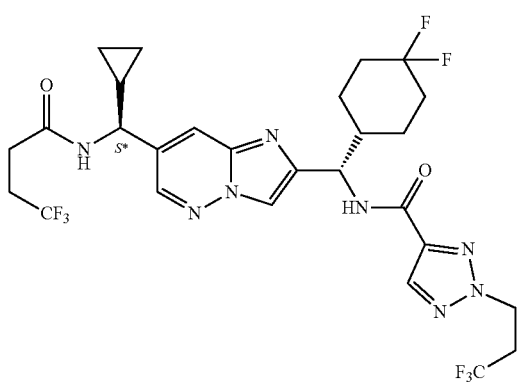 [SMILES: O=C(CCC(F)(F)F)N[C@H](c1cnn2cc([C@@H](NC(=O)c3cnn(CCC(F)(F)F)n3)C3CCC(F)(F)CC3)nc2c1)C1CC1]

TABLE 1A-continued
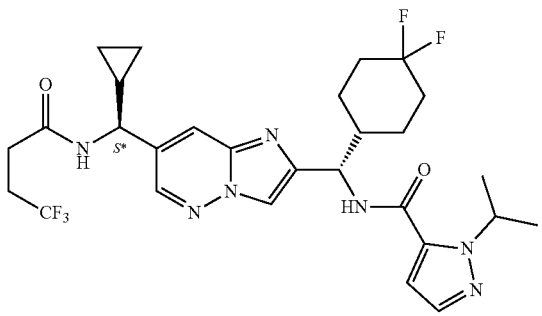 [SMILES: CC(C)n1nccc1C(=O)N[C@H](c1cn2ncc([C@@H](NC(=O)CCC(F)(F)F)C3CC3)cc2n1)C1CCC(F)(F)CC1]
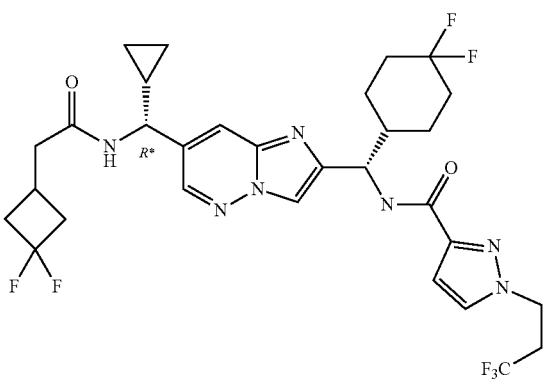
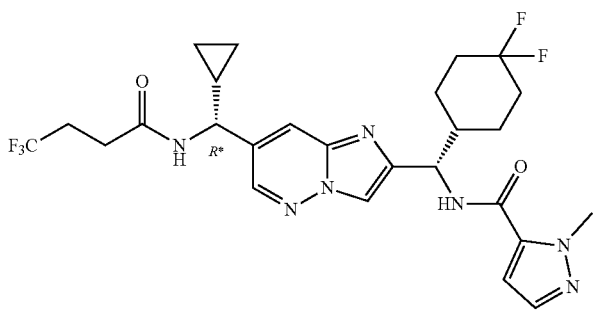 [SMILES: Cn1nccc1C(=O)N[C@H](c1cn2ncc([C@H](NC(=O)CCC(F)(F)F)C3CC3)cc2n1)C1CCC(F)(F)CC1]
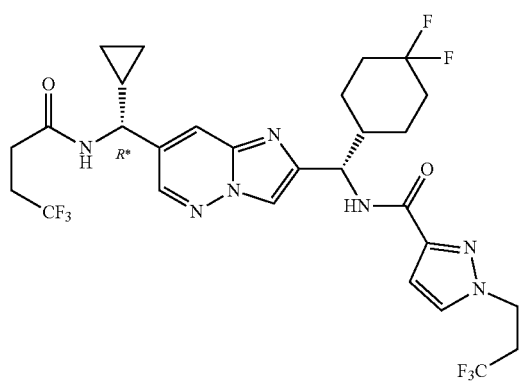

TABLE 1A-continued
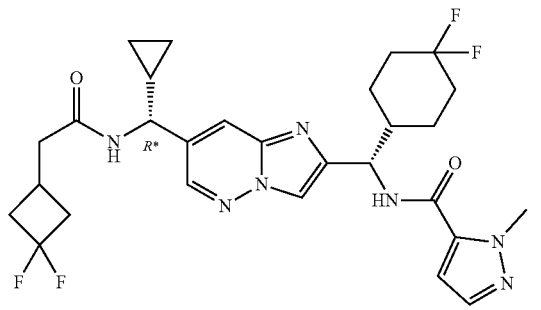 [SMILES: Cn1nccc1C(=O)N[C@H](c1cn2ncc([C@H](NC(=O)CC3CC(F)(F)C3)C3CC3)cc2n1)C1CCC(F)(F)CC1]
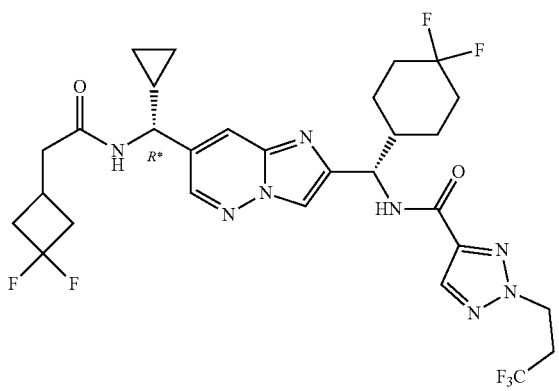 [SMILES: O=C(CC1CC(F)(F)C1)N[C@@H](c1cnn2cc([C@@H](NC(=O)c3cnn(CCC(F)(F)F)n3)C3CCC(F)(F)CC3)nc2c1)C1CC1]
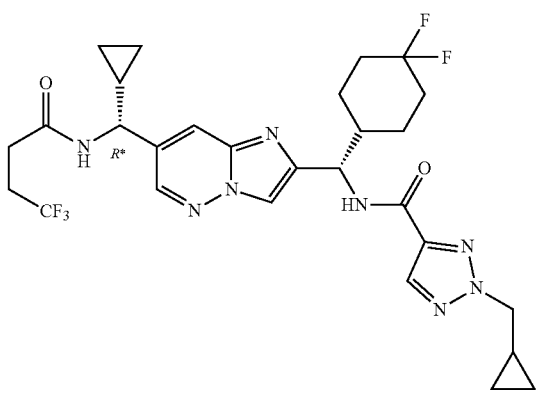 [SMILES: O=C(CCC(F)(F)F)N[C@@H](c1cnn2cc([C@@H](NC(=O)c3cnn(CC4CC4)n3)C3CCC(F)(F)CC3)nc2c1)C1CC1]
TABLE 1B
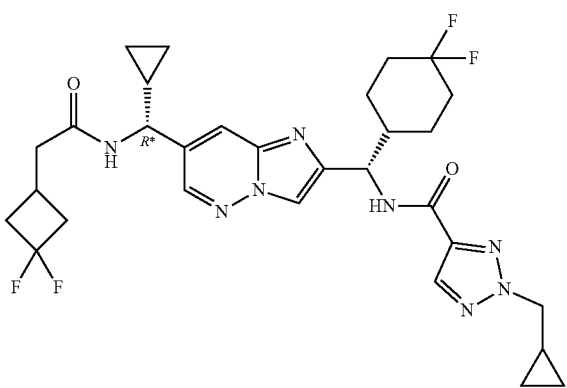 [SMILES: O=C(CC1CC(F)(F)C1)N[C@@H](c1cnn2cc([C@@H](NC(=O)c3cnn(CC4CC4)n3)C3CCC(F)(F)CC3)nc2c1)C1CC1]

TABLE 1B-continued
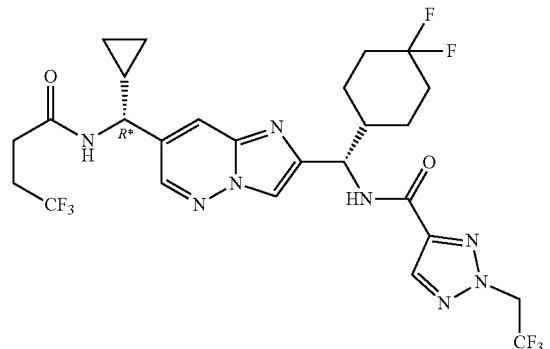 [SMILES: O=C(CCC(F)(F)F)N[C@@H](c1cnn2cc([C@@H](NC(=O)c3cnn(CC(F)(F)F)n3)C3CCC(F)(F)CC3)nc2c1)C1CC1]
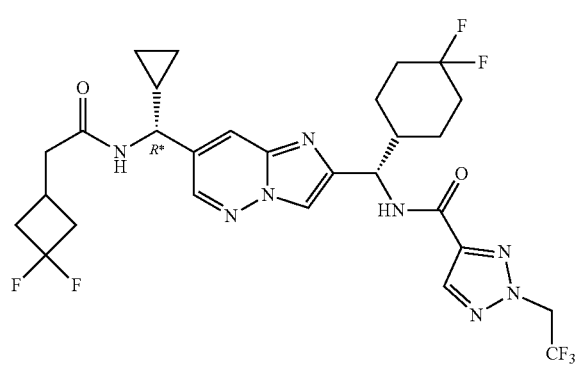 [SMILES: O=C(CC1CC(F)(F)C1)N[C@@H](c1cnn2cc([C@@H](NC(=O)c3cnn(CC(F)(F)F)n3)C3CCC(F)(F)CC3)nc2c1)C1CC1]
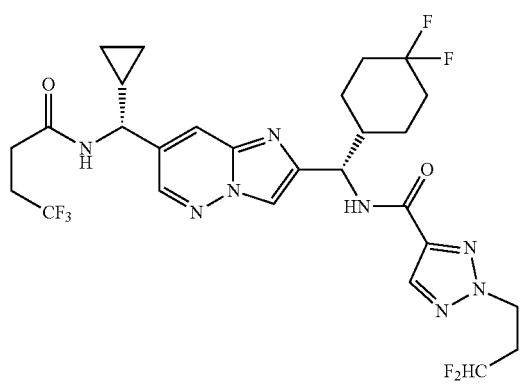 [SMILES: O=C(CCC(F)(F)F)N[C@@H](c1cnn2cc([C@@H](NC(=O)c3cnn(CCC(F)F)n3)C3CCC(F)(F)CC3)nc2c1)C1CC1]
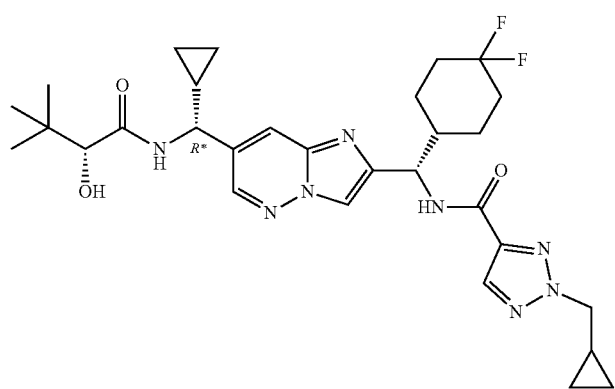 [SMILES: CC(C)(C)[C@@H](O)C(=O)N[C@@H](c1cnn2cc([C@@H](NC(=O)c3cnn(CC4CC4)n3)C3CCC(F)(F)CC3)nc2c1)C1CC1]

TABLE 1B-continued
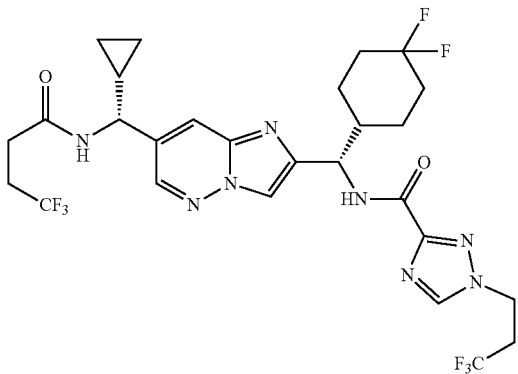 [SMILES: O=C(CCC(F)(F)F)N[C@@H](c1cnn2cc([C@@H](NC(=O)c3ncn(CCC(F)(F)F)n3)C3CCC(F)(F)CC3)nc2c1)C1CC1]
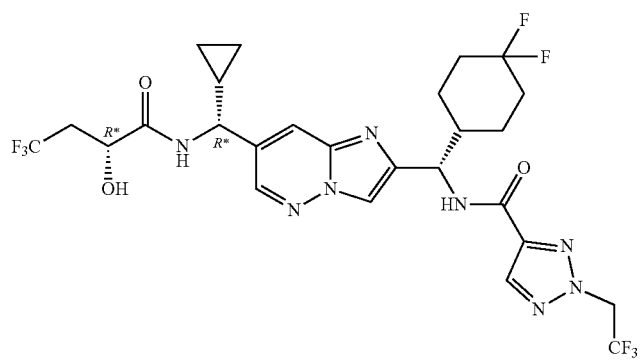 [SMILES: O=C(N[C@H](c1cn2ncc([C@H](NC(=O)[C@H](O)CC(F)(F)F)C3CC3)cc2n1)C1CCC(F)(F)CC1)c1cnn(CC(F)(F)F)n1]
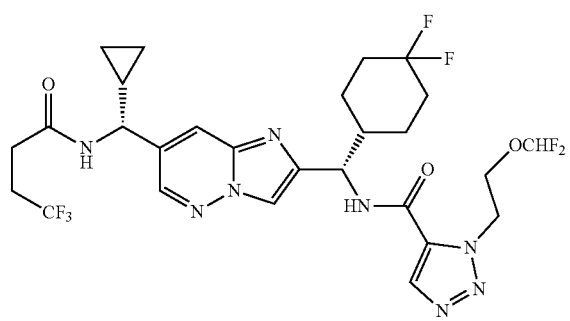 [SMILES: O=C(CCC(F)(F)F)N[C@@H](c1cnn2cc([C@@H](NC(=O)c3cnnn3CCOC(F)F)C3CCC(F)(F)CC3)nc2c1)C1CC1]
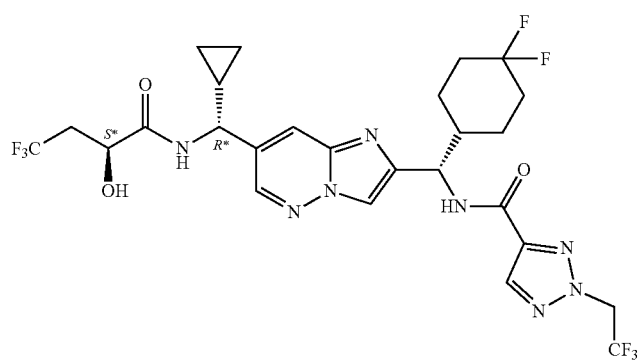 [SMILES: O=C(N[C@H](c1cn2ncc([C@H](NC(=O)[C@@H](O)CC(F)(F)F)C3CC3)cc2n1)C1CCC(F)(F)CC1)c1cnn(CC(F)(F)F)n1]

TABLE 1B-continued
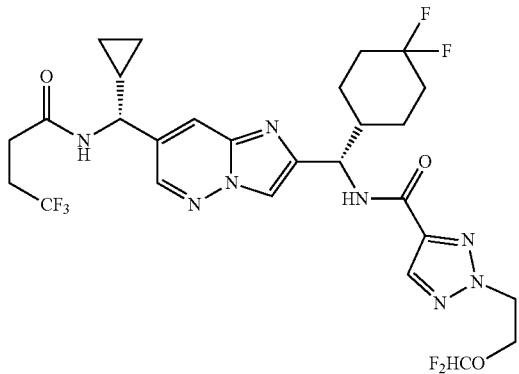 [SMILES: O=C(CCC(F)(F)F)N[C@@H](c1cnn2cc([C@@H](NC(=O)c3cnn(CCOC(F)F)n3)C3CCC(F)(F)CC3)nc2c1)C1CC1]
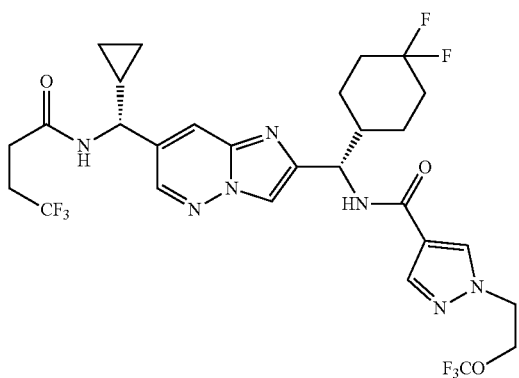 [SMILES: O=C(CCC(F)(F)F)N[C@@H](c1cnn2cc([C@@H](NC(=O)c3cnn(CCOC(F)(F)F)c3)C3CCC(F)(F)CC3)nc2c1)C1CC1]
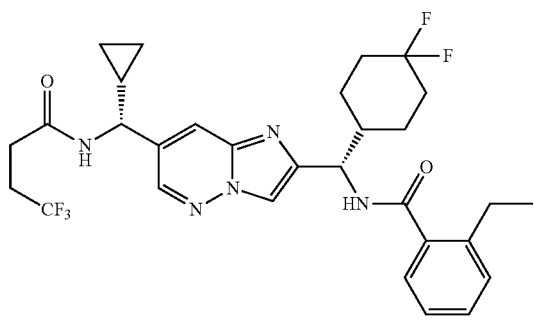 [SMILES: CCc1ccccc1C(=O)N[C@H](c1cn2ncc([C@H](NC(=O)CCC(F)(F)F)C3CC3)cc2n1)C1CCC(F)(F)CC1]
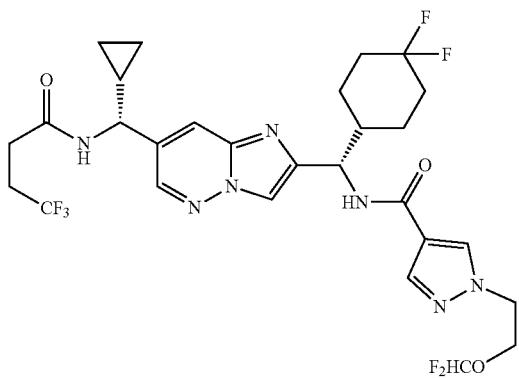 [SMILES: O=C(CCC(F)(F)F)N[C@@H](c1cnn2cc([C@@H](NC(=O)c3cnn(CCOC(F)F)c3)C3CCC(F)(F)CC3)nc2c1)C1CC1]

TABLE 1B-continued
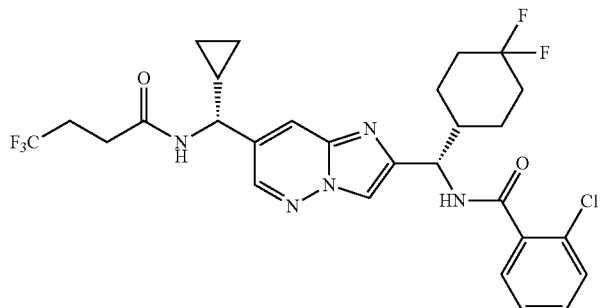
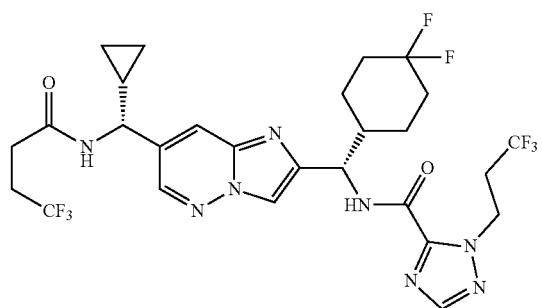 [SMILES: O=C(CCC(F)(F)F)N[C@@H](c1cnn2cc([C@@H](NC(=O)c3ncnn3CCC(F)(F)F)C3CCC(F)(F)CC3)nc2c1)C1CC1]
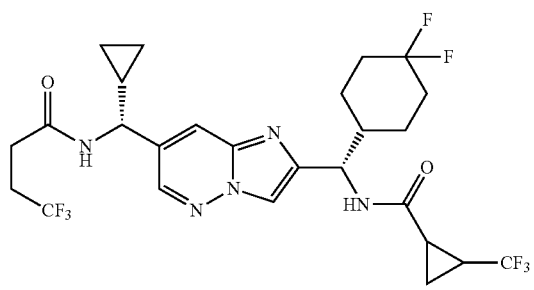 [SMILES: O=C(CCC(F)(F)F)N[C@@H](c1cnn2cc([C@@H](NC(=O)C3CC3C(F)(F)F)C3CCC(F)(F)CC3)nc2c1)C1CC1]
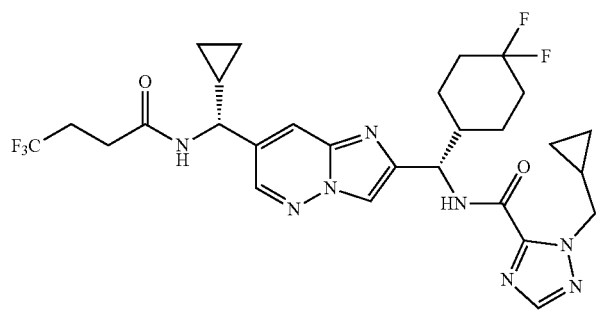 [SMILES: O=C(CCC(F)(F)F)N[C@@H](c1cnn2cc([C@@H](NC(=O)c3ncnn3CC3CC3)C3CCC(F)(F)CC3)nc2c1)C1CC1]
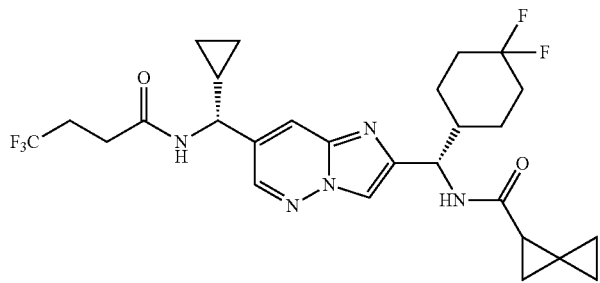 [SMILES: O=C(CCC(F)(F)F)N[C@@H](c1cnn2cc([C@@H](NC(=O)C3CC34CC4)C3CCC(F)(F)CC3)nc2c1)C1CC1]

TABLE 1B-continued
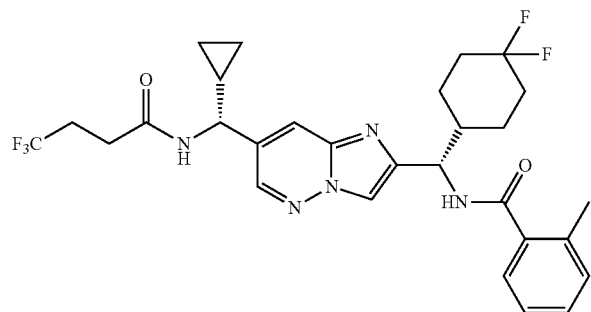 [SMILES: Cc1ccccc1C(=O)N[C@H](c1cn2ncc([C@H](NC(=O)CCC(F)(F)F)C3CC3)cc2n1)C1CCC(F)(F)CC1]
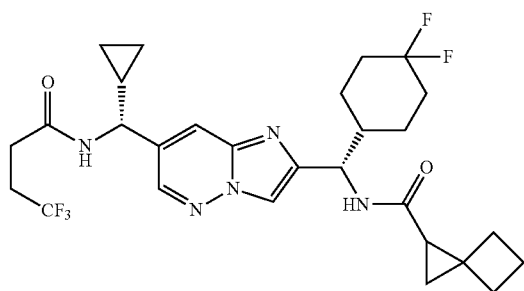
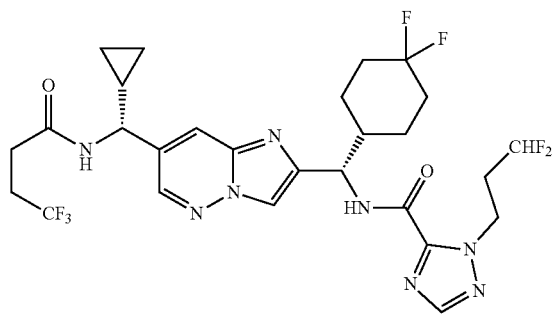 [SMILES: O=C(CCC(F)(F)F)N[C@@H](c1cnn2cc([C@@H](NC(=O)c3ncnn3CCC(F)F)C3CCC(F)(F)CC3)nc2c1)C1CC1]
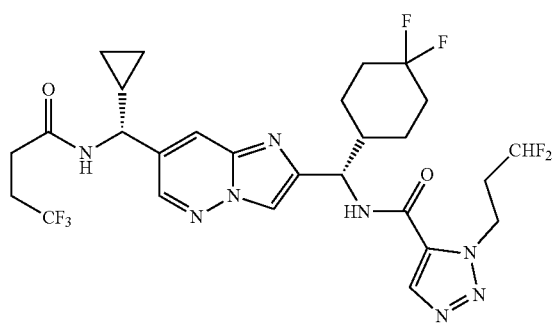 [SMILES: O=C(CCC(F)(F)F)N[C@@H](c1cnn2cc([C@@H](NC(=O)c3cnnn3CCC(F)F)C3CCC(F)(F)CC3)nc2c1)C1CC1]
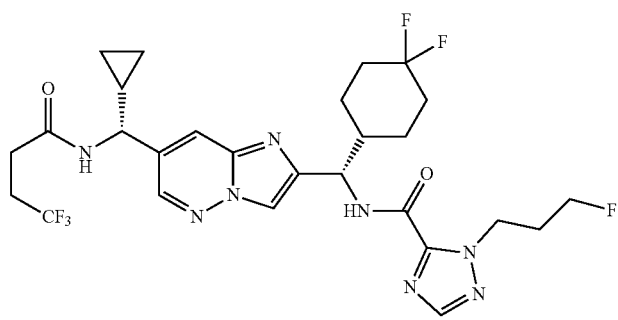 [SMILES: O=C(CCC(F)(F)F)N[C@@H](c1cnn2cc([C@@H](NC(=O)c3ncnn3CCCF)C3CCC(F)(F)CC3)nc2c1)C1CC1]

TABLE 1B-continued
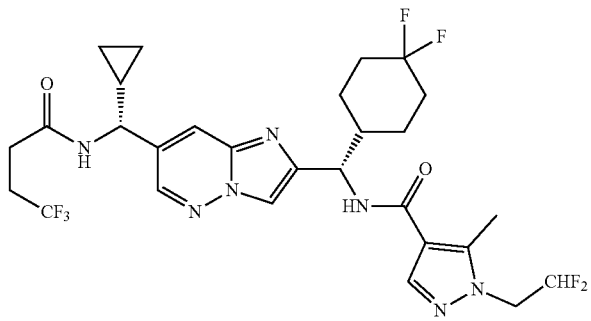 [SMILES: Cc1c(C(=O)N[C@H](c2cn3ncc([C@H](NC(=O)CCC(F)(F)F)C4CC4)cc3n2)C2CCC(F)(F)CC2)cnn1CC(F)F]
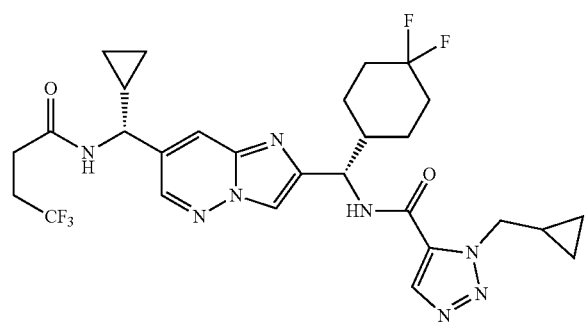 [SMILES: O=C(CCC(F)(F)F)N[C@@H](c1cnn2cc([C@@H](NC(=O)c3cnnn3CC3CC3)C3CCC(F)(F)CC3)nc2c1)C1CC1]
TABLE 1C
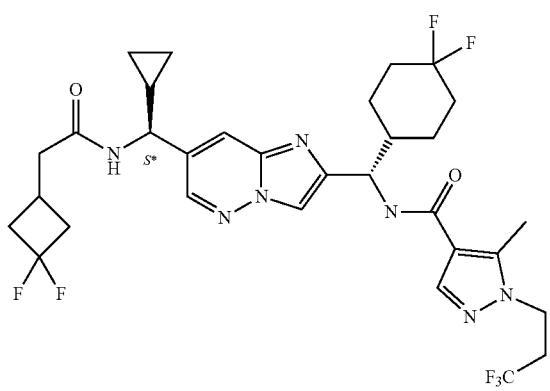
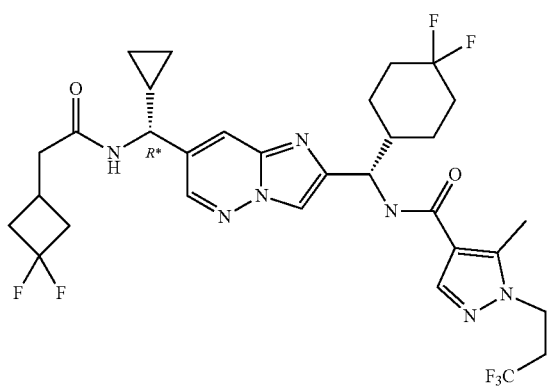

TABLE 1C-continued
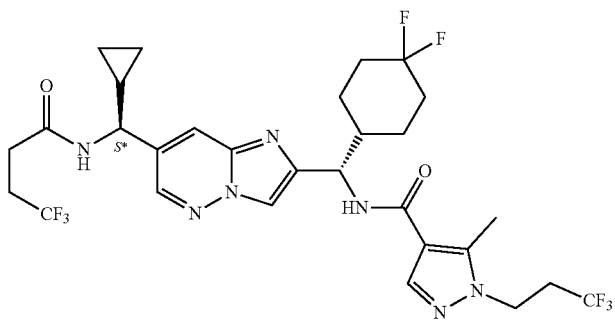 [SMILES: Cc1c(C(=O)N[C@H](c2cn3ncc([C@@H](NC(=O)CCC(F)(F)F)C4CC4)cc3n2)C2CCC(F)(F)CC2)cnn1CCC(F)(F)F]
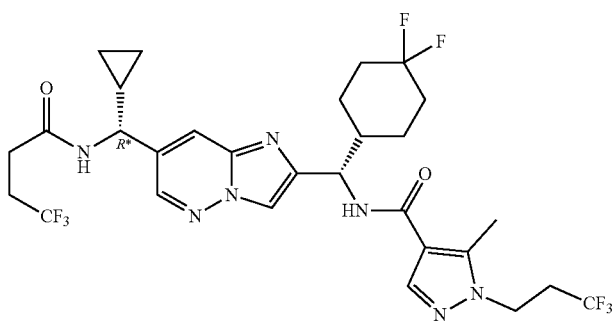 [SMILES: Cc1c(C(=O)N[C@H](c2cn3ncc([C@H](NC(=O)CCC(F)(F)F)C4CC4)cc3n2)C2CCC(F)(F)CC2)cnn1CCC(F)(F)F]
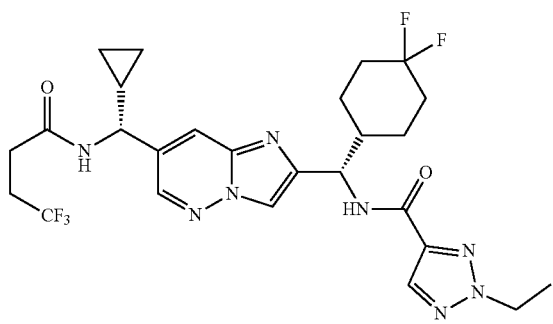 [SMILES: CCn1ncc(C(=O)N[C@H](c2cn3ncc([C@H](NC(=O)CCC(F)(F)F)C4CC4)cc3n2)C2CCC(F)(F)CC2)n1]
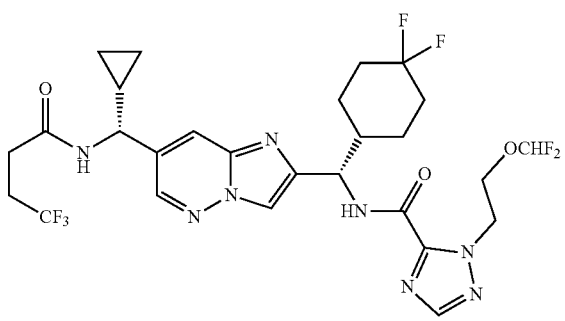 [SMILES: O=C(CCC(F)(F)F)N[C@@H](c1cnn2cc([C@@H](NC(=O)c3ncnn3CCOC(F)F)C3CCC(F)(F)CC3)nc2c1)C1CC1]
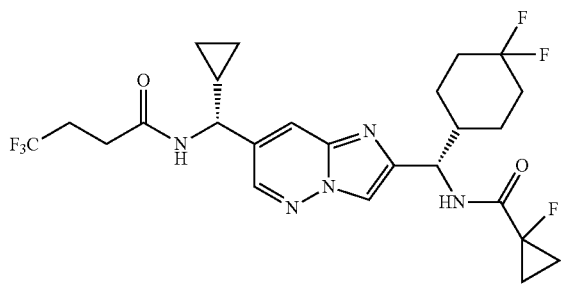 [SMILES: O=C(CCC(F)(F)F)N[C@@H](c1cnn2cc([C@@H](NC(=O)C3(F)CC3)C3CCC(F)(F)CC3)nc2c1)C1CC1]

TABLE 1C-continued
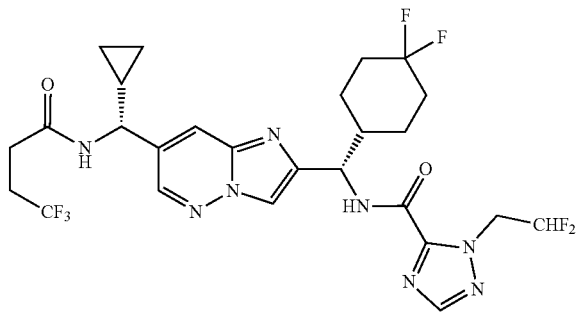 [SMILES: O=C(CCC(F)(F)F)N[C@@H](c1cnn2cc([C@@H](NC(=O)c3ncnn3CC(F)F)C3CCC(F)(F)CC3)nc2c1)C1CC1]
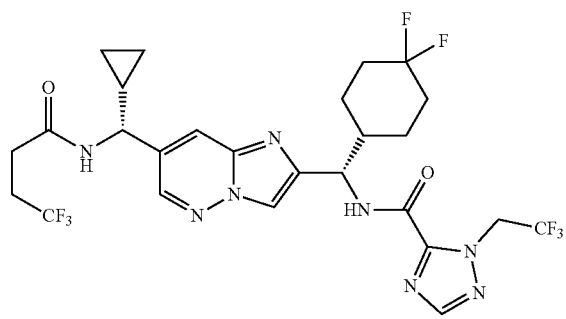 [SMILES: O=C(CCC(F)(F)F)N[C@@H](c1cnn2cc([C@@H](NC(=O)c3ncnn3CC(F)(F)F)C3CCC(F)(F)CC3)nc2c1)C1CC1]
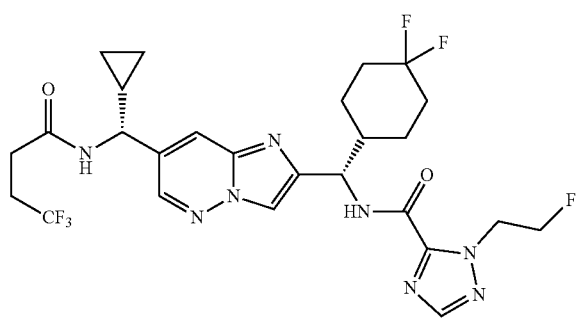 [SMILES: O=C(CCC(F)(F)F)N[C@@H](c1cnn2cc([C@@H](NC(=O)c3ncnn3CCF)C3CCC(F)(F)CC3)nc2c1)C1CC1]
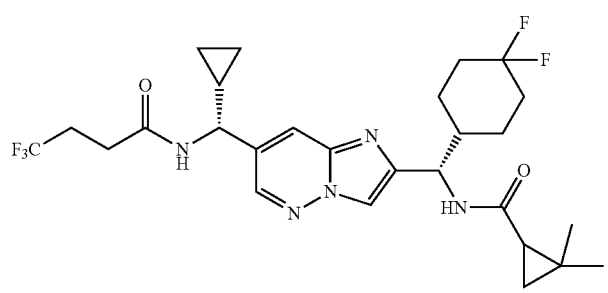 [SMILES: CC1(C)CC1C(=O)N[C@H](c1cn2ncc([C@H](NC(=O)CCC(F)(F)F)C3CC3)cc2n1)C1CCC(F)(F)CC1]
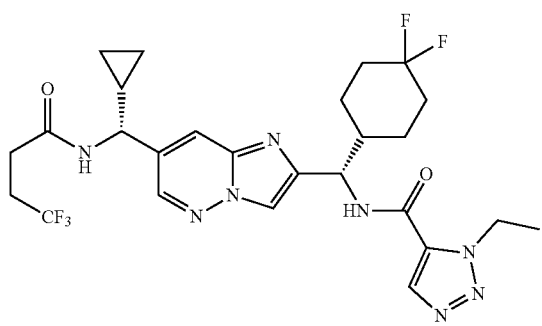 [SMILES: CCn1nncc1C(=O)N[C@H](c1cn2ncc([C@H](NC(=O)CCC(F)(F)F)C3CC3)cc2n1)C1CCC(F)(F)CC1]

TABLE 1C-continued
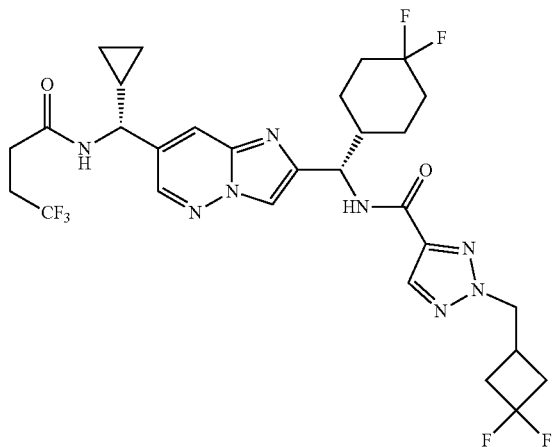 [SMILES: O=C(CCC(F)(F)F)N[C@@H](c1cnn2cc([C@@H](NC(=O)c3cnn(CC4CC(F)(F)C4)n3)C3CCC(F)(F)CC3)nc2c1)C1CC1]
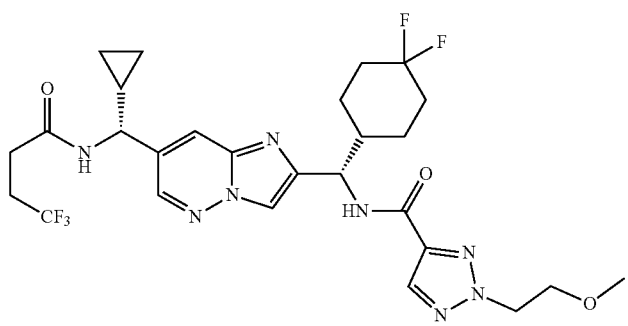 [SMILES: COCCn1ncc(C(=O)N[C@H](c2cn3ncc([C@H](NC(=O)CCC(F)(F)F)C4CC4)cc3n2)C2CCC(F)(F)CC2)n1]
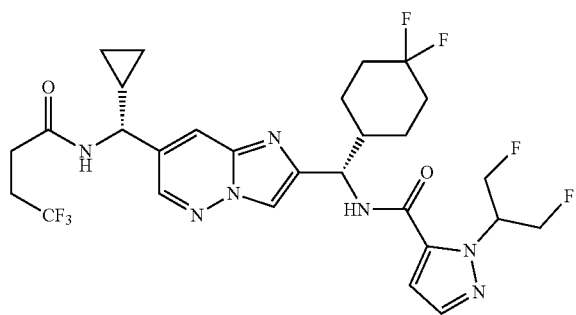 [SMILES: O=C(CCC(F)(F)F)N[C@@H](c1cnn2cc([C@@H](NC(=O)c3ccnn3C(CF)CF)C3CCC(F)(F)CC3)nc2c1)C1CC1]
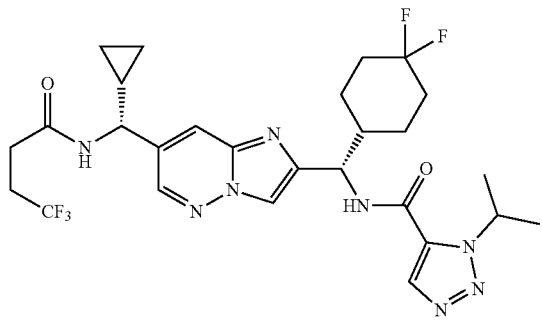 [SMILES: CC(C)n1nncc1C(=O)N[C@H](c1cn2ncc([C@H](NC(=O)CCC(F)(F)F)C3CC3)cc2n1)C1CCC(F)(F)CC1]

TABLE 1C-continued
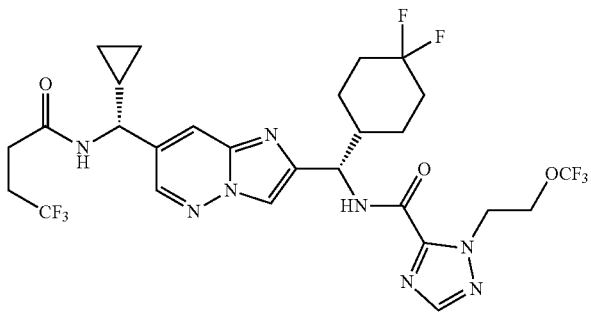
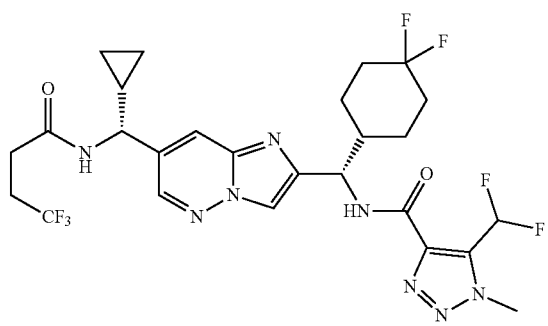 [SMILES: Cn1nnc(C(=O)N[C@H](c2cn3ncc([C@H](NC(=O)CCC(F)(F)F)C4CC4)cc3n2)C2CCC(F)(F)CC2)c1C(F)F]
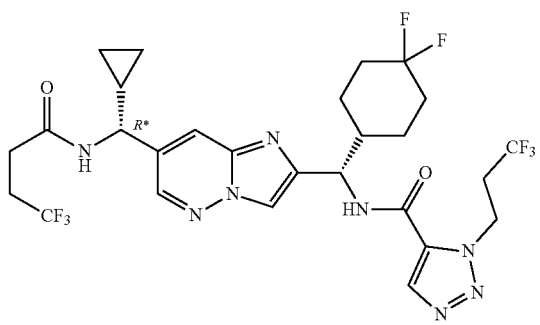 [SMILES: O=C(CCC(F)(F)F)N[C@@H](c1cnn2cc([C@@H](NC(=O)c3cnnn3CCC(F)(F)F)C3CCC(F)(F)CC3)nc2c1)C1CC1]
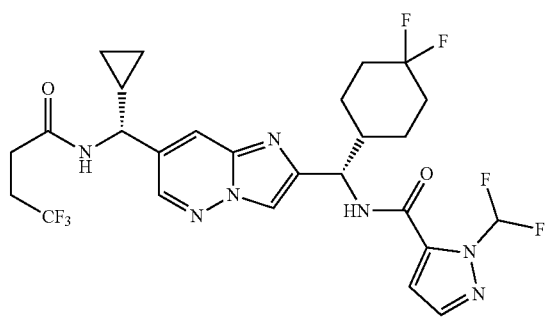 [SMILES: O=C(CCC(F)(F)F)N[C@@H](c1cnn2cc([C@@H](NC(=O)c3ccnn3C(F)F)C3CCC(F)(F)CC3)nc2c1)C1CC1]
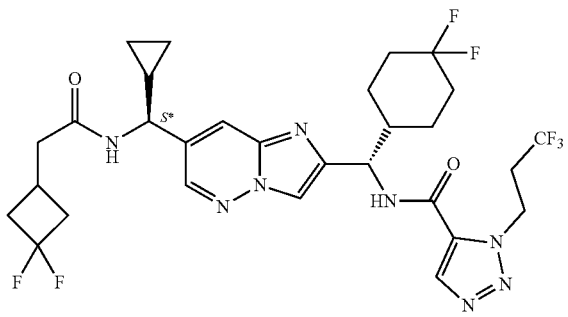 [SMILES: O=C(CC1CC(F)(F)C1)N[C@H](c1cnn2cc([C@@H](NC(=O)c3cnnn3CCC(F)(F)F)C3CCC(F)(F)CC3)nc2c1)C1CC1]

TABLE 1C-continued
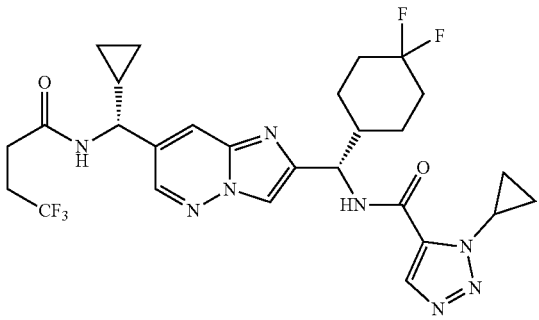 [SMILES: O=C(CCC(F)(F)F)N[C@@H](c1cnn2cc([C@@H](NC(=O)c3cnnn3C3CC3)C3CCC(F)(F)CC3)nc2c1)C1CC1]
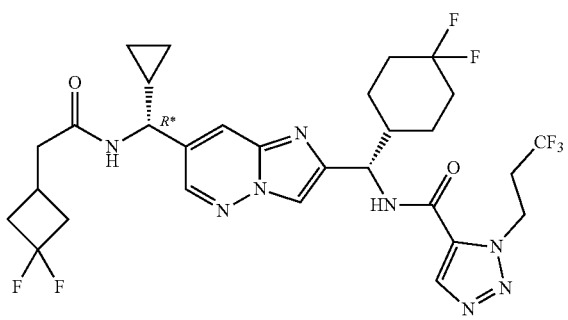 [SMILES: O=C(CC1CC(F)(F)C1)N[C@@H](c1cnn2cc([C@@H](NC(=O)c3cnnn3CCC(F)(F)F)C3CCC(F)(F)CC3)nc2c1)C1CC1]
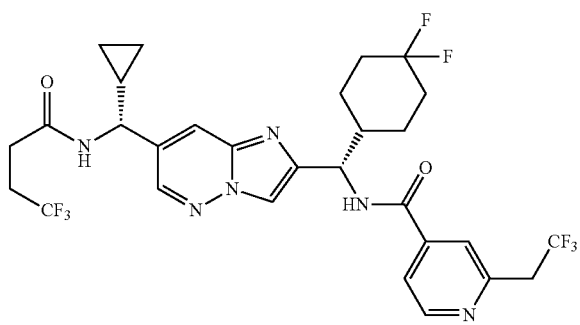 [SMILES: O=C(CCC(F)(F)F)N[C@@H](c1cnn2cc([C@@H](NC(=O)c3ccnc(CC(F)(F)F)c3)C3CCC(F)(F)CC3)nc2c1)C1CC1]
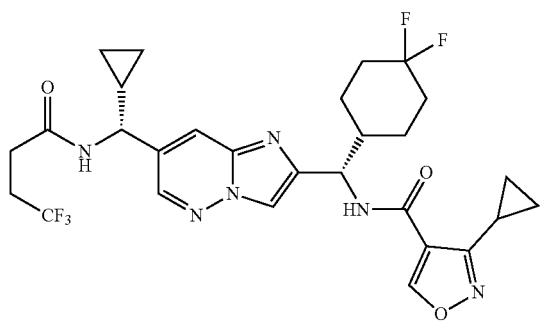 [SMILES: O=C(CCC(F)(F)F)N[C@@H](c1cnn2cc([C@@H](NC(=O)c3conc3C3CC3)C3CCC(F)(F)CC3)nc2c1)C1CC1]

TABLE 1D
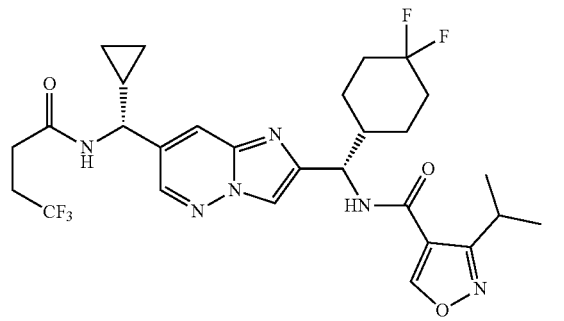
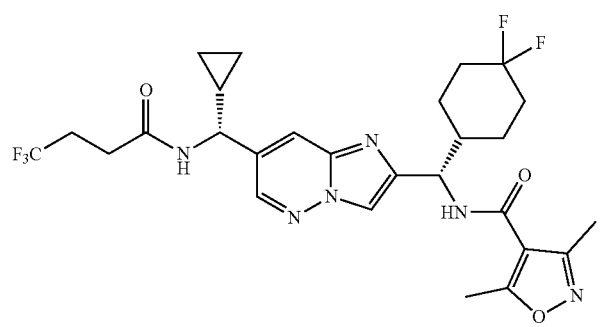 [SMILES: Cc1noc(C)c1C(=O)N[C@H](c1cn2ncc([C@H](NC(=O)CCC(F)(F)F)C3CC3)cc2n1)C1CCC(F)(F)CC1]
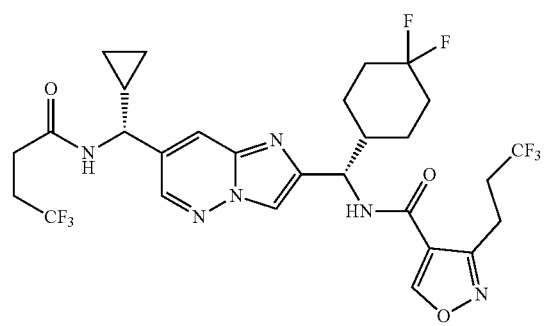 [SMILES: O=C(CCC(F)(F)F)N[C@@H](c1cnn2cc([C@@H](NC(=O)c3conc3CCC(F)(F)F)C3CCC(F)(F)CC3)nc2c1)C1CC1]
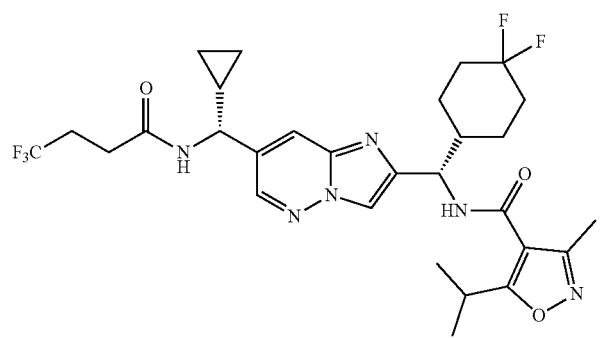 [SMILES: Cc1noc(C(C)C)c1C(=O)N[C@H](c1cn2ncc([C@H](NC(=O)CCC(F)(F)F)C3CC3)cc2n1)C1CCC(F)(F)CC1]
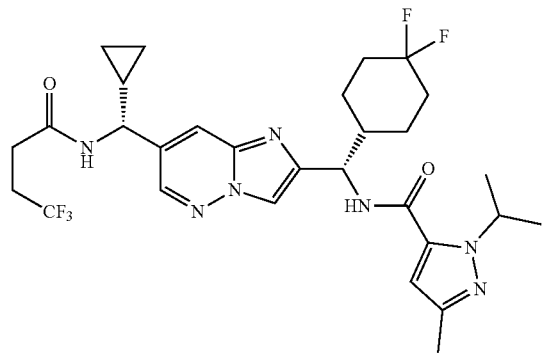 [SMILES: Cc1cc(C(=O)N[C@H](c2cn3ncc([C@H](NC(=O)CCC(F)(F)F)C4CC4)cc3n2)C2CCC(F)(F)CC2)n(C(C)C)n1]

TABLE 1D-continued
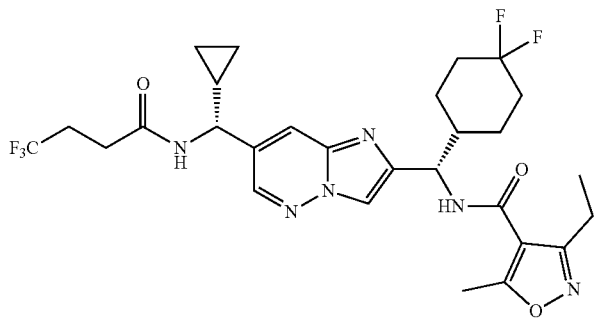 [SMILES: CCc1noc(C)c1C(=O)N[C@H](c1cn2ncc([C@H](NC(=O)CCC(F)(F)F)C3CC3)cc2n1)C1CCC(F)(F)CC1]
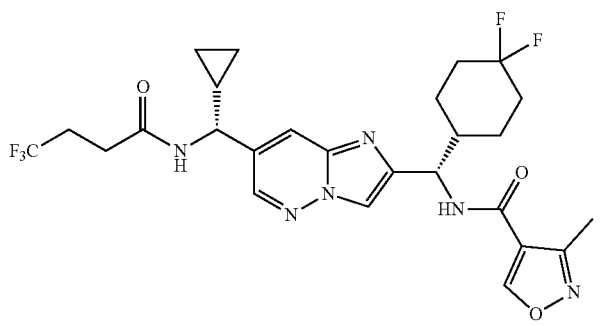
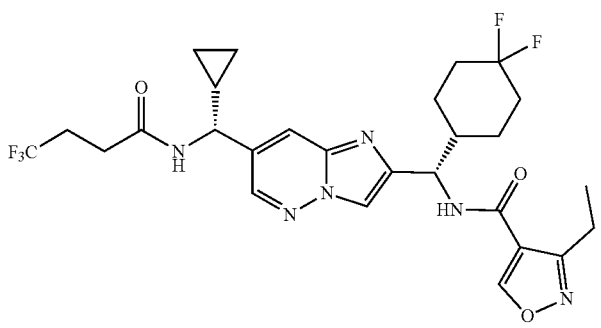 [SMILES: CCc1nocc1C(=O)N[C@H](c1cn2ncc([C@H](NC(=O)CCC(F)(F)F)C3CC3)cc2n1)C1CCC(F)(F)CC1]
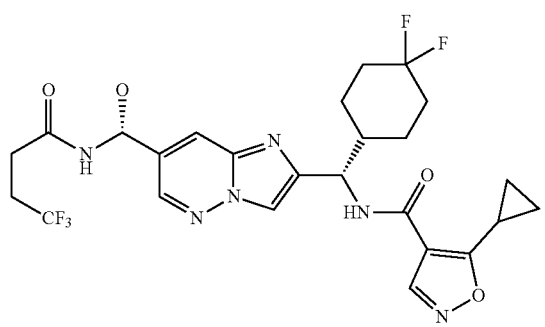
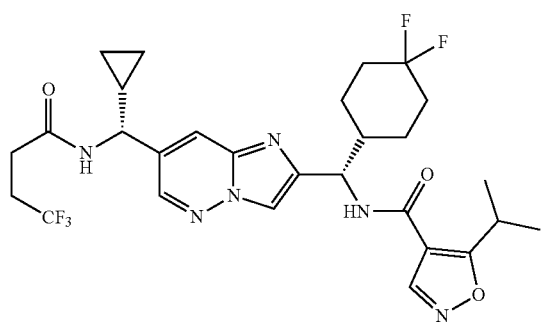 [SMILES: CC(C)c1oncc1C(=O)N[C@H](c1cn2ncc([C@H](NC(=O)CCC(F)(F)F)C3CC3)cc2n1)C1CCC(F)(F)CC1]

TABLE 1D-continued
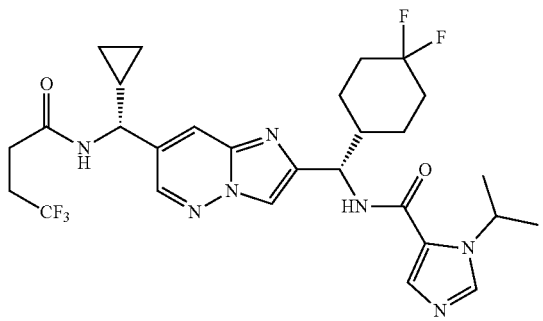 [SMILES: CC(C)n1cncc1C(=O)N[C@H](c1cn2ncc([C@H](NC(=O)CCC(F)(F)F)C3CC3)cc2n1)C1CCC(F)(F)CC1]
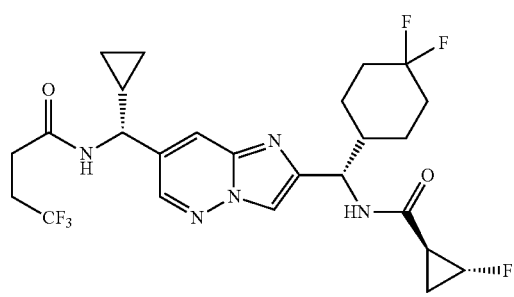 [SMILES: O=C(CCC(F)(F)F)N[C@@H](c1cnn2cc([C@@H](NC(=O)[C@@H]3C[C@H]3F)C3CCC(F)(F)CC3)nc2c1)C1CC1]
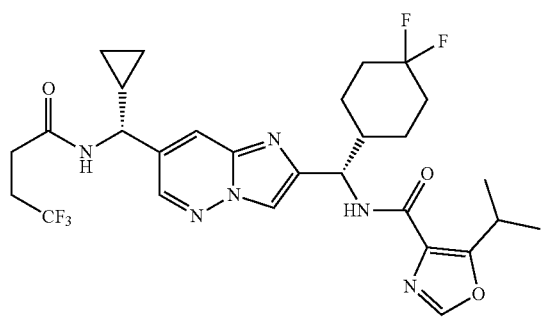 [SMILES: CC(C)c1ocnc1C(=O)N[C@H](c1cn2ncc([C@H](NC(=O)CCC(F)(F)F)C3CC3)cc2n1)C1CCC(F)(F)CC1]
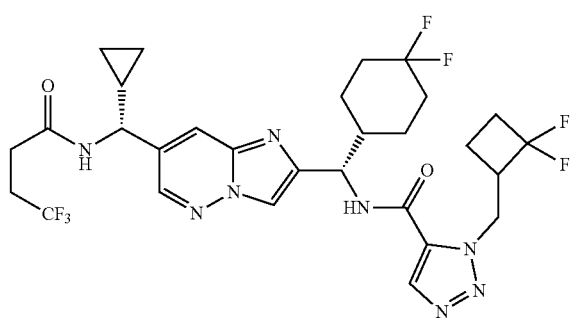 [SMILES: O=C(CCC(F)(F)F)N[C@@H](c1cnn2cc([C@@H](NC(=O)c3cnnn3CC3CCC3(F)F)C3CCC(F)(F)CC3)nc2c1)C1CC1]
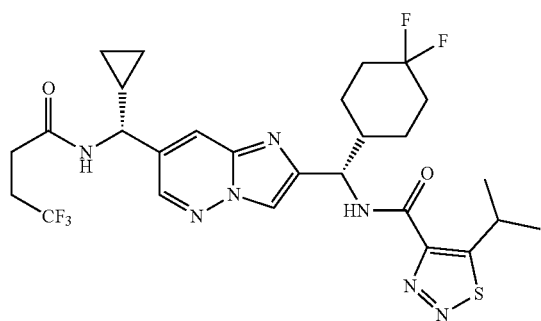

TABLE 1D-continued
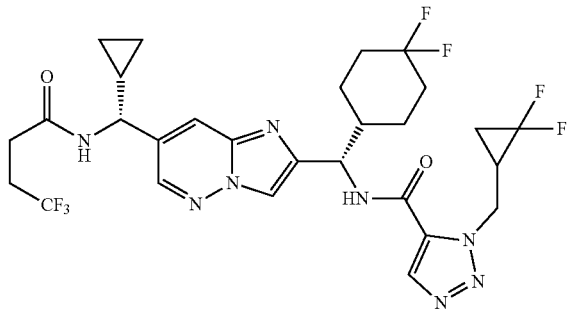 [SMILES: O=C(CCC(F)(F)F)N[C@@H](c1cnn2cc([C@@H](NC(=O)c3cnnn3CC3CC3(F)F)C3CCC(F)(F)CC3)nc2c1)C1CC1]
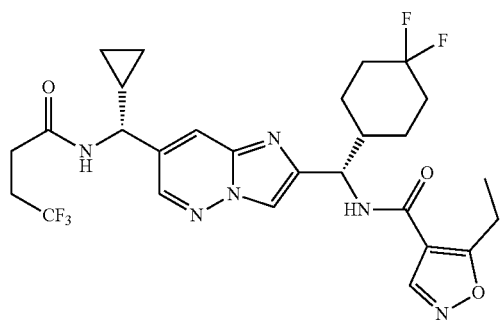 [SMILES: CCc1oncc1C(=O)N[C@H](c1cn2ncc([C@H](NC(=O)CCC(F)(F)F)C3CC3)cc2n1)C1CCC(F)(F)CC1]
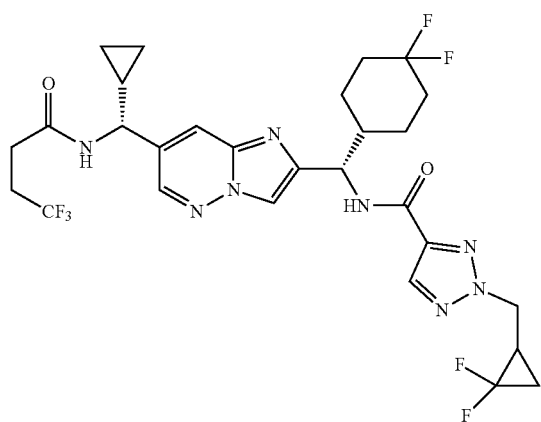 [SMILES: O=C(CCC(F)(F)F)N[C@@H](c1cnn2cc([C@@H](NC(=O)c3cnn(CC4CC4(F)F)n3)C3CCC(F)(F)CC3)nc2c1)C1CC1]
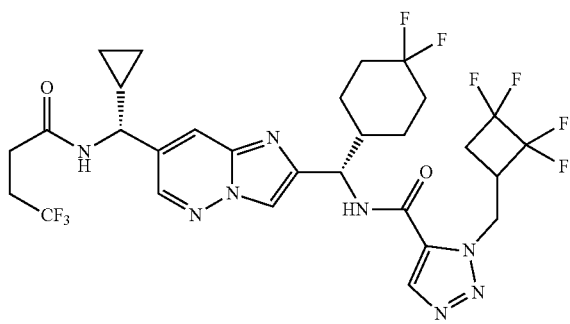 [SMILES: O=C(CCC(F)(F)F)N[C@@H](c1cnn2cc([C@@H](NC(=O)c3cnnn3CC3CC(F)(F)C3(F)F)C3CCC(F)(F)CC3)nc2c1)C1CC1]

TABLE 1D-continued
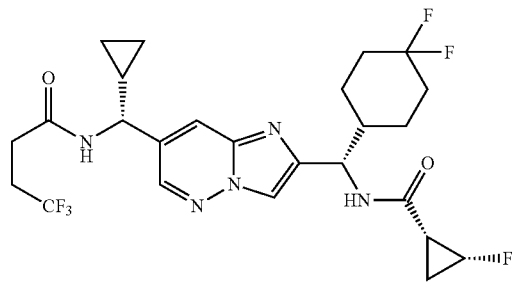 [SMILES: O=C(CCC(F)(F)F)N[C@@H](c1cnn2cc([C@@H](NC(=O)[C@H]3C[C@H]3F)C3CCC(F)(F)CC3)nc2c1)C1CC1]
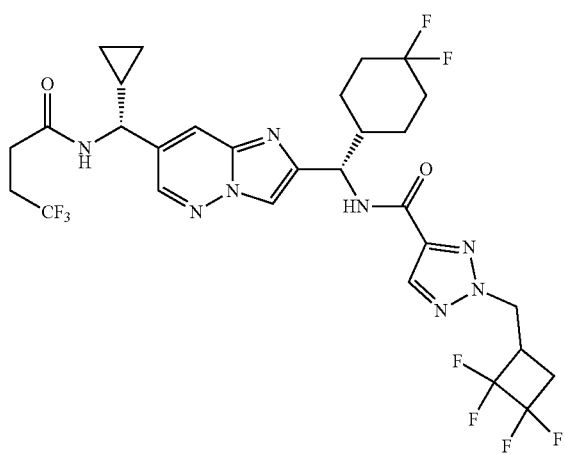 [SMILES: O=C(CCC(F)(F)F)N[C@@H](c1cnn2cc([C@@H](NC(=O)c3cnn(CC4CC(F)(F)C4(F)F)n3)C3CCC(F)(F)CC3)nc2c1)C1CC1]
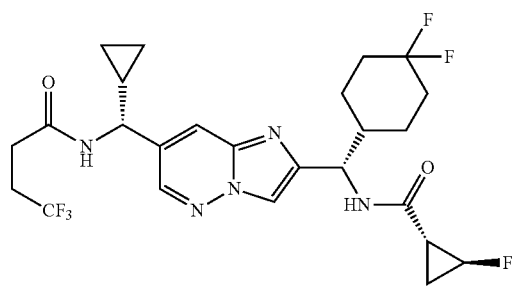 [SMILES: O=C(CCC(F)(F)F)N[C@@H](c1cnn2cc([C@@H](NC(=O)[C@H]3C[C@@H]3F)C3CCC(F)(F)CC3)nc2c1)C1CC1]
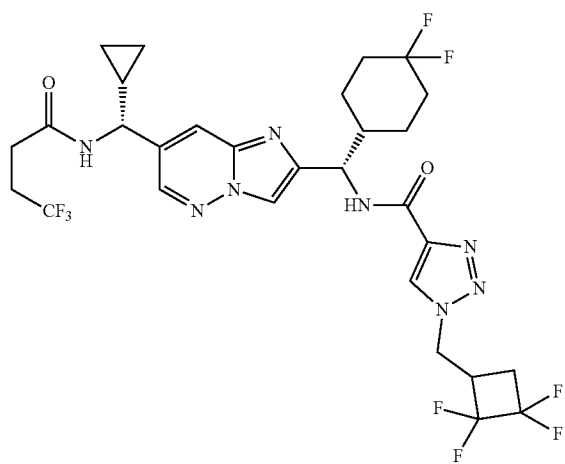 [SMILES: O=C(CCC(F)(F)F)N[C@@H](c1cnn2cc([C@@H](NC(=O)c3cn(CC4CC(F)(F)C4(F)F)nn3)C3CCC(F)(F)CC3)nc2c1)C1CC1]

TABLE 1D-continued
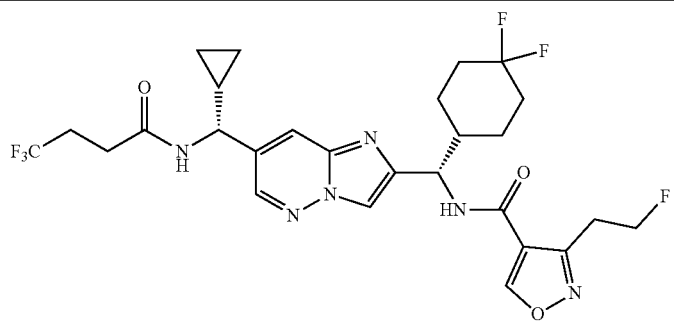
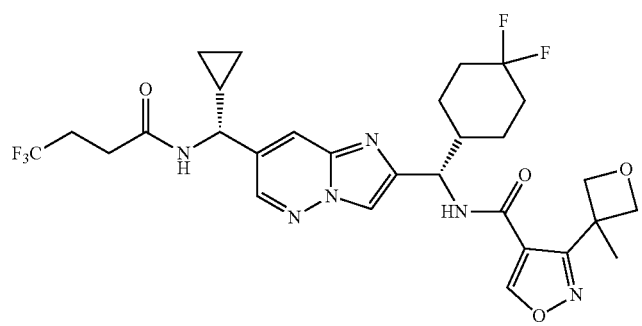 [SMILES: CC1(c2nocc2C(=O)N[C@H](c2cn3ncc([C@H](NC(=O)CCC(F)(F)F)C4CC4)cc3n2)C2CCC(F)(F)CC2)COC1]
TABLE 1E
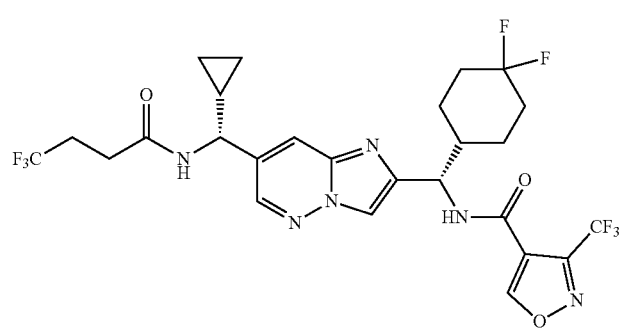 [SMILES: O=C(CCC(F)(F)F)N[C@@H](c1cnn2cc([C@@H](NC(=O)c3conc3C(F)(F)F)C3CCC(F)(F)CC3)nc2c1)C1CC1]
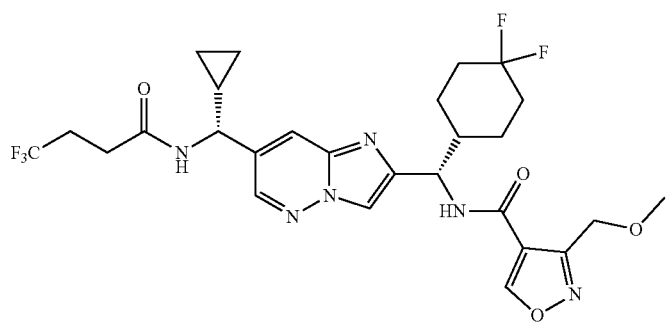 [SMILES: COCc1nocc1C(=O)N[C@H](c1cn2ncc([C@H](NC(=O)CCC(F)(F)F)C3CC3)cc2n1)C1CCC(F)(F)CC1]

TABLE 1E-continued
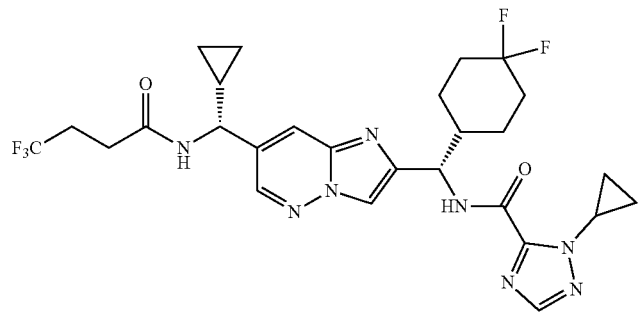 [SMILES: O=C(CCC(F)(F)F)N[C@@H](c1cnn2cc([C@@H](NC(=O)c3ncnn3C3CC3)C3CCC(F)(F)CC3)nc2c1)C1CC1]
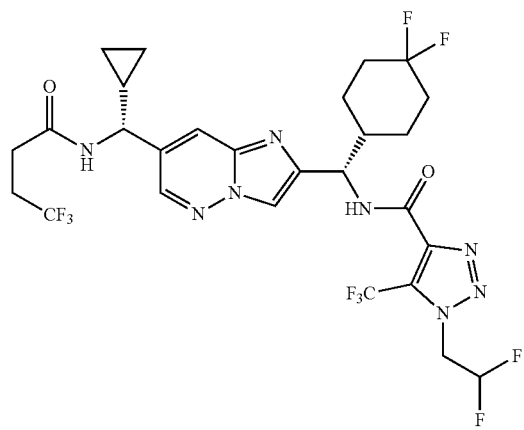 [SMILES: O=C(CCC(F)(F)F)N[C@@H](c1cnn2cc([C@@H](NC(=O)c3nnn(CC(F)F)c3C(F)(F)F)C3CCC(F)(F)CC3)nc2c1)C1CC1]
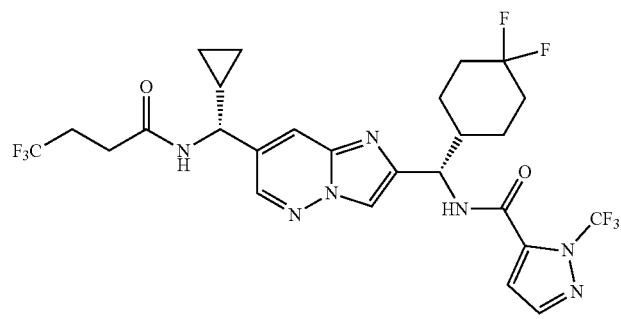 [SMILES: O=C(CCC(F)(F)F)N[C@@H](c1cnn2cc([C@@H](NC(=O)c3ccnn3C(F)(F)F)C3CCC(F)(F)CC3)nc2c1)C1CC1]
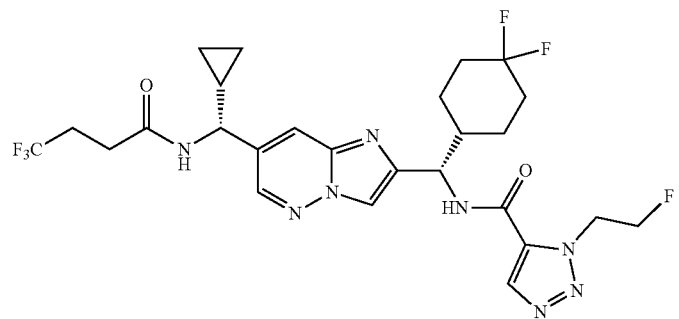 [SMILES: O=C(CCC(F)(F)F)N[C@@H](c1cnn2cc([C@@H](NC(=O)c3cnnn3CCF)C3CCC(F)(F)CC3)nc2c1)C1CC1]

TABLE 1E-continued
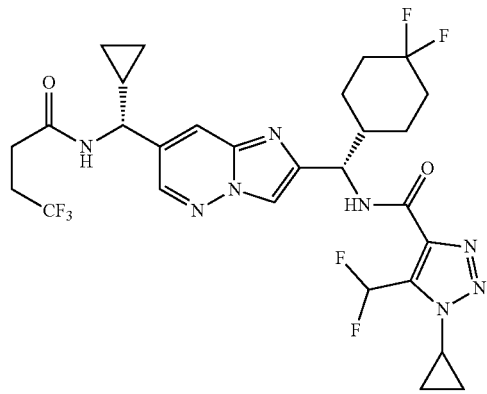 [SMILES: O=C(CCC(F)(F)F)N[C@@H](c1cnn2cc([C@@H](NC(=O)c3nnn(C4CC4)c3C(F)F)C3CCC(F)(F)CC3)nc2c1)C1CC1]
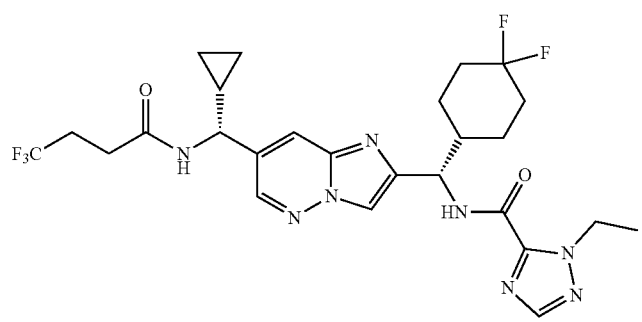 [SMILES: CCn1ncnc1C(=O)N[C@H](c1cn2ncc([C@H](NC(=O)CCC(F)(F)F)C3CC3)cc2n1)C1CCC(F)(F)CC1]
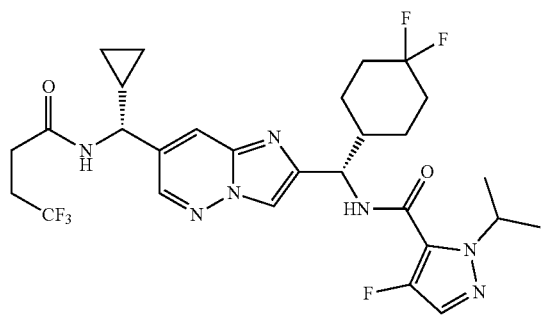 [SMILES: CC(C)n1ncc(F)c1C(=O)N[C@H](c1cn2ncc([C@H](NC(=O)CCC(F)(F)F)C3CC3)cc2n1)C1CCC(F)(F)CC1]
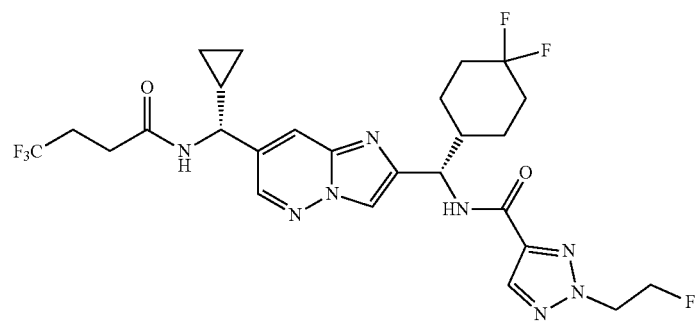 [SMILES: O=C(CCC(F)(F)F)N[C@@H](c1cnn2cc([C@@H](NC(=O)c3cnn(CCF)n3)C3CCC(F)(F)CC3)nc2c1)C1CC1]

TABLE 1E-continued
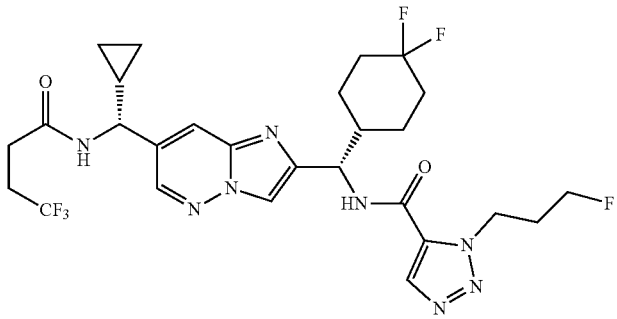 [SMILES: O=C(CCC(F)(F)F)N[C@@H](c1cnn2cc([C@@H](NC(=O)c3cnnn3CCCF)C3CCC(F)(F)CC3)nc2c1)C1CC1]
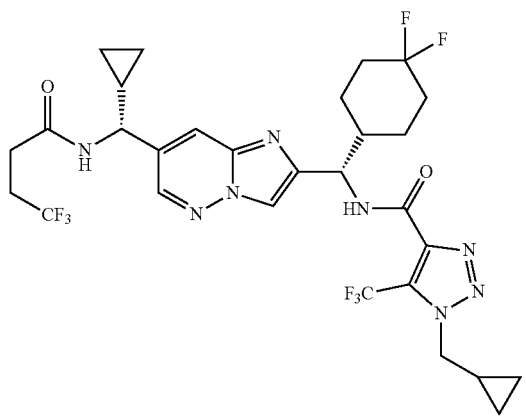 [SMILES: O=C(CCC(F)(F)F)N[C@@H](c1cnn2cc([C@@H](NC(=O)c3nnn(CC4CC4)c3C(F)(F)F)C3CCC(F)(F)CC3)nc2c1)C1CC1]
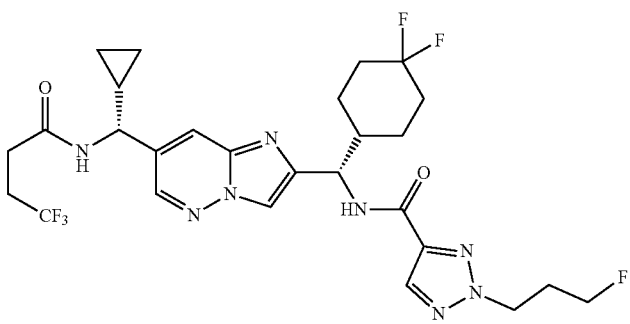 [SMILES: O=C(CCC(F)(F)F)N[C@@H](c1cnn2cc([C@@H](NC(=O)c3cnn(CCCF)n3)C3CCC(F)(F)CC3)nc2c1)C1CC1]
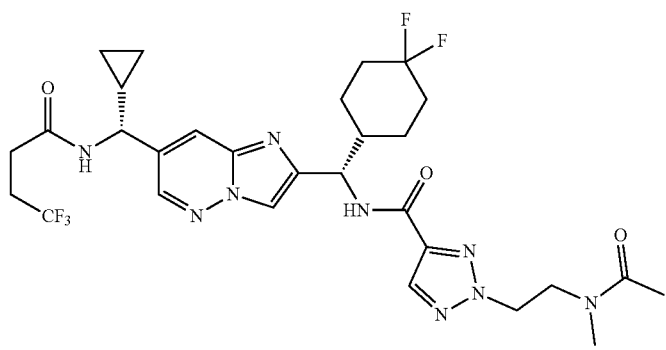 [SMILES: CC(=O)N(C)CCn1ncc(C(=O)N[C@H](c2cn3ncc([C@H](NC(=O)CCC(F)(F)F)C4CC4)cc3n2)C2CCC(F)(F)CC2)n1]

TABLE 1E-continued
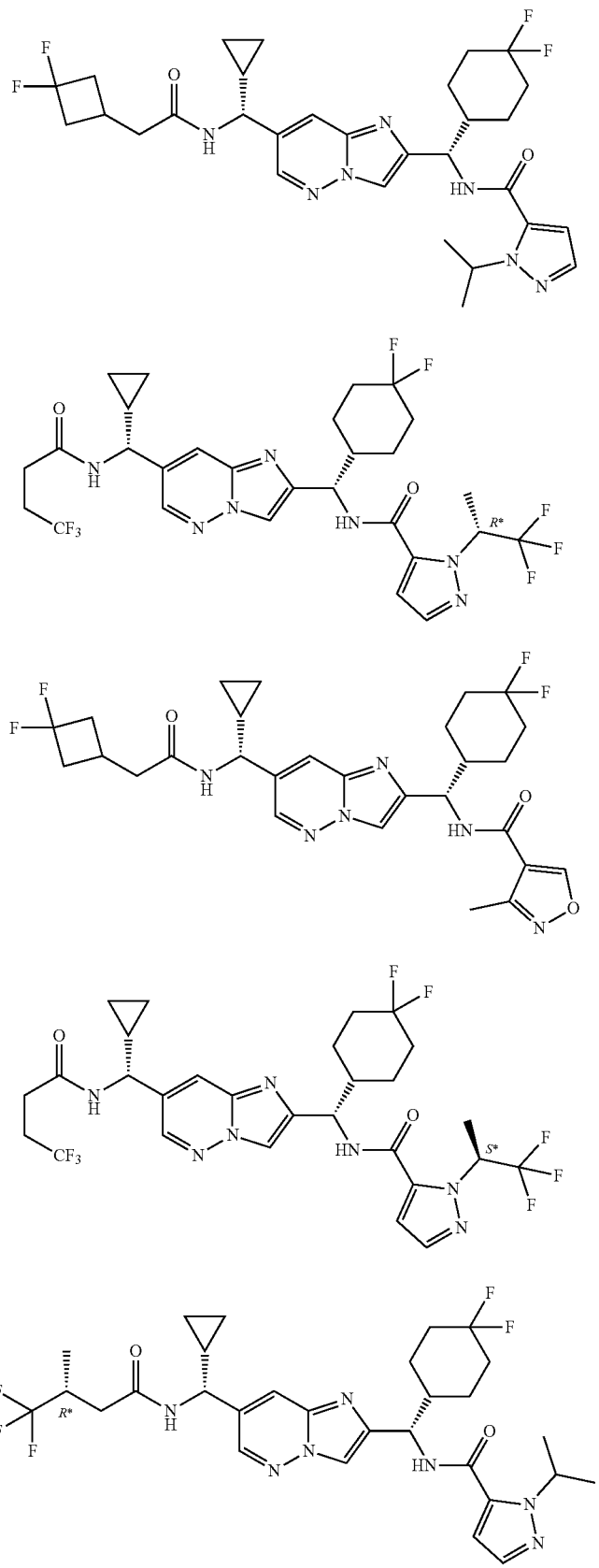

TABLE 1E-continued
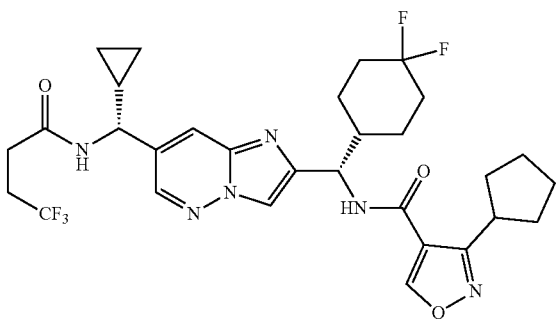 [SMILES: O=C(CCC(F)(F)F)N[C@@H](c1cnn2cc([C@@H](NC(=O)c3conc3C3CCCC3)C3CCC(F)(F)CC3)nc2c1)C1CC1]
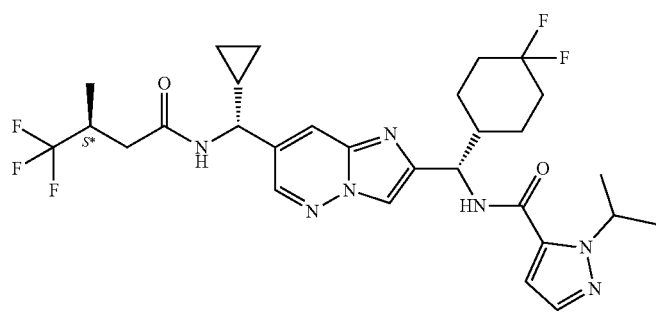 [SMILES: CC(C)n1nccc1C(=O)N[C@H](c1cn2ncc([C@H](NC(=O)C[C@H](C)C(F)(F)F)C3CC3)cc2n1)C1CCC(F)(F)CC1]
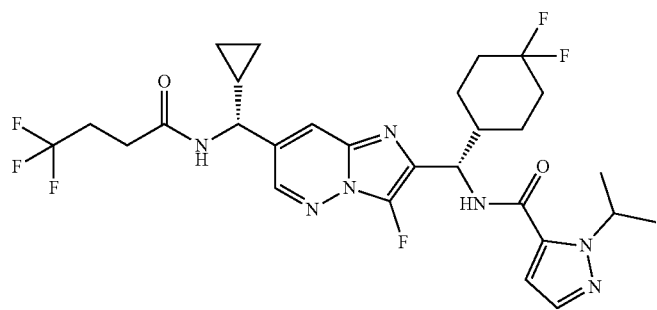 [SMILES: CC(C)n1nccc1C(=O)N[C@H](c1nc2cc([C@H](NC(=O)CCC(F)(F)F)C3CC3)cnn2c1F)C1CCC(F)(F)CC1]
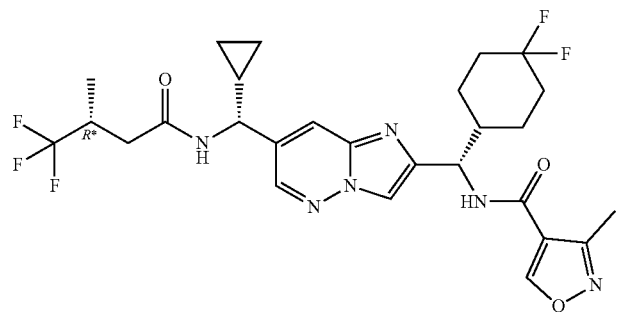 [SMILES: Cc1nocc1C(=O)N[C@H](c1cn2ncc([C@H](NC(=O)C[C@@H](C)C(F)(F)F)C3CC3)cc2n1)C1CCC(F)(F)CC1]
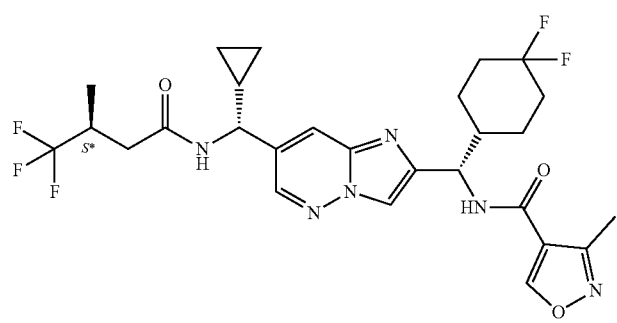

TABLE 1E-continued
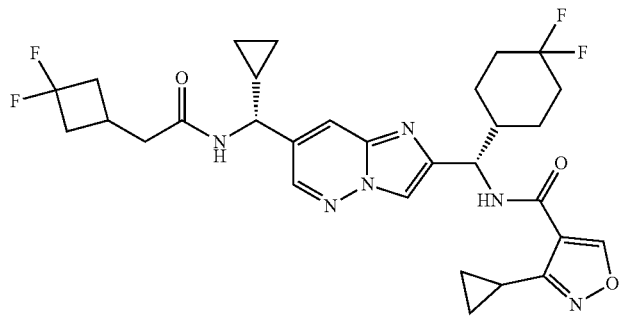 [SMILES: O=C(CC1CC(F)(F)C1)N[C@@H](c1cnn2cc([C@@H](NC(=O)c3conc3C3CC3)C3CCC(F)(F)CC3)nc2c1)C1CC1]
TABLE 1F
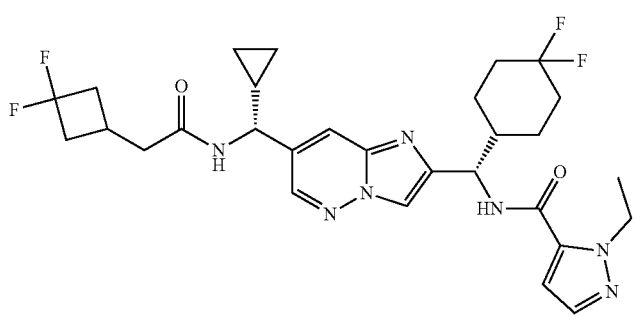 [SMILES: CCn1nccc1C(=O)N[C@H](c1cn2ncc([C@H](NC(=O)CC3CC(F)(F)C3)C3CC3)cc2n1)C1CCC(F)(F)CC1]
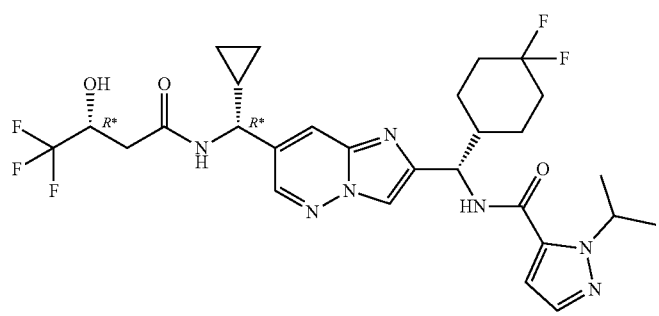 [SMILES: CC(C)n1nccc1C(=O)N[C@H](c1cn2ncc([C@H](NC(=O)C[C@@H](O)C(F)(F)F)C3CC3)cc2n1)C1CCC(F)(F)CC1]
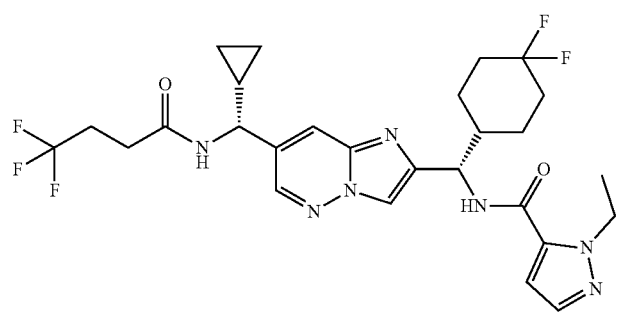 [SMILES: CCn1nccc1C(=O)N[C@H](c1cn2ncc([C@H](NC(=O)CCC(F)(F)F)C3CC3)cc2n1)C1CCC(F)(F)CC1]

TABLE 1F-continued
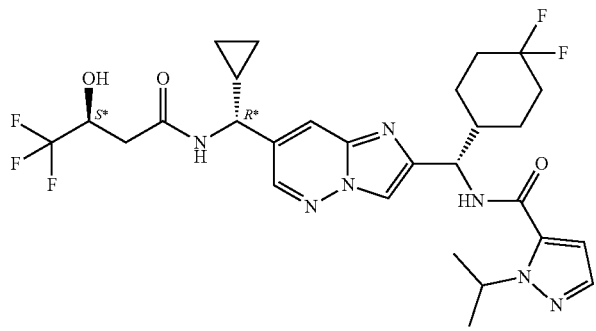 [SMILES: CC(C)n1nccc1C(=O)N[C@H](c1cn2ncc([C@H](NC(=O)C[C@H](O)C(F)(F)F)C3CC3)cc2n1)C1CCC(F)(F)CC1]
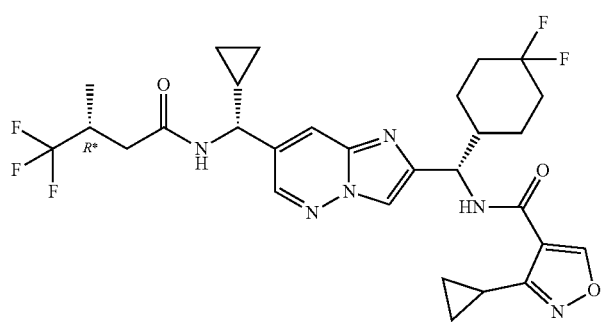 [SMILES: C[C@H](CC(=O)N[C@@H](c1cnn2cc([C@@H](NC(=O)c3conc3C3CC3)C3CCC(F)(F)CC3)nc2c1)C1CC1)C(F)(F)F]
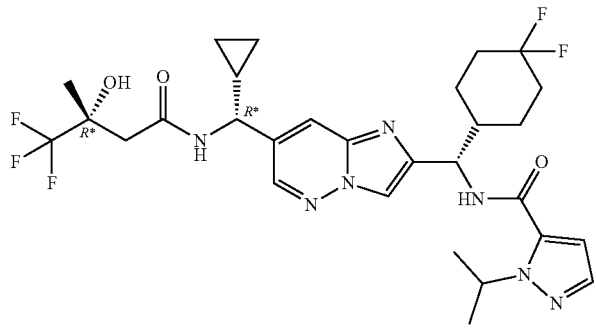 [SMILES: CC(C)n1nccc1C(=O)N[C@H](c1cn2ncc([C@H](NC(=O)C[C@@](C)(O)C(F)(F)F)C3CC3)cc2n1)C1CCC(F)(F)CC1]
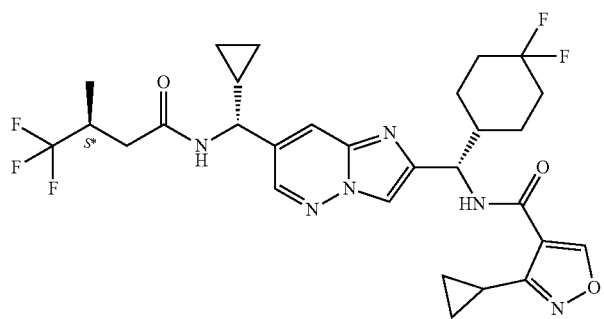 [SMILES: C[C@@H](CC(=O)N[C@@H](c1cnn2cc([C@@H](NC(=O)c3conc3C3CC3)C3CCC(F)(F)CC3)nc2c1)C1CC1)C(F)(F)F]

TABLE 1F-continued
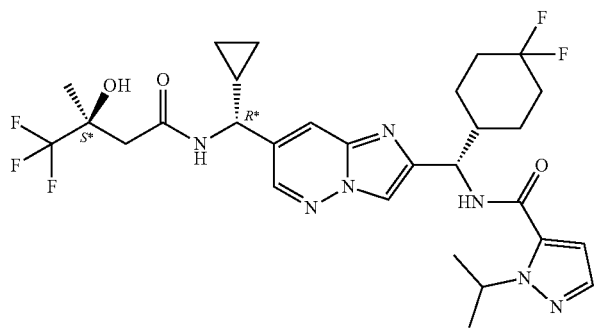 [SMILES: CC(C)n1nccc1C(=O)N[C@H](c1cn2ncc([C@H](NC(=O)C[C@](C)(O)C(F)(F)F)C3CC3)cc2n1)C1CCC(F)(F)CC1]
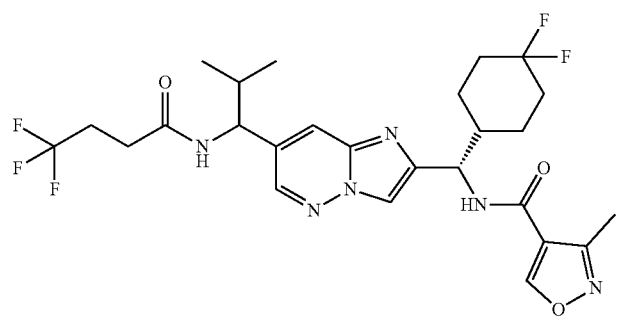 [SMILES: Cc1nocc1C(=O)N[C@H](c1cn2ncc(C(NC(=O)CCC(F)(F)F)C(C)C)cc2n1)C1CCC(F)(F)CC1]
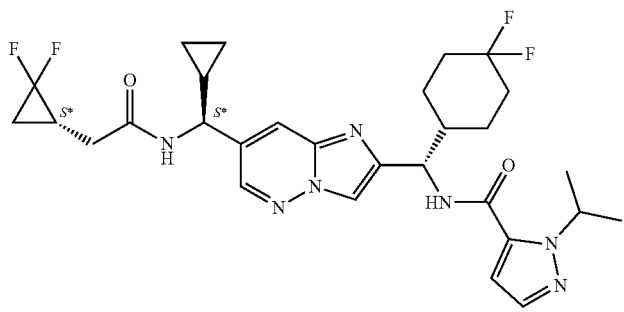 [SMILES: CC(C)n1nccc1C(=O)N[C@H](c1cn2ncc([C@@H](NC(=O)C[C@@H]3CC3(F)F)C3CC3)cc2n1)C1CCC(F)(F)CC1]
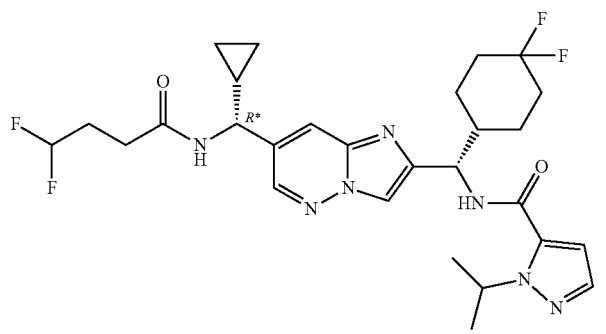 [SMILES: CC(C)n1nccc1C(=O)N[C@H](c1cn2ncc([C@H](NC(=O)CCC(F)F)C3CC3)cc2n1)C1CCC(F)(F)CC1]
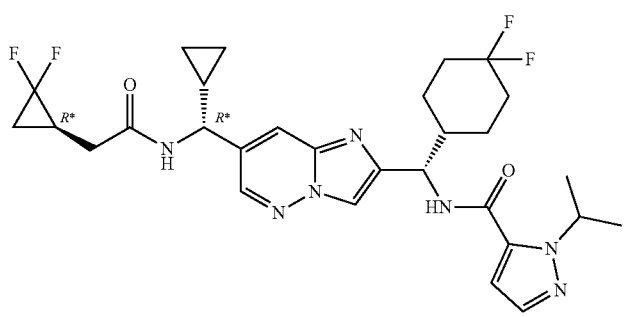 [SMILES: CC(C)n1nccc1C(=O)N[C@H](c1cn2ncc([C@H](NC(=O)C[C@H]3CC3(F)F)C3CC3)cc2n1)C1CCC(F)(F)CC1]

TABLE 1F-continued
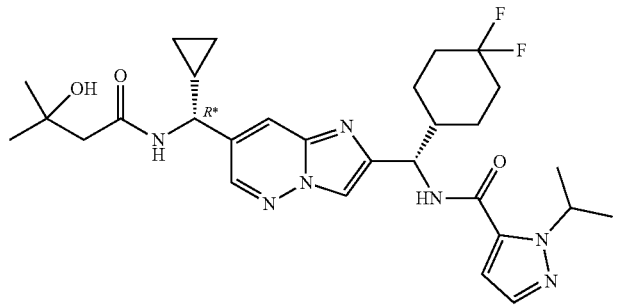 [SMILES: CC(C)n1nccc1C(=O)N[C@H](c1cn2ncc([C@H](NC(=O)CC(C)(C)O)C3CC3)cc2n1)C1CCC(F)(F)CC1]
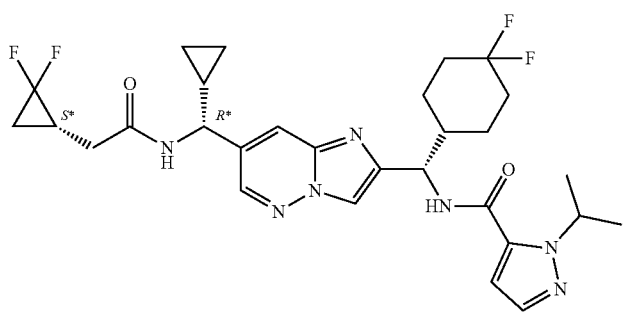 [SMILES: CC(C)n1nccc1C(=O)N[C@H](c1cn2ncc([C@H](NC(=O)C[C@@H]3CC3(F)F)C3CC3)cc2n1)C1CCC(F)(F)CC1]
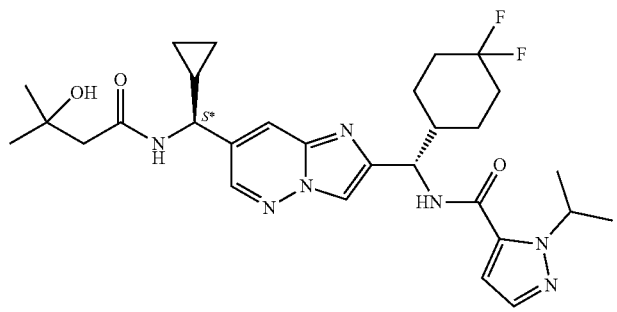 [SMILES: CC(C)n1nccc1C(=O)N[C@H](c1cn2ncc([C@@H](NC(=O)CC(C)(C)O)C3CC3)cc2n1)C1CCC(F)(F)CC1]
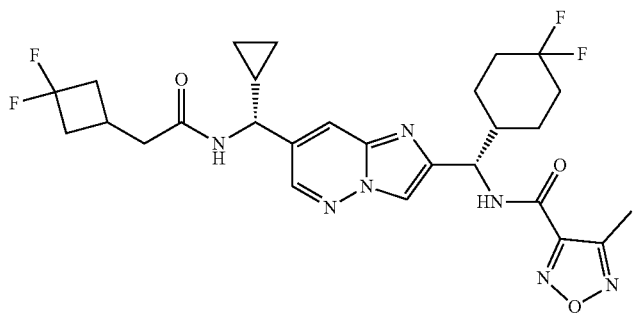 [SMILES: Cc1nonc1C(=O)N[C@H](c1cn2ncc([C@H](NC(=O)CC3CC(F)(F)C3)C3CC3)cc2n1)C1CCC(F)(F)CC1]
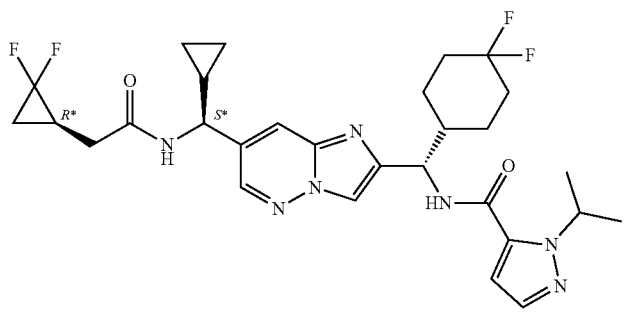 [SMILES: CC(C)n1nccc1C(=O)N[C@H](c1cn2ncc([C@@H](NC(=O)C[C@H]3CC3(F)F)C3CC3)cc2n1)C1CCC(F)(F)CC1]

TABLE 1F-continued
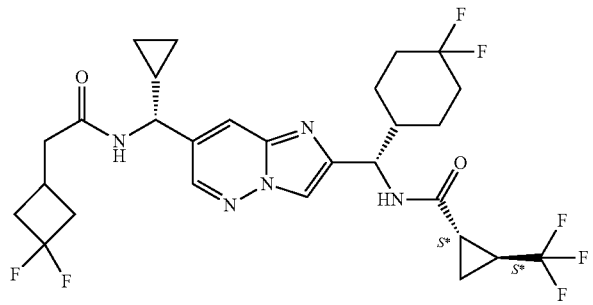 [SMILES: O=C(CC1CC(F)(F)C1)N[C@@H](c1cnn2cc([C@@H](NC(=O)[C@H]3C[C@@H]3C(F)(F)F)C3CCC(F)(F)CC3)nc2c1)C1CC1]
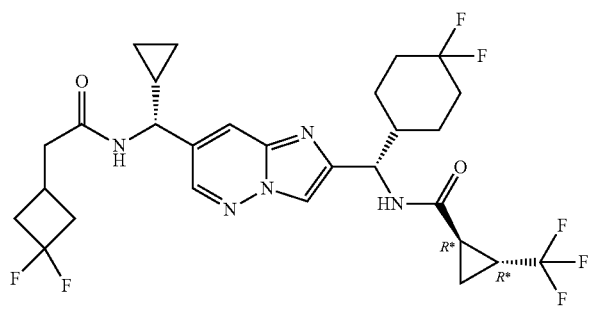 [SMILES: O=C(CC1CC(F)(F)C1)N[C@@H](c1cnn2cc([C@@H](NC(=O)[C@@H]3C[C@H]3C(F)(F)F)C3CCC(F)(F)CC3)nc2c1)C1CC1]
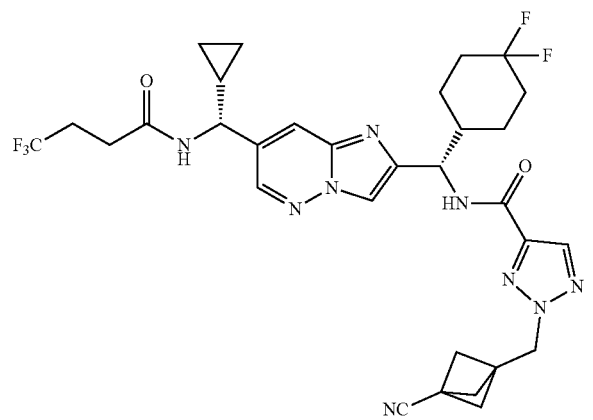 [SMILES: N#CC12CC(Cn3ncc(C(=O)N[C@H](c4cn5ncc([C@H](NC(=O)CCC(F)(F)F)C6CC6)cc5n4)C4CCC(F)(F)CC4)n3)(C1)C2]
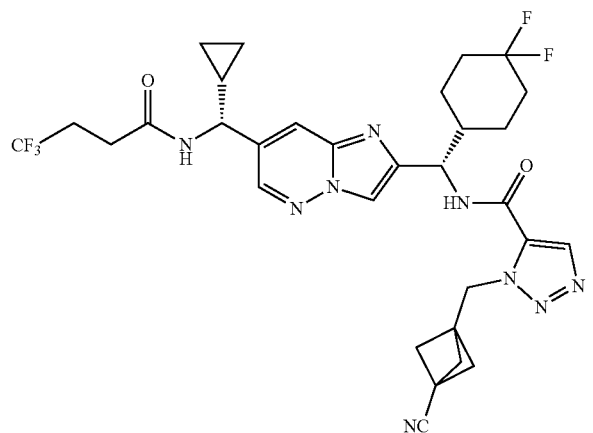 [SMILES: N#CC12CC(Cn3nncc3C(=O)N[C@H](c3cn4ncc([C@H](NC(=O)CCC(F)(F)F)C5CC5)cc4n3)C3CCC(F)(F)CC3)(C1)C2]

TABLE 1F-continued
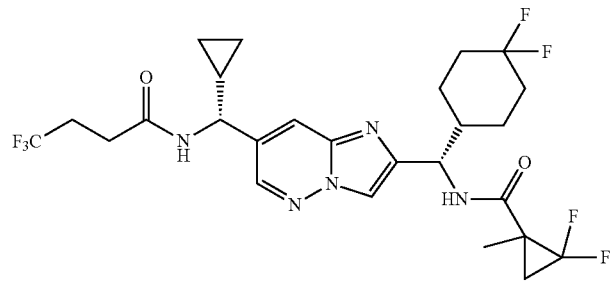 [SMILES: CC1(C(=O)N[C@H](c2cn3ncc([C@H](NC(=O)CCC(F)(F)F)C4CC4)cc3n2)C2CCC(F)(F)CC2)CC1(F)F]
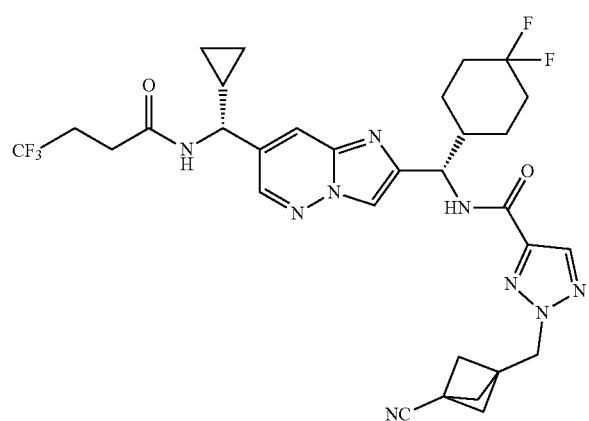 [SMILES: N#CC12CC(Cn3ncc(C(=O)N[C@H](c4cn5ncc([C@H](NC(=O)CCC(F)(F)F)C6CC6)cc5n4)C4CCC(F)(F)CC4)n3)(C1)C2]
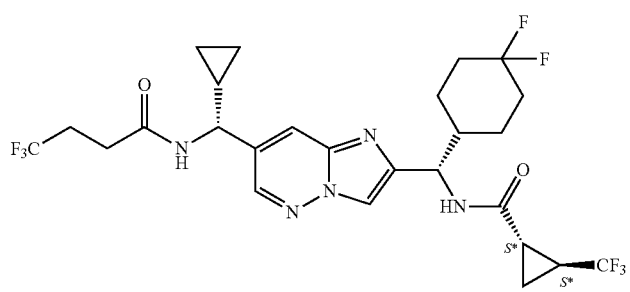 [SMILES: O=C(CCC(F)(F)F)N[C@@H](c1cnn2cc([C@@H](NC(=O)[C@H]3C[C@@H]3C(F)(F)F)C3CCC(F)(F)CC3)nc2c1)C1CC1]
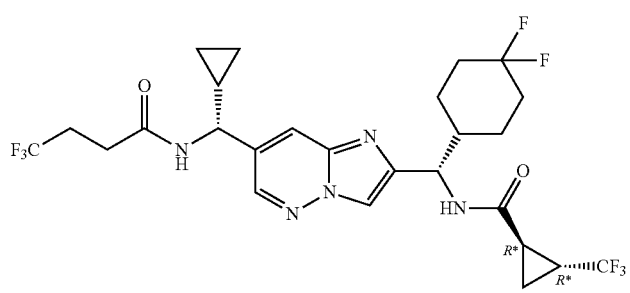 [SMILES: O=C(CCC(F)(F)F)N[C@@H](c1cnn2cc([C@@H](NC(=O)[C@@H]3C[C@H]3C(F)(F)F)C3CCC(F)(F)CC3)nc2c1)C1CC1]

TABLE 1G
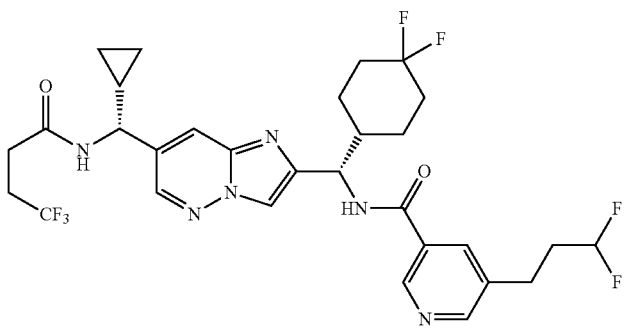 [SMILES: O=C(CCC(F)(F)F)N[C@@H](c1cnn2cc([C@@H](NC(=O)c3cncc(CCC(F)F)c3)C3CCC(F)(F)CC3)nc2c1)C1CC1]
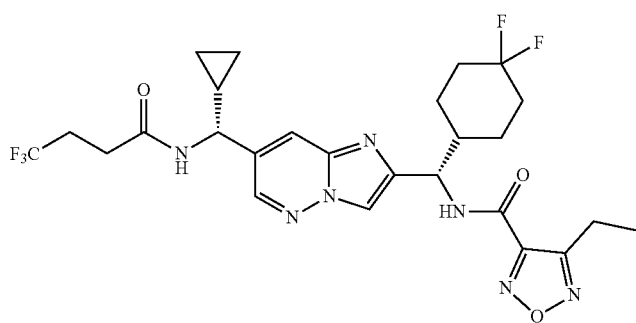 [SMILES: CCc1nonc1C(=O)N[C@H](c1cn2ncc([C@H](NC(=O)CCC(F)(F)F)C3CC3)cc2n1)C1CCC(F)(F)CC1]
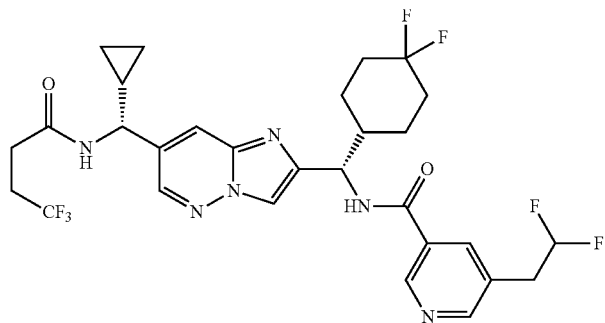 [SMILES: O=C(CCC(F)(F)F)N[C@@H](c1cnn2cc([C@@H](NC(=O)c3cncc(CC(F)F)c3)C3CCC(F)(F)CC3)nc2c1)C1CC1]
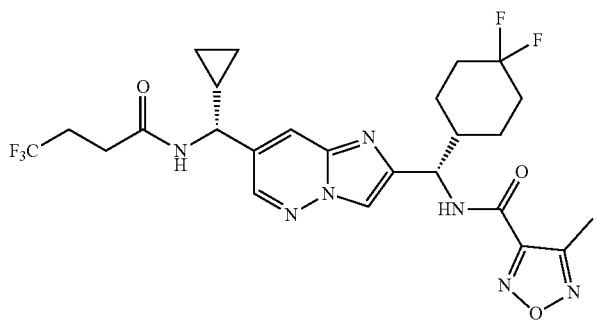
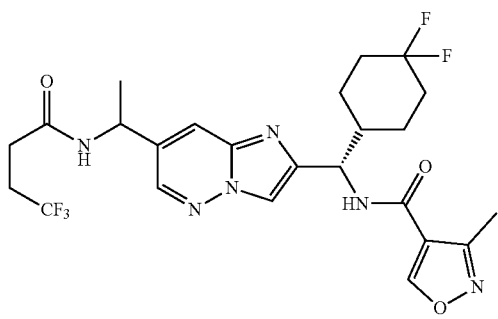 [SMILES: Cc1nocc1C(=O)N[C@H](c1cn2ncc(C(C)NC(=O)CCC(F)(F)F)cc2n1)C1CCC(F)(F)CC1]

TABLE 1G-continued
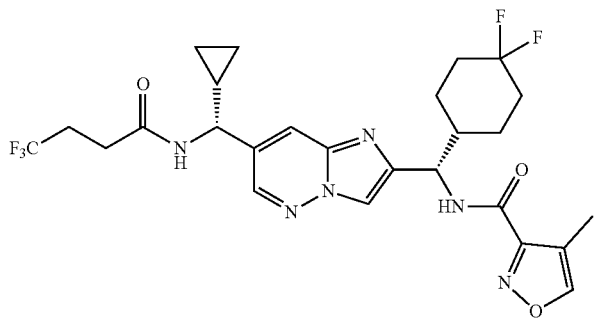 [SMILES: Cc1conc1C(=O)N[C@H](c1cn2ncc([C@H](NC(=O)CCC(F)(F)F)C3CC3)cc2n1)C1CCC(F)(F)CC1]
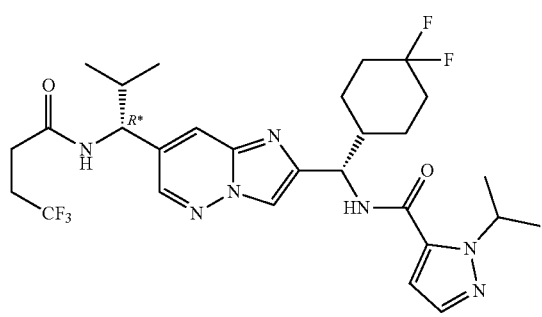 [SMILES: CC(C)[C@@H](NC(=O)CCC(F)(F)F)c1cnn2cc([C@@H](NC(=O)c3ccnn3C(C)C)C3CCC(F)(F)CC3)nc2c1]
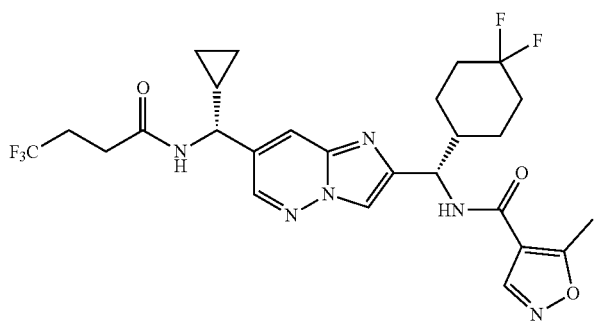 [SMILES: Cc1oncc1C(=O)N[C@H](c1cn2ncc([C@H](NC(=O)CCC(F)(F)F)C3CC3)cc2n1)C1CCC(F)(F)CC1]
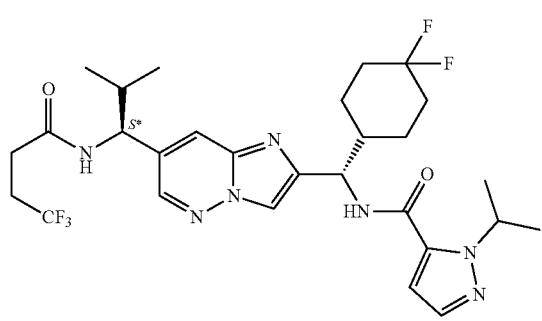 [SMILES: CC(C)[C@H](NC(=O)CCC(F)(F)F)c1cnn2cc([C@@H](NC(=O)c3ccnn3C(C)C)C3CCC(F)(F)CC3)nc2c1]
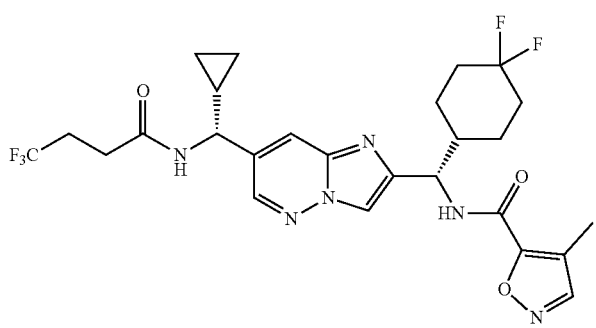 [SMILES: Cc1cnoc1C(=O)N[C@H](c1cn2ncc([C@H](NC(=O)CCC(F)(F)F)C3CC3)cc2n1)C1CCC(F)(F)CC1]

TABLE 1G-continued
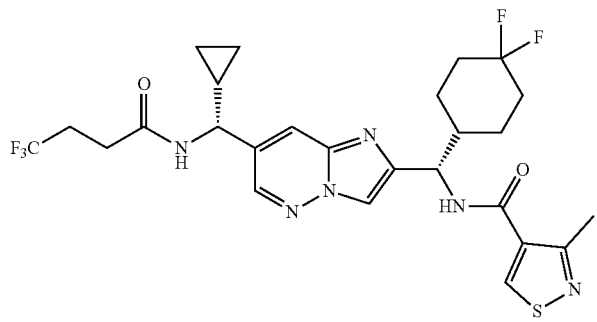 [SMILES: Cc1nscc1C(=O)N[C@H](c1cn2ncc([C@H](NC(=O)CCC(F)(F)F)C3CC3)cc2n1)C1CCC(F)(F)CC1]
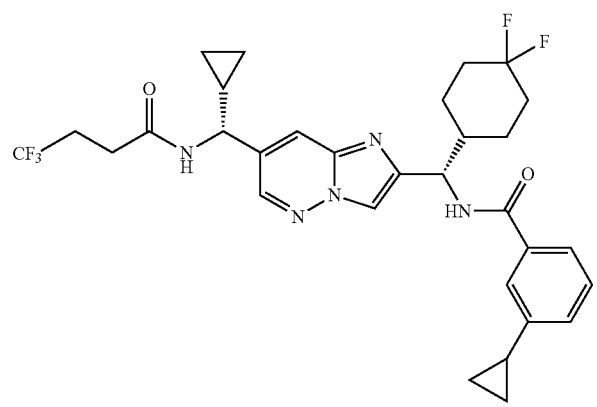 [SMILES: O=C(CCC(F)(F)F)N[C@@H](c1cnn2cc([C@@H](NC(=O)c3cccc(C4CC4)c3)C3CCC(F)(F)CC3)nc2c1)C1CC1]
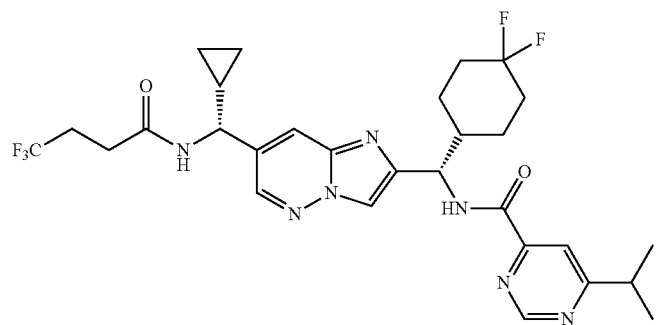
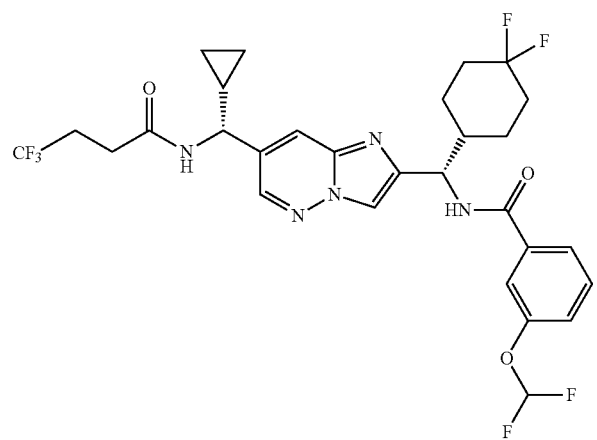 [SMILES: O=C(CCC(F)(F)F)N[C@@H](c1cnn2cc([C@@H](NC(=O)c3cccc(OC(F)F)c3)C3CCC(F)(F)CC3)nc2c1)C1CC1]

TABLE 1G-continued
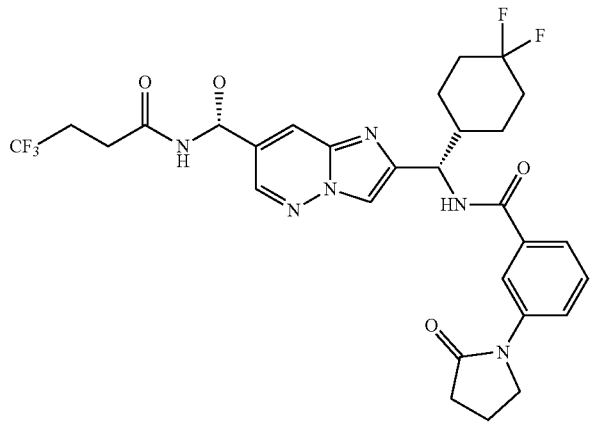
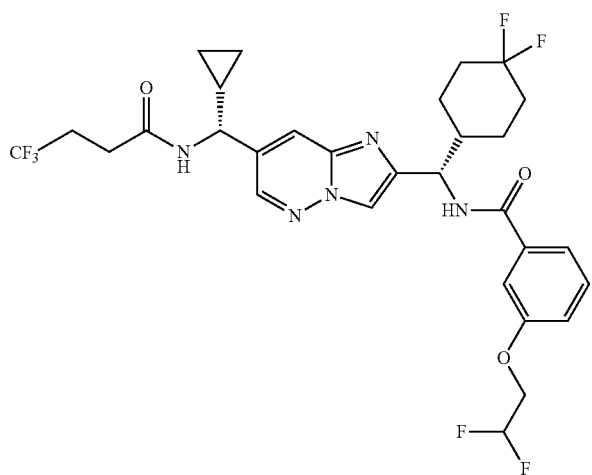 [SMILES: O=C(CCC(F)(F)F)N[C@@H](c1cnn2cc([C@@H](NC(=O)c3cccc(OCC(F)F)c3)C3CCC(F)(F)CC3)nc2c1)C1CC1]
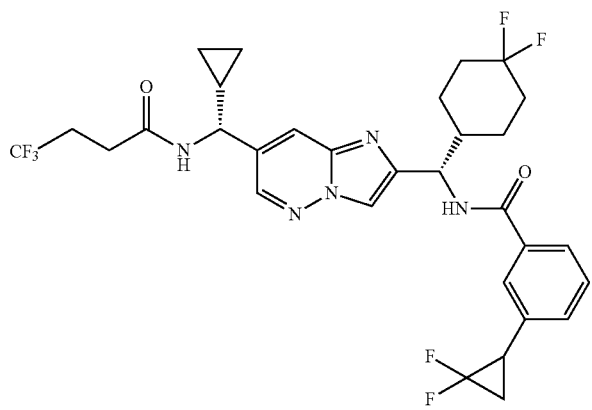 [SMILES: O=C(CCC(F)(F)F)N[C@@H](c1cnn2cc([C@@H](NC(=O)c3cccc(C4CC4(F)F)c3)C3CCC(F)(F)CC3)nc2c1)C1CC1]

TABLE 1G-continued
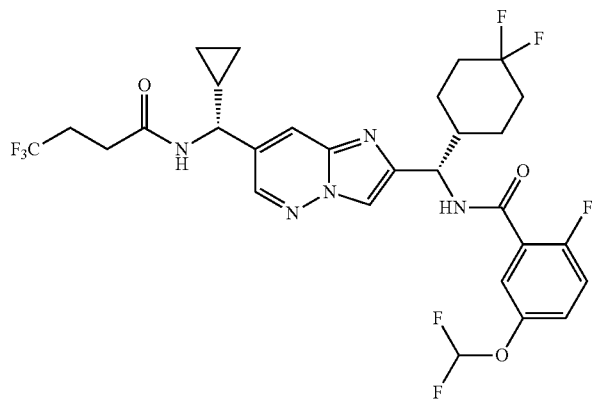 [SMILES: O=C(CCC(F)(F)F)N[C@@H](c1cnn2cc([C@@H](NC(=O)c3cc(OC(F)F)ccc3F)C3CCC(F)(F)CC3)nc2c1)C1CC1]
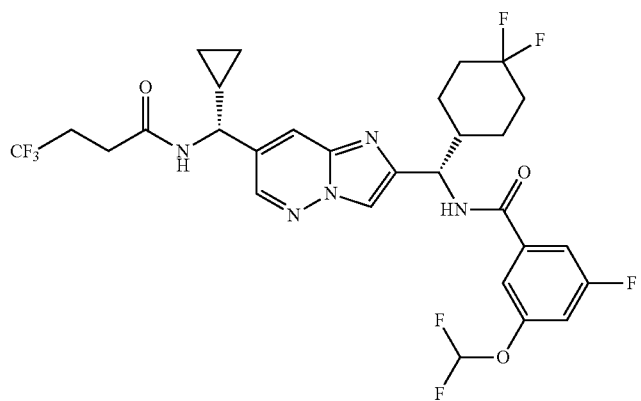 [SMILES: O=C(CCC(F)(F)F)N[C@@H](c1cnn2cc([C@@H](NC(=O)c3cc(F)cc(OC(F)F)c3)C3CCC(F)(F)CC3)nc2c1)C1CC1]
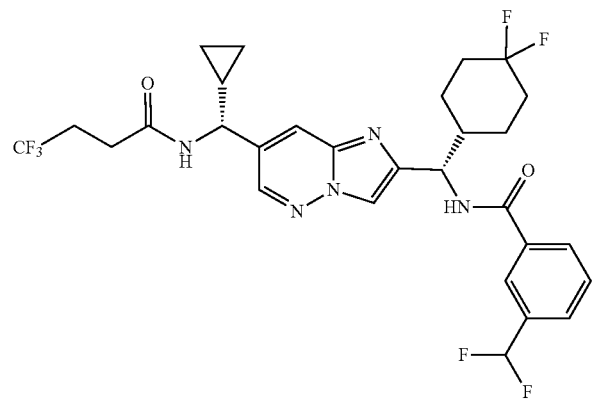 [SMILES: O=C(CCC(F)(F)F)N[C@@H](c1cnn2cc([C@@H](NC(=O)c3cccc(C(F)F)c3)C3CCC(F)(F)CC3)nc2c1)C1CC1]
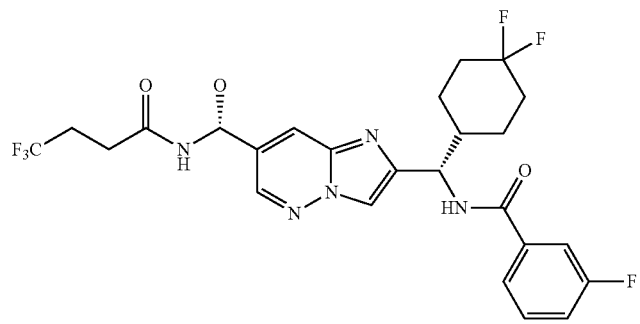

TABLE 1G-continued
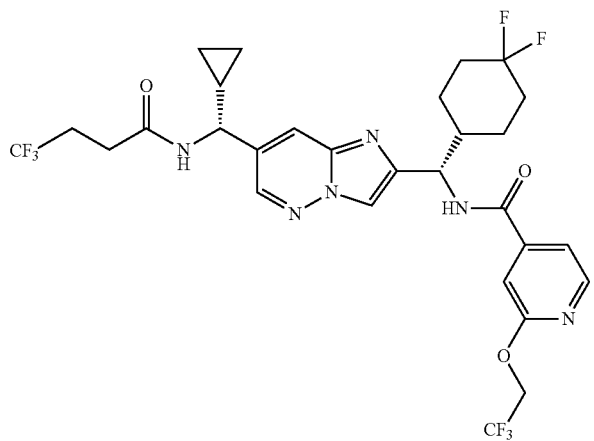 [SMILES: O=C(CCC(F)(F)F)N[C@@H](c1cnn2cc([C@@H](NC(=O)c3ccnc(OCC(F)(F)F)c3)C3CCC(F)(F)CC3)nc2c1)C1CC1]
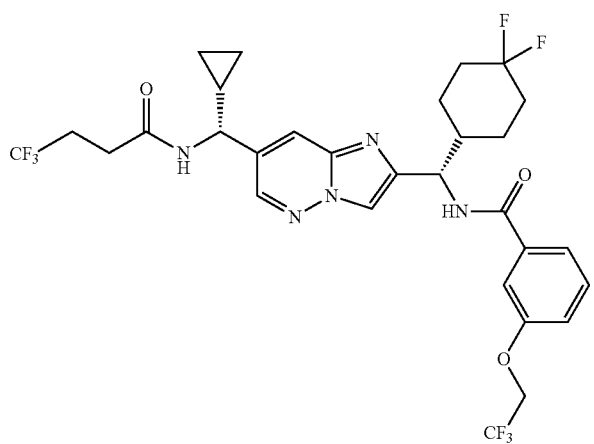
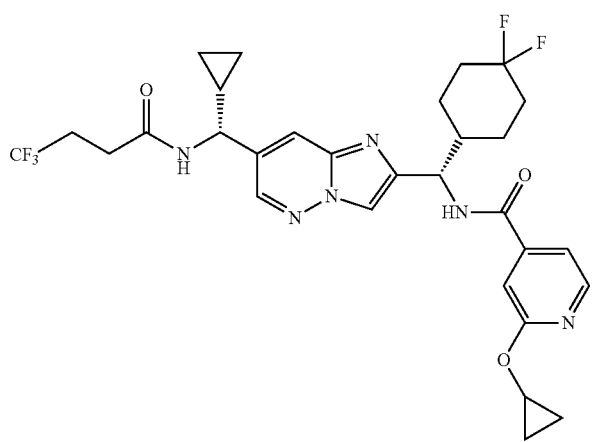 [SMILES: O=C(CCC(F)(F)F)N[C@@H](c1cnn2cc([C@@H](NC(=O)c3ccnc(OC4CC4)c3)C3CCC(F)(F)CC3)nc2c1)C1CC1]

TABLE 1G-continued
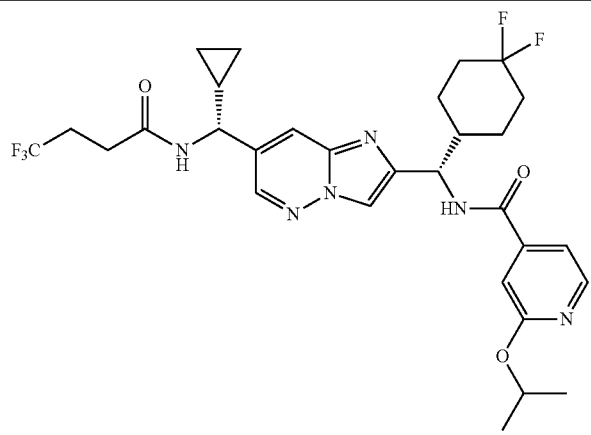
20
TABLE 1H
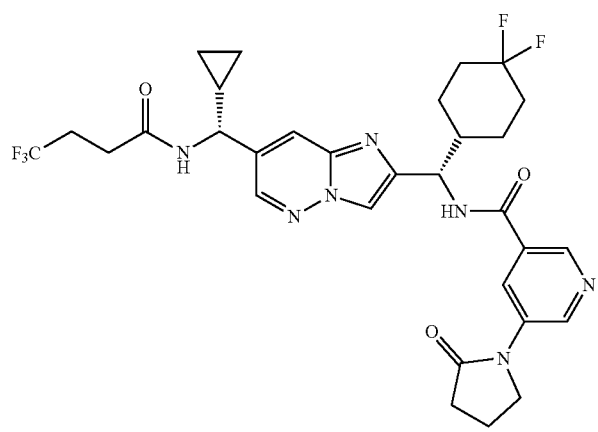 [SMILES: O=C(CCC(F)(F)F)N[C@@H](c1cnn2cc([C@@H](NC(=O)c3cncc(N4CCCC4=O)c3)C3CCC(F)(F)CC3)nc2c1)C1CC1]
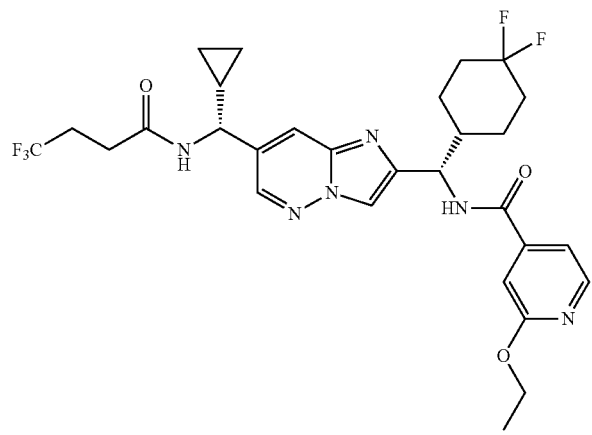 [SMILES: CCOc1cc(C(=O)N[C@H](c2cn3ncc([C@H](NC(=O)CCC(F)(F)F)C4CC4)cc3n2)C2CCC(F)(F)CC2)ccn1]

TABLE 1H-continued
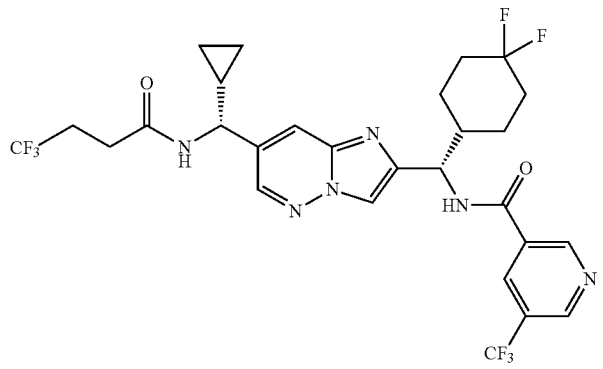 [SMILES: O=C(CCC(F)(F)F)N[C@@H](c1cnn2cc([C@@H](NC(=O)c3cncc(C(F)(F)F)c3)C3CCC(F)(F)CC3)nc2c1)C1CC1]
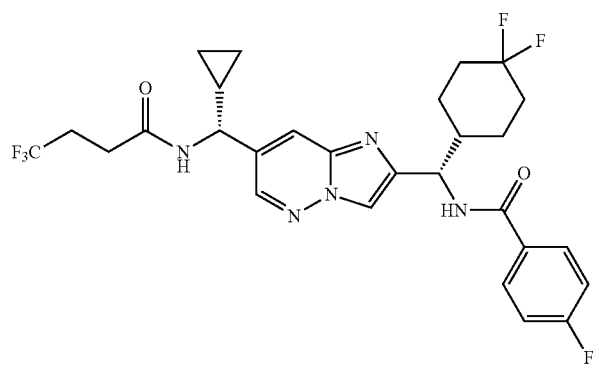 [SMILES: O=C(CCC(F)(F)F)N[C@@H](c1cnn2cc([C@@H](NC(=O)c3ccc(F)cc3)C3CCC(F)(F)CC3)nc2c1)C1CC1]
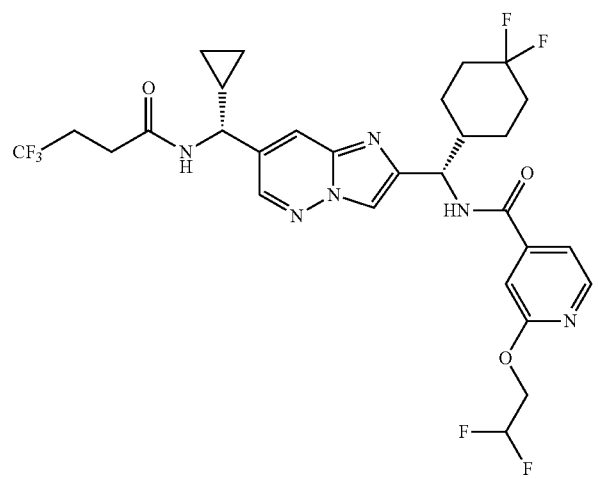

TABLE 1H-continued
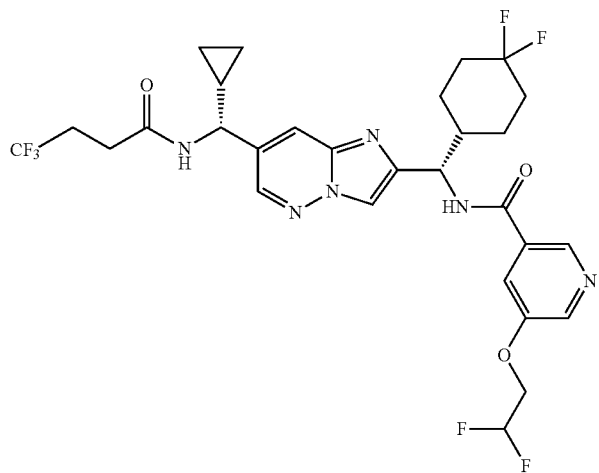 [SMILES: O=C(CCC(F)(F)F)N[C@@H](c1cnn2cc([C@@H](NC(=O)c3cncc(OCC(F)F)c3)C3CCC(F)(F)CC3)nc2c1)C1CC1]
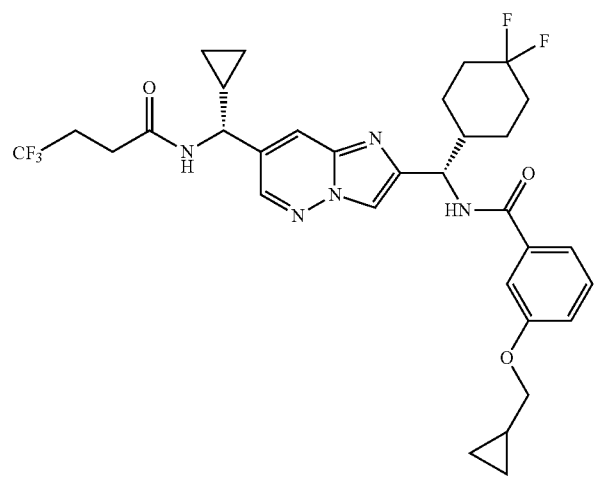 [SMILES: O=C(CCC(F)(F)F)N[C@@H](c1cnn2cc([C@@H](NC(=O)c3cccc(OCC4CC4)c3)C3CCC(F)(F)CC3)nc2c1)C1CC1]
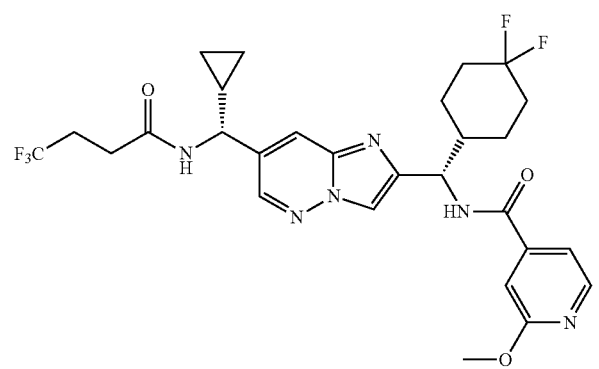 [SMILES: COc1cc(C(=O)N[C@H](c2cn3ncc([C@H](NC(=O)CCC(F)(F)F)C4CC4)cc3n2)C2CCC(F)(F)CC2)ccn1]

TABLE 1H-continued
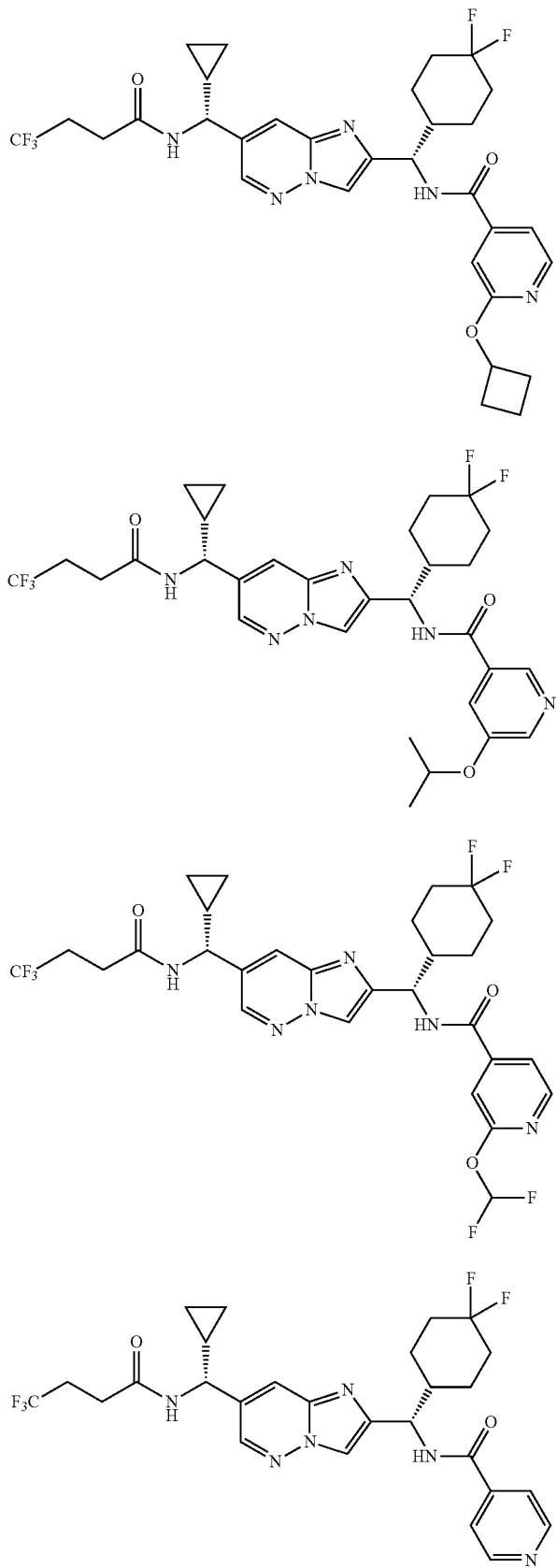

TABLE 1H-continued
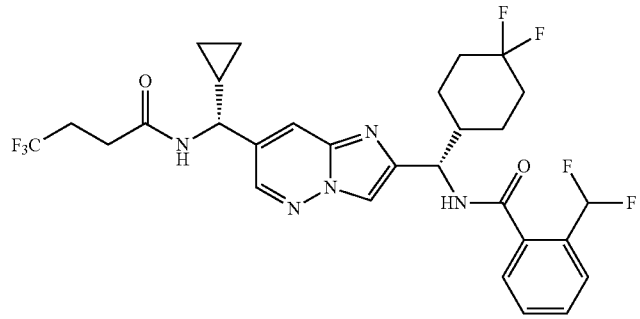 [SMILES: O=C(CCC(F)(F)F)N[C@@H](c1cnn2cc([C@@H](NC(=O)c3ccccc3C(F)F)C3CCC(F)(F)CC3)nc2c1)C1CC1]
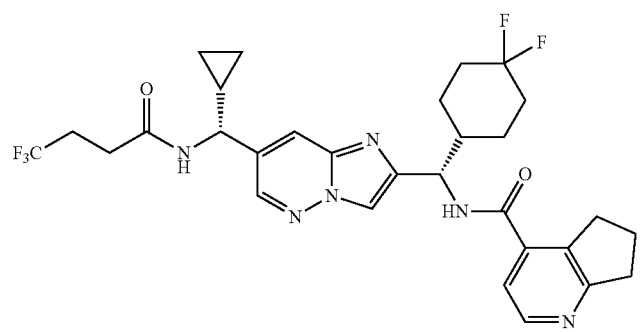 [SMILES: O=C(CCC(F)(F)F)N[C@@H](c1cnn2cc([C@@H](NC(=O)c3ccnc4c3CCC4)C3CCC(F)(F)CC3)nc2c1)C1CC1]
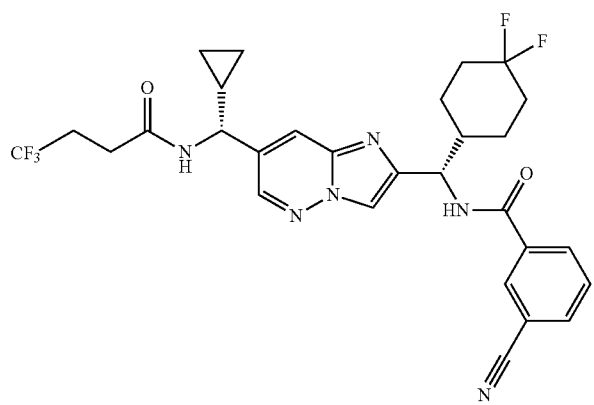 [SMILES: N#Cc1cccc(C(=O)N[C@H](c2cn3ncc([C@H](NC(=O)CCC(F)(F)F)C4CC4)cc3n2)C2CCC(F)(F)CC2)c1]
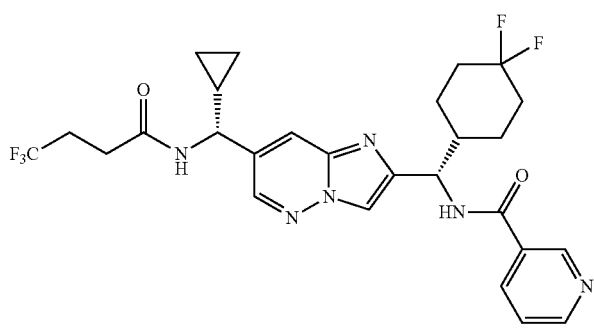

TABLE 1H-continued
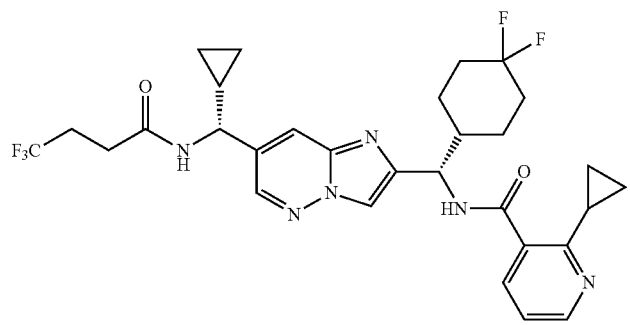 [SMILES: O=C(CCC(F)(F)F)N[C@@H](c1cnn2cc([C@@H](NC(=O)c3cccnc3C3CC3)C3CCC(F)(F)CC3)nc2c1)C1CC1]
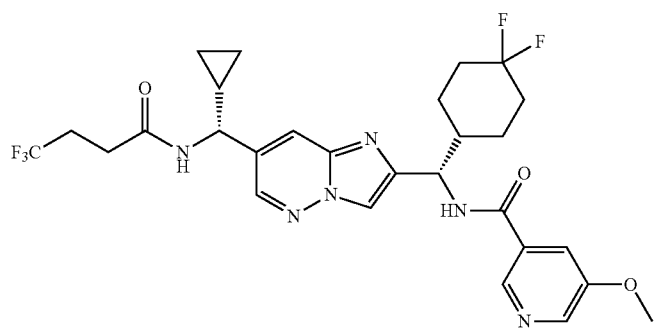 [SMILES: COc1cncc(C(=O)N[C@H](c2cn3ncc([C@H](NC(=O)CCC(F)(F)F)C4CC4)cc3n2)C2CCC(F)(F)CC2)c1]
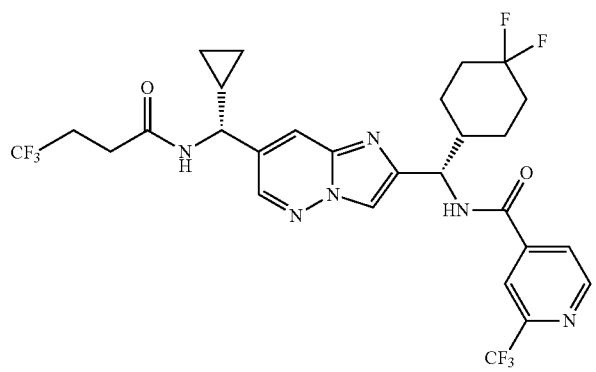 [SMILES: O=C(CCC(F)(F)F)N[C@@H](c1cnn2cc([C@@H](NC(=O)c3ccnc(C(F)(F)F)c3)C3CCC(F)(F)CC3)nc2c1)C1CC1]
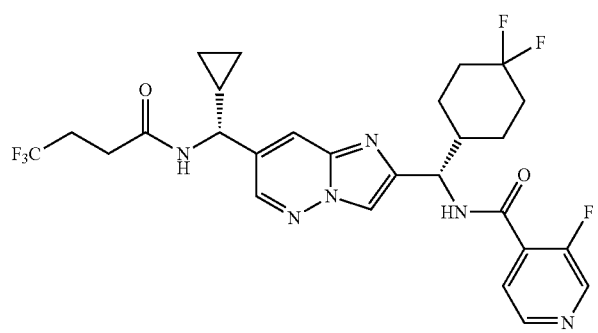 [SMILES: O=C(CCC(F)(F)F)N[C@@H](c1cnn2cc([C@@H](NC(=O)c3ccncc3F)C3CCC(F)(F)CC3)nc2c1)C1CC1]

TABLE 1H-continued
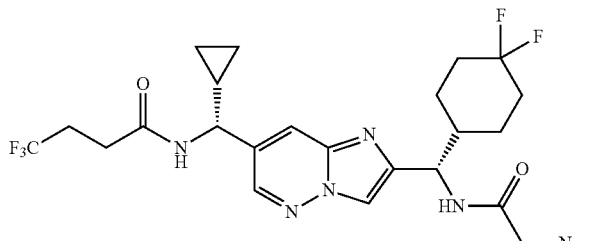
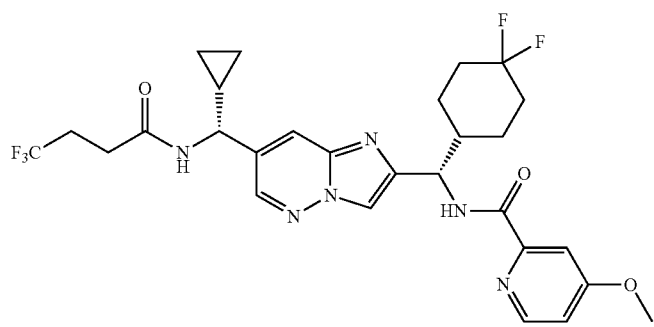 [SMILES: COc1ccnc(C(=O)N[C@H](c2cn3ncc([C@H](NC(=O)CCC(F)(F)F)C4CC4)cc3n2)C2CCC(F)(F)CC2)c1]
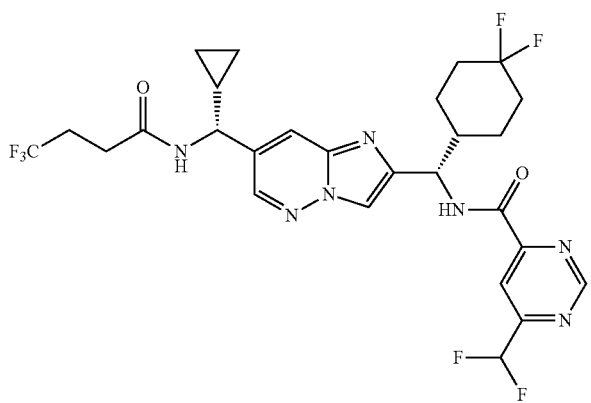 [SMILES: O=C(CCC(F)(F)F)N[C@@H](c1cnn2cc([C@@H](NC(=O)c3cc(C(F)F)ncn3)C3CCC(F)(F)CC3)nc2c1)C1CC1]
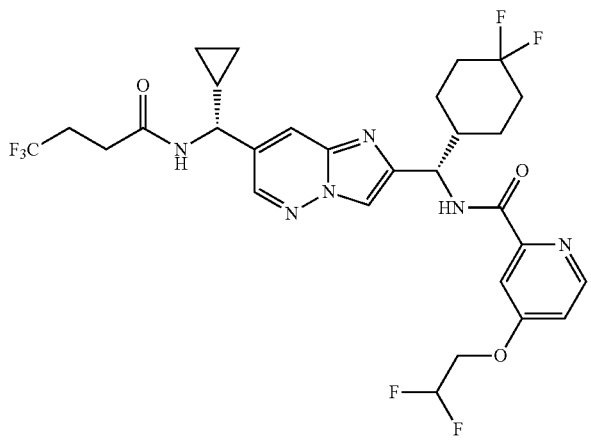 [SMILES: O=C(CCC(F)(F)F)N[C@@H](c1cnn2cc([C@@H](NC(=O)c3cc(OCC(F)F)ccn3)C3CCC(F)(F)CC3)nc2c1)C1CC1]

TABLE 1H-continued
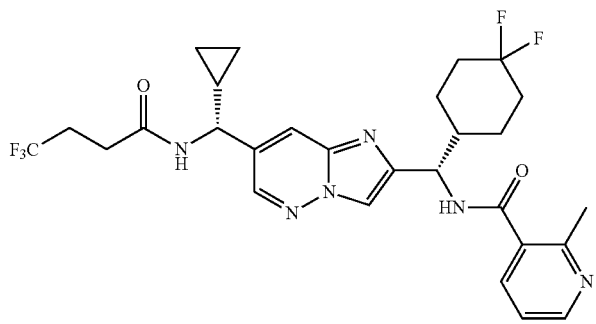 [SMILES: Cc1ncccc1C(=O)N[C@H](c1cn2ncc([C@H](NC(=O)CCC(F)(F)F)C3CC3)cc2n1)C1CCC(F)(F)CC1]
TABLE 1I
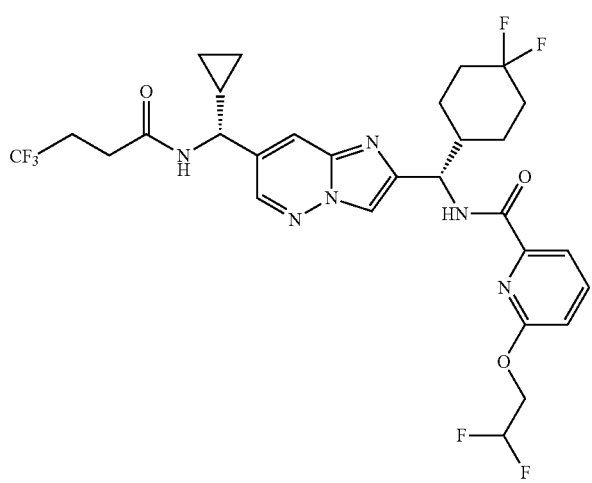
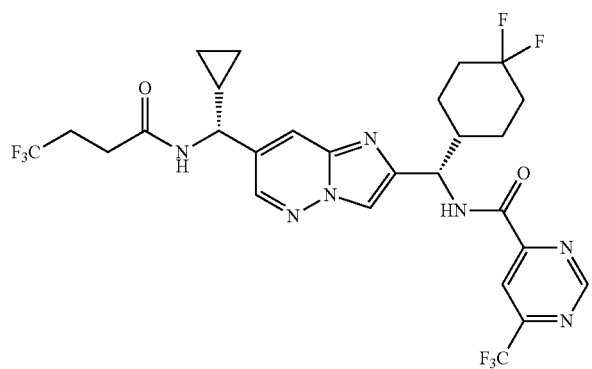 [SMILES: O=C(CCC(F)(F)F)N[C@@H](c1cnn2cc([C@@H](NC(=O)c3cc(C(F)(F)F)ncn3)C3CCC(F)(F)CC3)nc2c1)C1CC1]

TABLE 1I-continued
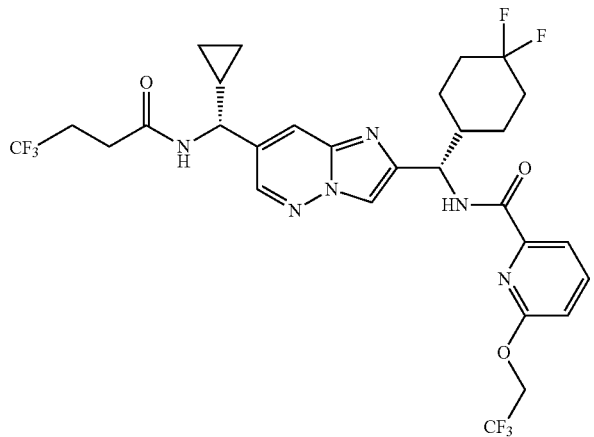
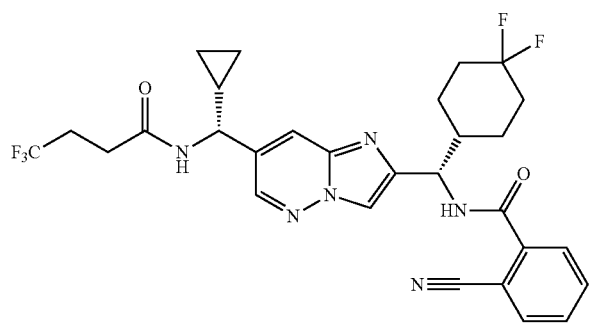 [SMILES: N#Cc1ccccc1C(=O)N[C@H](c1cn2ncc([C@H](NC(=O)CCC(F)(F)F)C3CC3)cc2n1)C1CCC(F)(F)CC1]
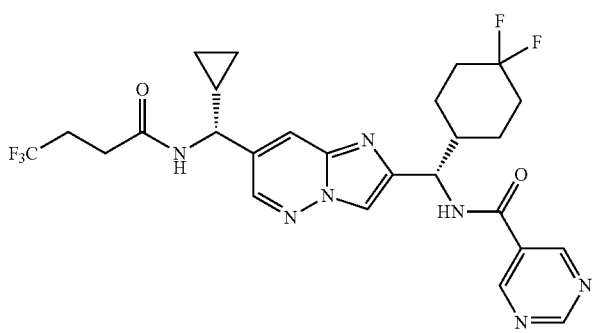 [SMILES: O=C(CCC(F)(F)F)N[C@@H](c1cnn2cc([C@@H](NC(=O)c3cncnc3)C3CCC(F)(F)CC3)nc2c1)C1CC1]
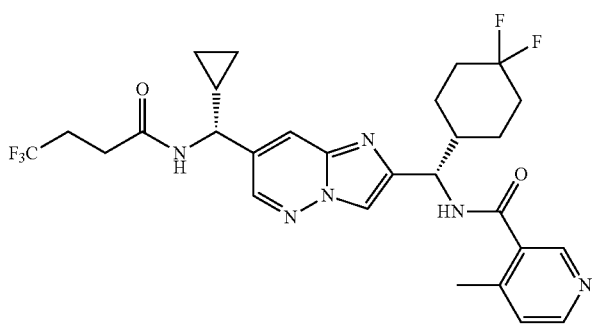 [SMILES: Cc1ccncc1C(=O)N[C@H](c1cn2ncc([C@H](NC(=O)CCC(F)(F)F)C3CC3)cc2n1)C1CCC(F)(F)CC1]

TABLE 1I-continued
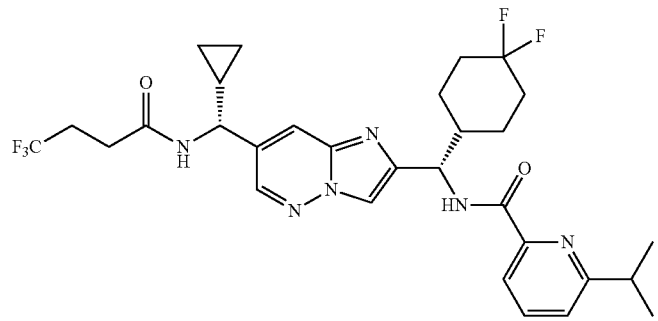 [SMILES: CC(C)c1cccc(C(=O)N[C@H](c2cn3ncc([C@H](NC(=O)CCC(F)(F)F)C4CC4)cc3n2)C2CCC(F)(F)CC2)n1]
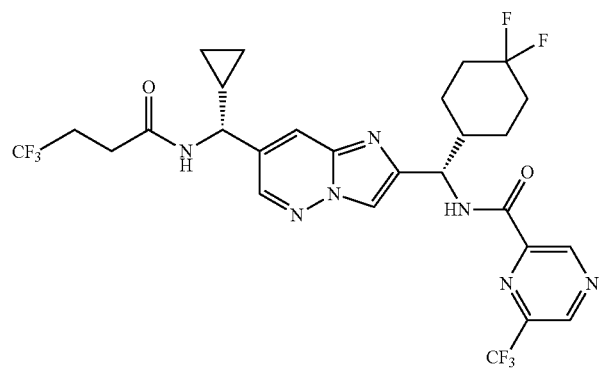 [SMILES: O=C(CCC(F)(F)F)N[C@@H](c1cnn2cc([C@@H](NC(=O)c3cncc(C(F)(F)F)n3)C3CCC(F)(F)CC3)nc2c1)C1CC1]
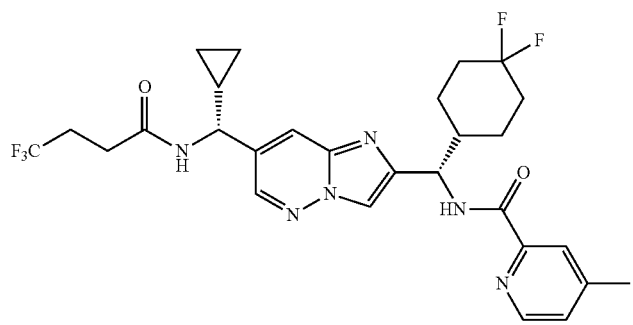
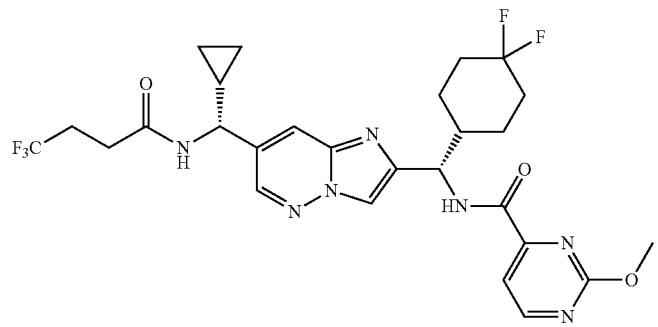 [SMILES: COc1nccc(C(=O)N[C@H](c2cn3ncc([C@H](NC(=O)CCC(F)(F)F)C4CC4)cc3n2)C2CCC(F)(F)CC2)n1]

TABLE 1I-continued
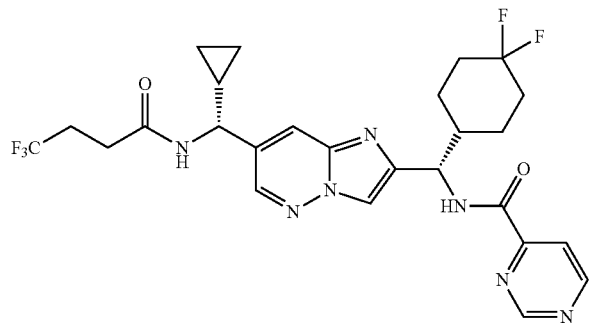 [SMILES: O=C(CCC(F)(F)F)N[C@@H](c1cnn2cc([C@@H](NC(=O)c3ccncn3)C3CCC(F)(F)CC3)nc2c1)C1CC1]
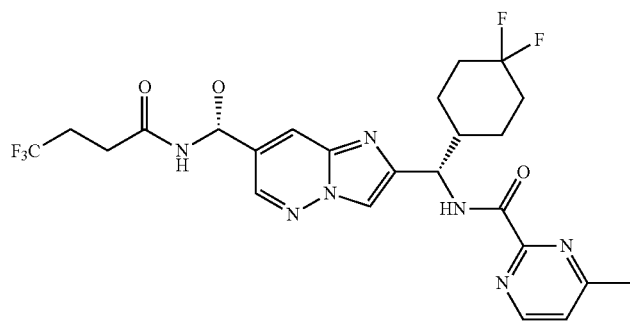
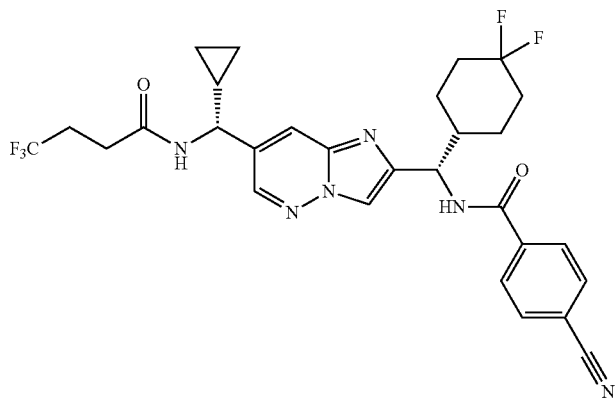 [SMILES: N#Cc1ccc(C(=O)N[C@H](c2cn3ncc([C@H](NC(=O)CCC(F)(F)F)C4CC4)cc3n2)C2CCC(F)(F)CC2)cc1]
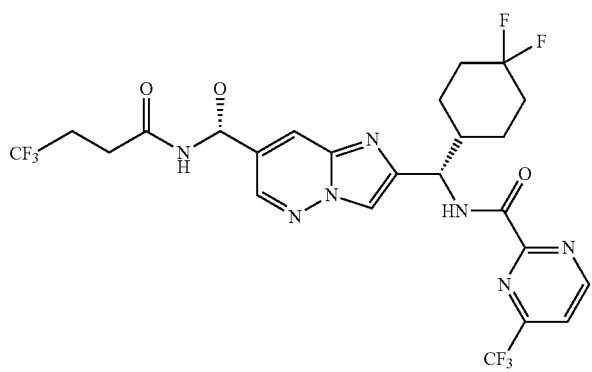

TABLE 1I-continued
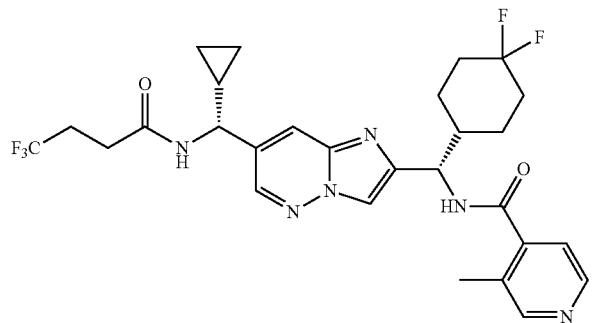 [SMILES: Cc1cnccc1C(=O)N[C@H](c1cn2ncc([C@H](NC(=O)CCC(F)(F)F)C3CC3)cc2n1)C1CCC(F)(F)CC1]
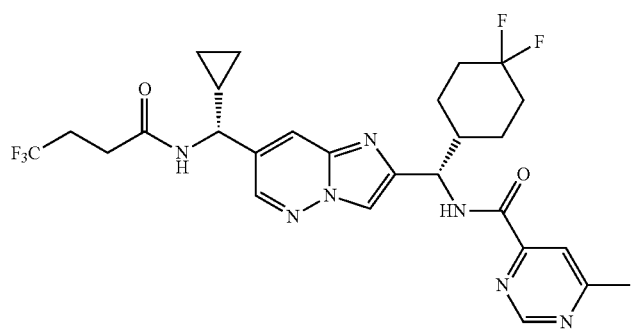 [SMILES: Cc1cc(C(=O)N[C@H](c2cn3ncc([C@H](NC(=O)CCC(F)(F)F)C4CC4)cc3n2)C2CCC(F)(F)CC2)ncn1]
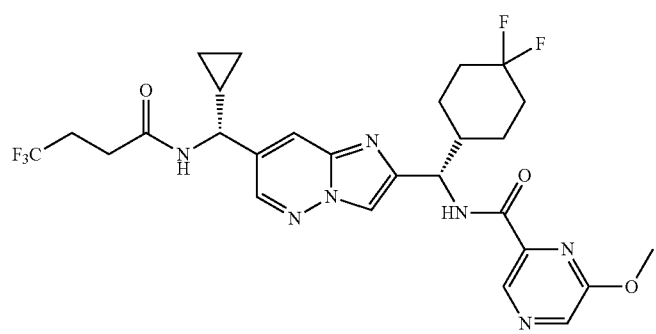 [SMILES: COc1cncc(C(=O)N[C@H](c2cn3ncc([C@H](NC(=O)CCC(F)(F)F)C4CC4)cc3n2)C2CCC(F)(F)CC2)n1]
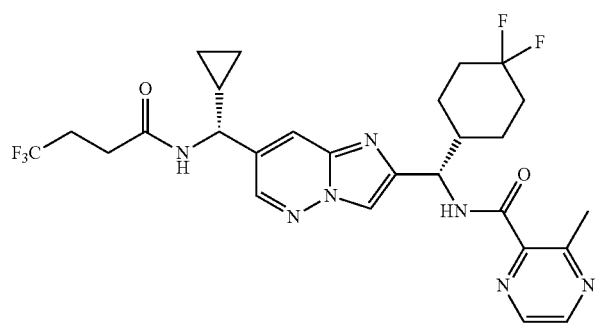 [SMILES: Cc1nccnc1C(=O)N[C@H](c1cn2ncc([C@H](NC(=O)CCC(F)(F)F)C3CC3)cc2n1)C1CCC(F)(F)CC1]

TABLE 1I-continued
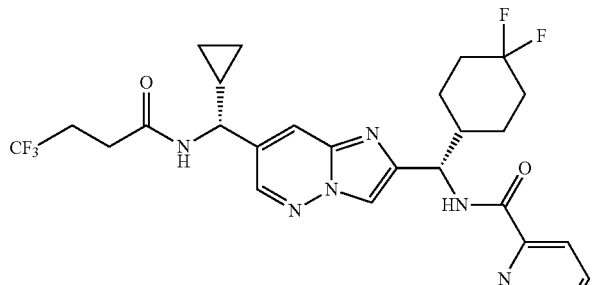
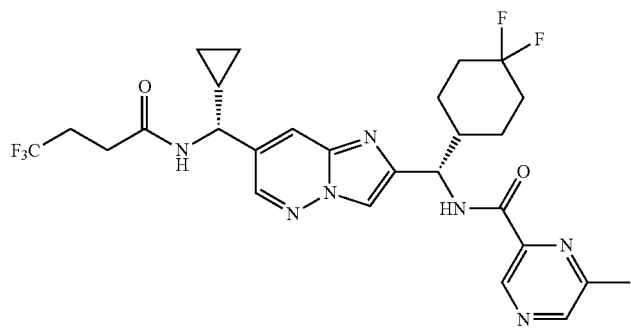 [SMILES: Cc1cncc(C(=O)N[C@H](c2cn3ncc([C@H](NC(=O)CCC(F)(F)F)C4CC4)cc3n2)C2CCC(F)(F)CC2)n1]
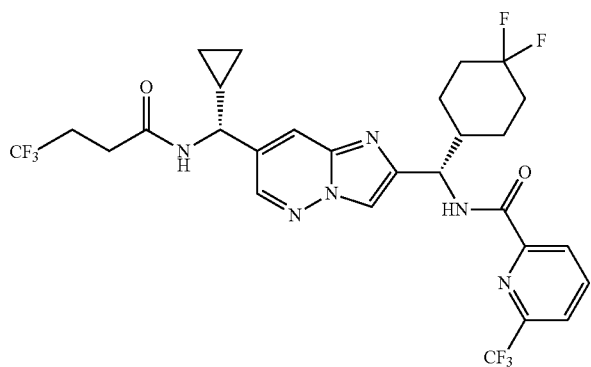 [SMILES: O=C(CCC(F)(F)F)N[C@@H](c1cnn2cc([C@@H](NC(=O)c3cccc(C(F)(F)F)n3)C3CCC(F)(F)CC3)nc2c1)C1CC1]
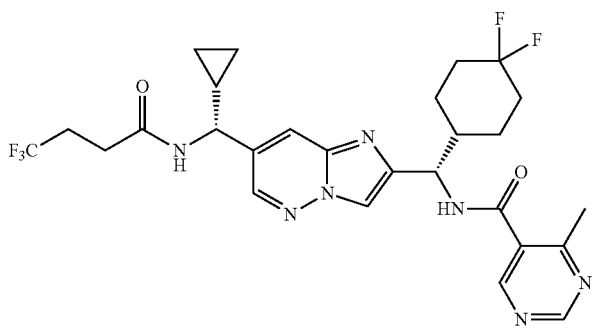 [SMILES: Cc1ncncc1C(=O)N[C@H](c1cn2ncc([C@H](NC(=O)CCC(F)(F)F)C3CC3)cc2n1)C1CCC(F)(F)CC1]

TABLE 1I-continued
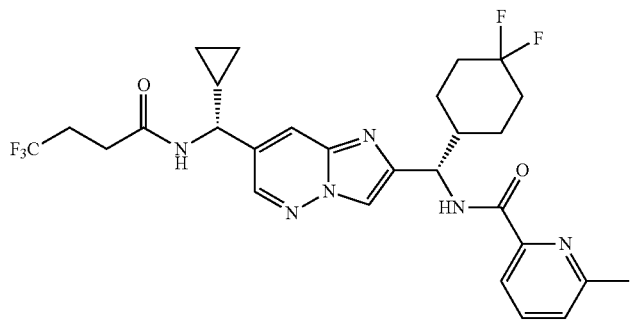 [SMILES: Cc1cccc(C(=O)N[C@H](c2cn3ncc([C@H](NC(=O)CCC(F)(F)F)C4CC4)cc3n2)C2CCC(F)(F)CC2)n1]
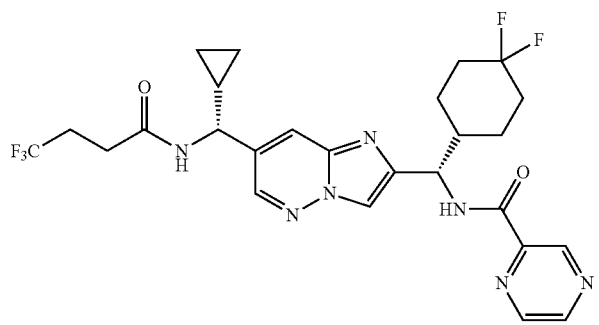 [SMILES: O=C(CCC(F)(F)F)N[C@@H](c1cnn2cc([C@@H](NC(=O)c3cnccn3)C3CCC(F)(F)CC3)nc2c1)C1CC1]
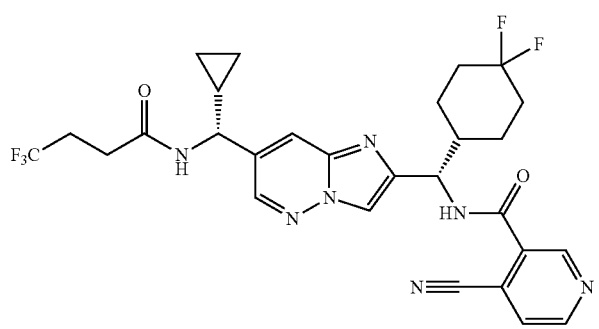 [SMILES: N#Cc1ccncc1C(=O)N[C@H](c1cn2ncc([C@H](NC(=O)CCC(F)(F)F)C3CC3)cc2n1)C1CCC(F)(F)CC1]
TABLE 1J
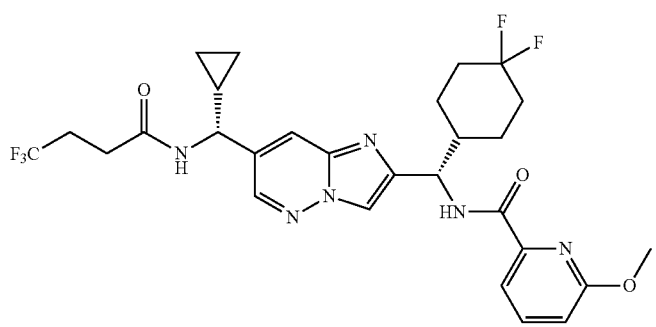

TABLE 1J-continued
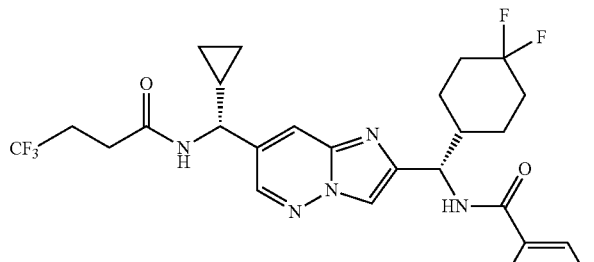
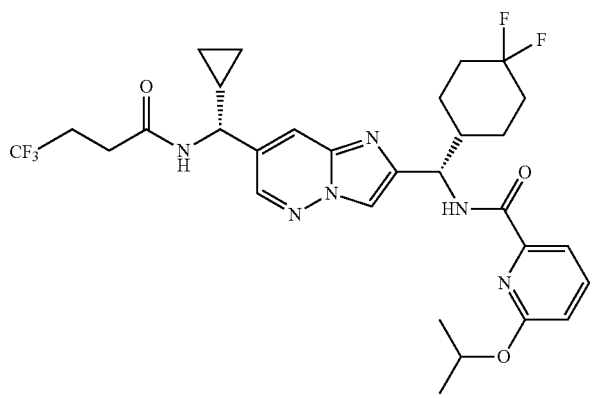 [SMILES: CC(C)Oc1cccc(C(=O)N[C@H](c2cn3ncc([C@H](NC(=O)CCC(F)(F)F)C4CC4)cc3n2)C2CCC(F)(F)CC2)n1]
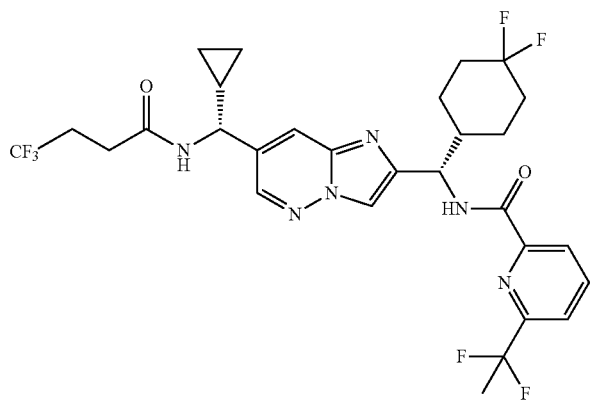 [SMILES: CC(F)(F)c1cccc(C(=O)N[C@H](c2cn3ncc([C@H](NC(=O)CCC(F)(F)F)C4CC4)cc3n2)C2CCC(F)(F)CC2)n1]
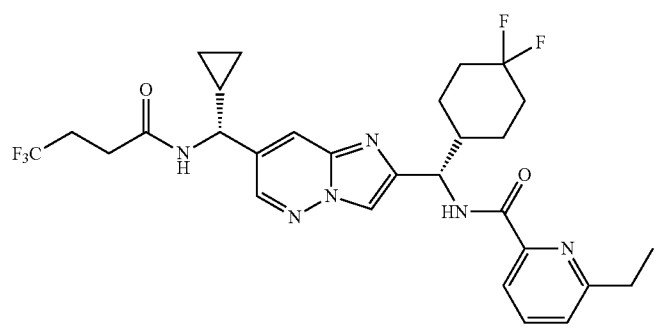

TABLE 1J-continued
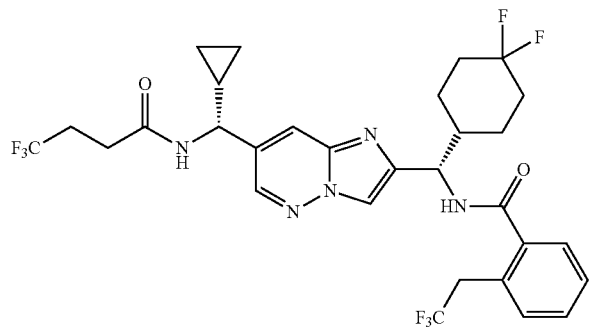 [SMILES: O=C(CCC(F)(F)F)N[C@@H](c1cnn2cc([C@@H](NC(=O)c3ccccc3CC(F)(F)F)C3CCC(F)(F)CC3)nc2c1)C1CC1]
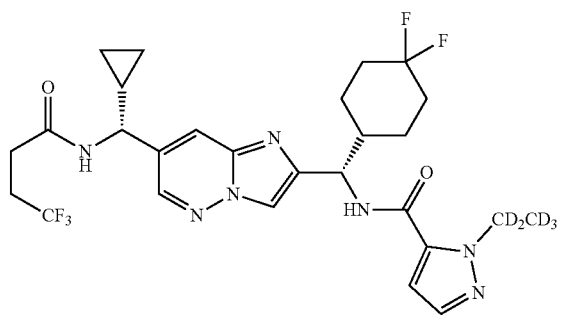
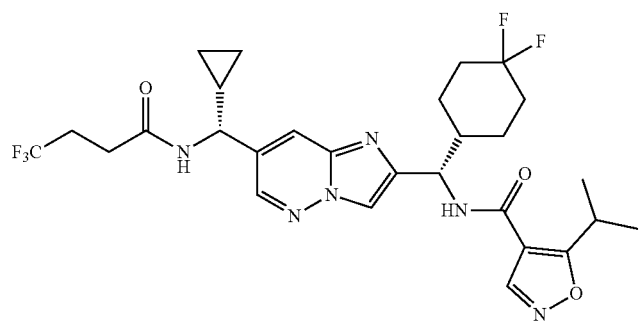 [SMILES: CC(C)c1oncc1C(=O)N[C@H](c1cn2ncc([C@H](NC(=O)CCC(F)(F)F)C3CC3)cc2n1)C1CCC(F)(F)CC1]
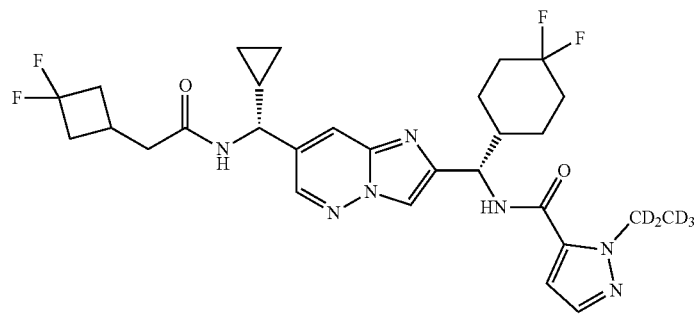

In some embodiments, disclosed herein is a compound of Formula I, or a pharmaceutically acceptable salt thereof, selected from the group consisting of the compounds in Table 1A, Table 1B, Table 1C, Table 1D, Table 1E, Table 1F, Table 1G, Table 1H, Table 1I and Table 1J.

In some embodiments, disclosed herein is a compound of Formula I, or a pharmaceutically acceptable salt thereof, selected from the group consisting of:

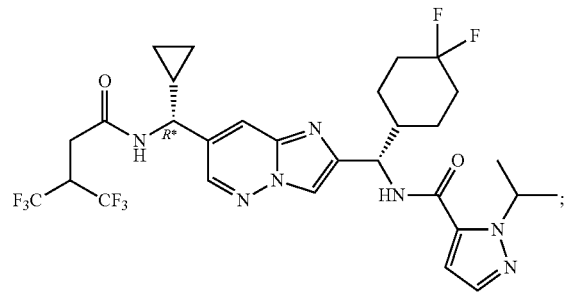
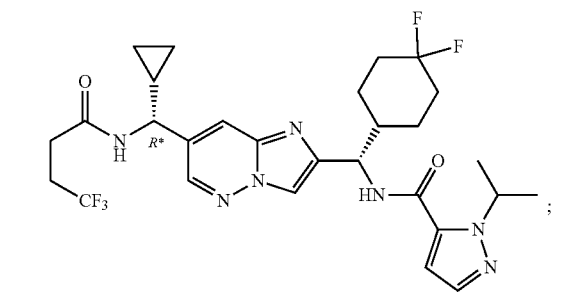
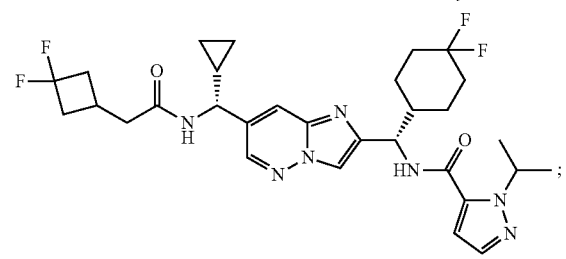
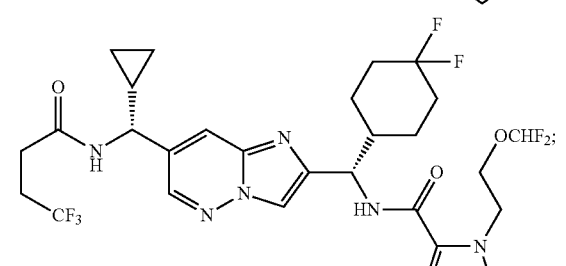
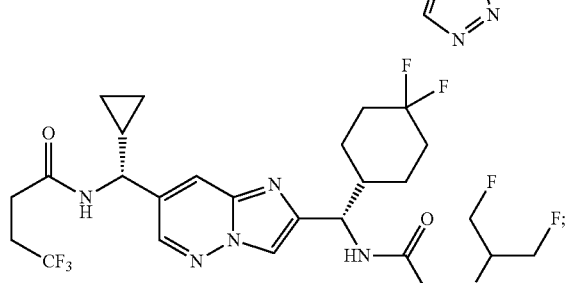
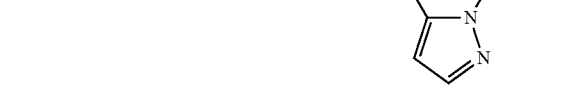

-continued

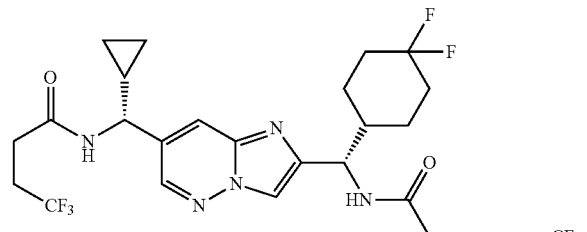
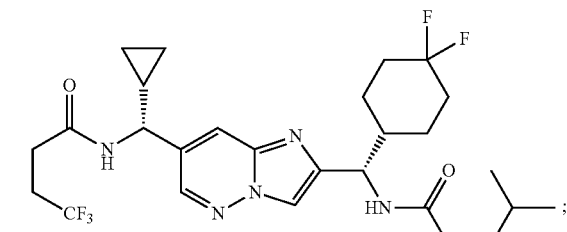
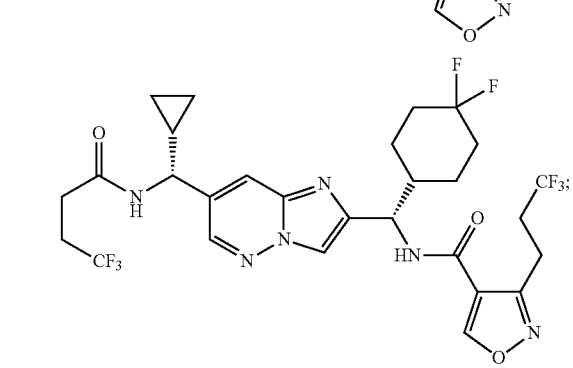
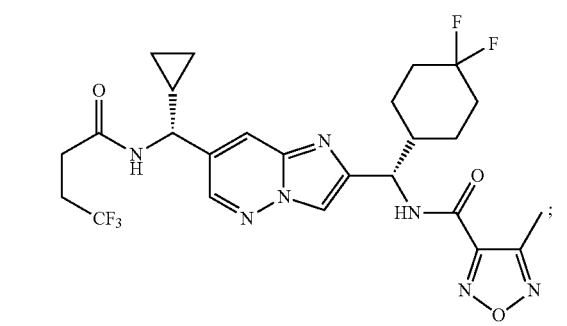
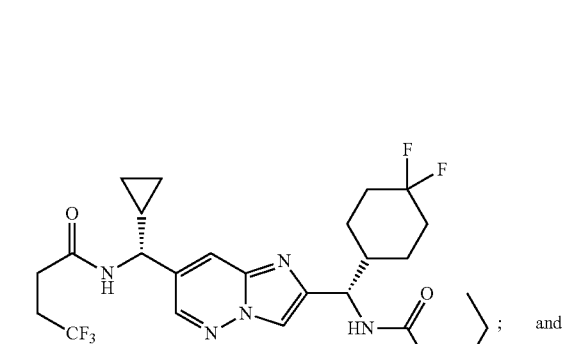

and

-continued

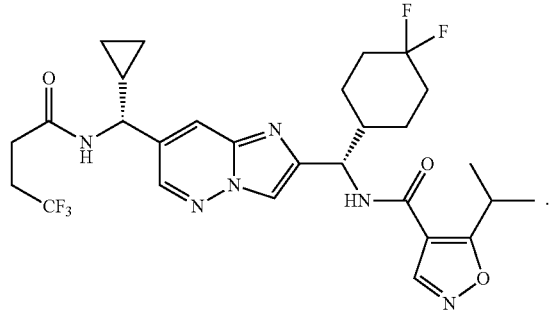 [SMILES: CC(C)c1oncc1C(=O)N[C@H](c1cn2ncc([C@H](NC(=O)CCC(F)(F)F)C3CC3)cc2n1)C1CCC(F)(F)CC1]

In some embodiments, disclosed herein is a compound of Formula I, which is

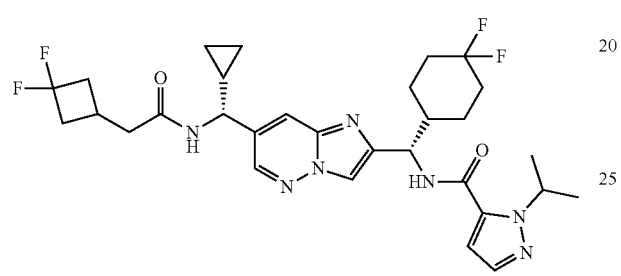

or a pharmaceutically acceptable salt thereof.

In some embodiments, disclosed herein is a compound of Formula I, which is

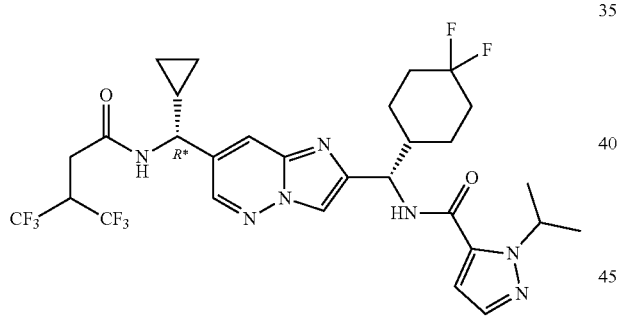

or a pharmaceutically acceptable salt thereof.

In some embodiments, disclosed herein is a compound of Formula I, which is

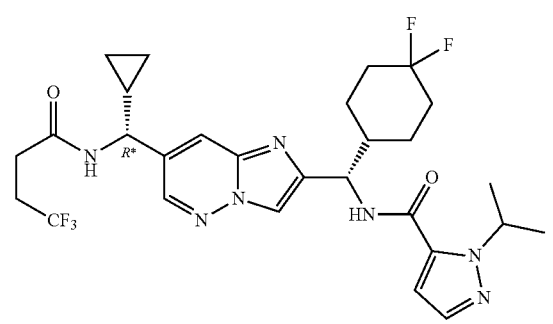 [SMILES: CC(C)n1nccc1C(=O)N[C@H](c1cn2ncc([C@H](NC(=O)CCC(F)(F)F)C3CC3)cc2n1)C1CCC(F)(F)CC1]

or a pharmaceutically acceptable salt thereof.

In some embodiments, disclosed herein is a compound of Formula I, which is

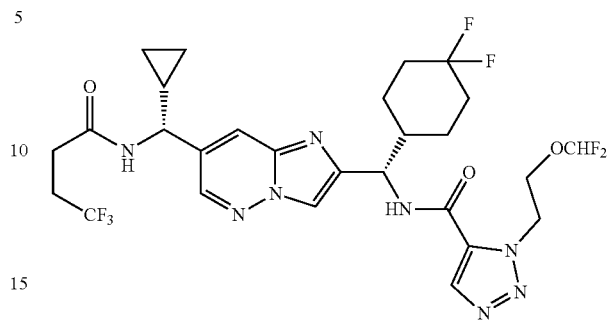

or a pharmaceutically acceptable salt thereof.

In some embodiments, disclosed herein is a compound of Formula I, which is

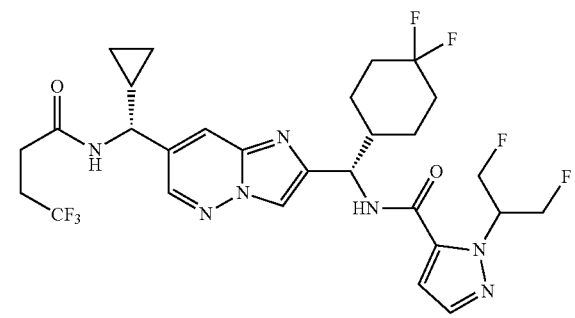 [SMILES: O=C(CCC(F)(F)F)N[C@@H](c1cnn2cc([C@@H](NC(=O)c3ccnn3C(CF)CF)C3CCC(F)(F)CC3)nc2c1)C1CC1]

or a pharmaceutically acceptable salt thereof.

In some embodiments, disclosed herein is a compound of Formula I, which is

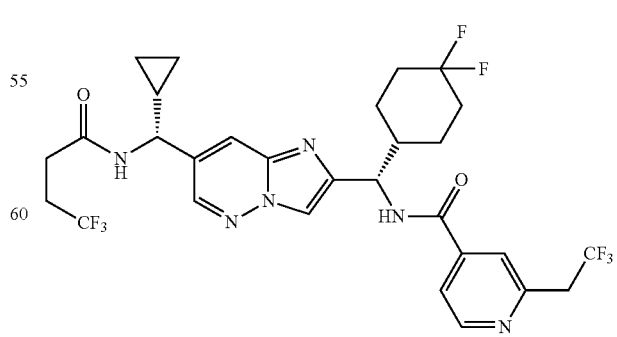

or pharmaceutically acceptable salt thereof.

In some embodiments, disclosed herein is a compound of Formula I, which is

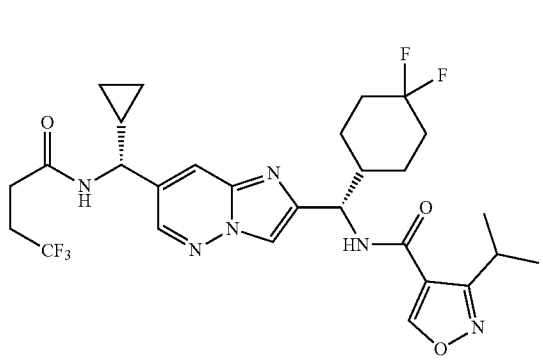 [SMILES: CC(C)c1nocc1C(=O)N[C@H](c1cn2ncc([C@H](NC(=O)CCC(F)(F)F)C3CC3)cc2n1)C1CCC(F)(F)CC1]

or a pharmaceutically acceptable salt thereof.

In some embodiments, disclosed herein is a compound of Formula I, which is

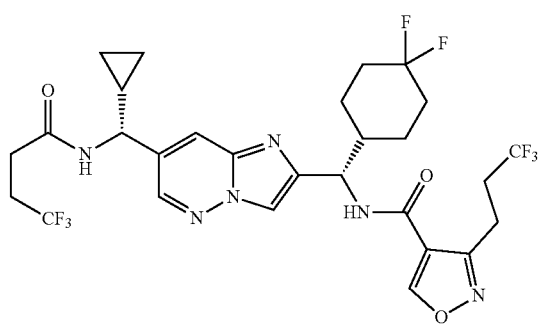 [SMILES: O=C(CCC(F)(F)F)N[C@@H](c1cnn2cc([C@@H](NC(=O)c3conc3CCC(F)(F)F)C3CCC(F)(F)CC3)nc2c1)C1CC1]

or a pharmaceutically acceptable salt thereof.

In some embodiments, disclosed herein is a compound of Formula I, which is

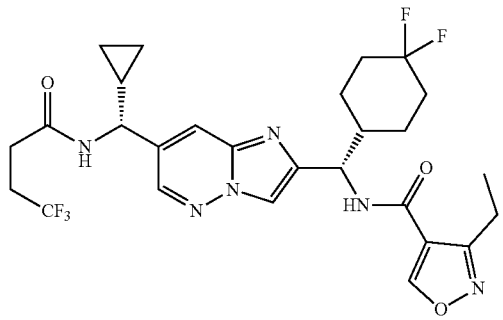 [SMILES: CCc1nocc1C(=O)N[C@H](c1cn2ncc([C@H](NC(=O)CCC(F)(F)F)C3CC3)cc2n1)C1CCC(F)(F)CC1]

or a pharmaceutically acceptable salt thereof.

In some embodiments disclosed herein is a compound of Formula I, which is

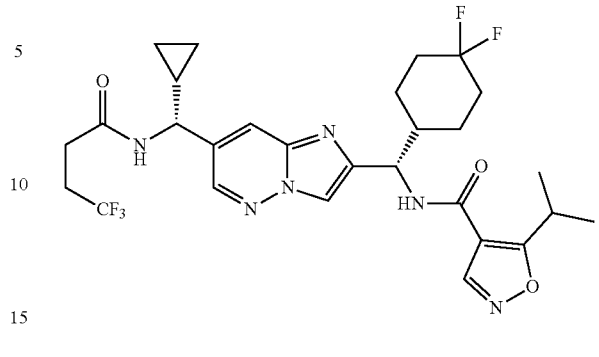

or a pharmaceutically acceptable salt thereof.

In some embodiments, disclosed herein is a compound of Formula I, which is

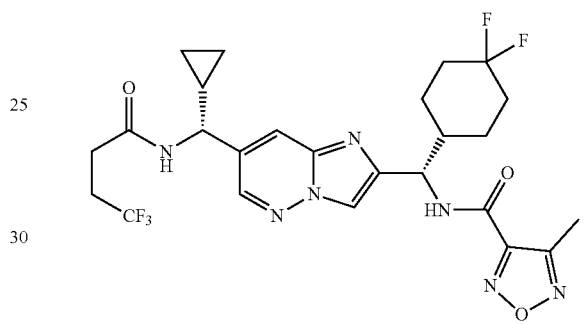

or a pharmaceutically acceptable salt thereof.

In some embodiments, disclosed herein is a pharmaceutical composition, comprising a compound of Formula I, or a pharmaceutically acceptable salt thereof, and a pharmaceutically acceptable carrier. In some embodiments, the pharmaceutical composition is formulated for oral administration (e.g., a tablet or capsule).

In some embodiments, disclosed herein is a pharmaceutical composition made by mixing a compound of Formula I, or a pharmaceutically acceptable salt thereof, and a pharmaceutically acceptable carrier.

In some embodiments, disclosed herein is a process for making a pharmaceutical composition comprising mixing a compound of Formula I, or a pharmaceutically acceptable salt thereof, and a pharmaceutically acceptable carrier.

The present application also discloses compounds of Formula I'. All compounds of Formula I are compounds of Formula I'. Some compounds of Formula I' are compounds of Formula I.

Accordingly, disclosed herein is a compound of Formula I':

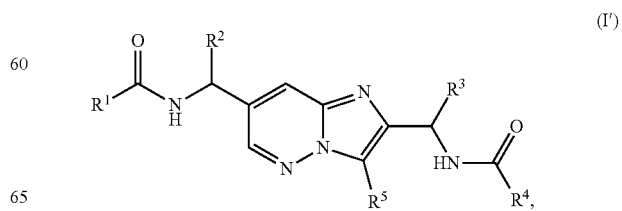

(I')

or a pharmaceutically acceptable salt thereof, wherein:
$R^1$ is —$C_{(1-6)}$alkyl, —$C_{(0-2)}$alkyl$C_{(3-6)}$cycloalkyl, —$C_{(0-2)}$alkyl-cyclopropyl-$C_{(1-3)}$perfluoroalkyl, or a 5- to 6-membered heterocyclyl having 1 to 2 nitrogen atoms;
   wherein the —$C_{(1-6)}$alkyl is unsubstituted or substituted with one to six $R^{1a}$ groups;
   wherein the —$C_{(0-2)}$alkyl$C_{(3-6)}$cycloalkyl is unsubstituted or substituted with one to six $R^{1b}$ groups; and
   wherein the 5- to 6-membered heterocyclyl is unsubstituted or substituted with one to three $R^{1c}$ groups;
$R^2$ is H, —$C_{(3-5)}$cycloalkyl, —$C_{(1-4)}$alkyl, or a 6-membered heterocycle having 1 to 2 oxygen atoms; wherein the —$C_{(1-4)}$alkyl is unsubstituted or substituted with one to six $R^{2a}$ groups; and wherein the —$C_{(3-5)}$cycloalkyl is unsubstituted or substituted with —CN;
$R^{1a}$, $R^{1b}$ and $R^{2a}$ are each independently fluorine, —$C_{(3-5)}$cycloalkyl, —CN, —OH, —$OC_{(1-3)}$alkyl or —$OC_{(3-4)}$cycloalkyl, wherein the —$OC_{(1-3)}$alkyl and —$OC_{(3-4)}$cycloalkyl groups are unsubstituted or substituted with one to three fluorine atoms;
each $R^{1c}$ is independently —$OCH_3$, —$OCF_3$, —$OCHF_2$, or —$C_{(1-4)}$alkyl that is unsubstituted or substituted with one to six fluorine atoms;
$R^3$ is —$C_{(0-1)}$alkyl$C_{(3-6)}$cycloalkyl, —$C_{(3-6)}$alkyl or —$C_{(1-2)}$alkyl-O—$C_{(1-3)}$alkyl, wherein the —$C_{(0-1)}$alkyl$C_{(3-6)}$cycloalkyl, —$C_{(3-6)}$alkyl and —$C_{(1-2)}$alkyl-O—$C_{(1-3)}$alkyl are unsubstituted or substituted with one to five $R^{3a}$ groups each independently selected from fluorine, —$CH_3$—$CHF_2$, —$CF_3$, OH and =O;
$R^4$ is —$C_{(3-6)}$cycloalkyl, phenyl, or a 5 to 6-membered heteroaryl having 1 to 4 heteroatoms selected from N, O, and S;
   wherein the $C_{(3-6)}$cycloalkyl is unsubstituted or substituted with one to three $R^{4a}$ groups each independently selected from halogen, —$OC_{(1-3)}$alkyl, and —$C_{(1-4)}$alkyl wherein the —$OC_{(1-3)}$alkyl, and —$C_{(1-4)}$alkyl are unsubstituted or substituted with one to three fluorine atoms;
   alternatively, two $R^{4a}$ groups attached to the same ring atom can be combined with the atom to which they are attached to form a $C_{(3-6)}$cycloalkyl;
   wherein the phenyl is unsubstituted or substituted with one to three $R^{4b}$ groups each independently selected from halogen, —CN, —$C_{(0-2)}$alkyl-$C_{(3-4)}$cycloalkyl, —$OC_{(0-2)}$alkyl-$C_{(3-4)}$cycloalkyl, —$OC_{(1-3)}$alkyl, —$C_{(1-4)}$alkyl and a 3 to 6-membered heterocyclyl having 1 to 2 heteroatoms selected from N and O, wherein the —$OC_{(1-3)}$alkyl, —$C_{(0-2)}$alkyl-$C_{(3-4)}$cycloalkyl and —$C_{(1-4)}$alkyl are unsubstituted or substituted with one to three fluorine atoms, and wherein the heterocyclyl is unsubstituted or substituted with 1 oxo;
   wherein the 5- to 6-membered heteroaryl is unsubstituted or substituted with one or two $R^{4c}$ groups;
each $R^{4c}$ is independently halogen, —CN, —OH, —$N(R^{4c1})(R^{4c2})$, —$C_{(0-2)}$alkyl$C_{(3-6)}$cycloalkyl, —$OC_{(0-2)}$alkyl-$C_{(3-4)}$cycloalkyl, —$C_{(1-4)}$alkyl, —$OC_{(1-3)}$alkyl, or a 3 to 6-membered heterocyclyl having 1 to 2 heteroatoms selected from N and O, wherein the —$C_{(0-2)}$alkyl$C_{(3-6)}$cycloalkyl, —$C_{(1-4)}$alkyl, —$OC_{(1-3)}$alkyl and heterocyclyl groups are unsubstituted or substituted with one to six $R^{4d}$ groups;
   alternatively, two $R^{4c}$ groups attached to adjacent ring atoms can be combined to form a $C_{(4-6)}$cycloalkyl;
each $R^{4d}$ is independently fluorine, —CN, —OH, oxo, —$C_{(1-3)}$alkyl, —$OC_{(1-3)}$alkyl, —$OC_{(3-4)}$cycloalkyl, —$C_{(0-2)}$alkyl-$N(R^{4d1})(R^{4d2})$, —$C_{(0-2)}$alkyl-$N(C_{(1-4)}$alkyl)C(O)($C_{(1-4)}$alkyl) or a 3- to 6-membered heterocyclyl having 1 to 2 heteroatoms selected from N and O, wherein the —$C_{(1-3)}$alkyl, —$OC_{(1-3)}$alkyl, —$OC_{(3-4)}$cycloalkyl and heterocyclyl groups are unsubstituted or substituted with one to three fluorine atoms;
$R^{4c1}$, $R^{4c2}$, $R^{4d1}$ and $R^{4d2}$ are each independently H or —$C_{(1-3)}$alkyl, wherein the —$C_{(1-3)}$alkyl is unsubstituted or substituted with one to six groups selected from fluorine and chlorine;
   alternatively $R^{4d1}$ and $R^{4d2}$ can be combined with the atom to which they are attached to form a 3- to 6-membered heterocyclyl having 1 to 3 heteroatoms selected from N, O and S, wherein the heterocyclyl is unsubstituted or substituted with 1 to 4 fluorine atoms; and
$R^5$ is hydrogen or halogen;
wherein:
   when $R^4$ is 1,2,4-triazolyl, then $R^4$ is and
   when $R^4$ is a substituted 6-membered heteroaryl, the substituted heteroaryl is unsubstituted at the para-position.

In some embodiments, disclosed herein is a compound of Formula I', or a pharmaceutically acceptable salt thereof, wherein:
$R^1$ is —$C_{(1-6)}$alkyl, —$C_{(0-2)}$alkyl$C_{(3-6)}$cycloalkyl, —$C_{(0-2)}$alkyl-cyclopropyl-$C_{(1-3)}$perfluoroalkyl, pyrrolidinyl or piperidinyl;
   wherein the —$C_{(1-6)}$alkyl is unsubstituted or substituted with one to six $R^{1a}$ groups;
   wherein the —$C_{(0-2)}$alkyl$C_{(3-6)}$cycloalkyl is unsubstituted or substituted with one to six $R^{1b}$ groups; and
   wherein the piperidinyl and pyrrolidinyl are unsubstituted or substituted with one to three $R^{1c}$ groups;
$R^{1a}$ and $R^{1b}$ are each independently —OH, —$OCH_3$, —$OCF_3$, —$OCHF_2$, or fluorine;
each $R^{1c}$ is independently —$C_{(1-2)}$alkyl that is unsubstituted or substituted with one to three fluorine atoms;
$R^2$ is H, —$C_{(3-5)}$cycloalkyl, —$C_{(1-4)}$alkyl or a 6-membered heterocycle having 1 to 2 oxygen atoms; wherein the —$C_{(3-5)}$cycloalkyl is unsubstituted or substituted with —CN;
$R^3$ is —$C_{(5-6)}$cycloalkyl that is unsubstituted or substituted with one to two fluorine atoms;
$R^4$ is —$C_{(3-4)}$cycloalkyl, phenyl, or a 5-membered heteroaryl having 1 to 4 heteroatoms selected from N, O, and S;
   wherein the $C_{(3-6)}$cycloalkyl is unsubstituted or substituted with one to three $R^{4a}$ groups each independently selected from halogen and $C_{(1-4)}$alkyl that is unsubstituted or substituted with one to three fluorine atoms;
   alternatively, two $R^{4a}$ groups attached to the same ring atom can be combined with the atom to which they are attached to form a $C_{(3-6)}$cycloalkyl;
   wherein the phenyl is unsubstituted or substituted with one or two $R^{4b}$ groups each independently selected from halogen, —CN, —C$_{(0-2)}$alkyl-C$_{(3-4)}$cycloalkyl, —OC$_{(0-2)}$alkyl-C$_{(3-4)}$cycloalkyl, —OC$_{(1-3)}$alkyl, C$_{(1-4)}$alkyl, and a 3 to 6-membered heterocyclyl having 1 to 2 heteroatoms selected from N and O, wherein the —OC$_{(1-3)}$alkyl, —C$_{(0-2)}$alkyl-C$_{(3-4)}$cycloalkyl and —C$_{(1-4)}$alkyl are unsubstituted or substituted with one to three fluorine atoms, and wherein the heterocyclyl is unsubstituted or substituted with 1 oxo;

wherein the 5-membered heteroaryl is unsubstituted or substituted with one or two R$^{4c}$ groups;

each R$^{4c}$ is independently halogen, —CN, —C$_{(0-2)}$alkyl C$_{(3-6)}$cycloalkyl, —OC$_{(0-2)}$alkyl-C$_{(3-4)}$cycloalkyl, —C$_{(1-4)}$alkyl, —OC$_{(1-3)}$alkyl, or a 3 to 6-membered heterocyclyl having 1 to 2 heteroatoms selected from N and O, wherein the —C$_{(0-2)}$alkylC$_{(3-6)}$cycloalkyl, —C$_{(1-4)}$alkyl, —OC$_{(1-3)}$alkyl and heterocyclyl groups are unsubstituted or substituted with one to six R$^{4d}$ groups;

each R$^{4d}$ is independently fluorine, —CN, oxo, —C$_{(1-3)}$alkyl, —OC$_{(1-3)}$alkyl, —OC$_{(3-4)}$cycloalkyl, —C$_{(0-2)}$alkyl-N(R$^{4d1}$)(R$^{4d2}$), or —C$_{(0-2)}$alkyl-N(C$_{(1-4)}$alkyl)C(O)(C$_{(1-4)}$alkyl), wherein the —C$_{(1-3)}$alkyl, —OC$_{(1-3)}$alkyl and —OC$_{(3-4)}$cycloalkyl groups are unsubstituted or substituted with one to three fluorine atoms;

R$^{4d1}$ and R$^{4d2}$ are each independently H or —C$_{(1-3)}$alkyl, wherein the —C$_{(1-3)}$alkyl is unsubstituted or substituted with one to six groups selected from fluorine and chlorine;

alternatively R$^{4d1}$ and R$^{4d2}$ can be combined with the atom to which they are attached to form a 3 to 6 membered heterocyclyl having 1 to 3 heteroatoms selected from N, O and S, wherein the heterocyclyl is unsubstituted or substituted with 1 to 4 fluorine atoms; and R$^5$ is hydrogen or fluorine;

wherein when R$^4$ is 1,2,4-triazolyl, then R$^4$ is

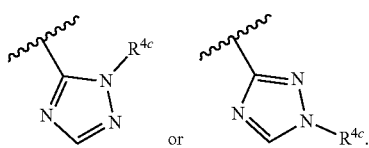

In some embodiments, disclosed herein is a compound of Formula I', or a pharmaceutically acceptable salt thereof, wherein:

R$^1$ is —C$_{(1-6)}$alkyl, —C$_{(0-2)}$alkylC$_{(3-6)}$cycloalkyl, —C$_{(0-2)}$alkyl-cyclopropyl-C$_{(1-3)}$perfluoroalkyl, pyrrolidinyl, or piperidinyl;

wherein the —C$_{(1-6)}$alkyl is unsubstituted or substituted with one to six R$^{1a}$ groups;

wherein the —C$_{(0-2)}$alkylC$_{(3-6)}$cycloalkyl is unsubstituted or substituted with one to six R$^{1b}$ groups; and wherein the pyrrolidinyl and piperidinyl are unsubstituted or substituted with one to three R$^{1c}$ groups;

R$^{1a}$ and R$^{1b}$ are each independently —OH, —OCH$_3$, —OCF$_3$, —OCHF$_2$, or fluorine;

each R$^{1c}$ is independently —C$_{(1-2)}$alkyl that is unsubstituted or substituted with one to three fluorine atoms;

R$^2$ is H, —C$_{(3-5)}$cycloalkyl, or —C$_{(1-4)}$alkyl; wherein the —C$_{(3-5)}$cycloalkyl is unsubstituted or substituted with —CN;

R$^3$ is —C$_{(5-6)}$cycloalkyl that is unsubstituted or substituted with one to two fluorine atoms;

R$^4$ is —C$_{(3-4)}$cycloalkyl, phenyl, or a 5-membered heteroaryl having 1 to 4 heteroatoms selected from N, O, and S;

wherein the C$_{(3-6)}$cycloalkyl is unsubstituted or substituted with one to three R$^{4a}$ groups each independently selected from halogen and C$_{(1-4)}$alkyl that is unsubstituted or substituted with one to three fluorine atoms;

alternatively, two R$^{4a}$ groups attached to the same ring atom can be combined with the atom to which they are attached to form a C$_{(3-6)}$cycloalkyl;

wherein the phenyl is unsubstituted or substituted with one or two R$^{4b}$ groups each independently selected from halogen, —CN, —C$_{(0-2)}$alkyl-C$_{(3-4)}$cycloalkyl, —OC$_{(0-2)}$alkyl-C$_{(3-4)}$cycloalkyl, —OC$_{(1-3)}$alkyl, C$_{(1-4)}$alkyl, and a 3 to 6-membered heterocyclyl having 1 to 2 heteroatoms selected from N and O, wherein the —OC$_{(1-3)}$alkyl, —C$_{(0-2)}$alkyl-C$_{(3-4)}$cycloalkyl and —C$_{(1-4)}$alkyl are unsubstituted or substituted with one to three fluorine atoms, and wherein the heterocyclyl is unsubstituted or substituted with 1 oxo;

wherein the 5-membered heteroaryl is unsubstituted or substituted with one or two R$^{4c}$ groups;

each R$^{4c}$ is independently halogen, —CN, —C$_{(0-2)}$alkyl C$_{(3-6)}$cycloalkyl, —OC$_{(0-2)}$alkyl-C$_{(3-4)}$cycloalkyl, —C$_{(1-4)}$alkyl, —OC$_{(1-3)}$alkyl, or a 3 to 6-membered heterocyclyl having 1 to 2 heteroatoms selected from N and O, wherein the —C$_{(0-2)}$alkylC$_{(3-6)}$cycloalkyl, —C$_{(1-4)}$alkyl, —OC$_{(1-3)}$alkyl and heterocyclyl groups are unsubstituted or substituted with one to six R$^{4d}$ groups;

each R$^{4d}$ is independently fluorine, —CN, oxo, —C$_{(1-3)}$alkyl, —OC$_{(1-3)}$alkyl, —OC$_{(3-4)}$cycloalkyl, —C$_{(0-2)}$alkyl-N(R$^{4d1}$)(R$^{4d2}$), or —C$_{(0-2)}$alkyl-N(C$_{(1-4)}$alkyl)C(O)(C$_{(1-4)}$alkyl), wherein the —C$_{(1-3)}$alkyl, —OC$_{(1-3)}$alkyl and —OC$_{(3-4)}$cycloalkyl groups are unsubstituted or substituted with one to three fluorine atoms;

R$^{4d1}$ and R$^{4d2}$ are each independently H or —C$_{(1-3)}$alkyl, wherein the —C$_{(1-3)}$alkyl is unsubstituted or substituted with one to six groups selected from fluorine and chlorine;

alternatively R$^{4d1}$ and R$^{4d2}$ can be combined with the atom to which they are attached to form a 3 to 6 membered heterocyclyl having 1 to 3 heteroatoms selected from N, O and S, wherein the heterocyclyl is unsubstituted or substituted with 1 to 4 fluorine atoms; and R$^5$ is hydrogen or fluorine;

wherein when R$^4$ is 1,2,4-triazolyl, then R$^4$ is

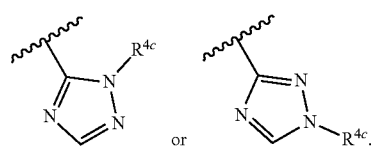

In some embodiments, disclosed herein is a compound of Formula I', or a pharmaceutically acceptable salt thereof, wherein:
- $R^1$ is —$C_{(1-6)}$alkyl, —$C_{(1-2)}$alkyl$C_{(3-6)}$cycloalkyl, —$C_{(0-2)}$alkyl-cyclopropyl-$CF_3$, pyrrolidinyl, or piperidinyl:
  - wherein the —$C_{(1-6)}$alkyl is unsubstituted or substituted with one to six $R^{1a}$ groups;
  - wherein the —$C_{(1-2)}$alkyl$C_{(3-6)}$cycloalkyl is unsubstituted or substituted with one to four fluorine atoms; and
  - wherein the pyrrolidinyl and piperidinyl are unsubstituted or substituted with —$C_{(1-2)}$alkyl that is unsubstituted or substituted with one to three fluorine atoms;
- each $R^{1a}$ is independently —OH, —$OCH_3$, —$OCF_3$, —$OCHF_2$, or fluorine;
- $R^2$ is H, —$C_{(3-5)}$cycloalkyl, or —$C_{(1-3)}$alkyl; wherein the —$C_{(3-5)}$cycloalkyl is unsubstituted or substituted with —CN; $R^3$ is cyclohexyl that is unsubstituted or substituted with one to two fluorine atoms;
- $R^4$ is —$C_{(3-4)}$cycloalkyl, spiropentanyl, spirohexanyl, spiroheptanyl, spirooctanyl, phenyl, pyrrolyl, pyrazolyl, oxazolyl, oxadiazolyl, isoxazolyl, triazolyl, tetrazolyl, imidazolyl, thienyl, thiazolyl, isothiazolyl or thiadiazolyl; wherein the —$C_{(3-4)}$cycloalkyl is unsubstituted or substituted with one to three groups selected from halogen, and $C_{(1-2)}$alkyl that is unsubstituted or substituted with one to three fluorine atoms; wherein the phenyl is unsubstituted or substituted with one or two groups selected from halogen, —CN, —$C_{(0-2)}$alkyl-$C_{(3-4)}$cycloalkyl, —$OC_{(0-2)}$alkyl-$C_{(3-4)}$cycloalkyl, —$OC_{(1-3)}$alkyl, $C_{(1-4)}$alkyl, and a 3 to 6-membered heterocyclyl having 1 to 2 heteroatoms selected from N and O, wherein the —$OC_{(1-3)}$alkyl, —$C_{(0-2)}$alkyl-$C_{(3-4)}$cycloalkyl and —$C_{(1-4)}$alkyl are unsubstituted or substituted with one to three fluorine atoms, and wherein the heterocyclyl is unsubstituted or substituted with 1 oxo;
  - wherein the pyrazolyl, oxazolyl, oxadiazolyl, isoxazolyl, triazolyl, tetrazolyl, imidazolyl, thiazolyl, isothiazolyl and thiadiazolyl are substituted with one or two $R^{4c}$ groups;
  - each $R^{4c}$ is independently halogen, —CN, —$C_{(0-2)}$alkyl$C_{(3-6)}$cycloalkyl, —$OC_{(0-2)}$alkyl-$C_{(3-4)}$cycloalkyl, —$C_{(1-4)}$alkyl, —$OC_{(1-3)}$alkyl, or a 3 to 6-membered heterocyclyl having 1 to 2 heteroatoms selected from N and O, wherein the —$C_{(0-2)}$alkyl $C_{(3-6)}$cycloalkyl, —$C_{(1-4)}$alkyl, —$OC_{(1-3)}$alkyl and heterocyclyl groups are unsubstituted or substituted with one to four $R^{4d}$ groups;
- each $R^{4d}$ is independently —$OCH_3$, —$OCF_3$, —$OCHF_2$, or fluorine; and
- $R^5$ is hydrogen or fluorine;
- wherein
  - when $R^4$ is 1,2,4-triazolyl, then $R^4$ is

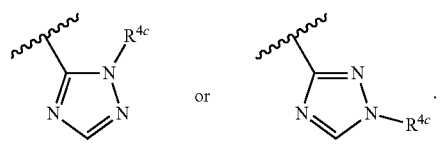

In some embodiments, disclosed herein is a compound of Formula I', or a pharmaceutically acceptable salt thereof, wherein:

$R^1$ is —$C_{(3-5)}$alkyl,

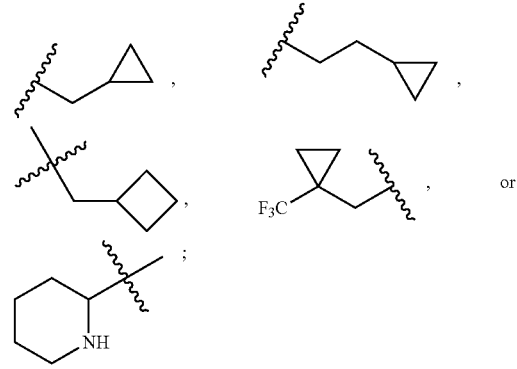

wherein the —$C_{(3-5)}$alkyl is unsubstituted or substituted with one to six $R^{1a}$ groups;

wherein the

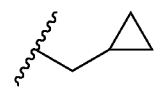

is unsubstituted or substituted with one to four fluorine atoms;

wherein the

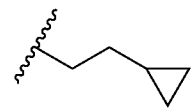 [SMILES: *CCC1CC1]

is unsubstituted or substituted with one to four fluorine atoms;

wherein the

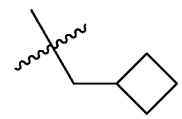

is unsubstituted or substituted with one to four fluorine atoms; and wherein the

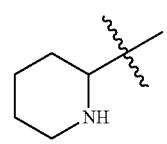 [SMILES: *C1CCCCN1]

is unsubstituted or substituted with —$C_{(1-2)}$alkyl that is unsubstituted or substituted with one to three fluorine atoms;
each $R^{1a}$ is independently —OH or fluorine;
$R^2$ is H, methyl, isopropyl, cyclopropyl, or cyclobutyl; wherein the cyclopropyl and cyclobutyl are unsubstituted or substituted with —CN;
$R^3$ is cyclohexyl or

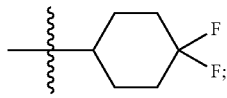

$R^4$ is cyclopropyl, spiropentanyl, spirohexanyl, phenyl, pyrazolyl, oxazolyl, isoxazolyl, 1,2,5-oxadiazolyl, triazolyl, tetrazolyl, imidazolyl, thienyl, thiazolyl, isothiazolyl, 1,2,3-thiadiazolyl or 1,2,5-thiadiazolyl;
  wherein the cyclopropyl is unsubstituted or substituted with one to three groups selected from fluorine and $C_{(1-2)}$alkyl that is unsubstituted or substituted with one to three fluorine atoms;
  wherein the phenyl is unsubstituted or substituted with one to two groups selected from chlorine and $C_{(1-2)}$alkyl that is unsubstituted or substituted with one to three fluorine atoms;
  wherein the 1,2,3-thiadiazolyl is unsubstituted or substituted with $C_{(1-3)}$alkyl, wherein the $C_{(1-3)}$alkyl is unsubstituted or substituted with one to three fluorine atoms;
  wherein the pyrazolyl, oxazolyl, isoxazolyl, 1,2,5-oxadiazolyl, triazolyl, tetrazolyl, imidazolyl, thiazolyl, isothiazolyl, or 1,2,5-thiadiazolyl are unsubstituted or substituted with one or two $R^{4c}$ groups;
each $R^{4c}$ is independently —$C_{(0-1)}$alkyl$C_{(3-4)}$cycloalkyl, or —$C_{(1-4)}$alkyl, wherein the —$C_{(0-1)}$alkyl$C_{(3-4)}$cycloalkyl and —$C_{(1-4)}$alkyl groups are unsubstituted or substituted with one to four $R^{4d}$ groups;
each $R^{4d}$ is independently —$OCH_3$, —$OCF_3$, —$OCHF_2$, or fluorine; and
$R^5$ is hydrogen or fluorine;
wherein
  when $R^4$ is 1,2,4-triazolyl, then $R^4$ is

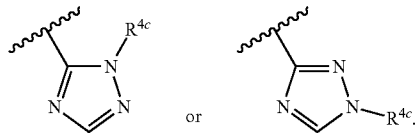

In some embodiments, disclosed herein is a compound of Formula I', or a pharmaceutically acceptable salt thereof, wherein:
$R^1$ is —$C_{(3-5)}$alkyl,

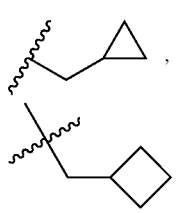, 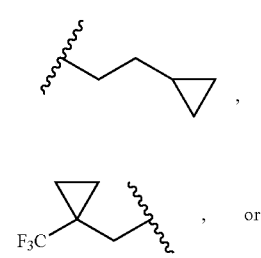, or

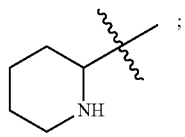;

wherein the —$C_{(3-5)}$alkyl is substituted with one to six $R^{1a}$ groups;
wherein the

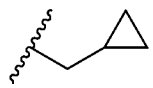

is unsubstituted or substituted with one to two fluorine atoms;
wherein the

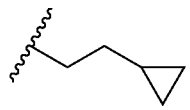 [SMILES: *CCC1CC1]

is unsubstituted or substituted with one to four fluorine atoms;
wherein the

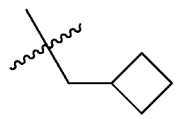 [SMILES: *CC1CCC1]

is substituted with two fluorine atoms; and
wherein the

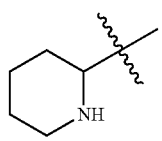 [SMILES: *C1CCCCN1]

is substituted with —$CF_3$;
each $R^{1a}$ is independently —OH or fluorine;
$R^2$ is H, methyl, isopropyl, cyclopropyl, or cyclobutyl; wherein the cyclopropyl and cyclobutyl are unsubstituted or substituted with —CN;
$R^3$ is cyclohexyl or

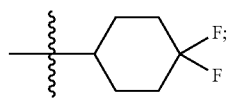

$R^4$ is cyclopropyl, spiropentanyl, spirohexanyl, phenyl, pyrazolyl, oxazolyl, isoxazolyl, 1,2,5-oxadiazolyl, triazolyl, tetrazolyl, imidazolyl, 1,2,3-thiadiazolyl or 1,2,5-thiadiazolyl;
  wherein the cyclopropyl is substituted with one to two groups selected from fluorine and $C_{(1)}$alkyl that is unsubstituted or substituted with three fluorine atoms; wherein the phenyl is unsubstituted or substituted with -chlorine, or —C$_{(1-2)}$alkyl; wherein the 1,2,3-thiadiazolyl and 1,2,5-thiadiazolyl are substituted with C$_{(2-3)}$alkyl;

wherein the pyrazolyl, oxazolyl, isoxazolyl, 1,2,5-oxadiazolyl, triazolyl, tetrazolyl and imidazolyl are substituted with one or two R$^{4c}$ groups;

each R$^{4c}$ is independently —C$_{(0-1)}$alkylC$_{(3-4)}$cycloalkyl, or —C$_{(1-3)}$alkyl, wherein the —C$_{(0-1)}$alkylC$_{(3-4)}$cycloalkyl and —C$_{(1-3)}$alkyl groups are unsubstituted or substituted with one to four R$^{4d}$ groups;

each R$^{4d}$ is independently —OCH$_3$, —OCF$_3$, —OCHF$_2$, or fluorine; and

R$^5$ is hydrogen;

wherein when R$^4$ is 1,2,4-triazolyl, then R$^4$ is

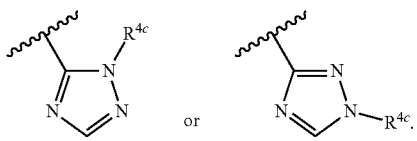

or

All embodiments described hereinabove with respect to the compounds of Formula I are incorporated herein by reference with respect to the compounds of Formula I'. Accordingly, any definitions for variables R$^1$, R$^2$, R$^3$, R$^4$, and/or R$^5$ that apply to Formula I also apply to Formula I'. Certain embodiments of the compound of Formula I' are also provided below.

In some embodiments, disclosed herein is a compound of Formula I', or a pharmaceutically acceptable salt thereof, wherein:

R$^1$ is —C$_{(1-6)}$alkyl, —C$_{(0-2)}$alkylC$_{(3-6)}$cycloalkyl, —C$_{(0-2)}$alkyl-cyclopropyl-C$_{(1-3)}$perfluoroalkyl, pyrrolidinyl, or piperidinyl;
wherein the —C$_{(1-6)}$alkyl is unsubstituted or substituted with one to six R$^{1a}$ groups;
wherein the —C$_{(0-2)}$alkylC$_{(3-6)}$cycloalkyl is unsubstituted or substituted with one to six R$^{1b}$ groups; and
wherein the pyrrolidinyl and piperidinyl are unsubstituted or substituted with one to three R$^{1c}$ groups.

In some embodiments, disclosed herein is a compound of Formula I', or a pharmaceutically acceptable salt thereof, wherein:

R$^1$ is —C$_{(1-6)}$alkyl, —C$_{(0-2)}$alkylC$_{(3-6)}$cycloalkyl, —CH$_2$-cyclopropyl-C$_{(1-3)}$perfluoroalkyl, pyrrolidinyl or piperidinyl;
wherein the —C$_{(1-6)}$alkyl is unsubstituted or substituted with one to six R$^{1a}$ groups;
wherein the —C$_{(0-2)}$alkylC$_{(3-6)}$cycloalkyl is unsubstituted or substituted with one to six R$^{1b}$ groups; and
wherein the pyrrolidinyl and piperidinyl are unsubstituted or substituted with one to three R$^{1c}$ groups.

In some embodiments, disclosed herein is a compound of Formula I', or a pharmaceutically acceptable salt thereof, wherein:

R$^1$ is —C$_{(3-6)}$alkyl, —C$_{(0-2)}$alkylC$_{(3-6)}$cycloalkyl, —C$_{(0-2)}$alkyl-cyclopropyl-C$_{(1-3)}$perfluoroalkyl, pyrrolidinyl, or piperidinyl;
wherein the —C$_{(1-6)}$alkyl is unsubstituted or substituted with one to six R$^{1a}$ groups;
wherein the —C$_{(0-2)}$alkylC$_{(3-6)}$cycloalkyl is unsubstituted or substituted with one to four R$^{1b}$ groups; and
wherein the pyrrolidinyl and piperidinyl are substituted with one R$^{1c}$ group;

each R$^{1a}$ is independently fluorine, —CN, —OH, —OC$_{(1-3)}$alkyl, or —OC$_{(3-4)}$cycloalkyl, wherein the —OC$_{(1-3)}$alkyl and —OC$_{(3-4)}$cycloalkyl groups are unsubstituted or substituted with one to three fluorine atoms;

each R$^{1b}$ is independently fluorine;

R$^{1c}$ is —C$_{(1-4)}$alkyl that is substituted with one to three fluorine atoms.

In some embodiments, disclosed herein is a compound of Formula I', or a pharmaceutically acceptable salt thereof, wherein:

R$^1$ is —C$_{(3-6)}$alkyl, —C$_{(1-2)}$alkylC$_{(3-6)}$cycloalkyl, or —C$_{(1-2)}$alkyl-cyclopropyl-CF$_3$;
wherein the —C$_{(1-6)}$alkyl is unsubstituted or substituted with one to six R$^{1a}$ groups;
wherein the —C$_{(1-2)}$alkylC$_{(3-6)}$cycloalkyl is unsubstituted or substituted with one or two R$^{1b}$ groups;
each R$^{1a}$ is independently fluorine;
each R$^{1b}$ is independently fluorine.

In some embodiments disclosed herein is a compound of Formula I', or a pharmaceutically acceptable salt thereof, wherein R$^1$ is —C$_{(0-2)}$alkylC$_{(3-6)}$cycloalkyl that is unsubstituted or substituted with one to three R$^{1b}$ groups, wherein each R$^{1b}$ is independently fluorine. In some embodiments disclosed herein is a compound of Formula I', or a pharmaceutically acceptable salt thereof, wherein R$^1$ is —CH$_2$C$_{(3-6)}$cycloalkyl that is unsubstituted or substituted with one to three R$^{1b}$ groups, wherein each R$^{1b}$ is independently fluorine.

In some embodiments, disclosed herein is a compound of Formula I', or a pharmaceutically acceptable salt thereof, wherein R$^1$ is:

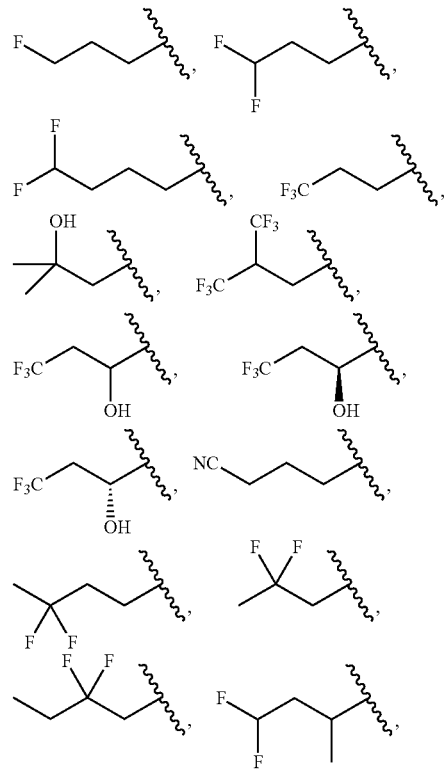

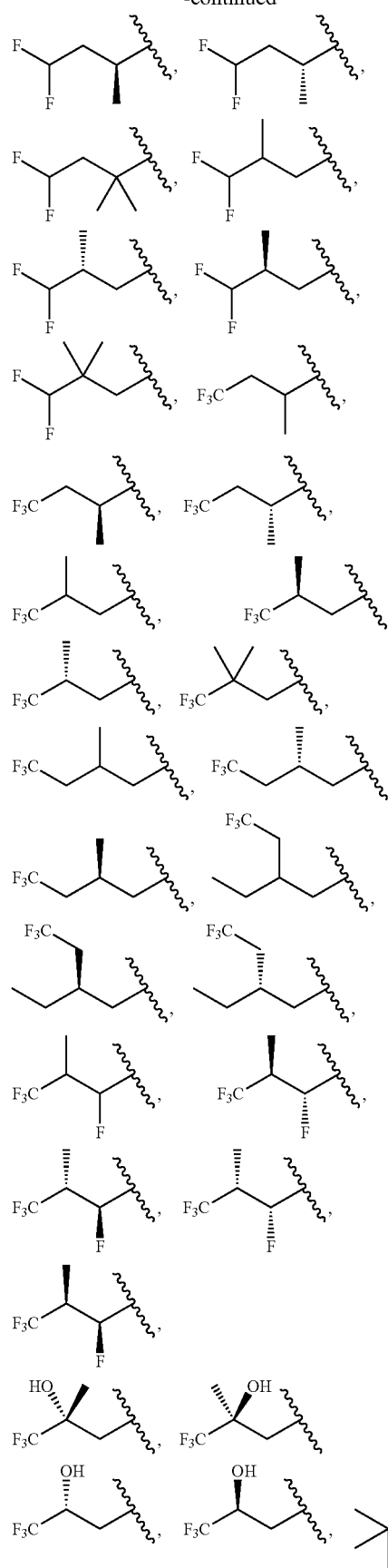
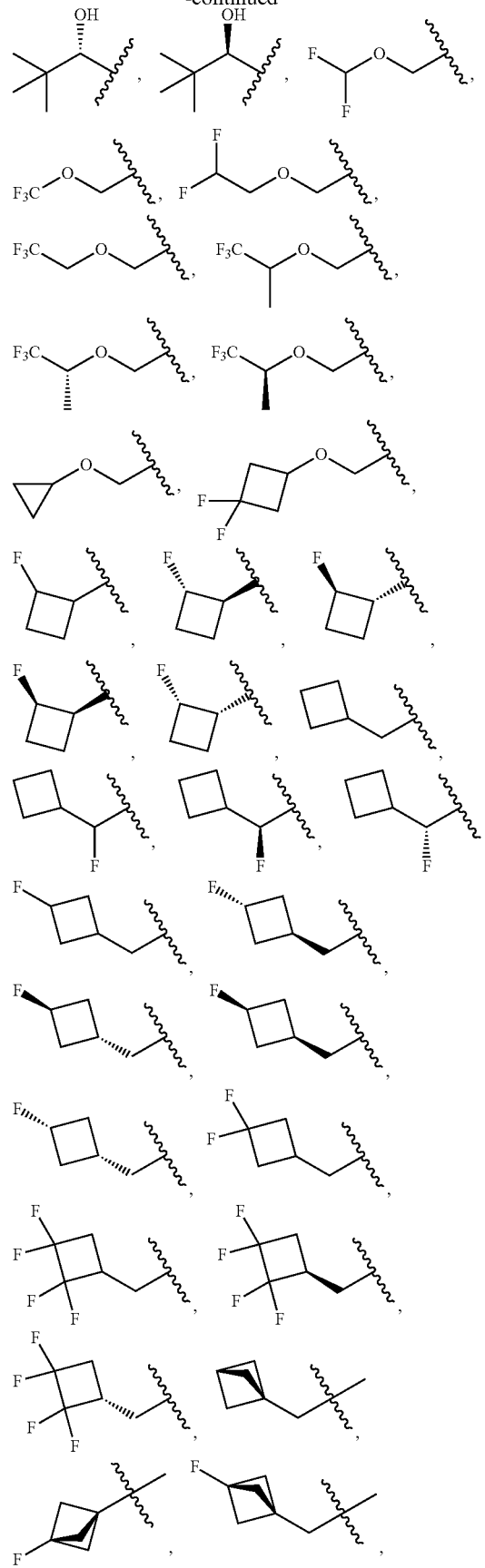

-continued

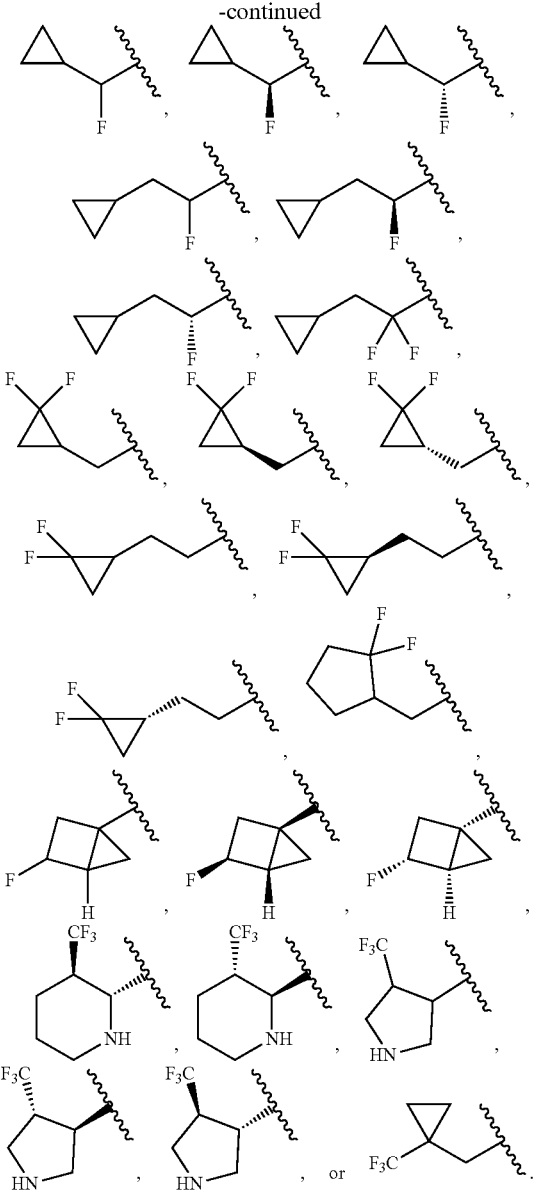

In some embodiments, disclosed herein is a compound of Formula I', or a pharmaceutically acceptable salt thereof, wherein R¹ is:

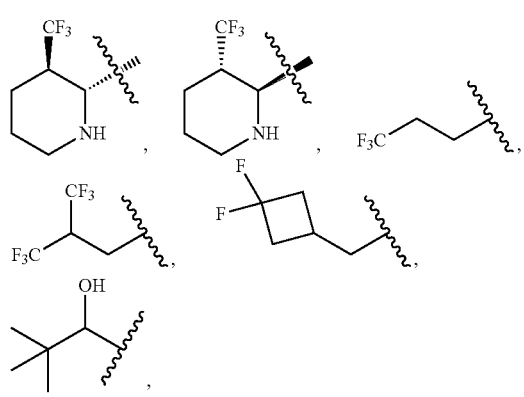

-continued

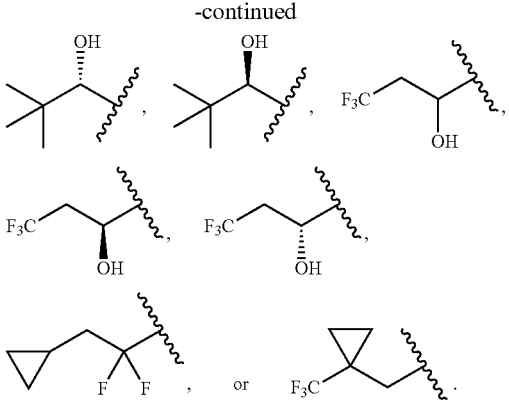

In some embodiments, disclosed herein is a compound of Formula I', or a pharmaceutically acceptable salt thereof, wherein R¹ is:

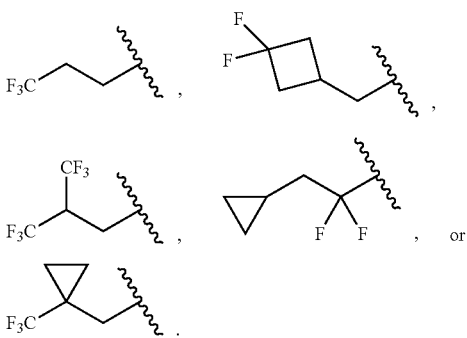

In some embodiments, disclosed herein is a compound of Formula I', or a pharmaceutically acceptable salt thereof, wherein R¹ is:

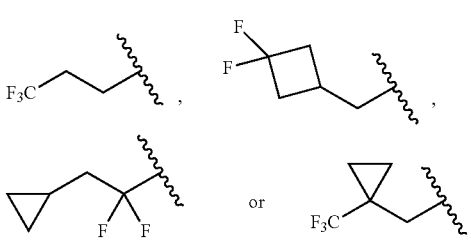

In some embodiments, disclosed herein is a compound of Formula I', or a pharmaceutically acceptable salt thereof, wherein R¹ is:

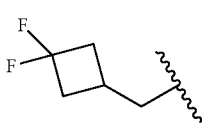

In some embodiments, disclosed herein is a compound of Formula I', or a pharmaceutically acceptable salt thereof, wherein R¹ is:

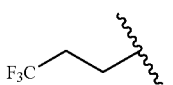

In some embodiments, disclosed herein is a compound of Formula I', or a pharmaceutically acceptable salt thereof, wherein $R^1$ is

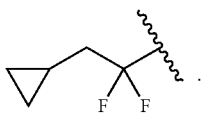 [SMILES: *C(F)(F)CC1CC1]

In some embodiments, disclosed herein is a compound of Formula I', or a pharmaceutically acceptable salt thereof, wherein $R^1$ is:

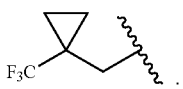

In some embodiments, disclosed herein is a compound of Formula I', or a pharmaceutically acceptable salt thereof, wherein $R^2$ is H, cyclopropyl, cyclobutyl, —$C_{(1-3)}$alkyl, or tetrahydropyran,
wherein the cyclopropyl and cyclobutyl are unsubstituted or substituted with —CN;
wherein the —$C_{(1-3)}$alkyl is substituted with one to three $R^{2a}$ groups; and
wherein each $R^{2a}$ is independently fluorine, —$C_{(3-4)}$cycloalkyl, —CN, —OH, or —$OC_{(1-3)}$alkyl.

In some embodiments, disclosed herein is a compound of Formula I', or a pharmaceutically acceptable salt thereof, wherein $R^2$ is H, methyl, ethyl, isopropyl, trifluoromethyl, cyclopropyl, cyclobutyl, tetrahydropyranyl,

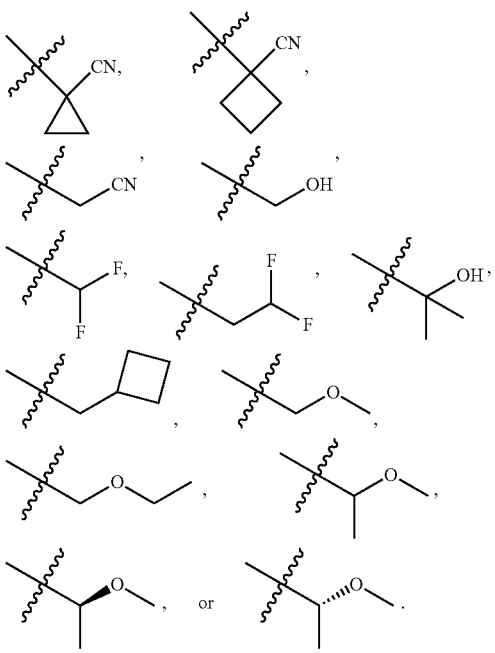

In some embodiments, disclosed herein is a compound of Formula I', or a pharmaceutically acceptable salt thereof, wherein $R^2$ is H, methyl, isopropyl, cyclopropyl, cyclobutyl, or tetrahydropyran; wherein the cyclopropyl and cyclobutyl are unsubstituted or substituted with —CN.

In some embodiments, disclosed herein is a compound of Formula I', or a pharmaceutically acceptable salt thereof, wherein $R^2$ is H, methyl, isopropyl, cyclopropyl, or cyclobutyl; wherein the cyclopropyl and cyclobutyl are unsubstituted or substituted with —CN.

In some embodiments, disclosed herein is a compound of Formula I', or a pharmaceutically acceptable salt thereof, wherein $R^2$ is cyclopropyl or cyclobutyl, wherein the cyclopropyl and cyclobutyl are unsubstituted or substituted with —CN.

In some embodiments, disclosed herein is a compound of Formula I', or a pharmaceutically acceptable salt thereof, wherein $R^2$ is unsubstituted cyclopropyl. In some embodiments, disclosed herein is a compound of Formula I', or a pharmaceutically acceptable salt thereof, wherein $R^2$ is cyclopropyl substituted with —CN. In some embodiments, disclosed herein is a compound of Formula I', or a pharmaceutically acceptable salt thereof, wherein $R^2$ is:

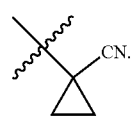

In some embodiments, disclosed herein is a compound of Formula I', or a pharmaceutically acceptable salt thereof, wherein $R^2$ is unsubstituted cyclobutyl. In some embodiments, disclosed herein is a compound of Formula I', or a pharmaceutically acceptable salt thereof, wherein $R^2$ is cyclobutyl substituted with —CN. In some embodiments, disclosed herein is a compound of Formula I', or a pharmaceutically acceptable salt thereof, wherein $R^2$ is:

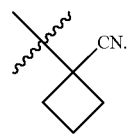 [SMILES: *C1(C#N)CCC1]

In some embodiments, disclosed herein is a compound of Formula I', or a pharmaceutically acceptable salt thereof, which is a compound of formula I'a:

(I'a)

In some embodiments, disclosed herein is a compound of Formula I', or a pharmaceutically acceptable salt thereof, which is a compound of formula I'b:

(I'b)

wherein $R^{3a}$ is fluorine and n is 0, 1, or 2. In some embodiments, $R^{3a}$ is fluorine and n is 2.

In some embodiments, disclosed herein is a compound of Formula I', or a pharmaceutically acceptable salt thereof, which is a compound of formula I'b-1:

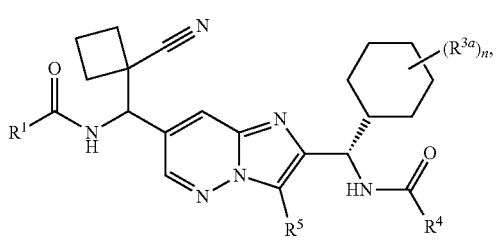

(I'b-1)

wherein $R^{3a}$ is fluorine and n is 2.

In some embodiments, disclosed herein is a compound of Formula I', or a pharmaceutically acceptable salt thereof, which is a compound of formula I'b-2a:

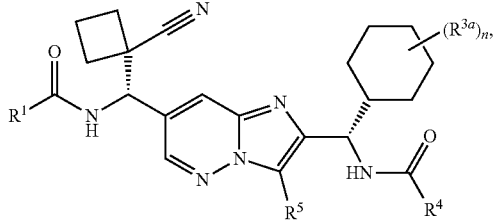

(I'b-2a)

wherein $R^{3a}$ is fluorine and n is 2.

In some embodiments, disclosed herein is a compound of Formula I', or a pharmaceutically acceptable salt thereof, which is a compound of formula I'b-2b:

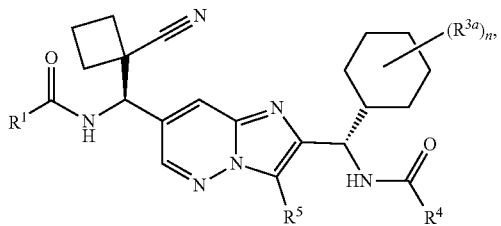

(I'b-2b)

wherein $R^{3a}$ is fluorine and n is 2.

In some embodiments, disclosed herein is a compound of Formula I', or a pharmaceutically acceptable salt thereof, which is a compound of formula I'b-3a:

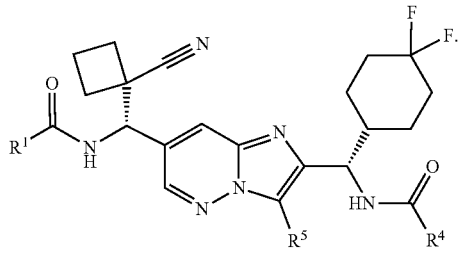

(I'b-3a)

In some embodiments, disclosed herein is a compound of Formula I', or a pharmaceutically acceptable salt thereof, which is a compound of formula I'b-3b:

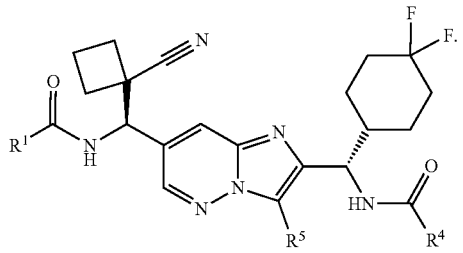

(I'b-3b)

In some embodiments, disclosed herein is a compound of Formula I', or a pharmaceutically acceptable salt thereof, which is a compound of formula I'c:

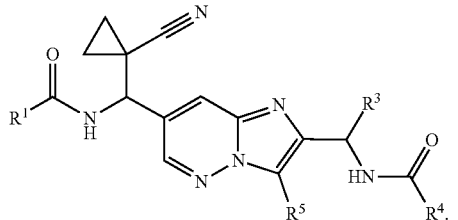

(I'c)

In some embodiments, disclosed herein is a compound of Formula I', or a pharmaceutically acceptable salt thereof, which is a compound of formula I'd:

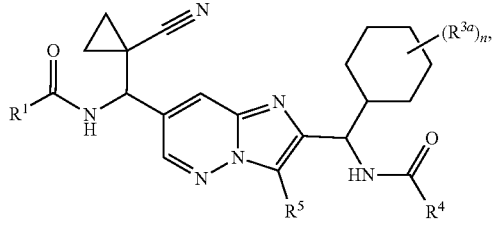

(I'd)

wherein $R^{3a}$ is fluorine and n is 0, 1, or 2. In some embodiments, $R^{3a}$ is fluorine and n is 2.

In some embodiments, disclosed herein is a compound of Formula I', or a pharmaceutically acceptable salt thereof, which is a compound of formula I'd-1:

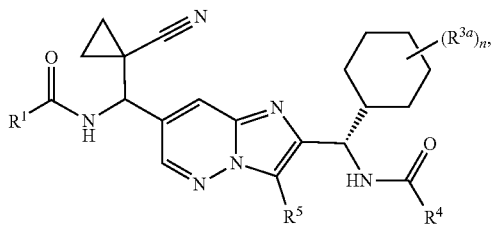

(I'd-1)

wherein R³ᵃ is fluorine and n is 2.

In some embodiments, disclosed herein is a compound of Formula I', or a pharmaceutically acceptable salt thereof, which is a compound of formula I'd-2a:

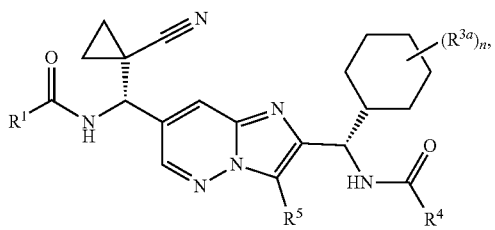

(I'd-2a)

wherein R³ᵃ is fluorine and n is 2.

In some embodiments, disclosed herein is a compound of Formula I', or a pharmaceutically acceptable salt thereof, which is a compound of formula I'd-2b:

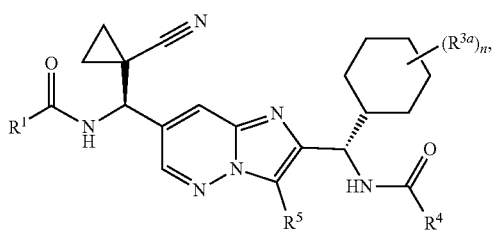

(I'd-2b)

wherein R³ᵃ is fluorine and n is 2.

In some embodiments, disclosed herein is a compound of Formula I', or a pharmaceutically acceptable salt thereof, which is a compound of formula I'd-3a:

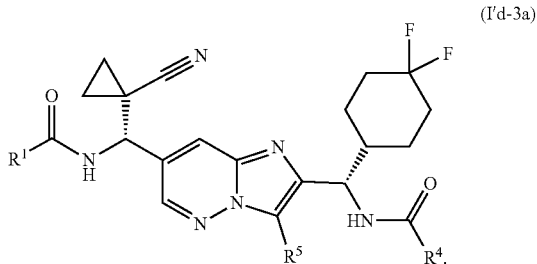

(I'd-3a)

In some embodiments, disclosed herein is a compound of Formula I', or a pharmaceutically acceptable salt thereof, which is a compound of formula I'd-3b:

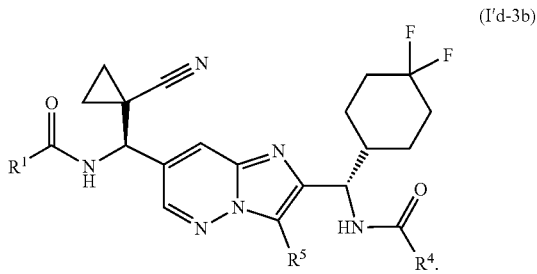

(I'd-3b)

In some embodiments, disclosed herein is a compound of Formula I', or a pharmaceutically acceptable salt thereof, wherein R³ is $C_{(3-6)}$cycloalkyl, —$C_{(3-6)}$alkyl or —$CH_2$—O—$C_{(1-3)}$alkyl, wherein the $C_{(3-6)}$cycloalkyl, —$C_{(3-6)}$alkyl and —$CH_2$—O—$C_{(1-3)}$alkyl are unsubstituted or substituted with one to three R³ᵃ groups each independently selected from fluorine, —$CH_3$, and —$CF_3$.

In some embodiments, disclosed herein is a compound of Formula I', or a pharmaceutically acceptable salt thereof, wherein R³ is:

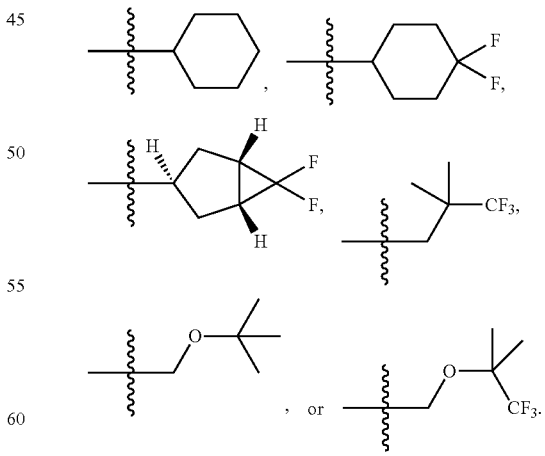

In some embodiments, disclosed herein is a compound of Formula I', or a pharmaceutically acceptable salt thereof, wherein R³ is

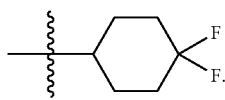

In some embodiments, disclosed herein is a compound of Formula I', or a pharmaceutically CF$_3$ acceptable salt thereof, wherein R$^3$ is

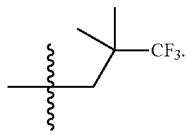 [SMILES: *CC(C)(C)C(F)(F)F]

In some embodiments, disclosed herein is a compound of Formula I', or a pharmaceutically acceptable salt thereof, wherein R$^3$ is

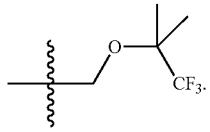

In some embodiments, disclosed herein is a compound of Formula I', or a pharmaceutically acceptable salt thereof, which is a compound of formula I'e:

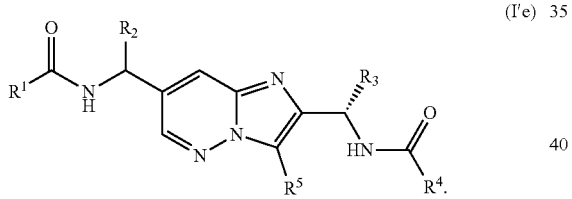

(I'e)

In some embodiments, disclosed herein is a compound of Formula I', or a pharmaceutically acceptable salt thereof, wherein:
R$^4$ is —C$_{(3-6)}$cycloalkyl that is unsubstituted or substituted with one to three R$^{4a}$ groups; and
each R$^{4a}$ is independently selected from fluorine and —C$_{(1-4)}$alkyl, wherein the —C$_{(1-4)}$alkyl is unsubstituted or substituted with one to three fluorine atoms; alternatively, two R$^{4a}$ groups attached to the same ring atom can be combined with the atom to which they are attached to form a C$_{(3-6)}$cycloalkyl.

In some embodiments, disclosed herein is a compound of Formula I', or a pharmaceutically acceptable salt thereof, wherein:
R$^4$ is —C$_{(3-6)}$cycloalkyl that is unsubstituted or substituted with one to three R$^{4a}$ groups; and
each R$^{4a}$ is independently selected from fluorine, CH$_3$, CH$_2$F, CF$_2$H, and CF$_3$; alternatively, two R$^{4a}$ groups attached to the same ring atom can be combined with the atom to which they are attached to form a cyclopropyl, cyclobutyl, or cyclopentyl.

In some embodiments, disclosed herein is a compound of Formula I', or a pharmaceutically acceptable salt thereof, wherein R$^4$ is:

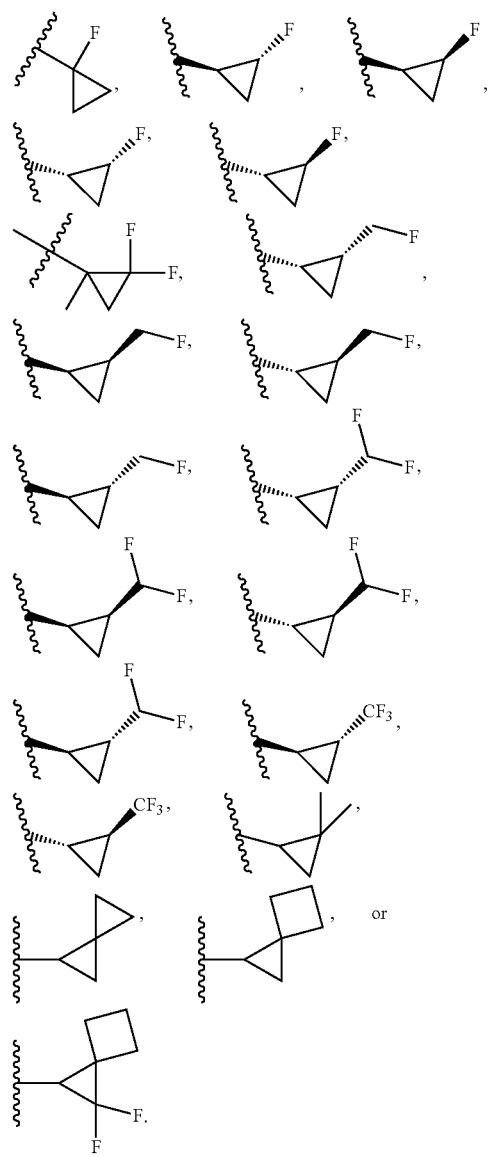

In some embodiments, disclosed herein is a compound of Formula I', or a pharmaceutically acceptable salt thereof, wherein:
R$^4$ is a 5 to 6-membered heteroaryl having 1 to 4 heteroatoms selected from N, O, and S, that is substituted with one or two R$^{4c}$ groups;
each R$^{4c}$ is independently halogen, —CN, —NH$_2$, —N(CH$_3$)$_2$, —C$_{(0-2)}$alkylC$_{(3-6)}$cycloalkyl, —OC$_{(0-2)}$alkyl-C$_{(3-4)}$cycloalkyl, —C$_{(1-4)}$alkyl, —OC$_{(1-3)}$alkyl, or a 3 to 6-membered heterocyclyl having 1 to 2 heteroatoms selected from N and O, wherein the —C$_{(0-2)}$alkylC$_{(3-6)}$cycloalkyl, —C$_{(1-4)}$alkyl, —OC$_{(1-3)}$alkyl and heterocyclyl groups are unsubstituted or substituted with one to six R$^{4d}$ groups; alternatively, two R$^{4c}$ groups attached to adjacent ring atoms can be combined to form a C$_{(4-6)}$cycloalkyl;
each R$^{4d}$ is independently fluorine, —CN, —OH, oxo, —C$_{(1-3)}$alkyl, —OC$_{(1-3)}$alkyl, —OC$_{(3-4)}$cycloalkyl, —C$_{(0-2)}$alkyl-N(R$^{4d1}$)(R$^{4d2}$), —C$_{(0-2)}$alkyl-N(C$_{(1-4)}$alkyl)C(O)(C$_{(1-4)}$alkyl), or a 3- to 6-membered heterocyclyl having 1 to 2 heteroatoms selected from N and O, wherein the —C$_{(1-3)}$alkyl, —OC$_{(1-3)}$alkyl, —OC$_{(3-4)}$cycloalkyl, and heterocyclyl groups are unsubstituted or substituted with one to three fluorine atoms; and R$^{4d1}$ and R$^{4d2}$ are each independently H or —C$_{(1-3)}$alkyl, wherein the —C$_{(1-3)}$alkyl is unsubstituted or substituted with one to six groups selected from fluorine and chlorine;

alternatively R$^{4d1}$ and R$^{4d2}$ can be combined with the atom to which they are attached to form a 3 to 6 membered heterocyclyl having 1 to 3 heteroatoms selected from N, O and S, wherein the heterocyclyl is unsubstituted or substituted with 1 to 4 fluorine atoms;

wherein
when R$^4$ is 1,2,4-triazolyl, then R$^4$ is 1H-1,2,4-triazolyl, and
when R$^4$ is a 6-membered heteroaryl, the heteroaryl is unsubstituted at the para-position.

In some embodiments, disclosed herein is a compound of Formula I', or a pharmaceutically acceptable salt thereof, wherein:

each R$^{4c}$ is independently fluorine, —CN, —OH, —NH$_2$, N(CH$_3$)$_2$, methyl, ethyl, isopropyl, —CD$_3$, —CD$_2$CD$_3$, —OCH$_3$, —OCH$_2$CH$_3$, —OCH(CH$_3$)$_2$, —OC(CH$_3$)$_3$, CH(CH$_3$)OH, —CHF$_2$, —CF$_3$, —CH$_2$CH$_2$F, —CH$_2$CHF$_2$, —CH$_2$CF$_3$, —CF$_2$CH$_3$, —CH$_2$CH$_2$CH$_2$F, —CH$_2$CH$_2$CHF$_2$, —CH$_2$CH$_2$CF$_3$, —CH(CH$_3$)CHF$_2$, —CH(CH$_3$)CF$_3$, —CH(CH$_2$F)$_2$, —CH$_2$CF$_2$CH$_3$, —CH$_2$CH$_2$CF$_2$CH$_3$, —CH$_2$OCH$_3$, —CH$_2$CH$_2$OCH$_3$, —CH$_2$CH$_2$OCHF$_2$, —CH$_2$CH$_2$OCF$_3$, —CH$_2$OCHF$_2$, —OCHF$_2$, —OCH$_2$CHF$_2$, —OCH$_2$CH$_2$F, —OCH$_2$CF$_3$, cyclopropyl, cyclobutyl, cyclopentyl, —CH$_2$-cyclopropyl, —O—cyclopropyl, —O-cyclobutyl,

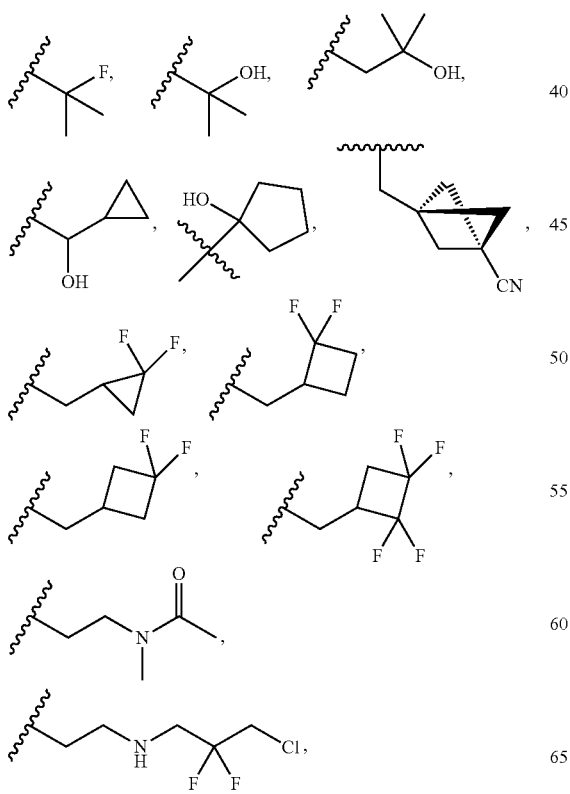

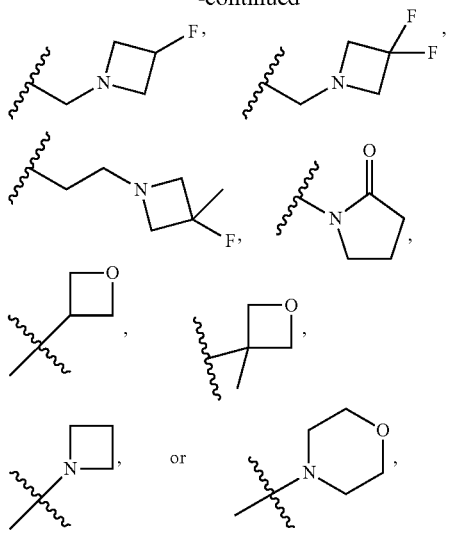

alternatively two R$^{4c}$ groups attached to adjacent ring atoms can be combined to form the group:

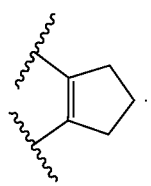 [SMILES: *C1=C(*)CCC1 ; "."]

In some embodiments, disclosed herein is a compound of Formula I', or a pharmaceutically acceptable salt thereof, wherein:

R$^4$ is oxazolyl, isoxazolyl or oxadiazolyl that is substituted with one or two R$^{4c}$ groups, wherein each R$^{4c}$ is independently —OH, —NH$_2$, —N(CH$_3$)$_2$, —C$_{(0-1)}$alkylC$_{(3-5)}$cycloalkyl, —OC$_{(3-4)}$cycloalkyl, —C$_{(1-3)}$alkyl, —OC$_{(1-3)}$alkyl,

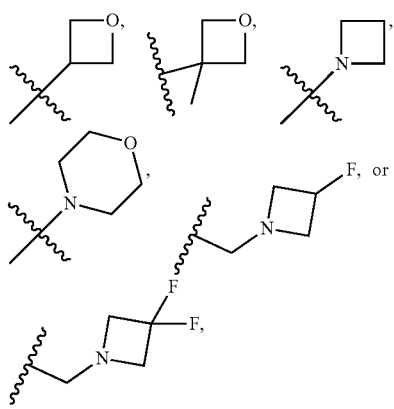

wherein the —C$_{(0-1)}$alkylC$_{(3-5)}$cycloalkyl, —C$_{(1-3)}$alkyl, and —OC$_{(1-3)}$alkyl groups are unsubstituted or substituted with one to three groups selected from —OH, —OCH$_3$, —OCHF$_2$, —CH$_3$, and fluorine.

In some embodiments, disclosed herein is a compound of Formula I', or a pharmaceutically acceptable salt thereof, wherein
  R⁴ is oxazolyl, isoxazolyl, or oxadiazolyl (e.g., 1,2,5-oxadiazolyl) that is unsubstituted or substituted with one or two R⁴ᶜ groups,
  wherein each R⁴ᶜ is independently cyclopropyl, —C₍₁₋₃₎alkyl, or —OC₍₁₋₃₎alkyl, wherein the cyclopropyl, —C₍₁₋₃₎alkyl, and —OC₍₁₋₃₎alkyl groups are unsubstituted or substituted with one to three fluorine atoms.

In some embodiments, disclosed herein is a compound of Formula I', or a pharmaceutically acceptable salt thereof, wherein R⁴ is
  isoxazolyl substituted with one or two R⁴ᶜ groups each independently methyl, ethyl, isopropyl, —CF₃, —CH₂CH₂F, —CH₂CH₂CF₃, —CH₂OCH₃, cyclopropyl, cyclopentyl, or

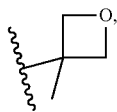

oxazolyl substituted with one isopropyl, or
  oxadiazolyl substituted with one methyl, ethyl, —OCH₂CHF₂, or cyclopropyl.

In some embodiments, disclosed herein is a compound of Formula I', or a pharmaceutically acceptable salt thereof, wherein R⁴ is 1,2,5-oxadiazolyl substituted with cyclopropyl.

In some embodiments, disclosed herein is a compound of Formula I', or a pharmaceutically acceptable salt thereof, wherein R⁴ is:

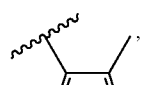 ,  , 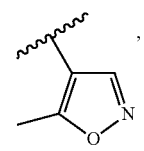 ,

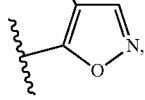 , 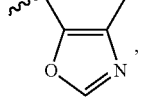 , 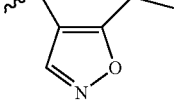 ,

 ,  ,

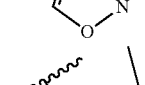 , 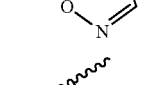 ,

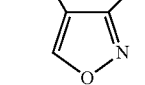 , 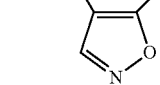 ,

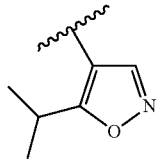 , 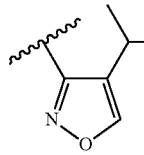 , 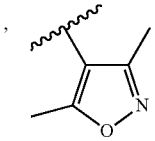 ,

-continued

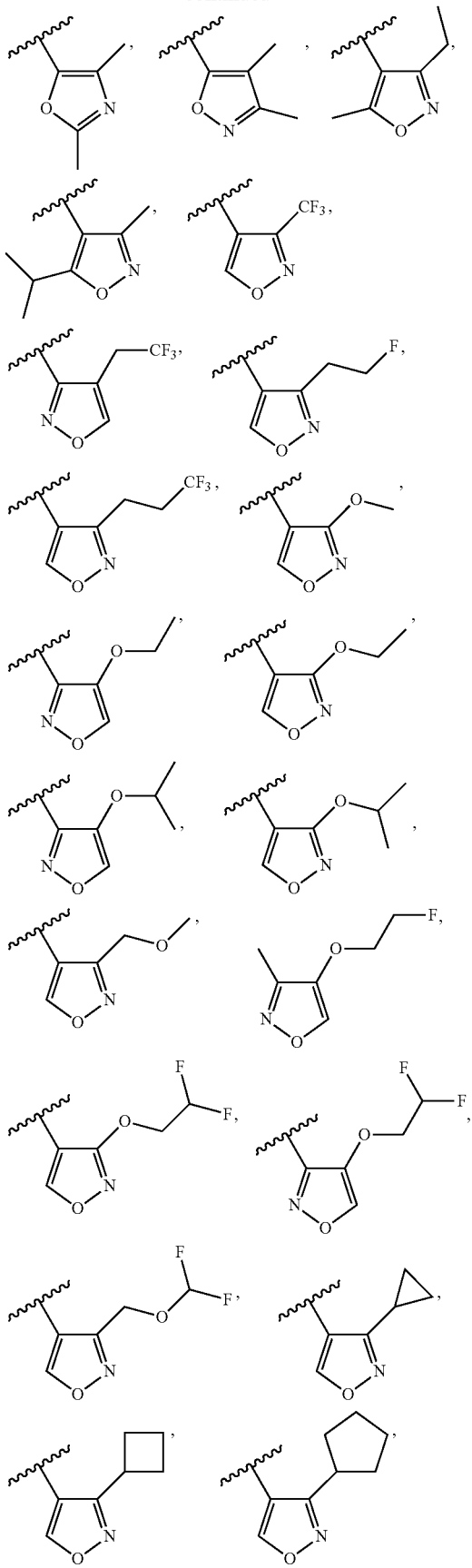

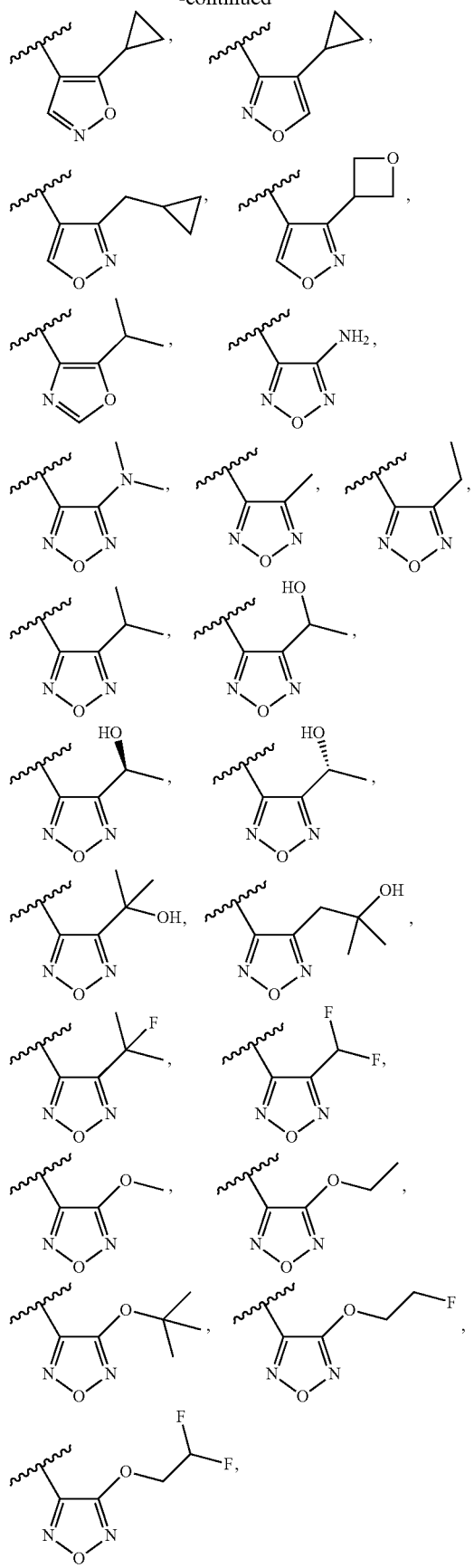
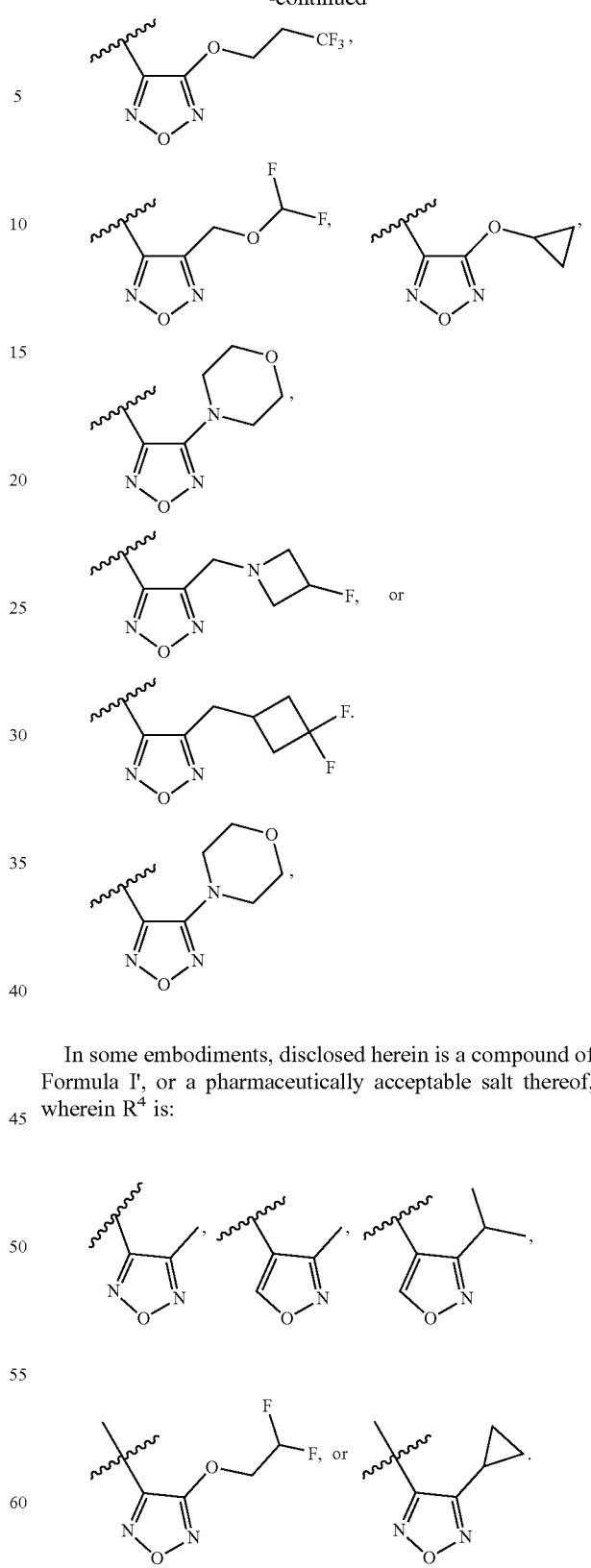
In some embodiments, disclosed herein is a compound of Formula I', or a pharmaceutically acceptable salt thereof, wherein $R^4$ is:
In some embodiments, disclosed herein is a compound of Formula I', or a pharmaceutically acceptable salt thereof, wherein $R^4$ is:

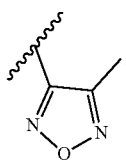

In some embodiments, disclosed herein is a compound of Formula I', or a pharmaceutically acceptable salt thereof, wherein R⁴ is:

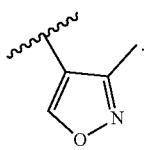 [SMILES: *c1conc1C]

In some embodiments, disclosed herein is a compound of Formula I', or a pharmaceutically acceptable salt thereof, wherein R⁴ is:

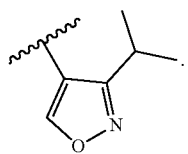 [SMILES: *c1conc1C(C)C]

In some embodiments, disclosed herein is a compound of Formula I', or a pharmaceutically acceptable salt thereof, wherein R⁴ is:

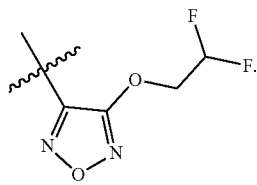 [SMILES: *c1nonc1OCC(F)F]

In some embodiments, disclosed herein is a compound of Formula I', or a pharmaceutically acceptable salt thereof, wherein R⁴ is:

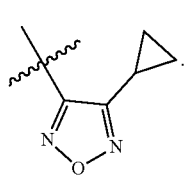 [SMILES: *c1nonc1C1CC1]

In some embodiments, disclosed herein is a compound of Formula I', or a pharmaceutically acceptable salt thereof, which is a compound of Formula I'f:

(I'f)

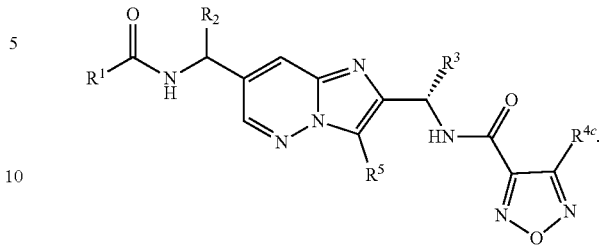

In some embodiments, disclosed herein is a compound of Formula I', or a pharmaceutically acceptable salt thereof, which is a compound of Formula I'g:

(I'g)

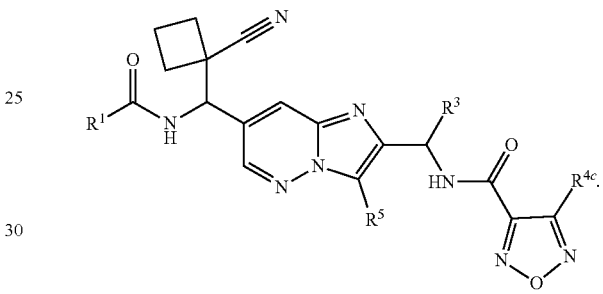

In some embodiments, disclosed herein is a compound of Formula I', or a pharmaceutically acceptable salt thereof, which is a compound of Formula I'h:

(I'h)

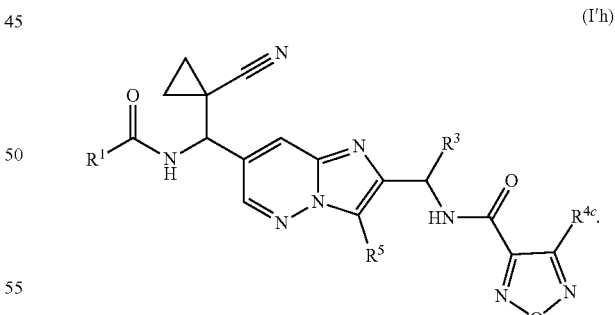

In some embodiments, disclosed herein is a compound of Formula I', or a pharmaceutically acceptable salt thereof, which is a compound of Formula I'i:

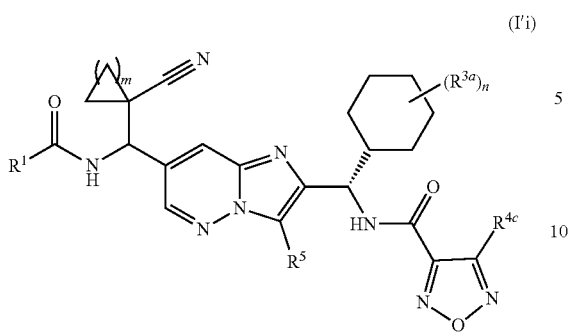

(I'i)

wherein R³ᵃ is fluorine, n is 2, and m is 1 or 2.

In some embodiments, disclosed herein is a compound of Formula I', or a pharmaceutically acceptable salt thereof, wherein:

R⁴ is pyrazolyl or imidazolyl that is unsubstituted or substituted with one or two R⁴ᶜ groups, wherein each R⁴ᶜ is independently fluorine, cyclopropyl, or —C₍₁₋₃₎ alkyl, wherein the —C₍₁₋₃₎alkyl is unsubstituted or substituted with one to three groups selected from —CHF₂, —CF₃, —OCHF₂, —OCF₃ and fluorine.

In some embodiments, disclosed herein is a compound of Formula I', or a pharmaceutically acceptable salt thereof, wherein R⁴ is pyrazolyl or imidazolyl that is substituted with one or two R⁴ᶜ groups, wherein each R⁴ᶜ is independently —C₍₁₋₃₎alkyl that is unsubstituted or substituted with one to three groups selected from —CHF₂, —CF₃, —OCHF₂, —OCF₃ and fluorine.

In some embodiments, disclosed herein is a compound of Formula I', or a pharmaceutically acceptable salt thereof, wherein R⁴ is pyrazolyl substituted with one or two R⁴ᶜ groups each independently cyclopropyl, methyl, ethyl, isopropyl, —CD₃, —CD₂CD₃, fluorine, —CHF₂, —CF₃, —CH₂CHF₂, —CH₂CF₃, —CH(CH₃)CF₃, —CH(CH₂F)₂, —CH₂CH₂OCHF₂, or —CH₂CH₂OCF₃, or imidazolyl substituted with one methyl or isopropyl.

In some embodiments, disclosed herein is a compound of Formula I', or a pharmaceutically acceptable salt thereof, wherein R⁴ is pyrazolyl substituted with one —C₍₁₋₃₎alkyl.

In some embodiments, disclosed herein is a compound of Formula I', or a pharmaceutically acceptable salt thereof, wherein R⁴ is pyrazolyl substituted with isopropyl, —CD₃, or -CD₂CD₃.

In some embodiments, disclosed herein is a compound of Formula I', or a pharmaceutically acceptable salt thereof, wherein R⁴ is:

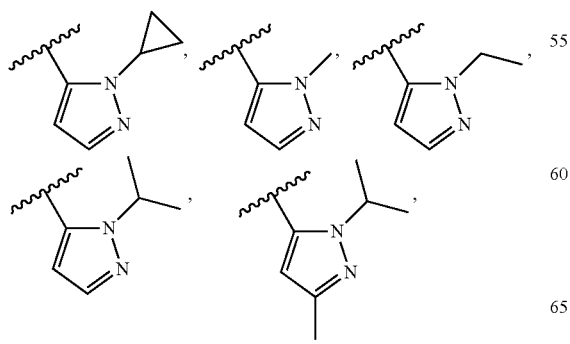

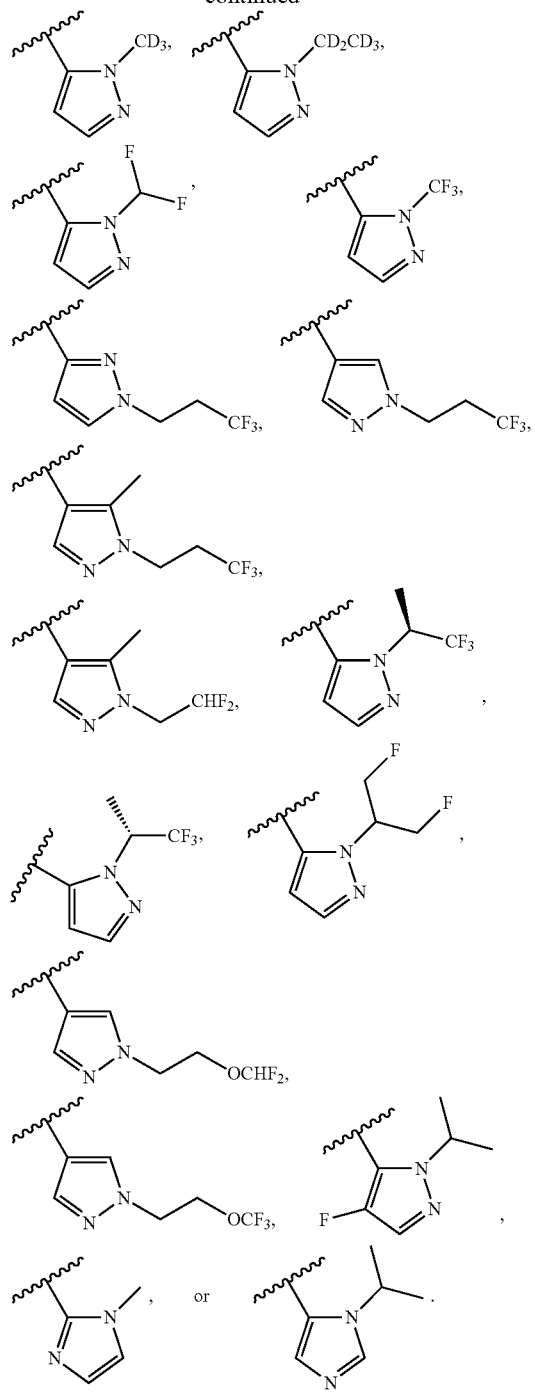

In some embodiments, disclosed herein is a compound of Formula I', or a pharmaceutically acceptable salt thereof, wherein R⁴ is:

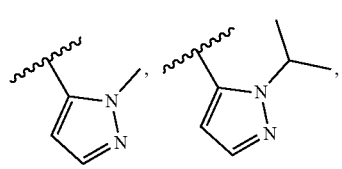

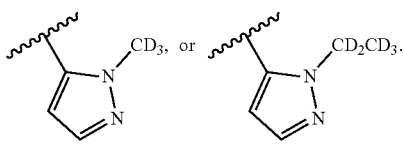

In some embodiments, disclosed herein is a compound of Formula I', or a pharmaceutically acceptable salt thereof, wherein $R^4$ is

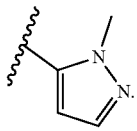

In some embodiments, disclosed herein is a compound of Formula I', or a pharmaceutically acceptable salt thereof, wherein $R^4$ is

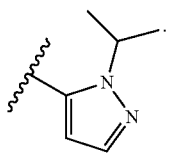

In some embodiments, disclosed herein is a compound of Formula I', or a pharmaceutically acceptable salt thereof, wherein $R^4$ is

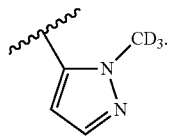 [SMILES: *c1ccnn1C([2H])([2H])[2H]]

In some embodiments, disclosed herein is a compound of Formula I', or a pharmaceutically acceptable salt thereof, wherein $R^4$ is

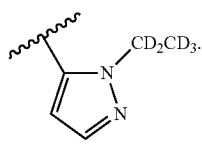

In some embodiments, disclosed herein is a compound of Formula I', or a pharmaceutically acceptable salt thereof, wherein:

$R^4$ is triazolyl that is unsubstituted or substituted with one or two $R^{4c}$ groups; each $R^{4c}$ is independently —$C_{(0-1)}$alkyl$C_{(3-4)}$cycloalkyl, —$C_{(1-4)}$alkyl,

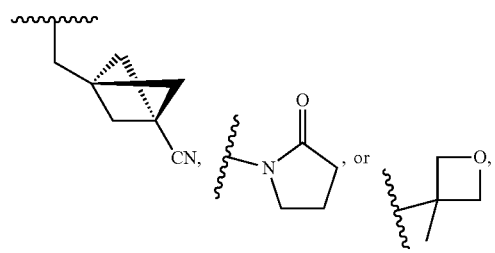

wherein the —$C_{(0-1)}$alkyl$C_{(3-4)}$cycloalkyl and —$C_{(1-3)}$alkyl groups are unsubstituted or substituted with one to four $R^{4d}$ groups; and each $R^{4d}$ is independently —$OCH_3$, —$OCF_3$, —$OCHF_2$, fluorine,

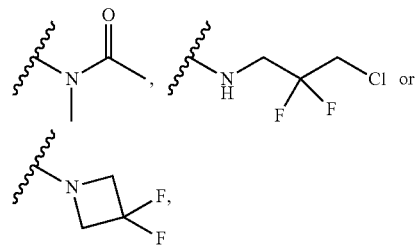

wherein when $R^4$ is 1,2,4-triazolyl, then $R^4$ is

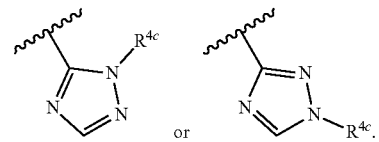

Alternatively, when $R^4$ is 1,2,4-triazolyl, then $R^4$ is 1H-1,2,4-triazolyl.

In some embodiments, disclosed herein is a compound of Formula I', or a pharmaceutically acceptable salt thereof, wherein:

$R^4$ is triazolyl that is unsubstituted or substituted with one or two $R^{4c}$ groups; and each $R^4$, is independently methyl, ethyl, isopropyl, —$CH_2CH_2OCH_3$, —$CHF_2$, —$CF_3$, —$CH_2CH_2F$, —$CH_2CHF_2$, —$CH_2CF_3$, —$CH_2CH_2CH_2F$, —$CH_2CH_2CHF_2$, —$CH_2CH_2CF_3$, —$CH(CH_3)CHF_2$, —$CH(CH_3)CF_3$—$CH_2CF_2CH_3$, —$CH_2CH_2CF_2CH_3$, —$CH_2CH_2OCHF_2$, —$CH_2CH_2OCF_3$, cyclopropyl, —$CH_2$-cyclopropyl,

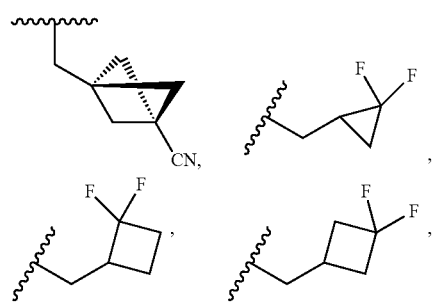

217
-continued
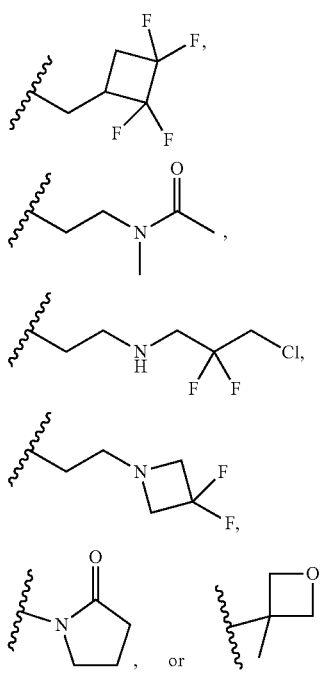
wherein when R⁴ is 1,2,4-triazolyl, then R⁴ is
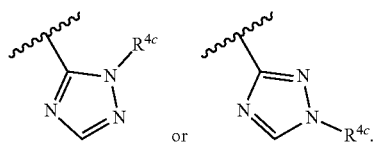
In some embodiments, disclosed herein is a compound of Formula I', or a pharmaceutically acceptable salt thereof, wherein R⁴ is:
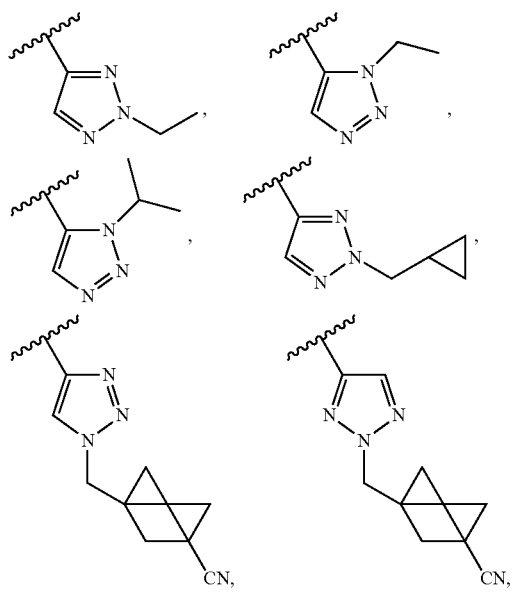
218
-continued
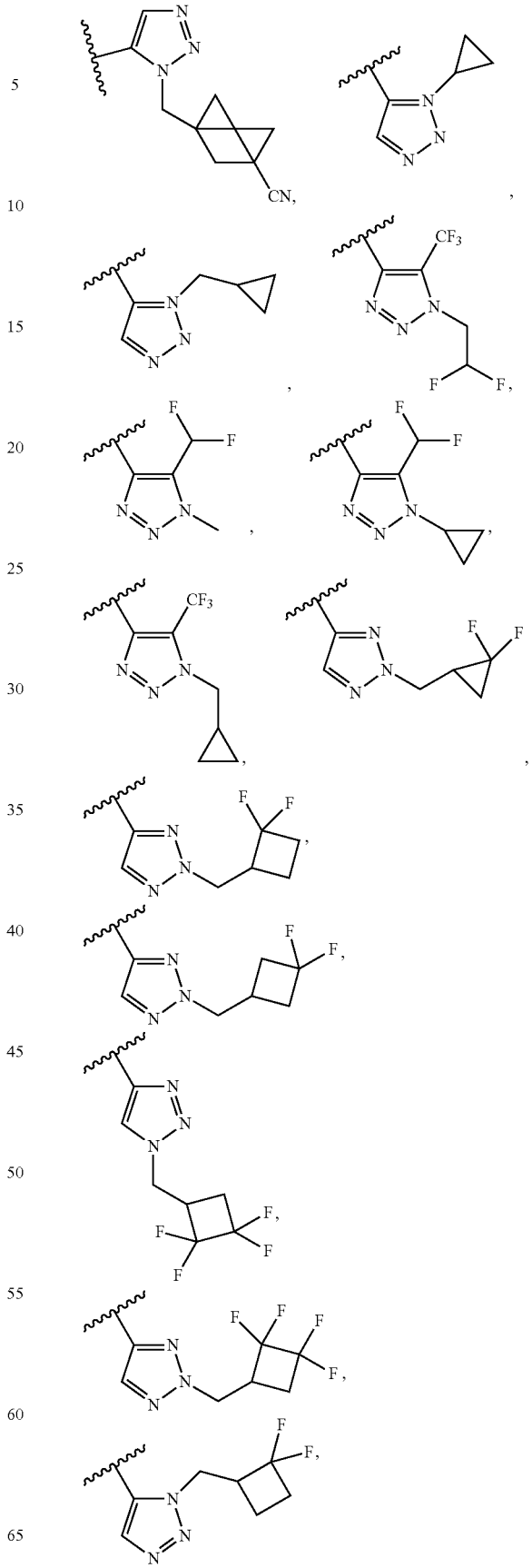

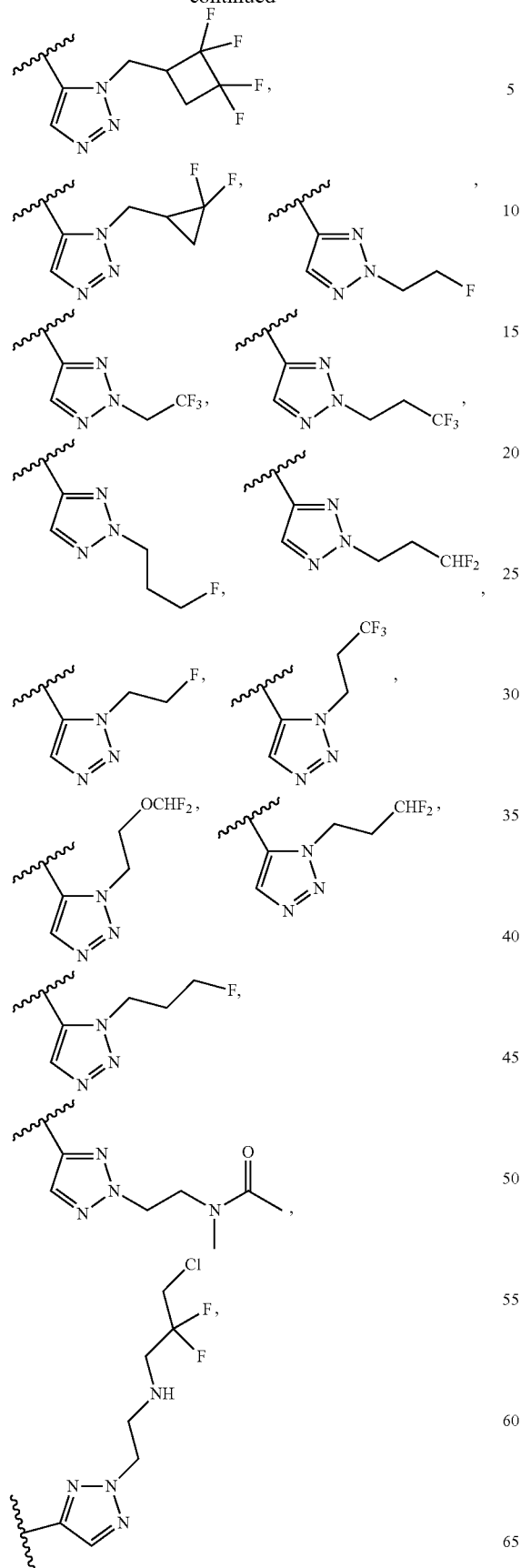
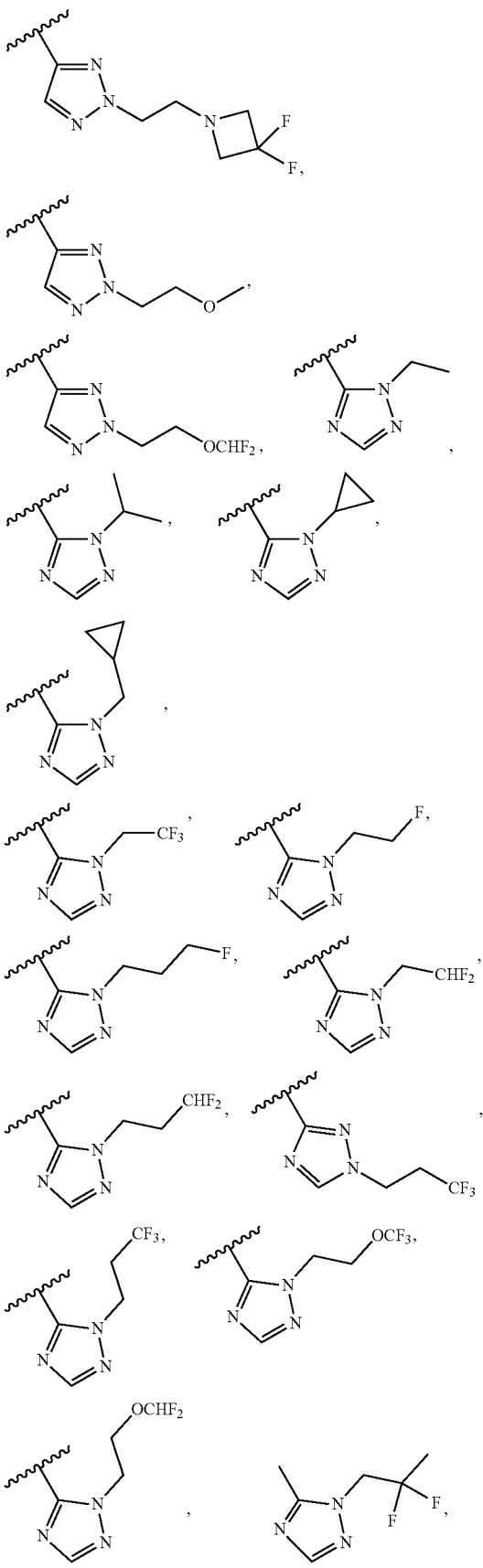

-continued

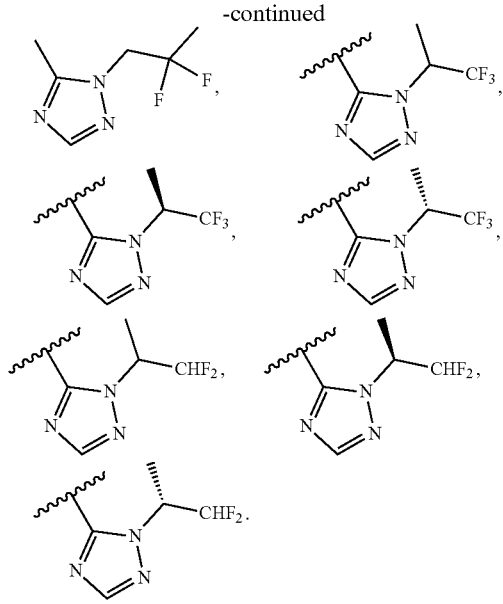

In some embodiments, disclosed herein is a compound of Formula I', or a pharmaceutically acceptable salt thereof, wherein $R^4$ is thienyl, thiazolyl, or thiadiazolyl, each substituted with methyl, isopropyl or cyclopropyl.

In some embodiments, disclosed herein is a compound of Formula I', or a pharmaceutically acceptable salt thereof, wherein $R^4$ is thienyl substituted with isopropyl, thiazolyl substituted with isopropyl, or thiadiazolyl substituted with methyl, isopropyl or cyclopropyl.

In some embodiments, disclosed herein is a compound of Formula I', or a pharmaceutically acceptable salt thereof, wherein $R^4$ is:

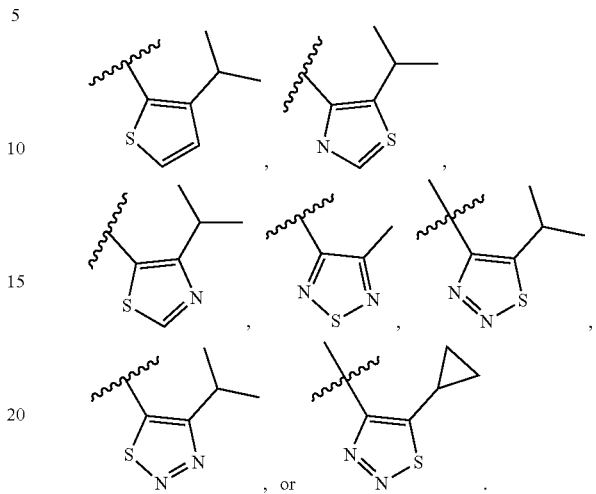

In some embodiments, disclosed herein is a compound of Formula I', or a pharmaceutically acceptable salt thereof, wherein $R^4$ is

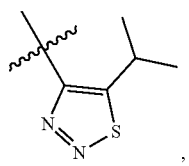 [SMILES: *c1nnsc1C(C)C]

TABLE 2A

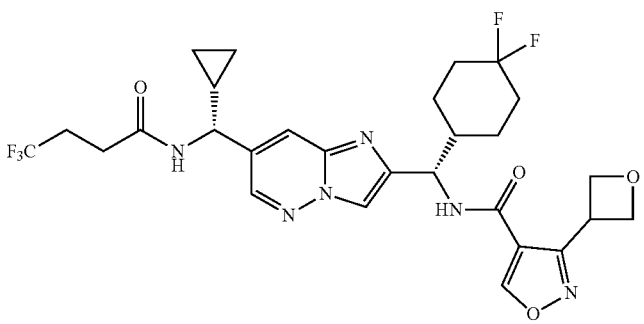 [SMILES: O=C(CCC(F)(F)F)N[C@@H](c1cnn2cc([C@@H](NC(=O)c3conc3C3COC3)C3CCC(F)(F)CC3)nc2c1)C1CC1]

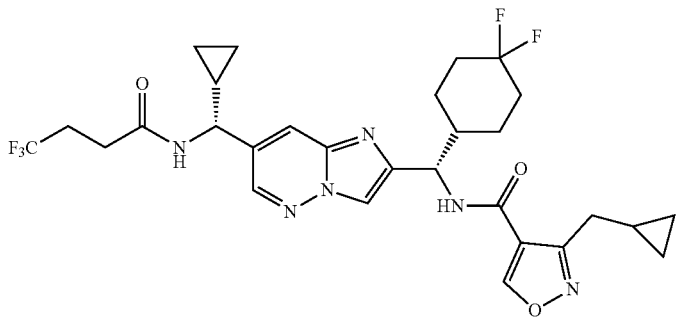 [SMILES: O=C(CCC(F)(F)F)N[C@@H](c1cnn2cc([C@@H](NC(=O)c3conc3CC3CC3)C3CCC(F)(F)CC3)nc2c1)C1CC1]

TABLE 2A-continued
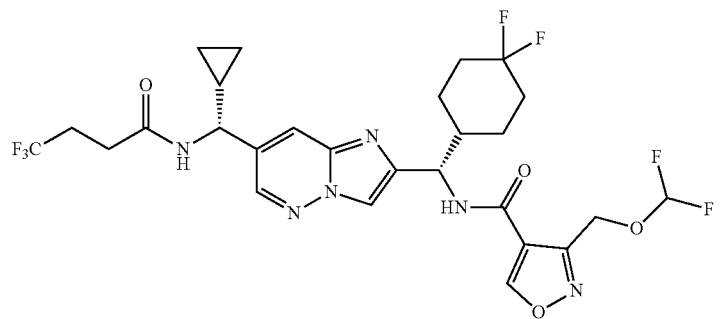 [SMILES: O=C(CCC(F)(F)F)N[C@@H](c1cnn2cc([C@@H](NC(=O)c3conc3COC(F)F)C3CCC(F)(F)CC3)nc2c1)C1CC1]
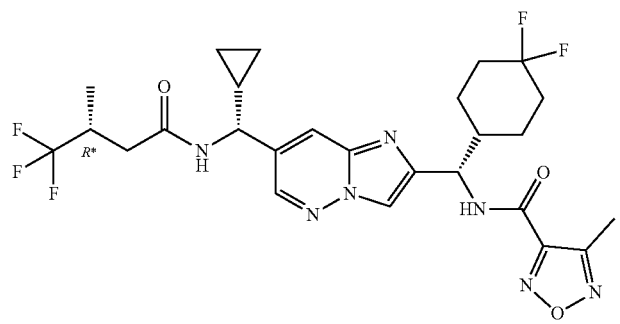 [SMILES: Cc1nonc1C(=O)N[C@H](c1cn2ncc([C@H](NC(=O)C[C@@H](C)C(F)(F)F)C3CC3)cc2n1)C1CCC(F)(F)CC1]
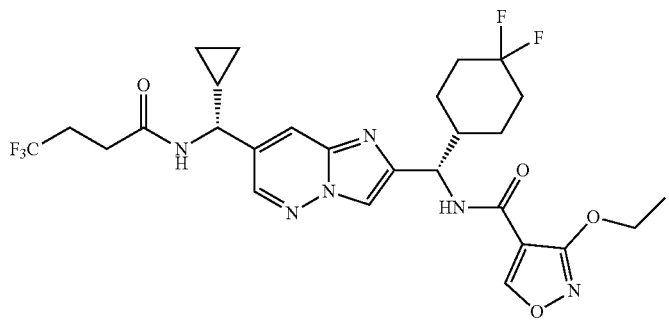 [SMILES: CCOc1nocc1C(=O)N[C@H](c1cn2ncc([C@H](NC(=O)CCC(F)(F)F)C3CC3)cc2n1)C1CCC(F)(F)CC1]
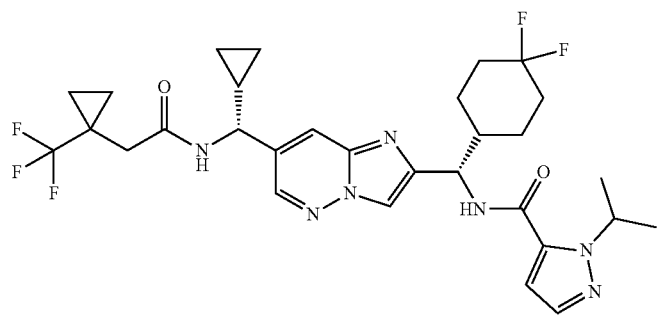 [SMILES: CC(C)n1nccc1C(=O)N[C@H](c1cn2ncc([C@H](NC(=O)CC3(C(F)(F)F)CC3)C3CC3)cc2n1)C1CCC(F)(F)CC1]
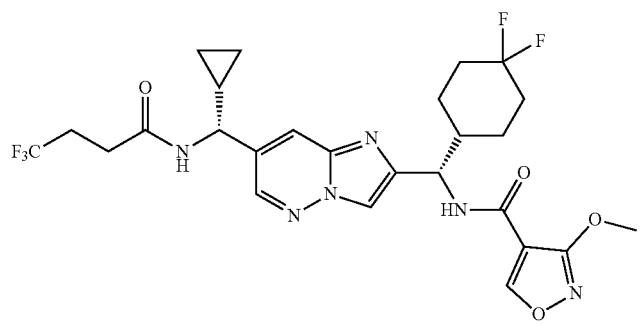 [SMILES: COc1nocc1C(=O)N[C@H](c1cn2ncc([C@H](NC(=O)CCC(F)(F)F)C3CC3)cc2n1)C1CCC(F)(F)CC1]

TABLE 2A-continued
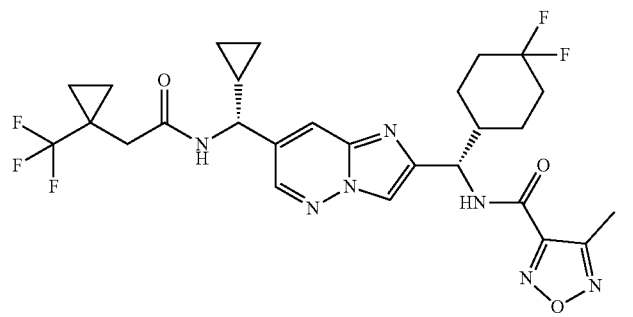 [SMILES: Cc1nonc1C(=O)N[C@H](c1cn2ncc([C@H](NC(=O)CC3(C(F)(F)F)CC3)C3CC3)cc2n1)C1CCC(F)(F)CC1]
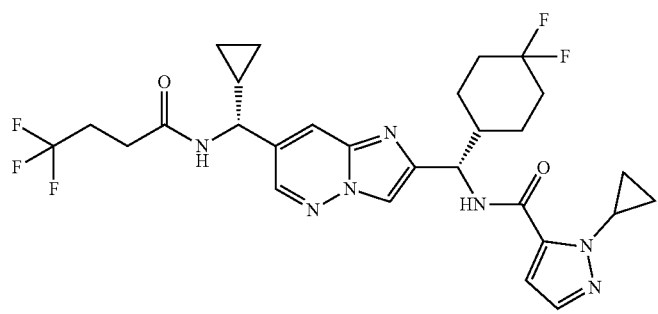 [SMILES: O=C(CCC(F)(F)F)N[C@@H](c1cnn2cc([C@@H](NC(=O)c3ccnn3C3CC3)C3CCC(F)(F)CC3)nc2c1)C1CC1]
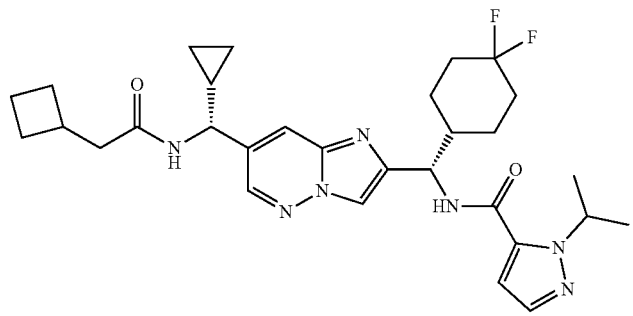 [SMILES: CC(C)n1nccc1C(=O)N[C@H](c1cn2ncc([C@H](NC(=O)CC3CCC3)C3CC3)cc2n1)C1CCC(F)(F)CC1]
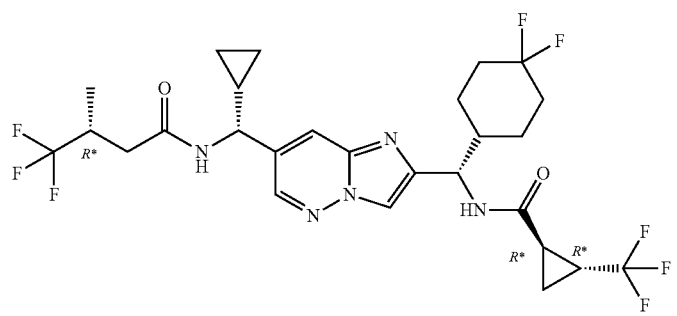 [SMILES: C[C@H](CC(=O)N[C@@H](c1cnn2cc([C@@H](NC(=O)[C@@H]3C[C@H]3C(F)(F)F)C3CCC(F)(F)CC3)nc2c1)C1CC1)C(F)(F)F]
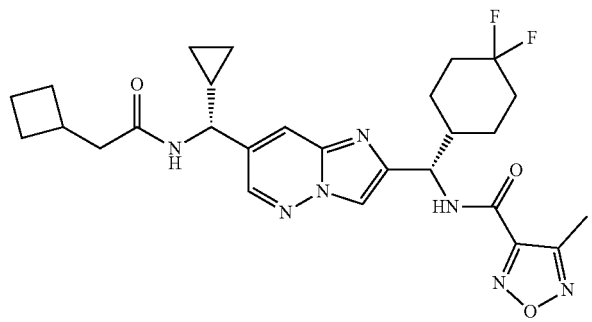 [SMILES: Cc1nonc1C(=O)N[C@H](c1cn2ncc([C@H](NC(=O)CC3CCC3)C3CC3)cc2n1)C1CCC(F)(F)CC1]

TABLE 2A-continued
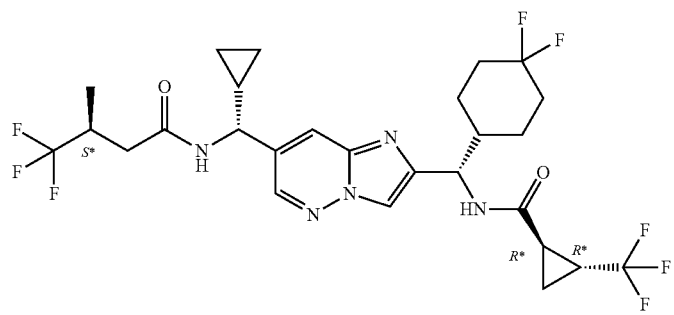 [SMILES: C[C@@H](CC(=O)N[C@@H](c1cnn2cc([C@@H](NC(=O)[C@@H]3C[C@H]3C(F)(F)F)C3CCC(F)(F)CC3)nc2c1)C1CC1)C(F)(F)F]
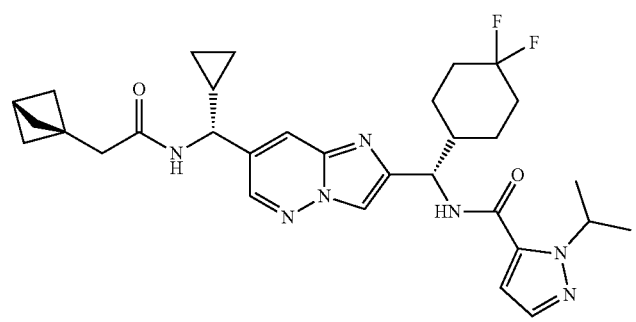
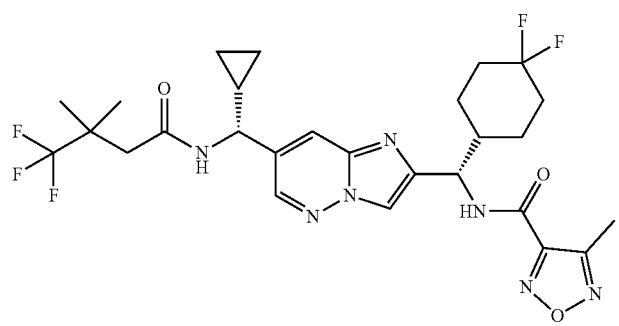 [SMILES: Cc1nonc1C(=O)N[C@H](c1cn2ncc([C@H](NC(=O)CC(C)(C)C(F)(F)F)C3CC3)cc2n1)C1CCC(F)(F)CC1]
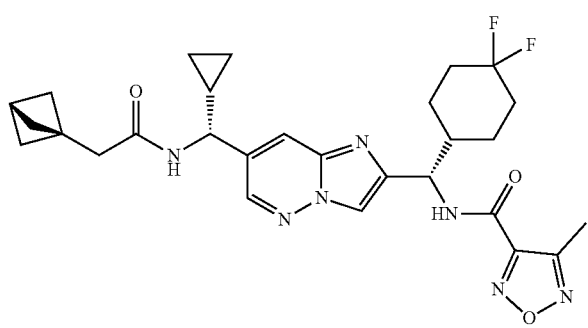
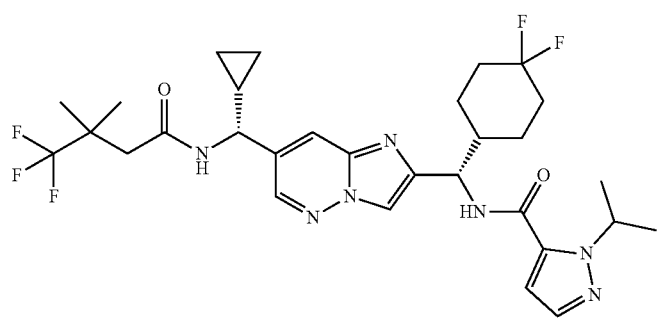 [SMILES: CC(C)n1nccc1C(=O)N[C@H](c1cn2ncc([C@H](NC(=O)CC(C)(C)C(F)(F)F)C3CC3)cc2n1)C1CCC(F)(F)CC1]

TABLE 2A-continued
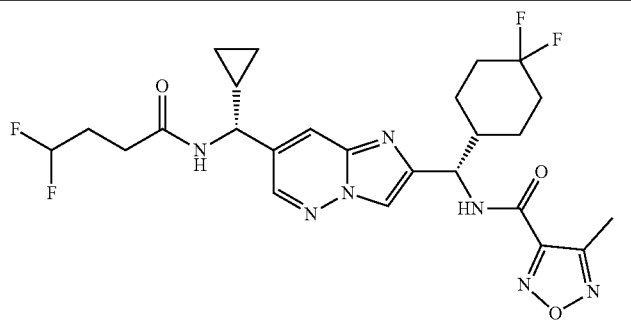
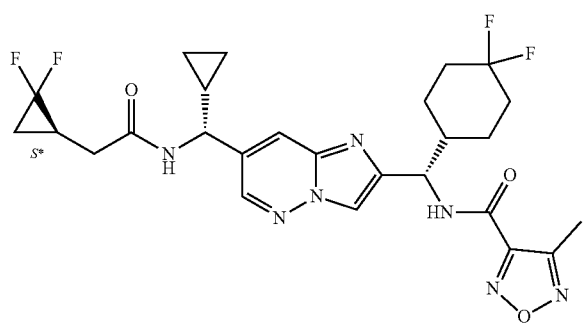 [SMILES: Cc1nonc1C(=O)N[C@H](c1cn2ncc([C@H](NC(=O)C[C@H]3CC3(F)F)C3CC3)cc2n1)C1CCC(F)(F)CC1]
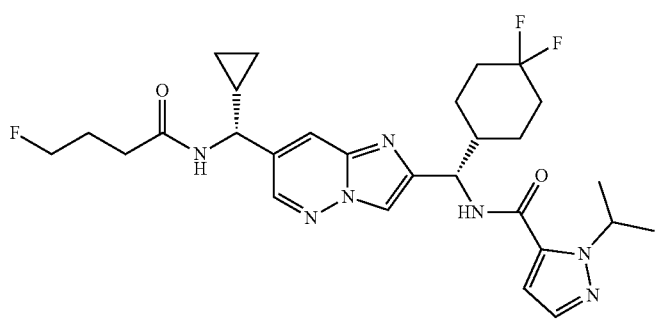 [SMILES: CC(C)n1nccc1C(=O)N[C@H](c1cn2ncc([C@H](NC(=O)CCCF)C3CC3)cc2n1)C1CCC(F)(F)CC1]
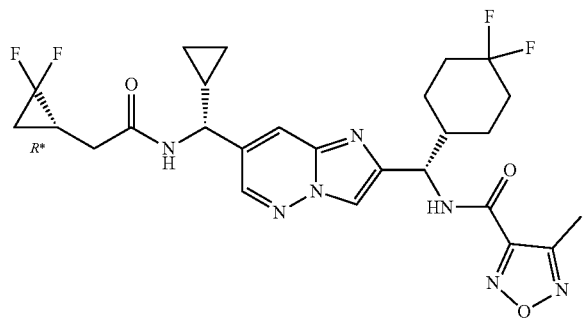 [SMILES: Cc1nonc1C(=O)N[C@H](c1cn2ncc([C@H](NC(=O)C[C@@H]3CC3(F)F)C3CC3)cc2n1)C1CCC(F)(F)CC1]
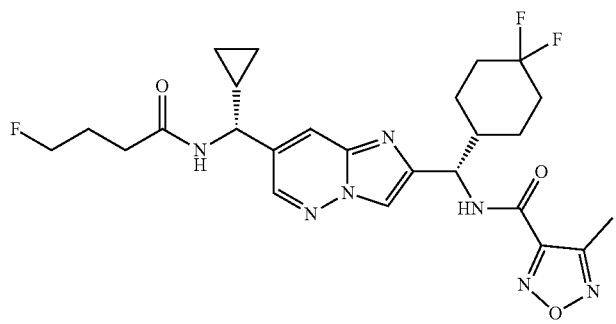 [SMILES: Cc1nonc1C(=O)N[C@H](c1cn2ncc([C@H](NC(=O)CCCF)C3CC3)cc2n1)C1CCC(F)(F)CC1]

TABLE 2A-continued
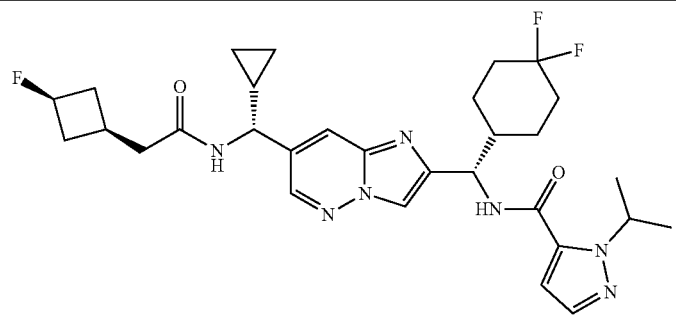
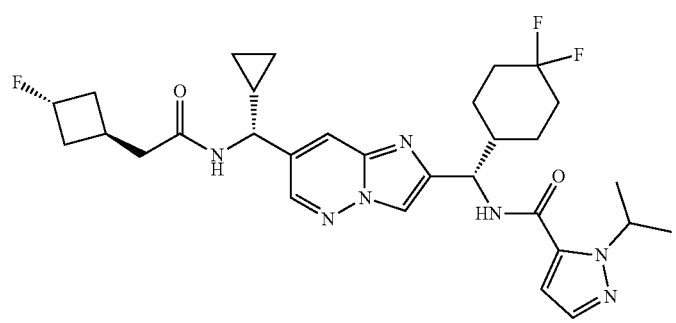 [SMILES: CC(C)n1nccc1C(=O)N[C@H](c1cn2ncc([C@H](NC(=O)C[C@H]3C[C@H](F)C3)C3CC3)cc2n1)C1CCC(F)(F)CC1]
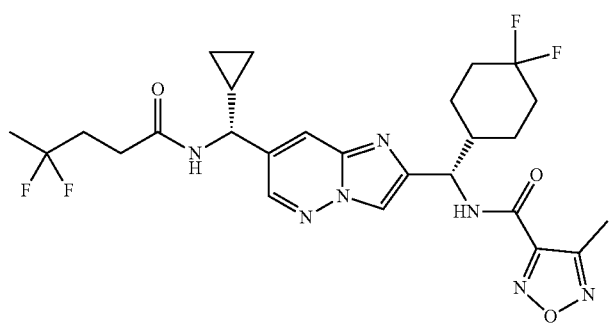 [SMILES: Cc1nonc1C(=O)N[C@H](c1cn2ncc([C@H](NC(=O)CCC(C)(F)F)C3CC3)cc2n1)C1CCC(F)(F)CC1]
TABLE 2B
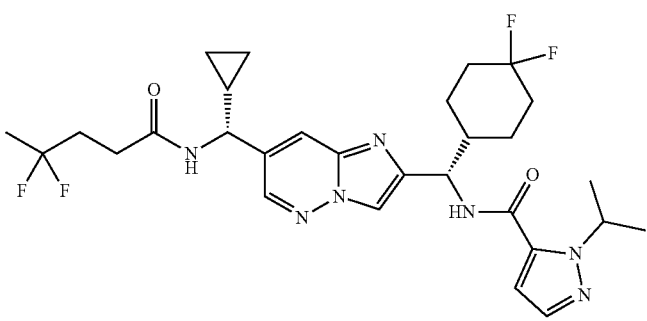 [SMILES: CC(C)n1nccc1C(=O)N[C@H](c1cn2ncc([C@H](NC(=O)CCC(C)(F)F)C3CC3)cc2n1)C1CCC(F)(F)CC1]

TABLE 2B-continued
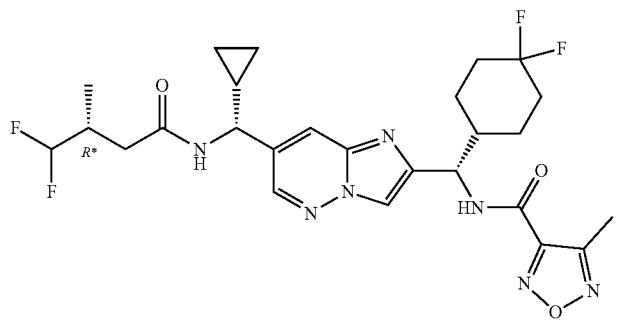 [SMILES: Cc1nonc1C(=O)N[C@H](c1cn2ncc([C@H](NC(=O)C[C@@H](C)C(F)F)C3CC3)cc2n1)C1CCC(F)(F)CC1]
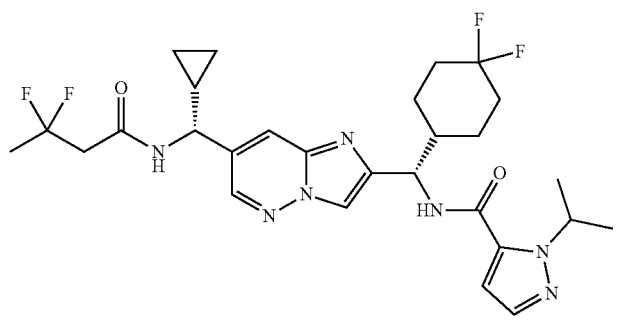 [SMILES: CC(C)n1nccc1C(=O)N[C@H](c1cn2ncc([C@H](NC(=O)CC(C)(F)F)C3CC3)cc2n1)C1CCC(F)(F)CC1]
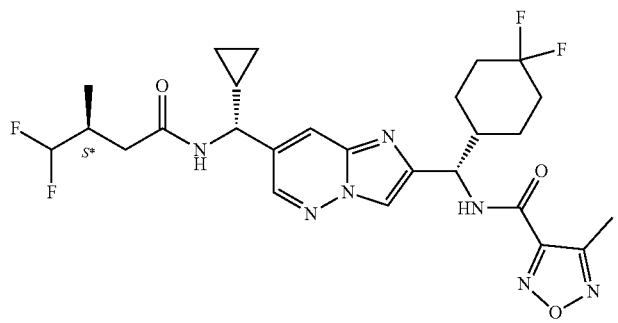 [SMILES: Cc1nonc1C(=O)N[C@H](c1cn2ncc([C@H](NC(=O)C[C@H](C)C(F)F)C3CC3)cc2n1)C1CCC(F)(F)CC1]
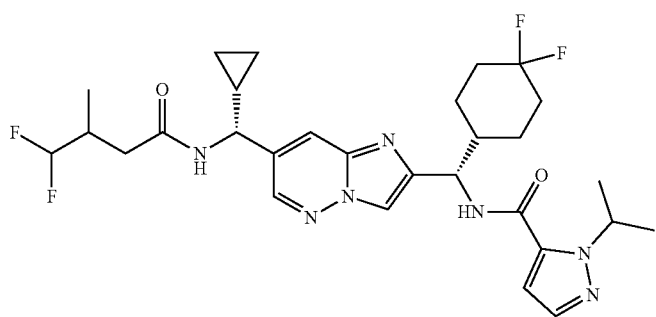 [SMILES: CC(CC(=O)N[C@@H](c1cnn2cc([C@@H](NC(=O)c3ccnn3C(C)C)C3CCC(F)(F)CC3)nc2c1)C1CC1)C(F)F]
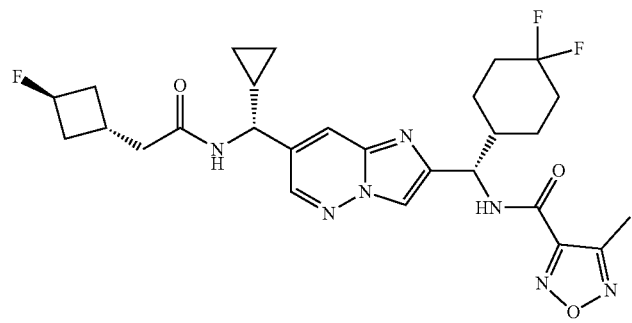 [SMILES: Cc1nonc1C(=O)N[C@H](c1cn2ncc([C@H](NC(=O)C[C@H]3C[C@H](F)C3)C3CC3)cc2n1)C1CCC(F)(F)CC1]

TABLE 2B-continued
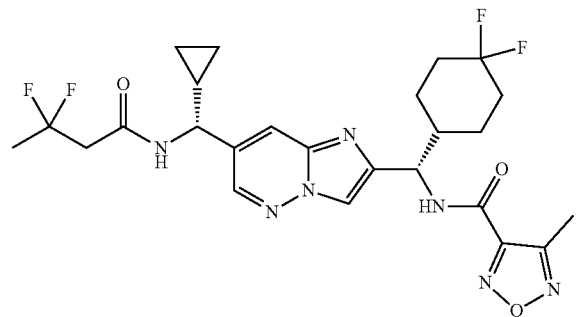 [SMILES: Cc1nonc1C(=O)N[C@H](c1cn2ncc([C@H](NC(=O)CC(C)(F)F)C3CC3)cc2n1)C1CCC(F)(F)CC1]
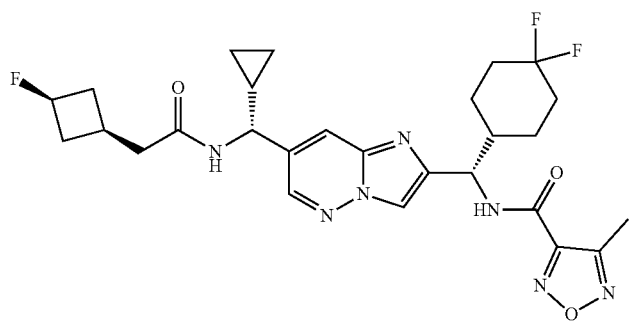 [SMILES: Cc1nonc1C(=O)N[C@H](c1cn2ncc([C@H](NC(=O)C[C@H]3C[C@@H](F)C3)C3CC3)cc2n1)C1CCC(F)(F)CC1]
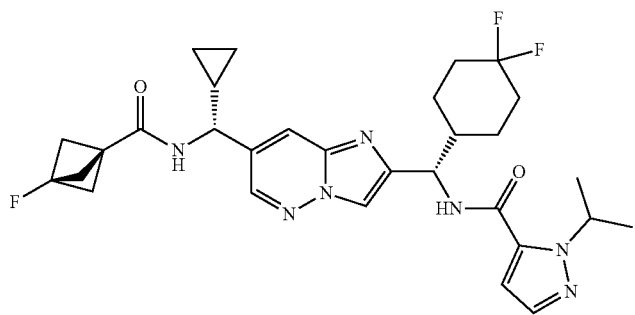 [SMILES: CC(C)n1nccc1C(=O)N[C@H](c1cn2ncc([C@H](NC(=O)[C@]34C[C@](F)(C3)C4)C3CC3)cc2n1)C1CCC(F)(F)CC1]
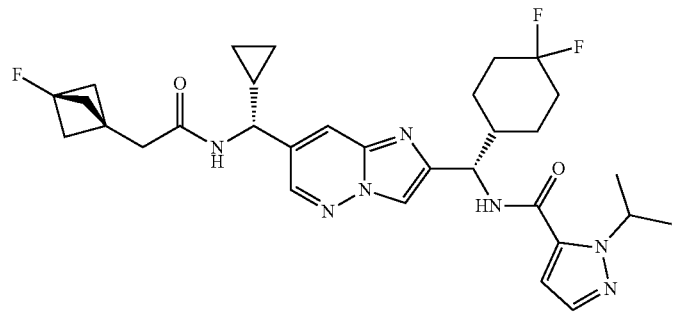 [SMILES: CC(C)n1nccc1C(=O)N[C@H](c1cn2ncc([C@H](NC(=O)C[C@]34C[C@](F)(C3)C4)C3CC3)cc2n1)C1CCC(F)(F)CC1]
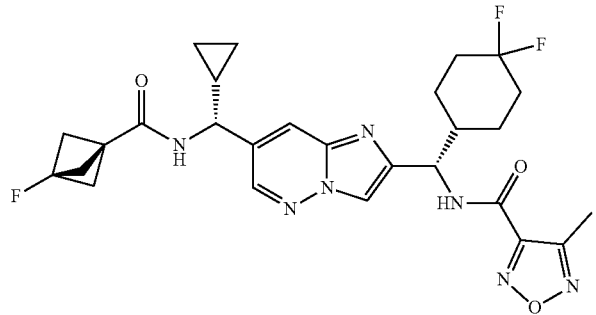 [SMILES: Cc1nonc1C(=O)N[C@H](c1cn2ncc([C@H](NC(=O)[C@]34C[C@](F)(C3)C4)C3CC3)cc2n1)C1CCC(F)(F)CC1]

TABLE 2B-continued
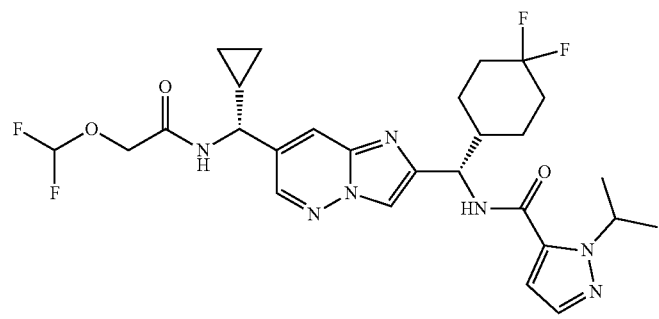 [SMILES: CC(C)n1nccc1C(=O)N[C@H](c1cn2ncc([C@H](NC(=O)COC(F)F)C3CC3)cc2n1)C1CCC(F)(F)CC1]
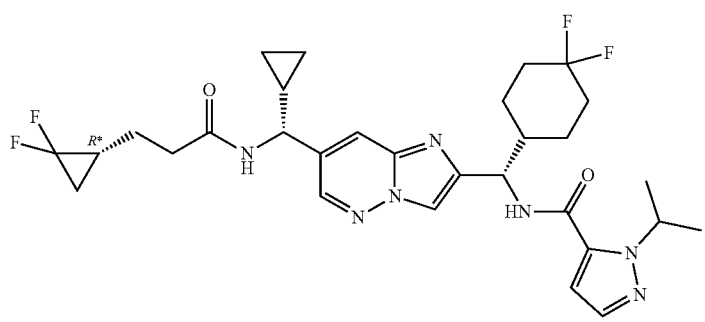 [SMILES: CC(C)n1nccc1C(=O)N[C@H](c1cn2ncc([C@H](NC(=O)CC[C@@H]3CC3(F)F)C3CC3)cc2n1)C1CCC(F)(F)CC1]
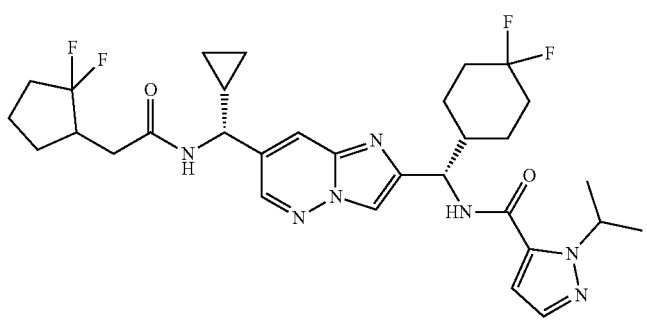 [SMILES: CC(C)n1nccc1C(=O)N[C@H](c1cn2ncc([C@H](NC(=O)CC3CCCC3(F)F)C3CC3)cc2n1)C1CCC(F)(F)CC1]
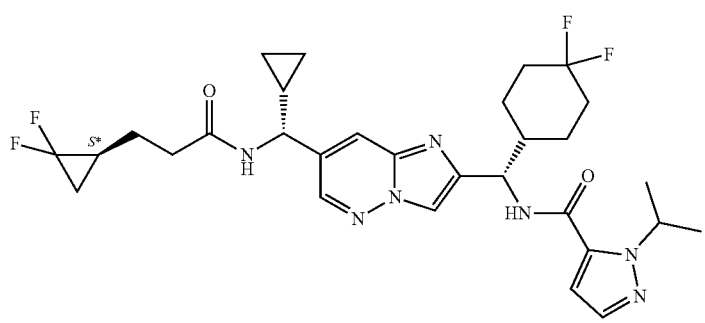 [SMILES: CC(C)n1nccc1C(=O)N[C@H](c1cn2ncc([C@H](NC(=O)CC[C@H]3CC3(F)F)C3CC3)cc2n1)C1CCC(F)(F)CC1]
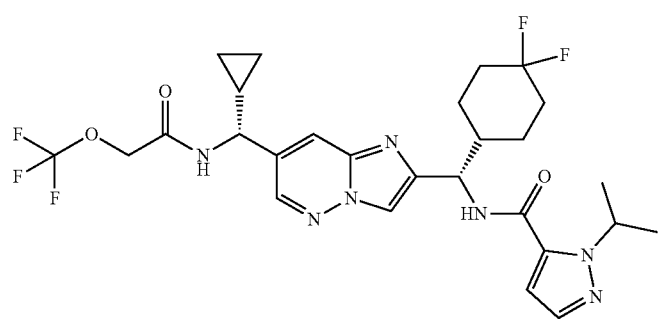 [SMILES: CC(C)n1nccc1C(=O)N[C@H](c1cn2ncc([C@H](NC(=O)COC(F)(F)F)C3CC3)cc2n1)C1CCC(F)(F)CC1]

TABLE 2B-continued
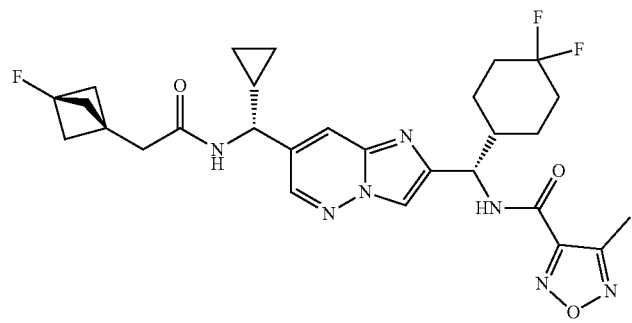 [SMILES: Cc1nonc1C(=O)N[C@H](c1cn2ncc([C@H](NC(=O)C[C@]34C[C@](F)(C3)C4)C3CC3)cc2n1)C1CCC(F)(F)CC1]
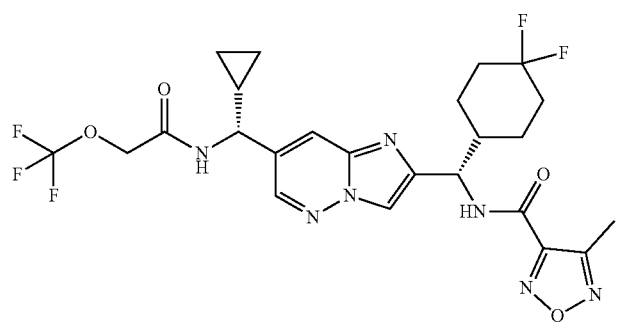 [SMILES: Cc1nonc1C(=O)N[C@H](c1cn2ncc([C@H](NC(=O)COC(F)(F)F)C3CC3)cc2n1)C1CCC(F)(F)CC1]
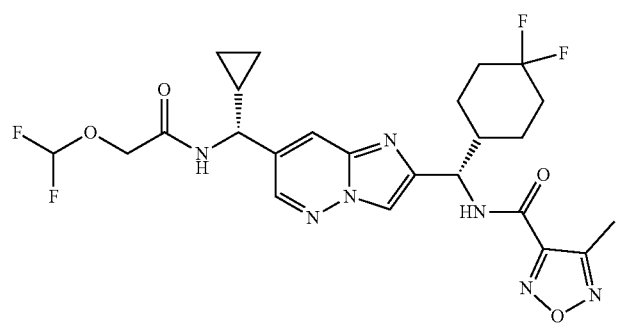 [SMILES: Cc1nonc1C(=O)N[C@H](c1cn2ncc([C@H](NC(=O)COC(F)F)C3CC3)cc2n1)C1CCC(F)(F)CC1]
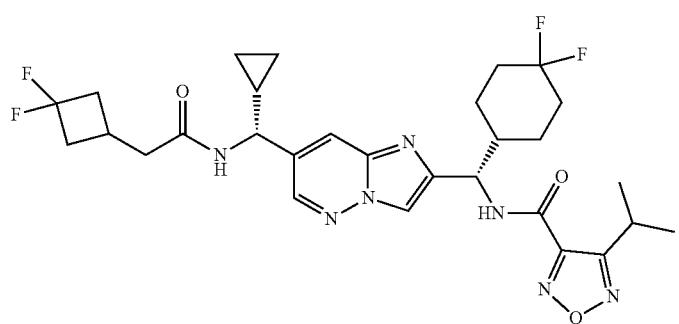 [SMILES: CC(C)c1nonc1C(=O)N[C@H](c1cn2ncc([C@H](NC(=O)CC3CC(F)(F)C3)C3CC3)cc2n1)C1CCC(F)(F)CC1]
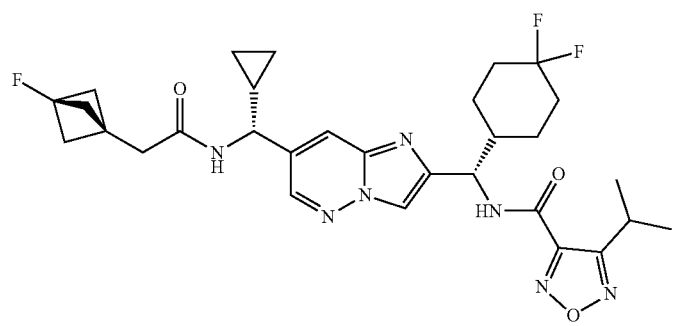 [SMILES: CC(C)c1nonc1C(=O)N[C@H](c1cn2ncc([C@H](NC(=O)C[C@]34C[C@](F)(C3)C4)C3CC3)cc2n1)C1CCC(F)(F)CC1]

TABLE 2B-continued
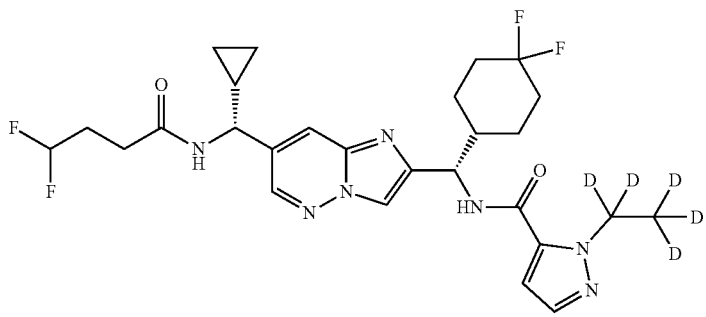 [SMILES: [2H]C([2H])([2H])C([2H])([2H])n1nccc1C(=O)N[C@H](c1cn2ncc([C@H](NC(=O)CCC(F)F)C3CC3)cc2n1)C1CCC(F)(F)CC1]
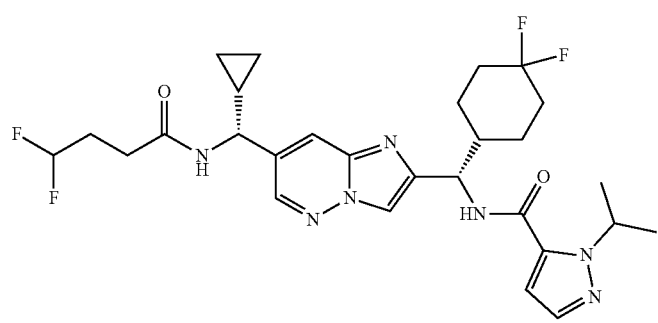 [SMILES: CC(C)n1nccc1C(=O)N[C@H](c1cn2ncc([C@H](NC(=O)CCC(F)F)C3CC3)cc2n1)C1CCC(F)(F)CC1]
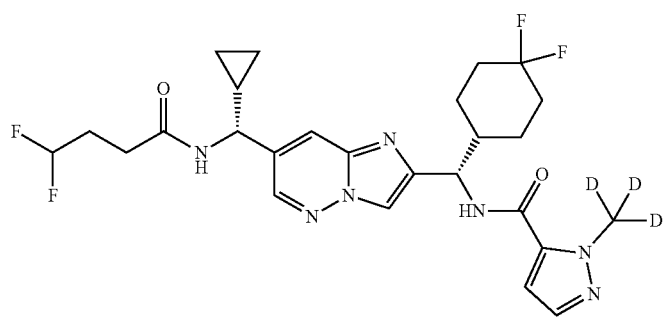 [SMILES: [2H]C([2H])([2H])n1nccc1C(=O)N[C@H](c1cn2ncc([C@H](NC(=O)CCC(F)F)C3CC3)cc2n1)C1CCC(F)(F)CC1]
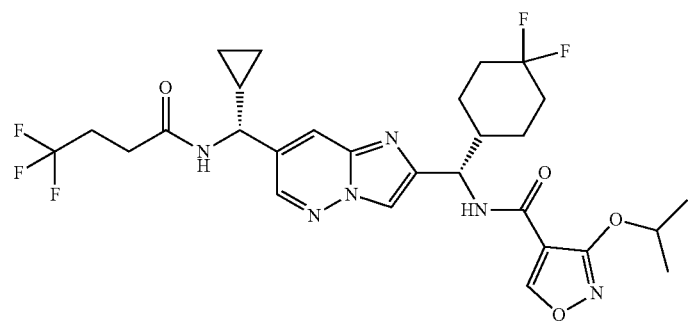 [SMILES: CC(C)Oc1nocc1C(=O)N[C@H](c1cn2ncc([C@H](NC(=O)CCC(F)(F)F)C3CC3)cc2n1)C1CCC(F)(F)CC1]

TABLE 2C
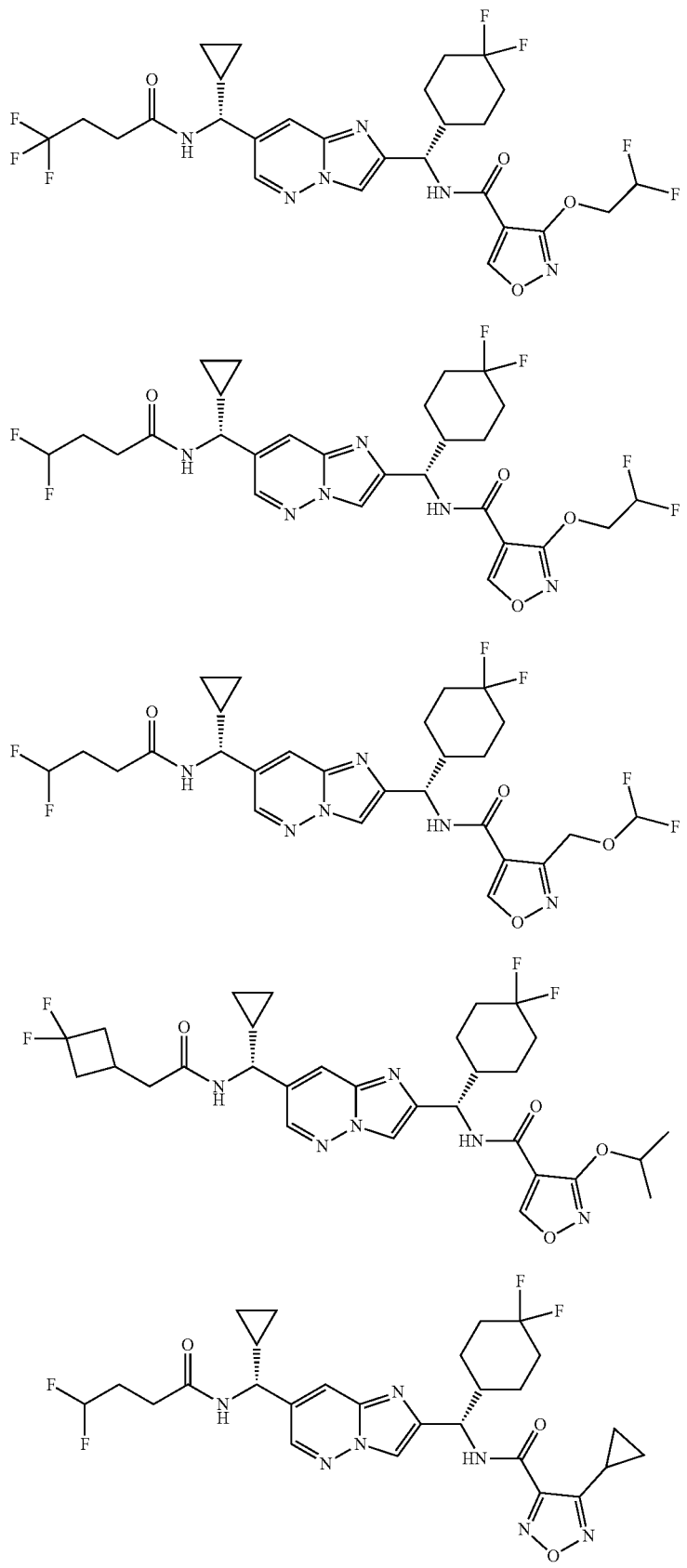

TABLE 2C-continued
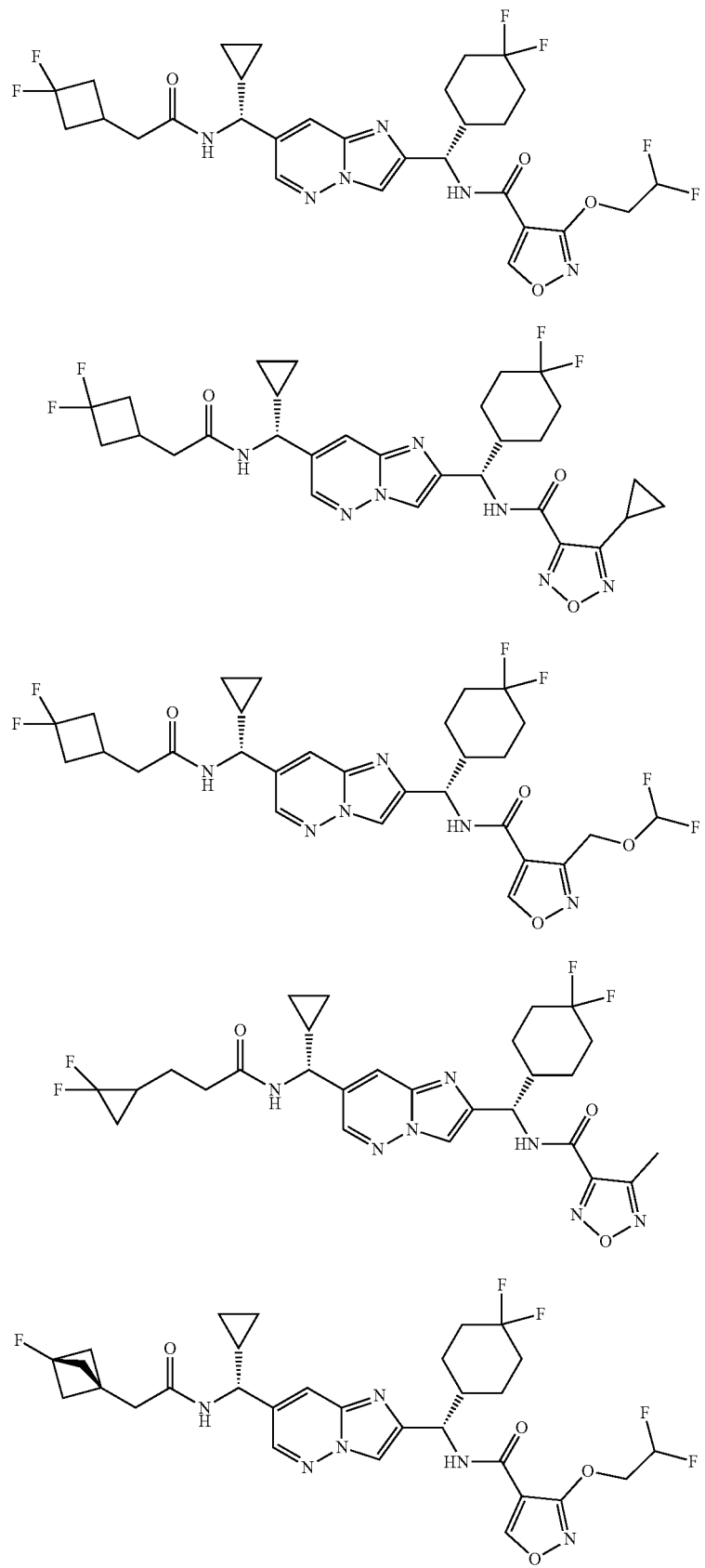

TABLE 2C-continued
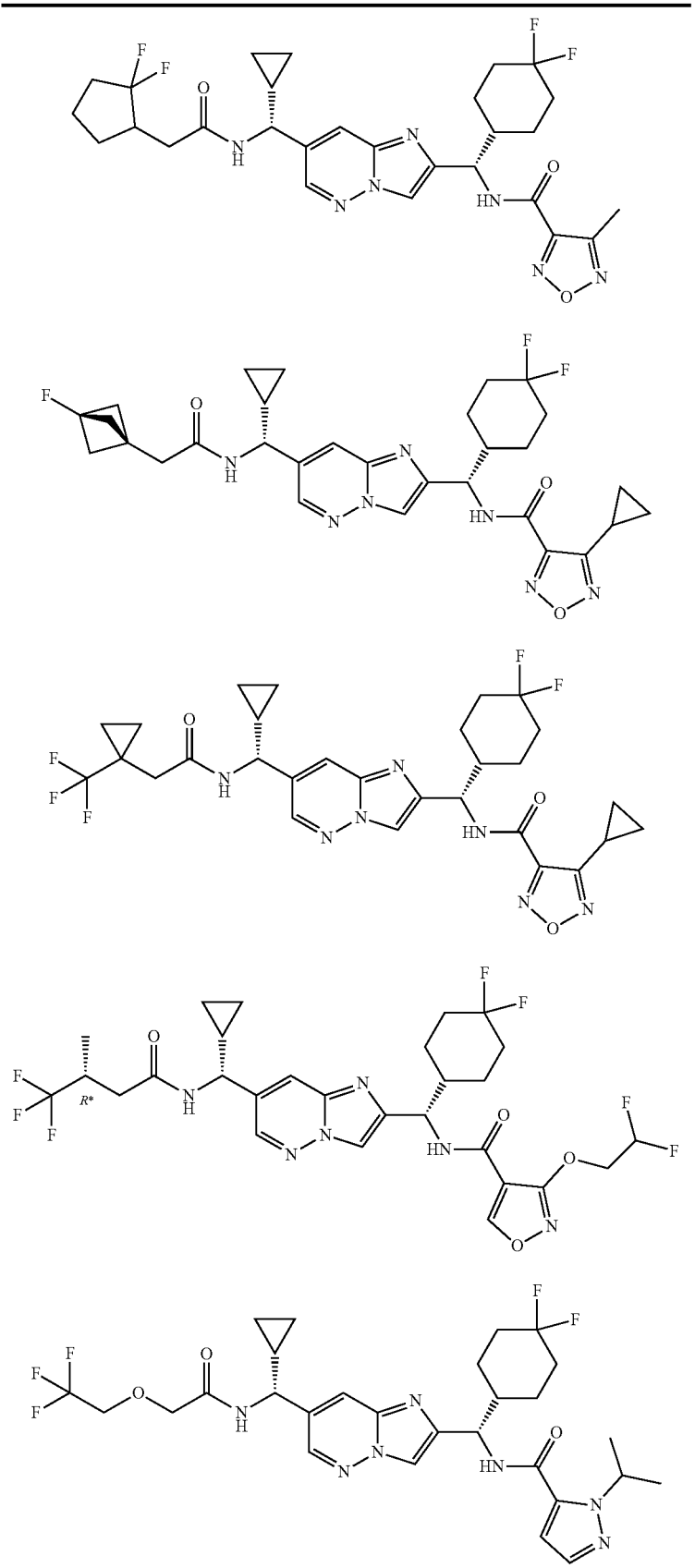

TABLE 2C-continued
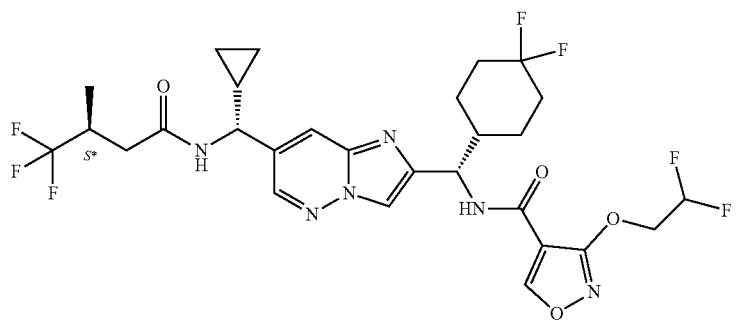 [SMILES: C[C@@H](CC(=O)N[C@@H](c1cnn2cc([C@@H](NC(=O)c3conc3OCC(F)F)C3CCC(F)(F)CC3)nc2c1)C1CC1)C(F)(F)F]
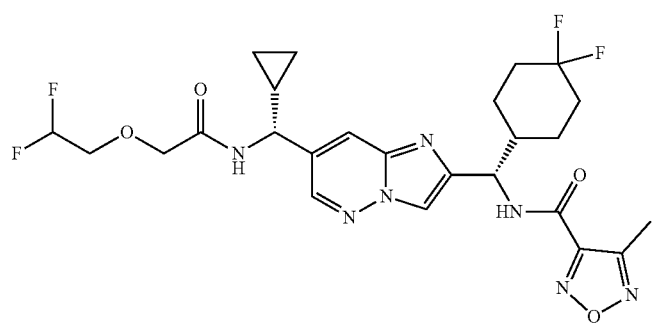 [SMILES: Cc1nonc1C(=O)N[C@H](c1cn2ncc([C@H](NC(=O)COCC(F)F)C3CC3)cc2n1)C1CCC(F)(F)CC1]
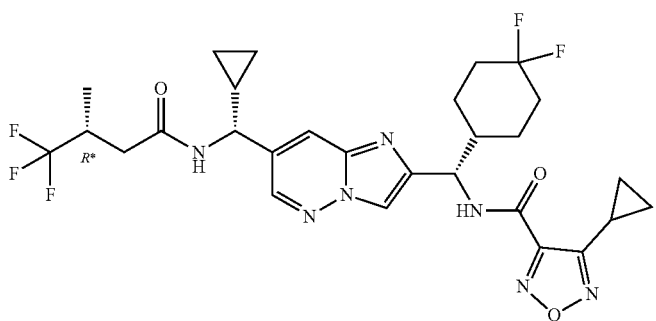 [SMILES: C[C@H](CC(=O)N[C@@H](c1cnn2cc([C@@H](NC(=O)c3nonc3C3CC3)C3CCC(F)(F)CC3)nc2c1)C1CC1)C(F)(F)F]
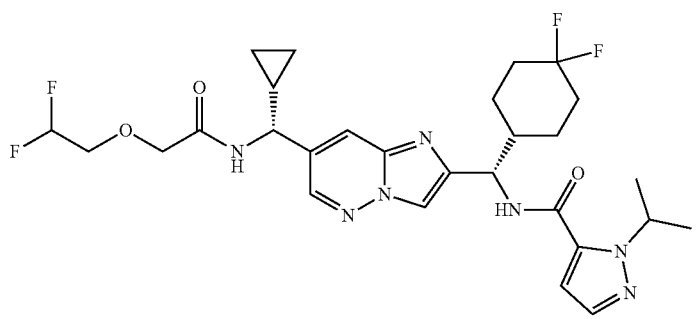 [SMILES: CC(C)n1nccc1C(=O)N[C@H](c1cn2ncc([C@H](NC(=O)COCC(F)F)C3CC3)cc2n1)C1CCC(F)(F)CC1]
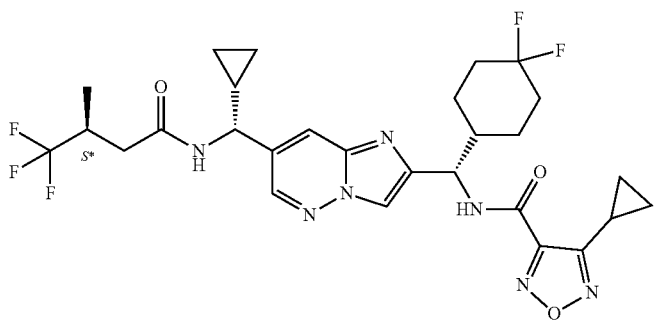 [SMILES: C[C@@H](CC(=O)N[C@@H](c1cnn2cc([C@@H](NC(=O)c3nonc3C3CC3)C3CCC(F)(F)CC3)nc2c1)C1CC1)C(F)(F)F]

TABLE 2C-continued
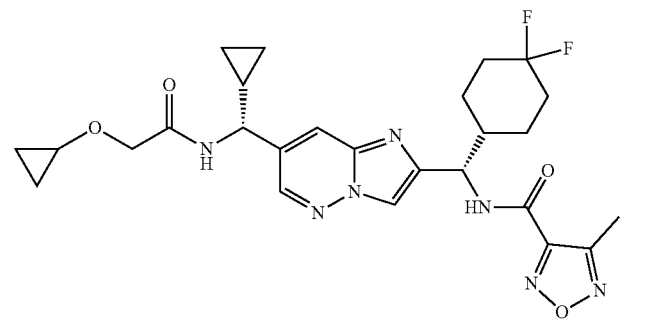 [SMILES: Cc1nonc1C(=O)N[C@H](c1cn2ncc([C@H](NC(=O)COC3CC3)C3CC3)cc2n1)C1CCC(F)(F)CC1]
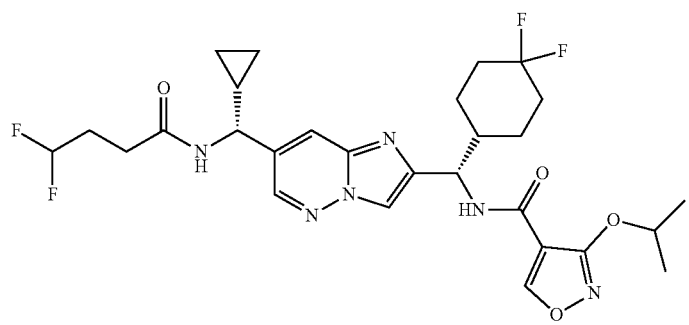 [SMILES: CC(C)Oc1nocc1C(=O)N[C@H](c1cn2ncc([C@H](NC(=O)CCC(F)F)C3CC3)cc2n1)C1CCC(F)(F)CC1]
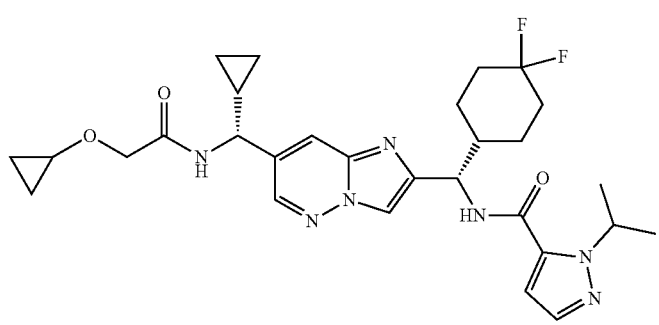 [SMILES: CC(C)n1nccc1C(=O)N[C@H](c1cn2ncc([C@H](NC(=O)COC3CC3)C3CC3)cc2n1)C1CCC(F)(F)CC1]
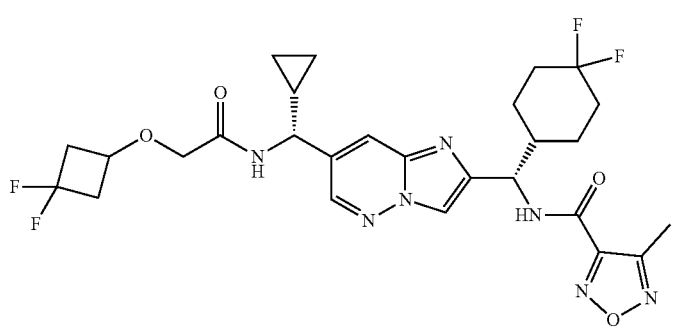 [SMILES: Cc1nonc1C(=O)N[C@H](c1cn2ncc([C@H](NC(=O)COC3CC(F)(F)C3)C3CC3)cc2n1)C1CCC(F)(F)CC1]
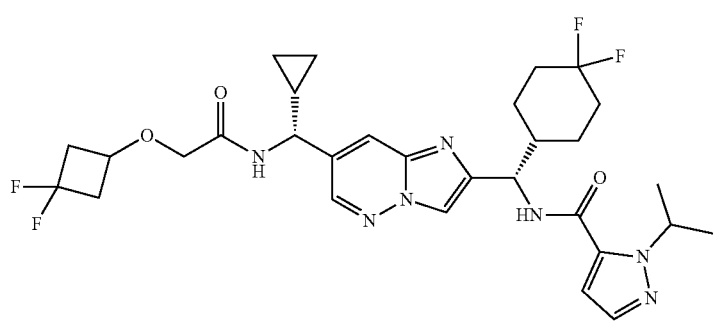 [SMILES: CC(C)n1nccc1C(=O)N[C@H](c1cn2ncc([C@H](NC(=O)COC3CC(F)(F)C3)C3CC3)cc2n1)C1CCC(F)(F)CC1]

TABLE 2D
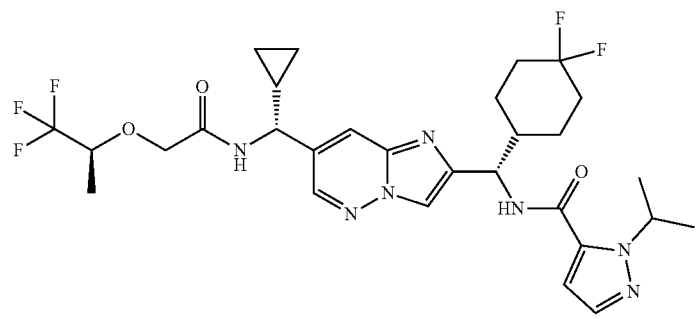 [SMILES: CC(C)n1nccc1C(=O)N[C@H](c1cn2ncc([C@H](NC(=O)CO[C@@H](C)C(F)(F)F)C3CC3)cc2n1)C1CCC(F)(F)CC1]
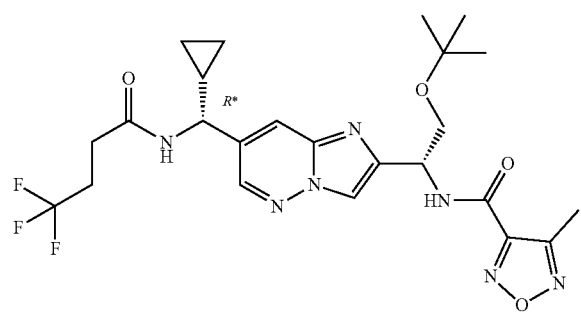 [SMILES: Cc1nonc1C(=O)N[C@@H](COC(C)(C)C)c1cn2ncc([C@H](NC(=O)CCC(F)(F)F)C3CC3)cc2n1]
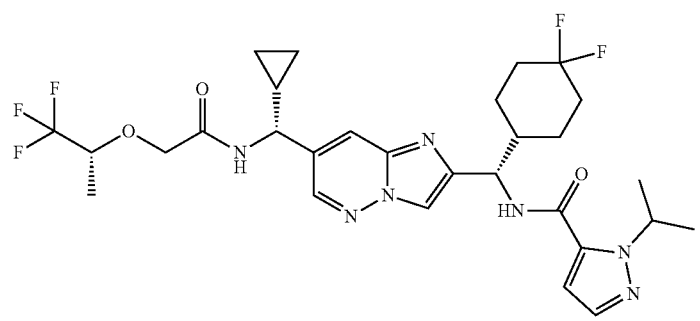 [SMILES: CC(C)n1nccc1C(=O)N[C@H](c1cn2ncc([C@H](NC(=O)CO[C@H](C)C(F)(F)F)C3CC3)cc2n1)C1CCC(F)(F)CC1]
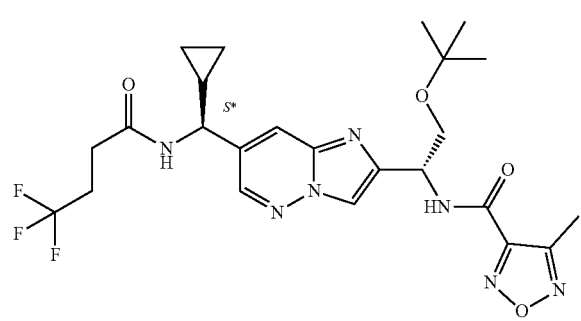 [SMILES: Cc1nonc1C(=O)N[C@@H](COC(C)(C)C)c1cn2ncc([C@@H](NC(=O)CCC(F)(F)F)C3CC3)cc2n1]
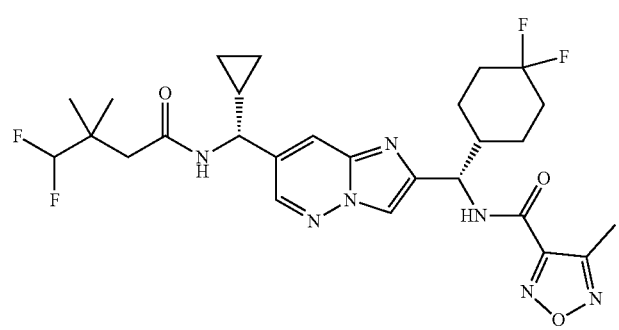 [SMILES: Cc1nonc1C(=O)N[C@H](c1cn2ncc([C@H](NC(=O)CC(C)(C)C(F)F)C3CC3)cc2n1)C1CCC(F)(F)CC1]

TABLE 2D-continued
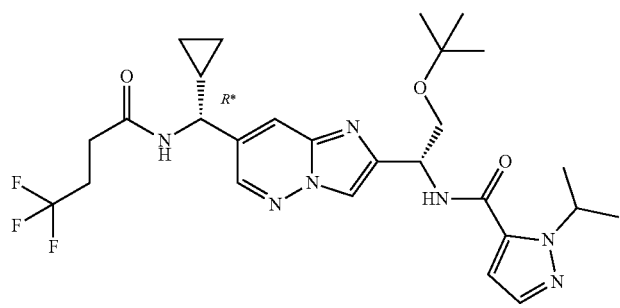 [SMILES: CC(C)n1nccc1C(=O)N[C@@H](COC(C)(C)C)c1cn2ncc([C@H](NC(=O)CCC(F)(F)F)C3CC3)cc2n1]
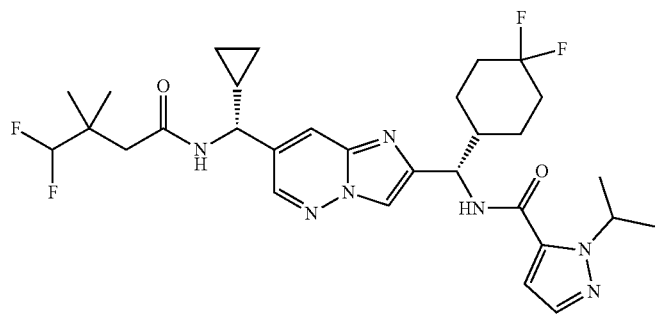 [SMILES: CC(C)n1nccc1C(=O)N[C@H](c1cn2ncc([C@H](NC(=O)CC(C)(C)C(F)F)C3CC3)cc2n1)C1CCC(F)(F)CC1]
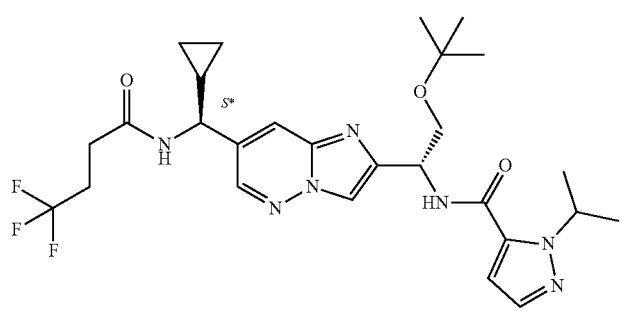 [SMILES: CC(C)n1nccc1C(=O)N[C@@H](COC(C)(C)C)c1cn2ncc([C@@H](NC(=O)CCC(F)(F)F)C3CC3)cc2n1]
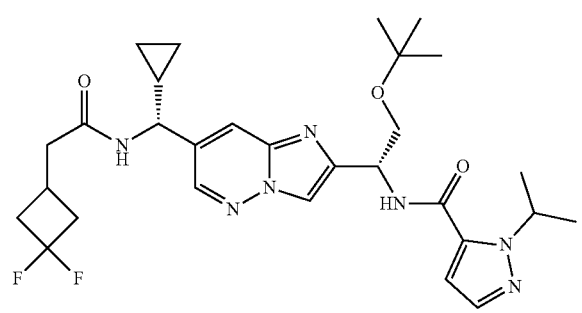 [SMILES: CC(C)n1nccc1C(=O)N[C@@H](COC(C)(C)C)c1cn2ncc([C@H](NC(=O)CC3CC(F)(F)C3)C3CC3)cc2n1]
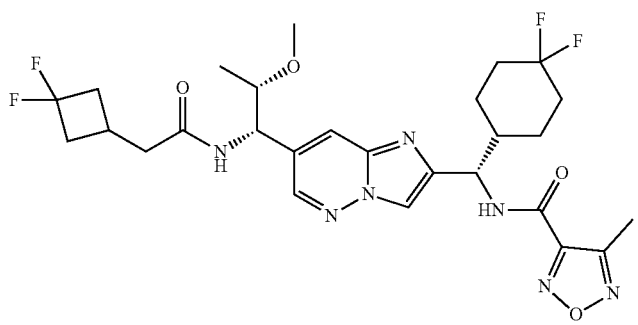 [SMILES: CO[C@@H](C)[C@@H](NC(=O)CC1CC(F)(F)C1)c1cnn2cc([C@@H](NC(=O)c3nonc3C)C3CCC(F)(F)CC3)nc2c1]

TABLE 2D-continued
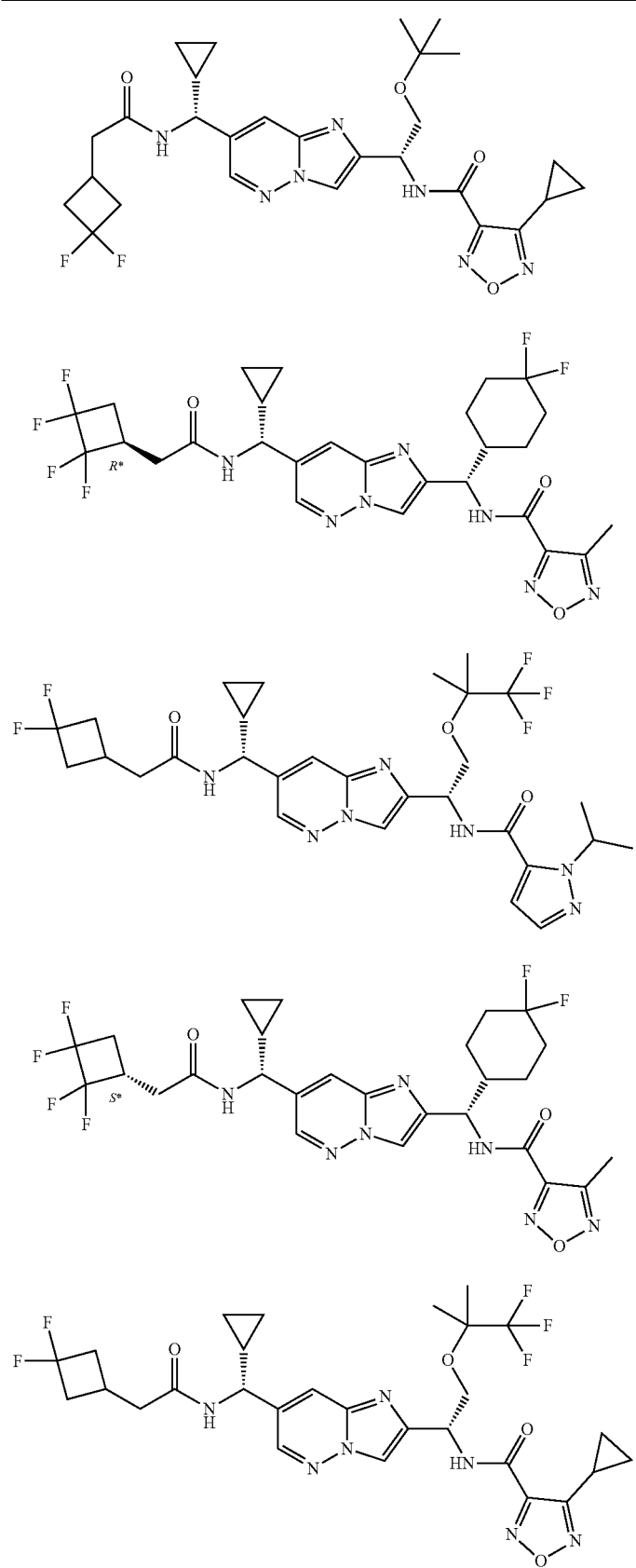

TABLE 2D-continued
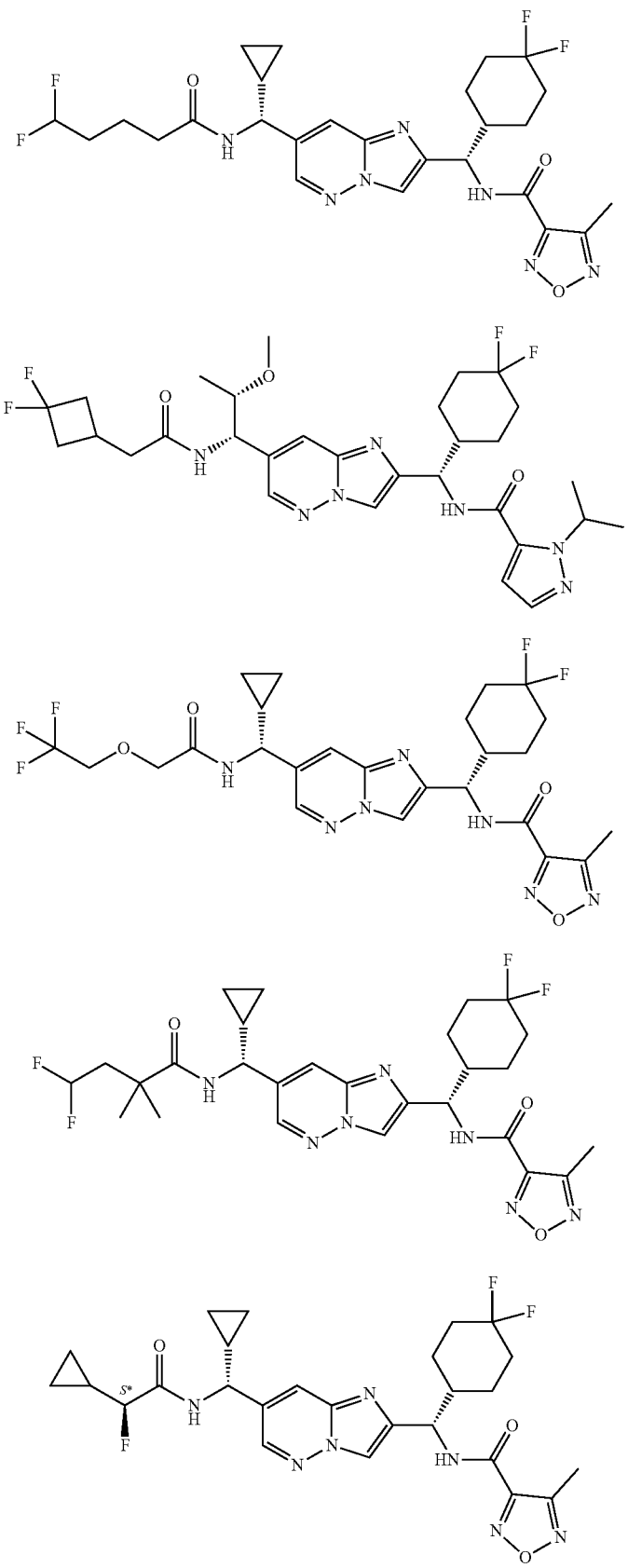

TABLE 2D-continued
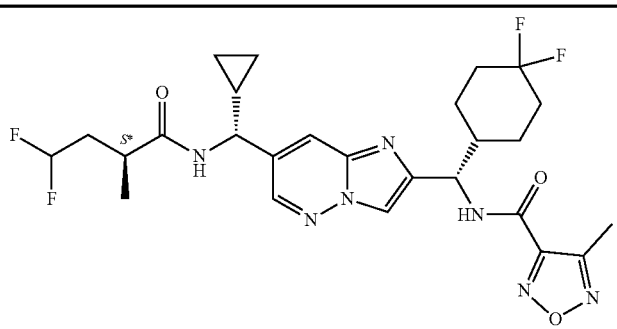
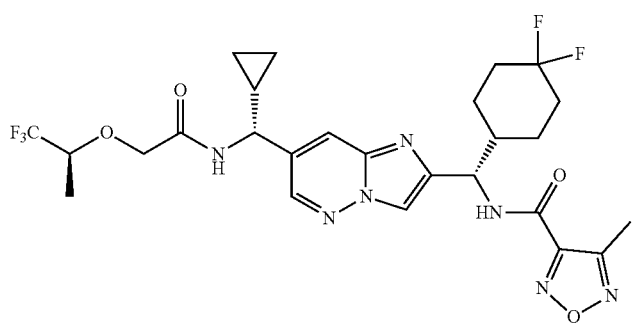 [SMILES: Cc1nonc1C(=O)N[C@H](c1cn2ncc([C@H](NC(=O)CO[C@@H](C)C(F)(F)F)C3CC3)cc2n1)C1CCC(F)(F)CC1]
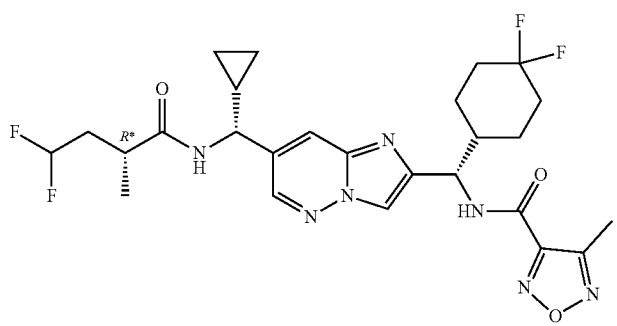 [SMILES: Cc1nonc1C(=O)N[C@H](c1cn2ncc([C@H](NC(=O)[C@H](C)CC(F)F)C3CC3)cc2n1)C1CCC(F)(F)CC1]
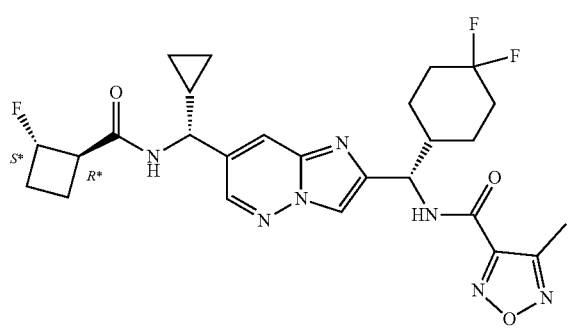 [SMILES: Cc1nonc1C(=O)N[C@H](c1cn2ncc([C@H](NC(=O)[C@H]3CC[C@@H]3F)C3CC3)cc2n1)C1CCC(F)(F)CC1]
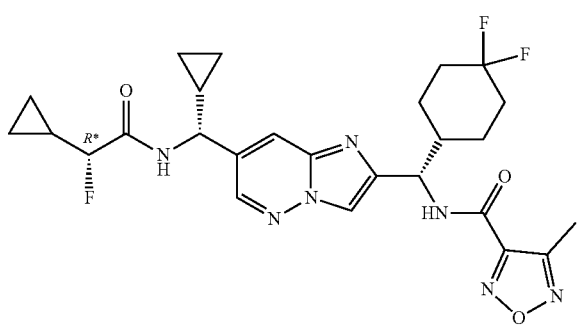 [SMILES: Cc1nonc1C(=O)N[C@H](c1cn2ncc([C@H](NC(=O)[C@H](F)C3CC3)C3CC3)cc2n1)C1CCC(F)(F)CC1]

TABLE 2E
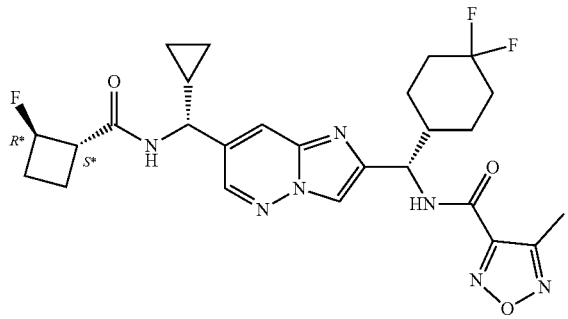 [SMILES: Cc1nonc1C(=O)N[C@H](c1cn2ncc([C@H](NC(=O)[C@@H]3CC[C@H]3F)C3CC3)cc2n1)C1CCC(F)(F)CC1]
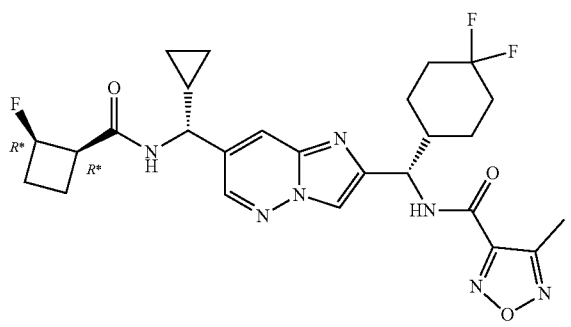 [SMILES: Cc1nonc1C(=O)N[C@H](c1cn2ncc([C@H](NC(=O)[C@H]3CC[C@H]3F)C3CC3)cc2n1)C1CCC(F)(F)CC1]
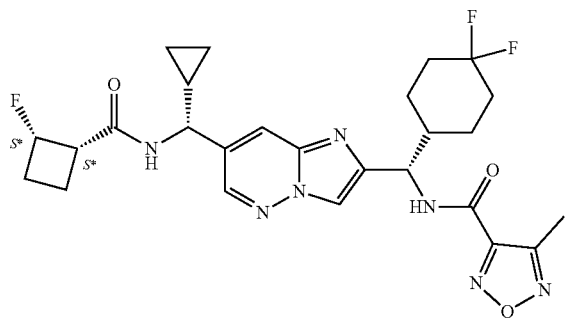 [SMILES: Cc1nonc1C(=O)N[C@H](c1cn2ncc([C@H](NC(=O)[C@@H]3CC[C@@H]3F)C3CC3)cc2n1)C1CCC(F)(F)CC1]
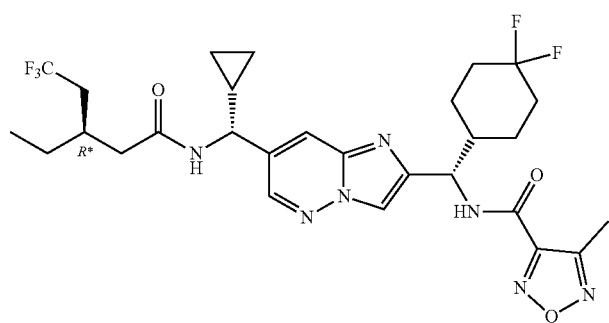 [SMILES: CC[C@H](CC(=O)N[C@@H](c1cnn2cc([C@@H](NC(=O)c3nonc3C)C3CCC(F)(F)CC3)nc2c1)C1CC1)CC(F)(F)F]

TABLE 2E-continued
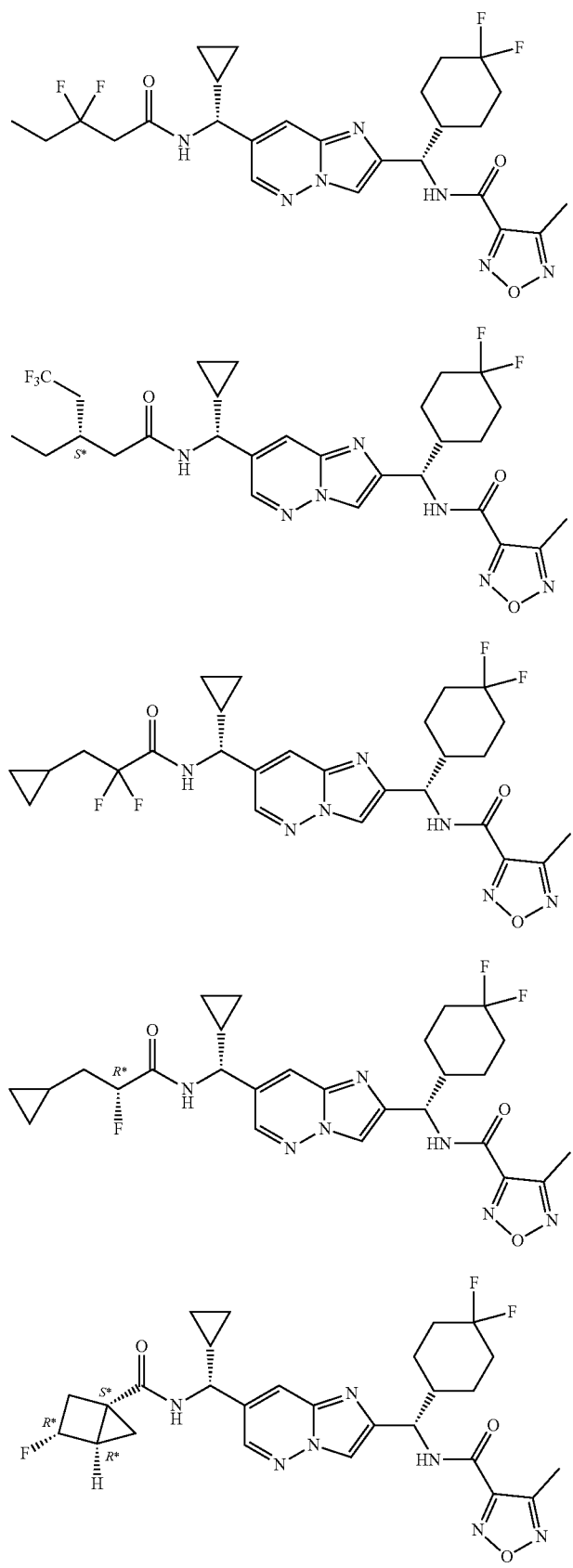

TABLE 2E-continued
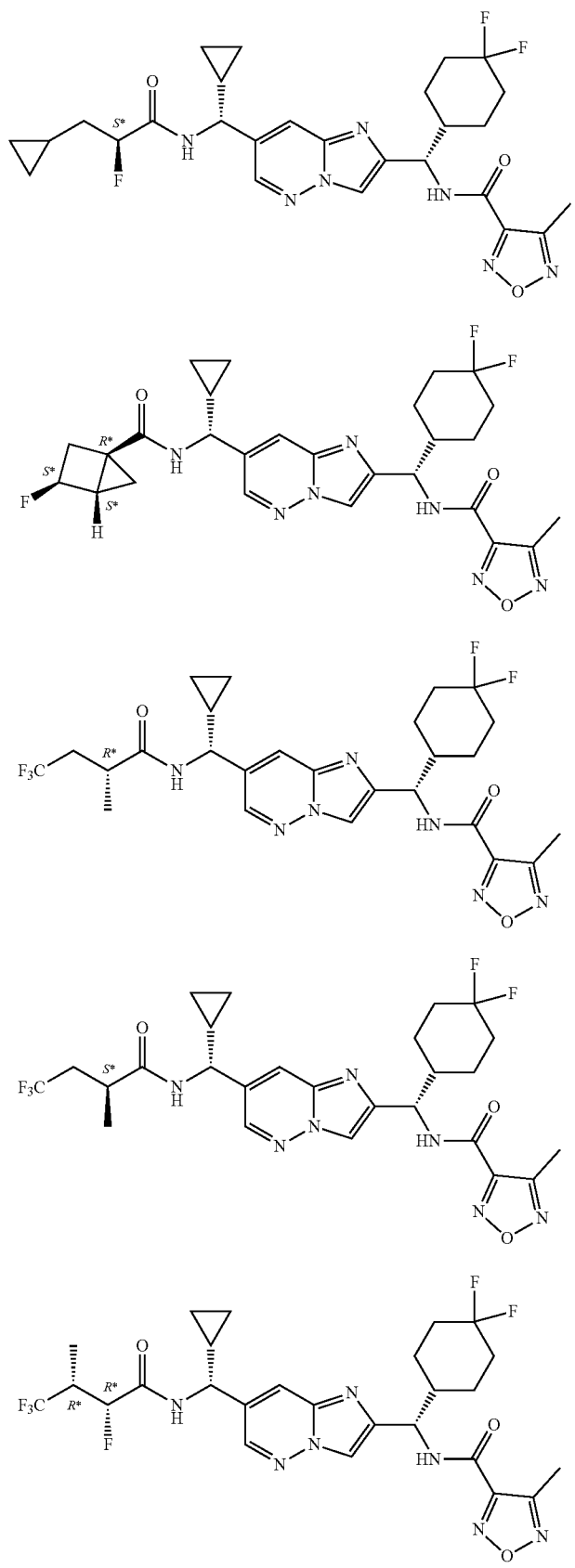

TABLE 2E-continued
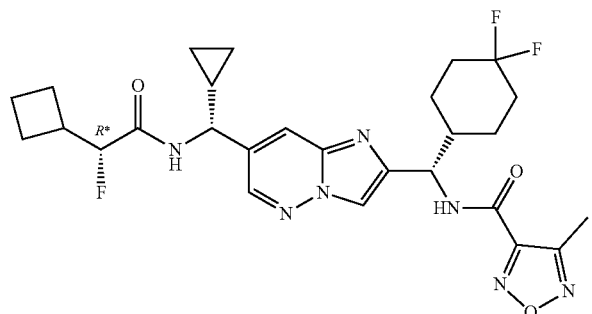
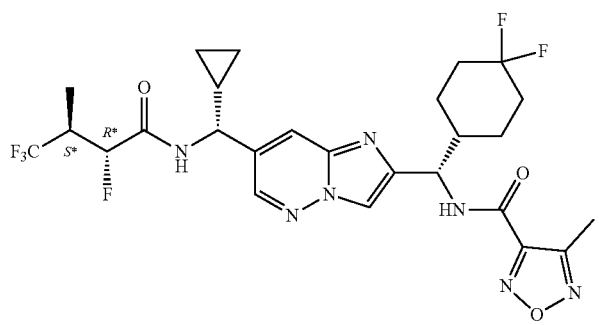 [SMILES: Cc1nonc1C(=O)N[C@H](c1cn2ncc([C@H](NC(=O)[C@H](F)[C@H](C)C(F)(F)F)C3CC3)cc2n1)C1CCC(F)(F)CC1]
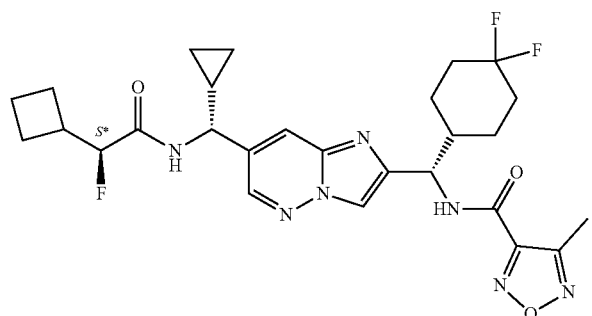
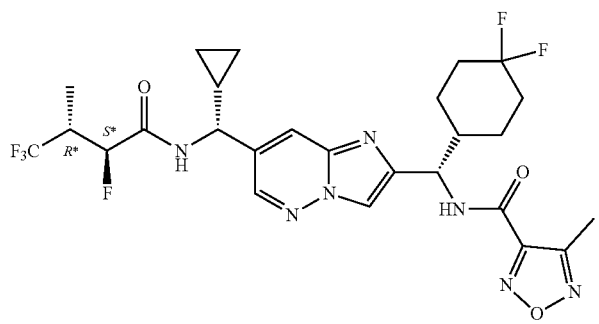 [SMILES: Cc1nonc1C(=O)N[C@H](c1cn2ncc([C@H](NC(=O)[C@@H](F)[C@@H](C)C(F)(F)F)C3CC3)cc2n1)C1CCC(F)(F)CC1]
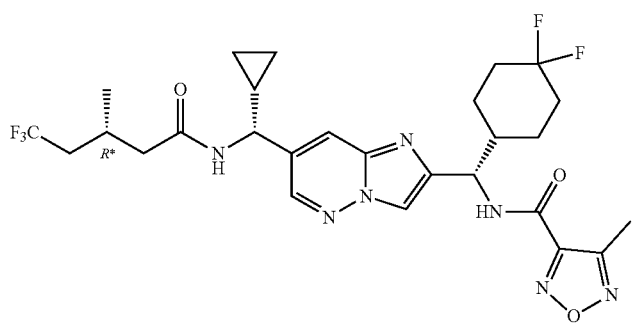 [SMILES: Cc1nonc1C(=O)N[C@H](c1cn2ncc([C@H](NC(=O)C[C@@H](C)CC(F)(F)F)C3CC3)cc2n1)C1CCC(F)(F)CC1]

TABLE 2E-continued
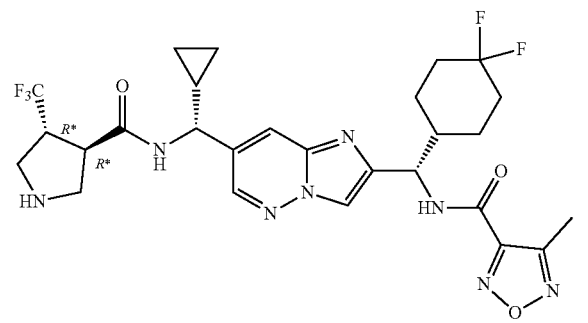 [SMILES: Cc1nonc1C(=O)N[C@H](c1cn2ncc([C@H](NC(=O)[C@H]3CNC[C@@H]3C(F)(F)F)C3CC3)cc2n1)C1CCC(F)(F)CC1]
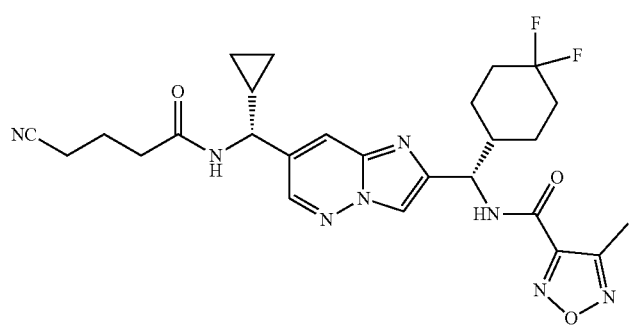 [SMILES: Cc1nonc1C(=O)N[C@H](c1cn2ncc([C@H](NC(=O)CCCC#N)C3CC3)cc2n1)C1CCC(F)(F)CC1]
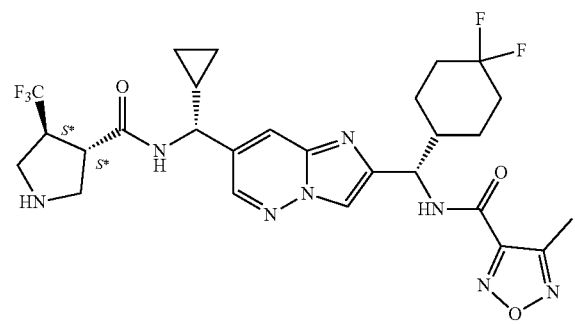 [SMILES: Cc1nonc1C(=O)N[C@H](c1cn2ncc([C@H](NC(=O)[C@@H]3CNC[C@H]3C(F)(F)F)C3CC3)cc2n1)C1CCC(F)(F)CC1]
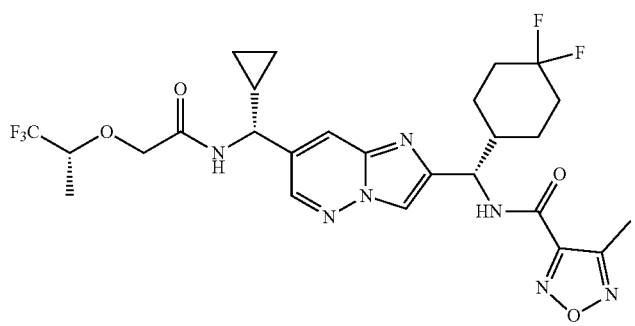
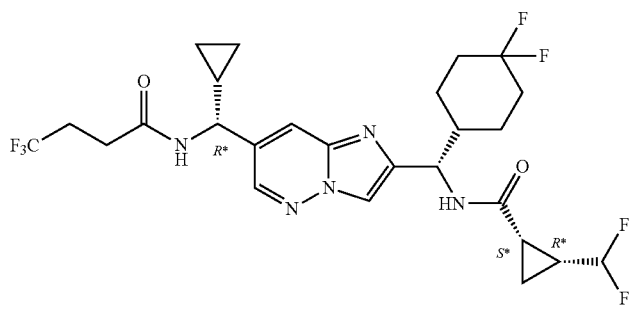 [SMILES: O=C(CCC(F)(F)F)N[C@@H](c1cnn2cc([C@@H](NC(=O)[C@H]3C[C@H]3C(F)F)C3CCC(F)(F)CC3)nc2c1)C1CC1]

TABLE 2E-continued
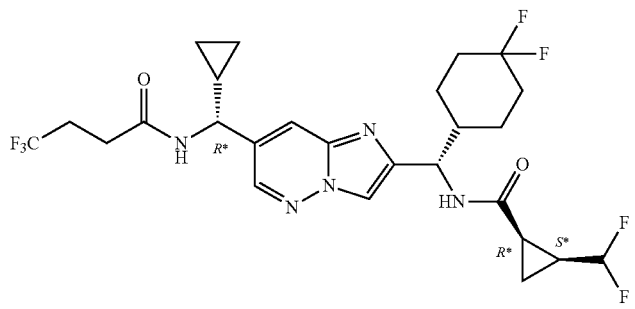 [SMILES: O=C(CCC(F)(F)F)N[C@@H](c1cnn2cc([C@@H](NC(=O)[C@@H]3C[C@@H]3C(F)F)C3CCC(F)(F)CC3)nc2c1)C1CC1]
15
TABLE 2F
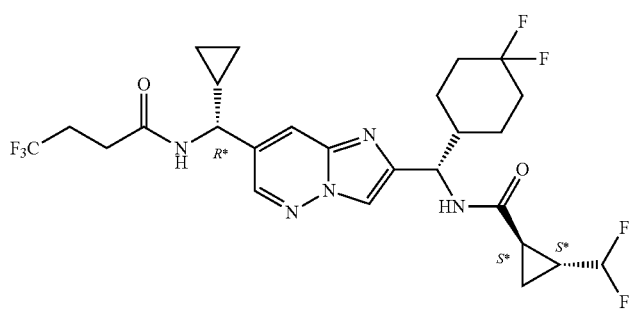 [SMILES: O=C(CCC(F)(F)F)N[C@@H](c1cnn2cc([C@@H](NC(=O)[C@@H]3C[C@H]3C(F)F)C3CCC(F)(F)CC3)nc2c1)C1CC1]
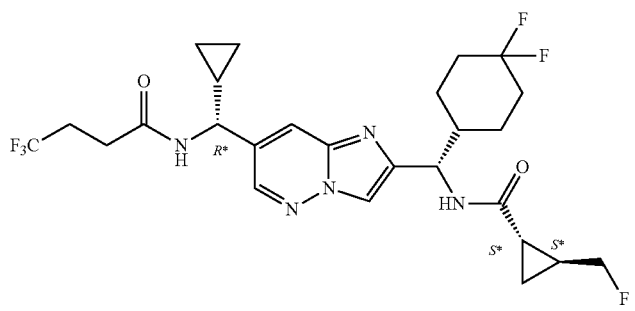 [SMILES: O=C(CCC(F)(F)F)N[C@@H](c1cnn2cc([C@@H](NC(=O)[C@H]3C[C@@H]3CF)C3CCC(F)(F)CC3)nc2c1)C1CC1]
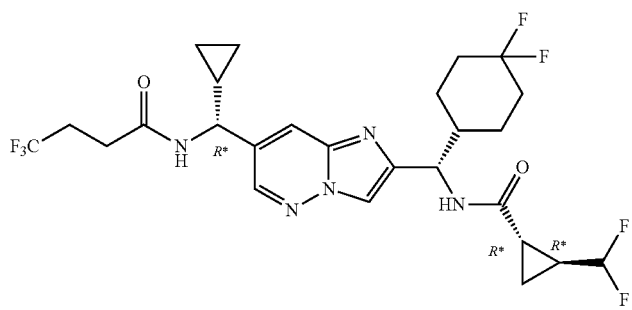 [SMILES: O=C(CCC(F)(F)F)N[C@@H](c1cnn2cc([C@@H](NC(=O)[C@H]3C[C@@H]3C(F)F)C3CCC(F)(F)CC3)nc2c1)C1CC1]

TABLE 2F-continued
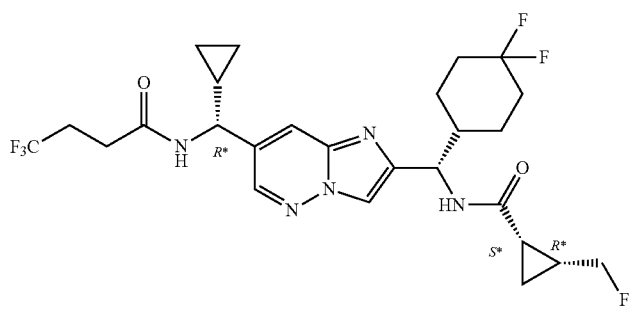 [SMILES: O=C(CCC(F)(F)F)N[C@@H](c1cnn2cc([C@@H](NC(=O)[C@H]3C[C@H]3CF)C3CCC(F)(F)CC3)nc2c1)C1CC1]
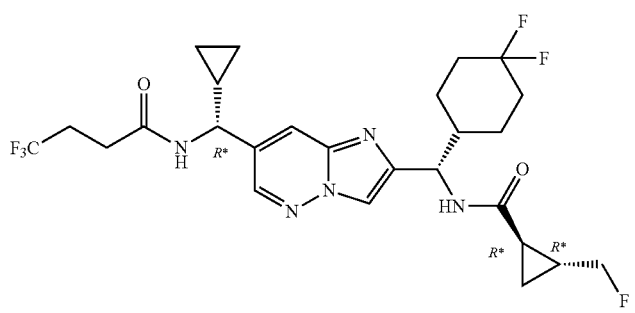 [SMILES: O=C(CCC(F)(F)F)N[C@@H](c1cnn2cc([C@@H](NC(=O)[C@@H]3C[C@H]3CF)C3CCC(F)(F)CC3)nc2c1)C1CC1]
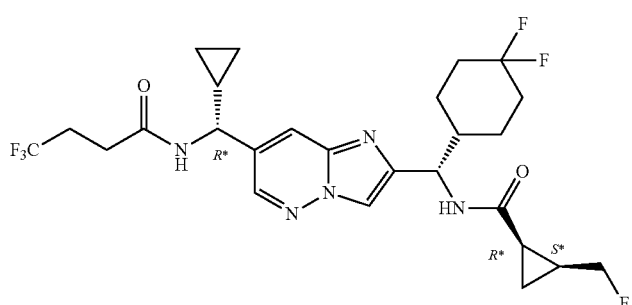
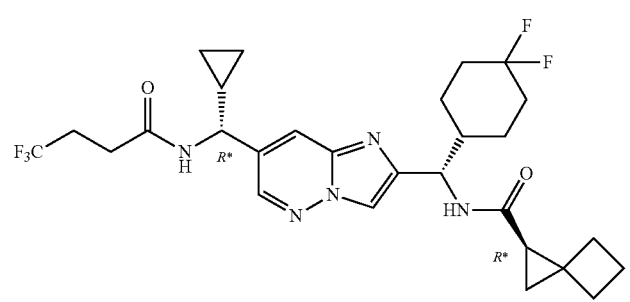 [SMILES: O=C(CCC(F)(F)F)N[C@@H](c1cnn2cc([C@@H](NC(=O)[C@@H]3CC34CCC4)C3CCC(F)(F)CC3)nc2c1)C1CC1]
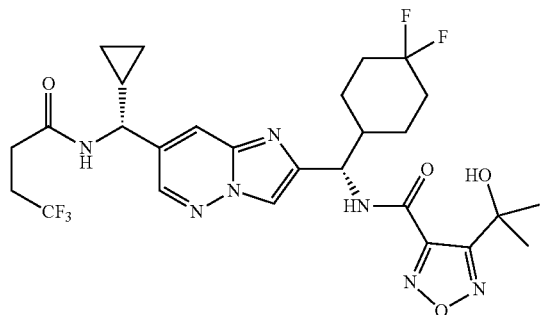 [SMILES: CC(C)(O)c1nonc1C(=O)N[C@H](c1cn2ncc([C@H](NC(=O)CCC(F)(F)F)C3CC3)cc2n1)C1CCC(F)(F)CC1]

TABLE 2F-continued
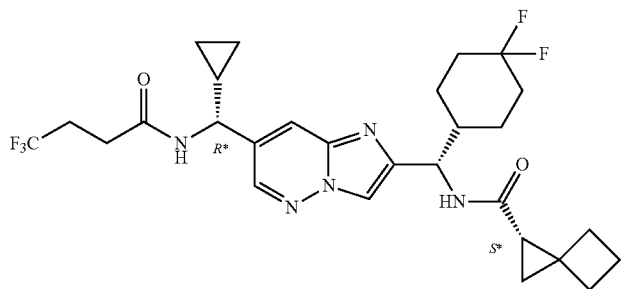
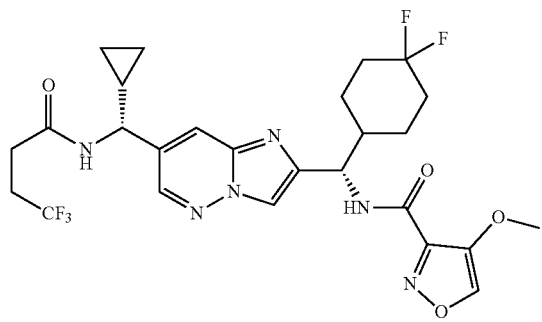 [SMILES: COc1conc1C(=O)N[C@H](c1cn2ncc([C@H](NC(=O)CCC(F)(F)F)C3CC3)cc2n1)C1CCC(F)(F)CC1]
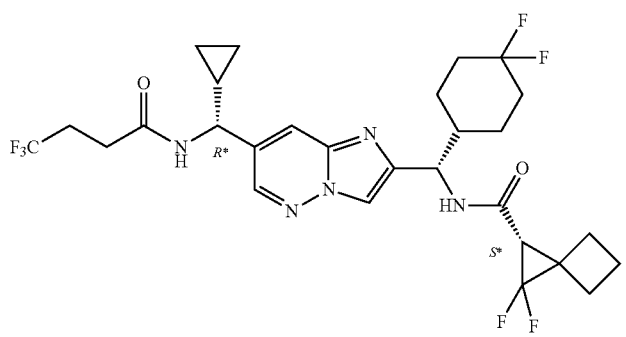 [SMILES: O=C(CCC(F)(F)F)N[C@@H](c1cnn2cc([C@@H](NC(=O)[C@H]3C(F)(F)C34CCC4)C3CCC(F)(F)CC3)nc2c1)C1CC1]
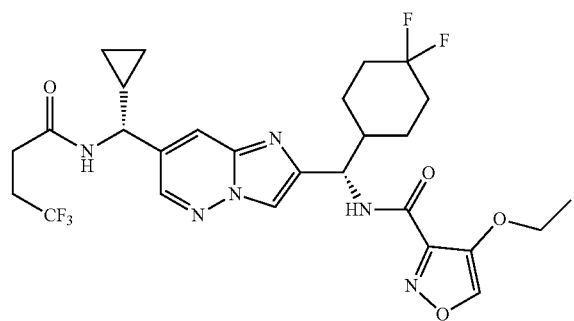 [SMILES: CCOc1conc1C(=O)N[C@H](c1cn2ncc([C@H](NC(=O)CCC(F)(F)F)C3CC3)cc2n1)C1CCC(F)(F)CC1]
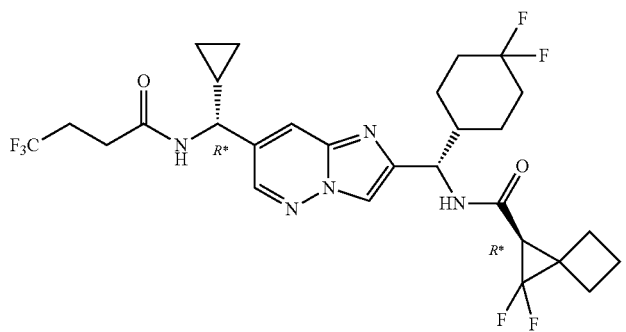 [SMILES: O=C(CCC(F)(F)F)N[C@@H](c1cnn2cc([C@@H](NC(=O)[C@@H]3C(F)(F)C34CCC4)C3CCC(F)(F)CC3)nc2c1)C1CC1]

TABLE 2F-continued
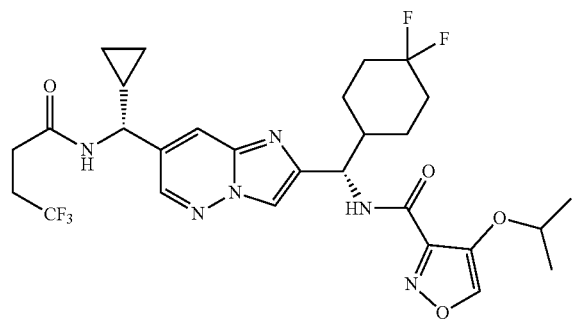 [SMILES: CC(C)Oc1conc1C(=O)N[C@H](c1cn2ncc([C@H](NC(=O)CCC(F)(F)F)C3CC3)cc2n1)C1CCC(F)(F)CC1]
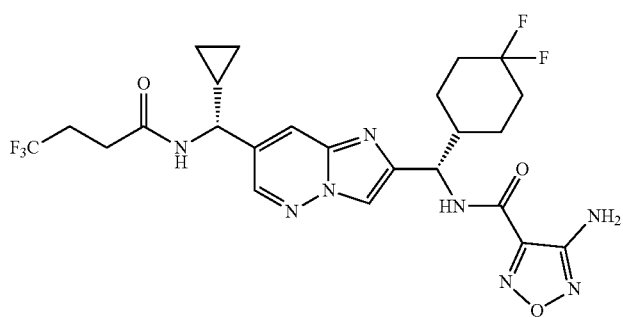 [SMILES: Nc1nonc1C(=O)N[C@H](c1cn2ncc([C@H](NC(=O)CCC(F)(F)F)C3CC3)cc2n1)C1CCC(F)(F)CC1]
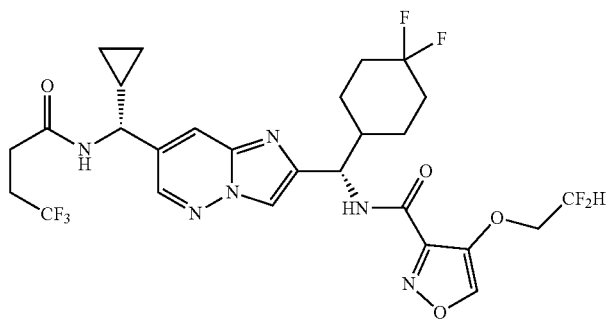 [SMILES: O=C(CCC(F)(F)F)N[C@@H](c1cnn2cc([C@@H](NC(=O)c3nocc3OCC(F)F)C3CCC(F)(F)CC3)nc2c1)C1CC1]
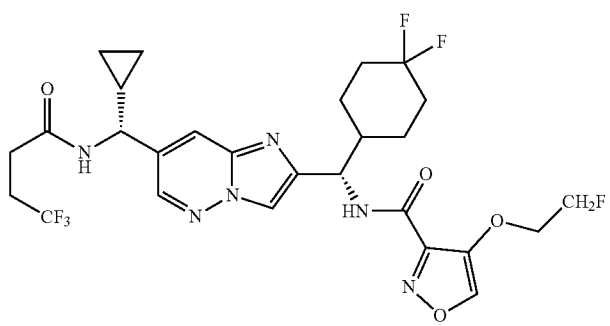
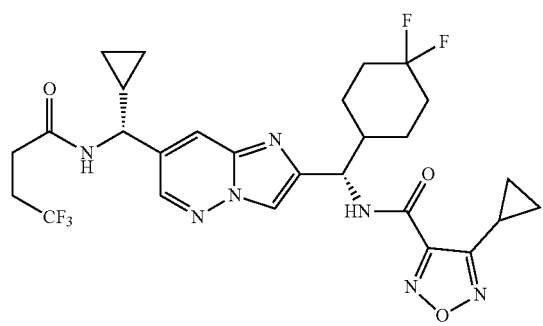 [SMILES: O=C(CCC(F)(F)F)N[C@@H](c1cnn2cc([C@@H](NC(=O)c3nonc3C3CC3)C3CCC(F)(F)CC3)nc2c1)C1CC1]

TABLE 2F-continued
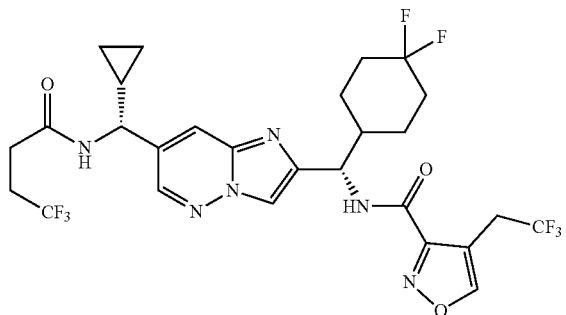 [SMILES: O=C(CCC(F)(F)F)N[C@@H](c1cnn2cc([C@@H](NC(=O)c3nocc3CC(F)(F)F)C3CCC(F)(F)CC3)nc2c1)C1CC1]
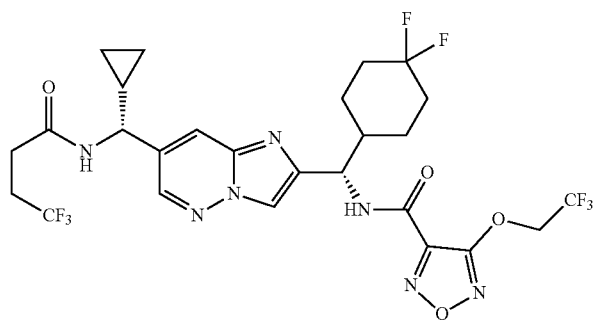 [SMILES: O=C(CCC(F)(F)F)N[C@@H](c1cnn2cc([C@@H](NC(=O)c3nonc3OCC(F)(F)F)C3CCC(F)(F)CC3)nc2c1)C1CC1]
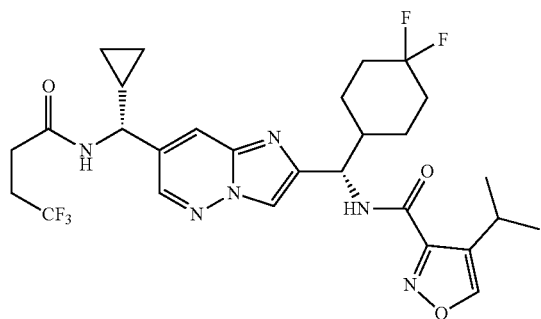 [SMILES: CC(C)c1conc1C(=O)N[C@H](c1cn2ncc([C@H](NC(=O)CCC(F)(F)F)C3CC3)cc2n1)C1CCC(F)(F)CC1]
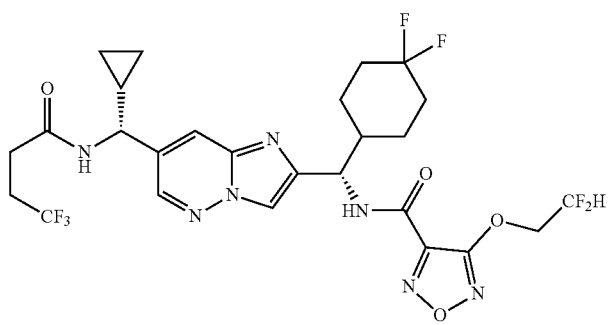 [SMILES: O=C(CCC(F)(F)F)N[C@@H](c1cnn2cc([C@@H](NC(=O)c3nonc3OCC(F)F)C3CCC(F)(F)CC3)nc2c1)C1CC1]
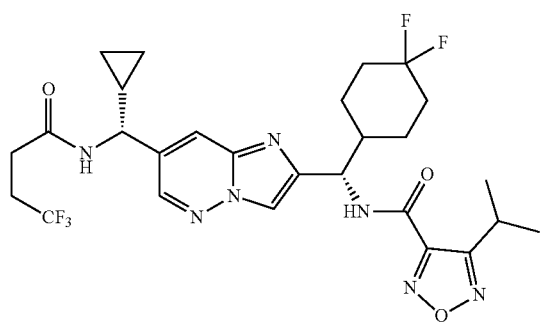 [SMILES: CC(C)c1nonc1C(=O)N[C@H](c1cn2ncc([C@H](NC(=O)CCC(F)(F)F)C3CC3)cc2n1)C1CCC(F)(F)CC1]

TABLE 2F-continued
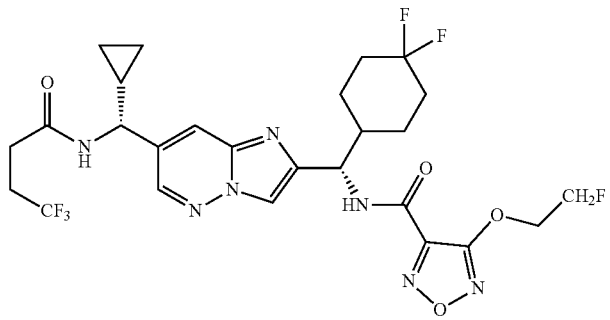
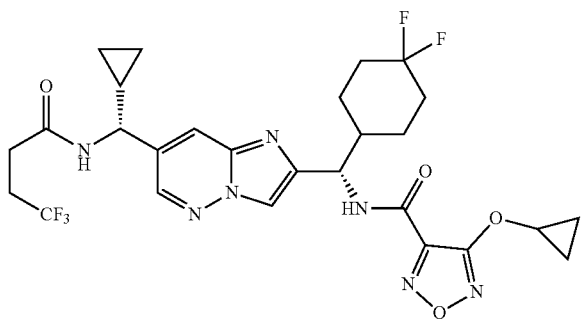 [SMILES: O=C(CCC(F)(F)F)N[C@@H](c1cnn2cc([C@@H](NC(=O)c3nonc3OC3CC3)C3CCC(F)(F)CC3)nc2c1)C1CC1]
TABLE 2G
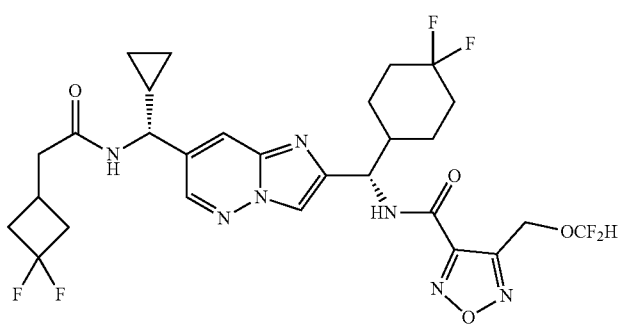
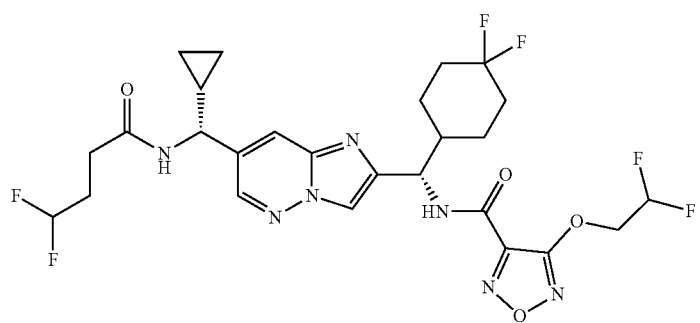 [SMILES: O=C(CCC(F)F)N[C@@H](c1cnn2cc([C@@H](NC(=O)c3nonc3OCC(F)F)C3CCC(F)(F)CC3)nc2c1)C1CC1]

TABLE 2G-continued
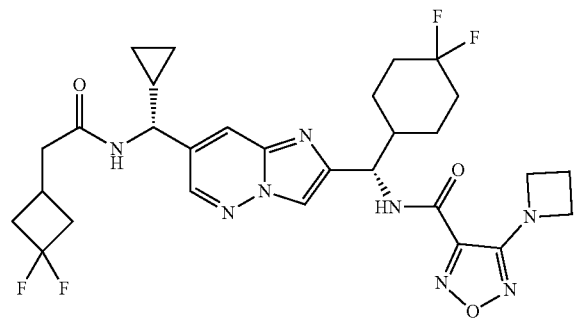 [SMILES: O=C(CC1CC(F)(F)C1)N[C@@H](c1cnn2cc([C@@H](NC(=O)c3nonc3N3CCC3)C3CCC(F)(F)CC3)nc2c1)C1CC1]
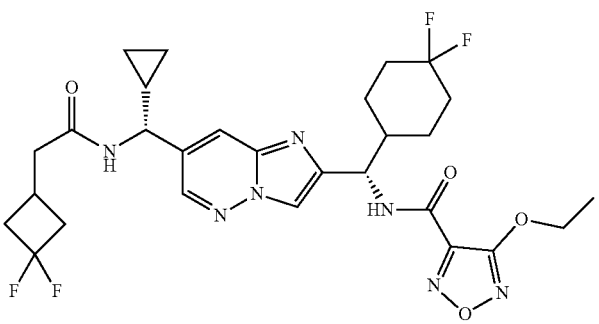 [SMILES: CCOc1nonc1C(=O)N[C@H](c1cn2ncc([C@H](NC(=O)CC3CC(F)(F)C3)C3CC3)cc2n1)C1CCC(F)(F)CC1]
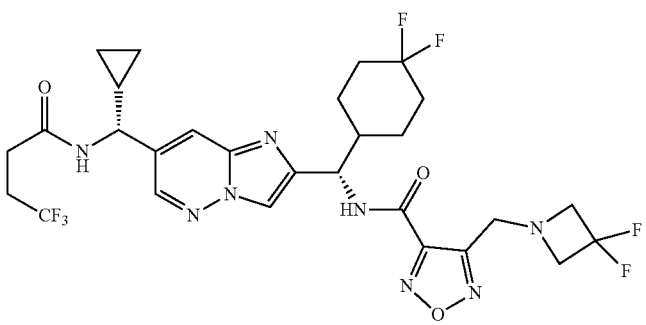 [SMILES: O=C(CCC(F)(F)F)N[C@@H](c1cnn2cc([C@@H](NC(=O)c3nonc3CN3CC(F)(F)C3)C3CCC(F)(F)CC3)nc2c1)C1CC1]
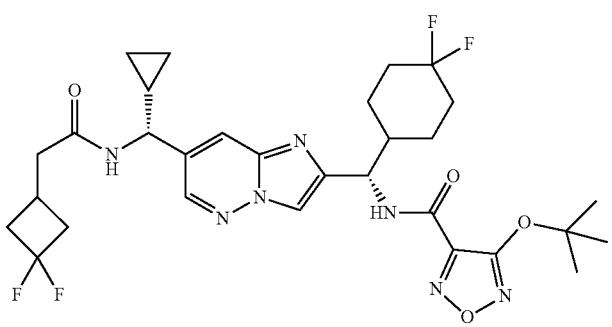 [SMILES: CC(C)(C)Oc1nonc1C(=O)N[C@H](c1cn2ncc([C@H](NC(=O)CC3CC(F)(F)C3)C3CC3)cc2n1)C1CCC(F)(F)CC1]
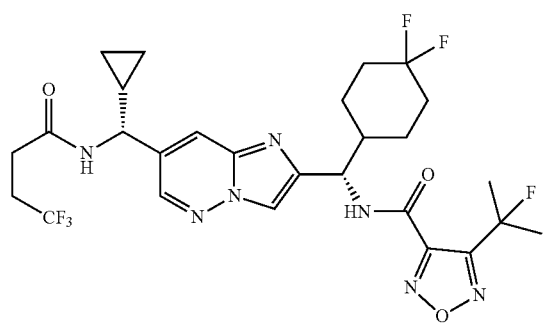 [SMILES: CC(C)(F)c1nonc1C(=O)N[C@H](c1cn2ncc([C@H](NC(=O)CCC(F)(F)F)C3CC3)cc2n1)C1CCC(F)(F)CC1]

TABLE 2G-continued
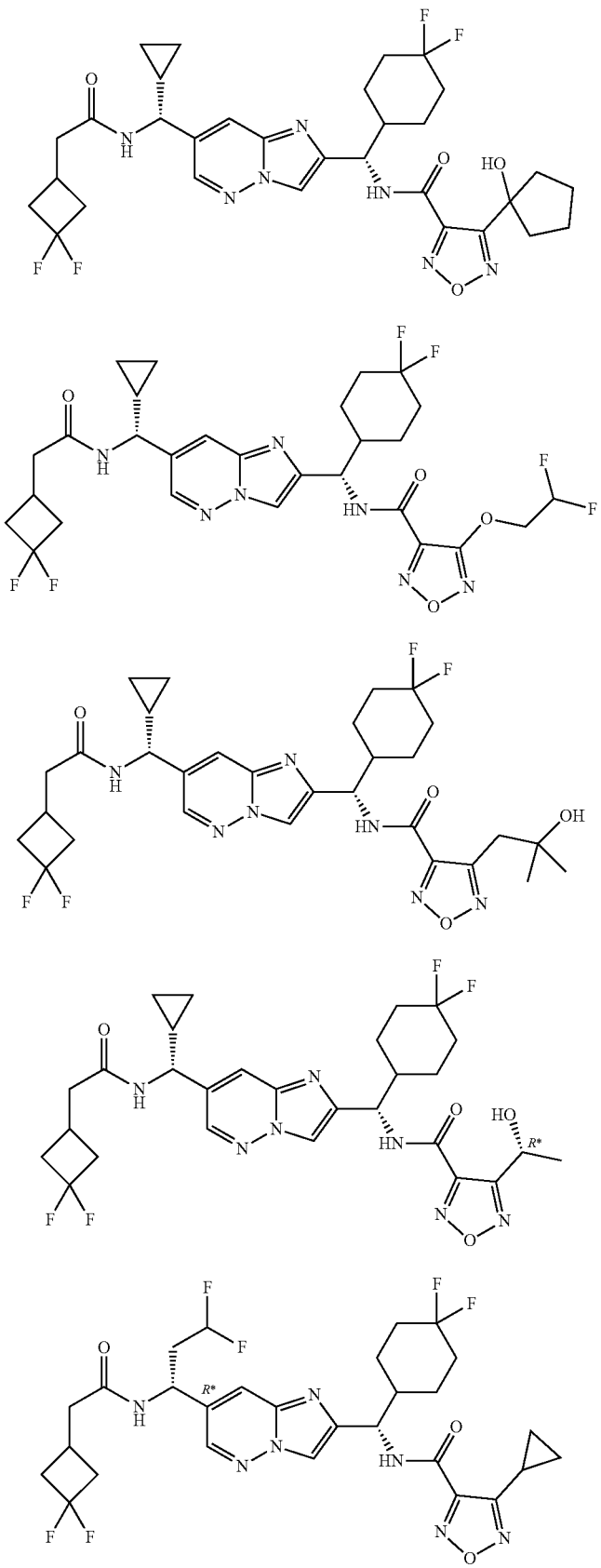

TABLE 2G-continued
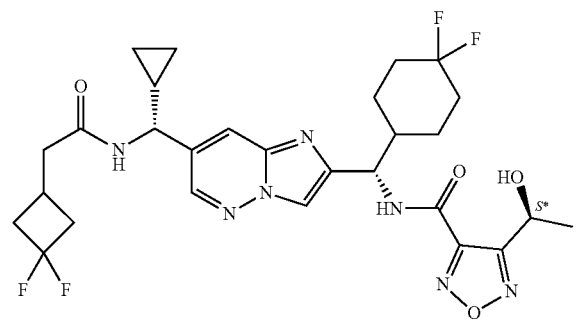 [SMILES: C[C@H](O)c1nonc1C(=O)N[C@H](c1cn2ncc([C@H](NC(=O)CC3CC(F)(F)C3)C3CC3)cc2n1)C1CCC(F)(F)CC1]
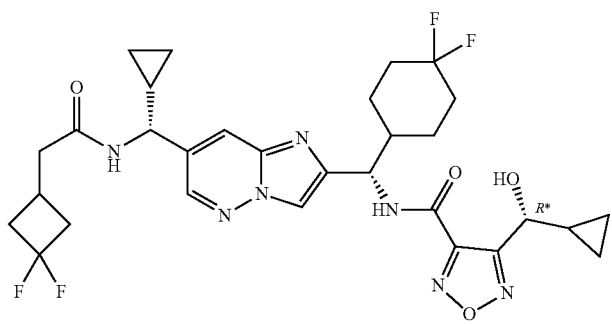 [SMILES: O=C(CC1CC(F)(F)C1)N[C@@H](c1cnn2cc([C@@H](NC(=O)c3nonc3[C@H](O)C3CC3)C3CCC(F)(F)CC3)nc2c1)C1CC1]
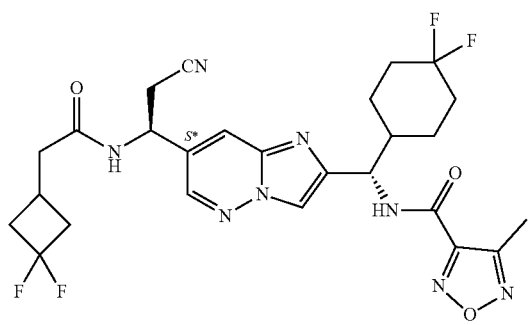 [SMILES: Cc1nonc1C(=O)N[C@H](c1cn2ncc([C@H](CC#N)NC(=O)CC3CC(F)(F)C3)cc2n1)C1CCC(F)(F)CC1]
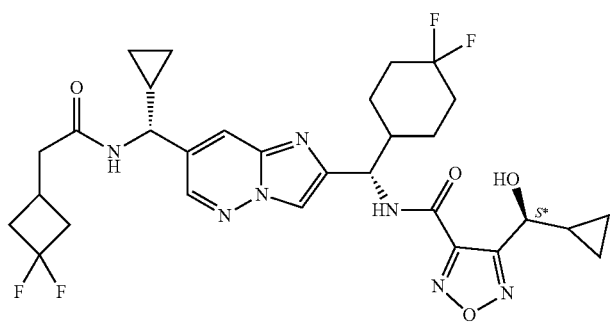 [SMILES: O=C(CC1CC(F)(F)C1)N[C@@H](c1cnn2cc([C@@H](NC(=O)c3nonc3[C@@H](O)C3CC3)C3CCC(F)(F)CC3)nc2c1)C1CC1]
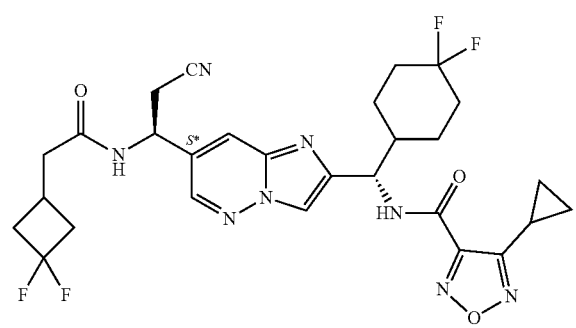 [SMILES: N#CC[C@H](NC(=O)CC1CC(F)(F)C1)c1cnn2cc([C@@H](NC(=O)c3nonc3C3CC3)C3CCC(F)(F)CC3)nc2c1]

TABLE 2G-continued
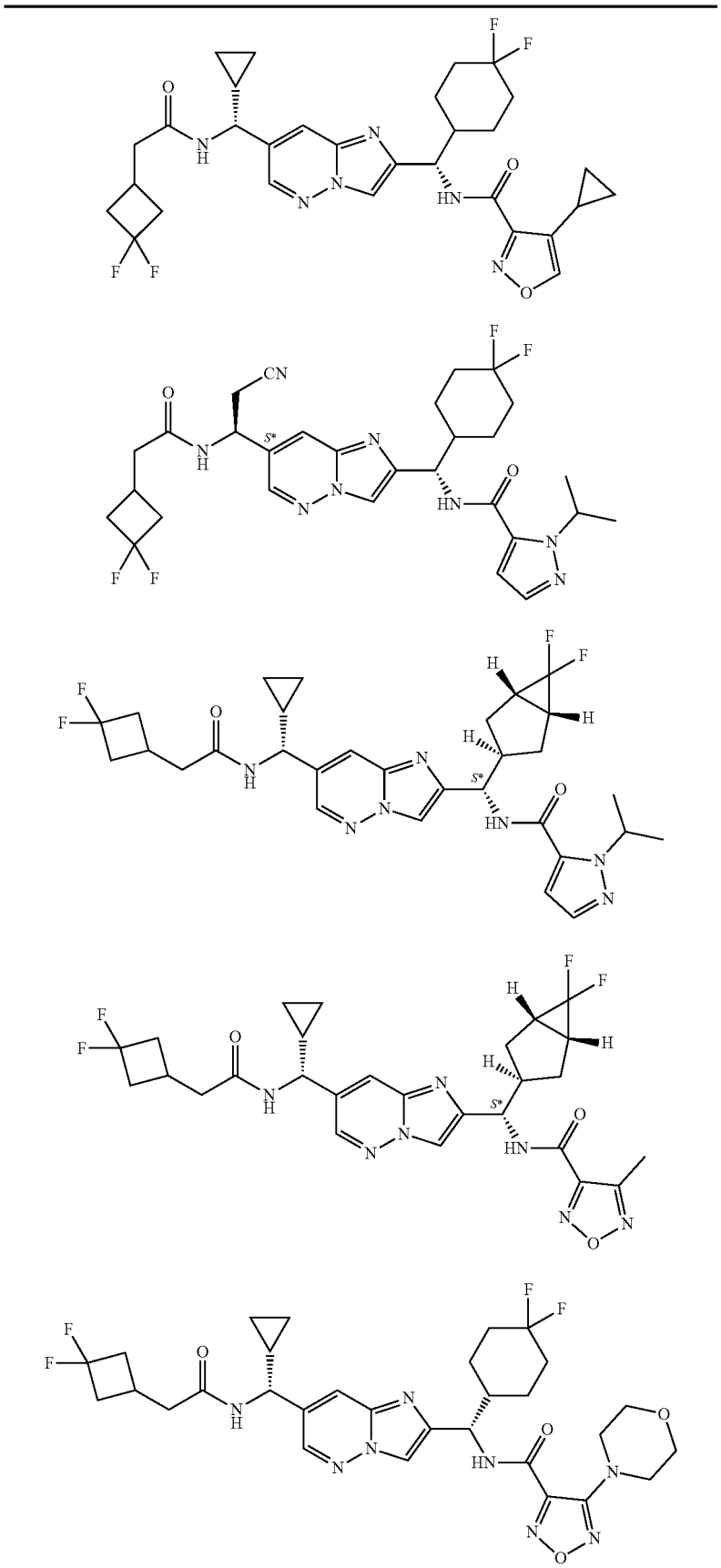

TABLE 2G-continued
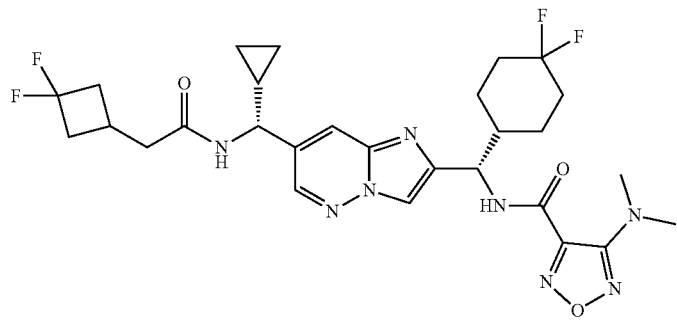 [SMILES: CN(C)c1nonc1C(=O)N[C@H](c1cn2ncc([C@H](NC(=O)CC3CC(F)(F)C3)C3CC3)cc2n1)C1CCC(F)(F)CC1]
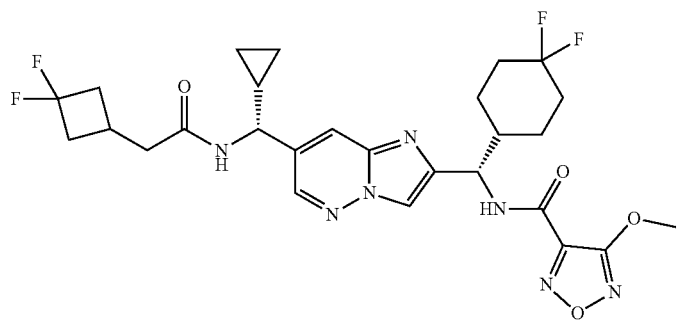 [SMILES: COc1nonc1C(=O)N[C@H](c1cn2ncc([C@H](NC(=O)CC3CC(F)(F)C3)C3CC3)cc2n1)C1CCC(F)(F)CC1]
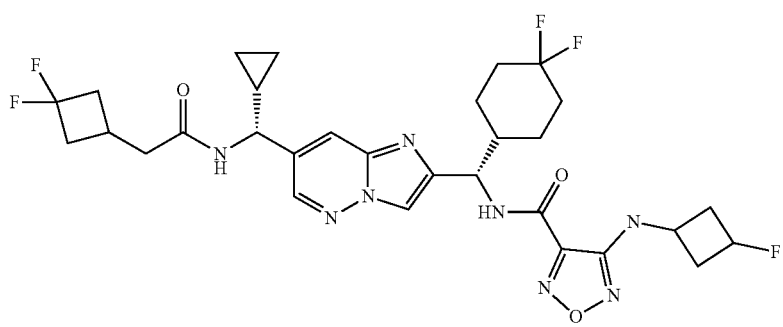 [SMILES: O=C(CC1CC(F)(F)C1)N[C@@H](c1cnn2cc([C@@H](NC(=O)c3nonc3NC3CC(F)C3)C3CCC(F)(F)CC3)nc2c1)C1CC1]
TABLE 2H
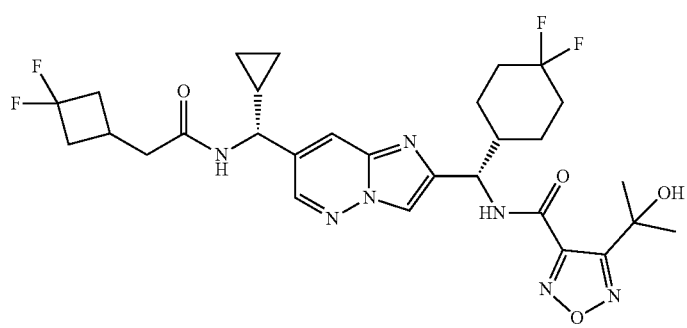 [SMILES: CC(C)(O)c1nonc1C(=O)N[C@H](c1cn2ncc([C@H](NC(=O)CC3CC(F)(F)C3)C3CC3)cc2n1)C1CCC(F)(F)CC1]

TABLE 2H-continued
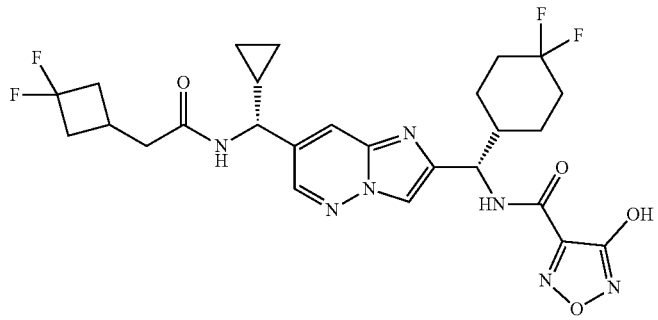 [SMILES: O=C(CC1CC(F)(F)C1)N[C@@H](c1cnn2cc([C@@H](NC(=O)c3nonc3O)C3CCC(F)(F)CC3)nc2c1)C1CC1]
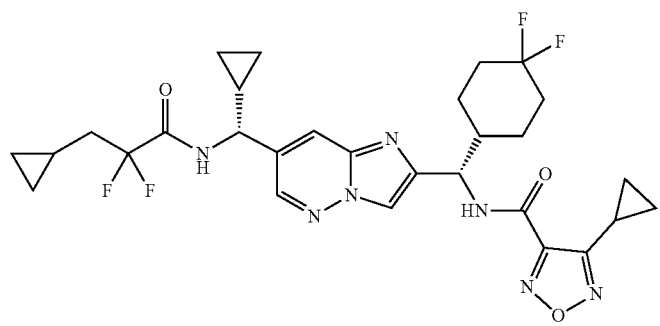 [SMILES: O=C(N[C@H](c1cn2ncc([C@H](NC(=O)C(F)(F)CC3CC3)C3CC3)cc2n1)C1CCC(F)(F)CC1)c1nonc1C1CC1]
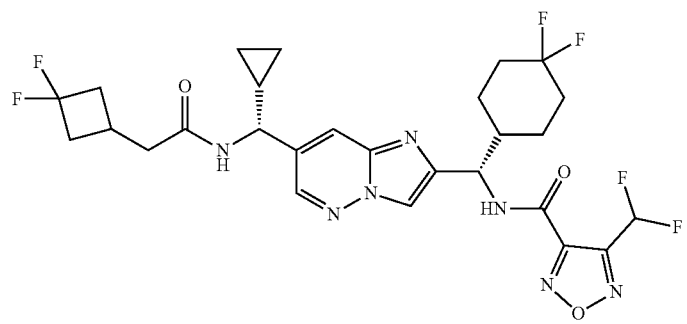 [SMILES: O=C(CC1CC(F)(F)C1)N[C@@H](c1cnn2cc([C@@H](NC(=O)c3nonc3C(F)F)C3CCC(F)(F)CC3)nc2c1)C1CC1]
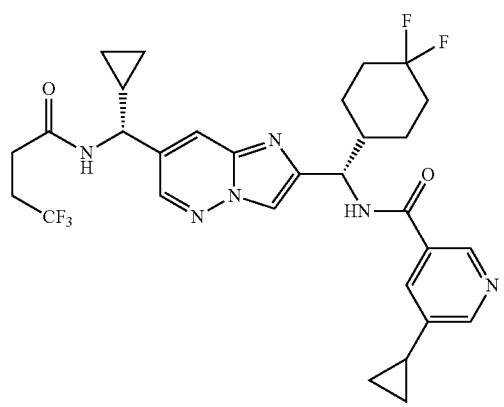 [SMILES: O=C(CCC(F)(F)F)N[C@@H](c1cnn2cc([C@@H](NC(=O)c3cncc(C4CC4)c3)C3CCC(F)(F)CC3)nc2c1)C1CC1]

TABLE 2H-continued
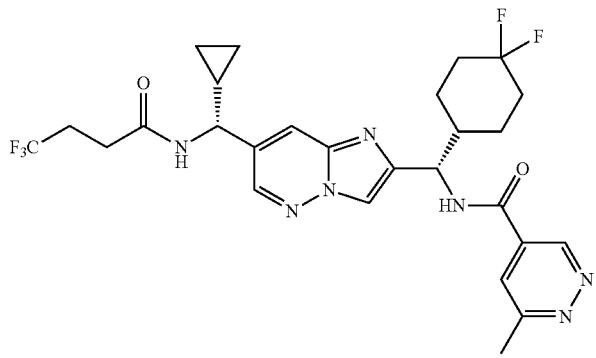 [SMILES: Cc1cc(C(=O)N[C@H](c2cn3ncc([C@H](NC(=O)CCC(F)(F)F)C4CC4)cc3n2)C2CCC(F)(F)CC2)cnn1]
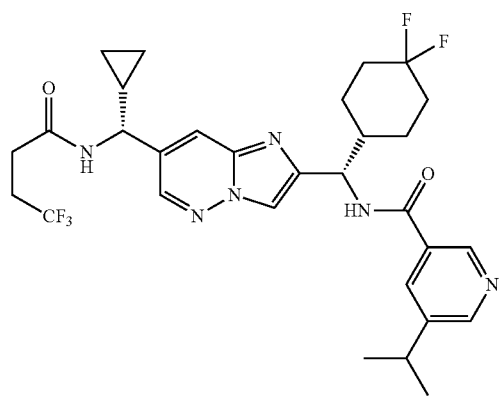 [SMILES: CC(C)c1cncc(C(=O)N[C@H](c2cn3ncc([C@H](NC(=O)CCC(F)(F)F)C4CC4)cc3n2)C2CCC(F)(F)CC2)c1]
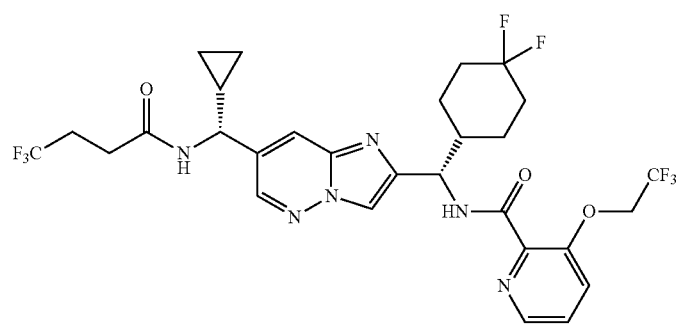 [SMILES: O=C(CCC(F)(F)F)N[C@@H](c1cnn2cc([C@@H](NC(=O)c3ncccc3OCC(F)(F)F)C3CCC(F)(F)CC3)nc2c1)C1CC1]
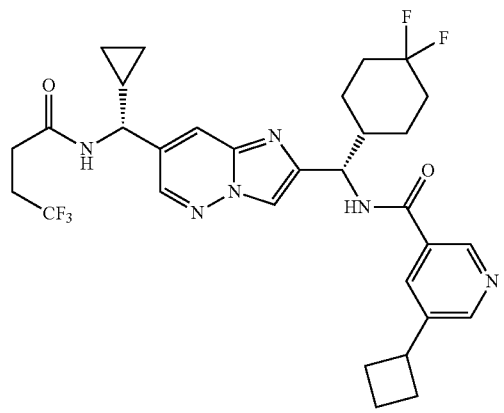 [SMILES: O=C(CCC(F)(F)F)N[C@@H](c1cnn2cc([C@@H](NC(=O)c3cncc(C4CCC4)c3)C3CCC(F)(F)CC3)nc2c1)C1CC1]

TABLE 2H-continued
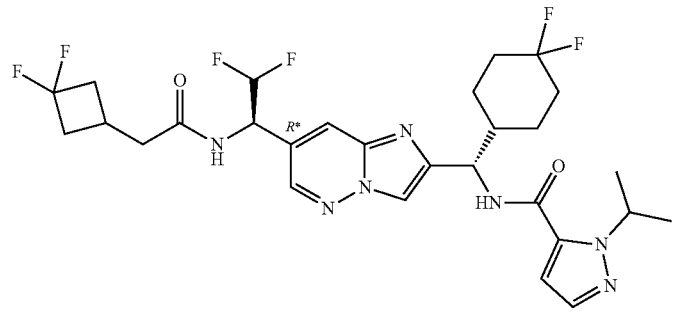 [SMILES: CC(C)n1nccc1C(=O)N[C@H](c1cn2ncc([C@@H](NC(=O)CC3CC(F)(F)C3)C(F)F)cc2n1)C1CCC(F)(F)CC1]
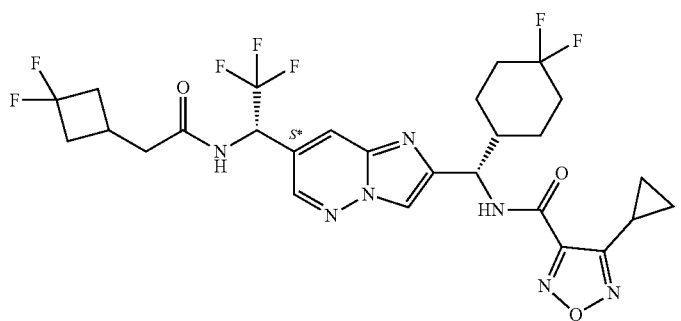 [SMILES: O=C(CC1CC(F)(F)C1)N[C@@H](c1cnn2cc([C@@H](NC(=O)c3nonc3C3CC3)C3CCC(F)(F)CC3)nc2c1)C(F)(F)F]
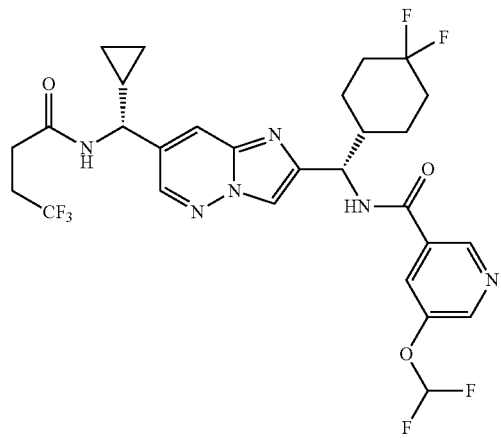 [SMILES: O=C(CCC(F)(F)F)N[C@@H](c1cnn2cc([C@@H](NC(=O)c3cncc(OC(F)F)c3)C3CCC(F)(F)CC3)nc2c1)C1CC1]
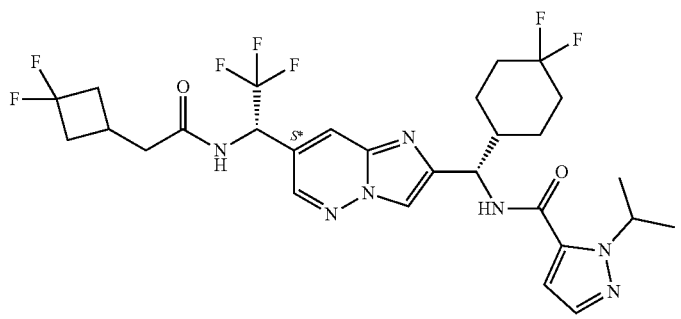 [SMILES: CC(C)n1nccc1C(=O)N[C@H](c1cn2ncc([C@H](NC(=O)CC3CC(F)(F)C3)C(F)(F)F)cc2n1)C1CCC(F)(F)CC1]

TABLE 2H-continued
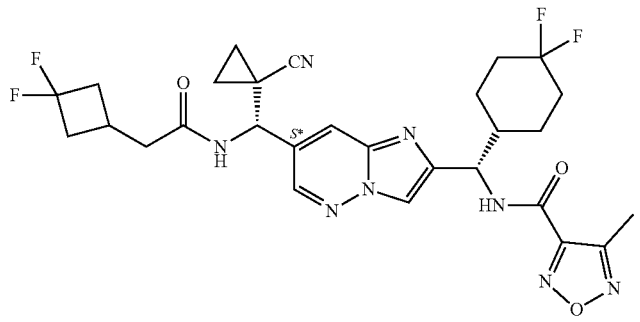 [SMILES: Cc1nonc1C(=O)N[C@H](c1cn2ncc([C@H](NC(=O)CC3CC(F)(F)C3)C3(C#N)CC3)cc2n1)C1CCC(F)(F)CC1]
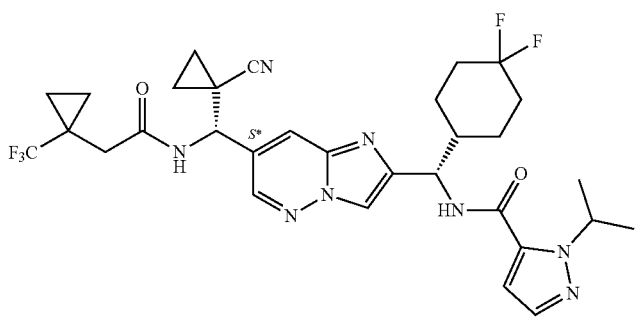 [SMILES: CC(C)n1nccc1C(=O)N[C@H](c1cn2ncc([C@H](NC(=O)CC3(C(F)(F)F)CC3)C3(C#N)CC3)cc2n1)C1CCC(F)(F)CC1]
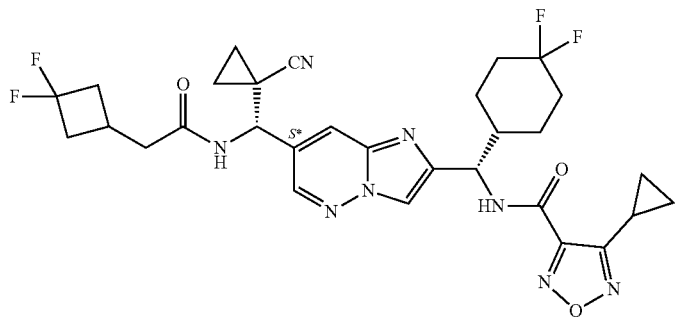 [SMILES: N#CC1([C@@H](NC(=O)CC2CC(F)(F)C2)c2cnn3cc([C@@H](NC(=O)c4nonc4C4CC4)C4CCC(F)(F)CC4)nc3c2)CC1]
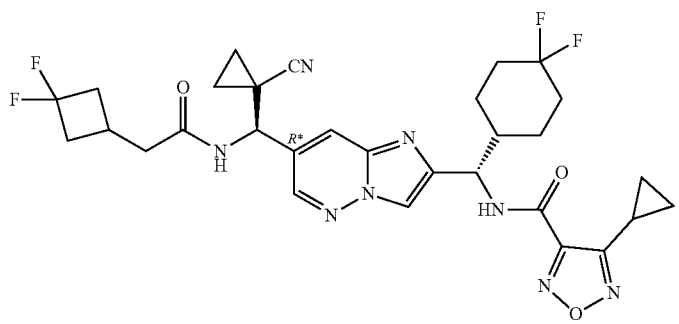 [SMILES: N#CC1([C@H](NC(=O)CC2CC(F)(F)C2)c2cnn3cc([C@@H](NC(=O)c4nonc4C4CC4)C4CCC(F)(F)CC4)nc3c2)CC1]

TABLE 2H-continued
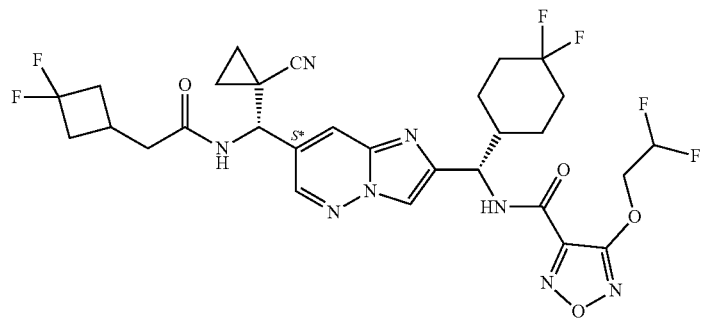 [SMILES: N#CC1([C@@H](NC(=O)CC2CC(F)(F)C2)c2cnn3cc([C@@H](NC(=O)c4nonc4OCC(F)F)C4CCC(F)(F)CC4)nc3c2)CC1]
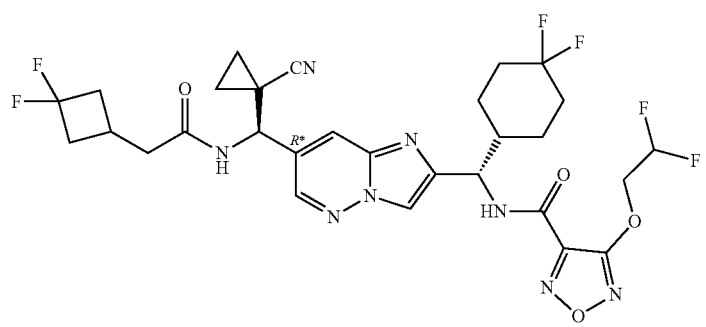 [SMILES: N#CC1([C@H](NC(=O)CC2CC(F)(F)C2)c2cnn3cc([C@@H](NC(=O)c4nonc4OCC(F)F)C4CCC(F)(F)CC4)nc3c2)CC1]
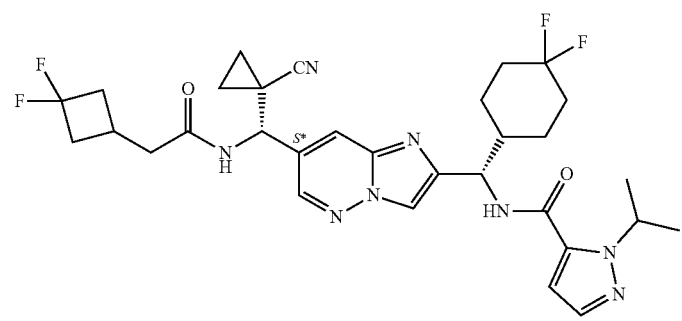 [SMILES: CC(C)n1nccc1C(=O)N[C@H](c1cn2ncc([C@H](NC(=O)CC3CC(F)(F)C3)C3(C#N)CC3)cc2n1)C1CCC(F)(F)CC1]
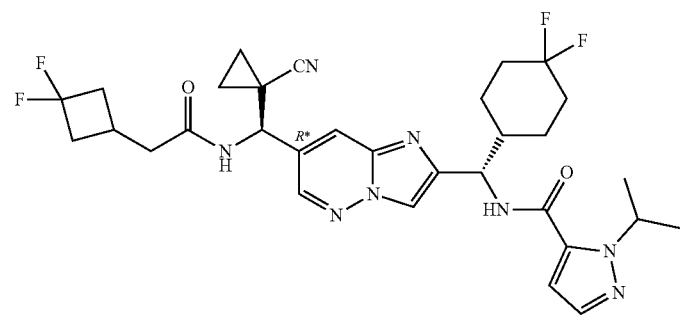 [SMILES: CC(C)n1nccc1C(=O)N[C@H](c1cn2ncc([C@@H](NC(=O)CC3CC(F)(F)C3)C3(C#N)CC3)cc2n1)C1CCC(F)(F)CC1]
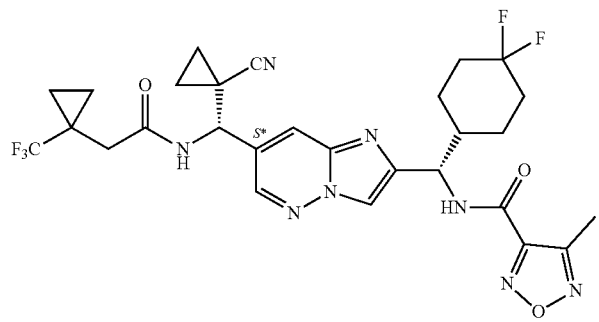 [SMILES: Cc1nonc1C(=O)N[C@H](c1cn2ncc([C@H](NC(=O)CC3(C(F)(F)F)CC3)C3(C#N)CC3)cc2n1)C1CCC(F)(F)CC1]

TABLE 2H-continued
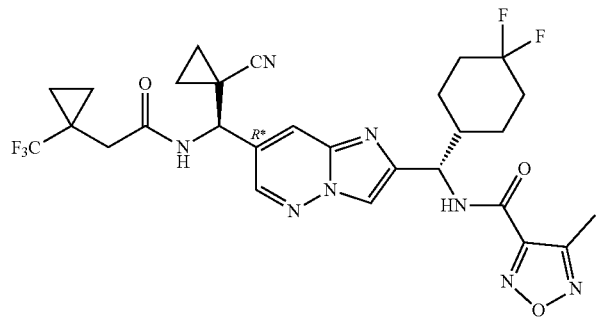 [SMILES: Cc1nonc1C(=O)N[C@H](c1cn2ncc([C@@H](NC(=O)CC3(C(F)(F)F)CC3)C3(C#N)CC3)cc2n1)C1CCC(F)(F)CC1]
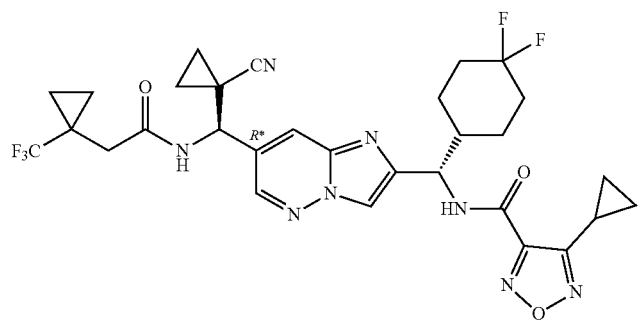 [SMILES: N#CC1([C@H](NC(=O)CC2(C(F)(F)F)CC2)c2cnn3cc([C@@H](NC(=O)c4nonc4C4CC4)C4CCC(F)(F)CC4)nc3c2)CC1]
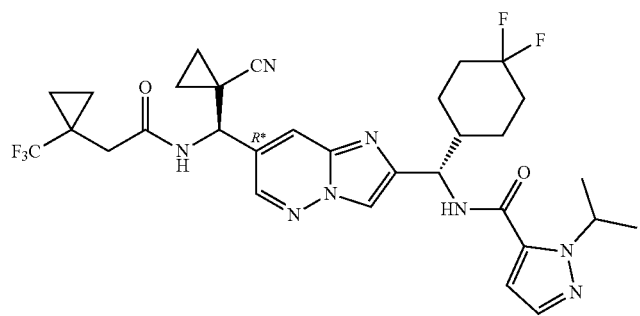 [SMILES: CC(C)n1nccc1C(=O)N[C@H](c1cn2ncc([C@@H](NC(=O)CC3(C(F)(F)F)CC3)C3(C#N)CC3)cc2n1)C1CCC(F)(F)CC1]
TABLE 2I
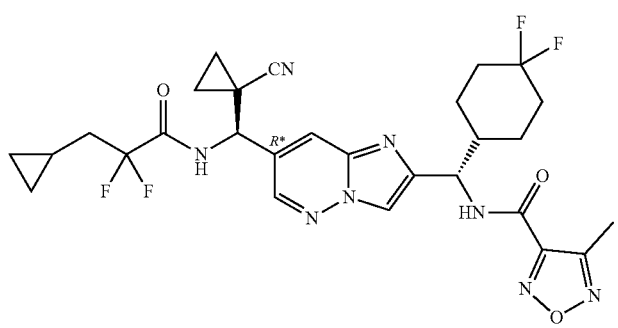 [SMILES: Cc1nonc1C(=O)N[C@H](c1cn2ncc([C@@H](NC(=O)C(F)(F)CC3CC3)C3(C#N)CC3)cc2n1)C1CCC(F)(F)CC1]

TABLE 2I-continued
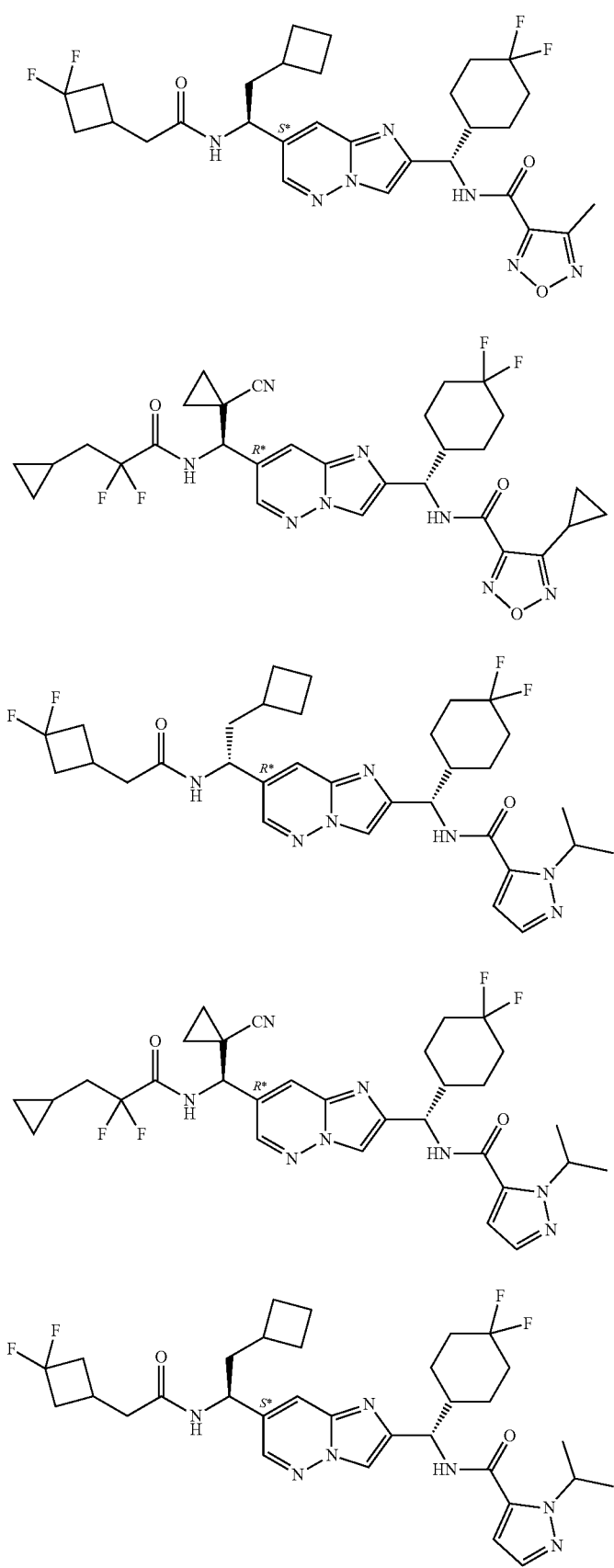

TABLE 2I-continued
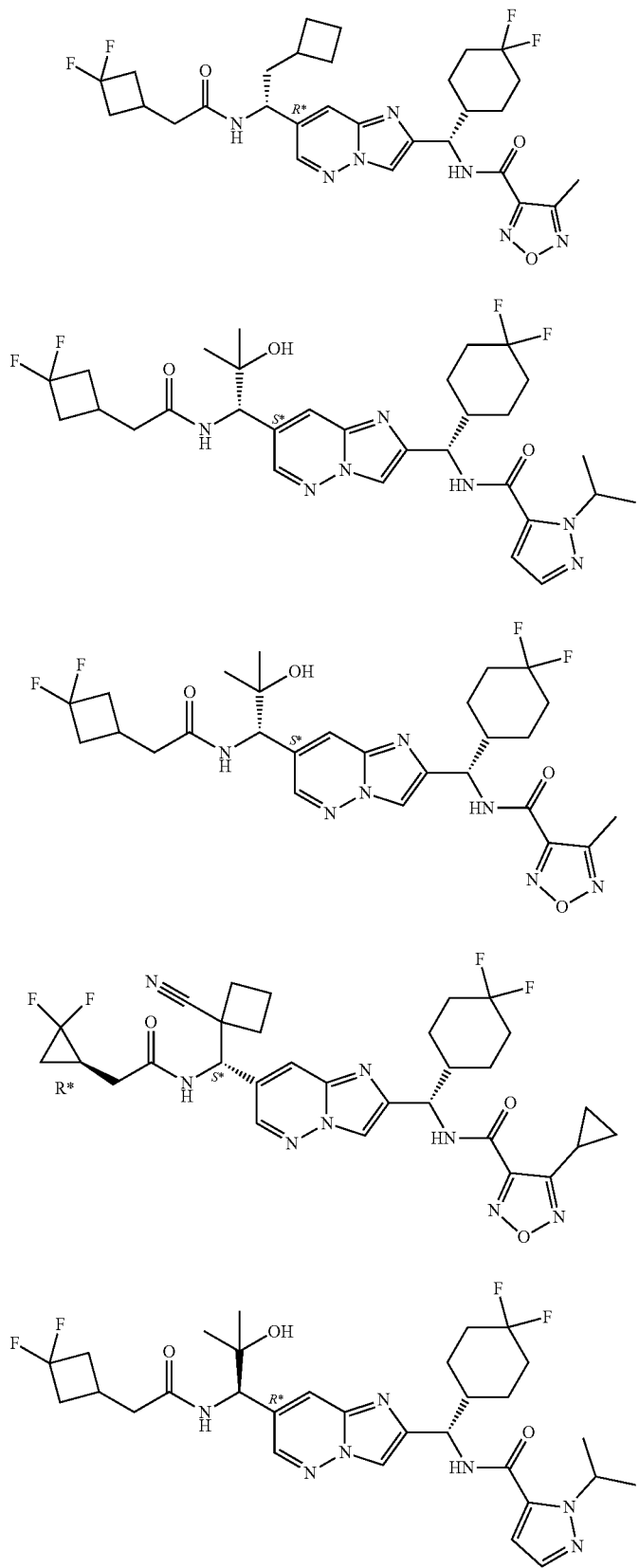

TABLE 2I-continued
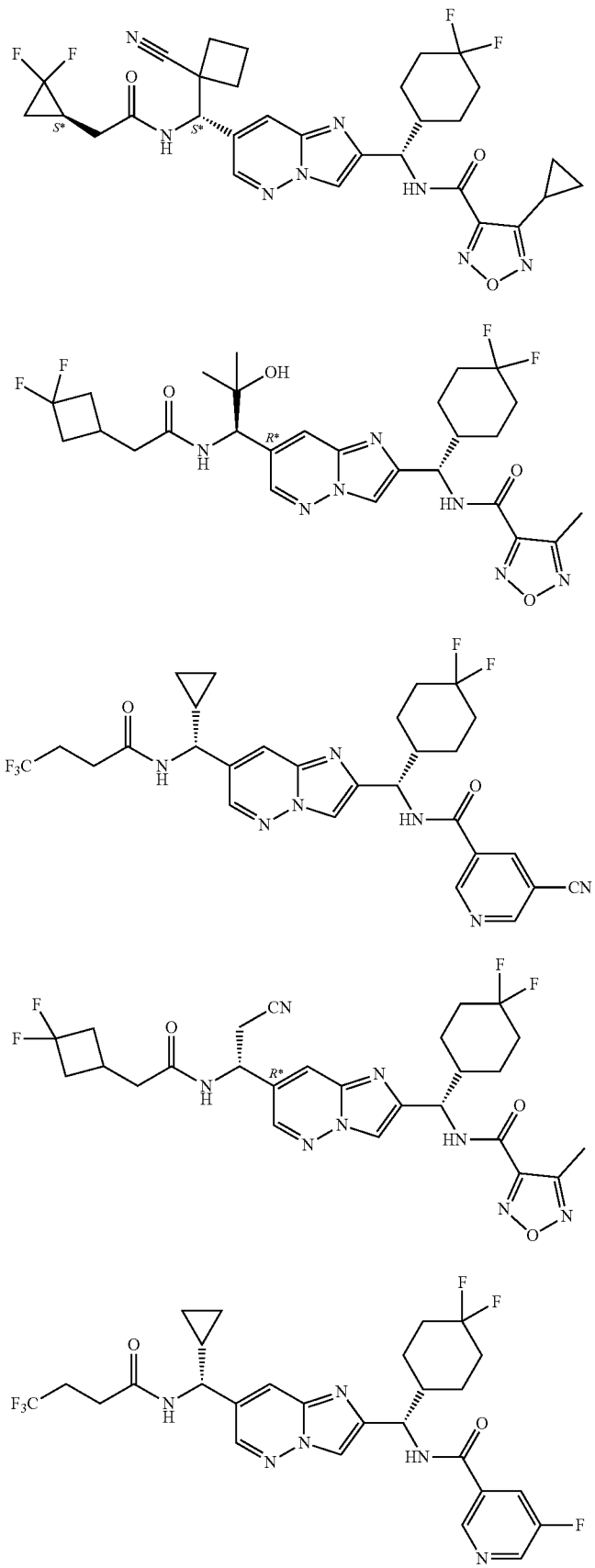

TABLE 2I-continued
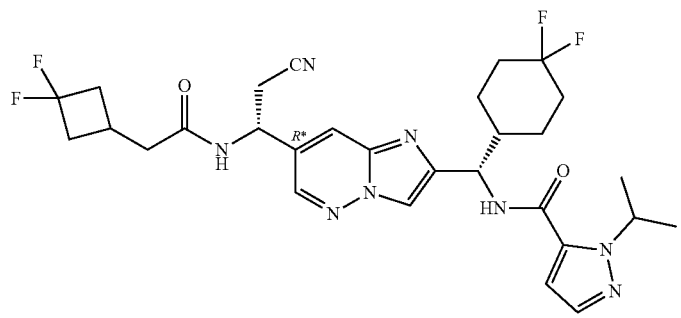 [SMILES: CC(C)n1nccc1C(=O)N[C@H](c1cn2ncc([C@@H](CC#N)NC(=O)CC3CC(F)(F)C3)cc2n1)C1CCC(F)(F)CC1]
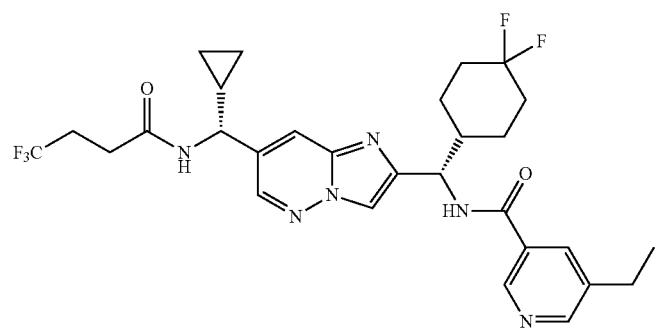 [SMILES: CCc1cncc(C(=O)N[C@H](c2cn3ncc([C@H](NC(=O)CCC(F)(F)F)C4CC4)cc3n2)C2CCC(F)(F)CC2)c1]
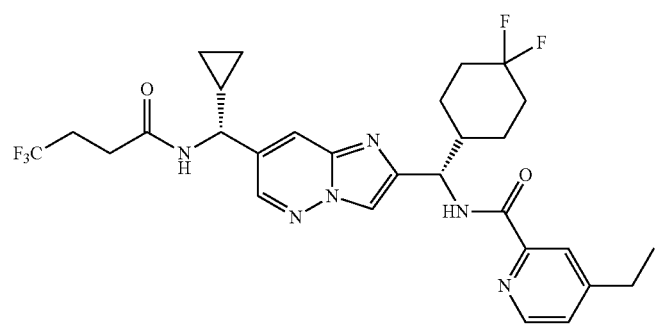 [SMILES: CCc1ccnc(C(=O)N[C@H](c2cn3ncc([C@H](NC(=O)CCC(F)(F)F)C4CC4)cc3n2)C2CCC(F)(F)CC2)c1]
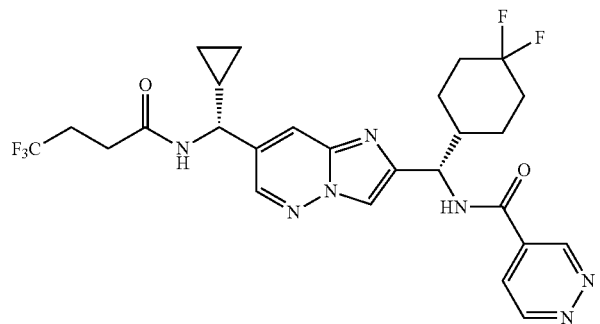 [SMILES: O=C(CCC(F)(F)F)N[C@@H](c1cnn2cc([C@@H](NC(=O)c3ccnnc3)C3CCC(F)(F)CC3)nc2c1)C1CC1]

TABLE 2I-continued
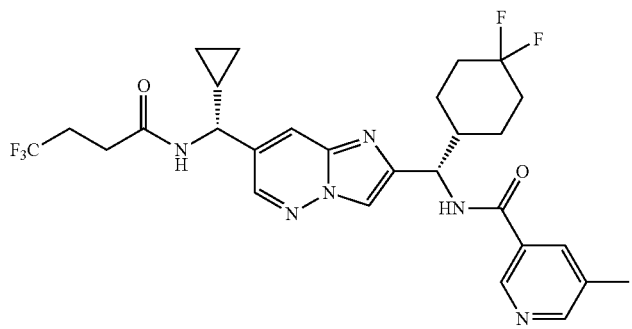 [SMILES: Cc1cncc(C(=O)N[C@H](c2cn3ncc([C@H](NC(=O)CCC(F)(F)F)C4CC4)cc3n2)C2CCC(F)(F)CC2)c1]
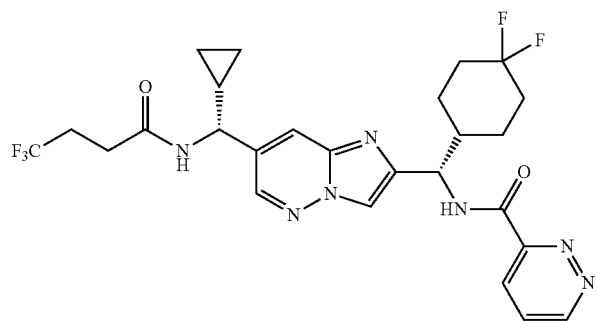 [SMILES: O=C(CCC(F)(F)F)N[C@@H](c1cnn2cc([C@@H](NC(=O)c3cccnn3)C3CCC(F)(F)CC3)nc2c1)C1CC1]
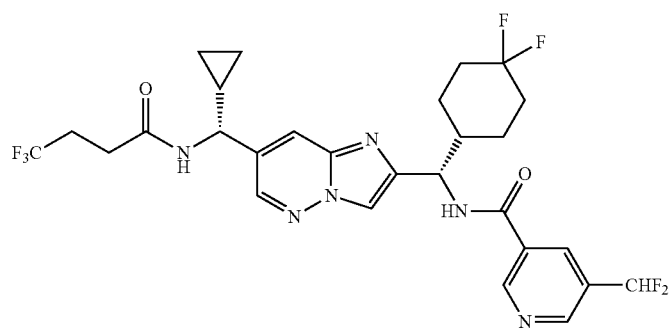 [SMILES: O=C(CCC(F)(F)F)N[C@@H](c1cnn2cc([C@@H](NC(=O)c3cncc(C(F)F)c3)C3CCC(F)(F)CC3)nc2c1)C1CC1]
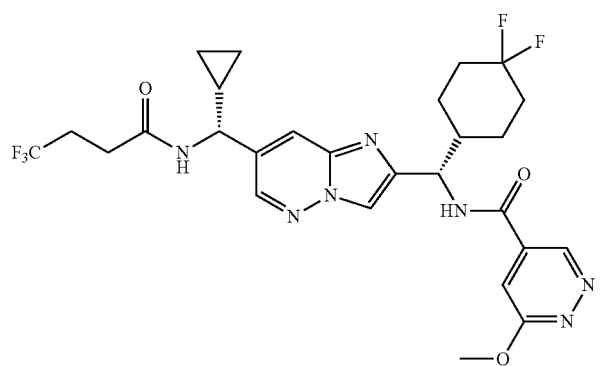 [SMILES: COc1cc(C(=O)N[C@H](c2cn3ncc([C@H](NC(=O)CCC(F)(F)F)C4CC4)cc3n2)C2CCC(F)(F)CC2)cnn1]

TABLE 2I-continued
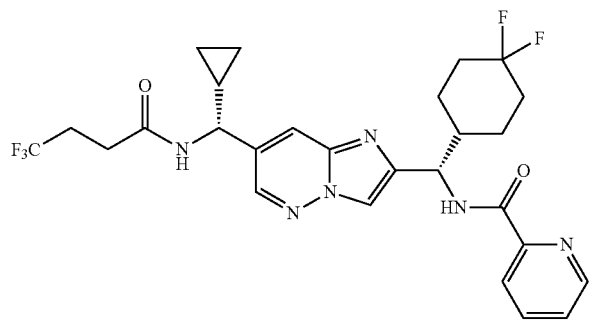 [SMILES: O=C(CCC(F)(F)F)N[C@@H](c1cnn2cc([C@@H](NC(=O)c3ccccn3)C3CCC(F)(F)CC3)nc2c1)C1CC1]
TABLE 2J
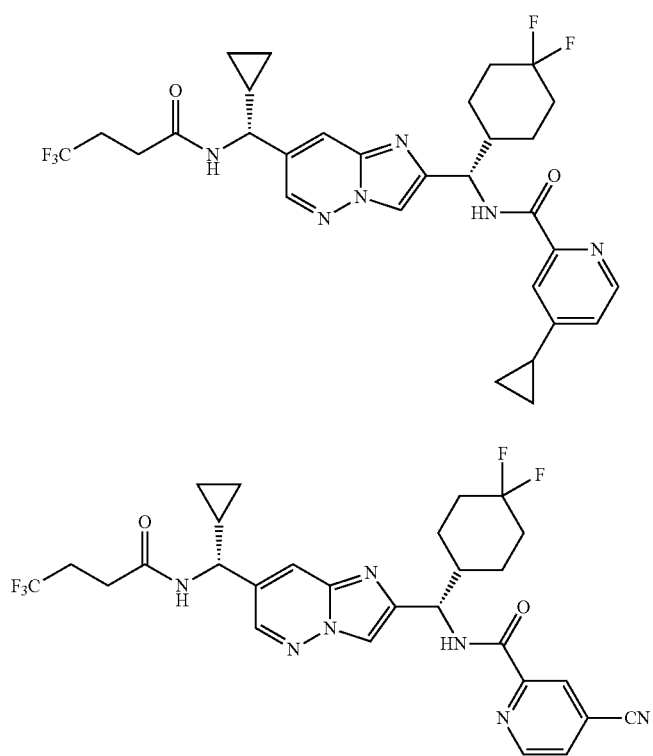
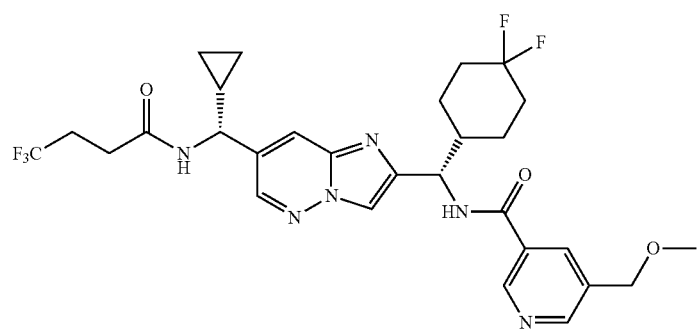 [SMILES: COCc1cncc(C(=O)N[C@H](c2cn3ncc([C@H](NC(=O)CCC(F)(F)F)C4CC4)cc3n2)C2CCC(F)(F)CC2)c1]

TABLE 2J-continued
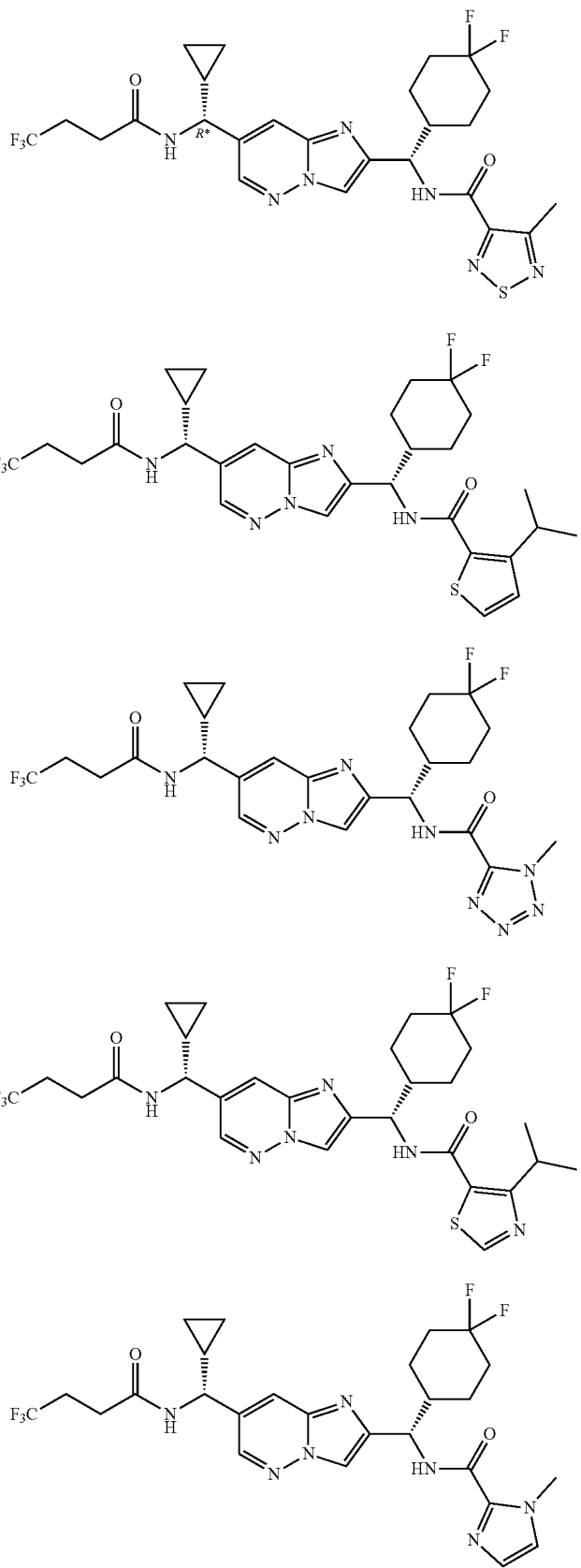

TABLE 2J-continued
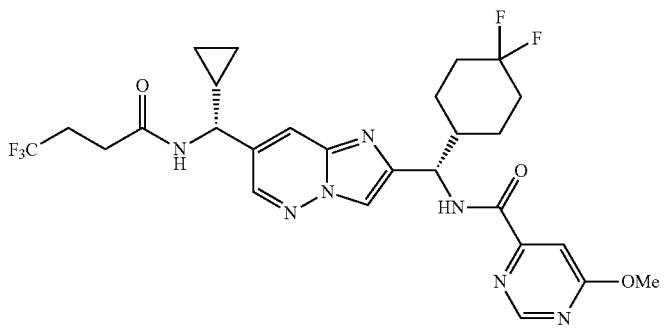 [SMILES: COc1cc(C(=O)N[C@H](c2cn3ncc([C@H](NC(=O)CCC(F)(F)F)C4CC4)cc3n2)C2CCC(F)(F)CC2)ncn1]
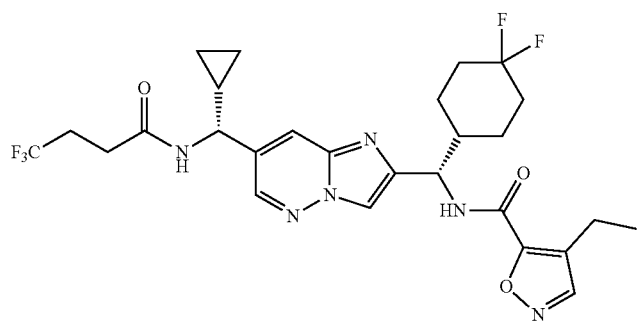 [SMILES: CCc1cnoc1C(=O)N[C@H](c1cn2ncc([C@H](NC(=O)CCC(F)(F)F)C3CC3)cc2n1)C1CCC(F)(F)CC1]
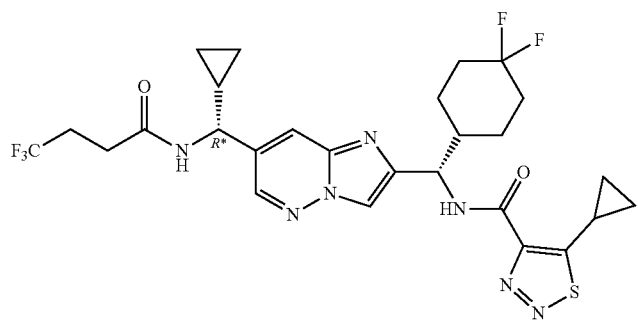 [SMILES: O=C(CCC(F)(F)F)N[C@@H](c1cnn2cc([C@@H](NC(=O)c3nnsc3C3CC3)C3CCC(F)(F)CC3)nc2c1)C1CC1]
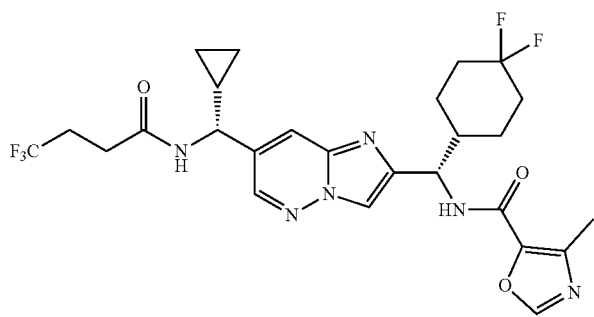 [SMILES: Cc1ncoc1C(=O)N[C@H](c1cn2ncc([C@H](NC(=O)CCC(F)(F)F)C3CC3)cc2n1)C1CCC(F)(F)CC1]
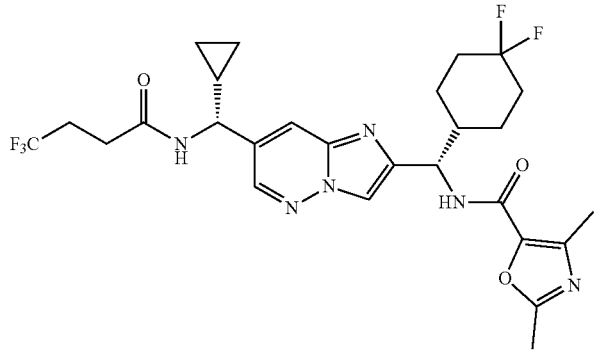 [SMILES: Cc1nc(C)c(C(=O)N[C@H](c2cn3ncc([C@H](NC(=O)CCC(F)(F)F)C4CC4)cc3n2)C2CCC(F)(F)CC2)o1]

TABLE 2J-continued
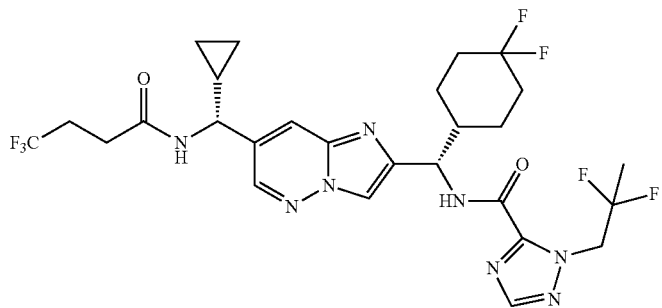 [SMILES: CC(F)(F)Cn1ncnc1C(=O)N[C@H](c1cn2ncc([C@H](NC(=O)CCC(F)(F)F)C3CC3)cc2n1)C1CCC(F)(F)CC1]
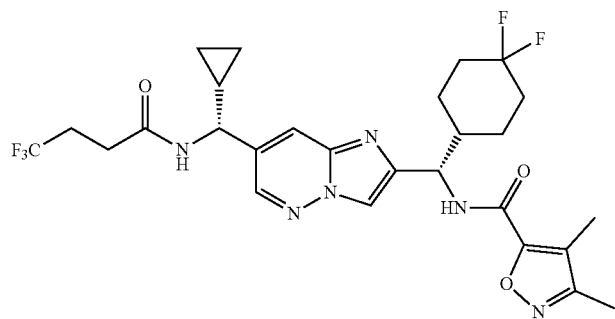 [SMILES: Cc1noc(C(=O)N[C@H](c2cn3ncc([C@H](NC(=O)CCC(F)(F)F)C4CC4)cc3n2)C2CCC(F)(F)CC2)c1C]
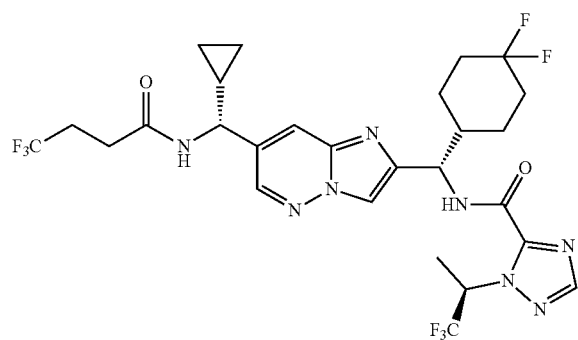 [SMILES: C[C@@H](n1ncnc1C(=O)N[C@H](c1cn2ncc([C@H](NC(=O)CCC(F)(F)F)C3CC3)cc2n1)C1CCC(F)(F)CC1)C(F)(F)F]
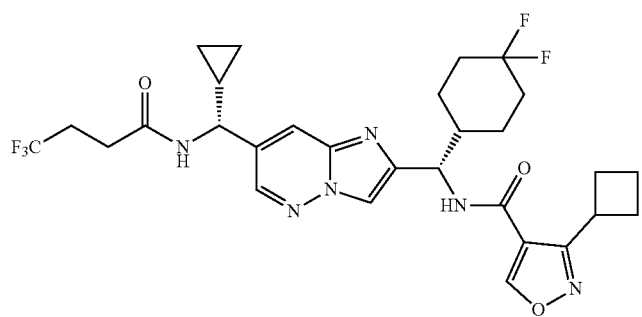 [SMILES: O=C(CCC(F)(F)F)N[C@@H](c1cnn2cc([C@@H](NC(=O)c3conc3C3CCC3)C3CCC(F)(F)CC3)nc2c1)C1CC1]

TABLE 2J-continued
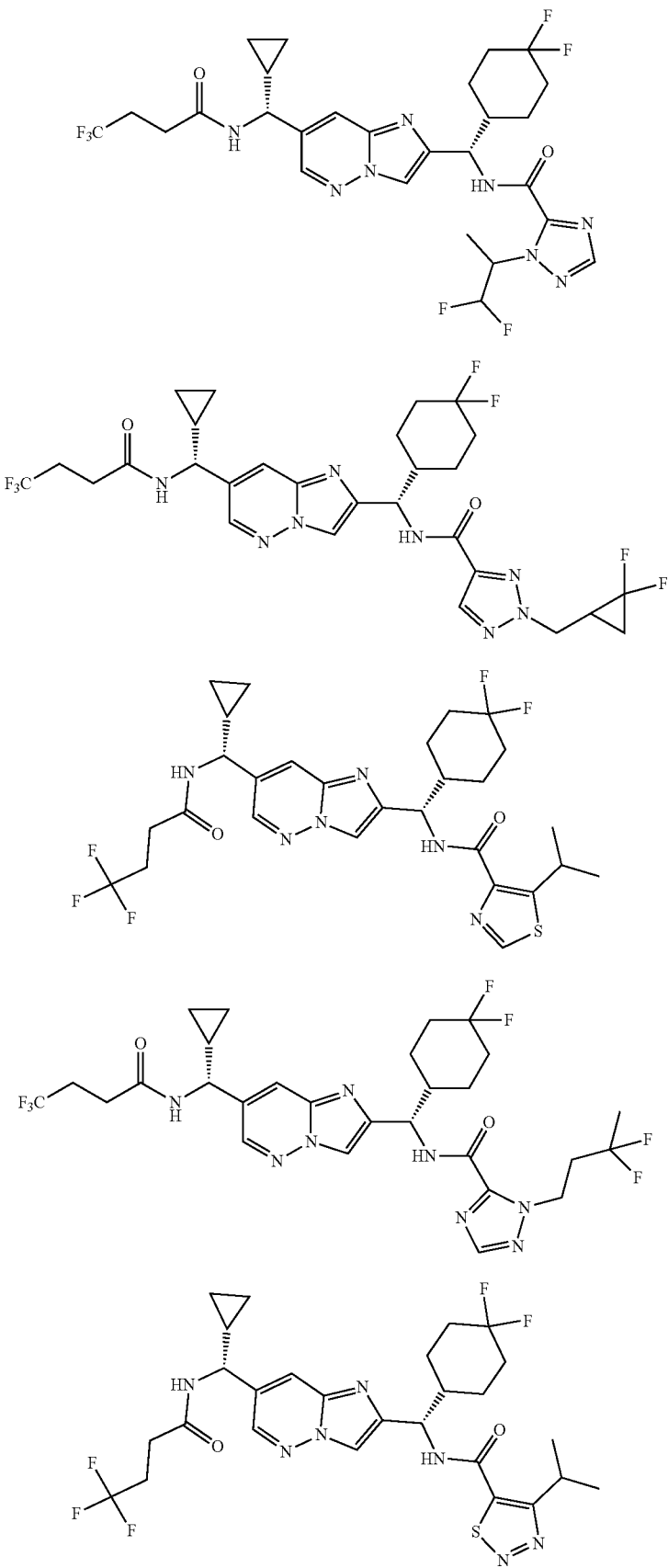

TABLE 2J-continued
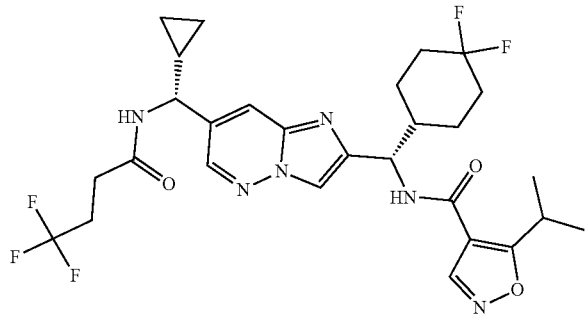 [SMILES: CC(C)c1oncc1C(=O)N[C@H](c1cn2ncc([C@H](NC(=O)CCC(F)(F)F)C3CC3)cc2n1)C1CCC(F)(F)CC1]
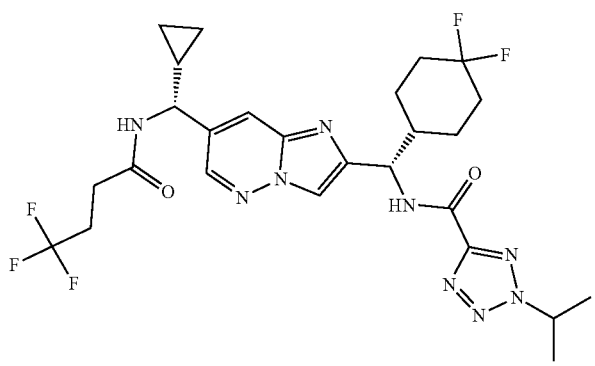 [SMILES: CC(C)n1nnc(C(=O)N[C@H](c2cn3ncc([C@H](NC(=O)CCC(F)(F)F)C4CC4)cc3n2)C2CCC(F)(F)CC2)n1]
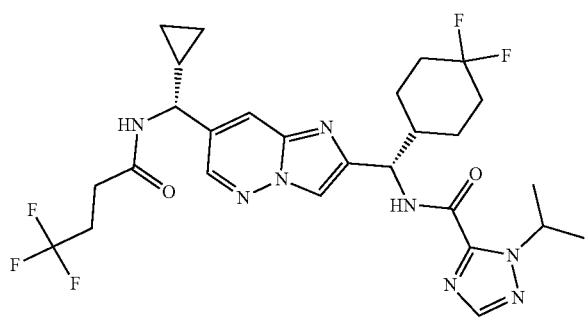 [SMILES: CC(C)n1ncnc1C(=O)N[C@H](c1cn2ncc([C@H](NC(=O)CCC(F)(F)F)C3CC3)cc2n1)C1CCC(F)(F)CC1]
TABLE 2K
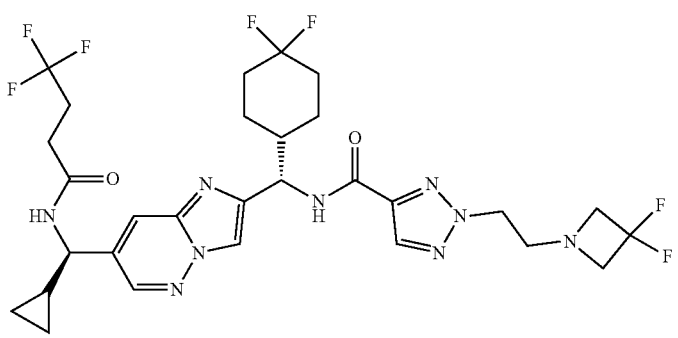 [SMILES: O=C(CCC(F)(F)F)N[C@@H](c1cnn2cc([C@@H](NC(=O)c3cnn(CCN4CC(F)(F)C4)n3)C3CCC(F)(F)CC3)nc2c1)C1CC1]

TABLE 2K-continued
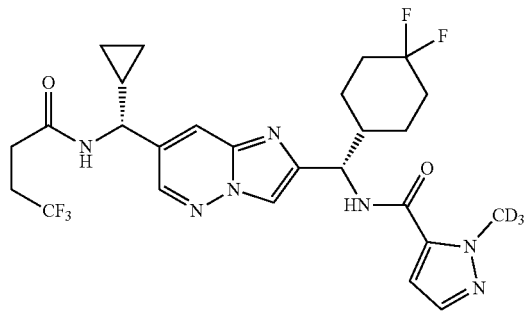 [SMILES: [2H]C([2H])([2H])n1nccc1C(=O)N[C@H](c1cn2ncc([C@H](NC(=O)CCC(F)(F)F)C3CC3)cc2n1)C1CCC(F)(F)CC1]
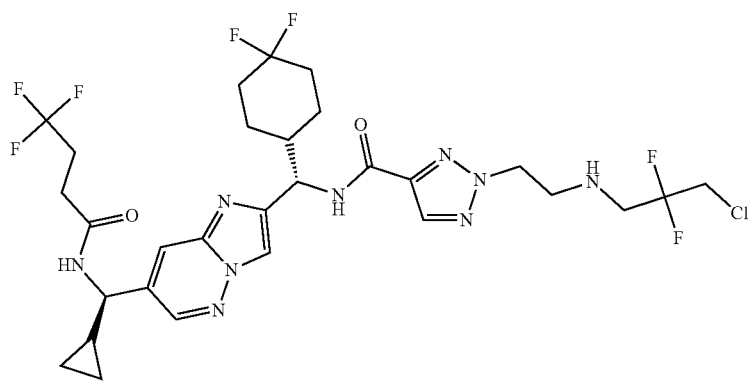 [SMILES: O=C(CCC(F)(F)F)N[C@@H](c1cnn2cc([C@@H](NC(=O)c3cnn(CCNCC(F)(F)CCl)n3)C3CCC(F)(F)CC3)nc2c1)C1CC1]
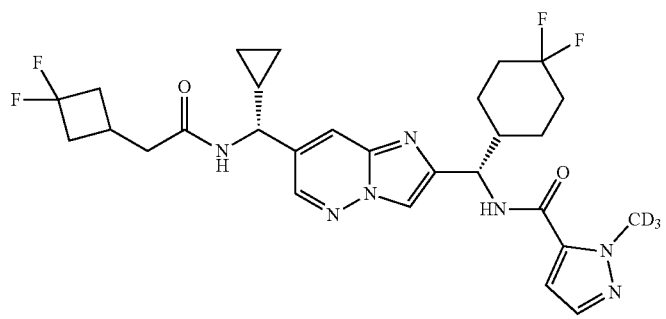 [SMILES: [2H]C([2H])([2H])n1nccc1C(=O)N[C@H](c1cn2ncc([C@H](NC(=O)CC3CC(F)(F)C3)C3CC3)cc2n1)C1CCC(F)(F)CC1]
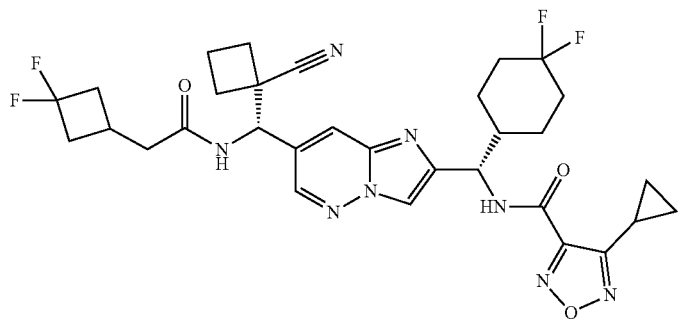 [SMILES: N#CC1([C@@H](NC(=O)CC2CC(F)(F)C2)c2cnn3cc([C@@H](NC(=O)c4nonc4C4CC4)C4CCC(F)(F)CC4)nc3c2)CCC1]

TABLE 2K-continued
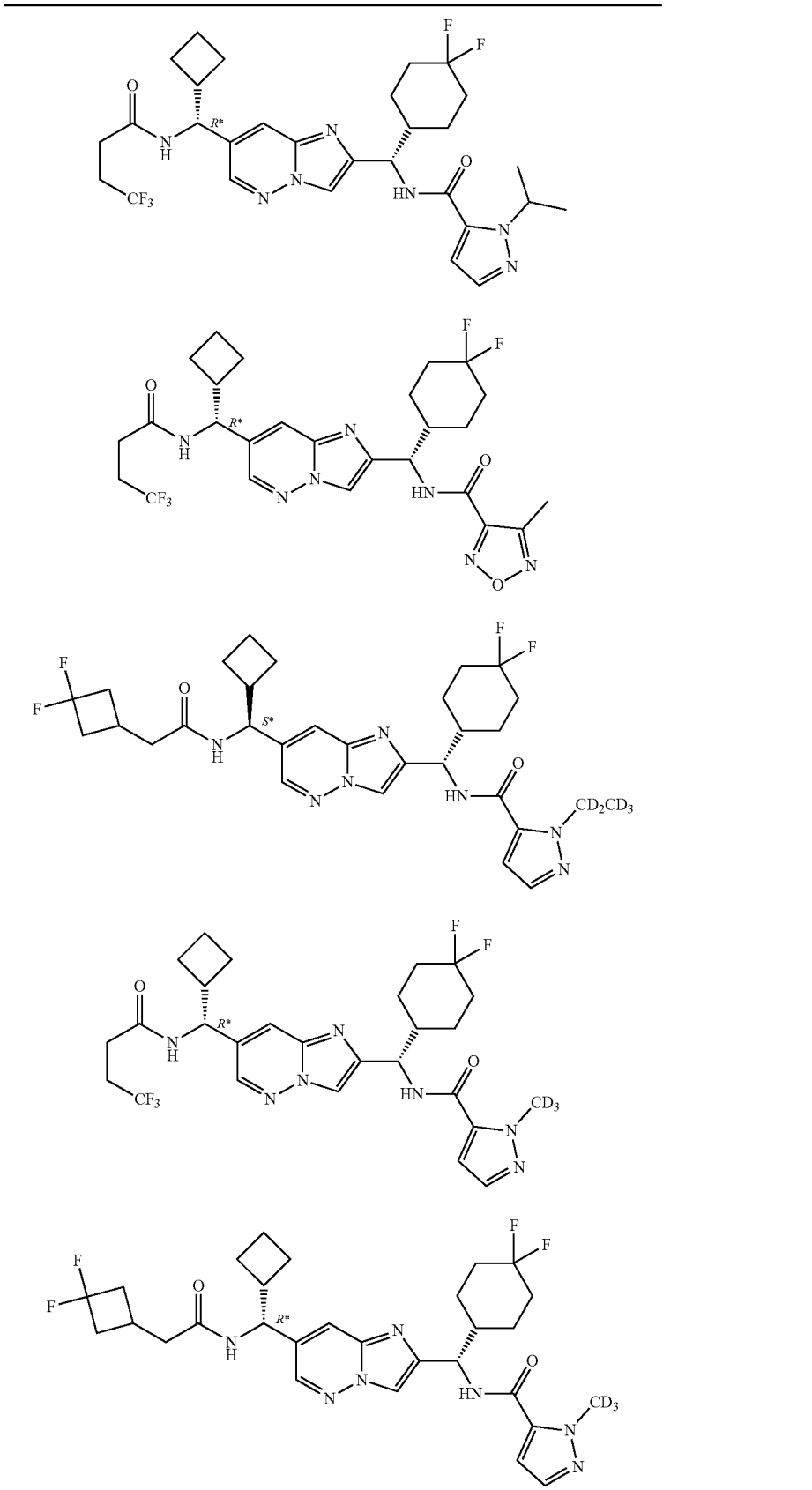

TABLE 2K-continued
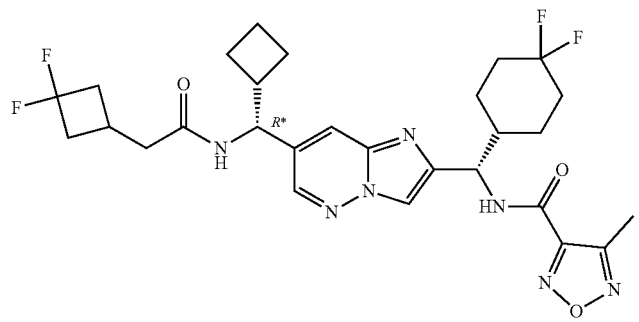 [SMILES: Cc1nonc1C(=O)N[C@H](c1cn2ncc([C@H](NC(=O)CC3CC(F)(F)C3)C3CCC3)cc2n1)C1CCC(F)(F)CC1]
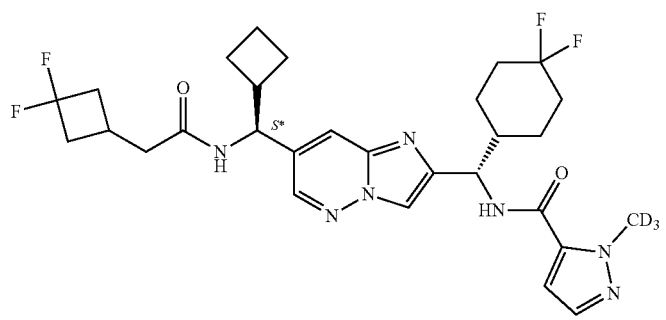 [SMILES: [2H]C([2H])([2H])n1nccc1C(=O)N[C@H](c1cn2ncc([C@@H](NC(=O)CC3CC(F)(F)C3)C3CCC3)cc2n1)C1CCC(F)(F)CC1]
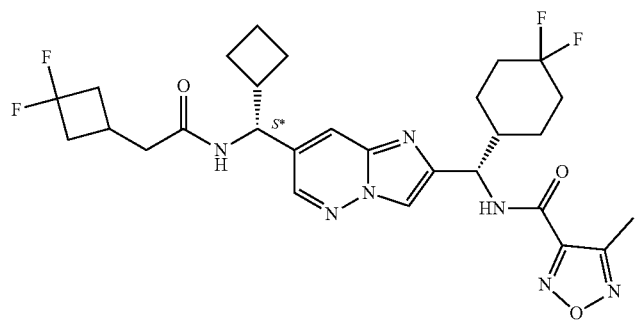 [SMILES: Cc1nonc1C(=O)N[C@H](c1cn2ncc([C@H](NC(=O)CC3CC(F)(F)C3)C3CCC3)cc2n1)C1CCC(F)(F)CC1]
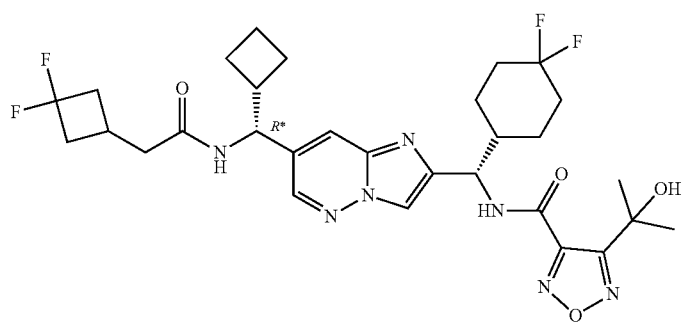 [SMILES: CC(C)(O)c1nonc1C(=O)N[C@H](c1cn2ncc([C@H](NC(=O)CC3CC(F)(F)C3)C3CCC3)cc2n1)C1CCC(F)(F)CC1]
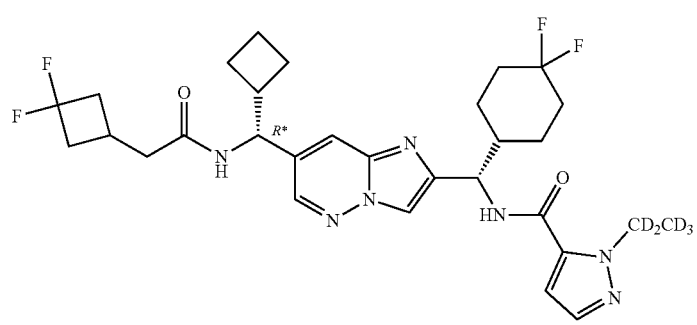

TABLE 2K-continued
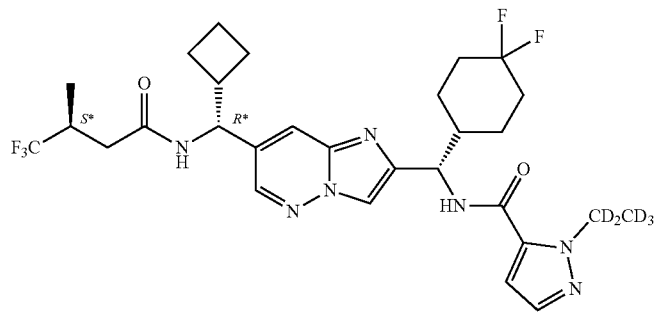
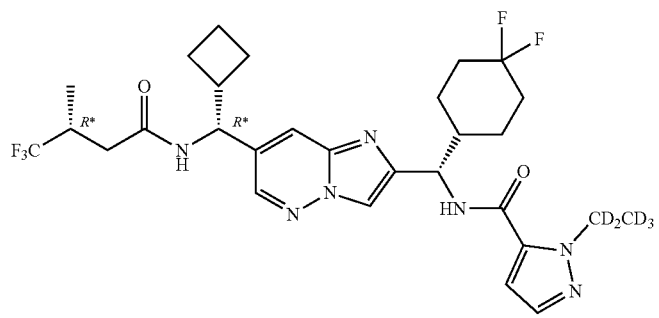
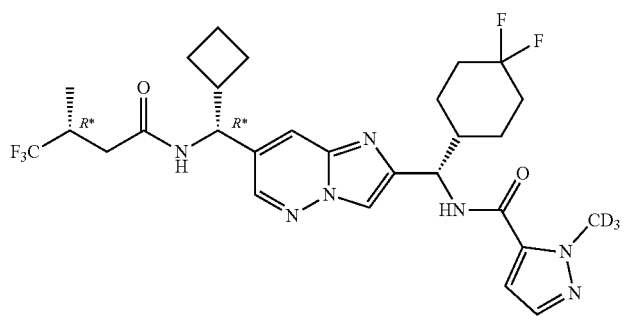 [SMILES: [2H]C([2H])([2H])n1nccc1C(=O)N[C@H](c1cn2ncc([C@H](NC(=O)C[C@@H](C)C(F)(F)F)C3CCC3)cc2n1)C1CCC(F)(F)CC1]
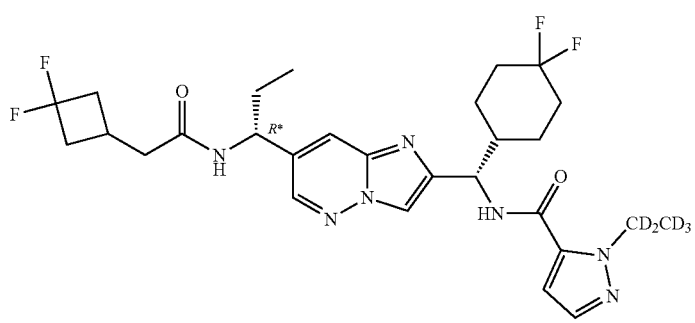
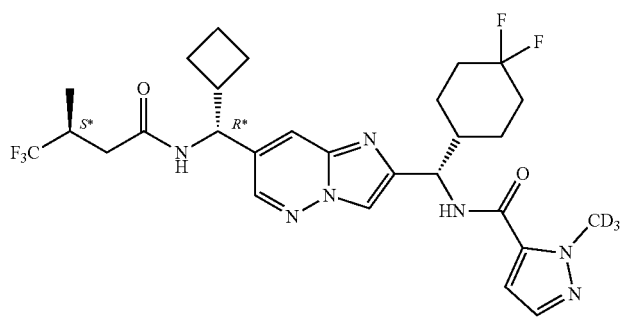 [SMILES: [2H]C([2H])([2H])n1nccc1C(=O)N[C@H](c1cn2ncc([C@H](NC(=O)C[C@H](C)C(F)(F)F)C3CCC3)cc2n1)C1CCC(F)(F)CC1]

TABLE 2K-continued
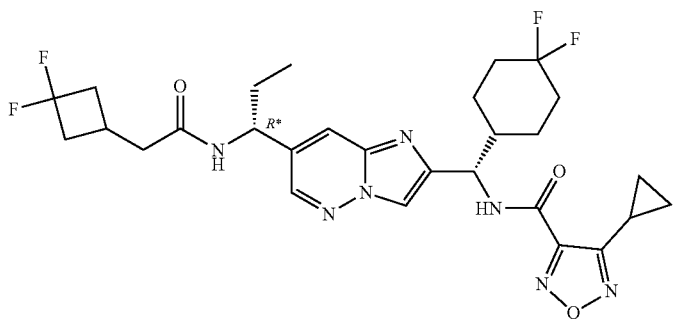 [SMILES: CC[C@@H](NC(=O)CC1CC(F)(F)C1)c1cnn2cc([C@@H](NC(=O)c3nonc3C3CC3)C3CCC(F)(F)CC3)nc2c1]
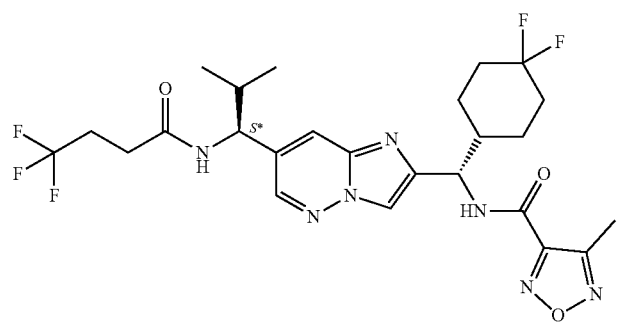 [SMILES: Cc1nonc1C(=O)N[C@H](c1cn2ncc([C@@H](NC(=O)CCC(F)(F)F)C(C)C)cc2n1)C1CCC(F)(F)CC1]
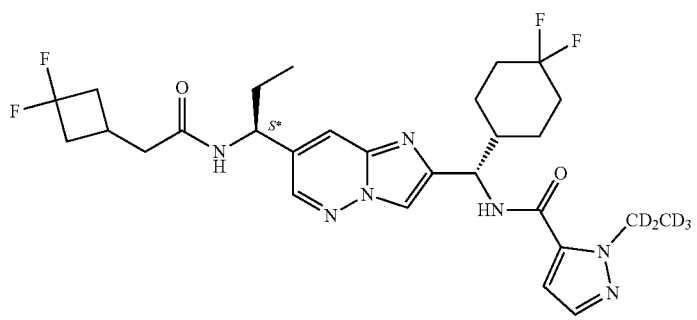
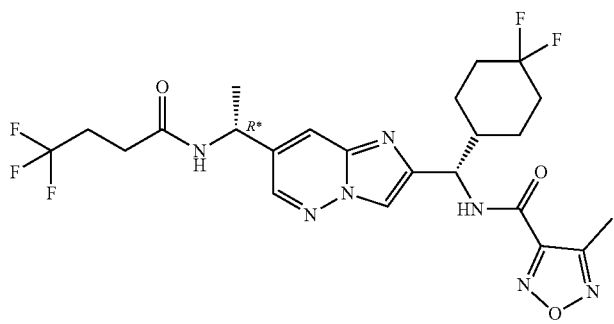 [SMILES: Cc1nonc1C(=O)N[C@H](c1cn2ncc([C@@H](C)NC(=O)CCC(F)(F)F)cc2n1)C1CCC(F)(F)CC1]
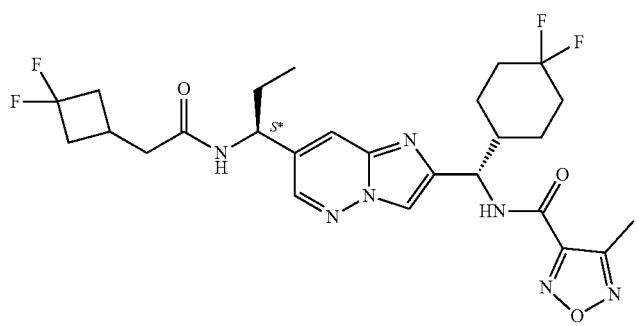 [SMILES: CC[C@H](NC(=O)CC1CC(F)(F)C1)c1cnn2cc([C@@H](NC(=O)c3nonc3C)C3CCC(F)(F)CC3)nc2c1]

TABLE 2L
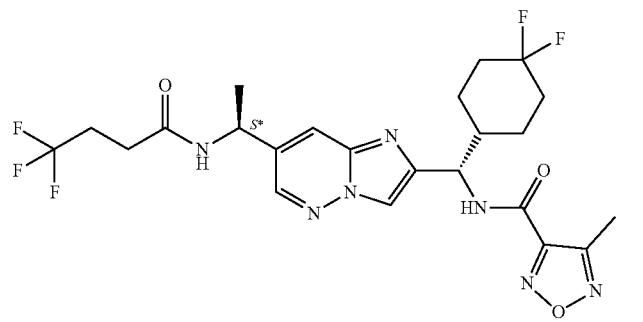 [SMILES: Cc1nonc1C(=O)N[C@H](c1cn2ncc([C@H](C)NC(=O)CCC(F)(F)F)cc2n1)C1CCC(F)(F)CC1]
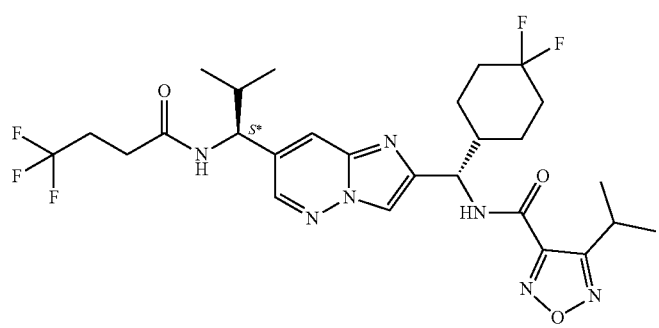 [SMILES: CC(C)c1nonc1C(=O)N[C@H](c1cn2ncc([C@@H](NC(=O)CCC(F)(F)F)C(C)C)cc2n1)C1CCC(F)(F)CC1]
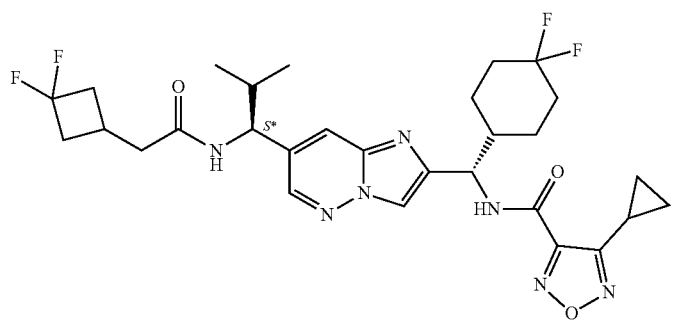 [SMILES: CC(C)[C@H](NC(=O)CC1CC(F)(F)C1)c1cnn2cc([C@@H](NC(=O)c3nonc3C3CC3)C3CCC(F)(F)CC3)nc2c1]
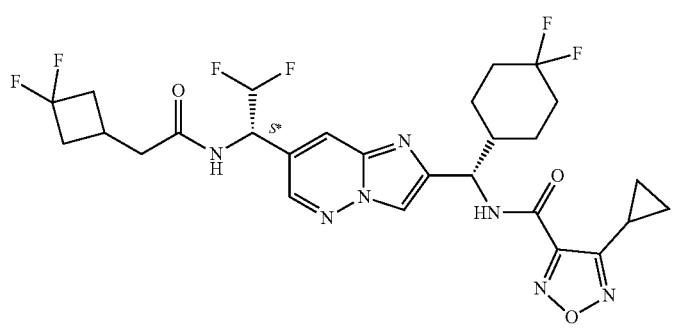 [SMILES: O=C(CC1CC(F)(F)C1)N[C@@H](c1cnn2cc([C@@H](NC(=O)c3nonc3C3CC3)C3CCC(F)(F)CC3)nc2c1)C(F)F]
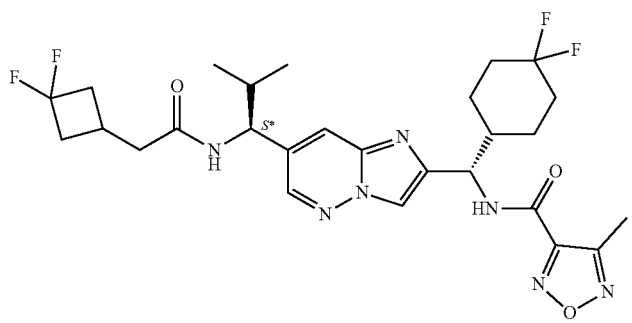 [SMILES: Cc1nonc1C(=O)N[C@H](c1cn2ncc([C@@H](NC(=O)CC3CC(F)(F)C3)C(C)C)cc2n1)C1CCC(F)(F)CC1]

TABLE 2L-continued
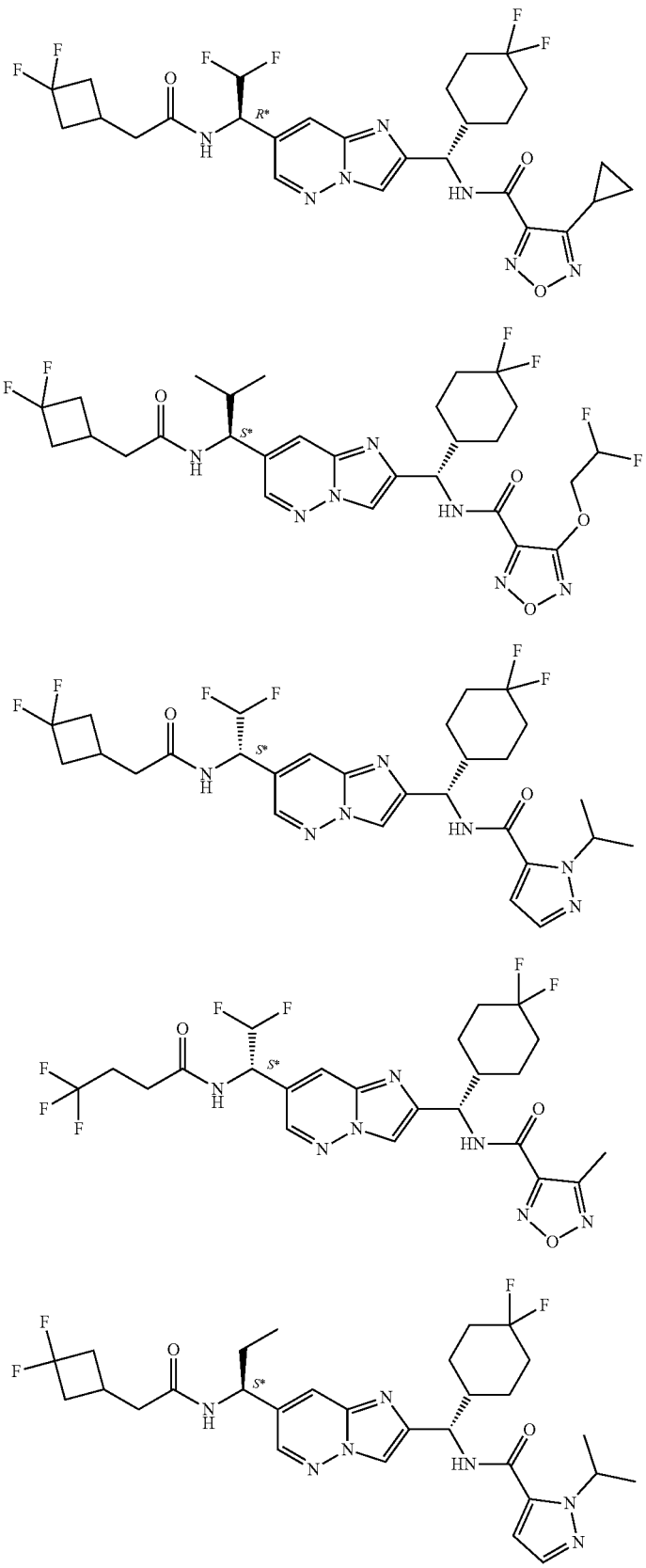

TABLE 2L-continued
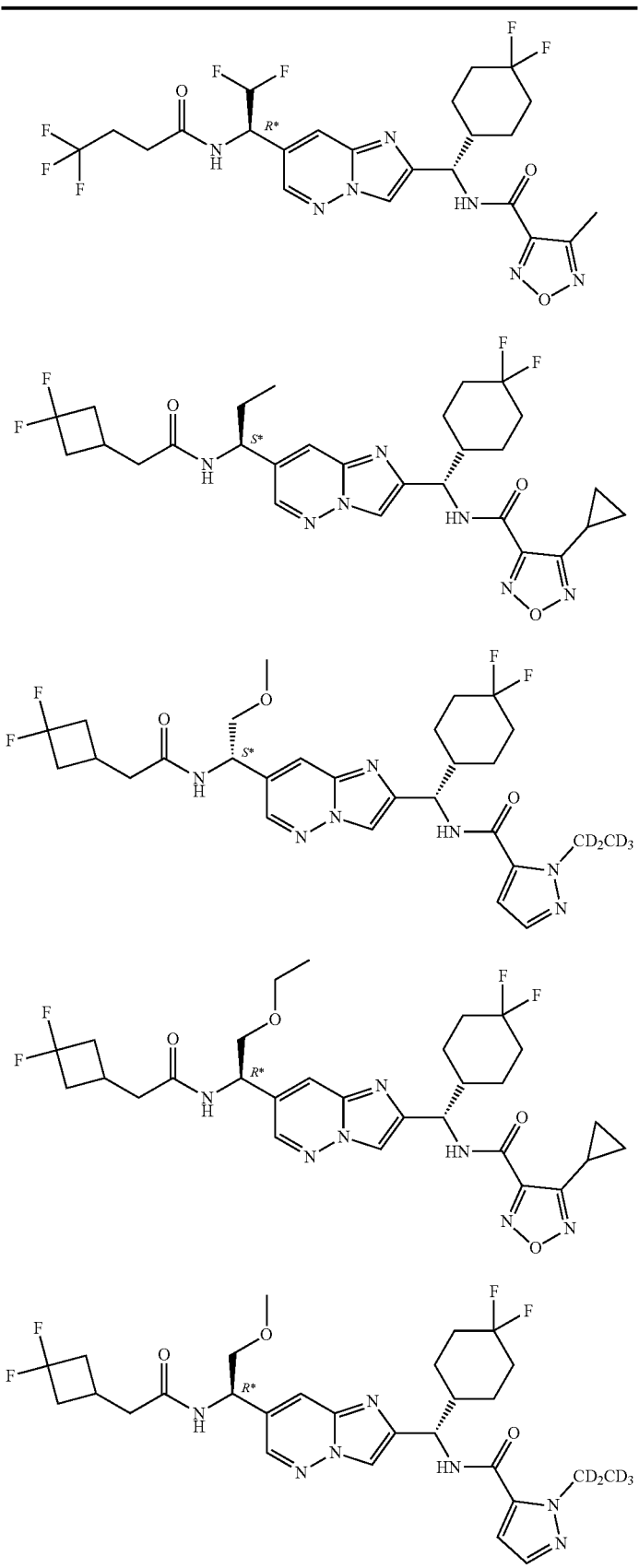

TABLE 2L-continued
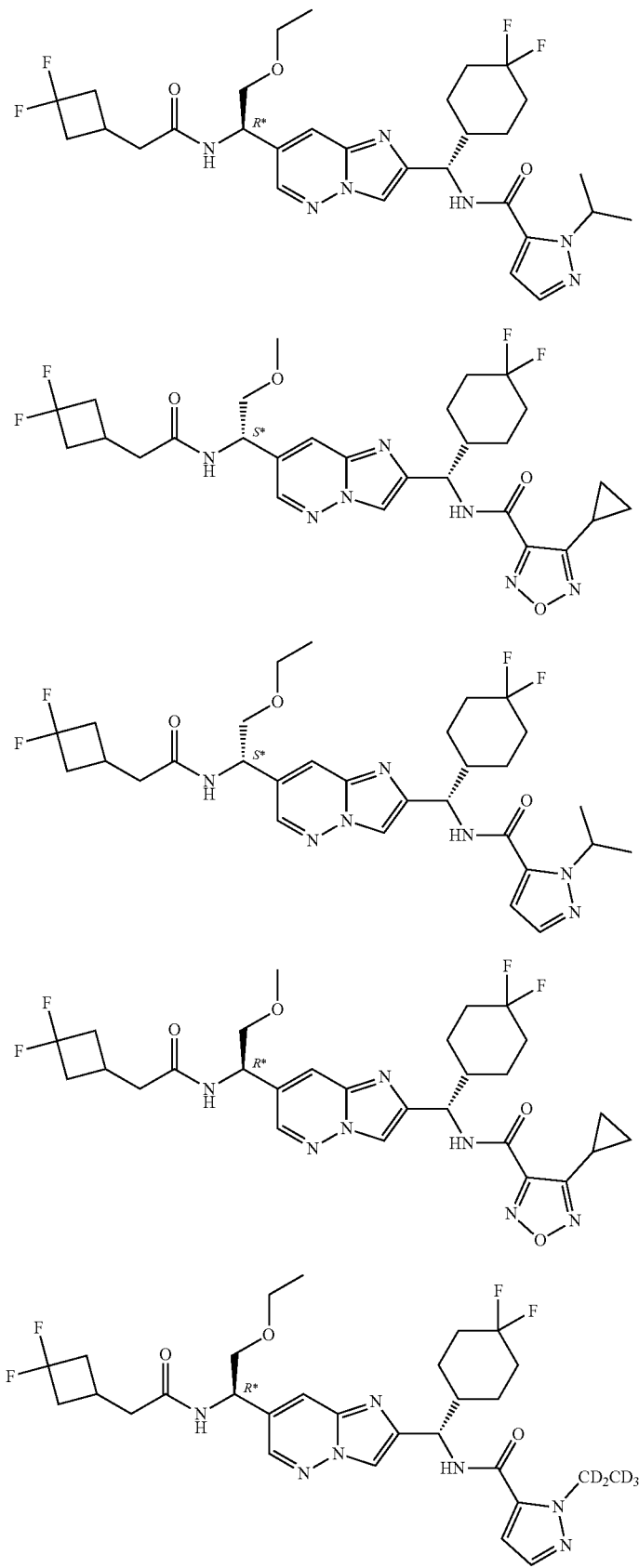

TABLE 2L-continued
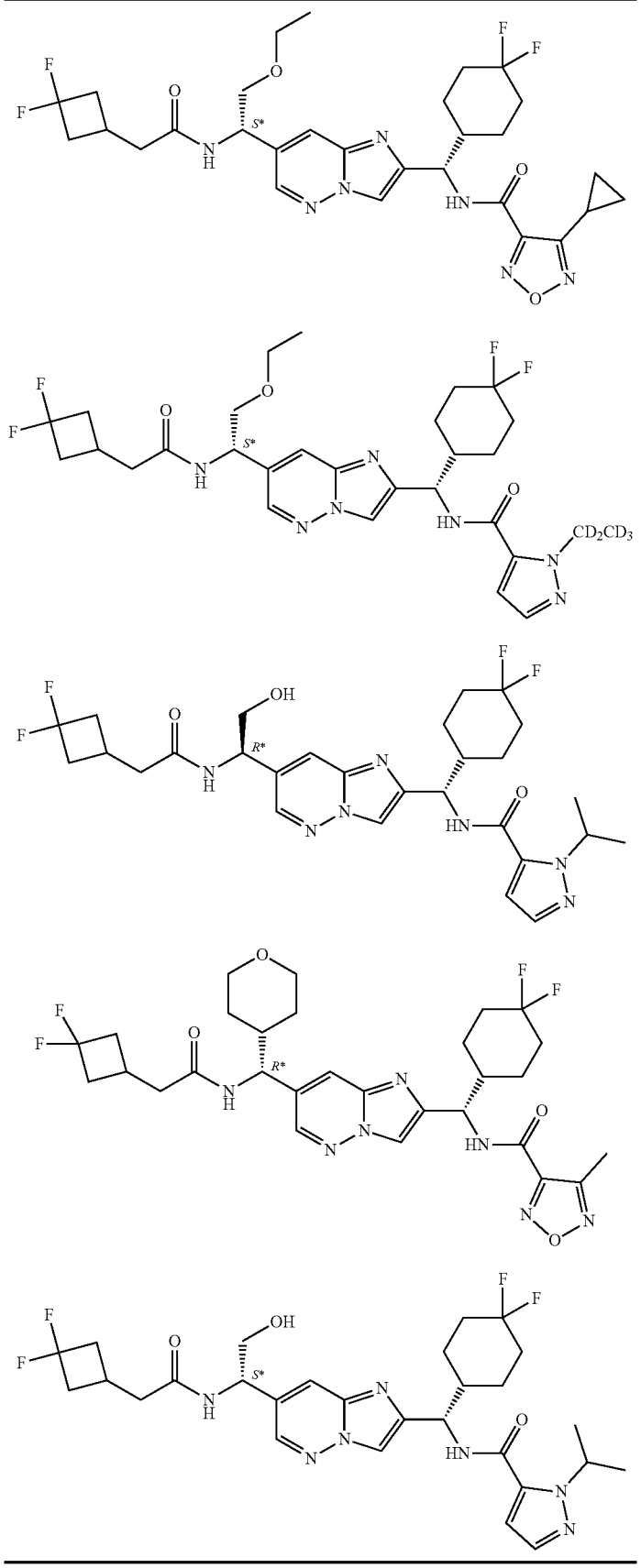

TABLE 2M
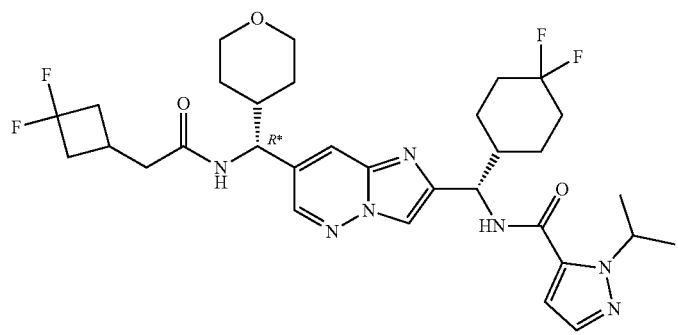 [SMILES: CC(C)n1nccc1C(=O)N[C@H](c1cn2ncc([C@H](NC(=O)CC3CC(F)(F)C3)C3CCOCC3)cc2n1)C1CCC(F)(F)CC1]
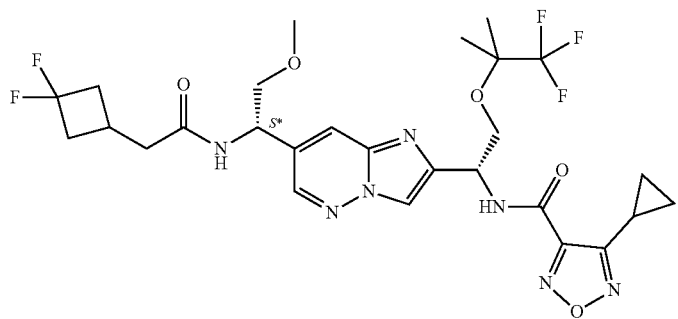 [SMILES: COC[C@@H](NC(=O)CC1CC(F)(F)C1)c1cnn2cc([C@H](COC(C)(C)C(F)(F)F)NC(=O)c3nonc3C3CC3)nc2c1]
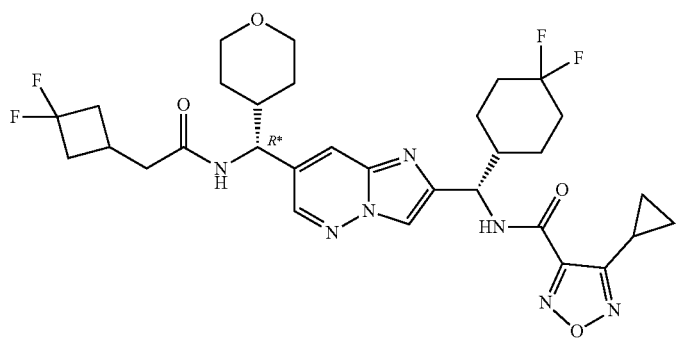 [SMILES: O=C(CC1CC(F)(F)C1)N[C@@H](c1cnn2cc([C@@H](NC(=O)c3nonc3C3CC3)C3CCC(F)(F)CC3)nc2c1)C1CCOCC1]
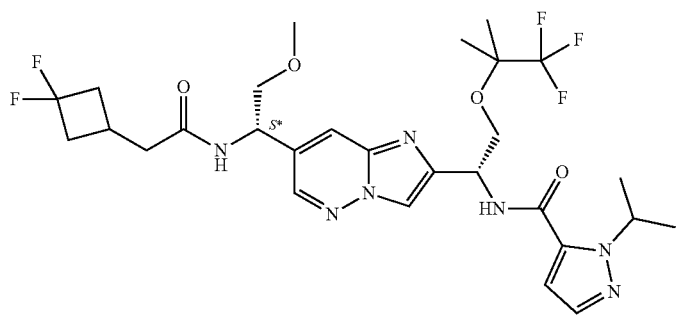 [SMILES: COC[C@@H](NC(=O)CC1CC(F)(F)C1)c1cnn2cc([C@H](COC(C)(C)C(F)(F)F)NC(=O)c3ccnn3C(C)C)nc2c1]

TABLE 2M-continued
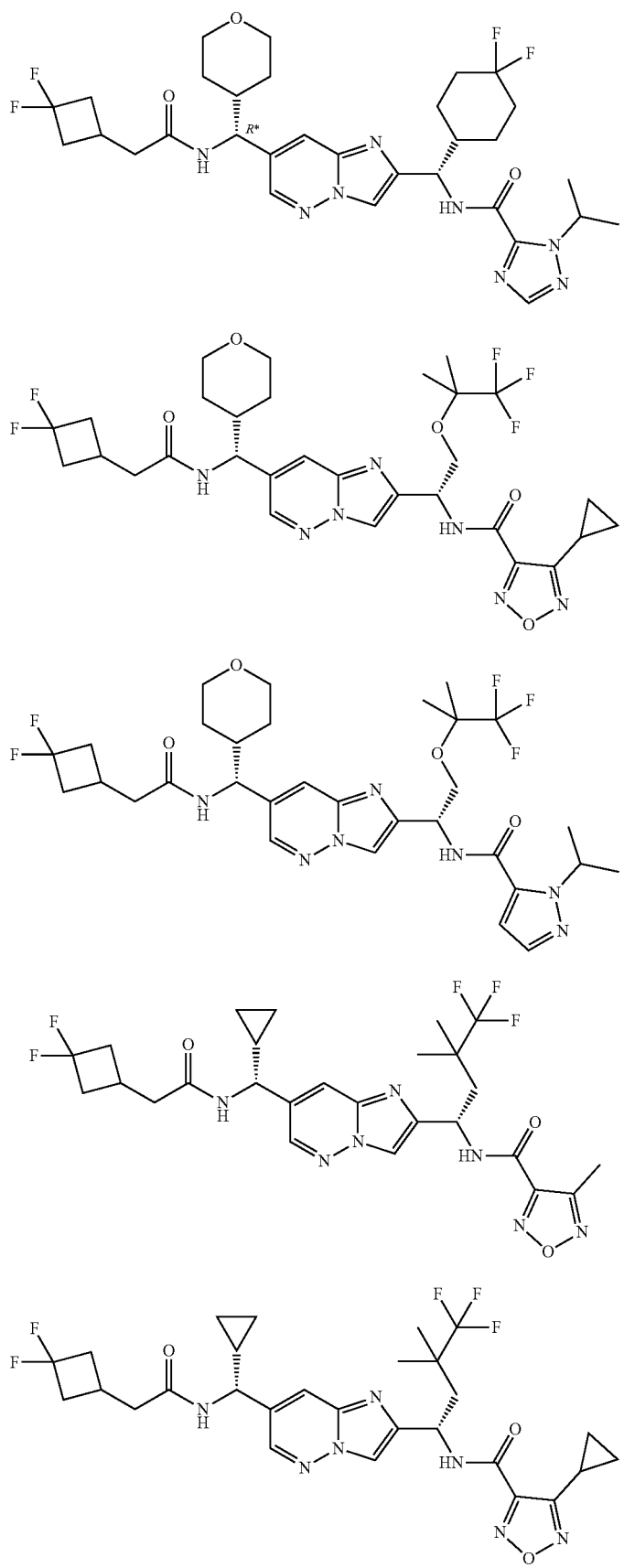

TABLE 2M-continued

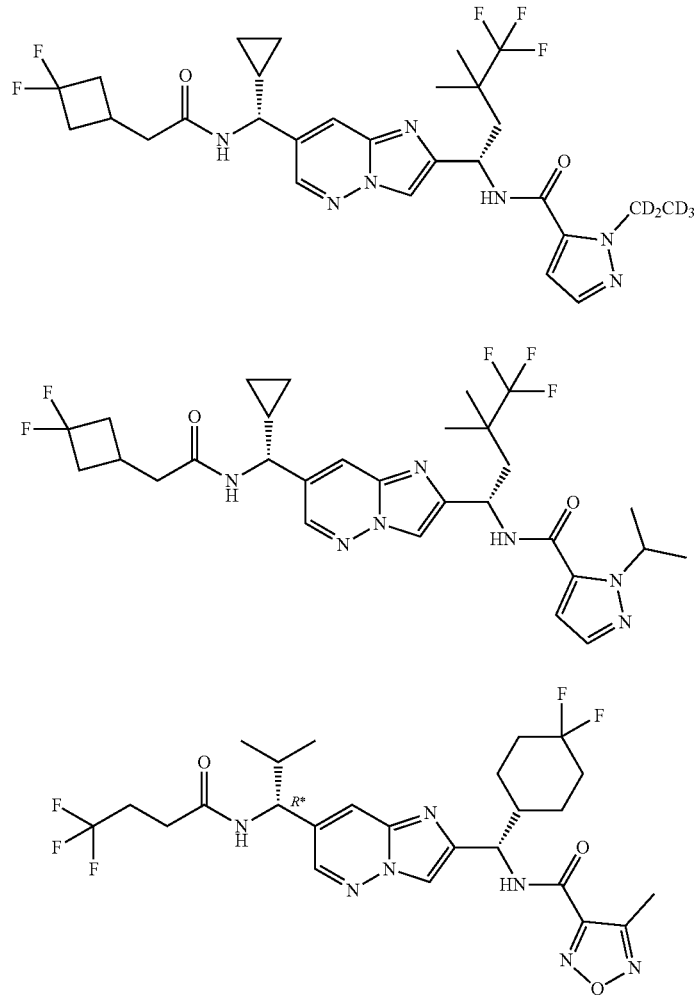

In some embodiments, disclosed herein is a compound of Formula I', or a pharmaceutically acceptable salt thereof, selected from the group consisting of the compounds in Table 2A, Table 2B, Table 2C, Table 2D, Table 2E, Table 2F, Table 2G, Table 2H, Table 2I, Table 2J, Table 2K, and Table 2M.

In some embodiments, disclosed herein is a compound of Formula I', or a pharmaceutically acceptable salt thereof, selected from the group consisting of:

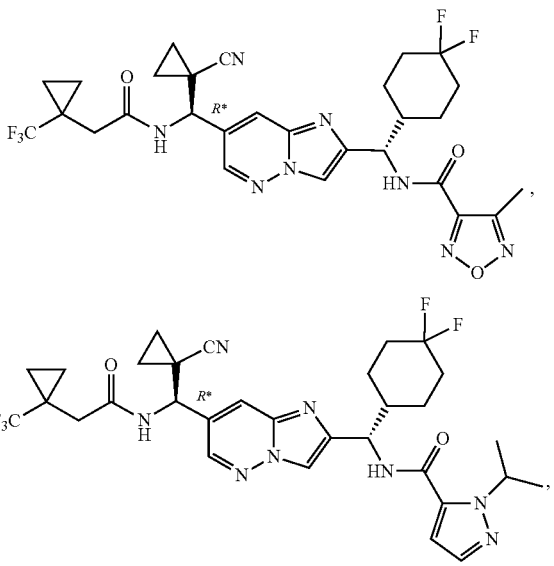

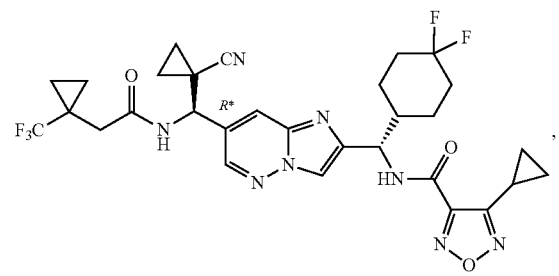
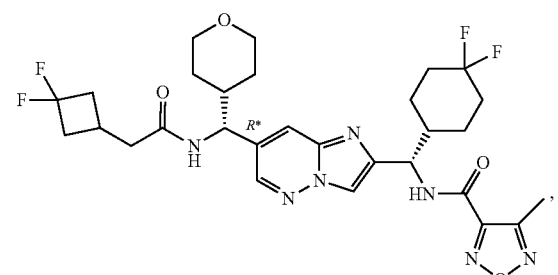
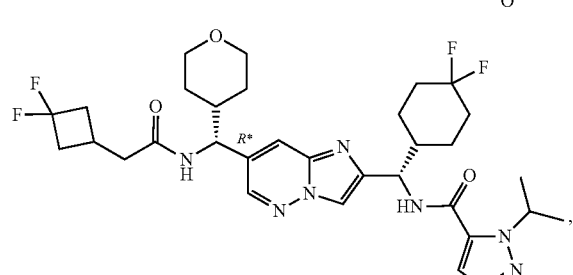
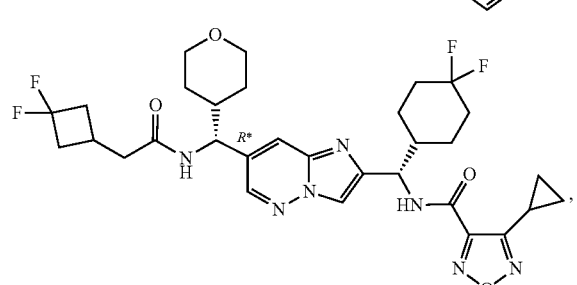
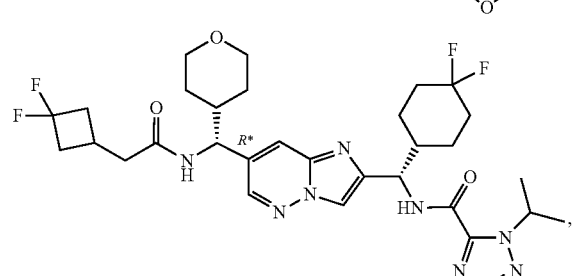
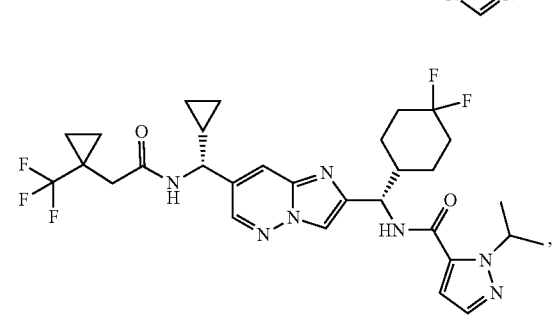
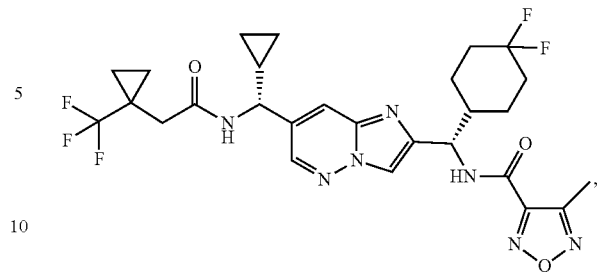
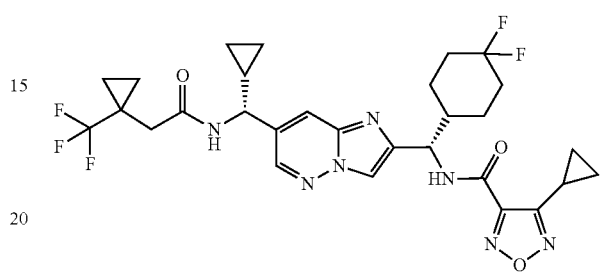
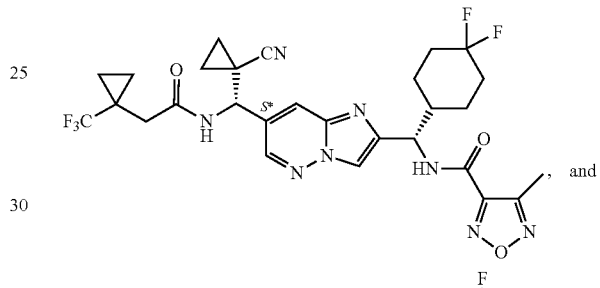, and
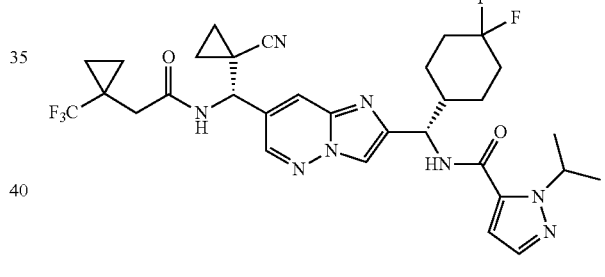
In some embodiments, disclosed herein is a compound of Formula I that is
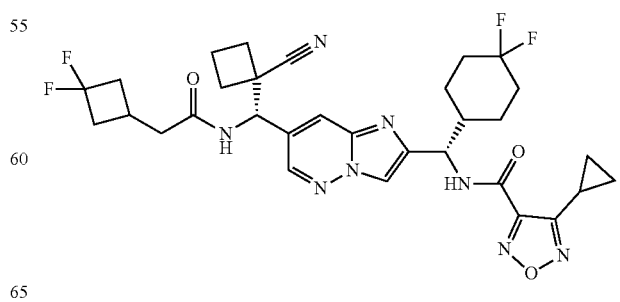
or a pharmaceutically acceptable salt thereof.

In some embodiments, disclosed herein is a compound of Formula I' that is

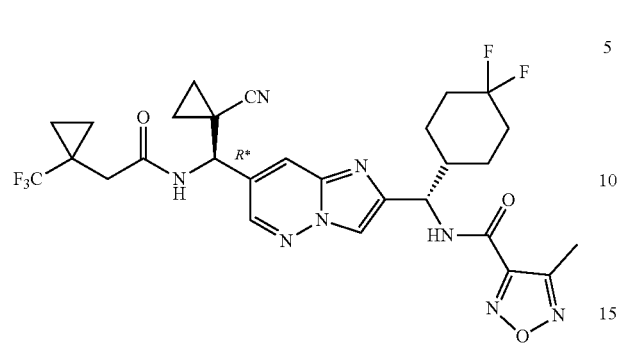

or a pharmaceutically acceptable salt thereof.

In some embodiments, disclosed herein is a compound of Formula I' that is

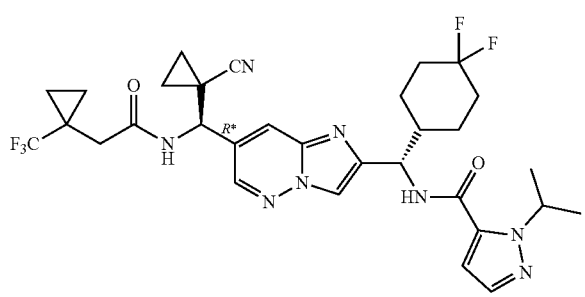 [SMILES: CC(C)n1nccc1C(=O)N[C@H](c1cn2ncc([C@@H](NC(=O)CC3(C(F)(F)F)CC3)C3(C#N)CC3)cc2n1)C1CCC(F)(F)CC1]

or a pharmaceutically acceptable salt thereof.

In some embodiments, disclosed herein is a compound of Formula I' that is

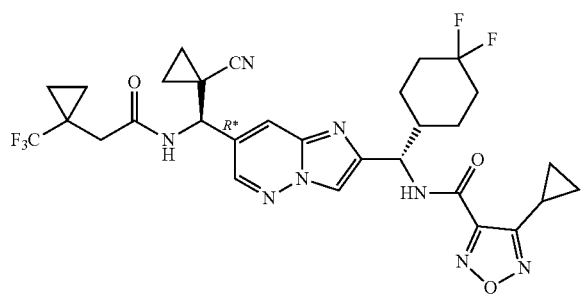 [SMILES: N#CC1([C@H](NC(=O)CC2(C(F)(F)F)CC2)c2cnn3cc([C@@H](NC(=O)c4nonc4C4CC4)C4CCC(F)(F)CC4)nc3c2)CC1]

or a pharmaceutically acceptable salt thereof.

In some embodiments, disclosed herein is a compound of Formula I' that is

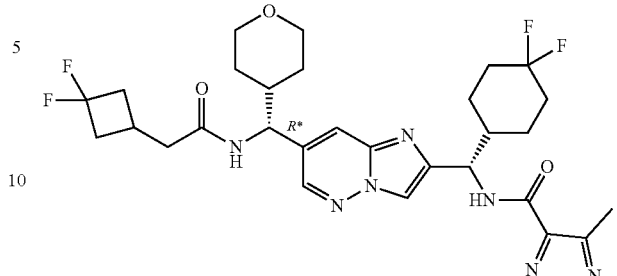

or a pharmaceutically acceptable salt thereof.

In some embodiments, disclosed herein is a compound of Formula I' that is

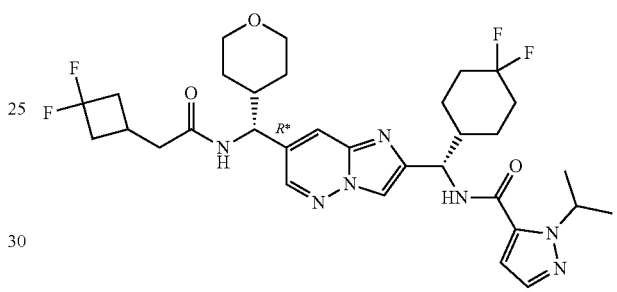

or a pharmaceutically acceptable salt thereof.

In some embodiments, disclosed herein is a compound of Formula I' that is

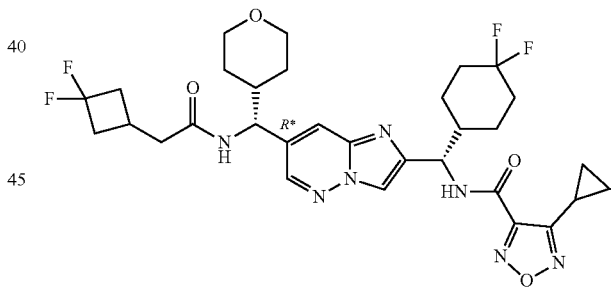

or a pharmaceutically acceptable salt thereof.

In some embodiments, disclosed herein is a compound of Formula I' that is

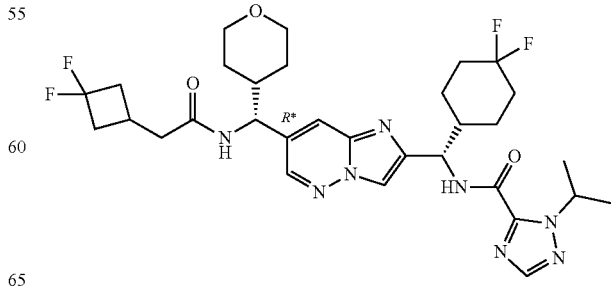

or a pharmaceutically acceptable salt thereof.

In some embodiments, disclosed herein is a compound of Formula I' that is

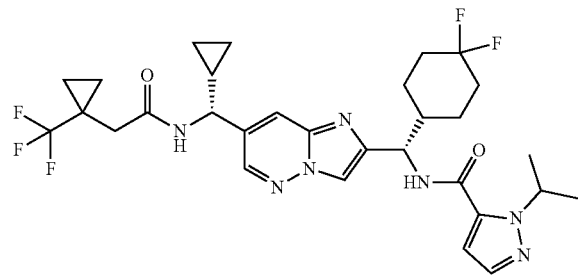 [SMILES: CC(C)n1nccc1C(=O)N[C@H](c1cn2ncc([C@H](NC(=O)CC3(C(F)(F)F)CC3)C3CC3)cc2n1)C1CCC(F)(F)CC1]

In some embodiments, disclosed herein is a compound of Formula I' that is

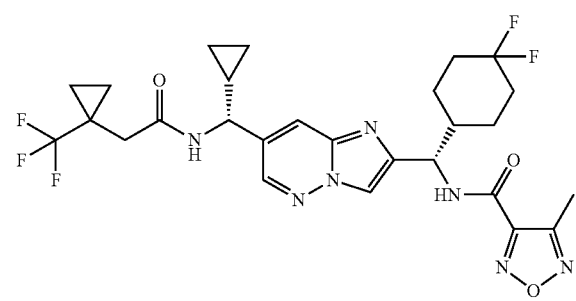 [SMILES: Cc1nonc1C(=O)N[C@H](c1cn2ncc([C@H](NC(=O)CC3(C(F)(F)F)CC3)C3CC3)cc2n1)C1CCC(F)(F)CC1]

or a pharmaceutically acceptable salt thereof.

In some embodiments, disclosed herein is a compound of Formula I' that is

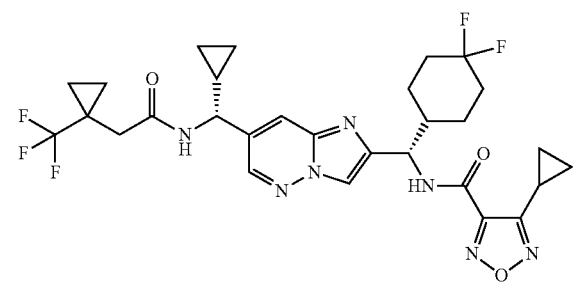 [SMILES: O=C(CC1(C(F)(F)F)CC1)N[C@@H](c1cnn2cc([C@@H](NC(=O)c3nonc3C3CC3)C3CCC(F)(F)CC3)nc2c1)C1CC1]

or a pharmaceutically acceptable salt thereof.

In some embodiments, disclosed herein is a compound of Formula I' that is

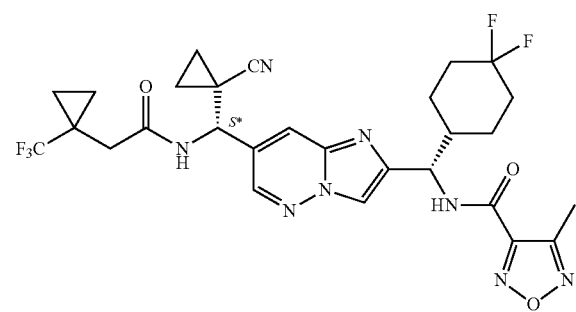 [SMILES: Cc1nonc1C(=O)N[C@H](c1cn2ncc([C@H](NC(=O)CC3(C(F)(F)F)CC3)C3(C#N)CC3)cc2n1)C1CCC(F)(F)CC1]

or a pharmaceutically acceptable salt thereof.

In some embodiments, disclosed herein is a compound of Formula I' that is

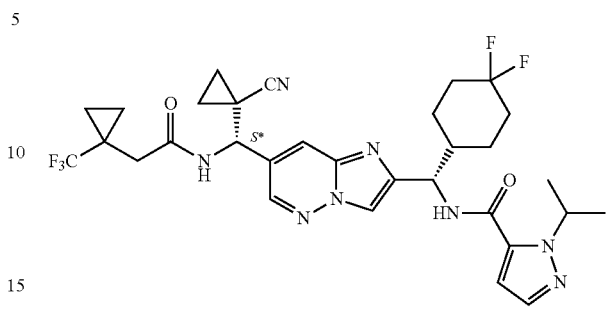

or a pharmaceutically acceptable salt thereof.

In some embodiments, disclosed herein is a pharmaceutical composition, comprising a compound of Formula I', or a pharmaceutically acceptable salt thereof, and a pharmaceutically acceptable carrier. In some embodiments, the pharmaceutical composition is formulated for oral administration (e.g., a tablet or capsule).

In some embodiments, disclosed herein is a pharmaceutical composition made by mixing a compound of Formula I', or a pharmaceutically acceptable salt thereof, and a pharmaceutically acceptable carrier.

In some embodiments, disclosed herein is a process for making a pharmaceutical composition comprising mixing a compound of Formula I', or a pharmaceutically acceptable salt thereof, and a pharmaceutically acceptable carrier.

III. Therapeutic Use

The present application is also directed to a method for treating and/or ameliorating a IL-17 mediated inflammatory syndrome, disorder or disease comprising administering to a subject in need thereof an effective amount of a compound of Formula I, or pharmaceutically acceptable salt thereof, composition thereof, or medicament thereof.

The present application is also directed to a method for treating and/or ameliorating a IL-17 mediated inflammatory syndrome, disorder or disease comprising administering to a subject in need thereof an effective amount of a compound of Formula I', or pharmaceutically acceptable salt thereof, composition thereof, or medicament thereof.

In some embodiments, disclosed herein is a method for treating or ameliorating an IL-17A mediated inflammatory syndrome, disorder, or disease comprising administering to a subject in need thereof a therapeutically effective amount of a compound of Formula I, or a pharmaceutically acceptable salt thereof.

In some embodiments, disclosed herein is a method for treating or ameliorating an IL-17A mediated inflammatory syndrome, disorder, or disease comprising administering to a subject in need thereof a therapeutically effective amount of a compound of Formula I', or a pharmaceutically acceptable salt thereof.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigold, atopic dermatitis, vitiligo, multiple sclerosis, asthma, uveitis, chronic obstructive pulmonary disorder, multiple myeloma, and systemic lupus erythematosus.

In some embodiments, disclosed herein is a method for treating and/or ameliorating an IL-17A mediated inflammatory syndrome, disorder, or disease comprising administering to a subject in need thereof a therapeutically effective amount of a compound of Formula I', or a pharmaceutically acceptable salt thereof, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigold, atopic dermatitis, vitiligo, multiple sclerosis, asthma, uveitis, chronic obstructive pulmonary disorder, multiple myeloma, and systemic lupus erythematosus.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is psoriasis.

In some embodiments, disclosed herein is a method for treating and/or ameliorating an IL-17A mediated inflammatory syndrome, disorder, or disease comprising administering to a subject in need thereof a therapeutically effective amount of a compound of Formula I', or a pharmaceutically acceptable salt thereof, wherein the IL-17A mediated inflammatory syndrome, disorder, or disease is psoriasis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is psoriatic arthritis.

In some embodiments, disclosed herein is a method for treating and/or ameliorating an IL-17A mediated inflammatory syndrome, disorder, or disease comprising administering to a subject in need thereof a therapeutically effective amount of a compound of Formula I', or a pharmaceutically acceptable salt thereof, wherein the IL-17A mediated inflammatory syndrome, disorder, or disease is psoriatic arthritis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is rheumatoid arthritis.

In some embodiments, disclosed herein is a method for treating and/or ameliorating an IL-17A mediated inflammatory syndrome, disorder, or disease comprising administering to a subject in need thereof a therapeutically effective amount of a compound of Formula I', or a pharmaceutically acceptable salt thereof, wherein the IL-17A mediated inflammatory syndrome, disorder, or disease is rheumatoid arthritis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is ankylosing spondylitis.

In some embodiments, disclosed herein is a method for treating and/or ameliorating an IL-17A mediated inflammatory syndrome, disorder, or disease comprising administering to a subject in need thereof a therapeutically effective amount of a compound of Formula I', or a pharmaceutically acceptable salt thereof, wherein the IL-17A mediated inflammatory syndrome, disorder, or disease is ankylosing spondylitis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is hidradenitis suppurativa.

In some embodiments, disclosed herein is a method for treating and/or ameliorating an IL-17A mediated inflammatory syndrome, disorder, or disease comprising administering to a subject in need thereof a therapeutically effective amount of a compound of Formula I', or a pharmaceutically acceptable salt thereof, wherein the IL-17A mediated inflammatory syndrome, disorder, or disease is hidradenitis suppurativa.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is bullous pemphigold.

In some embodiments, disclosed herein is a method for treating and/or ameliorating an IL-17A mediated inflammatory syndrome, disorder, or disease comprising administering to a subject in need thereof a therapeutically effective amount of a compound of Formula I', or a pharmaceutically acceptable salt thereof, wherein the IL-17A mediated inflammatory syndrome, disorder, or disease is bullous pemphigold.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is atopic dermatitis.

In some embodiments, disclosed herein is a method for treating and/or ameliorating an IL-17A mediated inflammatory syndrome, disorder, or disease comprising administering to a subject in need thereof a therapeutically effective amount of a compound of Formula I', or a pharmaceutically acceptable salt thereof, wherein the IL-17A mediated inflammatory syndrome, disorder, or disease is atopic dermatitis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is vitiligo.

In some embodiments, disclosed herein is a method for treating and/or ameliorating an IL-17A mediated inflammatory syndrome, disorder, or disease comprising administering to a subject in need thereof a therapeutically effective amount of a compound of Formula I', or a pharmaceutically acceptable salt thereof, wherein the IL-17A mediated inflammatory syndrome, disorder, or disease is vitiligo.

In some embodiments, disclosed herein is a method for treating or ameliorating and/an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is multiple sclerosis.

In some embodiments, disclosed herein is a method for treating or ameliorating and/an IL-17A mediated inflammatory syndrome, disorder, or disease comprising administering to a subject in need thereof a therapeutically effective amount of a compound of Formula I', or a pharmaceutically acceptable salt thereof, wherein the IL-17A mediated inflammatory syndrome, disorder, or disease is multiple sclerosis.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is systemic lupus erythematosus.

In some embodiments, disclosed herein is a method for treating and/or ameliorating an IL-17A mediated inflammatory syndrome, disorder, or disease comprising administering to a subject in need thereof a therapeutically effective amount of a compound of Formula I', or a pharmaceutically acceptable salt thereof, wherein the IL-17A mediated inflammatory syndrome, disorder, or disease is systemic lupus erythematosus.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is asthma.

In some embodiments, disclosed herein is a method for treating and/or ameliorating an IL-17A mediated inflammatory syndrome, disorder, or disease comprising administering to a subject in need thereof a therapeutically effective amount of a compound of Formula I', or a pharmaceutically acceptable salt thereof, wherein the IL-17A mediated inflammatory syndrome, disorder, or disease is asthma.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is uveitits.

In some embodiments, disclosed herein is a method for treating and/or ameliorating an IL-17A mediated inflammatory syndrome, disorder, or disease comprising administering to a subject in need thereof a therapeutically effective amount of a compound of Formula I', or a pharmaceutically acceptable salt thereof, wherein the IL-17A mediated inflammatory syndrome, disorder, or disease is uveitits.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is chronic obstructive pulmonary disorder.

In some embodiments, disclosed herein is a method for treating and/or ameliorating an IL-17A mediated inflammatory syndrome, disorder, or disease comprising administering to a subject in need thereof a therapeutically effective amount of a compound of Formula I', or a pharmaceutically acceptable salt thereof, wherein the IL-17A mediated inflammatory syndrome, disorder, or disease is chronic obstructive pulmonary disorder.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is multiple myeloma.

In some embodiments, disclosed herein is a method for treating and/or ameliorating an IL-17A mediated inflammatory syndrome, disorder, or disease comprising administering to a subject in need thereof a therapeutically effective amount of a compound of Formula I', or a pharmaceutically acceptable salt thereof, wherein the IL-17A mediated inflammatory syndrome, disorder, or disease is multiple myeloma.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigold, atopic dermatitis, vitiligo, multiple sclerosis, asthma, uveitis, chronic obstructive pulmonary disorder, multiple myeloma, and systemic lupus erythematosus, wherein the compound of Formula I or the pharmaceutically acceptable salt thereof is administered orally (e.g., as a tablet or capsule).

In some embodiments, disclosed herein is a method for treating and/or ameliorating an IL-17A mediated inflammatory syndrome, disorder, or disease comprising administering to a subject in need thereof a therapeutically effective amount of a compound of Formula I', or a pharmaceutically acceptable salt thereof, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigold, atopic dermatitis, vitiligo, multiple sclerosis, asthma, uveitis, chronic obstructive pulmonary disorder, multiple myeloma, and systemic lupus erythematosus, wherein the compound of Formula I' or the pharmaceutically acceptable salt thereof is administered orally (e.g., as a tablet or capsule).

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigold, atopic dermatitis, vitiligo, multiple sclerosis, asthma, uveitis, chronic obstructive pulmonary disorder, multiple myeloma, and systemic lupus erythematosus, wherein the therapeutically effective amount is a dose of about 10 mg to 300 mg QD. In some embodiments, the therapeutically effective amount is a dose of about 20 mg to 200 mg QD. In some embodiments, the therapeutically effective amount is a dose of about 50 mg to 100 mg QD.

In some embodiments, disclosed herein is a method for treating and/or ameliorating an IL-17A mediated inflammatory syndrome, disorder, or disease comprising administering to a subject in need thereof a therapeutically effective amount of a compound of Formula I', or a pharmaceutically acceptable salt thereof, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigold, atopic dermatitis, vitiligo, multiple sclerosis, asthma, uveitis, chronic obstructive pulmonary disorder, multiple myeloma, and systemic lupus erythematosus, wherein the therapeutically effective amount is a dose of about 10 mg to 300 mg QD. In some embodiments, the therapeutically effective amount is a dose of about 20 mg to 200 mg QD. In some embodiments, the therapeutically effective amount is a dose of about 50 mg to 100 mg QD.

In some embodiments, disclosed herein is a method for treating and/or ameliorating an IL-17A mediated inflammatory syndrome, disorder, or disease comprising administering to a subject in need thereof a therapeutically effective amount of a compound of Formula I, or a pharmaceutically acceptable salt thereof, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigold, atopic dermatitis, vitiligo, multiple sclerosis, asthma, uveitis, chronic obstructive pulmonary disorder, multiple myeloma, and systemic lupus erythematosus, wherein the therapeutically effective amount is a dose of about 10 mg to 300 mg BID. In some embodiments, the therapeutically effective amount is a dose of about 20 mg to 200 mg BID. In some embodiments, the therapeutically effective amount is a dose of about 50 mg to 100 mg BID.

In some embodiments, disclosed herein is a method for treating and/or ameliorating an IL-17A mediated inflammatory syndrome, disorder, or disease comprising administering to a subject in need thereof a therapeutically effective amount of a compound of Formula I', or a pharmaceutically acceptable salt thereof, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous pemphigold, atopic dermatitis, vitiligo, multiple sclerosis, asthma, uveitis, chronic obstructive pulmonary disorder, multiple myeloma, and systemic lupus erythematosus, wherein the therapeutically effective amount is a dose of about 10 mg to 300 mg BID. In some embodiments, the therapeutically effective amount is a dose of about 20 mg to 200 mg BID. In some embodiments, the therapeutically effective amount is a dose of about 50 mg to 100 mg BID.

In some embodiments, disclosed herein is the use of a therapeutically effective amount of compound of Formula I, or a pharmaceutically acceptable salt thereof, for treating and/or ameliorating an IL-17A mediated inflammatory syndrome, disorder, or disease selected from the group consisting of: psoriasis, psoriatic arthritis, rheumatoid arthritis, ankylosing spondylitis, hidradenitis suppurativa, bullous pemphigold, atopic dermatitis, vitiligo, multiple sclerosis, asthma, uveitis, chronic obstructive pulmonary disorder, multiple myeloma, and systemic lupus erythematosus.

In some embodiments, disclosed herein is the use of a therapeutically effective amount of compound of Formula I', or a pharmaceutically acceptable salt thereof, for treating and/or ameliorating an IL-17A mediated inflammatory syndrome, disorder, or disease selected from the group consisting of: psoriasis, psoriatic arthritis, rheumatoid arthritis, ankylosing spondylitis, hidradenitis suppurativa, bullous pemphigold, atopic dermatitis, vitiligo, multiple sclerosis, asthma, uveitis, chronic obstructive pulmonary disorder, multiple myeloma, and systemic lupus erythematosus.

In some embodiments, disclosed herein is the use of a compound of Formula I, or pharmaceutically acceptable salt thereof, in the manufacture of a medicament for treating and/or ameliorating an IL-17A mediated inflammatory syndrome, disorder, or disease selected from the group consisting of: psoriasis, psoriatic arthritis, rheumatoid arthritis, ankylosing spondylitis, hidradenitis suppurativa, bullous pemphigold, atopic dermatitis, vitiligo, multiple sclerosis, asthma, uveitis, chronic obstructive pulmonary disorder, multiple myeloma, and systemic lupus erythematosus.

In some embodiments, disclosed herein is the use of a compound of Formula I', or pharmaceutically acceptable salt thereof, in the manufacture of a medicament for treating and/or ameliorating an IL-17A mediated inflammatory syndrome, disorder, or disease selected from the group consisting of: psoriasis, psoriatic arthritis, rheumatoid arthritis, ankylosing spondylitis, hidradenitis suppurativa, bullous pemphigold, atopic dermatitis, vitiligo, multiple sclerosis, asthma, uveitis, chronic obstructive pulmonary disorder, multiple myeloma, and systemic lupus erythematosus.

In some embodiments, disclosed herein is a method for treating and/or ameliorating an IL-17 mediated inflammatory syndrome, disorder or disease comprising administering to a subject in need thereof a therapeutically effective amount of a compound of Formula I, or pharmaceutically acceptable salt thereof, a composition thereof, or a medicament thereof.

In some embodiments, disclosed herein is a method for treating and/or ameliorating an IL-17 mediated inflammatory syndrome, disorder or disease comprising administering to a subject in need thereof a therapeutically effective amount of a compound of Formula I', or pharmaceutically acceptable salt thereof, a composition thereof, or a medicament thereof.

In some embodiments, disclosed herein is a method of treating and/or ameliorating an IL-17 mediated inflammatory syndrome, disorder or disease, wherein the syndrome, disorder or disease is selected from the group consisting of: psoriasis, psoriatic arthritis, rheumatoid arthritis, ankylosing spondylitis, hidradenitis suppurativa, atopic dermatitis, vitiligo, multiple sclerosis, asthma, allergic asthma, steroid resistant asthma, neutrophilic asthma, chronic obstructive pulmonary disease, uveitis, multiple myeloma, and systemic lupus erythematosus, comprising administering to a subject in need thereof a therapeutically effective amount of a compound of Formula I, or pharmaceutically acceptable salt thereof, a composition thereof, or a medicament thereof.

In some embodiments, disclosed herein is a method of treating and/or ameliorating an IL-17 mediated inflammatory syndrome, disorder or disease, wherein the syndrome, disorder or disease is selected from the group consisting of: psoriasis, psoriatic arthritis, rheumatoid arthritis, ankylosing spondylitis, hidradenitis suppurativa, atopic dermatitis, vitiligo, multiple sclerosis, asthma, allergic asthma, steroid resistant asthma, neutrophilic asthma, chronic obstructive pulmonary disease, uveitis, multiple myeloma, and systemic lupus erythematosus, comprising administering to a subject in need thereof a therapeutically effective amount of a compound of Formula I', or pharmaceutically acceptable salt thereof, a composition thereof, or a medicament thereof.

In some embodiments, disclosed herein is a method of treating or ameliorating an IL-17 mediated inflammatory syndrome, disorder or disease, wherein the syndrome, disorder or disease is selected from the group consisting of: psoriasis, psoriatic arthritis, and ankylosing spondylitis, comprising administering to a subject in need thereof a therapeutically effective amount of a compound of Formula I, or pharmaceutically acceptable salt thereof, a composition thereof, or a medicament thereof.

In some embodiments, disclosed herein is a method of treating or ameliorating an IL-17 mediated inflammatory syndrome, disorder or disease, wherein the syndrome, disorder or disease is selected from the group consisting of: psoriasis, psoriatic arthritis, and ankylosing spondylitis, comprising administering to a subject in need thereof a therapeutically effective amount of a compound of Formula I', or pharmaceutically acceptable salt thereof, a composition thereof, or a medicament thereof.

In some embodiments, disclosed herein are methods of modulating IL-17 activity in a mammal by administration of a therapeutically effective amount of at least one compound of Formula I, or pharmaceutically acceptable salt thereof.

In some embodiments, disclosed herein are methods of modulating IL-17 activity in a mammal by administration of a therapeutically effective amount of at least one compound of Formula I', or pharmaceutically acceptable salt thereof.

Also disclosed herein is a method of inhibiting production of interleukin-17, comprising administering to a subject in need thereof a therapeutically effective amount of a compound of Formula I, or pharmaceutically acceptable salt thereof.

Also disclosed herein is a method of inhibiting production of interleukin-17, comprising administering to a subject in need thereof a therapeutically effective amount of a compound of Formula I', or pharmaceutically acceptable salt thereof.

IV. Combination Therapy

A compound of Formula I, or pharmaceutically acceptable salt thereof, a composition thereof, or a medicament thereof may also be used in combination with one or more additional therapeutic agents. Likewise, a compound of Formula I', or pharmaceutically acceptable salt thereof, a composition thereof, or a medicament thereof may be used in combination with one or more additional therapeutic agents.

In some embodiments, the one or more additional therapeutic agents is selected from the group consisting of anti-inflammatory agents, immunomodulatory agents, and immunosuppressive agents.

In some embodiments, the one or more additional therapeutic agents is selected from the group consisting of:
anti-TNFalpha agents such as infliximab (Remicade®), adalimumab (Humira®), certolizumab pegol (Cimzia®), golimumab (Simponi®), etanercept (Enbrel®), thalidomide (Immunoprin®), lenalidomide (Revlimid®), and pomalidomide (Pomalyst®/Imnovid®);
anti-p40 antibody agents such as ustekinumab (Stelara®); and
anti-p19 antibody agents such as guselkumab (Tremfya®), tildrakizumab (Ilumya™/Ilumetri), risankizumab (Skyrizi™), and mirikizumab.

In some embodiments, disclosed herein is a method of treating and/or ameliorating an IL-17 mediated inflammatory syndrome, disorder or disease, in a subject in need thereof comprising administering to the subject a therapeutically effective amount of the compound of Formula I, or pharmaceutically acceptable salt thereof, composition thereof, or medicament thereof in a combination therapy with one or more additional therapeutic agents, such as anti-inflammatory agents, immunomodulatory agents, or immunosuppressive agents, wherein said syndrome, disorder or disease is selected from the group consisting of psoriasis, psoriatic arthritis, rheumatoid arthritis, ankylosing spondylitis, hidradenitis suppurativa, atopic dermatitis, vitiligo, multiple sclerosis, asthma, allergic asthma, steroid resistant asthma, neutrophilic asthma, chronic obstructive pulmonary disease, uveitis, multiple myeloma, and systemic lupus erythematosus.

In some embodiments, disclosed herein is a method of treating and/or ameliorating an IL-17 mediated inflammatory syndrome, disorder or disease, in a subject in need thereof comprising administering to the subject a therapeutically effective amount of the compound of Formula I', or pharmaceutically acceptable salt thereof, composition thereof, or medicament thereof in a combination therapy with one or more additional therapeutic agents, such as anti-inflammatory agents, immunomodulatory agents, or immunosuppressive agents, wherein said syndrome, disorder or disease is selected from the group consisting of psoriasis, psoriatic arthritis, rheumatoid arthritis, ankylosing spondylitis, hidradenitis suppurativa, atopic dermatitis, vitiligo, multiple sclerosis, asthma, allergic asthma, steroid resistant asthma, neutrophilic asthma, chronic obstructive pulmonary disease, uveitis, multiple myeloma, and systemic lupus erythematosus.

In some embodiments, disclosed herein is a method of treating and/or ameliorating an IL-17 mediated inflammatory syndrome, disorder or disease, in a subject in need thereof comprising administering to the subject a therapeutically effective amount of the compound of Formula I, or pharmaceutically acceptable salt thereof, composition thereof, or medicament thereof in a combination therapy with one or more additional therapeutic agents, such as anti-inflammatory agents, or immunosuppressive agents, wherein said syndrome, disorder or disease is psoriasis, psoriatic arthritis, ankylosing spondylitis. In some embodiments, the IL-17 mediated inflammatory syndrome, disorder or disease is psoriasis. In some embodiments, the IL-17 mediated inflammatory syndrome, disorder or disease is psoriatic arthritis. In some embodiments, the IL-17 mediated inflammatory syndrome, disorder or disease is ankylosing spondylitis.

In some embodiments, disclosed herein is a method of treating and/or ameliorating an IL-17 mediated inflammatory syndrome, disorder or disease, in a subject in need thereof comprising administering to the subject a therapeutically effective amount of the compound of Formula I', or pharmaceutically acceptable salt thereof, composition thereof, or medicament thereof in a combination therapy with one or more additional therapeutic agents, such as anti-inflammatory agents, or immunosuppressive agents, wherein said syndrome, disorder or disease is psoriasis, psoriatic arthritis, ankylosing spondylitis. In some embodiments, the IL-17 mediated inflammatory syndrome, disorder or disease is psoriasis. In some embodiments, the IL-17 mediated inflammatory syndrome, disorder or disease is psoriatic arthritis. In some embodiments, the IL-17 mediated inflammatory syndrome, disorder or disease is ankylosing spondylitis.

Dosage Regimen

When employed as IL-17A modulators, the compounds disclosed herein may be administered in an effective amount within the dosage range of about 0.5 mg to about 1 g, preferably between about 0.5 mg to about 500 mg, in single or divided daily doses. In some embodiments, the dosage amount is about 5 mg to 400 mg. In some embodiments, the dosage amount is about 10 mg to 300 mg. In some embodiments, the dosage amount is about 0.5, 1, 5, 10, 15, 20, 25, 30, 35, 40, 45, 50, 55, 60, 65, 70, 75, 80, 85, 90, 95, or 100 mg of a compound of Formula I, or pharmaceutically acceptable salt thereof. In some embodiments, the dosage amount is about 100, 105, 110, 115, 120, 125, 130, 135, 140, 145, 150, 155, 160, 165, 170, 175, 180, 185, 190, 195, or 200 mg of a compound of Formula I, or pharmaceutically acceptable salt thereof. In some embodiments, the dosage amount is about 200, 205, 210, 215, 220, 225, 230, 235, 240, 245, 250, 255, 260, 265, 270, 275, 280, 285, 290, 295, or 300 mg of a compound of Formula I, or pharmaceutically acceptable salt thereof. In some embodiments, the dosage amount is about 300, 315, 320, 325, 330, 335, 340, 345, 350, 355, 360, 365, 370, 375, 380, 385, 390, 395, or 400 mg of a compound of Formula I, or pharmaceutically acceptable salt thereof. In some embodiments, the dosage amount is about 400, 405, 410, 415, 420, 425, 430, 435, 440, 445, 450, 455, 460, 465, 470, 475, 480, 485, 490, 495, or 500 mg of a compound of Formula I, or pharmaceutically acceptable salt thereof. In some embodiments, the dosage amount is about 10 mg to 300 mg. In some embodiments, the dosage amount is about 0.5, 1, 5, 10, 15, 20, 25, 30, 35, 40, 45, 50, 55, 60, 65, 70, 75, 80, 85, 90, 95, or 100 mg of a compound of Formula I', or pharmaceutically acceptable salt thereof. In some embodiments, the dosage amount is about 100, 105, 110, 115, 120, 125, 130, 135, 140, 145, 150, 155, 160, 165, 170, 175, 180, 185, 190, 195, or 200 mg of a compound of Formula I', or pharmaceutically acceptable salt thereof. In some embodiments, the dosage amount is about 200, 205, 210, 215, 220, 225, 230, 235, 240, 245, 250, 255, 260, 265, 270, 275, 280, 285, 290, 295, or 300 mg of a compound of Formula I', or pharmaceutically acceptable salt thereof. In some embodiments, the dosage amount is about 300, 305, 310, 315, 320, 325, 330, 335, 340, 345, 350, 355, 360, 365, 370, 375, 380, 385, 390, 395, or 400 mg of a compound of Formula I', or pharmaceutically acceptable salt thereof. In some embodiments, the dosage amount is about 400, 405, 410, 415, 420, 425, 430, 435, 440, 445, 450, 455, 460, 465, 470, 475, 480, 485, 490, 495, or 500 mg of a compound of Formula I', or pharmaceutically acceptable salt thereof.

In some embodiments, a compound of Formula I, or pharmaceutically acceptable salt thereof, may be administered in an effective amount within the dosage range of about 10 mg to 300 mg QD. In some embodiments, a compound of Formula I, or pharmaceutically acceptable salt thereof, may be administered in an effective amount within the dosage range of about 20 mg to 200 mg QD. In some embodiments, a compound of Formula I, or pharmaceutically acceptable salt thereof, may be administered in an effective amount within the dosage range of about 50 mg to 100 mg QD.

In some embodiments, a compound of Formula I', or pharmaceutically acceptable salt thereof, may be administered in an effective amount within the dosage range of about 10 mg to 300 mg QD. In some embodiments, a compound of Formula I', or pharmaceutically acceptable salt thereof, may be administered in an effective amount within the dosage range of about 20 mg to 200 mg QD. In some embodiments, a compound of Formula I', or pharmaceutically acceptable salt thereof, may be administered in an effective amount within the dosage range of about 50 mg to 100 mg QD.

In some embodiments, a compound of Formula I, or pharmaceutically acceptable salt thereof, may be administered in an effective amount within the dosage range of about 10 mg to 300 mg BID. In some embodiments, a compound of Formula I, or pharmaceutically acceptable salt thereof, may be administered in an effective amount within the dosage range of about 20 mg to 200 mg BID. In some embodiments, a compound of Formula I, or pharmaceutically acceptable salt thereof, may be administered in an effective amount within the dosage range of about 50 mg to 100 mg BID.

In some embodiments, a compound of Formula I', or pharmaceutically acceptable salt thereof, may be administered in an effective amount within the dosage range of about 10 mg to 300 mg BID. In some embodiments, a compound of Formula I', or pharmaceutically acceptable salt thereof, may be administered in an effective amount within the dosage range of about 20 mg to 200 mg BID. In some embodiments, a compound of Formula I', or pharmaceutically acceptable salt thereof, may be administered in an effective amount within the dosage range of about 50 mg to 100 mg BID.

The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Pharmaceutically Acceptable Salts

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethylpropane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine, or zinc.

Pharmaceutical Compositions

The compounds of Formula I, or pharmaceutically acceptable salt thereof, may be formulated into pharmaceutical compositions comprising any known pharmaceutically acceptable carriers. The compounds of Formula I', or pharmaceutically acceptable salts thereof, may likewise be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Similarly, the pharmaceutically-acceptable salts of the compounds of Formula I' also include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, topical, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

Also disclosed herein is a method of making a pharmaceutical composition comprising mixing a pharmaceutically acceptable carrier with any of the compounds of Formula I, or pharmaceutically acceptable salt thereof. Further disclosed herein is a method of making a pharmaceutical composition comprising mixing a pharmaceutically acceptable carrier with any of the compounds of Formula I', or pharmaceutically acceptable salt thereof. Additionally, the present application includes pharmaceutical compositions made by mixing a pharmaceutically acceptable carrier with any of the compounds of the present invention.

EXAMPLES

Abbreviations

Herein and throughout the application, the following abbreviations may be used.
Å Angstrom
Ac acetyl
acac acetylacetone
ACN acetonitrile
BAST Bis(2-methoxyethyl)aminosulfur trifluoride
Boc tert-butyloxycarbonyl
br broad
Bs para-bromophenylsulfonyl (brosyl)
Bu butyl
Bz benzoate
CAM ceric ammomium molybdate
COD or cod cyclooctadiene
δ NMR chemical shift in parts per million downfield from a standard
d doublet
d day(s)
DAST (diethylamino)sulfur trifluoride
dba dibenzylideneacetone
DBU 1,8-diazabicyclo[5.4.0]undec-7-ene
DCM dichloromethane
DEA diethylamine
DIAD diisopropyl azodicarboxylate
DIBAL-H diisobutylaluminum hydride
DIPEA N,N-diisopropylethylamine (Hünig's base)
DMA N,N-dimethylacetamide
DMAP 4-(dimethylamino)pyridine
DME 1,2-dimethoxyethane
DMF N,N-dimethylformamide
DMP Dess-Martin Periodinane
DMSO dimethyl sulfoxide
DPPE ethylenebis(diphenylphosphine)
dppf 1,1'-bis(diphenylphosphino)ferrocene
ELSD evaporative light scattering detector
EDCI 1-ethyl-3-(3-dimethylaminopropyl) carbodiimide hydrochloride
ESI electrospray ionization
Et ethyl
EtOAc ethyl acetate
Fmoc fluorenylmethyloxycarbonyl
g gram(s)
h hour(s)
HATU O-(7-azabenzotriazol-1-yl)-N,N,N',N'-tetramethyluronium hexafluorophosphate
HOAt 1-hydroxy-7-azabenzotriazole
HOBt 1-hydroxybenzotriazole
HPLC high pressure liquid chromatography
Hz Hertz
i iso
J coupling constant (NMR spectroscopy)
L liter(s)
LC liquid chromatography
LDA lithium diisopropylamide
m milli or multiplet
m/z mass-to-charge ratio M+ parent molecular ion
M molar (moles/liter) or mega
Me methyl
MeCN acetonitrile
min minute(s)
μ micro
Ms methanesulfonyl
MS mass spectrometry
MTBE tert-butyl methyl ether
NCS N-chlorosuccinimide
n normal
n nano
N normal (equivalent concentration)
NMM N-methyl morpholine
NMR nuclear magnetic resonance
NPA n-propylamine
Pd/C palladium on carbon
Ph phenyl
PPTS pyridinium p-toluenesulfonate
Pr propyl
Psi pounds per square inch
Pd(dtbpf)Cl$_2$ [1,1'-bis(di-tert-butylphosphino)ferrocene]dichloropalladium(II)
q quartet
Rochelle salt sodium potassium tartrate
rt room temperature
RuPhos PD G3 (2-Dicyclohexylphosphino-2',6'-diisopropoxy-1,1'-biphenyl)[2-(2'-amino-1,1'-biphenyl)]palladium(II) methanesulfonate
s singlet
SFC supercritical fluid chromatography
t tert
t triplet
TBAT tetrabutylammonium difluorotriphenylsilicate
TBD triazabicyclodecene
TEA triethylamine
TFA trifluoroacetic acid
THF tetrahydrofuran
TLC thin layer chromatography
TMP tetramethylpiperidinyl
Ts para-toluenesulfonyl (tosyl)
XPhos 2-dicyclohexylphosphino-2',4',6'-triisopropylbiphenyl
XPhos Pd G1 (2-Dicyclohexylphosphino-2',4',6'-triisopropyl-1,1'-biphenyl)[2-(2-aminoethyl)phenyl]palladium(II) chloride, (XPhos) palladium(II) phenethylamine chloride, Chloro(2-dicyclohexylphosphino-2',4',6'-triisopropyl-1,1'-biphenyl)[2-(2-aminoethyl)phenyl)]palladium(II)
XtalFluor-E® (diethylamino)difluorosulfonium tetrafluoroborate In some embodiments, provided herein are processes and intermediates disclosed herein that are useful for preparing a compound of the disclosure or pharmaceutically acceptable salts thereof.

General Schemes

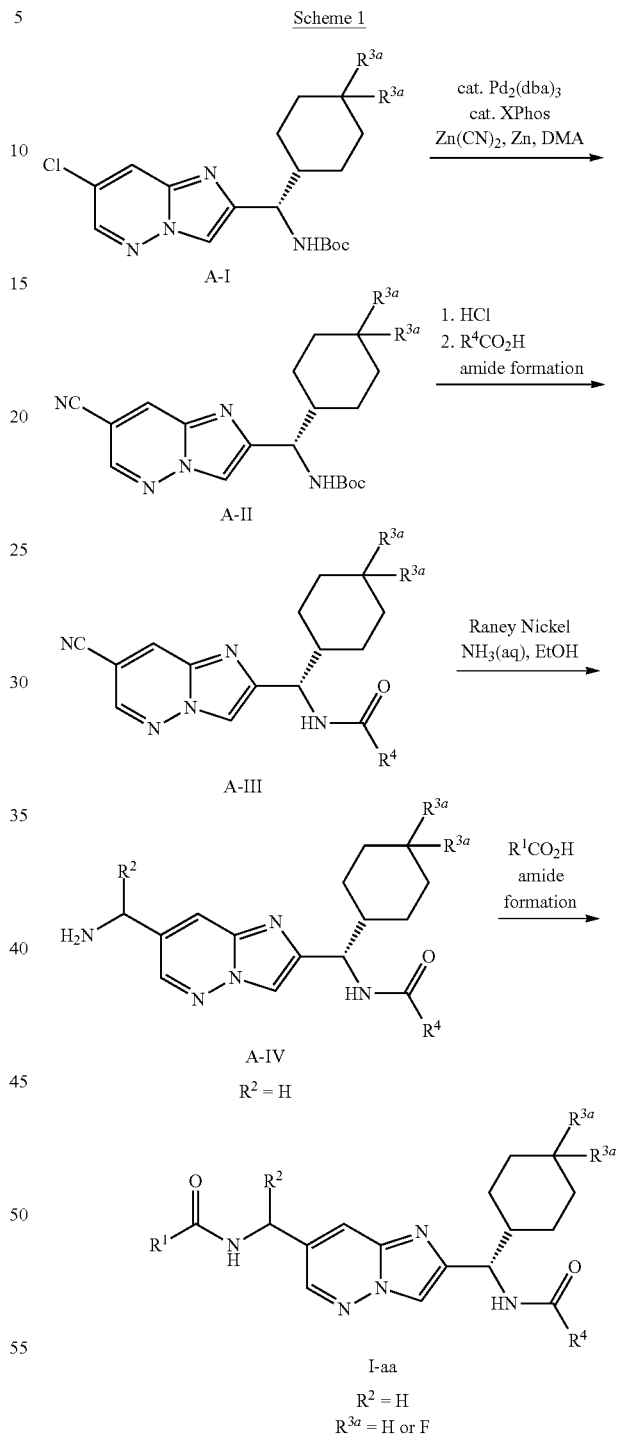

Scheme 1

Certain compounds of formula I-aa in the present invention can be prepared, for example, according to Scheme 1. Cyanation of A-I using reagents such as zinc cyanide in the presence of a catalyst, such as Pd$_2$(dba)$_3$, affords nitriles A-II. Removal of the Boc group under acidic conditions, such as aqueous hydrochloric acid, afforded an amine that was subsequently coupled to a carboxylic acid through the use of a coupling agent, such as HATU or EDCI, in the presence of a base, such as DIPEA, in a solvent, such as DMF, MeCN, or DCM, with or without an additive, such as HOBt, to yield amides A-III. Reduction of the nitrile of A-III with hydrogen in the presence of a catalyst, such as Raney nickel affords the corresponding primary amines A-IV, which can be coupled to carboxylic acids in a manner analogous to the conversion of A-II to A-III to give compounds of the general structure I-aa shown in Scheme 1.

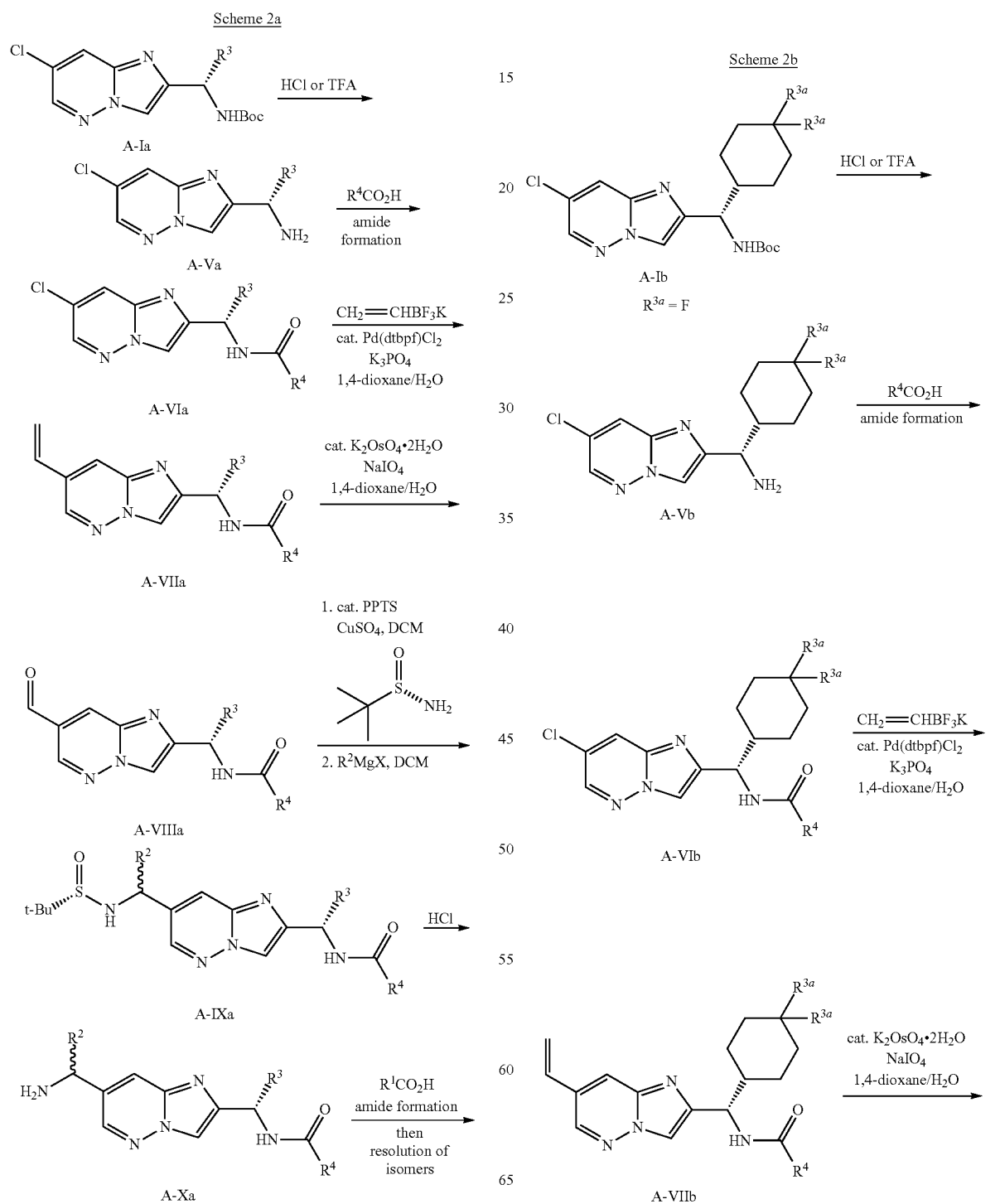

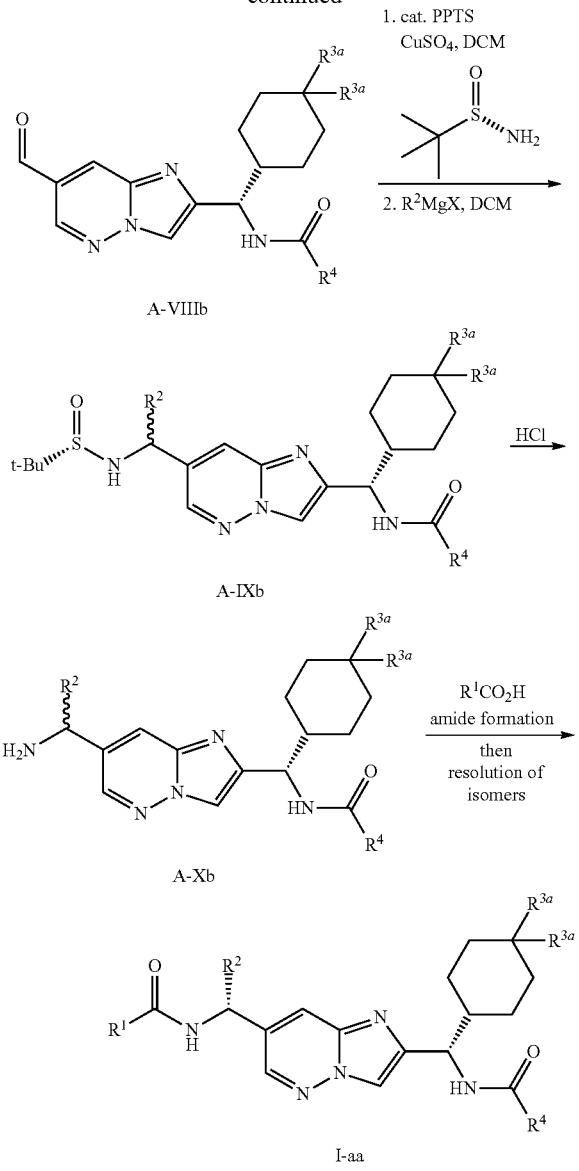

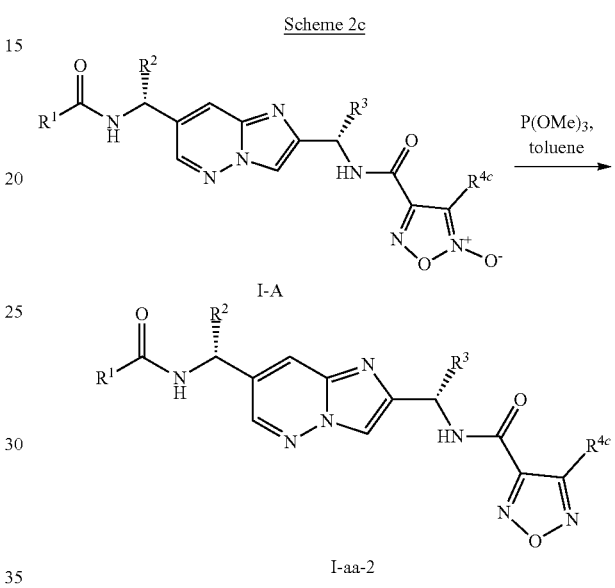

philic carbon-containing reagents, such as alkyl magnesium halides, yields sulfinamides of general structure A-IX. Conversion of compounds of structure A-IX to A-X could be conducted under acidic conditions, such as aqueous hydrochloric acid, and subsequently converted to compounds of general structure I-aa-1 and I-aa in a manner analogous to the conversion of A-IT to A-III. Compounds of general structure I-aa obtained as mixtures of isomers were subjected to additional purification techniques, such as HPLC or SFC using columns with a chiral stationary phase, to give single-isomer products I-aa-1 and I-aa.

Compounds I-aa-2 can be prepared by the reaction shown in Scheme 2c. Treatment of N-oxides I-A with trimethyl phosphite in toluene generates compounds I-aa-2.

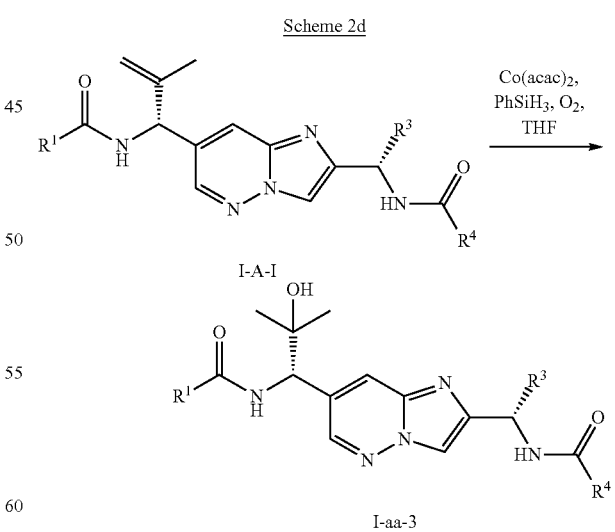

Certain compounds of general structure I-aa-1 and I-aa in the present invention can also be prepared according to Scheme 2a and 2b, respectively. Removal of the Boc group of compounds of type A-Ia or A-Ib under acidic conditions, such as aqueous hydrochloric acid or TFA, affords amines of type A-V (e.g., A-Va and A-Vb). Amides of formula A-VIa and A-VIb can be formed from A-Va and A-Vb, respectively, in a manner analogous to the conversion of A-II to A-III (see Scheme 1). Conversion of compounds of type A-VI to A-VII was conducted using a reagent mixture capable of transferring a vinyl group, such as potassium trifluoro(vinyl)borate, in the presence of a catalyst, such as Pd(dtbpf)Cl$_2$. Compounds of general structure A-VII could be converted to compounds of structure A-VIII through the oxidative cleavage of the vinyl substituent using reagents, such as sodium periodate, in the presence of a catalyst, such as potassium osmate, in a solvent, such as aqueous 1,4-dioxane. Subsequent condensation of compounds of general structure A-VIII with (S)-(−)-2-methyl-2-propanesulfinamide gives the corresponding sulfinimide, that upon addition of nucleo- Compounds I-aa-3 can be prepared as shown Scheme 2d. Hydration of the olefin within I-A-I using reagents such as Co(acac)$_2$, (cobalt(II) acetylacetonate), and PhSiH$_3$ (phenylsilane) in an oxygenated atmosphere in THF provides compounds I-aa-3.

Scheme 3

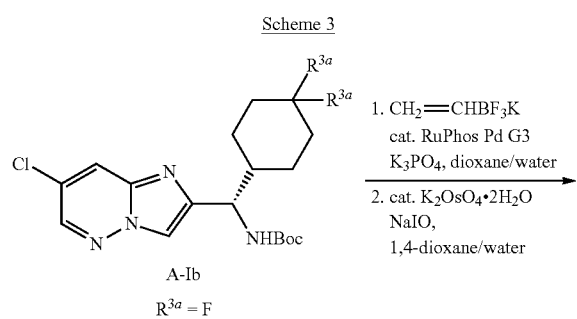

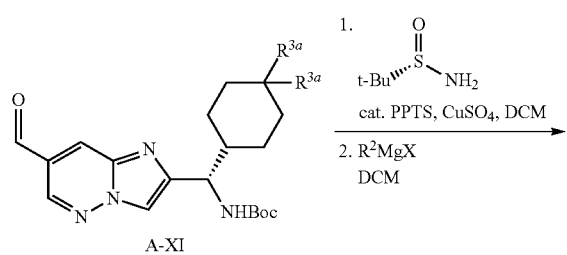

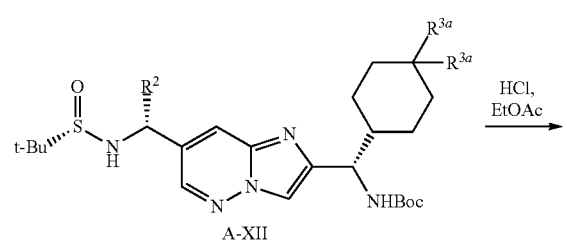

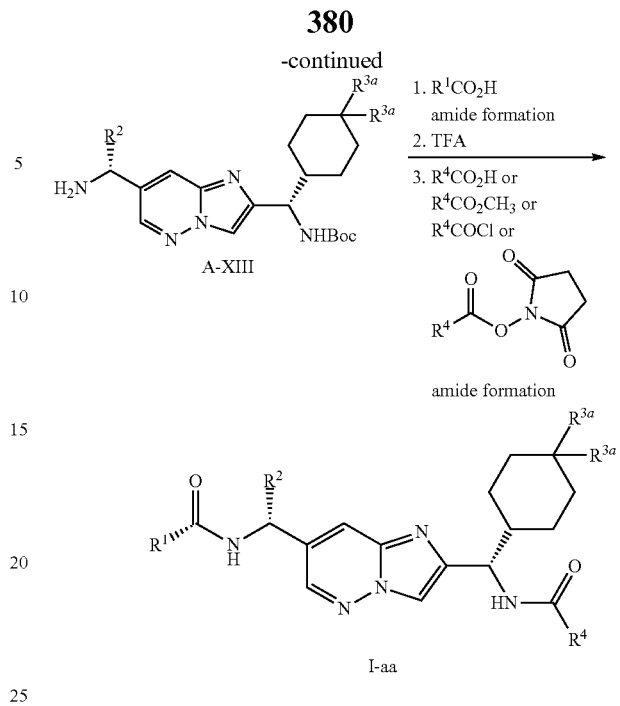

The compounds of formula I-aa in the present invention can also be prepared according to Scheme 3 in which the relative order of transformations is reversed compared to Scheme 2b. Aldehydes of formula A-XI can be formed from A-I (e.g., A-Ib) in a manner analogous to the conversion of A-VI to A-VIII. Similarly, compounds of general structure A-XII can be formed from A-XI in a manner analogous to the conversion of A-VIII to A-IX. Selective removal of the sulfinamide functionality from compounds of general structure A-XII under acidic conditions such, as aqueous hydrochloric acid in EtOAc, yields amines of general structure A-XIII. Acylation of A-XIII, followed by removal of the Boc group, and amide formation to give compounds of general structure I-aa could be conducted as described in the preceding schemes, though in some cases they were prepared (i) using an acid chloride in a solvent such as DCM, (ii) by direct conversion of an ester to an amide by heating with $Al(CH_3)_3$ in a solvent such as toluene or (iii) by conversion of the N-hydroxy succinate ester in the presence of DIPEA in a solvent such as acetonitrile.

Scheme 3a

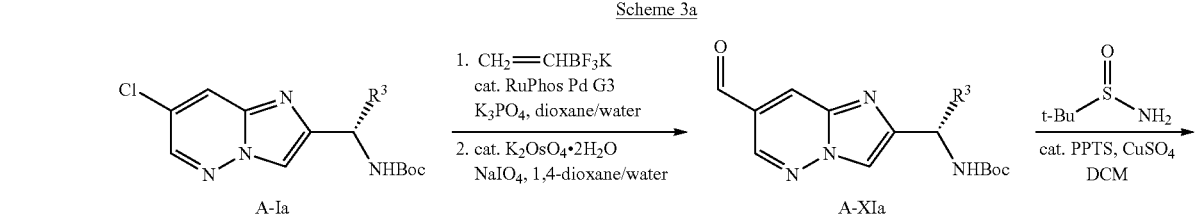

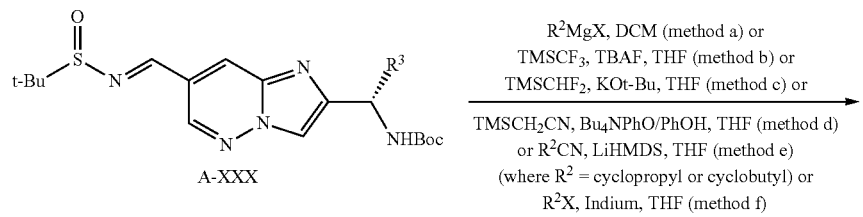

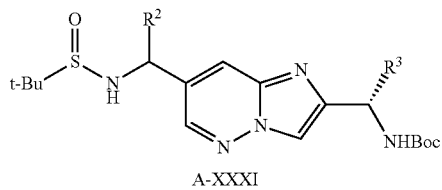

A-XXXI

Compounds of the general structure A-XXXI can be made as shown in Scheme 3a. Following a sequence similar to that shown in Scheme 3 chlorides A-Ia can be converted in a two step sequence to the corresponding aldehydes A-XIa. Condensation of compounds A-XIa with either (R)- or (S)-2-methyl-2-propanesulfinamide gives the corresponding sulfinimides A-XXX. Addition of grinard reagents, such as $R^2MgX$ (X=halide), in a solvent such as DCM (method a) to A-XXX yields compounds of the general formula A-XXXI. Addition of nucleophilic carbon-containing reagents such as $TMSCF_3$ to A-XXX in the presence of reagents such as TBAF in solvents such as THF (method b) yields compounds of the general formula A-XXXI. Alternatively, addition of nucleophilic carbon-containing reagent such as $TMSCHF_2$ in the presence of reagents such as potassium tert-butoxide in solvents such as THE (method c) affords compounds of the general formula A-XXXI. Trimethylsilylacteonitrile can be metallated using reagents such as tetra-butylammonium phenolate in a solvent such as THE (method d) to afford sulfinamides of general structure A-XXXI. Cycloalkyl nitriles can be deprotonated using bases such as LiHMDS in a solvent such as THE (method e) and upon addition to A-XXX provide compounds A-XXXI. Addition of indium reagents to A-XXX, such as allyl indium formed by in situ treatment of allyl bromide and indium in THE (method f), provides compounds A-XXXI.

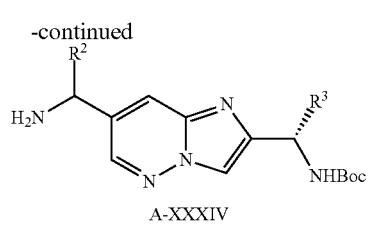

A-XXXIV

The compounds of formula A-XXXIV can be prepared according to Scheme 3b. Ketones of formula A-XXXIII can be formed from A-Ia using a vinyl transferring agent such as a 4,4,5,5-tetramethyl-vinyl-1,3,2-dioxaborolane (J-III), in the presence of a catalyst, such as RuPhos Pd G3, followed by oxidative cleavage of the vinyl substituent using reagents such as sodium periodate in the presence of a catalyst such as potassium osmate in a solvent such as aqueous 1,4-dioxane. Reductive amination using reagents such as ammonium formate in the presence of a reducing agent such as sodium cyanoborohydride with an additive such as acetic acid in a solvent such as methanol yields amines of general structure A-XXXIV.

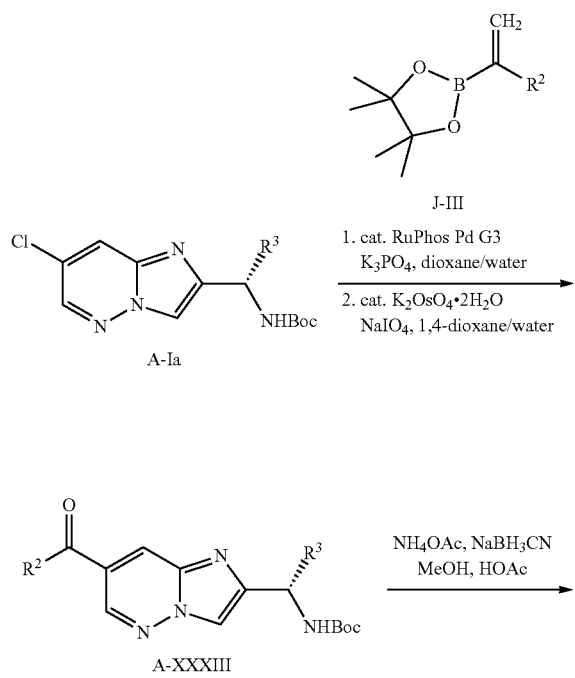

Scheme 3b

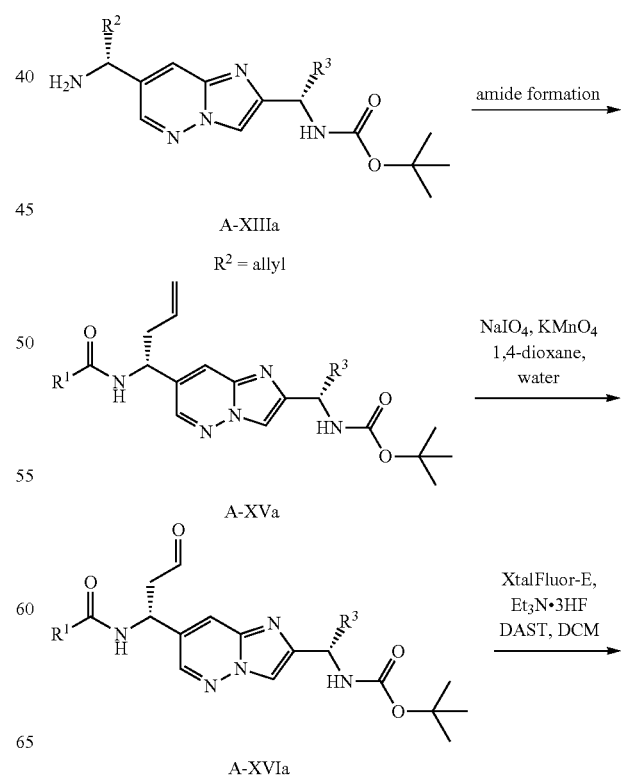

Scheme 3c as HCl in a solvent such as EtOAc then affords the corresponding amine hydrochloride salts A-XIXa. Sequential amide bond formation using conditions mentioned above and Fmoc deprotection using a reagent such as piperdine in a solvent such as DCM then affords amines A-Xaa.

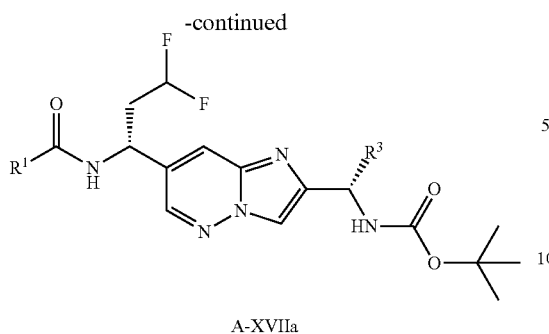

A-XVIIa

Amides of the structure A-XVIIa can be prepared as shown in Scheme 3c. Amide formation from amines A-XIIIa can be performed as described in previous schemes to provide A-XVa. Oxidative cleavage of the olefin within A-XVa using reagents such as sodium periodate and potassium permanganate in solvents such as 1,4-dioxane and water affords corresponding aldehydes A-XVIa. Treatment of A-XVIa with XtalFluor-E® in the presence of reagents such as triethylamine trihydrofluoride and DAST in solvents such as DCM then yields the corresponding geminally difluorinated products A-XVIIa. These may then be converted to analogs 1-aa using the sequence shown in Scheme 3.

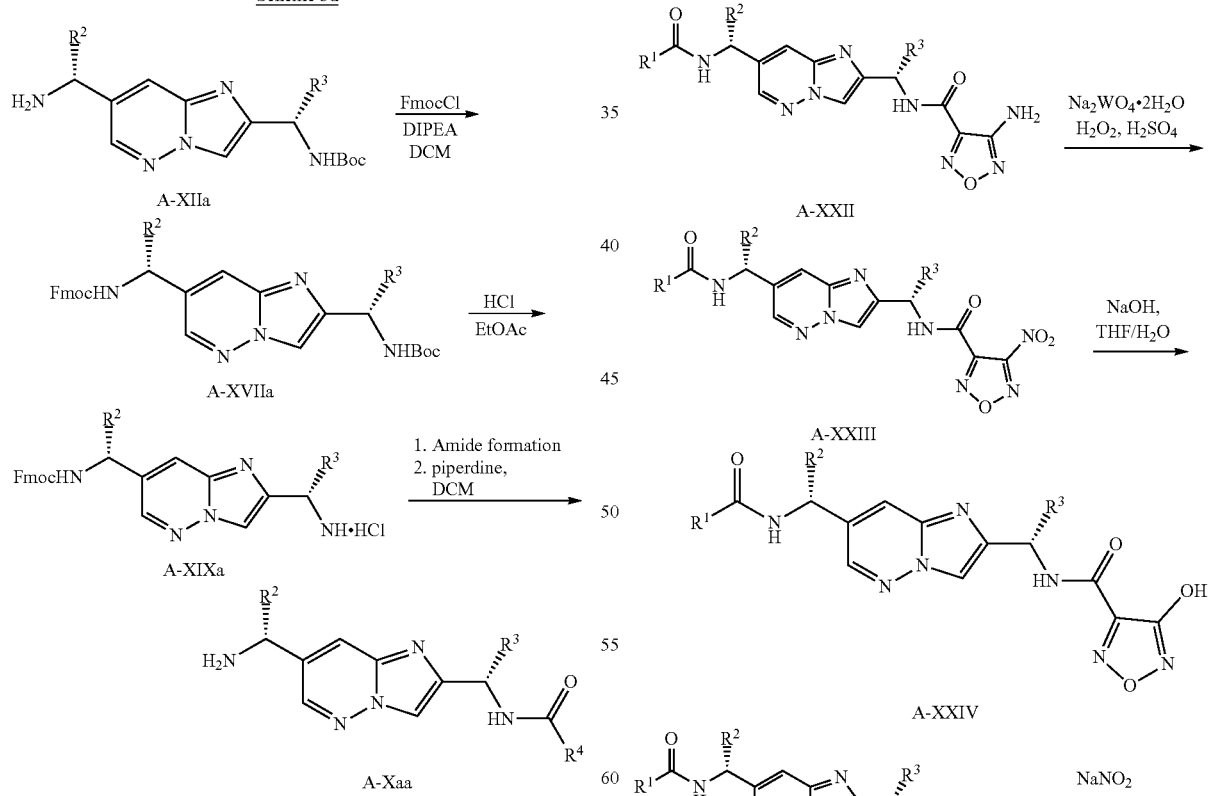

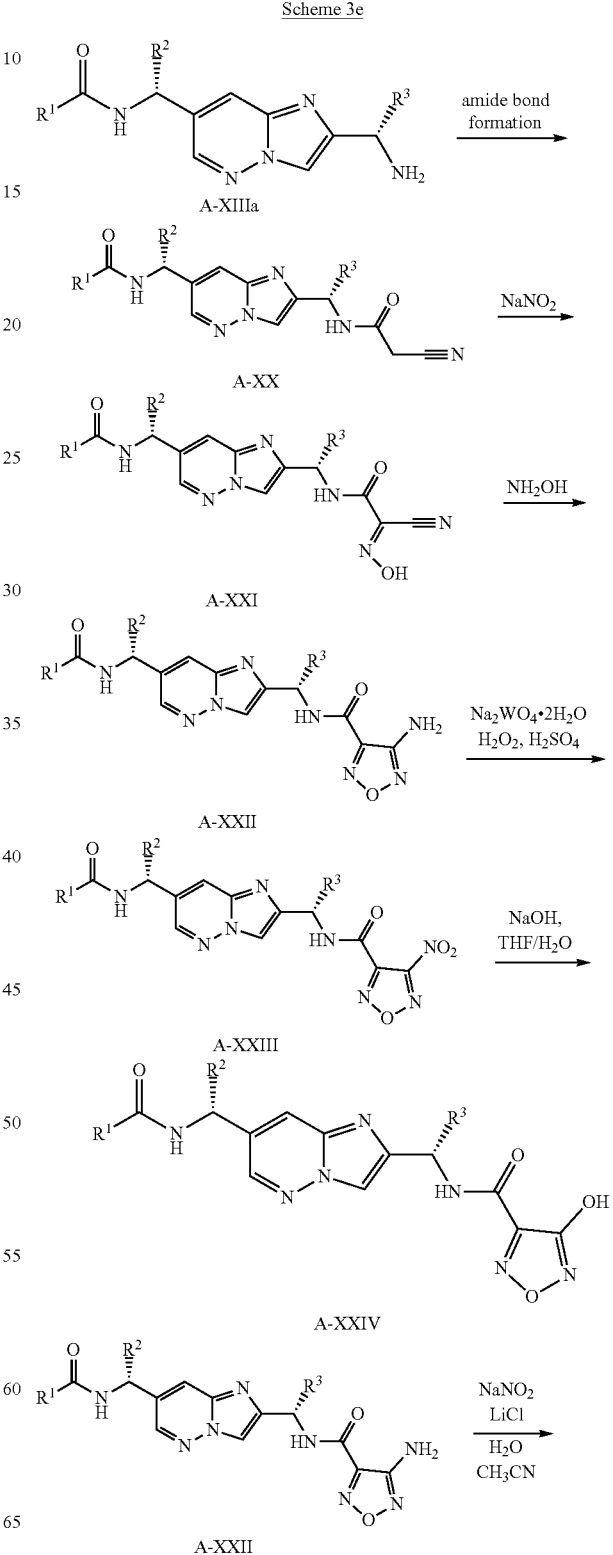

Compounds of the general formula A-Xaa can be prepared using sequence shown in Scheme 3d. Protection of the amine within A-XIIIa using FmocCl in the presence of DIPEA in a solvent such as DCM then affords carbamates A-XVIIIa. Deprotection of the Boc group using an acid such

385

-continued

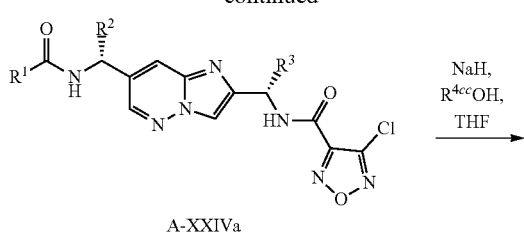

A-XXIVa

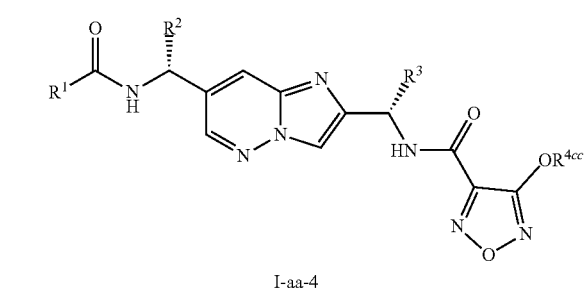

I-aa-4

Compounds I-aa, such as I-aa-4, can be prepared as shown in Scheme 3e. Amide bond formation using conditions as described above using cyanoacetic acid yields amides A-XX. Treatment of A-XX with $NaNO_2$ in the presence of HCl in a solvent such as acetonitrile yields oximes A-XXI. Subsequent treatment of A-XXI with hydroxylamine in THF then affords oxadiazoles A-XXII. Oxidation of the amine within A-XXII using $Na_2WO_4 \cdot 2H_2O$ in the presence of hydrogen peroxide and sulfuric acid then generates the nitro compounds A-XXIII. Displacement of the nitro group in A-XXIII with a hydroxyl group can be achieved using sodium hydroxide in a solvent such as $THF/H_2O$ to afford oxadiazoles A-XXIV. Treatment of amines A-XXII with $NaNO_2$ in the presence of LiCl in solvents such as water and $CH_3CN$ affords the chlorides A-XXIVa. Treatment of chlorides A-XXIVa with aliphatic alcohols, $R^{4cc}$ OH, in the presence of a base such as sodium hydride in a solvent such as THF affords compounds I-aa-4, wherein $R^{4c}$, is $C_{(1-3)}$alkyl or $C_{(0-2)}$alkyl-$C_{(3-4)}$cycloalkyl and wherein $R^{4cc}$ is unsubstituted or substituted with one to six $R^{4d}$ groups.

Scheme 3f

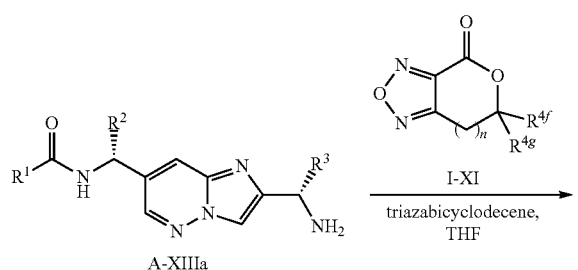

A-XIIIa

386

-continued

A-XXV
where n is 0
and $R^{4f}$ and $R^{4g}$ are H

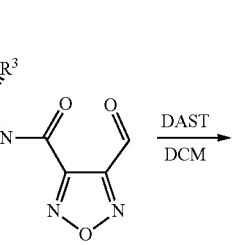

A-XXVI

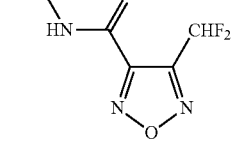

I-aa-5

Additional oxadiazole containing analogs can be prepared by the route shown in Scheme 3f. Treatment of amines A-XIIIa with lactones I-XI in solvents such as DCM, or in the presence of triazabicyclodecene and in solvents such as THF affords amides A-XXV. In the case where A-XXV contains a primary alcohol, oxidation using DMP can generate the corresponding aldehydes A-XXVI. Treatment of A-XXVI with DAST in a solvent such as DCM then affords compounds I-aa-5.

Scheme 3g

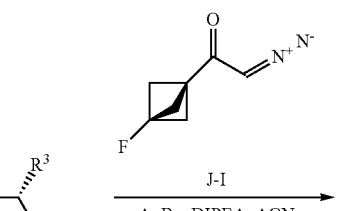

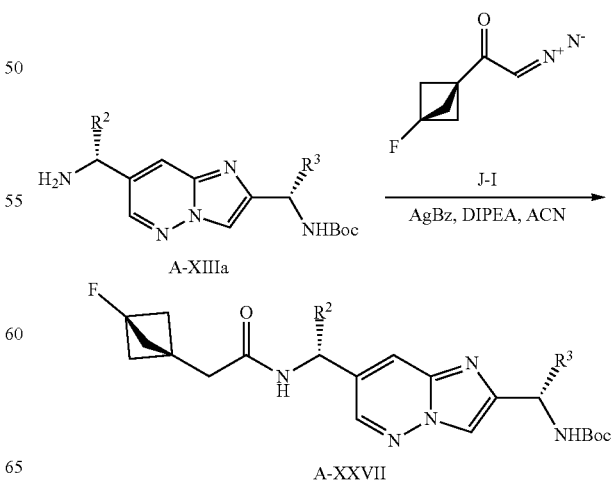

A-XXVII

Amides of the general formula A-XXVII can be prepared by the method shown in Scheme 3g. Treatment of amines A-XIIIa with diazo-1-(3-fluorobicyclo[1.1.1]pentan-1-yl)ethan-1-one J-I in the presence of DIPEA and silver benzoate (AgBz) in CH₃CN affords homologated amides A-XXVII.

Compounds of formula A-I can be prepared according to the route in Scheme 4. Chloromethyl ketones B-I are converted to the corresponding iodomethyl ketones B-II under conditions of halide interconversion, such as sodium iodide in acetone. Cyclocondensation with 5-chloropyridazin-3-amine then affords the imidazopyridazines A-I.

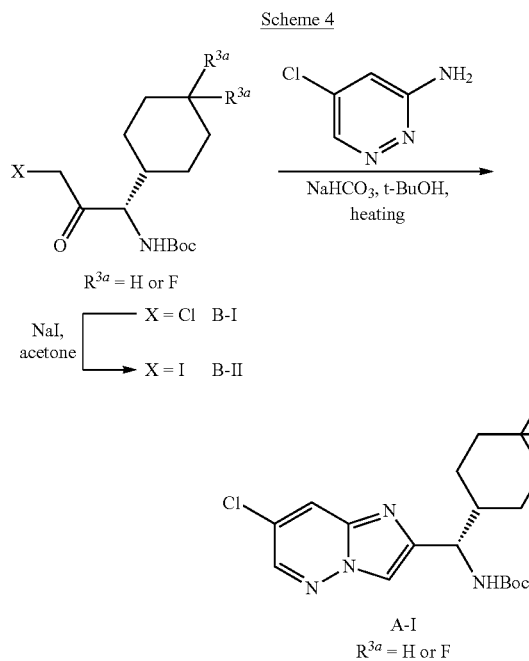

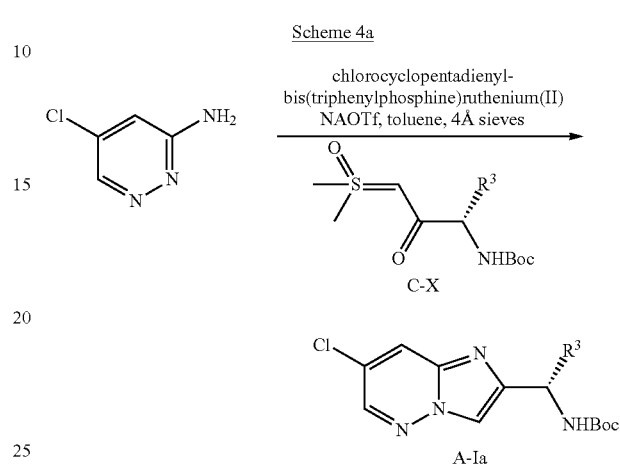

Compounds of formula A-Ia can be prepared according to the route in Scheme 4a. Ylides of general structure C-X undergo cyclocondensation with 5-chloropyridazin-3-amine in the presence of a catalyst such as chlorocyclopentadienylbis(triphenylphosphine)ruthenium(II) in the presence of additives such as sodium triflate and 4 Å molecular sieves in a solvent such as toluene to afford imidazopyridazines A-Ia.

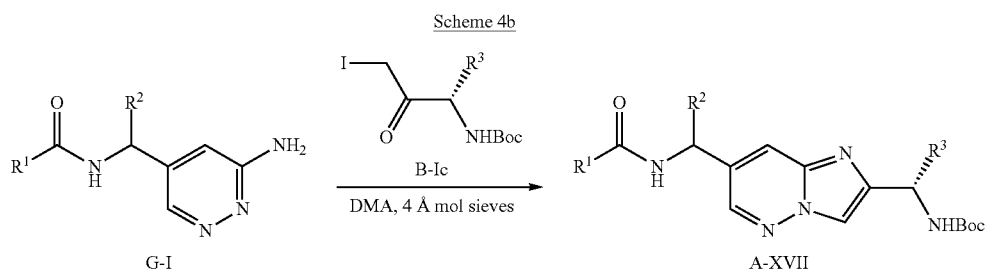

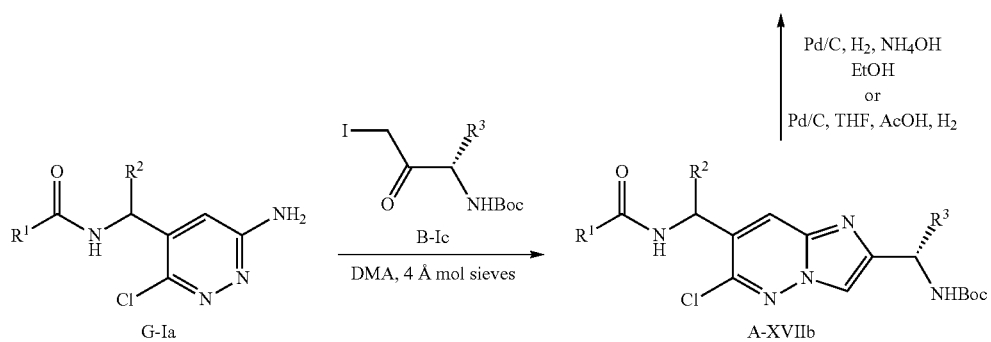

Compounds of the general structure A-XVII can be prepared as shown in Scheme 4b. Cyclocondensation of aminopyridazines G-I with iodoketones B-Ic in a solvent such as DMA in the presence of 4 Å molecular sieves affords compounds A-XVII. Alternatively, chlorinated compounds G-Ia can undergo cyclocondensation with iodoketones B-Ic under similar conditions to generate chlorinated aminopyridazines A-XVIIb. Hydrogenation using palladium catalysis in the presence of hydrogen gas and ammonium formate in ethanol, or in the presence of hydrogen gas and acetic acid in a solvent such as THF then yields compounds A-XVII.

hydrogen source, such as hydrogen gas, in the presence of a catalyst, such as Pd/C, yields racemic B-IV. Treatment of B-IV with (dimethyl(oxo)-$\lambda^6$-sulfanylidene)methane, formed by deprotonation of trimethylsulfoxonium iodide with a base, such as sodium tert-butoxide, affords ylides B-V. Cyclocondensation of B-V with 5-chloropyridazin-3-amine in the presence of a catalyst, such as di-µ-chlorobis[(1,2,5,6-η)-1,5-cyclooctadiene]diiridium, followed by resolution of the enantiomers affords compounds A-Ib.

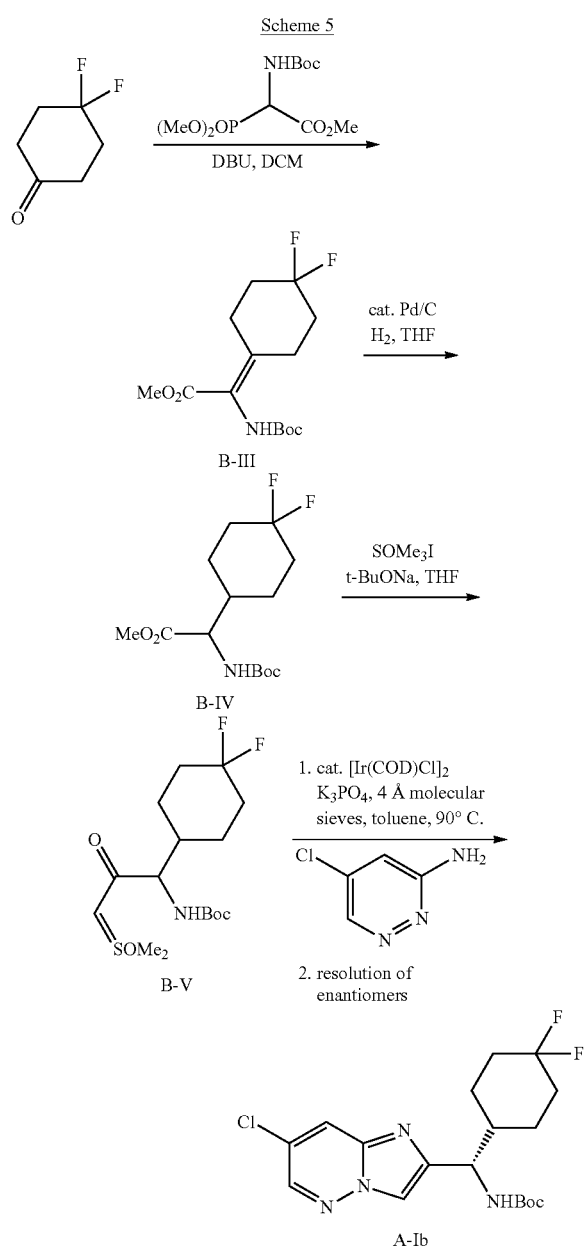

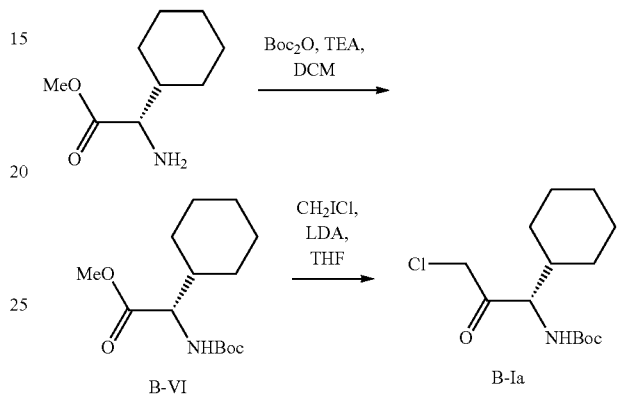

Chloromethyl ketones B-Ia may also be prepared by the route outlined in Scheme 6. Treatment of methyl (S)-2-amino-2-cyclohexylacetate with di-tert-butyl dicarbonate with or without a base, such as TEA, in a solvent, such as DCM, affords B-VI which can be subsequently converted to the chloromethyl ketones B-Ia upon treatment with chloroiodomethane treated with LDA in an aprotic solvent, such as THF.

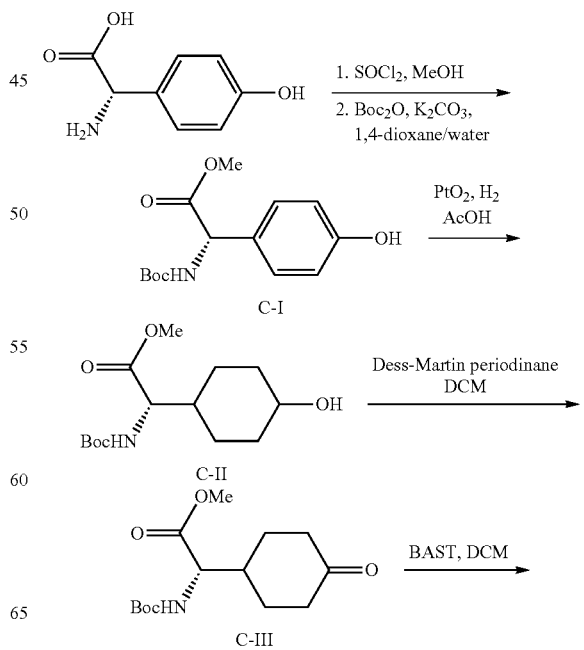

Alternatively, A-I (e.g., A-Ib) can be prepared as shown in Scheme 5. Treatment of 4,4-difluorocyclohexyl ketone with methyl 2-((tert-butoxycarbonyl)amino)-2-(dimethoxyphosphoryl)acetate and a base, such as DBU, affords corresponding tetrasubstituted olefins B-III. Reduction of B-III with a -continued

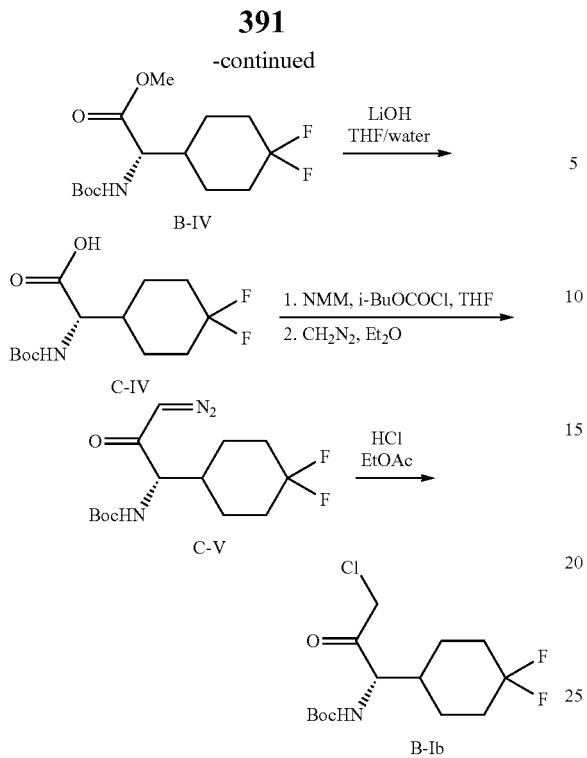

Alternatively, compounds of general structure B-Ib can be prepared according to Scheme 7. (S)-2-Amino-2-(4-hydroxyphenyl)acetic acid can be converted to C-I by esterifying the acid under acidic conditions, such as thionyl chloride in dry methanol, and subsequent treatment with di-tert-butyl dicarbonate in the presence of a mild base, such as potassium carbonate, in a solvent mixture, such as water and 1,4-dioxane. Reduction of the phenyl ring of C-I using a hydrogen source, such as hydrogen gas, and a catalyst, such as platinum(IV) oxide, in a solvent, such as HOAc, gives C-II. Oxidation of the alcohol of C-II with an oxidant, such as DMP, affords ketones C-III.

Conversion of C-III to geminal difluorides B-IV can be achieved by treatment with deoxygenative fluorinating reagents, such as BAST (bis(2-methoxyethyl)aminosulfur trifluoride), in a solvent, such as DCM. Saponification of the ester using a base, such as lithium hydroxide, furnishes the corresponding acids C-IV, which upon conversion to a mixed anhydride by treatment with a reagent such as isobutyl chloroformate followed by addition of diazomethane yields corresponding diazoketones C-V. C-V could be converted to B-Ib by treatment with aqueous hydrochloric acid.

Scheme 7b

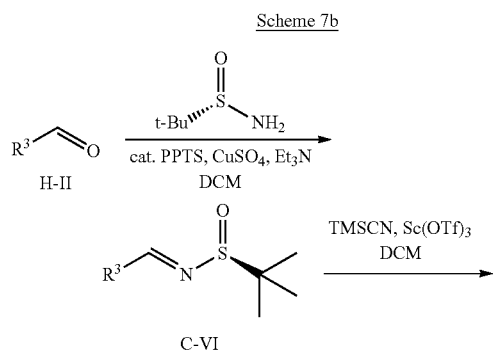

-continued

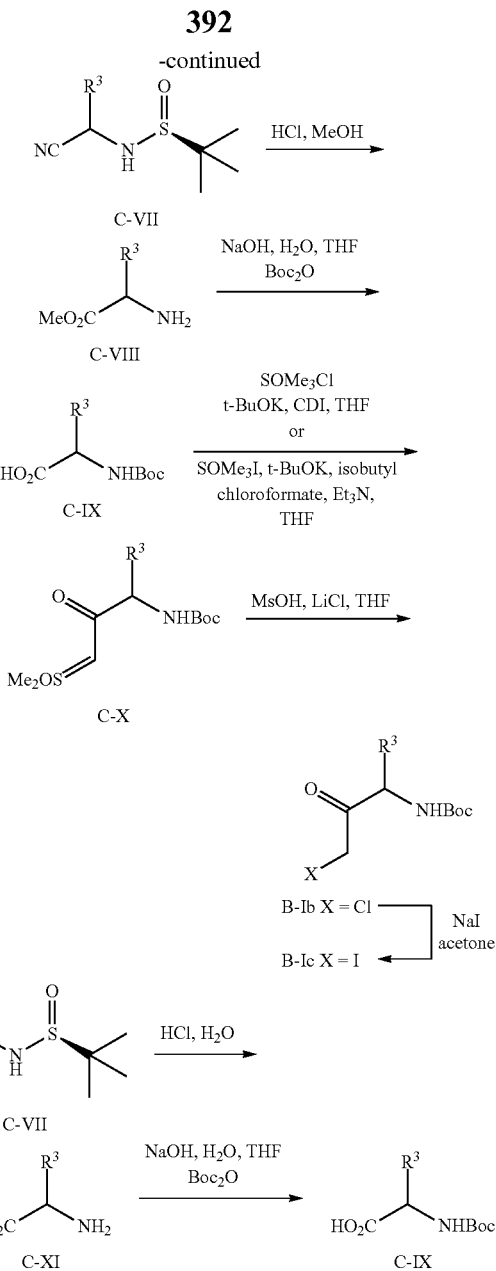

Compounds of the general formula B-Ic and C-IX can be prepared as shown in Scheme 7b. Condensation of aldehydes H-II with (S)-(−)-2-methyl-2-propanesulfinamide gives corresponding sulfinimides C-VI. Cyanation using TMSCN in the presence of scandium triflate then affords nitriles C-VII. Subsequent treatment with HCl in methanol then affords esters C-VIII. Coincident ester saponification and Boc protection of the amine then yields C-IX. Activation of the carboxylic acid within C-IX using a reagent such as CDI or isobutylchloroformate in the presence of a base such as potassium tert-butoxide in a solvent such as THF then generates ylides of the structure C-X. Treatment of ylides C-X with methanesulfonic acid in the presence of lithium chloride in a solvent such as THF then provides the chloromethyl ketones B-Ib, that can be converted to the corresponding iodides by treatment with sodium iodide in acetone to yield compounds B-Ic. Alternatively, acids C-IX can be prepared from nitriles C-VII by treatment with aqueous HCl and subsequent treatment of resulting amino acids C-XI with sodium hydroxide and Boc anhydride to afford protected amino acids C-IX.

Scheme 8

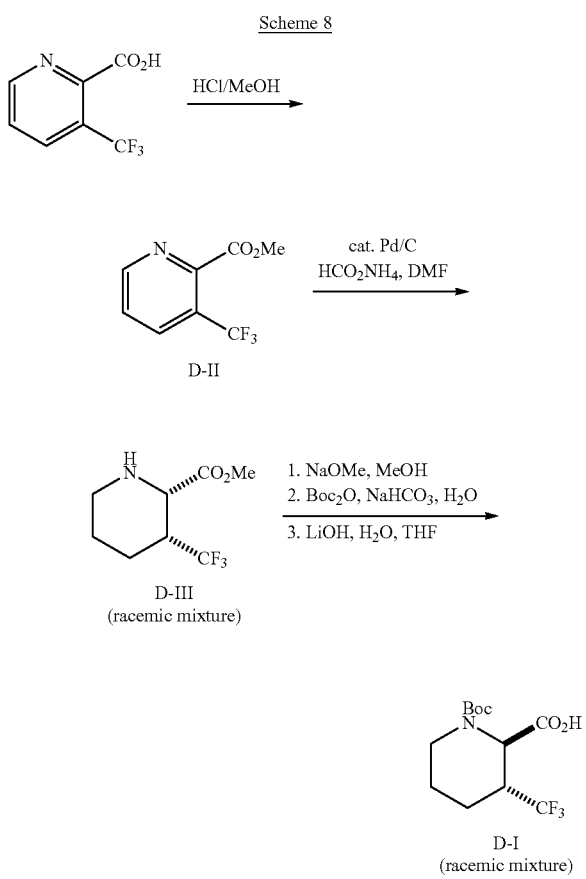

Trans-1-(tert-butoxycarbonyl)-3-(trifluoromethyl)piperidine-2-carboxylic acid D-I can be prepared as shown in Scheme 8. Esterification of 3-(trifluoromethyl)picolinic acid in acidic methanol yields ester D-II. Reduction of the pyridine ring D-II using a hydrogen source, such as ammonium formate, in the presence of a catalyst, such as palladium on carbon, afforded racemic piperidine D-III. D-I could then be prepared by epimerizing the 2-position of D-III under basic conditions, such as sodium methoxide in methanol, followed by treatment with di-tert-butyl dicarbonate with a base such as aqueous sodium bicarbonate, and then converting the ester to the corresponding acid under alkaline conditions, such as with aqueous LiOH in a solvent such as THF.

Scheme 9

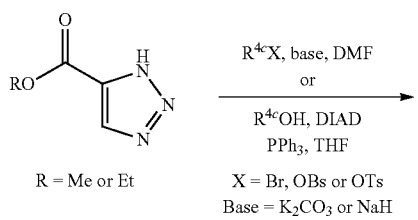

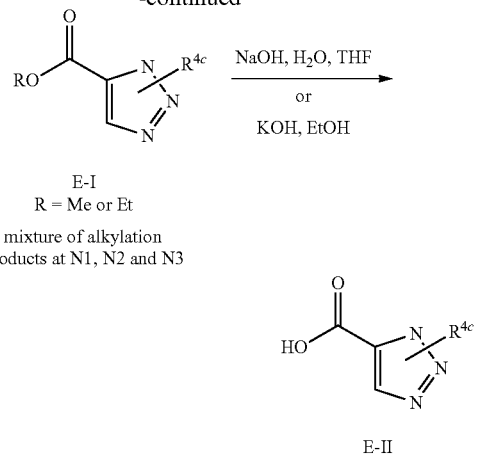

Substituted 1,2,3-triazole-5-carboxylic acids E-II can be prepared as shown in Scheme 9. Methyl or ethyl 1H-1,2,3-triazole-5-carboxylate can be alkylated by treating the ester with a base such as potassium carbonate or sodium hydride and an alkylating agent such as alkyl bromide, brosylate or tosylate in a solvent such as DMF to yield a mixture of 1,2,3-triazoles-5-carboxylates E-I alkylated at the N1, N2 or N3 positions that could be separated by silica gel chromatography. Alternatively, alkylation can be accomplished by treatment of methyl or ethyl 1H-1,2,3-triazole-5-carboxylate with an alcohol using Mitsunobu conditions, such as DIAD and triphenylphosphine in a solvent such as THF, to provide E-I. Hydrolysis of the ester with aqueous base such as sodium hydroxide or potassium hydroxide in a solvent such as THF or EtOH leads to the carboxylic acids E-II.

Scheme 10

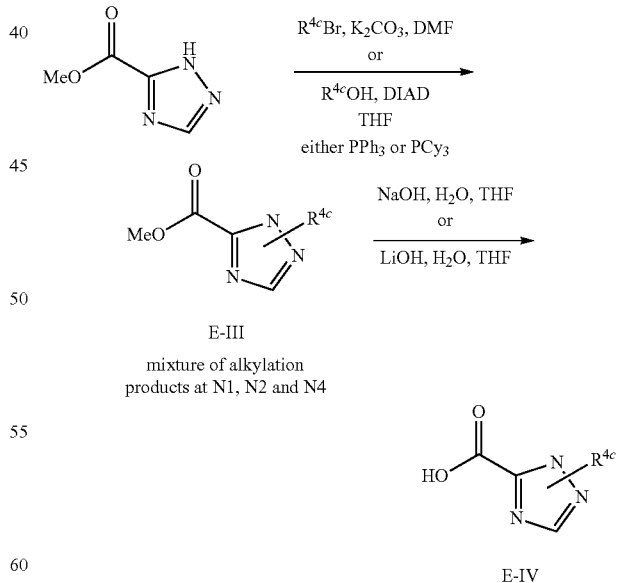

Scheme 10 shows that substituted 1,2,4-triazole-5-carboxylic acids E-IV can be prepared in a similar sequence as described in Scheme 9 using methyl 1,2,4-triazole-5-carboxylate as the starting material wherein PCy$_3$ is tricyclohexylphosphine.

Scheme 11

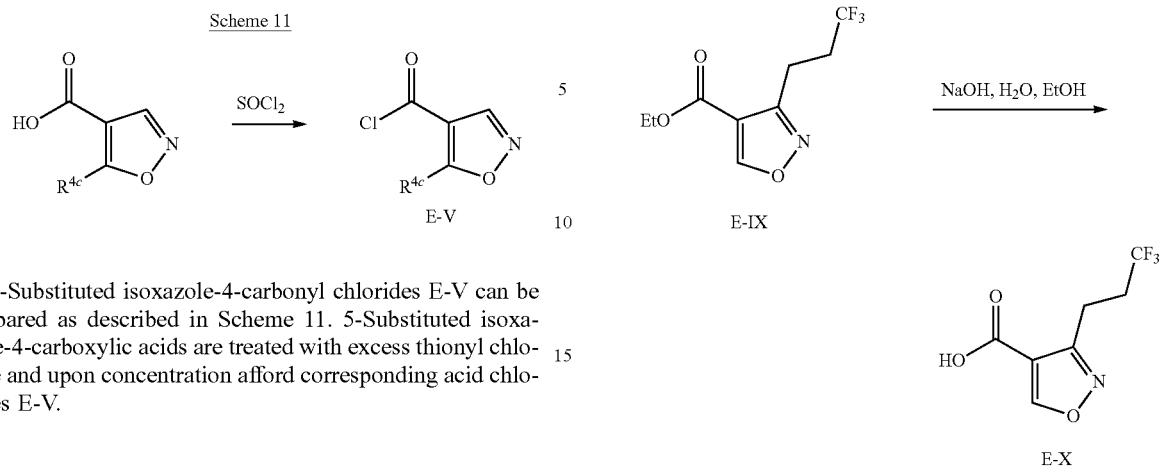

5-Substituted isoxazole-4-carbonyl chlorides E-V can be prepared as described in Scheme 11. 5-Substituted isoxazole-4-carboxylic acids are treated with excess thionyl chloride and upon concentration afford corresponding acid chlorides E-V.

Scheme 12

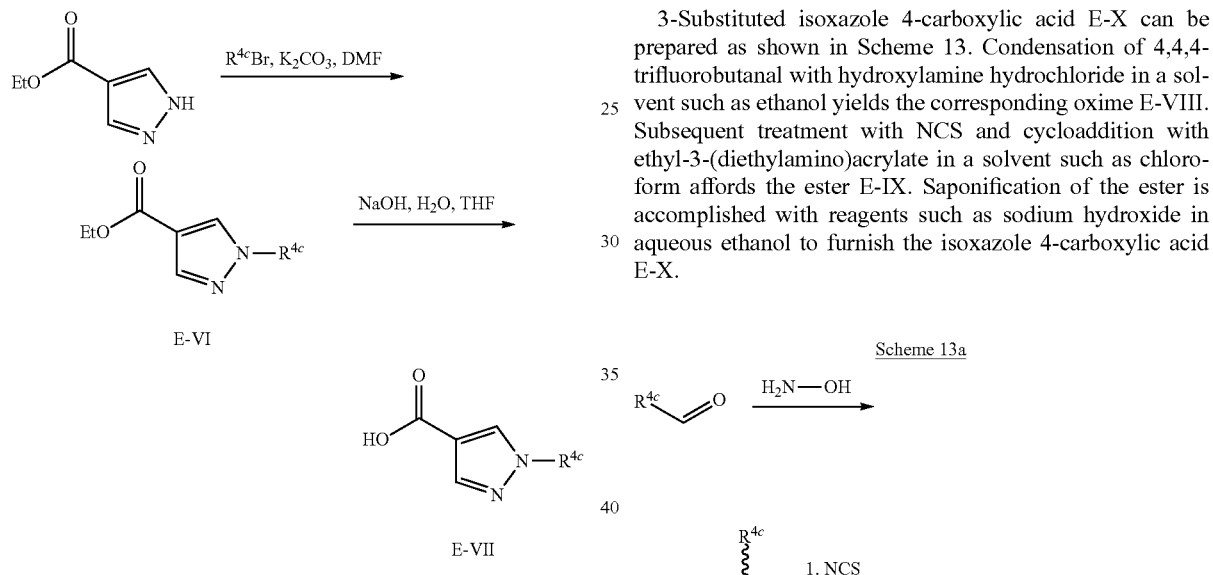

Scheme 12 shows that substituted 1,2-pyrazole-4-carboxylic acids E-VII can be prepared in a similar sequence as described in Scheme 9.

Scheme 13

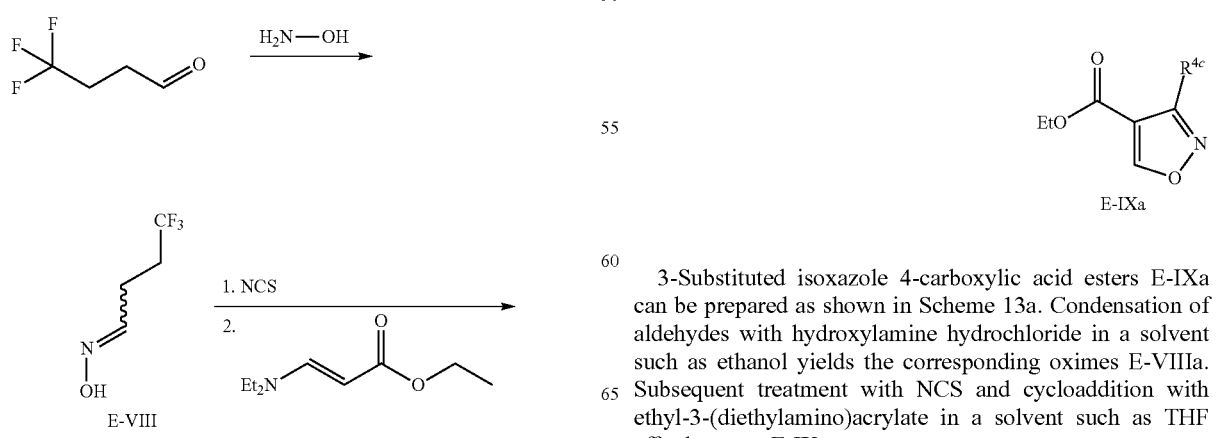

3-Substituted isoxazole 4-carboxylic acid E-X can be prepared as shown in Scheme 13. Condensation of 4,4,4-trifluorobutanal with hydroxylamine hydrochloride in a solvent such as ethanol yields the corresponding oxime E-VIII. Subsequent treatment with NCS and cycloaddition with ethyl-3-(diethylamino)acrylate in a solvent such as chloroform affords the ester E-IX. Saponification of the ester is accomplished with reagents such as sodium hydroxide in aqueous ethanol to furnish the isoxazole 4-carboxylic acid E-X.

Scheme 13a

3-Substituted isoxazole 4-carboxylic acid esters E-IXa can be prepared as shown in Scheme 13a. Condensation of aldehydes with hydroxylamine hydrochloride in a solvent such as ethanol yields the corresponding oximes E-VIIIa. Subsequent treatment with NCS and cycloaddition with ethyl-3-(diethylamino)acrylate in a solvent such as THF affords esters E-IXa.

Scheme 13b

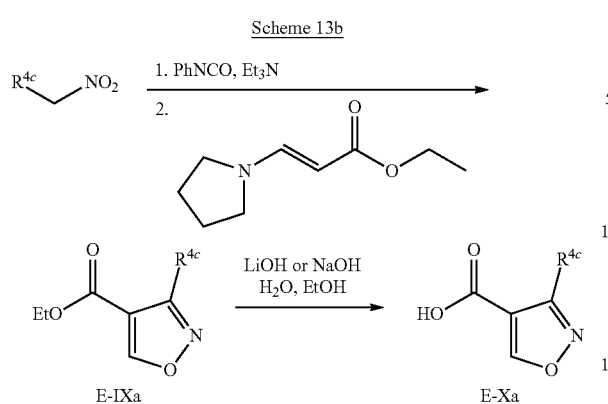

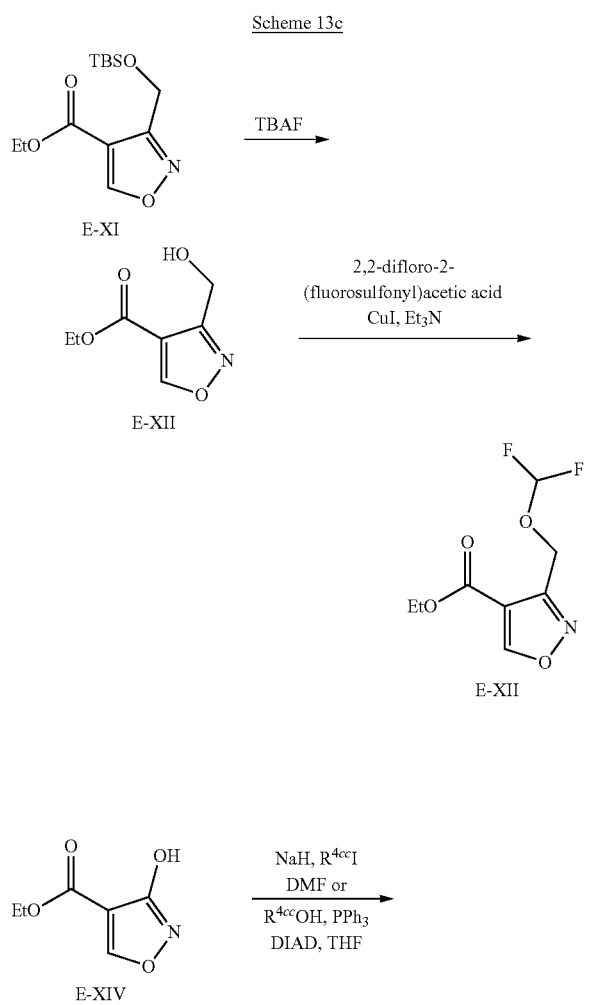

Isoxazoles E-Xa can be prepared by the process outlined in Scheme 13b. Treatment of a suitable nitroalkane with phenylisocyanate in the presence of Et₃N, followed by treatment with 3-pyrrolidin-1-yl-acrylic acid ethyl ester in the presence of triethyl amine in a solvent such as benzene affords corresponding esters E-IXa. Subsequent saponification using a reagent such as LiOH or NaOH in aqueous ethanol yields corresponding acids E-Xa.

Scheme 13c

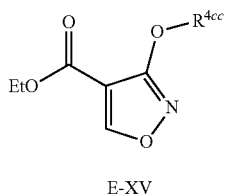

Isoxazole esters E-XIII and E-XV can be prepared by the route shown in Scheme 13c. Desilylation of ester E-XI using TBAF affords the alcohol E-XII. Difluoromethylation using 2,2-difluoro-2-(fluorosulfonyl)acetic acid in the presence of an additive such as CuI and a base such as Et₃N in a solvent such as CH₃CN affords the ester E-XIII. Ethyl 3-hydroxy-isoxazole-4-carboxylate E-XIV can be alkylated with iodo-alkanes in the presence of sodium hydride in a solvent such as DMF to afford ethers E-XV. Alternatively treatment of ethyl 3-hydroxyisoxazole-4-carboxylate E-XIV with aliphatic alcohols and reagents such as triphenyl phosphine and DIAD in a solvent such as THF provides ethers E-XV.

Scheme 13d

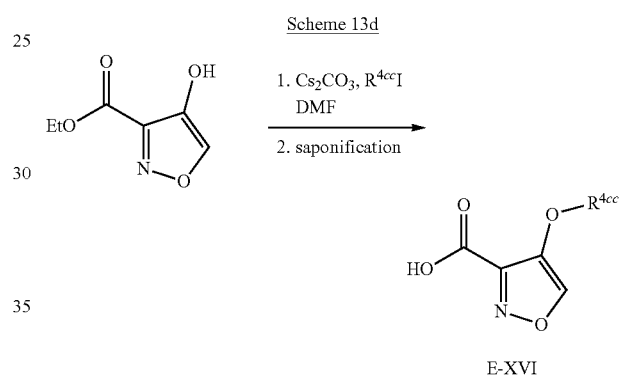

Isoxazole acids E-XVI can be prepared by the route shown in Scheme 13d. Alkylation of ethyl 4-hydroxyisoxazole-3-carboxylate using alkyl iodides in the presence of a base such as cesium carbonate in a solvent such as DMF affords the corresponding esters. Subsequent saponification using reagents such as LiOH in solvent mixtures such as THF and water affords isoxazole acids E-XVI.

Scheme 13e

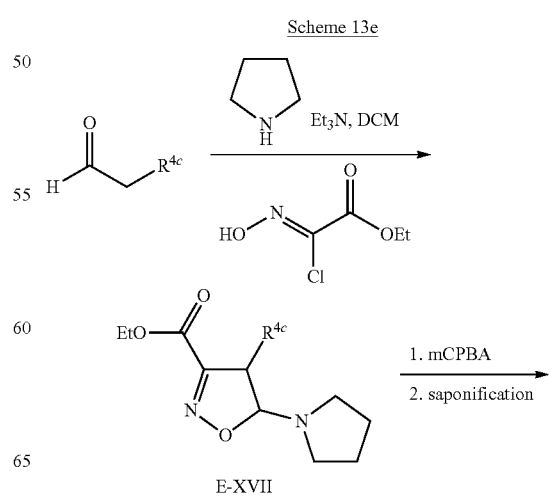

E-XVIII

4-Substituted isoxazole-3-carboxylic acids of the general formula E-XVIII can be prepared as shown in Scheme 13e. Condensation of a suitable aldehyde with ethyl 2-chloro-2-(hydroxyimino)acetate in the presence of pyrrolidine in a solvent such as DCM and a base such as triethylamine yields compounds E-XVII. Oxidation of the pyrrolidine within E-XVII using reagents such as mCPBA in solvents such as DCM then affords the corresponding isoxazole-3-carboxylic esters (structure not shown) that upon saponification using regents such as aqueous LiOH in solvents such as THF affords compounds of formula E-XVIII.

Scheme 14

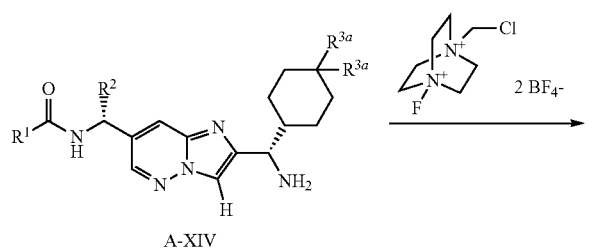

A-XIV

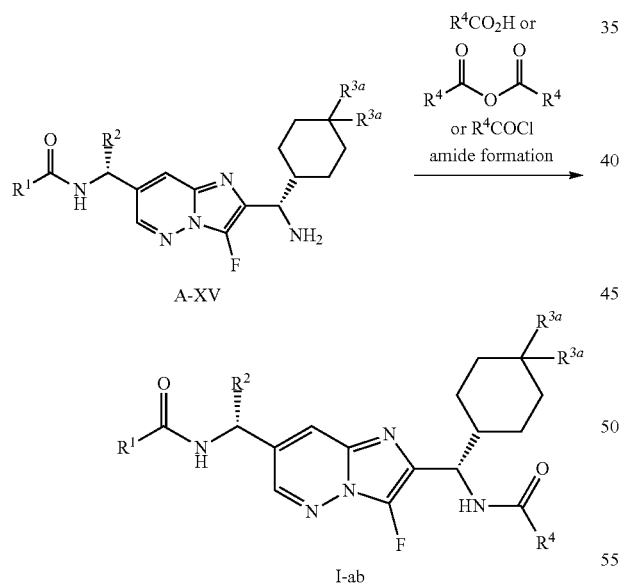

A-XV

I-ab

Compounds I-ab possessing an $R^5$=F may be prepared as shown in Scheme 14. Compounds A-XIV (prepared from A-VIII as shown in Scheme 3) may be treated with fluorinating reagent such as 1-chloromethyl-4-fluoro-1,4-diazoniabicyclo[2.2.2]octane bis(tetrafluoroborate) in a solvent such as acetonitrile to afford compounds with the structure A-XV with $R^5$=F. Subsequent amide bond formation as previously described then provides compounds I-ab.

Scheme 15

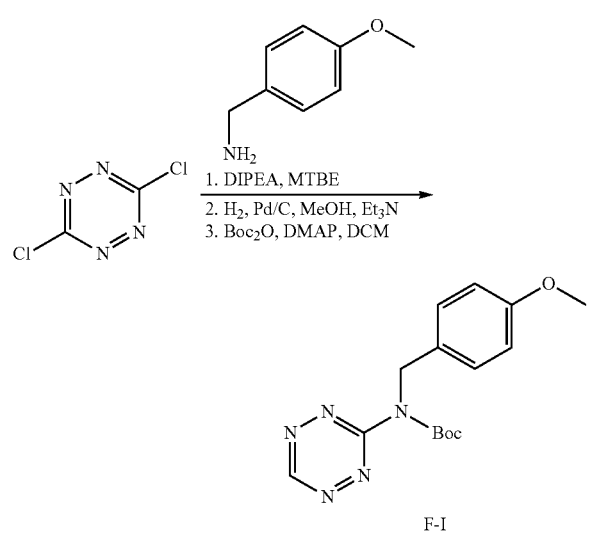

F-I

Functionalized tetrazines can be prepared as shown in Scheme 15. Treatment of 3,6-dichloro-1,2,4,5-tetrazine with (4-methoxyphenyl)methanamine in the presence of reagents such as DIPEA in a solvent such as MTBE yields the aminated product (not shown). Subsequent dechlorination reduction using palladium catalysis and Boc protection of the amine affords tetrazine F-I.

Scheme 16

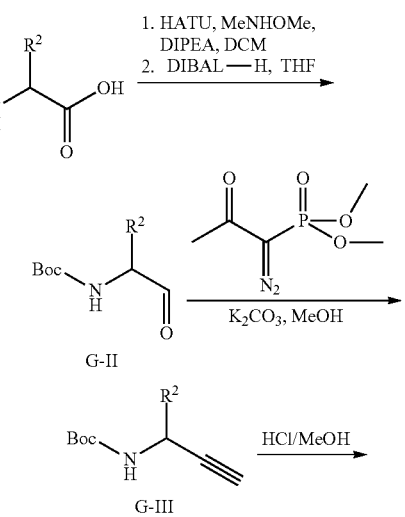

G-II

G-III

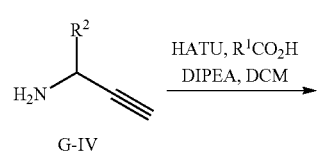

G-IV

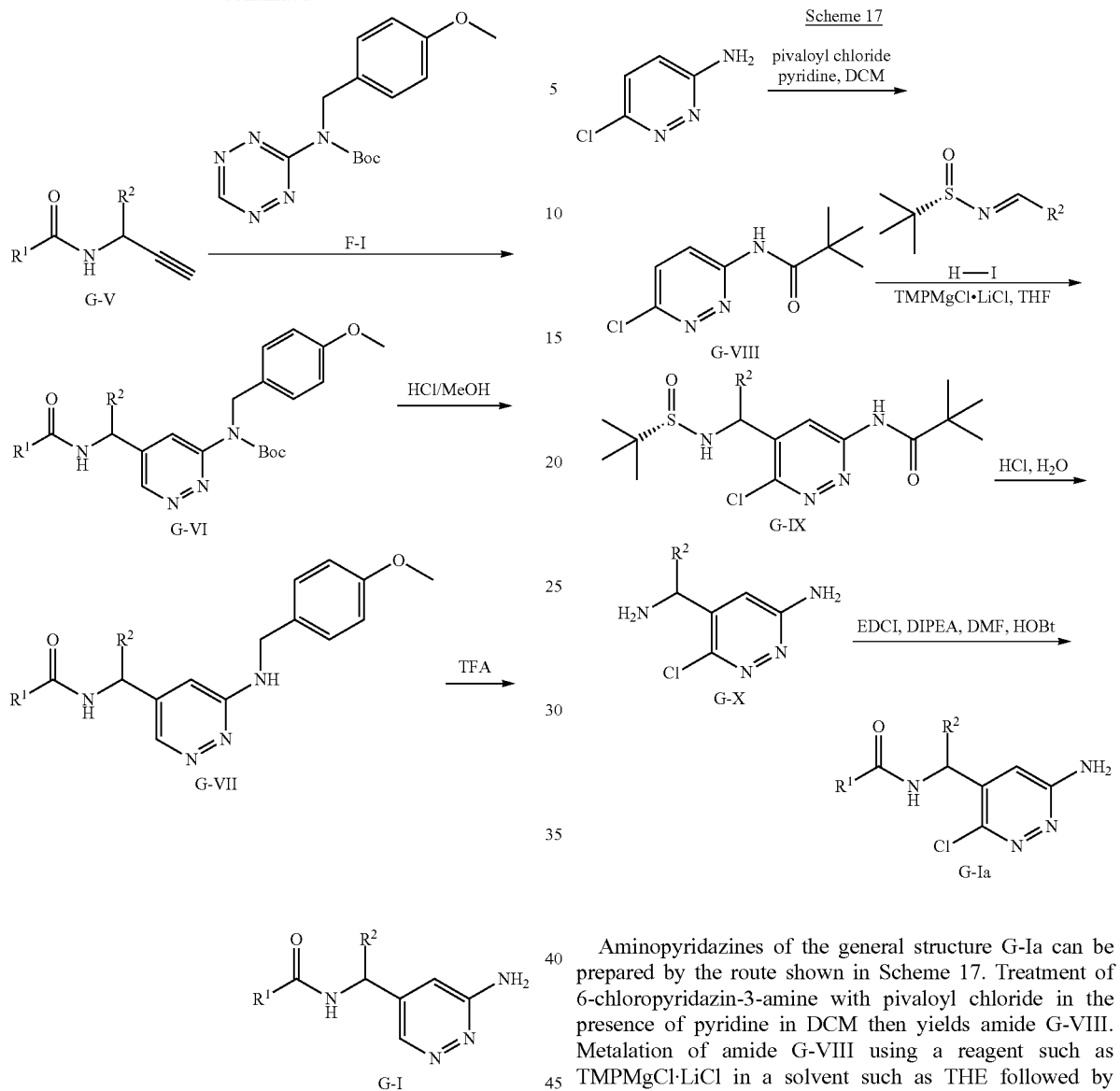

Aminopyridazines of the general structure G-I can be prepared by the route shown in Scheme 16. Conversion of Boc protected amino acids to the corresponding aldehydes by a two step process involving Weinreb amide formation and subsequent reduction using hydride reagents such as DIBAL-H in solvents such as THF affords aldehydes G-II. Treatment of aldehydes G-II with dimethyl (1-diazo-2-oxopropyl)phosphonate in a solvent such as methanol in the presence of a base such as potassium carbonate then affords alkynes G-III. Deprotection of the Boc group using hydrochloric acid in methanol provides amines G-IV. Subsequent amide bond formation with carboxylic acids using reagents such as HATU in solvents such as DCM in the presence of additives such as DIPEA then yields amides G-V. Condensation of G-V with tetrazine F-I under thermal conditions (60-115° C.) generates compounds G-VI. Deprotection of the Boc with HCl in methanol to give G-VII and subsequent deprotection of the 4-methoxybenzyl groups with TFA then affords aminopyridazines G-I.

Aminopyridazines of the general structure G-Ia can be prepared by the route shown in Scheme 17. Treatment of 6-chloropyridazin-3-amine with pivaloyl chloride in the presence of pyridine in DCM then yields amide G-VIII. Metalation of amide G-VIII using a reagent such as TMPMgCl·LiCl in a solvent such as THF followed by treatment with a sulfinimine H-I then affords sulfinamines G-IX. Removal of the sulfinimine and pivaloyl groups by acidic hydrolysis using reagents such as aqueous hydrochloric acid then affords diamines G-X. Subsequent amide bond formation generates aminopyridazines G-Ia.

Scheme 18

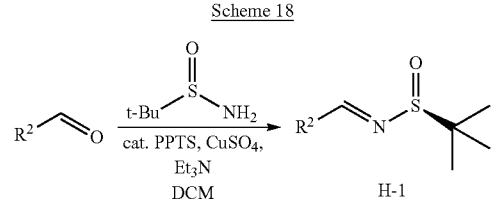

Sulfinimides H-I are prepared as shown in Scheme 18. Condensation of aldehydes with sulfimamides such as (S)-2-methylpropane-2-sulfinamide in the presence of reagents such as copper sulfate and PPTS in solvents such as DCM, THF and/or toluene yields sulfinimines H-I.

Scheme 19

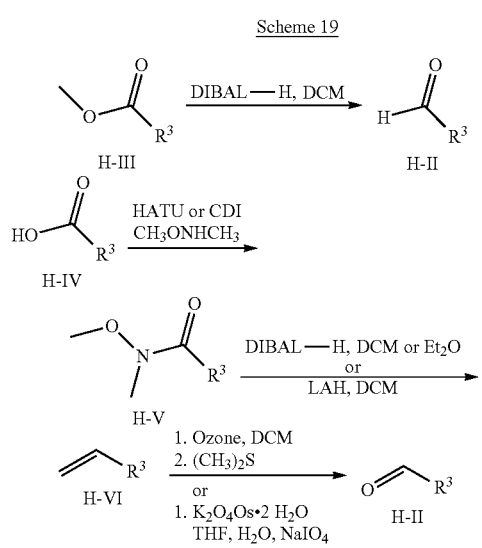

Aldehydes of the general structure H-IT are prepared as shown in Scheme 19. In some cases, carboxylic esters H-ITT can be reduced using reagents such as DIBAL-H in solvents such as DCM to afford aldehydes H-TI. Carboxylic acids H-IV can be converted to the corresponding amides H-V by treatment with N,O-dimethylhydroxylamine in the presence of reagents such as HATU or CDI and the presence of additives such as DIPEA in solvents such as DCM. Reduction of amides H-V using reducing agents such as DIBAL-H or lithium aluminum hydride in solvents such as DCM or ethyl ether afford the corresponding aldehydes H-II. Terminal olefins H-VI may be cleaved under oxidative conditions by treatment with reagents such as ozone in DCM followed by treatment with dimethyl sulfide to afford H-IT. Alternatively, treatment of H-VI with reagents such as potassium osmate dihydrate and sodium periodate in solvents such as THE and water afford aldehydes H-IT.

Scheme 20

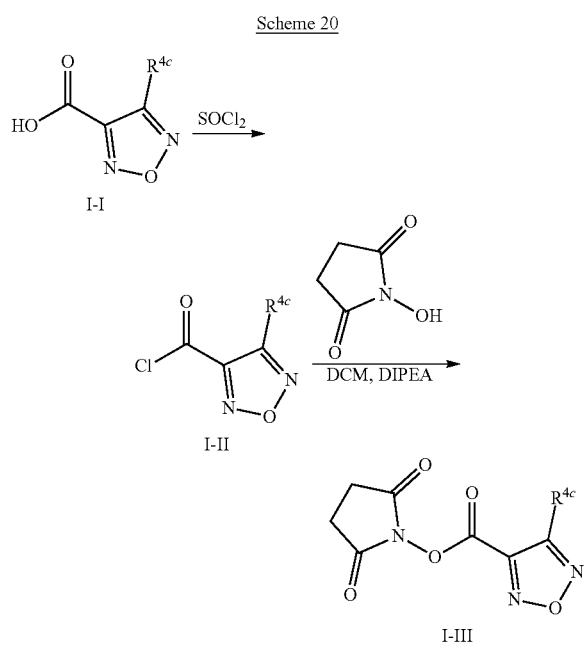

5-Substituted oxadiazole-4-carbonyl chlorides (I-IT) and N-hydroxysuccinate esters (I-ITT) can be prepared as described in Scheme 20. Acids I-I are treated with a chlorinating agent such as excess thionyl chloride and upon concentration this affords the corresponding acid chlorides I-IT. Subsequent reaction with N-hydroxysuccinimide affords the corresponding esters I-III.

Scheme 21

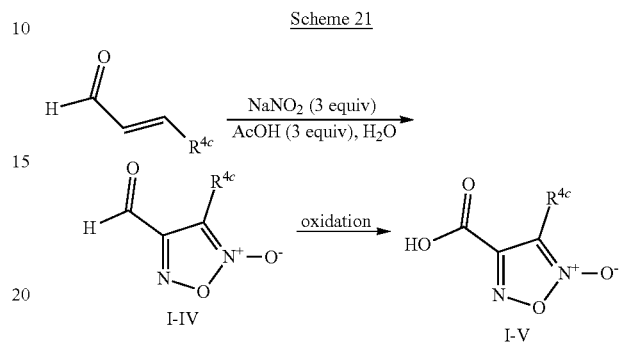

Oxadiazole acids I-V can be prepared as shown in Scheme 21. Treatment of α,β-unsaturated aldehydes with sodium nitrite in solvents such as acetic acid affords the corresponding oxadiazole formyl-1,2,5-oxadiazole 2-oxides I-IV. Oxidation of I-IV with a reagent such as Jones reagent in a solvent such as acetone affords the carboxylic acids I-V.

Scheme 22

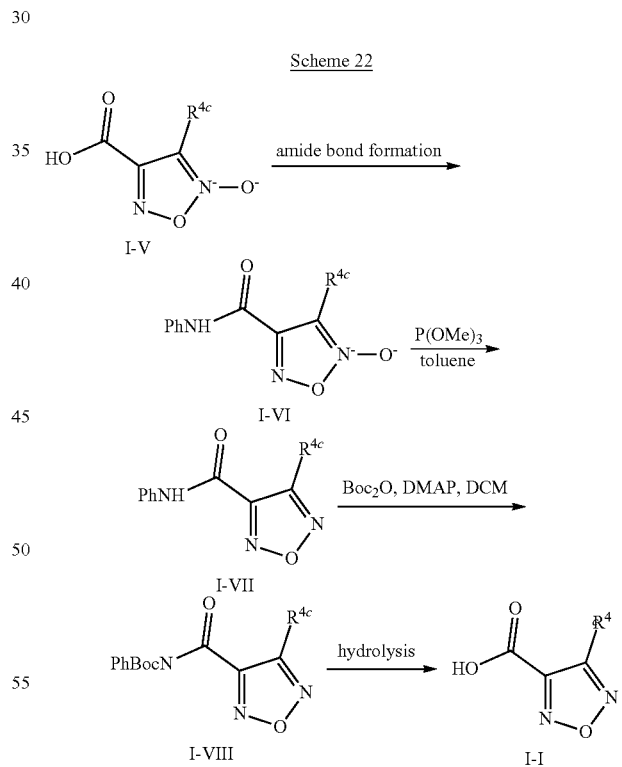

Oxadiaxole acids of the general formula I-I can be prepared as shown in Scheme 22. Treatment of acids I-V with aniline affords amides I-VI. Reduction with trimethyl phosphite in a solvent such as toluene then affords compounds I-VII. Subsequent treatment of I-VII with di-tert-butyl dicarbonate in the presence of DMAP in a solvent such as DCM affords compounds I-VIII. Treatment of I-VIII with LiOH in THF/water then yields acids I-I

Scheme 23

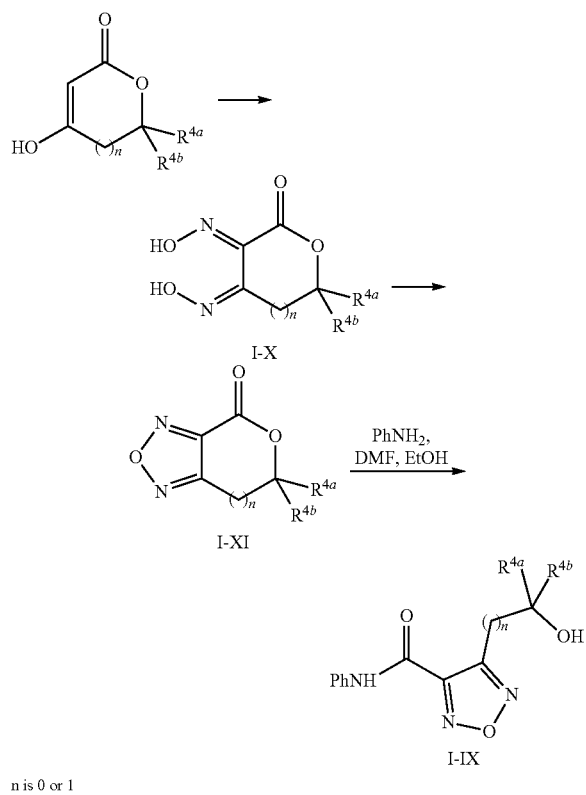

n is 0 or 1

Amides I-IX can be prepared by the route shown in Scheme 23. Lactones I-XI may be prepared using the procedures outlined in Pollet, P.; Gelin, S. Tetronic Acids and Derivatives; Part VI. A Convenient Synthesis of New 4-Oxo-2-phenyl-2H-4,6-dihydrofuro[3,4-d]triazole and 4-Oxo-4,6-dihydrofuro[3,4-c]furazan Systems. *Synthesis.* 1979, 12, 977. Treatment of lactones I-XI with aniline in a solvent mixture such as DMF and EtOH then affords the amides I-IX.

Scheme 24

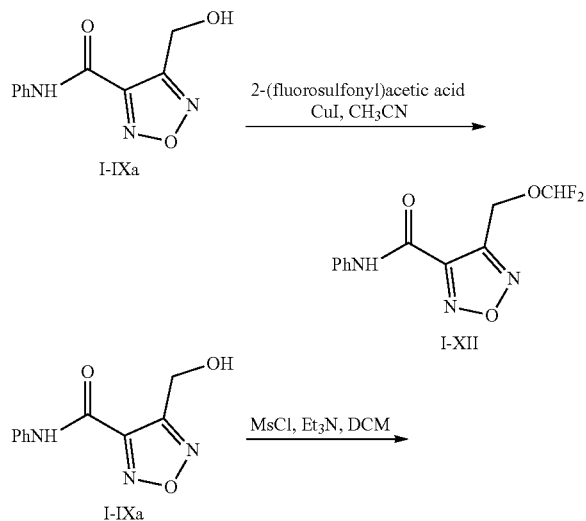

Oxadiazole amides may be prepared as shown in Scheme 24. Treatment of alcohol I-IXa with copper (I) iodide and 2-(fluorosulfonyl)acetic acid in a solvent such as acetonitrile provides the corresponding difluoromethyl ether I-XII. Activation of the hydroxyl in I-IXa using methansulfonyl chloride in the presence of $Et_3N$ in a solvent such as DCM affords I-XIII. Treatment of I-XIII with 3-presence of DIPEA in a solvent such as DCM affords I-XIV.

Scheme 25

Oxadiazole amides I-IXb and I-IXc can be prepared as shown in Scheme 25. Treatment of chloro-N-phenyl-1,2,5-oxadiazole-3-carboxamide with certain amines in the presence of DIPEA in 1,4-dioxane, or sodium hydride in THF, or neat affords amides I-IXb. Similarly, treatment of chloro-N-phenyl-1,2,5-oxadiazole-3-carboxamide with certain alcohols in the presence of sodium hydride in THF or, in the case of $R^{4cc}$=Me, sodium methoxide in methanol, yields amides I-IXc.

Scheme 26

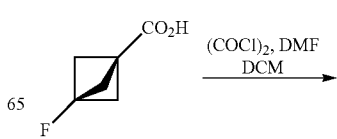

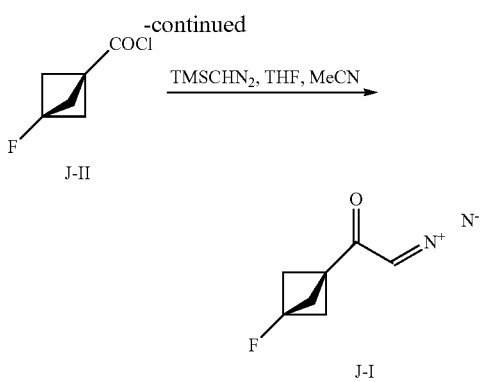

Diazoketone J-I can be prepared as shown in Scheme 26. Subjection of 3-fluorobicyclo[1.1.1]pentane-1-carboxylic acid to oxalyl chloride in the presence of DMF in a solvent such as DCM affords the corresponding acid chloride J-II. Subsequent treatment of J-II with (trimethylsilyl)diazomethane in THF and acetonitrile then affords the diazoketone J-I.

INTERMEDIATES

Intermediate 1

Methyl 3-(trifluoromethyl)picolinate

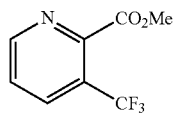

Methanol (600 mL) was cooled to 0° C. in an ice bath, and then AcCl (95 g, 1.2 mol) was added dropwise at a rate that maintained the internal temperature below 10° C. After the addition was complete, the resulting solution was allowed to warm to rt. Neat 3-(trifluoromethyl)pyridine-2-carboxylic acid (30 g, 160 mmol) was then added, and the resulting solution was heated at reflux temperature for 16 h. After this time, the reaction mixture was allowed to cool to rt and then concentrated. The residue was diluted with EtOAc and saturated aqueous NaHCO$_3$ solution, the layers were mixed and then separated, and the aqueous layer was extracted with EtOAc. The organic layers were combined, dried with anhydrous MgSO$_4$, and concentrated to afford the title compound as a yellow oil.

Intermediate 2

Methyl (cis-2,3)-3-(trifluoromethyl)piperidine-2-carboxylate

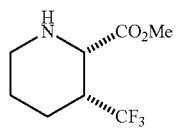

Methyl 3-(trifluoromethyl)picolinate (20 g, 97 mmol, Intermediate 1), HCO$_2$NH$_4$ (37 g, 0.58 mol), and Pd/C (9.0 g, 20% w/w, 17 mmol) were added to a reactor containing DMF (260 mL) under an atmosphere of nitrogen gas, and the resulting mixture was stirred at rt for 3 h. After this time, the mixture was filtered, and the filter cake was washed with MTBE. The combined filtrate and wash were diluted with water. The layers were mixed and then separated, and the aqueous layer was extracted twice with MTBE. The organic layers were combined and then concentrated to afford the title compound as a yellow oil.

Intermediate 3

(Trans-2,3)-1-(tert-butoxycarbonyl)-3-(trifluoromethyl)piperidine-2-carboxylic Acid

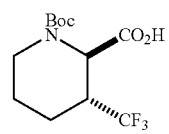

Sodium methoxide (2.6 g, 47 mmol) was added to a solution of methyl (cis-2,3)-3-(trifluoromethyl)piperidine-2-carboxylate (10 g, 47 mmol, Intermediate 2) in dry MeOH (100 mL), and the resulting solution was maintained at rt for 1 h. The solution was then warmed to 45° C. and maintained at that temperature overnight. The solution was then allowed to cool to rt and maintained at that temperature for an additional 24 h. After this time, a solution of aqueous HCl (80 mL, 1.0 M, 80 mmol) was added, and the mixture was partially concentrated to remove most of the MeOH. The resulting concentrated aqueous solution was diluted with water (220 mL), and then Boc$_2$O (46 g, 0.21 mol) and NaHCO$_3$ (18 g, 0.21 mol) were added. The resulting mixture was stirred at rt for 20 h. After this time, the pH of the reaction mixture was adjusted to pH 6-7 with 1 N aqueous HCl. The mixture was then diluted with THF (250 mL). Lithium hydroxide (3.95 g, 165 mmol) and water (75 mL) were added, and the resulting mixture was stirred at rt for 16 h. After this time, 1 N aqueous HCl was added to make the mixture acidic. The layers were separated, and the aqueous layer was extracted twice with EtOAc. The organic layers were combined and then concentrated to give a colorless solid. This solid was crystallized from EtOAc/n-heptane (250 mL, 1:4 v/v) to afford the title compound as a colorless crystalline solid.

Intermediate 4

Methyl (S)-2-((tert-butoxycarbonyl)amino)-2-cyclohexylacetate

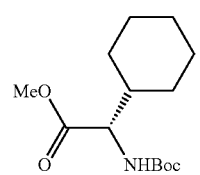 [SMILES: COC(=O)[C@@H](NC(=O)OC(C)(C)C)C1CCCCC1]

Di-tert-butyl dicarbonate (200 mL, 870 mmol) was added to a mixture of (S)-methyl 2-amino-2-cyclohexylacetate hydrochloride (120 g, 578 mmol) and TEA (240 mL, 1.73 mol) in DCM (1.5 L), and the resulting mixture was stirred at rt for 16 h. After this time, the pH of the mixture was adjusted to pH 5 by adding a saturated aqueous citric acid solution. The mixture was then poured into water (1 L) and extracted three times with DCM. The organic extracts were combined, dried over anhydrous $Na_2SO_4$, filtered, and concentrated. The residue was triturated with petroleum ether (350 mL) and then isolated by filtration to afford the title compound as a colorless solid.

Intermediate 5

Tert-Butyl (S)-(3-chloro-1-cyclohexyl-2-oxopropyl) carbamate

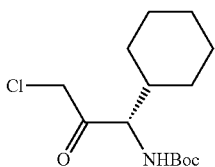

A solution of LDA was prepared by adding n-BuLi (194 mL, 2.5 M in hexane, 485 mmol) dropwise to a −70° C. solution of diisopropylamine (62.0 mL, 441 mmol) in THF (80 mL), and then allowing the resulting solution to warm to 0° C. (ice bath) over 30 min. This solution was then added dropwise to a −70° C. solution of methyl (S)-2-((tert-butoxycarbonyl)amino)-2-cyclohexylacetate (20 g, 74 mmol, Intermediate 4) and chloroiodomethane (21.6 mL, 295 mmol) in THF (120 mL). The resulting mixture was stirred at −70° C. for 3 h before it was quenched with a saturated aqueous $NH_4Cl$ solution (200 mL) and allowed to warm to rt. The resulting mixture was extracted three times with EtOAc. The organic extracts were combined, dried over anhydrous $Na_2SO_4$, filtered, and concentrated. The residue was purified by silica gel chromatography (20:1 to 5:1 petroleum ether/EtOAc) to afford the title compound as a black oil.

Intermediate 6

Tert-Butyl (S)-(1-cyclohexyl-3-iodo-2-oxopropyl) carbamate

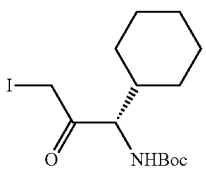

Sodium iodide (11.0 g, 73.4 mmol) was added to a solution of tert-butyl (S)-(3-chloro-1-cyclohexyl-2-oxopropyl)carbamate (35.0 g, 121 mmol, Intermediate 5) in acetone (150 mL), and the resulting mixture was stirred at rt for 48 h. The mixture was then concentrated, and the residue was diluted with EtOAc (150 mL). The resulting suspension was filtered, and the filter cake was washed with EtOAc. The filtrate and wash were combined and concentrated to afford the title compound, which was used directly in next step without further purification.

Intermediate 7

Methyl (S)-2-amino-2-(4-hydroxyphenyl)acetate Hydrochloride

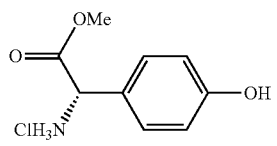

Thionyl chloride (711 g, 5.98 mol) was added to a solution of (S)-2-amino-2-(4-hydroxyphenyl)acetic acid (500 g, 2.99 mol) in MeOH (2.0 L) at 0° C. After the addition was complete, the mixture was stirred at 80° C. for 12 h. After this time, the mixture was allowed to cool to rt and then concentrated to afford the title compound as a yellow solid.

Intermediate 8

Methyl (S)-2-((tert-butoxycarbonyl)amino)-2-(4-hydroxyphenyl)acetate

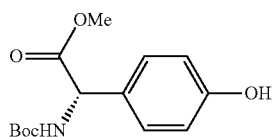

A solution of $K_2CO_3$ (508 g, 3.68 mol) in water (2.0 L) was added to a suspension of methyl (S)-2-amino-2-(4-hydroxyphenyl)acetate hydrochloride (400 g, 1.84 mol, Intermediate 7) in 1,4-dioxane (1.0 L), and the mixture was cooled to 0° C. Di-tert-butyl dicarbonate (421 g, 1.93 mol) was then added, and the mixture was allowed to warm to 18° C. and stirred for 12 h. After this time, the mixture was diluted with EtOAc, and the layers were mixed and then separated. The organic layer was washed with brine, dried with anhydrous $Na_2SO_4$, filtered, and then concentrated to give the title compound as a colorless solid.

Intermediate 9

Methyl (S)-2-((tert-butoxycarbonyl)amino)-2-(4-hydroxycyclohexyl)acetate

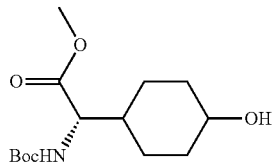 [SMILES: COC(=O)[C@@H](NC(=O)OC(C)(C)C)C1CCC(O)CC1]

Platinum dioxide (7.50 g, 33.1 mmol) was added to a solution of methyl (S)-2-((tert-butoxycarbonyl)amino)-2-(4-hydroxyphenyl)acetate (100 g, 355 mmol, Intermediate 8) in acetic acid (1.0 L), and the resulting mixture was stirred under an atmosphere of $H_2$ (48 psi) at 30° C. for 96 h. After this time, the reaction mixture was filtered, and the filtrate was concentrated to give a yellow oil. This oil was purified by gel silica chromatography (10:1 to 1:1 petroleum ether/EtOAc) to give the title compound as a colorless oil.

Intermediate 10

Methyl (S)-2-((tert-butoxycarbonyl)amino)-2-(4-oxocyclohexyl)acetate

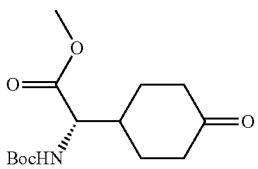

Dess-Martin periodinane (442 g, 1.04 mol) was added to a solution of methyl (S)-2-((tert-butoxycarbonyl)amino)-2-(4-hydroxycyclohexyl)acetate (200 g, 696 mmol, Intermediate 9) in DCM (2.0 L) at 0° C., and the resulting mixture was stirred at 10° C. for 12 h. After this time, a solution of Na$_2$SO$_3$ (400 g, 3.2 mol) in water (5 L) was added. The layers were mixed and then separated. The organic layer was washed with a saturated aqueous NaHCO$_3$ solution, followed by brine, dried with anhydrous Na$_2$SO$_4$, filtered, and then concentrated to give the title compound as a yellow oil.

Intermediate 11

Methyl (S)-2-((tert-butoxycarbonyl)amino)-2-(4,4-difluorocyclohexyl)acetate

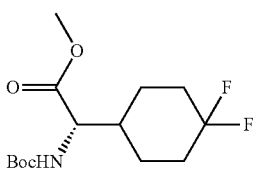

Bis(2-methoxyethyl)aminosulfur trifluoride (85.6 g, 387 mmol) was added dropwise to a solution of methyl (S)-2-((tert-butoxycarbonyl)amino)-2-(4-oxocyclohexyl)acetate (30.0 g, 105 mmol, Intermediate 10) in DCM (300 mL) at 0° C., and the resulting solution was stirred at 10° C. for 12 h. After this time, a cold saturated aqueous NaHCO$_3$ solution was added with stirring until the pH of the aqueous layer was maintained at pH 7. The layers were then separated, and the organic layer was washed with brine, dried with anhydrous Na$_2$SO$_4$, filtered, and concentrated to give a yellow oil. This oil was purified by gel silica chromatography (10:1 petroleum ether/EtOAc) to give the title compound as a yellow solid.

Intermediate 12

(S)-2-((tert-Butoxycarbonyl)amino)-2-(4,4-difluorocyclohexyl)acetic Acid

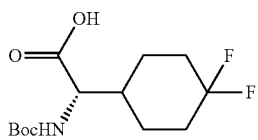

A solution of LiOH·H$_2$O (21.8 g, 520 mmol) in water (250 mL) was added to a solution of methyl (S)-2-((tert-butoxycarbonyl)amino)-2-(4,4-difluorocyclohexyl)acetate (80.0 g, 260 mmol, Intermediate 11) in THF (500 mL), and the mixture was stirred at 10° C. for 3 h. After this time, DCM (500 mL) was added, and the layers were mixed and then separated. The organic layer was discarded. The pH of the aqueous layer was adjusted to pH 2 with 1 M aqueous HCl, and the resulting mixture was extracted three times with DCM. The organic extracts were combined, dried with anhydrous Na$_2$SO$_4$, filtered, and concentrated to give the title compound as a yellow solid.

Intermediate 13

Tert-Butyl (S)-(3-diazo-1-(4,4-difluorocyclohexyl)-2-oxopropyl)carbamate

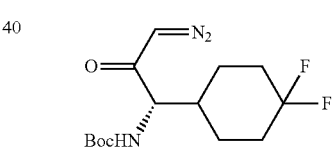

Isobutyl chloroformate (25.6 g, 187 mmol) was added dropwise to a solution of (S)-2-((tert-butoxycarbonyl)amino)-2-(4,4-difluorocyclohexyl)acetic acid (50.0 g, 170.4 mmol, Intermediate 12) and 4-methylmorpholine (18.9 g, 187 mmol) in THF (500 mL) at −20° C., then the resulting mixture was stirred at −20° C. for 30 min. After this time, the mixture was filtered. A solution of freshly prepared diazomethane in Et$_2$O* (1.8 L, approximately 3 equiv.) was then added to the filtrate at 0° C., the resulting solution was maintained at 0° C. for 12 h. After this time, the solution was partially concentrated to remove excess diazomethane, washed with water, dried with anhydrous Na$_2$SO$_4$, filtered, and concentrated to give a yellow solid. This solid was purified by gel silica chromatography (20:1 petroleum ether/EtOAc) to give the title compound as a light-yellow solid.

*Prepared according to de Boer, Th. J.; Backer, H. *J. Org. Synth.* 1956, 36, 16.

Intermediate 14

Tert-Butyl (S)-(3-chloro-1-(4,4-difluorocyclohexyl)-2-oxopropyl)carbamate

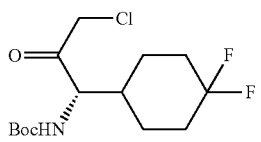

A solution of HCl in EtOAc (7.80 mL, 4.0 M, 31.2 mmol) was added to a solution of tert-butyl (S)-(3-diazo-1-(4,4-difluorocyclohexyl)-2-oxopropyl)carbamate (9.00 g, 28.3 mmol, Intermediate 13) in EtOAc (100 mL), and the mixture was stirred at 10° C. for 2 h. The mixture was then washed with a saturated aqueous $NaHCO_3$ solution, dried with anhydrous $Na_2SO_4$, filtered, and concentrated. The residue was purified by gel silica chromatography (10:1 petroleum ether/EtOAc) to afford a colorless solid. The solid was triturated with petroleum ether (200 mL) and then filtered, and the filter cake was dried under vacuum to give the title compound as a colorless solid.

Intermediate 15

Tert-Butyl (S)-(1-(4,4-difluorocyclohexyl)-3-iodo-2-oxopropyl)carbamate

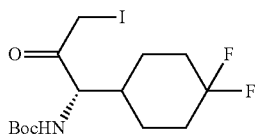 [SMILES: CC(C)(C)OC(=O)N[C@H](C(=O)CCl)C1CCC(F)(F)CC1]

The title compound was prepared as described for the synthesis of Intermediate 6, using tert-butyl (S)-(3-chloro-1-(4,4-difluorocyclohexyl)-2-oxopropyl)carbamate (Intermediate 14) in place of tert-butyl (S)-(3-chloro-1-cyclohexyl-2-oxopropyl)carbamate.

Intermediate 16

N-(5-Chloropyridazin-3-yl)-1,1-diphenylmethanimine

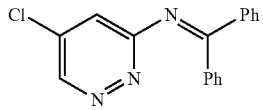 [SMILES: Clc1cnnc(N=C(c2ccccc2)c2ccccc2)c1]

A stirring mixture of $Cs_2CO_3$ (875 g, 2.68 mol), dppf (59.5 g, 107 mmol), and $Pd_2(dba)_3$ (49.2 g, 53.7 mmol) in DME (1.4 L) was warmed to 40° C., and then a solution of 3,5-dichloropyridazine (200 g, 1.34 mol) and benzophenone imine (243 g, 1.34 mol) in DME (600 mL) was added dropwise while maintaining an internal temperature of 40-45° C. When the addition was complete, the resulting mixture was stirred at 85° C. for 16 h. After this time, the reaction mixture was allowed to cool to rt and then filtered. The filter cake was washed with EtOAc, and the filtrate and wash were combined and concentrated. The residue was diluted with EtOAc (600 mL), and the resulting slurry was stirred at rt for 3 h. The mixture was filtered, and the filter cake was dried by aspiration to afford the title compound as a brown solid.

Intermediate 17

5-Chloropyridazin-3-amine

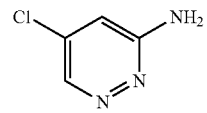

N-(5-Chloropyridazin-3-yl)-1,1-diphenylmethanimine (297 g, 84% w/w, 0.85 mol, Intermediate 16) was diluted with EtOAc (1.0 L) and water (700 mL). An aqueous HCl solution (300 mL, 5.0 N, 1.5 mol) was then added dropwise at 20° C., and the resulting mixture was stirred at 20° C. for 30 min. After this time, the mixture was filtered, and the filter pad was washed with 1 N aqueous HCl (100 mL). The layers of the combined filtrate and wash were separated, the aqueous layer was washed three times with EtOAc. The aqueous layers were combined, and the pH was adjusted to pH 8-9 using a 5 N aqueous NaOH solution. After stirring at 10-20° C. for 1 h, the precipitate was collected by filtration and washed with water to give crude title compound as a brown solid (134 g, 71% w/w). This material was combined with another batch obtained in a similar way (36.2 g, 56% w/w). The combined batches were diluted with aqueous HCl (2.0 L, 1.0 N, 2.0 mol) and stirred at rt for 30 min. The undissolved impurities were removed by filtration, and the filter pad was washed with water (100 mL). SiliaMetS® Thiol (20 g) was added to the combined filtrate and wash, and the resulting mixture was stirred at 40° C. for 2 h and then filtered. Two additional treatments with SiliaMetS® Thiol as described above were carried out. The pH of the final filtrate was adjusted to pH 9-10 using 5 N aqueous NaOH, and the resulting mixture was stirred at 10-20° C. for 1 h. The precipitate was isolated by filtration and then dried under vacuum to give the title compound as an off-white solid.

Intermediate 18

Methyl 2-((tert-butoxycarbonyl)amino)-2-(4,4-difluorocyclohexylidene)acetate

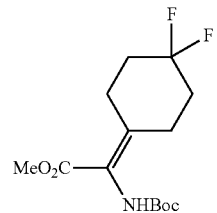 [SMILES: COC(=O)C(NC(=O)OC(C)(C)C)=C1CCC(F)(F)CC1]

A solution of 4,4-difluorocyclohexan-1-one (250 g, 1.86 mol) in DCM (500 mL) was added dropwise to a 0° C. (ice bath) stirring solution of methyl 2-((tert-butoxycarbonyl)amino)-2-(dimethoxyphosphoryl) acetate (582 g, 1.96 mol)

and DBU (289 g, 1.90 mol) in DCM (2.0 L) at a rate that maintained the internal temperature below 10° C. Then the reaction was allowed to warm to 20° C. and maintained at this temperature for 16 h. After this time, water (800 mL) was added, and the mixture was stirred for 30 min. The layers were separated, and the organic layer was washed three times with water and then concentrated. The residue was diluted with n-heptane (1 L), and the resulting slurry stirred and then filtered. The filter cake was dried under vacuum at 50° C. to give the title compound as an off-white solid.

Intermediate 19

Methyl 2-((tert-butoxycarbonyl)amino)-2-(4,4-difluorocyclohexyl)acetate

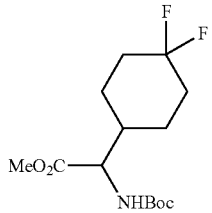 [SMILES: COC(=O)C(NC(=O)OC(C)(C)C)C1CCC(F)(F)CC1]

Methyl-2-((tert-butoxycarbonyl)amino)-2-(4,4-difluorocyclohexylidene)acetate (750.0 g, 2.46 mol, Intermediate 18) and Pd/C (75.0 g, 10% w/w, 71 mmol) were added to a reactor containing THF (6.0 L) under an atmosphere of nitrogen gas. The resulting mixture was hydrogenated using a balloon of $H_2$ at rt for 18 h. After this time, the reaction mixture was filtered, and the filter cake was rinsed with THF (1.5 L). The filtrate and rinse were combined and concentrated. The residue was diluted with n-heptane (3.75 L), and the resulting slurry was stirred and then filtered. The filter cake was dried under vacuum at 50° C. to give the title compound as an off-white solid.

Intermediate 20

Tert-Butyl (1-(4,4-difluorocyclohexyl)-3-(dimethyl (oxo)-$\lambda^6$-sulfanylidene)-2-oxopropyl) carbamate

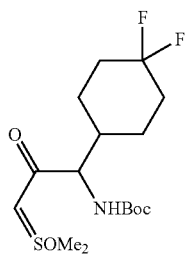

A suspension of trimethylsulfoxonium chloride (552 g, 4.29 mol) and potassium tert-butoxide (386 g, 3.44 mol) in THF (2.64 L) was stirred at 10-20° C. for 2 h. After this time, a solution of methyl 2-((tert-butoxycarbonyl)amino)-2-(4,4-difluorocyclohexyl)acetate (660 g, 2.15 mol, Intermediate 19) in THF (2.64 L) was added dropwise at a rate that maintained the internal temperature below 20° C. After the addition was complete, the resulting mixture was stirred at 10-20° C. for 48 h. After this time, a saturated aqueous NH$_4$Cl solution (1.32 L) was added dropwise. The resulting mixture was diluted with water (1.32 L) and stirred for 30 min. The mixture was then partially concentrated to remove THF, and the precipitate was isolated by filtration. The filter cake was suspended in water (1 L) and stirred for 2 h. The mixture was filtered, and the filter cake was dried under vacuum at 50° C. to give the title compound as an off-white solid.

Intermediate 21

Tert-Butyl N—[(S)-(7-chloroimidazo[1,2-b] pyridazin-2-yl)-(4,4-difluorocyclohexyl)methyl] carbamate

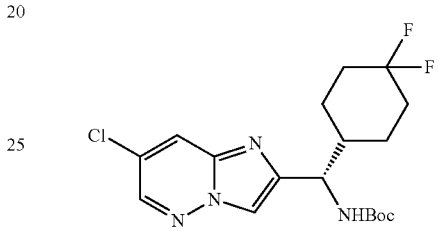

A mixture of 5-chloropyridazin-3-amine (15.0 g, 116 mmol, Intermediate 17), tert-butyl (1-(4,4-difluorocyclohexyl)-3-(dimethyl(oxo)-$\lambda^6$-sulfaneylidene)-2-oxopropyl) carbamate (46.8 g, 127 mmol, Intermediate 20), K$_3$PO$_4$ (1.23 g, 5.80 mmol), and 4 Å molecular sieves (3.0 g) in toluene (500 mL) was stirred at rt for 30 min. Then [Ir(cod)Cl]$_2$ (1.56 g, 2.32 mmol) was added under a nitrogen atmosphere, and the resulting mixture was heated to 95° C. and stirred at this temperature for 16 h. After this time, the reaction mixture was allowed to cool to 30° C. and then filtered. The filter pad was washed with EtOAc and then the combined filtrate and wash was concentrated. The residue was purified by silica gel chromatography (5:1 petroleum ether/EtOAc) to give a light-yellow solid. This solid was purified by SFC on a chiral stationary phase (Daicel CHIRALPAK® AS-H, 60:40 2 mM NH$_3$ in MeOH solution/CO$_2$) to give the S enantiomer as the second-eluting isomer. The desired fractions were concentrated, diluted with n-heptane (2.5 volumes), and stirred at rt for 1 h. The product was isolated by filtration and then dried under vacuum to give the title compound as a colorless solid.

Intermediate 21 Alternate Synthesis tert-Butyl (S)-(1-(4,4-difluorocyclohexyl)-3-iodo-2-oxopropyl)carbamate (500 mg, 1.98 mmol, Intermediate 15), 5-chloropyridazin-3-amine (171 mg, 1.32 mmol), NaHCO$_3$ (302 mg, 3.60 mmol), and t-BuOH (20 mL) were added to a 50 L round-bottomed flask. The resultant mixture was stirred at 135° C. for 20 h. After that time, the reaction was cooled to rt, then triturated with EtOAc (50 mL), filtered, and the filtrate concentrated to dryness under reduced pressure to afford the crude title product, which was purified by silica gel chromatography (10-100% petroleum ether: ethyl acetate) to afford the title compound as a white solid.

Intermediate 22

Tert-Butyl (S)-((7-chloroimidazo[1,2-b]pyridazin-2-yl)(cyclohexyl)methyl)carbamate

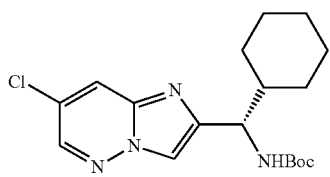 [SMILES: CC(C)(C)OC(=O)N[C@H](c1cn2ncc(Cl)cc2n1)C1CCCCC1]

5-Chloropyridazin-3-amine (1.5 g, 12 mmol, Intermediate 17) was added to a solution of tert-butyl (S)-(1-cyclohexyl-3-iodo-2-oxopropyl)carbamate (13.2 g, 34.6 mmol, Intermediate 6), and NaHCO$_3$ (3.89 g, 46.3 mmol) in t-BuOH (30 mL). The mixture was then stirred at 130° C. for 48 h. After this time, the mixture was allowed to cool to rt and then filtered through a pad of Celite®. The pad was rinsed with EtOAc, and the rinse was combined with the filtrate and diluted with water (50 mL). The layers were separated, and the aqueous layer was extracted three times with EtOAc. The organic extracts were combined, washed with brine, dried over anhydrous Na$_2$SO$_4$, filtered, and concentrated. The residue was purified by silica gel chromatography (1:0 to 4:1 petroleum ether/EtOAc) to afford the title compound as a brown oil.

Intermediate 23

Tert-Butyl (S)-((7-cyanoimidazo[1,2-b]pyridazin-2-yl)(cyclohexyl)methyl)carbamate

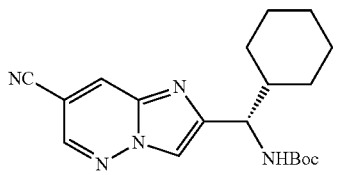 [SMILES: CC(C)(C)OC(=O)N[C@H](c1cn2ncc(C#N)cc2n1)C1CCCCC1]

A mixture of tert-butyl (S)-((7-chloroimidazo[1,2-b]pyridazin-2-yl)(cyclohexyl)methyl) carbamate (800 mg, 2.19 mmol, Intermediate 22), Zn(CN)$_2$ (644 mg, 5.48 mmol), and zinc powder (29 mg, 0.44 mmol) in DMA (8.0 mL) was sparged with argon for 5 min, and then Pd$_2$(dba)$_3$ (405 mg, 0.442 mmol) and XPhos (420 mg, 0.881 mmol) were added. The mixture was sparged with argon for another 5 min. The mixture was then stirred at 120° C. under microwave irradiation for 2 h. After this time, the mixture was allowed to cool to rt and then filtered through a pad of Celite®. The pad was rinsed with EtOAc, and the rinse was combined with the filtrate and diluted with water (30 mL). The layers were separated, and the aqueous layer was extracted three times with EtOAc. The organic extracts were combined, dried over anhydrous Na$_2$SO$_4$, filtered, and concentrated. The residue was purified by silica gel chromatography (2:1 petroleum ether/EtOAc) to afford the title compound as a brown oil.

Intermediate 24

(S)-2-(Amino(cyclohexyl)methyl)imidazo[1,2-b]pyridazine-7-carbonitrile Hydrochloride

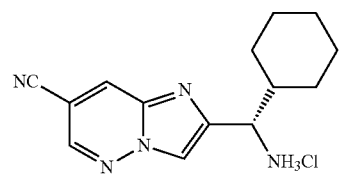

A solution of HCl (5.5 mL, 4.0 M in EtOAc, 22 mmol) was added to a 0° C. solution of tert-butyl (S)-((7-cyanoimidazo[1,2-b]pyridazin-2-yl)(cyclohexyl)methyl)carbamate (500 mg, 1.41 mmol, Intermediate 23) and EtOAc (5 mL), and the resulting mixture was stirred for 4 h at 0° C. The mixture was then concentrated to afford the title compound as a colorless solid.

Intermediate 25

(S)—N-((7-Cyanoimidazo[1,2-b]pyridazin-2-yl)(cyclohexyl)methyl)benzamide

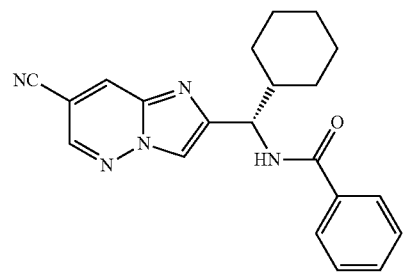 [SMILES: N#Cc1cnn2cc([C@@H](NC(=O)c3ccccc3)C3CCCCC3)nc2c1]

Neat HATU (156 mg, 0.410 mmol) was added to a 0° C. mixture of (S)-2-(amino(cyclohexyl)methyl)imidazo[1,2-b]pyridazine-7-carbonitrile hydrochloride (100 mg, 0.343 mmol, Intermediate 24), benzoic acid (50 mg, 0.41 mmol), and DIPEA (0.20 mL, 1.1 mmol) in DCM (2.0 mL), and the resulting mixture was stirred at 0° C. for 2 h. The mixture was then poured into water (10 mL) and extracted three times with DCM. The organic extracts were combined, washed with brine, dried over anhydrous Na$_2$SO$_4$, filtered, and concentrated. The residue was purified by silica gel chromatography (1:0 to 3:1 DCM/EtOAc) to afford the title compound as a yellow oil.

Intermediate 26

(S)—N-((7-(Aminomethyl)imidazo[1,2-b]pyridazin-2-yl)(cyclohexyl)methyl)benzamide

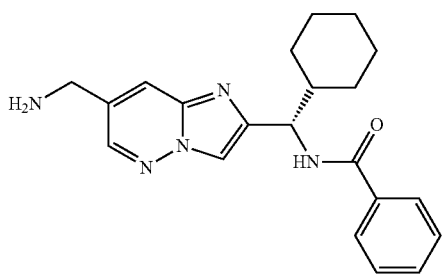 [SMILES: NCc1cnn2cc([C@@H](NC(=O)c3ccccc3)C3CCCCC3)nc2c1]

Raney®-Nickel (193 mg, slurry in water) was added to a mixture of (S)—N-((7-cyanoimidazo[1,2-b]pyridazin-2-yl)(cyclohexyl)methyl)benzamide (191 mg, 0.531 mmol, Intermediate 25) and aqueous NH$_4$OH (1.0 mL, 28% w/w ammonia, 15 mmol) in EtOH (10 mL). The reaction mixture was stirred under H$_2$ (15 psi) at rt for 2 h. After this time, the mixture was filtered through a pad of Celite®, and the pad was washed with EtOH. The filtrate and wash were combined and then concentrated to afford the title compound as a brown oil.

Intermediate 27

Tert-Butyl (trans-2,3)-2-(((2-((S)-benzamido(cyclohexyl)methyl)imidazo[1,2-b]pyridazin-7-yl)methyl)carbamoyl)-3-(trifluoromethyl)piperidine-1-carboxylate

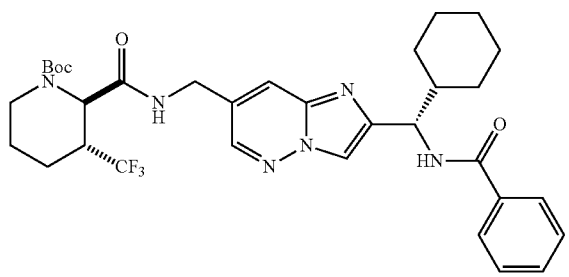

Neat HATU (399 mg, 1.05 mmol) was added to a solution of (S)—N-((7-(aminomethyl)imidazo[1,2-b]pyridazin-2-yl)(cyclohexyl)methyl)benzamide (350 mg, 0.963 mmol, Intermediate 26), (trans-2,3)-1-(tert-butoxycarbonyl)-3-(trifluoromethyl)piperidine-2-carboxylic acid (273 mg, 0.918 mmol, Intermediate 3) and DIPEA (0.47 mL, 2.7 mmol) in DCM (5 mL) at 0° C., and the resulting mixture was stirred at 0° C. for 2 h. The mixture was poured into water (30 mL) and then extracted three times with DCM. The organic extracts were combined, washed with brine, dried over anhydrous Na$_2$SO$_4$, filtered, and concentrated. The residue was purified by silica gel chromatography (1:0 to 1:2 petroleum ether/EtOAc) to afford the title compound, a diastereomeric mixture, as a yellow solid.

Intermediate 28

Tert-Butyl (trans-2R*,3R*)-2-(((2-((S)-benzamido(cyclohexyl)methyl)imidazo[1,2-b]pyridazin-7-yl)methyl)carbamoyl)-3-(trifluoromethyl)piperidine-1-carboxylate

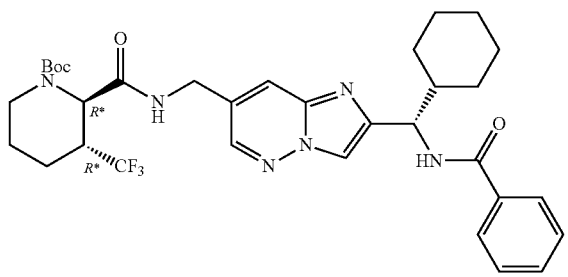 [SMILES: CC(C)(C)OC(=O)N1CCC[C@@H](C(F)(F)F)[C@@H]1C(=O)NCc1cnn2cc([C@@H](NC(=O)c3ccccc3)C3CCCCC3)nc2c1]

Intermediate 29

Tert-Butyl (trans-2S*,3S*)-2-(((2-((S)-benzamido(cyclohexyl)methyl)imidazo[1,2-b]pyridazin-7-yl)methyl)carbamoyl)-3-(trifluoromethyl)piperidine-1-carboxylate

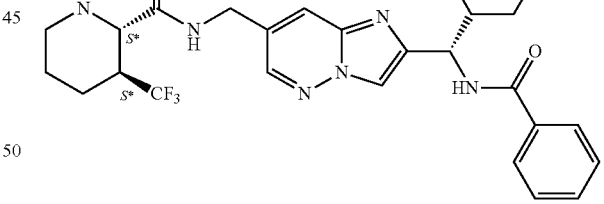

tert-Butyl (trans-2,3)-2-(((2-((S)-benzamido(cyclohexyl)methyl)imidazo[1,2-b]pyridazin-7-yl)methyl)carbamoyl)-3-(trifluoromethyl)piperidine-1-carboxylate (Intermediate 27) was purified by SFC using a chiral stationary phase (Daicel CHIRALPAK® IC, 45:55 EtOH (containing 0.1% (v/v) of 25% aqueous NH$_3$/CO$_2$) to give a pair of diastereomers. The first-eluting isomer was Intermediate 28, and the second-eluting isomer was Intermediate 29.

Intermediate 30

Tert-Butyl (trans-2,3)-2-(((2-((S)-cyclohexyl(1-methyl-1H-pyrazole-5-carboxamido)methyl) imidazo[1,2-b]pyridazin-7-yl)methyl)carbamoyl)-3-(trifluoromethyl)piperidine-1-carboxylate

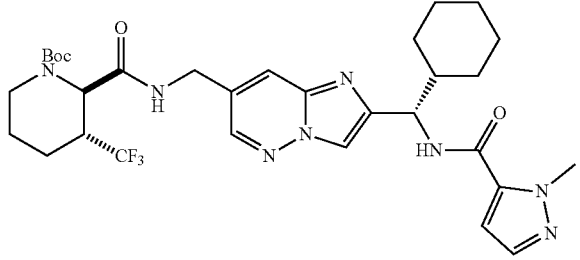

The title compound was prepared as described for the synthesis of Intermediate 27, using 1-methyl-1H-pyrazole-5-carboxylic acid in place of benzoic acid to afford the title compound as a brown solid.

Intermediate 31

Tert-Butyl (trans-2R*,3R*)-2-(((2-((S)-cyclohexyl(1-methyl-1H-pyrazole-5-carboxamido)methyl) imidazo[1,2-b]pyridazin-7-yl)methyl)carbamoyl)-3-(trifluoromethyl)piperidine-1-carboxylate

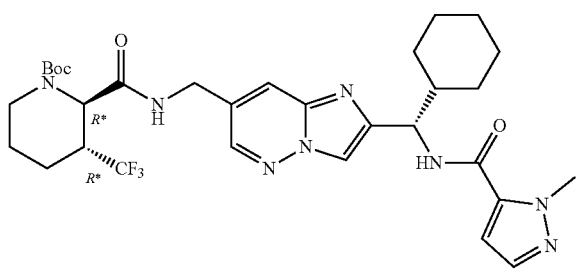 [SMILES: Cn1nccc1C(=O)N[C@H](c1cn2ncc(CNC(=O)[C@H]3[C@H](C(F)(F)F)CCCN3C(=O)OC(C)(C)C)cc2n1)C1CCCCC1]

tert-Butyl (trans-2,3)-2-(((2-((S)-cyclohexyl(1-methyl-1H-pyrazole-5-carboxamido)methyl) imidazo[1,2-b]pyridazin-7-yl)methyl)carbamoyl)-3-(trifluoromethyl)piperidine-1-carboxylate (Intermediate 30) was purified by SFC using a chiral stationary phase (Daicel CHIRALPAK® IC, 45:55 i-PrOH (containing 0.1% (v/v) of 25% aqueous $NH_3$)/$CO_2$) to give the title compound as the first-eluting isomer.

Intermediate 32

(S)-(7-Chloroimidazo[1,2-b]pyridazin-2-yl)(4,4-difluorocyclohexyl)methanamine

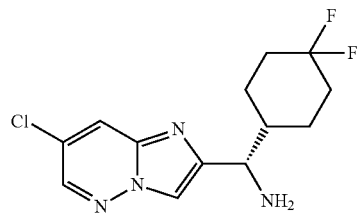 [SMILES: N[C@H](c1cn2ncc(Cl)cc2n1)C1CCC(F)(F)CC1]

Trifluoroacetic acid (8.0 mL, 100 mmol) was added to tert-butyl N—[(S)-(7-chloroimidazo[1,2-b]pyridazin-2-yl)-(4,4-difluorocyclohexyl)methyl]carbamate (2.00 g, 4.99 mmol, Intermediate 21), and the mixture was stirred at rt for 10 min. After this time, the resulting solution was concentrated and then diluted with a saturated aqueous $NaHCO_3$ solution and EtOAc. The layers were mixed and then separated, and the aqueous layer was extracted twice with EtOAc. The organic layers were combined, washed with brine, dried with anhydrous $MgSO_4$, filtered and concentrated to afford the title compound as an off-white solid.

Intermediate 33

(S)—N-((7-Chloroimidazo[1,2-b]pyridazin-2-yl)(4,4-difluorocyclohexyl)methyl)-1-(3,3,3-trifluoropropyl)-1H-pyrazole-4-carboxamide

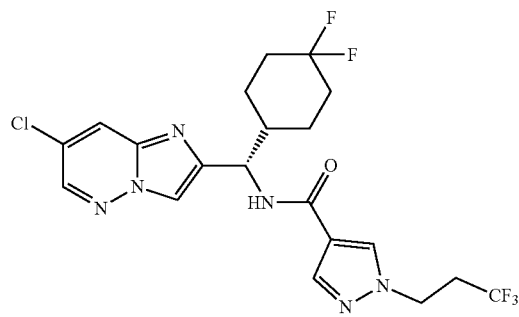 [SMILES: O=C(N[C@H](c1cn2ncc(Cl)cc2n1)C1CCC(F)(F)CC1)c1cnn(CCC(F)(F)F)c1]

Hunig's base (0.52 mL, 3.0 mmol) was added to a mixture of (S)-(7-chloroimidazo[1,2-b]pyridazin-2-yl)(4,4-difluorocyclohexyl)methanamine (750 mg, 2.49 mmol, Intermediate 32), 1-(3,3,3-trifluoropropyl)-1H-pyrazole-4-carboxylic acid (523 mg, 2.54 mmol) and HOBt (337 mg, 2.49 mmol) in MeCN (13 mL), and the suspension was stirred for 10 min. Then EDCI (478 mg, 2.49 mmol) was added, and the mixture was stirred at rt for 3 h. After this time, the suspension was filtered, and the filter cake was washed with MeCN/water (20 mL, 1:1 v/v) and then water (20 mL). The filtrate, which became heterogeneous as water was introduced, was combined with the filter cake and refiltered. The new cake was washed with water and then dried by aspiration. This cake was diluted with acetone (~10 mL) and then filtered. The filtrate was then concentrated to afford the title compound as an off-white solid.

Intermediate 34

(S)—N-((4,4-Difluorocyclohexyl)(7-vinylimidazo[1,2-b]pyridazin-2-yl)methyl)-1-(3,3,3-trifluoropropyl)-1H-pyrazole-4-carboxamide

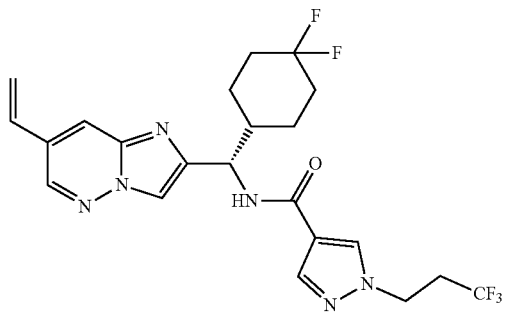 [SMILES: C=Cc1cnn2cc([C@@H](NC(=O)c3cnn(CCC(F)(F)F)c3)C3CCC(F)(F)CC3)nc2c1]

(S)—N-((7-Chloroimidazo[1,2-b]pyridazin-2-yl)(4,4-difluorocyclohexyl)methyl)-1-(3,3,3-trifluoropropyl)-1H-pyrazole-4-carboxamide (790 mg, 1.37 mmol, 85% w/w, Intermediate 33), potassium trifluoro(vinyl)borate (275 mg, 2.05 mmol), Pd(dtbpf)Cl₂ (180 mg, 0.27 mmol), and K₃PO₄ (870 mg, 4.1 mmol) were combined in a reactor, and the reactor was evacuated and backfilled with nitrogen three times. The mixture was then diluted with 1,4-dioxane and water (15 mL, 4:1 v/v), and the resulting mixture was sparged with argon for 15 min. The mixture was then stirred at 100° C. for 2.5 h. After this time, the reaction mixture was allowed to cool to rt and then was diluted with water and EtOAc. The layers were separated, and the aqueous layer was extracted twice with EtOAc. The organic layers were combined, washed with brine, dried with anhydrous MgSO₄, filtered and concentrated to afford a brown residue. This residue was purified by silica gel chromatography (50% to 100% EtOAc/hexanes, then 50% to 100% acetone/hexanes) to afford the title compound as a colorless solid.

Intermediate 35

(S)—N-((4,4-Difluorocyclohexyl)(7-formylimidazo[1,2-b]pyridazin-2-yl)methyl)-1-(3,3,3-trifluoropropyl)-1H-pyrazole-4-carboxamide

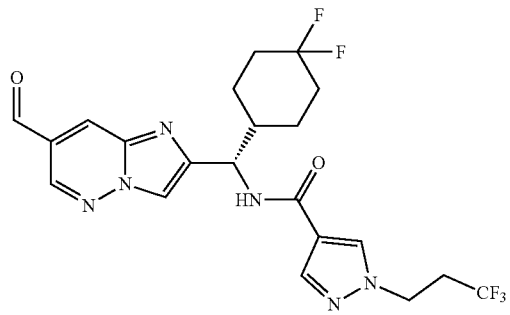 [SMILES: O=Cc1cnn2cc([C@@H](NC(=O)c3cnn(CCC(F)(F)F)c3)C3CCC(F)(F)CC3)nc2c1]

A solution of NaIO₄ (1.1 g, 5.2 mmol) in water (25 mL) was added to a solution of (S)—N-((4,4-difluorocyclohexyl)(7-vinylimidazo[1,2-b]pyridazin-2-yl)methyl)-1-(3,3,3-trifluoropropyl)-1H-pyrazole-4-carboxamide (500 mg, 1.04 mmol, Intermediate 34) in 1,4-dioxane (25 mL), and then K₂OsO₄·2H₂O (76 mg, 0.21 mmol) was added, and the resulting mixture was stirred at rt for 1.5 h. After this time, the resulting thick suspension was diluted with water and extracted three times with EtOAc. The organic layers were combined, washed with brine, dried with anhydrous MgSO₄, filtered and concentrated to give a brown residue. This residue was purified by silica gel chromatography (30% to 100% acetone/hexanes) to afford the title compound as a colorless solid.

Intermediate 36

N—((S)-(7-((E)-(((S)-tert-butylsulfinyl)imino)methyl)imidazo[1,2-b]pyridazin-2-yl)(4,4-difluorocyclohexyl)methyl)-1-(3,3,3-trifluoropropyl)-1H-pyrazole-4-carboxamide

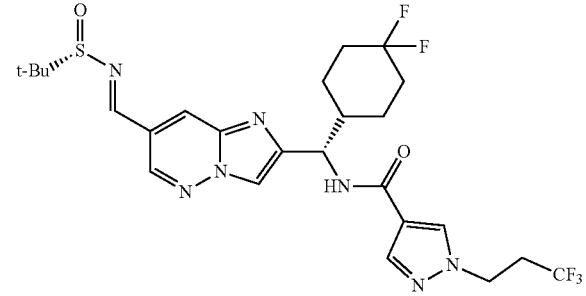 [SMILES: CC(C)(C)[S@](=O)/N=C/c1cnn2cc([C@@H](NC(=O)c3cnn(CCC(F)(F)F)c3)C3CCC(F)(F)CC3)nc2c1]

Copper(II) sulfate (311 mg, 1.95 mmol) and then PPTS (15 mg, 0.061 mmol) were added to a solution of (S)—N-((4,4-difluorocyclohexyl)(7-formylimidazo[1,2-b]pyridazin-2-yl)methyl)-1-(3,3,3-trifluoropropyl)-1H-pyrazole-4-carboxamide (310 mg, 0.61 mmol, Intermediate 35) and (S)-(−)-2-methyl-2-propanesulfinamide (77 mg, 0.64 mmol) in THF (2 mL), and the mixture was stirred at rt for 18 h. After this time, an additional portion of CuSO₄ (311 mg, 1.95 mmol) was added, and the mixture was stirred at 55° C. for 8 h and then at 45° C. for an additional 16 h. After this time, Celite® was added, and the mixture was filtered. The pad was washed with DCM, and the filtrate and wash were combined and then concentrated to give the title compound as a brown solid.

Intermediate 37

N-((1S)-(7-((((S)-tert-Butylsulfinyl)amino)(cyclopropyl)methyl)imidazo[1,2-b]pyridazin-2-yl)(4,4-difluorocyclohexyl)methyl)-1-(3,3,3-trifluoropropyl)-1H-pyrazole-4-carboxamide

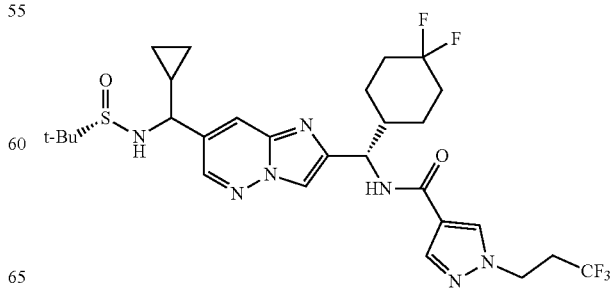

Intermediate 38

N-((1S)-(7-(Amino(cyclopropyl)methyl)imidazo[1,2-b]pyridazin-2-yl)(4,4-difluorocyclohexyl) methyl)-1-(3,3,3-trifluoropropyl)-1H-pyrazole-4-carboxamide A solution of cyclopropylmagnesium bromide (2.0 mL, 0.92 M in 2-MeTHF, 1.8 mmol) was added dropwise to a −78° C. stirring solution of N—((S)-(7-((((S)-tert-butylsulfinyl)imino) methyl)imidazo[1,2-b]pyridazin-2-yl)(4,4-difluorocyclohexyl)methyl)-1-(3,3,3-trifluoropropyl)-1H-pyrazole-4-carboxamide (360 mg, 0.61 mmol, Intermediate 36) in DCM (6.5 mL), and the resulting solution was allowed to slowly warm to 0° C. over 1 h. After this time, a saturated aqueous NH$_4$Cl solution and then water were added. The layers were mixed, and then separated. The aqueous layer was extracted twice with EtOAc. The organic layers were combined, washed with brine, dried with anhydrous MgSO$_4$, filtered, and concentrated to afford a brown foam. This foam was purified by silica gel chromatography (50% to 100% acetone/hexanes) to afford the title compound as a colorless film. $^1$H NMR analysis showed a 4:1 mixture of diastereomers.

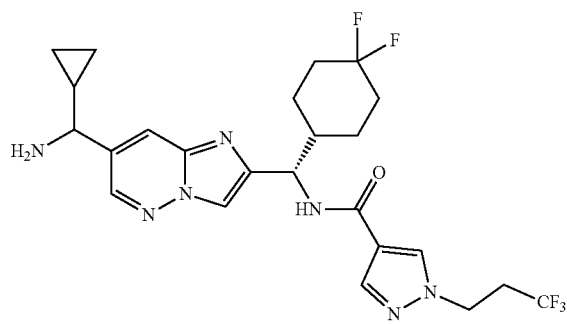 [SMILES: NC(c1cnn2cc([C@@H](NC(=O)c3cnn(CCC(F)(F)F)c3)C3CCC(F)(F)CC3)nc2c1)C1CC1]

A solution of HCl (0.32 mL, 4.0 M in dioxane, 1.3 mmol) was added to a solution of N-((1S)-(7-((((S)-tert-butylsulfinyl)amino)(cyclopropyl)methyl)imidazo[1,2-b]pyridazin-2-yl)(4,4-difluorocyclohexyl)methyl)-1-(3,3,3-trifluoropropyl)-1H-pyrazole-4-carboxamide (292 mg, 91% w/w, 0.420 mmol, Intermediate 37) in 1,4-dioxane (3.0 mL), and the mixture was stirred for 1.5 h. After this time, the resulting solution was concentrated. The residue was diluted with EtOAc and water. The layers were mixed and then separated, and the aqueous layer was washed with EtOAc. The organic layers were combined, extracted with water, and then discarded. The aqueous layers were combined, made basic with 15% aqueous NaOH, and extracted three times with EtOAc. The organic extracts were combined, dried with anhydrous MgSO$_4$, filtered, and concentrated to afford the title compound, a diastereomeric mixture, as an off-white solid.

Intermediate 39

N-((1S)-(7-(Cyclopropyl(4,4,4-trifluorobutanamido)methyl)imidazo[1,2-b]pyridazin-2-yl)(4,4-difluorocyclohexyl)methyl)-1-(3,3,3-trifluoropropyl)-1H-pyrazole-4-carboxamide

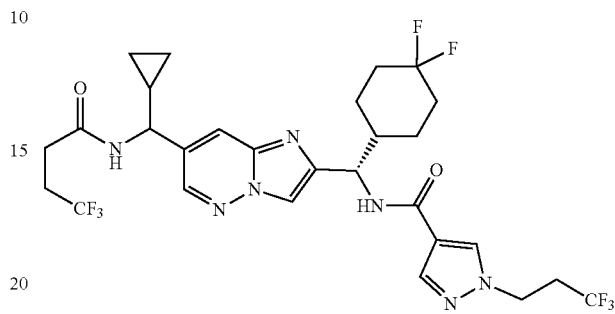

A mixture of N-((1S)-(7-(amino(cyclopropyl)methyl)imidazo[1,2-b]pyridazin-2-yl)(4,4-difluorocyclohexyl)methyl)-1-(3,3,3-trifluoropropyl)-1H-pyrazole-4-carboxamide (117 mg, 0.210 mmol, 96% w/w, Intermediate 38), 4,4,4-trifluorobutyric acid (34 mg, 0.24 mmol) and HOBt (29 mg, 0.21 mmol) was diluted with MeCN (1.2 mL). Hunig's base (0.044 mL, 0.26 mmol) and then EDCI (41 mg, 0.21 mmol) were added, and the resulting solution was maintained at rt for 30 min and then at 45° C. for 2 h. After this time, water and EtOAc were added. The layers were separated, and the aqueous layer was extracted twice with EtOAc. The organic layers were combined, washed with brine, dried with anhydrous MgSO$_4$, filtered, and concentrated. The residue was purified by silica gel chromatography (40% to 100% acetone/hexanes) to afford the title compound, a diastereomeric mixture, as a colorless film.

Intermediate 40

N-((1S)-(7-(Cyclopropyl(2-(3,3-difluorocyclobutyl)acetamido)methyl)imidazo[1,2-b]pyridazin-2-yl)(4,4-difluorocyclohexyl)methyl)-1-(3,3,3-trifluoropropyl)-1H-pyrazole-4-carboxamide

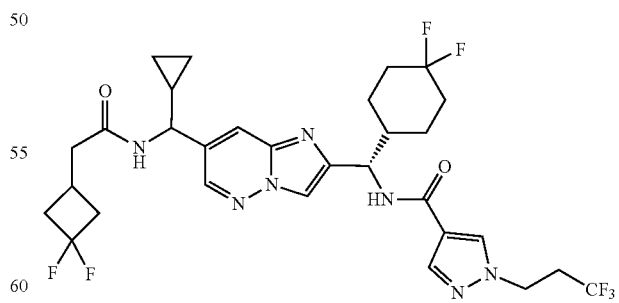

The title compound was prepared as described for the synthesis of Intermediate 39, using 2-(3,3-difluorocyclobutyl)acetic acid in place of 4,4,4-trifluorobutyric acid to afford the title compound, a diastereomeric mixture, as a colorless solid.

427

Intermediate 41

N-((1S)-(7-(Cyclopropyl(4,4,4-trifluoro-3-(trifluoromethyl)butanamido)methyl)imidazo[1,2-b]pyridazin-2-yl)(4,4-difluorocyclohexyl)methyl)-1-isopropyl-1H-pyrazole-5-carboxamide

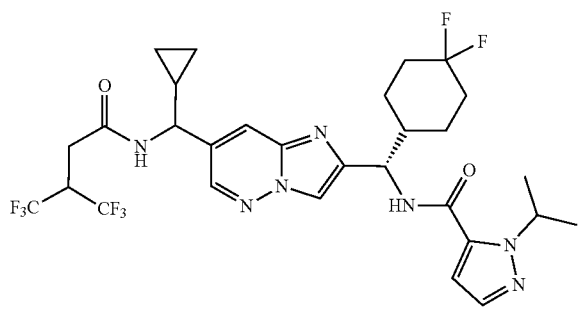 [SMILES: CC(C)n1nccc1C(=O)N[C@H](c1cn2ncc(C(NC(=O)CC(C(F)(F)F)C(F)(F)F)C3CC3)cc2n1)C1CCC(F)(F)CC1]

The title compound was prepared as described for the synthesis of Intermediate 39, using 1-isopropyl-1H-pyrazole-5-carboxylic acid in place of 1-(3,3,3-trifluoropropyl)-1H-pyrazole-4-carboxylic acid and 4,4,4-trifluoro-3-(trifluoromethyl)butanoic acid in place of 4,4,4-trifluorobutyric acid to afford the title compound, a diastereomeric mixture, as a colorless solid.

Intermediate 42

N-((1S)-(7-(Cyclopropyl(4,4,4-trifluorobutanamido)methyl)imidazo[1,2-b]pyridazin-2-yl)(4,4-difluorocyclohexyl)methyl)benzamide

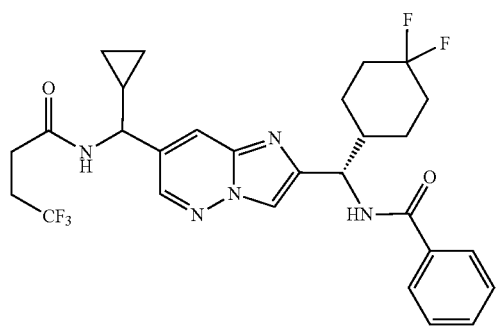 [SMILES: O=C(CCC(F)(F)F)NC(c1cnn2cc([C@@H](NC(=O)c3ccccc3)C3CCC(F)(F)CC3)nc2c1)C1CC1]

The title compound was prepared as described for the synthesis of Intermediate 39, using benzoic acid in place of 1-(3,3,3-trifluoropropyl)-1H-pyrazole-4-carboxylic acid to afford the title compound, a diastereomeric mixture, as a colorless solid.

428

Intermediate 43

N-((1S)-(7-(Cyclopropyl(4,4,4-trifluorobutanamido)methyl)imidazo[1,2-b]pyridazin-2-yl)(4,4-difluorocyclohexyl)methyl)-1-isopropyl-1H-pyrazole-5-carboxamide

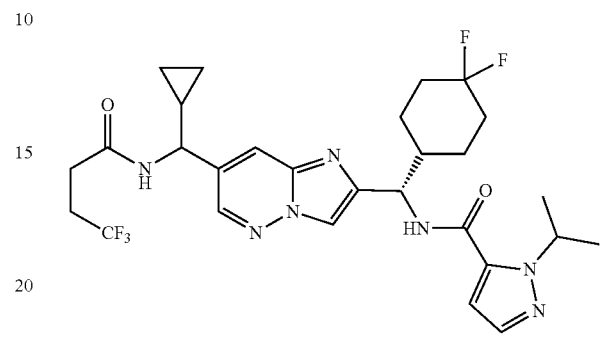

The title compound was prepared as described for the synthesis of Intermediate 58, using 1-isopropyl-1H-pyrazole-5-carboxylic acid in place of 1-(3,3,3-trifluoropropyl)-1H-pyrazole-4-carboxylic acid to afford the title compound, a diastereomeric mixture, as a colorless solid.

Intermediate 44

N-((1S)-(7-(Cyclopropyl(4,4,4-trifluoro-3-(trifluoromethyl)butanamido)methyl)imidazo[1,2-b]pyridazin-2-yl)(4,4-difluorocyclohexyl)methyl)benzamide

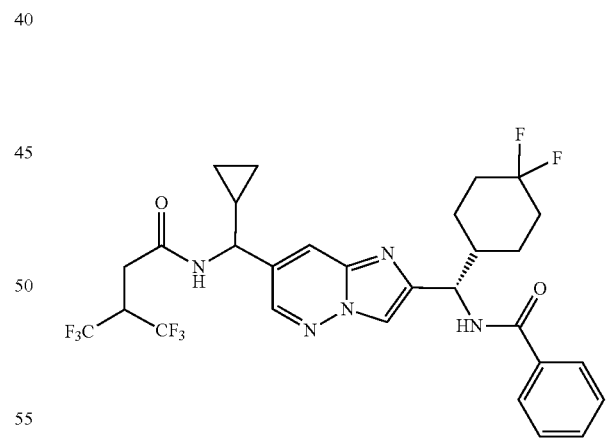

The title compound was prepared as described for the synthesis of Intermediate 39, using benzoic acid in place of 1-(3,3,3-trifluoropropyl)-1H-pyrazole-4-carboxylic acid and 4,4,4-trifluoro-3-(trifluoromethyl)butanoic acid in place of 4,4,4-trifluorobutyric acid to afford the title compound, a diastereomeric mixture, as a colorless solid.

Intermediate 45 tert-Butyl (S)-((4,4-difluorocyclohexyl)(7-vinylimidazo[1,2-b]pyridazin-2-yl)methyl)carbamate

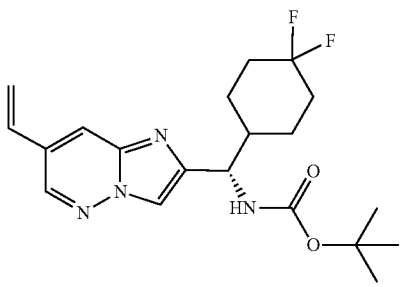 [SMILES: C=Cc1cnn2cc([C@@H](NC(=O)OC(C)(C)C)C3CCC(F)(F)CC3)nc2c1]

tert-Butyl N—[(S)-(7-chloroimidazo[1,2-b]pyridazin-2-yl)-(4,4-difluorocyclohexyl)methyl]carbamate (9.00 g, 22.5 mmol, Intermediate 21), potassium trifluoro(vinyl)borate (4.51 g, 33.7 mmol), and $K_3PO_4$ (14.3 g, 67.4 mmol) were added under a positive pressure of nitrogen gas to a reactor containing 1,4-dioxane and water (250 mL, 5:1 v/v, sparged with argon before use). The mixture was heated to reflux temperature (88° C.), and then a solution of RuPhos Pd G3 (470 mg, 0.56 mmol) in 1,4-dioxane (5 mL) was added, and the mixture was stirred at reflux temperature for 1.5 h. After this time, the mixture was allowed to cool to rt and then concentrated to remove most of the 1,4-dioxane. The residue was diluted with EtOAc and water, the layers were separated, and the aqueous layer was extracted twice with EtOAc. The organic layers were combined, washed with brine, dried with anhydrous $MgSO_4$, filtered and concentrated to afford the title compound as a brown foam.

Intermediate 46

Tert-Butyl (S)-((4,4-difluorocyclohexyl)(7-formylimidazo[1,2-b]pyridazin-2-yl)methyl)carbamate

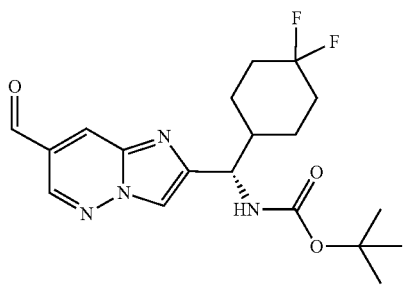 [SMILES: CC(C)(C)OC(=O)N[C@H](c1cn2ncc(C=O)cc2n1)C1CCC(F)(F)CC1]

A solution of $NaIO_4$ (24.0 g, 112 mmol) in water (540 mL) was added to a solution of tert-butyl (S)-((4,4-difluorocyclohexyl)(7-vinylimidazo[1,2-b]pyridazin-2-yl)methyl)carbamate (8.81 g, 22.5 mmol, Intermediate 45) in 1,4-dioxane (540 mL), and then $K_2OsO_4 \cdot 2H_2O$ (827 mg, 2.25 mmol) was added. The reaction immediately started to warm, so the reactor was placed in an ice bath for 15 min to maintain the temperature close to 30° C. After this time, the reaction mixture was stirred at rt for 1.75 h. After this time, the resulting thick suspension was filtered through Celite®, and the filter cake was washed with EtOAc. The filtrate and wash were combined, the layers were mixed and then separated, and the aqueous layer was extracted twice with EtOAc. The organic layers were combined, washed with a concentrated aqueous $Na_2S_2O_3$ solution and then washed with brine, dried with anhydrous $MgSO_4$, filtered and then concentrated to give a tan foam. This foam was purified by silica gel chromatography (20% to 50% acetone/hexanes) to afford the title compound as a pale-yellow foam.

Intermediate 47

Tert-Butyl ((S)-(7-((((S)-tert-butylsulfinyl)imino)methyl)imidazo[1,2-b]pyridazin-2-yl)(4,4-difluorocyclohexyl)methyl)carbamate

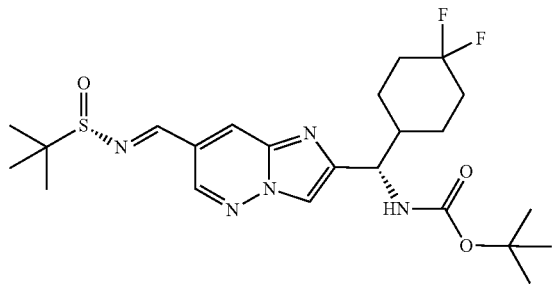 [SMILES: CC(C)(C)OC(=O)N[C@H](c1cn2ncc(/C=N/[S@@](=O)C(C)(C)C)cc2n1)C1CCC(F)(F)CC1]

A mixture of tert-butyl (S)-((4,4-difluorocyclohexyl)(7-formylimidazo[1,2-b]pyridazin-2-yl)methyl)carbamate (7.65 g, 19.4 mmol, Intermediate 46), (S)-(−)-2-methyl-2-propanesulfinamide (2.47 g, 20.4 mmol), $CuSO_4$ (9.91 g, 62.1 mmol) and PPTS (488 mg, 1.94 mmol) was diluted with THF (64 mL), and the mixture was stirred at 55° C. overnight. After this time, the mixture was diluted with DCM, Celite® was added, and the mixture was filtered. The filter pad was washed with DCM, and the filtrate and wash were combined and concentrated to give the title compound as an orange foam.

Intermediate 48

Tert-Butyl ((S)-(7-((R)-(((S)-tert-butylsulfinyl)amino)(cyclopropyl)methyl)imidazo[1,2-b]pyridazin-2-yl)(4,4-difluorocyclohexyl)methyl)carbamate

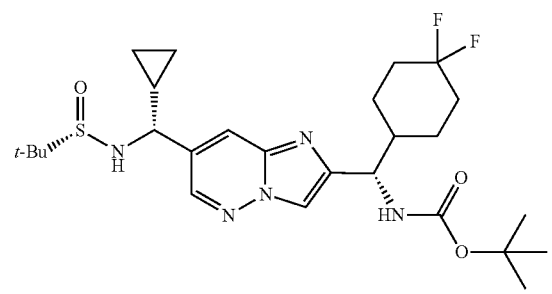 [SMILES: CC(C)(C)OC(=O)N[C@H](c1cn2ncc([C@H](N[S@@](=O)C(C)(C)C)C3CC3)cc2n1)C1CCC(F)(F)CC1]

A solution of tert-butyl ((S)-(7-((((S)-tert-butylsulfinyl)imino)methyl)imidazo[1,2-b]pyridazin-2-yl)(4,4-difluorocyclohexyl)methyl)carbamate (9.65 g, 19.4 mmol, Intermediate 47) in DCM (205 mL) was cooled to −78° C. A solution of cyclopropylmagnesium bromide in 2-MeTHF (51 mL, 0.88 M, 45 mmol) was then added at a rate that maintained the internal temperature below −60° C. When the addition was complete, the resulting solution was moved to an ice bath and allowed to slowly warm to 0° C. over 1 h. After this time, a saturated aqueous NH₄Cl solution was added. Enough water was then added to dissolve the precipitate that had formed upon adding the NH₄Cl solution, and the layers were mixed and then separated. The aqueous layer was extracted twice with EtOAc. The organic layers were combined, washed with brine, dried with anhydrous MgSO₄, filtered and then concentrated to afford a brown foam. This residue was purified twice by silica gel chromatography (30% to 70% acetone/hexanes) to afford the title compound as a colorless foam.

Intermediate 49

Tert-Butyl ((S)-(7-((R)-amino(cyclopropyl)methyl) imidazo[1,2-b]pyridazin-2-yl)(4,4-difluorocyclohexyl)methyl)carbamate

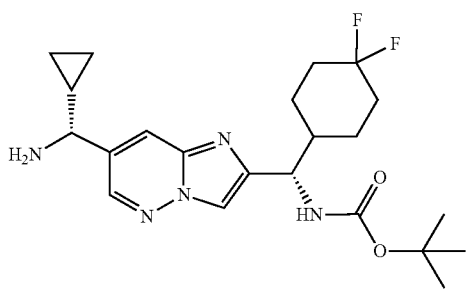 [SMILES: CC(C)(C)OC(=O)N[C@H](c1cn2ncc([C@H](N)C3CC3)cc2n1)C1CCC(F)(F)CC1]

A solution of HCl in 1,4-dioxane (6.7 mL, 4.0 M, 27 mmol) was added to a solution of tert-butyl ((S)-(7-((R)-(((S)-tert-butylsulfinyl)amino)(cyclopropyl)methyl)imidazo[1,2-b]pyridazin-2-yl)(4,4-difluorocyclohexyl)methyl)carbamate (6.64 g, 11.7 mmol, Intermediate 48) in EtOAc (58 mL), and the solution was stirred at rt for 20 h. After this time, additional HCl in 1,4-dioxane (0.29 mL, 4.0 M, 1.2 mmol) was added to the resulting suspension, and stirring was continued for 24 h. The suspension was then diluted with water (40 mL) and the layers were mixed and then separated. The organic layer was extracted twice with water (2×10 mL), and the aqueous layers were all combined and then washed with Et₂O (25 mL). The Et₂O wash was discarded. The aqueous layer was made basic with a 15% aqueous NaOH solution, and then extracted three times with EtOAc. The organic extracts were combined, dried with anhydrous MgSO₄, filtered and then concentrated to afford the title compound as a tan foam.

Intermediate 50

Tert-Butyl ((S)-(7-((R)-cyclopropyl(4,4,4-trifluorobutanamido)methyl)imidazo[1,2-b]pyridazin-2-yl) (4,4-difluorocyclohexyl)methyl)carbamate

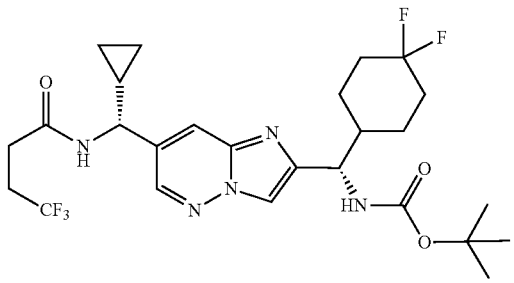 [SMILES: CC(C)(C)OC(=O)N[C@H](c1cn2ncc([C@H](NC(=O)CCC(F)(F)F)C3CC3)cc2n1)C1CCC(F)(F)CC1]

A flask was charged with a stir bar, tert-butyl ((S)-(7-((R)-amino(cyclopropyl)methyl)imidazo[1,2-b]pyridazin-2-yl)(4,4-difluorocyclohexyl)methyl) carbamate (500 mg, 1.11 mmol, Intermediate 49), 4,4,4-trifluorobutyric acid (171 mg, 1.17 mmol), HOBt (158 mg, 1.17 mmol), acetonitrile (50 mL), and Hunig's base (0.29 mL, 1.67 mmol) and the solution was stirred until homogenous (about 5 min). To the solution was added EDCI (224 mg, 1.17 mmol) and the mixture was stirred for 30 min. The reaction was heated to 45° C. and stirred for 1 h. The reaction was cooled to rt and quenched by the addition of water and ethyl acetate. The layers were separated, and the aqueous phase was further extracted with ethyl acetate (3×10 mL). The combined organics were washed with brine, dried over anhydrous MgSO₄, filtered and concentrated to yield the title compound as a white solid.

Intermediate 51

N—((R)-(2-((S)-Amino(4,4-difluorocyclohexyl) methyl)imidazo[1,2-b]pyridazin-7-yl) (cyclopropyl) methyl)-4,4,4-trifluorobutanamide

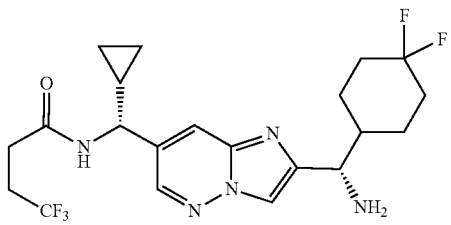 [SMILES: N[C@H](c1cn2ncc([C@H](NC(=O)CCC(F)(F)F)C3CC3)cc2n1)C1CCC(F)(F)CC1]

A vial was charged with a stir bar, tert-butyl ((S)-(7-((R)-cyclopropyl(4,4,4-trifluorobutanamido)methyl)imidazo[1,2-b]pyridazin-2-yl)(4,4-difluorocyclohexyl)methyl) carbamate (600 mg, 1.072 mmol, Intermediate 50) and TFA (3 mL, 39.2 mmol) then was stirred for 5 min. The reaction was condensed into a yellow oil and quenched by the careful addition of saturated aqueous NaHCO₃. The basic aqueous phase was extracted with ethyl acetate (2×15 mL). The combined organics were washed with brine, dried over anhydrous MgSO₄ filtered and condensed to yield the title compound as an off-white foam.

Intermediate 52

(S)—N-((7-Chloroimidazo[1,2-b]pyridazin-2-yl)(4,4-difluorocyclohexyl)methyl)-2-(3,3,3-trifluoropropyl)-2H-1,2,3-triazole-4-carboxamide

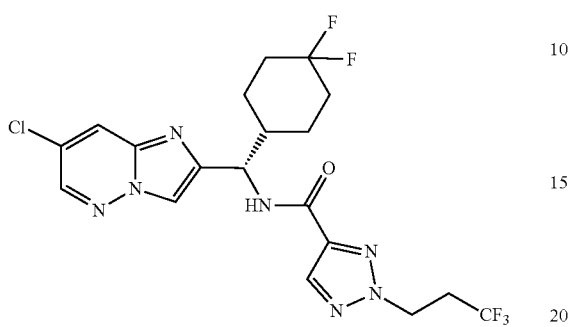

A flask was charged with a stir bar, (S)-(7-chloroimidazo[1,2-b]pyridazin-2-yl)(4,4-difluorocyclohexyl)methanamine (0.5 g, 1.48 mmol, Intermediate 32), 2-(3,3,3-trifluoropropyl)-2H-1,2,3-triazole-4-carboxylic acid (0.34 g, 1.63 mmol, Intermediate 76), HOBt (0.21 g, 1.56 mmol), acetonitrile (45 mL), and Hunig's base (1.02 mL, 0.75 g/mL, 5.93 mmol). The reaction was stirred for 5 min then EDCI (0.298 g, 1.56 mmol) was added to the solution. The reaction was stirred overnight. The reaction was partitioned between water and ethyl acetate. The layers were separated, and the aqueous phase was further extracted with ethyl acetate (3×3 mL). The combined organics were washed with brine, dried over anhydrous MgSO$_4$, filtered and condensed to afford the title compound as an off-white foam.

Intermediate 53

(S)—N-((4,4-Difluorocyclohexyl)(7-vinylimidazo[1,2-b]pyridazin-2-yl)methyl)-2-(3,3,3-trifluoropropyl)-2H-1,2,3-triazole-4-carboxamide

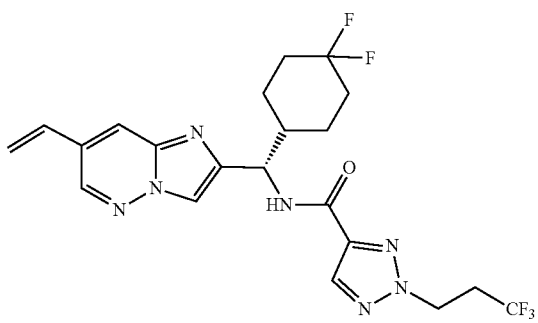 [SMILES: C=Cc1cnn2cc([C@@H](NC(=O)c3cnn(CCC(F)(F)F)n3)C3CCC(F)(F)CC3)nc2c1]

A microwave vial was charged with a stir bar, (S)—N-((7-chloroimidazo[1,2-b]pyridazin-2-yl)(4,4-difluorocyclohexyl)methyl)-2-(3,3,3-trifluoropropyl)-2H-1,2,3-triazole-4-carboxamide (460 mg, 0.935 mmol, Intermediate 52), potassium trifluoro(vinyl)borate (188 mg, 1.40 mmol), K$_3$PO$_4$ (596 mg, 2.81 mmol), and 1,4-dioxane and water (10 mL, 5:1 v/v). The reaction mixture was sparged with argon for 5 min and then Pd(dtbpf)Cl$_2$ (122 mg, 0.187 mmol) was added and the mixture was further sparged for 5 min with argon. The vial was sealed and heated to 100° C. with microwave irradiation and stirred for 2 h. After this time, the reaction was cooled to rt and diluted with water and ethyl acetate. The layers were separated, and the aqueous phase was extracted with ethyl acetate (3×5 mL). The combined organics were washed with brine, dried over anhydrous MgSO$_4$, filtered and condensed into a brown oil. The crude material was purified by silica gel chromatography (0-100% ethyl acetate/hexanes) to yield the title compound as a tan solid.

Intermediate 54

(S)—N-((4,4-Difluorocyclohexyl)(7-formylimidazo[1,2-b]pyridazin-2-yl)methyl)-2-(3,3,3-trifluoropropyl)-2H-1,2,3-triazole-4-carboxamide

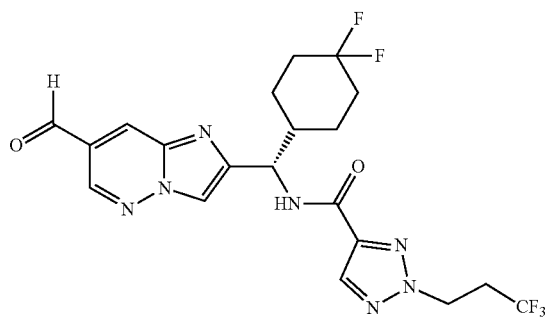 [SMILES: O=Cc1cnn2cc([C@@H](NC(=O)c3cnn(CCC(F)(F)F)n3)C3CCC(F)(F)CC3)nc2c1]

A flask was charged with a stir bar, (S)—N-((4,4-difluorocyclohexyl)(7-vinylimidazo[1,2-b]pyridazin-2-yl)methyl)-2-(3,3,3-trifluoropropyl)-2H-1,2,3-triazole-4-carboxamide (350 mg, 0.724 mmol, Intermediate 53), 1,4-dioxane and water (60 mL, 1:1 v/v) and K$_2$OsO$_4$·2H$_2$O (53.3 mg, 0.145 mmol). To the solution was added NaIO$_4$ (0.774 g, 3.62 mmol) and the reaction was stirred at rt for 1 h. After this time the resulting thick suspension was diluted with additional water and extracted with ethyl acetate (3×20 mL). The combined organics were washed with brine, dried over anhydrous MgSO$_4$ filtered and condensed into a brown residue. The crude material was purified by silica gel chromatography (10-100% ethyl acetate/hexanes) to afford the title compound as an off-white solid.

Intermediate 55

N—((S)-(7-((E)-(((S)-tert-Butylsulfinyl)imino)methyl)imidazo[1,2-b]pyridazin-2-yl)(4,4-difluorocyclohexyl)methyl)-2-(3,3,3-trifluoropropyl)-2H-1,2,3-triazole-4-carboxamide

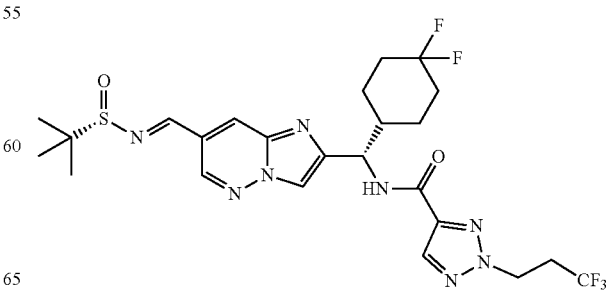

A vial was charged with a stir bar, N—((S)-(7-((E)-(((S)-tert-butylsulfinyl)imino)methyl)imidazo[1,2-b]pyridazin-2-yl)(4,4-difluorocyclohexyl)methyl)-2-(3,3,3-trifluoropropyl)-2H-1,2,3-triazole-4-carboxamide (280 mg, 0.57 mmol, Intermediate 54) (S)-2-methylpropane-2-sulfinamide (141 mg, 1.17 mmol), PPTS (39 mg, 0.15 mmol), copper(II) sulfate (956 mg, 5.99 mmol), and THF (2.5 mL). The vial was sealed and stirred overnight at 75° C. The mixture was cooled to rt and Celite® was added and the mixture was filtered with DCM washing. The filtrate and combined washings were condensed to afford the title compound as a glassy yellow solid.

Intermediate 56

N-((1S)-(7-((((S)-tert-Butylsulfinyl)amino)(cyclopropyl)methyl)imidazo[1,2-b]pyridazin-2-yl)(4,4-difluorocyclohexyl)methyl)-2-(3,3,3-trifluoropropyl)-2H-1,2,3-triazole-4-carboxamide

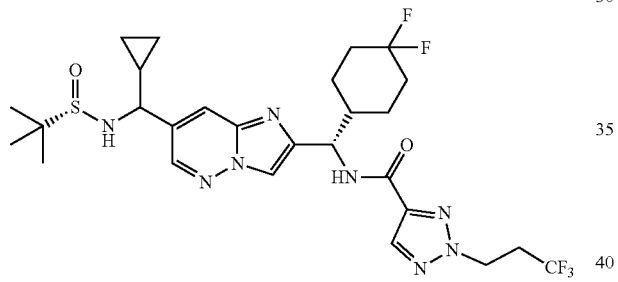

A flask was charged with N—((S)-(7-((E)-(((S)-tert-butylsulfinyl)imino)methyl)imidazo[1,2-b]pyridazin-2-yl)(4,4-difluorocyclohexyl)methyl)-2-(3,3,3-trifluoropropyl)-2H-1,2,3-triazole-4-carboxamide (180 mg, 0.306 mmol, Intermediate 55), and THF (3.25 mL). The flask was cooled to 0° C. and a solution of cyclopropylmagnesium bromide (0.950 mL, 1 M in 2-methyltetrahydrofuran, 0.948 mmol) was added dropwise. The reaction was allowed to warm to rt over 30 min. The reaction was poured over saturated aqueous NH₄Cl, and further diluted with water and ethyl acetate. The layers were separated, and the aqueous phase was extracted an additional time with ethyl acetate (10 mL). The combined organics were washed with brine, dried over anhydrous MgSO₄, filtered and condensed to afford the title compound as an off-white foam. ¹H NMR analysis showed a 3:1 mixture of diastereomers.

Intermediate 57

N-((1S)-(7-(Amino(cyclopropyl)methyl)imidazo[1,2-b]pyridazin-2-yl)(4,4-difluorocyclohexyl)methyl)-2-(3,3,3-trifluoropropyl)-2H-1,2,3-triazole-4-carboxamide

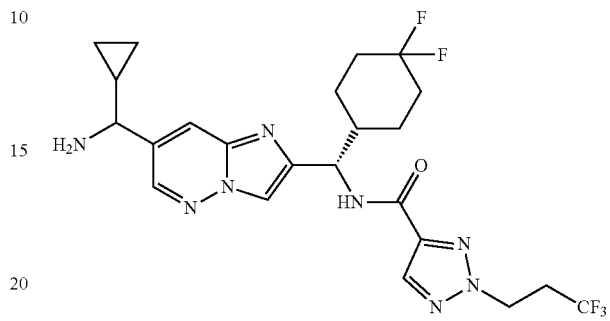

A flask was charged with a stir bar, N-((1S)-(7-((((S)-tert-butylsulfinyl)amino)(cyclopropyl)methyl)imidazo[1,2-b]pyridazin-2-yl)(4,4-difluorocyclohexyl) methyl)-2-(3,3,3-trifluoropropyl)-2H-1,2,3-triazole-4-carboxamide (175 mg, 0.27 mmol, Intermediate 56), 1,4-dioxane (2 mL), and HCl (0.21 mL, 4 M in dioxane). The reaction was stirred for 10 min, then condensed into an off-white residue. The crude was taken up in water and washed with hexanes (2×5 mL). The aqueous layer was made basic by the addition 1 N aqueous NaOH, then extracted with ethyl acetate (3×5 mL). The combined organics were washed with brine, dried over anhydrous MgSO₄, filtered and concentrated to afford the title compound, a diastereomeric mixture, as an off-white foam.

Intermediate 58

N-((1S)-(7-(Cyclopropyl(4,4,4-trifluorobutanamido)methyl)imidazo[1,2-b]pyridazin-2-yl)(4,4-difluorocyclohexyl)methyl)-2-(3,3,3-trifluoropropyl)-2H-1,2,3-triazole-4-carboxamide

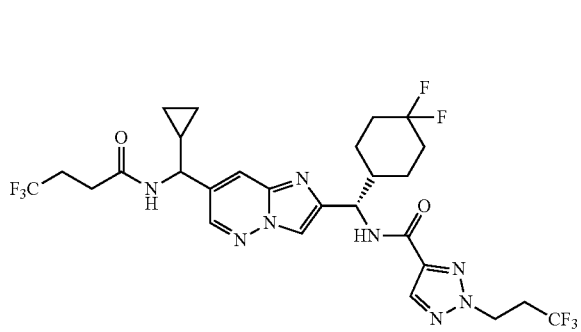

A vial was charged with a stir bar, 4,4,4-trifluorobutyric acid (40 mg, 0.27 mmol), HATU (105 mg, 0.27 mmol), and DMF (1 mL) then stirred for 5 min. To the stirred homogenous solution was added N-((1S)-(7-(amino(cyclopropyl)methyl)imidazo[1,2-b]pyridazin-2-yl)(4,4-difluorocyclohexyl)methyl)-2-(3,3,3-trifluoropropyl)-2H-1,2,3-triazole-4-carboxamide (110 mg, 0.21 mmol, Intermediate 57) and Hunig's base (0.072 mL, 0.42 mmol). The reaction was further stirred for 10 min then poured over water and diluted with ethyl acetate. The layers were separated, and the aqueous phase was further extracted with ethyl acetate (2×5 mL). The combined organics were washed with 10% aqueous lithium chloride then brine, dried over anhydrous $MgSO_4$, filtered and condensed into and glassy residue. The crude material was purified by silica gel chromatography, (0-100% (10% MeOH in ethyl acetate)/hexane) to yield a mixture of diastereomers as an off-white foam.

Intermediate 59

N-((1S)-(7-(Cyclopropyl(2-(3,3-difluorocyclobutyl) acetamido)methyl)imidazo[1,2-b]pyridazin-2-yl)(4, 4-difluorocyclohexyl)methyl)-1-(3,3,3-trifluoropropyl)-1H-pyrazole-3-carboxamide

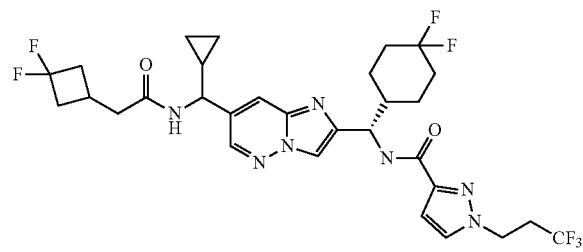 [SMILES: O=C(CC1CC(F)(F)C1)NC(c1cnn2cc([C@@H](NC(=O)c3ccn(CCC(F)(F)F)n3)C3CCC(F)(F)CC3)nc2c1)C1CC1]

The title compound was prepared as described for the synthesis of Intermediate 58, using 1-(3,3,3-trifluoropropyl)-1H-pyrazole-3-carboxylic acid in place of 2-(3,3,3-trifluoropropyl)-2H-1,2,3-triazole-4-carboxylic acid and 2-(3,3-difluorocyclobutyl)acetic acid in place of 4,4,4-trifluorobutanoic acid to afford the title compound, a diastereomeric mixture, as a glassy solid.

Intermediate 60

N-((1S)-(7-(Cyclopropyl(4,4,4-trifluorobutanamido) methyl)imidazo[1,2-b]pyridazin-2-yl)(4,4-difluorocyclohexyl)methyl)-1-(3,3,3-trifluoropropyl)-1H-pyrazole-3-carboxamide

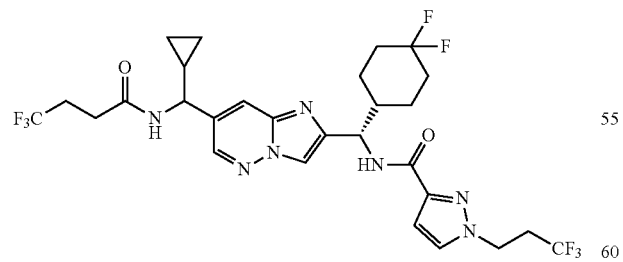

The title compound was prepared as described for the synthesis of Intermediate 59, using 4,4,4-trifluorobutanoic acid in place of 2-(3,3-difluorocyclobutyl)acetic acid to afford the title compound, a diastereomeric mixture, as a glassy solid.

Intermediate 61

N-((1S)-(7-(Cyclopropyl(2-(3,3-difluorocyclobutyl) acetamido)methyl)imidazo[1,2-b]pyridazin-2-yl)(4, 4-difluorocyclohexyl)methyl)-2-(3,3,3-trifluoropropyl)-2H-1,2,3-triazole-4-carboxamide

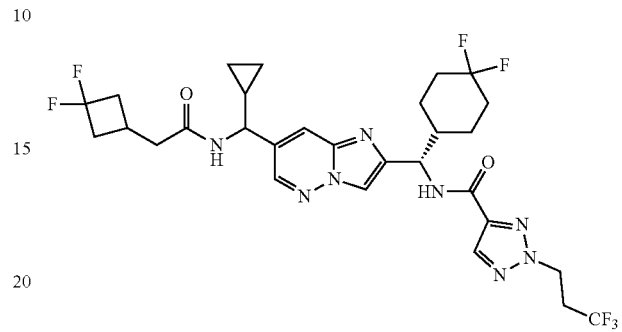

The title compound was prepared as described for the synthesis of Intermediate 58, using 2-(3,3-difluorocyclobutyl)acetic acid in place of 4,4,4-trifluorobutanoic acid to afford the title compound, a diastereomeric mixture, as a glassy solid.

Intermediate 62

N-((1S)-(7-(Cyclopropyl(4,4,4-trifluorobutanamido) methyl)imidazo[1,2-b]pyridazin-2-yl)(4,4-difluorocyclohexyl)methyl)-1-methyl-1H-pyrazole-5-carboxamide

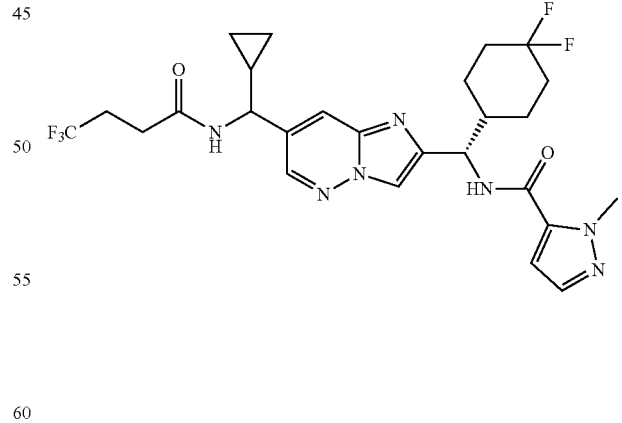

The title compound was prepared as described for the synthesis of Intermediate 58, using 1-methyl-1H-pyrazole-5-carboxylic acid in place of 2-(3,3,3-trifluoropropyl)-2H-1,2,3-triazole-4-carboxylic acid to afford the title compound, a mixture of diastereomers, as a glassy solid.

Intermediate 63

N-((1S)-(7-(Cyclopropyl(2-(3,3-difluorocyclobutyl)acetamido)methyl)imidazo[1,2-b]pyridazin-2-yl)(4,4-difluorocyclohexyl)methyl)-1-methyl-1H-pyrazole-5-carboxamide

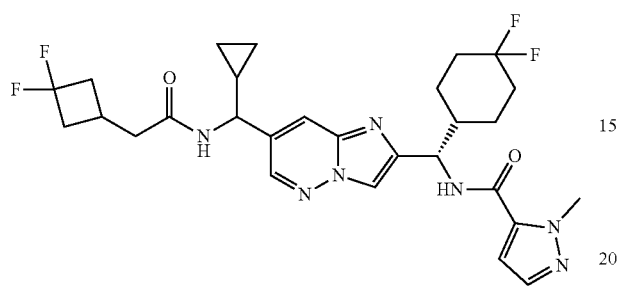

The title compound was prepared as described for the synthesis of Intermediate 62, using 2-(3,3-difluorocyclobutyl)acetic acid in place of 4,4,4-trifluorobutanoic acid to afford the title compound, a mixture of diastereomers, as a glassy solid.

Intermediate 64

N-((1S)-(7-(Cyclopropyl(4,4,4-trifluorobutanamido)methyl)imidazo[1,2-b]pyridazin-2-yl)(4,4-difluorocyclohexyl)methyl)-2-(cyclopropylmethyl)-2H-1,2,3-triazole-4-carboxamide

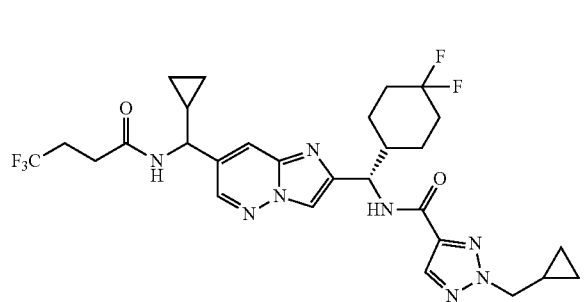 [SMILES: O=C(CCC(F)(F)F)NC(c1cnn2cc([C@@H](NC(=O)c3cnn(CC4CC4)n3)C3CCC(F)(F)CC3)nc2c1)C1CC1]

The title compound was prepared as described for the synthesis of Intermediate 58, using 2-(cyclopropylmethyl)-2H-1,2,3-triazole-4-carboxylic acid (Intermediate 106) in place of 2-(3,3,3-trifluoropropyl)-2H-1,2,3-triazole-4-carboxylic acid to afford the title compound, a mixture of diastereomers, as a glassy solid.

Intermediate 65

N-((1S)-(7-(Cyclopropyl(2-(3,3-difluorocyclobutyl)acetamido)methyl)imidazo[1,2-b]pyridazin-2-yl)(4,4-difluorocyclohexyl)methyl)-2-(cyclopropylmethyl)-2H-1,2,3-triazole-4-carboxamide

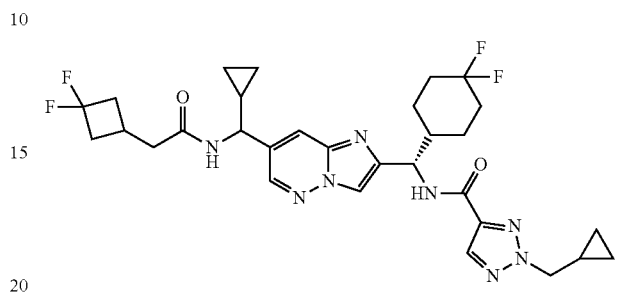

The title compound was prepared as described for the synthesis of Intermediate 64, using 2-(3,3-difluorocyclobutyl)acetic acid in place of 4,4,4-trifluorobutanoic acid to afford the title compound, a mixture of diastereomers, as a glassy solid.

Intermediate 66

N-((1S)-(7-(Cyclopropyl(4,4,4-trifluorobutanamido)methyl)imidazo[1,2-b]pyridazin-2-yl)(4,4-difluorocyclohexyl)methyl)-2-(2,2,2-trifluoroethyl)-2H-1,2,3-triazole-4-carboxamide

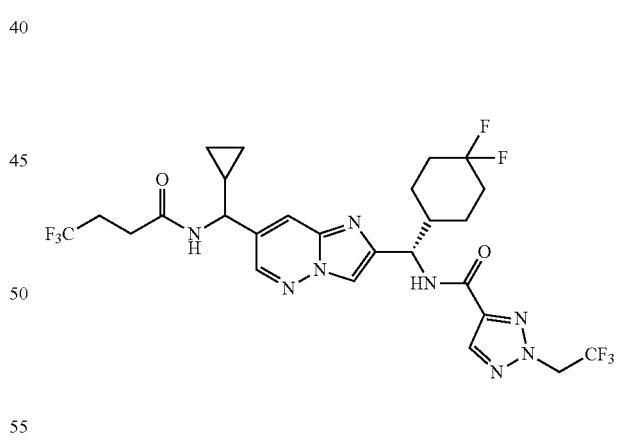

The title compound was prepared as described for the synthesis of Intermediate 58, using 2-(2,2,2-trifluoroethyl)-2H-1,2,3-triazole-4-carboxylic acid (Intermediate 104) in place of 2-(3,3,3-trifluoropropyl)-2H-1,2,3-triazole-4-carboxylic acid to afford the title compound, a mixture of diastereomers, as a glassy solid.

Intermediate 67

N-((1S)-(7-(Cyclopropyl(2-(3,3-difluorocyclobutyl)acetamido)methyl)imidazo[1,2-b]pyridazin-2-yl)(4,4-difluorocyclohexyl)methyl)-2-(2,2,2-trifluoroethyl)-2H-1,2,3-triazole-4-carboxamide

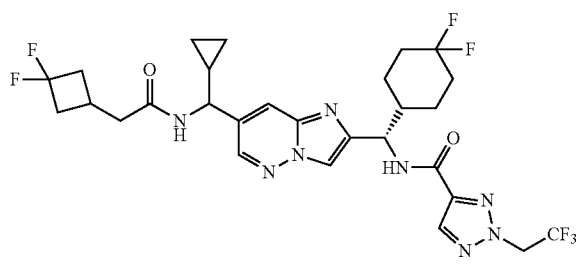 [SMILES: O=C(CC1CC(F)(F)C1)NC(c1cnn2cc([C@@H](NC(=O)c3cnn(CC(F)(F)F)n3)C3CCC(F)(F)CC3)nc2c1)C1CC1]

The title compound was prepared as described for the synthesis of Intermediate 66, using 2-(3,3-difluorocyclobutyl)acetic acid in place of 4,4,4-trifluorobutanoic acid to afford the title compound, a mixture of diastereomers, as a glassy solid.

Intermediate 68

N-((1S)-(7-(Cyclopropyl((R)-2-hydroxy-3,3-dimethylbutanamido)methyl)imidazo[1,2-b]pyridazin-2-yl)(4,4-difluorocyclohexyl)methyl)-2-(cyclopropylmethyl)-2H-1,2,3-triazole-4-carboxamide

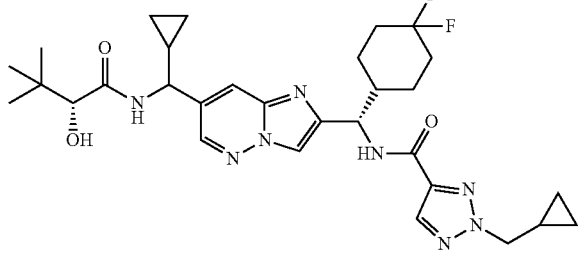

The title compound was prepared as described for the synthesis of Intermediate 64, using (R)-2-hydroxy-3,3-dimethylbutanoic acid in place of 4,4,4-trifluorobutanoic acid to afford the title compound, a mixture of diastereomers, as a glassy solid.

Intermediate 69

N-((1S)-(7-(Cyclopropyl(4,4,4-trifluoro-2-hydroxybutanamido)methyl)imidazo[1,2-b]pyridazin-2-yl)(4,4-difluorocyclohexyl)methyl)-2-(2,2,2-trifluoroethyl)-2H-1,2,3-triazole-4-carboxamide

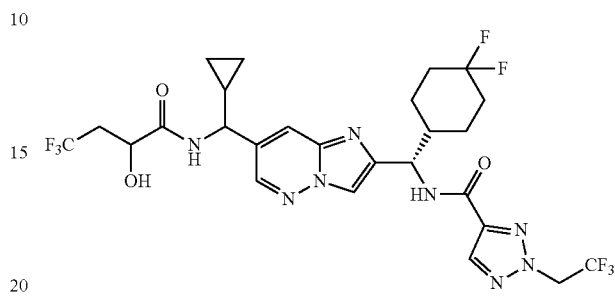

The title compound was prepared as described for the synthesis of Intermediate 66 using 4,4,4-trifluoro-2-hydroxybutanoic acid in place of 4,4,4-trifluorobutanoic acid to afford the title compound, a mixture of diastereomers, as a glassy solid.

Intermediate 70

(S)—N-((7-Cyanoimidazo[1,2-b]pyridazin-2-yl)(4,4-difluorocyclohexyl)methyl)-2-(3,3,3-trifluoropropyl)-2H-1,2,3-triazole-4-carboxamide

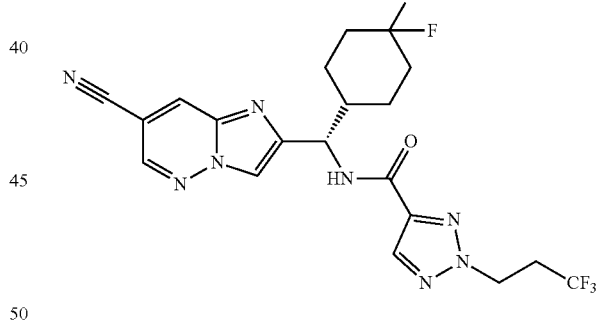

A microwave vial was charged with a stir bar, (S)—N-((7-chloroimidazo[1,2-b]pyridazin-2-yl)(4,4-difluorocyclohexyl)methyl)-2-(3,3,3-trifluoropropyl)-2H-1,2,3-triazole-4-carboxamide (1520 mg, 3.09 mmol, Intermediate 52), dicyanozinc (363 mg, 3.09 mmol), XPhos (76 mg, 0.155 mmol), XPhos Pd G1 (122 mg, 0.155 mmol), and NMP (15 mL). The vial was purged with argon for 5 min, sealed, warmed to 110° C. with microwave irradiation, and stirred for 2 h. The reaction was allowed to cool to rt before it was poured over water. The resulting suspension was stirred for 30 min then collected by filtration. The solids were dissolved in ethyl acetate, washed with brine, dried over anhydrous MgSO$_4$, filtered and condensed. The crude residue was purified by silica gel chromatography (0-100% (10% methanol in ethyl acetate)/hexanes) to afford the title compound as an off-white solid.

Intermediate 71

(S)—N-((7-(Aminomethyl)imidazo[1,2-b]pyridazin-2-yl)(4,4-difluorocyclohexyl)methyl)-2-(3,3,3-trifluoropropyl)-2H-1,2,3-triazole-4-carboxamide

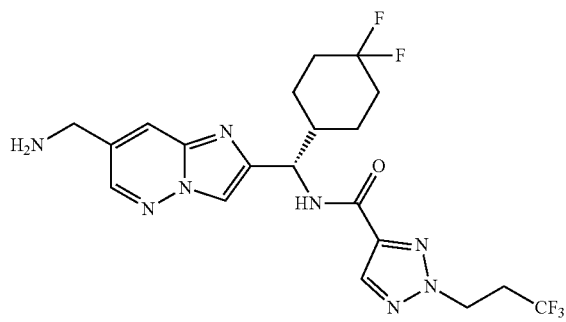 [SMILES: NCc1cnn2cc([C@@H](NC(=O)c3cnn(CCC(F)(F)F)n3)C3CCC(F)(F)CC3)nc2c1]

A flask was charged with a stir bar, (S)—N-((7-cyanoimidazo[1,2-b]pyridazin-2-yl)(4,4-difluorocyclohexyl)methyl)-2-(3,3,3-trifluoropropyl)-2H-1,2,3-triazole-4-carboxamide (400 mg, 0.83 mmol, Intermediate 70), Raney® Nickel (340 mg, 2.9 mmol), NH$_3$ (8 mL, 28% in water), and ethanol (24 mL). The flask was evacuated and backfilled with nitrogen three times before the flask was evacuated and placed under a hydrogen atmosphere. The reaction was stirred overnight at rt. The reaction was filtered through a pad of Celite® with MeOH washing. The combined filtrate and organic washes were condensed into a glassy brown solid. The material was purified by acidic HPLC (SunFire® Prep C18 OBD™ 5 μm, 30×250 mm column, 0-100% acetonitrile (0.05% TFA)/water (0.05% TFA)) to afford the title compound as an off white solid.

Intermediate 72

Methyl (4,4,4-trifluorobutanoyl)-D-leucinate

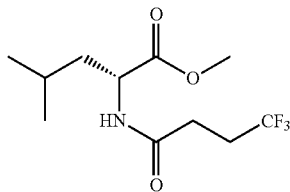 [SMILES: COC(=O)[C@@H](CC(C)C)NC(=O)CCC(F)(F)F]

A flask was charged with a stir bar, methyl D-leucinate (500 mg, 2.75 mmol), 4,4,4-trifluorobutyric acid (423 mg, 2.89 mmol), MeCN (50 mL), HOBt (390 mg, 2.89 mmol), and Hünig's base (1.2 mL, 6.88 mmol). The reaction was stirred for 10 min then EDCI (555 mg, 2.89 mmol) was added. The reaction was stirred at 45° C. for 2 h. The reaction was allowed to cool to rt, poured over water and extracted with ethyl acetate (3×15 mL). The combined organic extracts were washed with brine, dried over anhydrous MgSO$_4$ and condensed into a clear oil which was purified by silica gel chromatography (0-100% ethyl acetate/hexanes, ELSD detection, CAM staining for TLC visualization) to afford the title compound as a clear oil.

Intermediate 73

(4,4,4-Trifluorobutanoyl)-D-leucine

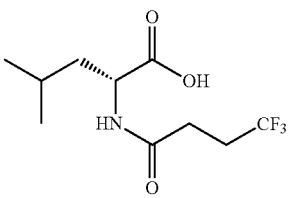 [SMILES: CC(C)C[C@@H](NC(=O)CCC(F)(F)F)C(=O)O]

A flask was charged with a stir bar, methyl (4,4,4-trifluorobutanoyl)-D-leucinate (650 mg, 2.40 mmol, Intermediate 72), ethanol (1 mL), water (1 mL), and lithium hydroxide (289 mg, 12.1 mmol). The reaction was stirred overnight at rt. The reaction was condensed to remove the ethanol and was diluted further with water. The reaction was made acidic (pH 5) by the addition of acetic acid. The aqueous phase was extracted with ethyl acetate (3×5 mL). The combined organic extracts were washed with brine, dried over anhydrous MgSO$_4$, filtered and condensed to afford the title compound as a white solid.

Intermediate 74

Methyl 2-(3,3,3-trifluoropropyl)-2H-1,2,3-triazole-4-carboxylate

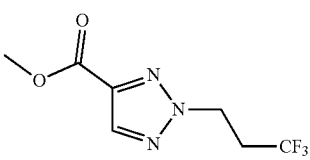

To a mixture of methyl 1H-1,2,3-triazole-4-carboxylate (5 g, 38.2 mmol), K$_2$CO$_3$ (5.27 g, 38.2 mmol) and DMF (49 mL) was added 3-bromo-1,1,1-trifluoropropane (4.07 mL, 38.2 mmol) and the resulting mixture was stirred at rt for 17 h. After that time the mixture was filtered through a pad of Celite®, rinsing with EtOAc and the filtrate concentrated under vacuum. The residue was partitioned between EtOAc (50 mL) and water (50 mL). The layers were separated and the aqueous further extracted with EtOAc (2×50 mL). The organic layers were combined, washed with brine (50 mL), dried over anhydrous Na$_2$SO$_4$, filtered and concentrated to dryness. The residue was purified by silica gel chromatography (0 to 75% EtOAc/hexanes; second eluting isomer) to provide the title compound as a white solid.

Intermediate 75

Methyl 1-(3,3,3-trifluoropropyl)-1H-1,2,3-triazole-5-carboxylate

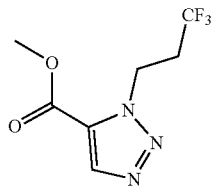

The title compound was prepared as described for the synthesis of Intermediate 74 and was the first eluting isomer isolated as a clear colorless oil.

Intermediate 76

2-(3,3,3-Trifluoropropyl)-2H-1,2,3-triazole-4-carboxylic acid

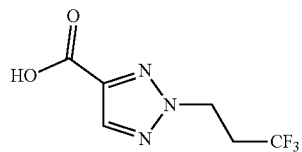

To a mixture of methyl 2-(3,3,3-trifluoropropyl)-2H-1,2,3-triazole-4-carboxylate (4.28 g, 19.2 mmol, Intermediate 74) in THF (58 mL) was added 2 M aqueous NaOH (58 mL, 115 mmol) and the mixture was stirred at rt for 15 h. After that time, the mixture was concentrated to remove the THF and then washed with EtOAc (2×50 mL). The aqueous layer was then acidified to pH 3 by the addition of 1 N aqueous HCl and extracted with 2-MeTHF (3×50 mL). The organic layers were combined, washed with brine (50 mL), dried over anhydrous $Na_2SO_4$, filtered and concentrated to dryness to provide the title compound as a white solid.

Intermediate 77

1-(3,3,3-Trifluoropropyl)-1H-1,2,3-triazole-5-carboxylic acid

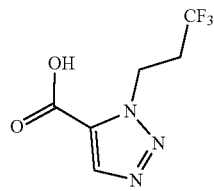

The title compound was prepared as described for the synthesis of Intermediate 76, using methyl 1-(3,3,3-trifluoropropyl)-1H-1,2,3-triazole-5-carboxylate (Intermediate 75) in place of methyl 2-(3,3,3-trifluoropropyl)-2H-1,2,3-triazole-4-carboxylate, to provide the title compound as a white solid.

Intermediate 78

Methyl 1-(3,3-difluoropropyl)-1H-1,2,4-triazole-5-carboxylate

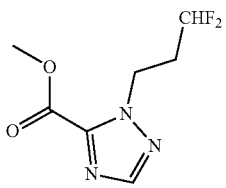

To a microwave vial was added methyl-1H-1,2,4-triazole-3-carboxylate (1.25 g, 9.64 mmol), 3,3-difluoropropan-1-ol (1.39 g, 14.5 mmol), $PPh_3$ (2.76 g, 10.5 mmol) and THF (16 mL). Then, DIAD (2 mL, 10.5 mmol) was added and the resulting mixture stirred at rt for 1 h. The reaction mixture was concentrated to dryness and the residue purified by silica gel chromatography (0 to 100% EtOAc/hexanes) to provide the title compound as a light yellow oil.

Intermediate 79

Methyl 1-(3-fluoropropyl)-1H-1,2,4-triazole-5-carboxylate

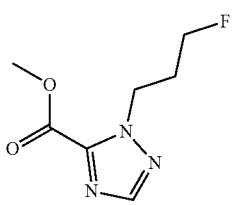

The title compound was prepared as described for the synthesis of Intermediate 78, using 3-fluoropropan-1-ol in place of 3,3-difluoropropan-1-ol, and cooling the mixture to 0° C. prior to addition of DIAD, to provide the title compound as a clear colorless oil.

Intermediate 80

1-(3-Fluoropropyl)-1H-1,2,4-triazole-5-carboxylic acid

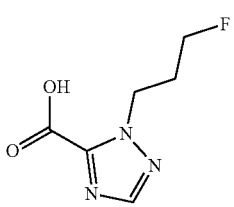 [SMILES: O=C(O)c1ncnn1CCCF]

A solution of methyl 1-(3-fluoropropyl)-1H-1,2,4-triazole-5-carboxylate (300 mg, 1.6 mmol, Intermediate 79) in THF (1.6 mL) was cooled to 0° C. and then 1 M aqueous LiOH (1.76 mL, 1.76 mmol) was added slowly. The resulting mixture was stirred at 0° C. for 1 h. After that time, the mixture was concentrated to remove THF and then washed with EtOAc (2×15 mL). The aqueous layer was acidified to pH 1.5 by the addition of 1 N aqueous HCl and a precipitate formed. The precipitate was collected by filtration, rinsed with water and dried under vacuum to provide the title compound as a white solid.

Intermediate 81

Methyl 1-(cyclopropylmethyl)-1H-1,2,3-triazole-5-carboxylate

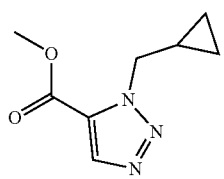

The title compound was prepared as described for the synthesis of Intermediate 74, using (bromomethyl)cyclopropane in place of 3-bromo-1,1,1-trifluoropropane to provide the title compound as a yellow oil.

Intermediate 82

1-(Cyclopropylmethyl)-1H-1,2,3-triazole-5-carboxylic acid

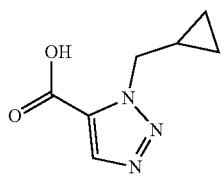 [SMILES: O=C(O)c1cnnn1CC1CC1]

The title compound was prepared as described for the synthesis of Intermediate 76, using methyl 1-(cyclopropylmethyl)-1H-1,2,3-triazole-5-carboxylate (Intermediate 81) in place of methyl 2-(3,3,3-trifluoropropyl)-2H-1,2,3-triazole-4-carboxylate to provide the title compound as a white solid.

Intermediate 83

Ethyl 1-(3,3-difluoropropyl)-1H-1,2,3-triazole-5-carboxylate

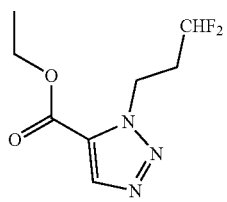

The title compound was prepared as described for the synthesis of Intermediate 78, using ethyl 1H-1,2,3-triazole-4-carboxylate in place of methyl-1H-1,2,4-triazole-3-carboxylate, cooling the mixture to 0° C. prior to addition of DIAD, and stirring at rt for 2.5 h instead of 1 h to provide the title compound as a yellow oil.

Intermediate 84

1-(3,3-Difluoropropyl)-1H-1,2,3-triazole-5-carboxylic Acid

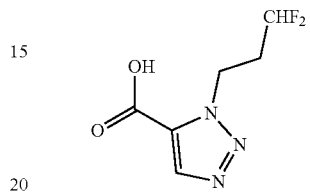

The title compound was prepared as described for the synthesis of Intermediate 76, using ethyl 1-(3,3-difluoropropyl)-1H-1,2,3-triazole-5-carboxylate (Intermediate 83) in place of methyl 2-(3,3,3-trifluoropropyl)-2H-1,2,3-triazole-4-carboxylate, and stirring at rt for 5 days instead of 15 h, to provide the title compound as a white solid.

Intermediate 85

(S)—N-((7-Chloroimidazo[1,2-b]pyridazin-2-yl)(4,4-difluorocyclohexyl)methyl)-5-methyl-1-(3,3,3-trifluoropropyl)-1H-pyrazole-4-carboxamide

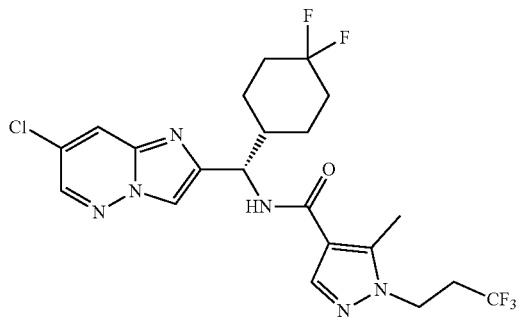 [SMILES: Cc1c(C(=O)N[C@H](c2cn3ncc(Cl)cc3n2)C2CCC(F)(F)CC2)cnn1CCC(F)(F)F]

A mixture of (S)-(7-chloroimidazo[1,2-b]pyridazin-2-yl)(4,4-difluorocyclohexyl)methanamine (75 mg, 0.25 mmol, Intermediate 32), 5-methyl-1-(3,3,3-trifluoropropyl)-1H-pyrazole-4-carboxylic acid (67 mg, 0.29 mmol), HOBt (35 mg, 0.26 mmol), DIPEA (52 µL, 0.3 mmol) and ACN (2.8 mL) was stirred until homogeneous. Then, EDCI (50 mg, 0.26 mmol) was added and the resulting mixture stirred at rt for 3.5 h. After this time, water was added to the mixture and the solution was extracted with EtOAc (2×15 mL). The organic layers were combined, washed with brine (20 mL), dried over anhydrous $Na_2SO_4$, filtered and concentrated to dryness to provide the title compound as a light brown solid.

Intermediate 86

(S)—N-((4,4-Difluorocyclohexyl)(7-vinylimidazo[1,2-b]pyridazin-2-yl)methyl)-5-methyl-1-(3,3,3-trifluoropropyl)-1H-pyrazole-4-carboxamide

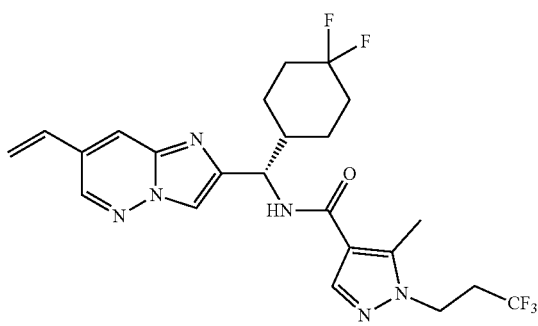 [SMILES: C=Cc1cnn2cc([C@@H](NC(=O)c3cnn(CCC(F)(F)F)c3C)C3CCC(F)(F)CC3)nc2c1]

To a microwave vial was added (S)—N-((7-chloroimidazo[1,2-b]pyridazin-2-yl)(4,4-difluorocyclohexyl)methyl)-5-methyl-1-(3,3,3-trifluoropropyl)-1H-pyrazole-4-carboxamide (985 mg, 1.95 mmol, Intermediate 85), potassium trifluoro(vinyl)borate (392 mg, 2.93 mmol), $K_3PO_4$ (1.24 g, 5.85 mmol) and 1,4-dioxane/water (5/1, 17 mL total) and the mixture sparged with nitrogen for 10 min. Then, Pd(dtbpf)$Cl_2$ (257 mg, 0.39 mmol) was added and the mixture sparged with nitrogen for 5 min. The vial was capped and stirred at 100° C. for 2 h. After that time, the mixture was cooled to rt, diluted with water and extracted with EtOAc (3×25 mL). The organic layers were combined, washed with brine (30 mL), dried over anhydrous $Na_2SO_4$, filtered and concentrated to dryness. The residue was purified by silica gel chromatography (0 to 100% EtOAc/hexanes) to provide the title compound as an amber oil.

Intermediate 87

(S)—N-((4,4-Difluorocyclohexyl)(7-formylimidazo[1,2-b]pyridazin-2-yl)methyl)-5-methyl-1-(3,3,3-trifluoropropyl)-1H-pyrazole-4-carboxamide

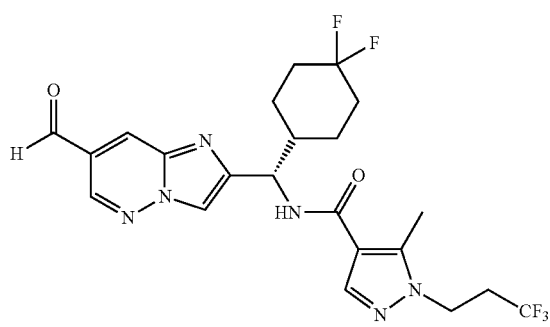 [SMILES: Cc1c(C(=O)N[C@H](c2cn3ncc(C=O)cc3n2)C2CCC(F)(F)CC2)cnn1CCC(F)(F)F]

To a mixture of (S)—N-((4,4-difluorocyclohexyl)(7-vinylimidazo[1,2-b]pyridazin-2-yl)methyl)-5-methyl-1-(3,3,3-trifluoropropyl)-1H-pyrazole-4-carboxamide (580 mg, 1.17 mmol, Intermediate 86) and $K_2OsO_4 \cdot 2H_2O$ (86 mg, 0.23 mmol) in 1,4-dioxane/water (1:1, 30 mL) was added $NaIO_4$ (1.25 g, 5.84 mmol) and the resulting mixture was stirred at rt for 1.5 h. After that time, another portion of $K_2OsO_4 \cdot 2H_2O$ (86 mg, 0.23 mmol) was added and the mixture stirred at 37° C. for 30 min. After that time, the mixture was cooled to rt, diluted with water (25 mL) and extracted with EtOAc (3×20 mL). The organic layers were combined, washed with brine (25 mL), dried over anhydrous $Na_2SO_4$, filtered and concentrated to dryness. The residue was purified by silica gel chromatography (0 to 100% EtOAc/hexanes) to provide the title compound as a yellow foam.

Intermediate 88

N—((S)-(7-((E)-(((S)-tert-Butylsulfinyl)imino)methyl)imidazo[1,2-b]pyridazin-2-yl)(4,4-difluorocyclohexyl)methyl)-5-methyl-1-(3,3,3-trifluoropropyl)-1H-pyrazole-4-carboxamide

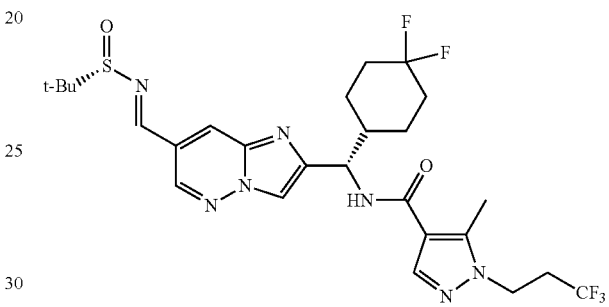

To a sealed tube was added (S)—N-((4,4-difluorocyclohexyl)(7-formylimidazo[1,2-b]pyridazin-2-yl)methyl)-5-methyl-1-(3,3,3-trifluoropropyl)-1H-pyrazole-4-carboxamide (418 mg, 0.84 mmol, Intermediate 87), pyridine 4-methylbenzenesulfonate (56 mg, 0.22 mmol), copper (II) sulfate (1.39 g, 8.72 mmol), (S)-(−)-2-methyl-2-propanesulfinamide (206 mg, 1.7 mmol) and THF (10.5 mL). The tube was capped and stirred at 80° C. for 16 h. After that time, the mixture was cooled to rt and filtered through a pad of Celite® rinsing with DCM. The filtrate was concentrated to dryness and the resulting residue purified by silica gel chromatography (0 to 100% EtOAc/hexanes) to provide the title compound as a yellow oil.

Intermediate 89

N-((1S)-(7-((((S)-tert-Butylsulfinyl)amino)(cyclopropyl)methyl)imidazo[1,2-b]pyridazin-2-yl)(4,4-difluorocyclohexyl)methyl)-5-methyl-1-(3,3,3-trifluoropropyl)-1H-pyrazole-4-carboxamide

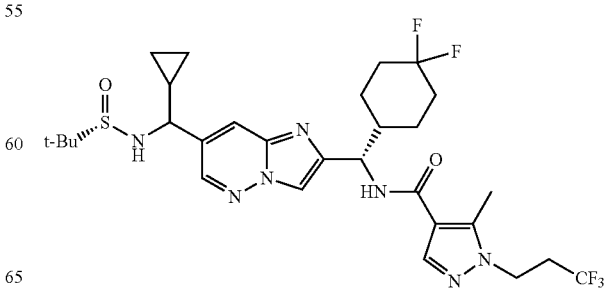

A solution of cyclopropylmagnesium bromide (1.9 mL, 1 M in 2-MeTHF, 1.9 mmol) was added dropwise to a −78° C. stirring solution of N—((S)-(7-((E)-(((S)-tert-butylsulfinyl)imino) methyl)imidazo[1,2-b]pyridazin-2-yl)(4,4-difluorocyclohexyl)methyl)-5-methyl-1-(3,3,3-trifluoropropyl)-1H-pyrazole-4-carboxamide (368 mg, 0.61 mmol, Intermediate 88) in DCM (6.5 mL), and the resulting solution was allowed to slowly warm to 0° C. over 1 h. Then, the solution was allowed to warm to rt over 1.5 h. After this time, a saturated aqueous aqueous NH₄Cl (25 mL) and then water (10 mL) were added. The layers were mixed, and then separated. The aqueous layer was extracted with EtOAc (2×20 mL). The organic layers were combined, washed with brine (20 mL), dried over anhydrous Na₂SO₄, filtered, and concentrated to dryness. The residue was purified by silica gel chromatography (0 to 100% (10% 2 M NH₃/MeOH in DCM)/DCM) to provide the title compound as a light yellow oil.

Intermediate 90

N-((1S)-(7-(Amino(cyclopropyl)methyl)imidazo[1,2-b]pyridazin-2-yl)(4,4-difluorocyclohexyl) methyl)-5-methyl-1-(3,3,3-trifluoropropyl)-1H-pyrazole-4-carboxamide

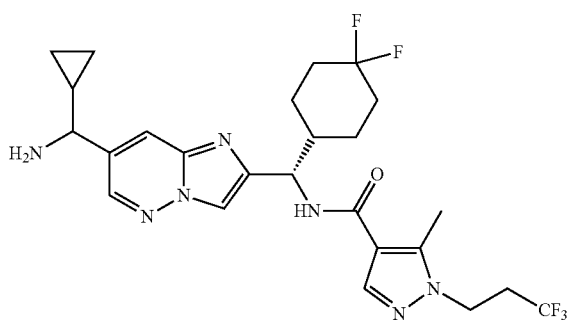 [SMILES: Cc1c(C(=O)N[C@H](c2cn3ncc(C(N)C4CC4)cc3n2)C2CCC(F)(F)CC2)cnn1CCC(F)(F)F]

A solution of HCl (0.21 mL, 4.0 M in dioxane, 0.84 mmol) was added to a solution of N-((1S)-(7-((((S)-tert-butylsulfinyl)amino)(cyclopropyl)methyl)imidazo[1,2-b]pyridazin-2-yl)(4,4-difluorocyclohexyl)methyl)-5-methyl-1-(3,3,3-trifluoropropyl)-1H-pyrazole-4-carboxamide (270 mg, 0.42 mmol, Intermediate 89) in EtOAc (4.5 mL), and the mixture was stirred for 30 min. Another aliquot of HCl solution (0.1 mL, 4.0 M in dioxane, 0.4 mmol) was added and the solution stirred at rt for 3 h. After this time, the resulting solution was concentrated, water (20 mL) was added and the mixture washed with hexane (2×20 mL). The aqueous layer was made basic by the addition of 1 N aqueous NaOH and then extracted with EtOAc (2×25 mL). The organic layers were combined, washed with brine (25 mL), dried over anhydrous Na₂SO₄, filtered and concentrated to dryness to provide the title compound, a diastereomeric mixture, as a yellow oil.

Intermediate 91

N-((1S)-(7-(Cyclopropyl(2-(3,3-difluorocyclobutyl)acetamido)methyl)imidazo[1,2-b]pyridazin-2-yl)(4,4-difluorocyclohexyl)methyl)-5-methyl-1-(3,3,3-trifluoropropyl)-1H-pyrazole-4-carboxamide

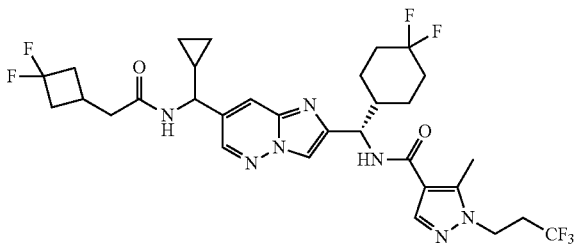 [SMILES: Cc1c(C(=O)N[C@H](c2cn3ncc(C(NC(=O)CC4CC(F)(F)C4)C4CC4)cc3n2)C2CCC(F)(F)CC2)cnn1CCC(F)(F)F]

A mixture of N-((1S)-(7-(amino(cyclopropyl)methyl)imidazo[1,2-b]pyridazin-2-yl)(4,4-difluorocyclohexyl)methyl)-5-methyl-1-(3,3,3-trifluoropropyl)-1H-pyrazole-4-carboxamide (102 mg, 0.19 mmol, Intermediate 90), 2-(3,3-difluorocyclobutyl)acetic acid (34 mg, 0.22 mmol), HOBt (27 mg, 0.2 mmol), DIPEA (39 μL, 0.23 mmol) and ACN (2.1 mL) was stirred until homogeneous. Then, EDCI (38 mg, 0.2 mmol) was added and the resulting mixture stirred at rt for 2 h. After this time, water was added and the mixture was extracted with EtOAc (2×20 mL). The organic layers were combined, washed with brine (25 mL), dried over anhydrous Na₂SO₄, filtered and concentrated to dryness. The residue was purified by silica gel chromatography (0 to 100% (10% 2 M NH₃ in MeOH/DCM)/DCM) to provide the title compound, a diastereomeric mixture, as a cream-colored solid.

Intermediate 92

N-((1S)-(7-(Cyclopropyl(4,4,4-trifluorobutanamido)methyl)imidazo[1,2-b]pyridazin-2-yl)(4,4-difluorocyclohexyl)methyl)-5-methyl-1-(3,3,3-trifluoropropyl)-1H-pyrazole-4-carboxamide

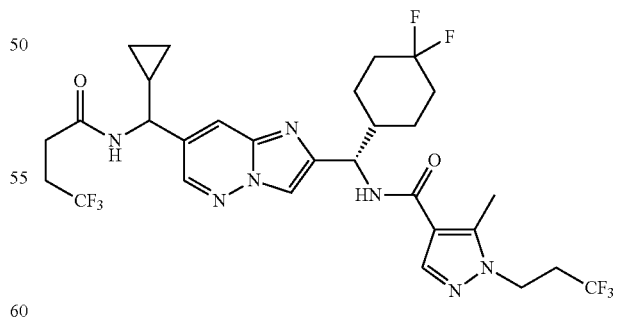

The title compound was prepared as described for the synthesis of Intermediate 91, using 4,4,4-trifluorobutyric acid in place of 2-(3,3-difluorocyclobutyl)acetic acid, and heating the mixture to 40° C. for 1.5 h after stirring at rt, to afford the title compound, a diastereomeric mixture, as a cream-colored solid.

Intermediate 93

Methyl 1-(cyclopropylmethyl)-1H-1,2,4-triazole-5-carboxylate

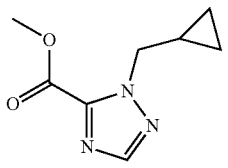

The title compound was prepared as described for the synthesis of Intermediate 74, using methyl-1H-1,2,4-triazole-3-carboxylate in place of methyl 1H-1,2,3-triazole-4-carboxylate and (bromomethyl)cyclopropane in place of 3-bromo-1,1,1-trifluoropropane, to provide the title compound as a light yellow oil.

Intermediate 94

1-(Cyclopropylmethyl)-1H-1,2,4-triazole-5-carboxylic Acid

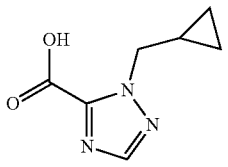 [SMILES: O=C(O)c1ncnn1CC1CC1]

To a mixture of methyl 1-(cyclopropylmethyl)-1H-1,2,4-triazole-5-carboxylate (500 mg, 2.76 mmol, Intermediate 93) in THF (2.76 mL) was added 2 M aqueous NaOH (2.76 mL, 5.52 mmol) and the mixture was stirred at rt for 2 h. After that time, the mixture was concentrated to remove the THF and then washed with EtOAc (2×15 mL). The aqueous layer was then acidified to pH 1-2 by the addition of 1 N aqueous HCl and a precipitate formed. The mixture was filtered and the filter cake rinsed with water and dried under vacuum to provide the title compound as a white solid.

Intermediate 95

Methyl 1-(3,3,3-trifluoropropyl)-1H-1,2,4-triazole-5-carboxylate

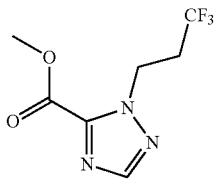

The title compound was prepared as described for the synthesis of Intermediate 78, using 3,3,3-trifluoropropan-1-ol in place of 3,3-difluoropropan-1-ol, and stirring at 120° C. in the microwave for 2 h instead of rt, to provide the title compound as a clear colorless oil.

Intermediate 96

1-(3,3,3-Trifluoropropyl)-1H-1,2,4-triazole-5-carboxylic Acid

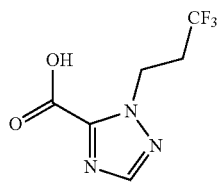 [SMILES: O=C(O)c1ncnn1CCC(F)(F)F]

The title compound was prepared as described for the synthesis of Intermediate 94, using methyl 1-(3,3,3-trifluoropropyl)-1H-1,2,4-triazole-5-carboxylate (Intermediate 95) in place of methyl 1-(cyclopropylmethyl)-1H-1,2,4-triazole-5-carboxylate, to provide the title compound as a white solid.

Intermediate 97

Ethyl 1-(2-(trifluoromethoxy)ethyl)-1H-pyrazole-4-carboxylate

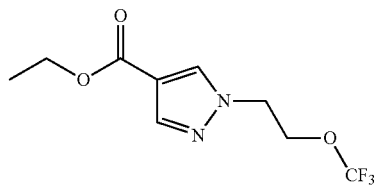 [SMILES: CCOC(=O)c1cnn(CCOC(F)(F)F)c1]

To a mixture of ethyl 1H-pyrazole-4-carboxylate (650 mg, 4.64 mmol), $K_2CO_3$ (641 mg, 4.64 mmol) and DMF (11 mL) was added 1-bromo-2-(trifluoromethoxy)ethane (0.56 mL, 4.64 mmol) and the resulting mixture was stirred at rt for 20 h. After that time the mixture was partitioned between EtOAc (30 mL) and water (30 mL). The layers were separated and the aqueous layer further extracted with EtOAc (2×30 mL). The organic layers were combined, washed with water (30 mL) followed by brine (30 mL), dried over anhydrous $Na_2SO_4$, filtered and concentrated to dryness. The residue was purified by silica gel chromatography (0 to 75% EtOAc/hexanes) to provide the title compound as a white solid.

Intermediate 98

1-(2-(Trifluoromethoxy)ethyl)-1H-pyrazole-4-carboxylic Acid

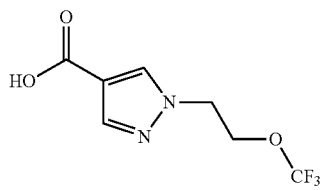

The title compound was prepared as described for the synthesis of Intermediate 76, using ethyl 1-(2-(trifluoromethoxy)ethyl)-1H-pyrazole-4-carboxylate (Intermediate 97) in place of methyl 2-(3,3,3-trifluoropropyl)-2H-1,2,3-triazole-4-carboxylate and stirring at 90° C. for 2 h after stirring at rt for 19 h, to provide the title compound as a white solid.

Intermediate 99

Ethyl 1-(2-(difluoromethoxy)ethyl)-1H-pyrazole-4-carboxylate

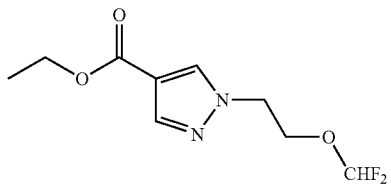 [SMILES: CCOC(=O)c1cnn(CCOC(F)F)c1]

The title compound was prepared as described in the synthesis of Intermediate 97, using 1-bromo-2-(difluoromethoxy)ethane in place of 1-bromo-2-(trifluoromethoxy)ethane to provide the title compound as a white solid.

Intermediate 100

1-(2-(Difluoromethoxy)ethyl)-1H-pyrazole-4-carboxylic Acid

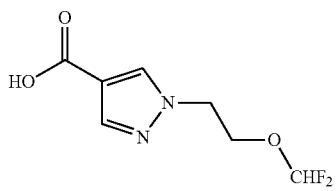 [SMILES: O=C(O)c1cnn(CCOC(F)F)c1]

The title compound was prepared as described for the synthesis of Intermediate 76, using ethyl 1-(2-(difluoromethoxy)ethyl)-1H-pyrazole-4-carboxylate (Intermediate 99) in place of methyl 2-(3,3,3-trifluoropropyl)-2H-1,2,3-triazole-4-carboxylate and stirring at 90° C. for 3 h after stirring at rt for 19 h, to provide the title compound as a white solid.

Intermediate 101

Ethyl 2-(3,3-difluoropropyl)-2H-1,2,3-triazole-4-carboxylate

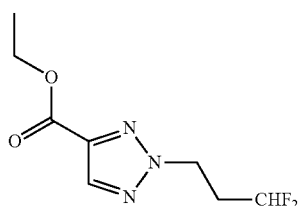

The title compound was prepared as described for the synthesis of Intermediate 78, using ethyl 1H-1,2,3-triazole-4-carboxylate in place of methyl-1H-1,2,4-triazole-3-carboxylate, cooling the mixture to 0° C. prior to addition of DIAD, and stirring at rt for 2.5 h instead of 1 h to provide the title compound as a clear colorless oil.

Intermediate 102

2-(3,3-Difluoropropyl)-2H-1,2,3-triazole-4-carboxylic Acid

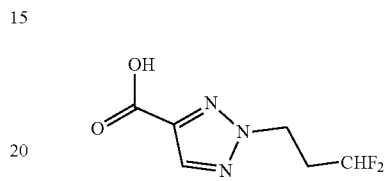

The title compound was prepared as described for the synthesis of Intermediate 76, using ethyl 2-(3,3-difluoropropyl)-2H-1,2,3-triazole-4-carboxylate (Intermediate 101) in place of methyl 2-(3,3,3-trifluoropropyl)-2H-1,2,3-triazole-4-carboxylate, and stirring at rt for 2 h instead of 15 h, to provide the title compound as a white solid.

Intermediate 103

Ethyl 2-(2,2,2-trifluoroethyl)-2H-1,2,3-triazole-4-carboxylate

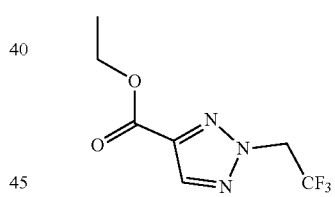

To a mixture of ethyl 1H-1,2,3-triazole-4-carboxylate (1 g, 6.73 mmol), Cs$_2$CO$_3$ (2.19 g, 6.73 mmol) and DMF (8.6 mL) was added 2-iodo-1,1,1-trifluoroethane (0.67 mL, 6.73 mmol) and the resulting mixture was stirred at 40° C. for 2.5 h. After that time, another aliquot of 2-iodo-1,1,1-trifluoroethane (0.67 mL, 6.73 mmol) was added and the mixture stirred at 60° C. for 3 d. After that time, the mixture was stirred at 80° C. for 3 d. After that time, the mixture was cooled to rt and filtered through a pad of Celite®, rinsing with EtOAc and the filtrate concentrated under vacuum. The residue was partitioned between EtOAc (30 mL) and water (30 mL). The layers were separated and the aqueous layer was further washed with EtOAc (2×30 mL). The organic layers were combined, washed with brine (50 mL), dried over anhydrous Na$_2$SO$_4$, filtered and concentrated to dryness. The residue was purified by silica gel chromatography (0 to 75% EtOAc/hexanes) to provide the title compound as a clear colorless oil.

Intermediate 104

2-(2,2,2-Trifluoroethyl)-2H-1,2,3-triazole-4-carboxylic Acid

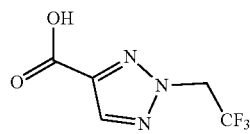 [SMILES: O=C(O)c1cnn(CC(F)(F)F)n1]

The title compound was prepared as described for the synthesis of Intermediate 76, using ethyl 2-(2,2,2-trifluoroethyl)-2H-1,2,3-triazole-4-carboxylate (Intermediate 103) in place of methyl 2-(3,3,3-trifluoropropyl)-2H-1,2,3-triazole-4-carboxylate, to provide the title compound as a white solid.

Intermediate 105

Methyl 2-(cyclopropylmethyl)-2H-1,2,3-triazole-4-carboxylate

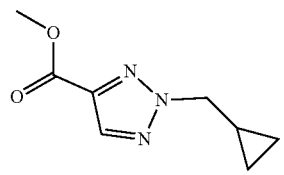

The title compound was prepared as described for the synthesis of Intermediate 74, using (bromomethyl)cyclopropane in place of 3-bromo-1,1,1-trifluoropropane, to provide the title compound as a clear colorless oil.

Intermediate 106

2-(Cyclopropylmethyl)-2H-1,2,3-triazole-4-carboxylic Acid

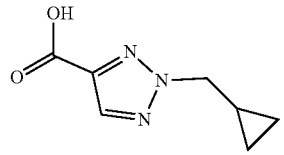 [SMILES: O=C(O)c1cnn(CC2CC2)n1]

The title compound was prepared as described for the synthesis of Intermediate 76, using methyl 2-(cyclopropylmethyl)-2H-1,2,3-triazole-4-carboxylate (Intermediate 105) in place of methyl 2-(3,3,3-trifluoropropyl)-2H-1,2,3-triazole-4-carboxylate to provide the title compound as a white solid.

Intermediate 107

Ethyl 2-(2-methoxyethyl)-2H-1,2,3-triazole-4-carboxylate

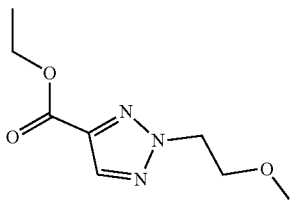

The title compound was prepared as described for the synthesis of Intermediate 74, using ethyl 1H-1,2,3-triazole-4-carboxylate in place of methyl 1H-1,2,3-triazole-4-carboxylate and 2-bromoethyl methyl ether in place of 3-bromo-1,1,1-trifluoropropane, to provide the title compound as a yellow oil.

Intermediate 108

2-(2-Methoxyethyl)-2H-1,2,3-triazole-4-carboxylic Acid

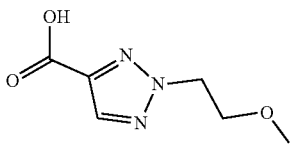

The title compound was prepared as described for the synthesis of Intermediate 76, using ethyl 2-(2-methoxyethyl)-2H-1,2,3-triazole-4-carboxylate (Intermediate 107) in place of methyl 2-(3,3,3-trifluoropropyl)-2H-1,2,3-triazole-4-carboxylate to provide the title compound as a yellow solid.

Intermediate 109

Ethyl 2-(2-(difluoromethoxy)ethyl)-2H-1,2,3-triazole-4-carboxylate

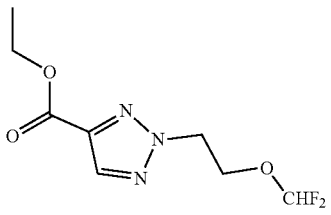 [SMILES: CCOC(=O)c1cnn(CCOC(F)F)n1]

The title compound was prepared as described for the synthesis of Intermediate 74, using ethyl 1H-1,2,3-triazole-4-carboxylate in place of methyl 1H-1,2,3-triazole-4-carboxylate and 1-bromo-2-(difluoromethoxy)ethane in place of 3-bromo-1,1,1-trifluoropropane, to provide the title compound as a yellow oil.

Intermediate 110

Ethyl 1-(2-(difluoromethoxy)ethyl)-1H-1,2,3-triazole-5-carboxylate

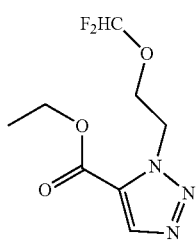

The title compound was prepared as described for the synthesis of Intermediate 74, using ethyl 1H-1,2,3-triazole-4-carboxylate in place of methyl 1H-1,2,3-triazole-4-carboxylate and 1-bromo-2-(difluoromethoxy)ethane in place of 3-bromo-1,1,1-trifluoropropane, to provide the title compound as a yellow oil.

Intermediate 111

2-(2-(Difluoromethoxy)ethyl)-2H-1,2,3-triazole-4-carboxylic Acid

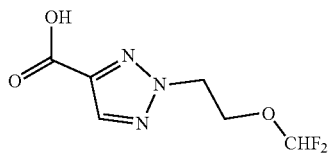

The title compound was prepared as described for the synthesis of Intermediate 76, using ethyl 2-(2-(difluoromethoxy)ethyl)-2H-1,2,3-triazole-4-carboxylate (Intermediate 109) in place of methyl 2-(3,3,3-trifluoropropyl)-2H-1,2,3-triazole-4-carboxylate to provide the title compound as a white solid.

Intermediate 112

1-(2-(Difluoromethoxy)ethyl)-1H-1,2,3-triazole-5-carboxylic Acid

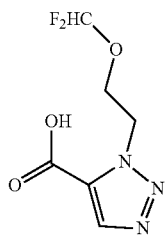 [SMILES: O=C(O)c1cnnn1CCOC(F)F]

The title compound was prepared as described for the synthesis of Intermediate 76, using ethyl 1-(2-(difluoromethoxy)ethyl)-1H-1,2,3-triazole-5-carboxylate (Intermediate 110) in place of methyl 2-(3,3,3-trifluoropropyl)-2H-1,2,3-triazole-4-carboxylate to provide the title compound as a white solid.

Intermediate 113

Methyl 1-(2,2-difluoroethyl)-1H-1,2,4-triazole-5-carboxylate

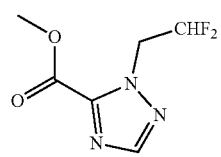

The title compound was prepared as described for the synthesis of Intermediate 74, using methyl-1H-1,2,4-triazole-3-carboxylate in place of methyl 1H-1,2,3-triazole-4-carboxylate and 2-bromo-1,1-difluoroethane in place of 3-bromo-1,1,1-trifluoropropane. An additional aliquot of 2-bromo-1,1-difluoroethane (1.03 mL, 11.6 mmol) was added to the mixture after stirring at rt for 17 h and stirring was continued for an additional 24 h to provide the title compound as a clear colorless oil.

Intermediate 114

Methyl 1-(2-fluoroethyl)-1H-1,2,4-triazole-5-carboxylate

The title compound was prepared as described for the synthesis of Intermediate 78, using 2-fluoroethanol in place of 3,3-difluoropropan-1-ol, and cooling the mixture to 0° C. prior to addition of DIAD, to provide the title compound as a clear colorless oil.

Intermediate 115

1-(1,3-Difluoropropan-2-yl)-1H-pyrazole-5-carboxylic Acid

The title compound was prepared as described for the synthesis of Intermediate 76, using methyl 1-(1,3-difluoropropan-2-yl)-1H-pyrazole-5-carboxylate (Intermediate 122) in place of methyl 2-(3,3,3-trifluoropropyl)-2H-1,2,3-triazole-4-carboxylate to provide the title compound as a white solid.

Intermediate 116

Methyl 1-(2,2,2-trifluoroethyl)-1H-1,2,4-triazole-5-carboxylate

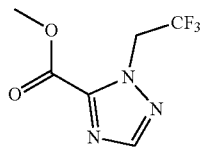

The title compound was prepared as described for the synthesis of Intermediate 78, using 2,2,2-trifluoroethanol in place of 3,3-difluoropropan-1-ol, and stirring at 120° C. in the microwave for 2 h instead of rt, to provide the title compound as a white solid.

Intermediate 117

Methyl 1-(3,3,3-trifluoropropyl)-1H-1,2,4-triazole-3-carboxylate

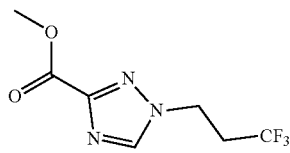

The title compound was prepared as described for the synthesis of Intermediate 78, using 3,3,3-trifluoropropan-1-ol in place of 3,3-difluoropropan-1-ol, and stirring at 120° C. in the microwave for 2 h instead of rt, to provide the title compound.

Intermediate 118

Methyl 2-((3,3-difluorocyclobutyl)methyl)-2H-1,2,3-triazole-4-carboxylate

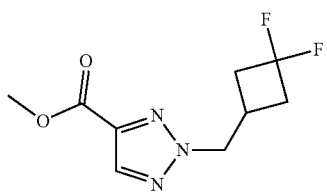 [SMILES: COC(=O)c1cnn(CC2CC(F)(F)C2)n1]

The title compound was prepared as described for the synthesis of Intermediate 74, using 3-(bromomethyl)-1,1-difluorocyclobutane in place of 3-bromo-1,1,1-trifluoropropane to provide the title compound as a clear colorless oil.

Intermediate 119

2-((3,3-Difluorocyclobutyl)methyl)-2H-1,2,3-triazole-4-carboxylic Acid

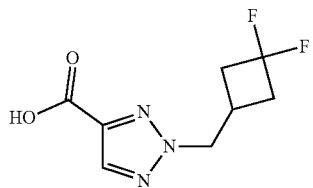 [SMILES: O=C(O)c1cnn(CC2CC(F)(F)C2)n1]

The title compound was prepared as described for the synthesis of Intermediate 76, using methyl 2-((3,3-difluorocyclobutyl)methyl)-2H-1,2,3-triazole-5-carboxylate (Intermediate 118) in place of methyl 2-(3,3,3-trifluoropropyl)-2H-1,2,3-triazole-4-carboxylate to provide the title compound as a white solid.

Intermediate 120

Methyl 1-(2-(difluoromethoxy)ethyl)-1H-1,2,4-triazole-5-carboxylate

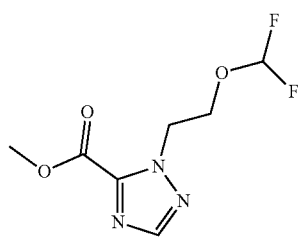

The title compound was prepared as described for the synthesis of Intermediate 74, using methyl-1H-1,2,4-triazole-3-carboxylate in place of methyl 1H-1,2,3-triazole-4-carboxylate and 1-bromo-2-(difluoromethoxy)ethane in place of 3-bromo-1,1,1-trifluoropropane, to provide the title compound as a clear colorless oil.

Intermediate 121

Methyl 1-(2-(trifluoromethoxy)ethyl)-1H-1,2,4-triazole-5-carboxylate

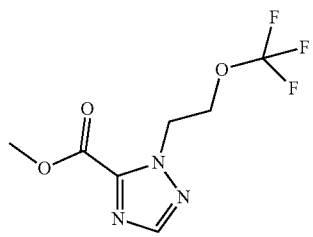 [SMILES: COC(=O)c1ncnn1CCOC(F)(F)F]

The title compound was prepared as described for the synthesis of Intermediate 74, using methyl-1H-1,2,4-triazole-3-carboxylate in place of methyl 1H-1,2,3-triazole-4- carboxylate and 1-bromo-2-(trifluoromethoxy)ethane in place of 3-bromo-1,1,1-trifluoropropane, to provide the title compound as a clear colorless oil.

Intermediate 122

Methyl 1-(1,3-difluoropropan-2-yl)-1H-pyrazole-5-carboxylate

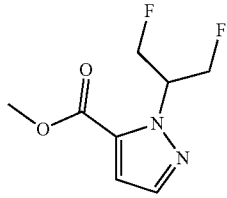

The title compound was prepared as described for the synthesis of Intermediate 78, using 1,3-difluoro-2-propanol in place of 3,3-difluoropropan-1-ol to provide the title compound as a clear light-yellow oil.

Intermediate 123

(S)—N-((7-Chloroimidazo[1,2-b]pyridazin-2-yl)(4,4-difluorocyclohexyl)methyl)-1-(3,3,3-trifluoropropyl)-1H-1,2,3-triazole-5-carboxamide

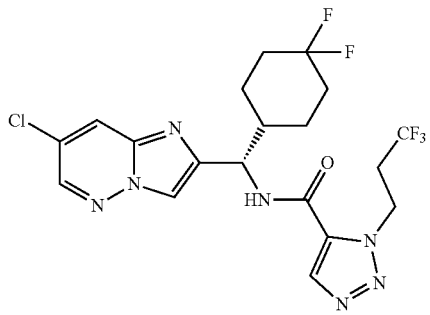 [SMILES: O=C(N[C@H](c1cn2ncc(Cl)cc2n1)C1CCC(F)(F)CC1)c1cnnn1CCC(F)(F)F]

A mixture containing (S)-(7-chloroimidazo[1,2-b]pyridazin-2-yl)(4,4-difluorocyclohexyl) methanamine (618 mg, 2.06 mmol, Intermediate 32), 1-(3,3,3-trifluoropropyl)-1H-1,2,3-triazole-5-carboxylic acid (571 mg, 2.73 mmol, Intermediate 77), HOBt (366 mg, 2.71 mmol), and EDCI (530 mg, 2.77 mol) in DIEPA (1.4 mL) and DMF (10 mL) was stirred at rt. After 3 h, the mixture was warmed to 40° C. After 1.5 h, the reaction was allowed to cool to rt and then portioned between water and ethyl acetate. The layers were separated. The organic layer was washed with water and then half-saturated sodium bicarbonate solution. The washed solution was dried over anhydrous sodium sulfate, filtered, and then concentrated under reduced pressure. The residue was purified by silica gel chromatography (hexanes/ethyl acetate) to afford the title compound as a white foam.

Intermediate 124

(S)—N-((4,4-Difluorocyclohexyl)(7-vinylimidazo[1,2-b]pyridazin-2-yl)methyl)-1-(3,3,3-trifluoropropyl)-1H-1,2,3-triazole-5-carboxamide

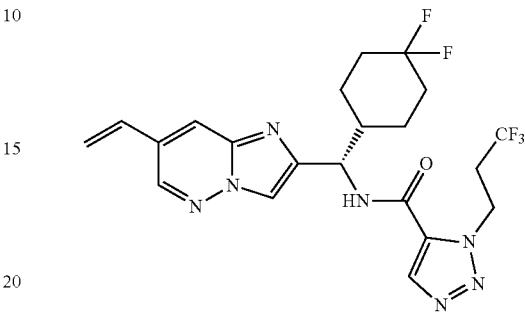

The title compound was prepared as described for the synthesis of Intermediate 34, using (S)—N-((7-chloroimidazo[1,2-b]pyridazin-2-yl)(4,4-difluorocyclohexyl)methyl)-1-(3,3,3-trifluoropropyl)-1H-1,2,3-triazole-5-carboxamide (Intermediate 123) in place of (S)—N-((7-chloroimidazo[1,2-b]pyridazin-2-yl)(4,4-difluorocyclohexyl)methyl)-1-(3,3,3-trifluoropropyl)-1H-pyrazole-4-carboxamide.

Intermediate 125

(S)—N-((4,4-Difluorocyclohexyl)(7-formylimidazo[1,2-b]pyridazin-2-yl)methyl)-1-(3,3,3-trifluoropropyl)-1H-1,2,3-triazole-5-carboxamide

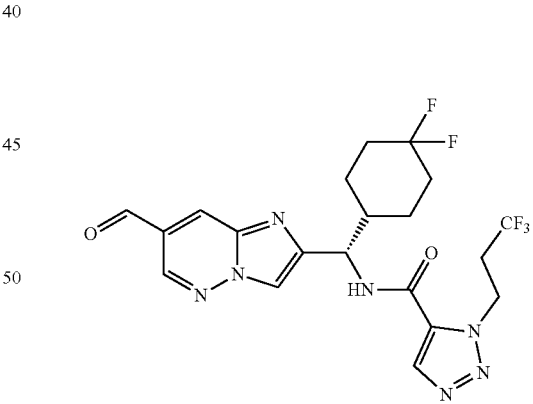

The title compound was prepared as described for the synthesis of Intermediate 35, using (S)—N-((4,4-difluorocyclohexyl)(7-vinylimidazo[1,2-b]pyridazin-2-yl)methyl)-1-(3,3,3-trifluoropropyl)-1H-1,2,3-triazole-5-carboxamide (Intermediate 124) in place of (S)—N-((4,4-difluorocyclohexyl)(7-vinylimidazo[1,2-b]pyridazin-2-yl)methyl)-1-(3,3,3-trifluoropropyl)-1H-pyrazole-4-carboxamide.

Intermediate 126

N—((S)-(7-((E)-(((S)-tert-Butylsulfinyl)imino)methyl)imidazo[1,2-b]pyridazin-2-yl)(4,4-difluorocyclohexyl)methyl)-1-(3,3,3-trifluoropropyl)-1H-1,2,3-triazole-5-carboxamide

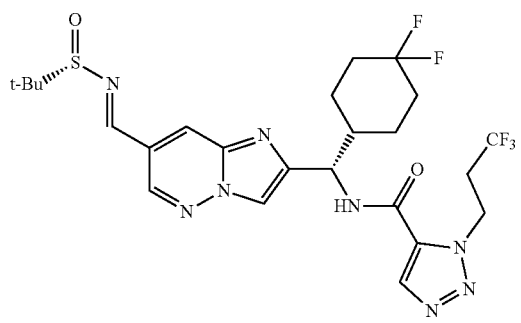 [SMILES: CC(C)(C)[S@](=O)/N=C/c1cnn2cc([C@@H](NC(=O)c3cnnn3CCC(F)(F)F)C3CCC(F)(F)CC3)nc2c1]

The title compound was prepared as described for the synthesis of Intermediate 36, using (S)—N-((4,4-difluorocyclohexyl)(7-formylimidazo[1,2-b]pyridazin-2-yl)methyl)-1-(3,3,3-trifluoropropyl)-1H-1,2,3-triazole-5-carboxamide (Intermediate 125) in place of (S)—N-((4,4-difluorocyclohexyl)(7-formylimidazo[1,2-b]pyridazin-2-yl)methyl)-1-(3,3,3-trifluoropropyl)-1H-pyrazole-4-carboxamide.

Intermediate 127

N-((1S)-(7-((((S)-tert-Butylsulfinyl)amino)(cyclopropyl)methyl)imidazo[1,2-b]pyridazin-2-yl)(4,4-difluorocyclohexyl)methyl)-1-(3,3,3-trifluoropropyl)-1H-1,2,3-triazole-5-carboxamide

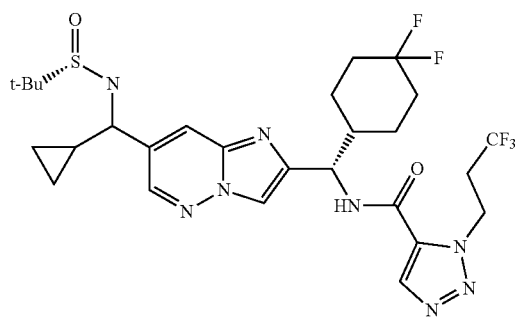 [SMILES: CC(C)(C)[S@](=O)NC(c1cnn2cc([C@@H](NC(=O)c3cnnn3CCC(F)(F)F)C3CCC(F)(F)CC3)nc2c1)C1CC1]

The title compound was prepared as described for the synthesis of Intermediate 37, using N—((S)-(7-((((S)-tert-butylsulfinyl)imino)methyl)imidazo[1,2-b]pyridazin-2-yl)(4,4-difluorocyclohexyl)methyl)-1-(3,3,3-trifluoropropyl)-1H-1,2,3-triazole-5-carboxamide (Intermediate 126) in place of N—((S)-(7-((((S)-tert-butylsulfinyl)imino)methyl)imidazo[1,2-b]pyridazin-2-yl)(4,4-difluorocyclohexyl)methyl)-1-(3,3,3-trifluoropropyl)-1H-pyrazole-4-carboxamide.

Intermediate 128

N-((1S)-(7-(Amino(cyclopropyl)methyl)imidazo[1,2-b]pyridazin-2-yl)(4,4-difluorocyclohexyl)methyl)-1-(3,3,3-trifluoropropyl)-1H-1,2,3-triazole-5-carboxamide

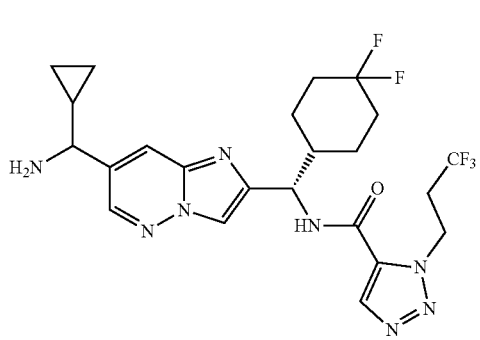 [SMILES: NC(c1cnn2cc([C@@H](NC(=O)c3cnnn3CCC(F)(F)F)C3CCC(F)(F)CC3)nc2c1)C1CC1]

The title compound was prepared as described for the synthesis of Intermediate 38, using N-((1S)-(7-((((S)-tert-butylsulfinyl)amino)(cyclopropyl)methyl)imidazo[1,2-b]pyridazin-2-yl)(4,4-difluorocyclohexyl)methyl)-1-(3,3,3-trifluoropropyl)-1H-1,2,3-triazole-5-carboxamide (Intermediate 127) in place of N-((1S)-(7-((((S)-tert-butylsulfinyl)amino)(cyclopropyl)methyl)imidazo[1,2-b]pyridazin-2-yl)(4,4-difluorocyclohexyl)methyl)-1-(3,3,3-trifluoropropyl)-1H-pyrazole-4-carboxamide.

Intermediate 129

N-((1S)-(7-(Cyclopropyl(4,4,4-trifluorobutanamido)methyl)imidazo[1,2-b]pyridazin-2-yl)(4,4-difluorocyclohexyl)methyl)-1-(3,3,3-trifluoropropyl)-1H-1,2,3-triazole-5-carboxamide

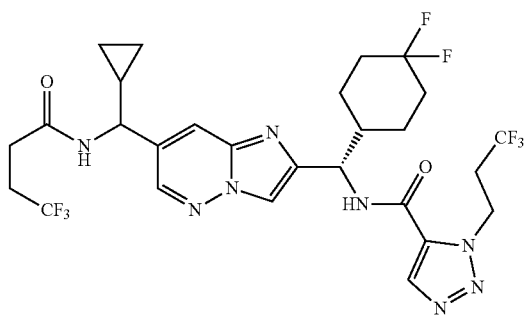 [SMILES: O=C(CCC(F)(F)F)NC(c1cnn2cc([C@@H](NC(=O)c3cnnn3CCC(F)(F)F)C3CCC(F)(F)CC3)nc2c1)C1CC1]

The title compound was prepared as described for the synthesis of Intermediate 39, using N-((1S)-(7-(amino(cyclopropyl)methyl)imidazo[1,2-b]pyridazin-2-yl)(4,4-difluorocyclohexyl)methyl)-1-(3,3,3-trifluoropropyl)-1H-1,2,3-triazole-5-carboxamide (Intermediate 128) in place of N-((1S)-(7-(amino(cyclopropyl)methyl)imidazo[1,2-b]pyridazin-2-yl)(4,4-difluorocyclohexyl)methyl)-1-(3,3,3-trifluoropropyl)-1H-pyrazole-4-carboxamide.

Intermediate 130

N-((1S)-(7-(Cyclopropyl(2-(3,3-difluorocyclobutyl)acetamido)methyl)imidazo[1,2-b]pyridazin-2-yl)(4,4-difluorocyclohexyl)methyl)-1-(3,3,3-trifluoropropyl)-1H-1,2,3-triazole-5-carboxamide

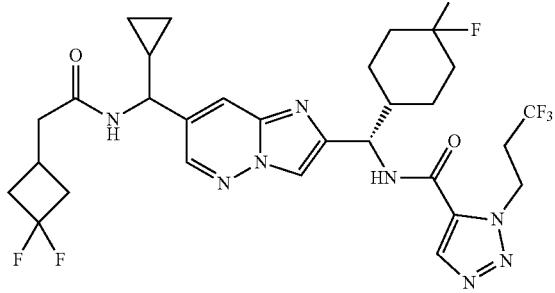

The title compound was prepared as described for the synthesis of Intermediate 39, using N-((1S)-(7-(amino(cyclopropyl)methyl)imidazo[1,2-b]pyridazin-2-yl)(4,4-difluorocyclohexyl)methyl)-1-(3,3,3-trifluoropropyl)-1H-1,2,3-triazole-5-carboxamide (Intermediate 128) in place of N-((1S)-(7-(amino(cyclopropyl)methyl)imidazo[1,2-b]pyridazin-2-yl)(4,4-difluorocyclohexyl)methyl)-1-(3,3,3-trifluoropropyl)-1H-pyrazole-4-carboxamide and 2-(3,3-difluorocyclobutyl)acetic acid in place of 4,4,4-trifluorobutyric acid.

Intermediate 131

Methyl 2-(2,2,2-trifluoro-1-hydroxyethyl)isonicotinate

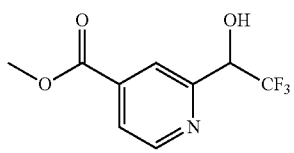 [SMILES: COC(=O)c1ccnc(C(O)C(F)(F)F)c1]

Trimethyl(trifluoromethyl)silane (14.5 g, 102 mmol) was added to a stirring, ice-water cooled solution of methyl 2-formylisonicotinate (16 g, 97 mmol) and CsF (22.1 g, 145 mmol). The mixture was allowed to warm to rt. After 2 h, the reaction mixture was poured into an aqueous, 2 M solution of HCl (20 mL) at 10° C. After 3 h, the mixture was extracted numerous times with ethyl acetate. The organic fractions were combined, dried over anhydrous Na$_2$SO$_4$, filtered and concentrated under vacuum to afford a residue. The residue was purified by silica gel chromatography (0 to 30% ethyl acetate/petroleum ether) to provide the title compound as a yellow solid.

Intermediate 132

2-(2,2,2-Trifluoro-1-((methylsulfonyl)oxy)ethyl) isonicotinate

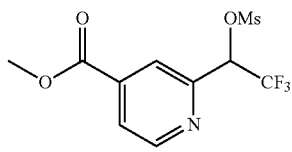 [SMILES: COC(=O)c1ccnc(C(OS(C)(=O)=O)C(F)(F)F)c1]

MsCl (8.4 g, 73 mmol) was added to a stirring solution of methyl 2-(2,2,2-trifluoro-1-hydroxyethyl)isonicotinate (10 g, 43 mmol Intermediate 131) and DIPEA (16.5 g, 128 mmol) in dichloromethane (100 mL). After 2 h, saturated aqueous sodium bicarbonate solution was added and the biphasic mixture was separated and the organics were washed with brine solution, dried over anhydrous Na$_2$SO$_4$, filtered and concentrated under vacuum to afford a residue. The residue was purified by silica gel chromatography (0 to 25% ethyl acetate/petroleum ether) to provide the title compound as a yellow oil.

Intermediate 133

Methyl 2-(2,2,2-trifluoroethyl)isonicotinate

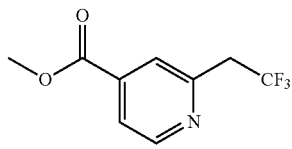

Palladium on carbon (2 g, 10% wt) was added to a stirring mixture of 2-(2,2,2-trifluoro-1-((methylsulfonyl)oxy)ethyl) isonicotinate (11.5 g, 36.7 mmol, Intermediate 132) in methanol (100 mL). The reaction mixture was placed under an atmosphere of hydrogen (15 psi). After 12 h, the mixture was filtered, and the filtrate was concentrated under reduce pressure to provide a residue. The residue was purified by silica gel chromatography (0 to 25%, ethyl acetate/petroleum ether) to provide the title compound as a colorless oil.

Intermediate 134

2-(2,2,2-Trifluoroethyl)isonicotinic Acid

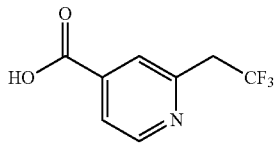

A mixture of methyl 2-(2,2,2-trifluoroethyl)isonicotinate (3.6 g, 16.4 mmol, Intermediate 133) and aqueous 12 M HCl solution (36 mL) was heated to 100° C. After 12 h, the mixture was concentrated under reduced pressure to provide the title compound as a white solid.

Intermediate 135

Ethyl 3-(3,3,3-trifluoropropyl)isoxazole-4-carboxylate

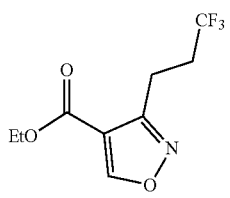 [SMILES: O=C(O)c1conc1CCC(F)(F)F]

NCS (392 mg, 2.93 mmol) was added to a solution of 4,4,4-trifluorobutanal oxime (394 mg, 2.79 mmol, Intermediate 154) and chloroform (2 mL). The reaction mixture was stirred at rt for 3 h. Ethyl-3-(diethylamino)acrylate (400 mg, 2.79 mmol) was added and the reaction mixture was stirred at rt for 16 h. The mixture was concentrated under reduced pressure, the residue was dispersed into a mixture of EtOAc (10 mL), then washed with water (10 mL) and brine (10 mL), dried over anhydrous $Na_2SO_4$, filtered, and concentrated to dryness under reduced pressure. Purification by preparative HPLC (Boston Green column, ODS 150×30 mm×5 µm (eluent: 50% to 80% (v/v) water/(0.2% formic acid)-ACN) and the resultant product was suspended in water (10 mL), frozen using dry ice/acetone, and then lyophilized to dryness to afford the title compound.

Intermediate 136

3-(3,3,3-Trifluoropropyl)isoxazole-4-carboxylic Acid

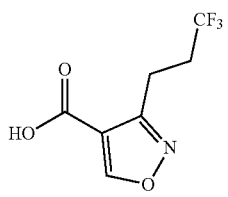

Sodium hydroxide (84 mg, 2.1 mmol) was added to a mixture consisting of ethyl 3-(3,3,3-trifluoropropyl)isoxazole-4-carboxylate (100 mg, 0.42 mmol, Intermediate 135), $H_2O$ (0.5 mL) and EtOH (2.5 mL). The resultant mixture was stirred at rt for 3 h, then concentrated under reduced pressure and the residue was diluted with water (10 mL). The resultant mixture was acidified with 1 N aqueous HCl to pH 3, frozen using dry ice/acetone, and then lyophilized to dryness to afford the title compound as a white solid.

Intermediate 137

(2,2,3,3-Tetrafluorocyclobutyl)methyl-p-toluenesulfonate

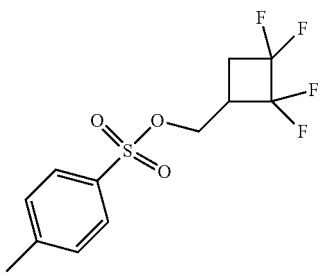 [SMILES: Cc1ccc(S(=O)(=O)OCC2CC(F)(F)C2(F)F)cc1]

(R/S) 2,2,3,3-Tetrafluorocyclobutylmethanol (0.921 g, 5.83 mmol), TsCl (1.37 g, 7.17 mmol), DCM (6.5 mL), pyridine (0.60 mL, 7.4 mmol), and a stir-bar were added to a 20 mL vial, and the resultant mixture stirred at rt for 22 h. The reaction mixture was then diluted with EtOAc, washed with 1 N NaOH, water, and brine, dried over anhydrous $MgSO_4$, filtered, and concentrated to dryness. The crude product was subjected to silica gel chromatography (0-100% (10% EtOAc in hexanes)/hexanes) to afford the title compound.

Intermediate 138

(2,2-Difluorocyclobutyl)methyl 4-bromobenzenesulfonate

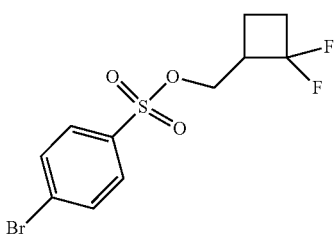 [SMILES: O=S(=O)(OCC1CCC1(F)F)c1ccc(Br)cc1]

(R/S) (2,2-Difluorocyclobutyl)methanol (994 mg, 8.14 mmol), 4-bromobenzenesulfonyl chloride (2.34 g, 9.16 mmol), a stir-bar, DCM (16.5 mL), and $Et_3N$ (1.80 mL, 13.0 mmol) were added to a 40 mL vial, and the resultant mixture stirred at rt for 22 h. The mixture was then diluted with EtOAc, washed with 1 N HCl and brine, dried over anhydrous $MgSO_4$, filtered, and concentrated to dryness to give the crude product. Subjecting the crude product to silica gel chromatography (0-20% EtOAc/hexanes) afforded the title compound as a white solid.

Intermediate 139

Ethyl 1-((2,2-difluorocyclobutyl)methyl)-1H-1,2,3-triazole-5-carboxylate

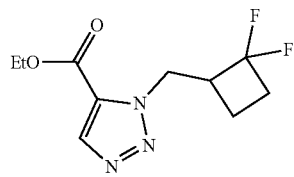 [SMILES: O=C(O)c1cnnn1CC1CCC1(F)F]

Intermediate 140

Ethyl 2-((2,2-difluorocyclobutyl)methyl)-2H-1,2,3-triazole-4-carboxylate

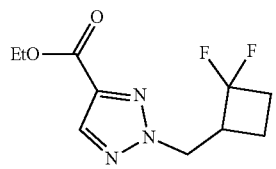 [SMILES: O=C(O)c1cnn(CC2CCC2(F)F)n1]

NaH (60% dispersion in mineral oil, 145 mg, 3.62 mmol), a stir-bar, and DMF (5 mL) were added to a nitrogen-purged 100 mL round-bottomed flask. The mixture was then treated with a solution, via syringe, consisting of (R/S) (2,2-difluorocyclobutyl)methyl 4-bromobenzenesulfonate (1.01 g, 2.95 mmol, Intermediate 138), ethyl 1H-1,2,3-triazole-5-carboxylate (457 mg, 3.24 mmol), and DMF (5.0 mL), dropwise over two min. The flask that had held the brosylate and triazole was rinsed with DMF (5 mL), and the DMF added to the reaction vessel via syringe. Stirring was continued at rt for 5 min before heating the reaction mixture at 80° C. for 18.6 h. The flask was then cooled to rt, and the excess NaH slowly quenched with water. The quenched reaction mixture was then diluted with EtOAc, washed with water (×3), dried over anhydrous MgSO₄, filtered, and concentrated to dryness to give a yellow-brown oil. The oil was subjected to silica gel chromatography (0-30% EtOAc/hexanes; Intermediate 140 eluted ahead of Intermediate 139) to give both title compounds.

Intermediate 141

Ethyl 1-((2,2,3,3-tetrafluorocyclobutyl)methyl)-1H-1,2,3-triazole-5-carboxylate

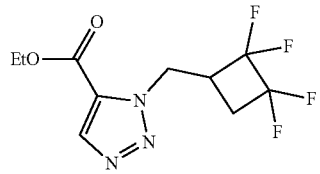 [SMILES: O=C(O)c1cnnn1CC1CC(F)(F)C1(F)F]

Intermediate 142

Ethyl 2-((2,2,3,3-tetrafluorocyclobutyl)methyl)-2H-1,2,3-triazole-4-carboxylate

Intermediate 143

Ethyl 1-((2,2,3,3-tetrafluorocyclobutyl)methyl)-1H-1,2,3-triazole-4-carboxylate

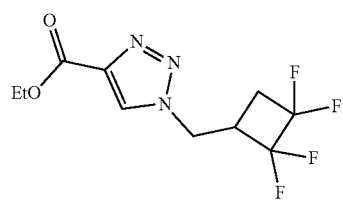

(R/S) (2,2,3,3-Tetrafluorocyclobutyl)methyl-p-toluenesulfonate (603 mg, 1.93 mmol, Intermediate 137), ethyl 1H-1,2,3-triazole-5-carboxylate (281 mg, 1.99 mmol), K₂CO₃ (546 mg, 3.95 mmol), a stir-bar, and DMF (4 mL) were added to a 20 mL vial and the mixture stirred at rt for 15 h. The reaction was diluted with EtOAc, washed water (×3) and brine, dried over anhydrous MgSO₄, filtered, and concentrated to dryness. The crude product was subjected to silica gel chromatography (0-100% EtOAc/hexanes; elution order: Intermediate 142 then Intermediate 141 then Intermediate 143) to give the title compounds.

Intermediate 144

Ethyl 1-((2,2-difluorocyclopropyl)methyl)-1H-1,2,3-triazole-5-carboxylate

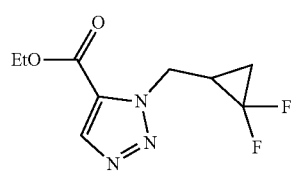

Intermediate 145

Ethyl 2-((2,2-difluorocyclopropyl)methyl)-2H-1,2,3-triazole-4-carboxylate

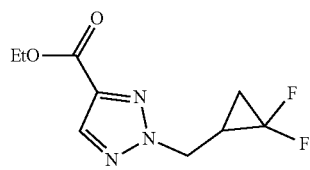

Triphenylphosphine (3.03 g, 11.6 mmol), a stir-bar, and THF (13.0 mL) were added to a nitrogen-purged 100 mL round-bottomed flask. The flask was cooled to 0° C. and treated with DIAD (2.2 mL, 11 mmol) drop-wise over 6 min, during which time the PPh₃/DIAD complex precipitated. The heterogeneous mixture was stirred for 10 min before adding a solution of 2,2-difluorocyclopropylmethanol (1.01 g, 9.32 mmol) and ethyl 1H-1,2,3-triazole-4-carboxylate (1.33 g, 9.41 mmol) in THF (10 mL) drop-wise over 9 min. The mixture was stirred an additional 14 h, and gradually warmed to rt. The reaction mixture was concentrated to dryness, taken up in EtOAc, washed with 1 N NaOH and brine, dried over anhydrous MgSO₄, filtered, and concentrated to dryness to afford a viscous oil. The crude product was subjected to silica gel chromatography (0-25% EtOAc/hexanes; Intermediate 145 elutes ahead of Intermediate 144) to give both title compounds.

Intermediate 146

1-((2,2-Difluorocyclobutyl)methyl)-1H-1,2,3-triazole-5-carboxylic Acid

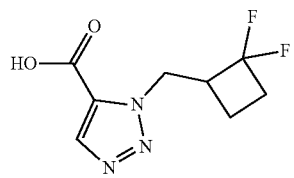

Ethyl 1-((2,2-difluorocyclobutyl)methyl)-1H-1,2,3-triazole-5-carboxylate (94.9 mg, 0.387 mmol, Intermediate 139), a stir-bar, THF (1.2 mL), and 2 N NaOH (aq) (1.2 mL, 2.4 mmol) were added to a 20 mL vial, and the mixture stirred at rt for 21 h. The THF was removed in vacuo and the resultant aqueous solution was adjusted to approximately pH 1 by treatment with 1 N aqueous HCl. The white solid that precipitated upon acidification was isolated via vacuum filtration and proved to be pure title compound. The filtrate was extracted with EtOAc (25 mL×2) and the combined extracts dried over anhydrous MgSO₄, filtered, and concentrated to dryness to afford additional pure title compound.

Intermediate 147

2-((2,2-Difluorocyclobutyl)methyl)-2H-1,2,3-triazole-4-carboxylic Acid

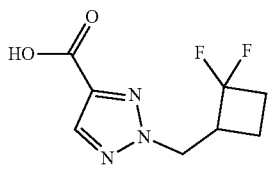

The title compound was prepared as described in the synthesis of Intermediate 146 using ethyl 2-((2,2-difluorocyclobutyl)methyl)-2H-1,2,3-triazole-4-carboxylate (Intermediate 140) in place of ethyl 1-((2,2-difluorocyclobutyl)methyl)-1H-1,2,3-triazole-5-carboxylate to provide the title compound.

Intermediate 148

1-((2,2,3,3-Tetrafluorocyclobutyl)methyl)-1H-1,2,3-triazole-5-carboxylic Acid

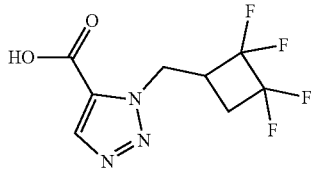

The title compound was prepared as described in the synthesis of Intermediate 146 using ethyl 1-((2,2,3,3-tetrafluorocyclobutyl)methyl)-1H-1,2,3-triazole-5-carboxylate (Intermediate 141) in place of ethyl 1-((2,2-difluorocyclobutyl)methyl)-1H-1,2,3-triazole-5-carboxylate to provide the title compound.

Intermediate 149

2-((2,2,3,3-Tetrafluorocyclobutyl)methyl)-2H-1,2,3-triazole-4-carboxylic Acid

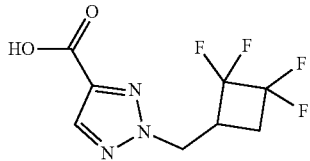 [SMILES: O=C(O)c1cnn(CC2CC(F)(F)C2(F)F)n1]

The title compound was prepared as described in the synthesis of Intermediate 146 using ethyl 2-((2,2,3,3-tetrafluorocyclobutyl)methyl)-2H-1,2,3-triazole-4-carboxylate (Intermediate 142) in place of ethyl 1-((2,2-difluorocyclobutyl)methyl)-1H-1,2,3-triazole-5-carboxylate to provide the title compound.

Intermediate 150

1-((2,2,3,3-Tetrafluorocyclobutyl)methyl)-1H-1,2,3-triazole-4-carboxylic Acid

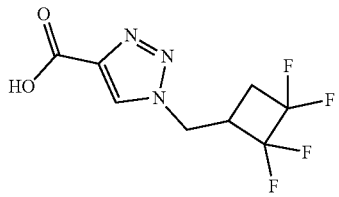 [SMILES: O=C(O)c1cn(CC2CC(F)(F)C2(F)F)nn1]

The title compound was prepared as described in the synthesis of Intermediate 146 using ethyl 1-((2,2,3,3-tetrafluorocyclobutyl)methyl)-1H-1,2,3-triazole-4-carboxylate (Intermediate 143) in place of ethyl 1-((2,2-difluorocyclobutyl)methyl)-1H-1,2,3-triazole-5-carboxylate to provide the title compound as a white solid.

Intermediate 151

1-((2,2-Difluorocyclopropyl)methyl)-1H-1,2,3-triazole-5-carboxylic Acid

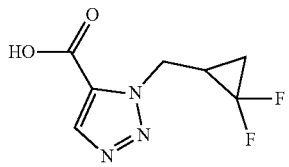 [SMILES: O=C(O)c1cnnn1CC1CC1(F)F]

The title compound was prepared as described in the synthesis of Intermediate 146 using ethyl 1-((2,2-difluorocyclopropyl)methyl)-1H-1,2,3-triazole-5-carboxylate (Intermediate 144) in place of ethyl 1-((2,2-difluorocyclobutyl)methyl)-1H-1,2,3-triazole-5-carboxylate to provide the title compound as a white solid.

Intermediate 152

2-((2,2-Difluorocyclopropyl)methyl)-2H-1,2,3-triazole-4-carboxylic Acid

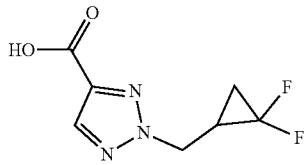

The title compound was prepared as described in the synthesis of Intermediate 146 using ethyl 2-((2,2-difluorocyclopropyl)methyl)-2H-1,2,3-triazole-4-carboxylate (Intermediate 145) in place of ethyl 1-((2,2-difluorocyclobutyl)methyl)-1H-1,2,3-triazole-5-carboxylate to provide the title compound as a white solid.

Intermediate 153

1-(3,3,3-Trifluoropropyl)-1H-1,2,4-triazole-3-carboxylic Acid

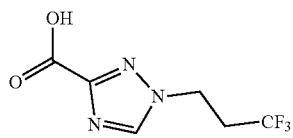 [SMILES: O=C(O)c1ncn(CCC(F)(F)F)n1]

The title compound was prepared as described for the synthesis of Intermediate 94, using methyl 1-(3,3,3-trifluoropropyl)-1H-1,2,4-triazole-3-carboxylate (Intermediate 117) in place of methyl 1-(cyclopropylmethyl)-1H-1,2,4-triazole-5-carboxylate, to provide the title compound.

Intermediate 154

(EZ)-4,4,4-Trifluorobutanal Oxime

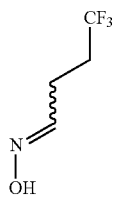

Potassium carbonate (3.29 g, 23.8 mmol) was added to a mixture of 4,4,4-trifluorobutanal (2 g, 15.9 mmol), hydroxylamine hydrochloride (1.21 g, 17.5 mmol) and EtOH (20 mL) and the resulting mixture was stirred at rt for 16 h. After that time, the mixture was concentrated to dryness, diluted with water (10 mL) and extracted with DCM (3×10 mL). The organic layers were combined, washed with brine (20 mL), dried over anhydrous Na$_2$SO$_4$, filtered and concentrated to dryness to provide the title compound as a colorless oil.

Intermediate 155

Ethyl 3-(2-fluoroethyl)isoxazole-4-carboxylate

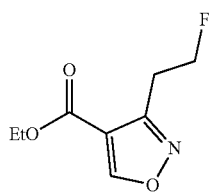 [SMILES: O=C(O)c1conc1CCF]

To a mixture of 3-pyrrolidin-1-yl-acrylic acid ethyl ester (1 g, 5.79 mmol), 1-fluoro-3-nitropropane (758 mg, 6.37 mmol) and phenyl isocyanate (1.27 mL, 11.6 mmol) was added a solution of triethylamine (0.14 mL, 1.04 mmol) in benzene (4.2 mL) and the resulting mixture was stirred at rt for 5 h followed by 85° C. for 30 min. The mixture was cooled to rt, the diphenylurea by-product was removed by filtration and the filtrate was concentrated to dryness to provide the title compound as a yellow oil/yellow solid.

Intermediate 156

3-(2-Fluoroethyl)isoxazole-4-carboxylic Acid

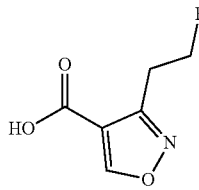

A solution of ethyl 3-(2-fluoroethyl)isoxazole-4-carboxylate (2.01 g, 5.8 mmol, Intermediate 155) in THF (5.8 mL) was cooled to 0° C. in an ice bath. Then, 1 M aqueous LiOH (6.4 mL, 6.4 mmol) was added slowly and the resulting mixture was stirred at 0° C. for 1 h. The mixture was then allowed to warm to rt over 3 h and then concentrated to remove THF. The aqueous layer was extracted with EtOAc (2×10 mL) and the aqueous was then acidified to ~pH 1.5 by the addition of 1 N aqueous HCl. The aqueous layer was then saturated with salt and extracted with 2-MeTHF (5×10 mL). The organic layers were combined, dried over anhydrous Na$_2$SO$_4$, filtered and concentrated to dryness to provide the title compound as a yellow solid.

Intermediate 157

Methyl 1-(2-fluoroethyl)-1H-1,2,3-triazole-5-carboxylate

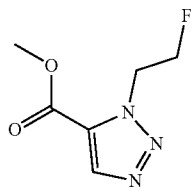

The title compound was prepared as described in the synthesis of Intermediate 74 using 1-bromo-2-fluoroethane in place of 3-bromo-1,1,1-trifluoropropane, to provide the title compound as a white solid.

Intermediate 158

Methyl 2-(2-fluoroethyl)-2H-1,2,3-triazole-4-carboxylate

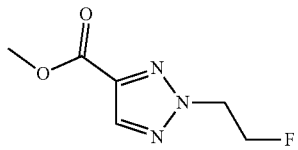

The title compound was prepared as described for the synthesis of Intermediate 157 and was isolated as a colorless oil.

Intermediate 159

1-(2-Fluoroethyl)-1H-1,2,3-triazole-5-carboxylic Acid

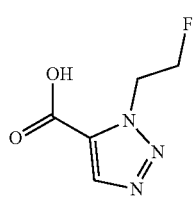 [SMILES: O=C(O)c1cnnn1CCF]

To a mixture of methyl 1-(2-fluoroethyl)-1H-1,2,3-triazole-5-carboxylate (1.15 g, 6.64 mmol, Intermediate 157) in THF (33 mL) was added 2 M aqueous NaOH (16.6 mL, 33.2 mmol) and the mixture was stirred at rt for 16 h. After that time, the mixture was concentrated to remove the THF and then washed with DCM (2×50 mL). The aqueous layer was then acidified to pH 3 by the addition of 1 N aqueous HCl and lyophilized to dryness. The crude residue was purified by preparatory HPLC (Welch Xtimate C18, 40×150 mm, 10 μm, 2-22% ACN/water+0.2% formic acid) to provide the title compound as a white solid.

Intermediate 160

2-(2-Fluoroethyl)-2H-1,2,3-triazole-4-carboxylic Acid

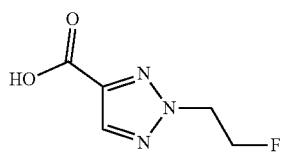 [SMILES: O=C(O)c1cnn(CCF)n1]

The title compound was prepared as described for the synthesis of Intermediate 159, using methyl 2-(2-fluoroethyl)-2H-1,2,3-triazole-4-carboxylate (Intermediate 158) in place of methyl 1-(2-fluoroethyl)-1H-1,2,3-triazole-5-carboxylate. The lyophilized solid was dissolved in DCM (200 mL), filtered and concentrated to dryness. The residue was further purified by preparatory HPLC (Welch Xtimate C18, 40×150 mm, 10 μm, 0-30% ACN/water+0.2% formic acid) followed by lyophilizing to provide the title compound as a white solid.

Intermediate 161

Methyl 1-cyclopropyl-1H-1,2,4-triazole-5-carboxylate

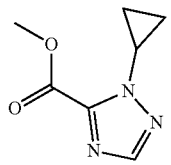

To a microwave vial was added methyl-1H-1,2,4-triazole-3-carboxylate (1.25 g, 9.64 mmol), cyclopropanol (0.85 mL, 12.5 mmol), PPh$_3$ (2.78 g, 10.6 mmol) and THF (16 mL). Then, DIAD (2.25 mL, 11.6 mmol) was added and the resulting mixture stirred at 120° C. in the microwave for 2 h. The reaction mixture was concentrated to dryness and the residue purified by silica gel chromatography (0 to 75% EtOAc/hexanes) to provide the title compound as a light yellow oil.

Intermediate 162

Methyl 1-(3-fluoropropyl)-1H-1,2,3-triazole-5-carboxylate

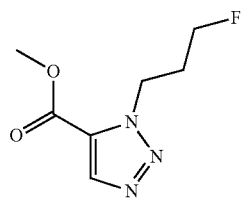

The title compound was prepared as described for the synthesis of Intermediate 74 using 1-bromo-3-fluoropropane in place of 3-bromo-1,1,1-trifluoropropane to provide the title compound as a clear colorless oil.

Intermediate 163

Methyl 2-(3-fluoropropyl)-2H-1,2,3-triazole-4-carboxylate

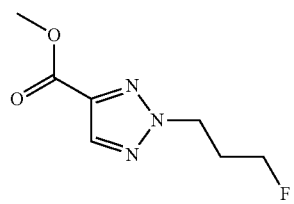

The title compound was prepared as described for the synthesis of Intermediate 74 using 1-bromo-3-fluoropropane in place of 3-bromo-1,1,1-trifluoropropane to provide the title compound as a clear colorless oil.

Intermediate 164

1-(3-Fluoropropyl)-1H-1,2,3-triazole-5-carboxylic Acid

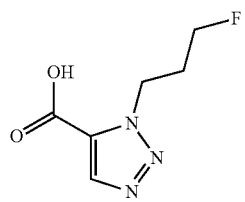 [SMILES: O=C(O)c1cnnn1CCCF]

The title compound was prepared as described for the synthesis of Intermediate 76, using methyl 1-(3-fluoropropyl)-1H-1,2,3-triazole-5-carboxylate (Intermediate 162) in place of methyl 2-(3,3,3-trifluoropropyl)-2H-1,2,3-triazole-4-carboxylate and purification by preparative HPLC (Welch Xtimate column, ODS 150×40 mm×10 μm (eluent: 8% to 80% (v/v) water/(0.2% formic acid)-ACN) to provide the title compound as a white solid.

Intermediate 165

2-(3-Fluoropropyl)-2H-1,2,3-triazole-4-carboxylic Acid

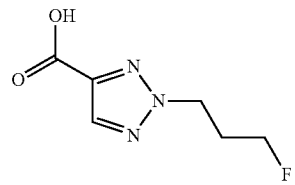 [SMILES: O=C(O)c1cnn(CCCF)n1]

The title compound was prepared as described for the synthesis of Intermediate 76, using methyl 2-(3-fluoropropyl)-2H-1,2,3-triazole-4-carboxylate (Intermediate 163) in place of methyl 2-(3,3,3-trifluoropropyl)-2H-1,2,3-triazole-4-carboxylate and purification by preparative HPLC (Welch Xtimate column, ODS 150×40 mm×10 μm (eluent: 0% to 40% (v/v) water/(0.2% formic acid)-ACN) to provide the title compound as a white solid.

Intermediate 166

Methyl 2-(2-(N-methylacetamido)ethyl)-2H-1,2,3-triazole-4-carboxylate

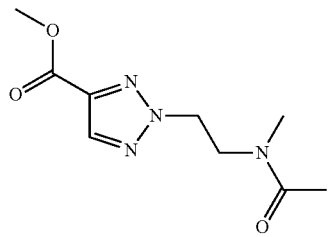 [SMILES: COC(=O)c1cnn(CCN(C)C(C)=O)n1]

The title compound was prepared as described for the synthesis of Intermediate 78, using methyl 1H-1,2,3-triazole-4-carboxylate in place of methyl-1H-1,2,4-triazole-3-carboxylate and using N-(2-hydroxyethyl)-N-methylacetamide in place of 3,3-difluoropropan-1-ol, and heating the mixture at 110° C. under microwave conditions for 1.5 h. The residue purified by silica gel chromatography (10 to 100% EtOAc/Hexanes) followed by preparative HPLC (Phenomenex Luna column, ODS 250×50 mm×10 μm (eluent: 1% to 25% (v/v) water/(0.2% formic acid)-ACN) to provide the title compound as a colorless solid.

Intermediate 167

2-(2-(N-Methylacetamido)ethyl)-2H-1,2,3-triazole-4-carboxylic Acid

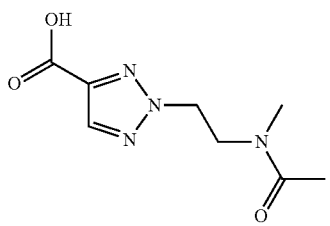

To a mixture of methyl 2-(2-(N-methylacetamido)ethyl)-2H-1,2,3-triazole-4-carboxylate (2.0 g, 8.84 mmol, Intermediate 166) in MeOH (40 mL) and water (8 mL) was added NaOH (1.77 g, 44.2 mmol) and the mixture was stirred at rt for 16 h. After that time, the mixture was concentrated to remove the MeOH and then washed with DCM (2×50 mL). The aqueous layer was then acidified to pH 4 by the addition of citric acid and concentrated under vacuum. Purification by preparative HPLC (Phenomenex Luna column, ODS 250×50 mm×10 μm (eluent: 1% to 25% (v/v) water/(0.2% formic acid)-ACN) to provide the title compound as a white solid.

Intermediate 168

Ethyl 1-(1,1,1-trifluoropropan-2-yl)-1H-pyrazole-5-carboxylate

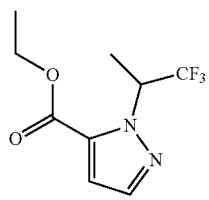 [SMILES: CCOC(=O)c1ccnn1C(C)C(F)(F)F]

A mixture of ethyl pyruvate (1.36 mL, 12.15 mmol) and N,N-dimethylformamide dimethyl acetal (1.73 mL, 12.15 mmol) was stirred at rt for 18 h. After that time, the mixture was added to a solution of (1,1,1-trifluoropropan-2-yl)hydrazine hydrochloride (1.0 g, 6.08 mmol) in EtOH (18 mL) and the mixture was stirred at 85° C. for 3 h. The mixture was concentrated under vacuum. The residue was purified by silica gel chromatography (20 to 100% EtOAc/Hexanes) to provide the title compound.

Intermediate 169

1-(1,1,1-Trifluoropropan-2-yl)-1H-pyrazole-5-carboxylic Acid

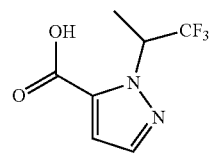

The title compound was prepared as described for the synthesis of Intermediate 76, using ethyl 1-(1,1,1-trifluoropropan-2-yl)-1H-pyrazole-5-carboxylate (Intermediate 168) in place of methyl 2-(3,3,3-trifluoropropyl)-2H-1,2,3-triazole-4-carboxylate to provide the title compound as a white solid.

Intermediate 170

N—((R)-(2-((S)-Amino(4,4-difluorocyclohexyl)methyl)-3-fluoroimidazo[1,2-b]pyridazin-7-yl)(cyclopropyl)methyl)-4,4,4-trifluorobutanamide

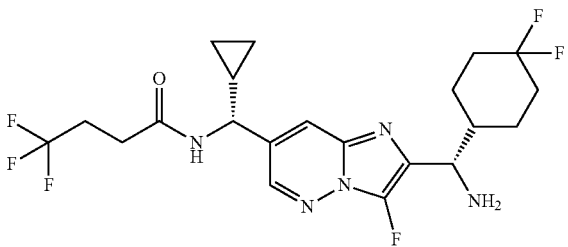 [SMILES: N[C@H](c1nc2cc([C@H](NC(=O)CCC(F)(F)F)C3CC3)cnn2c1F)C1CCC(F)(F)CC1]

A vial was charged with a stir bar, N—((R)-(2-((S)-amino(4,4-difluorocyclohexyl)methyl)imidazo[1,2-b]pyridazin-7-yl)(cyclopropyl)methyl)-4,4,4-trifluorobutanamide (200 mg, 0.44 mmol, Intermediate 51), MeCN (8 mL) and Selectfluor® (386 mg, 1.1 mmol). The reaction was stirred at rt for 3 h at which time it was quenched with water and extracted with ethyl acetate. The combined organics were washed with brine, dried over anhydrous MgSO₄, filtered and condensed. The crude material was purified by preparative HPLC (XBridge C18, 10% to 100% MeCN/aqueous NH₄OH (20 mM)). The product containing fractions were lyophlized to afford the title compound as a white powder.

Intermediate 171

N—((R)-(2-((S)-Amino(4,4-difluorocyclohexyl)methyl)imidazo[1,2-b]pyridazin-7-yl)(cyclopropyl)methyl)-2-(3,3-difluorocyclobutyl)acetamide

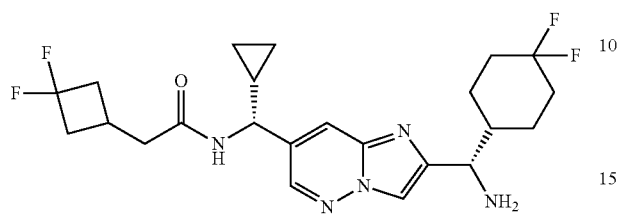

The title compound was prepared as described for the synthesis of Intermediate 51, using 2-(3,3-difluorocyclobutyl)acetic acid in place of 4,4,4-trifluorobutanoic acid.

Intermediate 172

N—((R)-(2-((S)-Amino(4,4-difluorocyclohexyl)methyl)imidazo[1,2-b]pyridazin-7-1)(cyclopropyl)methyl)-4,4,4-trifluoro-3-methylbutanamide

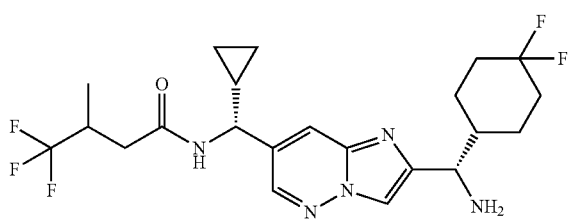 [SMILES: CC(CC(=O)N[C@@H](c1cnn2cc([C@@H](N)C3CCC(F)(F)CC3)nc2c1)C1CC1)C(F)(F)F]

The title compound was prepared as described for the synthesis of Intermediate 51, using 4,4,4-trifluoro-3-methylbutanoic acid in place of 4,4,4-trifluorobutanoic acid.

Intermediate 173

N-((1S)-(7-((1R)-Cyclopropyl(4,4,4-trifluoro-3-methylbutanamido)methyl)imidazo[1,2-b]pyridazin-2-yl)(4,4-difluorocyclohexyl)methyl)-1-isopropyl-1H-pyrazole-5-carboxamide

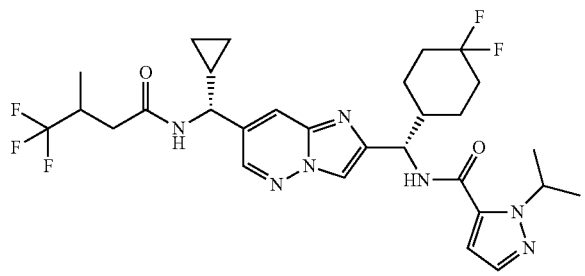 [SMILES: CC(C)n1nccc1C(=O)N[C@H](c1cn2ncc([C@H](NC(=O)CC(C)C(F)(F)F)C3CC3)cc2n1)C1CCC(F)(F)CC1]

A vial was charged with a stir bar, N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide (125 mg, 0.26 mmol, Intermediate 172), 1-isopropyl-1H-pyrazole-5-carboxylic acid (43 mg, 0.28 mmol), MeCN (2 mL), HOBt (37 mg, 0.28 mmol), and Hunig's base (68 μL, 0.28 mmol). The solution was heated to 40° C. and stirred for 5 min. To the solution was added EDCI (53 mg 0.28 mmol) and the reaction was further stirred for 30 min. The reaction was poured over water and extracted with ethyl acetate (3×5 mL). The combined organic extracts were washed with brine, dried over anhydrous MgSO₄, filtered and condensed. The crude material was purified using silica gel chromatography (0-100% (10% MeOH in ethyl acetate): hexane) to afford the title compound as a mixture of diastereomers.

Intermediate 174

N-((1S)-(7-((1R)-Cyclopropyl(4,4,4-trifluoro-3-methylbutanamido)methyl)imidazo[1,2-b]pyridazin-2-yl)(4,4-difluorocyclohexyl)methyl)-3-methylisoxazole-4-carboxamide

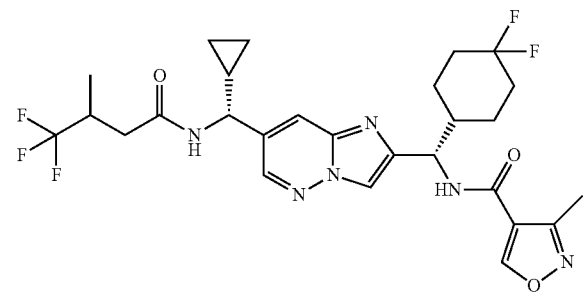 [SMILES: Cc1nocc1C(=O)N[C@H](c1cn2ncc([C@H](NC(=O)CC(C)C(F)(F)F)C3CC3)cc2n1)C1CCC(F)(F)CC1]

The title compound was prepared as described for Intermediate 173, using 3-methylisoxazole-4-carboxylic acid in place of 1-isopropyl-1H-pyrazole-5-carboxylic acid to afford the title compound as a mixture of diastereomers.

Intermediate 175

3-Cyclopropyl-N-((1S)-(7-((1R)-cyclopropyl(4,4,4-trifluoro-3-methylbutanamido)methyl)imidazo[1,2-b]pyridazin-2-yl)(4,4-difluorocyclohexyl)methyl)isoxazole-4-carboxamide

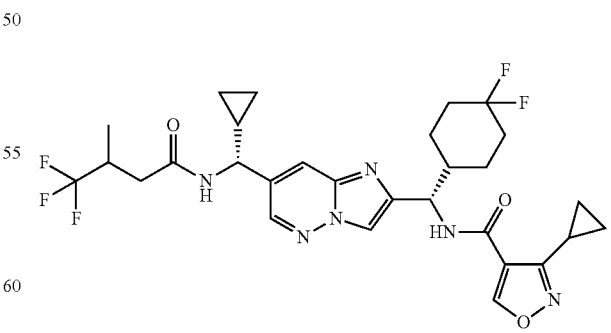

The title compound was prepared as described for Intermediate 173, using 3-cyclopropylisoxazole-4-carboxylic acid in place of 1-isopropyl-1H-pyrazole-5-carboxylic acid to afford the title compound as a mixture of diastereomers.

Intermediate 176

N-((1S)-(7-(Amino(cyclopropyl)methyl)imidazo[1,2-b]pyridazin-2-yl)(4,4-difluorocyclohexyl)methyl)-1-isopropyl-1H-pyrazole-5-carboxamide

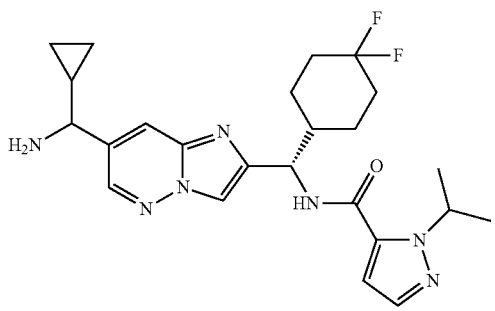 [SMILES: CC(C)n1nccc1C(=O)N[C@H](c1cn2ncc(C(N)C3CC3)cc2n1)C1CCC(F)(F)CC1]

The title compound was prepared as described for Intermediate 57 using 1-isopropyl-1H-pyrazole-5-carboxylic acid in place of 2-(3,3,3-trifluoropropyl)-2H-1,2,3-triazole-4-carboxylic acid to afford the title compound as a mixture of diastereomers.

Intermediate 177

N-((1S)-(7-(Cyclopropyl(4,4,4-trifluoro-3-hydroxybutanamido)methyl)imidazo[1,2-b]pyridazin-2-yl)(4,4-difluorocyclohexyl)methyl)-1-isopropyl-1H-pyrazole-5-carboxamide

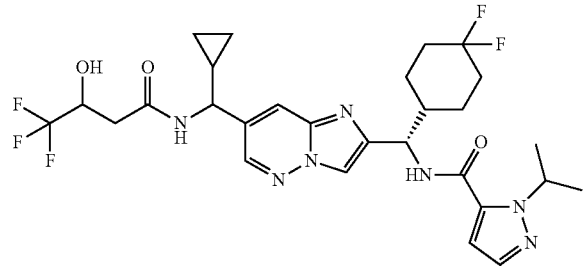 [SMILES: CC(C)n1nccc1C(=O)N[C@H](c1cn2ncc(C(NC(=O)CC(O)C(F)(F)F)C3CC3)cc2n1)C1CCC(F)(F)CC1]

A vial was charged with a stir bar, N-((1S)-(7-(amino(cyclopropyl)methyl)imidazo[1,2-b]pyridazin-2-yl)(4,4-difluorocyclohexyl)methyl)-1-isopropyl-1H-pyrazole-5-carboxamide (200 mg, 0.42 mmol, Intermediate 176), 4,4,4-trifluoro-3-hydroxybutanoic acid (70 mg, 0.45 mmol), MeCN (2 mL), HOBt (60 mg, 0.45 mmol), and Hunig's base (110 μL, 0.45 mmol). The solution was heated to 40° C. and stirred for 5 min. To the solution was added EDCI (85 mg 0.45 mmol) and the reaction was further stirred for 30 min. The reaction was poured over water and extracted with ethyl acetate (3×5 mL). The combined organic extracts were washed with brine, dried over anhydrous MgSO$_4$, filtered and condensed. The crude material was purified using silica gel chromatography (0-100% (10% MeOH in ethyl acetate): hexane) to afford the title compound as a mixture of diastereomers.

Intermediate 178

N-((1S)-(7-(Cyclopropyl(4,4,4-trifluoro-3-hydroxy-3-methylbutanamido)methyl)imidazo[1,2-b]pyridazin-2-yl)(4,4-difluorocyclohexyl)methyl)-1-isopropyl-1H-pyrazole-5-carboxamide

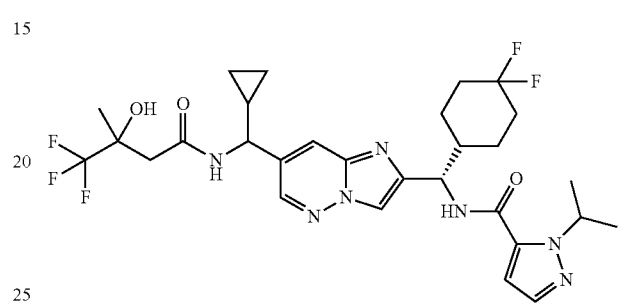

The title compound was prepared as described for Intermediate 177, using 4,4,4-trifluoro-3-hydroxy-3-methylbutanoic acid in place of 4,4,4-trifluoro-3-hydroxybutanoic acid to afford the title compound as a mixture of diastereomers.

Intermediate 179

N-((1S)-(7-(Cyclopropyl(4,4-difluorobutanamido)methyl)imidazo[1,2-b]pyridazin-2-yl)(4,4-difluorocyclohexyl)methyl)-1-isopropyl-1H-pyrazole-5-carboxamide

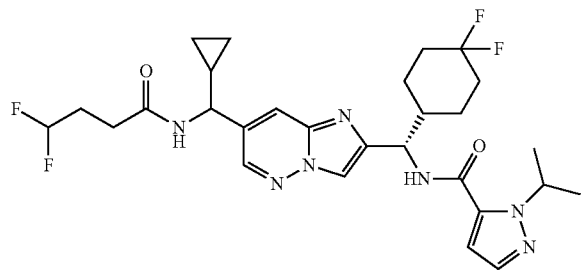 [SMILES: CC(C)n1nccc1C(=O)N[C@H](c1cn2ncc(C(NC(=O)CCC(F)F)C3CC3)cc2n1)C1CCC(F)(F)CC1]

The title compound was prepared as described for Intermediate 177, using 4,4-difluorobutanoic acid in place of 4,4,4-trifluoro-3-hydroxybutanoic acid to afford the title compound as a mixture of diastereomers.

Intermediate 180

N-((1S)-(7-(Cyclopropyl(3-hydroxy-3-methylbutanamido)methyl)imidazo[1,2-b]pyridazin-2-yl)(4,4-difluorocyclohexyl)methyl)-1-isopropyl-1H-pyrazole-5-carboxamide

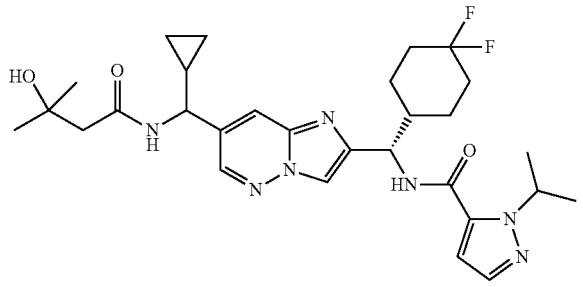 [SMILES: CC(C)n1nccc1C(=O)N[C@H](c1cn2ncc(C(NC(=O)CC(C)(C)O)C3CC3)cc2n1)C1CCC(F)(F)CC1]

The title compound was prepared as described for Intermediate 177, using 3-hydroxy-3-methylbutanoic acid in place of 4,4,4-trifluoro-3-hydroxybutanoic acid to afford the title compound as a mixture of diastereomers.

Intermediate 181

N-((1S)-(7-(Cyclopropyl(2-(2,2-difluorocyclopropyl)acetamido)methyl)imidazo[1,2-b]pyridazin-2-yl)(4,4-difluorocyclohexyl)methyl)-1-isopropyl-1H-pyrazole-5-carboxamide

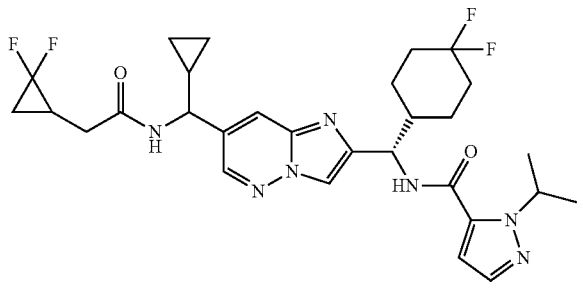 [SMILES: CC(C)n1nccc1C(=O)N[C@H](c1cn2ncc(C(NC(=O)CC3CC3(F)F)C3CC3)cc2n1)C1CCC(F)(F)CC1]

The title compound was prepared as described for Intermediate 177, using 2-(2,2-difluorocyclopropyl)acetic acid in place of 4,4,4-trifluoro-3-hydroxybutanoic acid to afford the title compound as a mixture of diastereomers.

Intermediate 182

(Trans-1,2)—N—((S)-(7-((R)-cyclopropyl(2-(3,3-difluorocyclobutyl)acetamido)methyl)imidazo[1,2-b]pyridazin-2-yl)(4,4-difluorocyclohexyl)methyl)-2-(trifluoromethyl)cyclopropane-1-carboxamide

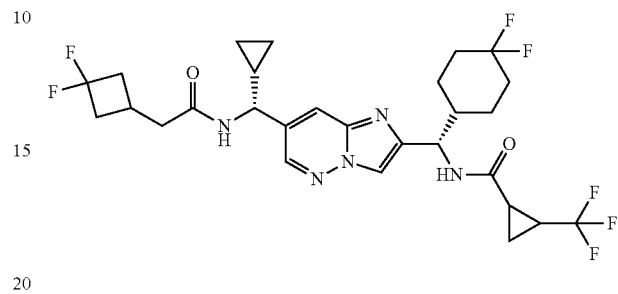

The title compound was prepared as described for Intermediate 173, using 2-(3,3-difluorocyclobutyl)acetic acid in place of 4,4,4-trifluoro-3-methylbutanoic acid, and (trans)-2-(trifluoromethyl)cyclopropane-1-carboxylic acid in place of 1-isopropyl-1H-pyrazole-5-carboxylic acid to afford the title compound as a mixture of diastereomers.

Intermediate 183

(3-Cyanobicyclo[1.1.1]pentan-1-yl)methyl 4-bromobenzenesulfonate

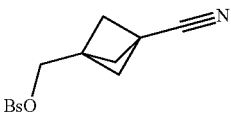

3-(Hydroxymethyl)bicyclo[1.1.1]pentane-1-carbonitrile (959 mg, 7.79 mmol), 4-bromobenzenesulfonyl chloride (2.23 g, 8.74 mmol), a stir-bar, DCM (16 mL), and Et$_3$N (1.7 mL, 12 mmol) were added to a 40 mL vial, and the resultant mixture stirred at rt for 22 h before diluting with EtOAc and washing with 1 N aqueous HCl and brine, drying over anhydrous MgSO$_4$, filtering, and concentrating to dryness to give the crude product. Silica gel chromatography (0-30% EtOAc/hexanes) afforded the title compound as a white solid.

Intermediate 184

Ethyl 1-((3-cyanobicyclo[1.1.1]pentan-1-yl)methyl)-1H-1,2,3-triazole-5-carboxylate

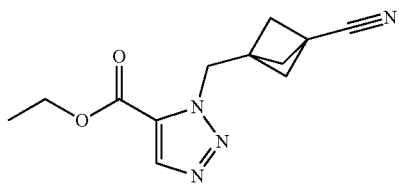 [SMILES: CCOC(=O)c1cnnn1CC12CC(C#N)(C1)C2]

Intermediate 185

Ethyl 2-((3-cyanobicyclo[1.1.1]pentan-1-yl)methyl)-2H-1,2,3-triazole-4-carboxylate

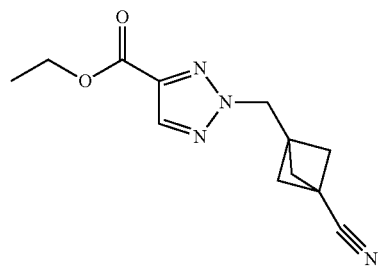 [SMILES: CCOC(=O)c1cnn(CC23CC(C#N)(C2)C3)n1]

Intermediate 186

Ethyl 1-((3-cyanobicyclo[1.1.1]pentan-1-yl)methyl)-1H-1,2,3-triazole-4-carboxylate

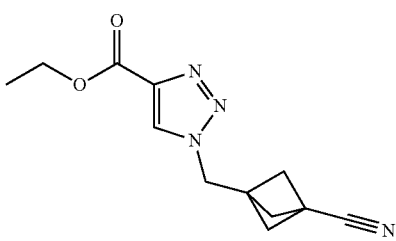 [SMILES: CCOC(=O)c1cn(CC23CC(C#N)(C2)C3)nn1]

NaH (60% dispersion in mineral oil, 154 mg, 3.84 mmol), a stir-bar and DMF (20 mL) were added to a nitrogen-purged 200 mL round-bottomed flask. The mixture was then treated with a solution consisting of (3-cyanobicyclo[1.1.1]pentan-1-yl)methyl 4-bromobenzenesulfonate (1004 mg, 2.94 mmol, Intermediate 183), ethyl 1H-1,2,3-triazole-5-carboxylate (460 mg, 3.26 mmol) and DMF (10 mL) drop-wise over 7 min. The flask that had held the cyanobicyclo[1.1.1]pentan-1-yl)methyl 4-bromobenzenesulfonate and ethyl 1H-1,2,3-triazole-5-carboxylate was rinsed with DMF (5 mL), and the resulting solution was transferred to the reaction vessel via syringe. Stirring was continued at rt for 5 min and then heated at 80° C. for 8 h. The mixture was cooled to rt, and the excess NaH slowly quenched with water. Once effervescence stopped, the mixture was diluted with EtOAc, washed with water (×3), dried over anhydrous MgSO$_4$, filtered, and concentrated to dryness to give a yellow-brown oil. The oil was subjected to silica gel chromatography (0-50% EtOAc/hexanes) to give three isomeric products. The first eluting product was Intermediate 186, the second eluting product was Intermediate 184, and the third eluting product was Intermediate 185.

Intermediate 187

1-((3-Cyanobicyclo[1.1.1]pentan-1-yl)methyl)-1H-1,2,3-triazole-5-carboxylic Acid

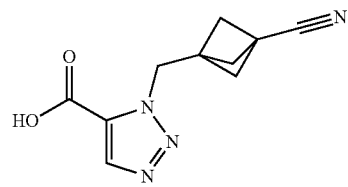 [SMILES: N#CC12CC(Cn3nncc3C(=O)O)(C1)C2]

Ethyl 1-((3-cyanobicyclo[1.1.1]pentan-1-yl)methyl)-1H-1,2,3-triazole-5-carboxylate (69.6 mg, 0.283 mmol, Intermediate 184), EtOH (0.66 mL), and a stir-bar were added to a 20 mL vial and the mixture was sonicated until a homogeneous solution was obtained. The mixture was then treated with 2 M KOH in EtOH (0.33 mL, 0.561 mmol) and heated at 60° C. for 24 h. The vial was cooled to rt, and the EtOH removed in vacuo. Water (2 mL) was added to the vial, and the mixture treated drop-wise with 1 N aqueous HCl until a white precipitate formed. The solid was isolated via vacuum filtration, and then air-dried to afford the title compound. The filtrate was subsequently extracted with EtOAc (25 mL×3), and the combined extracts were dried over anhydrous MgSO$_4$, filtered, and concentrated to dryness to afford title compound.

Intermediate 188

2-((3-Cyanobicyclo[1.1.1]pentan-1-yl)methyl)-2H-1,2,3-triazole-4-carboxylic Acid

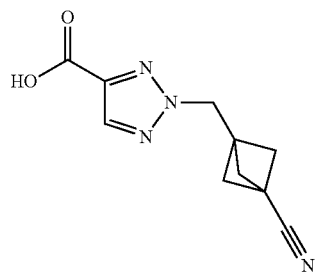 [SMILES: N#CC12CC(Cn3ncc(C(=O)O)n3)(C1)C2]

The title compound was prepared as described in the synthesis of Intermediate 187 using ethyl 2-((3-cyanobicyclo[1.1.1]pentan-1-yl)methyl)-2H-1,2,3-triazole-4-carboxylate (Intermediate 185) in place of ethyl 1-((3-cyanobicyclo[1.1.1]pentan-1-yl)methyl)-1H-1,2,3-triazole-5-carboxylate.

Intermediate 189

1-((3-Cyanobicyclo[1.1.1]pentan-1-yl)methyl)-1H-1,2,3-triazole-4-carboxylic Acid

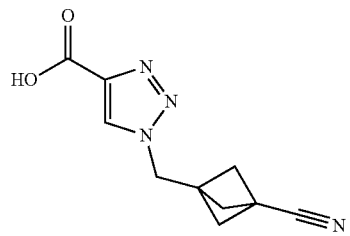 [SMILES: N#CC12CC(Cn3cc(C(=O)O)nn3)(C1)C2]

The title compound was prepared as described in the synthesis of Intermediate 187 using ethyl 1-((3-cyanobicyclo[1.1.1]pentan-1-yl)methyl)-1H-1,2,3-triazole-4-carboxylate (Intermediate 186) in place of ethyl 1-((3-cyanobicyclo[1.1.1]pentan-1-yl)methyl)-1H-1,2,3-triazole-5-carboxylate.

Intermediate 190

Methyl (E)-5-(2-(1,3-dioxolan-2-yl)vinyl)nicotinate

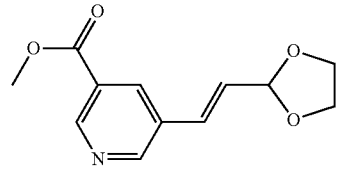 [SMILES: COC(=O)c1cncc(/C=C/C2OCCO2)c1]

Pd(OAc)$_2$ (1.1 g, 4.6 mmol) was added to a mixture containing methyl 5-bromonicotinate (10 g, 46 mmol), 2-vinyl-1,3-dioxolane (6.7 g, 67 mmol), Na$_2$CO$_3$ (5.4 g, 51 mmol) and DPPE (3.7 g, 9.3 mmol) in DMF (100 mL) at rt under N$_2$. The mixture was stirred at 110° C. overnight, whereupon it was cooled to rt and then concentrated under reduced pressure. The residue was partitioned between water and ethyl acetate. The layers were separated. The aqueous layer was extracted with ethyl acetate and the organic fractions were combined, washed with brine solution, dried over anhydrous Na$_2$SO$_4$, filtered, and concentrated. The residue was purified by silica gel chromatography (ethyl acetate/petroleum ether, 1:0 to 1:1) to provide the title compound.

Intermediate 191

Methyl 5-(2-(1,3-dioxolan-2-yl)ethyl)nicotinate

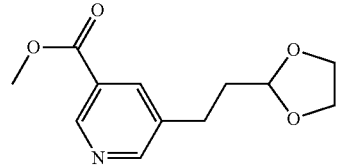 [SMILES: COC(=O)c1cncc(CCC2OCCO2)c1]

A mixture containing methyl (E)-5-(2-(1,3-dioxolan-2-yl)vinyl)nicotinate (1.5 g, 6.4 mmol, Intermediate 190) and palladium on carbon (100 mg, 10% by weight, 50% wet) in methanol (50 mL) was stirred under a hydrogen atmosphere and rt. After 1 h, the mixture was filtered, and the filtrate was concentrated to afford the title compound as a colorless liquid.

Intermediate 192

Methyl 5-(3-oxopropyl)nicotinate

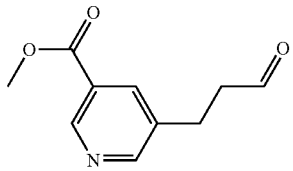

A mixture of methyl 5-(2-(1,3-dioxolan-2-yl)ethyl)nicotinate (1 g, 4 mmol, Intermediate 191) in 4 M HCl in ethyl acetate (10 mL) was stirred at rt. After 2 h, the mixture was poured onto water and then aqueous sodium bicarbonate solution was added until the pH~7. The mixture was extracted with ethyl acetate (3×10 mL). The organic fractions were combined, washed with brine solution, dried over anhydrous Na$_2$SO$_4$, filtered, and concentrated to provide the title compound as a colorless liquid.

Intermediate 193

Methyl 5-(3,3-difluoropropyl)nicotinate

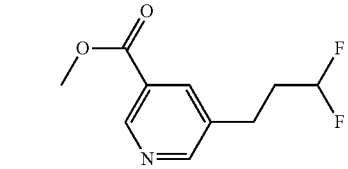

A mixture containing methyl 5-(3-oxopropyl)nicotinate (870 mg, 4.5 mmol, Intermediate 192) and DAST (0.87 mg, 5.4 mmol) in dichloromethane (10 mL) was stirred at rt overnight, whereupon aqueous sodium bicarbonate solution was added until the pH~7. The mixture was extracted with ethyl acetate (3×20 mL) and the organic fractions were combined, washed with brine solution, dried over anhydrous Na$_2$SO$_4$, filtered, and concentrated. The residue was purified by silica gel chromatography (0-50% ethyl acetate/petroleum ether) to provide the title compound.

Intermediate 194

5-(3,3-Difluoropropyl)nicotinic Acid

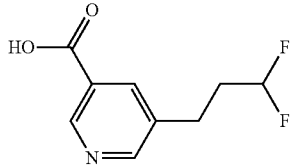 [SMILES: O=C(O)c1cncc(CCC(F)F)c1]

A mixture containing methyl 5-(3,3-difluoropropyl)nicotinate (550 mg, 2.6 mmol, Intermediate 193), lithium hydroxide monohydrate (215 mg, 5.1 mmol), methanol (5 mL), and water (5 mL) was stirred at rt. After 2 h, water was added and the mixture was extracted with ethyl acetate. The pH of the aqueous layer was adjusted to 3 by adding aqueous potassium hydrogen sulfate and then the mixture was extracted again with ethyl acetate (3×20 mL). The organic layers were combined, washed with brine, dried over anhydrous Na₂SO₄, filtered, and concentrated. The residue was purified by silica gel chromatography (0-100% ethyl acetate/petroleum ether) to provide the title compound.

Intermediate 195

Methyl 5-(2,2-difluorovinyl)nicotinate

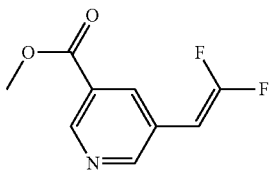

Sodium 2-chloro-2,2-difluoroacetate (1.7 g, 11 mmol) followed by triphenyl phosphine (2.4 g, 9.2 mmol) was added to a stirring solution of methyl 5-formylnicotinate (1 g, 6.1 mmol) in DMF (20 mL). The mixture was warmed to 110° C. After 35 min, the mixture was cooled to rt, whereupon ethyl acetate was added. The resulting mixture was washed with water, brine solution, dried over anhydrous Na₂SO₄, filtered, and concentrated. The residue was purified by silica gel chromatography (0-20% ethyl acetate/petroleum ether) to provide the title compound.

Intermediate 196

Methyl 5-(2,2-difluoroethyl)nicotinate

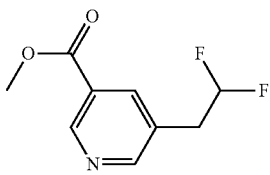

A mixture containing methyl 5-(2,2-difluorovinyl)nicotinate (1 g, 5.0 mmol, Intermediate 195) and palladium on carbon (200 mg, 10% by weight, 50% wet) in methanol (10 mL) was stirred under a hydrogen atmosphere at rt. After 2 h, the mixture was filtered, and the filtrate was concentrated. The residue was purified by silica gel chromatography (0-20% ethyl acetate/petroleum ether) to provide the title compound.

Intermediate 197

5-(2,2-Difluoroethyl)nicotinic Acid

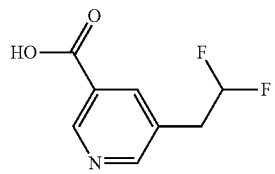 [SMILES: O=C(O)c1cncc(CC(F)F)c1]

A mixture containing methyl 5-(2,2-difluoroethyl)nicotinate (550 mg, 2.7 mmol, Intermediate 196), lithium hydroxide monohydrate (138 mg, 3.3 mmol), methanol (10 mL) and water (5 mL) was stirred at rt. After 2 h, the mixture was concentrated under reduced pressure to remove methanol and the pH was adjusted to 6 by adding aqueous 1 M HCl solution. The mixture was purified by preparative HPLC (YMC-Triart Prep C18 150×40 mm×7 μm, eluent: 1 to 30% (v/v) water-acetonitrile containing 0.225% v/v formic acid) to afford the title compound.

Intermediate 198

N-((1S)-(7-(1-Aminoethyl)imidazo[1,2-b]pyridazin-2-yl)(4,4-difluorocyclohexyl)methyl)-3-methylisoxazole-4-carboxamide

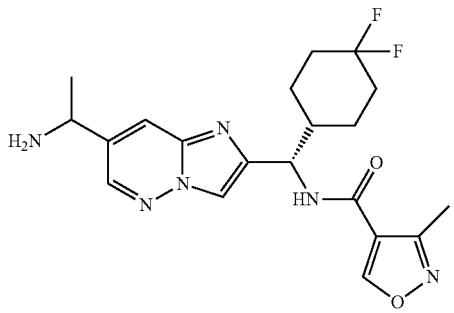 [SMILES: Cc1nocc1C(=O)N[C@H](c1cn2ncc(C(C)N)cc2n1)C1CCC(F)(F)CC1]

The title compound was prepared as described for Intermediate 38, using 3-methylisoxazole-4-carboxylic acid in place of 1-(3,3,3-trifluoropropyl)-1H-pyrazole-4-carboxylic acid and methylmagnesium bromide in place of cyclopropylmagnesium bromide.

Intermediate 199

N—((S)-(7-((R*)-1-(((S)-tert-Butylsulfinyl)amino)-2-methylpropyl)imidazo[1,2-b]pyridazin-2-yl)(4,4-difluorocyclohexyl)methyl)-1-isopropyl-1H-pyrazole-5-carboxamide

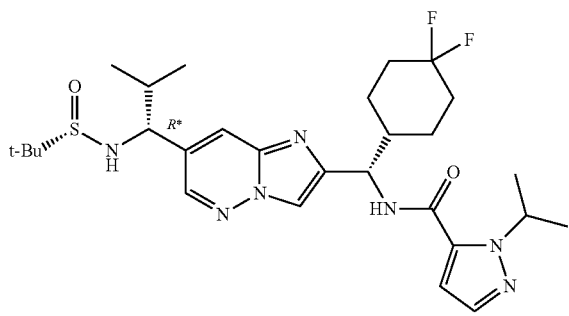 [SMILES: CC(C)[C@@H](N[S@@](=O)C(C)(C)C)c1cnn2cc([C@@H](NC(=O)c3ccnn3C(C)C)C3CCC(F)(F)CC3)nc2c1]

Intermediate 200

N—((S)-(7-((S*)-1-(((S)-tert-Butylsulfinyl)amino)-2-methylpropyl)imidazo[1,2-b]pyridazin-2-yl)(4,4-difluorocyclohexyl)methyl)-1-isopropyl-1H-pyrazole-5-carboxamide

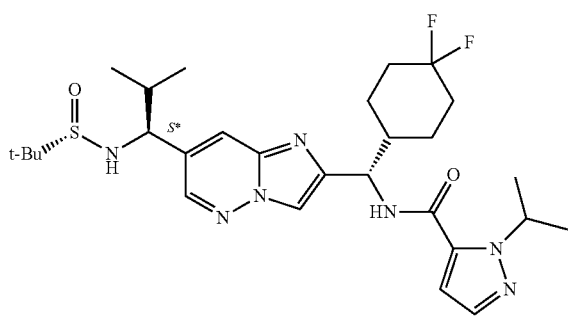 [SMILES: CC(C)[C@H](N[S@@](=O)C(C)(C)C)c1cnn2cc([C@@H](NC(=O)c3ccnn3C(C)C)C3CCC(F)(F)CC3)nc2c1]

The title compounds were prepared as described for Intermediate 37, using 1-isopropyl-1H-pyrazole-5-carboxylic acid in place of 1-(3,3,3-trifluoropropyl)-1H-pyrazole-4-carboxylic acid and isopropylmagnesium chloride in place of cyclopropylmagnesium bromide to form a pair of diastereomers. Purification by silica gel chromatography (petroleum ether/ethyl acetate) affords the title compounds. Intermediate 199 is the first eluting isomer, designated R*, and Intermediate 200 is the second eluting isomer, designated S*.

Intermediate 201

N—((S)-(7-((R*)-1-Amino-2-methylpropyl)imidazo[1,2-b]pyridazin-2-yl)(4,4-difluorocyclohexyl)methyl)-1-isopropyl-1H-pyrazole-5-carboxamide

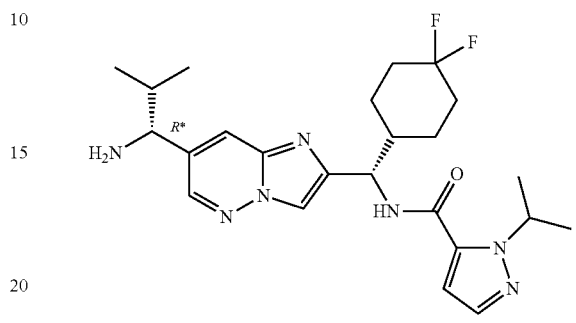

The title compound was prepared as described for Intermediate 38, using N—((S)-(7-((R*)-1-(((S)-tert-butylsulfinyl)amino)-2-methylpropyl)imidazo[1,2-b]pyridazin-2-yl)(4,4-difluorocyclohexyl)methyl)-1-isopropyl-1H-pyrazole-5-carboxamide (Intermediate 199) in place of N-((1S)-(7-((((S)-tert-butylsulfinyl)amino)(cyclopropyl)methyl)imidazo[1,2-b]pyridazin-2-yl)(4,4-difluorocyclohexyl)methyl)-1-(3,3,3-trifluoropropyl)-1H-pyrazole-4-carboxamide.

Intermediate 202

N—((S)-(7-((S*)-1-Amino-2-methylpropyl)imidazo[1,2-b]pyridazin-2-yl)(4,4-difluorocyclohexyl)methyl)-1-isopropyl-1H-pyrazole-5-carboxamide

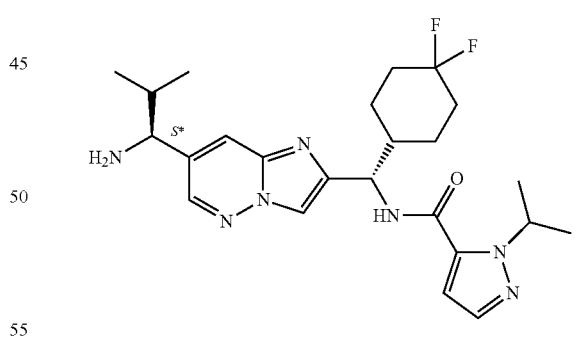

The title compound was prepared as described for Intermediate 38, using N—((S)-(7-((S*)-1-(((S)-tert-butylsulfinyl)amino)-2-methylpropyl)imidazo[1,2-b]pyridazin-2-yl)(4,4-difluorocyclohexyl)methyl)-1-isopropyl-1H-pyrazole-5-carboxamide (Intermediate 200) in place of N-((1S)-(7-((((S)-tert-butylsulfinyl)amino)(cyclopropyl)methyl)imidazo[1,2-b]pyridazin-2-yl)(4,4-difluorocyclohexyl)methyl)-1-(3,3,3-trifluoropropyl)-1H-pyrazole-4-carboxamide.

Intermediate 203

Ethyl 1-(ethyl-d5)-1H-pyrazole-5-carboxylate

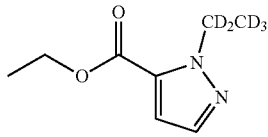

To a mixture of ethyl 1H-pyrazole-3-carboxylate (6.16 g, 44.0 mmol), K₂CO₃ (9.12 g, 66.0 mmol) and DMF (55 mL) was added bromoethane-d5 (5.0 g, 44.0 mmol) and the resulting mixture was stirred at rt for 15 h. The reaction mixture was partitioned between EtOAc and water. The layers were separated and the aqueous layer was further extracted with EtOAc. The organic layers were combined, washed with brine, dried over anhydrous Na₂SO₄, filtered and concentrated to dryness. This residue was purified by silica gel chromatography (10-60% EtOAc/hexanes) to afford the title compound as the first eluting fraction as a colorless oil.

Intermediate 204

1-(Ethyl-d5)-1H-pyrazole-5-carboxylic Acid

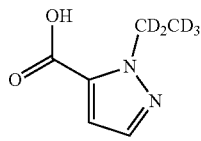

The title compound was prepared as described for the synthesis of Intermediate 76, using ethyl 1-(ethyl-d5)-1H-pyrazole-5-carboxylate (Intermediate 203) in place of methyl 2-(3,3,3-trifluoropropyl)-2H-1,2,3-triazole-4-carboxylate to provide the title compound as a white solid.

Intermediate 205

Ethyl 3-(oxetan-3-yl)isoxazole-4-carboxylate

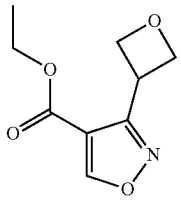

The title compound was prepared as described for the synthesis of Intermediate 155, using 3-(nitromethyl)oxetane in place of 1-fluoro-3-nitropropane to provide the title compound as an orange solid.

Intermediate 206

3-(Oxetan-3-yl)isoxazole-4-carboxylic Acid

The title compound was prepared as described for the synthesis of Intermediate 156, using ethyl 3-(oxetan-3-yl)isoxazole-4-carboxylate (Intermediate 205) in place of ethyl 3-(2-fluoroethyl)isoxazole-4-carboxylate to provide the title compound as a yellow solid.

Intermediate 207

Ethyl 3-(cyclopropylmethyl)isoxazole-4-carboxylate

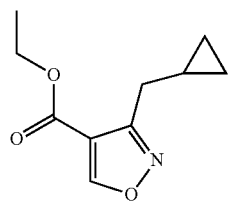

The title compound was prepared as described for the synthesis of Intermediate 155, using (2-nitroethyl)cyclopropane in place of 1-fluoro-3-nitropropane to provide the title compound as a yellow solid.

Intermediate 208

3-(Cyclopropylmethyl)isoxazole-4-carboxylic Acid

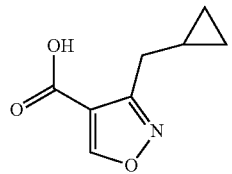 [SMILES: O=C(O)c1conc1CC1CC1]

The title compound was prepared as described for the synthesis of Intermediate 156, using ethyl 3-(cyclopropylmethyl)isoxazole-4-carboxylate (Intermediate 207) in place of ethyl 3-(2-fluoroethyl)isoxazole-4-carboxylate to provide the title compound as a light yellow solid.

Intermediate 209

(EZ)-2-((tert-Butyldimethylsilyl)oxy)acetaldehyde Oxime

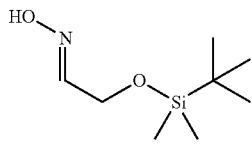

To a solution of (tert-butyldimethylsilyloxy)acetaldehyde (5 g, 28.7 mmol) in EtOH (200 mL) was added hydroxylamine hydrochloride (2.39 g, 34.4 mmol) and 2 M aqueous NaOH (17.2 mL, 34.4 mmol), and the resulting mixture was stirred at 90° C. overnight. The reaction mixture was concentrated and then partitioned between water (1 L) and EtOAc (200 mL). The aqueous layer was further extracted with EtOAc (2×200 mL), and then the combined organic layers were washed with brine (300 mL), dried over anhydrous Na$_2$SO$_4$, filtered, and concentrated to dryness. The residue was purified by silica gel chromatography (0-50% EtOAc/petroleum ether) to provide the title compound as a colorless liquid.

Intermediate 210

(EZ)-2-((tert-Butyldimethylsilyl)oxy)-N-hydroxyacetimidoyl Chloride

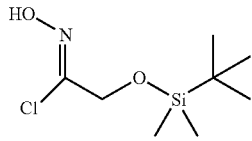

NCS (11.6 g, 87.2 mmol) was added to a solution of (EZ)-2-((tert-butyldimethylsilyl)oxy)acetaldehyde oxime (11 g, 58.1 mmol, Intermediate 209) in DMF (500 mL) and the resulting mixture was stirred at rt for 4 h. After that time, the mixture was concentrated to remove the DMF, and then water (500 mL) was added and the mixture was extracted with EtOAc (3×100 mL). The organic layers were combined, washed with brine (300 mL), dried over anhydrous Na$_2$SO$_4$, filtered, and concentrated to dryness to provide the title compound as a white liquid.

Intermediate 211

Ethyl 3-(((tert-butyldimethylsilyl)oxy)methyl)isoxazole-4-carboxylate

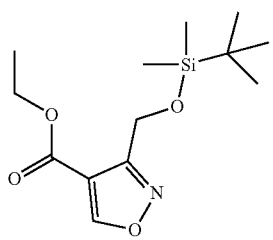 [SMILES: CCOC(=O)c1conc1CO[Si](C)(C)C(C)(C)C]

(E)-Ethyl 3-(pyrrolidin-1-yl)acrylate (7.56 g, 44.7 mmol) was added to a solution of (EZ)-2-((tert-butyldimethylsilyl)oxy)-N-hydroxyacetimidoyl chloride (10 g, 44.7 mmol, Intermediate 210) in THF (250 mL) and the resulting mixture was stirred at 80° C. for 16 h. The reaction was cooled to rt, water (500 mL) was added and the mixture was extracted with EtOAc (3×100 mL). The organic layers were combined, washed with brine (300 mL), dried over anhydrous Na$_2$SO$_4$, filtered, and concentrated to dryness to provide the title compound as a yellow liquid.

Intermediate 212

Ethyl 3-(hydroxymethyl)isoxazole-4-carboxylate

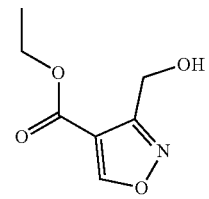

TBAF (54.7 mL, 54.7 mmol, 1 M in THF) was added to a solution of ethyl 3-(((tert-butyldimethylsilyl)oxy)methyl)isoxazole-4-carboxylate (12 g, 42 mmol, Intermediate 211) in DCM (160 mL), and the resulting mixture was stirred at rt for 2 h. After that time, water (1 L) was added and the mixture extracted with DCM (3×50 mL). The organic layers were combined, washed with brine (500 mL), dried over anhydrous Na$_2$SO$_4$, filtered, and concentrated to dryness. The residue was purified by silica gel chromatography (0-50% EtOAc/petroleum ether) to provide the title compound as a yellow liquid.

Intermediate 213

Ethyl 3-((difluoromethoxy)methyl)isoxazole-4-carboxylate

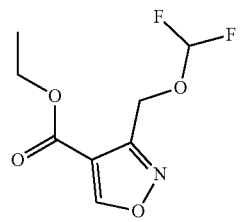

To a solution of ethyl 3-(hydroxymethyl)isoxazole-4-carboxylate (4 g, 23.4 mmol, Intermediate 212) in ACN (80 mL) at 50° C. were added CuI (0.89 g, 4.67 mmol) and TEA (2.92 mL, 21 mmol). Then, 2,2-difluoro-2-(fluorosulfonyl)acetic acid (7.25 mL, 70.1 mmol) was added slowly and the resulting mixture was stirred at 50° C. for 6 h. After that time, water (200 mL) was added and the mixture extracted with EtOAc (3×50 mL). The organic layers were combined, washed with brine (100 mL), dried over anhydrous Na$_2$SO$_4$, filtered, and concentrated to dryness. The residue was purified by silica gel chromatography (0-50% EtOAc/petroleum ether) to provide the title compound as a yellow liquid.

Intermediate 214

3-((Difluoromethoxy)methyl)isoxazole-4-carboxylic Acid

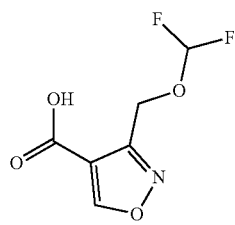 [SMILES: O=C(O)c1conc1COC(F)F]

A solution of ethyl 3-((difluoromethoxy)methyl)isoxazole-4-carboxylate (1.0 g, 4.5 mmol, Intermediate 213) in THF (20 mL) and water (20 mL) was cooled to 0° C. and then LiOH·H$_2$O (228 mg, 5.43 mmol) was added. The resulting mixture was stirred at rt for 2 h. After that time, water (100 mL) was added and the mixture was washed with petroleum ether (3×30 mL). The pH of the aqueous layer was adjusted to pH 3 by the addition of 1 N aqueous HCl, then the aqueous layer was extracted with EtOAc (3×30 mL). The organic layers were combined, washed with brine (50 mL), dried over anhydrous Na$_2$SO$_4$, filtered, and concentrated to dryness to provide the title compound as a yellow solid.

Intermediate 215

Ethyl 3-hydroxyisoxazole-4-carboxylate

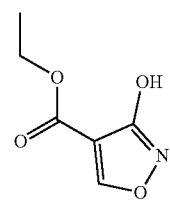

To a solution of diethyl 2-(ethoxymethylene)malonate (10 g, 46.3 mmol) in MeOH (60 mL) was added hydroxylamine hydrochloride (3.21 g, 46.3 mmol) and NaOMe (5.5 g, 101.7 mmol), and the resulting mixture was stirred at −5° C. for 30 min. The mixture was filtered, and the pH of the filtrate was adjusted to ~pH 2-3 by the addition of conc. HCl. The resulting precipitate was filtered off, and the filtrate was concentrated to dryness. The crude residue was taken up in DCM (30 mL), filtered, and the filtrate was concentrated to dryness. The residue was purified by silica gel chromatography (0-10% MeOH/DCM) to provide the title compound as a white solid.

Intermediate 216

Ethyl 3-ethoxyisoxazole-4-carboxylate

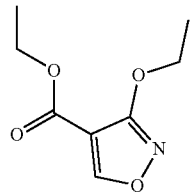

A mixture of ethyl 3-hydroxyisoxazole-4-carboxylate (2.0 g, 12.7 mmol, Intermediate 215), iodoethane (2.38 g, 15.3 mmol), NaH (0.46 g, 19.1 mmol) and DMF (30 mL) was stirred at 60° C. for 16 h. The mixture was added to water (20 mL) and extracted with EtOAc (20 mL). The organic layer was washed with water (3×20 mL) followed by brine (25 mL), dried over anhydrous Na$_2$SO$_4$, filtered and concentrated to dryness. The residue was purified by silica gel chromatography (0-20% EtOAc/petroleum ether) to provide the title compound as a white solid.

Intermediate 217

3-Ethoxyisoxazole-4-carboxylic Acid

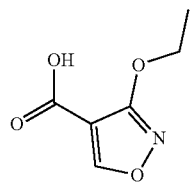

A solution of ethyl 3-ethoxyisoxazole-4-carboxylate (500 mg, 2.7 mmol, Intermediate 216) in EtOH (10 mL) and water (10 mL) was cooled to 0° C. and then LiOH·H$_2$O (125 mg, 2.97 mmol) was added. The resulting mixture was stirred at 0° C. for 1 h, then purified directly by preparative HPLC (Agela ASB 150×25 mm×5 μm column (water (0.05% HCl)/ACN)). The pure material was suspended in water (10 mL), frozen and lyophilized to provide the title compound as a white solid.

Intermediate 218

Ethyl 3-methoxyisoxazole-4-carboxylate

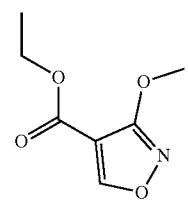

The title compound was prepared as described in the synthesis of Intermediate 216 using iodomethane in place of iodoethane, to provide the title compound as a white solid.

Intermediate 219

3-Methoxyisoxazole-4-carboxylic Acid

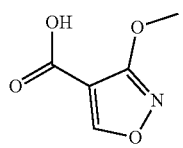

A solution of ethyl 3-methoxyisoxazole-4-carboxylate (523 mg, 3.06 mmol, Intermediate 218) in EtOH (6 mL) and water (6 mL) was cooled to 0° C. and then LiOH·H$_2$O (154 mg, 3.67 mmol) was added. The resulting mixture was stirred at 0° C. for 3 h, then ACN and 1 M aqueous HCl were added to reach a pH of ~7. The mixture was purified directly by preparative HPLC (Agela ASB 150×25 mm×5 μm column (10-40% ACN/water (0.05% HCl))). The pure material was suspended in water (10 mL), frozen and lyophilized to provide the title compound as a white solid.

Intermediate 220

N—((R)-(2-((S)-Amino(4,4-difluorocyclohexyl)methyl)imidazo[1,2-b]pyridazin-7-yl)(cyclopropyl)methyl)-2-((R*)-2,2-difluorocyclopropyl)acetamide

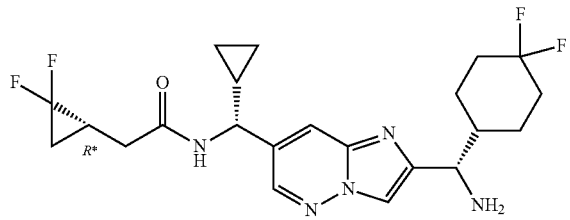 [SMILES: N[C@H](c1cn2ncc([C@H](NC(=O)C[C@@H]3CC3(F)F)C3CC3)cc2n1)C1CCC(F)(F)CC1]

Intermediate 221

N—((R)-(2-((S)-Amino(4,4-difluorocyclohexyl)methyl)imidazo[1,2-b]pyridazin-7-yl)(cyclopropyl)methyl)-2-((S*)-2,2-difluorocyclopropyl)acetamide

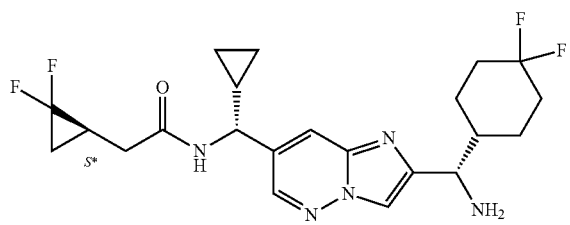 [SMILES: N[C@H](c1cn2ncc([C@H](NC(=O)C[C@H]3CC3(F)F)C3CC3)cc2n1)C1CCC(F)(F)CC1]

The title compounds were prepared as described for Intermediate 51 using 2-(2,2-difluorocyclopropyl)acetic acid in place of 4,4,4-trifluorobutanoic acid. The diastereomers were separated by SFC with a chiral stationary phase (Stationary phase: AS-H 2×15 mm, Mobile phase: 20% ethanol (with 0.2% NPA)/CO$_2$). The first eluting spot was Intermediate 220 and the second eluting spot was Intermediate 221.

Intermediate 222

4-Methyl-1,2,5-oxadiazole-3-carbonyl C

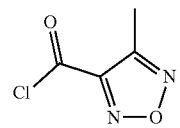

A round bottom flask was charged with a stir bar, 4-methyl-1,2,5-oxadiazole-3-carboxylic acid (6.4 g, 50 mmol), DCM (100 mL) and was cooled to 0° C. under a nitrogen atmosphere. To the solution was added oxalyl chloride (8.6 mL, 100 mmol) followed by DMF (0.4 mL, 5 mmol) dropwise. The reaction was stirred as it slowly warmed to rt. Once the gas evolution ceased the reaction was condensed into a yellow oil which was then taken up in 25 mL of dry DCM to be stored as a 2 M solution.

Intermediate 223

2,5-Dioxopyrrolidin-1-yl 4-methyl-1,2,5-oxadiazole-3-carboxylate

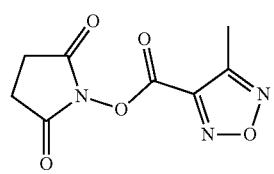 [SMILES: Cc1nonc1C(=O)ON1C(=O)CCC1=O]

A round bottom flask was charged with a stir bar, N-hydroxysuccinimide (1.8 g, 15 mmol), DCM (25 mL), and DIPEA (2.6 mL, 15 mmol), and cooled to 0° C. under a nitrogen atmosphere. To the solution was added a solution of 4-methyl-1,2,5-oxadiazole-3-carbonyl chloride (5 mL, 10 mmol, 2 M in DCM, Intermediate 222). The solution was allowed to warm to rt as it stirred for 1 h. The solution was washed with water, and brine, dried over anhydrous MgSO$_4$, filtered, and concentrated. The crude material was purified by silica gel chromatography (0-100% EtOAc (with 10% MeOH)/hexanes) to afford the title compound as an off white solid.

Intermediate 224

N—((R)-(2-((S)-Amino(4,4-difluorocyclohexyl)methyl)imidazo[1,2-b]pyridazin-7-yl)(cyclopropyl)methyl)-2-(bicyclo[1.1.1]pentan-1-yl)acetamide

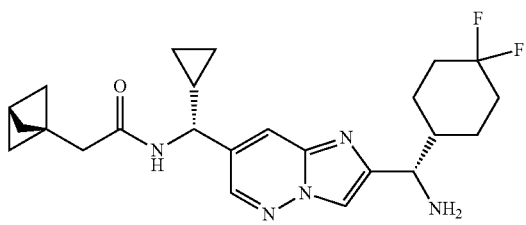

The title compound was prepared as described for Intermediate 51 using 2-(bicyclo[1.1.1]pentan-1-yl)acetic acid in place of 4,4,4-trifluorobutanoic acid to afford the title compound as a white solid.

Intermediate 225

3-Fluorobicyclo[1.1.1]pentane-1-carbonyl Chloride

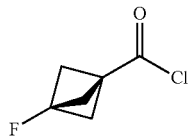

A vial was charged with a stir bar, 3-fluorobicyclo[1.1.1]pentane-1-carboxylic acid (300 mg, 2.3 mmol) and DCM (8 mL). To the solution was added oxalyl chloride (0.3 mL, 3.5 mmol) dropwise followed by 1 drop of DMF. The reaction was stirred until gas evolution ceased, about 30 min. The reaction was concentrated to afford the title compound as a pale yellow solid.

Intermediate 226

2-Diazo-1-(3-fluorobicyclo[1.1.1]pentan-1-yl)ethan-1-one

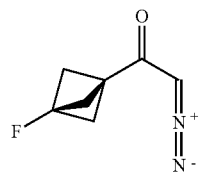

A round bottom flask was charged with a stir bar, 3-fluorobicyclo[1.1.1]pentane-1-carbonyl chloride (342 mg, 2.3 mmol, Intermediate 225), THF (4 mL), and MeCN (4 mL). The reaction was placed under a nitrogen atmosphere and cooled to 0° C. To the reaction was added (trimethylsilyl)diazomethane (2.3 mL, 4.6 mmol, 2 M in hexanes). The reaction was stirred for 3 h then concentrated, diluted with diethyl ether and washed with 0.5 M aqueous citric acid followed by 5% aqueous sodium bicarbonate. The combined organics were washed with brine, dried over anhydrous MgSO$_4$, filtered and concentrated to dryness. The crude material was purified by silica gel chromatography (0-100% EtOAc/hexanes) to afford the title compound as an orange solid.

Intermediate 227

Tert-Butyl ((S)-(7-((R)-cyclopropyl(2-(3-fluorobicyclo[1.1.1]pentan-1-yl)acetamido)methyl)imidazo[1,2-b]pyridazin-2-yl)(4,4-difluorocyclohexyl)methyl)carbamate

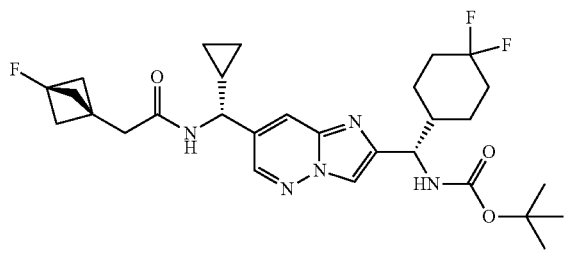 [SMILES: CC(C)(C)OC(=O)N[C@H](c1cn2ncc([C@H](NC(=O)C[C@]34C[C@](F)(C3)C4)C3CC3)cc2n1)C1CCC(F)(F)CC1]

A vial was charged with a stir bar, tert-butyl ((S)-(7-((R)-amino(cyclopropyl)methyl)imidazo[1,2-b]pyridazin-2-yl)(4,4-difluorocyclohexyl)methyl)carbamate (466 mg, 1.1 mmol, Intermediate 49), MeCN (9.5 mL), 2-diazo-1-(3-fluorobicyclo[1.1.1]pentan-1-yl)ethan-1-one (150 mg, 0.97 mmol, Intermediate 226), DIPEA (0.5 mL, 2.9 mmol), and silver benzoate (22 mg, 0.1 mmol). The reaction was stirred overnight at 45° C. The reaction was poured over water and extracted with EtOAc (3×5 mL). The combined organic layers were washed with brine, dried over anhydrous MgSO$_4$, filtered, and concentrated. The crude material was purified by silica gel chromatography (0-100% EtOAc (with 10% MeOH)/hexanes) to afford the title compound as a white solid.

Intermediate 228

N—((R)-(2-((S)-Amino(4,4-difluorocyclohexyl)methyl)imidazo[1,2-b]pyridazin-7-yl)(cyclopropyl)methyl)-2-(3-fluorobicyclo[1.1.1]pentan-1-yl)acetamide

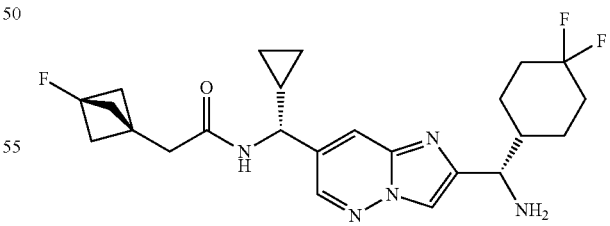

The material was prepared as described for Intermediate 51 using tert-butyl ((S)-(7-((R)-cyclopropyl(2-(3-fluorobicyclo[1.1.1]pentan-1-yl)acetamido)methyl)imidazo[1,2-b]pyridazin-2-yl)(4,4-difluorocyclohexyl)methyl)carbamate (Intermediate 227) in place of tert-butyl ((S)-(7-((R)-cyclopropyl(4,4,4-trifluorobutanamido)methyl)imidazo[1,2-b]pyridazin-2-yl)(4,4-difluorocyclohexyl)methyl) carbamate to afford the title compound as a white foam.

Intermediate 229

N—((R)-(2-((S)-Amino(4,4-difluorocyclohexyl)methyl)imidazo[1,2-b]pyridazin-7-yl)(cyclopropyl)methyl)-4,4,4-trifluoro-3-methylbutanamide

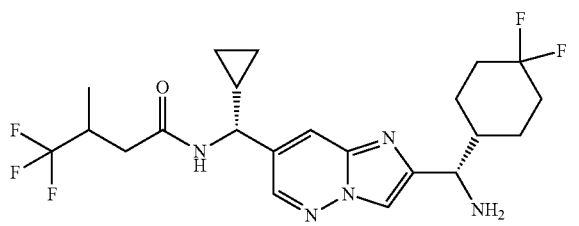 [SMILES: CC(CC(=O)N[C@@H](c1cnn2cc([C@@H](N)C3CCC(F)(F)CC3)nc2c1)C1CC1)C(F)(F)F]

The title compound was prepared as described for Intermediate 51 using 4,4,4-trifluoro-3-methylbutanoic acid in place of 4,4,4-trifluorobutanoic acid to afford the title compound as a white solid.

Intermediate 230

N—((R)-(2-((S)-Amino(4,4-difluorocyclohexyl)methyl)imidazo[1,2-b]pyridazin-7-yl)(cyclopropyl)methyl)-2-(1-(trifluoromethyl)cyclopropyl)acetamide

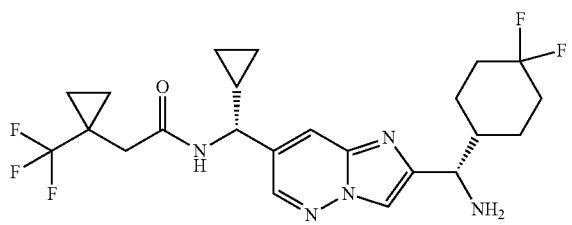 [SMILES: N[C@H](c1cn2ncc([C@H](NC(=O)CC3(C(F)(F)F)CC3)C3CC3)cc2n1)C1CCC(F)(F)CC1]

The title compound was prepared as described for Intermediate 51 using 2-(1-(trifluoromethyl)cyclopropyl)acetic acid in place of 4,4,4-trifluorobutanoic acid to afford the title compound as a white solid.

Intermediate 231

Tert-Butyl ((S)-(7-((R)-cyclopropyl(2-(2,2,2-trifluoroethoxy)acetamido)methyl)imidazo[1,2-b]pyridazin-2-yl)(4,4-difluorocyclohexyl)methyl)carbamate

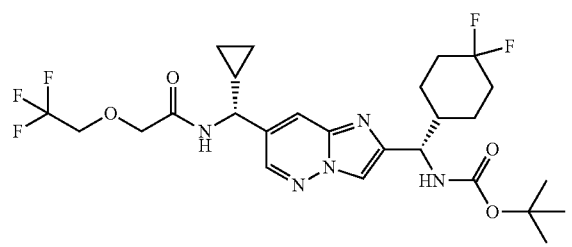 [SMILES: CC(C)(C)OC(=O)N[C@H](c1cn2ncc([C@H](NC(=O)COCC(F)(F)F)C3CC3)cc2n1)C1CCC(F)(F)CC1]

To a solution of 2-(2,2,2-trifluoroethoxy)acetic acid (0.1 g, 0.63 mmol), tert-butyl ((S)-(7-((R)-amino(cyclopropyl)methyl)imidazo[1,2-b]pyridazin-2-yl)(4,4-difluorocyclohexyl)methyl)carbamate (303 mg, 0.70 mmol, Intermediate 49), EDCI (242 mg, 1.26 mmol) and HOBt (103 mg, 0.76 mmol) in DCM (3 mL) was added Hünig's base (0.33 mL, 1.9 mmol). The mixture was stirred at rt overnight. The mixture was concentrated under reduced pressure to give a residue. The residue was purified by silica gel chromatography (0-2% MeOH/DCM) to afford the title compound as a white powder.

Intermediate 232

N—((R)-(2-((S)-Amino(4,4-difluorocyclohexyl)methyl)imidazo[1,2-b]pyridazin-7-yl)(cyclopropyl)methyl)-2-(2,2,2-trifluoroethoxy)acetamide Hydrochloride

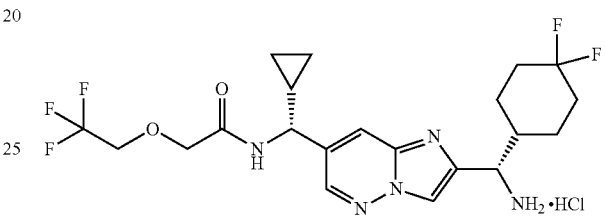

To a solution of tert-butyl ((S)-(7-((R)-cyclopropyl(2-(2,2,2-trifluoroethoxy)acetamido)methyl)imidazo[1,2-b]pyridazin-2-yl)(4,4-difluorocyclohexyl)methyl)carbamate (300 mg, 0.52 mmol, Intermediate 231) in MeOH (3 mL) was added HCl (3.0 mL, 12 mmol, 4 M solution in EtOAc). The mixture was stirred at rt overnight. The mixture was concentrated under reduced pressure to give the crude hydrochloride salt as a white solid.

Intermediate 233

N—((R)-(2-((S)-Amino(4,4-difluorocyclohexyl)methyl)imidazo[1,2-b]pyridazin-7-yl)(cyclopropyl)methyl)-2-(2,2-difluoroethoxy)acetamide

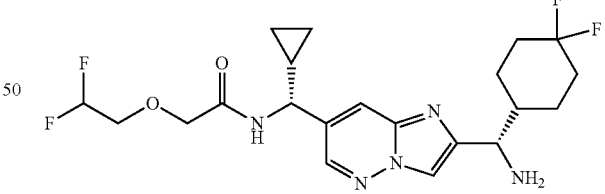

The title compound was prepared as described for the synthesis of Intermediate 232 using 2-(2,2-difluoroethoxy)acetic acid in place of 2-(2,2,2-trifluoroethoxy)acetic acid. The crude residue was taken up in water and washed with hexanes. The resulting aqueous phase was made basic by the addition of 1 N aqueous NaOH and extracted with DCM. The organic phase was dried over anhydrous Na$_2$SO$_4$, filtered, and concentrated. The crude material was purified by preparative HPLC (Stationary phase: Boston Prime C18 (150×30 mm×5 m), Mobile phase: 35-65% MeCN/water (0.05% NH$_4$OH+10 mM NH$_4$HCO$_3$)) to afford the title compound as a white powder.

Intermediate 234

2-Cyclopropoxyacetic Acid

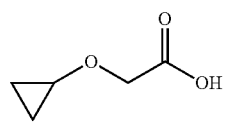

To a solution of cyclopropanol (10 g, 0.17 mol) in THF (150 mL) was added NaH (14 g of a 60% dispersion in mineral oil, 0.36 mmol) at 0° C. The reaction was stirred for 2 h at rt. Then, 2-bromoacetic acid (20 g, 0.14 mmol) was added and the reaction was stirred at rt for 20 h. The mixture was slowly added to ice water (300 mL) and stirred until a clear solution was obtained. The solution was extracted with Et$_2$O (200 mL). The aqueous layer was acidified with concentrated HCl (30 mL) to pH=1 and extracted with Et$_2$O (3×50 mL). The combined organic extracts were dried over anhydrous Na$_2$SO$_4$, filtered, and concentrated under reduced pressure to give the title compound as a brown liquid.

Intermediate 235

Tert-Butyl ((S)-(7-((R)-cyclopropyl(2-(3,3-difluoro-cyclobutoxy)acetamido)methyl)imidazo[1,2-b]pyridazin-2-yl)(4,4-difluorocyclohexyl)methyl)carbamate

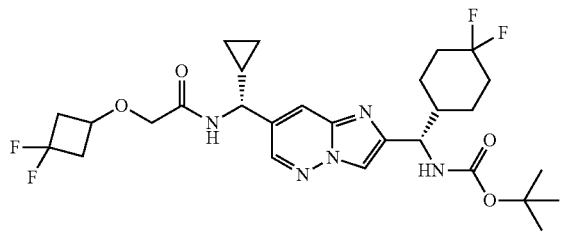 [SMILES: CC(C)(C)OC(=O)N[C@H](c1cn2ncc([C@H](NC(=O)COC3CC(F)(F)C3)C3CC3)cc2n1)C1CCC(F)(F)CC1]

The title compound was prepared as described for Intermediate 231 using 2-(3,3-difluorocyclobutoxy)acetic acid in place of 2-(2,2,2-trifluoroethoxy)acetic acid to afford the title compound as a white powder.

Intermediate 236

(S)-(7-((R)-Cyclopropyl(2-(3,3-difluorocyclobutoxy)acetamido)methyl)imidazo[1,2-b]pyridazin-2-yl)(4,4-difluorocyclohexyl)methanaminium Trifluoroacetate

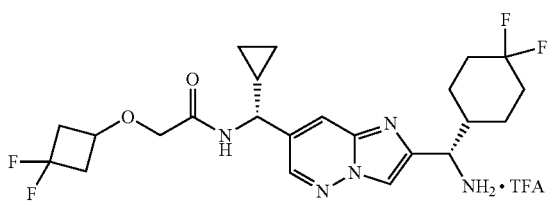 [SMILES: N[C@H](c1cn2ncc([C@H](NC(=O)COC3CC(F)(F)C3)C3CC3)cc2n1)C1CCC(F)(F)CC1]

tert-Butyl ((S)-(7-((R)-cyclopropyl(2-(3,3-difluorocyclobutoxy)acetamido)methyl) imidazo[1,2-b]pyridazin-2-yl)(4,4-difluorocyclohexyl)methyl)carbamate (232 mg, 0.40 mmol, Intermediate 235) and TFA (6 mL) were stirred at 25° C. for 0.5 h. The reaction mixture was concentrated to dryness under reduced pressure to afford the title trifluoroacetate salt as a brown oil.

Intermediate 237

Diethyl 2-(1,1-difluoropropan-2-ylidene)malonate

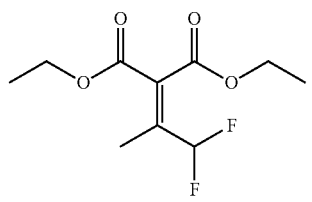 [SMILES: CCOC(=O)C(C(=O)OCC)=C(C)C(F)F]

A round bottom flask charged with a stir bar and THF (350 mL) was cooled to 0° C. under a N$_2$ atmosphere. To the solution was added TiCl$_4$ (23.7 g, 0.13 mol) dropwise and a yellow suspension was observed. To the resulting suspension was added CCl$_4$ (6.3 mL, 65.6 mmol) dropwise, followed by diethyl malonate (10.0 g, 62.4 mmol) and 1,1-difluoropropan-2-one (7.05 g, 74.9 mmol) at 0° C. The reaction was stirred for 1 h at 0° C., then pyridine (40.4 mL, 0.5 mol) was added dropwise. The mixture was stirred at 0° C. for 1 h then warmed to rt and stirred overnight. The mixture was poured into water (1.6 L) and extracted with MTBE (150 mL×3), washed with brine (200 mL), dried over anhydrous Na$_2$SO$_4$, filtered, and concentrated. The residue was purified by silica gel chromatography (0-10% EtOAc/petroleum ether) to afford the title compound as a colorless liquid.

Intermediate 238

Diethyl 2-(1,1-difluoro-2-methylpropan-2-yl)malonate

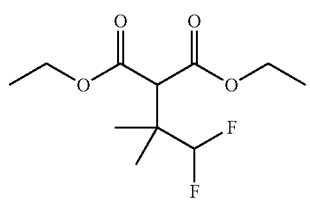 [SMILES: CCOC(=O)C(C(=O)OCC)C(C)(C)C(F)F]

To a solution of diethyl 2-(1,1-difluoropropan-2-ylidene)malonate (2.00 g, 8.5 mmol, Intermediate 237) in DCM (20 mL) and THF (5 mL) was added CuI (2.4 g, 12.7 mmol) followed by MeMgBr (8.5 mL, 25.4 mmol, 3 M in Et$_2$O) dropwise at −20° C. The dark mixture was stirred at −20° C. for 1 h. The solution was poured into ice-water (50 mL) and treated with saturated aqueous NH$_4$Cl (50 mL). Then the mixture was stirred for 30 min at 15° C. The solids were removed by filtration and the filtrate was extracted with DCM (30 mL×3). The organic phase was washed with brine (30 mL), dried over anhydrous Na$_2$SO$_4$, filtered, and concentrated under vacuum. The residue was purified by silica gel chromatography (0-10% EtOAc/petroleum ether) to afford the title compound as a colorless liquid.

Intermediate 239

4,4-Difluoro-3,3-dimethylbutanoic Acid

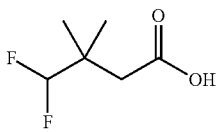

To a solution of diethyl 2-(1,1-difluoro-2-methylpropan-2-yl)malonate (1.3 g, 8.5 mmol, Intermediate 238) in DMSO (13 mL), LiOH·H$_2$O (1.1 g, 25.8 mmol) in H$_2$O (2 mL) was added, then the yellow solution was stirred at 90° C. for 16 h. The reaction was cooled to 20° C. and diluted with EtOAc (60 mL) and H$_2$O (60 mL). The layers were separated, and the aqueous phase was washed with EtOAc (30 mL×2). The resulting aqueous phase was adjusted to pH=2 with concentrated HCl and extracted with EtOAc (50 mL×3). The organic layer was washed with brine (50 mL), dried over anhydrous Na$_2$SO$_4$, filtered, and concentrated under vacuum. The residue was purified by silica gel chromatography (0-10% EtOAc/petroleum ether) to afford the title compound as a colorless liquid.

Intermediate 240

Tert-Butyl (S)-(1-(tert-butoxy)-4-(dimethyl(oxo)-λ$^6$-sulfaneylidene)-3-oxobutan-2-yl)carbamate

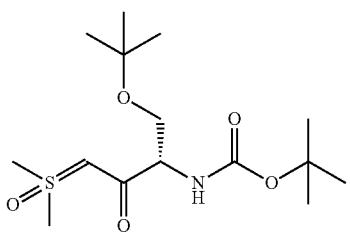 [SMILES: CC(C)(C)OC[C@H](NC(=O)OC(C)(C)C)C(=O)C=S(C)(C)=O]

To a suspension of trimethylsulfoxonium iodide (14.5 g, 65.9 mmol) in THF (155 mL) was added potassium tert-butoxide (7.29 g, 64.3 mmol). The mixture was heated to 80° C. for 2 h then cooled to 0° C. In a separate flask a solution of isobutyl chloroformate (5.00 mL, 38.3 mmol) in THF (115 mL) was cooled to 0° C. then a solution of N-(tert-butoxycarbonyl)-O-(tert-butyl)-L-serine (10.0 g, 38.3 mmol) and triethylamine (5.30 mL, 38.3 mmol) in THF (45 mL) was added dropwise utilizing an addition funnel. The resulting suspension was filtered then added to the previous mixture dropwise over 30 min utilizing an addition funnel while maintaining the reaction temperature at 0° C. The reaction was stirred at this temperature for 2 h then quenched with water. The mixture was extracted with EtOAc (3×200 mL) then the combined organic extracts were washed with brine, dried over anhydrous MgSO$_4$, filtered, and concentrated to afford the title compound.

Intermediate 241

Tert-Butyl (R)-(2-(tert-butoxy)-1-(7-chloroimidazo[1,2-b]pyridazin-2-yl)ethyl)carbamate

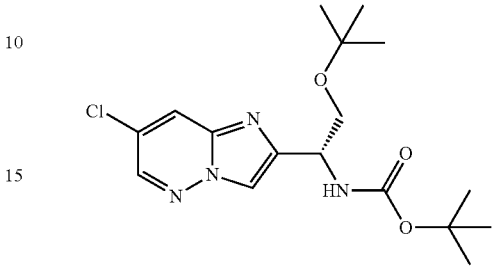

An oven dried round bottom flask was charged with 5-chloropyridazin-3-amine (3.89 g, 30.0 mmol, Intermediate 17), tert-butyl (S)-(1-(tert-butoxy)-4-(dimethyl(oxo)-26-sulfaneylidene)-3-oxobutan-2-yl)carbamate (11.1 g, 33.1 mmol, Intermediate 240), chlorocyclopentadienylbis(triphenylphosphine)ruthenium (II) (551 mg, 0.758 mmol), sodium trifluoromethanesulfonate (273 mg, 1.59 mmol) and 4 Å molecular sieves (7.8 g). Anhydrous toluene (100 mL) was added under an atmosphere of N$_2$ then the reaction was heated to 85° C. for 15 h. The mixture was allowed to cool to rt then filtered through diatomaceous earth (Celite®). The filter pad was washed with EtOAc and then the combined filtrate and wash was concentrated. The residue was purified by silica gel chromatography (0-40% EtOAc/hexanes) to provide the title compound.

Intermediate 242

Tert-Butyl (R)-(2-(tert-butoxy)-1-(7-vinylimidazo[1,2-b]pyridazin-2-yl)ethyl)carbamate

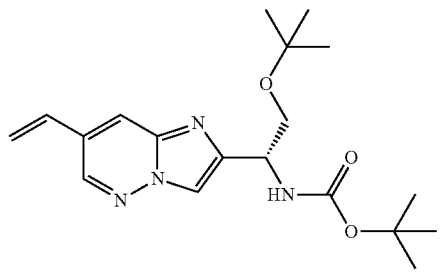 [SMILES: C=Cc1cnn2cc([C@H](COC(C)(C)C)NC(=O)OC(C)(C)C)nc2c1]

The title compound was prepared as described for the synthesis of Intermediate 45, using tert-butyl (R)-(2-(tert-butoxy)-1-(7-chloroimidazo[1,2-b]pyridazin-2-yl)carbamate (Intermediate 241) in place of tert-butyl N—[(S)-(7-chloroimidazo[1,2-b]pyridazin-2-yl)-(4,4-difluorocyclohexyl)methyl] carbamate.

Intermediate 243

Tert-Butyl (R)-(2-(tert-butoxy)-1-(7-formylimidazo[1,2-b]pyridazin-2-yl)ethyl)carbamate

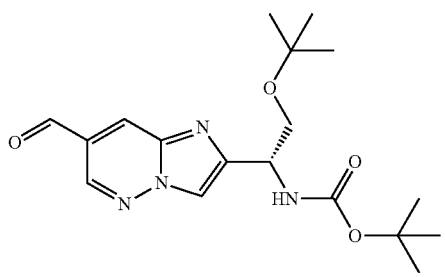 [SMILES: CC(C)(C)OC[C@H](NC(=O)OC(C)(C)C)c1cn2ncc(C=O)cc2n1]

The title compound was prepared as described for the synthesis of Intermediate 46, using tert-butyl (R)-(2-(tert-butoxy)-1-(7-vinylimidazo[1,2-b]pyridazin-2-yl)ethyl)carbamate (Intermediate 242) in place of tert-butyl (S)-((4,4-difluorocyclohexyl)(7-vinylimidazo[1,2-b]pyridazin-2-yl)methyl)carbamate.

Intermediate 244

Tert-Butyl ((R)-2-(tert-butoxy)-1-(7-((E)-(((S)-tert-butylsulfinyl)imino)methyl)imidazo[1,2-b]pyridazin-2-yl)ethyl)carbamate

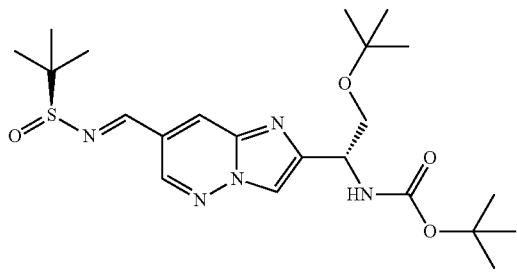 [SMILES: CC(C)(C)OC[C@H](NC(=O)OC(C)(C)C)c1cn2ncc(/C=N/[S@@](=O)C(C)(C)C)cc2n1]

The title compound was prepared as described for the synthesis of Intermediate 47, using tert-butyl (R)-(2-(tert-butoxy)-1-(7-formylimidazo[1,2-b]pyridazin-2-yl)ethyl)carbamate (Intermediate 243) in place of tert-butyl (S)-((4,4-difluorocyclohexyl)(7-formylimidazo[1,2-b]pyridazin-2-yl)methyl)carbamate.

Intermediate 245

Tert-Butyl ((1R)-2-(tert-butoxy)-1-(7-((((S)-tert-butylsulfinyl)amino)(cyclopropyl)methyl)imidazo[1,2-b]pyridazin-2-yl)ethyl)carbamate

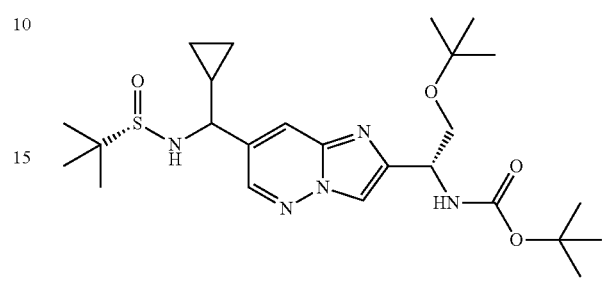

Intermediate 246

Tert-Butyl ((R)-2-(tert-butoxy)-1-(7-((R)-(((S)-tert-butylsulfinyl)amino)(cyclopropyl)methyl)imidazo[1,2-b]pyridazin-2-yl)ethyl)carbamate

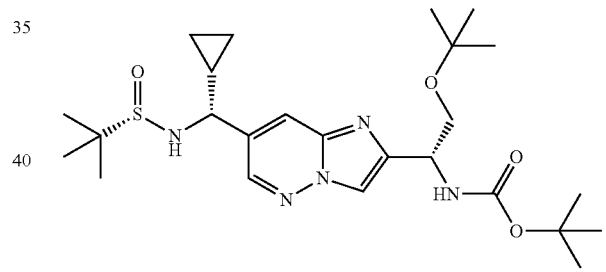

A solution of tert-butyl ((R)-2-(tert-butoxy)-1-(7-((E)-(((S)-tert-butylsulfinyl)imino)methyl)imidazo[1,2-b]pyridazin-2-yl)ethyl)carbamate (1.89 g, 4.06 mmol, Intermediate 244) in $CH_2Cl_2$ (53 mL) was cooled to −78° C. then cyclopropylmagnesium bromide (9.3 mL, 9.3 mmol, 1 M in 2-MeTHF) was added over 30 min utilizing a syringe pump. The reaction was maintained at this temperature for an additional 30 min then warmed to 0° C. and quenched by addition of a saturated aqueous $NH_4Cl$ solution. The mixture was warmed to rt, diluted with $H_2O$, then extracted with EtOAc. The combined organic extracts were dried over anhydrous $Na_2SO_4$, filtered, and concentrated to dryness. The residue was purified by silica gel chromatography (10-70% acetone/hexanes) to provide the title compounds. Intermediate 246 was further purified by trituration in 40% acetone/hexanes to provide the title compound as a single diastereomer.

Intermediate 247

Tert-Butyl ((1R)-1-(7-(amino(cyclopropyl)methyl)imidazo[1,2-b]pyridazin-2-yl)-2-(tert-butoxy)ethyl)carbamate

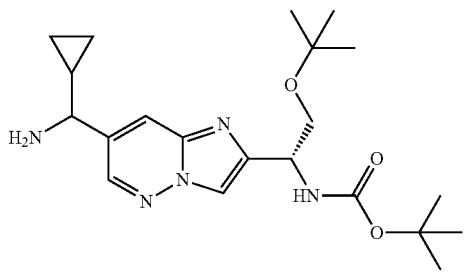 [SMILES: CC(C)(C)OC[C@H](NC(=O)OC(C)(C)C)c1cn2ncc(C(N)C3CC3)cc2n1]

A solution of HCl in 1,4-dioxane (0.19 mL, 0.77 mmol, 4.0 M) was added to a solution of tert-butyl ((1R)-2-(tert-butoxy)-1-(7-(((((S)-tert-butylsulfinyl)amino)(cyclopropyl)methyl)imidazo[1,2-b]pyridazin-2-yl)ethyl)carbamate (169 mg, 0.333 mmol, Intermediate 245) in EtOAc (2 mL), and the mixture was stirred at rt for 1 h. The suspension was then diluted with water (5 mL) and the layers were mixed and then separated. The organic layer was extracted with water (5 mL) and 1 M aqueous HCl (2 mL), and the aqueous layers were all combined and then washed with $Et_2O$ (10 mL). The $Et_2O$ wash was discarded. The aqueous layer was made basic with a 1 M aqueous NaOH solution, and then extracted three times with EtOAc. The organic extracts were combined, dried with anhydrous $Na_2SO_4$, filtered, and then concentrated to afford the title compound.

Intermediate 248

Tert-Butyl ((1R)-2-(tert-butoxy)-1-(7-(cyclopropyl(4,4,4-trifluorobutanamido)methyl)imidazo[1,2-b]pyridazin-2-yl)ethyl)carbamate

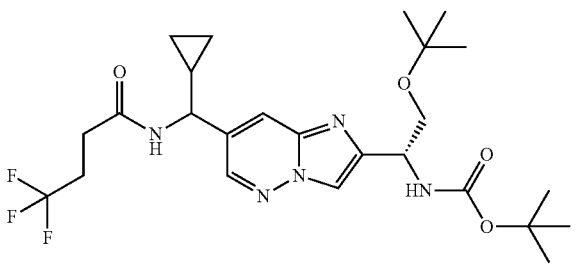 [SMILES: CC(C)(C)OC[C@H](NC(=O)OC(C)(C)C)c1cn2ncc(C(NC(=O)CCC(F)(F)F)C3CC3)cc2n1]

The title compound was prepared as described for the synthesis of Intermediate 50, using tert-butyl ((1R)-1-(7-(amino(cyclopropyl)methyl)imidazo[1,2-b]pyridazin-2-yl)-2-(tert-butoxy)ethyl)carbamate (Intermediate 247) in place of tert-butyl ((S)-(7-((R)-amino(cyclopropyl)methyl)imidazo[1,2-b]pyridazin-2-yl)(4,4-difluorocyclohexyl)methyl)carbamate.

Intermediate 249

N-((2-((R)-1-Amino-2-(tert-butoxy)ethyl)imidazo[1,2-b]pyridazin-7-yl)(cyclopropyl)methyl)-4,4,4-trifluorobutanamide

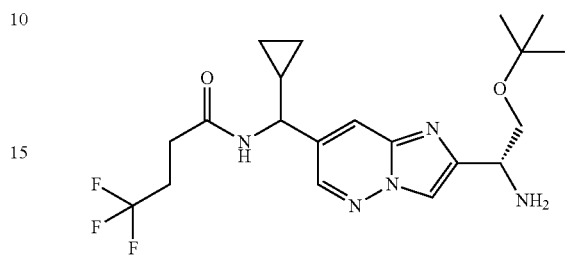

A solution of HCl in 1,4-dioxane (0.28 mL, 1.1 mmol, 4.0 M) was added to a solution of tert-butyl ((1R)-2-(tert-butoxy)-1-(7-(cyclopropyl(4,4,4-trifluorobutanamido)methyl)imidazo[1,2-b]pyridazin-2-yl)ethyl)carbamate (147 mg, 0.279 mmol, Intermediate 248) in EtOAc (1.4 mL) and the reaction stirred at rt for 1 h. At this time additional HCl in 1,4-dioxane (0.07 mL, 0.28 mmol, 4.0 M) was added and the reaction stirred at rt overnight. After 24 h additional HCl in 1,4-dioxane (0.07 mL, 0.28 mmol, 4.0 M) was added and the reaction stirred at rt overnight then extracted with $H_2O$, 1 M aqueous HCl, and $H_2O$. The combined aqueous extracts were basified with 1 M aqueous NaOH and extracted with EtOAc. The combined organic extracts were dried over anhydrous $Na_2SO_4$, filtered, and condensed to provide the title compound.

Intermediate 250

Tert-Butyl ((R)-1-(7-((R)-amino(cyclopropyl)methyl)imidazo[1,2-b]pyridazin-2-yl)-2-(tert-butoxy)ethyl)carbamate

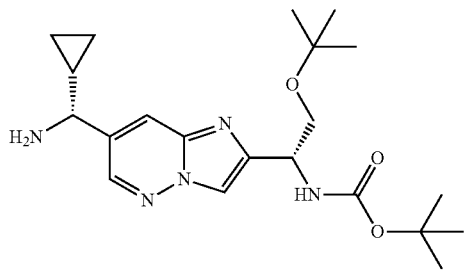

The title compound was prepared as described for the synthesis of Intermediate 247, using tert-butyl ((R)-2-(tert-butoxy)-1-(7-((R)-(((S)-tert-butylsulfinyl)amino)(cyclopropyl)methyl)imidazo[1,2-b]pyridazin-2-yl)ethyl)carbamate (Intermediate 246) in place of tert-butyl ((1R)-2-(tert-butoxy)-1-(7-(((((S)-tert-butylsulfinyl)amino)(cyclopropyl)methyl)imidazo[1,2-b]pyridazin-2-yl)ethyl)carbamate to provide the title compound.

Intermediate 251

Tert-Butyl ((R)-2-(tert-butoxy)-1-(7-((R)-cyclopropyl(2-(3,3-difluorocyclobutyl)acetamido)methyl)imidazo[1,2-b]pyridazin-2-yl)ethyl)carbamate

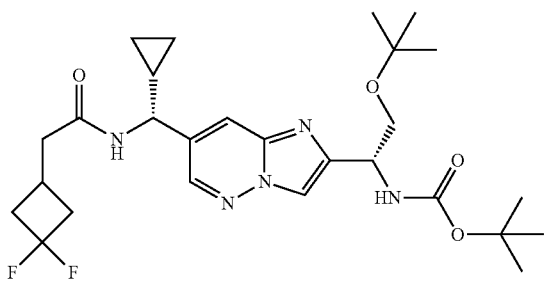 [SMILES: CC(C)(C)OC[C@H](NC(=O)OC(C)(C)C)c1cn2ncc([C@H](NC(=O)CC3CC(F)(F)C3)C3CC3)cc2n1]

The title compound was prepared as described for the synthesis of Intermediate 50, using tert-butyl ((R)-1-(7-((R)-amino(cyclopropyl)methyl)imidazo[1,2-b]pyridazin-2-yl)-2-(tert-butoxy)ethyl)carbamate (Intermediate 250) in place of tert-butyl ((S)-(7-((R)-amino(cyclopropyl)methyl)imidazo[1,2-b]pyridazin-2-yl)(4,4-difluorocyclohexyl)methyl)carbamate and 2-(3,3-difluorocyclobutyl)acetic acid in place of 4,4,4-trifluorobutyric acid.

Intermediate 252

N—((R)-(2-((R)-1-Amino-2-(tert-butoxy)ethyl)imidazo[1,2-b]pyridazin-7-yl)(cyclopropyl)methyl)-2-(3,3-difluorocyclobutyl)acetamide

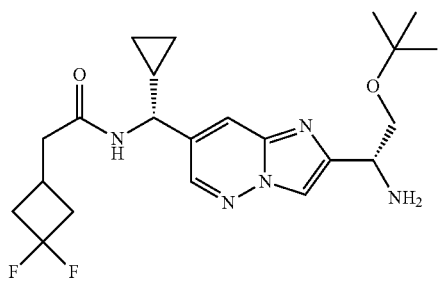 [SMILES: CC(C)(C)OC[C@H](N)c1cn2ncc([C@H](NC(=O)CC3CC(F)(F)C3)C3CC3)cc2n1]

To a solution of tert-butyl ((R)-2-(tert-butoxy)-1-(7-((R)-cyclopropyl(2-(3,3-difluorocyclobutyl)acetamido)methyl)imidazo[1,2-b]pyridazin-2-yl)ethyl)carbamate (508 mg, 0.948 mmol, Intermediate 251) in CH$_2$Cl$_2$ (1.8 mL) was added TFA (1 mL) and the reaction stirred at rt for 3 h. After this time 1 M aqueous NaOH (20 mL) was carefully added then the mixture was extracted with CH$_2$Cl$_2$. The combined organic extracts were dried over anhydrous Na$_2$SO$_4$, filtered and condensed to afford the title compound.

Intermediate 253

Tert-Butyl (S)-(4-chloro-3-oxo-1-((1,1,1-trifluoro-2-methylpropan-2-yl)oxy)butan-2-yl)carbamate

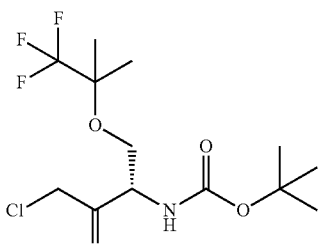

An oven dried round bottom flask was charged with anhydrous lithium chloride (212 mg, 5.01 mmol) and tert-butyl (S)-(4-(dimethyl(oxo)-$\lambda^6$-sulfaneylidene)-3-oxo-1-((1,1,1-trifluoro-2-methylpropan-2-yl)oxy)butan-2-yl)carbamate (780 mg, 2.00 mmol, Intermediate 282) under an N$_2$ atmosphere. Anhydrous THF (14 mL) was added, the reaction was cooled to 0° C., then methanesulfonic acid (143 μL, 2.20 mmol) was added dropwise. The reaction was maintained at 0° C. for 10 min then heated to 60° C. for 3 h. After this time the mixture was cooled to rt, diluted with H$_2$O, and extracted with 1:1 EtOAc:hexanes. The organic extracts were washed with brine, dried over anhydrous Na$_2$SO$_4$, filtered, and condensed to provide the title compound which was used without further purification.

Intermediate 254

Tert-Butyl (S)-(4-iodo-3-oxo-1-((1,1,1-trifluoro-2-methylpropan-2-yl)oxy)butan-2-yl)carbamate

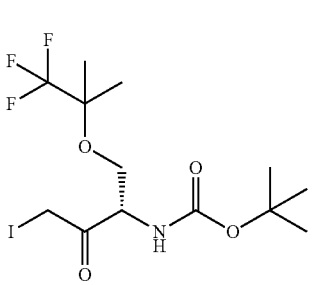 [SMILES: CC(C)(C)OC(=O)N[C@@H](COC(C)(C)C(F)(F)F)C(=O)CI]

A mixture of tert-butyl (S)-(4-chloro-3-oxo-1-((1,1,1-trifluoro-2-methylpropan-2-yl)oxy)butan-2-yl)carbamate (610 mg, 1.75 mmol, Intermediate 253) and NaI (2.63 g, 17.5 mmol) in acetone was stirred at rt for 1 h then diluted with EtOAc and filtered. The filtrate was washed with saturated aqueous sodium thiosulfate then dried over anhydrous Na$_2$SO$_4$, filtered, and condensed to afford the title compound which was used without further purification.

Intermediate 255

(S,E)-N-(Cyclopropylmethylene)-2-methylpropane-2-sulfinamide

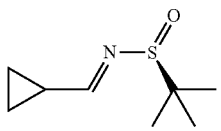

To a solution of cyclopropanecarboxaldehyde (24 mL, 320 mmol) and (S)-2-methylpropane-2-sulfinamide (35 g, 290 mmol) in CH$_2$Cl$_2$ (570 mL) was added copper(II) sulfate (138 g, 866 mmol) and PPTS (3.63 g, 14.4 mmol). The mixture was stirred at rt for 40 h then cyclopropanecarboxaldehyde (2.15 mL, 28.9 mmol) and copper(II) sulfate (23 g, 140 mmol) were added and the reaction stirred for an additional 72 h. After this time the mixture was filtered through diatomaceous earth (Celite®) and condensed. The residue was purified by filtration through silica gel (40% EtOAc/hexanes) to afford the title compound.

Intermediate 256

N-(6-Chloropyridazin-3-yl)pivalamide

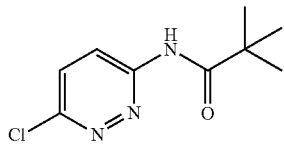

To a suspension of 6-chloropyridazin-3-amine (14.3 g, 110 mmol) and pyridine (17.8 mL, 221 mmol) in CH$_2$Cl$_2$ (286 mL) was added pivaloyl chloride (34.0 mL, 276 mmol) and the reaction stirred at rt overnight. The mixture was diluted with 1 N aqueous NaOH and stirred for 1 h then the layers were separated. The aqueous layer was extracted with CH$_2$Cl$_2$ then the combined organic layers were dried over anhydrous MgSO$_4$, filtered, and condensed. The residue was triturated with hexanes, filtered, and air dried to afford the title compound.

Intermediate 257

N-(5-((R)-(((S)-tert-Butylsulfinyl)amino)(cyclopropyl)methyl)-6-chloropyridazin-3-yl)pivalamide

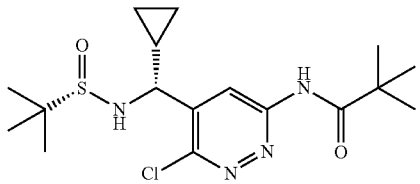 [SMILES: CC(C)(C)C(=O)Nc1cc([C@H](N[S@@](=O)C(C)(C)C)C2CC2)c(Cl)nn1]

A solution of N-(6-chloropyridazin-3-yl)pivalamide (26.0 g, 122 mmol, Intermediate 256) in THF (250 mL) was added via cannula transfer to a −40° C. solution of TMPMgCl·LiCl (361 mL, 316 mmol, 0.88 M in THF) over a period of 30 min. The reaction was maintained at −40° C. for 3 h then (S,E)-N-(cyclopropylmethylene)-2-methylpropane-2-sulfinamide (26.6 g, 146 mmol, Intermediate 255) was added and the reaction allowed to warm to rt. After 1.5 h an additional portion of (S,E)-N-(cyclopropylmethylene)-2-methylpropane-2-sulfinamide (6.6 g, 37 mmol, Intermediate 255) was added and the reaction was stirred at rt overnight. The reaction mixture was quenched with saturated aqueous NH$_4$Cl then partitioned between water and EtOAc. The aqueous layer was extracted twice with EtOAc then the combined organic layers were washed with brine, dried over anhydrous MgSO$_4$, filtered, and concentrated. Purification by silica gel chromatography (25-50% acetone/hexanes) provided the title compound.

Intermediate 258

(R)-5-(Amino(cyclopropyl)methyl)-6-chloropyridazin-3-amine

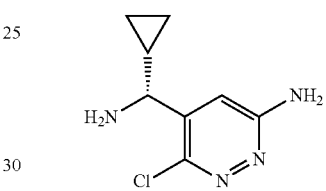

To a mixture of N-(5-((R)-(((S)-tert-butylsulfinyl)amino)(cyclopropyl)methyl)-6-chloropyridazin-3-yl)pivalamide (42.6 g, 93.5 mmol, Intermediate 257) in H$_2$O (181 mL) was added concentrated HCl (181 mL, 2170 mmol, 37% in H$_2$O). The reaction was stirred at 45° C. for 24 h then allowed to cool to rt and aged for 18 h. The resulting solution was then washed twice with EtOAc, and the organic layers were discarded. The pH was adjusted to pH 10-11 with solid Na$_2$CO$_3$ (114 g, 1080 mmol), brine was added, and the mixture was extracted with EtOAc, nBuOH, and 3:1 EtOAc: nBuOH. The organic layers were combined, dried over anhydrous MgSO$_4$, filtered, and concentrated. The concentrate was diluted with EtOAc, and the suspension was filtered through Celite® and then concentrated to provide the title compound.

Intermediate 259

(R)—N-((6-Amino-3-chloropyridazin-4-yl)(cyclopropyl)methyl)-2-(3,3-difluorocyclobutyl)acetamide

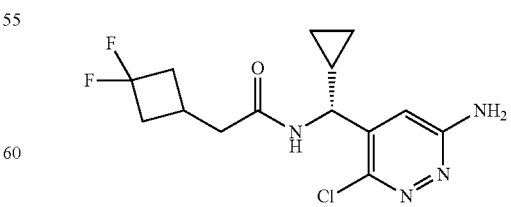

To a solution of (R)-5-(amino(cyclopropyl)methyl)-6-chloropyridazin-3-amine (11.8 g, 49.1 mmol, Intermediate 258), 2-(3,3-difluorocyclobutyl)acetic acid (8.11 g, 54.0 mmol), and HOBt (10.3 g, 54.0 mmol) in DMF (163 mL)

was added DIPEA (9.31 mL, 54.0 mmol) then EDCI (10.4 g, 54.0 mmol). The reaction was stirred at rt overnight then diluted with 500 mL of H$_2$O. The solids were filtered, washed with water, and air dried. Purification by SFC using a chiral stationary phase (Whelk 01 SS, 25:75 (MeOH/CO$_2$) provided the title compound.

Intermediate 260

Tert-Butyl ((R)-1-(6-chloro-7-((R)-cyclopropyl(2-(3,3-difluorocyclobutyl)acetamido)methyl)imidazo[1,2-b]pyridazin-2-yl)-2-((1,1,1-trifluoro-2-methylpropan-2-yl)oxy)ethyl)carbamate

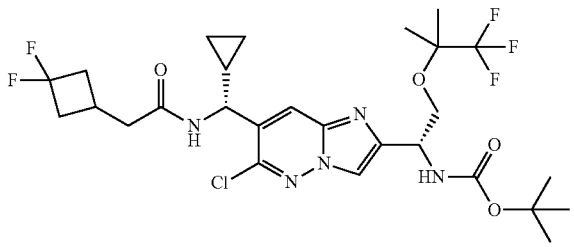 [SMILES: CC(C)(C)OC(=O)N[C@@H](COC(C)(C)C(F)(F)F)c1cn2nc(Cl)c([C@H](NC(=O)CC3CC(F)(F)C3)C3CC3)cc2n1]

An oven dried round bottom flask was charged with (R)—N-((6-amino-3-chloropyridazin-4-yl)(cyclopropyl)methyl)-2-(3,3-difluorocyclobutyl)acetamide (453 mg, 1.35 mmol, Intermediate 259), tert-butyl (S)-(4-iodo-3-oxo-1-((1,1,1-trifluoro-2-methylpropan-2-yl)oxy)butan-2-yl)carbamate (770 mg, 1.75 mmol, Intermediate 254), and activated 4 Å mol sieves under an N$_2$ atmosphere. DMA (18 mL) was added and the reaction heated to 45° C. for 12 h. After this time the mixture was filtered, the filtrate diluted with EtOAc, and washed with 5% aqueous LiCl then brine. The organics were dried over anhydrous Na$_2$SO$_4$ and condensed. Purification by silica gel chromatography (5-100% (10% MeOH/EtOAc)/hexanes) then a second purification by silica gel chromatography (10-100% EtOAc/hexanes) provided the title compound.

Intermediate 261

Tert-Butyl ((R)-1-(7-((R)-cyclopropyl(2-(3,3-difluorocyclobutyl)acetamido)methyl)imidazo[1,2-b]pyridazin-2-yl)-2-((1,1,1-trifluoro-2-methylpropan-2-yl)oxy)ethyl)carbamate

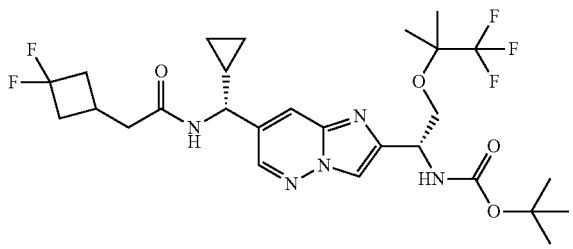 [SMILES: CC(C)(C)OC(=O)N[C@@H](COC(C)(C)C(F)(F)F)c1cn2ncc([C@H](NC(=O)CC3CC(F)(F)C3)C3CC3)cc2n1]

To a solution of tert-butyl ((R)-1-(6-chloro-7-((R)-cyclopropyl(2-(3,3-difluorocyclobutyl)acetamido)methyl)imidazo[1,2-b]pyridazin-2-yl)-2-((1,1,1-trifluoro-2-methylpropan-2-yl)oxy)ethyl)carbamate (330 mg, 0.529 mmol, Intermediate 260) and AcOH (1.6 mL) in THF (4.9 mL) was added Pd/C (130 mg, 0.106 mmol, 20% wt) under an N$_2$ atmosphere. The mixture was put under an H$_2$ atmosphere (balloon) and stirred at rt for 20 h then diluted with EtOAc, filtered through diatomaceous earth (Celite®), and condensed. The residue was taken up in EtOAc, washed three times with saturated aqueous NaHCO$_3$ followed by brine, then dried over anhydrous Na$_2$SO$_4$, filtered and condensed to provide the title compound.

Intermediate 262

N-(tert-Butoxycarbonyl)-O-methyl-D-threonine

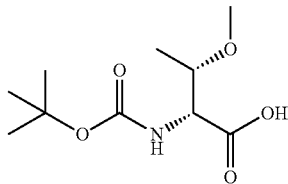 [SMILES: CO[C@@H](C)[C@@H](NC(=O)OC(C)(C)C)C(=O)O]

To a 0° C. solution of (2R,3S)-2-amino-3-methoxybutanoic acid (5 g, 37.5 mmol) in NaOH (75 mL, 1 M aqueous) and 1,4-dioxane (30 mL) was added dropwise a solution of di-tert-butyl dicarbonate (9.01 g, 41.31 mmol) in 1,4-dioxane (30 mL). The reaction mixture was stirred at 0° C. for 0.5 h, then was allowed to warm to rt. After 15 h the mixture was diluted with H$_2$O (30 mL), acidified to pH 2-3 with saturated aqueous citric acid, and extracted with EtOAc. The combined organic layers were washed with brine, dried over anhydrous Na$_2$SO$_4$, filtered and condensed to provide the title compound.

Intermediate 263

Tert-Butyl ((2R,3S)-3-methoxy-1-(methoxy(methyl)amino)-1-oxobutan-2-yl)carbamate

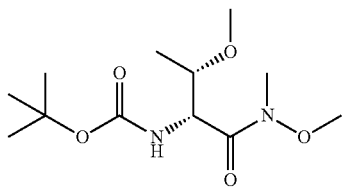 [SMILES: CO[C@@H](C)[C@@H](NC(=O)OC(C)(C)C)C(=O)N(C)OC]

To a solution of N-(tert-butoxycarbonyl)-O-methyl-D-threonine (7.86 g, 33.7 mmol, Intermediate 262) in CH$_2$Cl$_2$ (60 mL) was added HATU (25.6 g, 67.4 mmol), DIPEA (20.54 mL, 117.94 mmol) and N,O-dimethylhydroxylamine hydrochloride (4.93 g, 50.5 mmol). The resulting mixture was stirred at rt for 3 h then CH$_2$Cl$_2$ (30 mL) and saturated aqueous NH$_4$Cl (30 mL) were added and layers were separated. The aqueous phase was extracted with CH$_2$Cl$_2$ (30 mL×2). The combined organic layers were washed with saturated aqueous sodium bicarbonate solution (30 mL) and brine (30 mL), dried over anhydrous Na$_2$SO$_4$, filtered and condensed. The residue was purified by silica gel chromatography (0-30% EtOAc/petroleum ether) to afford the title compound.

Intermediate 264

Tert-Butyl ((2R,3S)-3-methoxy-1-oxobutan-2-yl)carbamate

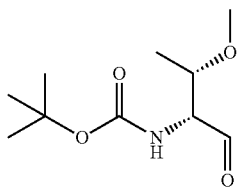

To a stirred −78° C. solution of tert-butyl ((2R,3S)-3-methoxy-1-(methoxy(methyl)amino)-1-oxobutan-2-yl)carbamate (7.78 g, 28.2 mmol, Intermediate 263) in THF (60 mL) was added DIBAL-H (70.4 mL, 70.4 mmol, 1 M in toluene) dropwise under $N_2$. The reaction was maintained at −78° C. for 3 h then quenched with saturated aqueous potassium sodium tartrate (70 mL) and warmed to 0° C. The mixture was stirred for 3 h then separated and the aqueous phase extracted with EtOAc (25 mL×3). The combined organic layers were washed with brine (25 mL), dried over anhydrous $Na_2SO_4$, filtered, and condensed to provide the title compound.

Intermediate 265

Tert-Butyl ((3S,4S)-4-methoxypent-1-yn-3-yl)carbamate

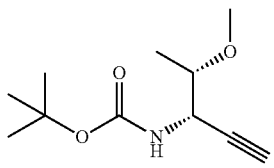

To a solution of tert-butyl ((2R,3S)-3-methoxy-1-oxobutan-2-yl)carbamate (6.1 g, 34 mmol, Intermediate 264) and $K_2CO_3$ (7.78 g, 56.3 mmol) in MeOH (90 mL) was added dimethyl (1-diazo-2-oxopropyl) phosphonate (6.48 g, 33.8 mmol). The mixture was stirred at rt overnight then filtered and condensed. Purification by silica gel chromatography (0-40% EtOAc/petroleum ether) provided the title compound.

Intermediate 266

(3S,4S)-4-Methoxypent-1-yn-3-amine hydrochloride

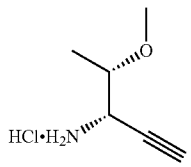

To a solution of tert-butyl ((3S,4S)-4-methoxypent-1-yn-3-yl)carbamate (7.64 g, 35.8 mmol, Intermediate 265) in MeOH (5 mL) was added HCl (51 mL, 204 mmol, 4 M in MeOH). The reaction was stirred at rt for 3 h then condensed to afford the title compound.

Intermediate 267

2-(3,3-Difluorocyclobutyl)-N-((3S,4S)-4-methoxypent-1-yn-3-yl)acetamide

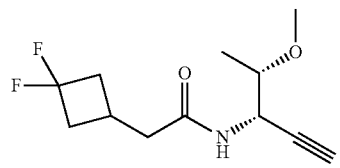 [SMILES: C#C[C@H](NC(=O)CC1CC(F)(F)C1)[C@H](C)OC]

To a solution of (3S,4S)-4-methoxypent-1-yn-3-amine hydrochloride (4.01 g, 26.8 mmol, Intermediate 266) in DCM (60 mL) was added 2-(3,3-difluorocyclobutyl)acetic acid (4.83 g, 32.2 mmol), HATU (15.3 g, 40.2 mmol) and DIPEA (22.8 mL, 134 mmol) slowly. The reaction was stirred at rt overnight then $CH_2Cl_2$ (30 mL) and saturated aqueous $NH_4Cl$ (30 mL) were added and layers were separated. The aqueous phase was extracted with $CH_2Cl_2$ (30 mL×2). The combined organic layers were washed with saturated aqueous sodium bicarbonate solution (30 mL) and brine (30 mL), dried over anhydrous $Na_2SO_4$, filtered and condensed. The residue was purified by silica gel chromatography (0-30% EtOAc/petroleum ether) to afford the title compound.

Intermediate 268

6-Chloro-N-(4-methoxybenzyl)-1,2,4,5-tetrazin-3-amine

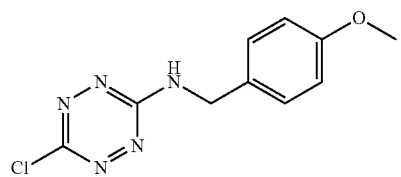 [SMILES: COc1ccc(CNc2nnc(Cl)nn2)cc1]

To a 0° C. solution of 3,6-dichloro-1,2,4,5-tetrazine (1.00 g, 6.62 mmol) in MTBE (20 mL) was added (4-methoxyphenyl)methanamine (909 mg, 6.63 mmol) in MTBE (10 mL) over 10 min under $N_2$. DIPEA (4.67 mL, 26.8 mmol) was added and the mixture was maintained at this temperature for 1 h then stirred at rt overnight. The reaction was condensed then purified by silica gel chromatography (0-20% EtOAc/petroleum ether) to provide the title compound.

Intermediate 269

N-(4-Methoxybenzyl)-1,2,4,5-tetrazin-3-amine

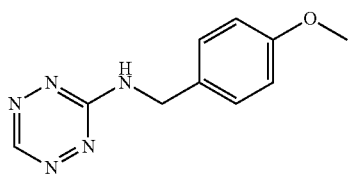 [SMILES: COc1ccc(CNc2nncnn2)cc1]

6-Chloro-N-(4-methoxybenzyl)-1,2,4,5-tetrazin-3-amine (1.00 g, 3.97 mmol, Intermediate 268), wet Pd/C (1 g, 10% Pd and 50% water), triethylamine (1.00 mL, 7.19 mmol), stir bar, and MeOH (30 mL) were added to a 100 mL hydrogenation bottle and the reaction vessel was purged with $H_2$ three times. The resultant mixture was stirred under $H_2$ (15 Psi) at rt for 2 h then filtered through a pad of diatomaceous earth (Celite®) and the pad washed with MeOH (150 mL). The filtrate was concentrated to dryness under reduced pressure. Purification by silica gel chromatography (0-30% EtOAc/petroleum ether) provided the title compound.

Intermediate 270

Tert-Butyl (4-methoxybenzyl)(1,2,4,5-tetrazin-3-yl)carbamate

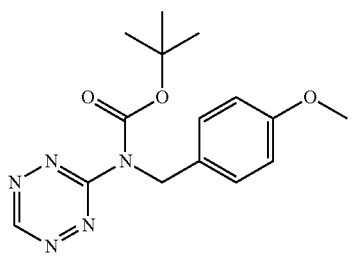 [SMILES: COc1ccc(CN(C(=O)OC(C)(C)C)c2nncnn2)cc1]

A mixture of N-(4-methoxybenzyl)-1,2,4,5-tetrazin-3-amine (1.60 g, 7.37 mmol, Intermediate 269), Boc$_2$O (2.42 g, 11.1 mmol), DMAP (91 mg, 0.74 mmol), and anhydrous DCM (40 mL) was stirred at rt overnight. The mixture was concentrated under reduced pressure then purified by silica gel chromatography (0-30% EtOAc/petroleum ether) to provide the title compound.

Intermediate 271

Tert-Butyl (5-((1S,2S)-1-(2-(3,3-difluorocyclobutyl)acetamido)-2-methoxypropyl)pyridazin-3-yl)(4-methoxybenzyl)carbamate

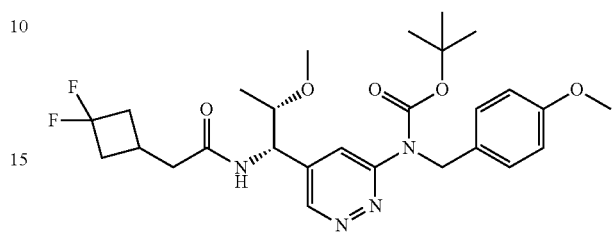

A 100 mL round bottom flask was charged with tert-butyl (4-methoxybenzyl)(1,2,4,5-tetrazin-3-yl)carbamate (14.8 g, 46.5 mmol, Intermediate 270), 2-(3,3-difluorocyclobutyl)-N-((3S,4S)-4-methoxypent-1-yn-3-yl)acetamide (4.01 g, 16.3 mmol, Intermediate 267) and put under an $N_2$ atmosphere. The reaction was heated to 60° C. then gradually to 115° C. at a rate of 5° C. every 10 min. After 3 h at 115° C. the reaction was cooled to rt and condensed. Purification by silica gel chromatography (0-70% EtOAc/petroleum ether) provided the title compound.

Intermediate 272

N-((1S,2S)-1-(6-Aminopyridazin-4-yl)-2-methoxypropyl)-2-(3,3-difluorocyclobutyl)acetamide

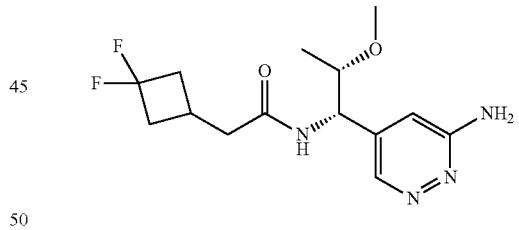

To a solution of tert-butyl (5-((1S,2S)-1-(2-(3,3-difluorocyclobutyl)acetamido)-2-methoxypropyl)pyridazin-3-yl)(4-methoxybenzyl)carbamate (8.0 g, 15 mmol, Intermediate 271) in MeOH (5 mL) was added HCl (35 mL, 140 mmol, 4 M in MeOH). The reaction was stirred at rt overnight then concentrated to dryness. The residue was treated with TFA (50 mL) and stirred at rt for 2 days then concentrated to dryness and neutralized with triethylamine (15 mL). The resulting mixture was condensed and purified by silica gel chromatography (0-70% EtOAc/petroleum ether). Further purification by SFC using a chiral stationary phase (DAICEL CHIRALPAK AD, 35:65 (0.1% NH$_4$OH in EtOH)/CO$_2$) provided the title compound.

Intermediate 273

Tert-Butyl ((S)-(7-((1S,2S)-1-(2-(3,3-difluorocyclobutyl)acetamido)-2-methoxypropyl)imidazo[1,2-b]pyridazin-2-yl)(4,4-difluorocyclohexyl)methyl)carbamate

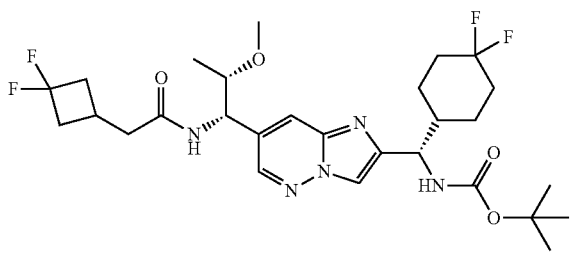 [SMILES: CO[C@@H](C)[C@@H](NC(=O)CC1CC(F)(F)C1)c1cnn2cc([C@@H](NC(=O)OC(C)(C)C)C3CCC(F)(F)CC3)nc2c1]

To a solution of tert-butyl (S)-(1-(4,4-difluorocyclohexyl)-3-iodo-2-oxopropyl)carbamate (272 mg, Intermediate 15) in DMA (5 mL) was added 4 Å molecular sieves (400 mg) and N-((1S,2S)-1-(6-aminopyridazin-4-yl)-2-methoxypropyl)-2-(3,3-difluorocyclobutyl)acetamide (136 mg, 0.43 mmol, Intermediate 272). The reaction was heated to 55° C. for 16 h under N₂ atmosphere then filtered over diatomaceous earth (Celite®) and the filter cake was washed with EtOAc. The filtrate was washed with H₂O and brine, dried over anhydrous Na₂SO₄, filtered, and condensed. Purification by silica gel chromatography (0-2% MeOH/CH₂Cl₂) provided the title compound.

Intermediate 274

N-((1S,2S)-1-(2-((S)-Amino(4,4-difluorocyclohexyl)methyl)imidazo[1,2-b]pyridazin-7-yl)-2-methoxypropyl)-2-(3,3-difluorocyclobutyl)acetamide Hydrochloride

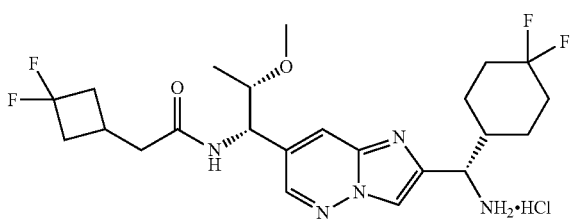

To a solution of tert-butyl ((S)-(7-((1S,2S)-1-(2-(3,3-difluorocyclobutyl)acetamido)-2-methoxypropyl)imidazo[1,2-b]pyridazin-2-yl)(4,4-difluorocyclohexyl)methyl)carbamate (105 mg, 0.18 mmol, Intermediate 273) in MeOH (3 mL) was added HCl (3.0 mL, 12 mmol, 4 M in 1,4-dioxane). The reaction was stirred at rt for 3 h then condensed to afford the title compound which was used without further purification.

Intermediate 275

2-((1,1,1-Trifluoro-2-methylpropan-2-yl)oxy)acetic Acid

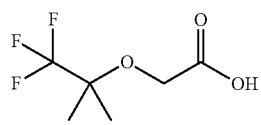

To a 0° C. solution of NaH (2.12 g, 78.1 mmol, 60% in mineral oil) in THF (80 mL) was added 1,1,1-trifluoro-2-methylpropan-2-ol (5.0 g, 39 mmol). The mixture was stirred at 0° C. for 1 h then a solution of 2-bromoacetic acid (6.51 g, 46.8 mmol) in THF (20 mL) was added dropwise. The reaction was warmed to rt then heated to 70° C. for 16 h. The mixture was condensed then H₂O (200 mL) was added. The aqueous layer was washed with CH₂Cl₂ (2×200 mL), acidified with 2 M aqueous HCl, then extracted with EtOAc (3×100 mL). The combined EtOAc extracts were dried over anhydrous Na₂SO₄, filtered and condensed to provide the title compound.

Intermediate 276

N-Methoxy-N-methyl-2-((1,1,1-trifluoro-2-methylpropan-2-yl)oxy)acetamide

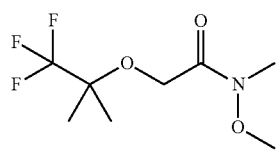

To a solution of 2-((1,1,1-trifluoro-2-methylpropan-2-yl)oxy)acetic acid (4 g, 21.5 mmol, Intermediate 275) in CH₂Cl₂ (40 mL) was added HATU (16.3 g, 43.0 mmol) and DIPEA (15.0 mL, 86.0 mmol) followed by N,O-dimethylhydroxylamine hydrochloride (3.14 g, 32.2 mmol). The resulting mixture was stirred at rt for 2 h then condensed. The residue was taken up in H₂O (200 mL) then extracted with EtOAc (3×100 mL). The combined organic extracts were washed with brine (200 mL), dried over anhydrous Na₂SO₄, filtered, and concentrated. Purification by silica gel chromatography (0-100% EtOAc/petroleum ether) provided the title compound.

Intermediate 277

2-((1,1,1-Trifluoro-2-methylpropan-2-yl)oxy)acetaldehyde

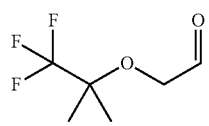

To a −78° C. solution of N-methoxy-N-methyl-2-((1,1,1-trifluoro-2-methylpropan-2-yl)oxy)acetamide (5.0 g, 22 mmol, Intermediate 276) in Et₂O (200 mL) was added DIBAL-H (65 mL, 65 mmol, 1 M in toluene). The reaction was stirred at this temperature for 1 h then quenched with 1 M aqueous HCl (10 mL). The resulting mixture was diluted with saturated aqueous Rochelle salt (100 mL) then extracted with Et₂O (3×50 mL). The combined organic extracts were washed with brine (2×100 mL), dried over anhydrous Na₂SO₄, filtered, and concentrated to provide the title compound which was used without further purification.

Intermediate 278

(S,E)-2-Methyl-N-(2-((1,1,1-trifluoro-2-methylpropan-2-yl)oxy)ethylidene)propane-2-sulfinamide

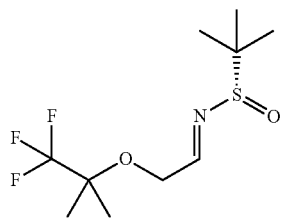 [SMILES: CC(C)(C)[S@](=O)/N=C/COC(C)(C)C(F)(F)F]

To a mixture of 2-((1,1,1-trifluoro-2-methylpropan-2-yl)oxy)acetaldehyde (3.5 g, 21 mmol, Intermediate 277), (S)-2-methylpropane-2-sulfinamide (3.0 g, 25 mmol), and CuSO₄ (9.9 g, 62 mmol) in CH₂Cl₂ (60 mL) was added PPTS (0.52 g, 2.1 mmol). The reaction was stirred at rt for 16 h then filtered through diatomaceous earth (Celite®). The filter cake was washed with EtOAc then the filtrate was condensed. Purification by silica gel chromatography (0-25% EtOAc/petroleum ether) provided the title compound.

Intermediate 279

(S)—N—((R)-1-Cyano-2-((1,1,1-trifluoro-2-methylpropan-2-yl)oxy)ethyl)-2-methylpropane-2-sulfinamide

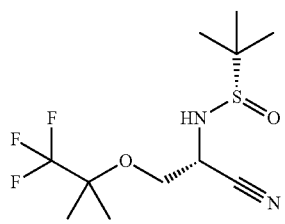 [SMILES: CC(C)(C)[S@](=O)N[C@H](C#N)COC(C)(C)C(F)(F)F]

A mixture of (S,E)-2-methyl-N-(2-((1,1,1-trifluoro-2-methylpropan-2-yl)oxy)ethylidene) propane-2-sulfinamide (6.0 g, 22 mmol, Intermediate 278), TMSCN (5.51 mL, 43.91 mmol), Sc(OTf)₃ (2.16 g, 4.39 mmol) and 4 Å molecular sieves (6 g) in DCM (60 mL) was stirred at rt for 48 h. The solution was filtered and concentrated under reduced pressure. Purification by silica gel chromatography (0-100% EtOAc/petroleum ether) provided the title compound.

Intermediate 280

O-(1,1,1-Trifluoro-2-methylpropan-2-yl)-L-serine

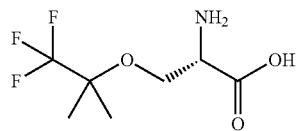

A mixture of (S)—N—((R)-1-cyano-2-((1,1,1-trifluoro-2-methylpropan-2-yl)oxy)ethyl)-2-methylpropane-2-sulfinamide (15 g, 50 mmol, Intermediate 279) in HCl (100 mL, 37% aqueous) was stirred at 80° C. for 16 h. The mixture was cooled to rt, aged at 0° C. for 16 h, then filtered. The resulting solid was triturated with EtOAc to provide the title compound.

Intermediate 281

N-(tert-Butoxycarbonyl)-O-(1,1,1-trifluoro-2-methylpropan-2-yl)-L-serine

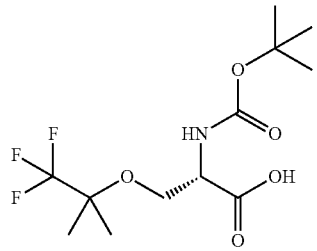 [SMILES: CC(C)(C)OC(=O)N[C@@H](COC(C)(C)C(F)(F)F)C(=O)O]

A mixture of O-(1,1,1-trifluoro-2-methylpropan-2-yl)-L-serine (9.00 g, 41.8 mmol, Intermediate 280), NaOH (3.18 g, 37.7 mmol), H₂O (36 mL), and THF (100 mL) was stirred at rt for 30 min then Boc₂O (8.22 g, 37.7 mmol) was added and the reaction stirred at rt for 16 h. The mixture was diluted with water (300 mL) and washed with EtOAc; the washes were discarded. The aqueous layer was acidified with 1 M aqueous HCl then extracted with EtOAc (3×100 mL). The combined organic layers were washed with brine, dried over anhydrous Na₂SO₄, filtered and condensed. The resulting solid was triturated with petroleum ether to provide the title compound.

Intermediate 282

Tert-Butyl (S)-(4-(dimethyl(oxo)-λ⁶-sulfaneylidene)-3-oxo-1-((1,1,1-trifluoro-2-methylpropan-2-yl)oxy)butan-2-yl)carbamate

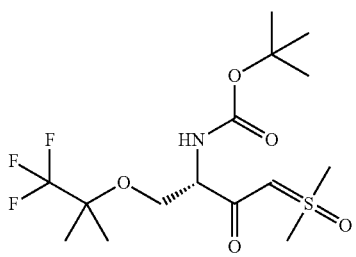 [SMILES: CC(C)(C)OC(=O)N[C@@H](COC(C)(C)C(F)(F)F)C(=O)C=S(C)(C)=O]

t-BuOK (2.38 mL, 2.38 mmol, 1 M in THF) was added to a suspension of trimethylsulfoxonium chloride (326 mg, 2.54 mmol) in THE (7.5 mL) and the resulting mixture was stirred at rt for 2 h. Separately, to a solution N-(tert-butoxycarbonyl)-O-(1,1,1-trifluoro-2-methylpropan-2-yl)-L-serine (500 mg, 1.59 mmol, Intermediate 281) in THE (5 mL) was added CDI (309 mg, 1.90 mmol) at 0° C. The mixture was stirred at 0° C. for 2 h then added to the first mixture dropwise over 5 min. The reaction was stirred at rt for 2 h then diluted with water (50 mL) and extracted with EtOAc (3×15 mL). The combined organic layers were washed with brine, dried over anhydrous MgSO₄, filtered, and concentrated. The residue was purified by silica gel chromatography (0-100% EtOAc/petroleum ether) then SFC (DAICEL CHIRALPAK AD, 25:75 (0.1% NH₄OH in EtOH)/CO₂) to provide the title compound.

Intermediate 283

Tert-Butyl ((S)-(7-((R)-((((9H-fluoren-9-yl)methoxy)carbonyl)amino)(cyclopropyl)methyl)imidazo[1,2-b]pyridazin-2-yl)(4,4-difluorocyclohexyl)methyl)carbamate

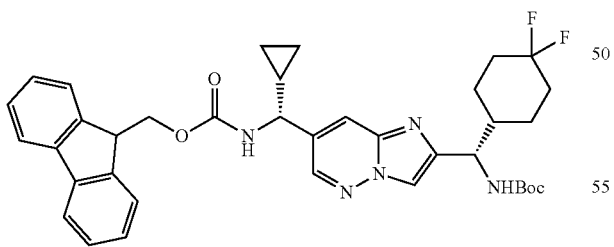

To a mixture of tert-butyl ((S)-(7-((R)-amino(cyclopropyl)methyl)imidazo[1,2-b]pyridazin-2-yl)(4,4-difluorocyclohexyl)methyl)carbamate (10 g, 22.96 mmol, Intermediate 49) in DCM (150 mL) were added DIPEA (7.2 mL, 41.3 mmol) and Fmoc-Cl (6.53 g, 25.26 mmol) and the resulting mixture stirred at rt for 2 h. The reaction was concentrated to dryness, then partitioned between water (20 mL) and EtOAc (20 mL). The aqueous layer was further extracted with EtOAc (2×20 mL) and the organic layers were combined, washed with brine (30 mL), dried over anhydrous Na₂SO₄, filtered and concentrated to dryness. The residue was purified by recrystallization using 5:1 petroleum ether/EtOAc (100 mL) to provide the title compound as a white solid.

Intermediate 284

(9H-Fluoren-9-yl)methyl ((R)-(2-((S)-amino(4,4-difluorocyclohexyl)methyl)imidazo[1,2-b]pyridazin-7-yl)(cyclopropyl)methyl)carbamate Hydrochloride

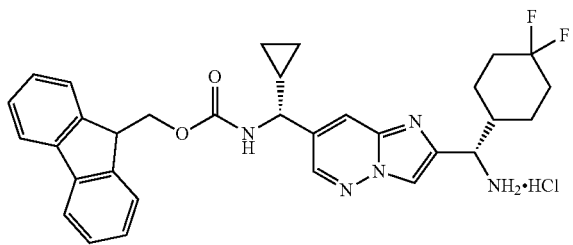

To a solution of HCl (200 mL, 201 mmol, 1 M in EtOAc) in EtOAc (200 mL) was added tert-butyl ((S)-(7-((R)-((((9H-fluoren-9-yl)methoxy)carbonyl)amino)(cyclopropyl)methyl)imidazo[1,2-b]pyridazin-2-yl)(4,4-difluorocyclohexyl)methyl)carbamate (12 g, 18.24 mmol, Intermediate 283), and the resulting mixture was stirred at rt overnight. The mixture was concentrated to dryness to provide the title compound as a yellow solid.

Intermediate 285

4-Methyl-1,2,5-oxadiazole-3-carbonyl Chloride

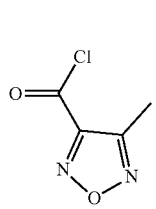

A mixture of 4-methyl-1,2,5-oxadiazole-3-carboxylic acid (1.5 g, 11.7 mmol), oxalyl chloride (1.49 g, 11.71 mmol), DMF (86 mL) and DCM (50 mL) was stirred at rt for 2 h and then used directly in the next reaction.

Intermediate 286

(9H-Fluoren-9-yl)methyl ((R)-cyclopropyl(2-((S)-(4,4-difluorocyclohexyl)(4-methyl-1,2,5-oxadiazole-3-carboxamido)methyl)imidazo[1,2-b]pyridazin-7-yl)methyl)carbamate

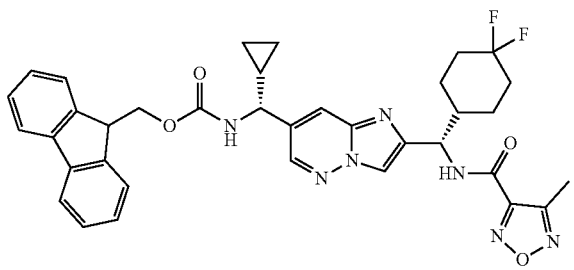 [SMILES: Cc1nonc1C(=O)N[C@H](c1cn2ncc([C@H](NC(=O)OCC3c4ccccc4-c4ccccc43)C3CC3)cc2n1)C1CCC(F)(F)CC1]

To a mixture of (9H-fluoren-9-yl)methyl ((R)-(2-((S)-amino(4,4-difluorocyclohexyl)methyl)imidazo[1,2-b]pyridazin-7-yl)(cyclopropyl)methyl)carbamate hydrochloride (5 g, 8.42 mmol, Intermediate 284) and TEA (4.7 mL, 33.7 mmol) in DCM (50 mL) was added 4-methyl-1,2,5-oxadiazole-3-carbonyl chloride (1.7 g, 11.6 mmol, Intermediate 285, solution in DCM and DMF) slowly. The resulting mixture was stirred at rt for 10 min, then combined with several other reactions and partitioned between water (100 mL) and DCM (200 mL). The layers were separated and the aqueous further extracted with DCM (3×100 mL). The organic layers were combined, washed with water (50 mL) and brine (50 mL), dried over anhydrous $Na_2SO_4$, filtered and concentrated to dryness. The crude residue was purified by silica gel chromatography (0-80% EtOAc/petroleum ether) to provide the title compound as a yellow solid.

Intermediate 287

N—((S)-(7-((R)-Amino(cyclopropyl)methyl)imidazo[1,2-b]pyridazin-2-yl)(4,4-difluorocyclohexyl)methyl)-4-methyl-1,2,5-oxadiazole-3-carboxamide

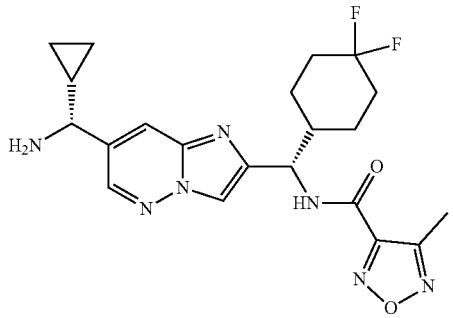 [SMILES: Cc1nonc1C(=O)N[C@H](c1cn2ncc([C@H](N)C3CC3)cc2n1)C1CCC(F)(F)CC1]

To a solution of piperidine (20 mL, 204 mmol) and DCM (100 mL) was added (9H-fluoren-9-yl)methyl ((R)-cyclopropyl(2-((S)-(4,4-difluorocyclohexyl)(4-methyl-1,2,5-oxadiazole-3-carboxamido)methyl)imidazo[1,2-b]pyridazin-7-yl)methyl)carbamate (8 g, 11.4 mmol, Intermediate 286) and the resulting mixture was stirred at rt for 2 h. The reaction was concentrated to dryness and purified by silica gel chromatography (0-10% MeOH/DCM) followed by recrystallization (4:1 petroleum ether/EtOAc, 150 mL) to provide the title compound.

Intermediate 288

Tert-Butyl (trans-3,4)-3-(((R)-cyclopropyl(2-((S)-(4,4-difluorocyclohexyl)(4-methyl-1,2,5-oxadiazole-3-carboxamido)methyl)imidazo[1,2-b]pyridazin-7-yl)methyl)carbamoyl)-4-(trifluoromethyl)pyrrolidine-1-carboxylate

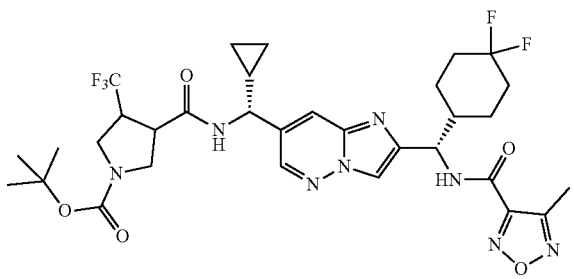 [SMILES: Cc1nonc1C(=O)N[C@H](c1cn2ncc([C@H](NC(=O)C3CN(C(=O)OC(C)(C)C)CC3C(F)(F)F)C3CC3)cc2n1)C1CCC(F)(F)CC1]

The title compound was prepared as described for the synthesis of Example 324, using trans (+/−) [4-(trifluoromethyl)pyrrolidine]-1,3-dicarboxylic acid 1-tert-butyl ester in place of (2,2,3,3-tetrafluorocyclobutyl)acetic acid, and running the reaction at 40° C. for 16 h instead of 2.5 h. The crude material was purified by preparative HPLC (Phenomenex Gemini-NX 150×30 mm, 5 μm column; 54-84% ACN/water (0.05% $NH_4OH$)) to provide the title compound as a mixture of diastereomers.

Intermediate 289 cis-2-(((4-Methoxybenzyl)oxy)carbonyl)cyclopropane-1-carboxylic acid

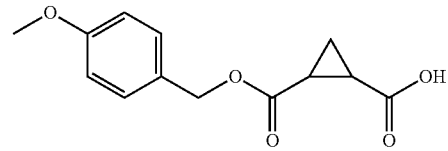 [SMILES: COc1ccc(COC(=O)C2CC2C(=O)O)cc1]

A mixture of cis-3-oxabicyclo[3.1.0]hexane-2,4-dione (5.00 g, 44.6 mmol), (4-methoxyphenyl)methanol (6.78 g, 49.1 mmol), DIPEA (15.5 mL, 89.2 mmol), and DCM (100 mL) was stirred at rt overnight. The solution was poured into aqueous HCl (1 N, 100 mL) and stirred at rt for 0.5 h. The phases were separated, and the aqueous mixture further extracted with DCM (2×50 mL). The combined extracts were washed with brine (100 mL), dried over anhydrous $Na_2SO_4$, filtered, and concentrated to dryness. The resultant crude product was subjected to silica gel chromatography (0-50% EtOAc/petroleum ether) to afford the title compound as a colorless liquid.

Intermediate 290

4-Methoxybenzyl cis-2-(hydroxymethyl)cyclopropane-1-carboxylate

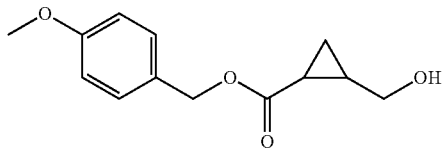 [SMILES: COc1ccc(COC(=O)C2CC2CO)cc1]

A solution consisting of cis-2-(((4-methoxybenzyl)oxy)carbonyl)cyclopropane-1-carboxylic acid (10.00 g, 39.96 mmol, Intermediate 289) and THF (300 mL) was cooled to 0° C. (ice/water bath), and then treated with $BH_3 \cdot THF$ (1 M in THF, 79.9 mL, 79.9 mmol), dropwise over 30 min. The resultant mixture was brought to rt, stirred overnight, re-cooled to 0° C. (ice/water bath), and treated with MeOH (50 mL), dropwise with stirring. Once effervescence had ceased, the mixture was further diluted with MeOH (50 mL) and concentrated to dryness under reduced pressure. The crude product was subjected to silica gel chromatography (0-50% EtOAc/petroleum ether) to afford the title compound as a colorless liquid.

Intermediate 291

4-Methoxybenzyl cis-2-formylcyclopropane-1-carboxylate

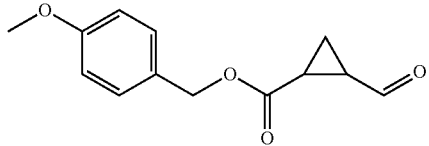

Oxalyl chloride (2.6 mL, 30 mmol) and anhydrous $CH_2Cl_2$ (100 mL) were added to a 500 mL three-necked round-bottomed flask equipped with mechanical stirrer, condensing tube, and thermometer. The flask was cooled to −78° C. (dry ice/ethanol bath) under a continuous flow of nitrogen, and then charged with a solution consisting of anhydrous DMSO (5.2 g, 66 mmol) and $CH_2Cl_2$ (20 mL) at such a rate that the temperature of the mixture did not exceed −70° C. (~40 min). Once addition was complete, the mixture was stirred for an additional 30 min before increasing the stir rate until vigorous, and treating it with 4-methoxybenzyl cis-2-(hydroxymethyl)cyclopropane-1-carboxylate (6.0 g, 25 mmol, Intermediate 290) dropwise and maintaining an internal temperature below −70° C. Stirring was continued for 1 h before treating the mixture with anhydrous triethylamine (17.6 mL, 127 mmol) at a rate that didn't significantly raise the temperature. Stirring was continued for 2 h before diluting the reaction mixture with water (100 mL) and extracting with DCM (3×50 mL). The combined organic extracts were washed with brine (100 mL), dried over anhydrous $Na_2SO_4$, filtered, and concentrated to dryness under reduced pressure to give the crude product, which was subjected to silica gel chromatography (100% DCM) to afford the title compound as a colorless oil.

Intermediate 292

4-Methoxybenzyl cis-2-(difluoromethyl)cyclopropane-1-carboxylate

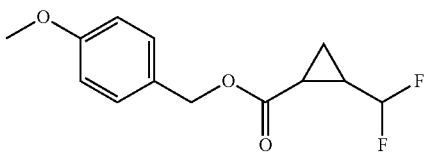 [SMILES: COc1ccc(COC(=O)C2CC2C(F)F)cc1]

4-Methoxybenzyl cis-2-formylcyclopropane-1-carboxylate (4.5 g, 19 mmol, Intermediate 291) and DCM (100 mL) were added to a 250 mL three-necked round-bottomed flask equipped with mechanical stirrer, condensing tube, and thermometer. The system was purged with nitrogen, charged with BAST (11 g, 48 mmol), and the resultant mixture stirred at 20° C. for 1 h. The mixture was then treated with ethanol (0.3 mL) and stirring continued for 24 h before pouring it into vigorously stirred saturated aqueous $NaHCO_3$ (150 mL). Once gas evolution ceased, the phases were separated, and the aqueous mixture extracted with $CH_2Cl_2$ (3×50 mL). The combined organic extracts were dried over anhydrous $Na_2SO_4$, filtered, and concentrated to dryness under reduced pressure. The crude product was subjected to silica gel chromatography (100% DCM) to provide the title compound as a colorless oil.

Intermediate 293 cis-2-(Difluoromethyl)cyclopropane-1-carboxylic Acid

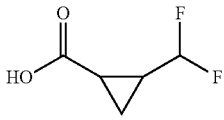

4-Methoxybenzyl cis-2-(difluoromethyl)cyclopropane-1-carboxylate (6.0 g, 23 mmol, Intermediate 292), THF (50 mL) and $H_2O$ (50 mL) were added to a 250 mL one-necked round-bottomed flask equipped with a mechanical stirrer, condensing tube, and a thermometer. $LiOH \cdot H_2O$ (1.2 g, 28 mmol) was added to the flask, and the resultant mixture stirred at 20° C. for 2 h. The reaction mixture was then treated with 1 N aqueous HCl until pH 3-4 and extracted with EtOAc (50 mL×3). The combined extracts were washed with brine (50 mL), dried over anhydrous $Na_2SO_4$, filtered, and concentrated to dryness under reduced pressure to give the crude product. The crude product was subjected to silica gel chromatography (10-20% EtOAc/petroleum ether) to give a white solid. The solid was suspended in n-hexane (5 mL), stirred at rt for 10 min, and re-isolated via vacuum filtration to afford the title compound as a white solid.

Intermediate 294 trans-2-(Ethoxycarbonyl)cyclopropane-1-carboxylic Acid

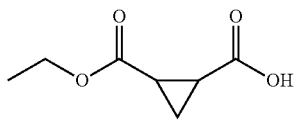

A solution of LiOH·H$_2$O (2.93 g, 69.8 mmol) and EtOH (100 mL) was added dropwise over the course of 1 h to a vigorously stirred solution of trans-diethyl cyclopropane-1,2-dicarboxylate (13.0 g, 69.8 mmol) in THE (400 mL) at rt and under a N$_2$ atmosphere. The resultant mixture was stirred at rt overnight and then concentrated to dryness. The residue was dissolved in water (100 mL), washed with petroleum ether (2×60 mL), treated with 2 N aqueous HCl until pH-2, and then extracted with EtOAc (3×100 mL). The combined EtOAc extracts were dried over anhydrous Na$_2$SO$_4$, filtered, and concentrated to dryness to provide the title compound as a colorless liquid.

Intermediate 295

Ethyl trans-2-(hydroxymethyl)cyclopropane-1-carboxylate

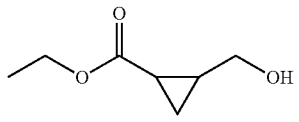

A solution consisting of trans-2-(ethoxycarbonyl)cyclopropane-1-carboxylic acid (5.50 g, 34.8 mmol, Intermediate 294) and THF (150 mL) was cooled to 0° C. (ice/water bath), and then treated with BH$_3$·THF (1 M in THF, 52.2 mL, 52.2 mmol), dropwise over 30 min. The resultant mixture was brought to rt, stirred overnight, re-cooled to 0° C. (ice/water bath), and treated with EtOH (30 mL), dropwise with stirring. Once effervescence had ceased, the mixture was further diluted with EtOH (100 mL) and concentrated to dryness under reduced pressure. The crude product was subjected to silica gel chromatography (0-50% EtOAc/petroleum ether) to afford the title compound as a colorless liquid.

Intermediate 296

Ethyl Trans-2-formylcyclopropane-1-carboxylate

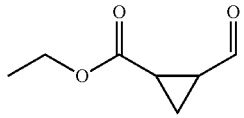

Oxalyl chloride (4.69 g, 37.0 mmol) and anhydrous CH$_2$Cl$_2$ (80 mL) were added to a 500 mL three-necked round-bottomed flask equipped with mechanical stirrer, condensing tube, and thermometer. The flask was cooled to −78° C. (dry ice/ethanol bath) under a continuous flow of nitrogen, and then charged with a solution consisting of anhydrous DMSO (6.26 g, 80.1 mmol) and CH$_2$Cl$_2$ (10 mL) at such a rate that the temperature of the mixture did not exceed −70° C. (~40 min). Once addition was complete, the mixture was stirred for an additional 30 min before increasing the stir rate until vigorous, and treating it with a solution consisting of ethyl trans-2-(hydroxymethyl)cyclopropane-1-carboxylate (4.44 g, 30.8 mmol, Intermediate 295) and DCM (10 mL) dropwise and maintaining an internal temperature below −70° C. Stirring was continued for 1 h before treating the mixture with anhydrous triethylamine (21.4 mL, 154 mmol) at a rate that didn't significantly raise the temperature. Stirring was continued for 2 h before diluting the reaction mixture with water (100 mL) and extracting with DCM (50 mL×3). The combined organic extracts were washed with brine (100 mL), dried over anhydrous Na$_2$SO$_4$, filtered, and concentrated to dryness under reduced pressure to give the crude product, which was subjected to silica gel chromatography (100% DCM) to afford the title compound as a colorless oil.

Intermediate 297

Ethyl trans-2-(difluoromethyl)cyclopropane-1-carboxylate

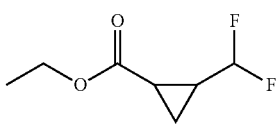

A solution consisting of ethyl trans-2-formylcyclopropane-1-carboxylate (3.0 g, 21 mmol, Intermediate 296) and DCM (30 mL) in a nitrogen-purged round-bottomed flask was treated with BAST (11.7 g, 52.8 mmol) at rt, and the resultant mixture stirred at 20° C. for 1 h. Ethanol (0.1 mL) was then added and stirring continued for 48 h before the mixture was poured into vigorously stirred saturated aqueous NaHCO$_3$ (150 mL). Once gas evolution ceased, the phases were separated, and the aqueous mixture extracted with CH$_2$Cl$_2$ (3×50 mL). The combined organic extracts were dried over anhydrous Na$_2$SO$_4$, filtered, and concentrated to dryness under reduced pressure. The crude product was subjected to silica gel chromatography (100% DCM) to provide the title compound as a colorless oil.

Intermediate 298 trans-2-(Difluoromethyl)cyclopropane-1-carboxylic Acid

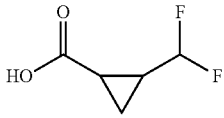

Ethyl trans-2-(difluoromethyl)cyclopropane-1-carboxylate (9.0 g, 55 mmol, Intermediate 297), THF (100 mL), and H₂O (100 mL) were added to a 500 mL one-necked round-bottomed flask equipped with a mechanical stirrer, condensing tube, and a thermometer. LiOH·H₂O (2.76 g, 65.8 mmol) was added to the flask, and the resultant mixture stirred at 20° C. for 16 h. The reaction mixture was then treated with 1 N aqueous HCl until pH 3-4 and extracted with EtOAc (200 mL×2). The combined organic extracts were washed with brine (300 mL), dried over anhydrous Na₂SO₄, filtered, and concentrated to dryness under reduced pressure to give the crude product. The crude product was subjected to silica gel chromatography (9-33% EtOAc/petroleum ether) to provide the title compound as a light-yellow oil.

Intermediate 299

4-Methoxybenzyl Cis-2-(fluoromethyl)cyclopropane-1-carboxylate

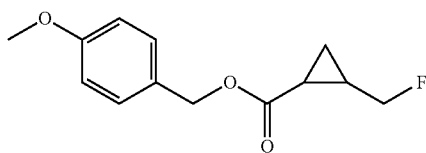 [SMILES: COc1ccc(COC(=O)C2CC2CF)cc1]

A solution consisting of 4-methoxybenzyl cis-2-(hydroxymethyl)cyclopropane-1-carboxylate (10.0 g, 42.3 mmol, Intermediate 290) and DCM (130 mL) was added to a solution consisting of BAST (14.9 mL, 84.7 mmol) and DCM (20 mL) at rt, and subsequently stirred overnight. The reaction mixture was carefully poured into saturated aqueous NaHCO₃ (200 mL) and extracted with DCM (100 mL×2). The combined organic extracts were washed with brine (100 mL), dried over anhydrous Na₂SO₄, filtered, and concentrated to dryness. The crude product was subjected to silica gel chromatography (0-9% EtOAc/petroleum ether) to afford the title compound as a colorless liquid.

Intermediate 300 cis-2-(Fluoromethyl)cyclopropane-1-carboxylic Acid

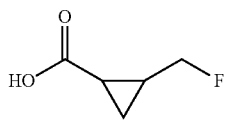

4-Methoxybenzyl cis-2-(fluoromethyl)cyclopropane-1-carboxylate (4.50 g, 18.9 mmol, Intermediate 299) was added to a solution consisting of NaOH (1.51 g, 37.8 mmol), THF (30 mL), MeOH (30 mL), and H₂O (30 mL) and the resulting mixture was stirred at 30° C. overnight. The solution was concentrated, diluted with water (100 mL), and extracted with EtOAc (30 mL×2). The aqueous phase was treated with 2 M aqueous HCl until pH 3, and then extracted with EtOAc (60 mL×3). The combined organic extracts were washed with brine (60 mL), dried over anhydrous Na₂SO₄, filtered, and concentrated to dryness. The resultant crude product was subjected to silica gel chromatography (0-33% EtOAc/petroleum ether) twice and washed with hexane to afford the title compound as a white solid.

Intermediate 301

Ethyl Trans-2-(fluoromethyl)cyclopropane-1-carboxylate

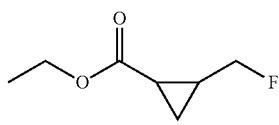

A solution consisting of ethyl trans-2-(hydroxymethyl)cyclopropane-1-carboxylate (8.00 g, 55.5 mmol, Intermediate 295) and DCM (120 mL) was added to a solution of consisting of BAST (19.50 mL, 111.0 mmol) and DCM (30 mL) at rt and stirred overnight. The mixture was poured into saturated aqueous NaHCO₃ (300 mL) and extracted with DCM (150 mL×2). The combined organic extracts were washed with brine (150 mL), dried over anhydrous Na₂SO₄, filtered, and concentrated to dryness. The resultant crude product was subjected to silica gel chromatography (0-9% EtOAc/petroleum ether) to afford the title compound as a colorless liquid.

Intermediate 302 trans-2-(Fluoromethyl)cyclopropane-1-carboxylic Acid

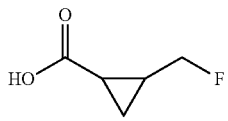

Ethyl trans-2-(fluoromethyl)cyclopropane-1-carboxylate (8.0 g, crude, Intermediate 301) was added to a solution consisting of LiOH·H₂O (2.3 g, 54.7 mmol), EtOH (50 mL), and H₂O (50 mL) and the resultant mixture stirred at rt for 2 h. The reaction mixture was concentrated, diluted with brine (60 mL), and extracted with petroleum ether (20 mL×2). The aqueous phase was then treated with 2 N aqueous HCl until pH 3, and then extracted with THF (30 mL×3). The combined THF extracts were concentrated to dryness, and the crude product subjected to silica gel chromatography (0-50% EtOAc/petroleum ether) to afford the title compound as a colorless liquid.

Intermediate 303

Ethyl 4-ethoxyisoxazole-3-carboxylate

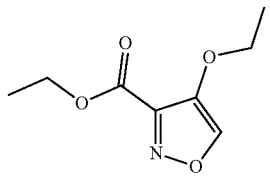

Ethyl 4-hydroxyisoxazole-3-carboxylate (250 mg, 1.6 mmol) was dissolved in DMF (4.2 mL) and then Cs$_2$CO$_3$ (780 mg, 2.4 mmol) and iodoethane (0.15 mL, 1.8 mmol) were sequentially added. The resultant mixture was stirred at 50° C. for 16 h, then quenched with water (50 mL). The biphasic mixture was extracted with EtOAc (3×25 mL). The combined organic layers were washed with brine twice, dried over anhydrous Na$_2$SO$_4$, filtered, and concentrated under reduced pressure. Purification by silica gel chromatography (0-100% EtOAc/hexanes) yielded the title compound as a pale-yellow oil.

Intermediate 304

Ethyl 4-isopropoxyisoxazole-3-carboxylate

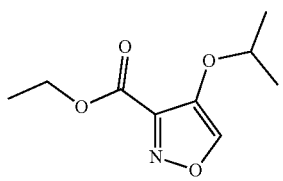

The title compound was prepared as described for the synthesis of Intermediate 303 using 2-iodopropane in place of iodoethane. Purification by silica gel chromatography (0-100% EtOAc/hexanes) yielded the title compound as a pale-yellow oil.

Intermediate 305

Ethyl 4-(2-fluoroethoxy)isoxazole-3-carboxylate

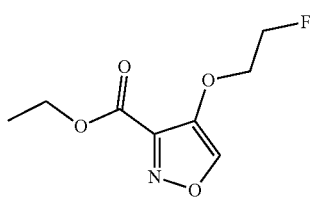

The title compound was prepared as described for the synthesis of Intermediate 303 using 1-fluoro-2-iodoethane in place of iodoethane. Purification by silica gel chromatography (0-100% EtOAc/hexanes) yielded the title compound as a pale-yellow oil.

Intermediate 306

Ethyl 4-(2,2-difluoroethoxy)isoxazole-3-carboxylate

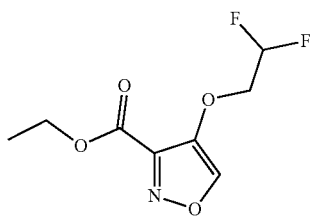

The title compound was prepared as described for the synthesis of Intermediate 303 using 1,1-difluoro-2-iodoethane in place of iodoethane. Purification by silica gel chromatography (0-100% EtOAc/hexanes) yielded the title compound as a pale-yellow oil.

Intermediate 307

4-Methoxyisoxazole-3-carboxylic Acid

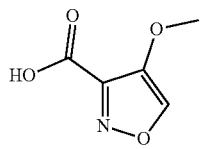

Ethyl 4-methoxyisoxazole-3-carboxylate (220 mg, 1.3 mmol) was dissolved in THF (0.76 mL) and had a solution of LiOH (62 mg, 2.6 mmol) in water (1.3 mL) added dropwise. The mixture stirred until full consumption of starting material (about 1 h), at which time the reaction was acidified with 1 N aqueous HCl and diluted with water (10 mL). The mixture was extracted with 20% IPA in CHCl$_3$ (15 mL×3). The combined organic layers were washed with brine, dried over anhydrous MgSO$_4$, filtered, and concentrated to afford the title compound as an off-white solid that was used without further purification.

Intermediate 308

4-Ethoxyisoxazole-3-carboxylic Acid

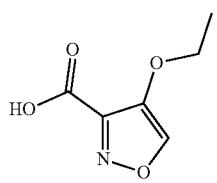

The title compound was prepared as described for the synthesis of Intermediate 307 using ethyl 4-ethoxyisoxazole-3-carboxylate (Intermediate 303) in place of ethyl 4-methoxyisoxazole-3-carboxylate.

Intermediate 309

4-Isopropoxyisoxazole-3-carboxylic A

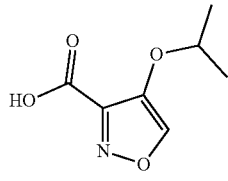

The title compound was prepared as described for the synthesis of Intermediate 307 using ethyl 4-isopropoxyisoxazole-3-carboxylate (Intermediate 304) in place of ethyl 4-methoxyisoxazole-3-carboxylate.

Intermediate 310

4-(2-Fluoroethoxy)isoxazole-3-carboxylic Acid

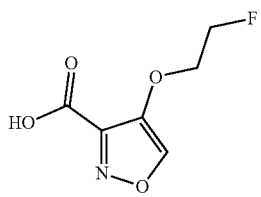 [SMILES: O=C(O)c1nocc1OCCF]

The title compound was prepared as described for the synthesis of Intermediate 307 using ethyl 4-(2-fluoroethoxy) isoxazole-3-carboxylate (Intermediate 305) in place of ethyl 4-methoxyisoxazole-3-carboxylate.

Intermediate 311

4-(2,2-Difluoroethoxy)isoxazole-3-carboxylic A

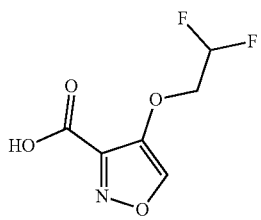 [SMILES: O=C(O)c1nocc1OCC(F)F]

The title compound was prepared as described for the synthesis of Intermediate 307 using ethyl 4-(2,2-difluoroethoxy)isoxazole-3-carboxylate (Intermediate 306) in place of ethyl 4-methoxyisoxazole-3-carboxylate.

Intermediate 312

Ethyl 4-cyclopropyl-5-(pyrrolidin-1-yl)-4,5-dihydroisoxazole-3-carboxylate

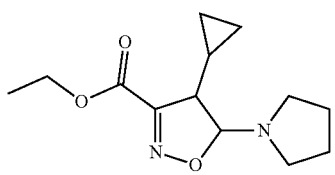 [SMILES: CCOC(=O)C1=NOC(N2CCCC2)C1C1CC1]

2-Cyclopropylacetaldehyde (1.5 g, 18 mmol) was added to a solution of pyrrolidine (1.6 mL, 19 mmol) and triethylamine (1.2 mL, 8.7 mmol) in DCM (44 mL) at 0° C. A solution of ethyl 2-chloro-2-(hydroxyimino)acetate (1.3 g, 8.7 mmol) in DCM (17 mL) was added in 5 portions over 5 min intervals. After 10 min, the ice bath was removed and the reaction was allowed to stir at rt for 1.5 h. The solution was then concentrated under reduced pressure and purified by silica gel chromatography (0-20% EtOAc/hexanes) to provide the title compound as a colorless oil.

Intermediate 313

Ethyl 4-cyclopropylisoxazole-3-carboxylate

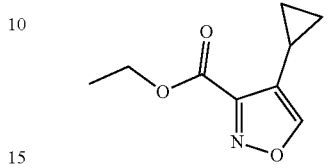

mCPBA (1.6 g, 7.4 mmol) was added to a solution of ethyl 4-cyclopropyl-5-(pyrrolidin-1-yl)-4,5-dihydroisoxazole-3-carboxylate (1.2 g, 4.6 mmol, Intermediate 312) in DCM (18 mL) at rt. The reaction was stirred at rt for 2 h and was subsequently quenched with a saturated aqueous solution of NaHCO$_3$. The biphasic mixture was transferred to a separatory funnel and extracted with EtOAc (3×20 mL). The combined organic layers were washed with a saturated aqueous solution of NaHCO$_3$ and brine, dried over anhydrous MgSO$_4$, filtered, and concentrated under reduced pressure. Purification by silica gel chromatography (0-45% EtOAc/hexanes) yielded the title compound as a low melting colorless solid.

Intermediate 314

4-Cyclopropylisoxazole-3-carboxylic Acid

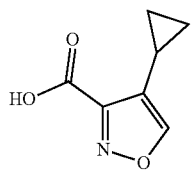 [SMILES: O=C(O)c1nocc1C1CC1]

The title compound was prepared as described for the synthesis of Intermediate 307 using ethyl 4-cyclopropylisoxazole-3-carboxylate (Intermediate 313) in place of ethyl 4-methoxyisoxazole-3-carboxylate. The crude product was purified by acidic preparative HPLC (Xbridge Prep C18, 5 μm, 50×100 mm, 5-95% MeCN (0.5% TFA) in water (0.5% TFA)) and the product containing fractions were diluted with water, frozen, and lyophilized to dryness to afford the title compound as a white solid.

Intermediate 315

Ethyl 5-(pyrrolidin-1-yl)-4-(2,2,2-trifluoroethyl)-4,5-dihydroisoxazole-3-carboxylate

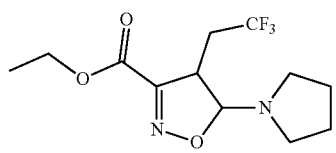 [SMILES: CCOC(=O)C1=NOC(N2CCCC2)C1CC(F)(F)F]

The title compound was prepared as described for the synthesis of Intermediate 312 using 4,4,4-trifluorobutyraldehyde in place of 2-cyclopropylacetaldehyde.

Intermediate 316

Ethyl 4-(2,2,2-trifluoroethyl)isoxazole-3-carboxylate

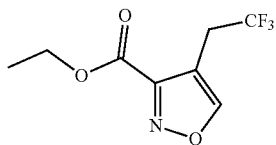

The title compound was prepared as described for the synthesis of Intermediate 313 using ethyl 5-(pyrrolidin-1-yl)-4-(2,2,2-trifluoroethyl)-4,5-dihydroisoxazole-3-carboxylate (Intermediate 315) in place of ethyl 4-cyclopropyl-5-(pyrrolidin-1-yl)-4,5-dihydroisoxazole-3-carboxylate.

Intermediate 317

4-(2,2,2-Trifluoroethyl)isoxazole-3-carboxylic Acid

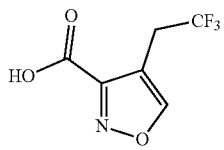

The title compound was prepared as described for the synthesis of Intermediate 307 using ethyl 4-(2,2,2-trifluoroethyl)isoxazole-3-carboxylate (Intermediate 316) in place of ethyl 4-methoxyisoxazole-3-carboxylate.

Intermediate 318

4-Isopropylisoxazole-3-carboxylic Acid

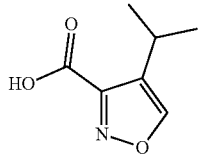

The title compound was prepared as described for the synthesis of Intermediate 307 using ethyl 4-isopropylisoxazole-3-carboxylate in place of ethyl 4-methoxyisoxazole-3-carboxylate.

Intermediate 319

4-Carboxy-3-isopropyl-1,2,5-oxadiazole 2-oxide

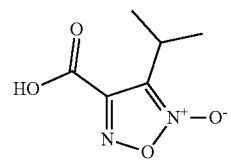

Jones reagent (2.3 mL, 4.6 mmol, 2 M) was added dropwise to a solution of 4-formyl-3-isopropyl-1,2,5-oxadiazole 2-oxide (450 mg, 2.9 mmol) in acetone (5.8 mL, 0.5 M) at 0° C. The reaction was warmed to rt and stirred until complete consumption of starting material was observed (typically 2 h). After this time, the reaction solution was cooled to 0° C., IPA (3 mL) was added, and stirred for an additional 30 min. The solution was then concentrated under reduced pressure to remove organic solvents and was diluted with water and $CH_2Cl_2$. The biphasic solution was then extracted with 20% IPA in $CH_2Cl_2$ solution (4×15 mL). The combined organic layers were washed with brine, dried over anhydrous $Na_2SO_4$, filtered, and concentrated under reduced pressure to afford the crude title compound which was used without further purification.

Intermediate 320

3-Cyclopropyl-4-formyl-1,2,5-oxadiazole 2-oxide

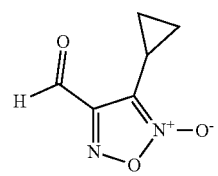

(E)-3-Cyclopropylacrylaldehyde (1.0 g, 10 mmol) was dissolved in glacial acetic acid (2.0 mL, 36 mmol) and cooled to 0° C. An aqueous solution of sodium nitrite (2.2 mL, 1.2 M) was then added dropwise via syringe pump (0.325 mL/min) and allowed to stir for 1 h at 0° C. The cooling bath was then removed and the reaction stirred at rt overnight. Upon complete consumption of starting material, the reaction was diluted with water (15 mL) and extracted with EtOAc (4×20 mL). The combined organic layers were washed with a saturated aqueous solution of $NaHCO_3$ and brine, dried over anhydrous $MgSO_4$, filtered, and concentrated under reduced pressure to afford the crude title compound. Purification by silica gel chromatography (0-60% EtOAc/hexanes) afforded the title compound as a pale-yellow oil.

Intermediate 321

4-Carboxy-3-cyclopropyl-1,2,5-oxadiazole 2-oxide

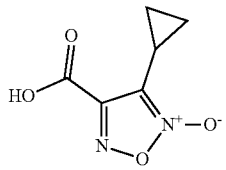

The title compound was prepared as described for the synthesis of Intermediate 319 using 3-cyclopropyl-4-formyl-1,2,5-oxadiazole 2-oxide (Intermediate 320) in place of 4-formyl-3-isopropyl-1,2,5-oxadiazole 2-oxide.

Intermediate 322

N—((R)-(2-((S)-(2-Cyanoacetamido)(4,4-difluorocyclohexyl)methyl)imidazo[1,2-b]pyridazin-7-yl)(cyclopropyl)methyl)-4,4,4-trifluorobutanamide

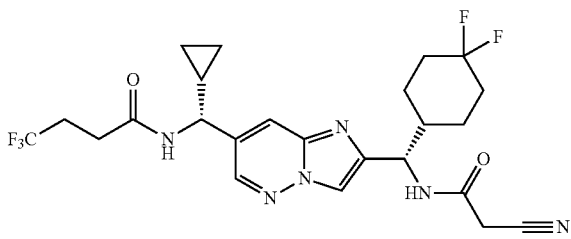 [SMILES: N#CCC(=O)N[C@H](c1cn2ncc([C@H](NC(=O)CCC(F)(F)F)C3CC3)cc2n1)C1CCC(F)(F)CC1]

The title compound was prepared as described for the synthesis of Example 32, using 2-cyanoacetic acid in place of 2-(3,3-difluoropropyl)-2H-1,2,3-triazole-4-carboxylic acid.

Intermediate 323

(E)-2-(((S)-(7-((R)-Cyclopropyl(4,4,4-trifluorobutanamido)methyl)imidazo[1,2-b]pyridazin-2-yl)(4,4-difluorocyclohexyl)methyl)amino)-N-hydroxy-2-oxoacetimidoyl Cyanide

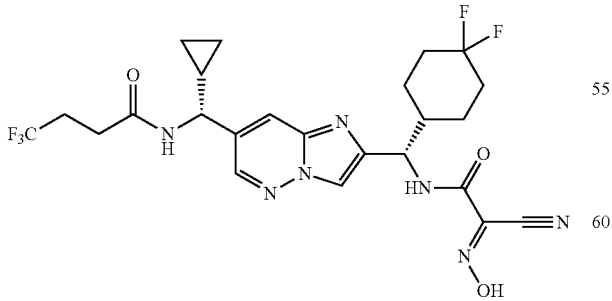

A solution of N—((R)-(2-((S)-(2-cyanoacetamido)(4,4-difluorocyclohexyl)methyl)imidazo[1,2-b]pyridazin-7-yl)(cyclopropyl)methyl)-4,4,4-trifluorobutanamide (280 mg, 0.53 mmol, Intermediate 322) in MeCN (2.7 mL) was charged with concentrated HCl (0.44 mL, 5.3 mmol). A solution of NaNO$_2$ (80 mg, 1.2 mmol) in water (0.17 mL) was added dropwise to the stirred reaction mixture at rt and was stirred until the complete consumption of starting material was observed (about 8 h). The reaction was then diluted with water and transferred to a separatory funnel. The aqueous layer was extracted with EtOAc (3×20 mL) and the combined organic layers were washed with brine, dried over anhydrous MgSO$_4$, filtered, and concentrated under reduced pressure. Purification by silica gel column chromatography (0-100% EtOAc/hexanes) afforded the title compound which was used without further characterization.

Intermediate 324

4-Chloro-N—((S)-(7-((R)-cyclopropyl(4,4,4-trifluorobutanamido)methyl)imidazo[1,2-b]pyridazin-2-yl)(4,4-difluorocyclohexyl)methyl)-1,2,5-oxadiazole-3-carboxamide

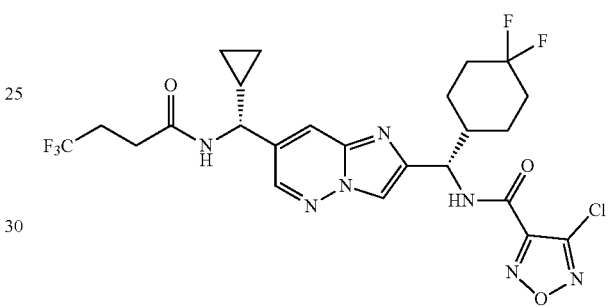

4-Amino-N—((S)-(7-((R)-cyclopropyl(4,4,4-trifluorobutanamido)methyl)imidazo[1,2-b]pyridazin-2-yl)(4,4-difluorocyclohexyl)methyl)-1,2,5-oxadiazole-3-carboxamide (165 mg, 0.29 mmol, Example 370) was dissolved in MeCN (1.3 mL), AcOH (1.3 mL), and concentrated HCl (0.73 mL). LiCl (37 mg, 0.87 mmol) was added and the mixture was cooled to 0° C. A solution of NaNO$_2$ (30 mg, 0.43 mmol) in water (62 μL) was added dropwise at 0° C. After 10 min the reaction was warmed to rt and allowed to stir for 1 h. The reaction was diluted with a saturated aqueous solution of NH$_4$Cl (5 mL) and water (15 mL), and transferred to a separatory funnel. The aqueous layer was then extracted with EtOAc (3×20 mL) and the combined organic layers were washed with brine, dried over anhydrous MgSO$_4$, filtered, and concentrated under reduced pressure. Purification by silica gel column chromatography (0-100% EtOAc/hexanes) afforded the title compound that was used without further characterization.

Intermediate 325

N-Phenyl-4-(2,2,2-trifluoroethoxy)-1,2,5-oxadiazole-3-carboxamide

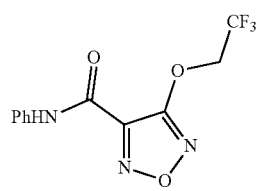

Procedure adapted from literature (Org. Lett. 2018, 20, 7, 2024-2027). A round bottom flask was charged with NaH (60 wt % suspension in mineral oil, 1.0 g, 27 mmol) and THF (60 mL). 2,2,2-Trifluoroethanol (1.3 g, 13.4 mmol) was added dropwise to the NaH suspension at rt and stirred for 5 min. 4-Chloro-N-phenyl-1,2,5-oxadiazole-3-carboxamide (2.0 g, 8.9 mmol) was then added as a solid and the mixture was heated at 50° C. for 1.25 h. The reaction was then cooled to rt and quenched slowly with 1 N aqueous HCl. The aqueous layer was extracted three times with EtOAc and the combined organic layers were washed with brine, dried over anhydrous MgSO$_4$, filtered, and concentrated under reduced pressure. Purification by silica gel column chromatography (0-17% EtOAc/hexanes) afforded the title compound as a pale-yellow solid.

Intermediate 326

Tert-Butyl phenyl(4-(2,2,2-trifluoroethoxy)-1,2,5-oxadiazole-3-carbonyl)carbamate

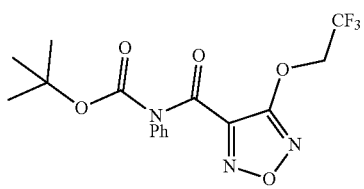

Boc anhydride (480 mg, 2.2 mmol) and DMAP (21 mg, 0.17 mmol) were added sequentially to a solution of N-phenyl-4-(2,2,2-trifluoroethoxy)-1,2,5-oxadiazole-3-carboxamide (500 mg, 1.7 mmol, Intermediate 325) in CH$_2$Cl$_2$ (8.7 mL) at rt and allowed to stir for 2 h. Upon complete consumption of starting material, the reaction was quenched with a saturated aqueous solution of NaHCO$_3$ (20 mL) and transferred to a separatory funnel. The biphasic mixture was extracted with EtOAc (3×20 mL) and the combined organic layers were washed with brine, dried over anhydrous MgSO$_4$, filtered, and concentrated under reduced pressure to afford the title compound which was used without further purification.

Intermediate 327

4-(2,2,2-Trifluoroethoxy)-1,2,5-oxadiazole-3-carboxylic Acid

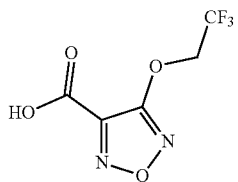 [SMILES: O=C(O)c1nonc1OCC(F)(F)F]

A solution of LiOH (230 mg, 9.6 mmol) in water (4.8 mL) was added dropwise to a solution of tert-butyl (4-(2,2,2-trifluoroethoxy)-1,2,5-oxadiazole-3-carbonyl)(phenyl)carbamate (670 mg, 1.7 mmol, Intermediate 326) in THF (6.4 mL) and the resulting mixture was heated to 35° C. After 1.5 h, the reaction was acidified to pH 1 with 1 N aqueous HCl (10 mL) and extracted with EtOAc (3×5 mL). The combined organic layers were washed with a saturated aqueous solution of NaHCO$_3$ and discarded. The new aqueous layer was slowly reacidified to pH 1 with 6 N aqueous HCl and extracted with EtOAc (3×20 mL). The new combined organic layers were dried over anhydrous Na$_2$SO$_4$, filtered, and concentrated under reduced pressure to afford the title compound as a hygroscopic solid. The title compound was diluted in MeCN and water, frozen, and lyophilized to dryness to generate a white powder.

Intermediate 328

4-(2,2-Difluoroethoxy)-N-phenyl-1,2,5-oxadiazole-3-carboxamide

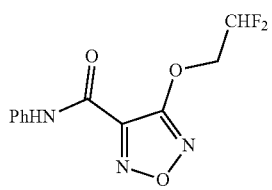

The title compound was prepared as described for the synthesis of Intermediate 325, using 2,2-difluoroethanol in place of 2,2,2-trifluoroethanol.

Intermediate 329

Tert-Butyl (4-(2,2-difluoroethoxy)-1,2,5-oxadiazole-3-carbonyl)(phenyl)carbamate

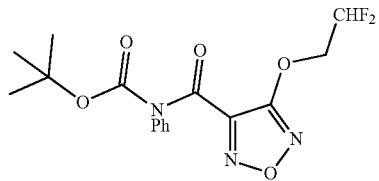

The title compound was prepared as described for the synthesis of Intermediate 326, using 4-(2,2-difluoroethoxy)-N-phenyl-1,2,5-oxadiazole-3-carboxamide (Intermediate 328) in place of N-phenyl-4-(2,2,2-trifluoroethoxy)-1,2,5-oxadiazole-3-carboxamide.

Intermediate 330

4-(2,2-Difluoroethoxy)-1,2,5-oxadiazole-3-carboxylic Acid

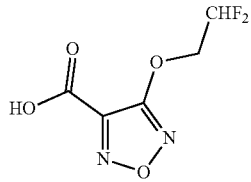 [SMILES: O=C(O)c1nonc1OCC(F)F]

The title compound was prepared as described for the synthesis of Intermediate 327, using tert-butyl (4-(2,2-difluoroethoxy)-1,2,5-oxadiazole-3-carbonyl)(phenyl)carbamate (Intermediate 329) in place of tert-butyl phenyl(4-(2,2,2-trifluoroethoxy)-1,2,5-oxadiazole-3-carbonyl)carbamate.

Intermediate 331

4-(Azetidin-1-yl)-N-phenyl-1,2,5-oxadiazole-3-carboxamide

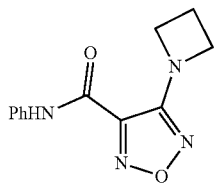

The title compound was prepared as described for the synthesis of Intermediate 325, using azetidine in place of 2,2,2-trifluoroethanol.

Intermediate 332

Tert-Butyl (4-(azetidin-1-yl)-1,2,5-oxadiazole-3-carbonyl)(phenyl)carbamate

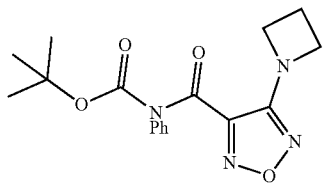

The title compound was prepared as described for the synthesis of Intermediate 326, using 4-(azetidin-1-yl)-N-phenyl-1,2,5-oxadiazole-3-carboxamide (Intermediate 331) in place of N-phenyl-4-(2,2,2-trifluoroethoxy)-1,2,5-oxadiazole-3-carboxamide.

Intermediate 333

4-(Azetidin-1-yl)-1,2,5-oxadiazole-3-carboxylic Acid

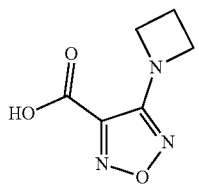

The title compound was prepared as described for the synthesis of Intermediate 327, using tert-butyl (4-(azetidin-1-yl)-1,2,5-oxadiazole-3-carbonyl)(phenyl)carbamate (Intermediate 332) in place of tert-butyl phenyl(4-(2,2,2-trifluoroethoxy)-1,2,5-oxadiazole-3-carbonyl)carbamate.

Intermediate 334

4-(tert-Butoxy)-N-phenyl-1,2,5-oxadiazole-3-carboxamide

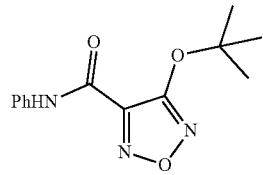

The title compound was prepared as described for the synthesis of Intermediate 325, using tert-butanol in place of 2,2,2-trifluoroethanol.

Intermediate 335

Tert-Butyl (4-(tert-butoxy)-1,2,5-oxadiazole-3-carbonyl)(phenyl)carbamate

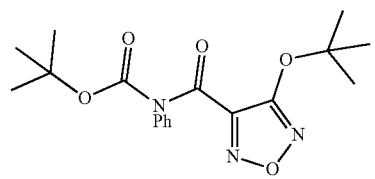

The title compound was prepared as described for the synthesis of Intermediate 326, using 4-(tert-butoxy)-N-phenyl-1,2,5-oxadiazole-3-carboxamide (Intermediate 334) in place of N-phenyl-4-(2,2,2-trifluoroethoxy)-1,2,5-oxadiazole-3-carboxamide.

Intermediate 336

4-(tert-Butoxy)-1,2,5-oxadiazole-3-carboxylic Acid

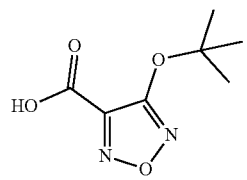

The title compound was prepared as described for the synthesis of Intermediate 327, using tert-butyl (4-(tert-butoxy)-1,2,5-oxadiazole-3-carbonyl)(phenyl)carbamate (Intermediate 335) in place of tert-butyl phenyl(4-(2,2,2-trifluoroethoxy)-1,2,5-oxadiazole-3-carbonyl)carbamate.

Intermediate 337

4-(tert-Butoxy)-1,2,5-oxadiazole-3-carbonyl Chloride

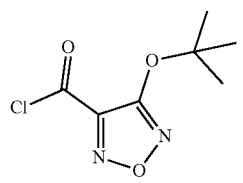

4-(tert-Butoxy)-1,2,5-oxadiazole-3-carboxylic acid (50 mg, 0.27 mmol, Intermediate 336) was dissolved in thionyl chloride (1.3 mL) and heated to 80° C. for 1.5 h. After this time the reaction was concentrated and used crude without further purification.

Intermediate 338

4-Ethoxy-N-phenyl-1,2,5-oxadiazole-3-carboxamide

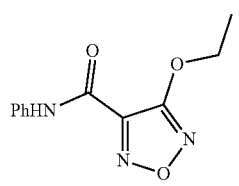

The title compound was prepared as described for the synthesis of Intermediate 325, using ethanol in place of 2,2,2-trifluoroethanol.

Intermediate 339

Tert-Butyl (4-ethoxy-1,2,5-oxadiazole-3-carbonyl)(phenyl)carbamate

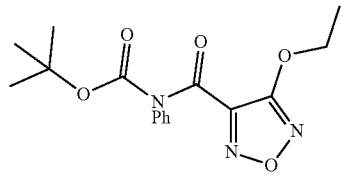

The title compound was prepared as described for the synthesis of Intermediate 326, using 4-ethoxy-N-phenyl-1,2,5-oxadiazole-3-carboxamide (Intermediate 338) in place of N-phenyl-4-(2,2,2-trifluoroethoxy)-1,2,5-oxadiazole-3-carboxamide.

Intermediate 340

4-Ethoxy-1,2,5-oxadiazole-3-carboxylic Acid

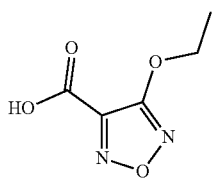

The title compound was prepared as described for the synthesis of Intermediate 327, using tert-butyl (4-ethoxy-1,2,5-oxadiazole-3-carbonyl)(phenyl)carbamate (Intermediate 339) in place of tert-butyl phenyl(4-(2,2,2-trifluoroethoxy)-1,2,5-oxadiazole-3-carbonyl)carbamate.

Intermediate 341

4-Ethoxy-1,2,5-oxadiazole-3-carbonyl Chloride

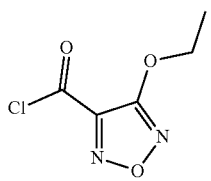

The title compound was prepared as described for the synthesis of Intermediate 337, using 4-ethoxy-1,2,5-oxadiazole-3-carboxylic acid (Intermediate 340) in place of 4-(tert-butoxy)-1,2,5-oxadiazole-3-carboxylic acid.

Intermediate 342

3,4-bis(Hydroxyimino)dihydrofuran-2(3H)-one

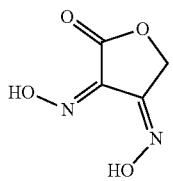

The title compound was synthesized from furan-2,4(3H,5H)-dione by the known procedure as described in Pollet, P.; Gelin, S. Tetronic Acids and Derivatives; Part VI. A Convenient Synthesis of New 4-Oxo-2-phenyl-2H-4,6-dihydrofuro[3,4-d]triazole and 4-Oxo-4,6-dihydrofuro[3,4-c]furazan Systems. *Synthesis.* 1979, 12, 977.

Intermediate 343

4H,6H-Furo[3,4-c][1,2,5]oxadiazol-4-one

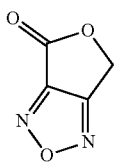

The title compound was synthesized from 3,4-bis(hydroxyimino)dihydrofuran-2(3H)-one (Intermediate 342) by the known procedure as described in Pollet, P.; Gelin, S. Tetronic Acids and Derivatives; Part VI. A Convenient Synthesis of New 4-Oxo-2-phenyl-2H-4,6-dihydrofuro[3,4-d]triazole and 4-Oxo-4,6-dihydrofuro[3,4-c]furazan Systems. *Synthesis*. 1979, 12, 977.

Intermediate 344

4-(Hydroxymethyl)-N-phenyl-1,2,5-oxadiazole-3-carboxamide

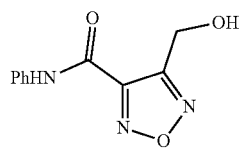

4H,6H-Furo[3,4-c][1,2,5]oxadiazol-4-one (500 mg, 4.0 mmol, Intermediate 343) was dissolved in DMF (2.5 mL) and further diluted with EtOH (20 mL). A solution of aniline (0.40 mL, 4.4 mmol) in EtOH (1.2 mL) was added dropwise and was stirred at rt for 30 min and then heated to 50° C. overnight. After this time the reaction was cooled to rt, concentrated and redissolved in EtOAc (5 mL). Water (20 mL) was added and the biphasic mixture was extracted with EtOAc (3×15 mL). The combined organic layers were washed with brine, dried over anhydrous MgSO$_4$, filtered, and concentrated. The crude product was then purified by silica gel chromatography (0-100% EtOAc/hexanes).

Intermediate 345

4-((Difluoromethoxy)methyl)-N-phenyl-1,2,5-oxadiazole-3-carboxamide

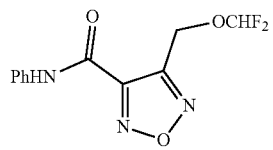

Under an inert atmosphere, 4-(hydroxymethyl)-N-phenyl-1,2,5-oxadiazole-3-carboxamide (640 mg, 2.9 mmol, Intermediate 344) was dissolved in MeCN (6.3 mL) and CuI (110 mg, 2.9 mmol) was added. The solution was heated to 50° C., followed by the dropwise addition of 2,2-difluoro-2-(fluorosulfonyl)acetic acid (0.45 mL, 4.4 mmol) in MeCN (2.2 mL) over 30 min. The reaction was stirred at rt overnight. After that time, the reaction was concentrated, redissolved in EtOAc, filtered over diatomaceous earth (Celite®), and concentrated. The crude product was purified by silica gel chromatography (0-100% EtOAc/hexanes) to afford the title compound as a yellow oil.

Intermediate 346

Tert-Butyl (4-((difluoromethoxy)methyl)-1,2,5-oxadiazole-3-carbonyl)(phenyl)carbamate

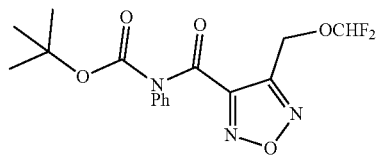

The title compound was prepared as described for the synthesis of Intermediate 326, using 4-((difluoromethoxy)methyl)-N-phenyl-1,2,5-oxadiazole-3-carboxamide (Intermediate 345) in place of N-phenyl-4-(2,2,2-trifluoroethoxy)-1,2,5-oxadiazole-3-carboxamide.

Intermediate 347

4-((Difluoromethoxy)methyl)-1,2,5-oxadiazole-3-carboxylic Acid

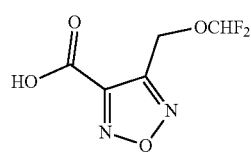 [SMILES: O=C(O)c1nonc1COC(F)F]

The title compound was prepared as described for the synthesis of Intermediate 327, using tert-butyl (4-((difluoromethoxy)methyl)-1,2,5-oxadiazole-3-carbonyl)(phenyl)carbamate (Intermediate 346) in place of tert-butyl phenyl (4-(2,2,2-trifluoroethoxy)-1,2,5-oxadiazole-3-carbonyl)carbamate.

Intermediate 348

4-Hydroxy-5,5-dimethylfuran-2(5H)-one

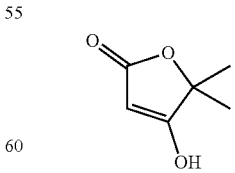

Ethyl acetate (5.0 mL, 51 mmol) and methyl-2-hydroxyisobutyrate (7.1 mL, 61 mmol) were dissolved in THF (88 mL). t-BuOK (12.6 g, 123 mmol) was added and the reaction was heated to 60° C. for 16 h. After this time, the reaction was cooled to rt, concentrated, and diluted with

Intermediate 349

3,4-Bis(hydroxyimino)-5,5-dimethyldihydrofuran-2(3H)-one

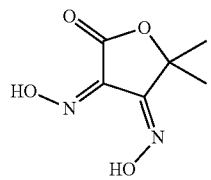

The title compound was prepared as described for the synthesis of Intermediate 342, using 4-hydroxy-5,5-dimethylfuran-2(5H)-one (Intermediate 348) in place of furan-2,4(3H,5H)-dione.

Intermediate 350

6,6-Dimethyl-4H,6H-furo[3,4-c][1,2,5]oxadiazol-4-one

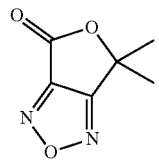

The title compound was prepared as described for the synthesis of Intermediate 343, using 3,4-bis(hydroxyimino)-5,5-dimethyldihydrofuran-2(3H)-one (Intermediate 349) in place of 3,4-bis(hydroxyimino)dihydrofuran-2(3H)-one.

Intermediate 351

4-Hydroxy-5-methylfuran-2(5H)-one

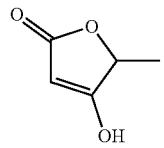

The title compound was prepared as described for the synthesis of Intermediate 348, using methyl acetate in place of ethyl acetate and methyl 2-hydroxypropanoate in place of methyl-2-hydroxyisobutyrate.

Intermediate 352

3,4-bis(Hydroxyimino)-5-methyldihydrofuran-2(3H)-one

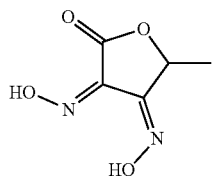

The title compound was prepared as described for the synthesis of Intermediate 342, using 4-hydroxy-5-methylfuran-2(5H)-one (Intermediate 351) in place of furan-2,4(3H,5H)-dione.

Intermediate 353

6-Methyl-4H,6H-furo[3,4-c][1,2,5]oxadiazol-4-one

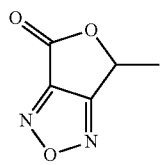

The title compound was prepared as described for the synthesis of Intermediate 343, using 3,4-bis(hydroxyimino)-5-methyldihydrofuran-2(3H)-one (Intermediate 352) in place of 3,4-bis(hydroxyimino)dihydrofuran-2(3H)-one.

Intermediate 354

5-Cyclopropyl-4-hydroxyfuran-2(5H)-one

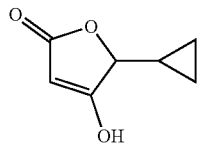

The title compound was prepared as described for the synthesis of Intermediate 351, using methyl 2-cyclopropyl-2-hydroxyacetate in place of methyl 2-hydroxypropanoate.

Intermediate 355

5-Cyclopropyl-3,4-bis(hydroxyimino)dihydrofuran-2(3H)-one

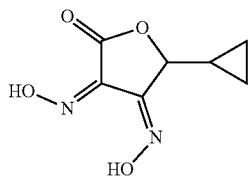 [SMILES: O=C1OC(C2CC2)C(=N/O)/C1=N/O]

The title compound was prepared as described for the synthesis of Intermediate 342, using 5-cyclopropyl-4-hydroxyfuran-2(5H)-one (Intermediate 354) in place of furan-2,4(3H,5H)-dione.

Intermediate 356

6-Cyclopropyl-4H,6H-furo[3,4-c][1,2,5]oxadiazol-4-one

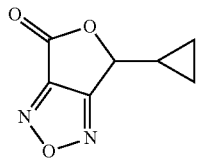 [SMILES: O=C1OC(C2CC2)c2nonc21]

The title compound was prepared as described for the synthesis of Intermediate 343, using 5-cyclopropyl-3,4-bis(hydroxyimino)dihydrofuran-2(3H)-one (Intermediate 355) in place of 3,4-bis(hydroxyimino)dihydrofuran-2(3H)-one.

Intermediate 357

3,4-Bis(hydroxyimino)-6,6-dimethyltetrahydro-2H-pyran-2-one

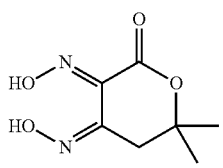

The title compound was prepared as described for the synthesis of Intermediate 342, using 6,6-dimethyldihydro-2H-pyran-2,4(3H)-dione in place of furan-2,4(3H,5H)-dione.

Intermediate 358

6,6-Dimethyl-6,7-dihydro-4H-pyrano[3,4-c][1,2,5]oxadiazol-4-one

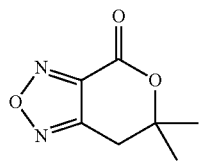

The title compound was prepared as described for the synthesis of Intermediate 343, using 3,4-bis(hydroxyimino)-6,6-dimethyltetrahydro-2H-pyran-2-one (Intermediate 357) in place of 3,4-bis(hydroxyimino)dihydrofuran-2(3H)-one.

Intermediate 359

N—((S)-(7-((R)-Cyclopropyl(4,4,4-trifluorobutanamido)methyl)imidazo[1,2-b]pyridazin-2-yl)(4,4-difluorocyclohexyl)methyl)-4-(hydroxymethyl)-1,2,5-oxadiazole-3-carboxamide

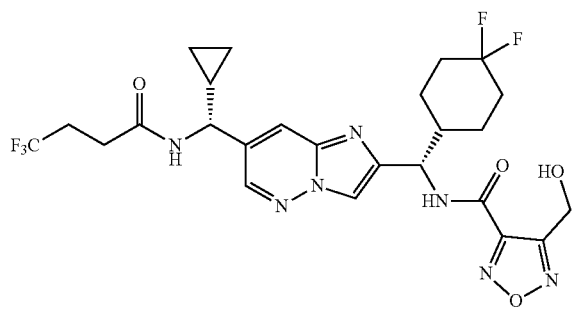 [SMILES: O=C(CCC(F)(F)F)N[C@@H](c1cnn2cc([C@@H](NC(=O)c3nonc3CO)C3CCC(F)(F)CC3)nc2c1)C1CC1]

N—((R)-(2-((S)-Amino(4,4-difluorocyclohexyl)methyl)imidazo[1,2-b]pyridazin-7-yl) (cyclopropyl)methyl)-4,4,4-trifluorobutanamide (100 mg, 0.22 mmol, Intermediate 51) was dissolved in DCM (0.87 mL). 4H,6H-Furo[3,4-c][1,2,5]oxadiazol-4-one (32 mg, 0.25 mmol, Intermediate 343) was added slowly and the reaction was stirred at rt for 15 h. After this time, the reaction was concentrated and directly purified by preparative basic HPLC (XBridge Prep C18 5 μm, 50×100 mm, 10-100 acetonitrile/water (with 20 mM NH₄OH)) to afford the title compound as a thin film.

Intermediate 360

4-(((S)-(7-((R)-Cyclopropyl(4,4,4-trifluorobutana-
mido)methyl)imidazo[1,2-b]pyridazin-2-yl)(4,4-
difluorocyclohexyl)methyl)carbamoyl)-3-isopropyl-
1,2,5-oxadiazole 2-oxide

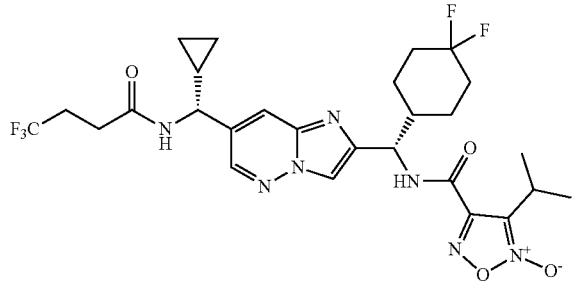 [SMILES: CC(C)c1c(C(=O)N[C@H](c2cn3ncc([C@H](NC(=O)CCC(F)(F)F)C4CC4)cc3n2)C2CCC(F)(F)CC2)no[n+]1[O-]]

The title compound was prepared as described for the synthesis of Example 32, using 4-carboxy-3-isopropyl-1,2,5-oxadiazole 2-oxide (Intermediate 319) in place of 2-(3,3-difluoropropyl)-2H-1,2,3-triazole-4-carboxylic acid to afford the title compound as an off-white powder.

Intermediate 361

3-Cyclopropyl-4-(((S)-(7-((R)-cyclopropyl(4,4,4-
trifluorobutanamido)methyl)imidazo[1,2-b]
pyridazin-2-yl)(4,4-difluorocyclohexyl)methyl)car-
bamoyl)-1,2,5-oxadiazole 2-oxide

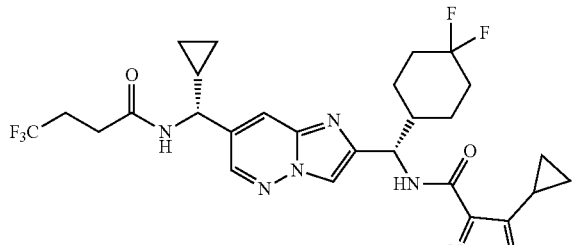

The title compound was prepared as described for the synthesis of Example 32, using 4-carboxy-3-cyclopropyl-1,2,5-oxadiazole 2-oxide (Intermediate 321) in place of 2-(3,3-difluoropropyl)-2H-1,2,3-triazole-4-carboxylic acid to afford the title compound as an off-white powder.

Intermediate 362

4-(2,2-Difluoroethoxy)-1,2,5-oxadiazole-3-carbonyl
Chloride

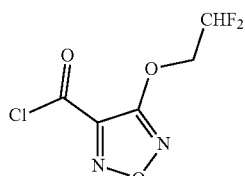

The title compound was prepared as described for the synthesis of Intermediate 337, using 4-(2,2-difluoroethoxy-1,2,5-oxadiazole-3-carboxylic acid (Intermediate 330) in place of 4-(tert-butoxy)-1,2,5-oxadiazole-3-carboxylic acid.

Intermediate 363

4-Hydroxy-1-oxaspiro[4.4]non-3-en-2-one

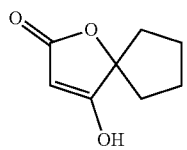 [SMILES: O=C1C=C(O)C2(CCCC2)O1]

The title compound was prepared as described for the synthesis of Intermediate 351, using methyl 1-hydroxycyclopentane-1-carboxylate in place of methyl 2-hydroxypropanoate.

Intermediate 364

3,4-Bis(hydroxyimino)-1-oxaspiro[4.4]nonan-2-one

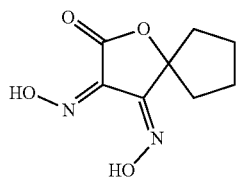 [SMILES: O=C1OC2(CCCC2)C(=N/O)/C1=N/O]

The title compound was prepared as described for the synthesis of Intermediate 342, using 4-hydroxy-1-oxaspiro[4.4]non-3-en-2-one (Intermediate 363) in place of furan-2,4(3H,5H)-dione.

Intermediate 365

6'H-Spiro[cyclopentane-1,4'-furo[3,4-c][1,2,5]oxadiazol]-6'-one

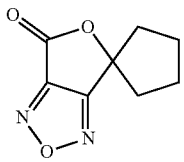 [SMILES: O=C1OC2(CCCC2)c2nonc21]

The title compound was prepared as described for the synthesis of Intermediate 343, using 5-4-hydroxy-1-oxaspiro[4.4]non-3-en-2-one (Intermediate 364) in place of 3,4-bis(hydroxyimino)dihydrofuran-2(3H)-one.

Intermediate 366

Tert-Butyl ((S)-(7-((S*)-1-(((R)-tert-butylsulfinyl)amino)-2-cyanoethyl)imidazo[1,2-b]pyridazin-2-yl)(4,4-difluorocyclohexyl)methyl)carbamate

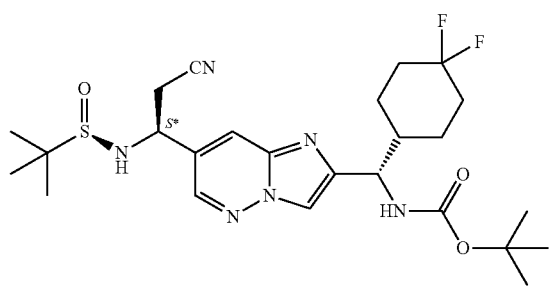 [SMILES: CC(C)(C)OC(=O)N[C@H](c1cn2ncc([C@H](CC#N)N[S@](=O)C(C)(C)C)cc2n1)C1CCC(F)(F)CC1]

A flask charged with tert-butyl ((S)-(7-((E)-(((R)-tert-butylsulfinyl)imino)methyl)imidazo[1,2-b]pyridazin-2-yl)(4,4-difluorocyclohexyl)methyl)carbamate (360 mg, 0.67 mmol, Intermediate 429) was dissolved in THF (9.5 mL). Tetra-butyl ammonium phenoxide (980 mg, 2.3 mmol) was added and the solution was cooled to −78° C. 2-Trimethylsilylacetonitrile (8.2 mL, 8.6 mmol) was added dropwise and stirred for 0.75 h. The reaction was quenched with cold water (20 mL) and extracted with EtOAc (3×20 mL). The combined organic layers were washed with brine, dried over anhydrous MgSO$_4$, filtered, and concentrated to dryness. The residue was purified by silica gel chromatography (0-100% EtOAc/hexanes) to afford the title compound as an off-white foam.

Intermediate 367

Tert-Butyl ((S)-(7-((S*)-1-amino-2-cyanoethyl)imidazo[1,2-b]pyridazin-2-yl)(4,4-difluorocyclohexyl)methyl)carbamate

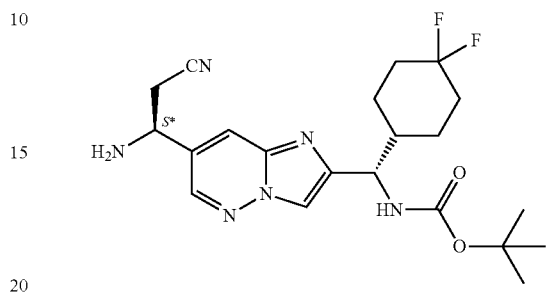

The title compound was prepared as described for the synthesis of Intermediate 49, using tert-butyl ((S)-(7-((S*)-1-(((R)-tert-butylsulfinyl)amino)-2-cyanoethyl)imidazo[1,2-b]pyridazin-2-yl)(4,4-difluorocyclohexyl)methyl)carbamate (Intermediate 366) in place of tert-butyl ((S)-(7-((R)-(((S)-tert-butylsulfinyl)amino)(cyclopropyl)methyl)imidazo[1,2-b]pyridazin-2-yl)(4,4-difluorocyclohexyl)methyl)carbamate.

Intermediate 368

Tert-Butyl ((S)-(7-((S*)-2-cyano--(2-(3,3-difluorocyclobutyl)acetamido)ethyl)imidazo[1,2-b]pyridazin-2-yl)(4,4-difluorocyclohexyl)methyl)carbamate

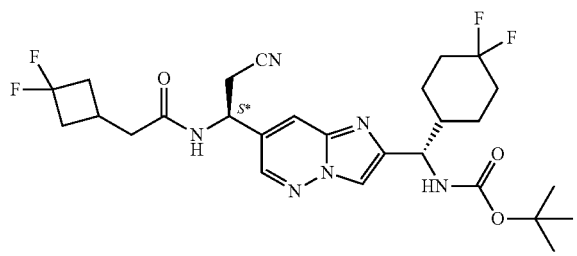 [SMILES: CC(C)(C)OC(=O)N[C@H](c1cn2ncc([C@H](CC#N)NC(=O)CC3CC(F)(F)C3)cc2n1)C1CCC(F)(F)CC1]

The title compound was prepared as described for the synthesis of Example 493, using tert-butyl ((S)-(7-((S*)-1-amino-2-cyanoethyl)imidazo[1,2-b]pyridazin-2-yl)(4,4-difluorocyclohexyl)methyl)carbamate (Intermediate 367) in place of N—((R*)-(2-((S)-amino(4,4-difluorocyclohexyl)methyl)imidazo[1,2-b]pyridazin-7-yl)(cyclobutyl)methyl)-2-(3,3-difluorocyclobutyl)acetamide and 2-(3,3-difluorocyclobutyl)acetic acid in place of 4-methyl-1,2,5-oxadiazole-3-carboxylic acid.

Intermediate 369

N—((S*)-1-(2-((S)-Amino(4,4-difluorocyclohexyl)methyl)imidazo[1,2-b]pyridazin-7-yl)-2-cyanoethyl)-2-(3,3-difluorocyclobutyl)acetamide

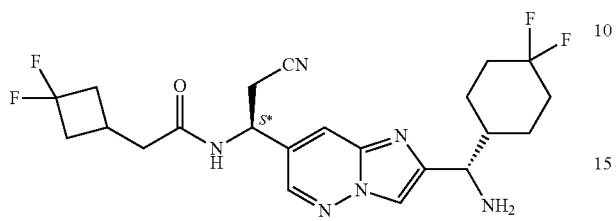

The title compound was prepare as described for the synthesis of Intermediate 51, using tert-butyl ((S)-(7-((S*)-2-cyano-1-(2-(3,3-difluorocyclobutyl)acetamido)ethyl)imidazo[1,2-b]pyridazin-2-yl)(4,4-difluorocyclohexyl)methyl)carbamate (Intermediate 368) in place of tert-butyl ((S)-(7-((R)-cyclopropyl(4,4,4-trifluorobutanamido)methyl)imidazo[1,2-b]pyridazin-2-yl)(4,4-difluorocyclohexyl)methyl) carbamate.

Intermediate 370

Tert-Butyl ((S)-(7-((R*)-1-(((S)-tert-butylsulfinyl)amino)but-3-en-1-yl)imidazo[1,2-b]pyridazin-2-yl)(4,4-difluorocyclohexyl)methyl)carbamate

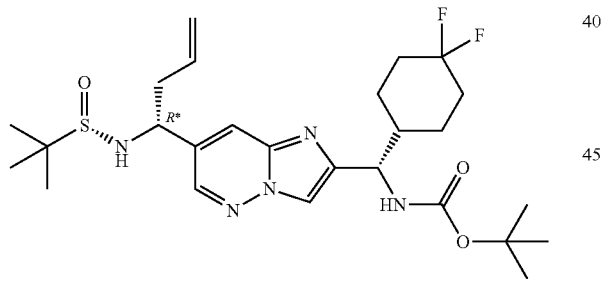

To a solution of tert-butyl ((S)-(7-((E)-(((S)-tert-butylsulfinyl)imino)methyl)imidazo[1,2-b]pyridazin-2-yl)(4,4-difluorocyclohexyl)methyl)carbamate (1.5 g, 3.0 mmol, Intermediate 47) in THF (7.5 mL), indium was added (520 mg, 4.5 mmol). Allyl bromide (0.39 mL, 4.5 mmol) was then added dropwise and the reaction was heated to 60° C. After 2 h the reaction was cooled to rt and diluted with water and EtOAc. The resultant emulsion was filtered through Celite® and extracted with EtOAc (2×20 mL). The combined organic layers were washed with brine, dried over anhydrous MgSO₄, filtered, and concentrated under reduced pressure. The crude product was purified by silica gel chromatography (30-100% acetone/hexanes) to afford the title compound.

Intermediate 371

Tert-Butyl ((S)-(7-((R*)-1-aminobut-3-en-1-yl)imidazo[1,2-b]pyridazin-2-yl)(4,4-difluorocyclohexyl)methyl)carbamate

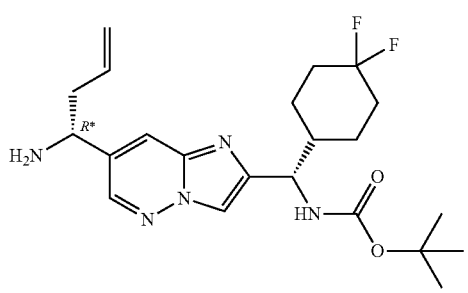 [SMILES: C=CC[C@@H](N)c1cnn2cc([C@@H](NC(=O)OC(C)(C)C)C3CCC(F)(F)CC3)nc2c1]

The title compound was prepared as described for the synthesis of Intermediate 49, using tert-butyl ((S)-(7-((R*)-1-(((S)-tert-butylsulfinyl)amino)but-3-en-1-yl)imidazo[1,2-b]pyridazin-2-yl)(4,4-difluorocyclohexyl)methyl)carbamate (Intermediate 370) in place of tert-butyl ((S)-(7-((R)-(((S)-tert-butylsulfinyl)amino)(cyclopropyl)methyl)imidazo[1,2-b]pyridazin-2-yl)(4,4-difluorocyclohexyl)methyl)carbamate.

Intermediate 372

Tert-Butyl ((S)-(7-((R*)-1-(2-(3,3-difluorocyclobutyl)acetamido)but-3-en-1-yl)imidazo[1,2-b]pyridazin-2-yl)(4,4-difluorocyclohexyl)methyl)carbamate

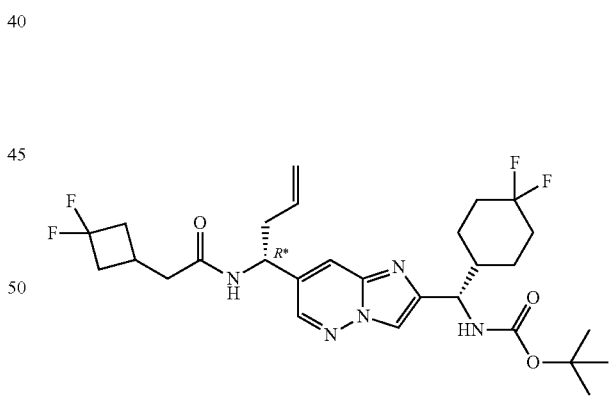

The title compound was prepared as described for the synthesis of Intermediate 439, using tert-butyl ((S)-(7-((R*)-1-aminobut-3-en-1-yl)imidazo[1,2-b]pyridazin-2-yl)(4,4-difluorocyclohexyl)methyl)carbamate (Intermediate 371) in place of N—((R*)-(2-((S)-amino(4,4-difluorocyclohexyl)methyl)imidazo[1,2-b]pyridazin-7-yl)(cyclobutyl)methyl)-2-(3,3-difluorocyclobutyl)acetamide.

Intermediate 373

Tert-Butyl ((S)-(7-((R*)-1-(2-(3,3-difluorocyclobutyl)acetamido)-3-oxopropyl)imidazo[1,2-b]pyridazin-2-yl)(4,4-difluorocyclohexyl)methyl)carbamate

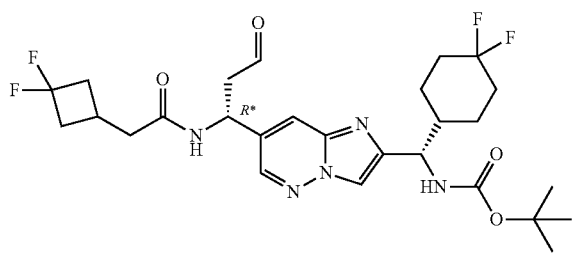 [SMILES: CC(C)(C)OC(=O)N[C@H](c1cn2ncc([C@@H](CC=O)NC(=O)CC3CC(F)(F)C3)cc2n1)C1CCC(F)(F)CC1]

The title compound was prepared as described for the synthesis of Intermediate 46, using tert-butyl ((S)-(7-((R*)-1-(2-(3,3-difluorocyclobutyl)acetamido)but-3-en-1-yl)imidazo[1,2-b]pyridazin-2-yl)(4,4-difluorocyclohexyl)methyl) carbamate (Intermediate 372) in place of tert-butyl (S)-((4,4-difluorocyclohexyl)(7-vinylimidazo[1,2-b]pyridazin-2-yl)methyl)carbamate.

Intermediate 374

Tert-Butyl ((S)-(7-((R*)-1-(2-(3,3-difluorocyclobutyl)acetamido)-3,3-difluoropropyl)imidazo[1,2-b]pyridazin-2-yl)(4,4-difluorocyclohexyl)methyl)carbamate

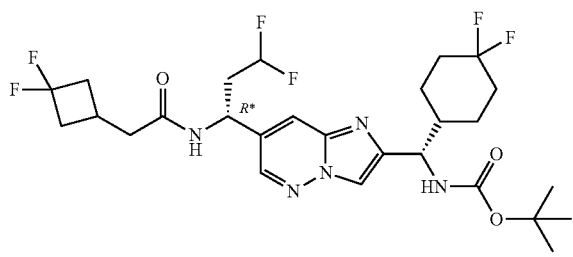 [SMILES: CC(C)(C)OC(=O)N[C@H](c1cn2ncc([C@@H](CC(F)F)NC(=O)CC3CC(F)(F)C3)cc2n1)C1CCC(F)(F)CC1]

To a solution of triethylamine trihydrofluoride (0.19 mL, 1.1 mmol) in DCM (1 mL) was added Xtalfluor-E® (190 mg, 0.85 mmol) followed by tert-butyl ((S)-(7-((R*)-1-(2-(3,3-difluorocyclobutyl)acetamido)-3-oxopropyl)imidazo[1,2-b]pyridazin-2-yl)(4,4-difluorocyclohexyl)methyl)carbamate (320 mg, 0.56 mmol, Intermediate 373). The reaction was allowed to stir at rt for 2.6 h, after which time the reaction was quenched with a saturated aqueous solution of NaHCO₃. The biphasic mixture was extracted with EtOAc (15 mL×3) and the combined organic layers were washed with brine, dried over anhydrous MgSO₄, filtered, and concentrated. Purification by preparative basic HPLC (XBridge Prep OBD, 5 μM C18, 10-100% acetonitrile/water (with 20 mM NH₄OH) followed by lyophilization provided the title compound as a white powder.

Intermediate 375

N—((R*)-1-(2-((S)-Amino(4,4-difluorocyclohexyl)methyl)imidazo[1,2-b]pyridazin-7-yl)-3,3-difluoropropyl)-2-(3,3-difluorocyclobutyl)acetamide

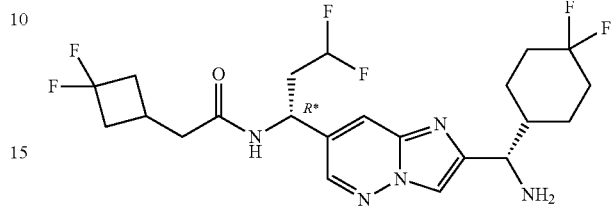

The title compound was prepared as described for the synthesis of Intermediate 51, using tert-butyl ((S)-(7-((R*)-1-(2-(3,3-difluorocyclobutyl)acetamido)-3,3-difluoropropyl)imidazo[1,2-b]pyridazin-2-yl)(4,4-difluorocyclohexyl)methyl)carbamate (Intermediate 374) in place of tert-butyl ((S)-(7-((R)-cyclopropyl(4,4,4-trifluorobutanamido)methyl)imidazo[1,2-b]pyridazin-2-yl)(4,4-difluorocyclohexyl)methyl) carbamate.

Intermediate 376

(1R,3s,5S)-6,6-Difluorobicyclo[3.1.0]hexane-3-carbaldehyde and (1R,3r,5S)-6,6-difluorobicyclo[3.1.0]hexane-3-carbaldehyde

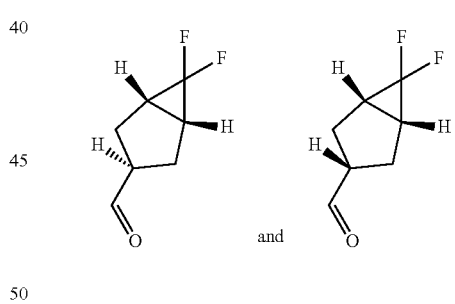

To a solution of methyl (1R,5S)-6,6-difluorobicyclo[3.1.0]hexane-3-carboxylate (3.4 g, 19 mmol) in DCM (60 mL) at −78° C. was added DIBAL-H (29 mL, 29 mmol, 1 M solution in toluene) dropwise and the resulting mixture was allowed to stir at rt for 2 h. After this time the reaction was quenched with a saturated aqueous solution of Rochelle Salt (100 mL). The biphasic mixture was transferred to a separatory funnel and extracted with CH₂Cl₂ (50 mL×4). The combined organic layers were washed with brine (50 mL), dried over anhydrous Na₂SO₄, filtered, and concentrated to remove CH₂Cl₂ to afford a crude mixture of the title compounds as a solution in toluene which was used without further purification.

Intermediate 377

(S)—N-((E)-((1R,3s,5S)-6,6-Difluorobicyclo[3.1.0]hexan-3-yl)methylene)-2-methylpropane-2-sulfinamide

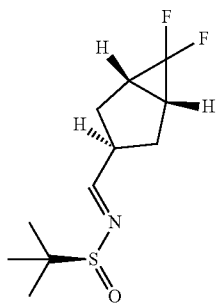 [SMILES: CC(C)(C)[S@](=O)/N=C/[C@@H]1C[C@@H]2[C@H](C1)C2(F)F]

The title compound was prepared as described for the synthesis of Intermediate 47, using (1R,3s,5S)-6,6-difluorobicyclo[3.1.0]hexane-3-carbaldehyde and (1R,3r,5S)-6,6-difluorobicyclo[3.1.0]hexane-3-carbaldehyde (Intermediate 376) in place of (S)-((4,4-difluorocyclohexyl)(7-formylimidazo[1,2-b]pyridazin-2-yl)methyl)carbamate. The title compound was purified by silica gel chromatography (5-20% EtOAc/petroleum ether).

Intermediate 378

(S)—N—((S*)-Cyano((1R,3s,5S)-6,6-difluorobicyclo[3.1.0]hexan-3-yl)methyl)-2-methylpropane-2-sulfinamide

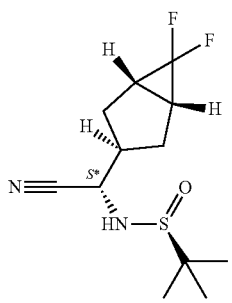 [SMILES: CC(C)(C)[S@](=O)N[C@H](C#N)[C@@H]1C[C@@H]2[C@H](C1)C2(F)F]

The title compound was prepared as described for the synthesis of Intermediate 279, using (S)—N—((E)-((1R,3s,5S)-6,6-difluorobicyclo[3.1.0]hexan-3-yl)methylene)-2-methylpropane-2-sulfinamide (Intermediate 377) in place of (S,E)-2-methyl-N-(2-((1,1,1-trifluoro-2-methylpropan-2-yl)oxy)ethylidene) propane-2-sulfinamide.

Intermediate 379

(S*)-2-Amino-2-((1R,3s,5S)-6,6-difluorobicyclo[3.1.0]hexan-3-yl)acetic Acid

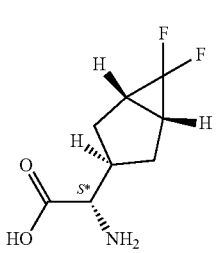 [SMILES: N[C@H](C(=O)O)[C@@H]1C[C@@H]2[C@H](C1)C2(F)F]

The title compound was prepared as described for the synthesis of Intermediate 280, using (S)—N—((S*)-cyano((1R,3s,5S)-6,6-difluorobicyclo[3.1.0]hexan-3-yl)methyl)-2-methylpropane-2-sulfinamide (Intermediate 378) in place of (S)—N—((R)-1-cyano-2-((1,1,1-trifluoro-2-methylpropan-2-yl)oxy)ethyl)-2-methylpropane-2-sulfinamide.

Intermediate 380

(S*)-2-((tert-Butoxycarbonyl)amino)-2-((1R,3s,5S)-6,6-difluorobicyclo[3.1.0]hexan-3-yl)acetic Acid

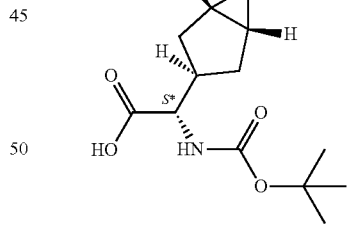

The title compound was prepared as described for the synthesis of Intermediate 281, using (S*)-2-amino-2-((1R,3s,5S)-6,6-difluorobicyclo[3.1.0]hexan-3-yl)acetic acid (Intermediate 379) in place of O-(1,1,1-trifluoro-2-methylpropan-2-yl)-L-serine.

Intermediate 381

Tert-Butyl ((S*)-1-((1R,3s,5S)-6,6-difluorobicyclo[3.1.0]hexan-3-yl)-3-(dimethyl(oxo)-$\lambda^6$-sulfaneylidene)-2-oxopropyl)carbamate

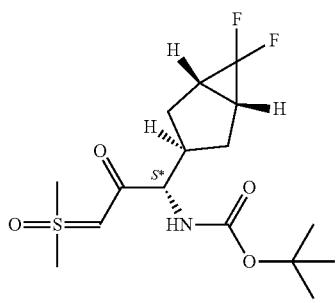 [SMILES: CC(C)(C)OC(=O)N[C@H](C(=O)C=S(C)(C)=O)[C@@H]1C[C@@H]2[C@H](C1)C2(F)F]

The title compound was prepared as described for the synthesis of Intermediate 282, using (S*)-2-((tert-butoxycarbonyl)amino)-2-((1R,3s,5S)-6,6-difluorobicyclo[3.1.0]hexan-3-yl)acetic acid (Intermediate 380) in place of N-(tert-butoxycarbonyl)-O-(1,1,1-trifluoro-2-methylpropan-2-yl)-L-serine. The residue was purified by silica gel chromatography (66-100% EtOAc/petroleum ether) followed by SFC (DAICEL CHIRALPAK AD, 10 μM 250×30 mm, Mobile phase: 45% (0.1% (25% aqueous NH$_4$OH) in EtOH), 55% CO$_2$) to provide the title compound.

Intermediate 382

Tert-Butyl ((S*)-3-chloro-1-((1R,3s,5S)-6,6-difluorobicyclo[3.1.0]hexan-3-yl)-2-oxopropyl)carbamate

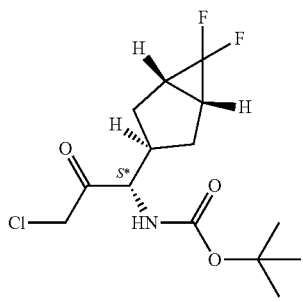 [SMILES: CC(C)(C)OC(=O)N[C@H](C(=O)CCl)[C@@H]1C[C@@H]2[C@H](C1)C2(F)F]

The title compound was prepared as described for the synthesis of Intermediate 253, using tert-butyl ((S*)-1-((1R,3s,5S)-6,6-difluorobicyclo[3.1.0]hexan-3-yl)-3-(dimethyl(oxo)-$\lambda^6$-sulfaneylidene)-2-oxopropyl)carbamate (Intermediate 381) in place of (S)-(4-(dimethyl(oxo)-$\lambda^6$-sulfaneylidene)-3-oxo-1-((1,1,1-trifluoro-2-methylpropan-2-yl)oxy)butan-2-yl)carbamate.

Intermediate 383

Tert-Butyl ((S*)-1-((1R,3s,5S)-6,6-difluorobicyclo[3.1.0]hexan-3-yl)-3-iodo-2-oxopropyl)carbamate

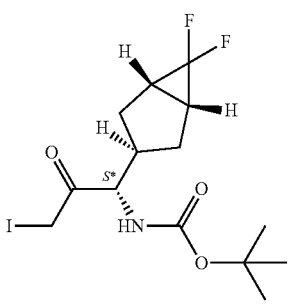 [SMILES: CC(C)(C)OC(=O)N[C@H](C(=O)CI)[C@@H]1C[C@@H]2[C@H](C1)C2(F)F]

The title compound was prepared as described for the synthesis of Intermediate 254, using tert-butyl ((S*)-3-chloro-1-((1R,3s,5S)-6,6-difluorobicyclo[3.1.0]hexan-3-yl)-2-oxopropyl)carbamate (Intermediate 382) in place of tert-butyl (S)-(4-chloro-3-oxo-1-((1,1,1-trifluoro-2-methylpropan-2-yl)oxy)butan-2-yl)carbamate.

Intermediate 384

Tert-Butyl ((S*)-(6-chloro-7-((R)-cyclopropyl(2-(3,3-difluorocyclobutyl)acetamido)methyl)imidazo[1,2-b]pyridazin-2-yl)((1R,3s,5S)-6,6-difluorobicyclo[3.1.0]hexan-3-yl)methyl)carbamate

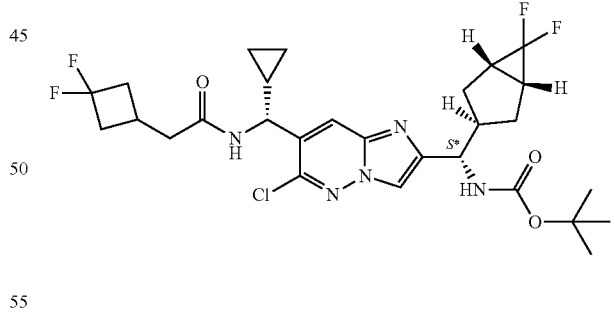

The title compound was prepared as described for the synthesis of Intermediate 260, using tert-butyl ((S*)-1-((1R,3s,5S)-6,6-difluorobicyclo[3.1.0]hexan-3-yl)-3-iodo-2-oxopropyl)carbamate (Intermediate 383) in place of tert-butyl (S)-(4-iodo-3-oxo-1-((1,1,1-trifluoro-2-methylpropan-2-yl)oxy)butan-2-yl)carbamate.

Intermediate 385

Tert-Butyl ((S*)-(7-((R)-cyclopropyl(2-(3,3-difluorocyclobutyl)acetamido)methyl)imidazo[1,2-b]pyridazin-2-yl)((1R,3s,5S)-6,6-difluorobicyclo[3.1.0]hexan-3-yl)methyl)carbamate

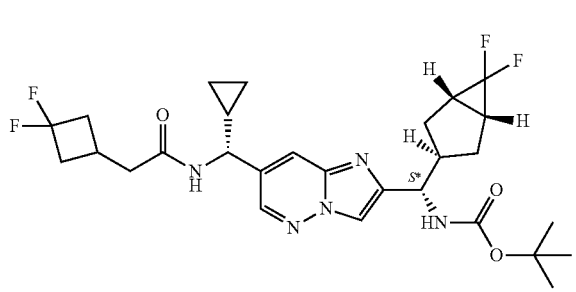 [SMILES: CC(C)(C)OC(=O)N[C@H](c1cn2ncc([C@H](NC(=O)CC3CC(F)(F)C3)C3CC3)cc2n1)[C@@H]1C[C@@H]2[C@H](C1)C2(F)F]

The title compound was prepared as described for the synthesis of Intermediate 261, using tert-butyl ((S*)-(6-chloro-7-((R)-cyclopropyl(2-(3,3-difluorocyclobutyl)acetamido)methyl)imidazo[1,2-b]pyridazin-2-yl)((1R,3s,5S)-6,6-difluorobicyclo[3.1.0]hexan-3-yl)methyl)carbamate (Intermediate 384) in place of tert-butyl ((R)-1-(6-chloro-7-((R)-cyclopropyl(2-(3,3-difluorocyclobutyl)acetamido)methyl)imidazo[1,2-b]pyridazin-2-yl)-2-((1,1,1-trifluoro-2-methylpropan-2-yl)oxy)ethyl)carbamate.

Intermediate 386

N—((R)-(2-((S*)-Amino((1R,3s,5S)-6,6-difluorobicyclo[3.1.0]hexan-3-yl)methyl)imidazo[1,2-b]pyridazin-7-yl)(cyclopropyl)methyl)-2-(3,3-difluorocyclobutyl)acetamide

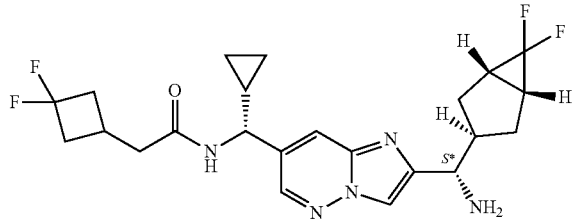 [SMILES: N[C@H](c1cn2ncc([C@H](NC(=O)CC3CC(F)(F)C3)C3CC3)cc2n1)[C@@H]1C[C@@H]2[C@H](C1)C2(F)F]

The title compound was prepared as described for the synthesis of Intermediate 51, using tert-butyl ((S*)-(7-((R)-cyclopropyl(2-(3,3-difluorocyclobutyl)acetamido)methyl)imidazo[1,2-b]pyridazin-2-yl)((1R,3s,5S)-6,6-difluorobicyclo[3.1.0]hexan-3-yl)methyl)carbamate (Intermediate 385) in place of tert-butyl ((S)-(7-((R)-cyclopropyl(4,4,4-trifluorobutanamido)methyl)imidazo[1,2-b]pyridazin-2-yl)(4,4-difluorocyclohexyl)methyl) carbamate.

Intermediate 387

4-(Dimethylamino)-N-phenyl-1,2,5-oxadiazole-3-carboxamide

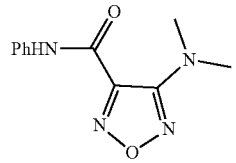

A mixture of 4-chloro-N-phenyl-1,2,5-oxadiazole-3-carboxamide (500 mg, 2.24 mmol), dimethylamine hydrochloride (0.91 g, 11.2 mmol) and DIPEA (3.9 mL, 22.4 mmol) in 1,4-dioxane (10 mL) was stirred at 100° C. for 16 h. After that time the mixture was concentrated to dryness and purified by silica gel chromatography (0-17% EtOAc/petroleum ether) to provide the title compound as a yellow solid.

Intermediate 388

Tert-Butyl (4-(dimethylamino)-1,2,5-oxadiazole-3-carbonyl)(phenyl)carbamate

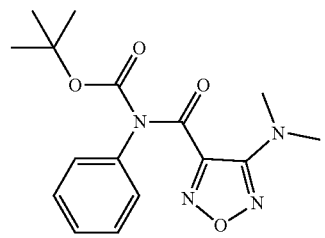 [SMILES: CN(C)c1nonc1C(=O)N(C(=O)OC(C)(C)C)c1ccccc1]

A mixture of Boc anhydride (0.56 g, 2.6 mmol), 4-(dimethylamino)-N-phenyl-1,2,5-oxadiazole-3-carboxamide (0.4 g, 1.7 mmol, Intermediate 387), DMAP (21 mg, 0.17 mmol) and DCM (10 mL) was stirred at rt for 16 h and the concentrated to dryness. The residue was purified by silica gel chromatography (0-25% EtOAc/hexanes) to provide the title compound as a white solid.

Intermediate 389

4-(Dimethylamino)-1,2,5-oxadiazole-3-carboxylic Acid

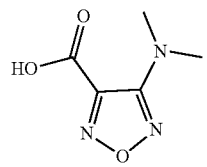

A mixture of tert-butyl (4-(dimethylamino)-1,2,5-oxadiazole-3-carbonyl)(phenyl)carbamate (0.1 g, 0.3 mmol, Intermediate 388) and LiOH·H$_2$O (15 mg, 0.36 mmol) in THF/water (1:1, 2 mL) was stirred at rt for 16 h. After that time, the mixture was diluted with water (100 mL) and extracted with EtOAc (2×50 mL). The pH of the aqueous phase was adjusted to pH=3 by the addition of saturated aqueous KHSO₄ followed by extraction with EtOAc (3×60 mL). The organic layers were combined, washed with brine (60 mL), dried over anhydrous Na$_2$SO$_4$, filtered and concentrated to dryness. The residue was triturated with n-hexane/DCM (50:1, 51 mL) at 30° C. for 30 min, then filtered and the filter cake washed with n-hexane (5 mL) followed by drying under vacuum to provide the title compound as a white solid.

Intermediate 390

(4-(Phenylcarbamoyl)-1,2,5-oxadiazol-3-yl)methyl Methanesulfonate

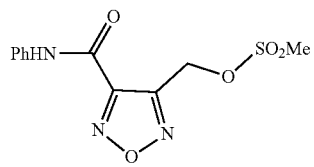

4-(Hydroxymethyl)-N-phenyl-1,2,5-oxadiazole-3-carboxamide (0.77 g, 3.5 mmol, Intermediate 344) was added to a mixture of TEA (1.7 mL, 12 mmol) in DCM (25 mL). The solution was cooled to 0° C. and then MsCl (0.48 g, 4.2 mmol) was added dropwise. The resulting mixture was stirred for 30 min, then quenched by the addition of saturated aqueous NaHCO₃ (60 mL). The mixture was extracted with DCM (3×50 mL), and the combined organic extracts were dried over anhydrous Na$_2$SO$_4$, filtered and concentrated to dryness to provide the title compound as a yellow solid.

Intermediate 391

4-((3-Fluoroazetidin-1-yl)methyl)-N-phenyl-1,2,5-oxadiazole-3-carboxamide

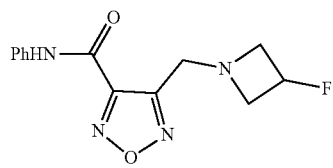

To a solution of (4-(phenylcarbamoyl)-1,2,5-oxadiazol-3-yl)methyl methanesulfonate (0.50 g, 1.7 mmol, Intermediate 390) in DCE (10 mL) was added 3-fluoroazetidine hydrochloride (225 mg, 2.02 mmol) followed by DIPEA (0.83 mL, 5.1 mmol), and the resulting mixture was stirred at 60° C. for 16 h. After that time, the mixture was diluted with DCM (50 mL) and quenched with water (30 mL). The layers were separated, and the aqueous layer further extracted with DCM (2×20 mL). The organic layers were combined, washed with brine (50 mL), dried over anhydrous Na$_2$SO$_4$, filtered and concentrated to dryness. The residue was purified by silica gel chromatography (0-5% EtOAc/petroleum ether) to provide the title compound as a yellow oil.

Intermediate 392

Tert-Butyl (4-((3-fluoroazetidin-1-yl)methyl)-1,2,5-oxadiazole-3-carbonyl)(phenyl)carbamate

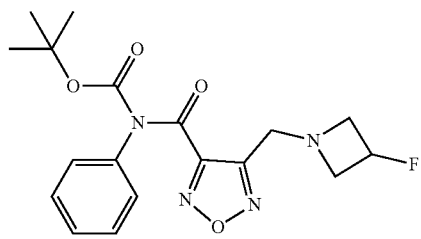 [SMILES: CC(C)(C)OC(=O)N(C(=O)c1nonc1CN1CC(F)C1)c1ccccc1]

The title compound was prepared as described for the synthesis of Intermediate 388, using 4-((3-fluoroazetidin-1-yl)methyl)-N-phenyl-1,2,5-oxadiazole-3-carboxamide (Intermediate 391) in place of 4-(dimethylamino)-N-phenyl-1,2,5-oxadiazole-3-carboxamide.

Intermediate 393

4-((3-Fluoroazetidin-1-yl)methyl)-1,2,5-oxadiazole-3-carboxylic Acid

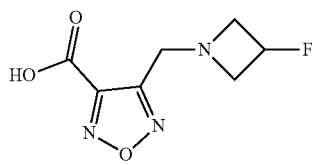 [SMILES: O=C(O)c1nonc1CN1CC(F)C1]

A mixture of tert-butyl (4-((3-fluoroazetidin-1-yl)methyl)-1,2,5-oxadiazole-3-carbonyl)(phenyl)carbamate (150 mg, 0.40 mmol, Intermediate 392) and LiOH·H₂O (25 mg, 0.60 mmol) in THF/water (1:1, 2 mL) was stirred at rt for 16 h. After that time, the mixture was diluted with water (40 mL) and extracted with MTBE (2×20 mL). The pH of the aqueous phase was adjusted to pH=3 by the addition of saturated aqueous KHSO₄, and then the solvent was removed by lyophilization. The residue was extracted with THF (3×30 mL), concentrated to dryness, washed with DCM (2×20 mL), and lyophilized again to provide the title compound as a colorless solid.

Intermediate 394

4-Morpholino-N-phenyl-1,2,5-oxadiazole-3-carboxamide

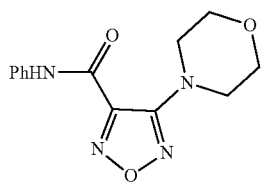

A mixture of 4-chloro-N-phenyl-1,2,5-oxadiazole-3-carboxamide (1.0 g, 4.5 mmol) and morpholine (4 mL) was stirred at 100° C. for 16 h. After that time, the mixture was poured into water (60 mL) and extracted with EtOAc (2×20 mL). The organic layers were combined, washed with brine (20 mL), dried over anhydrous Na$_2$SO$_4$, filtered and concentrated to dryness to provide the title compound as a yellow solid.

Intermediate 395

Tert-Butyl (4-morpholino-1,2,5-oxadiazole-3-carbonyl)(phenyl)carbamate

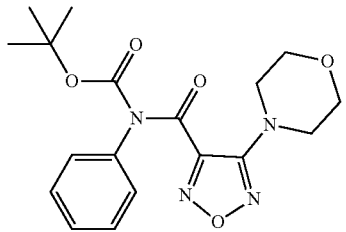 [SMILES: CC(C)(C)OC(=O)N(C(=O)c1nonc1N1CCOCC1)c1ccccc1]

The title compound was prepared as described for the synthesis of Intermediate 388 using 4-morpholino-N-phenyl-1,2,5-oxadiazole-3-carboxamide (Intermediate 394) in place of 4-(dimethylamino)-N-phenyl-1,2,5-oxadiazole-3-carboxamide.

Intermediate 396

4-Morpholino-1,2,5-oxadiazole-3-carboxylic Acid

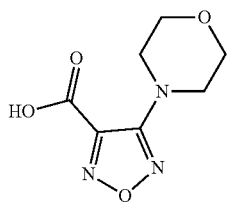 [SMILES: O=C(O)c1nonc1N1CCOCC1]

The title compound was prepared as described for the synthesis of Intermediate 393 using tert-butyl (4-morpholino-1,2,5-oxadiazole-3-carbonyl)(phenyl)carbamate (Intermediate 395) in place of tert-butyl (4-((3-fluoroazetidin-1-yl)methyl)-1,2,5-oxadiazole-3-carbonyl)(phenyl)carbamate.

Intermediate 397

4-Methoxy-N-phenyl-1,2,5-oxadiazole-3-carboxamide

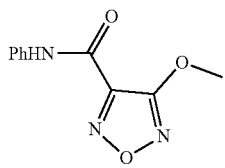

4-Chloro-N-phenyl-1,2,5-oxadiazole-3-carboxamide (6.00 g, 26.8 mmol) was added to a mixture of NaOMe (5.80 g, 107 mmol) in MeOH (200 mL) and the mixture was stirred at rt overnight. After that time, the mixture was concentrated to dryness and the residue partitioned between water (200 mL) and EtOAc (150 mL). The aqueous layer was further extracted with EtOAc (150 mL), the organic layers combined, washed with brine (200 mL), dried over anhydrous Na$_2$SO$_4$, filtered and concentrated to dryness. The residue was purified by silica gel chromatography (0-40% EtOAc/petroleum ether) to provide the title compound as a yellow solid.

Intermediate 398

Tert-Butyl (4-methoxy-1,2,5-oxadiazole-3-carbonyl)(phenyl)carbamate

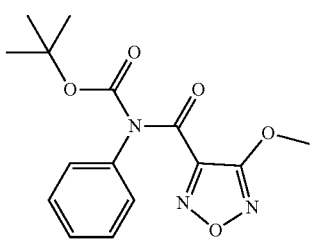 [SMILES: COc1nonc1C(=O)N(C(=O)OC(C)(C)C)c1ccccc1]

The title compound was prepared as described for the synthesis of Intermediate 388 using 4-methoxy-N-phenyl-1,2,5-oxadiazole-3-carboxamide (Intermediate 397) in place of 4-(dimethylamino)-N-phenyl-1,2,5-oxadiazole-3-carboxamide. The residue was purified by silica gel chromatography (0-25% EtOAc/petroleum ether) to provide the title compound as a white solid.

Intermediate 399

4-Methoxy-1,2,5-oxadiazole-3-carboxylic Acid

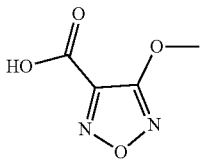

A mixture of tert-butyl (4-methoxy-1,2,5-oxadiazole-3-carbonyl)(phenyl)carbamate (5.52 g, 17.3 mmol, Intermediate 398) and LiOH·H$_2$O (1.09 g, 26.0 mmol) in THF/water (1:1, 55 mL) was stirred at rt overnight. After that time, the mixture was diluted with water (100 mL) and extracted with MTBE (2×100 mL). The pH of the aqueous phase was adjusted to pH=3 by the addition of saturated aqueous KHSO$_4$, and then extracted with EtOAc (2×100 mL). The organic layers were combined, washed with brine (150 mL), dried over anhydrous Na$_2$SO$_4$, filtered and concentrated to dryness to provide the title compound as an off-white solid.

Intermediate 400

Tert-Butyl ((S)-(7-((R)-cyclopropyl(3-cyclopropyl-2,2-difluoropropanamido)methyl)imidazo[1,2-b]pyridazin-2-yl)(4,4-difluorocyclohexyl)methyl)carbamate

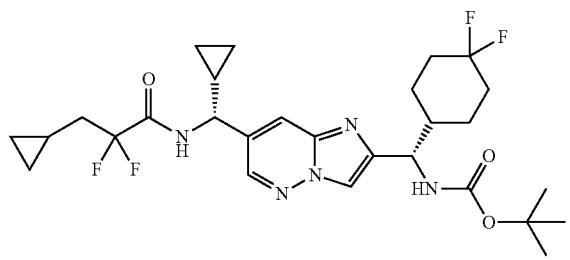 [SMILES: CC(C)(C)OC(=O)N[C@H](c1cn2ncc([C@H](NC(=O)C(F)(F)CC3CC3)C3CC3)cc2n1)C1CCC(F)(F)CC1]

To a solution of 3-cyclopropyl-2,2-difluoropropanoic acid (88 mg, 0.59 mmol), tert-butyl ((S)-(7-((R)-amino(cyclopropyl)methyl)imidazo[1,2-b]pyridazin-2-yl)(4,4-difluorocyclohexyl)methyl)carbamate (150 mg, 0.34 mmol, Intermediate 49), EDCI (130 mg, 0.69 mmol) and HOBt (61 mg, 0.45 mmol) in ACN (5 mL) was added DIPEA (0.18 mL, 1.03 mmol). The mixture was stirred at rt overnight and then concentrated to dryness. The residue was partitioned between DCM (50 mL) and water (30 mL), and the aqueous layer further extracted with DCM (2×20 mL). The organic layers were combined, washed with brine (50 mL), dried over anhydrous Na$_2$SO$_4$, filtered and concentrated to dryness. The residue was purified by silica gel chromatography (5% MeOH/DCM) to provide the title compound as a yellow oil.

Intermediate 401

N—((R)-(2-((S)-Amino(4,4-difluorocyclohexyl)methyl)imidazo[1,2-b]pyridazin-7-yl)(cyclopropyl)methyl)-3-cyclopropyl-2,2-difluoropropanamide

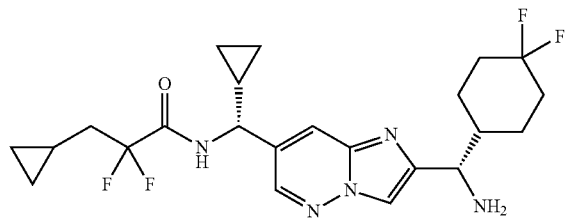 [SMILES: N[C@H](c1cn2ncc([C@H](NC(=O)C(F)(F)CC3CC3)C3CC3)cc2n1)C1CCC(F)(F)CC1]

A solution of HCl in 1,4-dioxane (2.15 mL, 8.59 mmol, 4 M) was added to a 0° C. solution of tert-butyl ((S)-(7-((R)-cyclopropyl(3-cyclopropyl-2,2-difluoropropanamido)methyl)imidazo[1,2-b]pyridazin-2-yl)(4,4-difluorocyclohexyl)methyl)carbamate (195 mg, 0.340 mmol, Intermediate 400) in 1,4-dioxane (2 mL). The reaction was stirred at rt for 4 h and then concentrated to dryness. The residue was diluted with water (5 mL) and the pH adjusted to pH=7 by the addition of saturated aqueous NaHCO$_3$ (5 mL). The mixture was extracted with DCM (3×10 mL) and the organic layers combined, washed with brine, dried over anhydrous Na$_2$SO$_4$, filtered and concentrated to dryness to provide the title compound as a white solid.

Intermediate 402

2-Cyano-N—((S)-(7-((R)-cyclopropyl(2-(3,3-difluorocyclobutyl)acetamido)methyl)imidazo[1,2-b]pyridazin-2-yl)(4,4-difluorocyclohexyl)methyl)acetamide

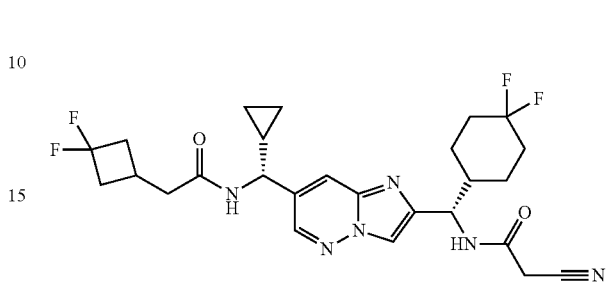

The title compound was prepared as described for the synthesis of Example 322 using N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide (Intermediate 171) in place of N-((1S,2S)-1-(2-((S)-amino(4,4-difluorocyclohexyl)methyl)imidazo[1,2-b]pyridazin-7-yl)-2-methoxypropyl)-2-(3,3-difluorocyclobutyl)acetamide hydrochloride and 2-cyanoacetic acid in place of 1-isopropyl-1H-pyrazole-5-carboxylic acid. The mixture was stirred at 30° C. for 16 h instead of rt overnight, and the residue was purified by silica gel chromatography (0-100% EtOAc/petroleum ether) to provide the title compound as a white solid.

Intermediate 403

(E)-2-(((S)-(7-((R)-Cyclopropyl(2-(3,3-difluorocyclobutyl)acetamido)methyl)imidazo[1,2-b]pyridazin-2-yl)(4,4-difluorocyclohexyl)methyl)amino)-N-hydroxy-2-oxoacetimidoyl Cyanide

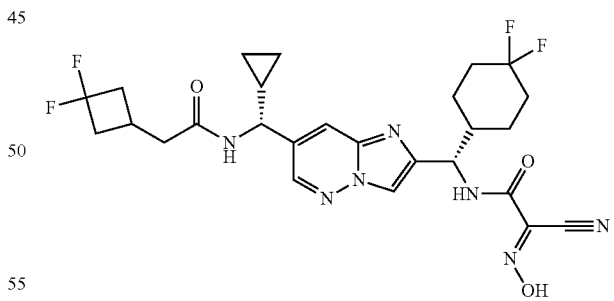

The title compound was prepared as described for the synthesis of Intermediate 323 using 2-cyano-N—((S)-(7-((R)-cyclopropyl(2-(3,3-difluorocyclobutyl)acetamido)methyl)imidazo[1,2-b]pyridazin-2-yl)(4,4-difluorocyclohexyl)methyl)acetamide (Intermediate 402) in place of N—((R)-(2-((S)-(2-cyanoacetamido)(4,4-difluorocyclohexyl)methyl)imidazo[1,2-b]pyridazin-7-yl)(cyclopropyl)methyl)-4,4,4-trifluorobutanamide. The mixture was stirred at rt for 16 h instead of 8 h, and the title compound was taken on crude, without any further purification.

Intermediate 404

4-Amino-N—((S)-(7-((R)-cyclopropyl(2-(3,3-difluorocyclobutyl)acetamido)methyl)imidazo[1,2-b]pyridazin-2-yl)(4,4-difluorocyclohexyl)methyl)-1,2,5-oxadiazole-3-carboxamide

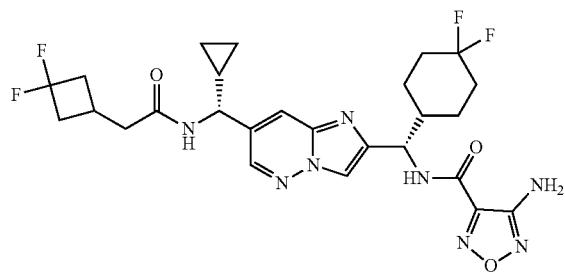 [SMILES: Nc1nonc1C(=O)N[C@H](c1cn2ncc([C@H](NC(=O)CC3CC(F)(F)C3)C3CC3)cc2n1)C1CCC(F)(F)CC1]

To a mixture of (E)-2-(((S)-(7-((R)-cyclopropyl(2-(3,3-difluorocyclobutyl)acetamido)methyl)imidazo[1,2-b]pyridazin-2-yl)(4,4-difluorocyclohexyl)methyl)amino)-N-hydroxy-2-oxoacetimidoyl cyanide (500 mg, 0.360 mmol, Intermediate 403) in THF (6 mL) was added hydroxylamine (117 mg, 1.77 mmol, 50% solution in water), and the resulting mixture stirred at 50° C. for 16 h. Then, Et$_3$N (2 mL, 14.4 mmol) was added and the mixture stirred at 120° C. in the microwave for 2 h. After that time, the mixture was concentrated to dryness and the residue purified by silica gel chromatography (0-100% EtOAc/petroleum ether) to provide the title compound as a white solid.

Intermediate 405

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-4-nitro-1,2,5-oxadiazole-3-carboxamide

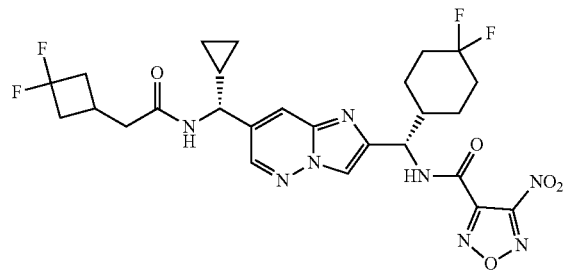

To a flask containing H$_2$SO$_4$ (1 mL) at 0° C. was added H$_2$O$_2$ (1 mL, 30% in water) followed by Na$_2$WO$_4$·2H$_2$O (57 mg, 0.17 mmol) and 4-amino-N—((S)-(7-((R)-cyclopropyl(2-(3,3-difluorocyclobutyl)acetamido)methyl)imidazo[1,2-b]pyridazin-2-yl)(4,4-difluorocyclohexyl)methyl)-1,2,5-oxadiazole-3-carboxamide (100 mg, 0.17 mmol, Intermediate 404). The resulting mixture was stirred at 30° C. for 16 h, then diluted with water (20 mL) and extracted with EtOAc (3×10 mL). The organic layers were combined, washed with brine (10 mL), dried over anhydrous Na$_2$SO$_4$, filtered and concentrated to dryness. The residue was purified by silica gel chromatography (0-100% EtOAc/petroleum ether) to provide the title compound as a white solid.

Intermediate 406

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-4-(hydroxymethyl)-1,2,5-oxadiazole-3-carboxamide

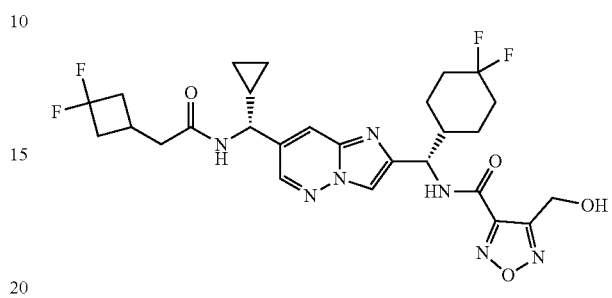

N—((R)-(2-((S)-Amino(4,4-difluorocyclohexyl)methyl)imidazo[1,2-b]pyridazin-7-yl)(cyclopropyl)methyl)-2-(3,3-difluorocyclobutyl)acetamide (250 mg, 0.54 mmol, Intermediate 171) was added to a mixture of 4H,6H-furo[3,4-c][1,2,5]oxadiazol-4-one (108 mg, 0.86 mmol, Intermediate 343) and TBD (22 mg, 0.16 mmol) in THF (8 mL) and the resulting mixture stirred at 75° C. overnight. After that time, the mixture was concentrated to dryness and purified by preparative HPLC (Boston Prime C18, 150×30 mm, 5 μm, 42 to 72% ACN/water (0.05% NH$_4$OH)) to provide the title compound as a white solid.

Intermediate 407

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-4-formyl-1,2,5-oxadiazole-3-carboxamide

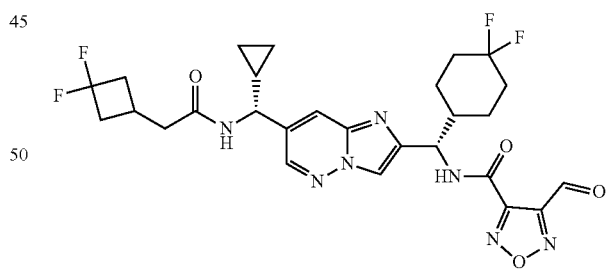

DMP (204 mg, 0.48 mmol was added to a solution of N—((S)-(7-((R)-cyclopropyl(2-(3,3-difluorocyclobutyl)acetamido)methyl)imidazo[1,2-b]pyridazin-2-yl)(4,4-difluorocyclohexyl)methyl)-4-(hydroxymethyl)-1,2,5-oxadiazole-3-carboxamide (143 mg, 0.24 mmol, Intermediate 406) in DCM (5 mL) at 0° C., and the resulting mixture was stirred at rt for 2 h. After that time, the mixture was filtered and the filtrate washed with brine (15 mL), dried over anhydrous Na$_2$SO$_4$, filtered and concentrated to dryness. The residue was purified by silica gel chromatography (0-2% MeOH/DCM) to provide the title compound as a colorless oil.

Intermediate 408

Tert-Butyl ((S')-(7-((R*)—(((S')-tert-butylsulfinyl)amino)(cyclopropyl)methyl)imidazo[1,2-b]pyridazin-2-yl)(4,4-difluorocyclohexyl)methyl)carbamate

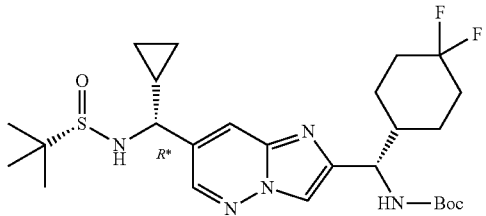 [SMILES: CC(C)(C)OC(=O)N[C@H](c1cn2ncc([C@H](N[S@@](=O)C(C)(C)C)C3CC3)cc2n1)C1CCC(F)(F)CC1]

The title compound was prepared as described for the synthesis of Intermediate 48, but the absolute stereochemistry was not assigned for this intermediate.

Intermediate 409

Tert-Butyl ((S)-(7-((R*)-amino(cyclopropyl)methyl)imidazo[1,2-b]pyridazin-2-yl)(4,4-difluorocyclohexyl)methyl)carbamate

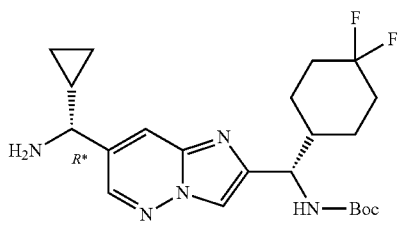 [SMILES: CC(C)(C)OC(=O)N[C@H](c1cn2ncc([C@H](N)C3CC3)cc2n1)C1CCC(F)(F)CC1]

The title compound was prepared as described for the synthesis of Intermediate 49, using tert-butyl ((S)-(7-((R*)—(((S)-tert-butylsulfinyl)amino)(cyclopropyl)methyl)imidazo[1,2-b]pyridazin-2-yl)(4,4-difluorocyclohexyl)methyl)carbamate (Intermediate 408) in place of tert-butyl ((S)-(7-((R)-(((S)-tert-butylsulfinyl)amino)(cyclopropyl)methyl)imidazo[1,2-b]pyridazin-2-yl)(4,4-difluorocyclohexyl)methyl)carbamate.

Intermediate 410

Tert-Butyl ((S)-(7-((R*)-cyclopropyl(4,4,4-trifluorobutanamido)methyl)imidazo[1,2-b]pyridazin-2-yl)(4,4-difluorocyclohexyl)methyl)carbamate

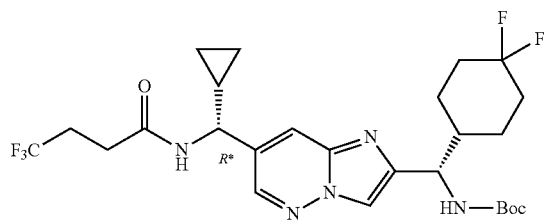 [SMILES: CC(C)(C)OC(=O)N[C@H](c1cn2ncc([C@H](NC(=O)CCC(F)(F)F)C3CC3)cc2n1)C1CCC(F)(F)CC1]

The title compound was prepared as described for the synthesis of Intermediate 50, using tert-butyl ((S)-(7-((R*)-amino(cyclopropyl)methyl)imidazo[1,2-b]pyridazin-2-yl)(4,4-difluorocyclohexyl)methyl)carbamate (Intermediate 409) in place of tert-butyl ((S)-(7-((R)-amino(cyclopropyl)methyl)imidazo[1,2-b]pyridazin-2-yl)(4,4-difluorocyclohexyl)methyl) carbamate.

Intermediate 411

N—((R*)-(2-((, S)-Amino(4,4-difluorocyclohexyl)methyl)imidazo[1,2-b]pyridazin-7-yl)(cyclopropyl)methyl)-4,4,4-trifluorobutanamide

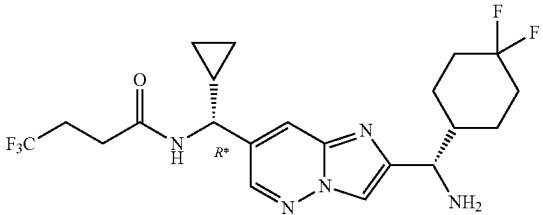 [SMILES: N[C@H](c1cn2ncc([C@H](NC(=O)CCC(F)(F)F)C3CC3)cc2n1)C1CCC(F)(F)CC1]

The title compound was prepared as described for the synthesis of Intermediate 51, using tert-butyl ((S)-(7-((R*)-cyclopropyl(4,4,4-trifluorobutanamido)methyl)imidazo[1,2-b]pyridazin-2-yl)(4,4-difluorocyclohexyl)methyl)carbamate (Intermediate 410) in place of tert-butyl ((S)-(7-((R)-cyclopropyl(4,4,4-trifluorobutanamido)methyl)imidazo[1,2-b]pyridazin-2-yl)(4,4-difluorocyclohexyl)methyl) carbamate.

Intermediate 412

Methyl 1-((2,2-difluorocyclopropyl)methyl)-1H-1,2,4-triazole-5-carboxylate

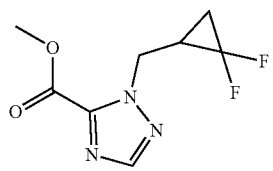

The title compound was prepared as described for the synthesis of Intermediate 161 using (2,2-difluorocyclopropyl)methanol in place of cyclopropanol to provide the title compound as a crystalline solid.

Intermediate 413

Lithium 1-((2,2-difluorocyclopropyl)methyl)-1H-1,2,4-triazole-5-carboxylate

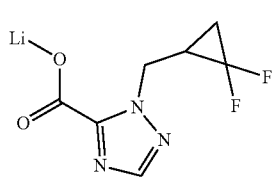

To a mixture of methyl 1-((2,2-difluorocyclopropyl)methyl)-1H-1,2,4-triazole-5-carboxylate (70 mg, 0.32 mmol, Intermediate 412) in THF (1.1 mL) at 0° C. was added 1 M aqueous LiOH (0.35 mL, 0.35 mmol) dropwise. The resulting mixture was stirred at 0° C. for 30 min and then concentrated to dryness to provide the title compound as a white solid.

Intermediate 414

Methyl 1-(3,3-difluorobutyl)-1H-1,2,4-triazole-5-carboxylate

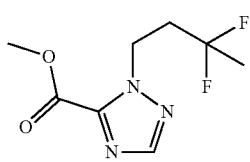

The title compound was prepared as described for the synthesis of Intermediate 161 using 3,3-difluorobutan-1-ol in place of cyclopropanol to provide the title compound as a crystalline solid.

Intermediate 415

Lithium 1-(3,3-difluorobutyl)-1H-1,2,4-triazole-5-carboxylate

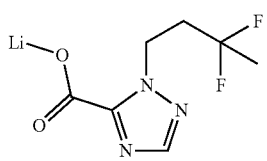

The title compound was prepared as described for the synthesis of Intermediate 413 using methyl 1-(3,3-difluorobutyl)-1H-1,2,4-triazole-5-carboxylate (Intermediate 414) in place of methyl 1-((2,2-difluorocyclopropyl)methyl)-1H-1,2,4-triazole-5-carboxylate to provide the title compound as a crystalline solid.

Intermediate 416

Methyl 1-(2,2-difluoropropyl)-1H-1,2,4-triazole-5-carboxylate

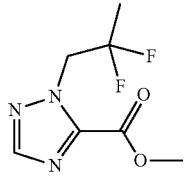

The title compound was prepared as described for the synthesis of Intermediate 161 using 2,2-difluoropropanol in place of cyclopropanol to provide the title compound as a crystalline solid.

Intermediate 417

Lithium 1-(2,2-difluoropropyl)-1H-1,2,4-triazole-5-carboxylate

The title compound was prepared as described for the synthesis of Intermediate 413 using methyl 1-(2,2-difluoropropyl)-1H-1,2,4-triazole-5-carboxylate (Intermediate 416) in place of methyl 1-((2,2-difluorocyclopropyl)methyl)-1H-1,2,4-triazole-5-carboxylate to provide the title compound as a crystalline solid.

Intermediate 418

Methyl (R)-1-(1,1,1-trifluoropropan-2-yl)-1H-1,2,4-triazole-5-carboxylate

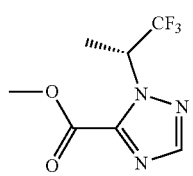

The title compound was prepared as described for the synthesis of Intermediate 161 using (R)-1,1,1-trifluoropropan-2-ol in place of cyclopropanol to provide the title compound as a crystalline solid.

Intermediate 419

Lithium (R)-1-(1,1,1-trifluoropropan-2-yl)-1H-1,2,4-triazole-5-carboxylate

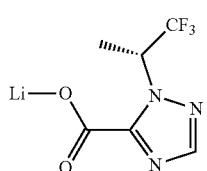

The title compound was prepared as described for the synthesis of Intermediate 413 using methyl (R)-1-(1,1,1-trifluoropropan-2-yl)-1H-1,2,4-triazole-5-carboxylate (Intermediate 418) in place of methyl 1-((2,2-difluorocyclopropyl)methyl)-1H-1,2,4-triazole-5-carboxylate to provide the title compound as a crystalline solid.

Intermediate 420

Methyl 1-(1,1-difluoropropan-2-yl)-1H-1,2,4-triazole-5-carboxylate

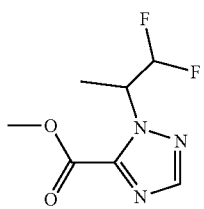

The title compound was prepared as described for the synthesis of Intermediate 161 using 1,1-difluoropropan-2-ol in place of cyclopropanol to provide the title compound as a crystalline solid.

Intermediate 421

Lithium 1-(1,1-difluoropropan-2-yl)-1H-1,2,4-triazole-5-carboxylate

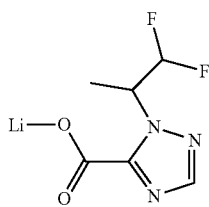

The title compound was prepared as described for the synthesis of Intermediate 413 using methyl 1-(1,1-difluoropropan-2-yl)-1H-1,2,4-triazole-5-carboxylate (Intermediate 420) in place of methyl 1-((2,2-difluorocyclopropyl)methyl)-1H-1,2,4-triazole-5-carboxylate to provide the title compound as a crystalline solid.

Intermediate 422

Methyl 1-isopropyl-1H-1,2,4-triazole-5-carboxylate

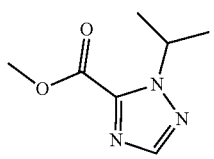

To a microwave vial was added methyl-1H-1,2,4-triazole-3-carboxylate (0.50 g, 3.9 mmol), propan-2-ol (0.47 g, 7.9 mmol), tricyclohexylphosphine (1.2 g, 4.3 mmol) and THF (8 mL). Then, di-tert-butyl azodicarboxylate (1.4 g, 6.1 mmol) was added and the resulting mixture stirred at 110° C. for 1.5 h. The reaction mixture was diluted with water (50 mL) and extracted with EtOAc (50 mL×2). The combined organic layers were dried over anhydrous $Na_2SO_4$, filtered and concentrated to dryness. The residue was purified by silica gel chromatography (0-50% EtOAc/petroleum ether) to provide the title compound as a light yellow oil.

Intermediate 423

Lithium 1-isopropyl-1H-1,2,4-triazole-5-carboxylate

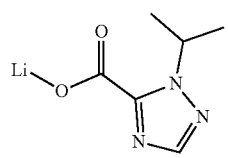

To a mixture of methyl 1-isopropyl-1H-1,2,4-triazole-5-carboxylate (200 mg, 1.182 mmol, Intermediate 422) in MeOH (5 mL) and water (1 mL) at rt was added LiOH—$H_2O$ (52 mg, 1.241 mmol) dropwise. The resulting mixture was stirred at rt for 40 min and then concentrated to dryness to provide the title compound as a white solid.

Intermediate 424

Ethyl 1-isopropyl-1H-tetrazole-5-carboxylate

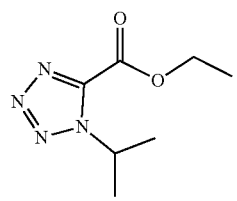

The title compound was prepared as described for the synthesis of Intermediate 97 using 2-iodopropane in place of 1-bromo-2-(trifluoromethoxy)ethane and ethyl 1H-tetrazole-5-carboxylate in place of ethyl 1H-pyrazole-4-carboxylate to provide the title compound as a yellow solid.

Intermediate 425

Lithium 1-isopropyl-1H-tetrazole-5-carboxylate

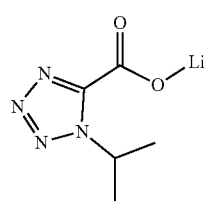

The title compound was prepared as described for the synthesis of Intermediate 423 using ethyl 1-isopropyl-1H-tetrazole-5-carboxylate (Intermediate 424) in place of methyl 1-isopropyl-1H-1,2,4-triazole-5-carboxylate to provide the title compound as a crystalline solid.

Intermediate 426

2-(3,3-Difluoroazetidin-1-yl)ethan-1-ol

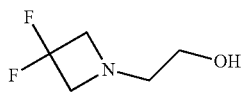

To a 100 mL flask was added MeCN (50 mL), 3,3-difluoroazetidine (5.00 g, 38.6 mmol, HCl salt), and 2-bromoethanol (4.82 g, 38.6 mmol). Following this, K$_2$CO$_3$ (16.0 g, 116 mmol) was added to the solution and left to stir at 80° C. for 16 hours. The reaction was filtered and concentrated to dryness. The residue purified by silica gel chromatography (0-100% EtOAc/petroleum ether) to provide the title compound as a yellow oil.

Intermediate 427

Methyl 2-(2-(3,3-difluoroazetidin-1-yl)ethyl)-2H-1,2,3-triazole-4-carboxylate

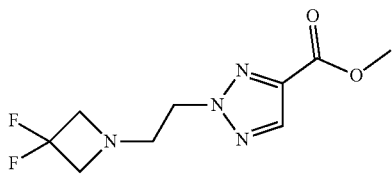 [SMILES: COC(=O)c1cnn(CCN2CC(F)(F)C2)n1]

The title compound was prepared as described for the synthesis of Intermediate 74, using 2-(3,3-difluoroazetidin-1-yl)ethan-1-ol (Intermediate 426) in place of 3-bromo-1,1,1-trifluoropropane, to provide the title compound as a clear oil.

Intermediate 428

Lithium 2-(2-(3,3-difluoroazetidin-1-yl)ethyl)-2H-1,2,3-triazole-4-carboxylate

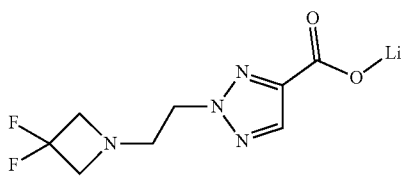

The title compound was prepared as described for the synthesis of Intermediate 423 using methyl 2-(2-(3,3-difluoroazetidin-1-yl)ethyl)-2H-1,2,3-triazole-4-carboxylate (Intermediate 427) in place of methyl 1-isopropyl-1H-1,2,4-triazole-5-carboxylate to provide the title compound as a crystalline solid.

Intermediate 429

Tert-Butyl ((S)-(7-((E)-(((R)-tert-butylsulfinyl)imino)methyl)imidazo[1,2-b]pyridazin-2-yl)(4,4-difluorocyclohexyl)methyl)carbamate

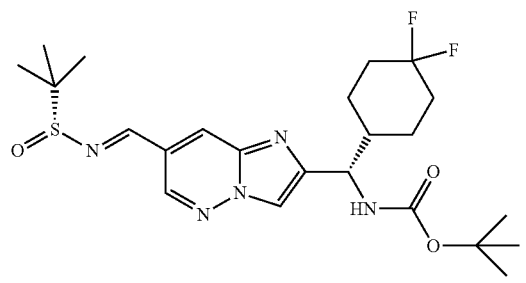 [SMILES: CC(C)(C)OC(=O)N[C@H](c1cn2ncc(/C=N/[S@](=O)C(C)(C)C)cc2n1)C1CCC(F)(F)CC1]

To a stirred solution of tert-butyl (S)-((4,4-difluorocyclohexyl)(7-formylimidazo[1,2-b]pyridazin-2-yl)methyl)carbamate (4.50 g, 11.4 mmol, Intermediate 46), (R)-(+)-2-methyl-2-propanesulfinamide (1.45 g, 12.0 mmol), pyridinium p-toluenesulfonate (287 mg, 1.14 mmol) in THF (38 mL) was added copper(II) sulfate (5.83 g, 36.5 mmol). The reaction mixture was heated at 60° C. for 16 h, allowed to cool to ambient temperature, diluted with DCM (40 mL), and filtered. The filtrate was concentrated and purified by silica gel chromatography (15-60% acetone/hexanes) to provide the title compound.

Intermediate 430

Tert-Butyl ((S)-(7-((S*)—(((R)-tert-butylsulfinyl)amino)(1-cyanocyclobutyl)methyl)imidazo[1,2-b]pyridazin-2-yl)(4,4-difluorocyclohexyl)methyl)carbamate

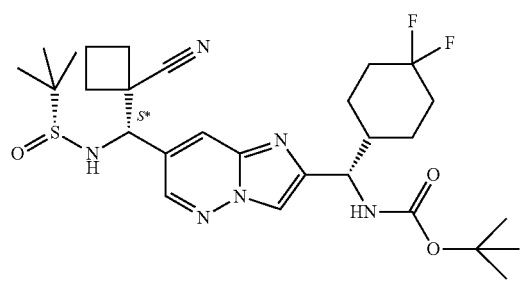 [SMILES: CC(C)(C)OC(=O)N[C@H](c1cn2ncc([C@H](N[S@](=O)C(C)(C)C)C3(C#N)CCC3)cc2n1)C1CCC(F)(F)CC1]

To an oven dried, N$_2$ flushed flask was added cyclobutanecarbonitrile (2.43 mL, 25.2 mmol) and THF (83.6 ml). The flask was cooled (0° C.) and LiHMDS (26.0 mL, 26.9 mmol, 1 M in THF) was added in a dropwise manner over 4 min. After a further 2 h at 0° C., the reaction mixture was treated with a solution of tert-butyl ((S)-(7-((E)-(((R)-tert-butylsulfinyl)imino)methyl)imidazo[1,2-b]pyridazin-2-yl)(4,4-difluorocyclohexyl)methyl) carbamate (4.18 g, 8.40 mmol, Intermediate 429) in THF (30 mL) in a dropwise manner over 5 min. Upon stirring at 0° C. for an additional 2 h the reaction mixture was quenched with saturated aqueous NH$_4$Cl (20 mL), allowed to warm to rt, and diluted with half saturated brine (100 mL) and EtOAc (100 mL). The layers were separated and the aqueous layer was extracted with EtOAc (3×50 mL). The combined organic layers were dried over anhydrous Na₂SO₄, filtered, and concentrated. The residue was purified by silica gel chromatography (10-70% acetone/hexanes (containing 0.1% TEA)) to give a mixture of diastereomers. The diastereomers were separated by SFC using a chiral stationary phase (Chiralpak IC 5 µm, 250×21 mm, Mobile phase: 20% EtOH, 80% CO₂). The second eluting diastereomer is the title compound shown above and is designated as the S* diastereomer: tert-butyl ((S)-(7-((S*)—(((R)-tert-butylsulfinyl)amino)(1-cyanocyclobutyl)methyl)imidazo[1,2-b]pyridazin-2-yl)(4,4-difluorocyclohexyl)methyl)carbamate. The first eluting diastereomer, tert-butyl ((S)-(7-((R*)—(((R)-tert-butylsulfinyl)amino)(1-cyanocyclobutyl)methyl)imidazo[1,2-b]pyridazin-2-yl)(4,4-difluorocyclohexyl)methyl)carbamate, is designated as the R* diastereomer.

Intermediate 431 tert-Butyl ((S)-(7-((S*)-amino(1-cyanocyclobutyl)methyl)imidazo[1,2-b]pyridazin-2-yl)(4,4-difluorocyclohexyl)methyl)carbamate

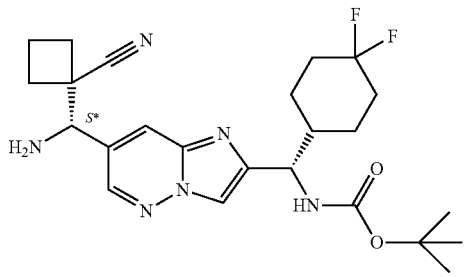 [SMILES: CC(C)(C)OC(=O)N[C@H](c1cn2ncc([C@H](N)C3(C#N)CCC3)cc2n1)C1CCC(F)(F)CC1]

To a stirred solution of tert-butyl ((S)-(7-((S*)—(((R)-tert-butylsulfinyl)amino)(1-cyanocyclobutyl)methyl)imidazo[1,2-b]pyridazin-2-yl)(4,4-difluorocyclohexyl)methyl) carbamate (1.53 g, 2.65 mmol, Intermediate 430) in EtOAc (26.5 mL) was added HCl (1.66 mL, 4 M in 1,4-dioxane). After stirring for 1.5 h at rt, an additional portion of HCl (0.60 mL, 4 M in 1,4-dioxane) was added. After an additional 1 h at rt, the reaction mixture was diluted with hexanes (50 mL), water (200 mL), and aqueous HCl (5 mL, 0.05 M). The layers were separated, and the organic layer was extracted with aqueous HCl (3×100 mL, 0.0005 M). The combined aqueous layers were washed with hexanes (100 mL), brought to pH ~11.5 with 3 M aqueous NaOH, diluted with brine (100 mL), and extracted with EtOAc (4×100 mL). The combined organic layers were dried over anhydrous Na₂SO₄, filtered, and concentrated to provide the title compound as a tan foam, that was used without further purification.

Intermediate 432

N—((S*)-(2-((S)-Amino(4,4-difluorocyclohexyl)methyl)imidazo[1,2-b]pyridazin-7-yl)(1-cyanocyclobutyl)methyl)-2-(3,3-difluorocyclobutyl)acetamide

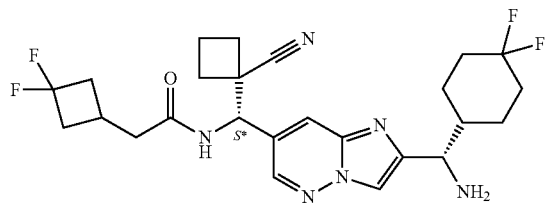 [SMILES: N#CC1([C@@H](NC(=O)CC2CC(F)(F)C2)c2cnn3cc([C@@H](N)C4CCC(F)(F)CC4)nc3c2)CCC1]

To a stirred solution of 2-(3,3-difluorocyclobutyl)acetic acid (475 mg, 3.16 mmol) and 1-propanephosphonic anhydride (1.66 mL, 2.78 mmol, 50% in EtOAc) in EtOAc (8.4 mL) was added N,N-diisopropylethylamine (0.867 mL, 5.06 mmol). After 5 min, tert-butyl ((S)-(7-((S*)-amino(1-cyanocyclobutyl)methyl)imidazo[1,2-b]pyridazin-2-yl)(4,4-difluorocyclohexyl)methyl) carbamate (600 mg, 1.26 mmol, Intermediate 431) was added as a solution in DCM (6 mL). After 16 h, the reaction mixture was diluted with aqueous HCl (40 mL, 0.05 M) and EtOAc (40 mL). The aqueous layer was extracted with EtOAc (3×20 mL). The organic layers were combined, washed with saturated aqueous NaHCO₃ (2×10 mL) and brine (10 mL), dried over anhydrous Na₂SO₄, filtered, and concentrated to dryness. The residue was dissolved in DCM (50 mL), cooled (0° C.) and treated with trifluoroacetic acid (25 mL). After 2.5 h at 0° C., the reaction mixture was concentrated to dryness, taken up in EtOAc (50 mL) and saturated aqueous NaHCO₃ (50 mL) and the pH was adjusted to ~11 with aqueous 3 M NaOH. The aqueous layer was extracted with EtOAc (3×20 mL). The combined organics were washed with brine (30 mL), dried over anhydrous Na₂SO₄, filtered, and concentrated to provide the title compound as a light-yellow solid which was used without further purification.

Intermediate 433

N—((S*)-(2-((S)-Amino(4,4-difluorocyclohexyl)methyl)imidazo[1,2-b]pyridazin-7-yl)(1-cyanocyclobutyl)methyl)-2-(2,2-difluorocyclopropyl)acetamide

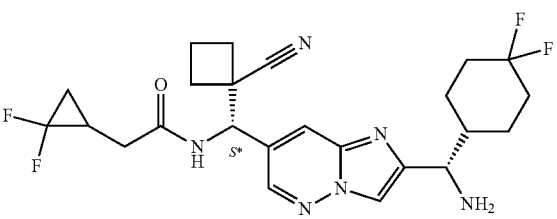 [SMILES: N#CC1([C@@H](NC(=O)CC2CC2(F)F)c2cnn3cc([C@@H](N)C4CCC(F)(F)CC4)nc3c2)CCC1]

The title compound was prepared as described for the synthesis of Intermediate 432, using 2-(2,2-difluorocyclopropyl)acetic acid in place of 2-(3,3-difluorocyclobutyl)acetic acid to provide the title compound as a off white solid.

Intermediate 434

Ethyl 1-(methyl-d₃)-1H-pyrazole-5-carboxylate

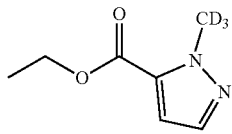

The title compound was prepared as described for the synthesis of Intermediate 203, using iodomethane-d₃ in place of bromoethane-ds to provide the title compound, the first eluting fraction, as a colorless oil.

Intermediate 435

1-(Methyl-d₃)-1H-pyrazole-5-carboxylic Acid

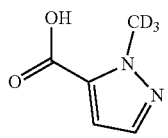 [SMILES: [2H]C([2H])([2H])n1nccc1C(=O)O]

The title compound was prepared as described for the synthesis of Intermediate 76, using ethyl 1-(methyl-d₃)-1H-pyrazole-5-carboxylate (Intermediate 434) in place of methyl 2-(3,3,3-trifluoropropyl)-2H-1,2,3-triazole-4-carboxylate to provide the title compound as a white solid.

Intermediate 436

Tert-Butyl ((S)-(7-((R*)—(((S)-tert-butylsulfinyl)amino)(cyclobutyl)methyl)imidazo[1,2-b]pyridazin-2-yl)(4,4-difluorocyclohexyl)methyl)carbamate

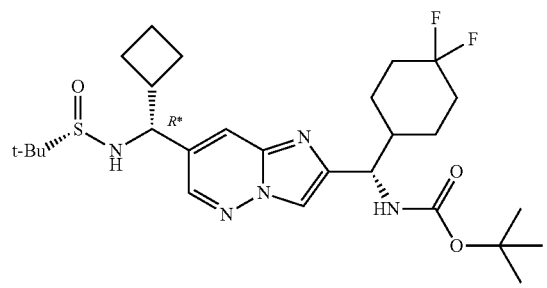 [SMILES: CC(C)(C)OC(=O)N[C@H](c1cn2ncc([C@H](N[S@@](=O)C(C)(C)C)C3CCC3)cc2n1)C1CCC(F)(F)CC1]

Intermediate 437

Tert-Butyl ((S)-(7-((S*)—(((S)-tert-butylsulfinyl)amino)(cyclobutyl)methyl)imidazo[1,2-b]pyridazin-2-yl)(4,4-difluorocyclohexyl)methyl)carbamate

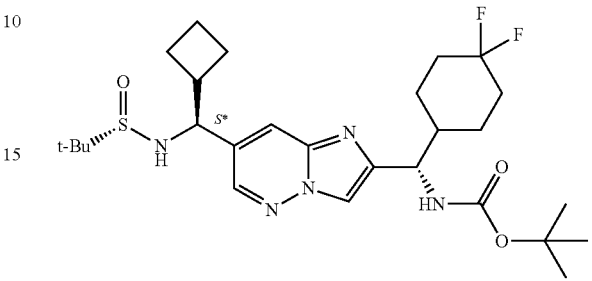

The title compounds were prepared as described for the synthesis of Intermediate 52, using cyclobutylmagnesium bromide in 0.5 M THF in place of cyclopropylmagnesium bromide in 2-MeTHF and further purification by SFC using a chiral stationary phase (Regis (S,S) Whelk-O® 1, 30:70 MeOH:IPA with 0.2% iPrNH₂/CO₂) to provide Intermediate 436 as the first eluting fraction and Intermediate 437 as the second eluting fraction.

Intermediate 438

Tert-Butyl ((S)-(7-((R*)-amino(cyclobutyl)methyl)imidazo[1,2-b]pyridazin-2-yl)(4,4-difluorocyclohexyl)methyl)carbamate

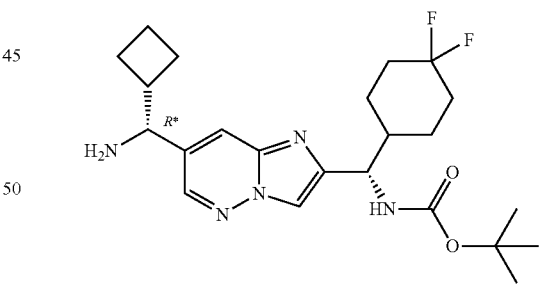

The title compound was prepared as described for the synthesis of Intermediate 49, using tert-butyl ((S)-(7-((R*)—(((S)-tert-butylsulfinyl)amino)(cyclobutyl)methyl)imidazo[1,2-b]pyridazin-2-yl)(4,4-difluorocyclohexyl)methyl)carbamate (Intermediate 436) in place of tert-butyl ((S)-(7-((((S)-tert-butylsulfinyl)imino)methyl)imidazo[1,2-b]pyridazin-2-yl)(4,4-difluorocyclohexyl)methyl)carbamate to provide the title compound as a white foam.

Intermediate 439

Tert-Butyl ((S)-(7-((R*)-cyclobutyl(4,4,4-trifluorobutanamido)methyl)imidazo[1,2-b]pyridazin-2-yl)(4,4-difluorocyclohexyl)methyl)carbamate

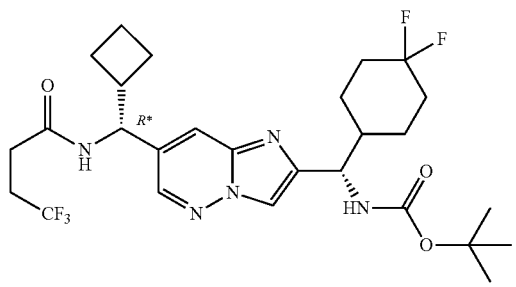 [SMILES: CC(C)(C)OC(=O)N[C@H](c1cn2ncc([C@H](NC(=O)CCC(F)(F)F)C3CCC3)cc2n1)C1CCC(F)(F)CC1]

The title compound was prepared as described for the synthesis of Intermediate 50, using tert-butyl ((S)-(7-((R*)-amino(cyclobutyl)methyl)imidazo[1,2-b]pyridazin-2-yl)(4,4-difluorocyclohexyl)methyl)carbamate (Intermediate 438) in place of tert-butyl ((S)-(7-((R)-amino(cyclopropyl)methyl)imidazo[1,2-b]pyridazin-2-yl)(4,4-difluorocyclohexyl)methyl) carbamate and purified by silica gel chromatography (0-100% EtOAc (with 10% MeOH)/hexanes) to provide the title compound.

Intermediate 440

N—((R*)-(2-((S)-Amino(4,4-difluorocyclohexyl)methyl)imidazo[1,2-b]pyridazin-7-yl) (cyclobutyl)methyl)-4,4,4-trifluorobutanamide

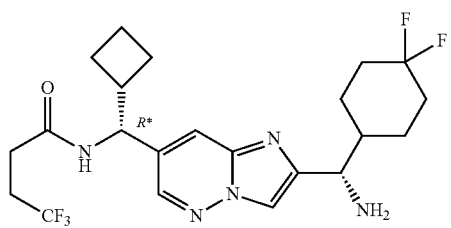 [SMILES: N[C@H](c1cn2ncc([C@H](NC(=O)CCC(F)(F)F)C3CCC3)cc2n1)C1CCC(F)(F)CC1]

A vial was charged with a stir bar, tert-butyl ((S)-(7-((R*)-cyclobutyl(4,4,4-trifluorobutanamido)methyl)imidazo[1,2-b]pyridazin-2-yl)(4,4-difluorocyclohexyl)methyl) carbamate (600 mg, 1.05 mmol, Intermediate 439), TFA (1.60 mL, 20.9 mmol) and DCM (2 mL) then was stirred for 5 min. The reaction was condensed and quenched by the careful addition of saturated aqueous NaHCO$_3$. The basic aqueous phase was partitioned with EtOAc. The organic phase was washed with 0.5 M aqueous NaOH, and then the aqueous phase was washed with EtOAc. The combined organics were washed with brine, dried over anhydrous Na$_2$SO$_4$, filtered and concentrated to dryness. The residue was purified by silica gel chromatography (0-100% DCM/(10% (2 M NH$_3$ in MeOH) in DCM)) to provide the title compound as a white foam.

Intermediate 441

Tert-Butyl ((S)-(7-((R*)-cyclobutyl(2-(3,3-difluorocyclobutyl)acetamido)methyl)imidazo[1,2-b]pyridazin-2-yl)(4,4-difluorocyclohexyl)methyl)carbamate

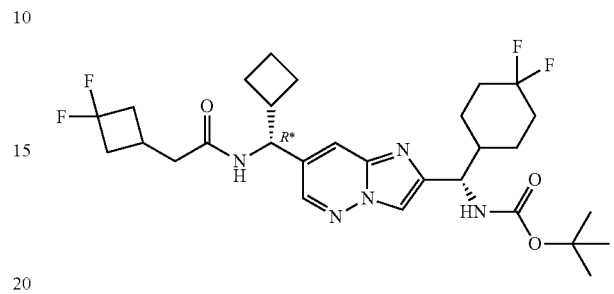

The title compound was prepared as described for the synthesis of Intermediate 50, using tert-butyl ((S)-(7-((R*)-amino(cyclobutyl)methyl)imidazo[1,2-b]pyridazin-2-yl)(4,4-difluorocyclohexyl)methyl)carbamate (Intermediate 438) in place of tert-butyl ((S)-(7-((R)-amino(cyclopropyl)methyl)imidazo[1,2-b]pyridazin-2-yl)(4,4-difluorocyclohexyl)methyl) carbamate and using 2-(3,3-difluorocyclobutyl)acetic acid in place of 4,4,4-trifluorobutanoic acid and purified by silica gel chromatography (5-90% MeOH/DCM) to provide the title compound.

Intermediate 442

N—((R*)-(2-((S)-Amino(4,4-difluorocyclohexyl)methyl)imidazo[1,2-b]pyridazin-7-yl) (cyclobutyl)methyl)-2-(3,3-difluorocyclobutyl)acetamide

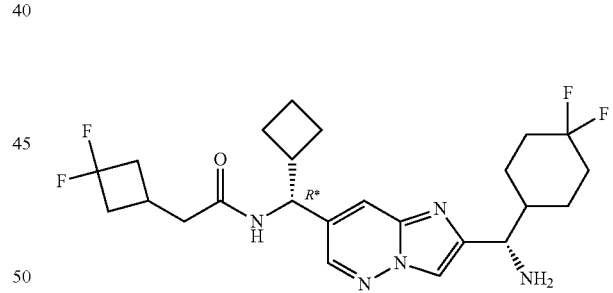

A solution of tert-butyl ((S)-(7-((R*)-cyclobutyl(2-(3,3-difluorocyclobutyl)acetamido)methyl)imidazo[1,2-b]pyridazin-2-yl)(4,4-difluorocyclohexyl)methyl)carbamate (250 mg, 0.43 mmol, Intermediate 441) in DCM (4 mL) was added dropwise HCl in 1,4-dioxane (1.25 mL, 4.0 M, 5.00 mmol) at 0° C. The resulting mixture was stirred at 25° C. for 12 h. The mixture was concentrated and basified with saturated aqueous NaHCO$_3$ (2 mL) until pH 8-9. The mixture was then extracted with EtOAc (3×10 mL). The organic layers were combined, washed with brine (5 mL) and dried over Na$_2$SO$_4$, filtered, and concentrated in vacuum to provide the title compound as a white solid.

Intermediate 443

N—((S*)-(2-((S)-Amino(4,4-difluorocyclohexyl)methyl)imidazo[1,2-b]pyridazin-7-yl) (cyclobutyl)methyl)-2-(3,3-difluorocyclobutyl)acetamide

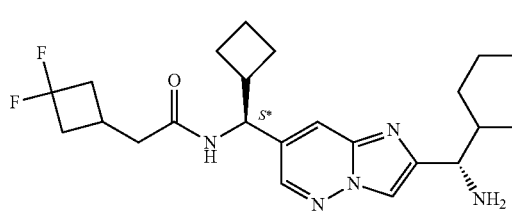

The title compound was prepared in the 4 step sequence described for the synthesis of Intermediate 442, using tert-butyl ((S)-(7-((S*)—(((S)-tert-butylsulfinyl)amino)(cyclobutyl)methyl)imidazo[1,2-b]pyridazin-2-yl)(4,4-difluorocyclohexyl)methyl)carbamate (Intermediate 437) in place of tert-butyl ((S)-(7-((R*)—(((S)-tert-butylsulfinyl)amino)(cyclobutyl)methyl)imidazo[1,2-b]pyridazin-2-yl)(4,4-difluorocyclohexyl)methyl)carbamate to provide the title compound.

Intermediate 444

Tert-Butyl ((S)-(7-((R*)-cyclobutyl(4,4,4-trifluoro-3-methylbutanamido)methyl)imidazo[1,2-b]pyridazin-2-yl)(4,4-difluorocyclohexyl)methyl)carbamate

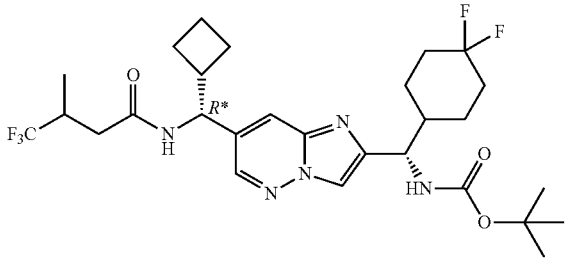 [SMILES: CC(CC(=O)N[C@@H](c1cnn2cc([C@@H](NC(=O)OC(C)(C)C)C3CCC(F)(F)CC3)nc2c1)C1CCC1)C(F)(F)F]

The title compound was prepared as described for the synthesis of Intermediate 50, using tert-butyl ((S)-(7-((R*)-amino(cyclobutyl)methyl)imidazo[1,2-b]pyridazin-2-yl)(4,4-difluorocyclohexyl)methyl)carbamate (Intermediate 438) in place of tert-butyl ((S)-(7-((R)-amino(cyclopropyl)methyl)imidazo[1,2-b]pyridazin-2-yl)(4,4-difluorocyclohexyl)methyl) carbamate and using 4,4,4-trifluoro-3-methylbutanoic acid in place of 4,4,4-trifluorobutanoic acid.

Intermediate 445

N—((R*)-(2-((S)-Amino(4,4-difluorocyclohexyl)methyl)imidazo[1,2-b]pyridazin-7-yl) (cyclobutyl)methyl)-4,4,4-trifluoro-3-methylbutanamide

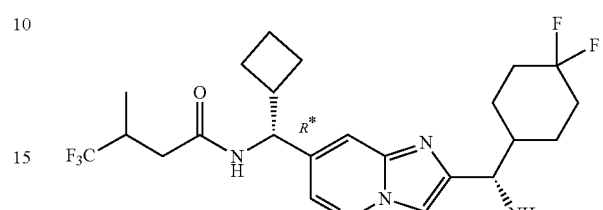

The title compound was prepared as described for the synthesis of Intermediate 442, using tert-butyl ((S)-(7-((R*)-cyclobutyl(4,4,4-trifluoro-3-methylbutanamido)methyl)imidazo[1,2-b]pyridazin-2-yl)(4,4-difluorocyclohexyl)methyl)carbamate (Intermediate 444) in place of tert-butyl ((S)-(7-((R*)-cyclobutyl(2-(3,3-difluorocyclobutyl)acetamido)methyl)imidazo[1,2-b]pyridazin-2-yl)(4,4-difluorocyclohexyl)methyl)carbamate.

Intermediate 446

Tert-Butyl ((S)-(7-((R*)-1-(((S)-tert-butylsulfinyl)amino)pent-4-en-1-yl)imidazo[1,2-b]pyridazin-2-yl)(4,4-difluorocyclohexyl)methyl)carbamate

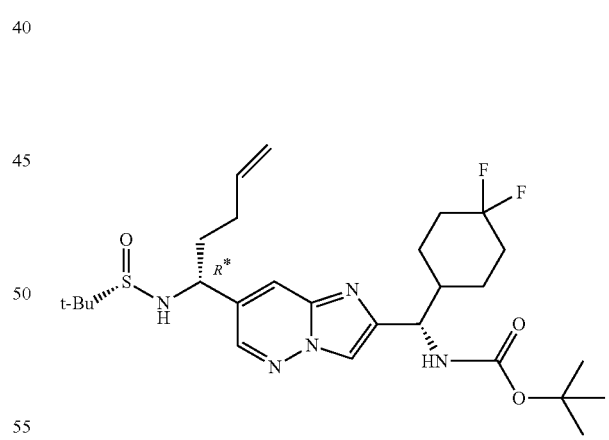

The title compound was prepared as described for the synthesis of Intermediate 53, using cyclopropylmethylmagnesium bromide 0.5 M in THF in place of cyclopropylmagnesium bromide in 2-MeTHF to provide the title compound.

Intermediate 447

N—((R*)-1-(2-((S)-Amino(4,4-difluorocyclohexyl)methyl)imidazo[1,2-b]pyridazin-7-yl)pent-4-en-1-yl)-4,4,4-trifluorobutanamide

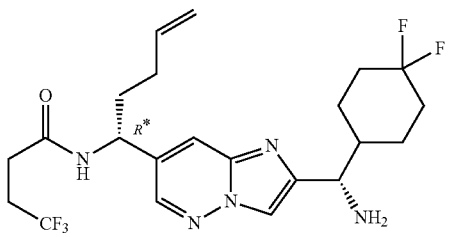 [SMILES: C=CCC[C@@H](NC(=O)CCC(F)(F)F)c1cnn2cc([C@@H](N)C3CCC(F)(F)CC3)nc2c1]

The title compound was prepared as described for the synthesis of Intermediate 440, using tert-butyl ((S)-(7-((R*)-1-(((S)-tert-butylsulfinyl)amino)pent-4-en-1-yl)imidazo[1,2-b]pyridazin-2-yl)(4,4-difluorocyclohexyl)methyl)carbamate (Intermediate 446) in place of tert-butyl ((S)-(7-((R*)-cyclobutyl(4,4,4-trifluorobutanamido)methyl)imidazo[1,2-b]pyridazin-2-yl)(4,4-difluorocyclohexyl)methyl) carbamate to provide the title compound.

Intermediate 448

Tert-Butyl ((S)-(7-((R*)-1-(((S)-tert-butylsulfinyl)amino)propyl)imidazo[1,2-b]pyridazin-2-yl)(4,4-difluorocyclohexyl)methyl)carbamate

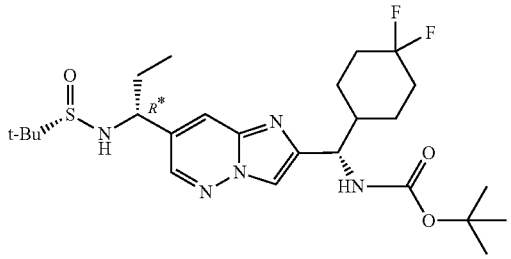

Intermediate 449

Tert-Butyl ((S)-(7-((S*)-1-(((S)-tert-butylsulfinyl)amino)propyl)imidazo[1,2-b]pyridazin-2-yl)(4,4-difluorocyclohexyl)methyl)carbamate

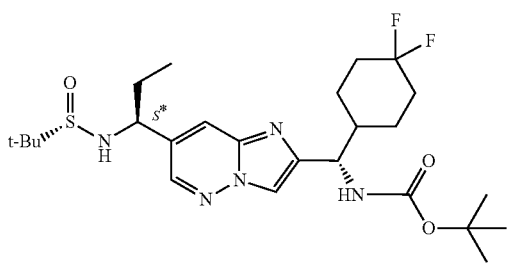 [SMILES: CC[C@H](N[S@@](=O)C(C)(C)C)c1cnn2cc([C@@H](NC(=O)OC(C)(C)C)C3CCC(F)(F)CC3)nc2c1]

The title compounds were prepared as described for the synthesis of Intermediate 54, using ethylmagnesium bromide 3.0 M in diethyl ether in place of cyclopropylmagnesium bromide in 2-MeTHF and further purification by SFC using a chiral stationary phase (Regis (S,S) Whelk-O® 1, 25:75 MeOH with 0.2% Et$_3$N/CO$_2$) to provide the title compounds, Intermediate 448 as the first eluting fraction and Intermediate 449 as the second eluting fraction.

Intermediate 450

N—((R*)-1-(2-((S)-Amino(4,4-difluorocyclohexyl)methyl)imidazo[1,2-b]pyridazin-7-yl)propyl)-2-(3,3-difluorocyclobutyl)acetamide

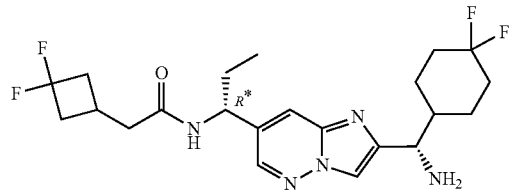 [SMILES: CC[C@@H](NC(=O)CC1CC(F)(F)C1)c1cnn2cc([C@@H](N)C3CCC(F)(F)CC3)nc2c1]

The title compound was prepared as described for the synthesis of Intermediate 440, using tert-butyl ((S)-(7-((R*)-1-(((S)-tert-butylsulfinyl)amino)propyl)imidazo[1,2-b]pyridazin-2-yl)(4,4-difluorocyclohexyl)methyl)carbamate (Intermediate 448) in place of tert-butyl ((S)-(7-((R*)-cyclobutyl(4,4,4-trifluorobutanamido)methyl)imidazo[1,2-b]pyridazin-2-yl)(4,4-difluorocyclohexyl)methyl) carbamate to provide the title compound.

Intermediate 451

N—((S*)-1-(2-((S)-Amino(4,4-difluorocyclohexyl)methyl)imidazo[1,2-b]pyridazin-7-yl)propyl)-2-(3,3-difluorocyclobutyl)acetamide

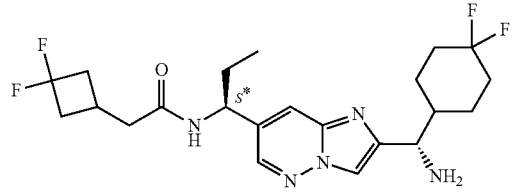 [SMILES: CC[C@H](NC(=O)CC1CC(F)(F)C1)c1cnn2cc([C@@H](N)C3CCC(F)(F)CC3)nc2c1]

The title compound was prepared as described for the synthesis of Intermediate 440, using tert-butyl ((S)-(7-((S*)-1-(((S)-tert-butylsulfinyl)amino)propyl)imidazo[1,2-b]pyridazin-2-yl)(4,4-difluorocyclohexyl)methyl)carbamate (Intermediate 449) in place of tert-butyl ((S)-(7-((R*)-cyclobutyl(4,4,4-trifluorobutanamido)methyl)imidazo[1,2-b]pyridazin-2-yl)(4,4-difluorocyclohexyl)methyl) carbamate to provide the title compound.

Intermediate 452

Tert-Butyl (S)-((4,4-difluorocyclohexyl)(7-(3-methoxyprop-1-en-2-yl)imidazo[1,2-b]pyridazin-2-yl)methyl)carbamate

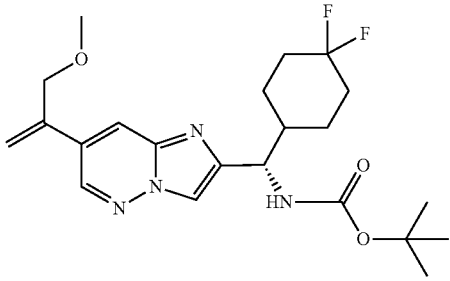 [SMILES: C=C(COC)c1cnn2cc([C@@H](NC(=O)OC(C)(C)C)C3CCC(F)(F)CC3)nc2c1]

A microwave vial was charged with a stir bar, tert-butyl N—[(S)-(7-chloroimidazo[1,2-b]pyridazin-2-yl)-(4,4-difluorocyclohexyl)methyl] carbamate (520 mg, 1.3 mmol, Intermediate 21), 2-(3-methoxyprop-1-en-2-yl)-4,4,5,5-tetramethyl-1,3,2-dioxaborolane (310 mg, 1.6 mmol), potassium phosphate tribasic (830 mg, 3.9 mmol), and 1,4-dioxane/water (5:1 v/v, 14.5 mL). The solution was sparged with Ar for 5 min and then RuPhos Pd G3 (29 mg, 0.035 mmol) was added. The reaction was heated in the microwave at 100° C. for 30 min. The reaction was concentrated to remove the 1,4-dioxane, then partitioned between additional water and ethyl acetate. The layers were separated and the aqueous phase was extracted twice with ethyl acetate. The combined organics were washed with brine, dried over anhydrous Na₂SO₄, filtered and condensed. Purification by silica gel chromatography (0-50% ethyl acetate (with 10% MeOH)/hexanes) provided the title compound.

Intermediate 453

Tert-Butyl (S)-((4,4-difluorocyclohexyl)(7-(2-methoxyacetyl)imidazo[1,2-b]pyridazin-2-yl)methyl)carbamate

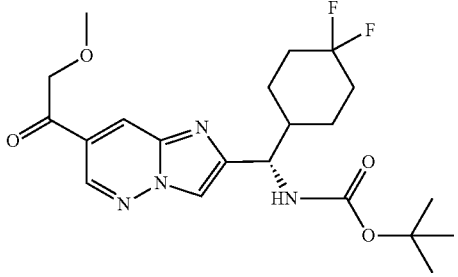 [SMILES: COCC(=O)c1cnn2cc([C@@H](NC(=O)OC(C)(C)C)C3CCC(F)(F)CC3)nc2c1]

The title compound was prepared as described for the synthesis of Intermediate 35, using tert-butyl (S)-((4,4-difluorocyclohexyl)(7-(3-methoxyprop-1-en-2-yl)imidazo[1,2-b]pyridazin-2-yl)methyl)carbamate (Intermediate 452) in place of (S)—N-((4,4-difluorocyclohexyl)(7-vinylimidazo[1,2-b]pyridazin-2-yl)methyl)-1-(3,3,3-trifluoropropyl)-1H-pyrazole-4-carboxamide to provide the title compound.

Intermediate 454

Tert-Butyl ((1S)-(7-(1-amino-2-methoxyethyl)imidazo[1,2-b]pyridazin-2-yl)(4,4-difluorocyclohexyl)methyl)carbamate

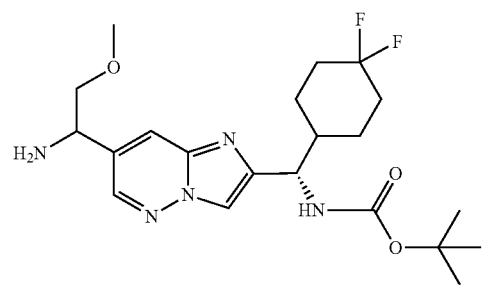 [SMILES: COCC(N)c1cnn2cc([C@@H](NC(=O)OC(C)(C)C)C3CCC(F)(F)CC3)nc2c1]

To a vial with tert-butyl (S)-((4,4-difluorocyclohexyl)(7-(2-methoxyacetyl)imidazo[1,2-b]pyridazin-2-yl)methyl)carbamate (300.0 mg, 0.680 mmol, Intermediate 453) in MeOH (6.84 mL) and AcOH (39 μL) was added NH₄OAc (1.06 g, 13.7 mmol). The mixture was heated to 100° C. in the microwave for 5 min. Then, sodium cyanoborohydride (129 mg, 2.05 mmol) was added and the reaction was heated at 130° C. for 5 min in the microwave. The reaction was partitioned between EtOAc and 1.0 N aqueous NaOH. The organic layer was washed with brine, dried over anhydrous Na₂SO₄, filtered and condensed to provide the title compound.

Intermediate 455

Tert-Butyl ((S)-(7-((R*)-1-(2-(3,3-difluorocyclobutyl)acetamido)-2-methoxyethyl)imidazo[1,2-b]pyridazin-2-yl)(4,4-difluorocyclohexyl)methyl)carbamate

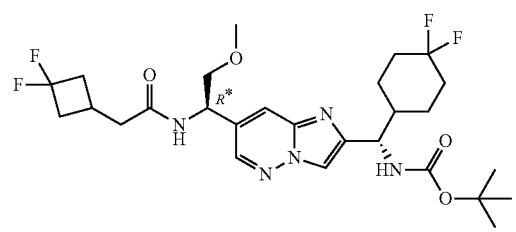 [SMILES: COC[C@H](NC(=O)CC1CC(F)(F)C1)c1cnn2cc([C@@H](NC(=O)OC(C)(C)C)C3CCC(F)(F)CC3)nc2c1]

Intermediate 456

Tert-Butyl ((S)-(7-((S*)-1-(2-(3,3-difluorocyclobutyl)acetamido)-2-methoxyethyl)imidazo[1,2-b]pyridazin-2-yl)(4,4-difluorocyclohexyl)methyl)carbamate

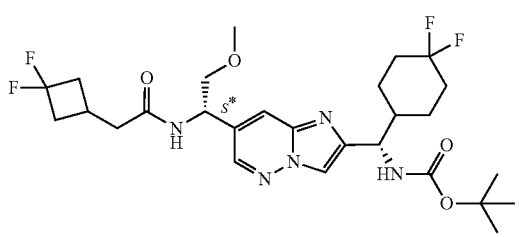 [SMILES: COC[C@@H](NC(=O)CC1CC(F)(F)C1)c1cnn2cc([C@@H](NC(=O)OC(C)(C)C)C3CCC(F)(F)CC3)nc2c1]

tert-Butyl ((1S)-(7-(1-amino-2-methoxyethyl)imidazo[1,2-b]pyridazin-2-yl)(4,4-difluorocyclohexyl)methyl)carbamate (350 mg, 0.8 mmol, Intermediate 454), TEA (330.0 µL, 2.39 mmol), 2-(3,3-difluorocyclobutyl)acetic acid (155 mg, 1.03 mmol), and DCM (15.8 mL) were added to a vial with stir bar. Then slowly, 1-propanephosphonic anhydride (380 mg, 1.19 mmol) was added. The reaction was stirred for 19 h at rt. The mixture was purified directly by silica gel chromatography (0-50% ethyl acetate (with 10% MeOH)/hexanes) to provide a mixture of diastereomers. The isomers were separated by SFC using a chiral stationary phase (Regis (S,S) Whelk-O® 1, 30:70 MeOH with 0.2% Et₃N/CO₂) to provide the title compounds. Intermediate 455 was the first-eluting fraction and Intermediate 456 was the second-eluting fraction.

Intermediate 457

N—((R*)-1-(2-((S)-Amino(4,4-difluorocyclohexyl)methyl)imidazo[1,2-b]pyridazin-7-yl)-2-methoxyethyl)-2-(3,3-difluorocyclobutyl)acetamide

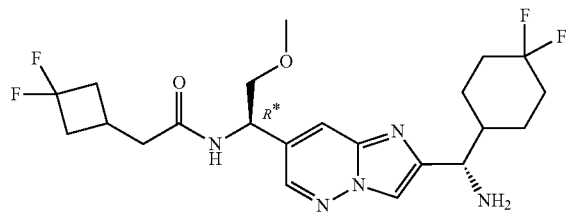 [SMILES: COC[C@H](NC(=O)CC1CC(F)(F)C1)c1cnn2cc([C@@H](N)C3CCC(F)(F)CC3)nc2c1]

The title compound was prepared as described for the synthesis of Intermediate 440, using tert-butyl ((S)-(7-((R*)-1-(2-(3,3-difluorocyclobutyl)acetamido)-2-methoxyethyl)imidazo[1,2-b]pyridazin-2-yl)(4,4-difluorocyclohexyl)methyl)carbamate (Intermediate 455) in place of tert-butyl ((S)-(7-((R*)-cyclobutyl(4,4,4-trifluorobutanamido)methyl)imidazo[1,2-b]pyridazin-2-yl)(4,4-difluorocyclohexyl)methyl) carbamate to provide the title compound.

Intermediate 458

N—((S*)-1-(2-((S)-Amino(4,4-difluorocyclohexyl)methyl)imidazo[1,2-b]pyridazin-7-yl)-2-methoxyethyl)-2-(3,3-difluorocyclobutyl)acetamide

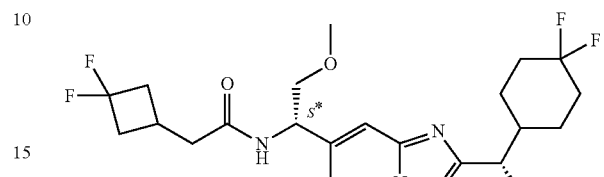

The title compound was prepared as described for the synthesis of Intermediate 440, using tert-butyl ((S)-(7-((S*)-1-(2-(3,3-difluorocyclobutyl)acetamido)-2-methoxyethyl)imidazo[1,2-b]pyridazin-2-yl)(4,4-difluorocyclohexyl)methyl)carbamate (Intermediate 456) in place of tert-butyl ((S)-(7-((R*)-cyclobutyl(4,4,4-trifluorobutanamido)methyl)imidazo[1,2-b]pyridazin-2-yl)(4,4-difluorocyclohexyl)methyl) carbamate to provide the title compound.

Intermediate 459

Tert-Butyl (S)-((4,4-difluorocyclohexyl)(7-(3-ethoxyprop-1-en-2-yl)imidazo[1,2-b]pyridazin-2-yl)methyl)carbamate

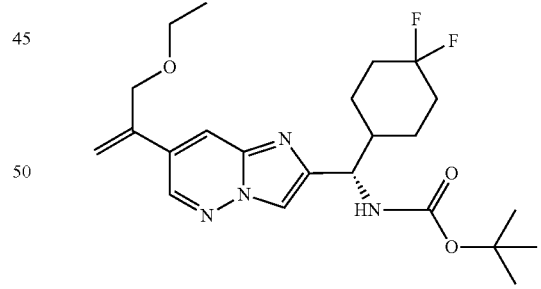

The title compound was prepared as described for the synthesis of Intermediate 18, using potassium (3-ethoxyprop-1-en-2-yl)trifluoroborate in place of 2-(3-methoxyprop-1-en-2-yl)-4,4,5,5-tetramethyl-1,3,2-dioxaborolane to provide the title compound.

Intermediate 460

Tert-Butyl (S)-((4,4-difluorocyclohexyl)(7-(2-ethoxyacetyl)imidazo[1,2-b]pyridazin-2-yl)methyl)carbamate

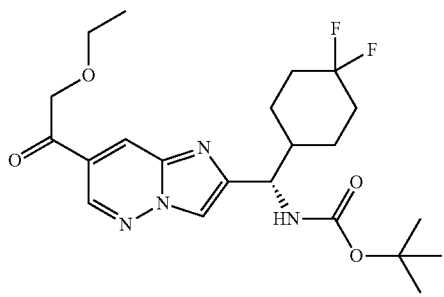 [SMILES: CCOCC(=O)c1cnn2cc([C@@H](NC(=O)OC(C)(C)C)C3CCC(F)(F)CC3)nc2c1]

The title compound was prepared as described for the synthesis of Intermediate 35, using tert-butyl (S)-((4,4-difluorocyclohexyl)(7-(3-ethoxyprop-1-en-2-yl)imidazo[1,2-b]pyridazin-2-yl)methyl)carbamate (Intermediate 459) in place of (S)—N-((4,4-difluorocyclohexyl)(7-vinylimidazo[1,2-b]pyridazin-2-yl)methyl)-1-(3,3,3-trifluoropropyl)-1H-pyrazole-4-carboxamide to provide the title compound.

Intermediate 461

Tert-Butyl ((1S)-(7-(1-amino-2-ethoxyethyl)imidazo[1,2-b]pyridazin-2-yl)(4,4-difluorocyclohexyl)methyl)carbamate

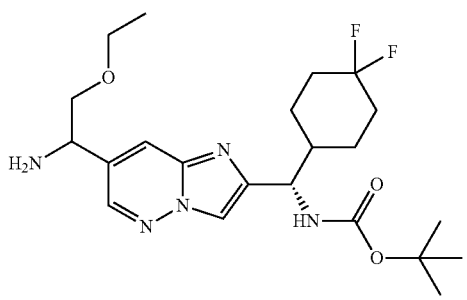 [SMILES: CCOCC(N)c1cnn2cc([C@@H](NC(=O)OC(C)(C)C)C3CCC(F)(F)CC3)nc2c1]

The title compound was prepared as described for the synthesis of Intermediate 454, using tert-butyl (S)-((4,4-difluorocyclohexyl)(7-(2-ethoxyacetyl)imidazo[1,2-b]pyridazin-2-yl)methyl)carbamate (Intermediate 460) in place of tert-butyl (S)-((4,4-difluorocyclohexyl)(7-(2-methoxyacetyl)imidazo[1,2-b]pyridazin-2-yl)methyl)carbamate.

Intermediate 462

Tert-Butyl ((S)-(7-((R*)-1-(2-(3,3-difluorocyclobutyl)acetamido)-2-ethoxyethyl)imidazo[1,2-b]pyridazin-2-yl)(4,4-difluorocyclohexyl)methyl)carbamate

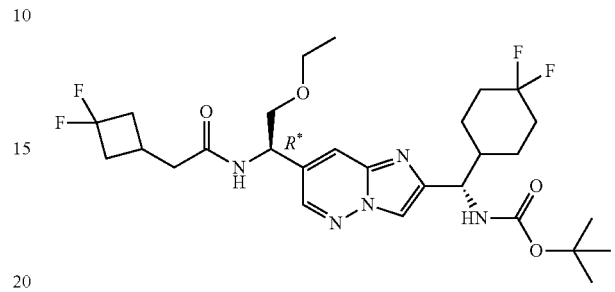

Intermediate 463

Tert-Butyl ((S)-(7-((S*)-1-(2-(3,3-difluorocyclobutyl)acetamido)-2-ethoxyethyl)imidazo[1,2-b]pyridazin-2-yl)(4,4-difluorocyclohexyl)methyl)carbamate

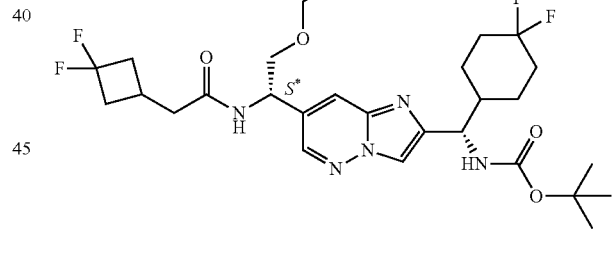

The title compound was prepared as described for the synthesis of Intermediate 456, using tert-butyl ((1S)-(7-(1-amino-2-ethoxyethyl)imidazo[1,2-b]pyridazin-2-yl)(4,4-difluorocyclohexyl)methyl)carbamate (Intermediate 461) in place of tert-butyl ((1S)-(7-(1-amino-2-methoxyethyl)imidazo[1,2-b]pyridazin-2-yl)(4,4-difluorocyclohexyl)methyl)carbamate. The isomers were separated by SFC using a chiral stationary phase (Regis (S,S) Whelk-O® 1, 20:80 MeOH/CO$_2$) to provide the title compounds, Intermediate 462 as the first eluting fraction and Intermediate 463 as the second eluting fraction.

Intermediate 464

N—((R*)-1-(2-((S)-Amino(4,4-difluorocyclohexyl)methyl)imidazo[1,2-b]pyridazin-7-yl)-2-ethoxyethyl)-2-(3,3-difluorocyclobutyl)acetamide

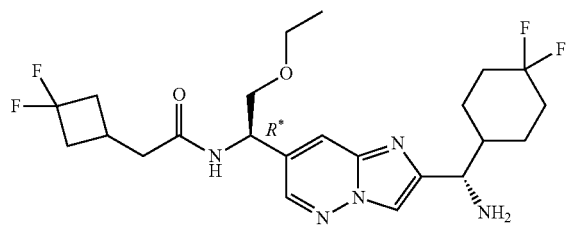 [SMILES: CCOC[C@H](NC(=O)CC1CC(F)(F)C1)c1cnn2cc([C@@H](N)C3CCC(F)(F)CC3)nc2c1]

The title compound was prepared as described for the synthesis of Intermediate 440, using tert-butyl ((S)-(7-((R*)-1-(2-(3,3-difluorocyclobutyl)acetamido)-2-ethoxyethyl)imidazo[1,2-b]pyridazin-2-yl)(4,4-difluorocyclohexyl)methyl)carbamate (Intermediate 462) in place of tert-butyl ((S)-(7-((R*)-cyclobutyl(4,4,4-trifluorobutanamido)methyl)imidazo[1,2-b]pyridazin-2-yl)(4,4-difluorocyclohexyl)methyl) carbamate to provide the title compound.

Intermediate 465

N—((S*)-1-(2-((S)-Amino(4,4-difluorocyclohexyl)methyl)imidazo[1,2-b]pyridazin-7-yl)-2-ethoxyethyl)-2-(3,3-difluorocyclobutyl)acetamide

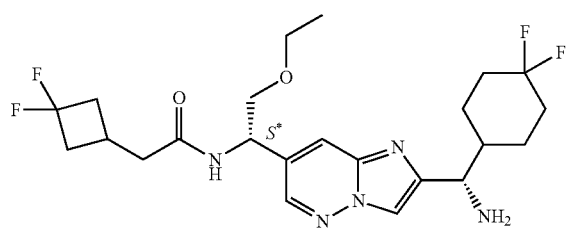 [SMILES: CCOC[C@@H](NC(=O)CC1CC(F)(F)C1)c1cnn2cc([C@@H](N)C3CCC(F)(F)CC3)nc2c1]

The title compound was prepared as described for the synthesis of Intermediate 440, using tert-butyl ((S)-(7-((S*)-1-(2-(3,3-difluorocyclobutyl)acetamido)-2-ethoxyethyl)imidazo[1,2-b]pyridazin-2-yl)(4,4-difluorocyclohexyl)methyl)carbamate (Intermediate 463) in place of tert-butyl ((S)-(7-((R*)-cyclobutyl(4,4,4-trifluorobutanamido)methyl)imidazo[1,2-b]pyridazin-2-yl)(4,4-difluorocyclohexyl)methyl) carbamate to provide the title compound.

Intermediate 466

(S)—N-((7-Chloroimidazo[1,2-b]pyridazin-2-yl)(4,4-difluorocyclohexyl)methyl)-1-isopropyl-1H-pyrazole-5-carboxamide

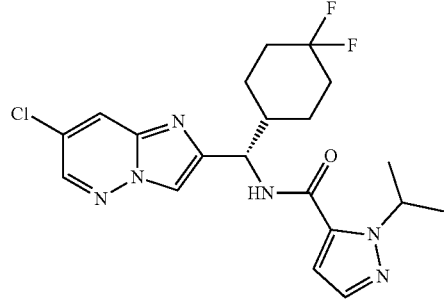 [SMILES: CC(C)n1nccc1C(=O)N[C@H](c1cn2ncc(Cl)cc2n1)C1CCC(F)(F)CC1]

The title compound was prepared as described for the synthesis of Example 506 using (S)-(7-chloroimidazo[1,2-b]pyridazin-2-yl)(4,4-difluorocyclohexyl)methanamine (Intermediate 32) in place of N—((R*)-1-(2-((S)-amino(4,4-difluorocyclohexyl)methyl)imidazo[1,2-b]pyridazin-7-yl)propyl)-2-(3,3-difluorocyclobutyl)acetamide and using 1-isopropyl-1H-pyrazole-5-carboxylic in place of 1-(ethylds)-1H-pyrazole-5-carboxylic acid to provide the title compound.

Intermediate 467

(S)—N-((7-(3-(Benzyloxy)prop-1-en-2-yl)imidazo[1,2-b]pyridazin-2-yl)(4,4-difluorocyclohexyl)methyl)-1-isopropyl-1H-pyrazole-5-carboxamide

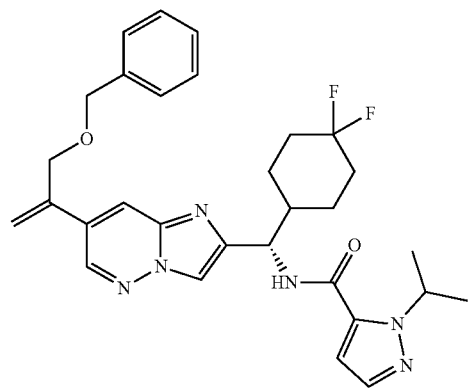 [SMILES: C=C(COCc1ccccc1)c1cnn2cc([C@@H](NC(=O)c3ccnn3C(C)C)C3CCC(F)(F)CC3)nc2c1]

The title compound was prepared as described for the synthesis of Intermediate 18, using potassium (3-(benzyloxy)prop-1-en-2-yl)trifluoroborate in place of 2-(3-methoxyprop-1-en-2-yl)-4,4,5,5-tetramethyl-1,3,2-dioxaborolane and (S)—N-((7-chloroimidazo[1,2-b]pyridazin-2-yl)(4,4-difluorocyclohexyl)methyl)-1-isopropyl-1H-pyrazole-5-carboxamide (Intermediate 466) in place of tert-butyl N—[(S)-(7-chloroimidazo[1,2-b]pyridazin-2-yl)-(4,4-difluorocyclohexyl)methyl]carbamate to provide the title compound.

Intermediate 468

(S)—N-((7-(2-(Benzyloxy)acetyl)imidazo[1,2-b]pyridazin-2-yl)(4,4-difluorocyclohexyl)methyl)-1-isopropyl-1H-pyrazole-5-carboxamide

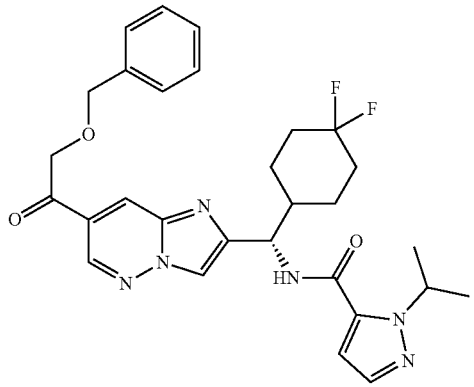 [SMILES: CC(C)n1nccc1C(=O)N[C@H](c1cn2ncc(C(=O)COCc3ccccc3)cc2n1)C1CCC(F)(F)CC1]

The title compound was prepared as described for the synthesis of Intermediate 35, using (S)—N-((7-(3-(benzyloxy)prop-1-en-2-yl)imidazo[1,2-b]pyridazin-2-yl)(4,4-difluorocyclohexyl)methyl)-1-isopropyl-1H-pyrazole-5-carboxamide (Intermediate 467) in place of (S)—N-((4,4-difluorocyclohexyl)(7-vinylimidazo[1,2-b]pyridazin-2-yl)methyl)-1-(3,3,3-trifluoropropyl)-1H-pyrazole-4-carboxamide to provide the title compound.

Intermediate 469

N-((1S)-(7-(1-Amino-2-(benzyloxy)ethyl)imidazo[1,2-b]pyridazin-2-yl)(4,4-difluorocyclohexyl)methyl)-1-isopropyl-1H-pyrazole-5-carboxamide

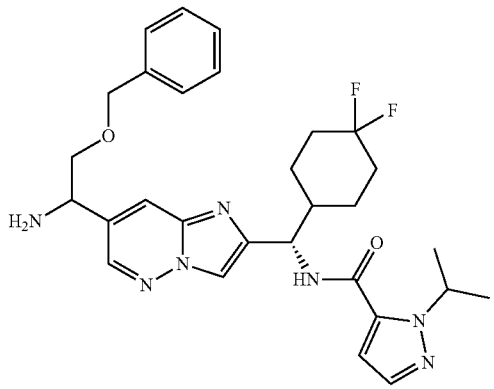 [SMILES: CC(C)n1nccc1C(=O)N[C@H](c1cn2ncc(C(N)COCc3ccccc3)cc2n1)C1CCC(F)(F)CC1]

The title compound was prepared as described for the synthesis of Intermediate 454, using (S)—N-((7-(2-(benzyloxy)acetyl)imidazo[1,2-b]pyridazin-2-yl)(4,4-difluorocyclohexyl)methyl)-1-isopropyl-1H-pyrazole-5-carboxamide (Intermediate 468) in place of tert-butyl (S)-((4,4-difluorocyclohexyl)(7-(2-methoxyacetyl)imidazo[1,2-b]pyridazin-2-yl)methyl)carbamate to provide the title compound.

Intermediate 470

N—((S)-(7-((R*)-2-(Benzyloxy)-1-(2-(3,3-difluorocyclobutyl)acetamido)ethyl)imidazo[1,2-b]pyridazin-2-yl)(4,4-difluorocyclohexyl)methyl)-1-isopropyl-1H-pyrazole-5-carboxamide

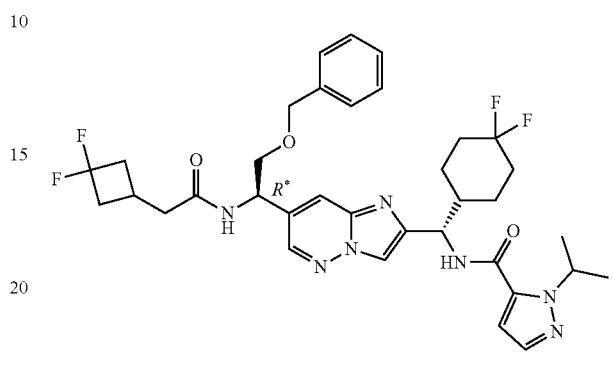

Intermediate 471

N—((S)-(7-((S*)-2-(Benzyloxy)-1-(2-(3,3-difluorocyclobutyl)acetamido)ethyl)imidazo[1,2-b]pyridazin-2-yl)(4,4-difluorocyclohexyl)methyl)-1-isopropyl-1H-pyrazole-5-carboxamide

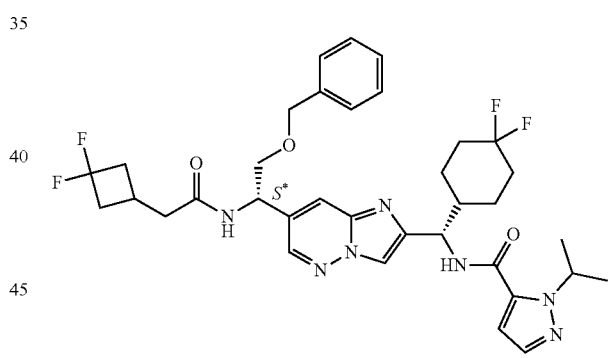

A vial was charged with a stir bar, 2-(3,3-difluorocyclobutyl)acetic acid (195 mg, 1.3 mmol), HATU (494 mg, 1.3 mmol), DIPEA (0.34 mL, 2.0 mmol) and CH₃CN (7 mL). The solution was stirred for 20 min then N-((1S)-(7-(1-amino-2-(benzyloxy)ethyl)imidazo[1,2-b]pyridazin-2-yl)(4,4-difluorocyclohexyl)methyl)-1-isopropyl-1H-pyrazole-5-carboxamide (551 mg, 1.0 mmol, Intermediate 469) was added and the reaction was stirred for a further 18 h. The mixture was partitioned between EtOAc and water. The organic layer was washed with brine, then dried over anhydrous Na₂SO₄, filtered, and concentrated to dryness. The crude material was purified by silica gel chromatography (0-100% ethyl acetate (with 10% MeOH)/hexanes) to provide the title compounds as a mixture of isomers. The isomers were separated by SFC using a chiral stationary phase (Chiralpak IA, 25:75 MeOH/CO₂) to provide the title compounds. Intermediate 470 was the first-eluting fraction and Intermediate 471 was the second-eluting fraction.

611

Intermediate 472

Tert-Butyl ((S)-(7-((R*)—(((S)-tert-butylsulfinyl)amino)(tetrahydro-2H-pyran-4-yl)methyl methyl)imidazo[1,2-b]pyridazin-2-yl)(4,4-difluorocyclohexyl)methyl)carbamate

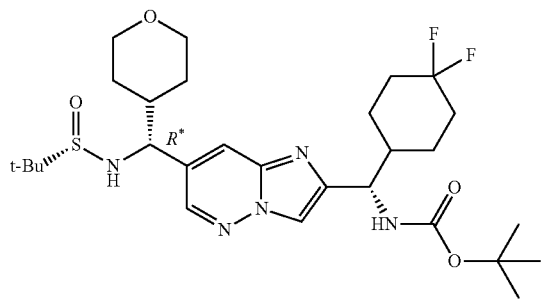 [SMILES: CC(C)(C)OC(=O)N[C@H](c1cn2ncc([C@H](N[S@@](=O)C(C)(C)C)C3CCOCC3)cc2n1)C1CCC(F)(F)CC1]

The title compound was prepared as described for the synthesis of Intermediate 55, using tetrahydropyran-4-yl-magnesium bromide 0.5 M in THF in place of cyclopropylmagnesium bromide in 2-MeTHF and further purification was accomplished by SFC using a chiral stationary phase (Regis (S,S) Whelk-O® 1, 30% MeOH:IPA with 0.2% iPrNH$_2$/70% CO$_2$) to provide the title compound.

Intermediate 473

Tert-Butyl ((S)-(7-((R*)-amino(tetrahydro-2H-pyran-4-yl)methyl)imidazo[1,2-b]pyridazin-2-yl)(4,4-difluorocyclohexyl)methyl)carbamate

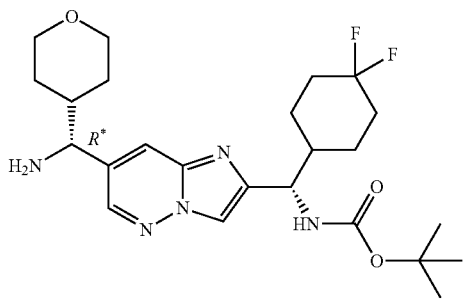 [SMILES: CC(C)(C)OC(=O)N[C@H](c1cn2ncc([C@H](N)C3CCOCC3)cc2n1)C1CCC(F)(F)CC1]

The title compound was prepared as described for the synthesis of Intermediate 49, using tert-butyl ((S)-(7-((R*)—(((S)-tert-butylsulfinyl)amino)(tetrahydro-2H-pyran-4-yl)methyl methyl)imidazo[1,2-b]pyridazin-2-yl)(4,4-difluorocyclohexyl)methyl)carbamate (Intermediate 472) in place of tert-butyl ((S)-(7-((R)-(((S)-tert-butylsulfinyl)amino)(cyclopropyl)methyl)imidazo[1,2-b]pyridazin-2-yl)(4,4-difluorocyclohexyl)methyl)carbamate to provide the title compound as a white foam.

612

Intermediate 474

Tert-Butyl ((S)-(7-((R*)-2-(3,3-difluorocyclobutyl)acetamido)(tetrahydro-2H-pyran-4-yl)methyl)imidazo[1,2-b]pyridazin-2-yl)(4,4-difluorocyclohexyl)methyl)carbamate

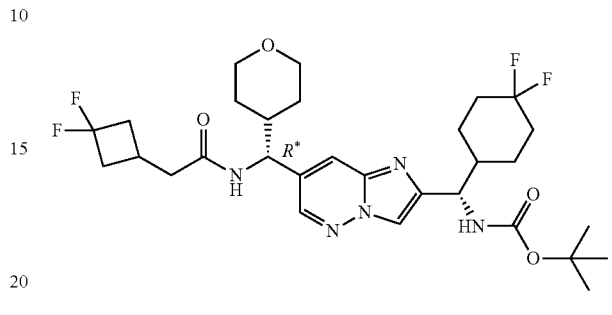

The title compound was prepared as described for the synthesis of Intermediate 50, using tert-butyl ((S)-(7-((R*)-amino(tetrahydro-2H-pyran-4-yl)methyl)imidazo[1,2-b]pyridazin-2-yl)(4,4-difluorocyclohexyl)methyl)carbamate (Intermediate 473) in place of tert-butyl ((S)-(7-((R)-amino(cyclopropyl)methyl)imidazo[1,2-b]pyridazin-2-yl)(4,4-difluorocyclohexyl)methyl) carbamate, 2-(3,3-difluorocyclobutyl)acetic acid in place of 4,4,4-trifluorobutyric acid and purification by silica gel chromatography (0-100% ethyl acetate (with 10% MeOH)/hexanes) to provide the title compound.

Intermediate 475

N—((R*)-(2-((S)-Amino(4,4-difluorocyclohexyl)methyl)imidazo[1,2-b]pyridazin-7-yl)(tetrahydro-2H-pyran-4-yl)methyl)-2-(3,3-difluorocyclobutyl)acetamide

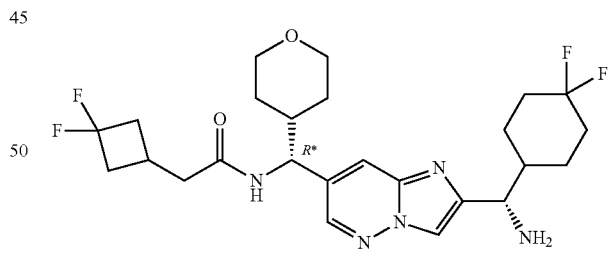

The title compound was prepared as described for the synthesis of Intermediate 440, using tert-butyl ((S)-(7-((R*)-(2-(3,3-difluorocyclobutyl)acetamido)(tetrahydro-2H-pyran-4-yl)methyl)imidazo[1,2-b]pyridazin-2-yl)(4,4-difluorocyclohexyl)methyl)carbamate (Intermediate 474) in place of tert-butyl ((S)-(7-((R*)-cyclobutyl(4,4,4-trifluorobutanamido)methyl)imidazo[1,2-b]pyridazin-2-yl)(4,4-difluorocyclohexyl)methyl) carbamate to provide the title compound.

Intermediate 476

Tert-Butyl (R)-(3-methoxy-1-(methoxy(methyl)amino)-1-oxopropan-2-yl)carbamate

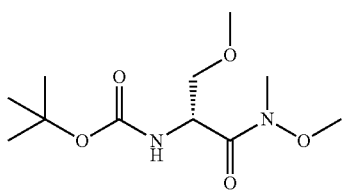 [SMILES: COC[C@@H](NC(=O)OC(C)(C)C)C(=O)N(C)OC]

The title compound was prepared as described for the synthesis of Intermediate 263, using (R)-2-((tert-butoxycarbonyl)amino)-3-methoxypropanoic acid in place of N-(tert-butoxycarbonyl)-O-methyl-D-threonine to provide the title compound.

Intermediate 477

Tert-Butyl (R)-(1-methoxy-3-oxopropan-2-yl)carbamate

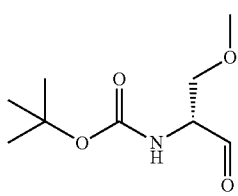

The title compound was prepared as described for the synthesis of Intermediate 264, using tert-butyl (R)-(1-methoxy-3-oxopropan-2-yl)carbamate (Intermediate 476) in place of tert-butyl ((2R,3S)-3-methoxy-1-(methoxy(methyl)amino)-1-oxobutan-2-yl)carbamate to provide the title compound.

Intermediate 478

Tert-Butyl (S)-(1-methoxybut-3-yn-2-yl)carbamate

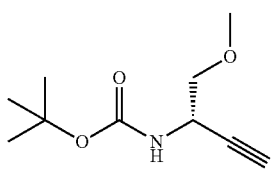

The title compound was prepared as described for the synthesis of Intermediate 265, using tert-butyl (R)-(1-methoxy-3-oxopropan-2-yl)carbamate (Intermediate 477) in place of tert-butyl ((2R,3S)-3-methoxy-1-oxobutan-2-yl)carbamate to provide the title compound.

Intermediate 479

(S)-1-Methoxybut-3-yn-2-amine Hydrochloride

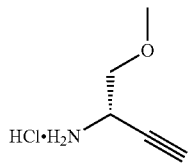

The title compound was prepared as described for the synthesis of Intermediate 266, using (S)-1-methoxybut-3-yn-2-amine (Intermediate 478) in place of tert-butyl ((3S,4S)-4-methoxypent-1-yn-3-yl)carbamate to provide the title compound.

Intermediate 480

(S)-2-(3,3-Difluorocyclobutyl)-N-(1-methoxybut-3-yn-2-yl)acetamide

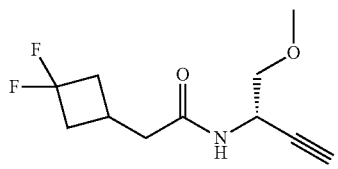 [SMILES: C#C[C@@H](COC)NC(=O)CC1CC(F)(F)C1]

The title compound was prepared as described for the synthesis of Intermediate 267, using (S)-1-methoxybut-3-yn-2-amine hydrochloride (Intermediate 479) in place of (3S,4S)-4-methoxypent-1-yn-3-amine hydrochloride.

Intermediate 481

Tert-Butyl (S)-(5-(1-(2-(3,3-difluorocyclobutyl)acetamido)-2-methoxyethyl)pyridazin-3-yl)(4-methoxybenzyl)carbamate

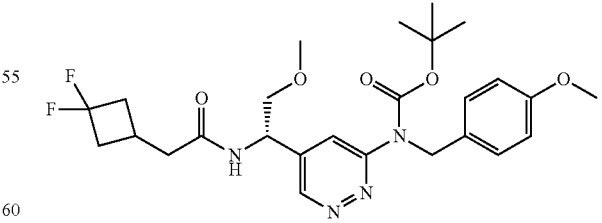

The title compound was prepared as described for the synthesis of Intermediate 271, using (S)-2-(3,3-difluorocyclobutyl)-N-(1-methoxybut-3-yn-2-yl)acetamide (Intermediate 480) in place of 2-(3,3-difluorocyclobutyl)-N-((3S,4S)-4-methoxypent-1-yn-3-yl)acetamide.

615

Intermediate 482

(S)—N-(1-(6-Aminopyridazin-4-yl)-2-methoxyethyl)-2-(3,3-difluorocyclobutyl)acetamide

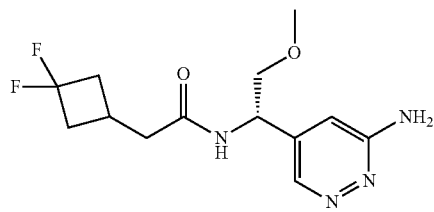 [SMILES: COC[C@@H](NC(=O)CC1CC(F)(F)C1)c1cnnc(N)c1]

The title compound was prepared as described for the synthesis of Intermediate 272, using tert-butyl (S)-(5-(1-(2-(3,3-difluorocyclobutyl)acetamido)-2-methoxyethyl)pyridazin-3-yl)(4-methoxybenzyl)carbamate (Intermediate 481) in place of tert-butyl (5-((1S,2S)-1-(2-(3,3-difluorocyclobutyl)acetamido)-2-methoxypropyl)pyridazin-3-yl)(4-methoxybenzyl)carbamate.

Intermediate 483

Tert-Butyl ((R)-1-(7-((S)-1-(2-(3,3-difluorocyclobutyl)acetamido)-2-methoxyethyl)imidazo[1,2-b]pyridazin-2-yl)-2-((1,1,1-trifluoro-2-methylpropan-2-yl)oxy)ethyl)carbamate

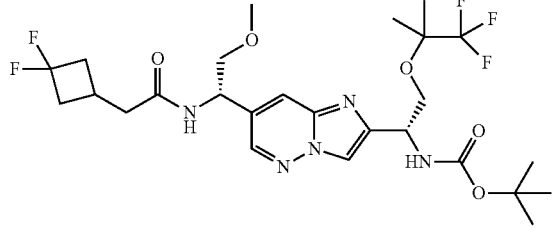

The title compound was prepared as described for the synthesis of Intermediate 273, using (S)—N-(1-(6-aminopyridazin-4-yl)-2-methoxyethyl)-2-(3,3-difluorocyclobutyl)acetamide (Intermediate 482) in place of N-((1S,2S)-1-(6-aminopyridazin-4-yl)-2-methoxypropyl)-2-(3,3-difluorocyclobutyl)acetamide, tert-butyl (S)-(4-iodo-3-oxo-1-((1,1,1-trifluoro-2-methylpropan-2-yl)oxy)butan-2-yl)carbamate (Intermediate 254) in place of tert-butyl (S)-(1-(4,4-difluorocyclohexyl)-3-iodo-2-oxopropyl)carbamate, and purification by silica gel chromatography (0-100% ethyl acetate (with 10% MeOH)/hexanes). Additional purification steps were performed by silica gel chromatography (10-100% ethyl acetate/hexanes) and preparative HPLC (XBridge Prep C18 5 µm, 50×100 mm column, 0-100% acetonitrile/water (with 20 mM NH$_4$OH)) to provide the title compound.

616

Intermediate 484

N—((S)-1-(2-((R)-1-Amino-2-((1,1,1-trifluoro-2-methylpropan-2-yl)oxy)ethyl)imidazo[1,2-b]pyridazin-7-yl)-2-methoxyethyl)-2-(3,3-difluorocyclobutyl)acetamide

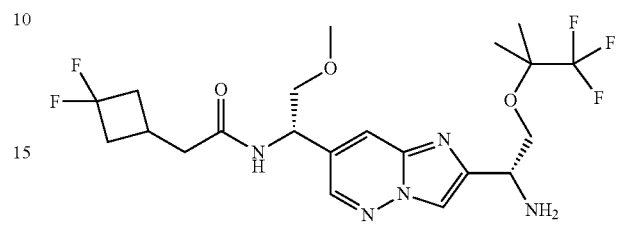

The title compound was prepared as described for the synthesis of Intermediate 440, using tert-butyl ((R)-1-(7-((S)-1-(2-(3,3-difluorocyclobutyl)acetamido)-2-methoxyethyl)imidazo[1,2-b]pyridazin-2-yl)-2-((1,1,1-trifluoro-2-methylpropan-2-yl)oxy)ethyl)carbamate (Intermediate 483) in place of tert-butyl ((S)-(7-((R*)-cyclobutyl(4,4,4-trifluorobutanamido)methyl)imidazo[1,2-b]pyridazin-2-yl)(4,4-difluorocyclohexyl)methyl) carbamate to provide the title compound.

Intermediate 485

(S,E)-2-Methyl-N-((tetrahydro-2H-pyran-4-yl)methylene)propane-2-sulfinamide

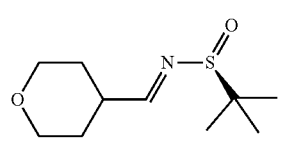

The title compound was prepared as described for the synthesis of Intermediate 255, using tetrahydro-2H-pyran-4-carbaldehyde in place of cyclopropanecarboxaldehyde to provide the title compound.

Intermediate 486

N-(5-((R)—(((S)-tert-Butylsulfinyl)amino)(tetrahydro-2H-pyran-4-yl)methyl))-6-chloropyridazin-3-yl)pivalamide

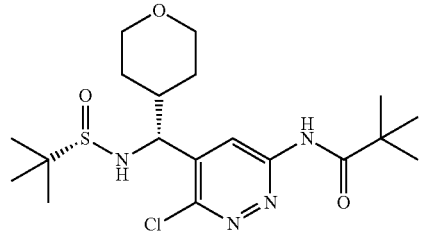 [SMILES: CC(C)(C)C(=O)Nc1cc([C@H](N[S@@](=O)C(C)(C)C)C2CCOCC2)c(Cl)nn1]

The title compound was prepared as described for the synthesis of Intermediate 257, using (S,E)-2-methyl-N-((tetrahydro-2H-pyran-4-yl)methylene)propane-2-sulfinamide (Intermediate 485) in place of (S,E)-N-(cyclopropylmethylene)-2-methylpropane-2-sulfinamide to provide the title compound.

Intermediate 487

(R)-5-(Amino(tetrahydro-2H-pyran-4-yl)methyl)-6-chloropyridazin-3-amine

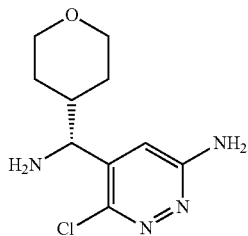 [SMILES: Nc1cc([C@H](N)C2CCOCC2)c(Cl)nn1]

The title compound was prepared as described for the synthesis of Intermediate 258, using N-(5-((R)—(((S)-tert-butylsulfinyl)amino)(tetrahydro-2H-pyran-4-yl)methyl))-6-chloropyridazin-3-yl)pivalamide (Intermediate 486) in place of N-(5-((R)—(((S)-tert-butylsulfinyl)amino)(cyclopropyl)methyl)-6-chloropyridazin-3-yl)pivalamide and additional extraction of the aqueous layer with 20% IPA in $CHCl_3$ (4×) to provide the title compound.

Intermediate 488

(R)—N-((6-Amino-3-chloropyridazin-4-yl)(tetrahydro-2H-pyran-4-yl)methyl)-2-(3,3-difluorocyclobutyl)acetamide

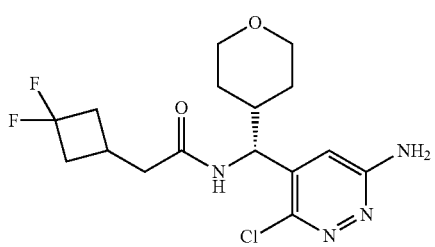 [SMILES: Nc1cc([C@H](NC(=O)CC2CC(F)(F)C2)C2CCOCC2)c(Cl)nn1]

The title compound was prepared as described for the synthesis of Intermediate 259, using (R)-5-(amino(tetrahydro-2H-pyran-4-yl)methyl)-6-chloropyridazin-3-amine (Intermediate 487) in place of (R)-5-(amino(cyclopropyl)methyl)-6-chloropyridazin-3-amine and purification by SFC using a chiral stationary phase (Chiralpak IB N3, 25:75 (MeOH/$CO_2$) provided the title compound.

Intermediate 489

Tert-Butyl ((R)-1-(6-chloro-7-((R)-(2-(3,3-difluorocyclobutyl)acetamido)(tetrahydro-2H-pyran-4-yl)methyl)imidazo[1,2-b]pyridazin-2-yl)-2-((1,1,1-trifluoro-2-methylpropan-2-yl)oxy)ethyl)carbamate

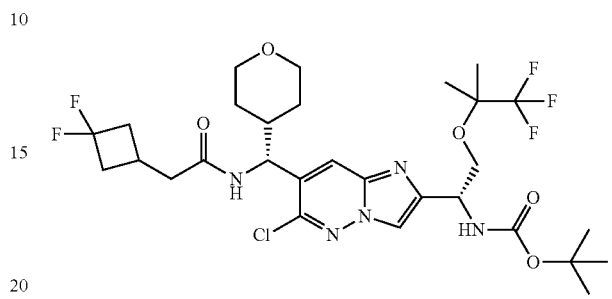

The title compound was prepared as described for the synthesis of Intermediate 260, using (R)—N-((6-amino-3-chloropyridazin-4-yl)(tetrahydro-2H-pyran-4-yl)methyl)-2-(3,3-difluorocyclobutyl)acetamide (Intermediate 488) in place of (R)—N-((6-amino-3-chloropyridazin-4-yl)(cyclopropyl)methyl)-2-(3,3-difluorocyclobutyl)acetamide. Purification by silica gel chromatography (0-100% acetone/hexanes) provided the title compound.

Intermediate 490

Tert-Butyl ((R)-1-(7-((R)-(2-(3,3-difluorocyclobutyl)acetamido)(tetrahydro-2H-pyran-4-yl)methyl)imidazo[1,2-b]pyridazin-2-yl)-2-((1,1,1-trifluoro-2-methylpropan-2-yl)oxy)ethyl)carbamate

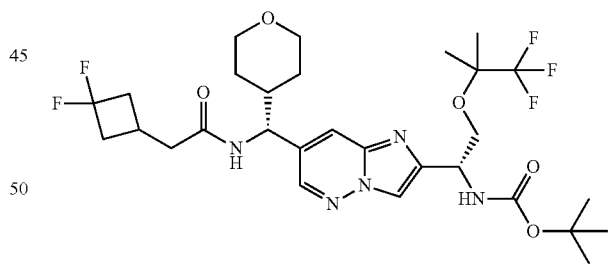

To a solution of tert-butyl ((R)-1-(6-chloro-7-((R)-(2-(3,3-difluorocyclobutyl)acetamido)(tetrahydro-2H-pyran-4-yl)methyl)imidazo[1,2-b]pyridazin-2-yl)-2-((1,1,1-trifluoro-2-methylpropan-2-yl)oxy)ethyl)carbamate (463 mg, 0.69 mmol, Intermediate 489) and $NH_4OH$ (1.5 mL) in EtOH (13-mL) was added Pd/C (147 mg, 0.14 mmol, 20% wt) under an $N_2$ atmosphere. The mixture was put under an $H_2$ atmosphere (balloon) and stirred at rt for 28 h then filtered through diatomaceous earth (Celite®), and concentrated. Purification by silica gel chromatography (0-100% acetone/hexanes) provided the title compound.

Intermediate 491

N—((R)-(2-((R)-1-Amino-2-((1,1,1-trifluoro-2-methylpropan-2-yl)oxy)ethyl)imidazo[1,2-b]pyridazin-7-yl)(tetrahydro-2H-pyran-4-yl)methyl)-2-(3,3-difluorocyclobutyl)acetamide

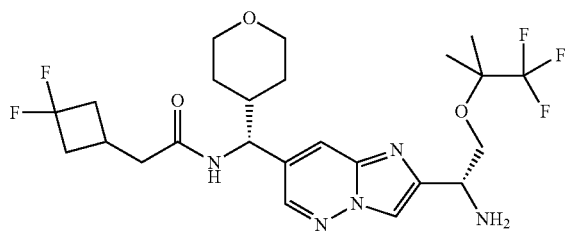 [SMILES: CC(C)(OC[C@H](N)c1cn2ncc([C@H](NC(=O)CC3CC(F)(F)C3)C3CCOCC3)cc2n1)C(F)(F)F]

The title compound was prepared as described for the synthesis of Intermediate 440, using tert-butyl ((R)-1-(7-((R)-(2-(3,3-difluorocyclobutyl)acetamido)(tetrahydro-2H-pyran-4-yl)methyl)imidazo[1,2-b]pyridazin-2-yl)-2-((1,1,1-trifluoro-2-methylpropan-2-yl)oxy)ethyl)carbamate (Intermediate 490) in place of tert-butyl ((S)-(7-((R*)-cyclobutyl(4,4,4-trifluorobutanamido)methyl)imidazo[1,2-b]pyridazin-2-yl)(4,4-difluorocyclohexyl)methyl) carbamate to provide the title compound.

Intermediate 492

(S,E)-2-Methyl-N-(4,4,4-trifluoro-3,3-dimethyl-butylidene)propane-2-sulfinamide

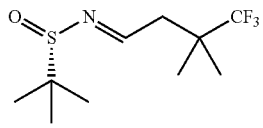 [SMILES: CC(C)(C)[S@](=O)/N=C/CC(C)(C)C(F)(F)F]

To a solution of 3,3,3-trifluoropropanal (140.0 g, 908.3 mmol) in DCM (1500 mL) was added (S)-2-methylpropane-2-sulfinamide (132.1 g, 1.09 mol), PPTS (23.1 g, 91.7 mmol) and CuSO₄ (430 g, 2.74 mol). The resulting mixture was stirred for 12 h at 30° C. The reaction was filtered through Celite®, then the filtrate was concentrated under reduced pressure to give a yellow oil. The yellow oil was purified by silica gel chromatography (0-10% EtOAc/petroleum ether) to obtain the title compound as a yellow oil.

Intermediate 493

(S)—N—((S)-1-Cyano-4,4,4-trifluoro-3,3-dimethyl-butyl)-2-methylpropane-2-sulfinamide

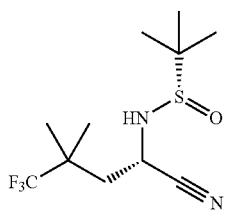 [SMILES: CC(C)(C)[S@](=O)N[C@H](C#N)CC(C)(C)C(F)(F)F]

The title compound was prepared as described for the synthesis of Intermediate 279, using (S,E)-2-methyl-N-(4,4,4-trifluoro-3,3-dimethylbutylidene)propane-2-sulfinamide (Intermediate 492) in place of (S,E)-2-methyl-N-(2-((1,1,1-trifluoro-2-methylpropan-2-yl)oxy)ethylidene) propane-2-sulfinamide to provide the title compound.

Intermediate 494

(S)-2-Amino-5,5,5-trifluoro-4,4-dimethylpentanoic Acid

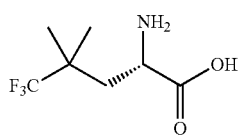

The title compound was prepared as described for the synthesis of Intermediate 280, using (S)—N—((S)-1-cyano-4,4,4-trifluoro-3,3-dimethylbutyl)-2-methylpropane-2-sulfinamide (Intermediate 493) in place of (S)—N—((R)-1-cyano-2-((1,1,1-trifluoro-2-methylpropan-2-yl)oxy)ethyl)-2-methylpropane-2-sulfinamide to provide the title compound.

Intermediate 495

(S)-2-((tert-Butoxycarbonyl)amino)-5,5,5-trifluoro-4,4-dimethylpentanoic Acid

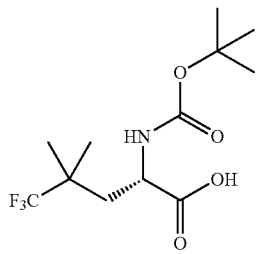 [SMILES: CC(C)(C)OC(=O)N[C@@H](CC(C)(C)C(F)(F)F)C(=O)O]

The title compound was prepared as described for the synthesis of Intermediate 281, using (S)-2-amino-5,5,5-trifluoro-4,4-dimethylpentanoic acid (Intermediate 494) in place of O-(1,1,1-trifluoro-2-methylpropan-2-yl)-L-serine to provide the title compound.

Intermediate 496

Tert-Butyl (S)-(1-(dimethyl(oxo)-λ⁶-sulfaney-lidene)-6,6,6-trifluoro-5,5-dimethyl-2-oxohexan-3-yl)carbamate

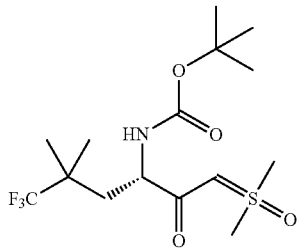

The title compound was prepared as described for the synthesis of Intermediate 282, using (S)-2-((tert-butoxycarbonyl)amino)-5,5,5-trifluoro-4,4-dimethylpentanoic acid (Intermediate 495) in place of N-(tert-butoxycarbonyl)-O-(1,1,1-trifluoro-2-methylpropan-2-yl)-L-serine to provide the title compound.

Intermediate 497

Tert-Butyl (S)-(1-chloro-6,6,6-trifluoro-5,5-dimethyl-2-oxohexan-3-yl)carbamate

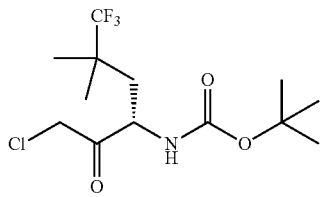 [SMILES: CC(C)(C)OC(=O)N[C@@H](CC(C)(C)C(F)(F)F)C(=O)CCl]

The title compound was prepared as described for the synthesis of Intermediate 253, using tert-butyl (S)-(1-(dimethyl(oxo)-λ⁶-sulfaneylidene)-6,6,6-trifluoro-5,5-dimethyl-2-oxohexan-3-yl)carbamate (Intermediate 496) in place of tert-butyl (S)-(4-(dimethyl(oxo)-λ⁶-sulfaneylidene)-3-oxo-1-((1,1,1-trifluoro-2-methylpropan-2-yl)oxy)butan-2-yl)carbamate to provide the title compound.

Intermediate 498

Tert-Butyl (S)-(6,6,6-trifluoro-1-iodo-5,5-dimethyl-2-oxohexan-3-yl)carbamate

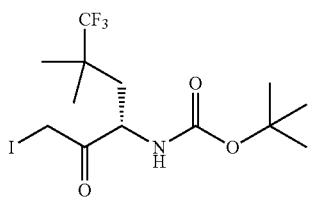 [SMILES: CC(C)(C)OC(=O)N[C@@H](CC(C)(C)C(F)(F)F)C(=O)CI]

The title compound was prepared as described for the synthesis of Intermediate 254, using tert-butyl (S)-(1-chloro-6,6,6-trifluoro-5,5-dimethyl-2-oxohexan-3-yl)carbamate (Intermediate 497) in place of tert-butyl (S)-(4-chloro-3-oxo-1-((1,1,1-trifluoro-2-methylpropan-2-yl)oxy)butan-2-yl)carbamate to provide the title compound.

Intermediate 499

Tert-Butyl ((S)-1-(6-chloro-7-((R)-cyclopropyl(2-(3,3-difluorocyclobutyl)acetamido)methyl)imidazo[1,2-b]pyridazin-2-yl)-4,4,4-trifluoro-3,3-dimethylbutyl)carbamate

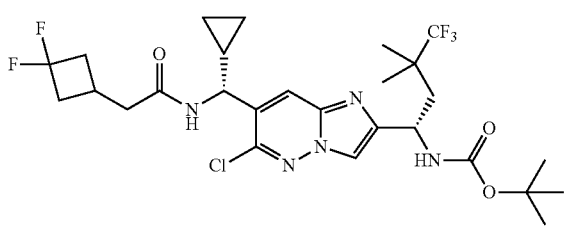 [SMILES: CC(C)(C)OC(=O)N[C@@H](CC(C)(C)C(F)(F)F)c1cn2nc(Cl)c([C@H](NC(=O)CC3CC(F)(F)C3)C3CC3)cc2n1]

The title compound was prepared as described for the synthesis of Intermediate 260, using tert-butyl (S)-(6,6,6-trifluoro-1-iodo-5,5-dimethyl-2-oxohexan-3-yl)carbamate (Intermediate 498) in place of tert-butyl (S)-(4-iodo-3-oxo-1-((1,1,1-trifluoro-2-methylpropan-2-yl)oxy)butan-2-yl)carbamate to provide the title compound.

Intermediate 500

Tert-Butyl ((S)-1-(7-((R)-cyclopropyl(2-(3,3-difluorocyclobutyl)acetamido)methyl)imidazo[1,2-b]pyridazin-2-yl)-4,4,4-trifluoro-3,3-dimethylbutyl)carbamate

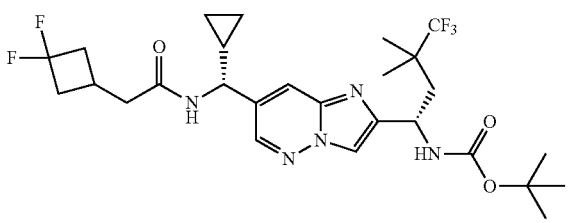 [SMILES: CC(C)(C)OC(=O)N[C@@H](CC(C)(C)C(F)(F)F)c1cn2ncc([C@H](NC(=O)CC3CC(F)(F)C3)C3CC3)cc2n1]

The title compound was prepared as described for the synthesis of Intermediate 490, using tert-butyl ((S)-1-(6-chloro-7-((R)-cyclopropyl(2-(3,3-difluorocyclobutyl)acetamido)methyl)imidazo[1,2-b]pyridazin-2-yl)-4,4,4-trifluoro-3,3-dimethylbutyl)carbamate (Intermediate 499) in place of tert-butyl ((R)-1-(6-chloro-7-((R)-(2-(3,3-difluorocyclobutyl)acetamido)(tetrahydro-2H-pyran-4-yl)methyl)imidazo[1,2-b]pyridazin-2-yl)-2-((1,1,1-trifluoro-2-methylpropan-2-yl)oxy)ethyl)carbamate to provide the title compound.

Intermediate 501

N—((R)-(2-((S)-1-Amino-4,4,4-trifluoro-3,3-dimethylbutyl)imidazo[1,2-b]pyridazin-7-yl)(cyclopropyl)methyl)-2-(3,3-difluorocyclobutyl)acetamide

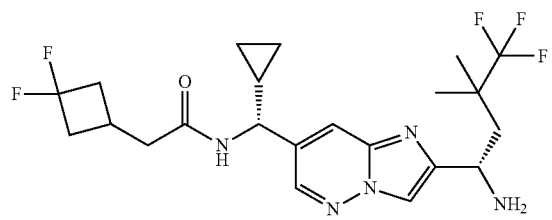 [SMILES: CC(C)(C[C@H](N)c1cn2ncc([C@H](NC(=O)CC3CC(F)(F)C3)C3CC3)cc2n1)C(F)(F)F]

The title compound was prepared as described for the synthesis of Intermediate 440, using tert-butyl ((S)-1-(7-((R)-cyclopropyl(2-(3,3-difluorocyclobutyl)acetamido)methyl)imidazo[1,2-b]pyridazin-2-yl)-4,4,4-trifluoro-3,3-dimethylbutyl)carbamate (Intermediate 500) in place of tert-butyl ((S)-(7-((R*)-cyclobutyl(4,4,4-trifluorobutanamido)methyl)imidazo[1,2-b]pyridazin-2-yl)(4,4-difluorocyclohexyl)methyl)carbamate to provide the title compound.

Intermediate 502

Tert-Butyl ((S)-(7-((R*)-1-(((S)-tert-butylsulfinyl)amino)-2-methylpropyl)imidazo[1,2-b]pyridazin-2-yl)(4,4-difluorocyclohexyl)methyl)carbamate

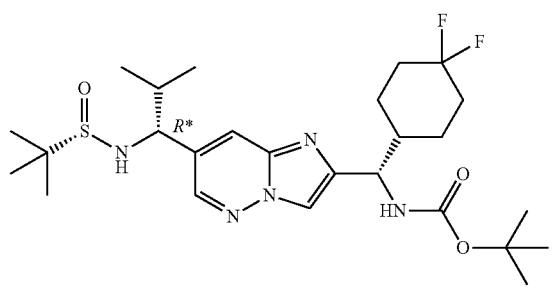 [SMILES: CC(C)[C@@H](N[S@@](=O)C(C)(C)C)c1cnn2cc([C@@H](NC(=O)OC(C)(C)C)C3CCC(F)(F)CC3)nc2c1]

The title compound was prepared as described for the synthesis of Intermediate 48, using isopropylmagnesium bromide in place of cyclopropylmagnesium bromide and is the first-eluting isomer.

Intermediate 503

Tert-Butyl ((S)-(7-((S*)-1-(((S)-tert-butylsulfinyl)amino)-2-methylpropyl)imidazo[1,2-b]pyridazin-2-yl)(4,4-difluorocyclohexyl)methyl)carbamate

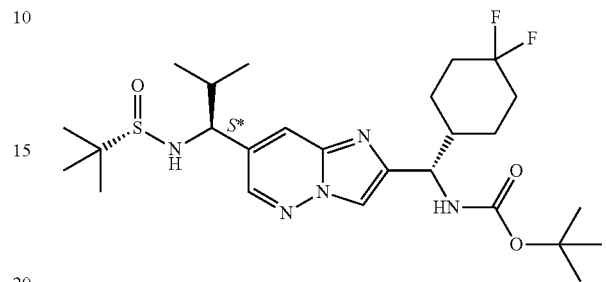

The title compound was prepared as described for the synthesis of Intermediate 48, using isopropylmagnesium bromide in place of cyclopropylmagnesium bromide and is the second-eluting isomer.

Intermediate 504

Tert-Butyl ((S)-(7-((R*)-1-(((S)-tert-butylsulfinyl)amino)ethyl)imidazo[1,2-b]pyridazin-2-yl)(4,4-difluorocyclohexyl)methyl)carbamate

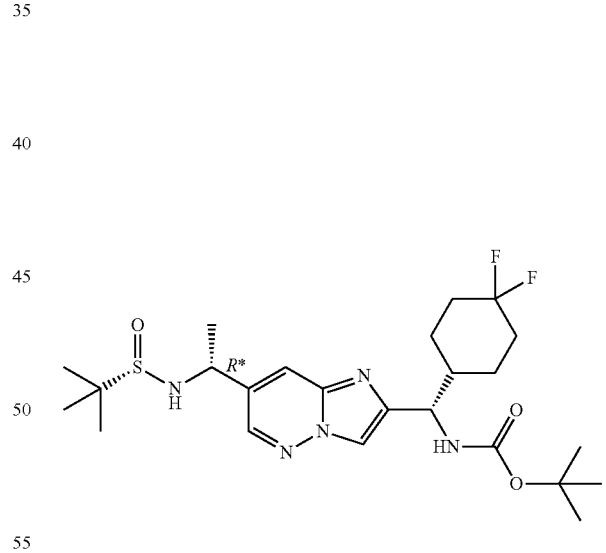

The title compound was prepared as described for the synthesis of Intermediate 48, using methylmagnesium bromide in place of cyclopropylmagnesium bromide and is the first-eluting isomer.

Intermediate 505

Tert-Butyl ((S)-(7-((S*)-1-(((S)-tert-butylsulfinyl)amino)ethyl)imidazo[1,2-b]pyridazin-2-yl)(4,4-difluorocyclohexyl)methyl)carbamate

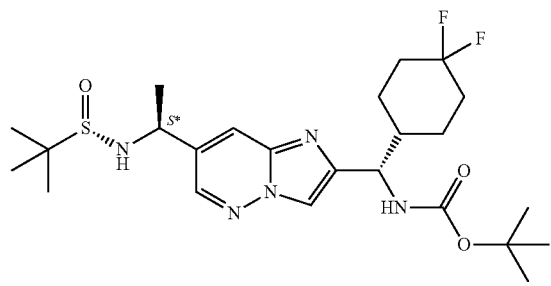 [SMILES: C[C@H](N[S@@](=O)C(C)(C)C)c1cnn2cc([C@@H](NC(=O)OC(C)(C)C)C3CCC(F)(F)CC3)nc2c1]

The title compound was prepared as described for the synthesis of Intermediate 48, using methylmagnesium bromide in place of cyclopropylmagnesium bromide and is the second-eluting isomer.

Intermediate 506

Tert-Butyl ((S)-(7-((R*)-1-amino-2-methylpropyl)imidazo[1,2-b]pyridazin-2-yl)(4,4-difluorocyclohexyl)methyl)carbamate

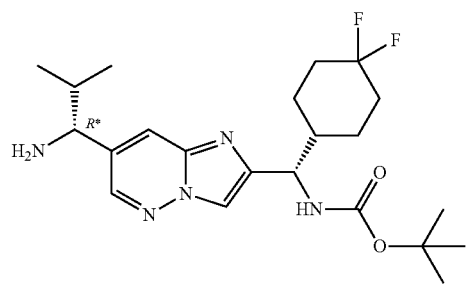 [SMILES: CC(C)[C@@H](N)c1cnn2cc([C@@H](NC(=O)OC(C)(C)C)C3CCC(F)(F)CC3)nc2c1]

The title compound was prepared as described for the synthesis of Intermediate 49 using tert-butyl ((S)-(7-((R*)-1-(((S)-tert-butylsulfinyl)amino)-2-methylpropyl)imidazo[1,2-b]pyridazin-2-yl)(4,4-difluorocyclohexyl)methyl)carbamate (Intermediate 502) in place of tert-butyl ((S)-(7-((R)—(((S)-tert-butylsulfinyl)amino)(cyclopropyl)methyl)imidazo[1,2-b]pyridazin-2-yl)(4,4-difluorocyclohexyl)methyl)carbamate to afford the title compound as an off-white foam.

Intermediate 507

Tert-Butyl ((S)-(7-((S*)-1-amino-2-methylpropyl)imidazo[1,2-b]pyridazin-2-yl)(4,4-difluorocyclohexyl)methyl)carbamate

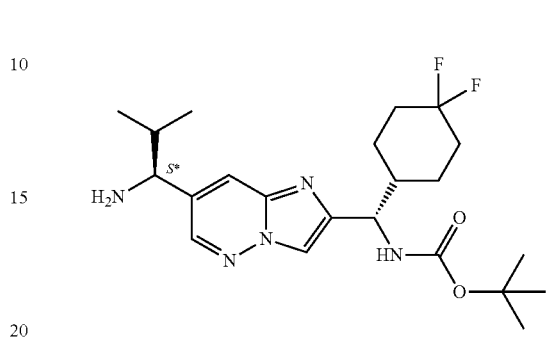

The title compound was prepared as described for the synthesis of Intermediate 49 using tert-butyl ((S)-(7-((S*)-1-(((S)-tert-butylsulfinyl)amino)-2-methylpropyl)imidazo[1,2-b]pyridazin-2-yl)(4,4-difluorocyclohexyl)methyl)carbamate (Intermediate 503) in place of tert-butyl ((S)-(7-((R)—(((S)-tert-butylsulfinyl)amino)(cyclopropyl)methyl)imidazo[1,2-b]pyridazin-2-yl)(4,4-difluorocyclohexyl)methyl)carbamate to afford the title compound as an off-white foam.

Intermediate 508

Tert-Butyl ((S)-(7-((R*)-1-aminoethyl)imidazo[1,2-b]pyridazin-2-yl)(4,4-difluorocyclohexyl)methyl)carbamate

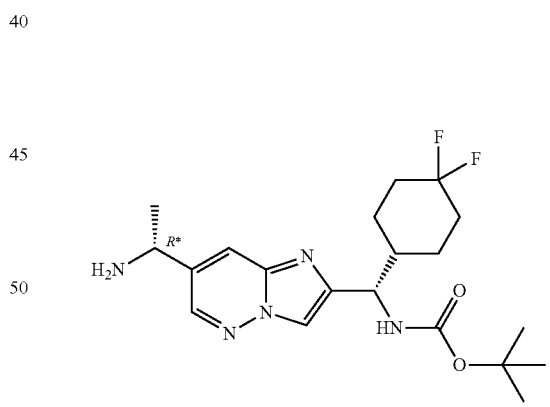

The title compound was prepared as described for the synthesis of Intermediate 49 using tert-butyl ((S)-(7-((R*)-1-(((S)-tert-butylsulfinyl)amino)ethyl)imidazo[1,2-b]pyridazin-2-yl)(4,4-difluorocyclohexyl)methyl)carbamate (Intermediate 504) in place of tert-butyl ((S)-(7-((R)—(((S)-tert-butylsulfinyl)amino)(cyclopropyl)methyl)imidazo[1,2-b]pyridazin-2-yl)(4,4-difluorocyclohexyl)methyl)carbamate to afford the title compound as an off-white foam.

Intermediate 509

Tert-Butyl ((S)-(7-((S*)-1-aminoethyl)imidazo[1,2-b]pyridazin-2-yl)(4,4-difluorocyclohexyl)methyl)carbamate

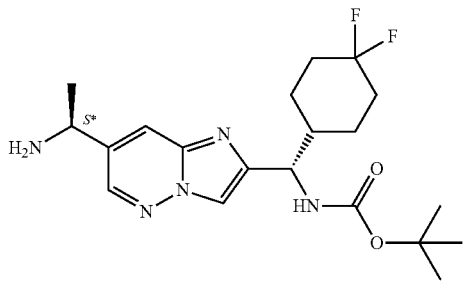 [SMILES: C[C@H](N)c1cnn2cc([C@@H](NC(=O)OC(C)(C)C)C3CCC(F)(F)CC3)nc2c1]

The title compound was prepared as described for the synthesis of Intermediate 49 using tert-butyl ((S)-(7-((S*)-1-(((S)-tert-butylsulfinyl)amino)ethyl)imidazo[1,2-b]pyridazin-2-yl)(4,4-difluorocyclohexyl)methyl)carbamate (Intermediate 505) in place of tert-butyl ((S)-(7-((R)—((S)-tert-butylsulfinyl)amino)(cyclopropyl)methyl)imidazo[1,2-b]pyridazin-2-yl)(4,4-difluorocyclohexyl)methyl)carbamate to afford the title compound as an off-white foam.

Intermediate 510

Tert-Butyl ((S)-(4,4-difluorocyclohexyl)(7-((R*)-2-methyl-1-(4,4,4-trifluorobutanamido)propyl)imidazo[1,2-b]pyridazin-2-yl)methyl)carbamate

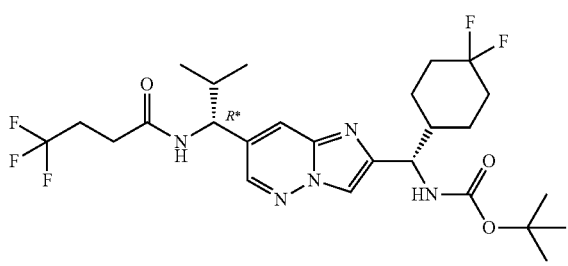 [SMILES: CC(C)[C@@H](NC(=O)CCC(F)(F)F)c1cnn2cc([C@@H](NC(=O)OC(C)(C)C)C3CCC(F)(F)CC3)nc2c1]

The title compound was prepared as described for the synthesis of Intermediate 50 using tert-butyl ((S)-(7-((R*)-1-amino-2-methylpropyl)imidazo[1,2-b]pyridazin-2-yl)(4,4-difluorocyclohexyl)methyl)carbamate (Intermediate 506) in place of tert-butyl ((S)-(7-((R)-amino(cyclopropyl)methyl)imidazo[1,2-b]pyridazin-2-yl)(4,4-difluorocyclohexyl)methyl) carbamate to afford the title compound as an off-white foam.

Intermediate 511

Tert-Butyl ((S)-(4,4-difluorocyclohexyl)(7-((S*)-2-methyl-1-(4,4,4-trifluorobutanamido)propyl)imidazo[1,2-b]pyridazin-2-yl)methyl)carbamate

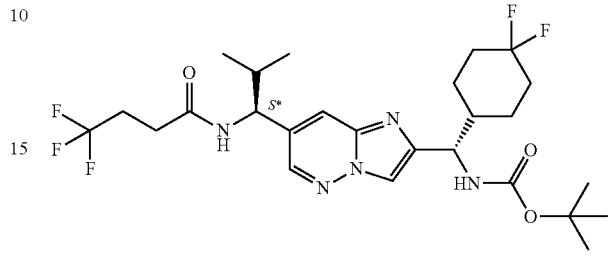

The title compound was prepared as described for the synthesis of Intermediate 50 using tert-butyl ((S)-(7-((S*)-1-amino-2-methylpropyl)imidazo[1,2-b]pyridazin-2-yl)(4,4-difluorocyclohexyl)methyl)carbamate (Intermediate 507) in place of tert-butyl ((S)-(7-((R)-amino(cyclopropyl)methyl)imidazo[1,2-b]pyridazin-2-yl)(4,4-difluorocyclohexyl)methyl) carbamate to afford the title compound as an off-white foam.

Intermediate 512

Tert-Butyl ((S)-(7-((S*)-1-(2-(3,3-difluorocyclobutyl)acetamido)-2-methylpropyl)imidazo[1,2-b]pyridazin-2-yl)(4,4-difluorocyclohexyl)methyl)carbamate

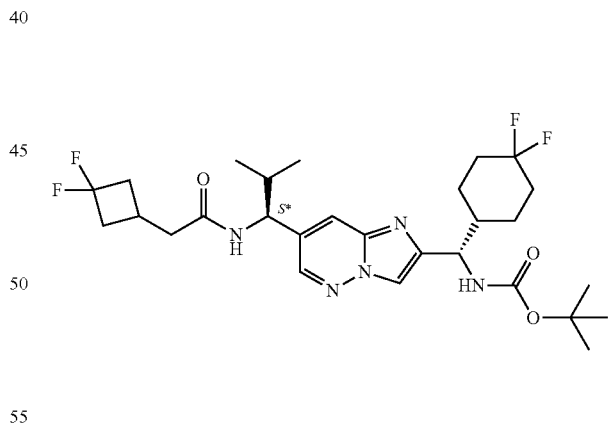

The title compound was prepared as described for the synthesis of Intermediate 50 using tert-butyl ((S)-(7-((S*)-1-amino-2-methylpropyl)imidazo[1,2-b]pyridazin-2-yl)(4,4-difluorocyclohexyl)methyl)carbamate (Intermediate 507) in place of tert-butyl ((S)-(7-((R)-amino(cyclopropyl)methyl)imidazo[1,2-b]pyridazin-2-yl)(4,4-difluorocyclohexyl)methyl) carbamate and 2-(3,3-difluorocyclobutyl)acetic acid in place of 4,4,4-trifluorobutanoic acid to afford the title compound as an off-white foam.

Intermediate 513

Tert-Butyl ((S)-(4,4-difluorocyclohexyl)(7-((R*)-1-(4,4-trifluorobutanamido)ethyl)imidazo[1,2-b]pyridazin-2-yl)methyl)carbamate

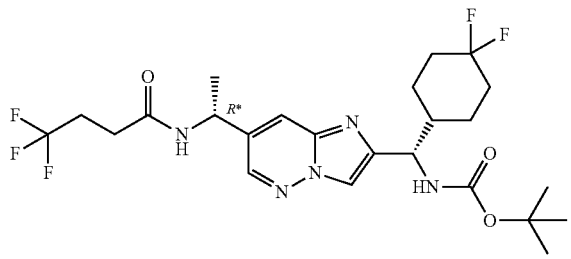 [SMILES: C[C@@H](NC(=O)CCC(F)(F)F)c1cnn2cc([C@@H](NC(=O)OC(C)(C)C)C3CCC(F)(F)CC3)nc2c1]

The title compound was prepared as described for the synthesis of Intermediate 50 using tert-butyl ((S)-(7-((R*)-1-aminoethyl)imidazo[1,2-b]pyridazin-2-yl)(4,4-difluorocyclohexyl)methyl)carbamate (Intermediate 508) in place of tert-butyl ((S)-(7-((R)-amino(cyclopropyl)methyl)imidazo[1,2-b]pyridazin-2-yl)(4,4-difluorocyclohexyl)methyl) carbamate to afford the title compound as an off-white foam.

Intermediate 514

Tert-Butyl ((S)-(4,4-difluorocyclohexyl)(7-((S*)-1-(4,4-trifluorobutanamido)ethyl)imidazo[1,2-b]pyridazin-2-yl)methyl)carbamate

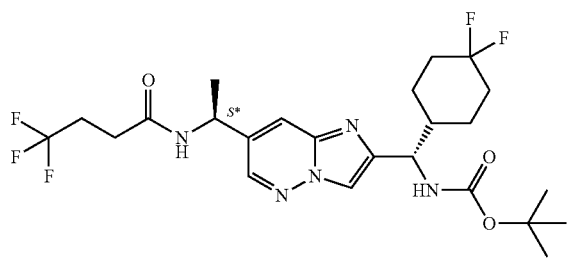 [SMILES: C[C@H](NC(=O)CCC(F)(F)F)c1cnn2cc([C@@H](NC(=O)OC(C)(C)C)C3CCC(F)(F)CC3)nc2c1]

The title compound was prepared as described for the synthesis of Intermediate 50 using tert-butyl ((S)-(7-((S*)-1-aminoethyl)imidazo[1,2-b]pyridazin-2-yl)(4,4-difluorocyclohexyl)methyl)carbamate (Intermediate 509) in place of tert-butyl ((S)-(7-((R)-amino(cyclopropyl)methyl)imidazo[1,2-b]pyridazin-2-yl)(4,4-difluorocyclohexyl)methyl) carbamate to afford the title compound as an off-white foam.

Intermediate 515

N—((R*)-1-(2-((S)-Amino(4,4-difluorocyclohexyl)methyl)imidazo[1,2-b]pyridazin-7-yl)-2-methylpropyl)-4,4,4-trifluorobutanamide

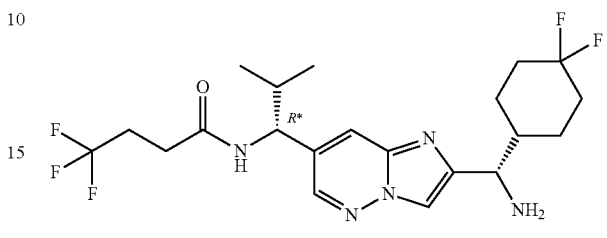

The title compound was prepared as described for the synthesis of Intermediate 51 using tert-butyl ((S)-(4,4-difluorocyclohexyl)(7-((R*)-2-methyl-1-(4,4,4-trifluorobutanamido)propyl)imidazo[1,2-b]pyridazin-2-yl)methyl)carbamate (Intermediate 510) in place of tert-butyl ((S)-(7-((R)-cyclopropyl(4,4,4-trifluorobutanamido)methyl)imidazo[1,2-b]pyridazin-2-yl)(4,4-difluorocyclohexyl)methyl) carbamate to afford the title compound as an off-white foam.

Intermediate 516

N—((S*)-1-(2-((S)-Amino(4,4-difluorocyclohexyl)methyl)imidazo[1,2-b]pyridazin-7-yl)-2-methylpropyl)-4,4,4-trifluorobutanamide

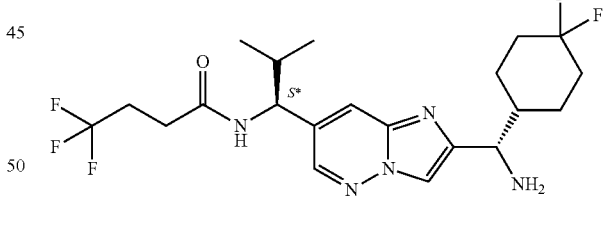

The title compound was prepared as described for the synthesis of Intermediate 51 using tert-butyl ((S)-(4,4-difluorocyclohexyl)(7-((S*)-2-methyl-1-(4,4,4-trifluorobutanamido)propyl)imidazo[1,2-b]pyridazin-2-yl)methyl)carbamate (Intermediate 511) in place of tert-butyl ((S)-(7-((R)-cyclopropyl(4,4,4-trifluorobutanamido)methyl)imidazo[1,2-b]pyridazin-2-yl)(4,4-difluorocyclohexyl)methyl) carbamate to afford the title compound as an off-white foam.

Intermediate 517

N—((S*)-1-(2-((S)-Amino(4,4-difluorocyclohexyl)methyl)imidazo[1,2-b]pyridazin-7-yl)-2-methylpropyl)-2-(3,3-difluorocyclobutyl)acetamide

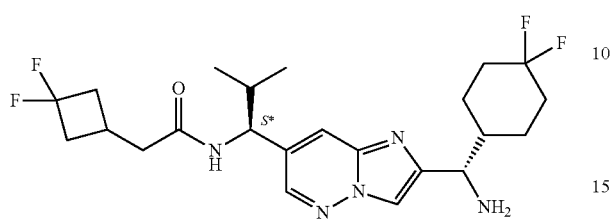

The title compound was prepared as described for the synthesis of Intermediate 51 using tert-butyl ((S)-(7-((S*)-1-(2-(3,3-difluorocyclobutyl)acetamido)-2-methylpropyl)imidazo[1,2-b]pyridazin-2-yl)(4,4-difluorocyclohexyl)methyl)carbamate (Intermediate 512) in place of tert-butyl ((S)-(7-((R)-cyclopropyl(4,4,4-trifluorobutanamido)methyl)imidazo[1,2-b]pyridazin-2-yl)(4,4-difluorocyclohexyl)methyl)carbamate to afford the title compound as an off-white foam.

Intermediate 518

4-(((S)-(4,4-Difluorocyclohexyl)(7-((S*)-2-methyl-1-(4,4,4-trifluorobutanamido)propyl)imidazo[1,2-b]pyridazin-2-yl)methyl)carbamoyl)-3-isopropyl-1,2,5-oxadiazole 2-oxide

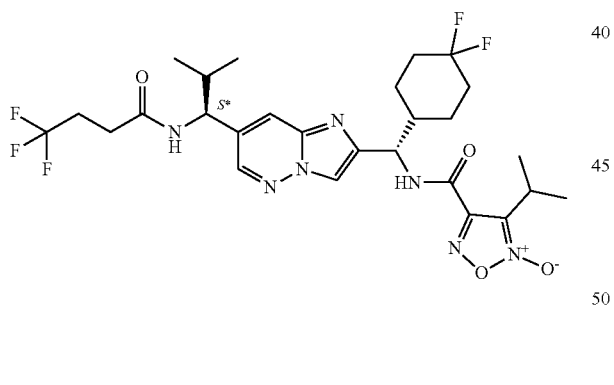

A vial was charged with a stir bar, 4-carboxy-3-isopropyl-1,2,5-oxadiazole 2-oxide (65.6 mg, 0.381 mmol, Intermediate 319), HATU (147 mg, 0.381 mmol) and DMF (1.5 mL). The solution was stirred for 5 min then N—((S*)-1-(2-((S)-amino(4,4-difluorocyclohexyl)methyl)imidazo[1,2-b]pyridazin-7-yl)-2-methylpropyl)-4,4,4-trifluorobutanamide (135.0 mg, 0.293 mmol, Intermediate 516) and Hunig's base (0.100 mL, 0.586 mmol) were added and the reaction was stirred for a further 30 min. The reaction was poured over water and diluted with ethyl acetate. The layers were separated the aqueous phase was further extracted with ethyl acetate (2×5 mL). The combined organic extracts were washed with 10% aqueous LiCl, then brine, dried over anhydrous MgSO₄, filtered, and concentrated to dryness to afford the title compound as an orange oil.

Intermediate 519

N—((R*)-1-(2-((S)-Amino(4,4-difluorocyclohexyl)methyl)imidazo[1,2-b]pyridazin-7-yl)ethyl)-4,4,4-trifluorobutanamide

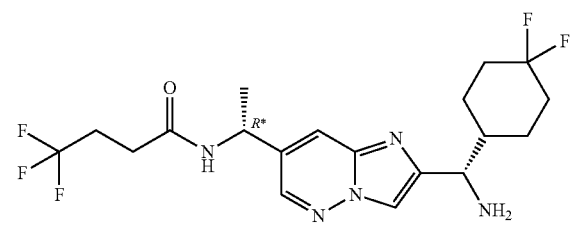 [SMILES: C[C@@H](NC(=O)CCC(F)(F)F)c1cnn2cc([C@@H](N)C3CCC(F)(F)CC3)nc2c1]

The title compound was prepared as described for the synthesis of Intermediate 51 using tert-butyl ((S)-(4,4-difluorocyclohexyl)(7-((R*)-1-(4,4,4-trifluorobutanamido)ethyl)imidazo[1,2-b]pyridazin-2-yl)methyl)carbamate (Intermediate 513) in place of tert-butyl ((S)-(7-((R)-cyclopropyl(4,4,4-trifluorobutanamido)methyl)imidazo[1,2-b]pyridazin-2-yl)(4,4-difluorocyclohexyl)methyl)carbamate to afford the title compound as an off-white foam.

Intermediate 520

N—((S*)-1-(2-((S)-Amino(4,4-difluorocyclohexyl)methyl)imidazo[1,2-b]pyridazin-7-yl)ethyl)-4,4,4-trifluorobutanamide

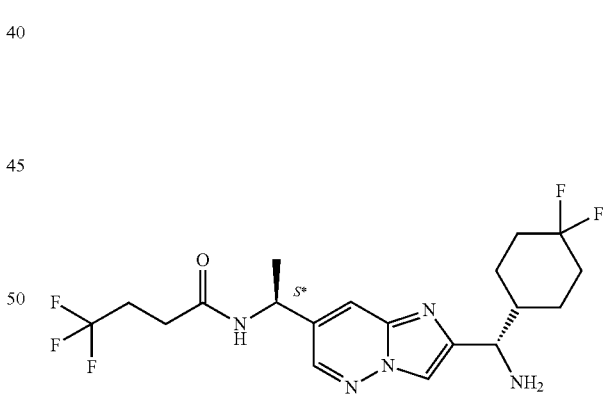

The title compound was prepared as described for the synthesis of Intermediate 51 using tert-butyl ((S)-(4,4-difluorocyclohexyl)(7-((S*)-1-(4,4,4-trifluorobutanamido)ethyl)imidazo[1,2-b]pyridazin-2-yl)methyl)carbamate (Intermediate 514) in place of tert-butyl ((S)-(7-((R)-cyclopropyl(4,4,4-trifluorobutanamido)methyl)imidazo[1,2-b]pyridazin-2-yl)(4,4-difluorocyclohexyl)methyl)carbamate to afford the title compound as an off-white foam.

Intermediate 521

Tert-Butyl ((1S)-(7-(1-(((S)-tert-butylsulfinyl)amino)-2,2-difluoroethyl)imidazo[1,2-b]pyridazin-2-yl)(4,4-difluorocyclohexyl)methyl)carbamate

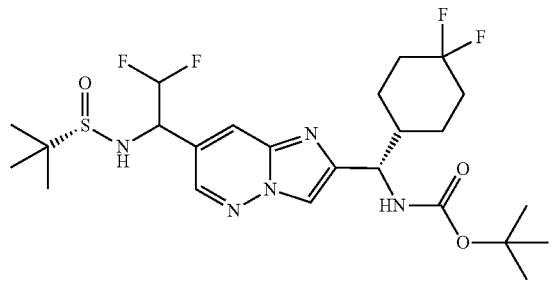 [SMILES: CC(C)(C)OC(=O)N[C@H](c1cn2ncc(C(N[S@@](=O)C(C)(C)C)C(F)F)cc2n1)C1CCC(F)(F)CC1]

A solution of tert-butyl ((S)-(7-(((((S)-tert-butylsulfinyl)imino)methyl)imidazo[1,2-b]pyridazin-2-yl)(4,4-difluorocyclohexyl)methyl)carbamate (5.00 g, 10.0 mmol, Intermediate 47) in THF (112 mL) was cooled to −78° C. Potassium tert-butoxide (3.34 g, 29.7 mmol) and (difluoromethyl)trimethylsilane (3.98 mL, 29.1 mmol) were then sequentially added to the reaction mixture and allowed to slowly warm to 0° C. over time. After 1 h, the contents were transferred to a separatory funnel and the organic layer was washed with water twice. The organic layer was then dried over anhydrous MgSO$_4$, filtered, and concentrated to afford a golden-yellow foam. This residue was purified by silica gel chromatography (30-70% acetone/hexanes) to afford the title compound as a yellow foam.

Intermediate 522

Tert-Butyl ((1S)-(7-(1-amino-2,2-difluoroethyl)imidazo[1,2-b]pyridazin-2-yl)(4,4-difluorocyclohexyl)methyl)carbamate

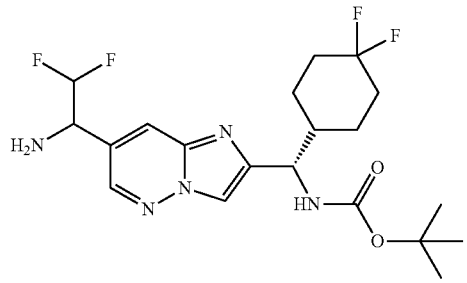 [SMILES: CC(C)(C)OC(=O)N[C@H](c1cn2ncc(C(N)C(F)F)cc2n1)C1CCC(F)(F)CC1]

The title compound was prepared as described for the synthesis of Intermediate 49 using tert-butyl ((1S)-(7-(1-(((S)-tert-butylsulfinyl)amino)-2,2-difluoroethyl)imidazo[1,2-b]pyridazin-2-yl)(4,4-difluorocyclohexyl)methyl)carbamate (Intermediate 521) in place of tert-butyl ((S)-(7-((R)—(((S)-tert-butylsulfinyl)amino)(cyclopropyl)methyl)imidazo[1,2-b]pyridazin-2-yl)(4,4-difluorocyclohexyl)methyl)carbamate to afford the title compound as an off-white foam.

Intermediate 523

Tert-Butyl ((1S)-(7-(2,2-difluoro-1-(4,4,4-trifluorobutanamido)ethyl)imidazo[1,2-b]pyridazin-2-yl)(4,4-difluorocyclohexyl)methyl)carbamate

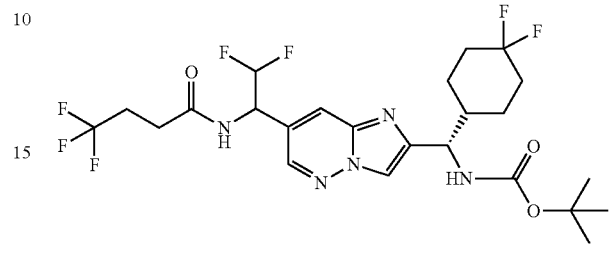

The title compound was prepared as described for the synthesis of Intermediate 50 using tert-butyl ((1S)-(7-(1-amino-2,2-difluoroethyl)imidazo[1,2-b]pyridazin-2-yl)(4,4-difluorocyclohexyl)methyl)carbamate (Intermediate 522) in place of tert-butyl ((S)-(7-((R)-amino(cyclopropyl)methyl)imidazo[1,2-b]pyridazin-2-yl)(4,4-difluorocyclohexyl)methyl)carbamate to afford the title compound as a white foam.

Intermediate 524

Tert-Butyl ((1S)-(7-(1-(2-(3,3-difluorocyclobutyl)acetamido)-2,2-difluoroethyl)imidazo[1,2-b]pyridazin-2-yl)(4,4-difluorocyclohexyl)methyl)carbamate

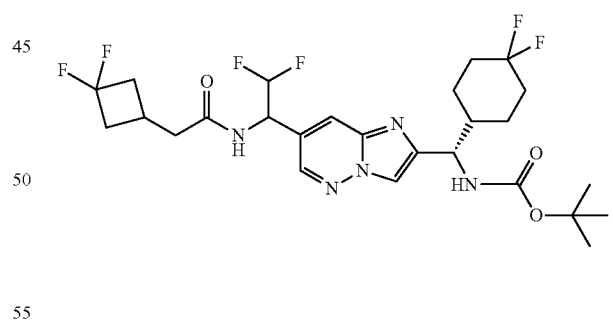

The title compound was prepared as described for the synthesis of Intermediate 50 using tert-butyl ((1S)-(7-(1-amino-2,2-difluoroethyl)imidazo[1,2-b]pyridazin-2-yl)(4,4-difluorocyclohexyl)methyl)carbamate (Intermediate 522) in place of tert-butyl ((S)-(7-((R)-amino(cyclopropyl)methyl)imidazo[1,2-b]pyridazin-2-yl)(4,4-difluorocyclohexyl)methyl)carbamate and 2-(3,3-difluorocyclobutyl)acetic acid in place of 4,4,4-trifluorobutanoic acid to afford the title compound as an off-white foam.

Intermediate 525

N-(1-(2-((S)-Amino(4,4-difluorocyclohexyl)methyl)imidazo[1,2-b]pyridazin-7-yl)-2,2-difluoroethyl)-4,4,4-trifluorobutanamide

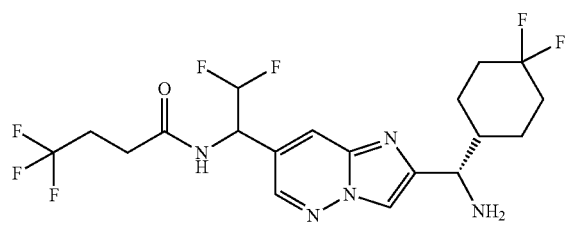 [SMILES: N[C@H](c1cn2ncc(C(NC(=O)CCC(F)(F)F)C(F)F)cc2n1)C1CCC(F)(F)CC1]

The title compound was prepared as described for the synthesis of Intermediate 51 using tert-butyl ((1S)-(7-(2,2-difluoro-1-(4,4,4-trifluorobutanamido)ethyl)imidazo[1,2-b]pyridazin-2-yl)(4,4-difluorocyclohexyl)methyl)carbamate (Intermediate 523) in place of tert-butyl ((S)-(7-((R)-cyclopropyl(4,4,4-trifluorobutanamido)methyl)imidazo[1,2-b]pyridazin-2-yl)(4,4-difluorocyclohexyl)methyl)carbamate to afford the title compound as an off-white foam.

Intermediate 526

N-(1-(2-((S)-Amino(4,4-difluorocyclohexyl)methyl)imidazo[1,2-b]pyridazin-7-yl)-2,2-difluoroethyl)-2-(3,3-difluorocyclobutyl)acetamide

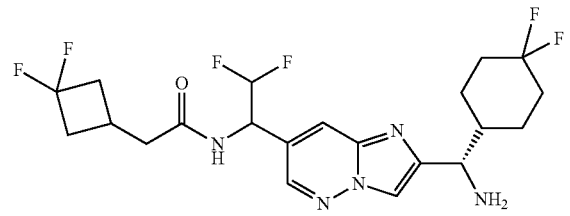 [SMILES: N[C@H](c1cn2ncc(C(NC(=O)CC3CC(F)(F)C3)C(F)F)cc2n1)C1CCC(F)(F)CC1]

The title compound was prepared as described for the synthesis of Intermediate 51 using tert-butyl ((1S)-(7-(1-(2-(3,3-difluorocyclobutyl)acetamido)-2,2-difluoroethyl)imidazo[1,2-b]pyridazin-2-yl)(4,4-difluorocyclohexyl)methyl)carbamate (Intermediate 524) in place of tert-butyl ((S)-(7-((R)-cyclopropyl(4,4,4-trifluorobutanamido)methyl)imidazo[1,2-b]pyridazin-2-yl)(4,4-difluorocyclohexyl)methyl)carbamate to afford the title compound as an off-white foam.

Intermediate 527

Tert-Butyl ((S)-(7-((S*)-1-(((R)-tert-butylsulfinyl)amino)-2,2,2-trifluoroethyl)imidazo[1,2-b]pyridazin-2-yl)(4,4-difluorocyclohexyl)methyl)carbamate

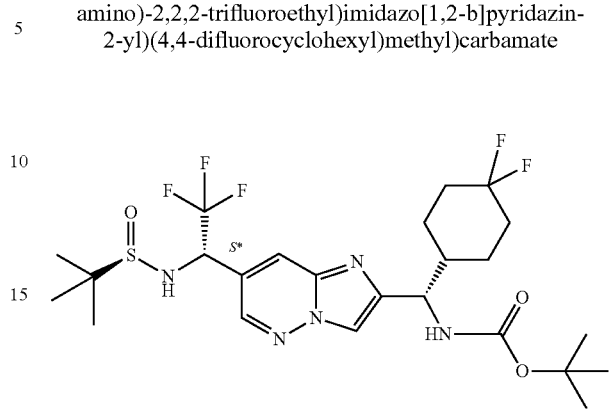

A flask was charged with a stir bar, tert-butyl ((S)-(7-((E)-(((R)-tert-butylsulfinyl)imino)methyl)imidazo[1,2-b]pyridazin-2-yl)(4,4-difluorocyclohexyl)methyl)carbamate (600 mg, 1.21 mmol, Intermediate 429), THF (24 mL), and TBAT (716 mg, 1.33 mmol) and the solution was cooled to −55° C. Trimethyl(trifluoromethyl)silane (214 μL, 1.45 mmol) was then added to the reaction mixture and the reaction was stirred for 4 h. The reaction was quenched by the addition of saturated aqueous NH$_4$Cl (10 mL) at −55° C. and the reaction mixture was allowed to warm to rt. The reaction mixture was poured into a separatory funnel and extracted with EtOAc (3×20 mL). The combined organic layers were washed with brine, dried over anhydrous MgSO$_4$, filtered, and concentrated to a yellow residue. This residue was purified by preparative acidic HPLC (Waters XSelect CSH C18, 5 μm, 19×100 mm, 35-55% MeCN/H$_2$O (with 0.16% TFA)). The product containing fractions were combined to afford the title compound as a white powder.

Intermediate 528

Tert-Butyl ((S)-(7-((S*)-1-amino-2,2,2-trifluoroethyl)imidazo[1,2-b]pyridazin-2-yl)(4,4-difluorocyclohexyl)methyl)carbamate

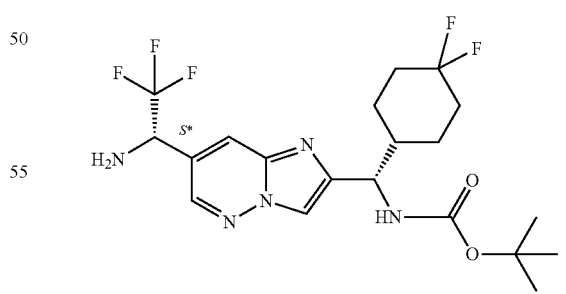

The title compound was prepared as described for the synthesis of Intermediate 49 using tert-butyl ((S)-(7-((S*)-1-(((R)-tert-butylsulfinyl)amino)-2,2,2-trifluoroethyl)imidazo[1,2-b]pyridazin-2-yl)(4,4-difluorocyclohexyl)methyl)carbamate (Intermediate 527) in place of tert-butyl ((S)-(7-((R)—(((S)-tert-butylsulfinyl)amino)(cyclopropyl)methyl)

imidazo[1,2-b]pyridazin-2-yl)(4,4-difluorocyclohexyl)methyl)carbamate to afford the title compound as an off-white foam.

Intermediate 529

Tert-Butyl ((S)-(7-((S*)-1-(2-(3,3-difluorocyclobutyl)acetamido)-2,2,2-trifluoroethyl)imidazo[1,2-b]pyridazin-2-yl)(4,4-difluorocyclohexyl)methyl)carbamate

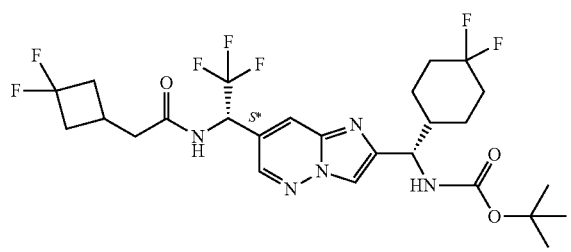 [SMILES: CC(C)(C)OC(=O)N[C@H](c1cn2ncc([C@H](NC(=O)CC3CC(F)(F)C3)C(F)(F)F)cc2n1)C1CCC(F)(F)CC1]

The title compound was prepared as described for the synthesis of Intermediate 50 using tert-butyl ((S)-(7-((S*)-1-amino-2,2,2-trifluoroethyl)imidazo[1,2-b]pyridazin-2-yl)(4,4-difluorocyclohexyl)methyl)carbamate (Intermediate 528) in place of tert-butyl ((S)-(7-((R)-amino(cyclopropyl)methyl)imidazo[1,2-b]pyridazin-2-yl)(4,4-difluorocyclohexyl)methyl) carbamate and 2-(3,3-difluorocyclobutyl)acetic acid in place of 4,4,4-trifluorobutanoic acid to afford the title compound as an off-white foam.

Intermediate 530

N—((S*)-1-(2-((S)-Amino(4,4-difluorocyclohexyl)methyl)imidazo[1,2-b]pyridazin-7-yl)-2,2,2-trifluoroethyl)-2-(3,3-difluorocyclobutyl)acetamide

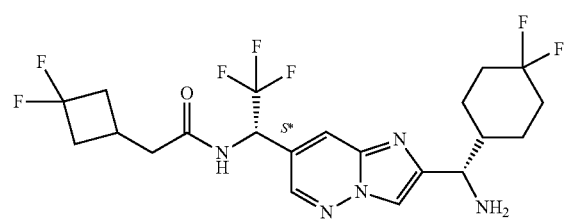 [SMILES: N[C@H](c1cn2ncc([C@H](NC(=O)CC3CC(F)(F)C3)C(F)(F)F)cc2n1)C1CCC(F)(F)CC1]

The title compound was prepared as described for the synthesis of Intermediate 51 using tert-butyl ((S)-(7-((S*)-1-(2-(3,3-difluorocyclobutyl)acetamido)-2,2,2-trifluoroethyl)imidazo[1,2-b]pyridazin-2-yl)(4,4-difluorocyclohexyl)methyl)carbamate (Intermediate 529) in place of tert-butyl ((S)-(7-((R)—(((S)-tert-butylsulfinyl)amino)(cyclopropyl)methyl)imidazo[1,2-b]pyridazin-2-yl)(4,4-difluorocyclohexyl)methyl)carbamate to afford the title compound as an off-white foam.

Intermediate 531

Tert-Butyl ((S)-(7-((S*)—(((S)-tert-butylsulfinyl)amino)(1-cyanocyclopropyl)methyl)imidazo[1,2-b]pyridazin-2-yl)(4,4-difluorocyclohexyl)methyl)carbamate

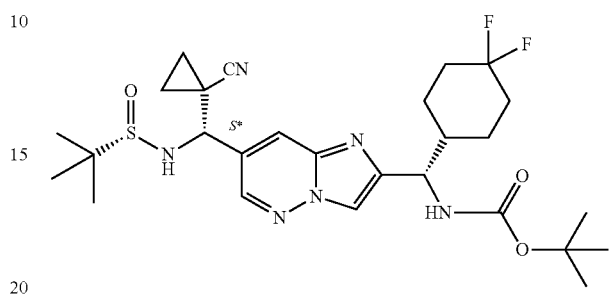

Intermediate 532

Tert-Butyl ((S)-(7-((R*)—(((S)-tert-butylsulfinyl)amino)(1-cyanocyclopropyl)methyl)imidazo[1,2-b]pyridazin-2-yl)(4,4-difluorocyclohexyl)methyl)carbamate

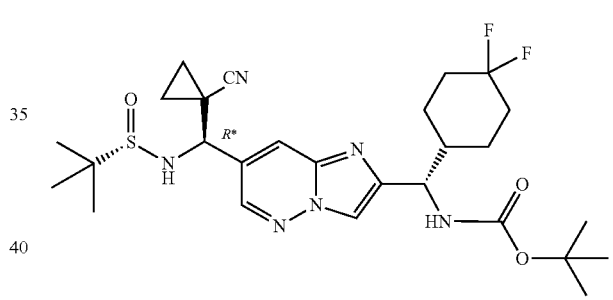

An oven-dried flask was charged a stir bar, cyclopropanecarbonitrile (1.78 mL, 24.1 mmol), and THF (60 mL) and the solution was cooled to 0° C. After 5 minutes at 0° C., LHMIDS (1.5 M solution in THF, 18.8 mL, 28.1 mmol) was added dropwise and the reaction allowed to stir for 1 h at 0° C. After 1 h, a solution of ((S)-(7-((((S)-tert-butylsulfinyl)imino)methyl)imidazo[1,2-b]pyridazin-2-yl)(4,4-difluorocyclohexyl)methyl)carbamate (4.00 g, 8.04 mmol, Intermediate 47) in THE (15 mL) was added dropwise to the reaction. The reaction was stirred for 2 h at 0° C. at which point it was quenched by addition of saturated aqueous NH$_4$Cl, and then diluted with water and EtOAc and allowed to stir for 5 min. The biphasic mixture was allowed to settle, and the layers were separated. The aqueous layer was washed with EtOAc (2×30 mL) and the combined organic layers were then washed with brine, dried with anhydrous MgSO$_4$, filtered and concentrated to dryness to give a yellow residue. The residue was purified by preparative basic HPLC (Waters XBridge BEH C18, 5 µm, 19×100 mm, (20-75% MeCN/H$_2$O (with 0.16% NH$_4$OH))). The product containing fractions were concentrated to a yellow residue that was subjected to a second round of purification by chiral SFC (Whelk O1 5 µm, 250×25 mm, Mobile phase: 20:80 MeOH/CO$_2$). The product containing fractions were concentrated to afford Intermediate 531 as the first-eluting isomer and Intermediate 532 as the second eluting isomer.

Intermediate 533

Tert-Butyl ((S)-(7-((S*)-amino(1-cyanocyclopropyl)methyl)imidazo[1,2-b]pyridazin-2-yl)(4,4-difluorocyclohexyl)methyl)carbamate

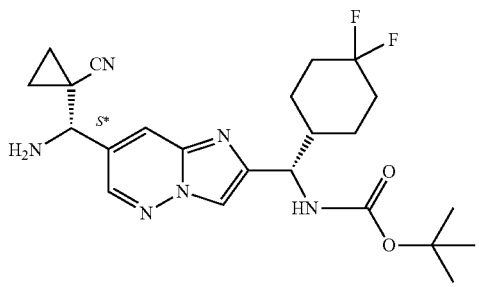

The title compound was prepared as described for the synthesis of Intermediate 49 using tert-butyl ((S)-(7-((S*)—(((S)-tert-butylsulfinyl)amino)(1-cyanocyclopropyl)methyl)imidazo[1,2-b]pyridazin-2-yl)(4,4-difluorocyclohexyl)methyl)carbamate (Intermediate 531) in place of tert-butyl ((S)-(7-((R)—(((S)-tert-butylsulfinyl)amino)(cyclopropyl)methyl)imidazo[1,2-b]pyridazin-2-yl)(4,4-difluorocyclohexyl)methyl)carbamate to afford the title compound as an off-white foam.

Intermediate 534

Tert-Butyl ((S)-(7-((R*)-amino(1-cyanocyclopropyl)methyl)imidazo[1,2-b]pyridazin-2-yl)(4,4-difluorocyclohexyl)methyl)carbamate

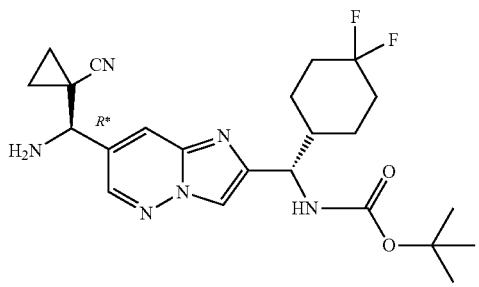

The title compound was prepared as described for the synthesis of Intermediate 49 using tert-butyl ((S)-(7-((R*)—(((S)-tert-butylsulfinyl)amino)(1-cyanocyclopropyl)methyl)imidazo[1,2-b]pyridazin-2-yl)(4,4-difluorocyclohexyl)methyl)carbamate (Intermediate 532) in place of tert-butyl ((S)-(7-((R)—(((S)-tert-butylsulfinyl)amino)(cyclopropyl)methyl)imidazo[1,2-b]pyridazin-2-yl)(4,4-difluorocyclohexyl)methyl)carbamate to afford the title compound as an off-white foam.

Intermediate 535

Tert-Butyl ((S)-(7-((S*)-(1-cyanocyclopropyl)(2-(3,3-difluorocyclobutyl)acetamido)methyl)imidazo[1,2-b]pyridazin-2-yl)(4,4-difluorocyclohexyl)methyl)carbamate

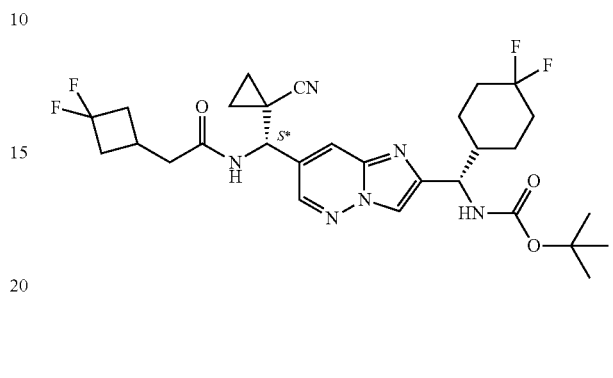

The title compound was prepared as described for the synthesis of Intermediate 50 using tert-butyl ((S)-(7-((S*)-amino(1-cyanocyclopropyl)methyl)imidazo[1,2-b]pyridazin-2-yl)(4,4-difluorocyclohexyl)methyl)carbamate (Intermediate 533) in place of tert-butyl ((S)-(7-((R)-amino(cyclopropyl)methyl)imidazo[1,2-b]pyridazin-2-yl)(4,4-difluorocyclohexyl)methyl) carbamate and 2-(3,3-difluorocyclobutyl)acetic acid in place of 4,4,4-trifluorobutanoic acid to afford the title compound as an off-white foam.

Intermediate 536

Tert-Butyl ((S)-(7-((S*)-(1-cyanocyclopropyl)(2-(1-(trifluoromethyl)cyclopropyl)acetamido)methyl)imidazo[1,2-b]pyridazin-2-yl)(4,4-difluorocyclohexyl)methyl)carbamate

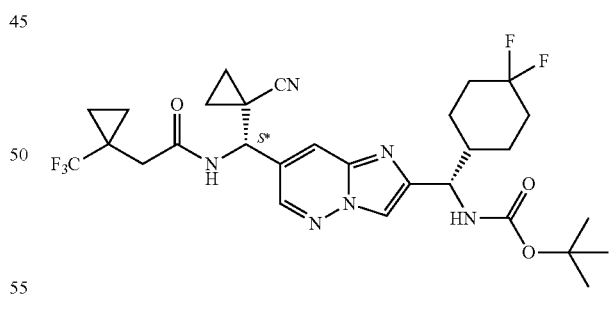

The title compound was prepared as described for the synthesis of Intermediate 50 using tert-butyl ((S)-(7-((S*)-amino(1-cyanocyclopropyl)methyl)imidazo[1,2-b]pyridazin-2-yl)(4,4-difluorocyclohexyl)methyl)carbamate (Intermediate 533) in place of tert-butyl ((S)-(7-((R)-amino(cyclopropyl)methyl)imidazo[1,2-b]pyridazin-2-yl)(4,4-difluorocyclohexyl)methyl) carbamate and 2-(1-(trifluoromethyl)cyclopropyl)acetic acid in place of 4,4,4-trifluorobutanoic acid to afford the title compound as an off-white foam.

Intermediate 537

Tert-Butyl ((S)-(7-((R*)-(1-cyanocyclopropyl)(2-(3,3-difluorocyclobutyl)acetamido)methyl)imidazo[1,2-b]pyridazin-2-yl)(4,4-difluorocyclohexyl)methyl)carbamate

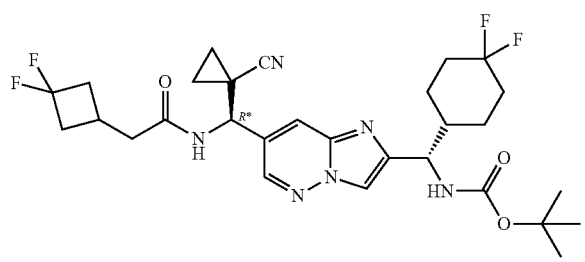 [SMILES: CC(C)(C)OC(=O)N[C@H](c1cn2ncc([C@@H](NC(=O)CC3CC(F)(F)C3)C3(C#N)CC3)cc2n1)C1CCC(F)(F)CC1]

The title compound was prepared as described for the synthesis of Intermediate 50 using tert-butyl ((S)-(7-((R*)-amino(1-cyanocyclopropyl)methyl)imidazo[1,2-b]pyridazin-2-yl)(4,4-difluorocyclohexyl)methyl)carbamate (Intermediate 534) in place of tert-butyl ((S)-(7-((R)-amino(cyclopropyl)methyl)imidazo[1,2-b]pyridazin-2-yl)(4,4-difluorocyclohexyl)methyl) carbamate and 2-(3,3-difluorocyclobutyl)acetic acid in place of 4,4,4-trifluorobutanoic acid to afford the title compound as an off-white foam.

Intermediate 538

Tert-Butyl ((S)-(7-((R*)-(1-cyanocyclopropyl)(2-(1-(trifluoromethyl)cyclopropyl)acetamido)methyl)imidazo[1,2-b]pyridazin-2-yl)(4,4-difluorocyclohexyl)methyl)carbamate

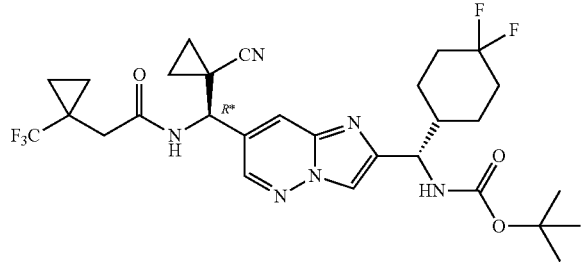 [SMILES: CC(C)(C)OC(=O)N[C@H](c1cn2ncc([C@@H](NC(=O)CC3(C(F)(F)F)CC3)C3(C#N)CC3)cc2n1)C1CCC(F)(F)CC1]

The title compound was prepared as described for the synthesis of Intermediate 50 using tert-butyl ((S)-(7-((R*)-amino(1-cyanocyclopropyl)methyl)imidazo[1,2-b]pyridazin-2-yl)(4,4-difluorocyclohexyl)methyl)carbamate (Intermediate 534) in place of tert-butyl ((S)-(7-((R)-amino(cyclopropyl)methyl)imidazo[1,2-b]pyridazin-2-yl)(4,4-difluorocyclohexyl)methyl) carbamate and 2-(1-(trifluoromethyl)cyclopropyl)acetic acid in place of 4,4,4-trifluorobutanoic acid to afford the title compound as an off-white foam.

Intermediate 539

Tert-Butyl ((S)-(7-((R*)-(1-cyanocyclopropyl)(3-cyclopropyl-2,2-difluoropropanamido)methyl)imidazo[1,2-b]pyridazin-2-yl)(4,4-difluorocyclohexyl)methyl)carbamate

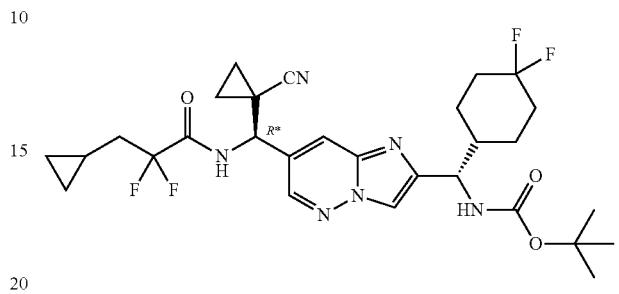

The title compound was prepared as described for the synthesis of Intermediate 50 using tert-butyl ((S)-(7-((R*)-amino(1-cyanocyclopropyl)methyl)imidazo[1,2-b]pyridazin-2-yl)(4,4-difluorocyclohexyl)methyl)carbamate (Intermediate 534) in place tert-butyl ((S)-(7-((R)-amino(cyclopropyl)methyl)imidazo[1,2-b]pyridazin-2-yl)(4,4-difluorocyclohexyl)methyl) carbamate and 3-cyclopropyl-2,2-difluoropropanoic acid in place of 4,4,4-trifluorobutanoic acid to afford the title compound as an off-white foam.

Intermediate 540

N—((S*)-(2-((S)-Amino(4,4-difluorocyclohexyl)methyl)imidazo[1,2-b]pyridazin-7-yl)(1-cyanocyclopropyl)methyl)-2-(3,3-difluorocyclobutyl)acetamide

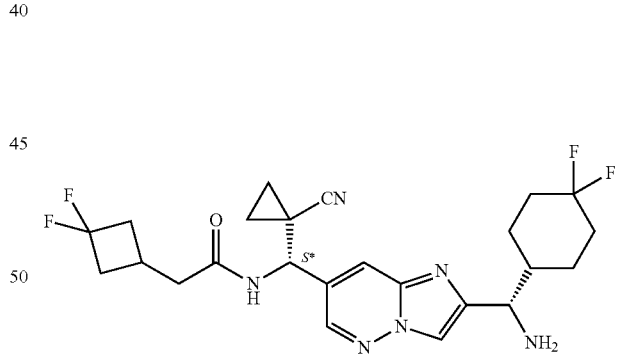

The title compound was prepared as described for the synthesis of Intermediate 51 using tert-butyl ((S)-(7-((S*)-(1-cyanocyclopropyl)(2-(3,3-difluorocyclobutyl)acetamido)methyl)imidazo[1,2-b]pyridazin-2-yl)(4,4-difluorocyclohexyl)methyl)carbamate (Intermediate 535) in place of tert-butyl ((S)-(7-((R)-cyclopropyl(4,4,4-trifluorobutanamido)methyl)imidazo[1,2-b]pyridazin-2-yl)(4,4-difluorocyclohexyl)methyl)carbamate to afford the title compound as a beige foam.

Intermediate 541

N—((S*)-(2-((S)-Amino(4,4-difluorocyclohexyl)methyl)imidazo[1,2-b]pyridazin-7-yl)(1-cyanocyclopropyl)methyl)-2-(1-(trifluoromethyl)cyclopropyl)acetamide

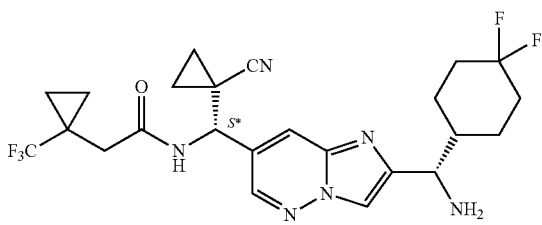 [SMILES: N#CC1([C@@H](NC(=O)CC2(C(F)(F)F)CC2)c2cnn3cc([C@@H](N)C4CCC(F)(F)CC4)nc3c2)CC1]

The title compound was prepared as described for the synthesis of Intermediate 51 using tert-butyl ((S)-(7-((S*)-(1-cyanocyclopropyl)(2-(1-(trifluoromethyl)cyclopropyl)acetamido)methyl)imidazo[1,2-b]pyridazin-2-yl)(4,4-difluorocyclohexyl)methyl)carbamate (Intermediate 536) in place of tert-butyl ((S)-(7-((R)-cyclopropyl(4,4,4-trifluorobutanamido)methyl)imidazo[1,2-b]pyridazin-2-yl)(4,4-difluorocyclohexyl)methyl)carbamate to afford the title compound as a beige foam.

Intermediate 542

N—((R*)-(2-((S)-Amino(4,4-difluorocyclohexyl)methyl)imidazo[1,2-b]pyridazin-7-yl)(1-cyanocyclopropyl)methyl)-2-(3,3-difluorocyclobutyl)acetamide

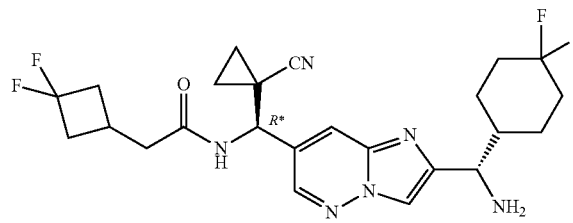

The title compound was prepared as described for the synthesis of Intermediate 51 using tert-butyl ((S)-(7-((R*)-(1-cyanocyclopropyl)(2-(3,3-difluorocyclobutyl)acetamido)methyl)imidazo[1,2-b]pyridazin-2-yl)(4,4-difluorocyclohexyl)methyl)carbamate (Intermediate 537) in place of tert-butyl ((S)-(7-((R)-cyclopropyl(4,4,4-trifluorobutanamido)methyl)imidazo[1,2-b]pyridazin-2-yl)(4,4-difluorocyclohexyl)methyl)carbamate to afford the title compound as a beige foam.

Intermediate 543

N—((R*)-(2-((S)-Amino(4,4-difluorocyclohexyl)methyl)imidazo[1,2-b]pyridazin-7-yl)(1-cyanocyclopropyl)methyl)-2-(1-(trifluoromethyl)cyclopropyl)acetamide

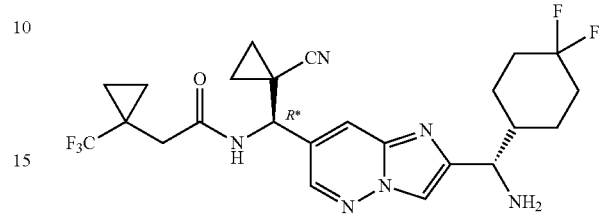

The title compound was prepared as described for the synthesis of Intermediate 51 using tert-butyl ((S)-(7-((R*)-(1-cyanocyclopropyl)(2-(1-(trifluoromethyl)cyclopropyl)acetamido)methyl)imidazo[1,2-b]pyridazin-2-yl)(4,4-difluorocyclohexyl)methyl)carbamate (Intermediate 538) in place of tert-butyl ((S)-(7-((R)-cyclopropyl(4,4,4-trifluorobutanamido)methyl)imidazo[1,2-b]pyridazin-2-yl)(4,4-difluorocyclohexyl)methyl)carbamate to afford the title compound as a beige foam.

Intermediate 544

N—((R*)-(2-((S)-Amino(4,4-difluorocyclohexyl)methyl)imidazo[1,2-b]pyridazin-7-yl)(1-cyanocyclopropyl)methyl)-3-cyclopropyl-2,2-difluoropropanamide

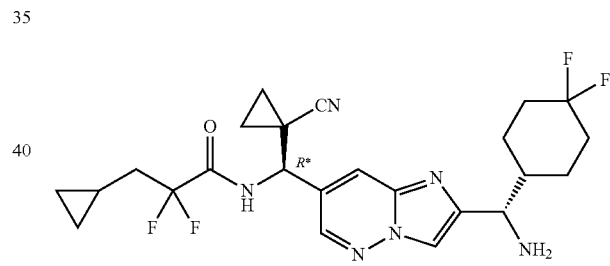

The title compound was prepared as described for the synthesis of Intermediate 51 using tert-butyl ((S)-(7-((R*)-(1-cyanocyclopropyl)(3-cyclopropyl-2,2-difluoropropanamido)methyl)imidazo[1,2-b]pyridazin-2-yl)(4,4-difluorocyclohexyl)methyl)carbamate (Intermediate 539) in place of tert-butyl ((S)-(7-((R)-cyclopropyl(4,4,4-trifluorobutanamido)methyl)imidazo[1,2-b]pyridazin-2-yl)(4,4-difluorocyclohexyl)methyl)carbamate to afford the title compound as a beige foam.

Intermediate 545

(Cyclobutylmethyl)magnesium Bromide

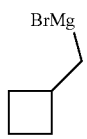

645

To a stirred suspension of magnesium powder (212 mg, 8.72 mmol) and iodine (85.2 mg, 0.34 mmol) in dry THF (10 mL) was added (bromomethyl)cyclobutane (1.00 g, 6.71 mmol) dropwise at rt. Upon reaction initiation, the residue was heated at reflux for 30 min, at which point the reaction mixture was allowed to cool to rt, and the resulting solution was used for the next step directly.

Intermediate 546

Tert-Butyl ((1S)-(7-(1-(((S)-tert-butylsulfinyl)amino)-2-cyclobutylethyl)imidazo[1,2-b]pyridazin-2-yl)(4,4-difluorocyclohexyl)methyl)carbamate

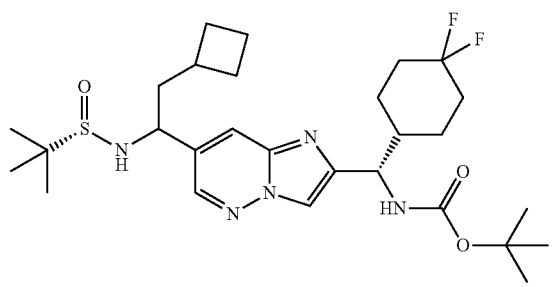 [SMILES: CC(C)(C)OC(=O)N[C@H](c1cn2ncc(C(CC3CCC3)N[S@@](=O)C(C)(C)C)cc2n1)C1CCC(F)(F)CC1]

The title compound was prepared as described for the synthesis of Intermediate 48, using (cyclobutylmethyl)magnesium bromide (Intermediate 545) in place of cyclopropylmagnesium bromide.

Intermediate 547

Tert-Butyl ((1S)-(7-(1-amino-2-cyclobutylethyl)imidazo[1,2-b]pyridazin-2-yl)(4,4-difluorocyclohexyl)methyl)carbamate

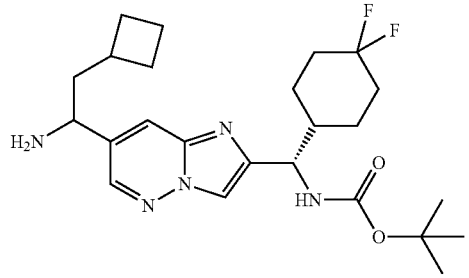 [SMILES: CC(C)(C)OC(=O)N[C@H](c1cn2ncc(C(N)CC3CCC3)cc2n1)C1CCC(F)(F)CC1]

The title compound was prepared as described for the synthesis of Intermediate 49 using tert-butyl ((1S)-(7-(1-(((S)-tert-butylsulfinyl)amino)-2-cyclobutylethyl)imidazo[1,2-b]pyridazin-2-yl)(4,4-difluorocyclohexyl)methyl)carbamate (Intermediate 546) in place of tert-butyl ((S)-(7-((R)-(((S)-tert-butylsulfinyl)amino)(cyclopropyl)methyl)imidazo[1,2-b]pyridazin-2-yl)(4,4-difluorocyclohexyl)methyl)carbamate to afford the title compound as a yellow solid.

646

Intermediate 548

Tert-Butyl ((1S)-(7-(2-cyclobutyl-1-(2-(3,3-difluorocyclobutyl)acetamido)ethyl)imidazo[1,2-b]pyridazin-2-yl)(4,4-difluorocyclohexyl)methyl)carbamate

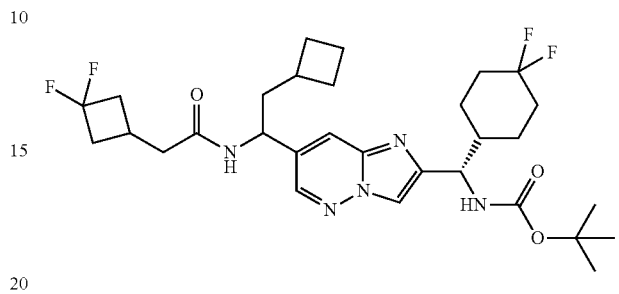

The title compound was prepared as described for the synthesis of Intermediate 50 using tert-butyl ((1S)-(7-(1-amino-2-cyclobutylethyl)imidazo[1,2-b]pyridazin-2-yl)(4,4-difluorocyclohexyl)methyl)carbamate (Intermediate 547) in place tert-butyl ((S)-(7-((R)-amino(cyclopropyl)methyl)imidazo[1,2-b]pyridazin-2-yl)(4,4-difluorocyclohexyl)methyl) carbamate and 2-(3,3-difluorocyclobutyl)acetic acid in place of 4,4,4-trifluorobutanoic acid to afford the title compound as an off-white foam.

Intermediate 549

N-(1-(2-((S)-Amino(4,4-difluorocyclohexyl)methyl)imidazo[1,2-b]pyridazin-7-yl)-2-cyclobutylethyl)-2-(3,3-difluorocyclobutyl)acetamide

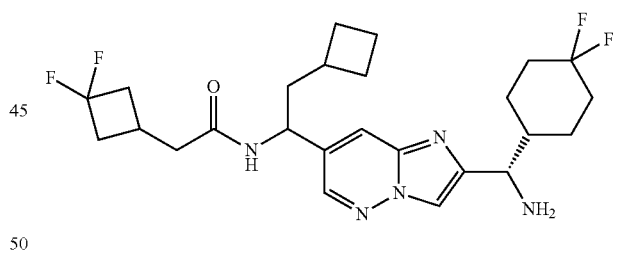

HCl (0.30 mL, 1.2 mmol, 4 M in 1,4-dioxane) was added to a solution of tert-butyl ((1S)-(7-(2-cyclobutyl-1-(2-(3,3-difluorocyclobutyl)acetamido)ethyl)imidazo[1,2-b]pyridazin-2-yl)(4,4-difluorocyclohexyl)methyl)carbamate (100 mg, 0.17 mmol, Intermediate 548) in 1,4-dioxane (0.6 mL) at 50° C. and the resulting mixture was stirred at 50° C. for 0.5 h. To the reaction mixture was added petroleum ether (10 mL) and water (10 mL) and the resulting mixture was allowed to stir for 5 min. Then, the reaction mixture was transferred to a separatory funnel and the layers separated. To the aqueous phase was added saturated aqueous NaHCO₃ solution to pH=8 and then it was extracted with EtOAc (2×20 mL). The combined organic layers were washed with brine (20 mL), dried over anhydrous sodium sulfate, filtered, and concentrated under reduced pressure to afford the title compound as a yellow solid.

Intermediate 550

Tert-Butyl ((S)-(7-((R*)-1-(((S)-tert-butylsulfinyl)amino)-2-methylallyl)imidazo[1,2-b]pyridazin-2-yl)(4,4-difluorocyclohexyl)methyl)carbamate

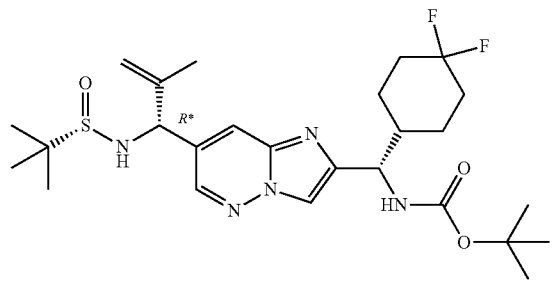 [SMILES: C=C(C)[C@@H](N[S@@](=O)C(C)(C)C)c1cnn2cc([C@@H](NC(=O)OC(C)(C)C)C3CCC(F)(F)CC3)nc2c1]

The title compound was prepared as described for the synthesis of Intermediate 48, using prop-1-en-2-ylmagnesium bromide in place of cyclopropylmagnesium bromide. An additional purification step was performed via SFC (Daicel Chiralpak AD, 250×30 mm, 10 m, 45% EtOH (containing 0.025% NH$_4$OH)/CO$_2$). Product containing fractions were combined to afford the title compound (first-eluting isomer) as a light-yellow oil.

Intermediate 551

Tert-Butyl ((S)-(7-((S*)-1-(((S)-tert-butylsulfinyl)amino)-2-methylallyl)imidazo[1,2-b]pyridazin-2-yl)(4,4-difluorocyclohexyl)methyl)carbamate

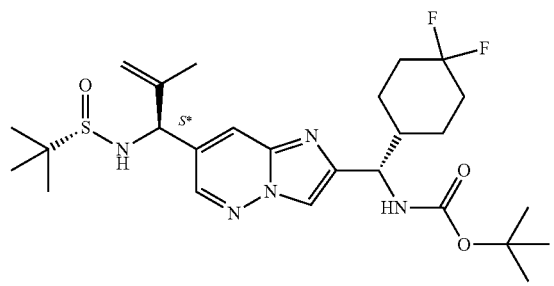 [SMILES: C=C(C)[C@H](N[S@@](=O)C(C)(C)C)c1cnn2cc([C@@H](NC(=O)OC(C)(C)C)C3CCC(F)(F)CC3)nc2c1]

The title compound was prepared as described for the synthesis of Intermediate 48, using prop-1-en-2-ylmagnesium bromide in place of cyclopropylmagnesium bromide. An additional purification step was performed via SFC (Daicel Chiralpak AD, 250×30 mm, 10 m, 45% EtOH (containing 0.025% NH$_4$OH)/CO$_2$). Product containing fractions were combined to afford the title compound (second-eluting isomer) as a light-yellow oil.

Intermediate 552

Tert-Butyl ((S)-(7-((R*)-1-Amino-2-methylallyl)imidazo[1,2-b]pyridazin-2-yl)(4,4-difluorocyclohexyl)methyl)carbamate

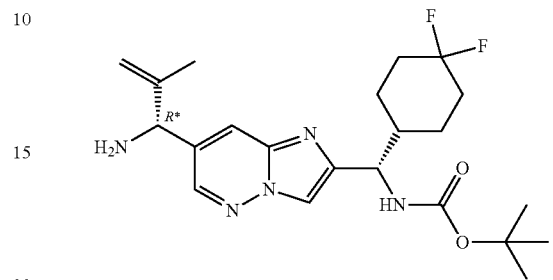

The title compound was prepared as described for the synthesis of Intermediate 49 using tert-butyl ((S)-(7-((R*)-1-(((S)-tert-butylsulfinyl)amino)-2-methylallyl)imidazo[1,2-b]pyridazin-2-yl)(4,4-difluorocyclohexyl)methyl)carbamate (Intermediate 550) in place of tert-butyl ((S)-(7-((R)—(((S)-tert-butylsulfinyl)amino)(cyclopropyl)methyl)imidazo[1,2-b]pyridazin-2-yl)(4,4-difluorocyclohexyl)methyl)carbamate to afford the title compound as a colorless oil.

Intermediate 553

Tert-Butyl ((S)-(7-((S*)-1-Amino-2-methylallyl)imidazo[1,2-b]pyridazin-2-yl)(4,4-difluorocyclohexyl)methyl)carbamate

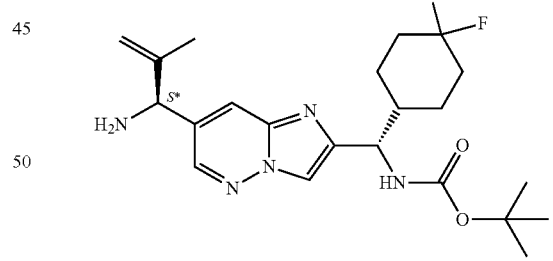

The title compound was prepared as described for the synthesis of Intermediate 49 using tert-butyl ((S)-(7-((S*)-1-(((S)-tert-butylsulfinyl)amino)-2-methylallyl)imidazo[1,2-b]pyridazin-2-yl)(4,4-difluorocyclohexyl)methyl)carbamate (Intermediate 551) in place of tert-butyl ((S)-(7-((R)—(((S)-tert-butylsulfinyl)amino)(cyclopropyl)methyl)imidazo[1,2-b]pyridazin-2-yl)(4,4-difluorocyclohexyl)methyl)carbamate to afford the title compound as a colorless oil.

649

Intermediate 554

Tert-Butyl ((S)-(7-((R*)-1-(2-(3,3-difluorocyclobutyl)acetamido)-2-methylallyl)imidazo[1,2-b]pyridazin-2-yl)(4,4-difluorocyclohexyl)methyl)carbamate

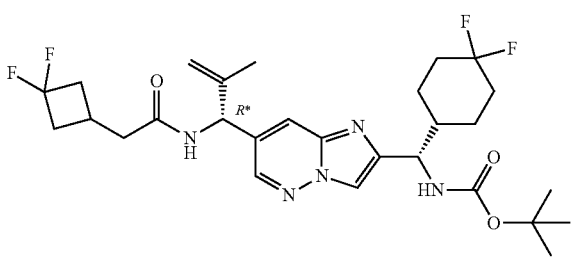 [SMILES: C=C(C)[C@@H](NC(=O)CC1CC(F)(F)C1)c1cnn2cc([C@@H](NC(=O)OC(C)(C)C)C3CCC(F)(F)CC3)nc2c1]

The title compound was prepared as described for the synthesis of Intermediate 50 using tert-butyl ((S)-(7-((R*)-1-amino-2-methylallyl)imidazo[1,2-b]pyridazin-2-yl)(4,4-difluorocyclohexyl)methyl)carbamate (Intermediate 552) in place of tert-butyl ((S)-(7-((R)-amino(cyclopropyl)methyl)imidazo[1,2-b]pyridazin-2-yl)(4,4-difluorocyclohexyl)methyl) carbamate and 2-(3,3-difluorocyclobutyl)acetic acid in place of 4,4,4-trifluorobutanoic acid to afford the title compound as a light-yellow oil.

Intermediate 555

Tert-Butyl ((S)-(7-((S*)-1-(2-(3,3-difluorocyclobutyl)acetamido)-2-methylallyl)imidazo[1,2-b]pyridazin-2-yl)(4,4-difluorocyclohexyl)methyl)carbamate

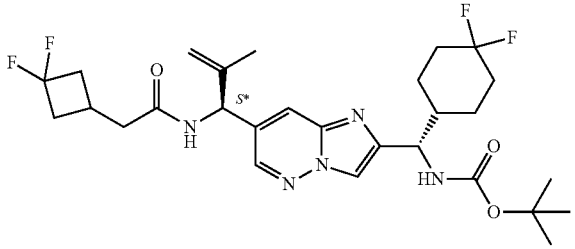 [SMILES: C=C(C)[C@H](NC(=O)CC1CC(F)(F)C1)c1cnn2cc([C@@H](NC(=O)OC(C)(C)C)C3CCC(F)(F)CC3)nc2c1]

The title compound was prepared as described for the synthesis of Intermediate 50 using tert-butyl ((S)-(7-((S*)-1-amino-2-methylallyl)imidazo[1,2-b]pyridazin-2-yl)(4,4-difluorocyclohexyl)methyl)carbamate (Intermediate 553) in place of tert-butyl ((S)-(7-((R)-amino(cyclopropyl)methyl)imidazo[1,2-b]pyridazin-2-yl)(4,4-difluorocyclohexyl)methyl) carbamate and 2-(3,3-difluorocyclobutyl)acetic acid in place of 4,4,4-trifluorobutanoic acid to afford the title compound as a light-yellow oil.

650

Intermediate 556

N—((R*)-1-(2-((S)-Amino(4,4-difluorocyclohexyl)methyl)imidazo[1,2-b]pyridazin-7-yl)-2-methylallyl)-2-(3,3-difluorocyclobutyl)acetamide

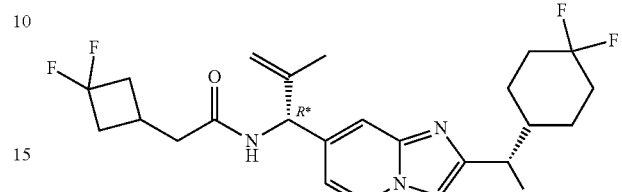

The title compound was prepared as described for the synthesis of Intermediate 549 using tert-butyl ((S)-(7-((R*)-1-(2-(3,3-difluorocyclobutyl)acetamido)-2-methylallyl)imidazo[1,2-b]pyridazin-2-yl)(4,4-difluorocyclohexyl)methyl)carbamate (Intermediate 554) in place of tert-butyl ((1S)-(7-(2-cyclobutyl-1-(2-(3,3-difluorocyclobutyl)acetamido)ethyl)imidazo[1,2-b]pyridazin-2-yl)(4,4-difluorocyclohexyl)methyl)carbamate to afford the title compound as a light-yellow oil.

Intermediate 557

N—((S*)-1-(2-((S)-Amino(4,4-difluorocyclohexyl)methyl)imidazo[1,2-b]pyridazin-7-yl)-2-methylallyl)-2-(3,3-difluorocyclobutyl)acetamide

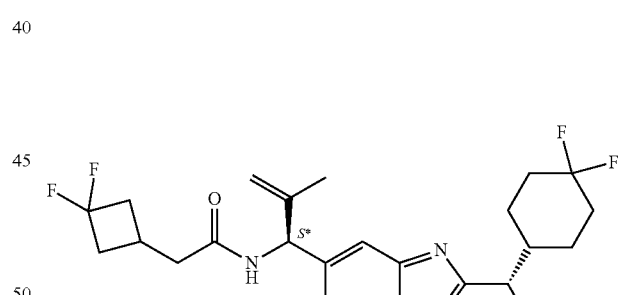

The title compound was prepared as described for the synthesis of Intermediate 549 using tert-butyl ((S)-(7-((S*)-1-(2-(3,3-difluorocyclobutyl)acetamido)-2-methylallyl)imidazo[1,2-b]pyridazin-2-yl)(4,4-difluorocyclohexyl)methyl)carbamate (Intermediate 555) in place of tert-butyl ((1S)-(7-(2-cyclobutyl-1-(2-(3,3-difluorocyclobutyl)acetamido)ethyl)imidazo[1,2-b]pyridazin-2-yl)(4,4-difluorocyclohexyl)methyl)carbamate to afford the title compound as a light-yellow oil.

Intermediate 558

N—((S)-(7-((R*)-1-(2-(3,3-Difluorocyclobutyl)acet-amido)-2-methylallyl)imidazo[1,2-b]pyridazin-2-yl)(4,4-difluorocyclohexyl)methyl)-1-isopropyl-1H-pyrazole-5-carboxamide

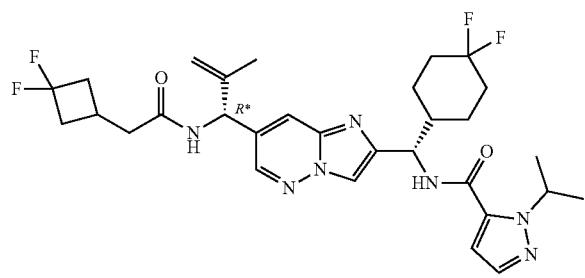 [SMILES: C=C(C)[C@@H](NC(=O)CC1CC(F)(F)C1)c1cnn2cc([C@@H](NC(=O)c3ccnn3C(C)C)C3CCC(F)(F)CC3)nc2c1]

The title compound was prepare as described or the synthesis of Example 38 using N—((R*)-1-(2-((S)-amino(4,4-difluorocyclohexyl)methyl)imidazo[1,2-b]pyridazin-7-yl)-2-methylallyl)-2-(3,3-difluorocyclobutyl)acetamide (Intermediate 556) in place of N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide and 1-isopropyl-1H-pyrazole-5-carboxylic acid in place of 1-(3,3,3-trifluoropropyl)-1H-1,2,4-triazole-5-carboxylic acid to afford the title compound as a colorless oil.

Intermediate 559

N—((S)-(7-((R*)-1-(2-(3,3-Difluorocyclobutyl)acet-amido)-2-methylallyl)imidazo[1,2-b]pyridazin-2-yl)(4,4-difluorocyclohexyl)methyl)-4-methyl-1,2,5-oxadiazole-3-carboxamide

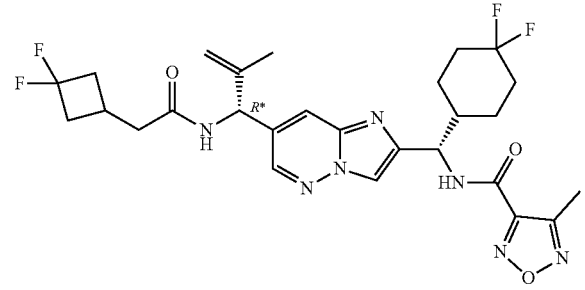 [SMILES: C=C(C)[C@@H](NC(=O)CC1CC(F)(F)C1)c1cnn2cc([C@@H](NC(=O)c3nonc3C)C3CCC(F)(F)CC3)nc2c1]

The title compound was prepared as described for the synthesis of Example 38 using N—((R*)-1-(2-((S)-amino(4,4-difluorocyclohexyl)methyl)imidazo[1,2-b]pyridazin-7-yl)-2-methylallyl)-2-(3,3-difluorocyclobutyl)acetamide (Intermediate 556) in place of N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide and 4-methyl-1,2,5-oxadiazole-3-carboxylic acid in place of 1-(3,3,3-trifluoropropyl)-1H-1,2,4-triazole-5-carboxylic acid to afford the title compound as a colorless oil.

Intermediate 560

N—((S)-(7-((S*)-1-(2-(3,3-Difluorocyclobutyl)acet-amido)-2-methylallyl)imidazo[1,2-b]pyridazin-2-yl)(4,4-difluorocyclohexyl)methyl)-1-isopropyl-1H-pyrazole-5-carboxamide

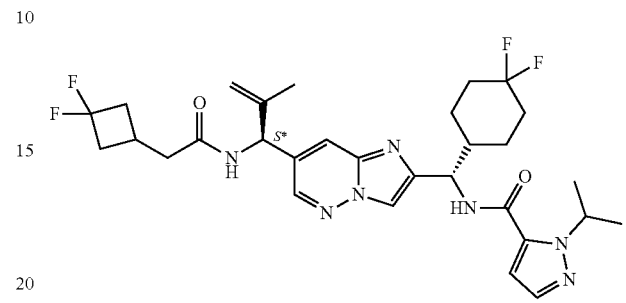

The title compound was prepared as described for the synthesis of Example 38 using N—((S*)-1-(2-((S)-amino(4,4-difluorocyclohexyl)methyl)imidazo[1,2-b]pyridazin-7-yl)-2-methylallyl)-2-(3,3-difluorocyclobutyl)acetamide (Intermediate 557) in place of N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide and 1-isopropyl-1H-pyrazole-5-carboxylic acid in place of 1-(3,3,3-trifluoropropyl)-1H-1,2,4-triazole-5-carboxylic acid to afford the title compound as a colorless oil.

Intermediate 561

N—((S)-(7-((S*)-1-(2-(3,3-Difluorocyclobutyl)acet-amido)-2-methylallyl)imidazo[1,2-b]pyridazin-2-yl)(4,4-difluorocyclohexyl)methyl)-4-methyl-1,2,5-oxadiazole-3-carboxamide

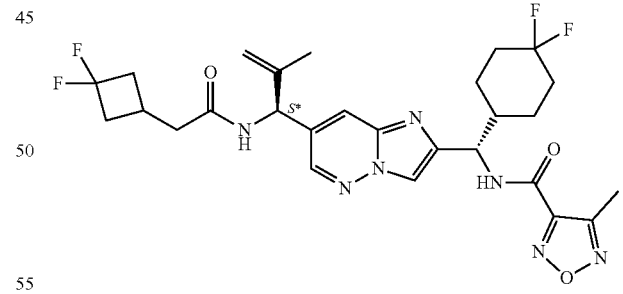

The title compound was prepared as described for the synthesis of Example 38 using N—((S*)-1-(2-((S)-amino(4,4-difluorocyclohexyl)methyl)imidazo[1,2-b]pyridazin-7-yl)-2-methylallyl)-2-(3,3-difluorocyclobutyl)acetamide (Intermediate 557) in place of N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide and 4-methyl-1,2,5-oxadiazole-3-carboxylic acid in place of 1-(3,3,3-trifluoropropyl)-1H-1,2,4-triazole-5-carboxylic acid to afford the title compound as a colorless oil.

Intermediate 562

Tert-Butyl ((S)-(7-((R*)-1-(((S)-tert-butylsulfinyl)amino)-2-cyanoethyl)imidazo[1,2-b]pyridazin-2-yl)(4,4-difluorocyclohexyl)methyl)carbamate

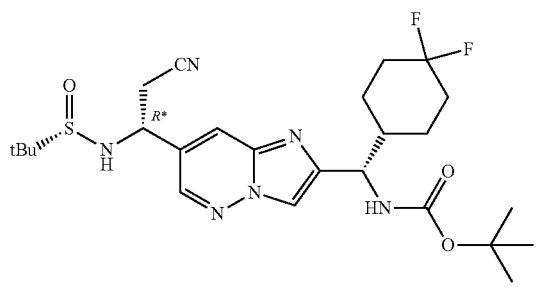 [SMILES: CC(C)(C)OC(=O)N[C@H](c1cn2ncc([C@@H](CC#N)N[S@@](=O)C(C)(C)C)cc2n1)C1CCC(F)(F)CC1]

tert-Butyl ((S)-(7-((E)-(((S)-tert-butylsulfinyl)imino)methyl)imidazo[1,2-b]pyridazin-2-yl)(4,4-difluorocyclohexyl)methyl)carbamate (500 mg, 1.01 mmol, Intermediate 47) was dissolved in THF (5 mL), and then tetra-butyl ammonium phenoxide (442 mg, 1.04 mmol) was added and the resulting solution was cooled to −78° C. 2-Trimethylsilylacetonitrile (0.62 mL, 4.52 mmol) was added dropwise and the mixture stirred for 0.75 h at −78° C. The reaction was quenched with cold water (20 mL) and extracted with EtOAc (3×20 mL). The combined organic layers were washed with brine, dried over anhydrous MgSO₄, filtered, and concentrated to dryness. The residue was purified by silica gel chromatography (0-100% EtOAc/hexanes) to afford the title compound as an off-white foam.

Intermediate 563

Tert-Butyl ((S)-(7-((R*)-1-amino-2-cyanoethyl)imidazo[1,2-b]pyridazin-2-yl)(4,4-difluorocyclohexyl)methyl)carbamate

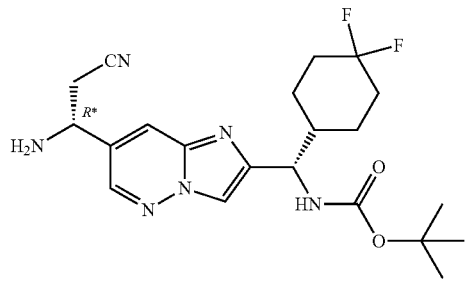 [SMILES: CC(C)(C)OC(=O)N[C@H](c1cn2ncc([C@H](N)CC#N)cc2n1)C1CCC(F)(F)CC1]

The title compound was prepared as described for the synthesis of Intermediate 49, using tert-butyl ((S)-(7-((R*)-1-(((S)-tert-butylsulfinyl)amino)-2-cyanoethyl)imidazo[1,2-b]pyridazin-2-yl)(4,4-difluorocyclohexyl)methyl)carbamate (Intermediate 562) in place of tert-butyl ((S)-(7-((R)-(((S)-tert-butylsulfinyl)amino)(cyclopropyl)methyl)imidazo[1,2-b]pyridazin-2-yl)(4,4-difluorocyclohexyl)methyl)carbamate to afford the title compound.

Intermediate 564

Tert-Butyl ((S)-(7-((R*)-2-cyano-1-(2-(3,3-difluorocyclobutyl)acetamido)ethyl)imidazo[1,2-b]pyridazin-2-yl)(4,4-difluorocyclohexyl)methyl)carbamate

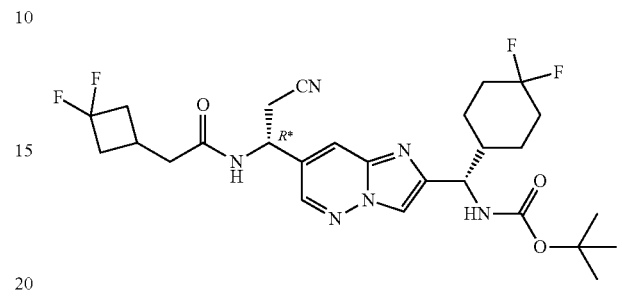

The title compound was prepared as described for the synthesis of Intermediate 439, using tert-butyl ((S)-(7-((R*)-1-amino-2-cyanoethyl)imidazo[1,2-b]pyridazin-2-yl)(4,4-difluorocyclohexyl)methyl)carbamate (Intermediate 563) in place of tert-butyl ((S)-(7-((R*)-amino(cyclobutyl)methyl)imidazo[1,2-b]pyridazin-2-yl)(4,4-difluorocyclohexyl)methyl)carbamate and 2-(3,3-difluorocyclobutyl)acetic acid in place of 4-methyl-1,2,5-oxadiazole-3-carboxylic acid to afford the title compound.

Intermediate 565

N—((R*)-1-(2-((S)-Amino(4,4-difluorocyclohexyl)methyl)imidazo[1,2-b]pyridazin-7-yl)-2-cyanoethyl)-2-(3,3-difluorocyclobutyl)acetamide

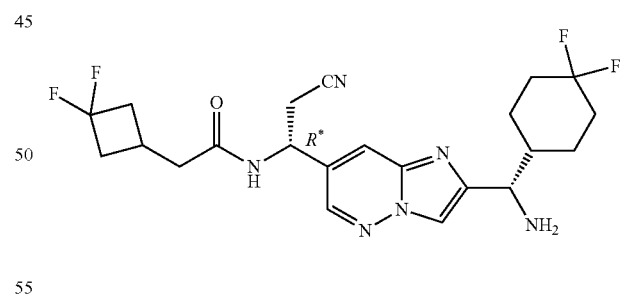

The title compound was prepared as described for the synthesis of Intermediate 51, using tert-butyl ((S)-(7-((R*)-2-cyano-1-(2-(3,3-difluorocyclobutyl)acetamido)ethyl)imidazo[1,2-b]pyridazin-2-yl)(4,4-difluorocyclohexyl)methyl)carbamate (Intermediate 564) in place of tert-butyl ((S)-(7-((R)-cyclopropyl(4,4,4-trifluorobutanamido)methyl)imidazo[1,2-b]pyridazin-2-yl)(4,4-difluorocyclohexyl)methyl) carbamate to afford the title compound.

Intermediate 566

3-Isopropyl-4-(phenylcarbamoyl)-1,2,5-oxadiazole 2-oxide

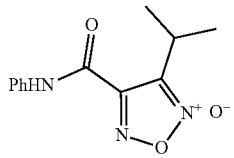

To a solution of 4-carboxy-3-isopropyl-1,2,5-oxadiazole 2-oxide (400 mg, 2.32 mmol, Intermediate 319) in DMF (11.6 mL) were added DIPEA (0.80 mL, 4.65 mmol) and HATU (1.17 g, 3.02 mmol) sequentially. The mixture was stirred for 3 min followed by the addition of aniline (0.30 mL, 3.25 mmol). The resulting mixture was stirred at rt for 2 h, then poured into a separatory funnel filled with water and was extracted with EtOAc (3×25 mL). The combined organic layers were washed with brine twice, dried over anhydrous MgSO$_4$, filtered, and concentrated under reduced pressure. The crude title compound was purified by silica gel chromatography (0-50% EtOAc/hexanes) to afford the title compound as a white solid.

Intermediate 567

4-Isopropyl-N-phenyl-1,2,5-oxadiazole-3-carboxamide

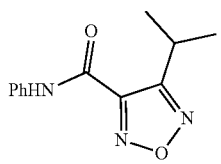

3-Isopropyl-4-(phenylcarbamoyl)-1,2,5-oxadiazole 2-oxide (630 mg, 2.55 mmol, Intermediate 566) was dissolved in toluene (12.7 mL) and was degassed with an inert N$_2$ atmosphere. Trimethyl phosphite (6.0 mL, 51 mmol) was then added, dropwise, and the reaction was heated to 120° C. and stirred at that temperature for 12 h. The reaction was then cooled to rt and poured into a separatory funnel filled with 1 N aqueous HCl (50 mL). The biphasic mixture was extracted with EtOAc (3×50 mL) and the combined organic layers were washed with brine, dried over anhydrous MgSO$_4$, filtered, and concentrated under reduced pressure. The crude title compound was purified by silica gel chromatography (0-50% EtOAc/hexanes) to afford the pure title compound as an off-white solid.

Intermediate 568

Tert-Butyl (4-isopropyl-1,2,5-oxadiazole-3-carbonyl)(phenyl)carbamate

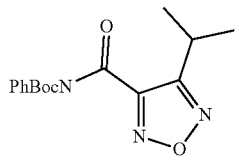

A flask was charged with 4-isopropyl-N-phenyl-1,2,5-oxadiazole-3-carboxamide (460 mg, 2.0 mmol, Intermediate 567) and DCM (10 mL). Di-tert-butyl dicarbonate (480 mg, 2.2 mmol) and DMAP (24 mg, 0.2 mmol) were sequentially added and the resultant solution was stirred at rt for 1 h. Silica gel was then added, and the resulting slurry was concentrated to dryness. Purification by silica gel chromatography (0-50% EtOAc/hexanes) afforded the title compound as a white solid.

Intermediate 569

4-Isopropyl-1,2,5-oxadiazole-3-carboxylic Acid

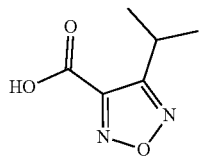

LiOH (10 mg, 0.43 mmol) was dissolved in deionized water (0.2 mL) and was added to a solution of tert-butyl (4-isopropyl-1,2,5-oxadiazole-3-carbonyl)(phenyl)carbamate (110 mg, 0.33 mmol, Intermediate 568) in THF (0.33 mL). The resulting reaction was stirred at rt for 1 h. The reaction was quenched with 1 N aqueous HCl (5 mL) and extracted with EtOAc (3×5 mL). The combined organic layers were then extracted with a saturated aqueous solution of NaHCO$_3$ (10 mL) and the organic layers were discarded. The basic aqueous layer was then slowly acidified to ~pH 1 with 6 N aqueous HCl and extracted with EtOAc (3×10 mL). The combined organic layers were then dried with anhydrous Na$_2$SO$_4$, filtered, and concentrated under reduced pressure to afford the crude title compound and was used without further purification.

Intermediate 570

4-Cyclopropyl-1,2,5-oxadiazole-3-carboxylic Acid

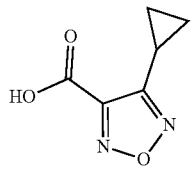

The title compound was prepared as described for the synthesis of Intermediate 569, using 3-cyclopropyl-4-formyl-1,2,5-oxadiazole 2-oxide (Intermediate 321) in place of 4-carboxy-3-isopropyl-1,2,5-oxadiazole 2-oxide.

Intermediate 571

Ethyl 3-isopropoxyisoxazole-4-carboxylate

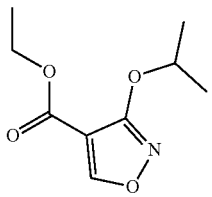

Isopropanol (363 mg, 6.0 mmol) was added to a solution of ethyl 3-hydroxyisoxazole-4-carboxylate (1.0 g, 4.83 mmol, Intermediate 215) in THF (80 mL) followed by triphenylphosphine (1.68 g, 6.28 mmol) and the resulting solution was allowed to stir for 2 min at rt. DIAD (1.27 g, 6.28 mmol) was then added dropwise. After stirring for 16 h the reaction mixture was concentrated and the crude product was purified by silica gel chromatography (0-30% ether/petroleum ether) to afford the title compound.

Intermediate 572

3-Isopropoxyisoxazole-4-carboxylic Acid

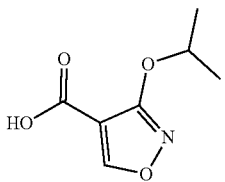

The title compound was prepared as described for the synthesis of Intermediate 217, using ethyl 3-isopropoxyisoxazole-4-carboxylate (Intermediate 571) in place of ethyl 3-ethoxyisoxazole-4-carboxylate.

Intermediate 573

3-(2,2-Difluoroethoxy)isoxazole-4-carboxylic Acid

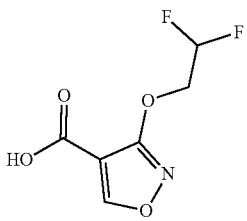 [SMILES: O=C(O)c1conc1OCC(F)F]

The title compound was prepared as described for the synthesis of Intermediate 572, using 2,2-difluoroethanol in place of isopropanol.

EXAMPLES

Example 1

(Trans-2R*,3R*)—N-((2-((S)-benzamido(cyclohexyl)methyl)imidazo[1,2-b]pyridazin-7-yl)methyl)-3-(trifluoromethyl)piperidine-2-carboxamide Hydrochloride

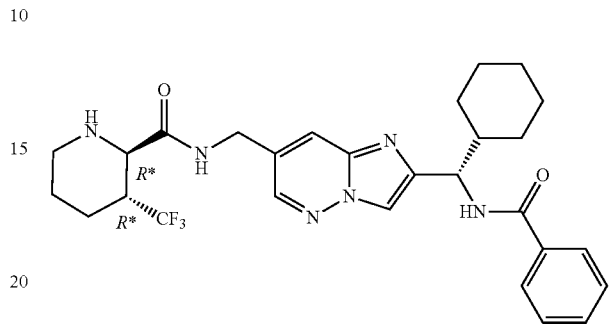

Hydrochloric acid (0.92 mL, 4.0 M in EtOAc, 3.7 mmol) was added to a 0° C. solution of tert-butyl (trans-2R*,3R*)-2-(((2-((S)-benzamido(cyclohexyl)methyl)imidazo[1,2-b]pyridazin-7-yl)methyl)carbamoyl)-3-(trifluoromethyl)piperidine-1-carboxylate (150 mg, 0.233 mmol, Intermediate 28) in EtOAc (2 mL), and the resulting mixture was stirred at 0° C. for 2 h. The mixture was then concentrated. The residue was purified by preparative HPLC (Agela ASB C18, 25% to 55% MeCN/aqueous HCl (0.006 N)) to afford the title compound as hydrochloride salt as a colorless solid. $^1$H NMR (400 MHz, DMSO-$d_6$) δ 10.50-10.69 (m, 1H), 9.64 (t, J=5.6 Hz, 1H), 9.02-9.16 (m, 1H), 8.80 (d, J=8.8 Hz, 1H), 8.70 (s, 1H), 8.42 (s, 1H), 8.21 (s, 1H), 7.87-7.94 (m, 2H), 7.44-7.55 (m, 3H), 5.17 (t, J=8.7 Hz, 1H), 4.61 (dd, J=6.2, 16.3 Hz, 1H), 4.44 (dd, J=5.0, 16.3 Hz, 1H), 3.84-3.87 (m, 1H), 3.24 (d, J=12.2 Hz, 1H), 2.84-2.99 (m, 2H), 2.01-2.11 (m, 2H), 1.61-1.88 (m, 6H), 1.46-1.52 (m, 1H), 0.90-1.29 (m, 6H). MS (ESI) m/z: [M+H]$^+$ Found 543.3.

Example 2

(Trans-2S*,3S*)—N-((2-((S)-benzamido(cyclohexyl)methyl)imidazo[1,2-b]pyridazin-7-yl)methyl)-3-(trifluoromethyl)piperidine-2-carboxamide Hydrochloride

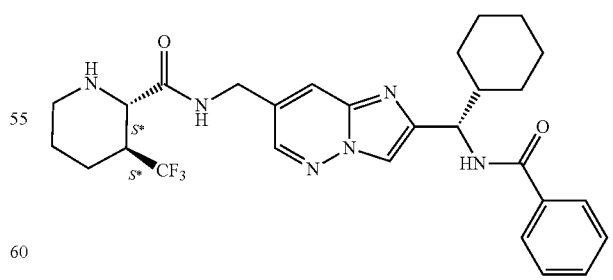

The title compound was prepared as described for the synthesis of Example 1, using tert-butyl (trans-2S*,3S*)-2-(((2-((S)-benzamido(cyclohexyl)methyl)imidazo[1,2-b]pyridazin-7-yl)methyl) carbamoyl)-3-(trifluoromethyl)piperidine-1-carboxylate (Intermediate 29) in place of tert-butyl (trans-2R*,3R*)-2-(((2-((S)-benzamido(cyclohexyl)methyl) imidazo[1,2-b]pyridazin-7-yl)methyl)carbamoyl)-3-(trifluoromethyl)piperidine-1-carboxylate to afford the title compound as a hydrochloride salt as a colorless solid. ¹H NMR (400 MHz, DMSO-d₆) δ 10.80-10.95 (m, 1H), 9.68-9.79 (m, 1H), 9.00-9.18 (m, 1H), 8.89 (d, J=8.3 Hz, 1H), 8.81 (s, 1H), 8.51 (s, 1H), 8.30 (s, 1H), 7.94 (d, J=7.3 Hz, 2H), 7.45-7.56 (m, 3H), 5.20 (t, J=8.7 Hz, 1H), 4.63 (dd, J=5.9, 15.9 Hz, 1H), 4.47 (dd, J=5.0, 16.3 Hz, 1H), 3.87 (t, J=10.9 Hz, 1H), 3.23 (d, J=10.5 Hz, 1H), 2.81-3.00 (m, 2H), 2.01-2.12 (m, 2H), 1.62-1.87 (m, 6H), 1.42-1.54 (m, 1H), 1.01-1.25 (m, 6H). MS (ESI) m/z: [M+H]⁺ Found 543.3.

Example 3

(Trans-2R*,3R*)—N-((2-((S)-cyclohexyl(1-methyl-1H-pyrazole-5-carboxamido)methyl)imidazo[1,2-b]pyridazin-7-yl)methyl)-3-(trifluoromethyl)piperidine-2-carboxamide Hydrochloride

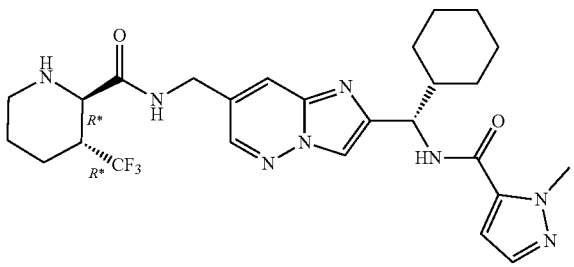 [SMILES: Cn1nccc1C(=O)N[C@H](c1cn2ncc(CNC(=O)[C@@H]3NCCC[C@H]3C(F)(F)F)cc2n1)C1CCCCC1]

The title compound was prepared as described for the synthesis of Example 1, using tert-butyl (trans-2R*,3R*)-2-(((2-((S)-cyclohexyl(1-methyl-1H-pyrazole-5-carboxamido)methyl)imidazo[1,2-b]pyridazin-7-yl)methyl)carbamoyl)-3-(trifluoromethyl)piperidine-1-carboxylate (Intermediate 31) in place of tert-butyl (trans-2R*,3R*)-2-(((2-((S)-benzamido(cyclohexyl)methyl)imidazo[1,2-b]pyridazin-7-yl)methyl)carbamoyl)-3-(trifluoromethyl)piperidine-1-carboxylate to afford the title compound as an hydrochloride salt as a colorless solid. ¹H NMR (400 MHz, DMSO-d₆) δ 11.05 (d, J=10.2 Hz, 1H), 9.81 (t, J=5.8 Hz, 1H), 9.17-9.01 (m, 2H), 8.92 (d, J=1.9 Hz, 1H), 8.64 (s, 1H), 8.39 (s, 1H), 7.47 (d, J=2.0 Hz, 1H), 7.18 (d, J=2.1 Hz, 1H), 5.18 (t, J=8.9 Hz, 1H), 4.66 (dd, J=16.6, 6.3 Hz, 1H), 4.49 (dd, J=16.6, 5.2 Hz, 1H), 4.02 (s, 3H), 3.89 (t, J=10.8 Hz, 1H), 3.27-3.17 (m, 1H), 2.99-2.80 (m, 2H), 2.12-2.00 (m, 2H), 1.92-1.55 (m, 7H), 1.52-1.43 (m, 2H), 1.21-0.92 (m, 5H). MS (ESI) m/z: [M+H]⁺ Found 547.3.

Example 4

N—((S)-(7-((R)-Cyclopropyl(4,4,4-trifluorobutanamido)methyl)imidazo[1,2-b]pyridazin-2-yl)(4,4-difluorocyclohexyl)methyl)-2-(2,2-difluorocyclobutyl)methyl)-2H-1,2,3-triazole-4-carboxamide

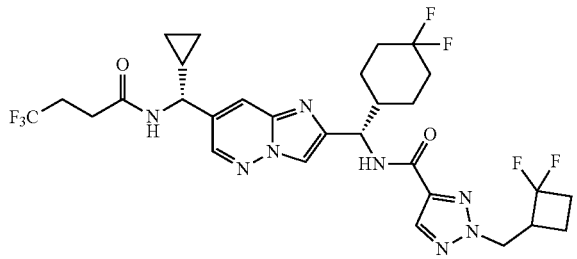 [SMILES: O=C(CCC(F)(F)F)N[C@@H](c1cnn2cc([C@@H](NC(=O)c3cnn(CC4CCC4(F)F)n3)C3CCC(F)(F)CC3)nc2c1)C1CC1]

N—((R)-2-((S)-Amino(4,4-difluorocyclohexyl)methyl) imidazo[1,2-b]pyridazin-7-yl)(cyclopropyl)methyl)-4,4,4-trifluorobutanamide (100.3 mg, 0.218 mmol, Intermediate 51), 2-((2,2-difluorocyclobutyl)methyl)-2H-1,2,3-triazole-4-carboxylic acid (63 mg, 0.29 mmol, Intermediate 147), and a stir-bar were added to a 20 mL vial and subsequently treated with a freshly prepared stock solution consisting of: 0.071 M HOBt, 0.071 M EDCI, ACN (4.0 mL), and 0.15 M DIPEA. The mixture was stirred at rt for 67 h before it was concentrated to dryness, and the resultant amber-colored oil subjected to silica gel chromatography (0-100% EtOAc/hexanes) to afford the title compound as a white solid. ¹H NMR (400 MHz, CD₃OD) δ 8.30 (d, J=2.1 Hz, 1H), 7.98 (s, 1H), 7.84 (s, 1H), 7.83-7.80 (m, 1H), 7.54 (d, J=9.1 Hz, 1H), 6.79 (d, J=7.1 Hz, 1H), 5.29-5.20 (m, 1H), 4.67 (ddd, J=13.9, 7.1, 1.0 Hz, 1H), 4.46 (dd, J=13.9, 8.3 Hz, 1H), 4.33-4.26 (m, 1H), 3.49-3.34 (m, 1H), 2.56-2.36 (m, 6H), 2.18-2.05 (m, 2H), 2.04-1.96 (m, 1H), 1.97-1.85 (m, 2H), 1.78-1.55 (m, 4H), 1.53-1.41 (m, 1H), 1.41-1.29 (m, 1H), 1.16-1.05 (m, 1H), 0.73-0.59 (m, 2H), 0.52-0.44 (m, 1H), 0.44-0.35 (m, 1H). MS (ESI) m/z: [M+H]⁺ Found 659.3.

Example 5

(S)—N-((4,4-Difluorocyclohexyl)(7-((4,4,4-trifluorobutanamido)methyl)imidazo[1,2-b]pyridazin-2-yl)methyl)benzamide

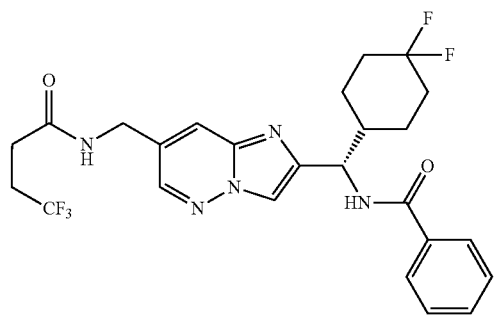 [SMILES: O=C(CCC(F)(F)F)NCc1cnn2cc([C@@H](NC(=O)c3ccccc3)C3CCC(F)(F)CC3)nc2c1]

The title compound was prepared as described for the synthesis of Intermediate 27, using tert-butyl (S)-(1-(4,4-difluorocyclohexyl)-3-iodo-2-oxopropyl)carbamate (Intermediate 15) in place of tert-butyl (S)-(1-cyclohexyl-3-iodo- 2-oxopropyl)carbamate and 4,4,4-trifluorobutanoic acid in place of (2RS,3RS)-1-(tert-butoxycarbonyl)-3-(trifluoromethyl)piperidine-2-carboxylic acid. Purification by preparative HPLC (Phenomenex Gemini C18, 40% to 70% MeCN/aqueous NH$_4$OH (0.05%)) afforded the title compound as a colorless solid. $^1$H NMR (400 MHz, DMSO-d$_6$) δ 8.78-8.66 (m, 2H), 8.41 (d, J=1.8 Hz, 1H), 8.22 (s, 1H), 7.92-7.82 (m, 3H), 7.57-7.50 (m, 1H), 7.49-7.43 (m, 2H), 5.27-5.15 (m, 1H), 4.37 (d, J=5.8 Hz, 2H), 2.60-2.52 (m, 2H), 2.49-2.43 (m, 2H), 2.25-2.13 (m, 1H), 2.09-1.93 (m, 2H), 1.92-1.69 (m, 3H), 1.66-1.56 (m, 1H), 1.46-1.33 (m, 1H), 1.31-1.21 (m, 1H). MS (ESI) m/z: [M+H]$^+$ Found 524.2.

Example 6

N—((S)-(7-((R*)-Cyclopropyl(4,4,4-trifluorobutanamido)methyl)imidazo[1,2-b]pyridazin-2-yl)(4,4-difluorocyclohexyl)methyl)-1-(3,3,3-trifluoropropyl)-1H-pyrazole-4-carboxamide

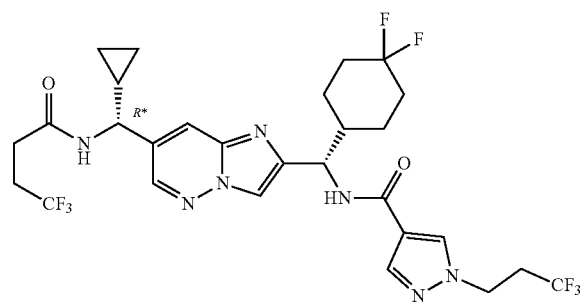 [SMILES: O=C(CCC(F)(F)F)N[C@@H](c1cnn2cc([C@@H](NC(=O)c3cnn(CCC(F)(F)F)c3)C3CCC(F)(F)CC3)nc2c1)C1CC1]

Example 7

N—((S)-(7-((S*)-Cyclopropyl(4,4,4-trifluorobutanamido)methyl)imidazo[1,2-b]pyridazin-2-yl)(4,4-difluorocyclohexyl)methyl)-1-(3,3,3-trifluoropropyl)-1H-pyrazole-4-carboxamide

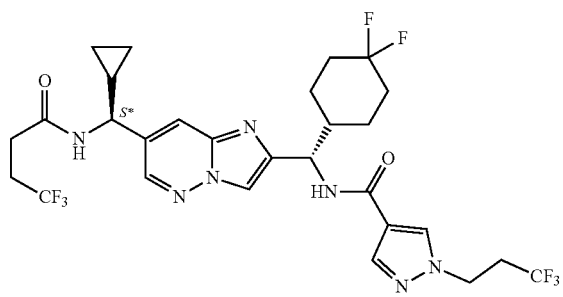 [SMILES: O=C(CCC(F)(F)F)N[C@H](c1cnn2cc([C@@H](NC(=O)c3cnn(CCC(F)(F)F)c3)C3CCC(F)(F)CC3)nc2c1)C1CC1]

N-((1S)-(7-(Cyclopropyl(4,4,4-trifluorobutanamido)methyl)imidazo[1,2-b]pyridazin-2-yl)(4,4-difluorocyclohexyl)methyl)-1-(3,3,3-trifluoropropyl)-1H-pyrazole-4-carboxamide (Intermediate 39) was purified by SFC using a chiral stationary phase (Regis (S,S) Whelk-O® 1, 25:75 MeOH/CO$_2$) to give a pair of diastereomers. The first-eluting isomer was re-purified by preparative HPLC (XBridge C18, 10% to 100% MeCN/aqueous NH$_4$OH (20 mM)) to give Example 6, the major diastereomer, as a colorless solid. The second-eluting isomer was re-purified by preparative HPLC (XBridge C18, 10% to 100% MeCN/aqueous NH$_4$OH (20 mM)) to give Example 7, the minor diastereomer, as a colorless solid. Example 6: $^1$H NMR (400 MHz, DMSO-d$_6$) δ 8.71 (d, J=7.7 Hz, 1H), 8.49 (d, J=1.9 Hz, 1H), 8.32 (s, 1H), 8.30 (d, J=9.2 Hz, 1H), 8.16 (s, 1H), 8.00 (s, 1H), 7.92 (d, J=0.8 Hz, 1H), 5.16 (t, J=8.6 Hz, 1H), 4.39 (t, J=6.8 Hz, 2H), 4.29 (t, J=8.4 Hz, 1H), 2.95-2.81 (m, 2H), 2.56-2.42 (m, 4H), 2.20-1.91 (m, 3H), 1.90-1.66 (m, 3H), 1.65-1.55 (m, 1H), 1.43-1.30 (m, 1H), 1.31-1.15 (m, 2H), 0.63-0.44 (m, 3H), 0.42-0.34 (m, 1H). MS (ESI) m/z: [M+H]$^+$ Found 650.3. Example 7: $^1$H NMR (400 MHz, DMSO-d$_6$) δ 8.71 (d, J=7.7 Hz, 1H), 8.48 (d, J=2.1 Hz, 1H), 8.32 (s, 1H), 8.29 (d, J=9.1 Hz, 1H), 8.16 (s, 1H), 7.99 (s, 1H), 7.92 (d, J=2.1 Hz, 1H), 5.16 (t, J=8.6 Hz, 1H), 4.39 (t, J=6.8 Hz, 2H), 4.29 (t, J=8.4 Hz, 1H), 2.94-2.81 (m, 2H), 2.49-2.42 (m, 4H), 2.20-2.09 (m, 1H), 2.09-1.91 (m, 2H), 1.91-1.66 (m, 3H), 1.65-1.55 (m, 1H), 1.44-1.31 (m, 1H), 1.31-1.14 (m, 2H), 0.63-0.44 (m, 3H), 0.42-0.34 (m, 1H). MS (ESI) m/z: [M+H]$^+$ Found 650.4.

Example 8

N—((S)-(7-((R*)-Cyclopropyl(2-(3,3-difluorocyclobutyl)acetamido)methyl)imidazo[1,2-b]pyridazin-2-yl)(4,4-difluorocyclohexyl)methyl)-1-(3,3,3-trifluoropropyl)-1H-pyrazole-4-carboxamide

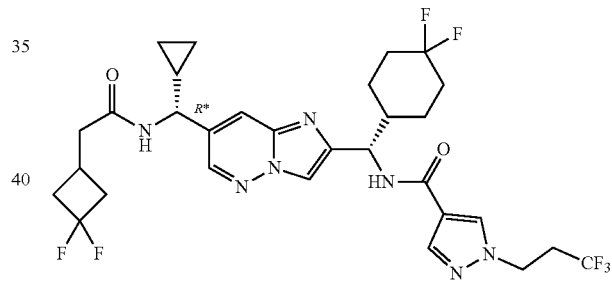

Example 9

N—((S)-(7-((S*)-Cyclopropyl(2-(3,3-difluorocyclobutyl)acetamido)methyl)imidazo[1,2-b]pyridazin-2-yl)(4,4-difluorocyclohexyl)methyl)-1-(3,3,3-trifluoropropyl)-1H-pyrazole-4-carboxamide

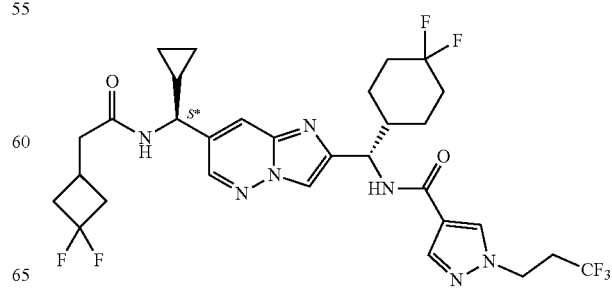

N-((1S)-(7-(Cyclopropyl(2-(3,3-difluorocyclobutyl)acetamido)methyl)imidazo[1,2-b]pyridazin-2-yl)(4,4-difluorocyclohexyl)methyl)-1-(3,3,3-trifluoropropyl)-1H-pyrazole-4-carboxamide (Intermediate 40) was purified by SFC using a chiral stationary phase (Regis (S,S) Whelk-O® 1, 35:65 MeOH/CO$_2$) to give a pair of diastereomers. The first-eluting isomer was re-purified by preparative HPLC (XBridge C18, 10% to 100% MeCN/aqueous NH$_4$OH (20 mM)) to give Example 8, the major diastereomer, as a colorless solid. The second-eluting isomer was re-purified by preparative HPLC (XBridge C18, 10% to 100% MeCN/aqueous NH$_4$OH (20 mM)) to give Example 9, the minor diastereomer, as a colorless solid. Example 8: $^1$H NMR (400 MHz, DMSO-d$_6$) δ 8.58 (d, J=7.8 Hz, 1H), 8.48 (d, J=2.1 Hz, 1H), 8.32 (s, 1H), 8.30 (d, J=9.2 Hz, 1H), 8.16 (s, 1H), 8.00-7.99 (m, 1H), 7.90 (d, J=2.0 Hz, 1H), 5.16 (t, J=8.6 Hz, 1H), 4.39 (t, J=6.8 Hz, 2H), 4.26 (t, J=8.4 Hz, 1H), 2.94-2.81 (m, 2H), 2.71-2.55 (m, 2H), 2.44-2.21 (m, 5H), 2.19-2.09 (m, 1H), 2.09-1.91 (m, 2H), 1.91-1.66 (m, 3H), 1.65-1.56 (m, 1H), 1.43-1.30 (m, 1H), 1.30-1.15 (m, 2H), 0.61-0.42 (m, 3H), 0.40-0.32 (m, 1H). MS (ESI) m/z: [M+H]$^+$ Found 658.3. Example 9: $^1$H NMR (400 MHz, DMSO-d$_6$) δ 8.58 (d, J=7.8 Hz, 1H), 8.47 (d, J=2.0 Hz, 1H), 8.32 (s, 1H), 8.29 (d, J=9.1 Hz, 1H), 8.16 (s, 1H), 7.99 (d, J=0.4 Hz, 1H), 7.90 (d, J=2.0 Hz, 1H), 5.16 (t, J=8.6 Hz, 1H), 4.39 (t, J=6.8 Hz, 2H), 4.26 (t, J=8.4 Hz, 1H), 2.95-2.81 (m, 2H), 2.71-2.54 (m, 2H), 2.43-2.21 (m, 5H), 2.20-2.09 (m, 1H), 2.08-1.90 (m, 2H), 1.90-1.65 (m, 3H), 1.65-1.55 (m, 1H), 1.44-1.31 (m, 1H), 1.31-1.14 (m, 2H), 0.62-0.42 (m, 3H), 0.40-0.32 (m, 1H). MS (ESI) m/z: [M+H]$^+$ Found 658.3.

Example 10

N-((S)-(7-((S*)-Cyclopropyl(4,4,4-trifluoro-3-(trifluoromethyl)butanamido)methyl)imidazo[1,2-b]pyridazin-2-yl)(4,4-difluorocyclohexyl)methyl)-1-isopropyl-1H-pyrazole-5-carboxamide

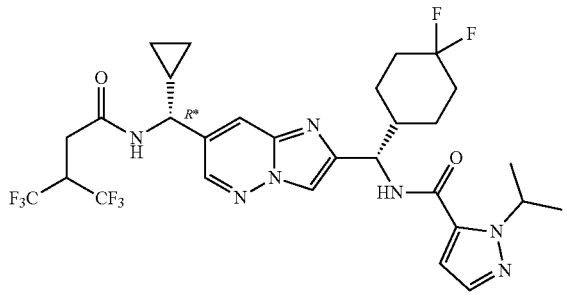

Example 11

N-((S)-(7-((S*)-Cyclopropyl(4,4,4-trifluoro-3-(trifluoromethyl)butanamido)methyl)imidazo[1,2-b]pyridazin-2-yl)(4,4-difluorocyclohexyl)methyl)-1-isopropyl-1H-pyrazole-5-carboxamide

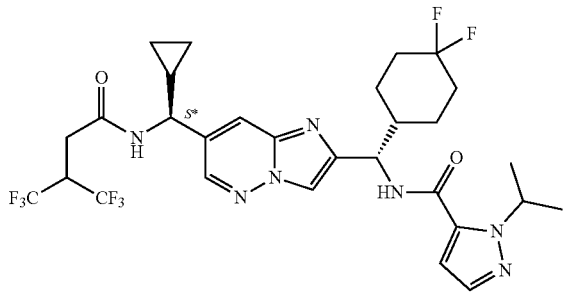 [SMILES: CC(C)n1nccc1C(=O)N[C@H](c1cn2ncc([C@@H](NC(=O)CC(C(F)(F)F)C(F)(F)F)C3CC3)cc2n1)C1CCC(F)(F)CC1]

N-((1S)-(7-(Cyclopropyl(4,4,4-trifluoro-3-(trifluoromethyl)butanamido)methyl)imidazo[1,2-b]pyridazin-2-yl)(4,4-difluorocyclohexyl)methyl)-1-isopropyl-1H-pyrazole-5-carboxamide (Intermediate 41) was purified by SFC using a chiral stationary phase (Regis (S,S) Whelk-O® 1, 30:70 MeOH (containing 0.1% (v/v) of 25% aqueous NH$_3$)/CO$_2$) to give a pair of diastereomers. The first-eluting isomer was Example 10, the major diastereomer. The second-eluting isomer was Example 11, the minor diastereomer. Example 10: $^1$H NMR (400 MHz, DMSO-d$_6$) δ 8.97 (d, J=7.6 Hz, 1H), 8.74 (d, J=9.0 Hz, 1H), 8.50 (d, J=2.0 Hz, 1H), 8.21 (s, 1H), 7.97-7.92 (m, 1H), 7.49 (d, J=2.0 Hz, 1H), 6.91 (d, J=2.0 Hz, 1H), 5.43-5.31 (m, 1H), 5.19-5.10 (m, 1H), 4.35-4.28 (m, 1H), 4.27-4.13 (m, 1H), 2.90-2.75 (m, 2H), 2.23-2.12 (m, 1H), 2.09-1.93 (m, 2H), 1.90-1.69 (m, 3H), 1.65-1.57 (m, 1H), 1.43-1.30 (m, 8H), 1.23-1.17 (m, 1H), 0.63-0.48 (m, 3H), 0.42-0.33 (m, 1H). MS (ESI) m/z: [M+H]$^+$ Found 664.3. Example 11: $^1$H NMR (400 MHz, DMSO-d$_6$) δ 9.01 (d, J=7.6 Hz, 1H), 8.74 (d, J=9.0 Hz, 1H), 8.50 (d, J=2.0 Hz, 1H), 8.21 (s, 1H), 7.99-7.92 (m, 1H), 7.49 (d, J=2.0 Hz, 1H), 6.92 (d, J=2.0 Hz, 1H), 5.43-5.30 (m, 1H), 5.20-5.09 (m, 1H), 4.34-4.27 (m, 1H), 4.27-4.14 (m, 1H), 2.90-2.75 (m, 2H), 2.23-2.12 (m, 1H), 2.07-1.93 (m, 2H), 1.90-1.71 (m, 3H), 1.65-1.57 (m, 1H), 1.45-1.31 (m, 8H), 1.23-1.17 (m, 1H), 0.65-0.50 (m, 3H), 0.43-0.32 (m, 1H). MS (ESI) m/z: [M+H]$^+$ Found 664.2.

Example 12

N—((S)-(7-((R*)-Cyclopropyl(4,4,4-trifluorobutanamido)methyl)imidazo[1,2-b]pyridazin-2-yl)(4,4-difluorocyclohexyl)methyl)benzamide

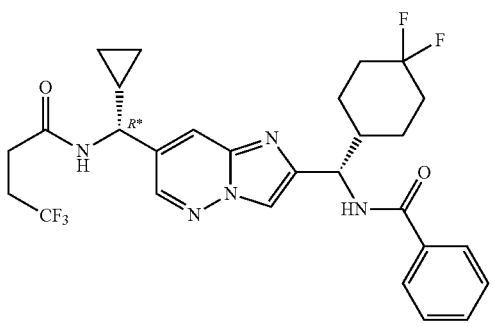 [SMILES: O=C(CCC(F)(F)F)N[C@@H](c1cnn2cc([C@@H](NC(=O)c3ccccc3)C3CCC(F)(F)CC3)nc2c1)C1CC1]

Example 13

N—((S)-(7-((S*)-Cyclopropyl(4,4,4-trifluorobutanamido)methyl)imidazo[1,2-b]pyridazin-2-yl)(4,4-difluorocyclohexyl)methyl)benzamide

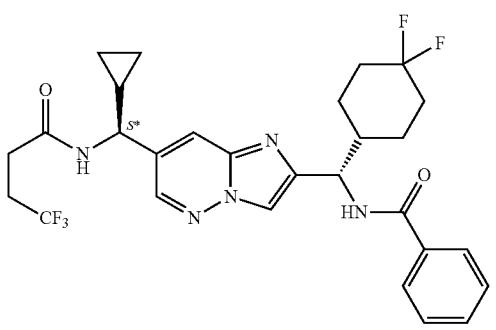 [SMILES: O=C(CCC(F)(F)F)N[C@H](c1cnn2cc([C@@H](NC(=O)c3ccccc3)C3CCC(F)(F)CC3)nc2c1)C1CC1]

N-((1S)-(7-(Cyclopropyl(4,4,4-trifluorobutanamido)methyl)imidazo[1,2-b]pyridazin-2-yl)(4,4-difluorocyclohexyl)methyl)benzamide (Intermediate 42) was purified by SFC using a chiral stationary phase (Daicel CHIRALPAK® AD-H, 35:65 i-PrOH (containing 0.1% (v/v) of 25% aqueous $NH_3$)/$CO_2$) to give a pair of diastereomers. The first-eluting isomer was Example 13, the minor diastereomer. The second-eluting isomer was Example 12, the major diastereomer. Example 12: $^1$H NMR (400 MHz, DMSO-$d_6$) δ 8.79-8.66 (m, 2H), 8.49 (d, J=2.0 Hz, 1H), 8.21 (s, 1H), 7.95-7.91 (m, 1H), 7.90-7.85 (m, 2H), 7.55-7.50 (m, 1H), 7.49-7.43 (m, 2H), 5.24-5.16 (m, 1H), 4.31-4.23 (m, 1H), 2.48-2.40 (m, 4H), 2.23-2.13 (m, 1H), 2.09-1.95 (m, 2H), 1.93-1.86 (m, 1H), 1.85-1.69 (m, 2H), 1.66-1.57 (m, 1H), 1.45-1.34 (m, 1H), 1.28-1.21 (m, 2H), 0.61-0.44 (m, 3H), 0.40-0.32 (m, 1H). MS (ESI) m/z: [M+H]$^+$ Found 564.2. Example 13: $^1$H NMR (400 MHz, DMSO-$d_6$) δ 8.76 (d, J=7.6 Hz, 1H), 8.71 (d, J=8.8 Hz, 1H), 8.49 (d, J=1.7 Hz, 1H), 8.21 (s, 1H), 7.94-7.90 (m, 1H), 7.89-7.84 (m, 2H), 7.56-7.50 (m, 1H), 7.49-7.42 (m, 2H), 5.23-5.16 (m, 1H), 4.30-4.24 (m, 1H), 2.48-2.42 (m, 4H), 2.24-2.13 (m, 1H), 2.07-1.95 (m, 2H), 1.93-1.86 (m, 1H), 1.85-1.67 (m, 2H), 1.66-1.56 (m, 1H), 1.44-1.34 (m, 1H), 1.29-1.23 (m, 2H), 0.61-0.44 (m, 3H), 0.40-0.31 (m, 1H). MS (ESI) m/z: [M+H]$^+$ Found 564.2.

Example 14

N—((S)-(7-((R*)-Cyclopropyl(4,4,4-trifluorobutanamido)methyl)imidazo[1,2-b]pyridazin-2-yl)(4,4-difluorocyclohexyl)methyl)-1-isopropyl-1H-pyrazole-5-carboxamide

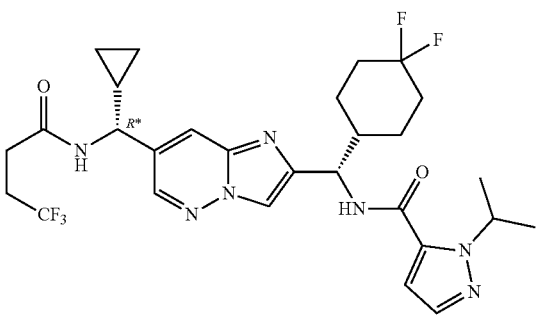 [SMILES: CC(C)n1nccc1C(=O)N[C@H](c1cn2ncc([C@H](NC(=O)CCC(F)(F)F)C3CC3)cc2n1)C1CCC(F)(F)CC1]

Example 15

N—((S)-(7-((S*)-Cyclopropyl(4,4,4-trifluorobutanamido)methyl)imidazo[1,2-b]pyridazin-2-yl)(4,4-difluorocyclohexyl)methyl)-1-isopropyl-1H-pyrazole-5-carboxamide

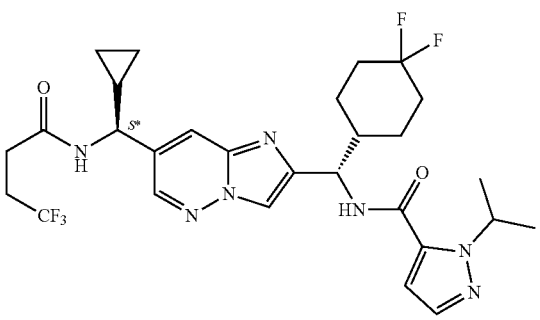 [SMILES: CC(C)n1nccc1C(=O)N[C@H](c1cn2ncc([C@@H](NC(=O)CCC(F)(F)F)C3CC3)cc2n1)C1CCC(F)(F)CC1]

N-((1S)-(7-(Cyclopropyl(4,4,4-trifluorobutanamido)methyl)imidazo[1,2-b]pyridazin-2-yl)(4,4-difluorocyclohexyl)methyl)-1-isopropyl-1H-pyrazole-5-carboxamide (Intermediate 43) was purified by SFC using a chiral stationary phase (Regis (S,S) Whelk-O® 1, 35:65 MeOH (containing 0.1% (v/v) of 25% aqueous $NH_3$)/$CO_2$) to give a pair of diastereomers. The first-eluting isomer was Example 14, the major diastereomer. The second-eluting isomer was Example 15, the minor diastereomer. Example 14: $^1$H NMR (400 MHz, DMSO-$d_6$) δ 8.79-8.70 (m, 2H), 8.51 (d, J=2.0 Hz, 1H), 8.20 (s, 1H), 7.96-7.91 (m, 1H), 7.49 (d, J=1.5 Hz, 1H), 6.92 (d, J=2.0 Hz, 1H), 5.44-5.30 (m, 1H), 5.20-5.11 (m, 1H), 4.33-4.24 (m, 1H), 2.50-2.43 (m, 4H), 2.23-2.12 (m, 1H), 2.10-1.93 (m, 2H), 1.92-1.68 (m, 3H), 1.66-1.58 (m, 1H), 1.44-1.27 (m, 8H), 1.23-1.17 (m, 2H), 0.62-0.46 (m, 3H), 0.42-0.34 (m, 1H). MS (ESI) m/z: [M+H]$^+$ Found 596.2. Example 15: $^1$H NMR (400 MHz, DMSO-$d_6$) δ 8.79-8.68 (m, 2H), 8.50 (d, J=1.7 Hz, 1H), 8.20 (s, 1H), 7.96-7.91 (m, 1H), 7.49 (d, J=1.7 Hz, 1H), 6.91 (d, J=2.0 Hz, 1H), 5.42-5.30 (m, 1H), 5.19-5.11 (m, 1H), 4.32-4.24 (m, 1H), 2.49-2.42 (m, 4H), 2.23-2.12 (m, 1H), 2.10-1.94 (m, 2H), 1.91-1.67 (m, 3H), 1.64-1.57 (m, 1H), 1.44-1.27 (m, 8H), 1.23-1.17 (m, 1H), 0.64-0.45 (m, 3H), 0.43-0.33 (m, 1H). MS (ESI) m/z: [M+H]⁺ Found 596.2.

Example 16

N—((S)-(7-((R*)-Cyclopropyl(4,4,4-trifluoro-3-(trifluoromethyl)butanamido)methyl)imidazo[1,2-b]pyridazin-2-yl)(4,4-difluorocyclohexyl)methyl)benzamide

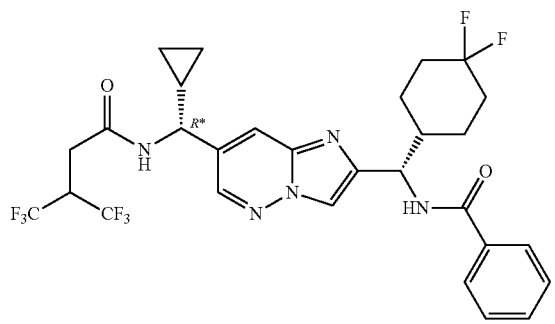 [SMILES: O=C(CC(C(F)(F)F)C(F)(F)F)N[C@@H](c1cnn2cc([C@@H](NC(=O)c3ccccc3)C3CCC(F)(F)CC3)nc2c1)C1CC1]

Example 17

N—((S)-(7-((S*)-Cyclopropyl(4,4,4-trifluoro-3-(trifluoromethyl)butanamido)methyl)imidazo[1,2-b]pyridazin-2-yl)(4,4-difluorocyclohexyl)methyl)benzamide

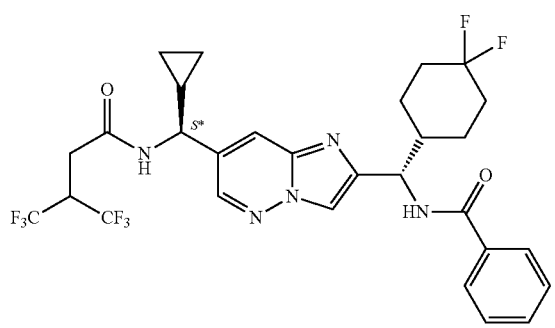 [SMILES: O=C(CC(C(F)(F)F)C(F)(F)F)N[C@H](c1cnn2cc([C@@H](NC(=O)c3ccccc3)C3CCC(F)(F)CC3)nc2c1)C1CC1]

N-((1S)-(7-(Cyclopropyl(4,4,4-trifluoro-3-(trifluoromethyl)butanamido)methyl)imidazo[1,2-b]pyridazin-2-yl)(4,4-difluorocyclohexyl)methyl)benzamide (Intermediate 44) was purified by SFC using a chiral stationary phase (Regis (S,S) Whelk-O® 1, 35:65 EtOH (containing 0.1% (v/v) of 25% aqueous NH₃)/CO₂) to give a pair of diastereomers. The first-eluting isomer was Example 16, the major diastereomer. The second-eluting isomer was Example 17, the minor diastereomer. Example 16: ¹H NMR (400 MHz, DMSO-d₆) δ 8.97 (d, J=7.6 Hz, 1H), 8.73 (d, J=9.0 Hz, 1H), 8.49 (d, J=2.0 Hz, 1H), 8.22 (s, 1H), 7.95 (d, J=1.7 Hz, 1H), 7.91-7.85 (m, 2H), 7.57-7.51 (m, 1H), 7.50-7.43 (m, 2H), 5.24-5.16 (m, 1H), 4.34-4.28 (m, 1H), 4.27-4.13 (m, 1H), 2.90-2.75 (m, 2H), 2.24-2.13 (m, 1H), 2.07-1.69 (m, 5H), 1.66-1.58 (m, 1H), 1.44-1.33 (m, 1H), 1.32-1.18 (m, 2H), 0.63-0.50 (m, 3H), 0.42-0.32 (m, 1H). MS (ESI) m/z: [M+H]⁺ Found 632.3. Example 17: ¹H NMR (400 MHz, DMSO-d₆) δ 8.98 (d, J=7.8 Hz, 1H), 8.73 (d, J=9.0 Hz, 1H), 8.49 (d, J=2.0 Hz, 1H), 8.23 (s, 1H), 7.96-7.92 (m, 1H), 7.91-7.84 (m, 2H), 7.57-7.50 (m, 1H), 7.49-7.41 (m, 2H), 5.24-5.17 (m, 1H), 4.34-4.27 (m, 1H), 4.26-4.13 (m, 1H), 2.89-2.76 (m, 2H), 2.25-2.12 (m, 1H), 2.05-1.71 (m, 5H), 1.66-1.58 (m, 1H), 1.45-1.33 (m, 1H), 1.30-1.22 (m, 2H), 0.62-0.50 (m, 3H), 0.41-0.33 (m, 1H). MS (ESI) m/z: [M+H]⁺ Found 632.3.

Example 18

N—((S)-(7-((R*)-Cyclopropyl(4,4,4-trifluorobutanamido)methyl)imidazo[1,2-b]pyridazin-2-yl)(4,4-difluorocyclohexyl)methyl)-2-(3,3,3-trifluoropropyl)-2H-1,2,3-triazole-4-carboxamide

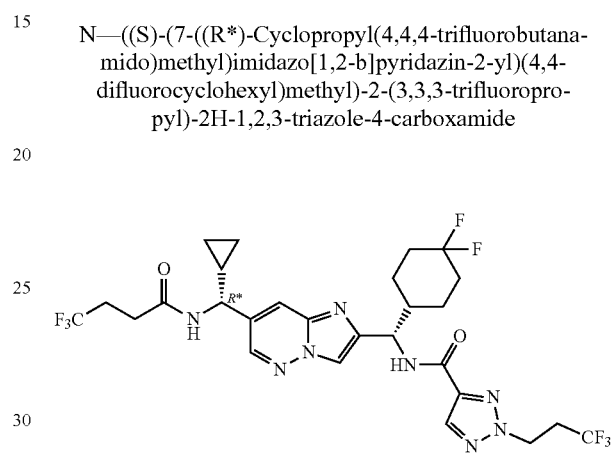

Example 19

N—((S)-(7-((S*)-Cyclopropyl(4,4,4-trifluorobutanamido)methyl)imidazo[1,2-b]pyridazin-2-yl)(4,4-difluorocyclohexyl)methyl)-2-(3,3,3-trifluoropropyl)-2H-1,2,3-triazole-4-carboxamide

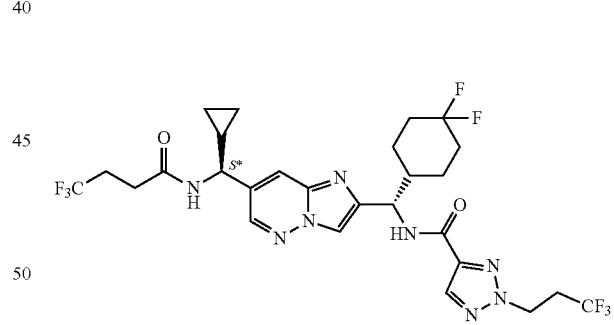

N—((S)-(7-(Cyclopropyl(4,4,4-trifluorobutanamido)methyl)imidazo[1,2-b]pyridazin-2-yl)(4,4-difluorocyclohexyl)methyl)-2-(3,3,3-trifluoropropyl)-2H-1,2,3-triazole-4-carboxamide (Intermediate 58) was resolved by SFC using a chiral stationary phase (Chiralpak IE, 5 μm, 250×21 mm, Mobile phase: 18% methanol, 82% CO₂, monitor at 220 nm) to give a pair of diastereomers. The first eluting fraction was condensed to afford Example 18, the major diastereomer, as a white powder. The second eluting fraction was condensed to afford Example 19, the minor diastereomer, as a white powder. Example 18: ¹H NMR (500 MHz, DMSO-d₆) δ 8.72 (d, J=7.6 Hz, 1H), 8.52 (d, J=9.1 Hz, 1H), 8.50 (d, J=2.0 Hz, 1H), 8.25-8.23 (m, 2H), 7.97-7.91 (m, 1H), 5.18 (t, J=8.8 Hz, 1H), 4.76 (t, J=6.6 Hz, 2H), 4.29 (t, J=8.4 Hz, 1H), 3.13-2.94 (m, 2H), 2.48-2.44 (m, 4H), 2.20-2.10 (m, 1H), 2.10-1.92 (m, 2H), 1.88 (br d, J=12.9 Hz, 1H), 1.85-1.67 (m, 2H), 1.58 (br d, J=13.6 Hz, 1H), 1.40-1.13 (m, 3H), 0.62-0.45 (m, 3H), 0.41-0.34 (m, 1H). MS (ESI) m/z: [M+H]⁺ Found 651.3. Example 19: ¹H NMR (500 MHz, DMSO-d₆) δ 8.71 (d, J=7.6 Hz, 1H), 8.59-8.45 (m, 2H), 8.28-8.17 (m, 2H), 8.04-7.85 (m, 1H), 5.17 (t, J=8.8 Hz, 1H), 4.76 (t, J=6.6 Hz, 2H), 4.29 (t, J=8.3 Hz, 1H), 3.13-2.96 (m, 2H), 2.48-2.42 (m, 4H), 2.20-2.10 (m, 1H), 2.10-1.93 (m, 2H), 1.93-1.85 (m, 1H), 1.85-1.67 (m, 2H), 1.58 (br d, J=12.4 Hz, 1H), 1.41-1.17 (m, 3H), 0.62-0.46 (m, 3H), 0.41-0.35 (m, 1H). MS (ESI) m/z: [M+H]⁺ Found 651.4.

Example 20

N—((S)-(7-((R*)-Cyclopropyl(2-(3,3-difluorocyclobutyl)acetamido)methyl)imidazo[1,2-b]pyridazin-2-yl)(4,4-difluorocyclohexyl)methyl)-1-(3,3,3-trifluoropropyl)-1H-pyrazole-3-carboxamide

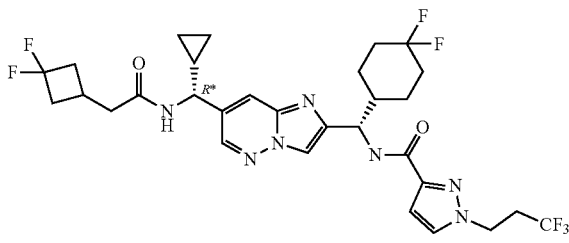 [SMILES: O=C(CC1CC(F)(F)C1)N[C@@H](c1cnn2cc([C@@H](NC(=O)c3ccn(CCC(F)(F)F)n3)C3CCC(F)(F)CC3)nc2c1)C1CC1]

N—((S)-(7-(Cyclopropyl(2-(3,3-difluorocyclobutyl)acetamido)methyl)imidazo[1,2-b]pyridazin-2-yl)(4,4-difluorocyclohexyl)methyl)-1-(3,3,3-trifluoropropyl)-1H-pyrazole-3-carboxamide (Intermediate 59) was resolved by SFC using a chiral stationary phase (Whelk-01 (S,S) 2×25 cm, mobile phase: 40% isopropanol (0.1% DEA/CO₂, 100 bar, 65 mL/min monitor at 220 nm) to yield a pair of diastereomers. The second eluting compound was condensed to afford the title compound, the major diastereomer, as a white powder. ¹H NMR (400 MHz, CD₃OD,) δ 8.47 (d, J=2.1 Hz, 1H), 8.12 (s, 1H), 7.93-7.83 (m, 1H), 7.75 (d, J=2.4 Hz, 1H), 6.75 (d, J=2.4 Hz, 1H), 5.26 (d, J=8.5 Hz, 1H), 4.50 (t, J=7.1 Hz, 2H), 4.28 (d, J=9.4 Hz, 1H), 2.95-2.83 (m, 2H), 2.78-2.64 (m, 2H), 2.56-2.46 (m, 3H), 2.39-2.16 (m, 3H), 2.15-1.96 (m, 3H), 1.91-1.69 (m, 2H), 1.68-1.60 (m, 1H), 1.56-1.34 (m, 2H), 1.32-1.23 (m, 1H), 0.77-0.68 (m, 2H), 0.56-0.46 (m, 2H). MS (ESI) m/z: [M+H]⁺ Found 658.3.

Example 21

N—((S)-(7-((R*)-Cyclopropyl(4,4,4-trifluorobutanamido)methyl)imidazo[1,2-b]pyridazin-2-yl)(4,4-difluorocyclohexyl)methyl)-1-(3,3,3-trifluoropropyl)-1H-pyrazole-3-carboxamide

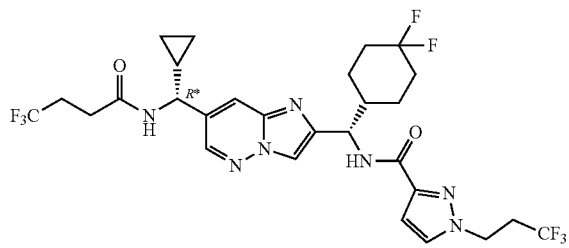 [SMILES: O=C(CCC(F)(F)F)N[C@@H](c1cnn2cc([C@@H](NC(=O)c3ccn(CCC(F)(F)F)n3)C3CCC(F)(F)CC3)nc2c1)C1CC1]

N—((S)-(7-(Cyclopropyl(4,4,4-trifluorobutanamido)methyl)imidazo[1,2-b]pyridazin-2-yl)(4,4-difluorocyclohexyl)methyl)-1-(3,3,3-trifluoropropyl)-1H-pyrazole-3-carboxamide (Intermediate 60) was resolved by SFC using a chiral stationary phase (Whelk-01 (S,S) 2×25 cm, mobile phase: 30% methanol (0.1% DEA/CO₂, 100 bar, 65 mL/min monitor at 220 nm) to yield a pair of diastereomers. The second eluting compound was condensed to afford the title compound, the major diastereomer, as a white powder. ¹H NMR (500 MHz, CD₃OD,) δ 8.48 (s, 1H), 8.12 (d, J=0.9 Hz, 1H), 7.90 (s, 1H), 7.79-7.64 (m, 1H), 6.75 (t, J=2.1 Hz, 1H), 5.26 (d, J=8.3 Hz, 1H), 4.55-4.42 (m, 2H), 4.29 (d, J=9.5 Hz, 1H), 2.96-2.83 (m, 2H), 2.62-2.44 (m, 4H), 2.27-1.95 (m, 4H), 1.90-1.68 (m, 2H), 1.66-1.60 (m, 1H), 1.57-1.34 (m, 2H), 1.33-1.23 (m, 1H), 0.77-0.68 (m, 2H), 0.55-0.49 (m, 2H). MS (ESI) m/z: [M+H]⁺ Found 650.3.

Example 22

N—((S)-(7-((R*)-Cyclopropyl(2-(3,3-difluorocyclobutyl)acetamido)methyl)imidazo[1,2-b]pyridazin-2-yl)(4,4-difluorocyclohexyl)methyl)-2-(3,3,3-trifluoropropyl)-2H-1,2,3-triazole-4-carboxamide

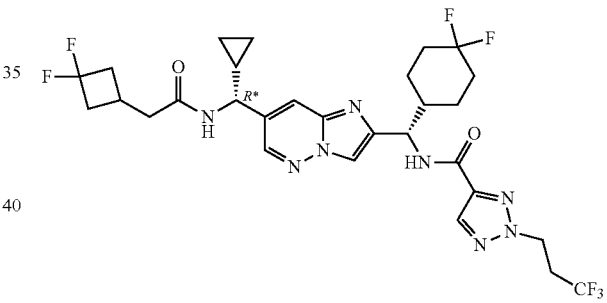

N—((S)-(7-(Cyclopropyl(2-(3,3-difluorocyclobutyl)acetamido)methyl)imidazo[1,2-b]pyridazin-2-yl)(4,4-difluorocyclohexyl)methyl)-2-(3,3,3-trifluoropropyl)-2H-1,2,3-triazole-4-carboxamide (Intermediate 61) was resolved by SFC using a chiral stationary phase (AD-H 3×25 cm, Mobile phase: 30% ethanol/CO₂, 100 bar, 65 mL/min, monitor at 220 nm) to yield a pair of diastereomers. The second eluting compound was condensed to afford the title compound, the major diastereomer, as a white powder. ¹H NMR (500 MHz, DMSO-d₆) δ 8.59 (d, J=7.8 Hz, 1H), 8.53 (d, J=9.1 Hz, 1H), 8.49 (d, J=2.0 Hz, 1H), 8.24 (d, J=1.8 Hz, 2H), 7.94 (s, 1H), 5.17 (t, J=8.8 Hz, 1H), 4.76 (t, J=6.6 Hz, 2H), 4.27 (t, J=8.4 Hz, 1H), 3.13-2.97 (m, 2H), 2.69-2.60 (m, 2H), 2.39 (br s, 3H), 2.35-2.23 (m, 2H), 2.20-2.11 (m, 1H), 2.09-1.93 (m, 2H), 1.93-1.85 (m, 1H), 1.85-1.67 (m, 2H), 1.64-1.54 (m, 1H), 1.42-1.15 (m, 3H), 0.62-0.42 (m, 3H 0.39-0.33 (m, 1H). MS (ESI) m/z: [M+H]⁺ Found 659.3.

Example 23

N—((S)-(7-((R*)-Cyclopropyl(4,4,4-trifluorobutanamido)methyl)imidazo[1,2-b]pyridazin-2-yl)(4,4-difluorocyclohexyl)methyl)-1-methyl-1H-pyrazole-5-carboxamide

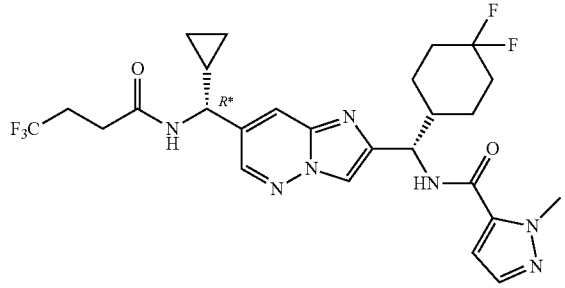 [SMILES: Cn1nccc1C(=O)N[C@H](c1cn2ncc([C@H](NC(=O)CCC(F)(F)F)C3CC3)cc2n1)C1CCC(F)(F)CC1]

N—((S)-(7-(Cyclopropyl(4,4,4-trifluorobutanamido)methyl)imidazo[1,2-b]pyridazin-2-yl)(4,4-difluorocyclohexyl)methyl)-1-methyl-1H-pyrazole-5-carboxamide (Intermediate 62) was resolved by SFC using a chiral stationary phase (Whelk-01 (S,S) 2×25 cm, mobile phase: 25% methanol/CO$_2$, 100 bar, 65 mL/min, monitor at 220 nm) to yield a pair of diastereomers. The first eluting compound was condensed to afford the title compound, the major diastereomer, as a white powder. $^1$H NMR (500 MHz, DMSO-d$_6$) δ 8.72-8.68 (m, 2H), 8.50 (d, J=2.0 Hz, 1H), 8.20 (s, 1H), 7.93 (d, J=2.0 Hz, 1H), 7.45 (d, J=2.0 Hz, 1H), 7.01 (d, J=2.1 Hz, 1H), 5.14 (t, J=8.7 Hz, 1H), 4.29 (t, J=8.4 Hz, 1H), 4.01 (s, 3H), 2.49-2.42 (m, 4H), 2.23-2.12 (m, 1H), 2.10-1.93 (m, 2H), 1.93-1.85 (m, 1H), 1.84-1.68 (m, 2H), 1.64-1.57 (m, 1H), 1.43-1.15 (m, 3H), 0.62-0.45 (m, 3H), 0.40-0.34 m, 1H). MS (ESI) m/z: [M+H]$^+$ Found 658.3.

Example 24

N—((S)-(7-((R*)-Cyclopropyl(2-(3,3-difluorocyclobutyl)acetamido)methyl)imidazo[1,2-b]pyridazin-2-yl)(4,4-difluorocyclohexyl)methyl)-1-methyl-1H-pyrazole-5-carboxamide

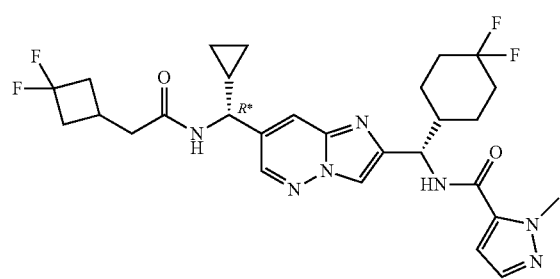 [SMILES: Cn1nccc1C(=O)N[C@H](c1cn2ncc([C@H](NC(=O)CC3CC(F)(F)C3)C3CC3)cc2n1)C1CCC(F)(F)CC1]

N—((S)-(7-(Cyclopropyl(2-(3,3-difluorocyclobutyl)acetamido)methyl)imidazo[1,2-b]pyridazin-2-yl)(4,4-difluorocyclohexyl)methyl)-1-methyl-1H-pyrazole-5-carboxamide (Intermediate 63) was resolved by SFC using a chiral stationary phase (Whelk-01 (S,S) 2×25 cm, mobile phase: 30% methanol/CO$_2$, 100 bar, 65 mL/min, monitor at 220 nm) to yield a pair of diastereomers. The first eluting compound was condensed to afford the title compound, the major diastereomer, as a white powder. $^1$H NMR (400 MHz, DMSO-d$_6$) δ 8.70 (d, J=9.0 Hz, 1H), 8.59 (d, J=7.9 Hz, 1H), 8.49 (d, J=2.0 Hz, 1H), 8.20 (s, 1H), 7.91 (d, J=2.0 Hz, 1H), 7.45 (d, J=2.0 Hz, 1H), 7.01 (d, J=2.0 Hz, 1H), 5.14 (t, J=8.7 Hz, 1H), 4.26 (t, J=8.3 Hz, 1H), 4.01 (s, 3H), 2.70-2.54 (m, 2H), 2.44-2.36 (m, 3H), 2.36-2.14 (m, 3H), 2.10-1.94 (m, 2H), 1.93-1.67 (m, 3H), 1.65-1.55 (m, 1H), 1.44-1.33 (m, 1H), 1.31-1.17 (m, 2H), 0.62-0.42 (m, 3H), 0.39-0.33 (m, 1H). MS (ESI) m/z: [M+H]$^+$ Found 576.3.

Example 25

N—((S)-(7-((R*)-Cyclopropyl(4,4,4-trifluorobutanamido)methyl)imidazo[1,2-b]pyridazin-2-yl)(4,4-difluorocyclohexyl)methyl)-2-(cyclopropylmethyl)-2H-1,2,3-triazole-4-carboxamide

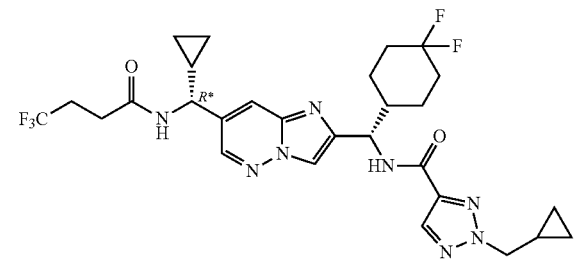 [SMILES: O=C(CCC(F)(F)F)N[C@@H](c1cnn2cc([C@@H](NC(=O)c3cnn(CC4CC4)n3)C3CCC(F)(F)CC3)nc2c1)C1CC1]

N—((S)-(7-(Cyclopropyl(4,4,4-trifluorobutanamido)methyl)imidazo[1,2-b]pyridazin-2-yl)(4,4-difluorocyclohexyl)methyl)-2-(cyclopropylmethyl)-2H-1,2,3-triazole-4-carboxamide (Intermediate 64) was resolved by SFC using a chiral stationary phase (Whelk-01 (S,S) 2×25 cm, mobile phase: 35% methanol (DEA)/CO$_2$, 100 bar, 65 mL/min, monitor at 220 nm) to yield a pair of diastereomers. The first eluting compound was condensed to afford the title compound, the major diastereomer, as a white powder. $^1$H NMR (500 MHz, DMSO-d$_6$) δ 8.71 (d, J=7.6 Hz, 1H), 8.50 (d, J=2.1 Hz, 1H), 8.47 (d, J=9.1 Hz, 1H), 8.24 (s, 1H), 8.18 (s, 1H), 7.95 (d, J=1.8 Hz, 1H), 5.18 (t, J=8.7 Hz, 1H), 4.35 (d, J=7.4 Hz, 2H), 4.29 (t, J=8.3 Hz, 1H), 2.49-2.42 (m, 4H), 2.19-2.10 (m, 1H), 2.09-1.93 (m, 2H), 1.92-1.85 (m, 1H), 1.85-1.66 (m, 2H), 1.62-1.53 (m, 1H), 1.41-1.30 (m, 2H), 1.29-1.17 (m, 2H), 0.61-0.47 (m, 5H), 0.45-0.34 (m, 3H). MS (ESI) m/z: [M+H]$^+$ Found 609.3.

Example 26

N—((S)-(7-((R*)-Cyclopropyl(2-(3,3-difluorocyclobutyl)acetamido)methyl)imidazo[1,2-b]pyridazin-2-yl)(4,4-difluorocyclohexyl)methyl)-2-(cyclopropylmethyl)-2H-1,2,3-triazole-4-carboxamide

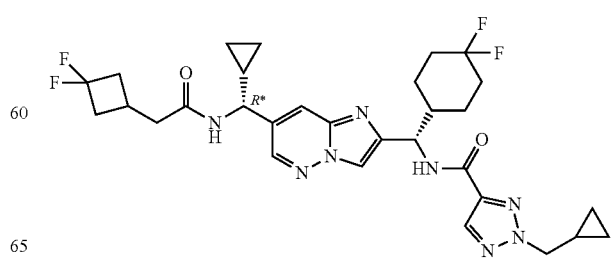

N—((S)-(7-(Cyclopropyl(2-(3,3-difluorocyclobutyl)acetamido)methyl)imidazo[1,2-b]pyridazin-2-yl)(4,4-difluorocyclohexyl)methyl)-2-(cyclopropylmethyl)-2H-1,2,3-triazole-4-carboxamide (Intermediate 65) was resolved using SFC with a chiral stationary phase (Whelk-01 (S,S) 2×25 cm, mobile phase: 35% methanol (DEA)/CO$_2$, 100 bar, 65 mL/min, monitor at 220 nm) to yield a pair of diastereomers. The first eluting compound was condensed to afford the title compound, the major diastereomer, as a white powder. $^1$H NMR (500 MHz, DMSO-d$_6$) δ 8.58 (d, J=7.9 Hz, 1H), 8.51-8.44 (m, 2H), 8.24 (s, 1H), 8.18 (s, 1H), 7.94 (d, J=1.9 Hz, 1H), 5.18 (t, J=8.7 Hz, 1H), 4.35 (d, J=7.3 Hz, 2H), 4.27 (t, J=8.4 Hz, 1H), 2.70-2.56 (m, 2H), 2.43-2.36 (m, 3H), 2.35-2.23 (m, 2H), 2.20-2.10 (m, 1H), 2.08-1.93 (m, 2H), 1.92-1.85 (m, 1H), 1.85-1.66 (m, 2H), 1.62-1.54 (m, 1H), 1.39-1.30 (m, 2H), 1.29-1.16 (m, 2H), 0.61-0.50 (m, 4H), 0.50-0.45 (m, 1H), 0.45-0.40 (m, 2H), 0.39-0.33 (m, 1H). MS (ESI) m/z: [M+H]$^+$ Found 617.3.

Example 27

N—((S)-(7-((R*)-Cyclopropyl(4,4,4-trifluorobutanamido)methyl)imidazo[1,2-b]pyridazin-2-yl)(4,4-difluorocyclohexyl)methyl)-2-(2,2,2-trifluoroethyl)-2H-1,2,3-triazole-4-carboxamide

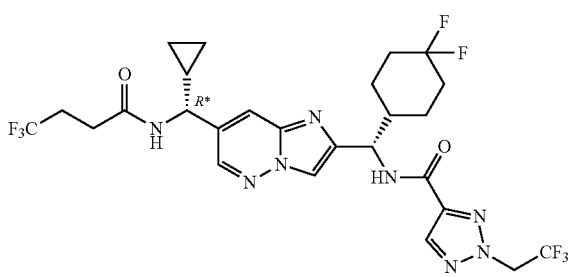 [SMILES: O=C(CCC(F)(F)F)N[C@@H](c1cnn2cc([C@@H](NC(=O)c3cnn(CC(F)(F)F)n3)C3CCC(F)(F)CC3)nc2c1)C1CC1]

N—((S)-(7-(Cyclopropyl(4,4,4-trifluorobutanamido)methyl)imidazo[1,2-b]pyridazin-2-yl)(4,4-difluorocyclohexyl)methyl)-2-(2,2,2-trifluoroethyl)-2H-1,2,3-triazole-4-carboxamide (Intermediate 66) was resolved by SFC using a chiral stationary phase (Whelk-01 (S,S) 2×25 cm, mobile phase: 30% methanol/CO$_2$, 100 bar, 65 mL/min, monitor at 220 nm) to yield a pair of diastereomers. The first eluting compound was condensed to afford the title compound, the major diastereomer, as a white powder. $^1$H NMR (500 MHz, DMSO-d$_6$) δ 8.71 (d, J=7.8 Hz, 1H), 8.63 (d, J=9.1 Hz, 1H), 8.50 (d, J=2.1 Hz, 1H), 8.39 (s, 1H), 8.25 (s, 1H), 7.95 (d, J=2.0 Hz, 1H), 5.64 (q, J=8.9 Hz, 2H), 5.18 (t, J=8.7 Hz, 1H), 4.29 (t, J=8.4 Hz, 1H), 2.48-2.42 (m, 4H), 2.22-2.11 (m, 1H), 2.09-1.93 (m, 2H), 1.93-1.86 (m, 1H), 1.85-1.67 (m, 2H), 1.62-1.54 (m, 1H), 1.40-1.17 (m, 3H), 0.62-0.46 (m, 3H), 0.42-0.34 (m, 1H). MS (ESI) m/z: [M+H]$^+$ Found 637.2.

Example 28

N—((S)-(7-((R*)-Cyclopropyl(2-(3,3-difluorocyclobutyl)acetamido)methyl)imidazo[1,2-b]pyridazin-2-yl)(4,4-difluorocyclohexyl)methyl)-2-(2,2,2-trifluoroethyl)-2H-1,2,3-triazole-4-carboxamide

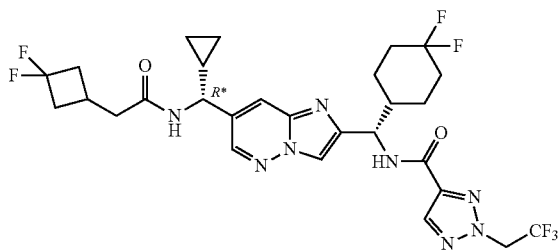 [SMILES: O=C(CC1CC(F)(F)C1)N[C@@H](c1cnn2cc([C@@H](NC(=O)c3cnn(CC(F)(F)F)n3)C3CCC(F)(F)CC3)nc2c1)C1CC1]

N—((S)-(7-(Cyclopropyl(2-(3,3-difluorocyclobutyl)acetamido)methyl)imidazo[1,2-b]pyridazin-2-yl)(4,4-difluorocyclohexyl)methyl)-2-(2,2,2-trifluoroethyl)-2H-1,2,3-triazole-4-carboxamide (Intermediate 67) was resolved by SFC using a chiral stationary phase (Whelk-01 (S,S) 2×25 cm, mobile phase: 35% methanol/CO$_2$, 100 bar, 65 mL/min, monitor at 220 nm) to yield a pair of diastereomers. The first eluting compound was condensed to afford the title compound, the major diastereomer, as a white powder. $^1$H NMR (500 MHz, DMSO-d$_6$) δ 8.64 (d, J=9.0 Hz, 1H), 8.59 (d, J=7.9 Hz, 1H), 8.50 (d, J=2.0 Hz, 1H), 8.39 (s, 1H), 8.25 (s, 1H), 7.94 (d, J=1.9 Hz, 1H), 5.64 (q, J=8.9 Hz, 2H), 5.18 (t, J=8.7 Hz, 1H), 4.27 (t, J=8.4 Hz, 1H), 2.72-2.55 (m, 2H), 2.44-2.36 (m, 3H), 2.36-2.23 (m, 2H), 2.21-2.12 (m, 1H), 2.09-1.93 (m, 2H), 1.94-1.85 (m, 1H), 1.85-1.66 (m, 2H), 1.62-1.54 (m, 1H), 1.43-1.30 (m, 1H), 1.30-1.15 (m, 2H), 0.61-0.50 (m, 2H), 0.50-0.44 (m, 1H), 0.40-0.33 (m, 1H). MS (ESI) m/z: [M+H]$^+$ Found 645.3.

Example 29

N—((S)-(7-((R*)-Cyclopropyl((R)-2-hydroxy-3,3-dimethylbutanamido)methyl)imidazo[1,2-b]pyridazin-2-yl)(4,4-difluorocyclohexyl)methyl)-2-(cyclopropylmethyl)-2H-1,2,3-triazole-4-carboxamide

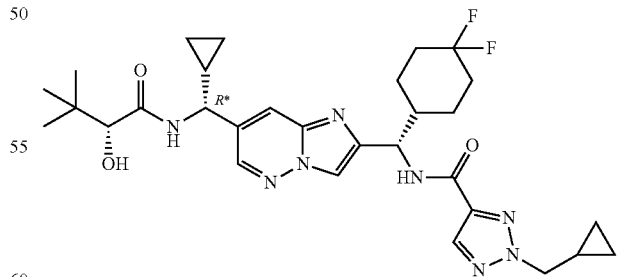

N—((S)-(7-(Cyclopropyl((R)-2-hydroxy-3,3-dimethylbutanamido)methyl)imidazo[1,2-b]pyridazin-2-yl)(4,4-difluorocyclohexyl)methyl)-2-(cyclopropylmethyl)-2H-1,2,3-triazole-4-carboxamide (Intermediate 68) was resolved by SFC using a chiral stationary phase (Whelk-01 (S,S) 2×25 cm, mobile phase: 30% isopropanol (0.1% DEA)/CO$_2$, 100 bar, 60 mL/min, monitor at 220 nm) to yield a pair of diastereomers. The first eluting compound was condensed to afford the title compound, the major diastereomer, as a white powder. $^1$H NMR (500 MHz, DMSO-d$_6$) δ 8.58 (d, J=2.1 Hz, 1H), 8.46 (d, J=9.1 Hz, 1H), 8.29 (d, J=8.4 Hz, 1H), 8.23 (s, 1H), 8.18 (s, 1H), 8.02 (d, J=2.0 Hz, 1H), 5.58 (d, J=5.3 Hz, 1H), 5.18 (t, J=8.6 Hz, 1H), 4.35 (d, J=7.3 Hz, 2H), 4.24 (t, J=9.1 Hz, 1H), 3.54 (d, J=5.4 Hz, 1H), 2.19-2.10 (m, 1H), 2.09-1.92 (m, 2H), 1.92-1.85 (m, 1H), 1.84-1.66 (m, 2H), 1.64-1.54 (m, 1H), 1.43-1.30 (m, 3H), 1.28-1.19 (m, 1H), 0.92 (s, 9H), 0.59-0.50 (m, 5H), 0.45-0.39 (m, 2H), 0.34-0.28 (m, 1H). MS (ESI) m/z: [M+H]$^+$ Found 599.3.

Example 30

N—((S)-(7-((R*)-Cyclopropyl((R*)-4,4,4-trifluoro-2-hydroxybutanamido)methyl)imidazo[1,2-b]pyridazin-2-yl)(4,4-difluorocyclohexyl)methyl)-2-(2,2,2-trifluoroethyl)-2H-1,2,3-triazole-4-carboxamide

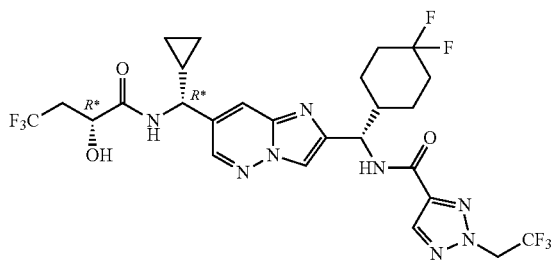 [SMILES: O=C(N[C@H](c1cn2ncc([C@H](NC(=O)[C@H](O)CC(F)(F)F)C3CC3)cc2n1)C1CCC(F)(F)CC1)c1cnn(CC(F)(F)F)n1]

Example 31

N—((S)-(7-((R*)-Cyclopropyl((S*)-4,4,4-trifluoro-2-hydroxybutanamido)methyl)imidazo[1,2-b]pyridazin-2-yl)(4,4-difluorocyclohexyl)methyl)-2-(2,2,2-trifluoroethyl)-2H-1,2,3-triazole-4-carboxamide

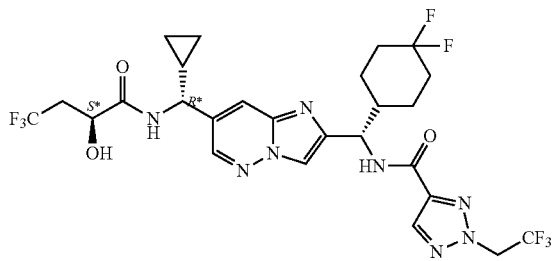 [SMILES: O=C(N[C@H](c1cn2ncc([C@H](NC(=O)[C@@H](O)CC(F)(F)F)C3CC3)cc2n1)C1CCC(F)(F)CC1)c1cnn(CC(F)(F)F)n1]

N-((1S)-(7-(Cyclopropyl(4,4,4-trifluoro-2-hydroxybutanamido)methyl)imidazo[1,2-b]pyridazin-2-yl)(4,4-difluorocyclohexyl)methyl)-2-(2,2,2-trifluoroethyl)-2H-1,2,3-triazole-4-carboxamide (Intermediate 69) was resolved by SFC using a chiral stationary phase (Whelk-01 (S,S) 2×25 cm, mobile phase: 30% isopropanol (0.1% DEA)/CO$_2$, 100 bar, 60 mL/min, monitor at 220 nm) to yield a set of four diastereomers. The first eluting fraction was condensed to afford Example 30, a co-major diastereomer, as a white powder. The third eluting fraction was condensed to afford Example 31, a co-major diastereomer, as a white powder. Example 30: $^1$H NMR (400 MHz, DMSO-d$_6$) δ 8.70 (d, J=8.1 Hz, 1H), 8.62 (d, J=9.0 Hz, 1H), 8.58 (d, J=2.0 Hz, 1H), 8.38 (s, 1H), 8.24 (s, 1H), 8.02 (d, J=2.0 Hz, 1H), 6.14 (d, J=6.3 Hz, 1H), 5.64 (q, J=8.8 Hz, 2H), 5.18 (t, J=8.6 Hz, 1H), 4.26-4.16 (m, 2H), 2.76-2.60 (m, 1H), 2.22-2.10 (m, 1H), 2.10-1.94 (m, 2H), 1.93-1.85 (m, 1H), 1.83-1.67 (m, 2H), 1.63-1.54 (m, 1H), 1.46-1.32 (m, 2H), 1.31-1.16 (m, 2H), 0.63-0.47 (m, 3H), 0.40-0.30 (m, 1H). MS (ESI) m/z: [M+H]$^+$ Found 653.2. Example 31: $^1$H NMR (400 MHz, DMSO-d$_6$) δ 8.71 (d, J=8.3 Hz, 1H), 8.63 (d, J=9.1 Hz, 1H), 8.57 (d, J=2.0 Hz, 1H), 8.38 (s, 1H), 8.24 (s, 1H), 8.00 (d, J=2.0 Hz, 1H), 6.16 (d, J=6.5 Hz, 1H), 5.64 (q, J=8.9 Hz, 2H), 5.18 (t, J=8.7 Hz, 1H), 4.32-4.16 (m, 2H), 2.71-2.57 (m, 1H), 2.22-2.11 (m, 1H), 2.09-1.94 (m, 2H), 1.93-1.86 (m, 1H), 1.84-1.66 (m, 2H), 1.62-1.53 (m, 1H), 1.47-1.32 (m, 2H), 1.31-1.18 (m, 2H), 0.61-0.46 (m, 3H), 0.41-0.32 (m, 1H). MS (ESI) m/z: [M+H]$^+$ Found 653.2.

Example 32

N—((S)-(7-((R)-Cyclopropyl(4,4,4-trifluorobutanamido)methyl)imidazo[1,2-b]pyridazin-2-yl)(4,4-difluorocyclohexyl)methyl)-2-(3,3-difluoropropyl)-2H-1,2,3-triazole-4-carboxamide

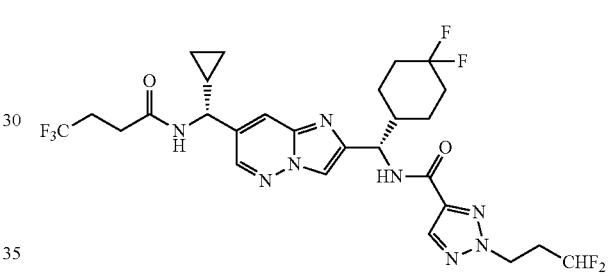

A vial was charged with a stir bar, 2-(3,3-difluoropropyl)-2H-1,2,3-triazole-4-carboxylic acid (54 mg, 0.28 mmol, Intermediate 102), HATU (110 mg, 0.28 mmol) and DMF (1 mL). The solution was stirred for 5 min then N—((R)-(2-((S)-amino(4,4-difluorocyclohexyl)methyl)imidazo[1,2-b]pyridazin-7-yl)(cyclopropyl)methyl)-4,4,4-trifluorobutanamide (100 mg, 0.22 mmol, Intermediate 51), and Hünig's base (0.075 mL, 0.42 mmol) were added and the reaction was stirred for a further 30 min. The reaction was poured over water and diluted with ethyl acetate. The layers were separated the aqueous phase was further extracted with ethyl acetate (2×5 mL). The combined organic extracts were washed with 10% aqueous LiCl, then brine, dried over anhydrous MgSO$_4$, filtered and condensed. The crude material was purified by silica gel chromatography (0-100% ethyl acetate (with 10% MeOH)/hexanes). The product containing fractions were condensed into a glassy solid. The material was further purified by reverse phase basic HPLC (Gemini® 5 μM C18 110 Å, 150×21.2 mm, 0-100% acetonitrile/water (with 20 mM NH$_4$OH). The product containing fractions were lyophilized to afford the title compound as a white powder. $^1$H NMR (500 MHz, DMSO-d$_6$) δ 8.71 (d, J=7.6 Hz, 1H), 8.54-8.48 (m, 2H), 8.24 (s, 1H), 8.21 (s, 1H), 7.97-7.94 (m, 1H), 6.37-6.05 (m, 1H), 5.17 (t, J=8.8 Hz, 1H), 4.65 (t, J=6.9 Hz, 2H), 4.29 (t, J=8.3 Hz, 1H), 2.59-2.52 (m, 2H), 2.49-2.43 (m, 4H), 2.21-2.11 (m, 1H), 2.09-1.93 (m, 1H), 1.92-1.85 (m, 1H), 1.85-1.66 (m, 2H), 1.62-1.54 (m, 1H), 1.42-1.30 (m, 1H), 1.29-1.17 (m, 1H), 0.61-0.55 (m, 1H), 0.55-0.46 (m, 2H), 0.42-0.32 (m, 1H). MS (ESI) m/z: [M+H]$^+$ Found 633.3.

Example 33

N—((S)-(7-((R)-Cyclopropyl(4,4,4-trifluorobutanamido)methyl)imidazo[1,2-b]pyridazin-2-yl)(4,4-difluorocyclohexyl)methyl)-1-(3,3,3-trifluoropropyl)-1H-1,2,4-triazole-3-carboxamide

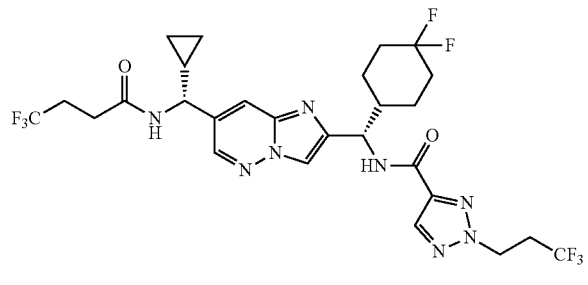 [SMILES: O=C(CCC(F)(F)F)N[C@@H](c1cnn2cc([C@@H](NC(=O)c3cnn(CCC(F)(F)F)n3)C3CCC(F)(F)CC3)nc2c1)C1CC1]

The title compound was prepared as described for Example 32 using 1-(3,3,3-trifluoropropyl)-1H-1,2,4-triazole-3-carboxylic acid (Intermediate 153) in place of 2-(3,3-difluoropropyl)-2H-1,2,3-triazole-4-carboxylic acid to afford the title compound as a white powder. $^1$H NMR (400 MHz, DMSO-$d_6$) δ 8.73 (s, 1H), 8.71 (d, J=7.6 Hz, 1H), 8.51 (d, J=2.0 Hz, 1H), 8.45 (d, J=9.1 Hz, 1H), 8.25 (s, 1H), 7.98 (d, J=2.0 Hz, 1H), 5.17 (t, J=8.6 Hz, 1H), 4.54 (t, J=6.8 Hz, 2H), 4.29 (t, J=8.3 Hz, 1H), 3.05-2.86 (m, 2H), 2.54 (br s, 1H), 2.49-2.44 (m, 3H), 2.18-2.06 (m, 1H), 2.06-1.91 (m, 2H), 1.91-1.84 (m, 1H), 1.83-1.64 (m, 2H), 1.63-1.53 (m, 1H), 1.39-1.27 (m, 1H), 1.26-1.16 (m, 2H), 0.62-0.46 (m, 3H), 0.42-0.33 (m, 1H). MS (ESI) m/z: [M+H]$^+$ Found 651.3.

Example 34

N—((S)-(7-((R)-Cyclopropyl(4,4,4-trifluorobutanamido)methyl)imidazo[1,2-b]pyridazin-2-yl)(4,4-difluorocyclohexyl)methyl)-1-(2-(difluoromethoxy)ethyl)-1H-1,2,3-triazole-5-carboxamide

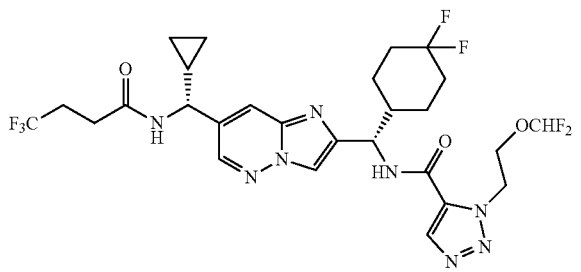 [SMILES: O=C(CCC(F)(F)F)N[C@@H](c1cnn2cc([C@@H](NC(=O)c3cnnn3CCOC(F)F)C3CCC(F)(F)CC3)nc2c1)C1CC1]

The title compound was prepared as described for Example 32 using 1-(2-(difluoromethoxy)ethyl)-1H-1,2,3-triazole-5-carboxylic acid (Intermediate 112) in place of 2-(3,3-difluoropropyl)-2H-1,2,3-triazole-4-carboxylic acid to afford the title compound as a white powder. $^1$H NMR (400 MHz, DMSO-$d_6$) δ 9.15 (d, J=8.9 Hz, 1H), 8.72 (d, J=7.6 Hz, 1H), 8.51 (d, J=2.1 Hz, 1H), 8.39 (s, 1H), 8.22 (s, 1H), 7.93 (d, J=2.0 Hz, 1H), 6.83-6.15 (m, 1H), 5.16 (t, J=8.6 Hz, 1H), 4.99-4.75 (m, 2H), 4.32-4.17 (m, 3H), 2.56-2.53 (m, 1H), 2.49-2.43 (m, 3H), 2.26-2.13 (m, 1H), 2.10-1.93 (m, 2H), 1.93-1.85 (m, 1H), 1.84-1.67 (m, 2H), 1.66-1.57 (m, 1H), 1.46-1.32 (m, 1H), 1.32-1.15 (m, 2H), 0.63-0.45 (m, 3H), 0.42-0.31 (m, 1H). MS (ESI) m/z: [M+H]$^+$ Found 649.3.

Example 35

N—((S)-(7-((R)-Cyclopropyl(4,4,4-trifluorobutanamido)methyl)imidazo[1,2-b]pyridazin-2-yl)(4,4-difluorocyclohexyl)methyl)-2-(2-(difluoromethoxy)ethyl)-2H-1,2,3-triazole-4-carboxamide

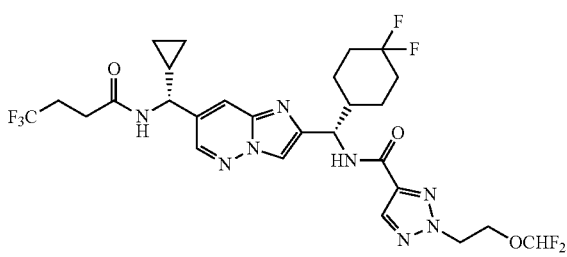 [SMILES: O=C(CCC(F)(F)F)N[C@@H](c1cnn2cc([C@@H](NC(=O)c3cnn(CCOC(F)F)n3)C3CCC(F)(F)CC3)nc2c1)C1CC1]

The title compound was prepared as described for Example 32 using 2-(2-(difluoromethoxy)ethyl)-2H-1,2,3-triazole-4-carboxylic acid (Intermediate 109) in place of 2-(3,3-difluoropropyl)-2H-1,2,3-triazole-4-carboxylic acid to afford the title compound as a white powder. $^1$H NMR (400 MHz, DMSO-$d_6$) δ=8.71 (d, J=7.8 Hz, 1H), 8.55-8.47 (m, 2H), 8.26-8.21 (m, 2H), 7.96 (d, J=2.0 Hz, 1H), 6.92-6.28 (m, 1H), 5.18 (t, J=8.7 Hz, 1H), 4.75 (t, J=5.1 Hz, 2H), 4.36 (t, J=5.1 Hz, 2H), 4.29 (t, J=8.4 Hz, 1H), 2.56-2.52 (m, 1H), 2.49-2.43 (m, 3H), 2.22-2.10 (m, 1H), 2.09-1.93 (m, 2H), 1.93-1.84 (m, 1H), 1.84-1.64 (m, 2H), 1.63-1.52 (m, 1H), 1.42-1.28 (m, 1H), 1.27-1.13 (m, 2H), 0.63-0.45 (m, 3H), 0.43-0.31 (m, 1H). MS (ESI) m/z: [M+H]$^+$ Found 649.3.

Example 36

N—((S)-(7-((R)-Cyclopropyl(4,4,4-trifluorobutanamido)methyl)imidazo[1,2-b]pyridazin-2-yl)(4,4-difluorocyclohexyl)methyl)-1-(2-(trifluoromethoxy)ethyl)-1H-pyrazole-4-carboxamide

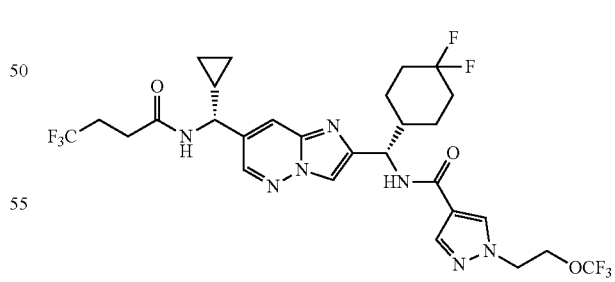

The title compound was prepared as described for Example 32 using 1-(2-(trifluoromethoxy)ethyl)-1H-pyrazole-4-carboxylic acid (Intermediate 98) in place of 2-(3,3-difluoropropyl)-2H-1,2,3-triazole-4-carboxylic acid to afford the title compound as a white powder $^1$H NMR (400 MHz, DMSO-$d_6$) δ 8.71 (d, J=7.6 Hz, 1H), 8.49 (d, J=2.1 Hz, 1H), 8.35-8.28 (m, 2H), 8.16 (s, 1H), 8.01 (d, J=0.6 Hz, 1H), 7.92 (d, J=2.1 Hz, 1H), 5.16 (t, J=8.7 Hz, 1H), 4.46 (s, 4H), 4.29 (t, J=8.4 Hz, 1H), 2.56-2.51 (m, 1H), 2.48-2.42 (m, 3H), 2.21-2.09 (m, 1H), 2.08-1.91 (m, 2H), 1.90-1.66 (m, 3H), 1.64-1.55 (m, 1H), 1.44-1.31 (m, 1H), 1.30-1.14 (m, 2H), 0.62-0.45 (m, 3H), 0.14-0.34 (m, 1H). MS (ESI) m/z: [M+H]+ Found 666.3.

Example 37

N—((S)-(7-((R)-Cyclopropyl(4,4,4-trifluorobutanamido)methyl)imidazo[1,2-b]pyridazin-2-yl)(4,4-difluorocyclohexyl)methyl)-1-(2-(difluoromethoxy)ethyl)-1H-pyrazole-4-carboxamide

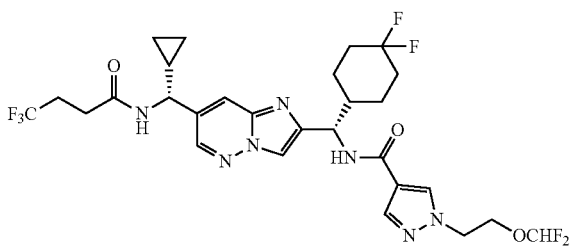 [SMILES: O=C(CCC(F)(F)F)N[C@@H](c1cnn2cc([C@@H](NC(=O)c3cnn(CCOC(F)F)c3)C3CCC(F)(F)CC3)nc2c1)C1CC1]

The title compound was prepared as described for Example 32 using 1-(2-(difluoromethoxy)ethyl)-1H-pyrazole-4-carboxylic acid (Intermediate 100) in place of 2-(3,3-difluoropropyl)-2H-1,2,3-triazole-4-carboxylic acid to afford the title compound as a white powder. 1H NMR (500 MHz, DMSO-d6) δ 8.71 (d, J=7.8 Hz, 1H), 8.49 (d, J=2.1 Hz, 1H), 8.30 (d, J=9.1 Hz, 1H), 8.27 (s, 1H), 8.16 (s, 1H), 7.98 (s, 1H), 7.92 (d, J=2.0 Hz, 1H), 6.64 (t, J=78.3 Hz, 1H), 5.16 (t, J=8.6 Hz, 1H), 4.41-4.32 (m, 2H), 4.29 (t, J=8.3 Hz, 1H), 4.19 (t, J=5.2 Hz, 2H), 2.56-2.51 (m, 1H), 2.48-2.43 (m, 3H), 2.20-2.09 (m, 1H), 2.09-1.91 (m, 2H), 1.90-1.67 (m, 3H), 1.64-1.56 (m, 1H), 1.42-1.31 (m, 1H), 1.29-1.15 (m, 2H), 0.61-0.44 (m, 3H), 0.40-0.34 (m, 1H). MS (ESI) m/z: [M+H]+ Found 648.3.

Example 38

N—((S)-(7-((R)-Cyclopropyl(4,4,4-trifluorobutanamido)methyl)imidazo[1,2-b]pyridazin-2-yl)(4,4-difluorocyclohexyl)methyl)-1-(3,3,3-trifluoropropyl)-1H-1,2,4-triazole-5-carboxamide

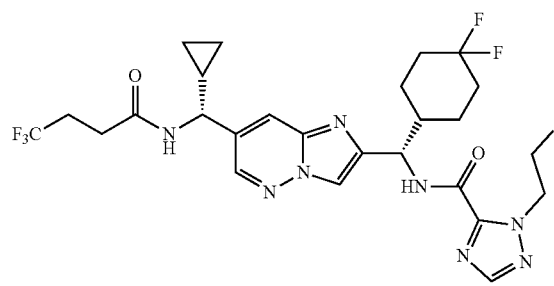

A vial was charged with a stir bar, N—((R)-2-((S)-amino(4,4-difluorocyclohexyl)methyl)imidazo[1,2-b]pyridazin-7-yl)(cyclopropyl)methyl)-4,4,4-trifluorobutanamide (100 mg, 0.218 mmol, Intermediate 51), MeCN (2 mL), HOBt (31 mg, 0.23 mmol), and 1-(3,3,3-trifluoropropyl)-1H-1,2,4-triazole-5-carboxylic acid (48 mg, 0.23 mmol, Intermediate 96). The reaction was stirred for 5 min then EDCI (44 mg, 0.23 mmol) and Hünig's base (0.056 mL, 0.33 mmol) were added and the reaction was stirred for 30 min at 40° C. The reaction was cooled to rt and poured over water and diluted with ethyl acetate. The layers were separated, and the aqueous phase was further extracted with ethyl acetate (2×5 mL). The combined organics were washed with brine, dried over anhydrous MgSO4, filtered and condensed into a glassy solid. The crude material was purified by silica gel chromatography (0-100% ethyl acetate (with 10% MeOH)/hexanes). The product containing fractions were condensed into an oily solid. The material was further purified by reverse phase basic HPLC (Gemini® 5 μM C18 110 Å, 150×21.2 mm, 0-100% acetonitrile/water (with 20 mM NH4OH). The product containing fractions were lyophilized to afford the title compound as a white powder. 1H NMR (400 MHz, DMSO-d6) δ 8.94 (d, J=9.3 Hz, 1H), 8.71 (d, J=7.8 Hz, 1H), 8.51 (d, J=2.0 Hz, 1H), 8.26 (s, 1H), 8.16 (s, 1H), 7.98 (d, J=2.0 Hz, 1H), 5.14 (t, J=8.6 Hz, 1H), 4.86 (t, J=6.8 Hz, 2H), 4.29 (t, J=8.3 Hz, 1H), 3.00-2.77 (m, 2H), 2.53 (m, 1H), 2.48-2.43 (m, 3H), 2.21-2.10 (m, 1H), 2.08-1.94 (m, 2H), 1.94-1.84 (m, 1H), 1.84-1.65 (m, 2H), 1.64-1.56 (m, 1H), 1.40-1.28 (m, 1H), 1.28-1.15 (m, 2H), 0.64-0.44 (m, 3H), 0.41-0.34 (m, 1H). MS (ESI) m/z: [M+H]+ Found 651.3.

Example 39

N—((S)-(7-((R)-Cyclopropyl(4,4,4-trifluorobutanamido)methyl)imidazo[1,2-b]pyridazin-2-yl)(4,4-difluorocyclohexyl)methyl)-1-(cyclopropylmethyl)-1H-1,2,4-triazole-5-carboxamide

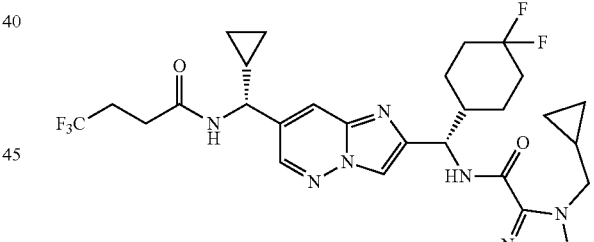

The title compound was prepared as described for Example 38 using 1-(cyclopropylmethyl)-1H-1,2,4-triazole-5-carboxylic acid (Intermediate 94) in place of 1-(3,3,3-trifluoropropyl)-1H-1,2,4-triazole-5-carboxylic acid to afford the title compound as a white powder. 1H NMR (500 MHz, DMSO-d6) δ 8.91 (d, J=9.1 Hz, 1H), 8.72 (d, J=7.8 Hz, 1H), 8.51 (d, J=2.0 Hz, 1H), 8.26 (s, 1H), 8.10 (s, 1H), 7.98 (s, 1H), 5.13 (t, J=8.6 Hz, 1H), 4.42 (d, J=7.3 Hz, 2H), 4.29 (t, J=8.3 Hz, 1H), 2.56-2.51 (m, 1H), 2.49-2.42 (m, 3H), 2.20-2.10 (m, 1H), 2.08-1.93 (m, 2H), 1.92-1.86 (m, 1H), 1.85-1.67 (m, 2H), 1.64-1.55 (m, 1H), 1.40-1.30 (m, 1H), 1.30-1.16 (m, 3H), 0.62-0.48 (m, 3H), 0.47-0.42 (m, 2H), 0.41-0.31 (m, 3H). MS (ESI) m/z: [M+H]+ Found 609.3.

Example 40

N—((S)-(7-((R)-Cyclopropyl(4,4,4-trifluorobutana-mido)methyl)imidazo[1,2-b]pyridazin-2-yl)(4,4-difluorocyclohexyl)methyl)-2-methylbenzamide

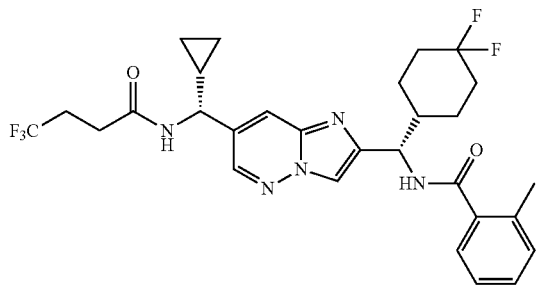 [SMILES: Cc1ccccc1C(=O)N[C@H](c1cn2ncc([C@H](NC(=O)CCC(F)(F)F)C3CC3)cc2n1)C1CCC(F)(F)CC1]

The title compound was prepared as described for Example 38 using 2-methylbenzoic acid in place of 1-(3,3,3-trifluoropropyl)-1H-1,2,4-triazole-5-carboxylic acid to afford the title compound as a white powder. $^1$H NMR (500 MHz, DMSO-$d_6$) δ 8.71 (d, J=7.8 Hz, 1H), 8.65 (d, J=9.1 Hz, 1H), 8.50 (d, J=2.0 Hz, 1H), 8.16 (s, 1H), 7.95 (d, J=2.0 Hz, 1H), 7.38-7.29 (m, 2H), 7.26-7.20 (m, 2H), 5.25-5.20 (m, 1H), 4.30 (t, J=8.4 Hz, 1H), 2.56-2.51 (m, 1H), 2.49-2.44 (m, 3H), 2.29 (s, 3H), 2.18-2.08 (m, 1H), 2.07-1.95 (m, 2H), 1.87-1.77 (m, 2H), 1.76-1.64 (m, 2H), 1.50-1.27 (m, 2H), 1.26-1.16 (m, 1H), 0.62-0.46 (m, 3H), 0.42-0.34 (m, 1H). MS (ESI) m/z: [M+H]$^+$ Found 578.2.

Example 41

N—((S)-(7-((R)-Cyclopropyl(4,4,4-trifluorobutana-mido)methyl)imidazo[1,2-b]pyridazin-2-yl)(4,4-difluorocyclohexyl)methyl)-2-ethylbenzamide

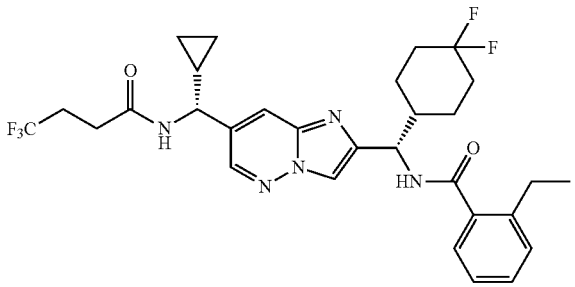 [SMILES: CCc1ccccc1C(=O)N[C@H](c1cn2ncc([C@H](NC(=O)CCC(F)(F)F)C3CC3)cc2n1)C1CCC(F)(F)CC1]

The title compound was prepared as described for Example 38 using 2-ethylbenzoic acid in place of 1-(3,3,3-trifluoropropyl)-1H-1,2,4-triazole-5-carboxylic acid to afford the title compound as a white powder. $^1$H NMR (500 MHz, DMSO-$d_6$) δ 8.72-8.67 (m, 2H), 8.50 (d, J=2.1 Hz, 1H), 8.15 (s, 1H), 7.94 (d, J=2.0 Hz, 1H), 7.38-7.33 (m, 1H), 7.32-7.16 (m, 3H), 5.25-5.20 (m, 1H), 4.30 (t, J=8.4 Hz, 1H), 2.73-2.59 (m, 2H), 2.54-2.51 (m, 1H), 2.49-2.43 (m, 3H), 2.17-2.08 (m, 1H), 2.07-1.95 (m, 2H), 1.86-1.76 (m, 2H), 1.75-1.64 (m, 2H), 1.48-1.28 (m, 2H), 1.25-1.16 (m, 1H), 1.09 (t, J=7.5 Hz, 3H), 0.63-0.46 (m, 3H), 0.42-0.33 (m, 1H). MS (ESI) m/z: [M+H]$^+$ Found 592.

Example 42

2-Chloro-N—((S)-(7-((R)-cyclopropyl(4,4,4-trifluorobutanamido)methyl)imidazo[1,2-b]pyridazin-2-yl)(4,4-difluorocyclohexyl)methyl)benzamide

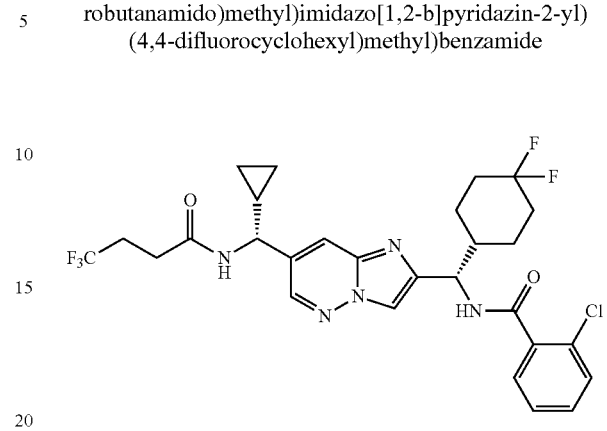

The title compound was prepared as described for Example 38 using 2-chlorobenzoic acid in place of 1-(3,3,3-trifluoropropyl)-1H-1,2,4-triazole-5-carboxylic acid to afford the title compound as a white powder. $^1$H NMR (500 MHz, DMSO-$d_6$) δ 8.89 (d, J=9.3 Hz, 1H), 8.71 (d, J=7.8 Hz, 1H), 8.50 (d, J=2.0 Hz, 1H), 8.15 (s, 1H), 7.99-7.83 (m, 1H), 7.52-7.48 (m, 1H), 7.47-7.36 (m, 3H), 5.31-5.14 m, 1H), 4.30 (t, J=8.4 Hz, 1H), 2.56-2.51 (m, 1H), 2.48-2.44 (m, 3H), 2.19-2.08 (m, 1H), 2.06-1.96 (m, 2H), 1.87-1.65 (m, 4H), 1.51-1.33 (m, 2H), 1.26-1.15 (m, 1H), 0.62-0.47 (m, 3H), 0.42-0.35 (m, 1H). MS (ESI) m/z: [M+H]$^+$ Found 598.1.

Example 43

(Trans-1,2)-N—((S)-(7-((R)-cyclopropyl(4,4,4-trifluorobutanamido)methyl)imidazo[1,2-b]pyridazin-2-yl)(4,4-difluorocyclohexyl)methyl)-2-(trifluoromethyl)cyclopropane-1-carboxamide

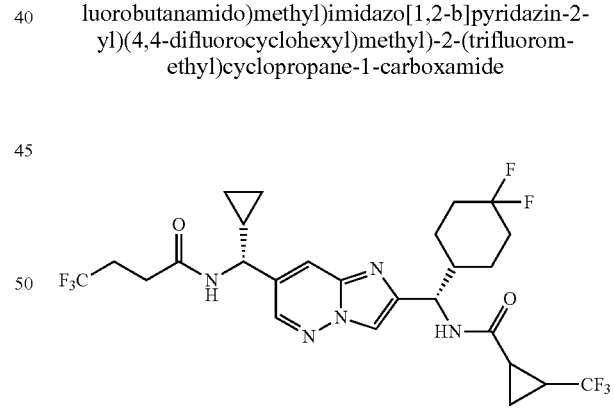

The title compound was prepared as described in the synthesis of Example 4, using racemic trans-2-(trifluoromethyl)cyclopropane-1-carboxylic acid in place of 2-((2,2-difluorocyclobutyl) methyl)-2H-1,2,3-triazole-4-carboxylic acid to afford a pair diastereomers compound as a white solid. $^1$H NMR (400 MHz, CD$_3$OD) δ 8.45 (dd, J=2.2, 1.0 Hz, 1H), 8.00 (s, 1H), 7.88-7.84 (m, 1H), 5.13-5.04 (m, 1H), 4.31-4.23 (m, 1H), 2.63-2.41 (m, 4H), 2.25-2.16 (m, 1H), 2.16-1.94 (m, 4H), 1.93-1.56 (m, 4H), 1.53-1.13 (m, 5H), 0.77-0.65 (m, 2H), 0.56-0.45 (m, 2H). MS (ESI) m/z: [M+H]$^+$ Found 596.4.

Example 44

N—((S)-(7-((R)-Cyclopropyl(4,4,4-trifluorobutanamido)methyl)imidazo[1,2-b]pyridazin-2-yl)(4,4-difluorocyclohexyl)methyl)spiro[2.2]pentane-1-carboxamide

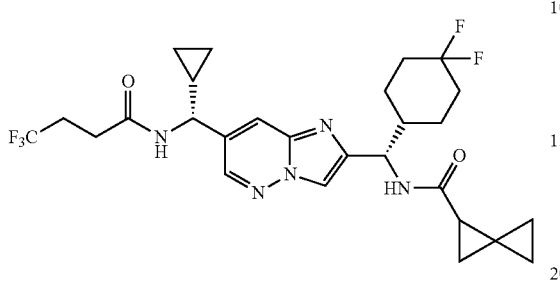

The title compound was prepared as described in the synthesis of Example 4, using spiro[2.2]pentane-1-carboxylic acid in place of 2-((2,2-difluorocyclobutyl)methyl)-2H-1,2,3-triazole-4-carboxylic acid to afford the title compound as a white solid. $^1$H NMR (500 MHz, CDCl$_3$) δ 8.36-8.27 (m, 1H), 7.86-7.72 (m, 2H), 6.39 (dd, J=13.0, 8.7 Hz, 1H), 6.07 (t, J 6.4 Hz, 1H), 5.15 (td, J=8.5, 7.1 Hz, 1H), 4.33 (dt, J=9.1, 7.4 Hz, 1H), 2.59-2.42 (m, 3H), 2.19-2.08 (m, 1H), 2.08-1.93 (m, 2H), 1.93-1.81 (m, 2H), 1.79-1.60 (m, 3H), 1.50-1.11 (m, 4H), 1.06-0.96 (m, 1H), 0.95-0.81 (m, 3H), 0.81-0.70 (m, 2H), 0.57-0.43 (m, 2H). MS (ESI) m/z: [M+H]$^+$ Found 554.3.

Example 45

N—((S)-(7-((R)-Cyclopropyl(4,4,4-trifluorobutanamido)methyl)imidazo[1,2-b]pyridazin-2-yl)(4,4-difluorocyclohexyl)methyl)spiro[2.3]hexane-1-carboxamide

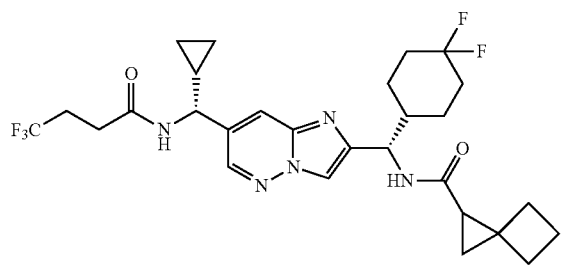 [SMILES: O=C(CCC(F)(F)F)N[C@@H](c1cnn2cc([C@@H](NC(=O)C3CC34CCC4)C3CCC(F)(F)CC3)nc2c1)C1CC1]

The title compound was prepared as described in the synthesis of Example 4, using spiro[2.3]hexane-1-carboxylic acid in place of 2-((2,2-difluorocyclobutyl)methyl)-2H-1,2,3-triazole-4-carboxylic acid to afford the title compound as a white solid. $^1$H NMR (500 MHz, CDCl$_3$) δ 8.32 (dd, J=8.1, 2.1 Hz, 1H), 7.88-7.76 (m, 2H), 6.44 (dd, J=14.5, 8.7 Hz, 1H), 6.15-6.04 (m, 1H), 5.23-5.08 (m, 1H), 4.39-4.27 (m, 1H), 2.62-2.41 (m, 4H), 2.27-1.83 (m, 7H), 1.81-1.55 (m, 4H), 1.53-1.38 (m, 1H), 1.38-1.11 (m, 4H), 0.97-0.83 (m, 1H), 0.81-0.69 (m, 2H), 0.57-0.42 (m, 2H). MS (ESI) m/z: [M+H]$^+$ Found 568.2.

Example 46

N—((S)-(7-((R)-Cyclopropyl(4,4,4-trifluorobutanamido)methyl)imidazo[1,2-b]pyridazin-2-yl)(4,4-difluorocyclohexyl)methyl)-1-(3,3-difluoropropyl)-1H-1,2,4-triazole-5-carboxamide

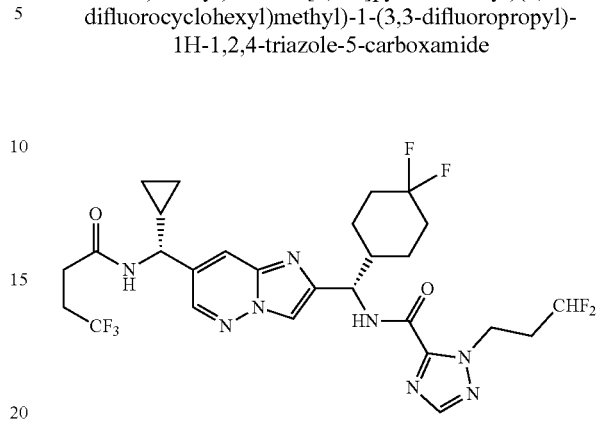

To a microwave vial was added N—((R)-(2-((S)-amino (4,4-difluorocyclohexyl) methyl) imidazo [1,2-b]pyridazin-7-yl)(cyclopropyl)methyl)-4,4,4-trifluorobutanamide (25 mg, 0.054 mmol, Intermediate 51), methyl 1-(3,3-difluoropropyl)-1H-1,2,4-triazole-5-carboxylate (17 mg, 0.082 mmol, Intermediate 78) and toluene (2 mL). Then, AlMe$_3$ (0.11 mL, 0.22 mmol, 2 M in toluene) was added dropwise and the resulting mixture stirred at 90° C. for 1 h. The mixture was then cooled to rt and quenched with 1 N aqueous HCl. The mixture was diluted with EtOAc (20 mL) and washed with 1 N aqueous HCl (20 mL). The aqueous was further extracted with EtOAc (20 mL) and then the organics were combined, dried over anhydrous Na$_2$SO$_4$, filtered and concentrated to dryness. The residue was purified by preparative HPLC (Xbridge C18, 30 to 100% ACN/ 20 mM aqueous NH$_4$OH solution) to provide the title compound as a white solid. $^1$H NMR (500 MHz, CDCl$_3$) δ 8.37-8.16 (m, 2H), 7.89-7.79 (m, 3H), 7.46-7.52 (m, 1H), 6.14-5.84 (m, 2H), 5.20 (dd, J=9.1, 7.6 Hz, 1H), 5.11-4.82 (m, 2H), 4.35-4.26 (m, 1H), 2.50-2.40 (m, 3H), 2.19-1.88 (m, 5H), 1.78-1.26 (m, 6H), 1.19-1.12 (m, 1H), 0.77-0.71 (m, 2H), 0.53-0.45 (m, 2H). MS (ESI) m/z: [M+H]$^+$ Found 633.2.

Example 47

N—((S)-(7-((R)-Cyclopropyl(4,4,4-trifluorobutanamido)methyl)imidazo[1,2-b]pyridazin-2-yl)(4,4-difluorocyclohexyl)methyl)-1-(3-fluoropropyl)-1H-1,2,4-triazole-5-carboxamide

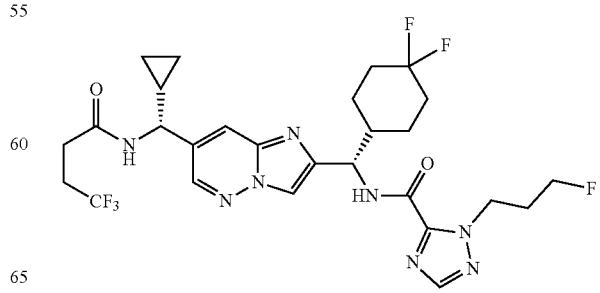

A mixture of N—((R)-(2-((S)-amino(4,4-difluorocyclohexyl)methyl)imidazo[1,2-b]pyridazin-7-yl)(cyclopropyl)methyl)-4,4,4-trifluorobutanamide (100 mg, 0.22 mmol, Intermediate 51), 1-(3-fluoropropyl)-1H-1,2,4-triazole-5-carboxylic acid (43 mg, 0.25 mmol, Intermediate 80), HOBt (31 mg, 0.23 mmol), DIPEA (45 μL, 0.26 mmol) and ACN (2.4 mL) was stirred until homogeneous. Then, EDCI (44 mg, 0.23 mmol) was added and the resulting mixture stirred at rt for 3 h followed by 40° C. for 18.5 h. After this time, the mixture was cooled to rt, water was added and the solution was extracted with EtOAc (2×20 mL). The organic layers were combined, washed with brine (20 mL), dried over anhydrous Na₂SO₄, filtered and concentrated to dryness. The residue was purified by preparative HPLC (Xbridge C18, 30 to 100% ACN/20 mM aqueous NH₄OH solution) to provide the title compound as a white solid. ¹H NMR (500 MHz, CDCl₃) δ 8.30 (d, J=2.1 Hz, 1H), 8.20 (d, J=9.1 Hz, 1H), 7.87-7.81 (m, 3H), 6.12 (d, J=7.0 Hz, 1H), 5.20 (dd, J=9.1, 7.6 Hz, 1H), 4.87-4.76 (m, 2H), 4.49 (dt, J=46.9, 5.7 Hz, 2H), 4.31 (dd, J=9.5, 6.9 Hz, 1H), 2.50-2.43 (m, 2H), 2.33-2.23 (m, 2H), 2.19-1.87 (m, 6H), 1.80-1.60 (m, 3H), 1.56-1.33 (m, 2H), 1.18-1.10 (m, 1H), 0.78-0.68 (m, 2H), 0.53-0.42 (m, 2H). MS (ESI) m/z: [M+H]⁺ Found 615.3.

Example 48

N—((S)-(7-((R)-Cyclopropyl(4,4,4-trifluorobutanamido)methyl)imidazo[1,2-b]pyridazin-2-yl)(4,4-difluorocyclohexyl)methyl)-1-(cyclopropylmethyl)-1H-1,2,3-triazole-5-carboxamide

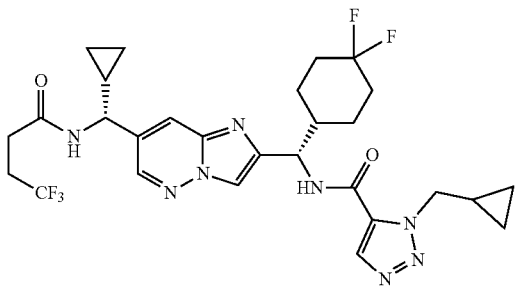 [SMILES: O=C(CCC(F)(F)F)N[C@@H](c1cnn2cc([C@@H](NC(=O)c3cnnn3CC3CC3)C3CCC(F)(F)CC3)nc2c1)C1CC1]

A mixture of 1-(cyclopropylmethyl)-1H-1,2,3-triazole-5-carboxylic acid (47 mg, 0.28 mmol, Intermediate 82), HATU (110 mg, 0.28 mmol), DIPEA (75 μL, 0.44 mmol) and DMF (1 mL) was stirred at rt for 5 min. Then, N—((R)-(2-((S)-amino(4,4-difluorocyclohexyl)methyl)imidazo[1,2-b]pyridazin-7-yl)(cyclopropyl)methyl)-4,4,4-trifluorobutanamide (100 mg, 0.22 mmol, Intermediate 51) was added and the resulting mixture stirred at rt for 1 h. After that time, the mixture was partitioned between saturated aqueous NaHCO₃ (20 mL) and EtOAc (20 mL). The aqueous layer was further extracted with EtOAc (20 mL), and then the organic layers were combined, washed with saturated aqueous NH₄Cl followed by brine, dried over anhydrous Na₂SO₄, filtered and concentrated to dryness. The residue was purified by preparative HPLC (Xbridge C18, 30 to 100% ACN/20 mM aqueous NH₄OH solution) to provide the title compound as a cream-colored solid. ¹H NMR (500 MHz, CDCl₃) δ 8.35 (d, J=2.2 Hz, 1H), 8.03 (s, 1H), 7.88-7.83 (m, 2H), 7.34 (d, J=8.5 Hz, 1H), 6.44 (d, J=6.9 Hz, 1H), 5.29-5.20 (m, 1H), 4.63-4.53 (m, 2H), 4.35-4.28 (m, 1H), 2.57-2.44 (m, 4H), 2.21-2.05 (m, 3H), 2.00-1.94 (m, 1H), 1.80-1.60 (m, 3H), 1.56-1.46 (m, 1H), 1.44-1.30 (m, 2H), 1.23-1.16 (m, 1H), 0.79-0.70 (m, 2H), 0.56-0.42 (m, 6H). MS (ESI) m/z: [M+H]⁺ Found 609.3.

Example 49

N—((S)-(7-((R)-Cyclopropyl(4,4,4-trifluorobutanamido)methyl)imidazo[1,2-b]pyridazin-2-yl)(4,4-difluorocyclohexyl)methyl)-1-(3,3-difluoropropyl)-1H-1,2,3-triazole-5-carboxamide

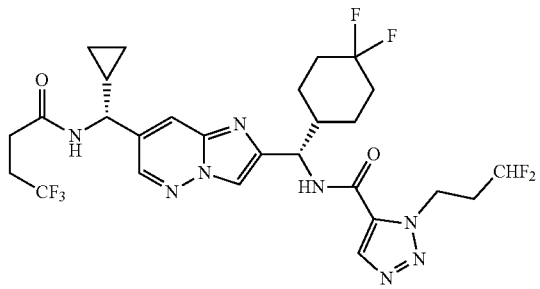 [SMILES: O=C(CCC(F)(F)F)N[C@@H](c1cnn2cc([C@@H](NC(=O)c3cnnn3CCC(F)F)C3CCC(F)(F)CC3)nc2c1)C1CC1]

The title compound was prepared as described for the synthesis of Example 48, using 1-(3,3-difluoropropyl)-1H-1,2,3-triazole-5-carboxylic acid (Intermediate 84) in place of 1-(cyclopropylmethyl)-1H-1,2,3-triazole-5-carboxylic acid to provide the title compound as a cream-colored solid. ¹H NMR (500 MHz, CDCl₃) δ 8.35 (d, J=2.1 Hz, 1H), 8.05 (s, 1H), 7.89-7.84 (m, 1H), 7.84-7.80 (m, 1H), 7.36 (d, J=8.5 Hz, 1H), 6.31 (d, J=6.8 Hz, 1H), 5.96 (tt, J=55.8, 4.3 Hz, 1H), 5.24 (t, J=8.0 Hz, 1H), 4.92 (t, J=7.0 Hz, 2H), 4.35-4.27 (m, 1H), 2.57-2.45 (m, 6H), 2.19-2.12 (m, 1H), 2.08-2.03 (m, 2H), 1.99-1.93 (m, 1H), 1.80-1.61 (m, 3H), 1.56-1.47 (m, 1H), 1.39-1.29 (m, 1H), 1.22-1.15 (m, 1H), 0.78-0.71 (m, 2H), 0.55-0.45 (m, 2H). MS (ESI) m/z: [M+H]⁺ Found 633.3.

Example 50

N—((S)-(7-((R)-Cyclopropyl(4,4,4-trifluorobutanamido)methyl)imidazo[1,2-b]pyridazin-2-yl)(4,4-difluorocyclohexyl)methyl)-1-(2,2-difluoroethyl)-5-methyl-1H-pyrazole-4-carboxamide

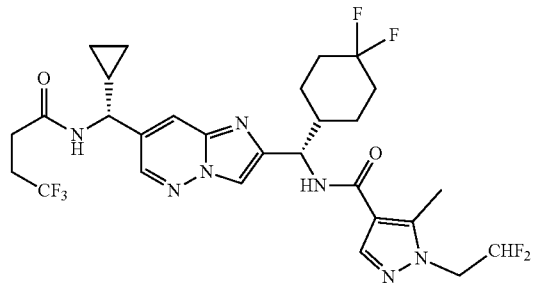 [SMILES: Cc1c(C(=O)N[C@H](c2cn3ncc([C@H](NC(=O)CCC(F)(F)F)C4CC4)cc3n2)C2CCC(F)(F)CC2)cnn1CC(F)F]

The title compound was prepared as described for the synthesis of Example 48, using 1-(2,2-difluoroethyl)-5-methyl-1H-pyrazole-4-carboxylic acid in place of 1-(cyclopropylmethyl)-1H-1,2,3-triazole-5-carboxylic acid to provide the title compound as a cream-colored solid. ¹H NMR (500 MHz, CDCl₃) δ 8.32 (d, J=2.1 Hz, 1H), 7.86-7.81 (m, 2H), 7.76 (s, 1H), 6.74 (d, J=8.5 Hz, 1H), 6.21-5.95 (m, 2H), 5.29-5.23 (m, 1H), 4.40 (td, J=13.2, 4.4 Hz, 2H), 4.35-4.30 (m, 1H), 2.59 (s, 3H), 2.56-2.45 (m, 4H), 2.17-1.94 (m, 4H), 1.79-1.64 (m, 3H), 1.56-1.46 (m, 1H), 1.40-1.30 (m, 1H), 1.20-1.13 (m, 1H), 0.80-0.71 (m, 2H), 0.54-0.45 (m, 2H). MS (ESI) m/z: [M+H]+ Found 632.3.

Example 51

N—((S)-(7-((S*)-Cyclopropyl(2-(3,3-difluorocyclobutyl)acetamido)methyl)imidazo[1,2-b]pyridazin-2-yl)(4,4-difluorocyclohexyl)methyl)-5-methyl-1-(3,3,3-trifluoropropyl)-1H-pyrazole-4-carboxamide

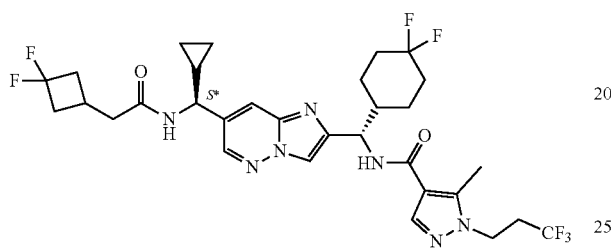

Example 52

N—((S)-(7-((R*)-Cyclopropyl(2-(3,3-difluorocyclobutyl)acetamido)methyl)imidazo[1,2-b]pyridazin-2-yl)(4,4-difluorocyclohexyl)methyl)-5-methyl-1-(3,3,3-trifluoropropyl)-1H-pyrazole-4-carboxamide

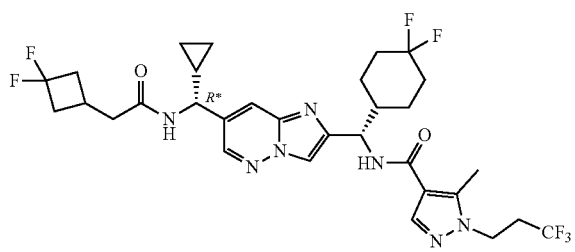 [SMILES: Cc1c(C(=O)N[C@H](c2cn3ncc([C@H](NC(=O)CC4CC(F)(F)C4)C4CC4)cc3n2)C2CCC(F)(F)CC2)cnn1CCC(F)(F)F]

N-((1S)-(7-(Cyclopropyl(2-(3,3-difluorocyclobutyl)acetamido)methyl)imidazo[1,2-b]pyridazin-2-yl)(4,4-difluorocyclohexyl)methyl)-5-methyl-1-(3,3,3-trifluoropropyl)-1H-pyrazole-4-carboxamide (Intermediate 91) was purified by SFC using a chiral stationary phase (Whelk-01 (R,R) (2×25 cm), 20% EtOH (0.1% DEA)/CO2) to give a pair of diastereomers. The first-eluting isomer was Example 51, the minor diastereomer, as a white solid. The second-eluting isomer was Example 52, the major diastereomer, as a white solid. Example 51: 1H NMR (500 MHz, CD3OD) δ 8.46 (d, J=2.0 Hz, 1H), 8.08 (s, 1H), 8.00 (s, 1H), 7.87 (s, 1H), 5.23 (d, J=8.5 Hz, 1H), 4.38 (t, J=7.0 Hz, 2H), 4.27 (d, J=9.3 Hz, 1H), 2.79 (dt, J=10.8, 7.0 Hz, 4H), 2.55 (s, 3H), 2.53-2.48 (m, 3H), 2.38-1.96 (m, 6H), 1.90-1.61 (m, 3H), 1.55-1.21 (m, 3H), 0.75-0.69 (m, 2H), 0.54-0.47 (m, 2H). MS (ESI) m/z: [M+H]+ Found 672.3. Example 52: 1H NMR (500 MHz, CD3OD) δ 8.46 (d, J=2.0 Hz, 1H), 8.08 (s, 1H), 8.01 (s, 1H), 7.88 (s, 1H), 5.25-5.04 (m, 1H), 4.38 (t, J=7.0 Hz, 2H), 4.27 (d, J=9.5 Hz, 1H), 2.78 (dt, J=10.8, 7.0 Hz, 4H), 2.55 (s, 3H), 2.53-2.48 (m, 3H), 0.75-0.69 (m, 2H), 0.49 (br t, J=4.5 Hz, 2H). MS (ESI) m/z: [M+H]+ Found 672.3.

Example 53

N—((S)-(7-((S*)-Cyclopropyl(4,4,4-trifluorobutanamido)methyl)imidazo[1,2-b]pyridazin-2-yl)(4,4-difluorocyclohexyl)methyl)-5-methyl-1-(3,3,3-trifluoropropyl)-1H-pyrazole-4-carboxamide

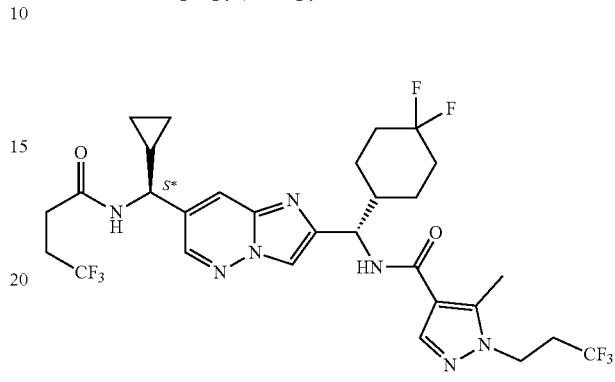

Example 54

N—((S)-(7-((R*)-Cyclopropyl(4,4,4-trifluorobutanamido)methyl)imidazo[1,2-b]pyridazin-2-yl)(4,4-difluorocyclohexyl)methyl)-5-methyl-1-(3,3,3-trifluoropropyl)-1H-pyrazole-4-carboxamide

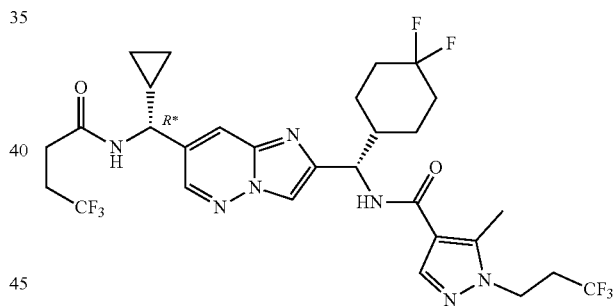

N-((1S)-(7-(Cyclopropyl(4,4,4-trifluorobutanamido)methyl)imidazo[1,2-b]pyridazin-2-yl)(4,4-difluorocyclohexyl)methyl)-5-methyl-1-(3,3,3-trifluoropropyl)-1H-pyrazole-4-carboxamide (Intermediate 92) was purified by SFC using a chiral stationary phase (Whelk-01 (R,R) (2×25 cm), 20% MeOH (0.1% DEA)/CO2) to give a pair of diastereomers. The first-eluting isomer was Example 53, the minor diastereomer, as a white solid. The second-eluting isomer was Example 54, the major diastereomer, as a white solid. Example 53: 1H NMR (400 MHz, CD3OD) δ 8.32 (d, J=2.3 Hz, 1H), 7.93 (s, 1H), 7.85 (s, 1H), 7.74 (d, J=2.0 Hz, 1H), 5.09 (d, J=8.5 Hz, 1H), 4.23 (t, J=7.0 Hz, 2H), 4.14 (d, J=9.5 Hz, 1H), 2.70-2.56 (m, 2H), 2.55-2.30 (m, 7H), 2.08-1.81 (m, 4H), 1.73-1.46 (m, 3H), 1.41-0.98 (m, 4H), 0.64-0.50 (m, 2H), 0.43-0.32 (m, 2H). MS (ESI) m/z: [M+H]+ Found 664.3. Example 54: 1H NMR (400 MHz, CD3OD) δ 8.46 (d, J=2.2 Hz, 1H), 8.08 (s, 1H), 8.00 (s, 1H), 7.88 (d, J=2.1 Hz, 1H), 5.23 (d, J=8.5 Hz, 1H), 4.37 (t, J=6.9 Hz, 2H), 4.29 (d, J=9.4 Hz, 1H), 2.84-2.71 (m, 2H), 2.60-2.57 (m, 1H), 2.57-2.54 (m, 4H), 2.54-2.45 (m, 2H), 2.22-1.95 (m, 4H), 1.86-1.59 (m, 3H), 1.54-1.33 (m, 2H), 1.29-1.21 (m, 1H), 0.75-0.66 (m, 2H), 0.54-0.46 (m, 2H). MS (ESI) m/z: [M+H]+ Found 664.3.

Example 55

N—((S)-(7-((R)-Cyclopropyl(4,4,4-trifluorobutanamido)methyl)imidazo[1,2-b]pyridazin-2-yl)(4,4-difluorocyclohexyl)methyl)-1-(2-(difluoromethoxy)ethyl)-1H-1,2,4-triazole-5-carboxamide

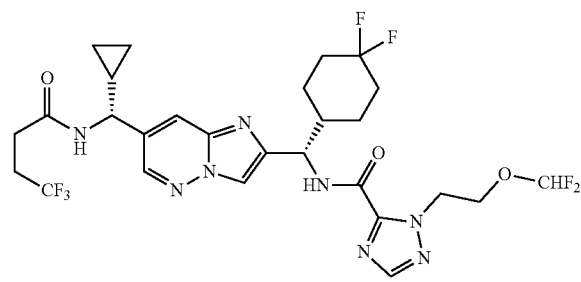 [SMILES: O=C(CCC(F)(F)F)N[C@@H](c1cnn2cc([C@@H](NC(=O)c3ncnn3CCOC(F)F)C3CCC(F)(F)CC3)nc2c1)C1CC1]

To a microwave vial was added N—((R)-(2-((S)-amino(4,4-difluorocyclohexyl)methyl)imidazo[1,2-b]pyridazin-7-yl)(cyclopropyl)methyl)-4,4,4-trifluorobutanamide (100 mg, 0.22 mmol, Intermediate 51) and toluene (7.3 mL). Then, AlMe₃ (0.44 mL, 0.87 mmol, 2 M in toluene) was added dropwise and the resulting mixture stirred at rt for 15 min. After that time, methyl 1-(2-(difluoromethoxy)ethyl)-1H-1,2,4-triazole-5-carboxylate (60 mg, 0.27 mmol, Intermediate 120) was added and the mixture stirred at 90° C. for 1 h. The mixture was then cooled to rt and quenched with 1 N aqueous HCl. The mixture was diluted with EtOAc (20 mL) and washed with 1 N aqueous HCl (20 mL). The aqueous was further extracted with EtOAc (20 mL) and then the organics were combined, dried over anhydrous Na₂SO₄, filtered and concentrated to dryness. The residue was purified by preparative HPLC (Xbridge C18, 30 to 100% ACN/20 mM aqueous NH₄OH solution) followed by preparative HPLC (Xbridge C18, 30 to 100% ACN/0.05% aqueous TFA solution) to provide the title compound as a white solid. ¹H NMR (500 MHz, CDCl₃) δ 8.60-8.53 (m, 1H), 8.50-8.17 (m, 2H), 7.97-7.86 (m, 2H), 7.69-7.62 (m, 1H), 6.11 (t, J=73.8 Hz, 1H), 5.23-5.14 (m, 1H), 4.94-4.84 (m, 2H), 4.32-4.20 (m, 3H), 2.54-2.40 (m, 4H), 2.25-2.20 (m, 1H), 2.05-2.00 (m, 2H), 1.84-1.60 (m, 3H), 1.53-1.33 (m, 2H), 1.27-1.11 (m, 2H), 0.74-0.68 (m, 2H), 0.52-0.41 (m, 2H). MS (ESI) m/z: [M+H]+ Found 649.2.

Example 56

N—((S)-(7-((R)-Cyclopropyl(4,4,4-trifluorobutanamido)methyl)imidazo[1,2-b]pyridazin-2-yl)(4,4-difluorocyclohexyl)methyl)-1-(2,2-difluoroethyl)-1H-1,2,4-triazole-5-carboxamide

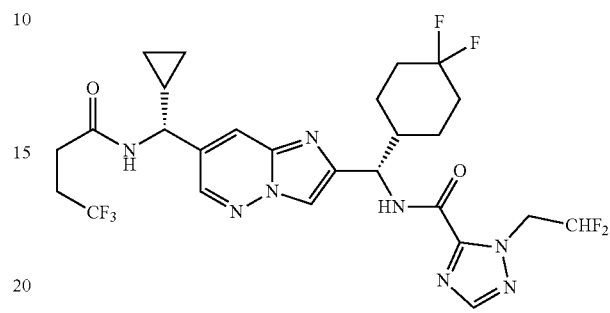

The title compound was prepared as described in the synthesis of Example 46, using methyl 1-(2,2-difluoroethyl)-1H-1,2,4-triazole-5-carboxylate (Intermediate 113) in place of methyl 1-(3,3-difluoropropyl)-1H-1,2,4-triazole-5-carboxylate to provide the title compound as a white solid. ¹H NMR (500 MHz, CDCl₃) δ 8.35-8.24 (m, 2H), 7.93-7.77 (m, 3H), 7.39-7.30 (m, 1H), 6.16 (tt, J=55.4, 4.3 Hz, 1H), 5.20-5.11 (m, 1H), 5.04 (td, J=13.0, 4.3 Hz, 2H), 4.31-4.20 (m, 1H), 2.53-2.38 (m, 5H), 2.12-1.91 (m, 3H), 1.76-1.58 (m, 3H), 1.52-1.33 (m, 2H), 1.19-1.08 (m, 1H), 0.71-0.63 (m, 2H), 0.50-0.38 (m, 2H). MS (ESI) m/z: [M+H]+ Found 619.0.

Example 57

N—((S)-(7-((R)-Cyclopropyl(4,4,4-trifluorobutanamido)methyl)imidazo[1,2-b]pyridazin-2-yl)(4,4-difluorocyclohexyl)methyl)-1-(2-fluoroethyl)-1H-1,2,4-triazole-5-carboxamide

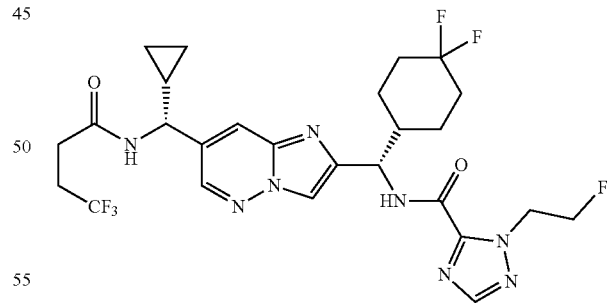

The title compound was prepared as described in the synthesis of Example 46, using methyl 1-(2-fluoroethyl)-1H-1,2,4-triazole-5-carboxylate (Intermediate 114) in place of methyl 1-(3,3-difluoropropyl)-1H-1,2,4-triazole-5-carboxylate to provide the title compound as a white solid. ¹H NMR (500 MHz, CDCl₃) δ 8.31 (d, J=2.1 Hz, 1H), 8.20 (d, J=9.1 Hz, 1H), 7.90 (s, 1H), 7.85 (d, J=2.2 Hz, 2H), 6.09 (d, J=6.9 Hz, 1H), 5.19 (dd, J=9.1, 7.6 Hz, 1H), 5.07-4.95 (m, 2H), 4.89-4.72 (m, 2H), 4.34-4.27 (m, 1H), 2.55-2.45 (m, 4H), 2.19-1.93 (m, 4H), 1.75-1.61 (m, 3H), 1.55-1.34 (m, 2H), 1.20-1.11 (m, 1H), 0.81-0.69 (m, 2H), 0.54-0.43 (m, 2H). MS (ESI) m/z: [M+H]+ Found 601.0.

Example 58

N—((S)-(7-((R)-Cyclopropyl(4,4,4-trifluorobutanamido)methyl)imidazo[1,2-b]pyridazin-2-yl)(4,4-difluorocyclohexyl)methyl)-1-ethyl-1H-1,2,3-triazole-5-carboxamide

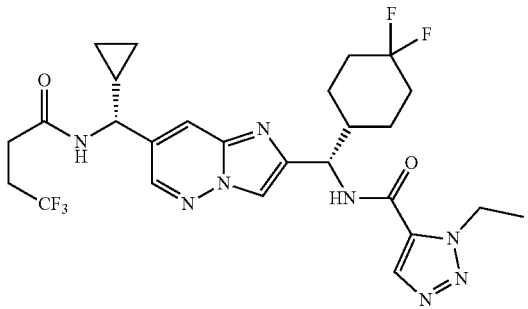 [SMILES: CCn1nncc1C(=O)N[C@H](c1cn2ncc([C@H](NC(=O)CCC(F)(F)F)C3CC3)cc2n1)C1CCC(F)(F)CC1]

The title compound was prepared as described in the synthesis of Example 47, using 1-ethyl-1H-1,2,3-triazole-5-carboxylic acid in place of 1-(3-fluoropropyl)-1H-1,2,4-triazole-5-carboxylic acid to provide the title compound as a white solid. $^1$H NMR (400 MHz, CDCl$_3$) δ 8.35 (d, J=2.1 Hz, 1H), 8.04 (s, 1H), 7.86 (s, 1H), 7.85-7.82 (m, 1H), 7.40 (d, J=8.6 Hz, 1H), 6.46 (d, J=6.9 Hz, 1H), 5.28-5.20 (m, 1H), 4.76 (q, J=7.2 Hz, 2H), 4.34-4.27 (m, 1H), 2.57-2.44 (m, 4H), 2.21-2.04 (m, 3H), 2.00-1.93 (m, 1H), 1.82-1.53 (m, 4H), 1.53-1.49 (m, 3H), 1.39-1.29 (m, 1H), 1.22-1.13 (m, 1H), 0.78-0.70 (m, 2H), 0.55-0.42 (m, 2H). MS (ESI) m/z: [M+H]+ Found 583.2.

Example 59

N—((S)-(7-((R)-Cyclopropyl(4,4,4-trifluorobutanamido)methyl)imidazo[1,2-b]pyridazin-2-yl)(4,4-difluorocyclohexyl)methyl)-2-ethyl-2H-1,2,3-triazole-4-carboxamide

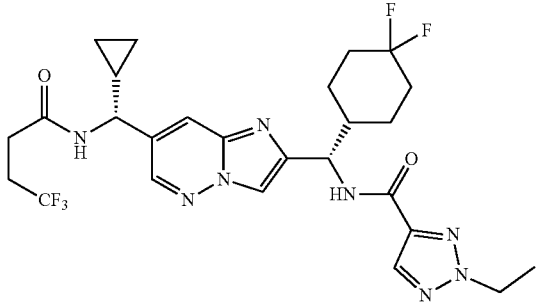 [SMILES: CCn1ncc(C(=O)N[C@H](c2cn3ncc([C@H](NC(=O)CCC(F)(F)F)C4CC4)cc3n2)C2CCC(F)(F)CC2)n1]

The title compound was prepared as described in the synthesis of Example 47, using 2-ethyl-2H-1,2,3-triazole-4-carboxylic acid in place of 1-(3-fluoropropyl)-1H-1,2,4-triazole-5-carboxylic acid, and stirring at 40° C. for 1.5 h instead of 18.5 h followed by rt for 18 h, to provide the title compound as a white solid. $^1$H NMR (400 MHz, CDCl$_3$) δ 8.31 (d, J=2.1 Hz, 1H), 8.01 (s, 1H), 7.88-7.82 (m, 2H), 7.53 (d, J=9.1 Hz, 1H), 6.22 (d, J=7.0 Hz, 1H), 5.34-5.25 (m, 1H), 4.47 (q, J=7.3 Hz, 2H), 4.34-4.28 (m, 1H), 2.55-2.45 (m, 4H), 2.17-1.94 (m, 4H), 1.72-1.63 (m, 2H), 1.58 (t, J=7.4 Hz, 3H), 1.54-1.36 (m, 2H), 1.19-1.11 (m, 1H), 0.78-0.69 (m, 2H), 0.53-0.44 (m, 2H). MS (ESI) m/z: [M+H]+ Found 583.2.

Example 60

N—((S)-(7-((R)-Cyclopropyl(4,4,4-trifluorobutanamido)methyl)imidazo[1,2-b]pyridazin-2-yl)(4,4-difluorocyclohexyl)methyl)-1-fluorocyclopropane-1-carboxamide

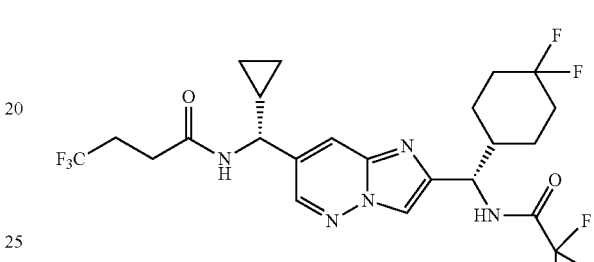

The title compound was prepared as described in the synthesis of Example 4, using 1-fluorocyclopropane-1-carboxylic acid in place of 2-((2,2-difluorocyclobutyl)methyl)-2H-1,2,3-triazole-4-carboxylic acid to afford the title compound as a white solid. $^1$H NMR (500 MHz, CDCl$_3$) δ 8.32 (d, J=2.1 Hz, 1H), 7.86-7.82 (m, 2H), 6.05 (d, J=7.0 Hz, 1H), 5.21-5.12 (m, 1H), 4.36-4.29 (m, 1H), 2.59-2.43 (m, 4H), 2.21-2.00 (m, 3H), 2.00-1.90 (m, 1H), 1.82-1.58 (m, 4H), 1.54-1.43 (m, 1H), 1.42-1.20 (m, 5H), 1.19-1.11 (m, 1H), 0.81-0.67 (m, 2H), 0.56-0.41 (m, 2H). MS (ESI) m/z: [M+H]+ Found 546.1.

Example 61

N—((S)-(7-((R)-Cyclopropyl(4,4,4-trifluorobutanamido)methyl)imidazo[1,2-b]pyridazin-2-yl)(4,4-difluorocyclohexyl)methyl)-1-(2,2,2-trifluoroethyl)-1H-1,2,4-triazole-5-carboxamide

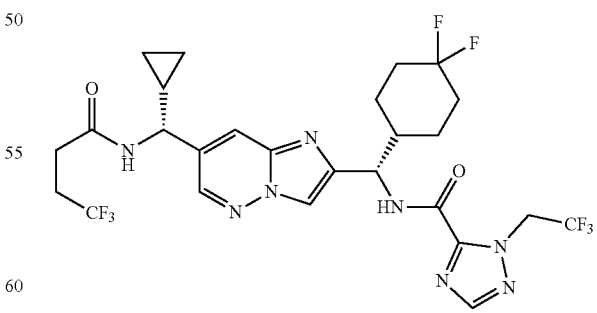

To a microwave vial was added N—((R)-(2-((S)-amino(4,4-difluorocyclohexyl)methyl) imidazo[1,2-b]pyridazin-7-yl)(cyclopropyl)methyl)-4,4,4-trifluorobutanamide (75 mg, 0.16 mmol, Intermediate 51), methyl 1-(2,2,2-trifluoroethyl)-1H-1,2,4-triazole-5-carboxylate (43 mg, 0.2 mmol, Intermediate 116) and toluene (5.5 mL). Then, AlMe₃ (0.33 mL, 0.65 mmol, 2 M in toluene) was added dropwise and the resulting mixture stirred at 90° C. for 2 h. The mixture was then cooled to rt and quenched with saturated aqueous Rochelle salt. After stirring at rt overnight, the mixture was partitioned between EtOAc (20 mL) and water (20 mL). The layers were separated and the aqueous further extracted with EtOAc (20 mL). The organic layers were combined, dried over anhydrous Na₂SO₄, filtered and concentrated to dryness. The residue was purified by preparative HPLC (Xbridge C18, 30 to 100% ACN/20 mM aqueous NH₄OH solution) to provide the title compound as a cream-colored solid. ¹H NMR (500 MHz, CDCl₃) δ 8.31 (d, J=2.2 Hz, 1H), 8.30-8.27 (m, 1H), 7.95 (s, 1H), 7.86 (s, 1H), 7.84-7.80 (m, 1H), 7.00 (d, J=7.2 Hz, 1H), 5.46-5.34 (m, 2H), 5.20-5.14 (m, 1H), 4.33-4.26 (m, 1H), 2.53-2.42 (m, 4H), 2.20-2.08 (m, 3H), 2.07-2.01 (m, 1H), 1.97-1.91 (m, 1H), 1.70-1.62 (m, 2H), 1.52-1.33 (m, 2H), 1.18-1.09 (m, 1H), 0.74-0.65 (m, 2H), 0.51-0.39 (m, 2H). MS (ESI) m/z: [M+H]⁺ Found 637.2.

Example 62

N—((S)-(7-((R)-Cyclopropyl(4,4,4-trifluorobutanamido)methyl)imidazo[1,2-b]pyridazin-2-yl)(4,4-difluorocyclohexyl)methyl)-2,2-dimethylcyclopropane-1-carboxamide

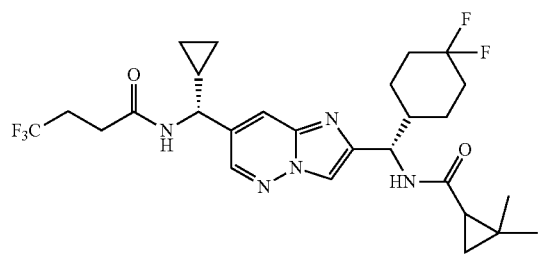 [SMILES: CC1(C)CC1C(=O)N[C@H](c1cn2ncc([C@H](NC(=O)CCC(F)(F)F)C3CC3)cc2n1)C1CCC(F)(F)CC1]

The title compound was prepared as described in the synthesis of Example 4, using 2,2-dimethylcyclopropane-1-carboxylic acid in place of 2-((2,2-difluorocyclobutyl)methyl)-2H-1,2,3-triazole-4-carboxylic acid to afford the title compound as a white solid. ¹H NMR (400 MHz, CD₃OD) δ 8.45 (d, J=2.1 Hz, 1H), 8.00-7.96 (m, 1H), 7.87-7.83 (m, 1H), 5.16-5.06 (m, 1H), 4.27 (d, J=9.4 Hz, 1H), 2.61-2.41 (m, 4H), 2.18-1.94 (m, 3H), 1.91-1.54 (m, 4H), 1.53-1.31 (m, 2H), 1.31-1.21 (m, 1H), 1.21-1.00 (m, 7H), 0.79-0.66 (m, 4H), 0.53-0.46 (m, 2H).

MS (ESI) m/z: [M+H]⁺ Found 556.2.

Example 63

N—((S)-(7-((R)-Cyclopropyl(4,4,4-trifluorobutanamido)methyl)imidazo[1,2-b]pyridazin-2-yl)(4,4-difluorocyclohexyl)methyl)-2-((3,3-difluorocyclobutyl)methyl)-2H-1,2,3-triazole-4-carboxamide

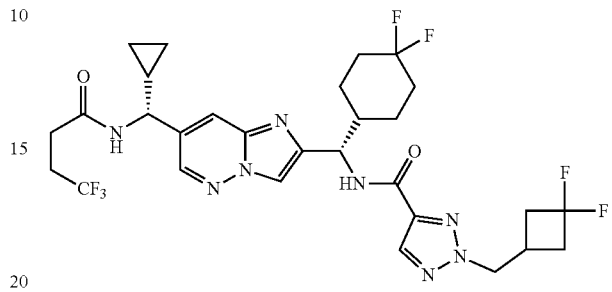

A vial was charged with a stir bar, 2-((3,3-difluorocyclobutyl)methyl)-2H-1,2,3-triazole-4-carboxylic acid (62 mg, 0.29 mmol, Intermediate 119), HATU (110 mg, 0.28 mmol), DIPEA (0.075 mL, 0.44 mmol) and DMF (1 mL, 12.91 mmol). The solution was stirred for 5 min then N—((R)-(2-((S)-amino(4,4-difluorocyclohexyl)methyl)imidazo[1,2-b]pyridazin-7-yl)(cyclopropyl)methyl)-4,4,4-trifluorobutanamide (100 mg, 0.218 mmol, Intermediate 51) was added and the reaction was stirred for a further 3 h. The mixture was partitioned between EtOAc and saturated aqueous NaHCO₃. The organic layer was washed with saturated aqueous ammonium chloride, brine, then dried over anhydrous Na₂SO₄, filtered and concentrated to dryness. The crude material was purified by silica gel chromatography (0-100% ethyl acetate (with 10% MeOH)/hexanes) to provide the title compound as a white solid. ¹H NMR (400 MHz, DMSO-d₆) δ 8.71 (d, J=7.7 Hz, 1H), 8.53-8.47 (m, 2H), 8.24 (s, 1H), 8.21 (s, 1H), 7.99-7.92 (m, 1H), 5.17 (t, J=8.7 Hz, 1H), 4.63 (d, J=6.5 Hz, 2H), 4.29 (t, J=8.3 Hz, 1H), 2.78-2.63 (m, 3H), 2.48-2.41 (m, 6H), 2.22-2.10 (m, 1H), 2.09-1.64 (m, 5H), 1.63-1.53 (m, 1H), 1.42-1.14 (m, 3H), 0.63-0.45 (m, 3H), 0.42-0.32 (m, 1H). MS (ESI) m/z: [M+H]⁺ Found 659.3.

Example 64

N—((S)-(7-((R)-Cyclopropyl(4,4,4-trifluorobutanamido)methyl)imidazo[1,2-b]pyridazin-2-yl)(4,4-difluorocyclohexyl)methyl)-2-(2-methoxyethyl)-2H-1,2,3-triazole-4-carboxamide

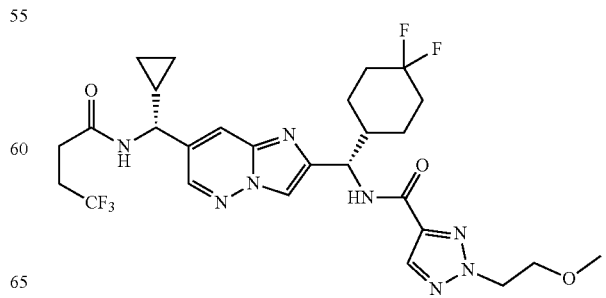

The title compound was prepared as described for the synthesis of Example 63, using 2-(2-methoxyethyl)-2H-1,2,3-triazole-4-carboxylic acid (Intermediate 108) in place of 2-((3,3-difluorocyclobutyl)methyl)-2H-1,2,3-triazole-4-carboxylic acid to provide the title compound as a white solid. ¹H NMR (400 MHz, DMSO-d₆) δ 8.71 (d, J=7.7 Hz, 1H), 8.53-8.44 (m, 2H), 8.24 (s, 1H), 8.19 (s, 1H), 8.00-7.91 (m, 1H), 5.18 (t, J=8.7 Hz, 1H), 4.69-4.59 (m, 2H), 4.29 (t, J=8.4 Hz, 1H), 3.84 (dd, J=5.6, 4.8 Hz, 2H), 3.21 (s, 3H), 2.48-2.42 (m, 5H), 2.20-2.09 (m, 1H), 2.09-1.63 (m, 4H), 1.64-1.52 (m, 1H), 1.42-1.14 (m, 3H), 0.62-0.45 (m, 3H), 0.42-0.32 (m, 1H). MS (ESI) m/z: [M+H]⁺ Found 613.3.

Example 65

N—((S)-(7-((R)-Cyclopropyl(4,4,4-trifluorobutanamido)methyl)imidazo[1,2-b]pyridazin-2-yl)(4,4-difluorocyclohexyl)methyl)-1-isopropyl-1H-1,2,3-triazole-5-carboxamide

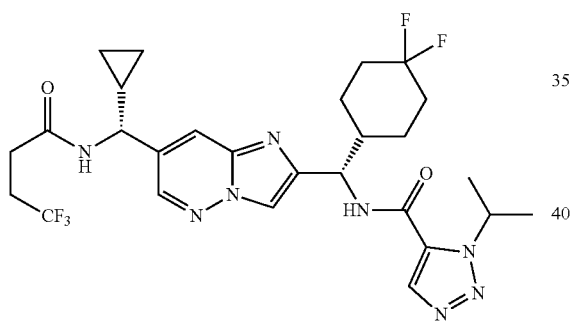

The title compound was prepared as described for the synthesis of Example 63, using 3-isopropyl-3H-1,2,3-triazole-4-carboxylic acid in place of 2-((3,3-difluorocyclobutyl)methyl)-2H-1,2,3-triazole-4-carboxylic acid to provide the title compound as a white solid. ¹H NMR (400 MHz, DMSO-d₆) δ 9.08 (d, J=8.9 Hz, 1H), 8.71 (d, J=7.7 Hz, 1H), 8.50 (d, J=2.1 Hz, 1H), 8.31 (s, 1H), 8.22 (s, 1H), 7.97-7.89 (m, 1H), 5.45-5.31 (m, 1H), 5.16 (t, J=8.6 Hz, 1H), 4.29 (t, J=8.3 Hz, 1H), 2.48-2.42 (m, 4H), 2.24-2.13 (m, 1H), 2.11-1.93 (m, 2H), 1.93-1.67 (m, 3H), 1.67-1.56 (m, 1H), 1.52-1.44 (m, 6H), 1.45-1.15 (m, 3H), 0.63-0.31 (m, 4H). MS (ESI) m/z: [M+H]⁺ Found 597.3.

Example 66

N—((S)-(7-((R)-Cyclopropyl(4,4,4-trifluorobutanamido)methyl)imidazo[1,2-b]pyridazin-2-yl)(4,4-difluorocyclohexyl)methyl)-5-(difluoromethyl)-1-methyl-1H-1,2,3-triazole-4-carboxamide

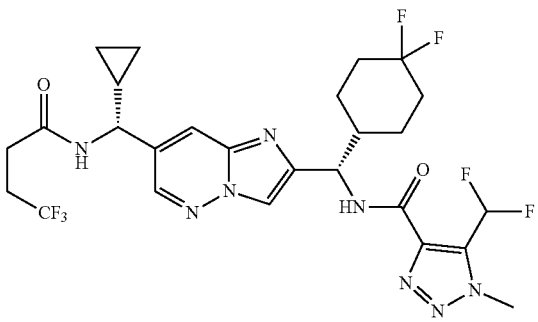 [SMILES: Cn1nnc(C(=O)N[C@H](c2cn3ncc([C@H](NC(=O)CCC(F)(F)F)C4CC4)cc3n2)C2CCC(F)(F)CC2)c1C(F)F]

The title compound was prepared as described for the synthesis of Example 63, using 5-(difluoromethyl)-1-methyl-1H-1,2,3-triazole-4-carboxylic acid in place of 2-((3,3-difluorocyclobutyl)methyl)-2H-1,2,3-triazole-4-carboxylic acid to provide the title compound as a white solid. ¹H NMR (400 MHz, DMSO-d₆) δ 8.92 (d, J=9.1 Hz, 1H), 8.71 (d, J=7.7 Hz, 1H), 8.50 (d, J=2.1 Hz, 1H), 8.26 (s, 1H), 7.97 (dd, J=1.9, 1.0 Hz, 1H), 7.65 (t, J=52.3 Hz, 1H), 5.17 (t, J=8.7 Hz, 1H), 4.29 (t, J=8.4 Hz, 1H), 4.22 (s, 3H), 2.48-2.42 (m, 4H), 2.23-2.11 (m, 1H), 2.11-1.64 (m, 5H), 1.65-1.54 (m, 1H), 1.42-1.13 (m, 3H), 0.62-0.44 (m, 3H), 0.43-0.32 (m, 1H). MS (ESI) m/z: [M+H]⁺ Found 619.2.

Example 67

N—((S)-(7-((R)-Cyclopropyl(4,4,4-trifluorobutanamido)methyl)imidazo[1,2-b]pyridazin-2-yl)(4,4-difluorocyclohexyl)methyl)-1-(difluoromethyl)-1H-pyrazole-5-carboxamide

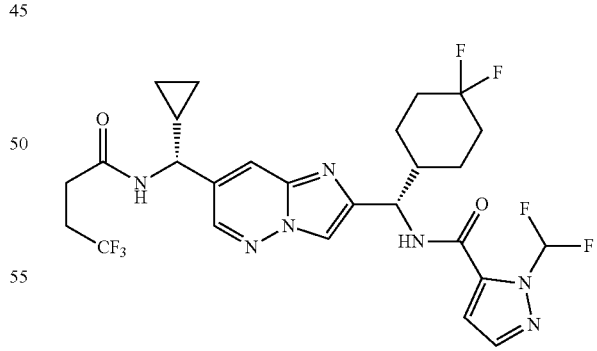

The title compound was prepared as described for the synthesis of Example 63, using 1-(difluoromethyl)-1H-pyrazole-5-carboxylic acid in place of 2-((3,3-difluorocyclobutyl)methyl)-2H-1,2,3-triazole-4-carboxylic acid to provide the title compound as a white solid. ¹H NMR (400 MHz, DMSO-d₆) δ 9.16 (d, J=8.9 Hz, 1H), 8.72 (d, J=7.9 Hz, 1H), 8.58-8.49 (m, 1H), 8.44-8.11 (m, 2H), 7.91 (d, J=23.7 Hz, 2H), 7.30 (s, 1H), 5.13 (t, J=8.8 Hz, 1H), 4.28 (t, J=8.4 Hz, 1H), 2.49-2.41 (m, 4H), 2.33-1.55 (m, 7H), 1.49-1.14 (m, 3H), 0.69-0.32 (m, 4H). MS (ESI) m/z: [M+H]+ Found 604.2.

Example 68

1-Cyclopropyl-N—((S)-(7-((R)-cyclopropyl(4,4,4-trifluorobutanamido)methyl)imidazo[1,2-b]pyridazin-2-yl)(4,4-difluorocyclohexyl)methyl)-1H-1,2,3-triazole-5-carboxamide

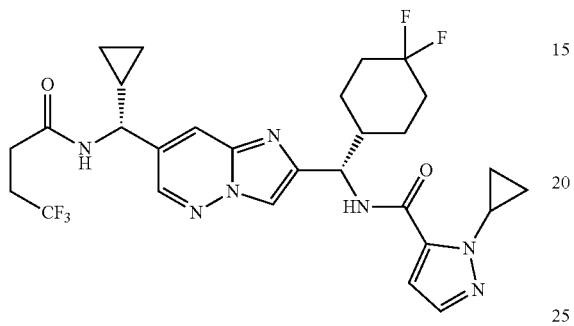

The title compound was prepared as described for the synthesis of Example 63, using 1-cyclopropyl-1H-1,2,3-triazole-5-carboxylic acid in place of 2-((3,3-difluorocyclobutyl)methyl)-2H-1,2,3-triazole-4-carboxylic acid to provide the title compound as a white solid. $^1$H NMR (400 MHz, DMSO-$d_6$) δ 9.07 (d, J=9.0 Hz, 1H), 8.71 (d, J=7.7 Hz, 1H), 8.51 (d, J=2.1 Hz, 1H), 8.27 (s, 1H), 8.23 (s, 1H), 7.94 (dd, J=1.9, 1.0 Hz, 1H), 5.18 (t, J=8.5 Hz, 1H), 4.34-4.25 (m, 2H), 2.49-2.42 (m, 4H), 2.25-2.12 (m, 1H), 2.10-1.57 (m, 5H), 1.47-1.03 (m, 8H), 0.63-0.45 (m, 3H), 0.42-0.33 (m, 1H). MS (ESI) m/z: [M+H]+ Found 595.3.

Example 69

N—((S)-(7-((R)-Cyclopropyl(4,4,4-trifluorobutanamido)methyl)imidazo[1,2-b]pyridazin-2-yl)(4,4-difluorocyclohexyl)methyl)-1-(1,3-difluoropropan-2-yl)-1H-pyrazole-5-carboxamide

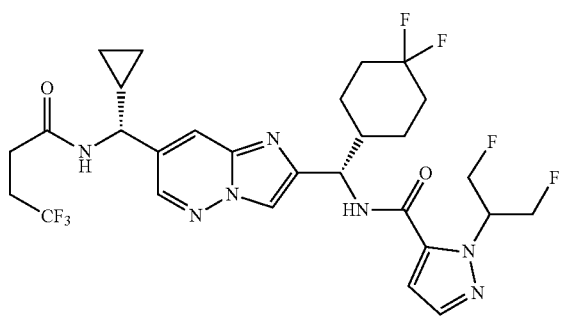 [SMILES: O=C(CCC(F)(F)F)N[C@@H](c1cnn2cc([C@@H](NC(=O)c3ccnn3C(CF)CF)C3CCC(F)(F)CC3)nc2c1)C1CC1]

The title compound was prepared as described for the synthesis of Example 63, using 1-(1,3-difluoropropan-2-yl)-1H-pyrazole-5-carboxylic acid (Intermediate 115) in place of 2-((3,3-difluorocyclobutyl)methyl)-2H-1,2,3-triazole-4-carboxylic acid to provide the title compound as a white solid. $^1$H NMR (400 MHz, DMSO-$d_6$) δ 8.84 (d, J=9.0 Hz, 1H), 8.71 (d, J=7.7 Hz, 1H), 8.50 (d, J=2.0 Hz, 1H), 8.19 (s, 1H), 7.97-7.90 (m, 1H), 7.62 (d, J=2.0 Hz, 1H), 7.10 (d, J=2.0 Hz, 1H), 6.03-5.85 (m, 1H), 5.14 (t, J=8.7 Hz, 1H), 4.94-4.66 (m, 4H), 4.29 (t, J=8.3 Hz, 1H), 2.48-2.43 (m, 4H), 2.25-2.12 (m, 1H), 2.06-1.92 (m, 2H), 1.92-1.67 (m, 3H), 1.67-1.56 (m, 1H), 1.45-1.13 (m, 3H), 0.62-0.45 (m, 3H), 0.42-0.32 (m, 1H). MS (ESI) m/z: [M+H]+ Found 632.2.

Example 70

N—((S)-(7-((R)-Cyclopropyl(4,4,4-trifluorobutanamido)methyl)imidazo[1,2-b]pyridazin-2-yl)(4,4-difluorocyclohexyl)methyl)-1-(2-(trifluoromethoxy)ethyl)-1H-1,2,4-triazole-5-carboxamide

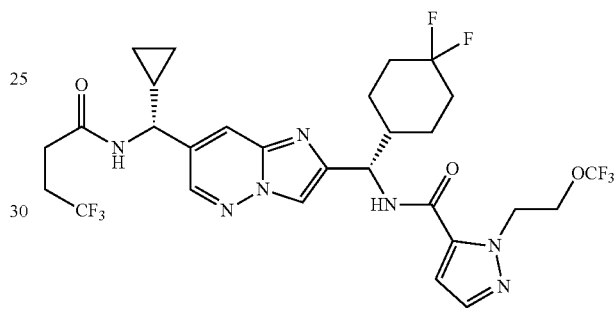

To a microwave vial was added N—((R)-(2-((S)-amino(4,4-difluorocyclohexyl)methyl)imidazo[1,2-b]pyridazin-7-yl)(cyclopropyl)methyl)-4,4,4-trifluorobutanamide (50 mg, 0.11 mmol, Intermediate 51), methyl 1-(2-(trifluoromethoxy)ethyl)-1H-1,2,4-triazole-5-carboxylate (39 mg, 0.16 mmol, Intermediate 121) and toluene (4 mL). Then, AlMe$_3$ (0.22 mL, 0.44 mmol, 2 M in toluene) was added dropwise and the vial was capped. The resulting mixture was heated to 90° C. for 1 h. The reaction was then quenched with water and acidified with 0.2 M aqueous HCl. The aqueous layer was extracted with DCM, brine and EtOAc. The organic layers were dried over anhydrous Na$_2$SO$_4$, filtered through a pad of Celite® and concentrated to dryness. The crude material was purified by silica gel chromatography (0-100% ethyl acetate (with 10% MeOH)/hexanes) and by basic reverse phase HPLC (ISCO ACCQ Prep, Gemini Prep NX-C18 5 μm column 21.5×150 mm, gradient 10-70% Acetonitrile: 20 mM ammonium hydroxide (aqueous) over 20 min). The purified fractions were concentrated to dryness to give the titled compound. $^1$H NMR (500 MHz, DMSO-$d_6$) δ 8.97 (d, J=9.2 Hz, 1H), 8.71 (d, J=7.7 Hz, 1H), 8.51 (d, J=2.1 Hz, 1H), 8.25 (s, 1H), 8.18 (s, 1H), 8.01-7.93 (m, 1H), 5.13 (t, J=8.6 Hz, 1H), 5.01-4.86 (m, 2H), 4.52-4.42 (m, 2H), 4.29 (t, J=8.4 Hz, 1H), 2.49-2.42 (m, 4H), 2.20-2.10 (m, 1H), 2.06-1.92 (m, 2H), 1.92-1.65 (m, 3H), 1.65-1.53 (m, 1H), 1.39-1.16 (m, 3H), 0.62-0.46 (m, 3H), 0.42-0.33 (m, 1H). MS (ESI) m/z: [M+H]+ Found 667.3.

Example 71

N—((S)-(7-((R*)-Cyclopropyl(4,4,4-trifluorobutanamido)methyl)imidazo[1,2-b]pyridazin-2-yl)(4,4-difluorocyclohexyl)methyl)-1-(3,3,3-trifluoropropyl)-1H-1,2,3-triazole-5-carboxamide

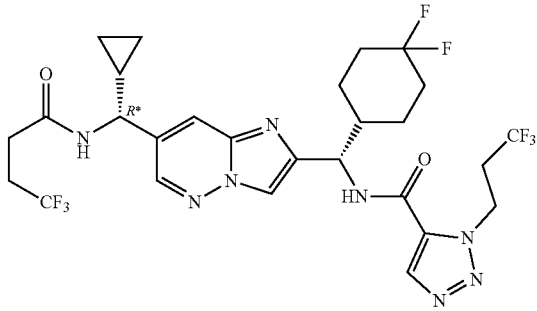 [SMILES: O=C(CCC(F)(F)F)N[C@@H](c1cnn2cc([C@@H](NC(=O)c3cnnn3CCC(F)(F)F)C3CCC(F)(F)CC3)nc2c1)C1CC1]

N-((1S)-(7-(Cyclopropyl(4,4,4-trifluorobutanamido)methyl)imidazo[1,2-b]pyridazin-2-yl)(4,4-difluorocyclohexyl)methyl)-1-(3,3,3-trifluoropropyl)-1H-1,2,3-triazole-5-carboxamide (Intermediate 129) was purified by SFC using a chiral stationary phase (Chiralpak IA, 9:1:90 methanol:isopropanol:$CO_2$ with 0.2% isopropylamine) to give a pair of diastereomers. The second eluting isomer (Example 71) was designated R*: $^1$H NMR (400 MHz, $CDCl_3$) δ 8.36 (d, J=2.0 Hz, 1H), 8.12 (s, 1H), 7.89-7.84 (m, 2H), 7.54 (d, J=8.7 Hz, 1H), 6.52 (d, J=6.9 Hz, 1H), 5.24 (t, J=8.1 Hz, 1H), 4.98 (t, J=7.3 Hz, 2H), 4.31 (dd, J=9.5, 6.8 Hz, 1H), 2.88-2.74 (m, 2H), 2.58-2.40 (m, 4H), 2.20-1.93 (m, 3H), 1.83-1.12 (m, 7H), 0.78-0.68 (m, 2H), 0.55-0.42 (m, 2H). MS (ESI) m/z: [M+H]$^+$ Found 651.2.

Example 72

N—((S)-(7-((S*)-Cyclopropyl(2-(3,3-difluorocyclobutyl)acetamido)methyl)imidazo[1,2-b]pyridazin-2-yl)(4,4-difluorocyclohexyl)methyl)-1-(3,3,3-trifluoropropyl)-1H-1,2,3-triazole-5-carboxamide

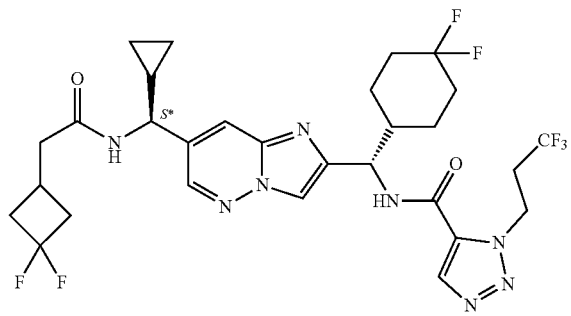 [SMILES: O=C(CC1CC(F)(F)C1)N[C@H](c1cnn2cc([C@@H](NC(=O)c3cnnn3CCC(F)(F)F)C3CCC(F)(F)CC3)nc2c1)C1CC1]

Example 73

N—((S)-(7-((R*)-Cyclopropyl(2-(3,3-difluorocyclobutyl)acetamido)methyl)imidazo[1,2-b]pyridazin-2-yl)(4,4-difluorocyclohexyl)methyl)-1-(3,3,3-trifluoropropyl)-1H-1,2,3-triazole-5-carboxamide

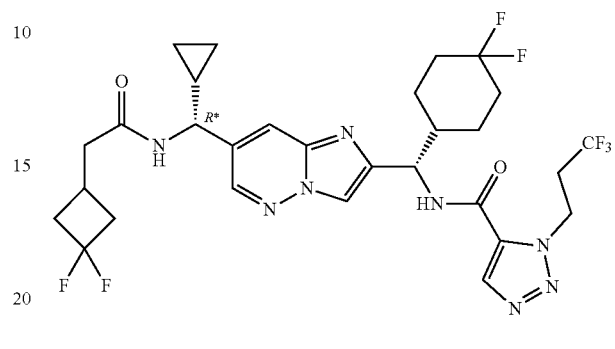

N-((1S)-(7-(Cyclopropyl(2-(3,3-difluorocyclobutyl)acetamido)methyl)imidazo[1,2-b]pyridazin-2-yl)(4,4-difluorocyclohexyl)methyl)-1-(3,3,3-trifluoropropyl)-1H-1,2,3-triazole-5-carboxamide (Intermediate 130) was purified by SFC using a chiral stationary phase (Whelk-O® 1 (S,S), 25% methanol, 75% $CO_2$) to give a pair of diastereomers. The first eluting isomer was Example 72 and designated S*. The second eluting isomer was Example 73 and designated R*. Example 72: $^1$H NMR (400 MHz, DMSO-$d_6$) δ 9.17 (d, J=8.9 Hz, 1H), 8.59 (d, J=7.8 Hz, 1H), 8.49 (d, J=2.0 Hz, 1H), 8.42 (s, 1H), 8.23 (s, 1H), 7.94-7.89 (m, 1H), 5.16 (t, J=8.7 Hz, 1H), 4.90 (td, J=6.9, 3.9 Hz, 2H), 4.26 (t, J=8.4 Hz, 1H), 2.99-2.84 (m, 2H), 2.71-2.57 (m, 2H), 2.42-2.13 (m, 6H), 2.10-1.55 (m, 6H), 1.44-1.14 (m, 3H), 0.61-0.42 (m, 3H), 0.40-0.32 (m, 1H). MS (ESI) m/z: [M+H]$^+$ Found 659.1. Example 73: $^1$H NMR (400 MHz, DMSO-$d_6$) δ 9.17 (d, J=8.9 Hz, 1H), 8.59 (d, J=7.8 Hz, 1H), 8.49 (d, J=2.0 Hz, 1H), 8.42 (s, 1H), 8.23 (s, 1H), 7.92 (d, J=2.0 Hz, 1H), 5.16 (t, J=8.6 Hz, 1H), 4.90 (td, J=6.9, 4.0 Hz, 2H), 4.26 (t, J=8.4 Hz, 1H), 2.99-2.85 (m, 2H), 2.62 (ddd, J=13.8, 7.7, 4.2 Hz, 2H), 2.42-2.15 (m, 6H), 2.10-1.56 (m, 6H), 1.44-1.14 (m, 3H), 0.61-0.42 (m, 3H), 0.41-0.32 (m, 1H). MS (ESI) m/z: [M+H]$^+$ Found 659.1.

Example 74

N—((S)-(7-((R)-Cyclopropyl(4,4,4-trifluorobutanamido)methyl)imidazo[1,2-b]pyridazin-2-yl)(4,4-difluorocyclohexyl)methyl)-2-(2,2,2-trifluoroethyl)isonicotinamide

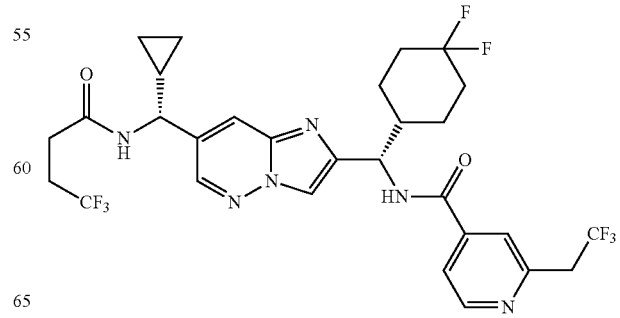

The title compound was prepared as described for the synthesis of Example 47, using 2-(2,2,2-trifluoroethyl)isonicotinic acid (Intermediate 134) in place of 1-(3-fluoropropyl)-1H-1,2,4-triazole-5-carboxylic acid. $^1$H NMR (400 MHz, DMSO-d$_6$) δ 9.08 (d, J=8.9 Hz, 1H), 8.73-8.69 (m, 2H), 8.50 (d, J=2.1 Hz, 1H), 8.23 (s, 1H), 7.93 (d, J=2.1 Hz, 1H), 7.84 (s, 1H), 7.80 (dd, J=5.1, 1.7 Hz, 1H), 5.19 (t, J=8.6 Hz, 1H), 4.28 (dd, J=9.0, 7.7 Hz, 1H), 3.89 (q, J=11.4 Hz, 2H), 2.49-2.44 (m, 4H), 2.26-1.14 (m, 10H), 0.63-0.45 (m, 3H), 0.43-0.32 (m, 1H). MS (ESI) m/z: [M+H]$^+$ Found 647.2.

Example 75

3-Cyclopropyl-N—((S)-(7-((R)-cyclopropyl(4,4,4-trifluorobutanamido)methyl)imidazo[1,2-b]pyridazin-2-yl)(4,4-difluorocyclohexyl)methyl)isoxazole-4-carboxamide

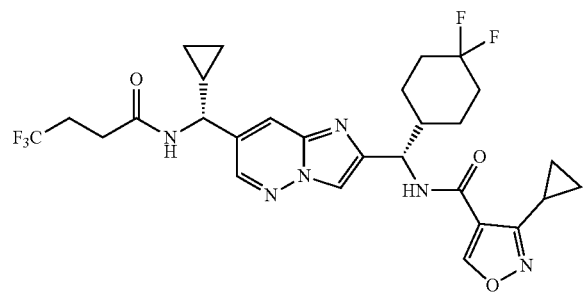 [SMILES: O=C(CCC(F)(F)F)N[C@@H](c1cnn2cc([C@@H](NC(=O)c3conc3C3CC3)C3CCC(F)(F)CC3)nc2c1)C1CC1]

DMF (3 mL), 3-cyclopropylisoxazole-4-carboxylic acid (42.4 mg, 0.28 mmol), Hünig's base (125 μL, 0.73 mmol) and HATU (97.8 mg, 0.26 mmol) were combined and stirred for 3 min, followed by the addition of N—((R)-(2-((S)-amino(4,4-difluorocyclohexyl)methyl)imidazo[1,2-b]pyridazin-7-yl)(cyclopropyl)methyl)-4,4,4-trifluorobutanamide (100.6 mg, 0.22 mmol, Intermediate 51).

The resulting mixture was stirred at rt overnight then transferred to a separatory funnel with ethyl acetate dilution. The aqueous phase was separated, then the organic phase was washed three times with deionized water. The organic phase was dried over anhydrous magnesium sulfate, filtered and concentrated under reduced pressure. Purification via silica gel chromatography (0-100% DCM/(10% (2 M NH$_3$ in MeOH) in DCM)) yielded the title compound. $^1$H NMR (500 MHz, CD$_3$OD) δ 9.05 (s, 1H), 8.46 (d, J=2.3 Hz, 1H), 8.09 (s, 1H), 7.85-7.90 (m, 1H), 5.25 (d, J=8.0 Hz, 1H), 4.28 (d, J=9.5 Hz, 1H), 2.45-2.61 (m, 4H), 2.32-2.40 (m, 1H), 2.13-2.24 (m, 1H), 1.92-2.13 (m, 3H), 1.61-1.87 (m, 3H), 1.34-1.53 (m, 2H), 1.22-1.30 (m, 1H), 0.92-1.05 (m, 4H), 0.66-0.74 (m, 2H), 0.46-0.52 (m, 2H). MS (ESI) m/z: [M+H]$^+$ Found 595.1.

Example 76

N—((S)-(7-((R)-Cyclopropyl(4,4,4-trifluorobutanamido)methyl)imidazo[1,2-b]pyridazin-2-yl)(4,4-difluorocyclohexyl)methyl)-3-isopropylisoxazole-4-carboxamide

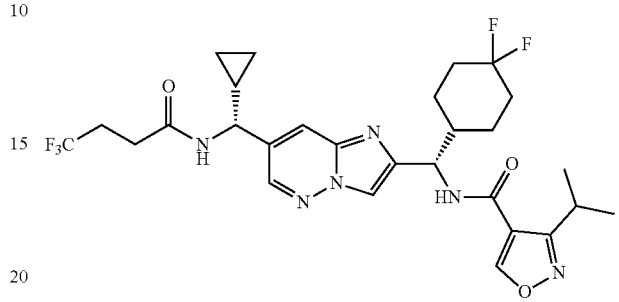

The title compound was prepared as described in the synthesis of Example 75, using 3-isopropylisoxazole-4-carboxylic acid in place of 3-cyclopropylisoxazole-4-carboxylic acid to provide the title compound. $^1$H NMR (500 MHz, CD$_3$OD) δ 9.06 (s, 1H), 8.46 (d, J=2.0 Hz, 1H), 8.08 (s, 1H), 7.85-7.88 (m, 1H), 5.22 (d, J=8.3 Hz, 1H), 4.28 (d, J=9.5 Hz, 1H), 3.40-3.50 (m, 1H), 2.45-2.61 (m, 4H), 1.91-2.23 (m, 4H), 1.61-1.86 (m, 3H), 1.44-1.54 (m, 1H), 1.34-1.44 (m, 1H), 1.24-1.30 (m, 7H), 0.66-0.74 (m, 2H), 0.46-0.53 (m, 2H). MS (ESI) m/z: [M+H]$^+$ Found 597.2.

Example 77

N—((S)-(7-((R)-Cyclopropyl(4,4,4-trifluorobutanamido)methyl)imidazo[1,2-b]pyridazin-2-yl)(4,4-difluorocyclohexyl)methyl)-3-(3,3,3-trifluoropropyl)isoxazole-4-carboxamide

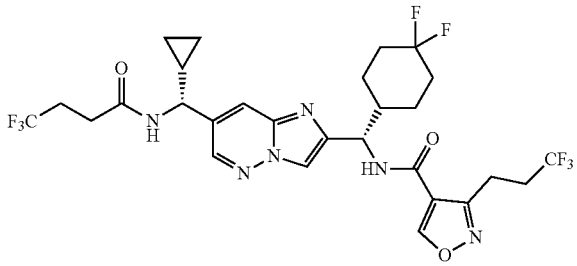 [SMILES: O=C(CCC(F)(F)F)N[C@@H](c1cnn2cc([C@@H](NC(=O)c3conc3CCC(F)(F)F)C3CCC(F)(F)CC3)nc2c1)C1CC1]

The title compound was prepared as described in the synthesis of Example 75, using 3-(3,3,3-trifluoropropyl)isoxazole-4-carboxylic acid (Intermediate 136) in place of 3-cyclopropylisoxazole-4-carboxylic acid to provide the title compound. $^1$H NMR (500 MHz, CD$_3$OD) δ 9.18 (s, 1H), 8.45 (d, J=2.3 Hz, 1H), 8.08 (s, 1H), 7.83-7.89 (m, 1H), 5.21 (d, J=8.5 Hz, 1H), 4.27 (d, J=9.5 Hz, 1H), 3.11-3.20 (m, 2H), 2.46-2.66 (m, 6H), 2.14-2.23 (m, 1H), 1.94-2.13 (m, 3H), 1.69-1.85 (m, 2H), 1.60-1.69 (m, 1H), 1.40-1.53 (m, 1H), 1.32-1.42 (m, 1H), 1.22-1.31 (m, 1H), 0.66-0.74 (m, 2H), 0.46-0.52 (m, 2H). MS (ESI) m/z: [M+H]$^+$ Found 651.1.

Example 78

N—((S)-(7-((R)-Cyclopropyl(4,4,4-trifluorobutanamido)methyl)imidazo[1,2-b]pyridazin-2-yl)(4,4-difluorocyclohexyl)methyl)-1-isopropyl-3-methyl-1H-pyrazole-5-carboxamide

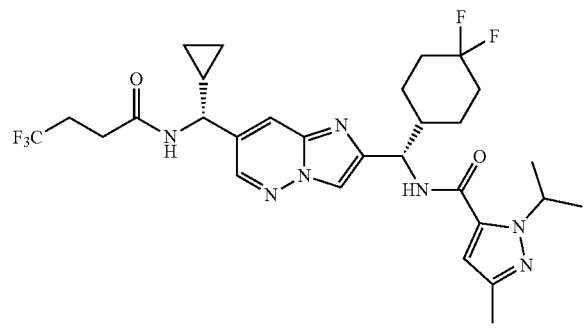 [SMILES: Cc1cc(C(=O)N[C@H](c2cn3ncc([C@H](NC(=O)CCC(F)(F)F)C4CC4)cc3n2)C2CCC(F)(F)CC2)n(C(C)C)n1]

The title compound was prepared as described in the synthesis of Example 75, using 1-isopropyl-3-methyl-1H-pyrazole-5-carboxylic acid in place of 3-cyclopropylisoxazole-4-carboxylic acid to provide the title compound. $^1$H NMR (500 MHz, CD$_3$OD) δ 8.46 (d, J=2.0 Hz, 1H), 8.08 (s, 1H), 7.84-7.91 (m, 1H), 6.54 (s, 1H), 5.25-5.34 (m, 1H), 5.22 (d, J=8.5 Hz, 1H), 4.28 (d, J=9.5 Hz, 1H), 2.45-2.61 (m, 4H), 2.25 (s, 3H), 2.14-2.23 (m, 1H), 1.91-2.14 (m, 3H), 1.59-1.87 (m, 3H), 1.34-1.53 (m, 8H), 1.22-1.30 (m, 1H), 0.66-0.74 (m, 2H), 0.46-0.53 (m, 2H). MS (ESI) m/z: [M+H]$^+$ Found 610.2.

Example 79

N—((S)-(7-((R)-Cyclopropyl(4,4,4-trifluorobutanamido)methyl)imidazo[1,2-b]pyridazin-2-yl)(4,4-difluorocyclohexyl)methyl)-3-methylisoxazole-4-carboxamide

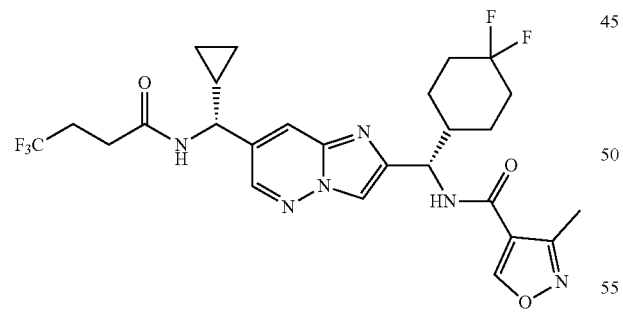

The title compound was prepared as described in the synthesis of Example 75, using 3-methylisoxazole-4-carboxylic acid in place of 3-cyclopropylisoxazole-4-carboxylic acid to provide the title compound. $^1$H NMR (500 MHz, CD$_3$OD) δ 9.11 (s, 1H), 8.46 (d, J=2.3 Hz, 1H), 8.08 (s, 1H), 7.84-7.89 (m, 1H), 5.22 (d, J=8.3 Hz, 1H), 4.28 (d, J=9.5 Hz, 1H), 2.45-2.60 (m, 4H), 2.42 (s, 3H), 1.92-2.23 (m, 4H), 1.59-1.87 (m, 3H), 1.43-1.54 (m, 1H), 1.32-1.42 (m, 1H), 1.21-1.30 (m, 1H), 0.66-0.74 (m, 2H), 0.46-0.53 (m, 2H). MS (ESI) m/z: [M+H]$^+$ Found 569.1.

Example 80

N—((S)-(7-((R)-Cyclopropyl(4,4,4-trifluorobutanamido)methyl)imidazo[1,2-b]pyridazin-2-yl)(4,4-difluorocyclohexyl)methyl)-3,5-dimethylisoxazole-4-carboxamide

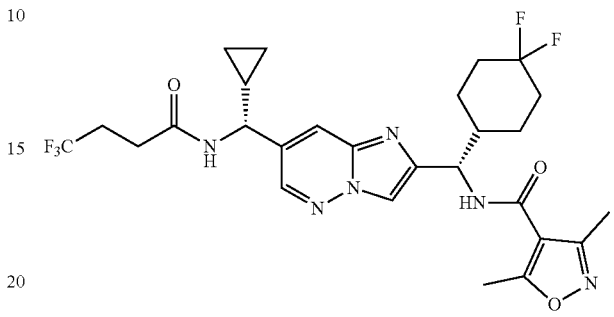

The title compound was prepared as described in the synthesis of Example 75, using 3,5-dimethylisoxazole-4-carboxylic acid in place of 3-cyclopropylisoxazole-4-carboxylic acid to provide the title compound. $^1$H NMR (400 MHz, CD$_3$OD) δ 8.46 (d, J=2.0 Hz, 1H), 8.07 (s, 1H), 7.84-7.91 (m, 1H), 5.26 (d, J=7.8 Hz, 1H), 4.27 (d, J=9.5 Hz, 1H), 2.43-2.62 (m, 7H), 2.33 (s, 3H), 1.90-2.26 (m, 4H), 1.61-1.89 (m, 3H), 1.34-1.58 (m, 2H), 1.19-1.32 (m, 1H), 0.63-0.77 (m, 2H), 0.46-0.54 (m, 2H). MS (ESI) m/z: [M+H]$^+$ Found 583.1.

Example 81

N—((S)-(7-((R)-Cyclopropyl(4,4,4-trifluorobutanamido)methyl)imidazo[1,2-b]pyridazin-2-yl)(4,4-difluorocyclohexyl)methyl)-5-isopropyl-3-methylisoxazole-4-carboxamide

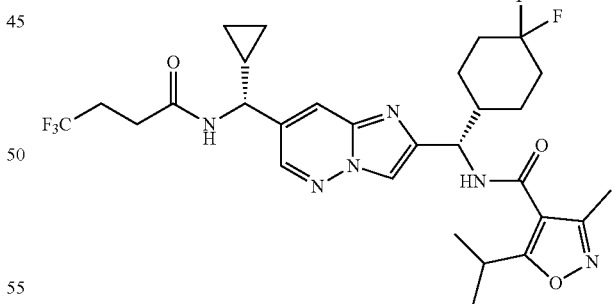

The title compound was prepared as described in the synthesis of Example 75, using 5-isopropyl-3-methylisoxazole-4-carboxylic acid in place of 3-cyclopropylisoxazole-4-carboxylic acid to provide the title compound. $^1$H NMR (400 MHz, CD$_3$OD) δ 8.46 (d, J=2.0 Hz, 1H), 8.05 (s, 1H), 7.84-7.90 (m, 1H), 5.26 (d, J=7.8 Hz, 1H), 4.27 (d, J=9.5 Hz, 1H), 3.33-3.43 (m, 1H), 2.43-2.62 (m, 4H), 2.30 (s, 3H), 1.98-2.25 (m, 3H), 1.88-1.98 (m, 1H), 1.61-1.88 (m, 3H), 1.35-1.57 (m, 2H), 1.22-1.31 (m, 7H), 0.65-0.76 (m, 2H), 0.45-0.55 (m, 2H). MS (ESI) m/z: [M+H]$^+$ Found 611.2.

Example 82

N—((S)-(7-((R)-Cyclopropyl(4,4,4-trifluorobutanamido)methyl)imidazo[1,2-b]pyridazin-2-yl)(4,4-difluorocyclohexyl)methyl)-3-ethyl-5-methylisoxazole-4-carboxamide

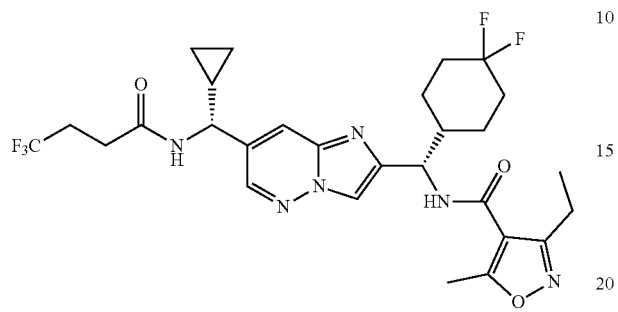

The title compound was prepared as described in the synthesis of Example 75, using 3-ethyl-5-methylisoxazole-4-carboxylic acid in place of 3-cyclopropylisoxazole-4-carboxylic acid to provide the title compound. $^1$H NMR (500 MHz, CD$_3$OD) δ 8.46 (d, J=2.0 Hz, 1H), 8.05 (s, 1H), 7.83-7.91 (m, 1H), 5.25 (d, J=8.0 Hz, 1H), 4.26 (d, J=9.5 Hz, 1H), 2.81 (s, 1H), 2.72-2.79 (m, 2H), 2.44-2.58 (m, 6H), 2.14-2.24 (m, 1H), 1.98-2.14 (m, 2H), 1.89-1.98 (m, 1H), 1.62-1.87 (m, 3H), 1.35-1.56 (m, 2H), 1.20-1.30 (m, 1H), 1.16 (t, J=7.5 Hz, 3H), 0.66-0.74 (m, 2H), 0.45-0.54 (m, 2H). MS (ESI) m/z: [M+H]$^+$ Found 597.2.

Example 83

N—((S)-(7-((R)-Cyclopropyl(4,4,4-trifluorobutanamido)methyl)imidazo[1,2-b]pyridazin-2-yl)(4,4-difluorocyclohexyl)methyl)-3-ethylisoxazole-4-carboxamide

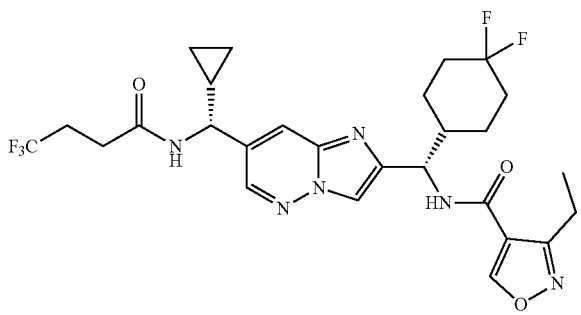 [SMILES: CCc1nocc1C(=O)N[C@H](c1cn2ncc([C@H](NC(=O)CCC(F)(F)F)C3CC3)cc2n1)C1CCC(F)(F)CC1]

The title compound was prepared as described in the synthesis of Example 75, using 3-ethylisoxazole-4-carboxylic acid in place of 3-cyclopropylisoxazole-4-carboxylic acid to provide the title compound. $^1$H NMR (500 MHz, CD$_3$OD) δ 9.10 (s, 1H), 8.46 (d, J=2.0 Hz, 1H), 8.08 (s, 1H), 7.85-7.89 (m, 1H), 5.22 (d, J=8.3 Hz, 1H), 4.28 (d, J=9.5 Hz, 1H), 2.79-2.95 (m, 3H), 2.45-2.61 (m, 4H), 1.92-2.24 (m, 4H), 1.60-1.87 (m, 3H), 1.43-1.54 (m, 1H), 1.32-1.43 (m, 1H), 1.20-1.26 (m, 3H), 0.66-0.74 (m, 2H), 0.46-0.53 (m, 2H). MS (ESI) m/z: [M+H]$^+$ Found 583.1.

Example 84

5-Cyclopropyl-N—((S)-(7-((R)-cyclopropyl(4,4,4-trifluorobutanamido)methyl)imidazo[1,2-b]pyridazin-2-yl)(4,4-difluorocyclohexyl)methyl)isoxazole-4-carboxamide

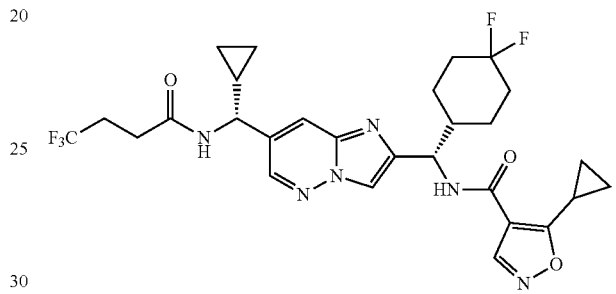

5-Cyclopropylisoxazole-4-carboxylic acid (40.3 mg, 0.26 mmol) and thionyl chloride (3 mL, 41.4 mmol) were combined and heated in a pre-equilibrated 80° C. oil bath for 2.5 h under a nitrogen atmosphere. The reaction was cooled to rt and the excess thionyl chloride was removed under reduced pressure to yield a thick amber oil. To the acid chloride was added DCM (4 mL) and the solution was cooled to 0° C. in an ice-water bath followed by the addition of Hünig's base (150 μL, 0.87 mmol) and N—((R)-(2-((S)-amino(4,4-difluorocyclohexyl)methyl)imidazo[1,2-b]pyridazin-7-yl)(cyclopropyl)methyl)-4,4,4-trifluorobutanamide (100.3 mg, 0.22 mmol, Intermediate 51) under a nitrogen atmosphere. The contents were stirred at 0° C. for 15 min, then the ice bath was removed and the mixture was allowed to warm to rt and stir at rt overnight. The mixture was then cooled to 0° C., quenched with deionized water, then transferred to a separatory funnel with ethyl acetate dilution. The aqueous phase was separated, then the organic phase was dried over anhydrous magnesium sulfate, filtered and concentrated under reduced pressure. Purification via silica gel chromatography (0-100% EtOAc/hexanes) yielded the title compound. $^1$H NMR (500 MHz, CD$_3$OD) δ 8.73 (s, 1H), 8.45 (d, J=2.3 Hz, 1H), 8.09 (s, 1H), 7.84-7.90 (m, 1H), 5.24 (d, J=8.5 Hz, 1H), 4.28 (d, J=9.3 Hz, 1H), 2.80-2.89 (m, 1H), 2.45-2.60 (m, 4H), 2.14-2.23 (m, 1H), 2.09 (td, J=3.3, 6.88 Hz, 1H), 1.95-2.05 (m, 2H), 1.68-1.85 (m, 2H), 1.59-1.68 (m, 1H), 1.43-1.54 (m, 1H), 1.32-1.42 (m, 1H), 1.21-1.31 (m, 1H), 1.11-1.20 (m, 4H), 0.66-0.74 (m, 2H), 0.45-0.53 (m, 2H). MS (ESI) m/z: [M+H]$^+$ Found 595.2.

Example 85

N—((S)-(7-((R)-Cyclopropyl(4,4,4-trifluorobutanamido)methyl)imidazo[1,2-b]pyridazin-2-yl)(4,4-difluorocyclohexyl)methyl)-1-isopropyl-1H-imidazole-5-carboxamide

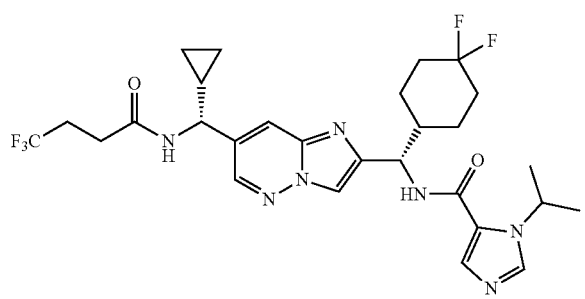 [SMILES: CC(C)n1cncc1C(=O)N[C@H](c1cn2ncc([C@H](NC(=O)CCC(F)(F)F)C3CC3)cc2n1)C1CCC(F)(F)CC1]

N-(3-Dimethylaminopropyl)-N-ethylcarbodiimide hydrochloride (50 mg, 0.26 mmol) was added to a solution consisting of 1-isopropyl-1H-imidazole-5-carboxylic acid (40 mg, 0.26 mmol), HOAt (36 mg, 0.26 mmol), Hünig's base (0.18 mL, 1.1 mmol) and dichloromethane (1 mL). The resultant mixture was stirred for 10 min at rt followed by the addition of N—((R)-(2-((S)-amino(4,4-difluorocyclohexyl)methyl)imidazo[1,2-b]pyridazin-7-yl)(cyclopropyl)methyl)-4,4,4-trifluorobutanamide (100 mg, 0.22 mmol, Intermediate 51). The resultant mixture was stirred for 16 h at rt. The reaction mixture was partitioned between saturated aqueous ammonium chloride (5 mL) and dichloromethane (5 mL). The layers were separated, and the aqueous phase was extracted with dichloromethane (5 mL×2). The combined organic extracts were washed with brine, dried over anhydrous $Na_2SO_4$, filtered and concentrated to dryness under reduced pressure to afford the crude product. Purification via preparatory HPLC (Boston Prime C18 column, 150×30 mm×5 μm column (eluent: 45% to 75% (v/v) ACN and $H_2O$ with 0.04% $NH_3$ in $H_2O$ and 10 mM $NH_4HCO_3$) and concentration of the fractions isolated the desired product that was suspended in water (10 mL), frozen using dry ice/ethanol, and then lyophilized to dryness to afford the title compound. $^1H$ NMR (400 MHz, DMSO-$d_6$) δ 8.77 (d, J=7.5 Hz, 1H), 8.61-8.48 (m, 2H), 8.20 (s, 1H), 8.01-7.91 (m, 2H), 7.69 (s, 1H), 5.23-5.09 (m, 2H), 4.35-4.24 (m, 1H), 2.51-2.44 (m, 4H), 2.23-2.11 (m, 1H), 2.11-1.94 (m, 2H), 1.92-1.68 (m, 3H), 1.67-1.58 (m, 1H), 1.45-1.34 (m, 7H), 1.32-1.17 (m, 2H), 0.64-0.46 (m, 3H), 0.43-0.34 (m, 1H). MS (ESI) m/z: [M+H]$^+$ Found 596.3.

Example 86

N—((S)-(7-((R)-Cyclopropyl(4,4,4-trifluorobutanamido)methyl)imidazo[1,2-b]pyridazin-2-yl)(4,4-difluorocyclohexyl)methyl)-5-isopropyloxazole-4-carboxamide

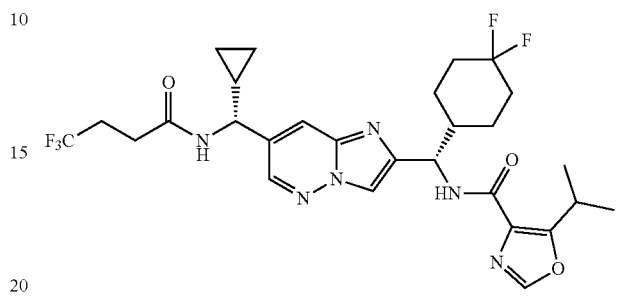

The title compound was prepared as described in the synthesis of Example 85, using 5-isopropyloxazole-4-carboxylic acid in place of 1-isopropyl-1H-imidazole-5-carboxylic acid to provide the title compound. $^1H$ NMR (400 MHz, DMSO-$d_6$) δ 8.77 (d, J=7.7 Hz, 1H), 8.53 (d, J=2.0 Hz, 1H), 8.38 (s, 1H), 8.27 (s, 1H), 8.16 (d, J=9.3 Hz, 1H), 8.03-7.98 (m, 1H), 5.20-5.12 (m, 1H), 4.34-4.25 (m, 1H), 3.85-3.74 (m, 1H), 2.51-2.44 (m, 4H), 2.13-1.93 (m, 3H), 1.91-1.65 (m, 3H), 1.64-1.53 (m, 1H), 1.41-1.29 (m, 1H), 1.26-1.17 (m, 8H), 0.64-0.47 (m, 3H), 0.43-0.35 (m, 1H). MS (ESI) m/z: [M+H]$^+$ Found 597.3.

Example 87

N—((S)-(7-((R)-Cyclopropyl(4,4,4-trifluorobutanamido)methyl)imidazo[1,2-b]pyridazin-2-yl)(4,4-difluorocyclohexyl)methyl)-5-isopropyl-1,2,3-thiadiazole-4-carboxamide

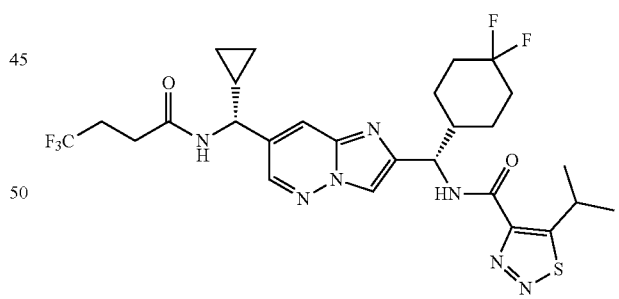

The title compound was prepared as described in the synthesis of Example 85, using 5-isopropyl-1,2,3-thiadiazole-4-carboxylic acid in place of 1-isopropyl-1H-imidazole-5-carboxylic acid to provide the title compound. $^1H$ NMR (400 MHz, DMSO-$d_6$) δ 9.08 (d, J=9.3 Hz, 1H), 8.75 (d, J=7.7 Hz, 1H), 8.51 (d, J=2.0 Hz, 1H), 8.28 (s, 1H), 8.00-7.95 (m, 1H), 5.29-5.21 (m, 1H), 4.32-4.23 (m, 1H), 4.14-4.02 (m, 1H), 2.48-2.44 (m, 4H), 2.24-2.11 (m, 1H), 2.08-1.89 (m, 3H), 1.88-1.70 (m, 2H), 1.68-1.58 (m, 1H), 1.45-1.36 (m, 1H), 1.34 (d, J=6.8 Hz, 3H), 1.31 (d, J=6.8 Hz, 3H), 1.27-1.14 (m, 2H), 0.63-0.46 (m, 3H), 0.42-0.33 (m, 1H). MS (ESI) m/z: [M+H]$^+$ Found 614.2.

Example 88

N—((S)-(7-((R)-Cyclopropyl(4,4,4-trifluorobutanamido)methyl)imidazo[1,2-b]pyridazin-2-yl)(4,4-difluorocyclohexyl)methyl)-5-ethylisoxazole-4-carboxamide

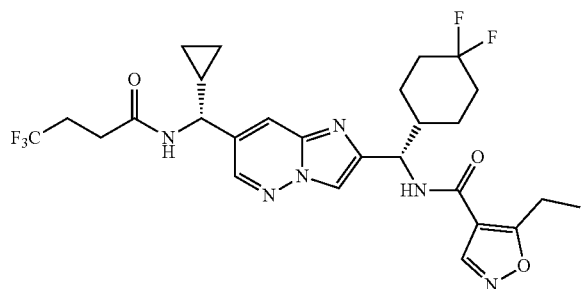

The title compound was prepared as described in the synthesis of Example 84, using 5-ethylisoxazole-4-carboxylic acid in place of 5-cyclopropylisoxazole-4-carboxylic acid to provide the title compound. $^1$H NMR (500 MHz, CD$_3$OD) δ 8.76 (s, 1H), 8.45 (d, J=2.0 Hz, 1H), 8.08 (s, 1H), 7.82-7.91 (m, 1H), 5.21 (d, J=8.5 Hz, 1H), 4.27 (d, J=9.3 Hz, 1H), 3.10 (q, J=7.8 Hz, 2H), 2.44-2.61 (m, 4H), 1.95-2.23 (m, 4H), 1.58-1.88 (m, 3H), 1.33-1.54 (m, 2H), 1.22-1.30 (m, 4H), 0.66-0.74 (m, 2H), 0.45-0.53 (m, 2H). MS (ESI) m/z: [M+H]$^+$ Found 583.1.

Example 89

N—((S)-(7-((R)-Cyclopropyl(4,4,4-trifluorobutanamido)methyl)imidazo[1,2-b]pyridazin-2-yl)(4,4-difluorocyclohexyl)methyl)-5-isopropylisoxazole-4-carboxamide

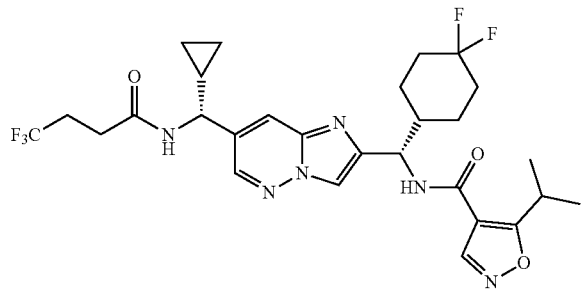 [SMILES: CC(C)c1oncc1C(=O)N[C@H](c1cn2ncc([C@H](NC(=O)CCC(F)(F)F)C3CC3)cc2n1)C1CCC(F)(F)CC1]

The title compound was prepared as described in the synthesis of Example 84, using 5-isopropylisoxazole-4-carboxylic acid in place of 5-cyclopropylisoxazole-4-carboxylic acid to provide the title compound. $^1$H NMR (500 MHz, CD$_3$OD) δ 8.76 (s, 1H), 8.46 (d, J=2.0 Hz, 1H), 8.09 (s, 1H), 7.83-7.92 (m, 1H), 5.23 (d, J=8.5 Hz, 1H), 4.28 (d, J=9.5 Hz, 1H), 3.75-3.89 (m, 1H), 2.45-2.62 (m, 4H), 2.14-2.24 (m, 1H), 2.05-2.13 (m, 1H), 1.94-2.05 (m, 2H), 1.70-1.85 (m, 2H), 1.58-1.70 (m, 1H), 1.42-1.54 (m, 1H), 1.23-1.39 (m, 8H), 0.66-0.74 (m, 2H), 0.46-0.53 (m, 2H). MS (ESI) m/z: [M+H]$^+$ Found 597.1.

Example 90

(1S,2R)—N—((S)-(7-((R)-Cyclopropyl(4,4,4-trifluorobutanamido)methyl)imidazo[1,2-b]pyridazin-2-yl)(4,4-difluorocyclohexyl)methyl)-2-fluorocyclopropane-1-carboxamide

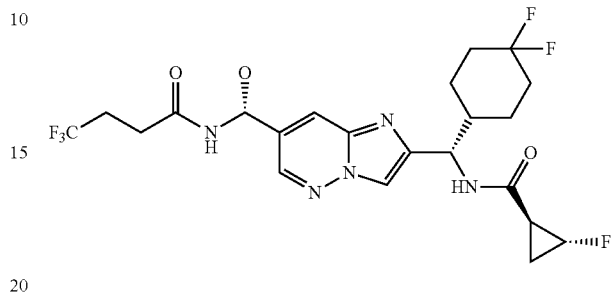

The title compound was prepared as described in the synthesis of Example 4, using (1S,2R)-2-fluorocyclopropane-1-carboxylic acid in place of 2-((2,2-difluorocyclobutyl)methyl)-2H-1,2,3-triazole-4-carboxylic acid to afford the title compound as a white solid. $^1$H NMR (400 MHz, CD$_3$OD) δ 8.45 (d, J=2.1 Hz, 1H), 7.99 (d, J=0.6 Hz, 1H), 7.85 (dd, J=2.0, 0.9 Hz, 1H), 5.07 (d, J=7.7 Hz, 1H), 4.88-4.65 (m, 1H), 4.27 (d, J=9.5 Hz, 1H), 2.64-2.41 (m, 4H), 2.26-1.94 (m, 4H), 1.93-1.84 (m, 1H), 1.84-1.68 (m, 2H), 1.68-1.57 (m, 1H), 1.54-1.10 (m, 5H), 0.77-0.66 (m, 2H), 0.56-0.44 (m, 2H). MS (ESI) m/z: [M+H]$^+$ Found 546.1.

Example 91

N—((S)-(7-((R)-Cyclopropyl(4,4,4-trifluorobutanamido)methyl)imidazo[1,2-b]pyridazin-2-yl)(4,4-difluorocyclohexyl)methyl)-1-((2,2-difluorocyclobutyl)methyl)-1H-1,2,3-triazole-5-carboxamide

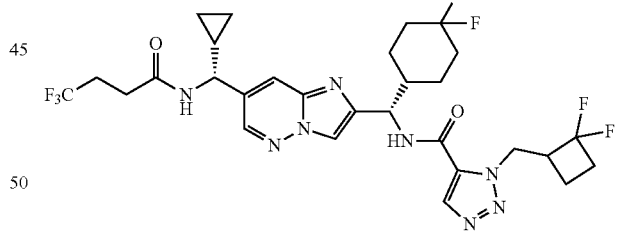

The title compound was prepared as described in the synthesis of Example 4, using 1-((2,2-difluorocyclobutyl)methyl)-1H-1,2,3-triazole-5-carboxylic acid (Intermediate 146) in place of 2-((2,2-difluorocyclobutyl)methyl)-2H-1,2,3-triazole-4-carboxylic acid to provide the title compound as a white solid. $^1$H NMR (400 MHz, CD$_3$OD) δ 8.46 (d, J=2.1 Hz, 1H), 8.21 (d, J 4.1 Hz, 1H), 8.10 (d, J=2.9 Hz, 1H), 7.91-7.82 (m, 1H), 5.22 (dd, J=8.6, 1.9 Hz, 1H), 5.05-4.91 (m, 1H), 4.81-4.74 (m, 1H), 4.26 (d, J=9.5 Hz, 1H), 3.51-3.34 (m, 1H), 2.63-2.35 (m, 6H), 2.31-2.16 (m, 1H), 2.16-1.94 (m, 3H), 1.92-1.79 (m, 2H), 1.79-1.70 (m, 1H), 1.70-1.56 (m, 2H), 1.56-1.31 (m, 2H), 1.31-1.18 (m, 1H), 0.71 (ddd, J=7.8, 4.5, 3.0 Hz, 2H), 0.55-0.45 (m, 2H). MS (ESI) m/z: [M+H]$^+$ Found 659.2.

Example 92

N—((S)-(7-((R)-Cyclopropyl(4,4,4-trifluorobutanamido)methyl)imidazo[1,2-b]pyridazin-2-yl)(4,4-difluorocyclohexyl)methyl)-1-((2,2-difluorocyclopropyl)methyl)-1H-1,2,3-triazole-5-carboxamide

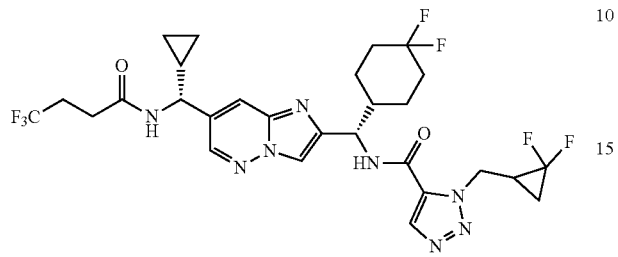

The title compound was prepared as described in the synthesis of Example 4, using 1-((2,2-difluorocyclopropyl)methyl)-1H-1,2,3-triazole-5-carboxylic acid (Intermediate 151) in place of 2-((2,2-difluorocyclobutyl)methyl)-2H-1,2,3-triazole-4-carboxylic acid to provide the title compound as a white solid. $^1$H NMR (500 MHz, CDCl$_3$) δ 8.34 (s, 1H), 8.11 (d, J=3.9 Hz, 1H), 7.85 (s, 1H), 7.82 (s, 1H), 7.67 (d, J=8.7 Hz, 1H), 6.88 (d, J=7.0 Hz, 1H), 5.26-5.18 (m, 1H), 5.01-4.85 (m, 1H), 4.79-4.61 (m, 1H), 4.35-4.22 (m, 1H), 3.17-2.79 (m, 1H), 2.61-2.35 (m, 4H), 2.35-2.19 (m, 1H), 2.19-1.86 (m, 4H), 1.80-1.55 (m, 3H), 1.55-1.27 (m, 3H), 1.20-1.02 (m, 1H), 0.75-0.62 (m, 2H), 0.54-0.35 (m, 2H). MS (ESI) m/z: [M+H]$^+$ Found 645.2.

Example 93

N—((S)-(7-((R)-Cyclopropyl(4,4,4-trifluorobutanamido)methyl)imidazo[1,2-b]pyridazin-2-yl)(4,4-difluorocyclohexyl)methyl)-2-((2,2-difluorocyclopropyl)methyl)-2H-1,2,3-triazole-4-carboxamide

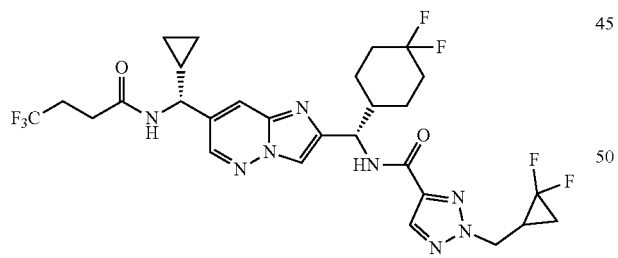

The title compound was prepared as described in the synthesis of Example 4, using 2-((2,2-difluorocyclopropyl)methyl)-2H-1,2,3-triazole-4-carboxylic acid (Intermediate 152) in place of 2-((2,2-difluorocyclobutyl)methyl)-2H-1,2,3-triazole-4-carboxylic acid to afford the title compound as a white solid. $^1$H NMR (500 MHz, CDCl$_3$) δ 8.30 (dd, J=2.1, 0.8 Hz, 1H), 8.01 (s, 1H), 7.84 (s, 1H), 7.81 (dd, J=2.1, 1.0 Hz, 1H), 7.60 (d, J=9.1 Hz, 1H), 6.85 (d, J=7.1 Hz, 1H), 5.25-5.22 (m, 1H), 4.59 (m, 1H), 4.44-4.36 (m, 1H), 4.28 (dd, J=9.4, 7.1 Hz, 1H), 2.55 (s, 2H), 2.52-2.38 (m, 4H), 2.26-2.14 (m, 1H), 2.14-2.04 (m, 1H), 1.97-1.89 (m, 1H), 1.78-1.59 (m, 3H), 1.59-1.41 (m, 2H), 1.40-1.28 (m, 2H), 1.17-1.05 (m, 1H), 0.73-0.59 (m, 2H), 0.52-0.35 (m, 2H). MS (ESI) m/z: [M+H]$^+$ Found 645.3.

Example 94

N—((S)-(7-((R)-Cyclopropyl(4,4,4-trifluorobutanamido)methyl)imidazo[1,2-b]pyridazin-2-yl)(4,4-difluorocyclohexyl)methyl)-1-((2,2,3,3-tetrafluorocyclobutyl)methyl)-1H-1,2,3-triazole-5-carboxamide

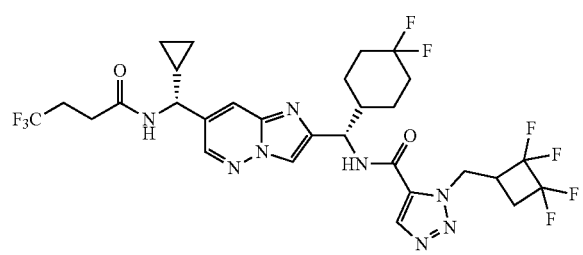 [SMILES: O=C(CCC(F)(F)F)N[C@@H](c1cnn2cc([C@@H](NC(=O)c3cnnn3CC3CC(F)(F)C3(F)F)C3CCC(F)(F)CC3)nc2c1)C1CC1]

The title compound was prepared as described in the synthesis of Example 4, using 1-((2,2,3,3-tetrafluorocyclobutyl)methyl)-1H-1,2,3-triazole-5-carboxylic acid (Intermediate 148) in place of 2-((2,2-difluorocyclobutyl)methyl)-2H-1,2,3-triazole-4-carboxylic acid to provide the title compound as a white solid. $^1$H NMR (500 MHz, CDCl$_3$) δ 8.34 (d, J=2.0 Hz, 1H), 8.10 (d, J 4.3 Hz, 1H), 7.86 (s, 1H), 7.83-7.76 (m, 1H), 7.61 (d, J=8.6 Hz, 1H), 6.59 (d, J=6.8 Hz, 1H), 5.26-5.18 (m, 1H), 5.10-5.01 (m, 1H), 4.91-482 (m, 1H), 4.33-4.24 (m, 1H), 3.51-3.32 (m, 1H), 2.80-2.66 (m, 1H), 2.65-2.32 (m, 4H), 2.20-1.99 (m, 3H), 1.99-1.89 (m, 1H), 1.81-1.56 (m, 3H), 1.56-1.44 (m, 1H), 1.39-1.27 (m, 1H), 1.21-1.11 (m, 1H), 0.79-0.65 (m, 2H), 0.56-0.39 (m, 2H). MS (ESI) m/z: [M+H]$^+$ Found 695.3.

Example 95

N—((S)-(7-((R)-Cyclopropyl(4,4,4-trifluorobutanamido)methyl)imidazo[1,2-b]pyridazin-2-yl)(4,4-difluorocyclohexyl)methyl)-2-((2,2,3,3-tetrafluorocyclobutyl)methyl)-2H-1,2,3-triazole-4-carboxamide

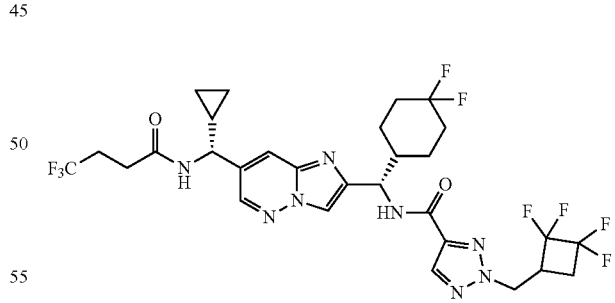

The title compound was prepared as described in the synthesis of Example 4, using 2-((2,2,3,3-tetrafluorocyclobutyl)methyl)-2H-1,2,3-triazole-5-carboxylic acid (Intermediate 149) in place of 2-((2,2-difluorocyclobutyl)methyl)-2H-1,2,3-triazole-4-carboxylic acid to provide the title compound as a white solid. $^1$H NMR (500 MHz, CDCl$_3$) δ 8.30 (d, J=2.2 Hz, 1H), 8.01 (d, J=0.8 Hz, 1H), 7.84 (s, 1H), 7.81 (dd, J=2.0, 1.0 Hz, 1H), 7.55 (dd, J=9.0, 1.7 Hz, 1H), 6.70 (dd, J=7.1, 1.6 Hz, 1H), 5.25-5.21 (m, 1H), 4.78-4.70 (m, 1H), 4.54 (dd, J=14.1, 8.5 Hz, 1H), 4.31-4.25

(m, 1H), 3.45-3.27 (m, 1H), 2.73-2.56 (m, 1H), 2.55-2.41 (m, 4H), 2.40-2.27 (m, 1H), 2.18-2.04 (m, 2H), 2.04-1.96 (m, 1H), 1.96-1.87 (m, 1H), 1.78-1.54 (m, 3H), 1.53-1.41 (m, 1H), 1.41-1.28 (m, 1H), 1.17-1.05 (m, 1H), 0.74-0.60 (m, 2H), 0.52-0.36 (m, 2H). MS (ESI) m/z: [M+H]⁺ Found 695.3.

Example 96

N—((S)-(7-((R)-Cyclopropyl(4,4,4-trifluorobutanamido)methyl)imidazo[1,2-b]pyridazin-2-yl)(4,4-difluorocyclohexyl)methyl)-1-((2,2,3,3-tetrafluorocyclobutyl)methyl)-1H-1,2,3-triazole-4-carboxamide

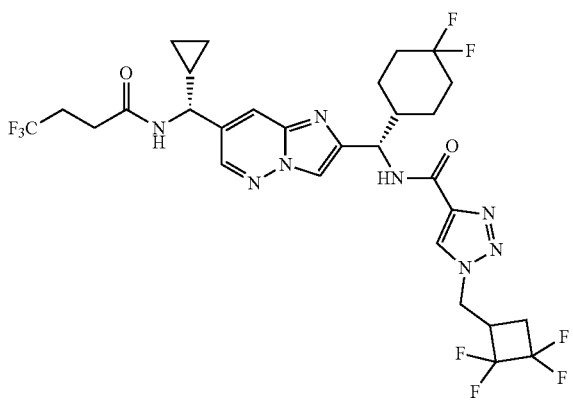 [SMILES: O=C(CCC(F)(F)F)N[C@@H](c1cnn2cc([C@@H](NC(=O)c3cn(CC4CC(F)(F)C4(F)F)nn3)C3CCC(F)(F)CC3)nc2c1)C1CC1]

The title compound was prepared as described in the synthesis of Example 4, using 1-((2,2,3,3-tetrafluorocyclobutyl)methyl)-1H-1,2,3-triazole-4-carboxylic acid (Intermediate 150) in place of 2-((2,2-difluorocyclobutyl)methyl)-2H-1,2,3-triazole-4-carboxylic acid to afford the title compound as a white solid. ¹H NMR (400 MHz, CD₃OD) δ 8.45 (d, J=2.1 Hz, 1H), 8.42 (s, 1H), 8.11 (s, 1H), 7.90-7.86 (m, 1H), 5.27 (d, J=8.3 Hz, 1H), 4.88-4.78 (m, 1H), 4.70 (dd, J=14.5, 7.2 Hz, 1H), 4.27 (d, J=9.5 Hz, 1H), 3.58-3.39 (m, 1H), 2.89-2.67 (m, 1H), 2.63-2.41 (m, 5H), 2.29-2.15 (m, 1H), 2.15-1.93 (m, 3H), 1.91-1.59 (m, 3H), 1.58-1.31 (m, 2H), 1.30-1.19 (m, 1H), 0.78-0.65 (m, 2H), 0.57-0.44 (m, 2H). MS (ESI) m/z: [M+H]⁺ Found 695.3.

Example 97

(1R,2R)—N—((S)-(7-((R)-Cyclopropyl(4,4,4-trifluorobutanamido)methyl)imidazo[1,2-b]pyridazin-2-yl)(4,4-difluorocyclohexyl)methyl)-2-fluorocyclopropane-1-carboxamide

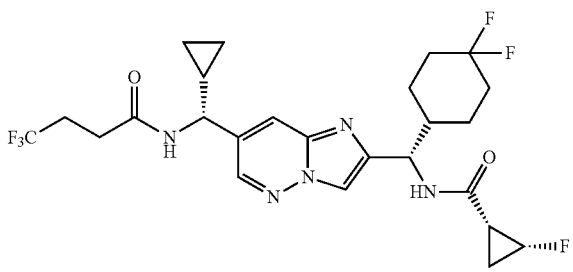 [SMILES: O=C(CCC(F)(F)F)N[C@@H](c1cnn2cc([C@@H](NC(=O)[C@H]3C[C@H]3F)C3CCC(F)(F)CC3)nc2c1)C1CC1]

The title compound was prepared as described in the synthesis of Example 4, using (1R,2R)-2-fluorocyclopropane-1-carboxylic acid in place of 2-((2,2-difluorocyclobutyl)methyl)-2H-1,2,3-triazole-4-carboxylic acid to afford the title compound as a white solid. ¹H NMR (400 MHz, CD₃OD) δ 8.45 (d, J=2.1 Hz, 1H), 7.97 (s, 1H), 7.85 (dd, J=2.0, 1.0 Hz, 1H), 5.23-5.08 (m, 1H), 4.94-4.62 (m, 1H), 4.27 (d, J=9.4 Hz, 1H), 2.61-2.41 (m, 4H), 2.23-1.96 (m, 3H), 1.96-1.89 (m, 1H), 1.89-1.74 (m, 2H), 1.74-1.59 (m, 3H), 1.53-1.31 (m, 2H), 1.31-1.19 (m, 1H), 1.16-1.04 (m, 1H), 0.76-0.64 (m, 2H), 0.56-0.43 (m, 2H). MS (ESI) m/z: [M+H]⁺ Found 546.1.

Example 98

(1R,2S)—N—((S)-(7-((R)-Cyclopropyl(4,4,4-trifluorobutanamido)methyl)imidazo[1,2-b]pyridazin-2-yl)(4,4-difluorocyclohexyl)methyl)-2-fluorocyclopropane-1-carboxamide

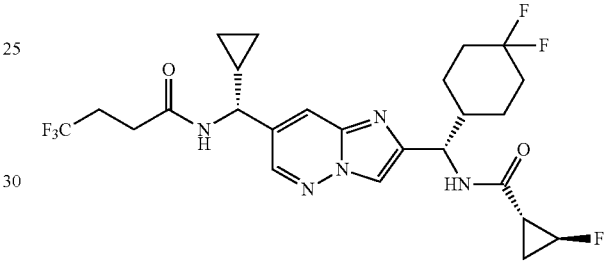

The title compound was prepared as described in the synthesis of Example 4, using (1R,2S)-2-fluorocyclopropane-1-carboxylic acid in place of 2-((2,2-difluorocyclobutyl)methyl)-2H-1,2,3-triazole-4-carboxylic acid to afford the title compound as a white solid. ¹H NMR (400 MHz, CD₃OD) δ 8.45 (d, J=2.1 Hz, 1H), 8.01 (s, 1H), 7.90-7.82 (m, 1H), 5.14-5.00 (m, 1H), 4.79-4.56 (m, 1H), 4.28 (d, J=9.4 Hz, 1H), 2.64-2.41 (m, 4H), 2.28-1.92 (m, 5H), 1.92-1.55 (m, 4H), 1.50-1.31 (m, 2H), 1.31-1.16 (m, 2H), 0.77-0.66 (m, 2H), 0.56-0.44 (m, 2H). MS (ESI) m/z: [M+H]⁺ Found 546.1.

Example 99

N—[(S)-[7-[(R)-Cyclopropyl-(4,4,4-trifluorobutanoylamino)methyl]imidazo[1,2-b]pyridazin-2-yl]-(4,4-difluorocyclohexyl)methyl]-3-(2-fluoroethyl)isoxazole-4-carboxamide

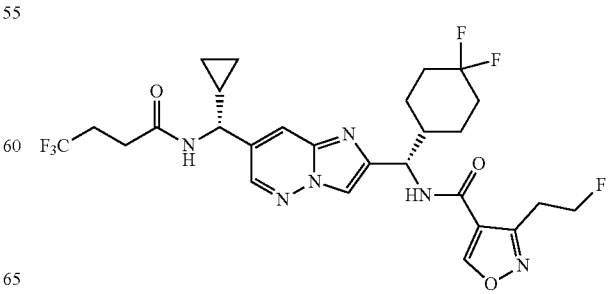

A mixture of N—((R)-(2-((S)-amino(4,4-difluorocyclohexyl)methyl)imidazo[1,2-b]pyridazin-7-yl)(cyclopropyl)methyl)-4,4,4-trifluorobutanamide (75 mg, 0.16 mmol, Intermediate 51), HOBt (23 mg, 0.17 mmol), DIPEA (0.034 mL, 0.2 mmol), 3-(2-fluoroethyl)isoxazole-4-carboxylic acid (30 mg, 0.19 mmol, Intermediate 156) and ACN (1.8 mL) was stirred until homogeneous. Then, EDCI (33 mg, 0.17 mmol) was added and the resulting mixture was stirred at rt for 2 h followed by 40° C. for 2 h. The reaction was cooled to rt, poured over water and extracted with EtOAc (2×20 mL). The organic layers were combined, washed with brine (20 mL), dried over anhydrous $Na_2SO_4$, filtered and concentrated to dryness. The residue was purified by reverse phase basic HPLC (Xbridge C18, 30 to 100% ACN/20 mM aqueous $NH_4OH$ solution) to provide the title compound as a white solid. $^1$H NMR (500 MHz, CDCl$_3$) δ 8.79 (s, 1H), 8.35 (d, J=2.1 Hz, 1H), 7.87-7.78 (m, 2H), 7.06-6.98 (m, 1H), 6.01 (d, J=6.8 Hz, 1H), 5.26 (t, J=7.8 Hz, 1H), 4.86 (td, J=6.2, 1.6 Hz, 1H), 4.76 (td, J=6.2, 1.6 Hz, 1H), 4.30 (dd, J=9.6, 6.7 Hz, 1H), 3.37 (dt, J=23.6, 6.1 Hz, 2H), 2.56-2.46 (m, 4H), 2.18-2.10 (m, 1H), 2.10-2.01 (m, 2H), 1.99-1.92 (m, 1H), 1.79-1.66 (m, 3H), 1.51-1.31 (m, 2H), 1.22-1.13 (m, 1H), 0.80-0.74 (m, 2H), 0.56-0.46 (m, 2H). MS (ESI) m/z: [M+H]$^+$ Found 601.2.

Example 100

N—[(S)-[7-[(R)-Cyclopropyl-(4,4,4-trifluorobutanoylamino)methyl]imidazo[1,2-b]pyridazin-2-yl]-(4,4-difluorocyclohexyl)methyl]-3-(3-methyloxetan-3-yl)isoxazole-4-carboxamide The title compound was prepared as described in the synthesis of Example 99 using 3-(3-methyloxetan-3-yl)-1,2-oxazole-4-carboxylic acid in place of 3-(2-fluoroethyl)isoxazole-4-carboxylic acid to provide the title compound. $^1$H NMR (500 MHz, CDCl$_3$) δ 8.75 (s, 1H), 8.34 (d, J=2.1 Hz, 1H), 7.83 (s, 1H), 7.82-7.78 (m, 1H), 6.96 (d, J=8.5 Hz, 1H), 6.05 (d, J=6.7 Hz, 1H), 5.21 (t, J=7.9 Hz, 1H), 5.11 (d, J=6.3 Hz, 1H), 5.06 (d, J=6.3 Hz, 1H), 4.65 (dd, J=6.3, 5.0 Hz, 2H), 4.30 (dd, J=9.5, 6.7 Hz, 1H), 2.58-2.46 (m, 4H), 2.17-1.90 (m, 4H), 1.80-1.74 (m, 4H), 1.69-1.61 (m, 2H), 1.53-1.29 (m, 2H), 1.21-1.14 (m, 1H), 0.81-0.72 (m, 2H), 0.56-0.45 (m, 2H). MS (ESI) m/z: [M+H]$^+$ Found 625.2.

Example 101

N—[(S)-[7-[(R)-Cyclopropyl-(4,4,4-trifluorobutanoylamino)methyl]imidazo[1,2-b]pyridazin-2-yl]-(4,4-difluorocyclohexyl)methyl]-3-(trifluoromethyl)isoxazole-4-carboxamide

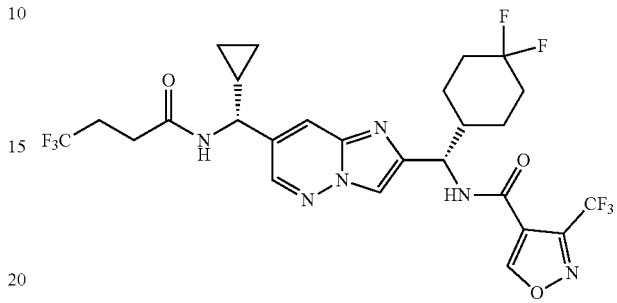

The title compound was prepared as described in the synthesis of Example 99 using 3-(trifluoromethyl)isoxazole-4-carboxylic acid in place of 3-(2-fluoroethyl)isoxazole-4-carboxylic acid to provide the title compound. $^1$H NMR (400 MHz, CDCl$_3$) δ 9.01-8.95 (m, 1H), 8.37-8.30 (m, 1H), 7.84 (s, 1H), 7.82-7.77 (m, 1H), 7.10 (d, J=8.3 Hz, 1H), 6.00 (d, J=6.8 Hz, 1H), 5.31-5.25 (m, 1H), 4.31 (dd, J=9.5, 6.8 Hz, 1H), 2.57-2.44 (m, 4H), 2.17-2.03 (m, 3H), 1.96-1.89 (m, 1H), 1.80-1.65 (m, 3H), 1.55-1.46 (m, 1H), 1.39-1.29 (m, 1H), 1.22-1.12 (m, 1H), 0.81-0.72 (m, 2H), 0.55-0.44 (m, 2H). MS (ESI) m/z: [M+H]$^+$ Found 623.2.

Example 102

N—[(S)-[7-[(R)-Cyclopropyl-(4,4,4-trifluorobutanoylamino)methyl]imidazo[1,2-b]pyridazin-2-yl]-(4,4-difluorocyclohexyl)methyl]-3-(methoxymethyl)isoxazole-4-carboxamide

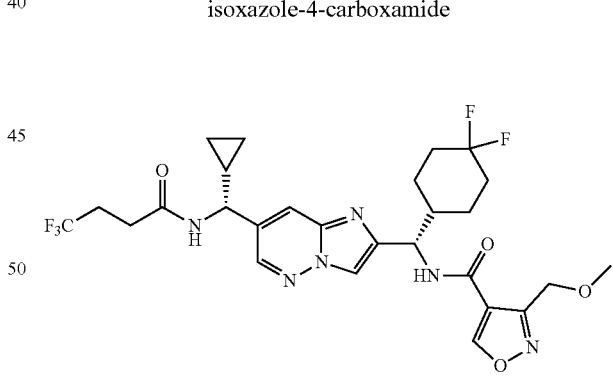

The title compound was prepared as described in the synthesis of Example 99 using 3-(methoxymethyl)-1,2-oxazole-4-carboxylic acid in place of 3-(2-fluoroethyl)isoxazole-4-carboxylic acid to provide the title compound. $^1$H NMR (500 MHz, CDCl$_3$) δ 8.95 (s, 1H), 8.57 (d, J=8.7 Hz, 1H), 8.31 (d, J=2.1 Hz, 1H), 7.83 (s, 1H), 7.80 (dd, J=2.1, 1.0 Hz, 1H), 6.04 (d, J=6.9 Hz, 1H), 5.36 (dd, J=8.7, 6.6 Hz, 1H), 4.76 (s, 2H), 4.32 (dd, J=9.5, 6.9 Hz, 1H), 3.53 (s, 3H), 2.56-2.47 (m, 4H), 2.18-2.10 (m, 2H), 1.90-1.83 (m, 1H), 1.78-1.65 (m, 4H), 1.51-1.42 (m, 1H), 1.21-1.12 (m, 1H), 0.79-0.71 (m, 2H), 0.53-0.44 (m, 2H). MS (ESI) m/z: [M+H]$^+$ Found 599.2.

Example 103

1-Cyclopropyl-N—((S)-(7-((R)-cyclopropyl(4,4,4-trifluorobutanamido)methyl)imidazo[1,2-b]pyridazin-2-yl)(4,4-difluorocyclohexyl)methyl)-1H-1,2,4-triazole-5-carboxamide

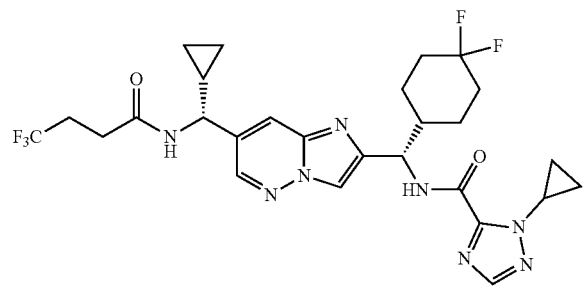 [SMILES: O=C(CCC(F)(F)F)N[C@@H](c1cnn2cc([C@@H](NC(=O)c3ncnn3C3CC3)C3CCC(F)(F)CC3)nc2c1)C1CC1]

The title compound was prepared as described in the synthesis of Example 61 using methyl 1-cyclopropyl-1H-1,2,4-triazole-5-carboxylate (Intermediate 161) in place of methyl 1-(2,2,2-trifluoroethyl)-1H-1,2,4-triazole-5-carboxylate. The material was further purified by chiral SFC (diethylaminopropyl 5 μm, 21.2×150 mm, 85% $CO_2$, 15% MeOH) to provide the title compound. $^1$H NMR (500 MHz, $CDCl_3$) δ 8.31 (d, J=2.1 Hz, 1H), 8.15 (d, J=9.1 Hz, 1H), 7.89-7.84 (m, 2H), 7.76 (s, 1H), 6.08 (d, J=6.9 Hz, 1H), 5.24 (dd, J=9.1, 7.6 Hz, 1H), 4.79-4.72 (m, 1H), 4.36-4.29 (m, 1H), 3.49 (s, 1H), 2.56-2.47 (m, 4H), 2.21-1.96 (m, 4H), 1.57-1.39 (m, 2H), 1.37-1.05 (m, 7H), 0.78-0.71 (m, 2H), 0.53-0.43 (m, 2H). MS (ESI) m/z: [M+H]$^+$ Found 595.2.

Example 104

N—((S)-(7-((R)-Cyclopropyl(4,4,4-trifluorobutanamido)methyl)imidazo[1,2-b]pyridazin-2-yl)(4,4-difluorocyclohexyl)methyl)-1-(trifluoromethyl)-1H-pyrazole-5-carboxamide

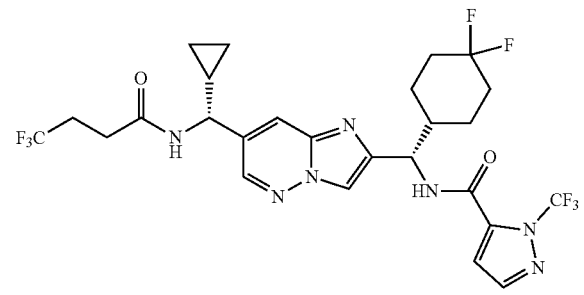 [SMILES: O=C(CCC(F)(F)F)N[C@@H](c1cnn2cc([C@@H](NC(=O)c3ccnn3C(F)(F)F)C3CCC(F)(F)CC3)nc2c1)C1CC1]

The title compound was prepared as described in the synthesis of Example 99 using 2-trifluoromethyl-2H-pyrazole-3-carboxylic acid in place of 3-(2-fluoroethyl)isoxazole-4-carboxylic acid to provide the title compound. $^1$H NMR (500 MHz, $CDCl_3$) δ 8.35 (d, J=2.1 Hz, 1H), 7.88-7.85 (m, 1H), 7.82-7.78 (m, 1H), 7.67 (d, J=1.8 Hz, 1H), 7.16 (d, J=8.5 Hz, 1H), 6.71 (dd, J=1.8, 0.9 Hz, 1H), 6.04 (d, J=6.7 Hz, 1H), 5.27 (dd, J=8.5, 7.2 Hz, 1H), 4.33-4.26 (m, 1H), 2.56-2.46 (m, 4H), 2.18-2.04 (m, 3H), 1.99-1.92 (m, 1H), 1.81-1.62 (m, 3H), 1.56-1.47 (m, 1H), 1.38-1.31 (m, 1H), 1.21-1.14 (m, 1H), 0.80-0.72 (m, 2H), 0.54-0.45 (m, 2H). MS (ESI) m/z: [M+H]$^+$ Found 622.1.

Example 105

N—((S)-(7-((R)-Cyclopropyl(4,4,4-trifluorobutanamido)methyl)imidazo[1,2-b]pyridazin-2-yl)(4,4-difluorocyclohexyl)methyl)-1-(2-fluoroethyl)-1H-1,2,3-triazole-5-carboxamide

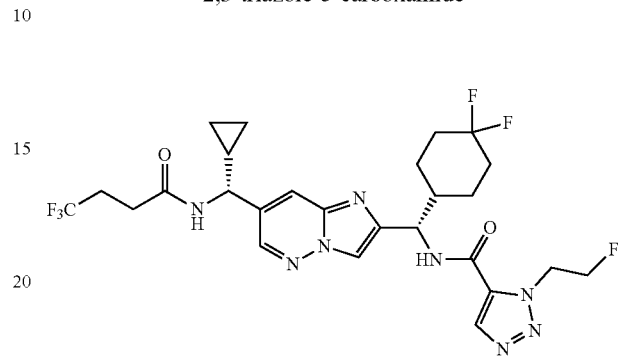

The title compound was prepared as described in the synthesis of Example 99 using 1-(2-fluoroethyl)-1H-1,2,3-triazole-5-carboxylic acid (Intermediate 159) in place of 3-(2-fluoroethyl)isoxazole-4-carboxylic acid to provide the title compound. $^1$H NMR (500 MHz, $CDCl_3$) δ 8.35 (d, J=2.1 Hz, 1H), 8.06 (s, 1H), 7.88-7.81 (m, 2H), 7.37 (d, J=8.6 Hz, 1H), 6.17 (d, J=6.8 Hz, 1H), 5.23 (dd, J=8.6, 7.7 Hz, 1H), 5.13-5.01 (m, 2H), 4.90-4.73 (m, 2H), 4.33-4.27 (m, 1H), 2.58-2.45 (m, 4H), 2.20-1.93 (m, 4H), 1.81-1.72 (m, 1H), 1.69-1.60 (m, 2H), 1.57-1.47 (m, 1H), 1.39-1.29 (m, 1H), 1.22-1.14 (m, 1H), 0.81-0.71 (m, 2H), 0.55-0.44 (m, 2H). MS (ESI) m/z: [M+H]$^+$ Found 601.2.

Example 106

N—((S)-(7-((R)-Cyclopropyl(4,4,4-trifluorobutanamido)methyl)imidazo[1,2-b]pyridazin-2-yl)(4,4-difluorocyclohexyl)methyl)-1-ethyl-1H-1,2,4-triazole-5-carboxamide

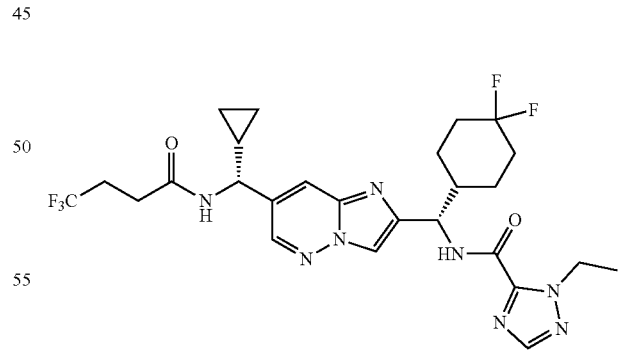

The title compound was prepared as described in the synthesis of Example 61 using methyl 1-ethyl-1H-1,2,4-triazole-5-carboxylate in place of methyl 1-(2,2,2-trifluoroethyl)-1H-1,2,4-triazole-5-carboxylate to provide the title compound. $^1$H NMR (500 MHz, $CDCl_3$) δ 8.31 (d, J=2.1 Hz, 1H), 8.16 (d, J=9.1 Hz, 1H), 7.89-7.82 (m, 3H), 5.98 (d, J=6.9 Hz, 1H), 5.22 (dd, J=9.1, 7.5 Hz, 1H), 4.76-4.65 (m, 2H), 4.35-4.28 (m, 1H), 2.57-2.46 (m, 4H), 2.21-1.95 (m, 4H), 1.79-1.64 (m, 3H), 1.54-1.38 (m, 5H), 1.21-1.12 (m, 1H), 0.80-0.69 (m, 2H), 0.53-0.45 (m, 2H). MS (ESI) m/z: [M+H]⁺ Found 583.3.

Example 107

N—((S)-(7-((R)-Cyclopropyl(4,4,4-trifluorobutanamido)methyl)imidazo[1,2-b]pyridazin-2-yl)(4,4-difluorocyclohexyl)methyl)-2-(2-fluoroethyl)-2H-1,2,3-triazole-4-carboxamide

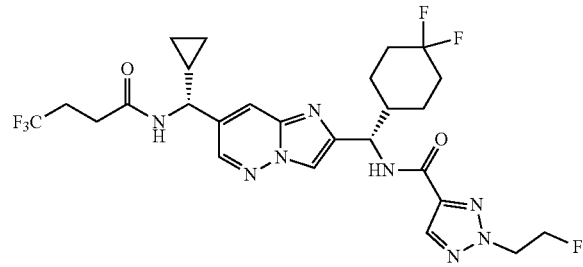 [SMILES: O=C(CCC(F)(F)F)N[C@@H](c1cnn2cc([C@@H](NC(=O)c3cnn(CCF)n3)C3CCC(F)(F)CC3)nc2c1)C1CC1]

The title compound was prepared as described in the synthesis of Example 99 using 2-(2-fluoroethyl)-2H-1,2,3-triazole-4-carboxylic acid (Intermediate 160) in place of 3-(2-fluoroethyl)isoxazole-4-carboxylic acid to provide the title compound. ¹H NMR (600 MHz, CDCl₃) δ 8.32 (d, J=2.1 Hz, 1H), 8.08 (s, 1H), 7.89-7.83 (m, 1H), 7.55 (d, J=9.1 Hz, 1H), 6.09 (d, J=6.9 Hz, 1H), 5.30 (dd, J=9.2, 7.6 Hz, 1H), 4.93 (dt, J=46.6, 4.9 Hz, 2H), 4.73 (dt, J=24.6, 5.0 Hz, 2H), 4.32 (dd, J=9.4, 6.9 Hz, 1H), 2.56-2.46 (m, 4H), 2.18-1.96 (m, 4H), 1.77-1.66 (m, 3H), 1.57-1.37 (m, 2H), 1.20-1.12 (m, 1H), 0.80-0.70 (m, 2H), 0.55-0.43 (m, 2H). MS (ESI) m/z: [M+H]⁺ Found 601.2.

Example 108

N—((S)-(7-((R)-Cyclopropyl(4,4,4-trifluorobutanamido)methyl)imidazo[1,2-b]pyridazin-2-yl)(4,4-difluorocyclohexyl)methyl)-1-(cyclopropylmethyl)-5-(trifluoromethyl)-1H-1,2,3-triazole-4-carboxamide

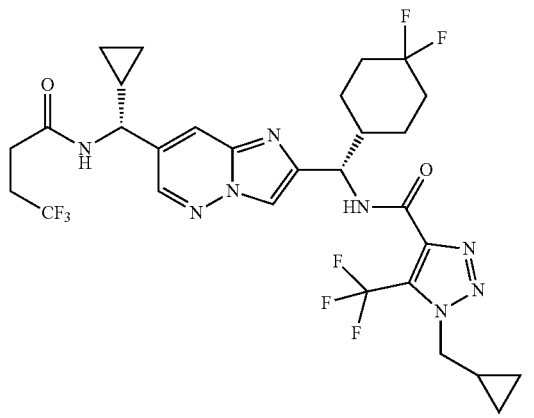 [SMILES: O=C(CCC(F)(F)F)N[C@@H](c1cnn2cc([C@@H](NC(=O)c3nnn(CC4CC4)c3C(F)(F)F)C3CCC(F)(F)CC3)nc2c1)C1CC1]

The title compound was prepared as described for the synthesis of Example 63, using 1-(cyclopropylmethyl)-5-(trifluoromethyl)-1H-1,2,3-triazole-4-carboxylic acid in place of 2-((3,3-difluorocyclobutyl)methyl)-2H-1,2,3-triaz-ole-4-carboxylic acid and acetonitrile in place of DMF to provide the title compound as a white solid. ¹H NMR (400 MHz, DMSO-d₆) δ 9.05 (d, J=9.2 Hz, 1H), 8.71 (d, J=7.7 Hz, 1H), 8.51 (d, J=2.1 Hz, 1H), 8.20 (s, 1H), 7.96 (d, J=2.0 Hz, 1H), 5.18 (t, J=8.4 Hz, 1H), 4.48 (d, J=7.4 Hz, 2H), 4.30 (t, J=8.4 Hz, 1H), 2.49-2.42 (m, 4H), 2.21-2.08 (m, 1H), 2.09-1.92 (m, 2H), 1.91-1.57 (m, 4H), 1.43-1.14 (m, 4H), 0.64-0.43 (m, 7H), 0.43-0.32 (m, 1H). MS (ESI) m/z: [M+H]⁺ Found 677.3.

Example 109

N—((S)-(7-((R)-Cyclopropyl(4,4,4-trifluorobutanamido)methyl)imidazo[1,2-b]pyridazin-2-yl)(4,4-difluorocyclohexyl)methyl)-1-(2,2-difluoroethyl)-5-(trifluoromethyl)-1H-1,2,3-triazole-4-carboxamide

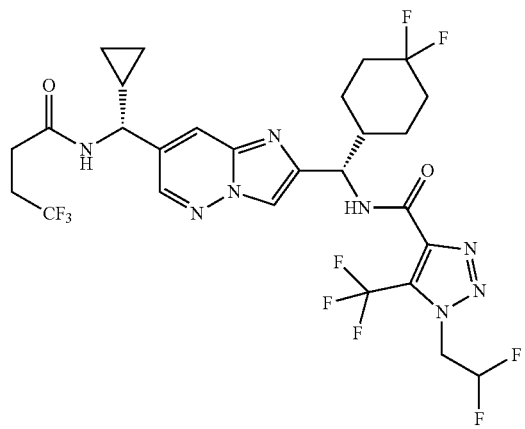 [SMILES: O=C(CCC(F)(F)F)N[C@@H](c1cnn2cc([C@@H](NC(=O)c3nnn(CC(F)F)c3C(F)(F)F)C3CCC(F)(F)CC3)nc2c1)C1CC1]

The title compound was prepared as described for the synthesis of Example 63, using 1-(2,2-difluoroethyl)-5-(trifluoromethyl)-1H-1,2,3-triazole-4-carboxylic acid in place of 2-((3,3-difluorocyclobutyl)methyl)-2H-1,2,3-triazole-4-carboxylic acid and acetonitrile in place of DMF to provide the title compound as a white solid. ¹H NMR (400 MHz, DMSO-d₆) δ 9.10 (d, J=9.1 Hz, 1H), 8.71 (d, J=7.7 Hz, 1H), 8.51 (d, J=2.1 Hz, 1H), 8.22 (s, 1H), 7.96 (d, J=2.0 Hz, 1H), 6.72-6.38 (m, 1H), 5.28-5.13 (m, 2H), 4.30 (t, J=8.4 Hz, 1H), 2.48-2.42 (m, 4H), 2.16 (d, J=10.3 Hz, 1H), 2.09-1.55 (m, 7H), 1.44-1.13 (m, 3H), 0.65-0.46 (m, 3H), 0.43-0.32 (m, 1H). MS (ESI) m/z: [M+H]⁺ Found 687.2.

Example 110

1-Cyclopropyl-N—((S)-(7-((R)-cyclopropyl(4,4,4-trifluorobutanamido)methyl)imidazo[1,2-b]pyridazin-2-yl)(4,4-difluorocyclohexyl)methyl)-5-(difluoromethyl)-1H-1,2,3-triazole-4-carboxamide

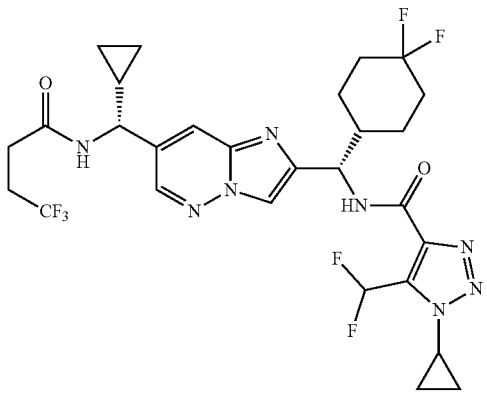 [SMILES: O=C(CCC(F)(F)F)N[C@@H](c1cnn2cc([C@@H](NC(=O)c3nnn(C4CC4)c3C(F)F)C3CCC(F)(F)CC3)nc2c1)C1CC1]

The title compound was prepared as described for the synthesis of Example 63, using 1-cyclopropyl-5-(difluoromethyl)-1H-1,2,3-triazole-4-carboxylic acid in place of 2-((3,3-difluorocyclobutyl)methyl)-2H-1,2,3-triazole-4-carboxylic acid and acetonitrile in place of DMF to provide the title compound as a white solid. $^1$H NMR (400 MHz, DMSO-d$_6$) δ 8.91 (d, J=9.1 Hz, 1H), 8.71 (d, J=7.7 Hz, 1H), 8.50 (d, J=2.1 Hz, 1H), 8.25 (s, 1H), 7.96 (dd, J=1.9, 1.0 Hz, 1H), 7.68 (t, J=52.3 Hz, 1H), 5.17 (t, J=8.6 Hz, 1H), 4.29 (t, J=8.4 Hz, 1H), 4.05-3.92 (m, 1H), 2.49-2.41 (m, 4H), 2.23-2.10 (m, 1H), 2.07-1.65 (m, 5H), 1.64-1.54 (m, 1H), 1.41-1.12 (m, 7H), 0.62-0.44 (m, 3H), 0.43-0.33 (m, 1H). MS (ESI) m/z: [M+H]$^+$ Found 645.3.

Example 111

N—((S)-(7-((R)-Cyclopropyl(4,4,4-trifluorobutanamido)methyl)imidazo[1,2-b]pyridazin-2-yl)(4,4-difluorocyclohexyl)methyl)-4-fluoro-1-isopropyl-1H-pyrazole-5-carboxamide

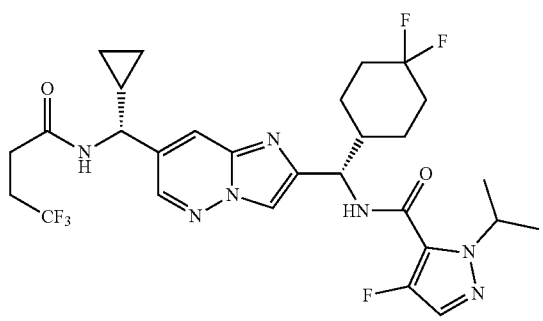 [SMILES: CC(C)n1ncc(F)c1C(=O)N[C@H](c1cn2ncc([C@H](NC(=O)CCC(F)(F)F)C3CC3)cc2n1)C1CCC(F)(F)CC1]

The title compound was prepared as described for the synthesis of Example 63, using 4-fluoro-1-isopropyl-1H-pyrazole-5-carboxylic acid in place of 2-((3,3-difluorocyclobutyl)methyl)-2H-1,2,3-triazole-4-carboxylic acid and acetonitrile in place of DMF to provide the title compound as a white solid. $^1$H NMR (400 MHz, DMSO-d$_6$) δ 8.71 (d, J=7.7 Hz, 1H), 8.68-8.60 (m, 1H), 8.51 (d, J=2.1 Hz, 1H), 8.17 (s, 1H), 7.98-7.92 (m, 1H), 7.60 (d, J=4.6 Hz, 1H), 5.24-5.15 (m, 1H), 5.05-4.91 (m, 1H), 4.30 (t, J=8.3 Hz, 1H), 2.49-2.43 (m, 4H), 2.19-2.09 (m, 1H), 2.06-1.92 (m, 2H), 1.88-1.61 (m, 4H), 1.42-1.26 (m, 8H), 1.26-1.13 (m, 1H), 0.64-0.46 (m, 3H), 0.43-0.33 (m, 1H). MS (ESI) m/z: [M+H]$^+$ Found 614.2.

Example 112

N—((S)-(7-((R)-Cyclopropyl(4,4,4-trifluorobutanamido)methyl)imidazo[1,2-b]pyridazin-2-yl)(4,4-difluorocyclohexyl)methyl)-1-(3-fluoropropyl)-1H-1,2,3-triazole-5-carboxamide

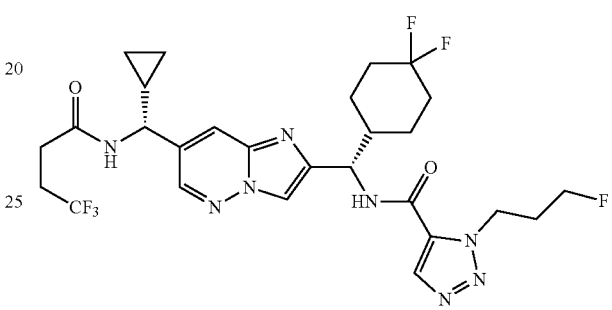

The title compound was prepared as described for the synthesis of Example 63, using 1-(3-fluoropropyl)-1H-1,2,3-triazole-5-carboxylic acid (Intermediate 164) in place of 2-((3,3-difluorocyclobutyl)methyl)-2H-1,2,3-triazole-4-carboxylic acid and acetonitrile in place of DMF to provide the title compound as a white solid. $^1$H NMR (400 MHz, DMSO-d$_6$) δ 9.10 (d, J=8.9 Hz, 1H), 8.71 (d, J=7.6 Hz, 1H), 8.50 (d, J=2.1 Hz, 1H), 8.38 (s, 1H), 8.22 (s, 1H), 7.96-7.90 (m, 1H), 5.16 (t, J=8.6 Hz, 1H), 4.73 (t, J=7.0 Hz, 2H), 4.49 (t, J=5.7 Hz, 1H), 4.37 (t, J=5.7 Hz, 1H), 4.28 (t, J=8.3 Hz, 1H), 2.48-2.41 (m, 4H), 2.24-2.09 (m, 3H), 2.09-1.67 (m, 5H), 1.66-1.56 (m, 1H), 1.45-1.14 (m, 3H), 0.63-0.45 (m, 3H), 0.42-0.33 (m, 1H). MS (ESI) m/z: [M+H]$^+$ Found 615.3.

Example 113

N—((S)-(7-((R)-Cyclopropyl(4,4,4-trifluorobutanamido)methyl)imidazo[1,2-b]pyridazin-2-yl)(4,4-difluorocyclohexyl)methyl)-2-(3-fluoropropyl)-2H-1,2,3-triazole-4-carboxamide

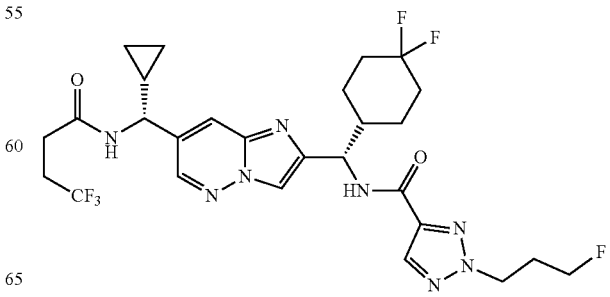

The title compound was prepare as described for the synthesis of Example 63, using 2-(3-fluoropropyl)-2H-1,2,3-triazole-4-carboxylic acid (Intermediate 165) in place of 2-((3,3-difluorocyclobutyl)methyl)-2H-1,2,3-triazole-4-carboxylic acid and acetonitrile in place of DMF to provide the title compound as a white solid. ¹H NMR (400 MHz, DMSO-d₆) δ 8.71 (d, J=7.7 Hz, 1H), 8.53-8.46 (m, 2H), 8.24 (s, 1H), 8.20 (s, 1H), 7.98-7.93 (m, 1H), 5.17 (t, J=8.7 Hz, 1H), 4.63-4.52 (m, 3H), 4.43 (t, J=5.7 Hz, 1H), 4.29 (t, J=8.4 Hz, 1H), 2.48-2.42 (m, 4H), 2.37-2.22 (m, 2H), 2.20-1.65 (m, 6H), 1.63-1.53 (m, 1H), 1.41-1.15 (m, 3H), 0.63-0.45 (m, 3H), 0.42-0.33 (m, 1H). MS (ESI) m/z: [M+H]⁺ Found 615.3.

Example 114

N—((S)-(7-((R)-Cyclopropyl(4,4,4-trifluorobutanamido)methyl)imidazo[1,2-b]pyridazin-2-yl)(4,4-difluorocyclohexyl)methyl)-2-(2-(N-methylacetamido)ethyl)-2H-1,2,3-triazole-4-carboxamide

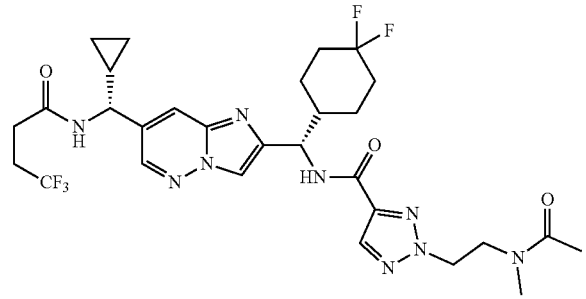 [SMILES: CC(=O)N(C)CCn1ncc(C(=O)N[C@H](c2cn3ncc([C@H](NC(=O)CCC(F)(F)F)C4CC4)cc3n2)C2CCC(F)(F)CC2)n1]

The title compound was prepared as described for the synthesis of Example 63, 2-(2-(N-methylacetamido)ethyl)-2H-1,2,3-triazole-4-carboxylic acid (Intermediate 167) in place of 2-((3,3-difluorocyclobutyl)methyl)-2H-1,2,3-triazole-4-carboxylic acid and acetonitrile in place of DMF to provide the title compound as a white solid. ¹H NMR (400 MHz, DMSO-d₆) δ 8.71 (d, J=7.7 Hz, 1H), 8.52-8.42 (m, 2H), 8.26-8.15 (m, 2H), 7.96 (d, J=2.1 Hz, 1H), 5.18 (t, J=8.7 Hz, 1H), 4.74-4.55 (m, 2H), 4.29 (t, J=8.4 Hz, 1H), 3.86-3.69 (m, 2H), 2.81-2.70 (m, 3H), 2.48-2.43 (m, 4H), 2.21-2.10 (m, 1H), 2.06-1.91 (m, 2H), 1.90 (s, 2H), 1.88-1.64 (m, 4H), 1.64-1.53 (m, 1H), 1.42-1.14 (m, 3H), 0.62-0.45 (m, 3H), 0.42-0.33 (m, 1H). MS (ESI) m/z: [M+H]⁺ Found 654.3.

Example 115

N—((S)-(7-((R)-Cyclopropyl(4,4,4-trifluorobutanamido)methyl)imidazo[1,2-b]pyridazin-2-yl)(4,4-difluorocyclohexyl)methyl)-1-((R*)-1,1,1-trifluoropropan-2-yl)-1H-pyrazole-5-carboxamide


Example 116

N—((S)-(7-((R)-Cyclopropyl(4,4,4-trifluorobutanamido)methyl)imidazo[1,2-b]pyridazin-2-yl)(4,4-difluorocyclohexyl)methyl)-1-((S*)-1,1,1-trifluoropropan-2-yl)-1H-pyrazole-5-carboxamide

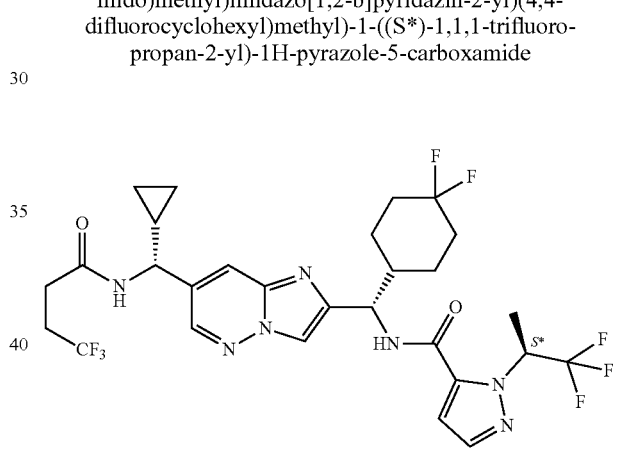

The title compounds were prepared as described for the synthesis of Example 63, using 1-(1,1,1-trifluoropropan-2-yl)-1H-pyrazole-5-carboxylic acid (Intermediate 169) in place of 2-((3,3-difluorocyclobutyl)methyl)-2H-1,2,3-triazole-4-carboxylic acid and acetonitrile in place of DMF to provide a mixture of diasteromers. The crude material was purified by silica gel chromatography (0 to 100% EtOAc (with 10% MeOH)/Hexanes) to give the separated title compounds with impurities. A second purification of each by preparative HPLC (ISCO ACCQ Prep, Gemini Prep NX-C18 5 μm column, 21.5×150 mm, gradient 10-70% Acetonitrile: 20 mM aqueous ammonium hydroxide over 20 min) gave purified title compounds. Example 115 was the first eluting isomer: ¹H NMR (400 MHz, DMSO-d₆) δ 8.93 (d, J=9.0 Hz, 1H), 8.71 (d, J=7.7 Hz, 1H), 8.50 (d, J=2.0 Hz, 1H), 8.17 (s, 1H), 7.95-7.89 (m, 1H), 7.68 (d, J=2.0 Hz, 1H), 7.19 (d, J=2.0 Hz, 1H), 6.42-6.29 (m, 1H), 5.14 (t, J=8.7 Hz, 1H), 4.29 (t, J=8.4 Hz, 1H), 2.49-2.41 (m, 4H), 2.25-2.12 (m, 1H), 2.12-1.71 (m, 5H), 1.68 (d, J=7.0 Hz, 3H), 1.65-1.55 (m, 1H), 1.46-1.14 (m, 3H), 0.63-0.45 (m, 3H), 0.41-0.31 (m, 1H). MS (ESI) m/z: [M+H]⁺ Found 650.2. Example 116 was the second eluting isomer: ¹H NMR (400 MHz, DMSO-d$_6$) δ 8.96 (d, J=9.0 Hz, 1H), 8.71 (d, J=7.6 Hz, 1H), 8.50 (d, J=2.1 Hz, 1H), 8.21 (s, 1H), 7.93 (dd, J=1.9, 1.0 Hz, 1H), 7.68 (d, J=2.0 Hz, 1H), 7.13 (d, J=2.0 Hz, 1H), 6.43-6.29 (m, 1H), 5.16 (t, J=8.7 Hz, 1H), 4.29 (t, J=8.4 Hz, 1H), 2.48-2.41 (m, 4H), 2.26-2.13 (m, 1H), 2.11-1.91 (m, 2H), 1.90-1.70 (m, 3H), 1.67 (d, J=7.0 Hz, 3H), 1.65-1.54 (m, 1H), 1.44-1.13 (m, 3H), 0.63-0.45 (m, 3H), 0.43-0.32 (m, 1H). MS (ESI) m/z: [M+H]$^+$ Found 650.3.

Example 117

3-Cyclopentyl-N—((R)-(7-((S)-cyclopropyl(4,4,4-trifluorobutanamido)methyl)imidazo[1,2-b]pyridazin-2-yl)(4,4-difluorocyclohexyl)methyl)isoxazole-4-carboxamide

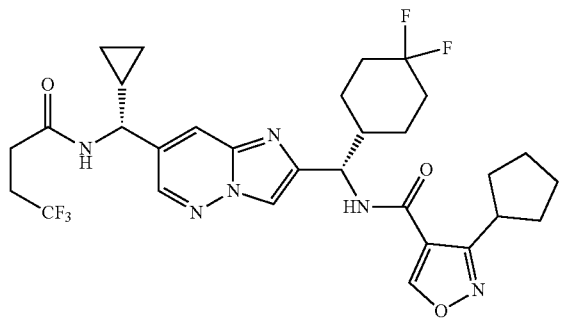 [SMILES: O=C(CCC(F)(F)F)N[C@@H](c1cnn2cc([C@@H](NC(=O)c3conc3C3CCCC3)C3CCC(F)(F)CC3)nc2c1)C1CC1]

A mixture of N—((R)-(2-((S)-amino(4,4-difluorocyclohexyl)methyl)imidazo[1,2-b]pyridazin-7-yl)(cyclopropyl)methyl)-4,4,4-trifluorobutanamide (75 mg, 0.16 mmol, Intermediate 51), 3-cyclopentyl-1,2-oxazole-4-carboxylic acid (34 mg, 0.19 mmol), HOBt (23 mg, 0.17 mmol), DIPEA (34 μL, 0.20 mmol) and ACN (1.8 mL) was stirred until homogeneous. Then, EDCI (33 mg, 0.17 mmol) was added and the resulting mixture stirred at rt for 5 h. After this time, water was added and the solution was extracted with EtOAc (2×20 mL). The organic layers were combined, washed with brine (20 mL), dried over anhydrous Na$_2$SO$_4$, filtered and concentrated to dryness. The residue was purified by preparative HPLC (Xbridge C18, 30 to 100% ACN/20 mM aqueous NH$_4$OH solution) to provide the title compound as a white solid. $^1$H NMR (500 MHz, CDCl$_3$) δ 8.70 (s, 1H), 8.34 (d, J=2.1 Hz, 1H), 7.84 (s, 1H), 7.79 (dd, J=2.1, 1.0 Hz, 1H), 6.89 (d, J=8.3 Hz, 1H), 6.00 (d, J=6.8 Hz, 1H), 5.30-5.21 (m, 1H), 4.31 (dd, J=9.6, 6.8 Hz, 1H), 3.50 (p, J=8.3 Hz, 1H), 2.61-2.46 (m, 4H), 2.20-2.01 (m, 5H), 1.95 (d, J=13.6 Hz, 1H), 1.89-1.75 (m, 4H), 1.71-1.66 (m, 3H), 1.54-1.46 (m, 1H), 1.39-1.31 (m, 1H), 1.26 (s, 1H), 1.21-1.15 (m, 1H), 0.91-0.82 (m, 1H), 0.82-0.71 (m, 2H), 0.51 (ddq, J=21.8, 9.2, 4.5 Hz, 2H). MS (ESI) m/z: [M+H]$^+$ Found 623.2.

Example 118

N—((S)-(7-((R)-Cyclopropyl(4,4,4-trifluorobutanamido)methyl)-3-fluoroimidazo[1,2-b]pyridazin-2-yl)(4,4-difluorocyclohexyl)methyl)-1-isopropyl-1H-pyrazole-5-carboxamide

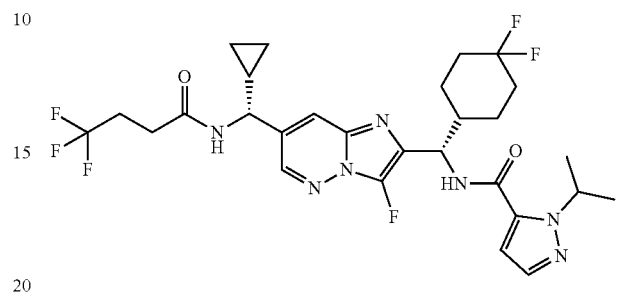

The title compound was prepared as described in Example 38, using N—((R)-(2-((S)-amino(4,4-difluorocyclohexyl)methyl)-3-fluoroimidazo[1,2-b]pyridazin-7-yl)(cyclopropyl)methyl)-4,4,4-trifluorobutanamide (Intermediate 170) in place of N—((R)-(2-((S)-amino(4,4-difluorocyclohexyl)methyl)imidazo[1,2-b]pyridazin-7-yl)(cyclopropyl)methyl)-4,4,4-trifluorobutanamide, and 1-isopropyl-1H-pyrazole-5-carboxylic acid in place of 1-(3,3,3-trifluoropropyl)-1H-1,2,4-triazole-5-carboxylic acid. The material was further purified by Preparative HPLC (XBridge C18, 10% to 100% MeCN/aqueous NH$_4$OH (20 mM)) to afford the title compound as a white solid. $^1$H NMR (500 MHz, DMSO-d$_6$) δ 8.84 (d, J=8.3 Hz, 1H), 8.72 (d, J=7.6 Hz, 1H), 8.60 (d, J=1.9 Hz, 1H), 7.93 (s, 1H), 7.47 (d, J=1.9 Hz, 1H), 6.90 (d, J=2.0 Hz, 1H), 5.36 (quin, J=6.6 Hz, 1H), 5.10 (t, J=8.8 Hz, 1H), 4.28 (t, J=8.4 Hz, 1H), 2.48-2.41 (m, 4H), 2.31-2.20 (m, 1H), 2.12-1.91 (m, 3H), 1.87-1.67 (m, 2H), 1.63-1.54 (m, 1H), 1.44-1.18 (m, 9H), 0.63-0.55 (m, 1H), 0.55-0.45 (m, 2H), 0.42-0.32 (m, 1H). MS (ESI) m/z: [M+H]$^+$ Found 614.3.

Example 119

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-1-isopropyl-1H-pyrazole-5-carboxamide

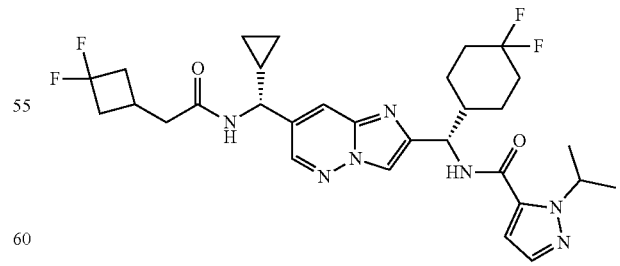

The title compound was prepared as described for the synthesis of Example 38, using N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide (Intermediate 171) in place of N—((R)-(2-((S)-amino(4,4- difluorocyclohexyl)methyl)imidazo[1,2-b]pyridazin-7-yl) (cyclopropyl)methyl)-4,4,4-trifluorobutanamide, and 1-isopropyl-1H-pyrazole-5-carboxylic acid in place of 1-(3,3,3-trifluoropropyl)-1H-1,2,4-triazole-5-carboxylic acid. $^1$H NMR (500 MHz, DMSO-d$_6$) δ 8.70 (d, J=9.1 Hz, 1H), 8.59 (d, J=7.8 Hz, 1H), 8.49 (d, J=2.0 Hz, 1H), 8.20 (s, 1H), 7.92 (d, J=2.0 Hz, 1H), 7.49 (d, J=1.9 Hz, 1H), 6.91 (d, J=2.0 Hz, 1H), 5.44-5.30 (m, 1H), 5.15 (t, J=8.7 Hz, 1H), 4.27 (t, J=8.4 Hz, 1H), 2.71-2.56 (m, 2H), 2.43-2.35 (m, 3H), 2.35-2.22 (m, 2H), 2.22-2.11 (m, 1H), 2.09-1.93 (m, 2H), 1.91-1.84 (m, 1H), 1.84-1.68 (m, 2H), 1.66-1.55 (m, 1H), 1.44-1.28 (m, 7H), 1.30-1.15 (m, 2H), 0.61-0.54 (m, 1H), 0.54-0.49 (m, 1H), 0.49-0.42 (m, 1H), 0.39-0.33 (m, 1H). MS (ESI) m/z: [M+H]$^+$ Found 604.3.

Example 120

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-3-methylisoxazole-4-carboxamide

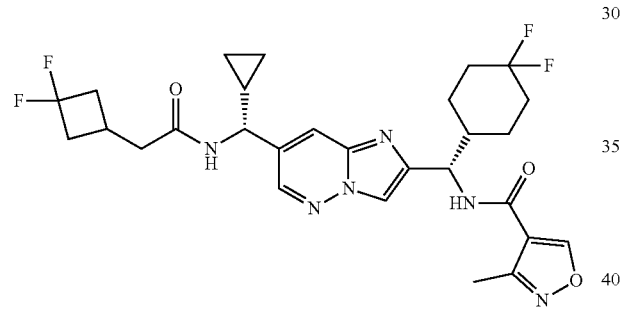

The title compound was prepared as described for the synthesis of Example 38 using N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide (Intermediate 171) in place of N—((R)-(2-((S)-amino(4,4-difluorocyclohexyl)methyl)imidazo[1,2-b]pyridazin-7-yl)(cyclopropyl)methyl)-4,4,4-trifluorobutanamide and 3-methylisoxazole-4-carboxylic acid in place of 1-(3,3,3-trifluoropropyl)-1H-1,2,4-triazole-5-carboxylic acid. $^1$H NMR (500 MHz, DMSO-d$_6$) δ 9.41 (s, 1H), 8.64 (d, J=9.0 Hz, 1H), 8.59 (d, J=7.8 Hz, 1H), 8.49 (d, J=2.0 Hz, 1H), 8.20 (s, 1H), 7.91 (d, J=2.0 Hz, 1H), 5.15 (t, J=8.4 Hz, 1H), 4.26 (t, J=8.4 Hz, 1H), 2.71-2.56 (m, 2H), 2.44-2.35 (m, 6H), 2.33-2.21 (m, 2H), 2.19-2.09 (m, 1H), 2.09-1.93 (m, 2H), 1.89-1.68 (m, 3H), 1.66-1.54 (m, 1H), 1.43-1.32 (m, 1H), 1.31-1.16 (m, 2H), 0.61-0.55 (m, 1H), 0.55-0.49 (m, 1H), 0.49-0.43 (m, 1H), 0.39-0.33 (m, 1H). MS (ESI) m/z: [M+H]$^+$ Found 577.2.

Example 121

N—((S)-(7-((R)-Cyclopropyl((R*)-4,4,4-trifluoro-3-methylbutanamido)methyl)imidazo[1,2-b]pyridazin-2-yl)(4,4-difluorocyclohexyl)methyl)-1-isopropyl-1H-pyrazole-5-carboxamide

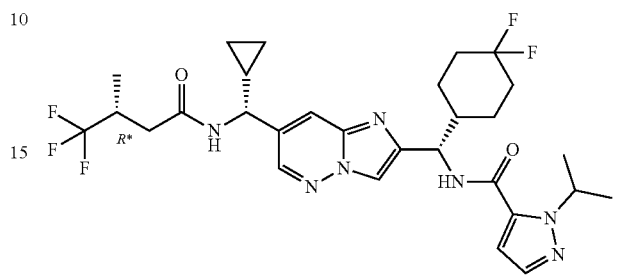

Example 122

N—((S)-(7-((R)-Cyclopropyl((S*)-4,4,4-trifluoro-3-methylbutanamido)methyl)imidazo[1,2-b]pyridazin-2-yl)(4,4-difluorocyclohexyl)methyl)-1-isopropyl-1H-pyrazole-5-carboxamide

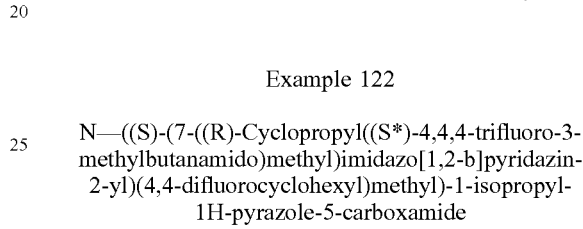

N-((1S)-(7-((1R)-Cyclopropyl(4,4,4-trifluoro-3-methylbutanamido)methyl)imidazo[1,2-b]pyridazin-2-yl)(4,4-difluorocyclohexyl)methyl)-1-isopropyl-1H-pyrazole-5-carboxamide (Intermediate 173) was purified by SFC using a chiral stationary phase (AS-H 2×25 cm, 15% IPA in CO$_2$, 100 bar, 65 mL/min) to afford a pair of diastereomers. Example 121 was the first eluting diastereomer: $^1$H NMR (500 MHz, DMSO-d$_6$) δ 8.76 (d, J=7.8 Hz, 1H), 8.71 (d, J=9.0 Hz, 1H), 8.49 (d, J=2.1 Hz, 1H), 8.20 (s, 1H), 7.93 (d, J=2.0 Hz, 1H), 7.48 (d, J=2.0 Hz, 1H), 6.91 (d, J=2.0 Hz, 1H), 5.36 (septet, J=6.6 Hz, 1H), 5.15 (t, J=8.6 Hz, 1H), 4.31 (t, J=8.4 Hz, 1H), 2.84-2.70 (m, 1H), 2.56-2.52 (m, 1H), 2.30-2.22 (m, 1H), 2.21-2.12 (m, 1H), 2.10-1.93 (m, 2H), 1.91-1.84 (m, 1H), 1.84-1.69 (m, 2H), 1.66-1.57 (m, 1H), 1.43-1.28 (m, 7H), 1.27-1.18 (m, 2H), 1.07 (d, J=7.0 Hz, 3H), 0.62-0.46 (m, 3H), 0.42-0.34 (m, 1H). MS (ESI) m/z: [M+H]$^+$ Found 610.3. Example 122 was the second eluting diastereomer: $^1$H NMR (500 MHz, DMSO-d$_6$) δ 8.77 (d, J=7.8 Hz, 1H), 8.71 (d, J=9.0 Hz, 1H), 8.50 (d, J=2.0 Hz, 1H), 8.20 (s, 1H), 7.94 (d, J=2.0 Hz, 1H), 7.48 (d, J=1.9 Hz, 1H), 6.91 (d, J=2.0 Hz, 1H), 5.36 (septet, J=6.6 Hz, 1H), 5.15 (t, J=8.6 Hz, 1H), 4.30 (t, J=8.4 Hz, 1H), 2.82-2.71 (m, 1H), 2.55-2.52 (m, 1H), 2.31-2.23 (m, 1H), 2.22-2.12 (m, 1H), 2.10-1.93 (m, 2H), 1.91-1.84 (m, 1H), 1.84-1.68 (m, 2H), 1.65-1.57 (m, 1H), 1.47-1.29 (m, 7H), 1.27-1.17 (m, 2H), 1.00 (d, J=6.9 Hz, 3H), 0.62-0.55 (m, 1H), 0.55-0.45 (m, 2H), 0.42-0.33 (m, 1H). MS (ESI) m/z: [M+H]⁺ Found 610.3.

Example 123

N—((S)-(7-((R)-Cyclopropyl((R*)-4,4,4-trifluoro-3-methylbutanamido)methyl)imidazo[1,2-b]pyridazin-2-yl)(4,4-difluorocyclohexyl)methyl)-3-methylisoxazole-4-carboxamide

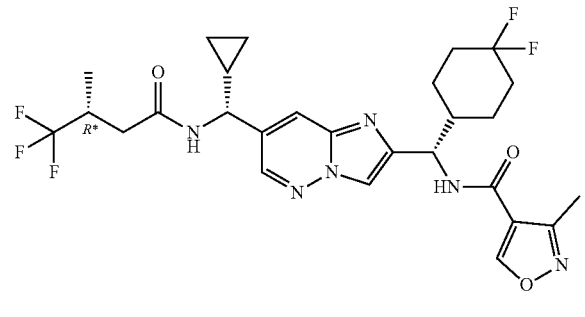 [SMILES: Cc1nocc1C(=O)N[C@H](c1cn2ncc([C@H](NC(=O)C[C@@H](C)C(F)(F)F)C3CC3)cc2n1)C1CCC(F)(F)CC1]

Example 124

N—((S)-(7-((R)-Cyclopropyl((S*)-4,4,4-trifluoro-3-methylbutanamido)methyl)imidazo[1,2-b]pyridazin-2-yl)(4,4-difluorocyclohexyl)methyl)-3-methylisoxazole-4-carboxamide

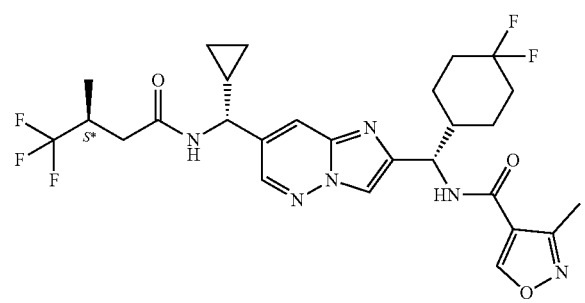 [SMILES: Cc1nocc1C(=O)N[C@H](c1cn2ncc([C@H](NC(=O)C[C@H](C)C(F)(F)F)C3CC3)cc2n1)C1CCC(F)(F)CC1]

N-((1S)-(7-((1R)-Cyclopropyl(4,4,4-trifluoro-3-methylbutanamido)methyl)imidazo[1,2-b]pyridazin-2-yl)(4,4-difluorocyclohexyl)methyl)-3-methylisoxazole-4-carboxamide (Intermediate 174) was separated by SFC using a chiral stationary phase (AS-H 2×25 cm, 10% IPA/CO₂, 100 bar, 70 mL/min) to afford a pair of diastereomers. Example 123 was the first eluting diastereomer: ¹H NMR (400 MHz, DMSO-d₆) δ 9.41 (s, 1H), 8.76 (d, J=7.8 Hz, 1H), 8.64 (d, J=9.0 Hz, 1H), 8.50 (d, J=2.0 Hz, 1H), 8.20 (s, 1H), 7.93 (d, J=2.0 Hz, 1H), 5.15 (t, J=8.4 Hz, 1H), 4.30 (t, J=8.4 Hz, 1H), 2.83-2.71 (m, 1H), 2.57-2.52 (m, 1H), 2.36 (s, 3H), 2.32-2.21 (m, 1H), 2.20-2.09 (m, 1H), 2.09-1.9 (m, 2H), 1.91-1.69 (m, 3H), 1.65-1.56 (m, 1H), 1.45-1.32 (m, 1H), 1.32-1.18 (m, 2H), 1.07 (d, J=7.0 Hz, 3H), 0.63-0.44 (m, 3H), 0.43-0.32 (m, 1H). MS (ESI) m/z: [M+H]⁺ Found 583.2. Example 124 was the second eluting diastereomer: ¹H NMR (400 MHz, DMSO-d₆) δ 9.41 (s, 1H), 8.77 (d, J=7.8 Hz, 1H), 8.65 (d, J=9.0 Hz, 1H), 8.51 (d, J=2.0 Hz, 1H), 8.20 (s, 1H), 7.93 (d, J=2.0 Hz, 1H), 5.15 (t, J=8.5 Hz, 1H), 4.30 (t, J=8.4 Hz, 1H), 2.85-2.96 (m, 1H), 2.56-2.52 (m, 1H), 2.36 (s, 3H), 2.31-2.22 (m, 1H), 2.20-2.08 (m, 1H), 2.07-1.92 (m, 2H), 1.91-1.67 (m, 3H), 1.67-1.55 (m, 1H), 1.45-1.32 (m, 1H), 1.32-1.18 (m, 2H), 1.00 (d, J=6.9 Hz, 3H), 0.63-0.45 (m, 3H), 0.43-0.32 (m, 1H). MS (ESI) m/z: [M+H]⁺ Found 583.3.

Example 125

3-Cyclopropyl-N—((S)-(7-((R)-cyclopropyl(2-(3,3-difluorocyclobutyl)acetamido)methyl)imidazo[1,2-b]pyridazin-2-yl)(4,4-difluorocyclohexyl)methyl)isoxazole-4-carboxamide

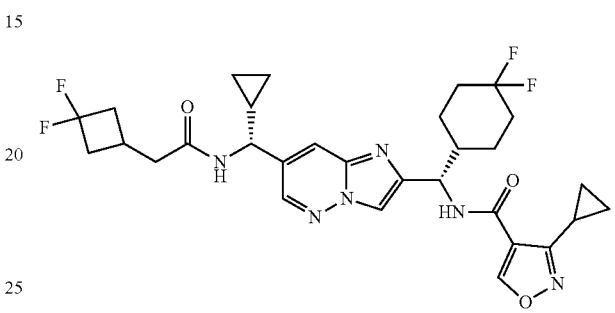

The title compound was prepared as described for the synthesis of Example 38 using N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide (Intermediate 171) in place of N—((R)-(2-((S)-amino(4,4-difluorocyclohexyl)methyl)imidazo[1,2-b]pyridazin-7-yl)(cyclopropyl)methyl)-4,4,4-trifluorobutanamide and 3-cyclopropylisoxazole-4-carboxylic acid in place of 1-(3,3,3-trifluoropropyl)-1H-1,2,4-triazole-5-carboxylic acid. ¹H NMR (400 MHz, DMSO-d₆) δ 9.35 (s, 1H), 8.65 (d, J=9.0 Hz, 1H), 8.59 (d, J=7.8 Hz, 1H), 8.49 (d, J=2.0 Hz, 1H), 8.21 (s, 1H), 7.92 (d, J=2.1 Hz, 1H), 5.17 (t, J=8.4 Hz, 1H), 4.27 (t, J=8.4 Hz, 1H), 2.73-2.54 (m, 2H), 2.48-2.22 (m, 6H), 2.20-2.09 (m, 1H), 2.09-1.93 (m, 2H), 1.91-1.67 (m, 3H), 1.67-1.57 (m, 1H), 1.47-1.33 (m, 1H), 1.33-1.15 (m, 2H), 1.05-0.93 (m, 2H), 0.93-0.82 (m, 2H), 0.62-0.43 (m, 3H), 0.41-0.32 (m, 1H). MS (ESI) m/z: [M+H]⁺ Found 603.3.

Example 126

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-1-ethyl-1H-pyrazole-5-carboxamide

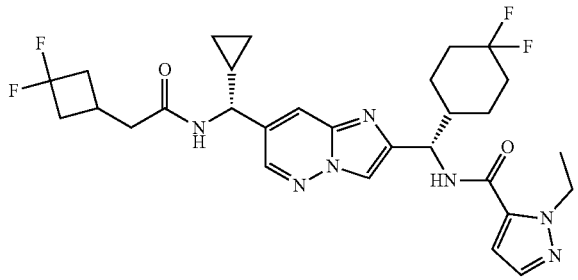 [SMILES: CCn1nccc1C(=O)N[C@H](c1cn2ncc([C@H](NC(=O)CC3CC(F)(F)C3)C3CC3)cc2n1)C1CCC(F)(F)CC1]

The title compound was prepared as described for the synthesis of Example 38 using N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide (Intermediate 171) in place of N—((R)-(2-((S)-amino(4,4-difluorocyclohexyl)methyl)imidazo[1,2-b]pyridazin-7-yl)(cyclopropyl)methyl)-4,4,4-trifluorobutanamide and 1-ethyl-1H-pyrazole-5-carboxylic acid in place of 1-(3,3,3-trifluoropropyl)-1H-1,2,4-triazole-5-carboxylic acid. $^1$H NMR (500 MHz, DMSO-$d_6$) δ 8.71 (d, J=9.0 Hz, 1H), 8.59 (d, J=7.8 Hz, 1H), 8.49 (d, J=2.1 Hz, 1H), 8.20 (s, 1H), 7.92 (d, J=2.0 Hz, 1H), 7.47 (d, J=2.0 Hz, 1H), 6.97 (d, J=2.0 Hz, 1H), 5.15 (t, J=8.7 Hz, 1H), 4.47-4.42 (m, 2H), 4.27 (t, J=8.4 Hz, 1H), 2.70-2.56 (m, 2H), 2.43-2.36 (m, 3H), 2.35-2.22 m, 2H), 2.22-2.12 (m, 1H), 2.10-1.93 (m, 2H), 1.91-1.84 (m, 1H), 1.84-1.68 (m, 2H), 1.65-1.55 (m, 1H), 1.43-1.33 (m, 1H), 1.32-1.17 (m, 5H), 0.61-0.49 (m, 2H), 0.49-0.41 (m, 1H), 0.40-0.32 (m, 1H). MS (ESI) m/z: [M+H]$^+$ Found 590.3.

Example 127

N—((S)-(7-((R)-Cyclopropyl(4,4,4-trifluorobutanamido)methyl)imidazo[1,2-b]pyridazin-2-yl)(4,4-difluorocyclohexyl)methyl)-1-ethyl-1H-pyrazole-5-carboxamide

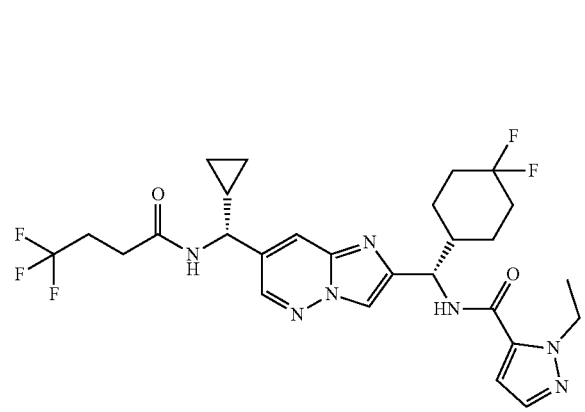 [SMILES: CCn1nccc1C(=O)N[C@H](c1cn2ncc([C@H](NC(=O)CCC(F)(F)F)C3CC3)cc2n1)C1CCC(F)(F)CC1]

The title compound was prepared as described for the synthesis of Example 38 using 1-ethyl-1H-pyrazole-5-carboxylic acid in place of 1-(3,3,3-trifluoropropyl)-1H-1,2,4-triazole-5-carboxylic acid. $^1$H NMR (500 MHz, DMSO-$d_6$) δ 8.74-8.67 (m, 2H), 8.50 (d, J=2.0 Hz, 1H), 8.20 (s, 1H), 7.93 (d, J=2.0 Hz, 1H), 7.47 (d, J=2.0 Hz, 1H), 6.98 (d, J=2.0 Hz, 1H), 5.15 (t, J=8.7 Hz, 1H), 4.48-4.41 (m, 2H), 4.29 (t, J=8.4 Hz, 1H), 2.48-2.43 (m, 1H), 2.48-2.42 (m, 3H), 2.23-2.12 (m, 1H), 2.10-1.93 (m, 2H), 1.92-1.84 (m, 1H), 1.84-1.68 (m, 2H), 1.66-1.57 (m, 1H), 1.44-1.33 (m, 1H), 1.30-1.16 (m, 5H), 0.62-0.46 (m, 3H), 0.43-0.31 (m, 1H). MS (ESI) m/z: [M+H]$^+$ Found 582.3.

Example 128

3-Cyclopropyl-N—((S)-(7-((R)-cyclopropyl((R*)-4,4,4-trifluoro-3-methylbutanamido)methyl)imidazo[1,2-b]pyridazin-2-yl)(4,4-difluorocyclohexyl)methyl)isoxazole-4-carboxamide

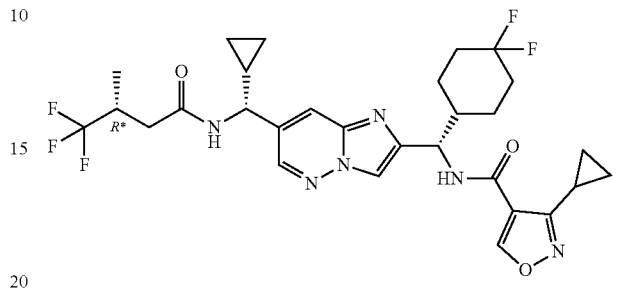

Example 129

3-Cyclopropyl-N—((S)-(7-((R)-cyclopropyl((S*)-4,4,4-trifluoro-3-methylbutanamido)methyl)imidazo[1,2-b]pyridazin-2-yl)(4,4-difluorocyclohexyl)methyl)isoxazole-4-carboxamide

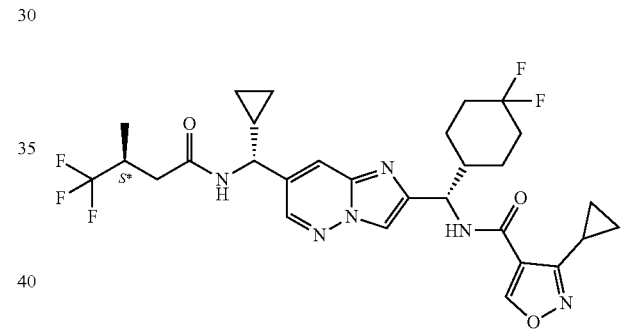

3-Cyclopropyl-N-((1S)-(7-((1R)-cyclopropyl(4,4,4-trifluoro-3-methylbutanamido)methyl)imidazo[1,2-b]pyridazin-2-yl)(4,4-difluorocyclohexyl)methyl)isoxazole-4-carboxamide (Intermediate 175) was separated by SFC with a chiral stationary phase (AS-H 2×25 cm, 15% IPA/CO$_2$, 65 mL/min) to afford a pair of diastereomers, which were both further purified by preparative HPLC (XBridge C18, 10% to 100% MeCN/aqueous NH$_4$OH (20 mM)). Example 128 was the first eluting diastereomer by SFC: $^1$H NMR (500 MHz, DMSO-$d_6$) δ 9.35 (s, 1H), 8.76 (d, J=7.9 Hz, 1H), 8.66 (d, J=9.0 Hz, 1H), 8.50 (d, J=2.0 Hz, 1H), 8.21 (s, 1H), 7.93 (d, J=2.0 Hz, 1H), 5.17 (t, J=8.4 Hz, 1H), 4.31 (t, J=8.4 Hz, 1H), 2.85-2.70 (m, 1H), 2.56-2.52 (m, 1H), 2.46-2.39 (m, 1H), 2.31-2.23 (m, 1H), 2.20-2.09 (m, 1H), 2.09-1.93 (m, 2H), 1.90-1.82 (m, 1H), 1.82-1.69 (m, 2H), 1.66-1.58 (m, 1H), 1.45-1.34 (m, 1H), 1.32-1.18 (m, 2H), 1.07 (d, J=6.9 Hz, 3H), 1.03-0.94 (m, 2H), 0.93-0.81 (m, 2H), 0.62-0.46 (m, 3H), 0.42-0.34 (m, 1H). MS (ESI) m/z: [M+H]$^+$ Found 609.2. Example 129 was the second eluting diastereomer by SFC: $^1$H NMR (500 MHz, DMSO-$d_6$) δ 9.35 (s, 1H), 8.77 (d, J=7.6 Hz, 1H), 8.66 (d, J=8.9 Hz, 1H), 8.51 (d, J=2.1 Hz, 1H), 8.22 (s, 1H), 7.93 (d, J=2.0 Hz, 1H), 5.17 (t, J=8.4 Hz, 1H), 4.30 (t, J=8.4 Hz, 1H), 2.85-2.70 (m, 1H), 2.56-2.51 (m, 1H), 2.46-2.40 (m, 1H), 2.31-2.23 (m, 1H), 2.19-2.10

(m, 1H), 2.09-1.92 (m, 2H), 1.91-1.83 (m, 1H), 1.82-1.68 (m, 2H), 1.66-1.58 (m, 1H), 1.44-1.34 (m, 1H), 1.32-1.17 (m, 2H), 1.04-0.96 (m, 5H), 0.93-0.82 (m, 2H), 0.62-0.56 (m, 1H), 0.56-0.46 (m, 2H), 0.42-0.34 (m, 1H). MS (ESI) m/z: [M+H]+ Found 609.3.

Example 130

N—((S)-(7-((R*)-Cyclopropyl((R*)-4,4,4-trifluoro-3-hydroxybutanamido)methyl)imidazo[1,2-b]pyridazin-2-yl)(4,4-difluorocyclohexyl)methyl)-1-isopropyl-1H-pyrazole-5-carboxamide

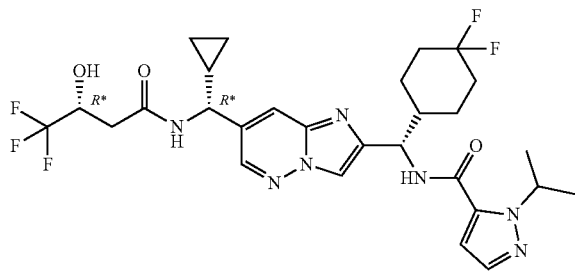 [SMILES: CC(C)n1nccc1C(=O)N[C@H](c1cn2ncc([C@H](NC(=O)C[C@@H](O)C(F)(F)F)C3CC3)cc2n1)C1CCC(F)(F)CC1]

Example 131

N—((S)-(7-((R*)-Cyclopropyl((S*)-4,4,4-trifluoro-3-hydroxybutanamido)methyl)imidazo[1,2-b]pyridazin-2-yl)(4,4-difluorocyclohexyl)methyl)-1-isopropyl-1H-pyrazole-5-carboxamide

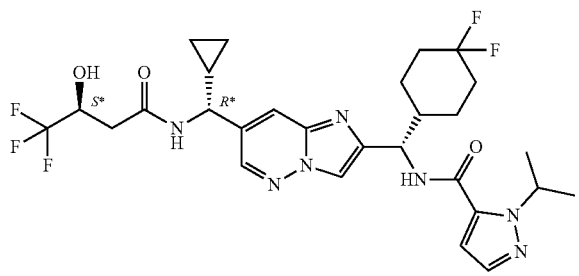 [SMILES: CC(C)n1nccc1C(=O)N[C@H](c1cn2ncc([C@H](NC(=O)C[C@H](O)C(F)(F)F)C3CC3)cc2n1)C1CCC(F)(F)CC1]

N-((1S)-(7-((1R*)-Cyclopropyl(4,4,4-trifluoro-3-hydroxybutanamido)methyl)imidazo[1,2-b]pyridazin-2-yl)(4,4-difluorocyclohexyl)methyl)-1-isopropyl-1H-pyrazole-5-carboxamide (Intermediate 177) was separated by SFC using a chiral stationary phase (Whelk-01 (R,R) 2×25 cm, 15% IPA/CO$_2$, 80 mL/min). The first eluting fraction was the major pair of diastereomers which was further subjected to SFC with a chiral stationary phase (Lux Cell-4 2×25 cm, 12% MeOH in CO$_2$, 80 mL/min). Example 130 was the first eluting diastereomer: $^1$H NMR (400 MHz, DMSO-d$_6$) δ 8.78 (d, J=7.8 Hz, 1H), 8.71 (d, J=9.1 Hz, 1H), 8.51 (d, J=2.0 Hz, 1H), 8.19 (s, 1H), 7.94 (d, J=1.9 Hz, 1H), 7.49 (d, J=2.0 Hz, 1H), 6.91 (d, J=2.0 Hz, 1H), 6.39 (s, 1H), 5.37 (td, J=6.6, 13.2 Hz, 1H), 5.15 (t, J=8.6 Hz, 1H), 4.38-4.23 (m, 2H), 2.21-2.11 (m, 1H), 2.10-1.93 (m, 3H), 1.92-1.79 (m, 2H), 1.78-1.69 (m, 1H), 1.66-1.56 (m, 1H), 1.45-1.28 (m, 8H), 1.28-1.17 (m, 2H), 0.63-0.48 (m, 3H), 0.44-0.33 (m, 1H). MS (ESI) m/z: [M+H]+ Found 612.3. Example 131 was the second eluting diastereomer: $^1$H NMR (400 MHz, DMSO-d$_6$) δ 8.78-8.65 (m, 2H), 8.50 (d, J=2.0 Hz, 1H), 8.19 (s, 1H), 7.94 (d, J=2.0 Hz, 1H), 7.48 (d, J=1.9 Hz, 1H), 6.91 (d, J=2.0 Hz, 1H), 6.44 (s, 1H), 5.36 (td, J=6.7, 13.3 Hz, 1H), 5.15 (t, J=8.6 Hz, 1H), 4.40-4.28 (m, 2H), 2.22-2.12 (m, 1H), 2.09-1.92 (m, 3H), 1.91-1.79 (m, 2H), 1.78-1.68 (m, 1H), 1.66-1.58 (m, 1H), 1.44-1.29 (m, 8H), 1.28-1.18 (m, 2H), 0.61-0.48 (m, 3H), 0.42-0.34 (m, 1H). MS (ESI) m/z: [M+H]+ Found 612.3.

Example 132

N—((S)-(7-((R*)-Cyclopropyl((R*)-4,4,4-trifluoro-3-hydroxy-3-methylbutanamido)methyl)imidazo[1,2-b]pyridazin-2-yl)(4,4-difluorocyclohexyl)methyl)-1-isopropyl-1H-pyrazole-5-carboxamide Example 133

N—((S)-(7-((R*)-Cyclopropyl((S*)-4,4,4-trifluoro-3-hydroxy-3-methylbutanamido)methyl)imidazo[1,2-b]pyridazin-2-yl)(4,4-difluorocyclohexyl)methyl)-1-isopropyl-1H-pyrazole-5-carboxamide N-((1S)-(7-((1R*)-Cyclopropyl(4,4,4-trifluoro-3-hydroxy-3-methylbutanamido)methyl)imidazo[1,2-b]pyridazin-2-yl)(4,4-difluorocyclohexyl)methyl)-1-isopropyl-1H-pyrazole-5-carboxamide (Intermediate 178) was separated using SFC with a chiral stationary phase (AD-H 2×25 cm, 15% IPA/CO$_2$, 65 mL/min). Example 132 was the first eluting diastereomer by SFC: $^1$H NMR (400 MHz, DMSO-d$_6$) δ 8.77-8.65 (m, 2H), 8.51 (d, J=2.0 Hz, 1H), 8.20 (s, 1H), 7.96 (d, J=2.0 Hz, 1H), 7.48 (d, J=2.0 Hz, 1H), 6.91 (d, J=2.0 Hz, 1H), 6.20 (s, 1H), 5.43-5.31 (m, 1H), 5.15 (t, J=8.6 Hz, 1H), 4.30 (t, J=8.4 Hz, 1H), 2.64-2.54 (m, 1H), 2.43 (d, J=13.8 Hz, 1H), 2.24-2.12 (m, 1H), 2.10-1.93 (m, 2H), 1.92-1.68 (m, 3H), 1.66-1.57 (m, 1H), 1.44-1.31 (m, 10H), 1.29-1.16 (m, 2H), 0.63-0.49 (m, 3H), 0.42-0.33 (m, 1H). MS (ESI) m/z: [M+H]+ Found 626.3. Example 133 was the second eluting diastereomer by SFC: $^1$H NMR (400

MHz, DMSO-d$_6$) δ 8.76-8.67 (m, 2H), 8.51 (d, J=2.1 Hz, 1H), 8.20 (s, 1H), 7.95 (d, J=2.0 Hz, 1H), 7.48 (d, J=1.9 Hz, 1H), 6.91 (d, J=2.0 Hz, 1H), 6.25 (s, 1H), 5.43-5.31 (m, 1H), 5.15 (t, J=8.6 Hz, 1H), 4.31 (t, J=8.2 Hz, 1H), 2.62-2.54 (m, 1H), 2.46-2.41 (m, 1H), 2.23-2.12 (m, 1H), 2.09-1.92 (m, 2H), 1.92-1.68 (m, 3H), 1.66-1.57 (m, 1H), 1.41-1.30 (m, 10H), 1.28-1.19 (m, 2H), 0.63-0.47 (m, 3H), 0.42-0.33 (m, 1H). MS (ESI) m/z: [M+H]$^+$ Found 626.3.

Example 134

N—((S)-(4,4-Difluorocyclohexyl)(7-(2-methyl-1-(4,4,4-trifluorobutanamido)propyl)imidazo[1,2-b]pyridazin-2-yl)methyl)-3-methylisoxazole-4-carboxamide

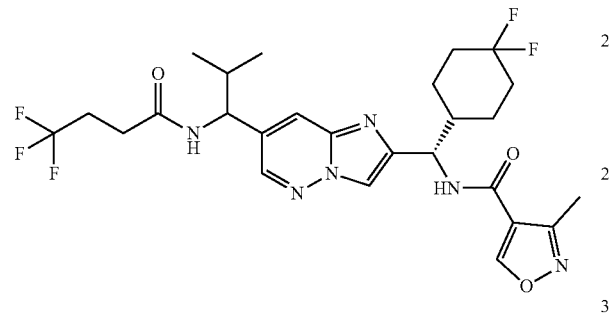

The title compound, a mixture of diastereomers, was prepared as described for the synthesis of Intermediate 39 using 3-methylisoxazole-4-carboxylic acid in place of 1-(3,3,3-trifluoropropyl)-1H-pyrazole-4-carboxylic acid and isopropylmagnesium bromide in place of cyclopropylmagnesium bromide. $^1$H NMR (500 MHz, DMSO-d$_6$) δ 9.43-9.39 (m, 1H), 8.67-8.62 (m, 1H), 8.52-8.44 (m, 1H), 8.47 (d, J=1.8 Hz, 1H), 8.20 (s, 1H), 7.88 (s, 1H), 5.18-5.10 (m, 1H), 4.74-4.66 (m, 1H), 2.49-2.42 (m, 4H), 2.36 (s, 3H), 2.19-2.10 (m, 1H), 2.10-2.02 (m, 2H), 2.02-1.93 (m, 1H), 1.91-1.84 (m, 1H), 1.84-1.70 (m, 2H), 1.65-1.58 (m, 1H), 1.44-1.34 (m, 1H), 1.31-1.21 (m, 1H), 0.93 (d, J=6.6 Hz, 3H), 0.82 (d, J=6.6 Hz, 3H). MS (ESI) m/z: [M+H]$^+$ Found 571.4.

Example 135

N-((1S)-(7-((R*)-Cyclopropyl(4,4-difluorobutanamido)methyl)imidazo[1,2-b]pyridazin-2-yl)(4,4-difluorocyclohexyl)methyl)-1-isopropyl-1H-pyrazole-5-carboxamide

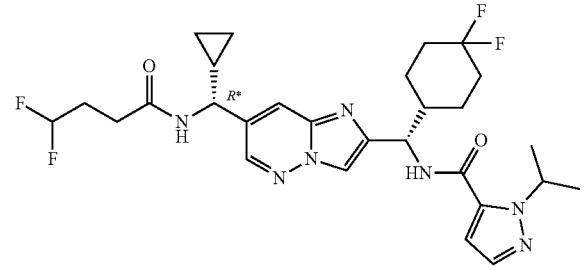 [SMILES: CC(C)n1nccc1C(=O)N[C@H](c1cn2ncc([C@H](NC(=O)CCC(F)F)C3CC3)cc2n1)C1CCC(F)(F)CC1]

N-((1S)-(7-(Cyclopropyl(4,4-difluorobutanamido)methyl)imidazo[1,2-b]pyridazin-2-yl)(4,4-difluorocyclohexyl)methyl)-1-isopropyl-1H-pyrazole-5-carboxamide (Intermediate 179) was separated by SFC using a chiral stationary phase (Whelk-01 (S,S), 5 μm, 250×21.2 mm, 40% IPA in CO$_2$). One fraction was further purified by SFC with a chiral stationary phase (Chiralpak IC, 5 μm, 250×21.2 mm, 40% IPA in CO$_2$) to afford the title compound. $^1$H NMR (500 MHz, DMSO-d$_6$) δ 8.71 (d, J=9.0 Hz, 1H), 8.65 (d, J=7.8 Hz, 1H), 8.51 (d, J=2.0 Hz, 1H), 8.20 (s, 1H), 7.93 (d, J=2.1 Hz, 1H), 7.49 (d, J=1.9 Hz, 1H), 6.91 (d, J=2.0 Hz, 1H), 6.26-5.91 (m, 1H), 5.37 (septet, J=6.6 Hz, 1H), 5.16 (t, J=8.6 Hz, 1H), 4.29 (t, J=8.4 Hz, 1H), 2.40-2.30 (m, 2H), 2.25-2.13 (m, 1H), 2.11-1.94 (m, 4H), 1.91-1.85 (m, 1H), 1.84-1.69 (m, 2H), 1.66-1.57 (m, 1H), 1.43-1.28 (m, 7H), 1.28-1.17 (m, 2H), 0.62-0.55 (m, 1H), 0.54-0.45 (m, 2H), 0.42-0.36 (m, 1H). MS (ESI) m/z: [M+H]$^+$ Found 578.3.

Example 136

N—((S)-(7-((R*)-Cyclopropyl(3-hydroxy-3-methylbutanamido)methyl)imidazo[1,2-b]pyridazin-2-yl)(4,4-difluorocyclohexyl)methyl)-1-isopropyl-1H-pyrazole-5-carboxamide

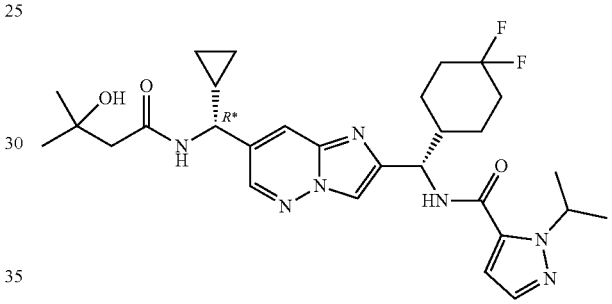

Example 137

N—((S)-(7-((S*)-Cyclopropyl(3-hydroxy-3-methylbutanamido)methyl)imidazo[1,2-b]pyridazin-2-yl)(4,4-difluorocyclohexyl)methyl)-1-isopropyl-1H-pyrazole-5-carboxamide

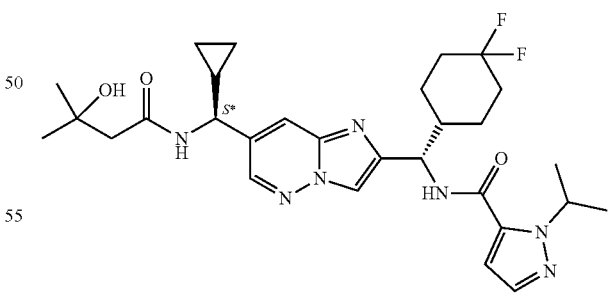

N-((1S)-(7-(Cyclopropyl(3-hydroxy-3-methylbutanamido)methyl)imidazo[1,2-b]pyridazin-2-yl)(4,4-difluorocyclohexyl)methyl)-1-isopropyl-1H-pyrazole-5-carboxamide (Intermediate 180) was separated using SFC with a chiral stationary phase (Whelk-01 SS3, 3 μm, 100×4.6 mm, 35% MeOH with 0.2% TEA/CO$_2$) to afford the title compounds. Example 136 was the first eluting diastereomer: $^1$H NMR (500 MHz, DMSO-d$_6$) δ 8.64 (d, J=9.1 Hz, 1H), 8.46-8.40

(m, 2H), 8.12 (s, 1H), 7.88 (d, J=1.8 Hz, 1H), 7.42 (d, J=1.9 Hz, 1H), 6.84 (d, J=2.0 Hz, 1H), 5.29 (septet, J=6.6 Hz, 1H), 5.08 (t, J=8.6 Hz, 1H), 4.64 (s, 1H), 4.22 (t, J=8.4 Hz, 1H), 2.28-2.17 (m, 2H), 2.14-2.06 (m, 1H), 2.02-1.86 (m, 2H), 1.85-1.77 (m, 1H), 1.77-1.62 (m, 2H), 1.59-1.50 (m, 1H), 1.36-1.22 (m, 7H), 1.21-1.11 (m, 2H), 1.10-1.03 (m, 6H), 0.55-0.40 (m, 3H), 0.34-0.26 (m, 1H). MS (ESI) m/z: [M+H]+ Found 572.3. Example 137 was the second eluting diastereomer: ¹H NMR (500 MHz, DMSO-d₆) δ 8.64 (d, J=9.0 Hz, 1H), 8.50-8.36 (m, 2H), 8.12 (s, 1H), 7.87 (s, 1H), 7.41 (d, J=1.9 Hz, 1H), 6.84 (d, J=1.9 Hz, 1H), 5.30 (septet, J=6.6 Hz, 1H), 5.08 (t, J=8.6 Hz, 1H), 4.64 (s, 1H), 4.23 (t, J=8.4 Hz, 1H), 2.26-2.17 (m, 2H), 2.15-2.05 (m, 1H), 2.03-1.85 (m, 2H), 1.85-1.77 (m, 1H), 1.77-1.60 (m, 2H), 1.59-1.48 (m, 1H), 1.36-1.22 (m, 7H), 1.21-1.11 (m, 2H), 1.10-1.03 (m, 6H), 0.56-0.39 (m, 3H), 0.35-0.25 (m, 1H). MS (ESI) m/z: [M+H]+ Found 572.3.

Example 138

N—((S)-(7-((S*)-Cyclopropyl(2-((R*)-2,2-difluorocyclopropyl)acetamido)methyl)imidazo[1,2-b]pyridazin-2-yl)(4,4-difluorocyclohexyl)methyl)-1-isopropyl-1H-pyrazole-5-carboxamide

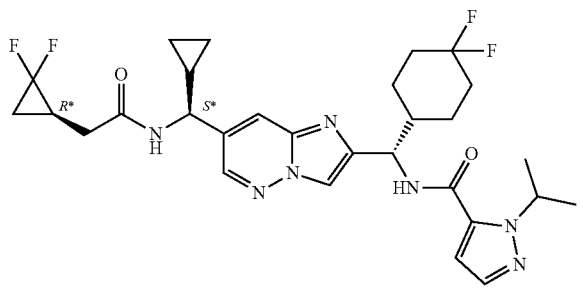 [SMILES: CC(C)n1nccc1C(=O)N[C@H](c1cn2ncc([C@@H](NC(=O)C[C@H]3CC3(F)F)C3CC3)cc2n1)C1CCC(F)(F)CC1]

Example 139

N—((S)-(7-((S*)-Cyclopropyl(2-((S*)-2,2-difluorocyclopropyl)acetamido)methyl)imidazo[1,2-b]pyridazin-2-yl)(4,4-difluorocyclohexyl)methyl)-1-isopropyl-1H-pyrazole-5-carboxamide

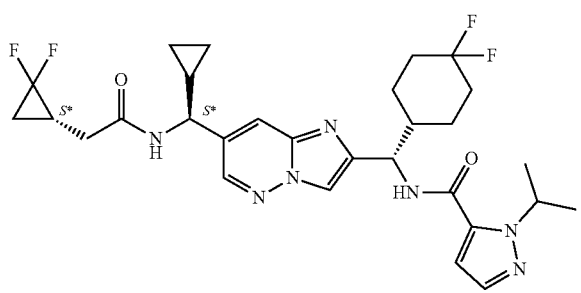 [SMILES: CC(C)n1nccc1C(=O)N[C@H](c1cn2ncc([C@@H](NC(=O)C[C@@H]3CC3(F)F)C3CC3)cc2n1)C1CCC(F)(F)CC1]

Example 140

N—((S)-(7-((R*)-Cyclopropyl(2-((R*)-2,2-difluorocyclopropyl)acetamido)methyl)imidazo[1,2-b]pyridazin-2-yl)(4,4-difluorocyclohexyl)methyl)-1-isopropyl-1H-pyrazole-5-carboxamide

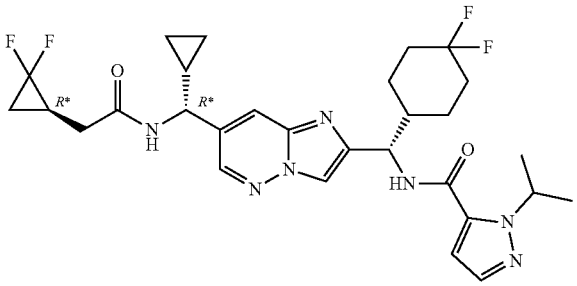 [SMILES: CC(C)n1nccc1C(=O)N[C@H](c1cn2ncc([C@H](NC(=O)C[C@H]3CC3(F)F)C3CC3)cc2n1)C1CCC(F)(F)CC1]

Example 141

N—((S)-(7-((R*)-Cyclopropyl(2-((S*)-2,2-difluorocyclopropyl)acetamido)methyl)imidazo[1,2-b]pyridazin-2-yl)(4,4-difluorocyclohexyl)methyl)-1-isopropyl-1H-pyrazole-5-carboxamide

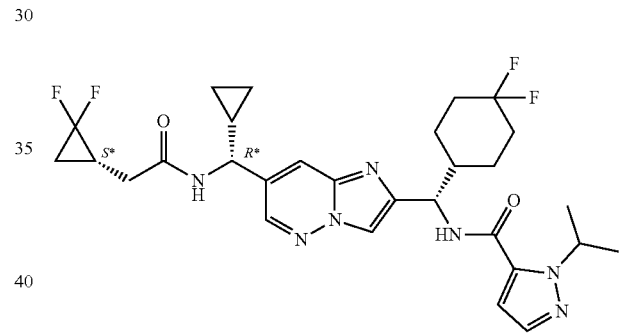

N-((1S)-(7-(Cyclopropyl(2-(2,2-difluorocyclopropyl)acetamido)methyl)imidazo[1,2-b]pyridazin-2-yl)(4,4-difluorocyclohexyl)methyl)-1-isopropyl-1H-pyrazole-5-carboxamide (Intermediate 181) was separated by SFC with a chiral stationary phase (Whelk-01 (S,S), 5 μm, 250×21.2 mm, 40% IPA/CO₂) to afford three fractions. Example 138, the second eluting fraction by SFC, was a minor diastereomer: ¹H NMR (500 MHz, DMSO-d₆) δ 8.71 (d, J=9.0 Hz, 1H), 8.60 (d, J=7.8 Hz, 1H), 8.50 (d, J=2.1 Hz, 1H), 8.21 (s, 1H), 7.93 (d, J=1.9 Hz, 1H), 7.49 (d, J=2.0 Hz, 1H), 6.91 (d, J=2.0 Hz, 1H), 5.37 (septet, J=6.6 Hz, 1H), 5.16 (t, J=8.6 Hz, 1H), 4.31 (t, J=8.3 Hz, 1H), 2.41-2.33 (m, 2H), 2.23-2.13 (m, 1H), 2.09-1.94 (m, 2H), 1.93-1.84 (m, 2H), 1.84-1.69 (m, 2H), 1.67-1.52 (m, 2H), 1.44-1.29 (m, 7H), 1.28-1.15 (m, 4H), 0.61-0.46 (m, 3H), 0.43-0.34 (m, 1H). MS (ESI) m/z: [M+H]+ Found 590.3. Example 139, the third eluting fraction by SFC, was a minor diastereomer: ¹H NMR (500 MHz, DMSO-d₆) δ 8.71 (d, J=9.1 Hz, 1H), 8.60 (d, J=7.8 Hz, 1H), 8.51 (d, J=2.1 Hz, 1H), 8.20 (s, 1H), 7.94 (d, J=2.0 Hz, 1H), 7.49 (d, J=1.9 Hz, 1H), 6.91 (d, J=2.0 Hz, 1H), 5.37 (septet, J=6.7 Hz, 1H), 5.15 (t, J=8.6 Hz, 1H), 4.30 (t, J=8.4 Hz, 1H), 2.44-2.33 (m, 2H), 2.23-2.12 (m, 1H), 2.10-1.93 (m, 2H), 1.92-1.70 (m, 4H), 1.66-1.59 (m, 1H), 1.58-1.49 (m, 1H), 1.44-1.28 (m, 7H), 1.26-1.16 (m, 3H), 0.62-0.45 (m, 3H), 0.43-0.34 (m, 1H). MS (ESI) m/z: [M+H]+ Found 590.3. The first eluting fraction was a mixture of diastereomers and was further purified by SFC using a chiral stationary phase (CHIRALPAK AD-H, 5 μm, 250×21.2 mm, 13% IPA/CO$_2$). Example 140, the first eluting fraction, was a major diastereomer: $^1$H NMR (500 MHz, DMSO-d$_6$) δ 8.71 (d, J=9.0 Hz, 1H), 8.60 (d, J=7.8 Hz, 1H), 8.51 (d, J=2.0 Hz, 1H), 8.21 (s, 1H), 7.93 (d, J=2.0 Hz, 1H), 7.49 (d, J=2.0 Hz, 1H), 6.91 (d, J=2.0 Hz, 1H), 5.37 (septet, J=6.6 Hz, 1H), 5.16 (t, J=8.6 Hz, 1H), 4.31 (t, J=8.3 Hz, 1H), 2.41-2.34 (m, 2H), 2.23-2.12 (m, 1H), 2.10-1.94 (m, 2H), 1.94-1.85 (m, 2H), 1.84-1.69 (m, 2H), 1.66-1.53 (m, 2H), 1.43-1.29 (m, 7H), 1.26-1.15 (m, 3H), 0.62-0.46 (m, 3H), 0.43-0.34 (m, 1H). MS (ESI) m/z: [M+H]+ Found 590.3. Example 141, the second eluting fraction, was a major diastereomer: $^1$H NMR (500 MHz, DMSO-d$_6$) δ 8.71 (d, J=9.0 Hz, 1H), 8.60 (d, J=7.8 Hz, 1H), 8.51 (d, J=2.0 Hz, 1H), 8.20 (s, 1H), 7.94 (d, J=2.0 Hz, 1H), 7.49 (d, J=1.9 Hz, 1H), 6.91 (d, J=2.0 Hz, 1H), 5.37 (septet, J=6.6 Hz, 1H), 5.15 (t, J=8.7 Hz, 1H), 4.30 (t, J=8.3 Hz, 1H), 2.43-2.30 (m, 2H), 2.23-2.13 (m, 1H), 2.11-1.93 (m, 2H), 1.92-1.69 (m, 4H), 1.67-1.59 (m, 1H), 1.58-1.49 (m, 1H), 1.44-1.31 (m, 7H), 1.26-1.15 (m, 3H), 0.63-0.45 (m, 3H), 0.42-0.34 (m, 1H). MS (ESI) m/z: [M+H]+ Found 590.3.

Example 142

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-4-methyl-1,2,5-oxadiazole-3-carboxamide

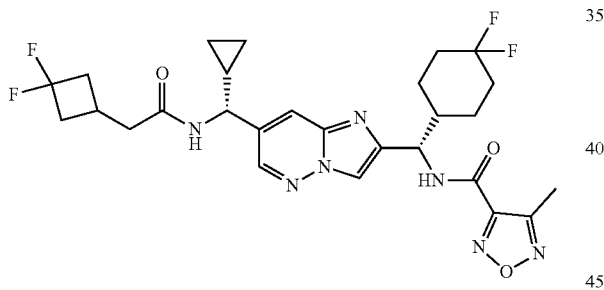

A flask was charged with a stir bar, 4-methyl-1,2,5-oxadiazole-3-carboxylic acid (154 mg, 1.2 mmol), and thionyl chloride (10.9 mL, 150 mmol). The resulting solution was heated to 80° C. and stirred for 1.5 hours. The mixture was condensed into an amber oil and taken up in dry DCM (1.2 mL) to make a 1M stock solution of 4-methyl-1,2,5-oxadiazole-3-carbonyl chloride. A vial was charged with N—((R)-2-((S)-amino(4,4-difluorocyclohexyl)methyl)imidazo[1,2-b]pyridazin-7-yl)(cyclopropyl)methyl)-2-(3,3-difluorocyclobutyl)acetamide (100 mg, 0.22 mmol, Intermediate 171), DCM (5 mL) and Hunig's base (150 μL, 0.86 mmol). The solution was cooled to 0° C., and 4-methyl-1,2,5-oxadiazole-3-carbonyl chloride (340 μL, 0.34 mmol, 1M in DCM)) was added and the solution was stirred for 1 h as it warmed to rt. The reaction was washed with water then brine, dried over anhydrous MgSO$_4$, filtered and condensed into a glassy solid. The crude material was purified by silica gel chromatography (0-100% (10% MeOH in ethyl acetate)/hexane). The material was further purified by preparative HPLC (XBridge C18, 10% to 100% MeCN/aqueous NH$_4$OH (20 mM)). The product containing fractions were lyophilzed to afford the title compound. $^1$H NMR (500 MHz, DMSO-d$_6$) δ 9.33 (d, J=9.0 Hz, 1H), 8.52 (d, J=7.8 Hz, 1H), 8.43 (d, J=1.9 Hz, 1H), 8.16 (s, 1H), 7.86 (d, J=1.3 Hz, 1H), 5.10 (t, J=8.6 Hz, 1H), 4.20 (t, J=8.4 Hz, 1H), 2.63-2.49 (m, 2H), 2.39 (s, 3H), 2.35-2.29 (m, 3H), 2.28-2.17 (m, 2H), 2.15-2.06 (m, 1H), 2.02-1.87 (m, 2H), 1.86-1.79 (m, 2H), 1.78-1.61 (m, 2H), 1.58-1.46 (m, 1H), 1.36-1.26 (m, 1H), 1.25-1.10 (m, 2H), 0.55-0.36 (m, 3H), 0.34-0.26 (m, 1H). MS (ESI) m/z: [M+H]+ Found 578.3.

Example 143

(Trans-1S*,2S*)—N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-2-(trifluoromethyl)cyclopropane-1-carboxamide

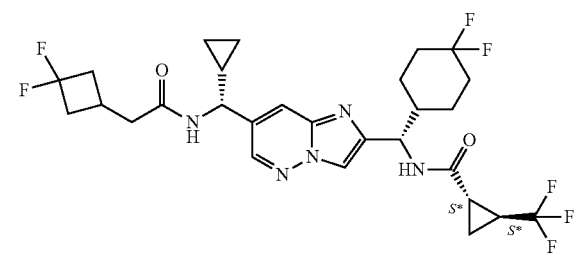 [SMILES: O=C(CC1CC(F)(F)C1)N[C@@H](c1cnn2cc([C@@H](NC(=O)[C@H]3C[C@@H]3C(F)(F)F)C3CCC(F)(F)CC3)nc2c1)C1CC1]

Example 144

(Trans-1R*,2R*)—N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-2-(trifluoromethyl)cyclopropane-1-carboxamide

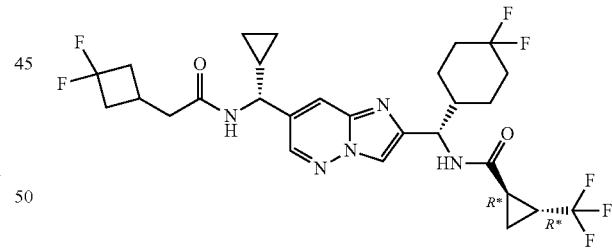

(Trans-1,2)-N—((S)-(7-((R)-cyclopropyl(2-(3,3-difluorocyclobutyl)acetamido)methyl)imidazo[1,2-b]pyridazin-2-yl)(4,4-difluorocyclohexyl)methyl)-2-(trifluoromethyl)cyclopropane-1-carboxamide (Intermediate 182) was separated using SFC with a chiral stationary phase (Chiralpak IA, 250×21 mm, 15% MeOH/CO$_2$) to afford the title compounds as single trans-diastereomers. Example 143 was the first eluting fraction by SFC. Example 143: $^1$H NMR (400 MHz, DMSO-d$_6$) δ 8.80 (d, J=9.1 Hz, 1H), 8.59 (d, J=7.8 Hz, 1H), 8.50 (d, J=2.0 Hz, 1H), 8.12 (s, 1H), 7.92 (d, J=2.0 Hz, 1H), 5.10-4.93 (m, 1H), 4.28 (t, J=8.4 Hz, 1H), 2.72-2.57 (m, 2H), 2.44-2.37 (m, 3H), 2.37-2.23 (m, 3H), 2.14-1.92 (m, 4H), 1.86-1.66 (m, 3H), 1.61-1.52 (m, 1H), 1.39-1.26 (m, 1H), 1.25-1.13 (m, 4H), 0.64-0.43 (m, 3H), 0.43-0.33 (m, 1H). MS (ESI) m/z: [M+H]+ Found 604.3. Example 144 was the second eluting fraction by SFC. Example 144: ¹H NMR (400 MHz, DMSO-d₆) δ 8.77 (d, J=9.1 Hz, 1H), 8.59 (d, J=7.8 Hz, 1H), 8.49 (d, J=2.0 Hz, 1H), 8.10 (s, 1H), 7.92 (d, J=2.0 Hz, 1H), 5.12-4.76 (m, 1H), 4.28 (t, J=8.4 Hz, 1H), 2.72-2.57 (m, 2H), 2.46-2.36 (m, 3H), 2.36-2.22 (m, 3H), 2.18-1.92 (m, 4H), 1.86-1.66 (m, 3H), 1.63-1.52 (m, 1H), 1.42-1.28 (m, 1H), 1.28-1.17 (m, 2H), 1.16-1.06 (m, 2H), 0.64-0.44 (m, 3H), 0.41-0.33 (m, 1H). MS (ESI) m/z: [M+H]+ Found 604.3.

Example 145

1-((3-Cyanobicyclo[1.1.1]pentan-1-yl)methyl)-N—((S)-(7-((R)-cyclopropyl(4,4,4-trifluorobutanamido)methyl)imidazo[1,2-b]pyridazin-2-yl)(4,4-difluorocyclohexyl)methyl)-1H-1,2,3-triazole-5-carboxamide

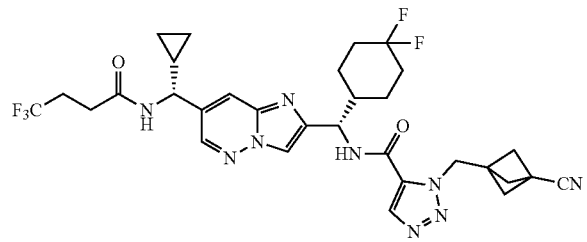 [SMILES: N#CC12CC(Cn3nncc3C(=O)N[C@H](c3cn4ncc([C@H](NC(=O)CCC(F)(F)F)C5CC5)cc4n3)C3CCC(F)(F)CC3)(C1)C2]

The title compound was prepared as described in the synthesis of Example 4, using 1-((3-cyanobicyclo[1.1.1]pentan-1-yl)methyl)-1H-1,2,3-triazole-5-carboxylic acid (Intermediate 187) in place of 2-((2,2-difluorocyclobutyl)methyl)-2H-1,2,3-triazole-4-carboxylic acid to afford the title compound as a white solid. ¹H NMR (500 MHz, CDCl₃) δ 8.31 (d, J=2.1 Hz, 1H), 7.99 (s, 1H), 7.94-7.90 (m, 2H), 7.01 (d, J=8.9 Hz, 1H), 6.43 (d, J=8.0 Hz, 1H), 5.15-5.08 (m, 1H), 4.92 (d, J=14.1 Hz, 1H), 4.72 (d, J=14.0 Hz, 1H), 4.53-4.46 (m, 1H), 2.58-2.39 (m, 4H), 2.26-2.14 (m, 1H), 2.13-2.03 (m, 2H), 1.87 (dd, J=9.5, 2.2 Hz, 3H), 1.81 (dd, J=9.5, 2.2 Hz, 3H), 1.76-1.59 (m, 4H), 1.58-1.48 (m, 1H), 1.45-1.32 (m, 1H), 1.23-1.14 (m, 1H), 0.82-0.67 (m, 2H), 0.59-0.49 (m, 1H), 0.46-0.35 (m, 1H). MS (ESI) m/z: [M+H]+ Found 660.3.

Example 146

2-((3-Cyanobicyclo[1.1.1]pentan-1-yl)methyl)-N—((S)-(7-((R)-cyclopropyl(4,4,4-trifluorobutanamido)methyl)imidazo[1,2-b]pyridazin-2-yl)(4,4-difluorocyclohexyl)methyl)-2H-1,2,3-triazole-4-carboxamide

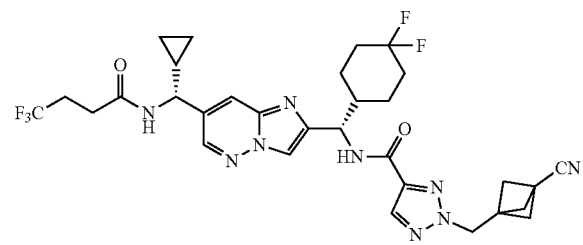 [SMILES: N#CC12CC(Cn3ncc(C(=O)N[C@H](c4cn5ncc([C@H](NC(=O)CCC(F)(F)F)C6CC6)cc5n4)C4CCC(F)(F)CC4)n3)(C1)C2]

The title compound was prepared as described in the synthesis of Example 4, using 2-((3-cyanobicyclo[1.1.1]pentan-1-yl)methyl)-2H-1,2,3-triazole-4-carboxylic acid (Intermediate 188) in place of 2-((2,2-difluorocyclobutyl)methyl)-2H-1,2,3-triazole-4-carboxylic to afford the title compound as a white solid. ¹H NMR (500 MHz, CDCl₃) δ 8.33 (d, J=2.1 Hz, 1H), 8.04 (s, 1H), 7.87 (d, J=0.7 Hz, 1H), 7.86-7.84 (m, 1H), 7.61 (d, J=8.9 Hz, 1H), 6.14 (d, J=7.0 Hz, 1H), 5.32-5.26 (m, 1H), 4.52 (d, J=2.8 Hz, 2H), 4.37-4.29 (m, 1H), 2.57-2.43 (m, 4H), 2.31-2.22 (m, 6H), 2.21-2.02 (m, 3H), 2.02-1.92 (m, 1H), 1.82-1.61 (m, 3H), 1.57-1.47 (m, 1H), 1.47-1.35 (m, 1H), 1.23-1.14 (m, 1H), 0.81-0.69 (m, 2H), 0.56-0.42 (m, 2H). MS (ESI) m/z: [M+H]+ Found 660.3.

Example 147

1-((3-Cyanobicyclo[1.1.1]pentan-1-yl)methyl)-N—((S)-(7-((R)-cyclopropyl(4,4,4-trifluorobutanamido)methyl)imidazo[1,2-b]pyridazin-2-yl)(4,4-difluorocyclohexyl)methyl)-1H-1,2,3-triazole-4-carboxamide

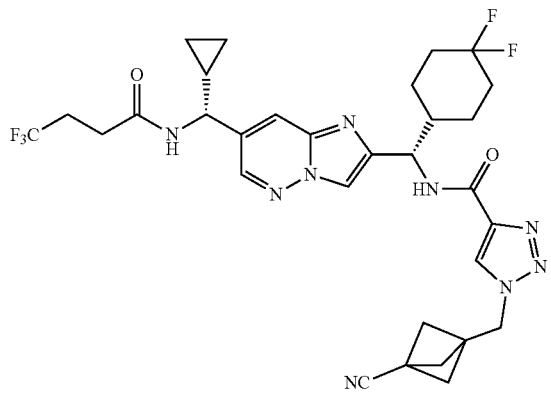 [SMILES: N#CC12CC(Cn3cc(C(=O)N[C@H](c4cn5ncc([C@H](NC(=O)CCC(F)(F)F)C6CC6)cc5n4)C4CCC(F)(F)CC4)nn3)(C1)C2]

The title compound was prepared as described in the synthesis of Example 4, using 1-((3-cyanobicyclo[1.1.1]pentan-1-yl)methyl)-1H-1,2,3-triazole-4-carboxylic acid (Intermediate 189) in place of 2-((2,2-difluorocyclobutyl)methyl)-2H-1,2,3-triazole-4-carboxylic acid to afford the title compound as a white solid. ¹H NMR (500 MHz, CDCl₃) δ 8.30 (d, J=2.2 Hz, 1H), 7.97 (s, 1H), 7.92 (d, J=9.2 Hz, 1H), 7.87 (s, 1H), 7.86-7.83 (m, 1H), 6.08 (d, J=6.9 Hz, 1H), 5.35-5.27 (m, 1H), 4.49 (d, J=1.3 Hz, 2H), 4.36-4.29 (m, 1H), 2.59-2.43 (m, 4H), 2.22 (s, 6H), 2.21-2.10 (m, 1H), 2.10-2.03 (m, 1H), 2.03-1.96 (m, 1H), 1.82-1.62 (m, 4H), 1.61-1.48 (m, 1H), 1.47-1.36 (m, 1H), 1.21-1.11 (m, 1H), 0.80-0.68 (m, 2H), 0.56-0.42 (m, 2H). MS (ESI) m/z: [M+H]+ Found 660.3.

Example 148

N—((S)-(7-((R)-Cyclopropyl(4,4,4-trifluorobutanamido)methyl)imidazo[1,2-b]pyridazin-2-yl)(4,4-difluorocyclohexyl)methyl)-2,2-difluoro-1-methyl-cyclopropane-1-carboxamide

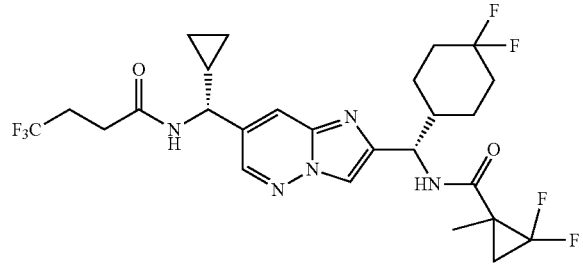 [SMILES: CC1(C(=O)N[C@H](c2cn3ncc([C@H](NC(=O)CCC(F)(F)F)C4CC4)cc3n2)C2CCC(F)(F)CC2)CC1(F)F]

The title compound was prepared as described in the synthesis of Example 4, using 2,2-difluoro-1-methylcyclopropane-1-carboxylic acid in place of 2-((2,2-difluorocyclobutyl)methyl)-2H-1,2,3-triazole-4-carboxylic acid to afford the title compound as a white solid. $^1$H NMR (500 MHz, CDCl$_3$) δ 8.35-8.31 (m, 1H), 7.83-7.81 (m, 1H), 7.80 (d, J=4.8 Hz, 1H), 6.81-6.67 (m, 1H), 6.10-6.01 (m, 1H), 5.18-5.07 (m, 1H), 4.38-4.28 (m, 1H), 2.60-2.44 (m, 4H), 2.22-2.09 (m, 2H), 2.09-1.95 (m, 2H), 1.92-1.83 (m, 1H), 1.81-1.55 (m, 3H), 1.54-1.44 (m, 1H), 1.49-1.36 (m, 3H), 1.36-1.22 (m, 2H), 1.22-1.13 (m, 1H), 0.83-0.69 (m, 2H), 0.58-0.44 (m, 2H). MS (ESI) m/z: [M+H]$^+$ Found 578.3.

Example 149

(Trans-1S*,2S*)—N—((S)-(7-((R)-Cyclopropyl(4,4,4-trifluorobutanamido)methyl)imidazo[1,2-b]pyridazin-2-yl)(4,4-difluorocyclohexyl)methyl)-2-(trifluoromethyl)cyclopropane-1-carboxamide

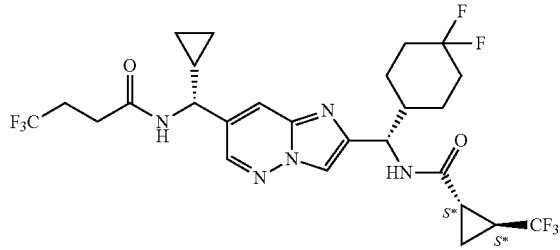 [SMILES: O=C(CCC(F)(F)F)N[C@@H](c1cnn2cc([C@@H](NC(=O)[C@H]3C[C@@H]3C(F)(F)F)C3CCC(F)(F)CC3)nc2c1)C1CC1]

Example 150

(Trans-1R*, 2R*)—N—((S)-(7-((R)-Cyclopropyl(4,4,4-trifluorobutanamido)methyl)imidazo[1,2-b]pyridazin-2-yl)(4,4-difluorocyclohexyl)methyl)-2-(trifluoromethyl)cyclopropane-1-carboxamide

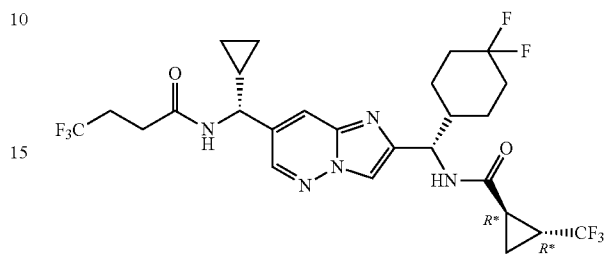

(Trans-1,2)-N—((S)-(7-((R)-Cyclopropyl(4,4,4-trifluorobutanamido)methyl)imidazo[1,2-b]pyridazin-2-yl)(4,4-difluorocyclohexyl)methyl)-2-(trifluoromethyl)cyclopropane-1-carboxamide (Example 43) was separated by SFC (ChiralPak IG 2×25 cm column, eluting with 12% IPA/CO$_2$, 100 bar, 70 mL/min, detection at 220 nm) to give two diastereomeric products as white solids. The first-eluting isomer was Example 149: $^1$H NMR (500 MHz, CD$_3$OD) δ 8.44 (d, J=2.1 Hz, 1H), 7.98 (d, J=0.6 Hz, 1H), 7.84 (dd, J=1.8, 0.8 Hz, 1H), 5.08 (d, J=7.7 Hz, 1H), 4.26 (d, J=9.4 Hz, 1H), 2.63-2.42 (m, 4H), 2.23-2.15 (m, 1H), 2.15-1.95 (m, 4H), 1.92-1.57 (m, 4H), 1.53-1.41 (m, 1H), 1.41-1.30 (m, 1H), 1.30-1.20 (m, 2H), 1.20-1.12 (m, 1H), 0.77-0.64 (m, 2H), 0.53-0.45 (m, 2H). MS (ESI) m/z: [M+H]$^+$ Found 596.3. The second-eluting isomer was Example 150: $^1$H NMR (500 MHz, CD$_3$OD) δ 8.45 (d, J=2.1 Hz, 1H), 7.99 (d, J=0.6 Hz, 1H), 7.86 (dd, J=2.0, 1.0 Hz, 1H), 5.08 (d, J=7.7 Hz, 1H), 4.27 (d, J=9.6 Hz, 1H), 2.62-2.42 (m, 4H), 2.23-2.16 (m, 1H), 2.16-1.96 (m, 4H), 1.92-1.83 (m, 1H), 1.83-1.66 (m, 2H), 1.66-1.57 (m, 1H), 1.50-1.32 (m, 2H), 1.32-1.20 (m, 3H), 0.76-0.67 (m, 2H), 0.55-0.45 (m, 2H). MS (ESI) m/z: [M+H]$^+$ Found 596.3.

Example 151

N—((S)-(7-((R)-Cyclopropyl(4,4,4-trifluorobutanamido)methyl)imidazo[1,2-b]pyridazin-2-yl)(4,4-difluorocyclohexyl)methyl)-5-(3,3-difluoropropyl)nicotinamide

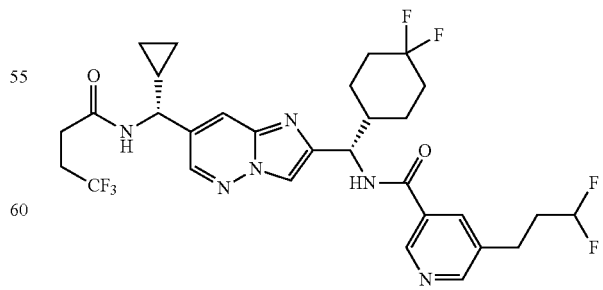

A mixture of N—((R)-(2-((S)-amino(4,4-difluorocyclohexyl)methyl)imidazo[1,2-b]pyridazin-7-yl)(cyclopropyl)methyl)-4,4,4-trifluorobutanamide (75 mg, 0.16 mmol, Intermediate 51), 5-(3,3-difluoropropyl)nicotinic acid (49 mg, 0.24 mmol, Intermediate 194), HOBt (42 mg, 0.27 mmol), DIPEA (0.12 mL, 0.69 mmol) and EDCI (50 mg, 0.26 mmol) in ACN (2 mL) was stirred at rt. After 48 h, the mixture was partitioned between ethyl acetate and saturated aqueous ammonium chloride solution. The layers were separated. The organic layer was washed with half-saturated aqueous sodium bicarbonate solution and then brine solution. The organic layer was dried over anhydrous Na$_2$SO$_4$, filtered and absorbed onto Celite® for purification by silica gel chromatography (hexanes/ethyl acetate) to provide the title compound as a white solid after lyophilization. $^1$H NMR (400 MHz, DMSO-d$_6$) δ 8.90 (d, J=8.9 Hz, 1H), 8.87 (d, J=2.1 Hz, 1H), 8.71 (d, J=7.7 Hz, 1H), 8.61 (d, J=2.2 Hz, 1H), 8.50 (d, J=2.1 Hz, 1H), 8.23 (s, 1H), 8.13 (t, J=2.1 Hz, 1H), 7.97-7.90 (m, 1H), 6.14 (tt, J=56.6, 4.3 Hz, 1H), 5.21 (t, J=8.6 Hz, 1H), 4.28 (t, J=8.4 Hz, 1H), 2.84-2.75 (m, 2H), 2.48-2.43 (m, 2H), 2.29-1.58 (m, 10H), 1.47-1.14 (m, 4H), 0.62-0.45 (m, 3H), 0.42-0.32 (m, 1H). MS (ESI) m/z: [M+H]$^+$ Found 643.2.

Example 152

N—((S)-(7-((R)-Cyclopropyl(4,4,4-trifluorobutanamido)methyl)imidazo[1,2-b]pyridazin-2-yl)(4,4-difluorocyclohexyl)methyl)-5-(2,2-difluoroethyl)nicotinamide

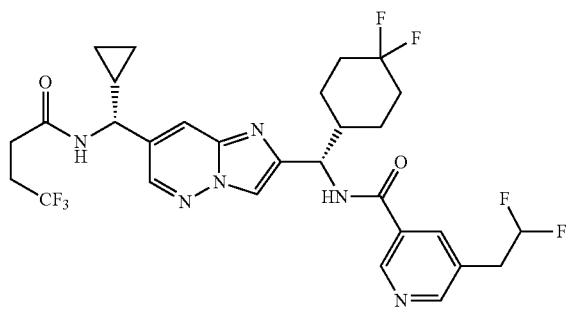 [SMILES: O=C(CCC(F)(F)F)N[C@@H](c1cnn2cc([C@@H](NC(=O)c3cncc(CC(F)F)c3)C3CCC(F)(F)CC3)nc2c1)C1CC1]

The title compound was prepared as described for the synthesis of Example 151, using 5-(2,2-difluoroethyl)nicotinic acid (Intermediate 197) in place of 5-(3,3-difluoropropyl)nicotinic acid to provide the title compound as a white solid. $^1$H NMR (600 MHz, DMSO-d$_6$) δ 8.99-8.92 (m, 2H), 8.71 (d, J=7.7 Hz, 1H), 8.64 (d, J=2.1 Hz, 1H), 8.50 (d, J=2.1 Hz, 1H), 8.23 (s, 1H), 8.16 (t, J=2.1 Hz, 1H), 7.93 (dd, J=1.9, 1.0 Hz, 1H), 6.33 (tt, J=56.3, 4.4 Hz, 1H), 5.21 (t, J=8.6 Hz, 1H), 4.29 (t, J=8.4 Hz, 1H), 3.36-3.25 (m, 2H), 2.49-2.42 (m, 4H), 2.24-2.16 (m, 1H), 2.10-1.87 (m, 3H), 1.84-1.70 (m, 2H), 1.67-1.59 (m, 1H), 1.45-1.36 (m, 1H), 1.32-1.17 (m, 2H), 0.64-0.43 (m, 3H), 0.41-0.33 (m, 1H). MS (ESI) m/z: [M+H]$^+$ Found 629.2.

Example 153

N-((1S)-(4,4-Difluorocyclohexyl)(7-(1-(4,4,4-trifluorobutanamido)ethyl)imidazo[1,2-b]pyridazin-2-yl)methyl)-3-methylisoxazole-4-carboxamide

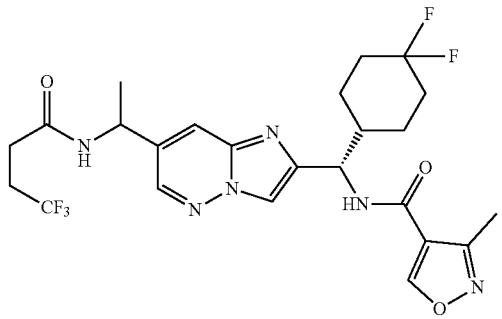 [SMILES: Cc1nocc1C(=O)N[C@H](c1cn2ncc(C(C)NC(=O)CCC(F)(F)F)cc2n1)C1CCC(F)(F)CC1]

The title compound was prepared as described for the synthesis of Intermediate 39 using N-((1S)-(7-(1-aminoethyl)imidazo[1,2-b]pyridazin-2-yl)(4,4-difluorocyclohexyl)methyl)-3-methylisoxazole-4-carboxamide (Intermediate 198) in place of N-((1S)-(7-(amino(cyclopropyl)methyl)imidazo[1,2-b]pyridazin-2-yl)(4,4-difluorocyclohexyl)methyl)-1-(3,3,3-trifluoropropyl)-1H-pyrazole-4-carboxamide. $^1$H NMR (600 MHz, DMSO-d6) δ 9.42-9.38 (m, 1H), 8.64 (d, J=9.0 Hz, 1H), 8.56 (d, J=7.4 Hz, 1H), 8.49-8.44 (m, 1H), 8.19 (s, 1H), 7.87-7.83 (m, 1H), 5.19-5.10 (m, 1H), 4.98 (p, J=7.0 Hz, 1H), 2.50-2.40 (m, 4H), 2.35 (s, 3H), 2.18-2.09 (m, 1H), 2.09-1.93 (m, 2H), 1.89-1.69 (m, 3H), 1.64-1.56 (m, 1H), 1.42 (d, J=7.0 Hz, 3H), 1.40-1.34 (m, 1H), 1.29-1.21 (m, 1H). MS (ESI) m/z: [M+H]$^+$ Found 543.2.

Example 154

N—((S)-(4,4-Difluorocyclohexyl)(7-((R*)-2-methyl-1-(4,4,4-trifluorobutanamido)propyl)imidazo[1,2-b]pyridazin-2-yl)methyl)-1-isopropyl-1H-pyrazole-5-carboxamide

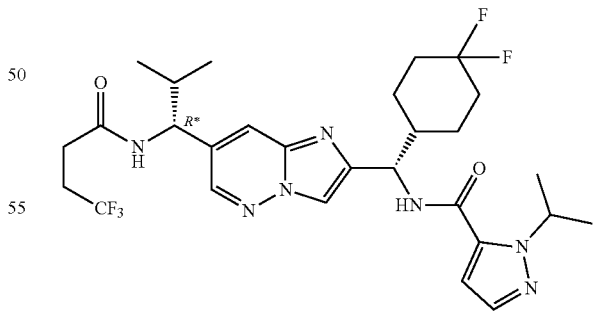

The title compound was prepared as described for the synthesis of Intermediate 58 using N—((S)-(7-((R*)-1-amino-2-methylpropyl)imidazo[1,2-b]pyridazin-2-yl)(4,4-difluorocyclohexyl)methyl)-1-isopropyl-1H-pyrazole-5-carboxamide (Intermediate 201) in place of N-((1S)-(7-(amino(cyclopropyl)methyl)imidazo[1,2-b]pyridazin-2-yl)(4,4-difluorocyclohexyl)methyl)-2-(3,3,3-trifluoropropyl)-

2H-1,2,3-triazole-4-carboxamide. ¹H NMR (400 MHz, CDCl₃) δ 8.17 (d, J=2.0 Hz, 1H), 7.79 (s, 1H), 7.61 (s, 1H), 7.42 (d, J=2.0 Hz, 1H), 7.04 (d, J=8.8 Hz, 1H), 6.52 (d, J=2.0 Hz, 1H), 5.89 (d, J=8.0 Hz, 1H), 5.41 (td, J=6.8, 13.2 Hz, 1H), 5.18 (t, J=8.0 Hz, 1H), 4.68 (t, J=8.0 Hz, 1H), 2.54-2.29 (m, 4H), 2.16-1.86 (m, 5H), 1.60 (d, J=12.0 Hz, 2H), 1.44 (d, J=6.8 Hz, 4H), 1.38 (d, J=6.8 Hz, 3H), 1.34-1.15 (m, 2H), 0.97 (d, J=6.8 Hz, 3H), 0.89 (d, J=6.8 Hz, 3H). MS (ESI) m/z: [M+H]⁺ Found 598.2.

Example 155

N—((S)-(4,4-Difluorocyclohexyl)(7-((S*)-2-methyl-1-(4,4-trifluorobutanamido)propyl)imidazo[1,2-b]pyridazin-2-yl)methyl)-1-isopropyl-1H-pyrazole-5-carboxamide

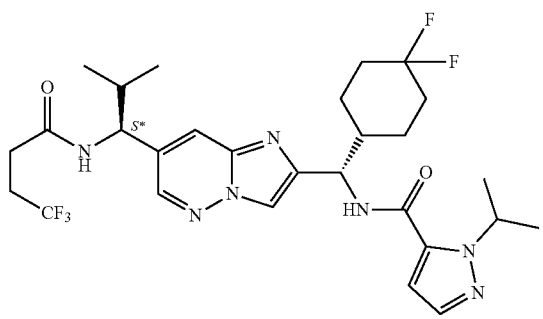 [SMILES: CC(C)[C@H](NC(=O)CCC(F)(F)F)c1cnn2cc([C@@H](NC(=O)c3ccnn3C(C)C)C3CCC(F)(F)CC3)nc2c1]

The title compound was prepared as described for the synthesis of Intermediate 58 using N—((S)-(7-((S*)-1-amino-2-methylpropyl)imidazo[1,2-b]pyridazin-2-yl)(4,4-difluorocyclohexyl)methyl)-1-isopropyl-1H-pyrazole-5-carboxamide (Intermediate 202) in place of N-((1S)-(7-(amino(cyclopropyl)methyl)imidazo[1,2-b]pyridazin-2-yl)(4,4-difluorocyclohexyl)methyl)-2-(3,3,3-trifluoropropyl)-2H-1,2,3-triazole-4-carboxamide. ¹H NMR (400 MHz, CDCl₃) δ 8.21 (d, J=2.0 Hz, 1H), 7.84 (s, 1H), 7.66 (s, 1H), 7.46 (d, J=2.0 Hz, 1H), 7.07 (d, J=8.0 Hz, 1H), 6.56 (d, J=2.0 Hz, 1H), 5.91 (d, J=8.0 Hz, 1H), 5.45 (td, J=6.4, 13.2 Hz, 1H), 5.22 (t, J=8.0 Hz, 1H), 4.72 (t, J=8.0 Hz, 1H), 2.58-2.35 (m, 4H), 2.19-1.91 (m, 5H), 1.76 (s, 2H), 1.49 (d, J=6.8 Hz, 4H), 1.42 (d, J=6.8 Hz, 3H), 1.38-1.21 (m, 2H), 1.03 (d, J=6.8 Hz, 3H), 0.93 (d, J=6.8 Hz, 3H). MS (ESI) m/z: [M+H]⁺ Found 598.2.

Example 156

N—((S)-(7-((R)-Cyclopropyl(4,4,4-trifluorobutanamido)methyl)imidazo[1,2-b]pyridazin-2-yl)(4,4-difluorocyclohexyl)methyl)-4-ethyl-1,2,5-oxadiazole-3-carboxamide

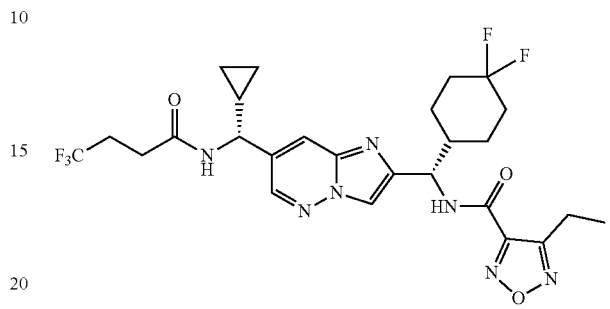

The title compound was prepared as described in the synthesis of Example 84, using 4-ethyl-1,2,5-oxadiazole-3-carboxylic acid in place of 5-cyclopropylisoxazole-4-carboxylic acid to provide the title compound. ¹H NMR (500 MHz, CD₃OD) δ 8.46 (d, J=2.0 Hz, 1H), 8.11 (s, 1H), 7.85-7.89 (m, 1H), 5.25 (d, J=8.5 Hz, 1H), 4.27 (d, J=9.5 Hz, 1H), 2.91-3.02 (m, 2H), 2.44-2.61 (m, 4H), 2.17-2.27 (m, 1H), 1.96-2.13 (m, 3H), 1.61-1.88 (m, 3H), 1.33-1.55 (m, 2H), 1.24-1.32 (m, 4H), 0.66-0.74 (m, 2H), 0.45-0.53 (m, 2H). MS (ESI) m/z: [M+H]⁺ Found 584.1.

Example 157

N—((S)-(7-((R)-Cyclopropyl(4,4,4-trifluorobutanamido)methyl)imidazo[1,2-b]pyridazin-2-yl)(4,4-difluorocyclohexyl)methyl)-4-methyl-1,2,5-oxadiazole-3-carboxamide

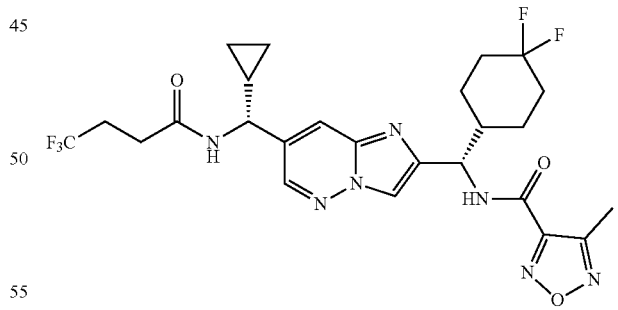

The title compound was prepared as described in the synthesis of Example 84, using 4-methyl-1,2,5-oxadiazole-3-carboxylic acid in place of 5-cyclopropylisoxazole-4-carboxylic acid to provide the title compound. ¹H NMR (500 MHz, CD₃OD) δ 8.46 (d, J=2.3 Hz, 1H), 8.11 (s, 1H), 7.85-7.90 (m, 1H), 5.25 (d, J=8.5 Hz, 1H), 4.24-4.31 (m, 1H), 2.52 (s, 7H), 2.16-2.27 (m, 1H), 1.95-2.14 (m, 3H), 1.58-1.88 (m, 3H), 1.32-1.54 (m, 2H), 1.21-1.31 (m, 1H), 0.66-0.74 (m, 2H), 0.46-0.53 (m, 2H). MS (ESI) m/z: [M+H]⁺ Found 570.1.

Example 158

N—((S)-(7-((R)-Cyclopropyl(4,4,4-trifluorobutanamido)methyl)imidazo[1,2-b]pyridazin-2-yl)(4,4-difluorocyclohexyl)methyl)-4-methylisoxazole-3-carboxamide

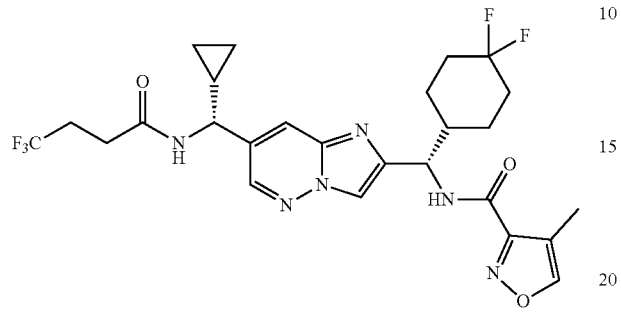

The title compound was prepared as described in the synthesis of Example 75, using 4-methylisoxazole-3-carboxylic acid in place of 3-cyclopropylisoxazole-4-carboxylic acid to provide the title compound. $^1$H NMR (500 MHz, CD$_3$OD) δ 8.50-8.52 (m, 1H), 8.45 (d, J=2.0 Hz, 1H), 8.10 (s, 1H), 7.85-7.89 (m, 1H), 5.24 (d, J=8.5 Hz, 1H), 4.27 (d, J=9.5 Hz, 1H), 2.44-2.60 (m, 4H), 2.14-2.21 (m, 4H), 1.95-2.14 (m, 3H), 1.59-1.87 (m, 3H), 1.33-1.54 (m, 2H), 1.22-1.29 (m, 1H), 0.66-0.74 (m, 2H), 0.46-0.52 (m, 2H). MS (ESI) m/z: [M+H]$^+$ Found 569.2.

Example 159

N—((S)-(7-((R)-Cyclopropyl(4,4,4-trifluorobutanamido)methyl)imidazo[1,2-b]pyridazin-2-yl)(4,4-difluorocyclohexyl)methyl)-5-methylisoxazole-4-carboxamide

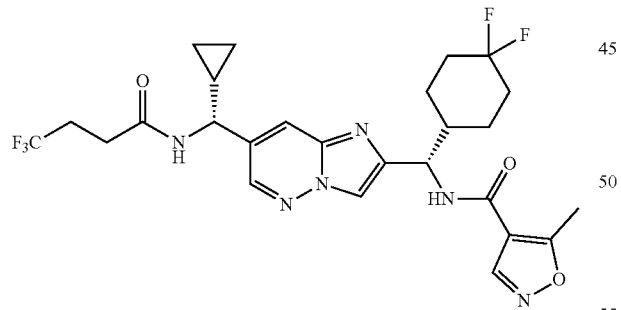

The title compound was prepared as described in the synthesis of Example 84, using 5-methylisoxazole-4-carboxylic acid in place of 5-cyclopropylisoxazole-4-carboxylic acid to provide the title compound. $^1$H NMR (500 MHz, CD$_3$OD) δ 8.73-8.77 (m, 1H), 8.45 (d, J=2.0 Hz, 1H), 8.08 (s, 1H), 7.84-7.89 (m, 1H), 5.21 (d, J=8.5 Hz, 1H), 4.27 (d, J=9.5 Hz, 1H), 2.64 (s, 3H), 2.42-2.59 (m, 4H), 1.94-2.24 (m, 4H), 1.67-1.87 (m, 2H), 1.58-1.67 (m, 1H), 1.42-1.52 (m, 1H), 1.31-1.42 (m, 1H), 1.20-1.30 (m, 1H), 0.66-0.74 (m, 2H), 0.46-0.53 (m, 2H). MS (ESI) m/z: [M+H]$^+$ Found 569.2.

Example 160

N—((S)-(7-((R)-Cyclopropyl(4,4,4-trifluorobutanamido)methyl)imidazo[1,2-b]pyridazin-2-yl)(4,4-difluorocyclohexyl)methyl)-4-methylisoxazole-5-carboxamide

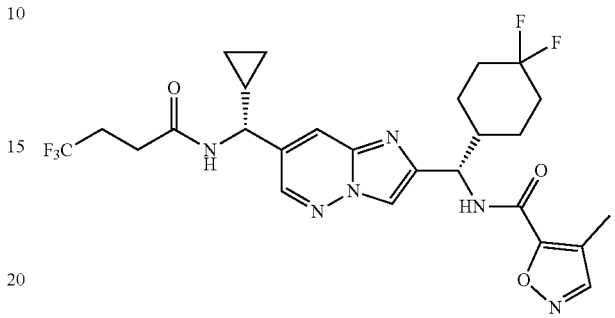

The title compound was prepared as described in the synthesis of Example 75, using 4-methylisoxazole-5-carboxylic acid in place of 3-cyclopropylisoxazole-4-carboxylic acid to provide the title compound. $^1$H NMR (500 MHz, CD$_3$OD) δ 8.45 (d, J=2.3 Hz, 1H), 8.37 (s, 1H), 8.10 (s, 1H), 7.84-7.91 (m, 1H), 5.22 (d, J=8.5 Hz, 1H), 4.28 (d, J=9.5 Hz, 1H), 2.45-2.61 (m, 4H), 2.28 (s, 3H), 2.16-2.26 (m, 1H), 1.95-2.14 (m, 3H), 1.57-1.88 (m, 3H), 1.42-1.53 (m, 1H), 1.31-1.42 (m, 1H), 1.20-1.31 (m, 1H), 0.66-0.74 (m, 2H), 0.46-0.52 (m, 2H). MS (ESI) m/z: [M+H]$^+$ Found 569.2.

Example 161

N—((S)-(7-((R)-Cyclopropyl(4,4,4-trifluorobutanamido)methyl)imidazo[1,2-b]pyridazin-2-yl)(4,4-difluorocyclohexyl)methyl)-3-methylisothiazole-4-carboxamide

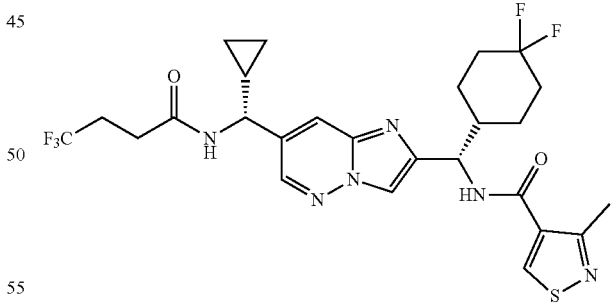

The title compound was prepared as described in the synthesis of Example 75, using 3-methylisothiazole-4-carboxylic acid in place of 3-cyclopropylisoxazole-4-carboxylic acid to provide the title compound. $^1$H NMR (500 MHz, CD$_3$OD) δ 9.27 (s, 1H), 8.46 (d, J=2.3 Hz, 1H), 8.09 (s, 1H), 7.84-7.89 (m, 1H), 5.25 (d, J=8.3 Hz, 1H), 4.27 (d, J=9.5 Hz, 1H), 2.43-2.59 (m, 7H), 1.94-2.26 (m, 4H), 1.62-1.88 (m, 3H), 1.34-1.57 (m, 2H), 1.20-1.31 (m, 1H), 0.66-0.74 (m, 2H), 0.46-0.53 (m, 2H). MS (ESI) m/z: [M+H]$^+$ Found 585.1.

Example 162

N—((S)-(7-((R)-Cyclopropyl(4,4,4-trifluorobutanamido)methyl)imidazo[1,2-b]pyridazin-2-yl)(4,4-difluorocyclohexyl)methyl)-6-isopropylpyrimidine-4-carboxamide

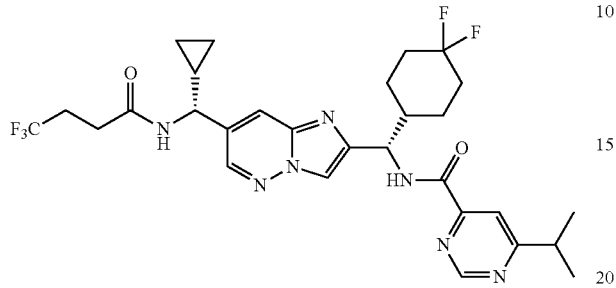

The title compound was prepared as described in the synthesis of Example 75, using 6-isopropylpyrimidine-4-carboxylic acid in place of 3-cyclopropylisoxazole-4-carboxylic acid to provide the title compound. $^1$H NMR (500 MHz, CD$_3$OD) δ 9.18 (d, J=1.3 Hz, 1H), 8.48 (d, J=2.0 Hz, 1H), 8.15 (s, 1H), 8.00 (d, J=1.3 Hz, 1H), 7.88-7.91 (m, 1H), 5.29 (d, J=8.5 Hz, 1H), 4.29 (d, J=9.5 Hz, 1H), 3.09-3.20 (m, 1H), 2.46-2.62 (m, 4H), 2.20-2.31 (m, 1H), 1.94-2.15 (m, 3H), 1.62-1.90 (m, 3H), 1.43-1.56 (m, 1H), 1.31-1.37 (m, 6H), 1.22-1.31 (m, 1H), 1.22-1.31 (m, 1H), 0.67-0.76 (m, 2H), 0.47-0.55 (m, 2H). MS (ESI) m/z: [M+H]$^+$ Found 608.3.

Example 163

N—((S)-(7-((R)-Cyclopropyl(4,4,4-trifluorobutanamido)methyl)imidazo[1,2-b]pyridazin-2-yl)(4,4-difluorocyclohexyl)methyl)-3-(2-oxopyrrolidin-1-yl)benzamide

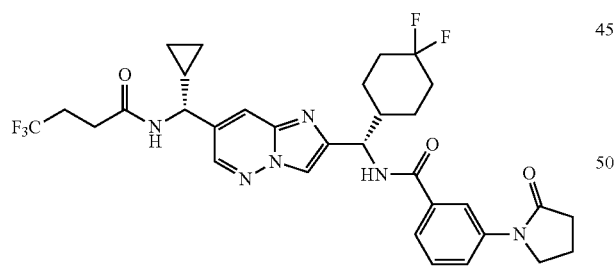

To a solution of N—((R)-(2-((S)-amino(4,4-difluorocyclohexyl)methyl)imidazo[1,2-b]pyridazin-7-yl)(cyclopropyl)methyl)-4,4,4-trifluorobutanamide (23 mg, 0.05 mmol, Intermediate 51) and 3-(2-oxopyrrolidin-1-yl)benzoic acid (13.3 mg, 0.065 mmol) in DMF (1 mL) was added EDCI (9.1 mg, 0.06 mmol), HOAt (7.3 g, 0.052 mmol) and DIPEA (16.5 mg, 0.12 mmol). The reaction mixture was stirred at rt for 24 h. The mixture was evaporated under high vacuum and the residue was dissolved in DMSO. The resulting solution was purified by HPLC (Waters X-bridge column C18 19×100 mm; deionized water and HPLC-grade methanol were used as eluent, gradient from 30-60 to 80-100% of methanol) to provide the title compound. $^1$H NMR (500 MHz, CD$_3$OD) δ 8.46 (d, J=2.1 Hz, 1H), 8.11 (s, 1H), 8.02 (t, J=1.9 Hz, 1H), 7.88 (d, J=2.1 Hz, 1H), 7.81-7.83 (m, 1H), 7.65-7.69 (m, 1H), 7.49 (t, J=7.9 Hz, 1H), 5.28 (d, J=8.6 Hz, 1H), 4.28 (d, J=9.5 Hz, 1H), 3.97 (t, J=7.1 Hz, 2H), 2.62 (t, J=8.1 Hz, 2H), 2.54-2.57 (m, 2H), 2.48-2.50 (m, 2H), 2.19-2.21 (m, 3H), 2.08-2.10 (m, 1H), 2.00-2.01 (m, 2H), 1.76-1.78 (m, 2H), 1.64-1.66 (m, 1H), 1.53-1.54 (m, 1H), 1.39-1.41 (m, 1H), 1.25-1.26 (m, 1H), 0.69-0.71 (m, 2H), 0.48-0.50 (m, 2H). MS (ESI) m/z: [M+H]$^+$ Found 647.2.

Example 164

N—((S)-(7-((R)-Cyclopropyl(4,4,4-trifluorobutanamido)methyl)imidazo[1,2-b]pyridazin-2-yl)(4,4-difluorocyclohexyl)methyl)-3-(2,2-difluorocyclopropyl)benzamide

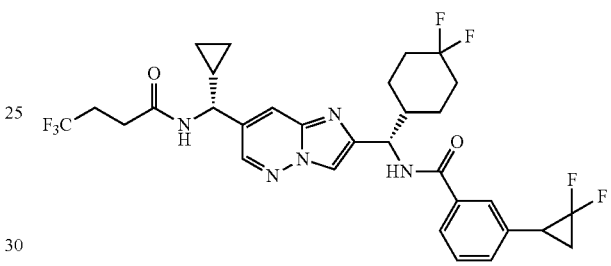

The title compound was prepared as described in the synthesis of Example 163, using 3-(2,2-difluorocyclopropyl)benzoic acid in place of 3-(2-oxopyrrolidin-1-yl)benzoic acid to provide the title compound. $^1$H NMR (500 MHz, CD$_3$OD) δ 8.44-8.46 (m, 1H), 8.10 (s, 1H), 7.88 (s, 1H), 7.73-7.75 (m, 2H), 7.41-7.44 (m, 2H), 5.28 (d, J=8.7 Hz, 1H), 4.28 (d, J=9.5 Hz, 1H), 2.91-2.93 (m, 1H), 2.56-2.58 (m, 2H), 2.48-2.50 (m, 2H), 2.21-2.23 (m, 1H), 2.09-2.11 (m, 1H), 2.00-2.01 (m, 2H), 1.89-1.91 (m, 1H), 1.78-1.80 (m, 3H), 1.62-1.64 (m, 1H), 1.50-1.52 (m, 1H), 1.37-1.39 (m, 1H), 1.22-1.25 (m, 1H), 0.68-0.70 (m, 2H), 0.48-0.50 (m, 2H). MS (ESI) m/z: [M+H]$^+$ Found 640.4.

Example 165

N—((S)-(7-((R)-Cyclopropyl(4,4,4-trifluorobutanamido)methyl)imidazo[1,2-b]pyridazin-2-yl)(4,4-difluorocyclohexyl)methyl)-3-(difluoromethoxy)-5-fluorobenzamide

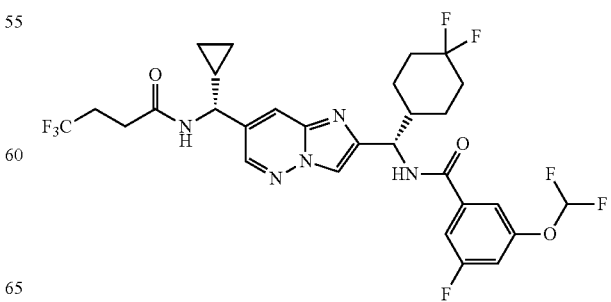

The title compound was prepared as described in the synthesis of Example 163, using 3-(difluoromethoxy)-5-fluorobenzoic acid in place of 3-(2-oxopyrrolidin-1-yl)benzoic acid to provide the title compound. $^1$H NMR (500 MHz, CD$_3$OD) δ 8.44-8.46 (m, 1H), 8.10 (s, 1H), 7.88 (s, 1H), 7.48-7.50 (m, 2H), 7.15 (m, 1H), 6.95 (t, J=73.2 Hz, 1H), 5.25 (d, J=8.8 Hz, 1H), 4.27 (d, J=9.5 Hz, 1H), 2.55-2.57 (m, 2H), 2.48-2.50 (m, 2H), 2.22-2.23 (m, 1H), 2.08-2.10 (m, 1H), 2.00-2.01 (m, 2H), 1.79-1.81 (m, 2H), 1.62-1.63 (m, 1H), 1.49-1.52 (m, 1H), 1.36-1.38 (m, 1H), 1.25-1.27 (m, 1H), 0.69-0.71 (m, 2H), 0.48-0.50 (m, 2H). MS (ESI) m/z: [M+H]$^+$ Found 648.2.

Example 166

3-Cyclopropyl-N—((S)-(7-((R)-cyclopropyl(4,4,4-trifluorobutanamido)methyl)imidazo[1,2-b]pyridazin-2-yl)(4,4-difluorocyclohexyl)methyl)benzamide

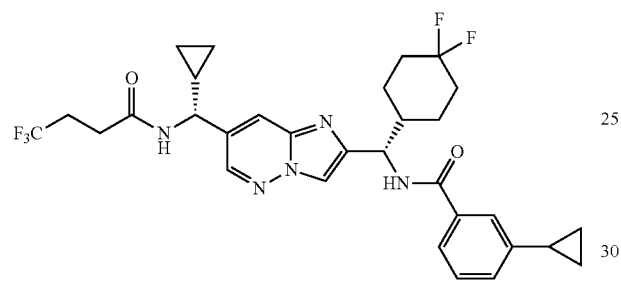

The title compound was prepared as described in the synthesis of Example 163, using 3-cyclopropylbenzoic acid in place of 3-(2-oxopyrrolidin-1-yl)benzoic acid to provide the title compound. $^1$H NMR (500 MHz, CD$_3$OD) δ 8.44-8.46 (m, 1H), 8.09-8.10 (m, 1H), 7.86-7.88 (m, 1H), 7.58-7.60 (m, 1H), 7.56-7.57 (m, 1H), 7.34-7.36 (m, 1H), 7.25-7.27 (m, 1H), 5.25-5.28 (m, 1H), 4.28-4.29 (m, 1H), 2.54-2.56 (m, 2H), 2.50-2.52 (m, 2H), 2.20-2.22 (m, 1H), 2.08-2.10 (m, 1H), 1.98-2.00 (m, 3H), 1.78-1.80 (m, 2H), 1.63-1.64 (m, 1H), 1.50-1.51 (m, 1H), 1.39-1.40 (m, 1H), 1.25-1.26 (m, 1H), 0.98-1.00 (m, 2H), 0.72-0.74 (m, 2H), 0.69-0.71 (m, 2H), 0.48-0.50 (m, 2H). MS (ESI) m/z: [M+H]$^+$ Found 604.4.

Example 167

N—((S)-(7-((R)-Cyclopropyl(4,4,4-trifluorobutanamido)methyl)imidazo[1,2-b]pyridazin-2-yl)(4,4-difluorocyclohexyl)methyl)-3-(difluoromethoxy)benzamide

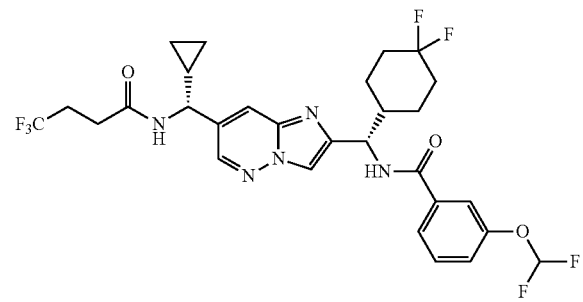

The title compound was prepared as described in the synthesis of Example 163, using 3-(difluoromethoxy)benzoic acid in place of 3-(2-oxopyrrolidin-1-yl)benzoic acid to provide the title compound. $^1$H NMR (500 MHz, CD$_3$OD) δ 8.43-8.46 (m, 1H), 8.11 (s, 1H), 7.86-7.88 (m, 1H), 7.72-7.75 (m, 1H), 7.61-7.63 (m, 1H), 7.51-7.53 (m, 1H), 7.33-7.35 (m, 1H), 6.89-6.92 (m, 1H), 5.27 (d, J=8.6 Hz, 1H), 4.28 (d, J=9.5 Hz, 1H), 2.55-2.56 (m, 2H), 2.46-2.49 (m, 2H), 2.21-2.23 (m, 1H), 2.09-2.11 (m, 1H), 2.00-2.01 (m, 2H), 1.76-1.79 (m, 2H), 1.61-1.64 (m, 1H), 1.48-1.51 (m, 1H), 1.39-1.41 (m, 1H), 1.25-1.26 (m, 1H), 0.70-0.72 (m, 2H), 0.48-0.50 (m, 2H). MS (ESI) m/z: [M+H]$^+$ Found 630.2.

Example 168

N—((S)-(7-((R)-Cyclopropyl(4,4,4-trifluorobutanamido)methyl)imidazo[1,2-b]pyridazin-2-yl)(4,4-difluorocyclohexyl)methyl)-3-(2,2-difluoroethoxy)benzamide

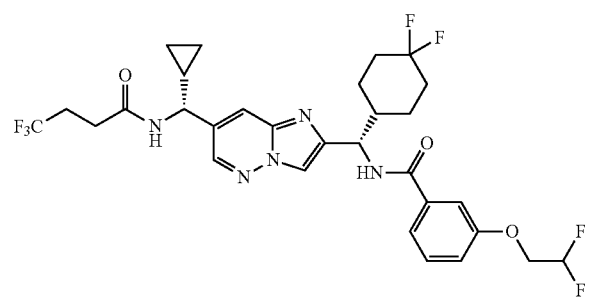 [SMILES: O=C(CCC(F)(F)F)N[C@@H](c1cnn2cc([C@@H](NC(=O)c3cccc(OCC(F)F)c3)C3CCC(F)(F)CC3)nc2c1)C1CC1]

The title compound was prepared as described in the synthesis of Example 163, using 3-(2,2-difluoroethoxy)benzoic acid in place of 3-(2-oxopyrrolidin-1-yl)benzoic acid to provide the title compound. $^1$H NMR (500 MHz, CD$_3$OD) δ 8.44-8.46 (m, 1H), 8.10 (s, 1H), 7.88 (s, 1H), 7.47-7.50 (m, 1H), 7.45-7.46 (m, 1H), 7.40-7.42 (m, 1H), 7.15-7.17 (m, 1H), 6.17-6.19 (m, 1H), 5.27 (d, J=8.8 Hz, 1H), 4.29-4.31 (m, 3H), 2.57-2.59 (m, 2H), 2.49-2.51 (m, 2H), 2.22-2.23 (m, 1H), 2.10-2.11 (m, 1H), 1.99-2.01 (m, 2H), 1.76-1.77 (m, 2H), 1.62-1.64 (m, 1H), 1.50-1.52 (m, 1H), 1.38-1.40 (m, 1H), 1.25-1.26 (m, 1H), 0.69-0.71 (m, 2H), 0.48-0.50 (m, 2H). MS (ESI) m/z: [M+H]$^+$ Found 644.3.

Example 169

N—((S)-(7-((R)-Cyclopropyl(4,4,4-trifluorobutanamido)methyl)imidazo[1,2-b]pyridazin-2-yl)(4,4-difluorocyclohexyl)methyl)-5-(difluoromethoxy)-2-fluorobenzamide

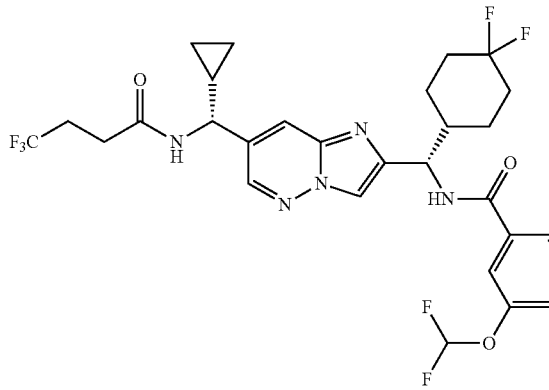

The title compound was prepared as described in the synthesis of Example 163, using 5-(difluoromethoxy)-2-fluorobenzoic acid in place of 3-(2-oxopyrrolidin-1-yl)benzoic acid to provide the title compound. $^1$H NMR (500 MHz, CD$_3$OD) δ 8.47 (d, J=2.3 Hz, 1H), 8.09 (s, 1H), 7.86-7.88 (m, 1H), 7.45-7.46 (m, 1H), 7.31-7.33 (m, 1H), 7.25-7.28 (m, 1H), 6.83 (t, J=73.5 Hz, 1H), 5.31 (d, J=7.9 Hz, 1H), 4.28 (d, J=9.5 Hz, 1H), 2.55-2.57 (m, 2H), 2.48-2.50 (m, 2H), 2.19-2.20 (m, 1H), 2.05-2.07 (m, 2H), 1.95-1.97 (m, 1H), 1.75-1.76 (m, 2H), 1.66-1.68 (m, 1H), 1.49-1.51 (m, 1H), 1.41-1.44 (m, 1H), 1.26-1.27 (m, 1H), 0.69-0.71 (m, 2H), 0.48-0.50 (m, 2H). MS (ESI) m/z: [M+H]$^+$ Found 648.4.

Example 170

N—((S)-(7-((R)-Cyclopropyl(4,4,4-trifluorobutanamido)methyl)imidazo[1,2-b]pyridazin-2-yl)(4,4-difluorocyclohexyl)methyl)-3-(difluoromethyl)benzamide

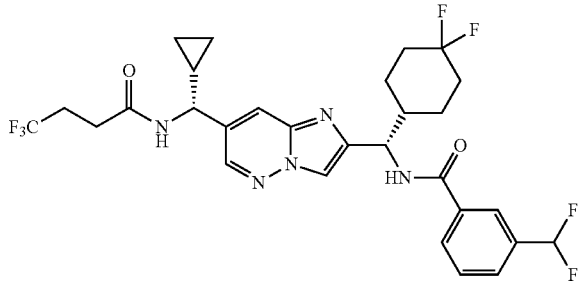 [SMILES: O=C(CCC(F)(F)F)N[C@@H](c1cnn2cc([C@@H](NC(=O)c3cccc(C(F)F)c3)C3CCC(F)(F)CC3)nc2c1)C1CC1]

The title compound was prepared as described in the synthesis of Example 163, using 3-(difluoromethyl)benzoic acid in place of 3-(2-oxopyrrolidin-1-yl)benzoic acid to provide the title compound. $^1$H NMR (500 MHz, CD$_3$OD) δ 8.46 (d, J=2.1 Hz, 1H), 8.11 (s, 1H), 8.04 (s, 1H), 8.00 (d, J=7.9 Hz, 1H), 7.88 (s, 1H), 7.73 (d, J=7.7 Hz, 1H), 7.61 (t, J=7.8 Hz, 1H), 6.84 (t, J=56.0 Hz, 1H), 5.29 (d, J=8.7 Hz, 1H), 4.28 (d, J=9.4 Hz, 1H), 2.56-2.57 (m, 2H), 2.48-2.50 (m, 2H), 2.22-2.24 (m, 1H), 2.09-2.11 (m, 1H), 2.02-2.04 (m, 2H), 1.78-1.80 (m, 2H), 1.64-1.65 (m, 1H), 1.52-1.54 (m, 1H), 1.41-1.43 (m, 1H), 1.25-1.27 (m, 1H), 0.69-0.71 (m, 2H), 0.48-0.50 (m, 2H). MS (ESI) m/z: [M+H]$^+$ Found 614.4.

Example 171

N—((S)-(7-((R)-Cyclopropyl(4,4,4-trifluorobutanamido)methyl)imidazo[1,2-b]pyridazin-2-yl)(4,4-difluorocyclohexyl)methyl)-2-(2,2,2-trifluoroethoxy)isonicotinamide

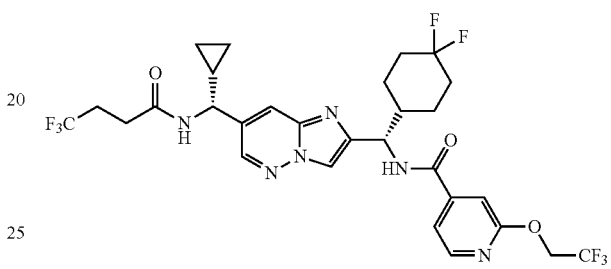

The title compound was prepared as described in the synthesis of Example 163, using 2-(2,2,2-trifluoroethoxy)isonicotinic acid in place of 3-(2-oxopyrrolidin-1-yl)benzoic acid to provide the title compound. $^1$H NMR (500 MHz, CD$_3$OD) δ 8.46 (d, J=2.1 Hz, 1H), 8.29 (d, J=5.3 Hz, 1H), 8.11 (s, 1H), 7.88 (s, 1H), 7.39-7.41 (m, 1H), 7.30 (s, 1H), 5.25 (d, J=8.6 Hz, 1H), 4.89-4.91 (m, 2H), 4.27 (d, J=9.4 Hz, 1H), 2.55-2.57 (m, 2H), 2.47-2.49 (m, 2H), 2.21-2.22 (m, 1H), 2.08-2.10 (m, 1H), 1.98-2.00 (m, 2H), 1.76-1.78 (m, 2H), 1.62-1.64 (m, 1H), 1.48-1.50 (m, 1H), 1.37-1.39 (m, 1H), 1.25-1.26 (m, 1H), 0.69-0.71 (m, 2H), 0.48-0.50 (m, 2H). MS (ESI) m/z: [M+H]$^+$ Found 663.2.

Example 172

2-Cyclopropoxy-N—((S)-(7-((R)-cyclopropyl(4,4,4-trifluorobutanamido)methyl)imidazo[1,2-b]pyridazin-2-yl)(4,4-difluorocyclohexyl)methyl)isonicotinamide

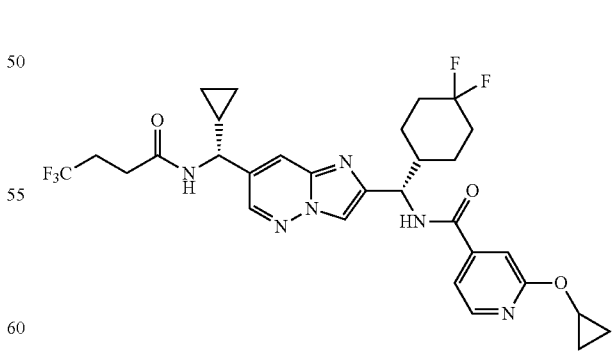

The title compound was prepared as described in the synthesis of Example 163, using 2-cyclopropoxyisonicotinic acid in place of 3-(2-oxopyrrolidin-1-yl)benzoic acid to provide the title compound. $^1$H NMR (500 MHz, CD$_3$OD) δ 8.46 (d, J=2.1 Hz, 1H), 8.28 (d, J=5.3 Hz, 1H), 8.10 (s, 1H), 7.86-7.88 (m, 1H), 7.33-7.36 (m, J=1.5 Hz, 1H), 7.27 (s, 1H), 5.26 (d, J=8.6 Hz, 1H), 4.27 (d, J=9.5 Hz, 1H), 4.18-4.20 (m, 1H), 2.54-2.56 (m, 2H), 2.47-2.49 (m, 2H), 2.20-2.23 (m, 1H), 2.08-2.10 (m, 1H), 1.97-2.00 (m, 2H), 1.74-1.77 (m, 2H), 1.63-1.65 (m, 1H), 1.50-1.52 (m, 1H), 1.41-1.43 (m, 1H), 1.25-1.26 (m, 1H), 0.81-0.83 (m, 2H), 0.70-0.73 (m, 4H), 0.48-0.50 (m, 2H). MS (ESI) m/z: [M+H]⁺ Found 621.2.

Example 173

N—((S)-(7-((R)-Cyclopropyl(4,4,4-trifluorobutanamido)methyl)imidazo[1,2-b]pyridazin-2-yl)(4,4-difluorocyclohexyl)methyl)-3-fluorobenzamide

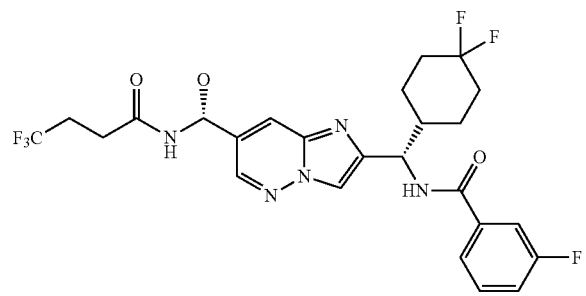

The title compound was prepared as described in the synthesis of Example 163, using 3-fluorobenzoic acid in place of 3-(2-oxopyrrolidin-1-yl)benzoic acid to provide the title compound. ¹H NMR (500 MHz, CD₃OD) δ 8.50 (d, J=2.1 Hz, 1H), 8.14 (s, 1H), 7.90 (s, 1H), 7.68 (d, J=7.8 Hz, 1H), 7.57-7.59 (m, 1H), 7.48-7.50 (m, 1H), 7.28-7.30 (m, 1H), 5.27 (d, J=8.6 Hz, 1H), 4.28 (d, J=9.5 Hz, 1H), 2.55-2.56 (m, 2H), 2.48-2.50 (m, 2H), 2.23-2.25 (m, 1H), 2.11-2.13 (m, 1H), 2.00-2.02 (m, 1H), 1.77-1.79 (m, 2H), 1.64-1.66 (m, 1H), 1.49-1.51 (m, 1H), 1.38-1.44 (m, 1H), 1.25-1.27 (m, 1H), 0.69-0.71 (m, 2H), 0.49-0.51 (m, 2H). MS (ESI) m/z: [M+H]⁺ Found 582.0.

Example 174

N—((S)-(7-((R)-Cyclopropyl(4,4,4-trifluorobutanamido)methyl)imidazo[1,2-b]pyridazin-2-yl)(4,4-difluorocyclohexyl)methyl)-3-(2,2,2-trifluoroethoxy)benzamide

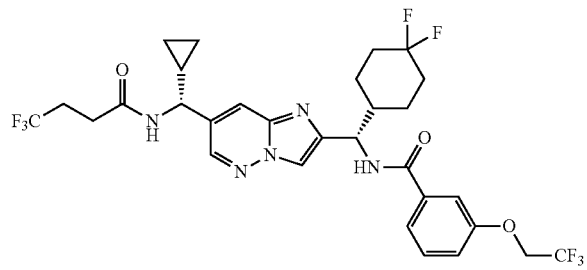 [SMILES: O=C(CCC(F)(F)F)N[C@@H](c1cnn2cc([C@@H](NC(=O)c3cccc(OCC(F)(F)F)c3)C3CCC(F)(F)CC3)nc2c1)C1CC1]

The title compound was prepared as described in the synthesis of Example 163, using 3-(2,2,2-trifluoroethoxy)benzoic acid in place of 3-(2-oxopyrrolidin-1-yl)benzoic acid to provide the title compound. ¹H NMR (500 MHz, CD₃OD) δ 8.46 (d, J=2.1 Hz, 1H), 8.10 (s, 1H), 7.88 (s, 1H), 7.53-7.54 (m, 1H), 7.48-7.50 (m, 1H), 7.44 (t, J=8.0 Hz, 1H), 7.17-7.20 (m, 1H), 5.27 (d, J=8.7 Hz, 1H), 4.60 (q, J=8.4 Hz, 2H), 4.27 (d, J=9.5 Hz, 1H), 2.55-2.56 (m, 2H), 2.47-2.49 (m, 2H), 2.22-2.24 (m, 1H), 2.08-2.10 (m, 1H), 2.00-2.02 (m, 2H), 1.78-1.80 (m, 2H), 1.62-1.64 (m, 1H), 1.48-1.50 (m, 1H), 1.37-1.39 (m, 1H), 1.25-1.26 (m, 1H), 0.69-0.71 (m, 2H), 0.48-0.50 (m, 2H). MS (ESI) m/z: [M+H]⁺ Found 662.0.

Example 175

N—((S)-(7-((R)-Cyclopropyl(4,4,4-trifluorobutanamido)methyl)imidazo[1,2-b]pyridazin-2-yl)(4,4-difluorocyclohexyl)methyl)-2-isopropoxyisonicotinamide

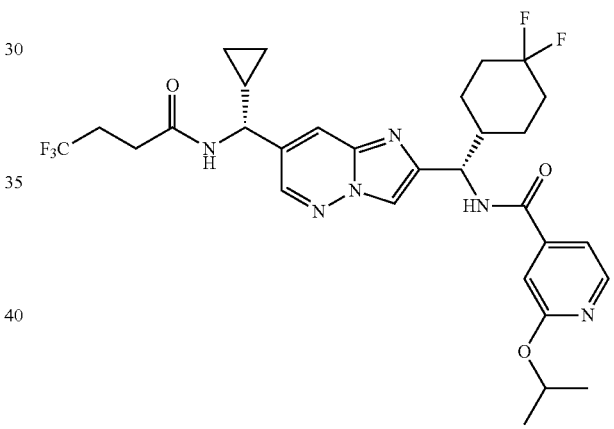

The title compound was prepared as described in the synthesis of Example 163, using 2-isopropoxyisonicotinic acid in place of 3-(2-oxopyrrolidin-1-yl)benzoic acid to provide the title compound. ¹H NMR (500 MHz, CD₃OD) δ 8.46 (d, J=2.0 Hz, 1H), 8.21 (d, J=5.3 Hz, 1H), 8.10 (s, 1H), 7.88 (s, 1H), 7.24 (d, J=5.3 Hz, 1H), 7.09 (s, 1H), 5.27-5.29 (m, 1H), 5.25 (d, J=11.4 Hz, 1H), 4.27 (d, J=9.4 Hz, 1H), 2.55-2.57 (m, 2H), 2.48-2.50 (m, 2H), 2.21-2.23 (m, 1H), 2.10-2.11 (m, 1H), 1.98-1.99 (m, 2H), 1.76-1.78 (m, 2H), 1.63-1.64 (m, 1H), 1.48-1.50 (m, 1H), 1.37-1.40 (m, 1H), 1.34 (d, J=6.1 Hz, 6H), 1.24-1.25 (m, 1H), 0.69-0.71 (m, 2H), 0.48-0.50 (m, 2H). MS (ESI) m/z: [M+H]⁺ Found 623.3.

Example 176

N—((S)-(7-((R)-Cyclopropyl(4,4,4-trifluorobutana-mido)methyl)imidazo[1,2-b]pyridazin-2-yl)(4,4-difluorocyclohexyl)methyl)-5-(2-oxopyrrolidin-1-yl)nicotinamide

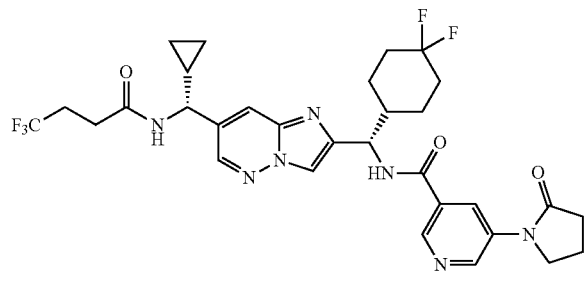 [SMILES: O=C(CCC(F)(F)F)N[C@@H](c1cnn2cc([C@@H](NC(=O)c3cncc(N4CCCC4=O)c3)C3CCC(F)(F)CC3)nc2c1)C1CC1]

The title compound was prepared as described in the synthesis of Example 163, using 5-(2-oxopyrrolidin-1-yl) nicotinic acid in place of 3-(2-oxopyrrolidin-1-yl)benzoic acid to provide the title compound. $^1$H NMR (500 MHz, CD$_3$OD) δ 9.07-9.08 (m, 1H), 8.76-8.77 (m, 1H), 8.44-8.46 (m, 2H), 8.12 (s, 1H), 7.88 (s, 1H), 5.29 (d, J=8.8 Hz, 1H), 4.28 (d, J=9.5 Hz, 1H), 3.99 (t, J=7.0 Hz, 2H), 2.63 (t, J=8.1 Hz, 2H), 2.54-2.56 (m, 2H), 2.48-2.50 (m, 2H), 2.20-2.23 (m, 3H), 2.09-2.11 (m, 1H), 2.01-2.03 (m, 2H), 1.76-1.79 (m, 2H), 1.65-1.66 (m, 1H), 1.50-1.52 (m, 1H), 1.39-1.41 (m, 1H), 1.25-1.26 (m, 1H), 0.69-0.71 (m, 2H), 0.48-0.50 (m, 2H). MS (ESI) m/z: [M+H]$^+$ Found 648.2.

Example 177

N—((S)-(7-((R)-Cyclopropyl(4,4,4-trifluorobutana-mido)methyl)imidazo[1,2-b]pyridazin-2-yl)(4,4-difluorocyclohexyl)methyl)-2-ethoxyisonicotinamide

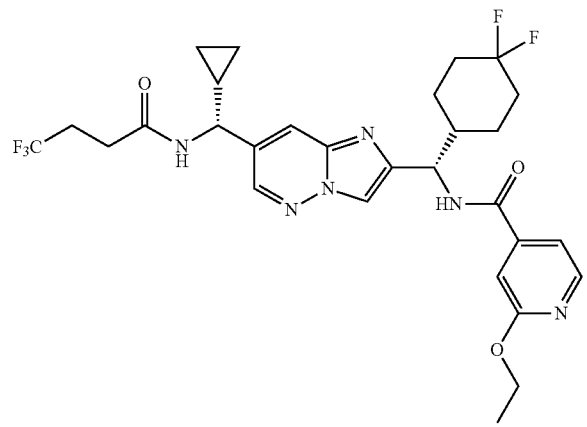

The title compound was prepared as described in the synthesis of Example 163, using 2-ethoxyisonicotinic acid in place of 3-(2-oxopyrrolidin-1-yl)benzoic acid to provide the title compound. $^1$H NMR (500 MHz, CD$_3$OD) δ 8.46-8.47 (m, 1H), 8.22 (d, J=5.3 Hz, 1H), 8.10 (s, 1H), 7.88 (s, 1H), 7.28-7.30 (m, 1H), 7.14 (s, 1H), 5.25 (d, J=8.7 Hz, 1H), 4.36 (q, J=7.0 Hz, 2H), 4.27 (d, J=9.4 Hz, 1H), 2.55-2.57 (m, 2H), 2.50-2.53 (m, 2H), 2.20-2.22 (m, 1H), 2.09-2.11 (m, 1H), 2.00-2.02 (m, 2H), 1.76-1.78 (m, 2H), 1.62-1.64 (m, 1H), 1.49-1.51 (m, 1H), 1.44-1.45 (m, 1H), 1.36-1.39 (t, J=7.1 Hz, 3H), 1.25-1.26 (m, 1H), 0.69-0.71 (m, 2H), 0.48-0.50 (m, 2H). MS (ESI) m/z: [M+H]$^+$ Found 609.2.

Example 178

N—((S)-(7-((R)-Cyclopropyl(4,4,4-trifluorobutana-mido)methyl)imidazo[1,2-b]pyridazin-2-yl)(4,4-difluorocyclohexyl)methyl)-5-(trifluoromethyl)nicotinamide

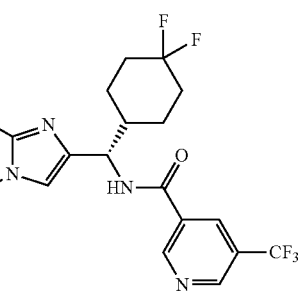

The title compound was prepared as described in the synthesis of Example 163, using 5-(trifluoromethyl)nicotinic acid in place of 3-(2-oxopyrrolidin-1-yl)benzoic acid to provide the title compound. $^1$H NMR (500 MHz, CD$_3$OD) δ 9.24-9.26 (m, 1H), 9.04 (s, 1H), 8.55-8.58 (m, 1H), 8.47 (d, J=2.1 Hz, 1H), 8.13 (s, 1H), 7.88 (s, 1H), 5.30 (d, J=8.6 Hz, 1H), 4.27 (d, J=9.5 Hz, 1H), 2.55-2.56 (m, 2H), 2.47-2.49 (m, 2H), 2.25-2.26 (m, 1H), 2.09-2.11 (m, 1H), 2.01-2.03 (m, 2H), 1.76-1.79 (m, 2H), 1.65-1.67 (m, 1H), 1.50-1.52 (m, 1H), 1.40-1.41 (m, 1H), 1.25-1.27 (m, 1H), 0.69-0.71 (m, 2H), 0.48-0.50 (m, 2H). MS (ESI) m/z: [M+H]$^+$ Found 633.2.

Example 179

N—((S)-(7-((R)-Cyclopropyl(4,4,4-trifluorobutana-mido)methyl)imidazo[1,2-b]pyridazin-2-yl)(4,4-difluorocyclohexyl)methyl)-2-(2,2-difluoroethoxy)isonicotinamide The title compound was prepared as described in the synthesis of Example 163, using 2-(2,2-difluoroethoxy) isonicotinic acid in place of 3-(2-oxopyrrolidin-1-yl)benzoic acid to provide the title compound. $^1$H NMR (500 MHz, CD$_3$OD) δ 8.46 (d, J=2.1 Hz, 1H), 8.27 (d, J=5.3 Hz, 1H), 8.10 (s, 1H), 7.88 (s, 1H), 7.35-7.37 (m, 1H), 7.25 (s, 1H), 6.19-6.21 (m, 1H), 5.25 (d, J=8.6 Hz, 1H), 4.55-4.57 (m, 2H), 4.27 (d, J=9.5 Hz, 1H), 2.54-2.56 (m, 2H), 2.48-2.50 (m, 2H), 2.20-2.22 (m, 1H), 2.08-2.10 (m, 1H), 1.99-2.01 (m, 2H), 1.77-1.79 (m, 2H), 1.64-1.66 (m, 1H), 1.49-1.51 (m, 1H), 1.39-1.41 (m, 1H), 1.25-1.26 (m, 1H), 0.69-0.71 (m, 2H), 0.48-0.50 (m, 2H). MS (ESI) m/z: [M+H]⁺ Found 645.2.

Example 180

N—((S)-(7-((R)-Cyclopropyl(4,4,4-trifluorobutanamido)methyl)imidazo[1,2-b]pyridazin-2-yl)(4,4-difluorocyclohexyl)methyl)-3-(cyclopropylmethoxy)benzamide

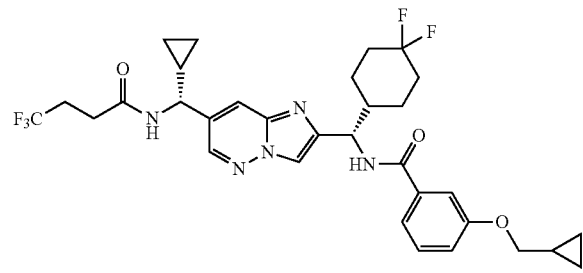 [SMILES: O=C(CCC(F)(F)F)N[C@@H](c1cnn2cc([C@@H](NC(=O)c3cccc(OCC4CC4)c3)C3CCC(F)(F)CC3)nc2c1)C1CC1]

The title compound was prepared as described in the synthesis of Example 163, using 3-(cyclopropylmethoxy) benzoic acid in place of 3-(2-oxopyrrolidin-1-yl)benzoic acid to provide the title compound. ¹H NMR (500 MHz, CD₃OD) δ 8.44-8.46 (m, 1H), 8.10 (s, 1H), 7.88 (s, 1H), 7.35-7.38 (m, 3H), 7.07-7.08 (m, 1H), 5.27 (d, J=8.6 Hz, 1H), 4.27 (d, J=9.5 Hz, 1H), 3.87 (d, J=6.9 Hz, 2H), 2.55-2.57 (m, 2H), 2.46-2.49 (m, 2H), 2.19-2.21 (m, 1H), 2.08-2.10 (m, 1H), 2.00-2.01 (m, 2H), 1.76-1.78 (m, 2H), 1.63-1.64 (m, 1H), 1.48-1.51 (m, 1H), 1.37-1.39 (m, 1H), 1.25-1.26 (m, 2H), 0.69-0.71 (m, 2H), 0.58-0.61 (m, 2H), 0.48-0.50 (m, 2H), 0.33-0.35 (m, 2H). MS (ESI) m/z: [M+H]⁺ Found 634.1.

Example 181

2-Cyclobutoxy-N—((S)-(7-((R)-cyclopropyl(4,4,4-trifluorobutanamido)methyl)imidazo[1,2-b]pyridazin-2-yl)(4,4-difluorocyclohexyl)methyl)isonicotinamide

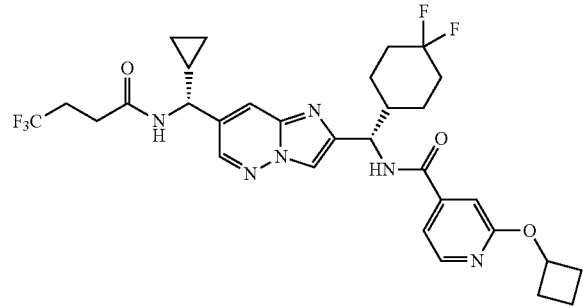 [SMILES: O=C(CCC(F)(F)F)N[C@@H](c1cnn2cc([C@@H](NC(=O)c3ccnc(OC4CCC4)c3)C3CCC(F)(F)CC3)nc2c1)C1CC1]

The title compound was prepared as described in the synthesis of Example 163, using 2-cyclobutoxyisonicotinic acid in place of 3-(2-oxopyrrolidin-1-yl)benzoic acid to provide the title compound. ¹H NMR (500 MHz, CD₃OD) δ 8.45-8.47 (m, 1H), 8.21 (d, J=5.3 Hz, 1H), 8.10 (s, 1H), 7.88 (s, 1H), 7.27 (d, J=5.3 Hz, 1H), 7.11 (s, 1H), 5.25 (d, J=8.6 Hz, 1H), 5.13-5.17 (m, 1H), 4.27 (d, J=9.5 Hz, 1H), 2.55-2.57 (m, 2H), 2.45-2.48 (m, 4H), 2.19-2.21 (m, 1H), 2.10-2.13 (m, 3H), 1.99-2.02 (m, 2H), 1.86-1.89 (m, 1H), 1.80-1.83 (m, 1H), 1.71-1.73 (m, 2H), 1.63-1.64 (m, 1H), 1.49-1.51 (m, 1H), 1.41-1.43 (m, 1H), 1.25-1.27 (m, 1H), 0.69-0.71 (m, 2H), 0.48-0.50 (m, 2H). MS (ESI) m/z: [M+H]⁺ Found 635.3.

Example 182

N—((S)-(7-((R)-Cyclopropyl(4,4,4-trifluorobutanamido)methyl)imidazo[1,2-b]pyridazin-2-yl)(4,4-difluorocyclohexyl)methyl)-4-fluorobenzamide

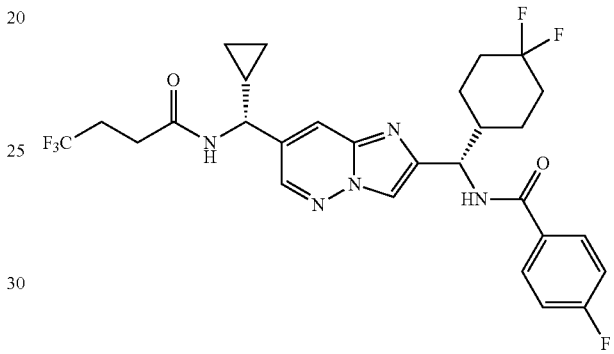

The title compound was prepared as described in the synthesis of Example 163, using 4-fluorobenzoic acid in place of 3-(2-oxopyrrolidin-1-yl)benzoic acid to provide the title compound. ¹H NMR (500 MHz, CD₃OD) δ 8.44-8.48 (m, 1H), 8.10 (s, 1H), 7.89-7.91 (m, 2H), 7.87 (s, 1H), 7.20 (t, J=8.8, 2H), 5.27 (d, J=8.6 Hz, 1H), 4.27 (d, J=9.5 Hz, 1H), 2.56-2.59 (m, 2H), 2.47-2.49 (m, 2H), 2.20-2.22 (m, 1H), 2.08-2.10 (m, 1H), 2.00-2.02 (m, 2H), 1.77-1.79 (m, 2H), 1.63-1.65 (m, 1H), 1.49-1.51 (m, 1H), 1.38-1.40 (m, 1H), 1.24-1.26 (m, 1H), 0.69-0.71 (m, 2H), 0.48-0.50 (m, 2H). MS (ESI) m/z: [M+H]⁺ Found 582.3.

Example 183

N—((S)-(7-((R)-Cyclopropyl(4,4,4-trifluorobutanamido)methyl)imidazo[1,2-b]pyridazin-2-yl)(4,4-difluorocyclohexyl)methyl)-5-(2,2-difluoroethoxy)nicotinamide

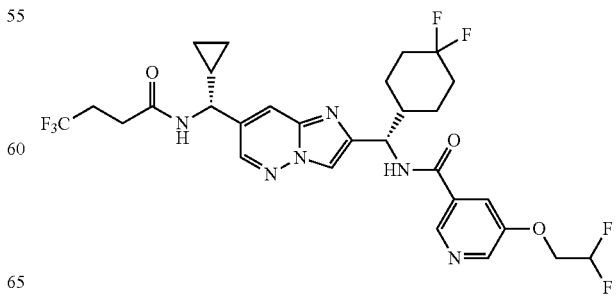

The title compound was prepared as described in the synthesis of Example 163, using 5-(2,2-difluoroethoxy) nicotinic acid in place of 3-(2-oxopyrrolidin-1-yl)benzoic acid to provide the title compound. $^1$H NMR (400 MHz, CDCl$_3$) δ 8.67 (s, 1H), 8.43 (d, J=2.9 Hz, 1H), 8.32 (d, J=2.2 Hz, 1H), 7.85 (s, 1H), 7.80 (s, 1H), 7.67-7.69 (m, 1H), 7.44 (d, J=8.5 Hz, 1H), 6.07-6.09 (m, 2H), 5.29 (t, J=8.0 Hz, 1H), 4.24-4.26 (m, 3H), 2.46-2.49 (m, 4H), 2.08-2.11 (m, 2H), 1.95-1.97 (m, 2H), 1.68-1.70 (m, 3H), 1.49-1.51 (m, 1H), 1.35-1.37 (m, 1H), 1.11-1.13 (m, 1H), 0.70-0.72 (m, 2H), 0.47-0.48 (m, 2H). MS (ESI) m/z: [M+H]$^+$ Found 645.2.

Example 184

N—((S)-(7-((R)-Cyclopropyl(4,4,4-trifluorobutanamido)methyl)imidazo[1,2-b]pyridazin-2-yl)(4,4-difluorocyclohexyl)methyl)-2-methoxyisonicotinamide

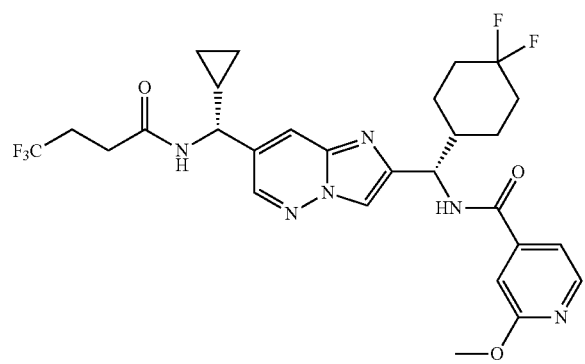 [SMILES: COc1cc(C(=O)N[C@H](c2cn3ncc([C@H](NC(=O)CCC(F)(F)F)C4CC4)cc3n2)C2CCC(F)(F)CC2)ccn1]

The title compound was prepared as described in the synthesis of Example 163, using 2-methoxyisonicotinic acid in place of 3-(2-oxopyrrolidin-1-yl)benzoic acid to provide the title compound. $^1$H NMR (500 MHz, CD$_3$OD) δ 8.46 (d, J=2.1 Hz, 1H), 8.25 (d, J=5.3 Hz, 1H), 8.10 (s, 1H), 7.87-7.88 (m, 1H), 7.30 (d, J=5.3 Hz, 1H), 7.17 (s, 1H), 5.25 (d, J=8.7 Hz, 1H), 4.27 (d, J=9.5 Hz, 1H), 3.95 (s, 3H), 2.57-2.59 (m, 2H), 2.50-2.51 (m, 2H), 2.20-2.22 (m, 1H), 2.09-2.11 (m, 1H), 2.01-2.03 (m, 2H), 1.78-1.80 (m, 2H), 1.64-1.65 (m, 1H), 1.48-1.50 (m, 1H), 1.37-1.39 (m, 1H), 1.25-1.26 (m, 1H), 0.69-0.71 (m, 2H), 0.48-0.50 (m, 2H). MS (ESI) m/z: [M+H]$^+$ Found 595.0.

Example 185

N—((S)-(7-((R)-Cyclopropyl(4,4,4-trifluorobutanamido)methyl)imidazo[1,2-b]pyridazin-2-yl)(4,4-difluorocyclohexyl)methyl)-5-isopropoxynicotinamide

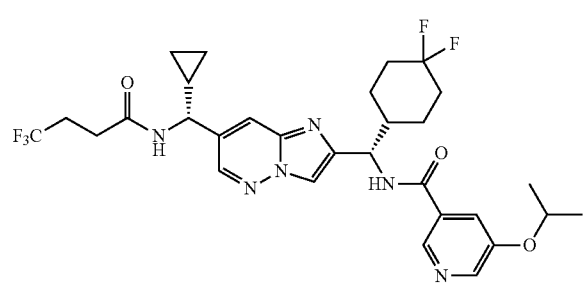 [SMILES: CC(C)Oc1cncc(C(=O)N[C@H](c2cn3ncc([C@H](NC(=O)CCC(F)(F)F)C4CC4)cc3n2)C2CCC(F)(F)CC2)c1]

The title compound was prepared as described in the synthesis of Example 163, using 5-isopropoxynicotinic acid in place of 3-(2-oxopyrrolidin-1-yl)benzoic acid to provide the title compound. $^1$H NMR (500 MHz, CD$_3$OD) δ 8.55-8.57 (m, 1H), 8.47 (d, J=2.2 Hz, 1H), 8.33 (d, J=2.8 Hz, 1H), 8.12 (s, 1H), 7.88 (s, 1H), 7.75-7.77 (m, 1H), 5.28 (d, J=8.6 Hz, 1H), 4.72-4.78 (m, 1H), 4.27 (d, J=9.5 Hz, 1H), 2.55-2.57 (m, 2H), 2.48-2.50 (m, 2H), 2.20-2.23 (m, 1H), 2.08-2.11 (m, 1H), 2.00-2.03 (m, 2H), 1.79-1.81 (m, 2H), 1.65-1.67 (m, 1H), 1.49-1.51 (m, 1H), 1.40-1.42 (m, 1H), 1.37 (d, J=6.0 Hz, 6H), 1.25-1.27 (m, 1H), 0.69-0.71 (m, 2H), 0.48-0.50 (m, 2H). MS (ESI) m/z: [M+H]$^+$ Found 623.2.

Example 186

N—((S)-(7-((R)-Cyclopropyl(4,4,4-trifluorobutanamido)methyl)imidazo[1,2-b]pyridazin-2-yl)(4,4-difluorocyclohexyl)methyl)-2-(difluoromethoxy)isonicotinamide

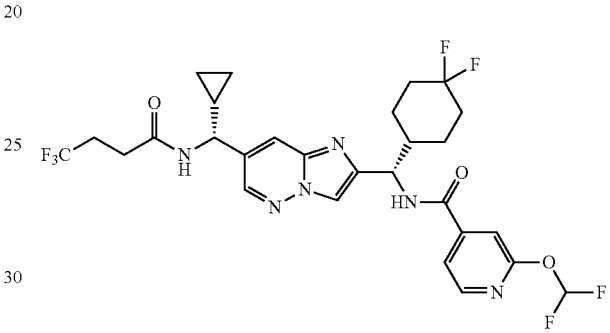

The title compound was prepared as described in the synthesis of Example 163, using 2-(difluoromethoxy)isonicotinic acid in place of 3-(2-oxopyrrolidin-1-yl)benzoic acid to provide the title compound. $^1$H NMR (500 MHz, CD$_3$OD) δ 8.47 (d, J=2.1 Hz, 1H), 8.34 (d, J=5.2 Hz, 1H), 8.11 (s, 1H), 7.88 (s, 1H), 7.55-7.57 (m, 2H), 7.36 (s, 1H), 5.26 (d, J=8.6 Hz, 1H), 4.27 (d, J=9.4 Hz, 1H), 2.54-2.56 (m, 2H), 2.50-2.52 (m, 2H), 2.21-2.23 (m, 1H), 2.09-2.11 (m, 1H), 1.99-2.01 (m, 2H), 1.77-1.79 (m, 2H), 1.63-1.65 (m, 1H), 1.48-1.50 (m, 1H), 1.37-1.39 (m, 1H), 1.25-1.26 (m, 1H), 0.70-0.72 (m, 2H), 0.48-0.50 (m, 2H). MS (ESI) m/z: [M+H]$^+$ Found 631.4.

Example 187

N—((S)-(7-((R)-Cyclopropyl(4,4,4-trifluorobutanamido)methyl)imidazo[1,2-b]pyridazin-2-yl)(4,4-difluorocyclohexyl)methyl)-2-(difluoromethyl)benzamide

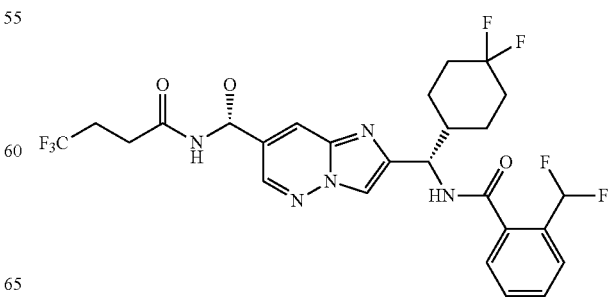

The title compound was prepared as described in the synthesis of Example 163, using 2-(difluoromethyl)benzoic acid in place of 3-(2-oxopyrrolidin-1-yl)benzoic acid to provide the title compound. ¹H NMR (500 MHz, CD₃OD) δ 8.47 (d, J=2.1 Hz, 1H), 8.09 (s, 1H), 7.88 (s, 1H), 7.72 (d, J=7.2 Hz, 1H), 7.60-7.62 (m, 1H), 7.57-7.59 (m, 2H), 7.12 (t, J=55.9 Hz, 1H), 5.28 (d, J=8.0 Hz, 1H), 4.28 (d, J=9.5 Hz, 1H), 2.55-2.57 (m, 2H), 2.51-2.53 (m, 2H), 2.18-2.20 (m, 1H), 2.06-2.08 (m, 2H), 1.95-1.97 (m, 1H), 1.78-1.81 (m, 1H), 1.73-1.75 (m, 1H), 1.67-1.69 (m, 1H), 1.53-1.55 (m, 1H), 1.45-1.48 (m, 1H), 1.25-1.27 (m, 1H), 0.69-0.71 (m, 2H), 0.48-0.51 (m, 2H). MS (ESI) m/z: [M+H]⁺ Found 614.4.

Example 188

3-Cyano-N—((S)-(7-((R)-cyclopropyl(4,4,4-trifluorobutanamido)methyl)imidazo[1,2-b]pyridazin-2-yl)(4,4-difluorocyclohexyl)methyl)benzamide

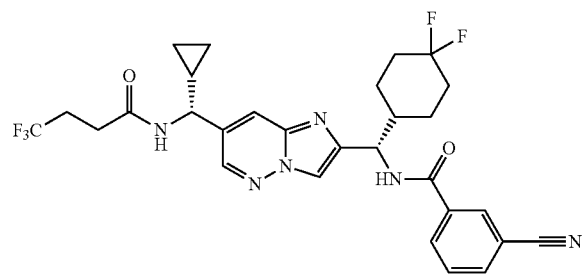 [SMILES: N#Cc1cccc(C(=O)N[C@H](c2cn3ncc([C@H](NC(=O)CCC(F)(F)F)C4CC4)cc3n2)C2CCC(F)(F)CC2)c1]

The title compound was prepared as described in the synthesis of Example 163, using 3-cyanobenzoic acid in place of 3-(2-oxopyrrolidin-1-yl)benzoic acid to provide the title compound. ¹H NMR (500 MHz, CD₃OD) δ 8.46 (d, J=2.1 Hz, 1H), 8.22 (s, 1H), 8.14 (d, J=8.0 Hz, 1H), 8.11 (s, 1H), 7.90 (d, J=7.7 Hz, 1H), 7.87-7.88 (m, 1H), 7.67 (t, J=7.8 Hz, 1H), 5.27 (d, J=8.6 Hz, 1H), 4.27 (d, J=9.5 Hz, 1H), 2.54-2.56 (m, 2H), 2.49-2.51 (m, 2H), 2.23-2.25 (m, 1H), 2.08-2.10 (m, 1H), 2.00-2.02 (m, 2H), 1.76-1.78 (m, 2H), 1.64-1.66 (m, 1H), 1.50-1.51 (m, 1H), 1.37-1.39 (m, 1H), 1.25-1.26 (m, 1H), 0.69-0.71 (m, 2H), 0.48-0.50 (m, 2H). MS (ESI) m/z: [M+H]⁺ Found 589.2.

Example 189

N—((S)-(7-((R)-Cyclopropyl(4,4,4-trifluorobutanamido)methyl)imidazo[1,2-b]pyridazin-2-yl)(4,4-difluorocyclohexyl)methyl)-5-methoxynicotinamide

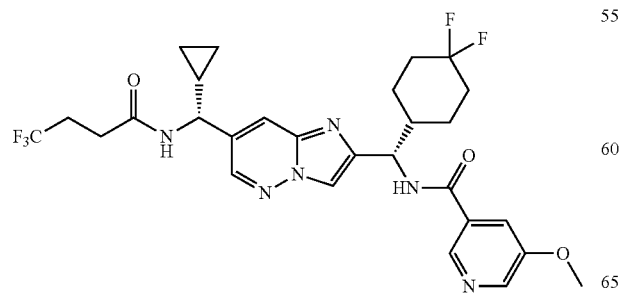

The title compound was prepared as described in the synthesis of Example 163, using 5-methoxynicotinic acid in place of 3-(2-oxopyrrolidin-1-yl)benzoic acid to provide the title compound. ¹H NMR (500 MHz, CD₃OD) δ 8.60 (s, 1H), 8.47 (d, J=2.1 Hz, 1H), 8.38 (d, J=2.8 Hz, 1H), 8.12 (s, 1H), 7.87-7.88 (m, 1H), 7.80-7.81 (m, 1H), 5.29 (d, J=8.6 Hz, 1H), 4.27 (d, J=9.5 Hz, 1H), 3.94 (s, 3H), 2.57-2.59 (m, 2H), 2.48-2.50 (m, 2H), 2.23-2.24 (m, 1H), 2.10-2.11 (m, 1H), 2.00-2.02 (m, 2H), 1.79-1.81 (m, 2H), 1.65-1.66 (m, 1H), 1.51-1.53 (m, 1H), 1.38-1.40 (m, 1H), 1.25-1.26 (m, 1H), 0.68-0.70 (m, 2H), 0.48-0.50 (m, 2H). MS (ESI) m/z: [M+H]⁺ Found 595.2.

Example 190

N—((S)-(7-((R)-Cyclopropyl(4,4,4-trifluorobutanamido)methyl)imidazo[1,2-b]pyridazin-2-yl)(4,4-difluorocyclohexyl)methyl)isonicotinamide

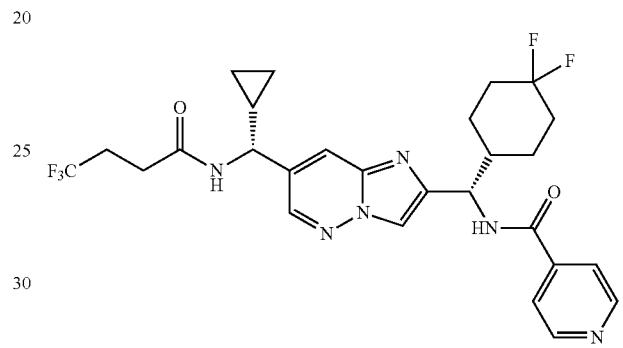

The title compound was prepared as described in the synthesis of Example 163, using isonicotinic acid in place of 3-(2-oxopyrrolidin-1-yl)benzoic acid to provide the title compound. ¹H NMR (500 MHz, CD₃OD) δ 8.68-8.72 (m, 2H), 8.47 (d, J=2.1 Hz, 1H), 8.12 (s, 1H), 7.84-7.88 (m, 1H), 7.78-7.82 (m, 2H), 5.28 (d, J=8.5 Hz, 1H), 4.27 (d, J=9.5 Hz, 1H), 2.51-2.55 (m, 2H), 2.45-2.50 (m, 2H), 2.20-2.24 (m, 1H), 2.05-2.10 (m, 1H), 1.95-2.01 (m, 2H), 1.76-1.79 (m, 2H), 1.63-1.66 (m, 1H), 1.50-1.52 (m, 1H), 1.36-1.40 (m, 1H), 1.24-1.28 (m, 1H), 0.70-0.71 (m, 2H), 0.48-0.50 (m, 2H). MS (ESI) m/z: [M+H]⁺ Found 565.2.

Example 191

N—((S)-(7-((R)-Cyclopropyl(4,4,4-trifluorobutanamido)methyl)imidazo[1,2-b]pyridazin-2-yl)(4,4-difluorocyclohexyl)methyl)-6,7-dihydro-5H-cyclopenta[b]pyridine-4-carboxamide

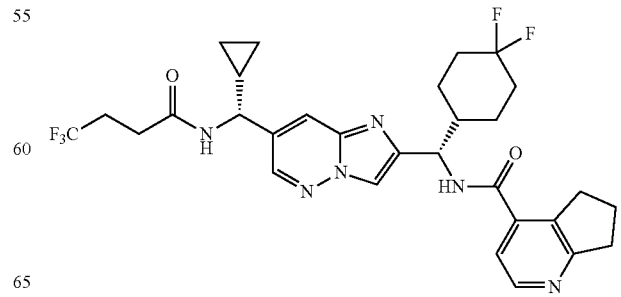

The title compound was prepared as described in the synthesis of Example 163, using 6,7-dihydro-5H-cyclopenta[b]pyridine-4-carboxylic acid in place of 3-(2-oxopyrrolidin-1-yl)benzoic acid to provide the title compound. $^1$H NMR (500 MHz, CD$_3$OD) δ 8.47 (d, J=2.1 Hz, 1H), 8.37 (d, J=5.2 Hz, 1H), 8.10 (s, 1H), 7.88 (s, 1H), 7.32 (d, J=5.2 Hz, 1H), 5.29 (d, J=8.1 Hz, 1H), 4.28 (d, J=9.5 Hz, 1H), 3.10 (t, J=7.5 Hz, 2H), 3.03 (t, J=7.7 Hz, 2H), 2.55-2.57 (m, 2H), 2.48-2.50 (m, 2H), 2.22-2.24 (m, 1H), 2.14-2.16 (m, 2H), 2.05-2.07 (m, 2H), 1.98-2.00 (m, 1H), 1.78-1.80 (m, 2H), 1.69-1.70 (m, 1H), 1.51-1.53 (m, 1H), 1.42-1.43 (m, 1H), 1.24-1.26 (m, 1H), 0.69-0.71 (m, 2H), 0.49-0.51 (m, 2H), 2 NH are not observed. MS (ESI) m/z: [M+H]$^+$ Found 605.4.

Example 192

N—((S)-(7-((R)-Cyclopropyl(4,4,4-trifluorobutanamido)methyl)imidazo[1,2-b]pyridazin-2-yl)(4,4-difluorocyclohexyl)methyl)nicotinamide

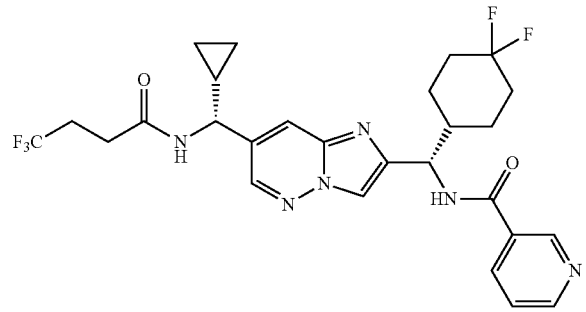

The title compound was prepared as described in the synthesis of Example 163, using nicotinic acid in place of 3-(2-oxopyrrolidin-1-yl)benzoic acid to provide the title compound. $^1$H NMR (500 MHz, CD$_3$OD) δ 9.01 (s, 1H), 8.70 (d, J=3.8 Hz, 1H), 8.49 (d, J=2.1 Hz, 1H), 8.28-8.32 (m, 1H), 8.14 (s, 1H), 7.90 (s, 1H), 7.55-7.59 (m, 1H), 5.30 (d, J=8.5 Hz, 1H), 4.27 (d, J=9.5 Hz, 1H), 2.55-2.58 (m, 2H), 2.48-2.53 (m, 2H), 2.25-2.29 (m, 1H), 2.10-2.12 (m, 1H), 2.00-2.03 (m, 2H), 1.80-1.85 (m, 2H), 1.65-1.69 (m, 1H), 1.51-1.54 (m, 1H), 1.39-1.41 (m, 1H), 1.25-1.27 (m, 1H), 0.68-0.71 (m, 2H), 0.49-0.51 (m, 2H). MS (ESI) m/z: [M+H]$^+$ Found 565.2.

Example 193

2-Cyclopropyl-N—((S)-(7-((R)-cyclopropyl(4,4,4-trifluorobutanamido)methyl)imidazo[1,2-b]pyridazin-2-yl)(4,4-difluorocyclohexyl)methyl)nicotinamide

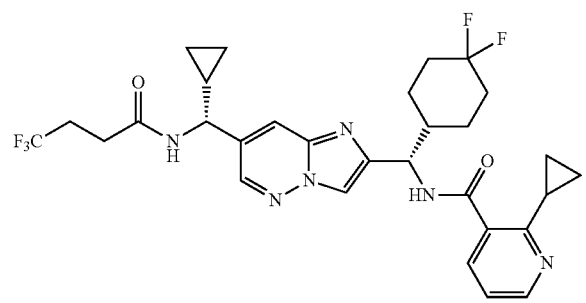 [SMILES: O=C(CCC(F)(F)F)N[C@@H](c1cnn2cc([C@@H](NC(=O)c3cccnc3C3CC3)C3CCC(F)(F)CC3)nc2c1)C1CC1]

The title compound was prepared as described in the synthesis of Example 163, using 2-cyclopropylnicotinic acid in place of 3-(2-oxopyrrolidin-1-yl)benzoic acid to provide the title compound. $^1$H NMR (500 MHz, CD$_3$OD) δ 8.48 (d, J=2.1 Hz, 1H), 8.41-8.43 (m, 1H), 8.09-8.11 (s, 1H), 7.87-7.89 (m, 1H), 7.69-7.70 (m, 1H), 7.19-7.21 (m, 1H), 5.33 (d, J=7.7 Hz, 1H), 4.27 (d, J=9.5 Hz, 1H), 2.55-2.57 (m, 2H), 2.49-2.51 (m, 2H), 2.21-2.23 (m, 2H), 2.06-2.08 (m, 2H), 1.97-1.99 (m, 1H), 1.78-1.80 (m, 2H), 1.73-1.75 (m, 1H), 1.53-1.55 (m, 1H), 1.45-1.47 (m, 1H), 1.26-1.27 (m, 1H), 1.05-1.06 (m, 2H), 0.92-0.94 (m, 2H), 0.69-0.71 (m, 2H), 0.49-0.51 (m, 2H). MS (ESI) m/z: [M+H]$^+$ Found 605.3.

Example 194

N—((S)-(7-((R)-Cyclopropyl(4,4,4-trifluorobutanamido)methyl)imidazo[1,2-b]pyridazin-2-yl)(4,4-difluorocyclohexyl)methyl)-2-(trifluoromethyl)isonicotinamide

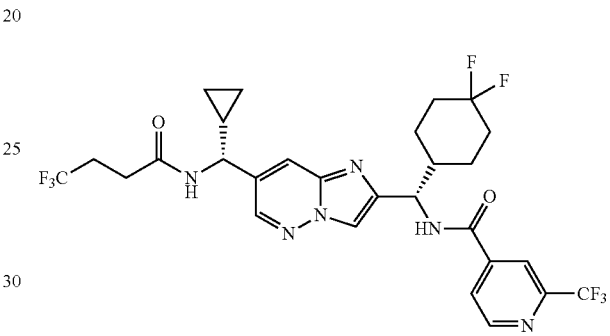

The title compound was prepared as described in the synthesis of Example 163, using 2-(trifluoromethyl)isonicotinic acid in place of 3-(2-oxopyrrolidin-1-yl)benzoic acid to provide the title compound. $^1$H NMR (500 MHz, CD$_3$OD) δ 8.87 (d, J=5.0 Hz, 1H), 8.45-8.47 (m, 1H), 8.21 (s, 1H), 8.13 (s, 1H), 8.00-8.03 (m, 1H), 7.88 (s, 1H), 5.28 (d, J=8.6 Hz, 1H), 4.27 (d, J=9.5 Hz, 1H), 2.55-2.57 (m, 2H), 2.48-2.50 (m, 2H), 2.23-2.26 (m, 1H), 2.09-2.11 (m, 1H), 2.00-2.03 (m, 2H), 1.76-1.79 (m, 2H), 1.64-1.66 (m, 1H), 1.50-1.52 (m, 1H), 1.40-1.42 (m, 1H), 1.25-1.26 (m, 1H), 0.69-0.71 (m, 2H), 0.48-0.50 (m, 2H). MS (ESI) m/z: [M+H]$^+$ Found 633.4.

Example 195

N—((S)-(7-((R)-Cyclopropyl(4,4,4-trifluorobutanamido)methyl)imidazo[1,2-b]pyridazin-2-yl)(4,4-difluorocyclohexyl)methyl)-3-fluoroisonicotinamide

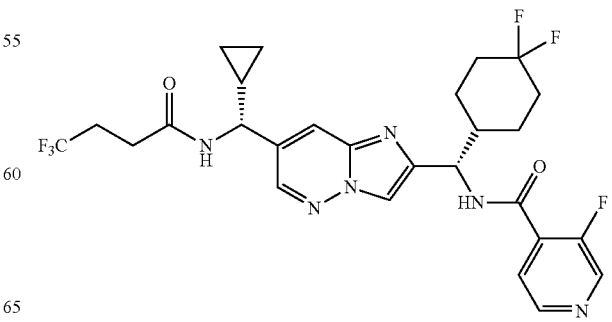

The title compound was prepared as described in the synthesis of Example 163, using 3-fluoroisonicotinic acid in place of 3-(2-oxopyrrolidin-1-yl)benzoic acid to provide the title compound. $^{1}$H NMR (500 MHz, CD$_{3}$OD) δ 8.61 (s, 1H), 8.51 (d, J=4.9 Hz, 1H), 8.47 (d, J=2.1 Hz, 1H), 8.09 (s, 1H), 7.88 (s, 1H), 7.63 (t, J=5.4 Hz, 1H), 5.32 (d, J=7.9 Hz, 1H), 4.28 (d, J=9.5 Hz, 1H), 2.54-2.56 (m, 2H), 2.49-2.51 (m, 2H), 2.23-2.25 (m, 1H), 2.07-2.09 (m, 2H), 1.96-1.98 (m, 1H), 1.80-1.82 (m, 1H), 1.74-1.76 (m, 1H), 1.68-1.70 (m, 1H), 1.49-1.52 (m, 1H), 1.41-1.44 (m, 1H), 1.25-1.27 (m, 1H), 0.69-0.71 (m, 2H), 0.49-0.51 (m, 2H). MS (ESI) m/z: [M+H]$^{+}$ Found 583.2.

Example 196

N—((S)-(7-((R)-Cyclopropyl(4,4,4-trifluorobutanamido)methyl)imidazo[1,2-b]pyridazin-2-yl)(4,4-difluorocyclohexyl)methyl)-4-methoxypicolinamide

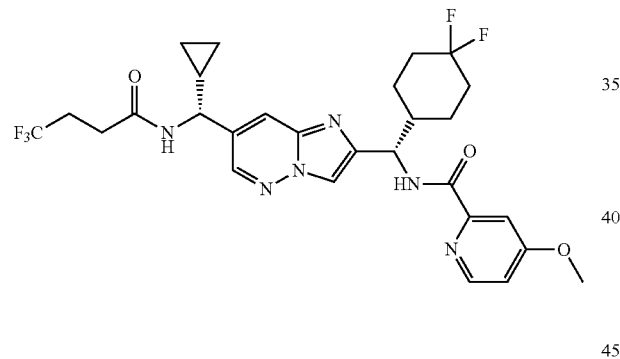

The title compound was prepared as described in the synthesis of Example 163, using 4-methoxypicolinic acid in place of 3-(2-oxopyrrolidin-1-yl)benzoic acid to provide the title compound. $^{1}$H NMR (500 MHz, CD$_{3}$OD) δ 8.45-8.46 (m, 2H), 8.12 (s, 1H), 7.88-7.89 (m, 1H), 7.64 (d, J=2.6 Hz, 1H), 7.08-7.10 (m, J=5.6 Hz, 1H), 5.26 (d, J=8.1 Hz, 1H), 4.28 (d, J=9.4 Hz, 1H), 3.93 (s, 3H), 2.54-2.56 (m, 2H), 2.50-2.52 (m, 2H), 2.21-2.20 (m, 1H), 2.06-2.07 (m, 2H), 1.95-1.97 (m, 1H), 1.75-1.78 (m, 2H), 1.63-1.65 (m, 1H), 1.49-1.50 (m, 1H), 1.38-1.40 (m, 1H), 1.25-1.26 (m, 1H), 0.70-0.71 (m, 2H), 0.48-0.50 (m, 2H). MS (ESI) m/z: [M+H]$^{+}$ Found 595.0.

Example 197

N—((S)-(7-((R)-Cyclopropyl(4,4,4-trifluorobutanamido)methyl)imidazo[1,2-b]pyridazin-2-yl)(4,4-difluorocyclohexyl)methyl)-4-(2,2-difluoroethoxy)picolinamide

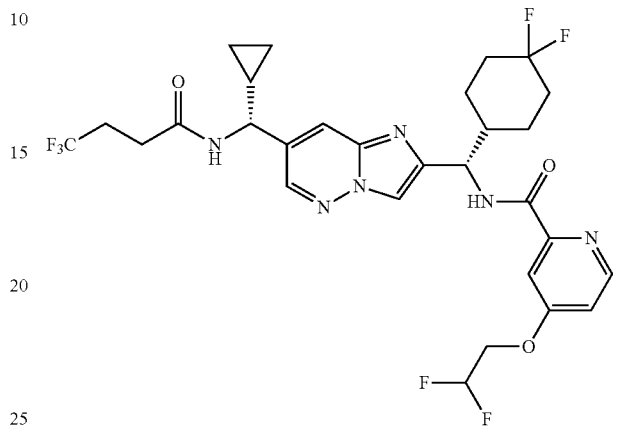

The title compound was prepared as described in the synthesis of Example 163, using 4-(2,2-difluoroethoxy)picolinic acid in place of 3-(2-oxopyrrolidin-1-yl)benzoic acid to provide the title compound. $^{1}$H NMR (500 MHz, CD$_{3}$OD) δ 8.50 (d, J=5.7 Hz, 1H), 8.46 (d, J=2.1 Hz, 1H), 8.12 (s, 1H), 7.89 (s, 1H), 7.69 (d, J=2.6 Hz, 1H), 7.17-7.18 (m, 1H), 6.22-6.23 (m, 1H), 5.26 (d, J=8.2 Hz, 1H), 4.40-4.42 (m, 2H), 4.28-4.30 (d, J=9.5 Hz, 1H), 2.55-2.57 (m, 2H), 2.49-2.51 (m, 2H), 2.22-2.24 (m, 1H), 2.03-2.05 (m, 3H), 1.77-1.80 (m, 2H), 1.65-1.66 (m, 1H), 1.48-1.50 (m, 1H), 1.39-1.41 (m, 1H), 1.25-1.26 (m, 1H), 0.69-0.71 (m, 2H), 0.49-0.51 (m, 2H). MS (ESI) m/z: [M+H]$^{+}$ Found 645.2.

Example 198

N—((S)-(7-((R)-Cyclopropyl(4,4,4-trifluorobutanamido)methyl)imidazo[1,2-b]pyridazin-2-yl)(4,4-difluorocyclohexyl)methyl)-4-(trifluoromethyl)picolinamide

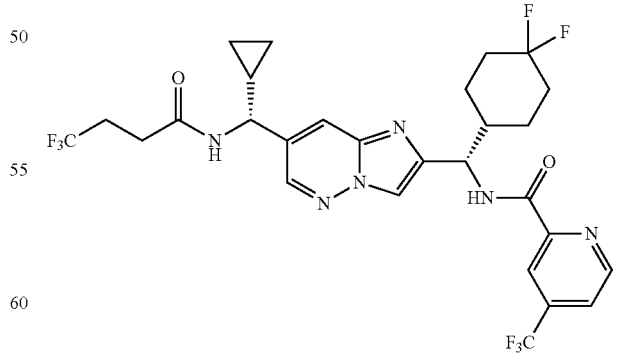

The title compound was prepared as described in the synthesis of Example 163, using 4-(trifluoromethyl)picolinic acid in place of 3-(2-oxopyrrolidin-1-yl)benzoic acid to provide the title compound. $^{1}$H NMR (500 MHz, CD$_{3}$OD)

δ 8.92 (d, J=5.0 Hz, 1H), 8.47 (d, J=2.1 Hz, 1H), 8.34 (s, 1H), 8.14 (s, 1H), 7.87-7.89 (m, 2H), 5.30 (d, J=8.3 Hz, 1H), 4.28 (d, J=9.5 Hz, 1H), 2.55-2.57 (m, 2H), 2.48-2.50 (m, 2H), 2.24-2.25 (m, 1H), 2.07-2.08 (m, 1H), 1.99 (d, J=16.2 Hz, 2H), 1.75-1.78 (m, 2H), 1.64-1.66 (m, 1H), 1.49-1.51 (m, 1H), 1.41-1.42 (m, 1H), 1.24-1.26 (m, 1H), 0.69-0.71 (m, 2H), 0.48-0.50 (m, 2H). MS (ESI) m/z: [M+H]+ Found 633.2.

Example 199

N—((S)-(7-((R)-Cyclopropyl(4,4,4-trifluorobutanamido)methyl)imidazo[1,2-b]pyridazin-2-yl)(4,4-difluorocyclohexyl)methyl)-6-(difluoromethyl)pyrimidine-4-carboxamide

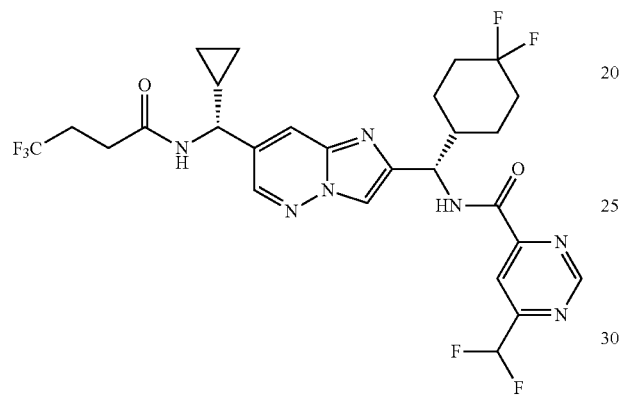

The title compound was prepared as described in the synthesis of Example 163, using 6-(difluoromethyl)pyrimidine-4-carboxylic acid in place of 3-(2-oxopyrrolidin-1-yl)benzoic acid to provide the title compound. ¹H NMR (500 MHz, CD₃OD) δ 9.41 (s, 1H), 8.47-8.48 (m, 1H), 8.30 (s, 1H), 8.15 (s, 1H), 7.89 (s, 1H), 6.81 (t, J=54.4 Hz, 1H), 5.30 (d, J=8.4 Hz, 1H), 4.27 (d, J=9.5 Hz, 1H), 2.57-2.55 (m, 2H), 2.48-2.50 (m, 2H), 2.23-2.26 (m, 1H), 2.09-2.11 (m, 1H), 1.97-1.99 (m, 2H), 1.78-1.80 (m, 2H), 1.65-1.66 (m, 1H), 1.49-1.51 (m, 1H), 1.37-1.39 (m, 1H), 1.24-1.25 (m, 1H), 0.69-0.71 (m, 2H), 0.48-0.50 (m, 2H). MS (ESI) m/z: [M+H]+ Found 616.4.

Example 200

N—((S)-(7-((R)-Cyclopropyl(4,4,4-trifluorobutanamido)methyl)imidazo[1,2-b]pyridazin-2-yl)(4,4-difluorocyclohexyl)methyl)-2-methylnicotinamide

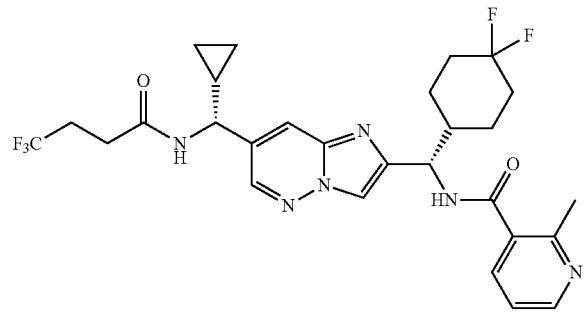

The title compound was prepared as described in the synthesis of Example 163, using 2-methylnicotinic acid in place of 3-(2-oxopyrrolidin-1-yl)benzoic acid to provide the title compound. ¹H NMR (500 MHz, CD₃OD) δ 8.48-8.51 (m, 2H), 8.12-8.10 (m, 1H), 7.86-7.89 (m, 1H), 7.78-7.80 (m, 1H), 7.31-7.34 (m, 1H), 5.29 (d, J=8.0 Hz, 1H), 4.28 (d, J=9.5 Hz, 1H), 2.56-2.58 (m, 2H), 2.55 (s, 3H), 2.49-2.52 (m, 2H), 2.19-2.21 (m, 1H), 2.06-2.08 (m, 2H), 1.97-1.99 (m, 1H), 1.77-1.79 (m, 2H), 1.68-1.70 (m, 1H), 1.51-1.55 (m, 1H), 1.44-1.45 (m, 1H), 1.26-1.28 (m, 1H), 0.69-0.72 (m, 2H), 0.49-0.51 (m, 2H). MS (ESI) m/z: [M+H]+ Found 579.2.

Example 201

N—((S)-(7-((R)-Cyclopropyl(4,4,4-trifluorobutanamido)methyl)imidazo[1,2-b]pyridazin-2-yl)(4,4-difluorocyclohexyl)methyl)-6-(2,2-difluoroethoxy)picolinamide

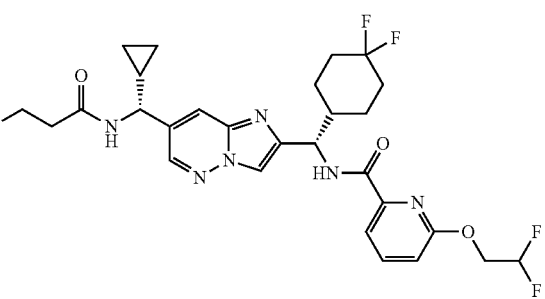

The title compound was prepared as described in the synthesis of Example 163, using 6-(2,2-difluoroethoxy)picolinic acid in place of 3-(2-oxopyrrolidin-1-yl)benzoic acid to provide the title compound. ¹H NMR (500 MHz, CD₃OD) δ 8.47 (d, J=2.2 Hz, 1H), 8.13 (s, 1H), 7.87-7.89 (m, 2H), 7.76 (d, J=7.3 Hz, 1H), 7.09 (d, J=8.3 Hz, 1H), 6.25-6.27 (m, 1H), 5.25 (d, J=8.2 Hz, 1H), 4.74-4.78 (m, 2H), 4.28 (d, J=9.5 Hz, 1H), 2.55-2.57 (m, 2H), 2.47-2.49 (m, 2H), 2.21-2.23 (m, 1H), 2.07-2.09 (m, 1H), 2.00-2.03 (m, 2H), 1.78-1.80 (m, 2H), 1.63-1.65 (m, 1H), 1.48-1.50 (m, 1H), 1.39-1.40 (m, 1H), 1.25-1.26 (m, 1H), 0.69-0.71 (m, 2H), 0.48-0.50 (m, 2H). MS (ESI) m/z: [M+H]+ Found 645.4.

Example 202

N—((S)-(7-((R)-Cyclopropyl(4,4,4-trifluorobutanamido)methyl)imidazo[1,2-b]pyridazin-2-yl)(4,4-difluorocyclohexyl)methyl)-6-(trifluoromethyl)pyrimidine-4-carboxamide

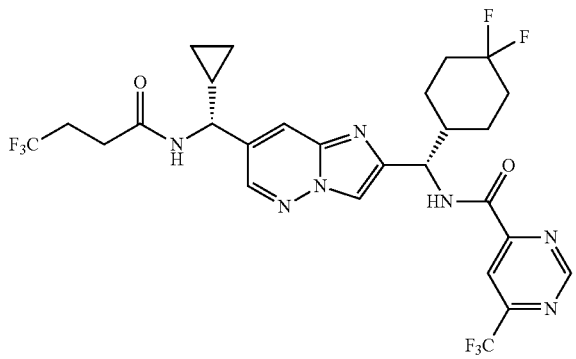 [SMILES: O=C(CCC(F)(F)F)N[C@@H](c1cnn2cc([C@@H](NC(=O)c3cc(C(F)(F)F)ccn3)C3CCC(F)(F)CC3)nc2c1)C1CC1]

The title compound was prepared as described in the synthesis of Example 163, using 6-(trifluoromethyl)pyrimidine-4-carboxylic acid in place of 3-(2-oxopyrrolidin-1-yl)benzoic acid to provide the title compound. $^1$H NMR (500 MHz, CD$_3$OD) δ 9.51 (s, 1H), 8.47 (d, J=2.1 Hz, 1H), 8.41 (d, J=1.4 Hz, 1H), 8.15 (s, 1H), 7.86-7.88 (m, 1H), 5.30 (d, J=8.4 Hz, 1H), 4.27 (d, J=9.5 Hz, 1H), 2.54-2.56 (m, 2H), 2.48-2.50 (m, 2H), 2.25-2.27 (m, 1H), 2.06-2.08 (m, 1H), 2.00-2.02 (m, 2H), 1.77-1.80 (m, 2H), 1.65-1.66 (m, 1H), 1.47-1.49 (m, 1H), 1.38-1.40 (m, 1H), 1.25-1.26 (m, 1H), 0.69-0.71 (m, 2H), 0.48-0.50 (m, 2H). MS (ESI) m/z: [M+H]$^+$ Found 634.4.

Example 203

N—((S)-(7-((R)-Cyclopropyl(4,4,4-trifluorobutanamido)methyl)imidazo[1,2-b]pyridazin-2-yl)(4,4-difluorocyclohexyl)methyl)-6-(2,2,2-trifluoroethoxy)picolinamide

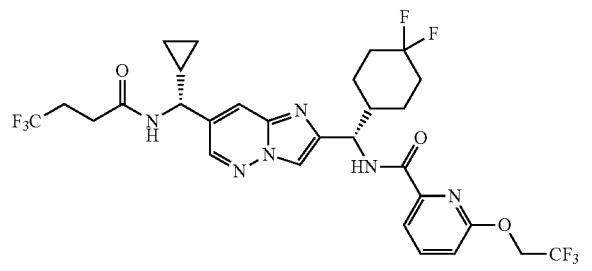 [SMILES: O=C(CCC(F)(F)F)N[C@@H](c1cnn2cc([C@@H](NC(=O)c3cccc(OCC(F)(F)F)n3)C3CCC(F)(F)CC3)nc2c1)C1CC1]

The title compound was prepared as described in the synthesis of Example 163, using 6-(2,2,2-trifluoroethoxy)picolinic acid in place of 3-(2-oxopyrrolidin-1-yl)benzoic acid to provide the title compound. $^1$H NMR (500 MHz, CD$_3$OD) δ 8.47 (d, J=2.1 Hz, 1H), 8.13 (s, 1H), 7.93 (t, J=7.8 Hz, 1H), 7.86-7.88 (m, 1H), 7.80 (d, J=7.3 Hz, 1H), 7.13 (d, J=8.2 Hz, 1H), 5.26 (d, J=8.5 Hz, 1H), 5.06-5.08 (m, 2H), 4.28 (d, J=9.4 Hz, 1H), 2.54-2.56 (m, 2H), 2.47-2.49 (m, 2H), 2.24-2.25 (m, 1H), 2.08-2.09 (m, 1H), 1.98-2.00 (m, 2H), 1.77-1.79 (m, 2H), 1.63-1.64 (m, 1H), 1.48-1.50 (m, 1H), 1.38-1.40 (m, 1H), 1.24-1.26 (m, 1H), 0.69-0.71 (m, 2H), 0.48-0.50 (m, 2H). MS (ESI) m/z: [M+H]$^+$ Found 663.2.

Example 204

N—((S)-(7-((R)-Cyclopropyl(4,4,4-trifluorobutanamido)methyl)imidazo[1,2-b]pyridazin-2-yl)(4,4-difluorocyclohexyl)methyl)pyrimidine-5-carboxamide

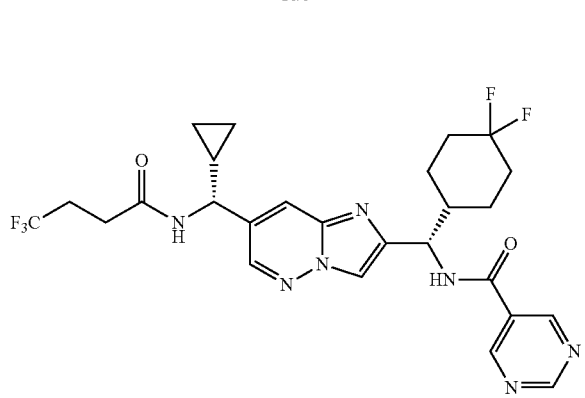

The title compound was prepared as described in the synthesis of Example 163, using pyrimidine-5-carboxylic acid in place of 3-(2-oxopyrrolidin-1-yl)benzoic acid to provide the title compound. $^1$H NMR (500 MHz, CD$_3$OD) δ 9.28 (s, 1H), 9.19 (s, 2H), 8.47 (d, J=2.1 Hz, 1H), 8.13 (s, 1H), 7.86-7.88 (m, 1H), 5.29 (d, J=8.4 Hz, 1H), 4.27 (d, J=9.5 Hz, 1H), 2.54-2.56 (m, 2H), 2.48-2.50 (m, 2H), 2.21-2.24 (m, 1H), 2.08-2.11 (m, 1H), 2.00-2.03 (m, 2H), 1.76-1.80 (m, 2H), 1.65-1.67 (m, 1H), 1.48-1.52 (m, 1H), 1.40-1.41 (m, 1H), 1.24-1.26 (m, 1H), 0.69-0.71 (m, 2H), 0.48-0.50 (m, 2H). MS (ESI) m/z: [M+H]$^+$ Found 566.2.

Example 205

N—((S)-(7-((R)-Cyclopropyl(4,4,4-trifluorobutanamido)methyl)imidazo[1,2-b]pyridazin-2-yl)(4,4-difluorocyclohexyl)methyl)-6-isopropylpicolinamide

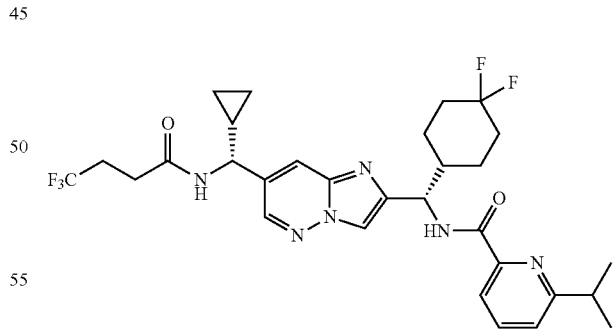

The title compound was prepared as described in the synthesis of Example 163, using 6-isopropylpicolinic acid in place of 3-(2-oxopyrrolidin-1-yl)benzoic acid to provide the title compound. $^1$H NMR (500 MHz, CD$_3$OD) δ 8.47 (d, J=2.1 Hz, 1H), 8.11 (s, 1H), 7.88-7.90 (m, 3H), 7.48 (d, J=7.6 Hz, 1H), 5.27 (d, J=8.0 Hz, 1H), 4.28 (d, J=9.5 Hz, 1H), 3.14-3.16 (m, 1H), 2.55-2.56 (m, 2H), 2.49-2.51 (m, 2H), 2.25-2.27 (m, 1H), 2.08-2.10 (m, 1H), 2.01-2.03 (m, 1H), 1.95-1.97 (m, 1H), 1.75-1.78 (m, 2H), 1.65-1.66 (m, 1H), 1.51-1.53 (m, 1H), 1.43-1.45 (m, 1H), 1.35-1.37 (m, 6H), 1.25-1.26 (m, 1H), 0.69-0.71 (m, 2H), 0.49-0.51 (m, 2H). MS (ESI) m/z: [M+H]⁺ Found 607.1.

Example 206

N—((S)-(7-((R)-Cyclopropyl(4,4,4-trifluorobutanamido)methyl)imidazo[1,2-b]pyridazin-2-yl)(4,4-difluorocyclohexyl)methyl)-4-methylpicolinamide

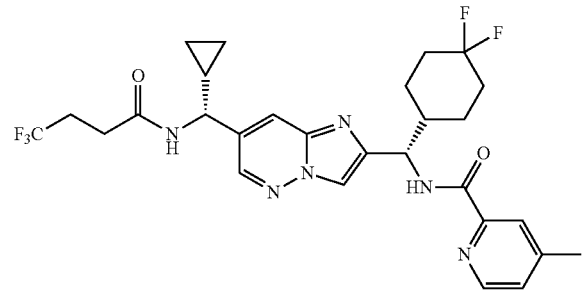 [SMILES: Cc1ccnc(C(=O)N[C@H](c2cn3ncc([C@H](NC(=O)CCC(F)(F)F)C4CC4)cc3n2)C2CCC(F)(F)CC2)c1]

The title compound was prepared as described in the synthesis of Example 163, using 4-methylpicolinic acid in place of 3-(2-oxopyrrolidin-1-yl)benzoic acid to provide the title compound. ¹H NMR (500 MHz, CD₃OD) δ 8.49 (d, J=4.9 Hz, 1H), 8.46 (d, J=2.1 Hz, 1H), 8.12 (s, 1H), 7.94 (s, 1H), 7.85-7.89 (m, 1H), 7.36-7.39 (m, 1H), 5.26 (d, J=8.1 Hz, 1H), 4.28 (d, J=9.5 Hz, 1H), 2.51-2.56 (m, 2H), 2.50-2.55 (m, 2H), 2.44 (s, 3H), 2.20-2.22 (m, 1H), 2.01-2.04 (m, 2H), 1.95-1.97 (m, 1H), 1.74-1.78 (m, 2H), 1.64-1.65 (m, 1H), 1.48-1.50 (m, 1H), 1.37-1.40 (m, 1H), 1.25-1.28 (m, 1H), 0.68-0.71 (m, 2H), 0.48-0.50 (m, 2H). MS (ESI) m/z: [M+H]⁺ Found 579.2.

Example 207

N—((S)-(7-((R)-Cyclopropyl(4,4,4-trifluorobutanamido)methyl)imidazo[1,2-b]pyridazin-2-yl)(4,4-difluorocyclohexyl)methyl)pyrimidine-4-carboxamide

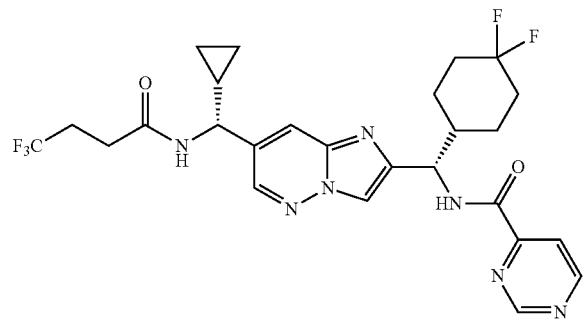 [SMILES: O=C(CCC(F)(F)F)N[C@@H](c1cnn2cc([C@@H](NC(=O)c3ccncn3)C3CCC(F)(F)CC3)nc2c1)C1CC1]

The title compound was prepared as described in the synthesis of Example 163, using pyrimidine-4-carboxylic acid in place of 3-(2-oxopyrrolidin-1-yl)benzoic acid to provide the title compound. ¹H NMR (400 MHz, CD₃OD) δ 9.28 (d, J=1.4 Hz, 1H), 9.01 (d, J=5.1 Hz, 1H), 8.45 (d, J=2.1 Hz, 1H), 8.12 (s, 1H), 8.05-8.10 (m, 1H), 7.87 (s, 1H), 5.26 (d, J=8.4 Hz, 1H), 4.26 (d, J=9.5 Hz, 1H), 2.51-2.54 (m, 2H), 2.44-2.49 (m, 2H), 2.21-2.28 (m, 1H), 2.01-2.05 (m, 1H), 1.94-1.97 (m, 1H), 1.74-1.78 (m, 2H), 1.62-1.68 (m, 1H), 1.44-1.48 (m, 2H), 1.20-1.24 (m, 1H), 0.65-0.69 (m, 2H), 0.45-0.48 (m, 2H). MS (ESI) m/z: [M+H]⁺ Found 566.1.

Example 208

2-Cyano-N—((S)-(7-((R)-cyclopropyl(4,4,4-trifluorobutanamido)methyl)imidazo[1,2-b]pyridazin-2-yl)(4,4-difluorocyclohexyl)methyl)benzamide

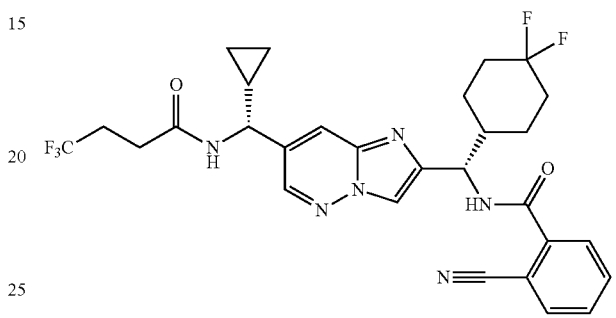

The title compound was prepared as described in the synthesis of Example 163, using 2-cyanobenzoic acid in place of 3-(2-oxopyrrolidin-1-yl)benzoic acid to provide the title compound. ¹H NMR (500 MHz, CD₃OD) δ 8.44-8.45 (m, 1H), 8.26-8.28 (m, 1H), 7.95-7.98 (m, 1H), 7.81-7.84 (m, 2H), 7.76-7.78 (m, 1H), 7.71-7.73 (m, 1H), 5.54-5.56 (m, 1H), 4.27-4.29 (m, 1H), 3.02-3.05 (m, 1H), 2.55-2.57 (m, 2H), 2.47-2.49 (m, 2H), 2.04-2.05 (m, 2H), 1.85-1.87 (m, 2H), 1.77-1.78 (m, 2H), 1.44-1.48 (m, 2H), 1.25-1.26 (m, 1H), 0.69-0.70 (m, 2H), 0.48-0.49 (m, 2H). MS (ESI) m/z: [M+H]⁺ Found 589.2.

Example 209

N—((S)-(7-((R)-Cyclopropyl(4,4,4-trifluorobutanamido)methyl)imidazo[1,2-b]pyridazin-2-yl)(4,4-difluorocyclohexyl)methyl)-4-methylnicotinamide

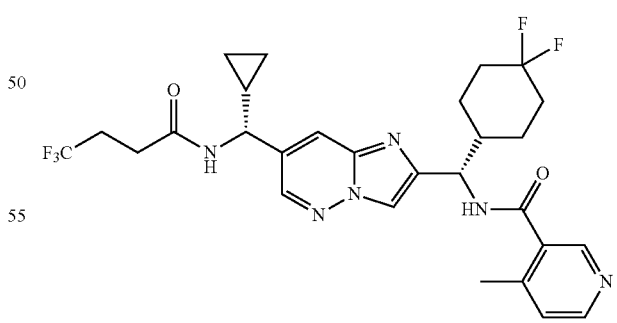

The title compound was prepared as described in the synthesis of Example 163, using 4-methylnicotinic acid in place of 3-(2-oxopyrrolidin-1-yl)benzoic acid to provide the title compound. ¹H NMR (500 MHz, CD₃OD) δ 8.50 (s, 1H), 8.48 (d, J=2.1 Hz, 1H), 8.46 (d, J=5.2 Hz, 1H), 8.10 (s, 1H), 7.86-7.89 (m, 1H), 7.35 (d, J=5.2 Hz, 1H), 5.31 (d, J=8.0 Hz, 1H), 4.28 (d, J=9.4 Hz, 1H), 2.57-2.59 (m, 2H), 2.49-2.51 (m, 2H), 2.41 (s, 3H), 2.19-2.22 (m, 1H), 2.08-2.10 (m, 2H), 1.96-1.98 (m, 1H), 1.82-1.85 (m, 1H), 1.75-1.77 (m, 1H), 1.68-1.70 (m, 1H), 1.55-1.58 (m, 1H), 1.44-1.46 (m, 1H), 1.27-1.29 (m, 1H), 0.70-0.72 (m, 2H), 0.49-0.51 (m, 2H). MS (ESI) m/z: [M+H]+ Found 579.2.

Example 210

N—((S)-(7-((R)-Cyclopropyl(4,4,4-trifluorobutanamido)methyl)imidazo[1,2-b]pyridazin-2-yl)(4,4-difluorocyclohexyl)methyl)-6-(trifluoromethyl)pyrazine-2-carboxamide

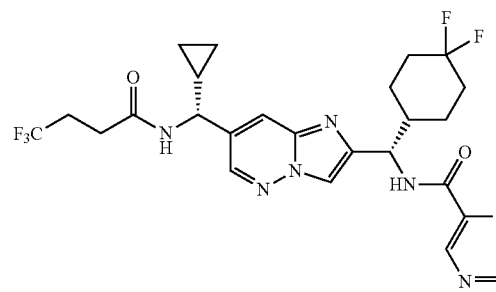

The title compound was prepared as described in the synthesis of Example 163, using 6-(trifluoromethyl)pyrazine-2-carboxylic acid in place of 3-(2-oxopyrrolidin-1-yl)benzoic acid to provide the title compound. ¹H NMR (500 MHz, CD₃OD) δ 9.52 (s, 1H), 9.25 (s, 1H), 8.47 (d, J=2.1 Hz, 1H), 8.15 (s, 1H), 7.89 (d, J=2.1 Hz, 1H), 5.30 (d, J=8.8 Hz, 1H), 4.28 (d, J=9.4 Hz, 1H), 2.54-2.56 (m, 2H), 2.47-2.49 (m, 2H), 2.27-2.28 (m, 1H), 2.08-2.10 (m, 1H), 2.00-2.02 (m, 2H), 1.76-1.78 (m, 2H), 1.59-1.62 (m, 1H), 1.49-1.50 (m, 1H), 1.38-1.40 (m, 1H), 1.25-1.26 (m, 1H), 0.69-0.71 (m, 2H), 0.48-0.50 (m, 2H). MS (ESI) m/z: [M+H]+ Found 634.4.

Example 211

N—((S)-(7-((R)-Cyclopropyl(4,4,4-trifluorobutanamido)methyl)imidazo[1,2-b]pyridazin-2-yl)(4,4-difluorocyclohexyl)methyl)-2-methoxypyrimidine-4-carboxamide

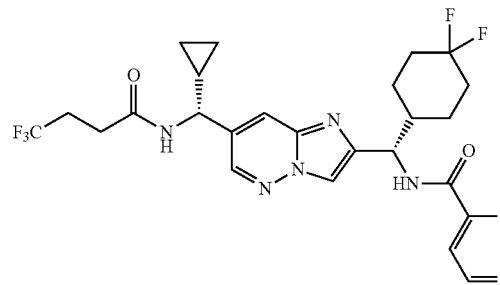

The title compound was prepared as described in the synthesis of Example 163, using 2-methoxypyrimidine-4-carboxylic acid in place of 3-(2-oxopyrrolidin-1-yl)benzoic acid to provide the title compound. ¹H NMR (500 MHz, CD₃OD) δ 8.79 (d, J=4.9 Hz, 1H), 8.47 (d, J=2.1 Hz, 1H), 8.14 (s, 1H), 7.87-7.89 (m, 1H), 7.68 (d, J=4.9 Hz, 1H), 5.25 (d, J=8.4 Hz, 1H), 4.28 (d, J=9.5 Hz, 1H), 4.11 (s, 3H), 2.54-2.56 (m, 2H), 2.49-2.51 (m, 2H), 2.25-2.26 (m, 1H), 2.03-2.04 (m, 1H), 1.97-1.98 (m, 2H), 1.77-1.78 (m, 2H), 1.64-1.65 (m, 1H), 1.46-1.48 (m, 2H), 1.26-1.27 (m, 1H), 0.70-0.72 (m, 2H), 0.48-0.50 (m, 2H). MS (ESI) m/z: [M+H]+ Found 596.0.

Example 212

N—((S)-(7-((R)-Cyclopropyl(4,4,4-trifluorobutanamido)methyl)imidazo[1,2-b]pyridazin-2-yl)(4,4-difluorocyclohexyl)methyl)-4-methylpyrimidine-2-carboxamide

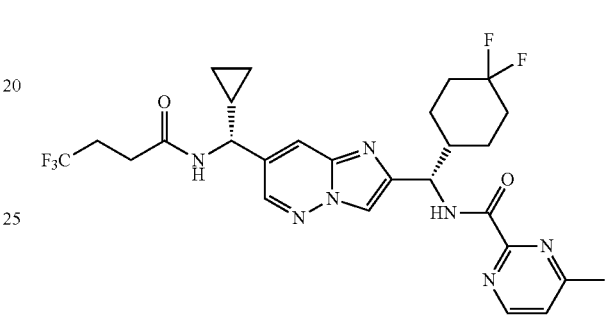

The title compound was prepared as described in the synthesis of Example 163, using 4-methylpyrimidine-2-carboxylic acid in place of 3-(2-oxopyrrolidin-1-yl)benzoic acid to provide the title compound. ¹H NMR (500 MHz, CD₃OD) δ 8.76 (d, J=5.1 Hz, 1H), 8.47 (d, J=2.1 Hz, 1H), 8.14 (s, 1H), 7.88-7.90 (m, 1H), 7.51 (d, J=5.1 Hz, 1H), 5.30 (d, J=8.4 Hz, 1H), 4.28 (d, J=9.5 Hz, 1H), 2.63 (s, 3H), 2.55-2.57 (m, 2H), 2.48-2.50 (m, 2H), 2.21-2.25 (m, 1H), 2.09-2.12 (m, 1H), 1.98-2.00 (m, 2H), 1.76-1.78 (m, 2H), 1.64-1.65 (m, 1H), 1.55-1.53 (m, 1H), 1.42-1.44 (m, 1H), 1.24-1.26 (m, 1H), 0.68-0.70 (m, 2H), 0.48-0.50 (m, 2H). MS (ESI) m/z: [M+H]+ Found 580.2.

Example 213

4-Cyano-N—((S)-(7-((R)-cyclopropyl(4,4,4-trifluorobutanamido)methyl)imidazo[1,2-b]pyridazin-2-yl)(4,4-difluorocyclohexyl)methyl)benzamide

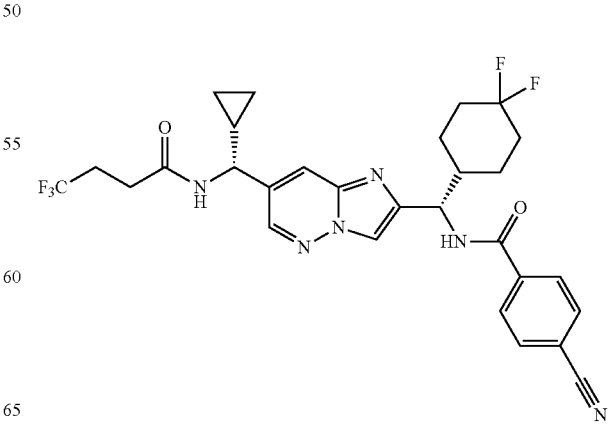

The title compound was prepared as described in the synthesis of Example 163, using 4-cyanobenzoic acid in place of 3-(2-oxopyrrolidin-1-yl)benzoic acid to provide the title compound. $^1$H NMR (500 MHz, CD$_3$OD) δ 8.47 (d, J=2.0 Hz, 1H), 8.11 (s, 1H), 7.95-7.98 (m, 2H), 7.87-7.88 (m, 1H), 7.83-7.85 (m, 2H), 5.28 (d, J=8.5 Hz, 1H), 4.27 (d, J=9.5 Hz, 1H), 2.55-2.57 (m, 2H), 2.48-2.50 (m, 2H), 2.24-2.25 (m, 1H), 2.09-2.11 (m, 1H), 2.01-2.03 (m, 2H), 1.76-1.79 (m, 2H), 1.64-1.66 (m, 1H), 1.50-1.53 (m, 1H), 1.39-1.40 (m, 1H), 1.25-1.26 (m, 1H), 0.70-0.72 (m, 2H), 0.48-0.50 (m, 2H). MS (ESI) m/z: [M+H]$^+$ Found 589.2.

Example 214

N—((S)-(7-((R)-Cyclopropyl(4,4,4-trifluorobutanamido)methyl)imidazo[1,2-b]pyridazin-2-yl)(4,4-difluorocyclohexyl)methyl)-3-methylisonicotinamide

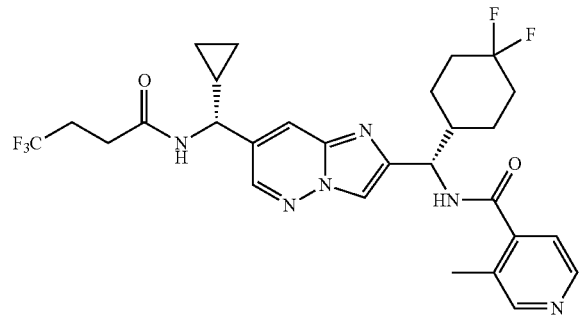 [SMILES: Cc1cnccc1C(=O)N[C@H](c1cn2ncc([C@H](NC(=O)CCC(F)(F)F)C3CC3)cc2n1)C1CCC(F)(F)CC1]

The title compound was prepared as described in the synthesis of Example 163, using 3-methylisonicotinic acid in place of 3-(2-oxopyrrolidin-1-yl)benzoic acid to provide the title compound. $^1$H NMR (500 MHz, CD$_3$OD) δ 8.46-8.48 (m, 2H), 8.45 (d, J=5.0 Hz, 1H), 8.10 (s, 1H), 7.87-7.89 (m, 1H), 7.37 (d, J=5.0 Hz, 1H), 5.30 (d, J=8.0 Hz, 1H), 4.28 (d, J=9.5 Hz, 1H), 2.56-2.58 (m, 2H), 2.49-2.51 (m, 2H), 2.35 (s, 3H), 2.20-2.22 (m, 1H), 2.06-2.08 (m, 2H), 1.96-1.99 (m, 1H), 1.81-1.83 (m, 1H), 1.74-1.76 (m, 1H), 1.68-1.70 (m, 1H), 1.49-1.51 (m, 2H), 1.24-1.26 (m, 1H), 0.70-0.72 (m, 2H), 0.48-0.51 (m, 2H). MS (ESI) m/z: [M+H]$^+$ Found 579.0.

Example 215

N—((S)-(7-((R)-Cyclopropyl(4,4,4-trifluorobutanamido)methyl)imidazo[1,2-b]pyridazin-2-yl)(4,4-difluorocyclohexyl)methyl)-6-methoxypyrazine-2-carboxamide

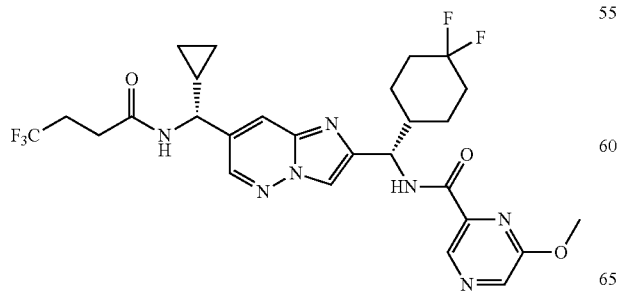

The title compound was prepared as described in the synthesis of Example 163, using 6-methoxypyrazine-2-carboxylic acid in place of 3-(2-oxopyrrolidin-1-yl)benzoic acid to provide the title compound. $^1$H NMR (500 MHz, CD$_3$OD) δ 8.75-8.77 (m, 1H), 8.47-8.48 (m, 1H), 8.42-8.44 (m, 1H), 8.14-8.16 (m, 1H), 7.86-7.88 (m, 1H), 5.27-5.29 (m, 1H), 4.26-4.28 (m, 1H), 4.11-4.13 (m, 3H), 2.55-2.56 (m, 2H), 2.47-2.49 (m, 2H), 2.24-2.26 (m, 1H), 2.09-2.10 (m, 1H), 2.00-2.01 (m, 2H), 1.77-1.79 (m, 2H), 1.65-1.66 (m, 1H), 1.44-1.45 (m, 2H), 1.25-1.26 (m, 1H), 0.69-0.71 (m, 2H), 0.48-0.50 (m, 2H). MS (ESI) m/z: [M+H]$^+$ Found 596.0.

Example 216

2-Cyclopropyl-N—((S)-(7-((R)-cyclopropyl(4,4,4-trifluorobutanamido)methyl)imidazo[1,2-b]pyridazin-2-yl)(4,4-difluorocyclohexyl)methyl)pyrimidine-4-carboxamide

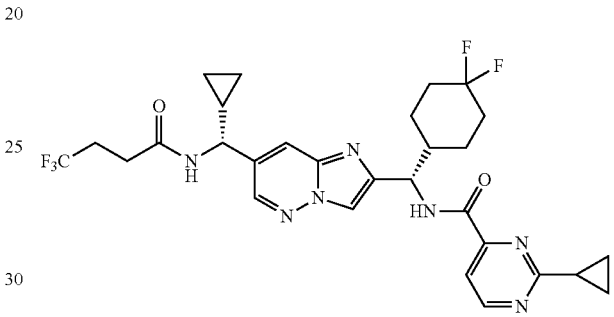

The title compound was prepared as described in the synthesis of Example 163, using 2-cyclopropylpyrimidine-4-carboxylic acid in place of 3-(2-oxopyrrolidin-1-yl)benzoic acid to provide the title compound. $^1$H NMR (500 MHz, CD$_3$OD) δ 8.81 (d, J=5.0 Hz, 1H), 8.47 (d, J=2.0 Hz, 1H), 8.13 (s, 1H), 7.88-7.90 (m, 1H), 7.78 (d, J=5.0 Hz, 1H), 5.25 (d, J=8.3 Hz, 1H), 4.28 (d, J=9.5 Hz, 1H), 2.57-2.59 (m, 2H), 2.48-2.50 (m, 2H), 2.34-2.36 (m, 1H), 2.21-2.24 (m, 1H), 2.10-2.11 (m, 1H), 1.97-1.99 (m, 2H), 1.75-1.77 (m, 2H), 1.62-1.64 (m, 1H), 1.47-1.49 (m, 1H), 1.38-1.40 (m, 1H), 1.25-1.26 (m, 1H), 1.19-1.21 (m, 1H), 1.16-1.18 (m, 1H), 1.12-1.14 (m, 1H), 0.70-0.72 (m, 2H), 0.48-0.50 (m, 2H). MS (ESI) m/z: [M+H]$^+$ Found 606.2.

Example 217

N—((S)-(7-((R)-Cyclopropyl(4,4,4-trifluorobutanamido)methyl)imidazo[1,2-b]pyridazin-2-yl)(4,4-difluorocyclohexyl)methyl)-4-(trifluoromethyl)pyrimidine-2-carboxamide

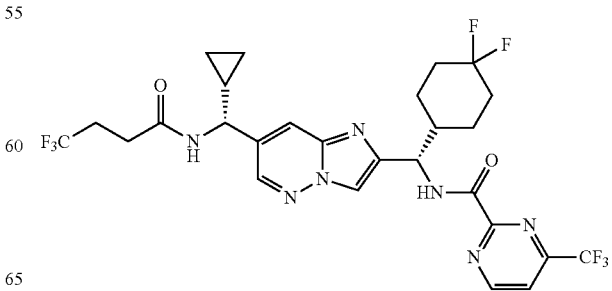

The title compound was prepared as described in the synthesis of Example 163, using 4-(trifluoromethyl)pyrimidine-2-carboxylic acid in place of 3-(2-oxopyrrolidin-1-yl)benzoic acid to provide the title compound. $^1$H NMR (500 MHz, CD$_3$OD) δ 9.25-9.27 (m, 1H), 8.44-8.47 (m, 1H), 8.15-8.16 (m, 1H), 8.06-8.07 (m, 1H), 7.87-7.89 (m, 1H), 5.31-5.33 (m, 1H), 4.27-4.28 (m, 1H), 2.55-2.57 (m, 2H), 2.48-2.50 (m, 2H), 2.27-2.28 (m, 1H), 2.08-2.10 (m, 1H), 2.00-2.02 (m, 2H), 1.78-1.80 (m, 2H), 1.65-1.66 (m, 1H), 1.49-1.51 (m, 1H), 1.39-1.41 (m, 1H), 1.25-1.26 (m, 1H), 0.68-0.70 (m, 2H), 0.48-0.50 (m, 2H). MS (ESI) m/z: [M+H]$^+$ Found 634.4.

Example 218

N—((S)-(7-((R)-Cyclopropyl(4,4,4-trifluorobutanamido)methyl)imidazo[1,2-b]pyridazin-2-yl)(4,4-difluorocyclohexyl)methyl)-6-methylpyrimidine-4-carboxamide

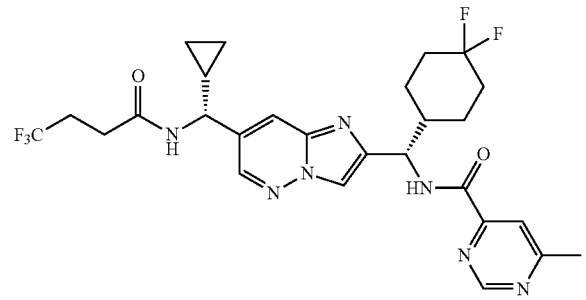 [SMILES: Cc1cc(C(=O)N[C@H](c2cn3ncc([C@H](NC(=O)CCC(F)(F)F)C4CC4)cc3n2)C2CCC(F)(F)CC2)ncn1]

The title compound was prepared as described in the synthesis of Example 163, using 6-methylpyrimidine-4-carboxylic acid in place of 3-(2-oxopyrrolidin-1-yl)benzoic acid to provide the title compound. $^1$H NMR (500 MHz, CD$_3$OD) δ 9.13 (s, 1H), 8.47 (d, J=2.1 Hz, 1H), 8.13 (s, 1H), 7.98 (s, 1H), 7.89 (s, 1H), 5.27 (d, J=8.3 Hz, 1H), 4.28 (d, J=9.5 Hz, 1H), 2.63 (s, 3H), 2.56-2.58 (m, 2H), 2.48-2.50 (m, 2H), 2.21-2.24 (m, 1H), 2.06-2.09 (m, 2H), 1.95-1.97 (m, 1H), 1.76-1.79 (m, 2H), 1.63-1.65 (m, 1H), 1.45-1.48 (m, 1H), 1.36-1.39 (m, 1H), 1.24-1.26 (m, 1H), 0.70-0.72 (m, 2H), 0.48-0.50 (m, 2H). MS (ESI) m/z: [M+H]$^+$ Found 580.2.

Example 219

N—((S)-(7-((R)-Cyclopropyl(4,4,4-trifluorobutanamido)methyl)imidazo[1,2-b]pyridazin-2-yl)(4,4-difluorocyclohexyl)methyl)-3-methylpyrazine-2-carboxamide

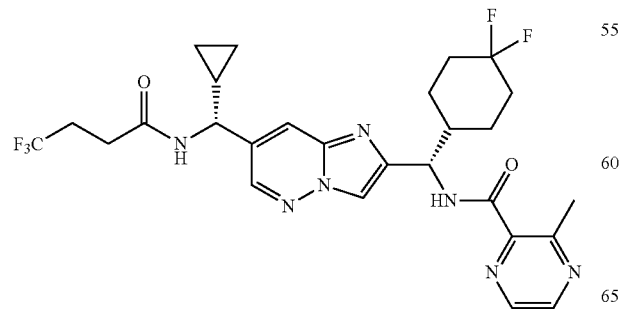

The title compound was prepared as described in the synthesis of Example 163, using 3-methylpyrazine-2-carboxylic acid in place of 3-(2-oxopyrrolidin-1-yl)benzoic acid to provide the title compound. $^1$H NMR (500 MHz, CD$_3$OD) δ 8.62 (d, J=2.4 Hz, 1H), 8.53-8.51 (m, 1H), 8.47 (d, J=2.2 Hz, 1H), 8.12 (s, 1H), 7.89-7.87 (m, 1H), 5.27 (d, J=8.3 Hz, 1H), 4.28 (d, J=9.5 Hz, 1H), 2.82 (s, 3H), 2.56-2.58 (m, 2H), 2.48-2.50 (m, 2H), 2.21-2.23 (m, 1H), 2.00-2.04 (m, 3H), 1.75-1.78 (m, 2H), 1.64-1.69 (m, 1H), 1.48-1.50 (m, 1H), 1.40-1.42 (m, 1H), 1.24-1.26 (m, 1H), 0.69-0.71 (m, 2H), 0.48-0.50 (m, 2H). MS (ESI) m/z: [M+H]$^+$ Found 580.0.

Example 220

N—((S)-(7-((R)-Cyclopropyl(4,4,4-trifluorobutanamido)methyl)imidazo[1,2-b]pyridazin-2-yl)(4,4-difluorocyclohexyl)methyl)-6-methylpyrazine-2-carboxamide

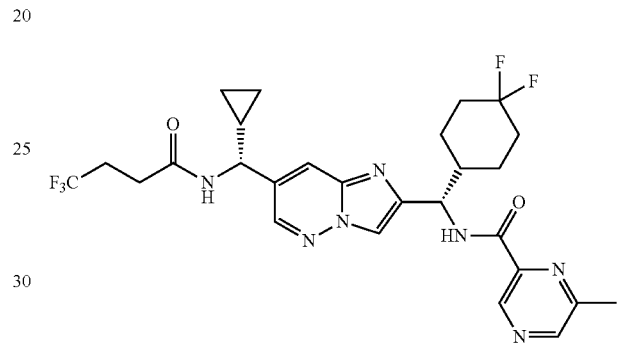

The title compound was prepared as described in the synthesis of Example 163, using 6-methylpyrazine-2-carboxylic acid in place of 3-(2-oxopyrrolidin-1-yl)benzoic acid to provide the title compound. $^1$H NMR (500 MHz, CD$_3$OD) δ 9.04 (s, 1H), 8.70 (s, 1H), 8.45-8.47 (m, 1H), 8.14 (s, 1H), 7.87-7.89 (m, 1H), 5.29 (d, J=8.5 Hz, 1H), 4.28 (d, J=9.5 Hz, 1H), 2.66 (s, 3H), 2.56-2.58 (m, 2H), 2.48-2.50 (m, 2H), 2.23-2.25 (m, 1H), 2.07-2.09 (m, 1H), 1.98-2.00 (m, 2H), 1.76-1.78 (m, 2H), 1.62-1.64 (m, 1H), 1.48-1.50 (m, 1H), 1.39-1.41 (m, 1H), 1.19-1.24 (m, 1H), 0.69-0.71 (m, 2H), 0.48-0.50 (m, 2H). MS (ESI) m/z: [M+H]$^+$ Found 580.2.

Example 221

N—((S)-(7-((R)-Cyclopropyl(4,4,4-trifluorobutanamido)methyl)imidazo[1,2-b]pyridazin-2-yl)(4,4-difluorocyclohexyl)methyl)-6-(trifluoromethyl)picolinamide

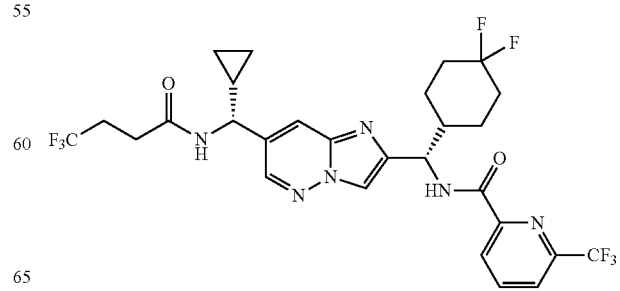

The title compound was prepared as described in the synthesis of Example 163, using 6-(trifluoromethyl)picolinic acid in place of 3-(2-oxopyrrolidin-1-yl)benzoic acid to provide the title compound. ¹H NMR (500 MHz, CD₃OD) δ 8.45-8.47 (m, 1H), 8.36 (d, J=7.9 Hz, 1H), 8.24 (t, J=7.9 Hz, 1H), 8.14 (s, 1H), 8.01 (d, J=7.8 Hz, 1H), 7.90 (s, 1H), 5.28 (d, J=8.8 Hz, 1H), 4.28 (d, J=9.6 Hz, 1H), 2.55-2.57 (m, 2H), 2.47-2.49 (m, 2H), 2.25-2.27 (m, 1H), 2.09-2.10 (m, 1H), 2.01-2.03 (m, 2H), 1.77-1.80 (m, 2H), 1.62-1.64 (m, 1H), 1.47-1.49 (m, 1H), 1.38-1.40 (m, 1H), 1.25-1.26 (m, 1H), 0.69-0.71 (m, 2H), 0.48-0.50 (m, 2H). MS (ESI) m/z: [M+H]⁺ Found 633.2.

Example 222

N—((S)-(7-((R)-Cyclopropyl(4,4,4-trifluorobutanamido)methyl)imidazo[1,2-b]pyridazin-2-yl)(4,4-difluorocyclohexyl)methyl)-4-methylpyrimidine-5-carboxamide

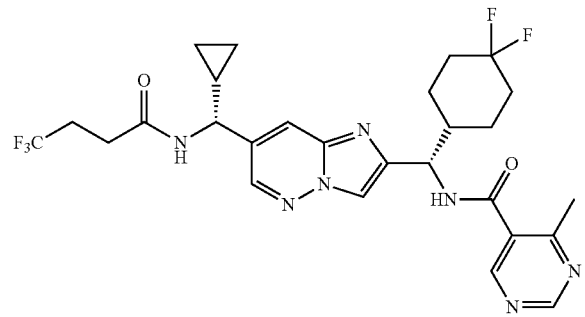 [SMILES: Cc1ncncc1C(=O)N[C@H](c1cn2ncc([C@H](NC(=O)CCC(F)(F)F)C3CC3)cc2n1)C1CCC(F)(F)CC1]

The title compound was prepared as described in the synthesis of Example 163, using 4-methylpyrimidine-5-carboxylic acid in place of 3-(2-oxopyrrolidin-1-yl)benzoic acid to provide the title compound. ¹H NMR (500 MHz, CD₃OD) δ 9.06 (s, 1H), 8.73 (s, 1H), 8.48 (d, J=2.1 Hz, 1H), 8.11 (s, 1H), 7.89 (s, 1H), 5.29 (d, J=7.9 Hz, 1H), 4.28 (d, J=9.4 Hz, 1H), 2.58-2.60 (m, 1H), 2.57 (s, 3H), 2.53-2.55 (m, 1H), 2.48-2.50 (m, 2H), 2.20-2.23 (m, 1H), 2.07-2.09 (m, 2H), 1.96-1.99 (m, 1H), 1.80-1.83 (m, 1H), 1.76-1.78 (m, 1H), 1.69-1.71 (m, 1H), 1.53-1.56 (m, 1H), 1.42-1.46 (m, 1H), 1.25-1.27 (m, 1H), 0.70-0.72 (m, 2H), 0.49-0.51 (m, 2H). MS (ESI) m/z: [M+H]⁺ Found 580.0.

Example 223

N—((S)-(7-((R)-Cyclopropyl(4,4,4-trifluorobutanamido)methyl)imidazo[1,2-b]pyridazin-2-yl)(4,4-difluorocyclohexyl)methyl)pyrazine-2-carboxamide

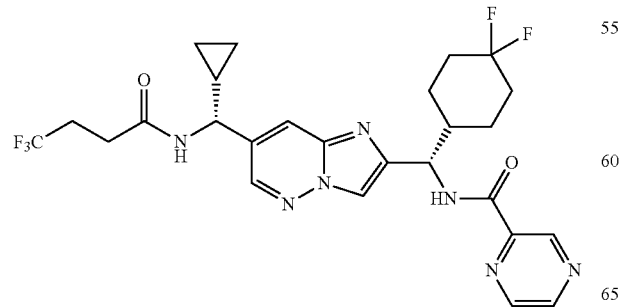

The title compound was prepared as described in the synthesis of Example 163, using pyrazine-2-carboxylic acid in place of 3-(2-oxopyrrolidin-1-yl)benzoic acid to provide the title compound. ¹H NMR (500 MHz, CD₃OD) δ 9.25 (s, 1H), 8.80 (d, J=2.5 Hz, 1H), 8.68-8.71 (m, 1H), 8.47 (d, J=2.1 Hz, 1H), 8.14 (s, 1H), 7.85-7.88 (m, 1H), 5.30 (d, J=8.3 Hz, 1H), 4.27 (d, J=9.4 Hz, 1H), 2.55-2.59 (m, 2H), 2.49-2.51 (m, 2H), 2.23-2.25 (m, 1H), 2.05-2.08 (m, 1H), 1.96-2.00 (m, 2H), 1.76-1.79 (m, 2H), 1.63-1.66 (m, 1H), 1.48-1.50 (m, 1H), 1.36-1.40 (m, 1H), 1.24-1.28 (m, 1H), 0.69-0.71 (m, 2H), 0.48-0.50 (m, 2H). MS (ESI) m/z: [M+H]⁺ Found 566.0.

Example 224

N—((S)-(7-((R)-Cyclopropyl(4,4,4-trifluorobutanamido)methyl)imidazo[1,2-b]pyridazin-2-yl)(4,4-difluorocyclohexyl)methyl)-6-methylpicolinamide

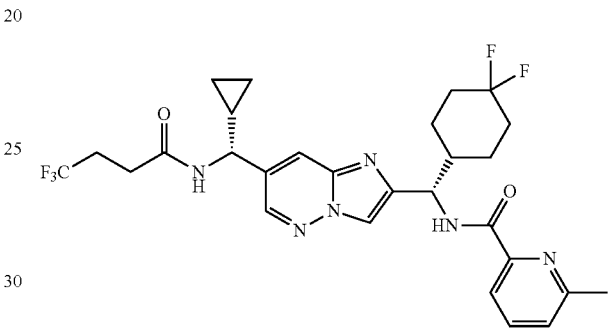

The title compound was prepared as described in the synthesis of Example 163, using 6-methylpicolinic acid in place of 3-(2-oxopyrrolidin-1-yl)benzoic acid to provide the title compound. ¹H NMR (500 MHz, CD₃OD) δ 8.47 (d, J=2.2 Hz, 1H), 8.13 (s, 1H), 7.87-7.90 (m, 2H), 7.83 (t, J=7.7 Hz, 1H), 7.43 (d, J=7.7 Hz, 1H), 5.26 (d, J=8.4 Hz, 1H), 4.28 (d, J=9.5 Hz, 1H), 2.61 (s, 3H), 2.55-2.58 (m, 2H), 2.47-2.56 (m, 2H), 2.20-2.23 (m, 1H), 2.06-2.09 (m, 1H), 1.98-2.00 (m, 2H), 1.75-1.77 (m, 2H), 1.60-1.63 (m, 1H), 1.48-1.50 (m, 1H), 1.38-1.40 (m, 1H), 1.24-1.26 (m, 1H), 0.69-0.71 (m, 2H), 0.48-0.50 (m, 2H). MS (ESI) m/z: [M+H]⁺ Found 579.2.

Example 225

4-Cyano-N—((S)-(7-((R)-cyclopropyl(4,4,4-trifluorobutanamido)methyl)imidazo[1,2-b]pyridazin-2-yl)(4,4-difluorocyclohexyl)methyl)nicotinamide

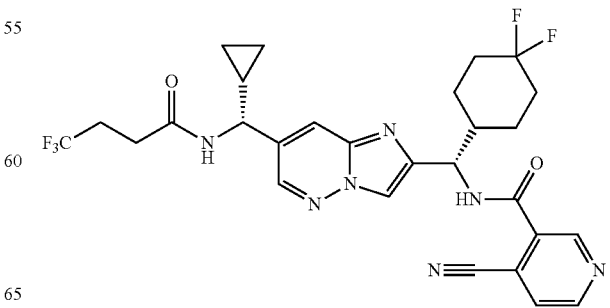

The title compound was prepared as described in the synthesis of Example 163, using 4-cyanonicotinic acid in place of 3-(2-oxopyrrolidin-1-yl)benzoic acid to provide the title compound. ¹H NMR (500 MHz, CD₃OD) δ 9.03-9.05 (m, 1H), 8.94-8.96 (m, 1H), 8.45-8.46 (m, 1H), 8.28-8.29 (m, 1H), 7.99-8.00 (m, 1H), 7.84-7.86 (m, 1H), 5.55-5.56 (m, 1H), 4.26-4.28 (m, 1H), 3.05-3.07 (m, 1H), 2.53-2.55 (m, 2H), 2.47-2.49 (m, 2H), 2.04-2.05 (m, 2H), 1.85-1.86 (m, 2H), 1.75-1.77 (m, 2H), 1.42-1.43 (m, 2H), 1.23-1.24 (m, 1H), 0.67-0.69 (m, 2H), 0.47-0.49 (m, 2H). MS (ESI) m/z: [M+H]⁺ Found 590.0.

Example 226

N—((S)-(7-((R)-Cyclopropyl(4,4,4-trifluorobutanamido)methyl)imidazo[1,2-b]pyridazin-2-yl)(4,4-difluorocyclohexyl)methyl)-6-methoxypicolinamide

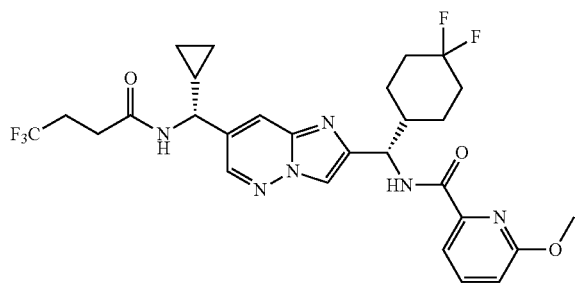

The title compound was prepared as described in the synthesis of Example 163, using 6-methoxypicolinic acid in place of 3-(2-oxopyrrolidin-1-yl)benzoic acid to provide the title compound. ¹H NMR (500 MHz, CD₃OD) δ 8.47 (d, J=2.1 Hz, 1H), 8.12 (s, 1H), 7.88 (s, 1H), 7.82 (t, J=7.8, 1H), 7.69 (d, J=7.3 Hz, 1H), 6.99 (d, J=8.3 Hz, 1H), 5.27 (d, J=8.0 Hz, 1H), 4.28 (d, J=9.5 Hz, 1H), 4.05 (s, 3H), 2.55-2.57 (m, 2H), 2.49-2.50 (m, 2H), 2.23-2.25 (m, 1H), 2.09-2.10 (m, 1H), 2.00-2.02 (m, 2H), 1.75-1.77 (m, 2H), 1.66-1.68 (m, 1H), 1.51-1.52 (m, 1H), 1.42-1.45 (m, 2H), 1.25-1.26 (m, 1H), 0.69-0.71 (m, 2H), 0.48-0.50 (m, 2H). MS (ESI) m/z: [M+H]⁺ Found 595.2.

Example 227

N—((S)-(7-((R)-Cyclopropyl(4,4,4-trifluorobutanamido)methyl)imidazo[1,2-b]pyridazin-2-yl)(4,4-difluorocyclohexyl)methyl)-6-isopropoxypicolinamide

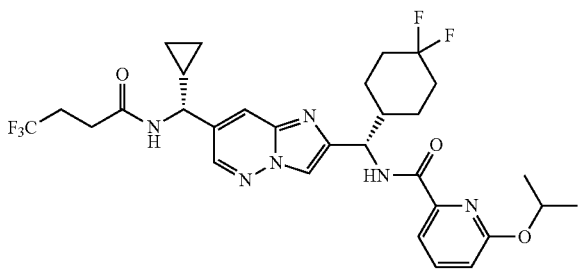 [SMILES: CC(C)Oc1cccc(C(=O)N[C@H](c2cn3ncc([C@H](NC(=O)CCC(F)(F)F)C4CC4)cc3n2)C2CCC(F)(F)CC2)n1]

The title compound was prepared as described in the synthesis of Example 163, using 6-isopropoxypicolinic acid in place of 3-(2-oxopyrrolidin-1-yl)benzoic acid to provide the title compound. ¹H NMR (500 MHz, CD₃OD) δ 8.45-8.47 (m, 1H), 8.11 (s, 1H), 7.87 (s, 1H), 7.79-7.81 (m, 1H), 7.63-7.65 (m, 1H), 6.90-6.92 (m, 1H), 5.45-5.47 (m, 1H), 5.25-5.27 (m, 1H), 4.25-4.28 (m, 1H), 2.56-2.59 (m, 2H), 2.48-2.50 (m, 2H), 2.21-2.23 (m, 1H), 2.05-2.07 (m, 2H), 1.91-1.94 (m, 1H), 1.79-1.82 (m, 2H), 1.69-1.71 (m, 1H), 1.48-1.50 (m, 1H), 1.37-1.40 (m, 7H), 1.25-1.26 (m, 1H), 0.69-0.71 (m, 2H), 0.48-0.50 (m, 2H). MS (ESI) m/z: [M+H]⁺ Found 623.3.

Example 228

N—((S)-(7-((R)-Cyclopropyl(4,4,4-trifluorobutanamido)methyl)imidazo[1,2-b]pyridazin-2-yl)(4,4-difluorocyclohexyl)methyl)-6-ethylpicolinamide

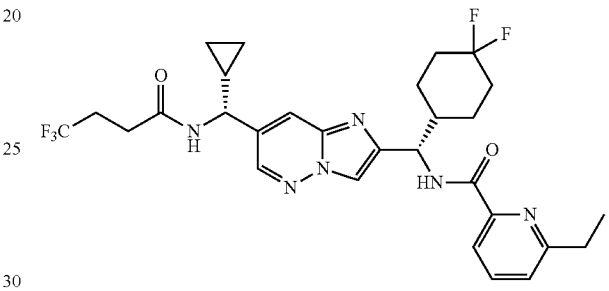

The title compound was prepared as described in the synthesis of Example 163, using 6-ethylpicolinic acid in place of 3-(2-oxopyrrolidin-1-yl)benzoic acid to provide the title compound. ¹H NMR (500 MHz, CD₃OD) δ 8.47 (d, J=2.0 Hz, 1H), 8.12 (s, 1H), 7.91-7.92 (m, 2H), 7.86 (t, J=7.7 Hz, 1H), 7.45 (d, J=7.7 Hz, 1H), 5.27 (d, J=8.3 Hz, 1H), 4.28 (d, J=9.4 Hz, 1H), 2.90 (q, J=7.6 Hz, 2H), 2.55-2.56 (m, 2H), 2.48-2.50 (m, 2H), 2.25-2.26 (m, 1H), 2.09-2.11 (m, 1H), 1.97-1.98 (m, 2H), 1.79-1.81 (m, 2H), 1.64 (d, J=13.7 Hz, 1H), 1.49-1.51 (m, 1H), 1.38-1.40 (m, 1H), 1.35 (t, J=7.6 Hz, 3H), 1.25-1.26 (m, 1H), 0.69-0.71 (m, 2H), 0.48-0.50 (m, 2H). MS (ESI) m/z: [M+H]⁺ Found 593.2.

Example 229

N—((S)-(7-((R)-Cyclopropyl(4,4,4-trifluorobutanamido)methyl)imidazo[1,2-b]pyridazin-2-yl)(4,4-difluorocyclohexyl)methyl)-6-(difluoromethyl)picolinamide

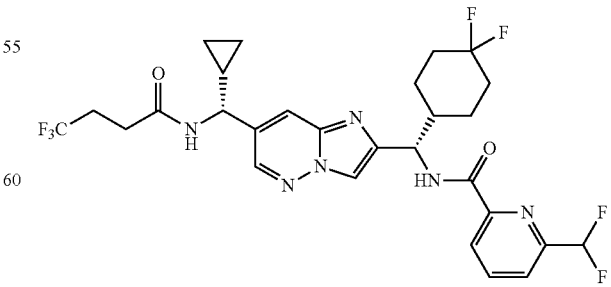

The title compound was prepared as described in the synthesis of Example 163, using 6-(difluoromethyl)picolinic acid in place of 3-(2-oxopyrrolidin-1-yl)benzoic acid to provide the title compound. ¹H NMR (500 MHz, CD₃OD) δ 8.47 (d, J=2.0 Hz, 1H), 8.25 (d, J=7.8 Hz, 1H), 8.17 (t, J=7.8 Hz, 1H), 8.14 (s, 1H), 7.87-7.89 (m, 2H), 6.83 (t, J=55.1 Hz, 1H), 5.28 (d, J=8.5 Hz, 1H), 4.28 (d, J=9.5 Hz, 1H), 2.54-2.56 (m, 2H), 2.47-2.49 (m, 2H), 2.24-2.26 (m, 1H), 2.07-2.09 (m, 1H), 2.00-2.01 (m, 2H), 1.76-1.78 (m, 2H), 1.63-1.65 (m, 1H), 1.47-1.49 (m, 1H), 1.38-1.39 (m, 1H), 1.24-1.26 (m, 1H), 0.69-0.71 (m, 2H), 0.48-0.50 (m, 2H). MS (ESI) m/z: [M+H]⁺ Found 615.4.

Example 230

N—((S)-(7-((R)-Cyclopropyl(4,4-trifluorobutanamido)methyl)imidazo[1,2-b]pyridazin-2-yl)(4,4-difluorocyclohexyl)methyl)-6-(1,1-difluoroethyl)picolinamide

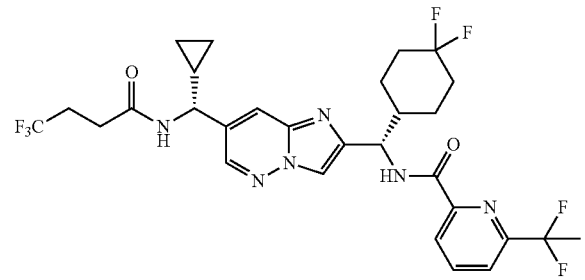 [SMILES: CC(F)(F)c1cccc(C(=O)N[C@H](c2cn3ncc([C@H](NC(=O)CCC(F)(F)F)C4CC4)cc3n2)C2CCC(F)(F)CC2)n1]

The title compound was prepared as described in the synthesis of Example 163, using 6-(1,1-difluoroethyl)picolinic acid in place of 3-(2-oxopyrrolidin-1-yl)benzoic acid to provide the title compound. ¹H NMR (500 MHz, CD₃OD) δ 8.47 (d, J=2.1 Hz, 1H), 8.21 (d, J=7.8 Hz, 1H), 8.12-8.14 (m, 2H), 7.90-7.93 (m, 2H), 5.28 (d, J=8.4 Hz, 1H), 4.28 (d, J=9.5 Hz, 1H), 2.55-2.56 (m, 2H), 2.45-2.48 (m, 2H), 2.24-2.27 (m, 1H), 2.10-2.15 (m, 4H), 2.00-2.01 (m, 2H), 1.80-1.83 (m, 2H), 1.63-1.67 (m, 1H), 1.48-1.50 (m, 1H), 1.38-1.40 (m, 1H), 1.25-1.26 (m, 1H), 0.69-0.71 (m, 2H), 0.48-0.50 (m, 2H). MS (ESI) m/z: [M+H]⁺ Found 629.2.

Example 231

N—((S)-(7-((R)-Cyclopropyl(4,4-trifluorobutanamido)methyl)imidazo[1,2-b]pyridazin-2-yl)(4,4-difluorocyclohexyl)methyl)-2-(2,2,2-trifluoroethyl)benzamide

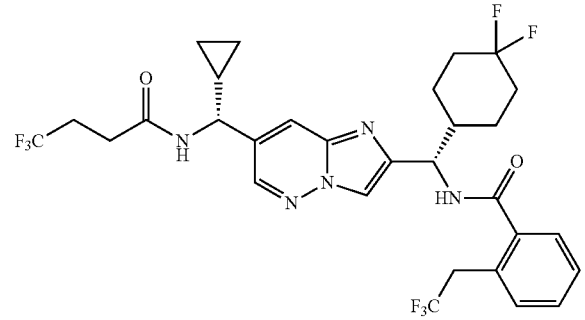 [SMILES: O=C(CCC(F)(F)F)N[C@@H](c1cnn2cc([C@@H](NC(=O)c3ccccc3CC(F)(F)F)C3CCC(F)(F)CC3)nc2c1)C1CC1]

The title compound was prepare as described in the synthesis of Example 163, using 2-(2,2,2-trifluoroethyl)benzoic acid in place of 3-(2-oxopyrrolidin-1-yl)benzoic acid to provide the title compound. ¹H NMR (500 MHz, CD₃OD) δ 8.47 (d, J=2.3 Hz, 1H), 8.07 (s, 1H), 7.88 (s, 1H), 7.50-7.52 (m, 1H), 7.47-7.48 (m, 1H), 7.41-7.44 (m, 2H), 5.27 (d, J=8.1 Hz, 1H), 4.28 (d, J=9.5 Hz, 1H), 3.74-3.78 (m, 2H), 2.54-2.58 (m, 2H), 2.48-2.50 (m, 2H), 2.19-2.21 (m, 1H), 2.06-2.08 (m, 2H), 1.98-2.00 (m, 1H), 1.76-1.78 (m, 2H), 1.66-1.68 (m, 1H), 1.50-1.52 (m, 1H), 1.42-1.44 (m, 1H), 1.24-1.26 (m, 1H), 0.70-0.72 (m, 2H), 0.48-0.51 (m, 2H). MS (ESI) m/z: [M+H]⁺ Found 646.4.

Example 232

N—((S)-(7-((R)-Cyclopropyl(4,4-trifluorobutanamido)methyl)imidazo[1,2-b]pyridazin-2-yl)(4,4-difluorocyclohexyl)methyl)-5-isopropylisoxazole-4-carboxamide

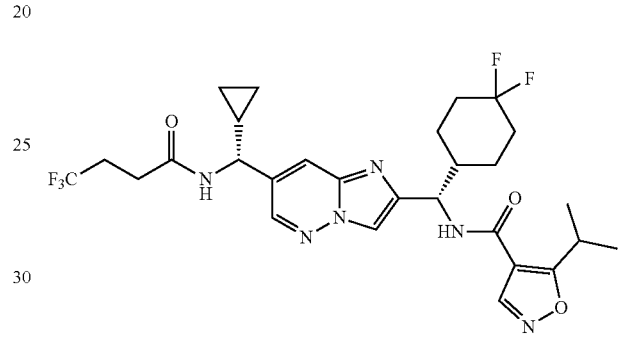

The title compound was prepared as described in the synthesis of Example 84, using 5-isopropylisoxazole-4-carboxylic acid in place of 5-cyclopropylisoxazole-4-carboxylic acid to provide the title compound. ¹H NMR (500 MHz, CD₃OD) δ 8.76 (s, 1H), 8.46 (d, J=2.0 Hz, 1H), 8.09 (s, 1H), 7.83-7.92 (m, 1H), 5.23 (d, J=8.5 Hz, 1H), 4.28 (d, J=9.5 Hz, 1H), 3.75-3.89 (m, 1H), 2.45-2.62 (m, 4H), 2.14-2.24 (m, 1H), 2.05-2.13 (m, 1H), 1.94-2.05 (m, 2H), 1.70-1.85 (m, 2H), 1.58-1.70 (m, 1H), 1.42-1.54 (m, 1H), 1.23-1.39 (m, 8H), 0.66-0.74 (m, 2H), 0.46-0.53 (m, 2H). MS (ESI) m/z: [M+H]⁺ Found 597.1.

Example 233

N—((S)-(7-((R)-Cyclopropyl(4,4-trifluorobutanamido)methyl)imidazo[1,2-b]pyridazin-2-yl)(4,4-difluorocyclohexyl)methyl)-1-(ethyl-d₅)-1H-pyrazole-5-carboxamide

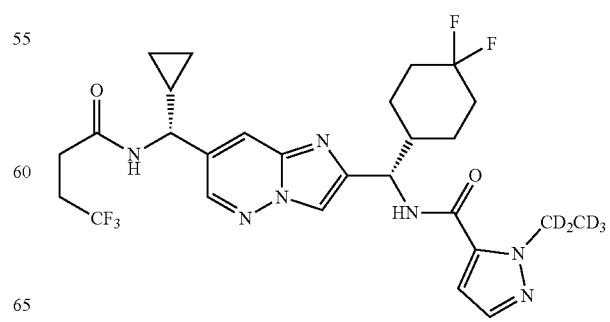

A vial was charged with a stir bar, N—((R)-(2-((S)-amino (4,4-difluorocyclohexyl)methyl)imidazo[1,2-b]pyridazin-7-yl)(cyclopropyl)methyl)-4,4,4-trifluorobutanamide (75 mg, 0.16 mmol, Intermediate 51), 1-(ethyl-d₅)-1H-pyrazole-5-carboxylic acid (23 mg, 0.16 mmol, Intermediate 204), MeCN (2.64 mL, 50.6 mmol), 1-methylimidazole (0.044 mL, 0.54 mmol), and chloro-N,N,N',N'-tetramethylformamidinium hexafluorophosphate (53 mg, 0.19 mmol). The reaction was stirred for 2 h at room temperature. The reaction mixture was filtered and purified directly by basic reverse phase HPLC (ISCO ACCQPrep, X-Bridge Prep C18 5 µm column 50×100 mm, gradient 10-70% 20 mM ammonium hydroxide (aq): Acetonitrile over 15 min) to provide the title compound as a white solid. $^1$H NMR (400 MHz, DMSO-d₆) δ 8.76-8.65 (m, 2H), 8.51 (d, J=2.1 Hz, 1H), 8.20 (s, 1H), 7.94 (d, J=2.0 Hz, 1H), 7.47 (d, J 2.0 Hz, 1H), 6.98 (d, J=2.1 Hz, 1H), 5.21-5.11 (m, 1H), 4.36-4.23 (m, 1H), 2.49-2.40 (m, 4H), 2.26-2.11 (m, 1H), 2.11-1.55 (m, 6H), 1.46-1.11 (m, 3H), 0.63-0.30 (m, 4H). MS (ESI) m/z: [M+H]⁺ Found 587.3.

Example 234

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-1-(ethyl-d₅)-1H-pyrazole-5-carboxamide

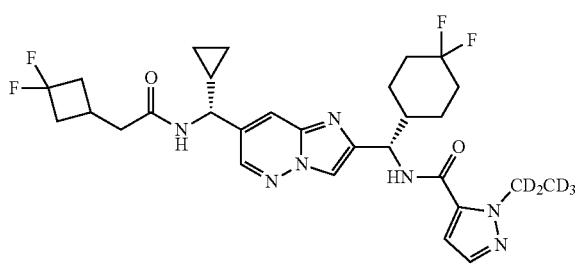

The title compound was prepared as described for the synthesis of Example 233, using N—((R)-(2-((S)-amino(4, 4-difluorocyclohexyl)methyl)imidazo[1,2-b]pyridazin-7-yl) (cyclopropyl)methyl)-2-(3,3-difluorocyclobutyl)acetamide (Intermediate 171) in place of N—((R)-(2-((S)-amino(4,4-difluorocyclohexyl)methyl)imidazo[1,2-b]pyridazin-7-yl) (cyclopropyl)methyl)-4,4,4-trifluorobutanamide and a second purification by silica gel chromatography (0-100% (10% MeOH/EtOAc)/hexanes) to provide the title compound as a white solid. $^1$H NMR (400 MHz, DMSO-d₆) δ 8.71 (d, J=9.0 Hz, 1H), 8.59 (d, J=7.8 Hz, 1H), 8.49 (d, J=2.1 Hz, 1H), 8.20 (s, 1H), 7.92 (d, J=2.0 Hz, 1H), 7.47 (d, J=2.0 Hz, 1H), 6.98 (d, J=2.1 Hz, 1H), 5.16 (t, J=8.7 Hz, 1H), 4.27 (t, J=8.4 Hz, 1H), 2.73-2.57 (m, 2H), 2.46-2.12 (m, 6H), 2.12-1.56 (m, 6H), 1.46-1.14 (m, 3H), 0.64-0.27 (m, 4H). MS (ESI) m/z: [M+H]⁺ Found 595.3.

Example 235

N—((S)-(7-((R)-Cyclopropyl(4,4,4-trifluorobutanamido)methyl)imidazo[1,2-b]pyridazin-2-yl)(4,4-difluorocyclohexyl)methyl)-3-(oxetan-3-yl)isoxazole-4-carboxamide

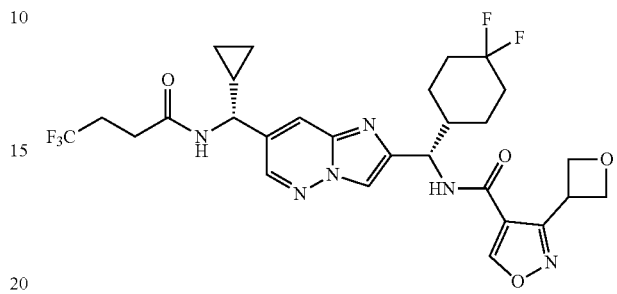

The title compound was prepared as described for the synthesis of Example 47, using 3-(oxetan-3-yl)isoxazole-4-carboxylic acid (Intermediate 206) in place of 1-(3-fluoropropyl)-1H-1,2,4-triazole-5-carboxylic acid, and the mixture was stirred at 40° C. for 2 h instead of rt for 3 h followed by 40° C. for 18.5 h, to provide the title compound as a white solid. $^1$H NMR (400 MHz, CDCl₃) δ 8.87 (s, 1H), 8.34 (d, J=2.1 Hz, 1H), 7.86-7.76 (m, 2H), 7.17 (d, J=8.6 Hz, 1H), 6.16 (d, J=6.7 Hz, 1H), 5.25-5.17 (m, 1H), 5.10-5.02 (m, 2H), 5.03-4.91 (m, 2H), 4.66-4.57 (m, 1H), 4.29 (dd, J=9.5, 6.7 Hz, 1H), 2.57-2.44 (m, 4H), 2.19-1.99 (m, 3H), 1.97-1.93 (m, 1H), 1.81-1.59 (m, 3H), 1.54-1.41 (m, 1H), 1.36-1.26 (m, 1H), 1.22-1.13 (m, 1H), 0.80-0.70 (m, 2H), 0.56-0.43 (m, 2H). MS (ESI) m/z: [M+H]⁺ Found 611.1.

Example 236

N—((S)-(7-((R)-Cyclopropyl(4,4,4-trifluorobutanamido)methyl)imidazo[1,2-b]pyridazin-2-yl)(4,4-difluorocyclohexyl)methyl)-3-(cyclopropylmethyl) isoxazole-4-carboxamide

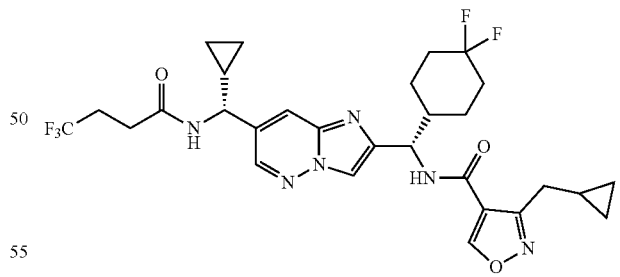

The title compound was prepared as described for the synthesis of Example 47, using 3-(cyclopropylmethyl)isoxazole-4-carboxylic acid (Intermediate 208) in place of 1-(3-fluoropropyl)-1H-1,2,4-triazole-5-carboxylic acid, and the mixture was stirred at rt for 2 h followed by 40° C. for 30 min instead of rt for 3 h followed by 40° C. for 18.5 h, to provide the title compound as a cream-colored solid. $^1$H NMR (500 MHz, CDCl₃) δ 8.74 (s, 1H), 8.34 (d, J=2.1 Hz, 1H), 7.84 (d, J=0.7 Hz, 1H), 7.82-7.75 (m, 1H), 6.99 (d, J=8.4 Hz, 1H), 6.08 (d, J=6.7 Hz, 1H), 5.29-5.22 (m, 1H), 4.34-4.27 (m, 1H), 2.86 (dd, J=7.0, 1.7 Hz, 2H), 2.56-2.47 (m, 4H), 2.16-1.94 (m, 4H), 1.75-1.59 (m, 3H), 1.54-1.44 (m, 1H), 1.38-1.29 (m, 1H), 1.21-1.12 (m, 2H), 0.80-0.72 (m, 2H), 0.54-0.46 (m, 4H), 0.26-0.21 (m, 2H). MS (ESI) m/z: [M+H]⁺ Found 609.2.

Example 237

N—((S)-(7-((R)-Cyclopropyl(4,4,4-trifluorobutanamido)methyl)imidazo[1,2-b]pyridazin-2-yl)(4,4-difluorocyclohexyl)methyl)-3-((difluoromethoxy)methyl)isoxazole-4-carboxamide

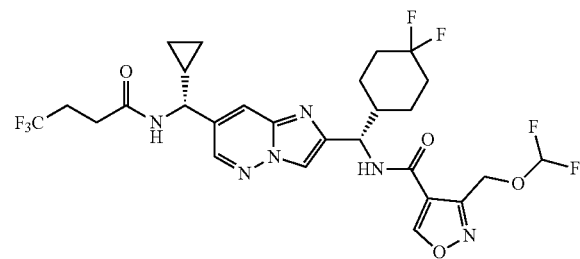 [SMILES: O=C(CCC(F)(F)F)N[C@@H](c1cnn2cc([C@@H](NC(=O)c3conc3COC(F)F)C3CCC(F)(F)CC3)nc2c1)C1CC1]

The title compound was prepared as described for the synthesis of Example 47, using 3-((difluoromethoxy)methyl)isoxazole-4-carboxylic acid (Intermediate 214) in place of 1-(3-fluoropropyl)-1H-1,2,4-triazole-5-carboxylic acid, and the mixture was stirred at 40° C. for 2 h instead of rt for 3 h followed by 40° C. for 18.5 h, to provide the title compound as a white solid. ¹H NMR (500 MHz, CDCl₃) δ 8.93 (s, 1H), 8.35 (d, J=2.2 Hz, 1H), 7.85 (s, 1H), 7.82-7.78 (m, 1H), 7.62-7.55 (m, 1H), 6.47 (t, J=73.3 Hz, 1H), 6.14 (d, J=6.7 Hz, 1H), 5.30-5.24 (m, 1H), 5.22 (d, J=1.9 Hz, 2H), 4.32-4.26 (m, 1H), 2.54-2.47 (m, 4H), 2.17-2.03 (m, 3H), 1.99-1.92 (m, 1H), 1.78-1.62 (m, 3H), 1.53-1.32 (m, 2H), 1.21-1.14 (m, 1H), 0.79-0.72 (m, 2H), 0.54-0.45 (m, 2H). MS (ESI) m/z: [M+H]⁺ Found 635.2.

Example 238

N—((S)-(7-((R)-Cyclopropyl(4,4,4-trifluorobutanamido)methyl)imidazo[1,2-b]pyridazin-2-yl)(4,4-difluorocyclohexyl)methyl)-3-ethoxyisoxazole-4-carboxamide

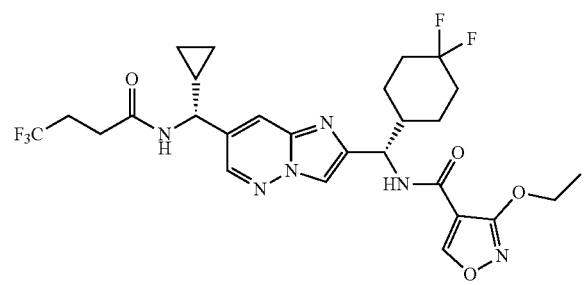 [SMILES: CCOc1nocc1C(=O)N[C@H](c1cn2ncc([C@H](NC(=O)CCC(F)(F)F)C3CC3)cc2n1)C1CCC(F)(F)CC1]

The title compound was prepared as described for the synthesis of Example 47, using 3-ethoxyisoxazole-4-carboxylic acid (Intermediate 217) in place of 1-(3-fluoropropyl)-1H-1,2,4-triazole-5-carboxylic acid, and the mixture was stirred at 40° C. for 2 h instead of rt for 3 h followed by 40° C. for 18.5 h, to provide the title compound as a white solid. ¹H NMR (500 MHz, CDCl₃) δ 8.71 (s, 1H), 8.33 (d, J=2.2 Hz, 1H), 7.83 (s, 1H), 7.82-7.79 (m, 1H), 7.55 (d, J=8.5 Hz, 1H), 6.17 (d, J=6.9 Hz, 1H), 5.28 (dd, J=8.5, 6.7 Hz, 1H), 4.53-4.44 (m, 2H), 4.35-4.29 (m, 1H), 2.55-2.46 (m, 4H), 2.19-2.06 (m, 3H), 1.91-1.87 (m, 1H), 1.77-1.65 (m, 3H), 1.58-1.53 (m, 3H), 1.51-1.38 (m, 2H), 1.20-1.13 (m, 1H), 0.79-0.70 (m, 2H), 0.54-0.44 (m, 2H). MS (ESI) m/z: [M+H]⁺ Found 599.2.

Example 239

N—((S)-(7-((R)-Cyclopropyl(4,4,4-trifluorobutanamido)methyl)imidazo[1,2-b]pyridazin-2-yl)(4,4-difluorocyclohexyl)methyl)-3-methoxyisoxazole-4-carboxamide

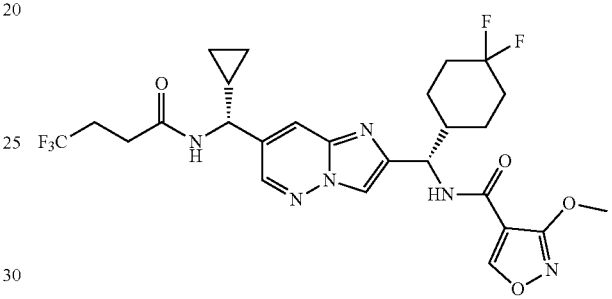

The title compound was prepared as described for the synthesis of Example 47, using 3-methoxyisoxazole-4-carboxylic acid (Intermediate 219) in place of 1-(3-fluoropropyl)-1H-1,2,4-triazole-5-carboxylic acid, and the mixture was stirred at 40° C. for 2 h instead of rt for 3 h followed by 40° C. for 18.5 h, to provide the title compound as a white solid. ¹H NMR (500 MHz, CDCl₃) δ 8.72 (s, 1H), 8.33 (d, J=2.1 Hz, 1H), 7.87-7.83 (m, 2H), 7.37 (d, J=8.7 Hz, 1H), 6.15 (d, J=6.9 Hz, 1H), 5.30-5.24 (m, 1H), 4.36-4.29 (m, 1H), 4.16 (s, 3H), 2.56-2.48 (m, 4H), 2.18-2.10 (m, 2H), 2.09-2.04 (m, 1H), 1.96-1.88 (m, 1H), 1.76-1.64 (m, 3H), 1.52-1.36 (m, 2H), 1.21-1.12 (m, 1H), 0.79-0.71 (m, 2H), 0.53-0.45 (m, 2H). MS (ESI) m/z: [M+H]⁺ Found 585.2.

Example 240

1-Cyclopropyl-N—((S)-(7-((R)-cyclopropyl(4,4,4-trifluorobutanamido)methyl)imidazo[1,2-b]pyridazin-2-yl)(4,4-difluorocyclohexyl)methyl)-1H-pyrazole-5-carboxamide

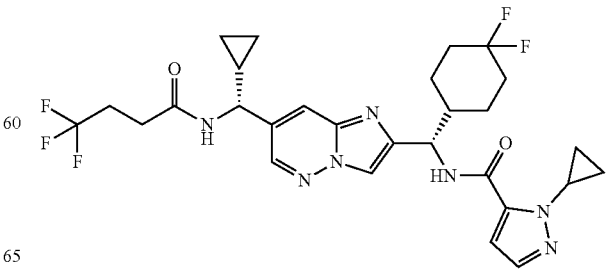

The title compound was prepared as described for the synthesis of Example 38 using 1-cyclopropyl-1H-pyrazole-5-carboxylic acid in place of 1-(3,3,3-trifluoropropyl)-1H-1,2,4-triazole-5-carboxylic acid. ¹H NMR (500 MHz, DMSO-d₆) δ 8.72 (dd, J=6.3, 8.3 Hz, 2H), 8.51 (d, J=2.1 Hz, 1H), 8.21 (s, 1H), 7.94 (d, H2.0 Hz, 1H), 7.41 (d, J=1.9 Hz, 1H), 6.92 (d, J=2.0 Hz, 1H), 5.18 (t, J=8.6 Hz, 1H), 4.43-4.37 (m, 1H), 4.30 (t, J=8.4 Hz, 1H), 2.56-2.52 (m, 1H), 2.47 (d, J=6.3 Hz, 3H), 2.24-2.13 (m, 1H), 2.11-1.94 (m, 2H), 1.93-1.85 (m, 1H), 1.85-1.68 (m, 2H), 1.68-1.59 (m, 1H), 1.46-1.34 (m, 1H), 1.33-1.17 (m, 2H), 1.11-0.99 (m, 2H), 0.97-0.85 (m, 2H), 0.62-0.46 (m, 3H), 0.41-0.34 (m, 1H). MS (ESI) m/z: [M+H]⁺ Found 594.3.

Example 241

(trans-1R*,2R*)—N—((S)-(7-((R)-Cyclopropyl((R*)-4,4,4-trifluoro-3-methylbutanamido)methyl)imidazo[1,2-b]pyridazin-2-yl)(4,4-difluorocyclohexyl)methyl)-2-(trifluoromethyl)cyclopropane-1-carboxamide

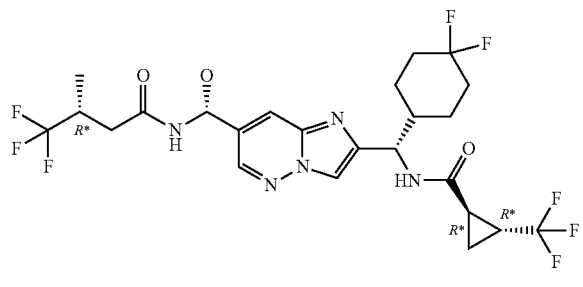

Example 242

(trans-1R*,2R*)—N—((S)-(7-((R)-Cyclopropyl((S*)-4,4,4-trifluoro-3-methylbutanamido)methyl)imidazo[1,2-b]pyridazin-2-yl)(4,4-difluorocyclohexyl)methyl)-2-(trifluoromethyl)cyclopropane-1-carboxamide

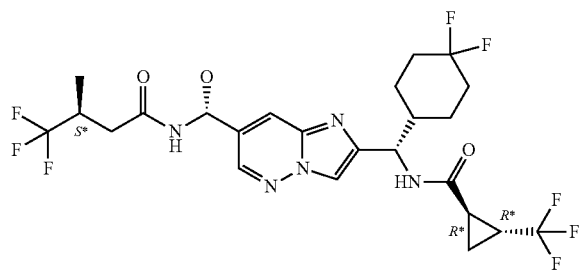

The title compounds were prepared as described for the synthesis of Example 38 using 4,4,4-trifluoro-3-methylbutanoic acid in place of 4,4,4-trifluorobutanoic acid, and trans-2-(trifluoromethyl)cyclopropane-1-carboxylic acid in place of 1-(3,3,3-trifluoropropyl)-1H-1,2,4-triazole-5-carboxylic acid. The resulting mixture of diastereomers were separated by SFC using a chiral stationary phase (Stationary phase: AD-H 2×25 cm, Mobile phase: 12% isopropanol/CO₂). The second eluting fraction afforded Example 241 as a white powder. The third eluting fraction afforded Example 242 as a white powder. Example 241: ¹H NMR (500 MHz, DMSO-d₆) δ 8.84-8.68 (m, 2H), 8.50 (d, J=2.0 Hz, 1H), 8.11 (s, 1H), 7.93 (d, J=2.0 Hz, 1H), 5.07-4.91 (m, 1H), 4.31 (t, J=8.4 Hz, 1H), 2.87-2.72 (m, 1H), 2.57-2.52 (m, 1H), 2.35-2.21 (m, 2H), 2.19-2.09 (m, 1H), 2.08-1.92 (m, 3H), 1.86-1.68 (m, 3H), 1.63-1.52 (m, 1H), 1.41-1.29 (m, 1H), 1.28-1.17 (m, 2H), 1.16-1.05 (m, 5H), 0.64-0.46 (m, 3H), 0.44-0.31 (m, 1H). MS (ESI) m/z: [M+H]⁺ Found 610.2. Example 242: ¹H NMR (500 MHz, DMSO-d₆) δ 8.86-8.71 (m, 2H), 8.51 (d, J 2.0 Hz, 1H), 8.11 (s, 1H), 7.94 (d, J=2.0 Hz, 1H), 5.12-4.85 (m, 1H), 4.31 (t, J=8.3 Hz, 1H), 2.85-2.70 (m, 1H), 2.57-2.52 (m, 1H), 2.35-2.23 (m, 2H), 2.17-2.09 (m, 1H), 2.08-1.92 (m, 3H), 1.85-1.68 (m, 3H), 1.62-1.50 (m, 1H), 1.40-1.28 (m, 1H), 1.27-1.19 (m, 2H), 1.17-1.05 (m, 2H), 1.01 (d, J=7.0 Hz, 3H), 0.64-0.45 (m, 3H), 0.43-0.35 (m, 1H). MS (ESI) m/z: [M+H]⁺ Found 610.3.

Example 243

N—((S)-(7-((R)-Cyclopropyl((R*)-4,4,4-trifluoro-3-methylbutanamido)methyl)imidazo[1,2-b]pyridazin-2-yl)(4,4-difluorocyclohexyl)methyl)-4-methyl-1,2,5-oxadiazole-3-carboxamide

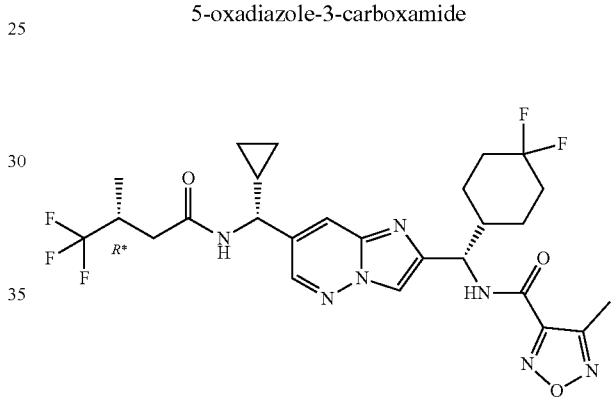

A vial was charged with a stir bar, N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide (150 mg, 0.32 mmol, Intermediate 229), DCM (7 mL), and Hünig's base (0.22 mL, 1.2 mmol). The vial was cooled to 0° C. and 4-methyl-1,2,5-oxadiazole-3-carbonyl chloride was added dropwise as a solution in DCM (0.5 mL, 0.5 mmol, 1 M in DCM, Intermediate 222). The reaction was stirred overnight as it warmed gradually to rt. The reaction was further diluted with DCM and quenched by the addition of water. The layers were separated, and the organic phase was washed with brine, dried over anhydrous MgSO₄, filtered and condensed. The crude material was purified by silica gel chromatography (0-100% EtOAc (with 10% MeOH)/hexanes). The material was further purified by basic preparative HPLC (Gemini® 5 μM C18 110 Å, 150×21.2 mm, 0-100% acetonitrile/water (with 20 mM NH₄OH). The diastereomers were separated by SFC with a chiral stationary phase (Stationary phase: Whelk 01 SS, 3 μm, 100×4.6 mm, Mobile phase: 12% methanol: isopropanol (1:1) with 0.2% isopropylamine, 88% CO₂). The third eluting peak was concentrated, taken up in minimal MeCN/water and lyophilized to afford the title compound as a white solid. ¹H NMR (500 MHz, DMSO-d₆) δ 9.41 (d, J=9.0 Hz, 1H), 8.77 (d, J 7.8 Hz, 1H), 8.52 (d, J=1.9 Hz, 1H), 8.24 (s, 1H), 7.96 (d, J=1.9 Hz, 1H), 5.19-5.13 (m, 1H), 4.36-4.22 (m, 1H), 2.82-2.70 (m, 1H), 2.47 (s, 3H), 2.31-2.23 (m, 1H), 2.22-

2.13 (m, 1H), 2.09-1.94 (m, 2H), 1.93-1.86 (m, 1H), 1.85-1.70 (m, 2H), 1.65-1.55 (m, 1H), 1.43-1.33 (m, 1H), 1.32-1.18 (m, 3H), 1.01 (d, J=7.1 Hz, 3H), 0.62-0.56 (m, 1H), 0.56-0.46 (m, 2H), 0.42-0.34 (m, 1H). MS (ESI) m/z: [M+H]⁺ Found 584.3.

Example 244

N—((S)-(7-((R)-Cyclopropyl(2-(1-(trifluoromethyl)cyclopropyl)acetamido)methyl)imidazo[1,2-b]pyridazin-2-yl)(4,4-difluorocyclohexyl)methyl)-1-isopropyl-1H-pyrazole-5-carboxamide

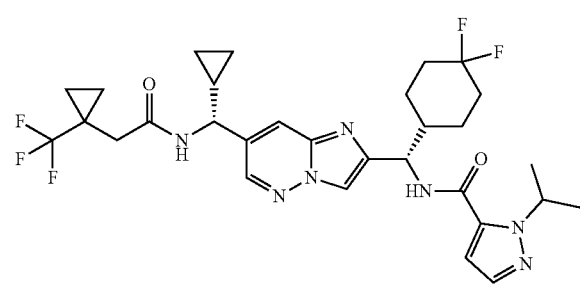 [SMILES: CC(C)n1nccc1C(=O)N[C@H](c1cn2ncc([C@H](NC(=O)CC3(C(F)(F)F)CC3)C3CC3)cc2n1)C1CCC(F)(F)CC1]

The title compound was prepared as described for the synthesis of Example 38 using 2-(1-(trifluoromethyl)cyclopropyl)acetic acid in place of 4,4,4-trifluorobutanoic acid, and 1-isopropyl-1H-pyrazole-5-carboxylic acid in place of 1-(3,3,3-trifluoropropyl)-1H-1,2,4-triazole-5-carboxylic acid. ¹H NMR (500 MHz, DMSO-d₆) δ 8.78-8.62 (m, 2H), 8.48 (d, J=2.0 Hz, 1H), 8.20 (s, 1H), 7.92 (d, J=1.9 Hz, 1H), 7.49 (d, J=1.9 Hz, 1H), 6.91 (d, J=1.9 Hz, 1H), 5.37 (spt, J=6.6 Hz, 1H), 5.19-5.07 (m, 1H), 4.31-4.19 (m, 1H), 2.56-2.52 (m, 1H), 2.48-2.44 (m, 1H), 2.24-2.13 (m, 1H), 2.10-1.93 (m, 2H), 1.92-1.84 (m, 1H), 1.84-1.69 (m, 2H), 1.66-1.58 (m, 1H), 1.43-1.31 (m, 7H), 1.31-1.18 (m, 2H), 0.95-0.85 (m, 4H), 0.63-0.46 (m, 3H), 0.41-0.32 (m, 1H). MS (ESI) m/z: [M+H]⁺ Found 622.3.

Example 245

N—((S)-(7-((R)-Cyclopropyl(2-(1-(trifluoromethyl)cyclopropyl)acetamido)methyl)imidazo[1,2-b]pyridazin-2-yl)(4,4-difluorocyclohexyl)methyl)-4-methyl-1,2,5-oxadiazole-3-carboxamide

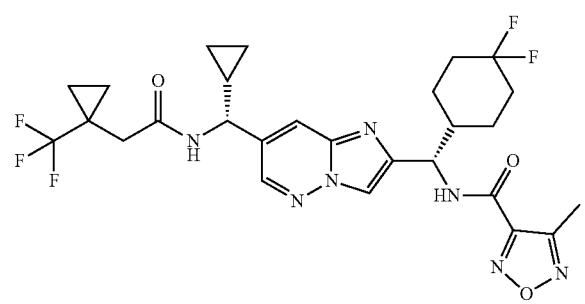 [SMILES: Cc1nonc1C(=O)N[C@H](c1cn2ncc([C@H](NC(=O)CC3(C(F)(F)F)CC3)C3CC3)cc2n1)C1CCC(F)(F)CC1]

A vial was charged with a stir bar, N—((R)-(2-((S)-amino(4,4-difluorocyclohexyl)methyl)imidazo[1,2-b]pyridazin-7-yl)(cyclopropyl)methyl)-2-(1-(trifluoromethyl)cyclopropyl)acetamide (150 mg, 0.31 mmol, Intermediate 230), 4-methyl-1,2,5-oxadiazole-3-carboxylic acid (38 mg, 0.29 mmol), and MeCN (5 mL). To this stirred solution was added 1-methylimidazole (83 µL, 1.0 mmol), and chloro-N,N,N',N'-tetramethylformamidinium hexafluorophosphate (99 mg, 0.35 mmol). The reaction was stirred for 15 min at rt. The crude reaction was poured over water and extracted with EtOAc (3×5 mL). The combined organics were washed with brine, dried over anhydrous MgSO₄, filtered and condensed. The resulting material was purified by silica gel chromatography (0-100% EtOAc (with 10% MeOH)/hexanes). The product containing fractions were concentrated, taken up in minimal MeCN/water and lyophilized to afford the title compound as a white powder. ¹H NMR (500 MHz, DMSO-d₆) δ 9.41 (d, J=9.0 Hz, 1H), 8.70 (d, J=7.8 Hz, 1H), 8.49 (d, J=2.0 Hz, 1H), 8.23 (s, 1H), 7.94 (d, J 1.9 Hz, 1H), 5.17 (t, J=8.5 Hz, 1H), 4.26 (t, J=8.4 Hz, 1H), 2.56-2.52 (m, 1H), 2.50-2.42 (m, 4H), 2.23-2.13 (m, 1H), 2.09-1.94 (m, 2H), 1.94-1.87 (m, 1H), 1.86-1.69 (m, 2H), 1.67-1.56 (m, 1H), 1.45-1.33 (m, 1H), 1.33-1.16 (m, 2H), 0.96-0.84 (m, 4H), 0.63-0.46 (m, 3H), 0.40-0.32 (m, 1H). MS (ESI) m/z: [M+H]⁺ Found 596.2.

Example 246

N—((S)-(7-((R)-(2-Cyclobutylacetamido)(cyclopropyl)methyl)imidazo[1,2-b]pyridazin-2-yl)(4,4-difluorocyclohexyl)methyl)-1-isopropyl-1H-pyrazole-5-carboxamide

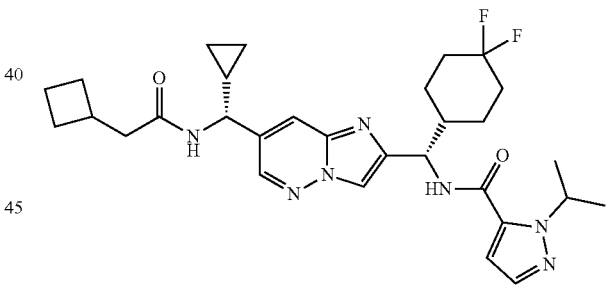

The title compound was prepared as described for the synthesis of Example 38 using 2-cyclobutylacetic acid in place of 4,4,4-trifluorobutanoic acid, and 1-isopropyl-1H-pyrazole-5-carboxylic acid in place of 1-(3,3,3-trifluoropropyl)-1H-1,2,4-triazole-5-carboxylic acid. ¹H NMR (500 MHz, DMSO-d₆) δ 8.70 (d, J=9.0 Hz, 1H), 8.47 (d, J=2.1 Hz, 1H), 8.45 (d, J=7.9 Hz, 1H), 8.19 (s, 1H), 7.92-7.87 (m, 1H), 7.48 (d, J=1.9 Hz, 1H), 6.90 (d, J=2.0 Hz, 1H), 5.34-5.25 (m, 1H), 5.14 (t, J=8.6 Hz, 1H), 4.26 (t, J=8.5 Hz, 1H), 2.60-2.53 (m, 1H), 2.31-2.22 (m, 2H), 2.21-2.12 (m, 1H), 2.09-2.02 (m, 1H), 2.01-1.92 (m, 3H), 1.91-1.84 (m, 1H), 1.84-1.71 (m, 4H), 1.70-1.58 (m, 3H), 1.43-1.31 (m, 7H), 1.30-1.14 (m, 2H), 0.60-0.43 (m, 3H), 0.38-0.31 (m, 1H). MS (ESI) m/z: [M+H]⁺ Found 568.3.

Example 247

N—((S)-(7-((R)-(2-Cyclobutylacetamido)(cyclopropyl)methyl)imidazo[1,2-b]pyridazin-2-yl)(4,4-difluorocyclohexyl)methyl)-4-methyl-1,2,5-oxadiazole-3-carboxamide

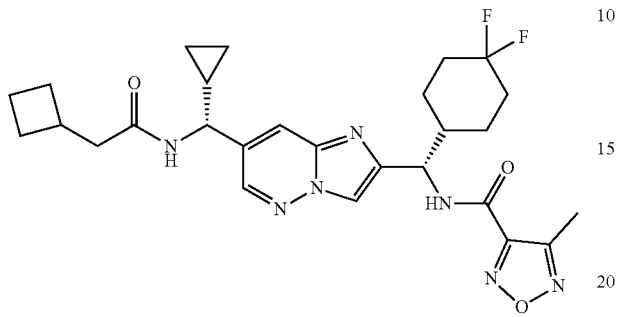

The title compound was prepared as described for the synthesis of Example 38 using 2-cyclobutylacetic acid in place of 4,4,4-trifluorobutanoic acid, and 4-methyl-1,2,5-oxadiazole-3-carboxylic acid in place of 1-(3,3,3-trifluoropropyl)-1H-1,2,4-triazole-5-carboxylic acid. $^1$H NMR (500 MHz, DMSO-d$_6$) δ 9.40 (d, J=8.9 Hz, 1H), 8.49 (d, J=2.0 Hz, 1H), 8.46 (d, J=7.9 Hz, 1H), 8.23 (s, 1H), 7.96-7.87 (m, 1H), 5.17 (t, J=8.6 Hz, 1H), 4.27 (t, J=8.4 Hz, 1H), 2.65-2.53 (m, 1H), 2.49-2.45 (m, 3H), 2.29-2.24 (m, 2H), 2.24-2.12 (m, 1H), 2.09-1.87 (m, 5H), 1.83-1.75 (m, 3H), 1.75-1.57 (m, 4H), 1.46-1.34 (m, 1H), 1.34-1.25 (m, 1H), 1.23-1.15 (m, 1H), 0.61-0.43 (m, 3H), 0.41-0.30 (m, 1H). MS (ESI) m/z: [M+H]$^+$ Found 542.3.

Example 248

N—((S)-(7-((R)-(2-(Cicyclo[1.1.1]pentan-1-yl)acetamido)(cyclopropyl)methyl)imidazo[1,2-b]pyridazin-2-yl)(4,4-difluorocyclohexyl)methyl)-1-isopropyl-1H-pyrazole-5-carboxamide

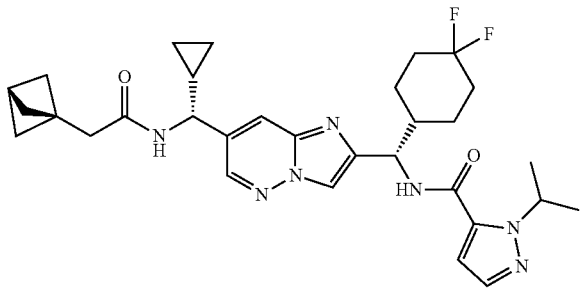

The title compound was prepared as described for the synthesis of Example 38 using 2-(bicyclo[1.1.1]pentan-1-yl)acetic acid in place of 4,4,4-trifluorobutanoic acid, and 1-isopropyl-1H-pyrazole-5-carboxylic acid in place of 1-(3,3,3-trifluoropropyl)-1H-1,2,4-triazole-5-carboxylic acid. $^1$H NMR (400 MHz, DMSO-d$_6$) δ 8.72 (d, J=9.0 Hz, 1H), 8.51 (d, J=2.0 Hz, 1H), 8.45 (d, J=7.9 Hz, 1H), 8.21 (s, 1H), 8.00-7.86 (m, 1H), 7.49 (d, J=1.9 Hz, 1H), 6.91 (d, J=2.0 Hz, 1H), 5.44-5.31 (m, 1H), 5.16 (t, J=8.6 Hz, 1H), 4.27 (t, J=8.6 Hz, 1H), 2.43 (s, 1H), 2.37-2.25 (m, 2H), 2.25-2.13 (m, 1H), 2.11-1.93 (m, 2H), 1.93-1.71 (m, 3H), 1.71-1.59 (m, 7H), 1.45-1.30 (m, 7H), 1.28-1.16 (m, 2H), 0.62-0.45 (m, 3H), 0.42-0.32 (m, 1H). MS (ESI) m/z: [M+H]$^+$ Found 580.3.

Example 249

N—((S)-(7-((R)-(2-(Bicyclo[1.1.1]pentan-1-yl)acetamido)(cyclopropyl)methyl)imidazo[1,2-b]pyridazin-2-yl)(4,4-difluorocyclohexyl)methyl)-4-methyl-1,2,5-oxadiazole-3-carboxamide

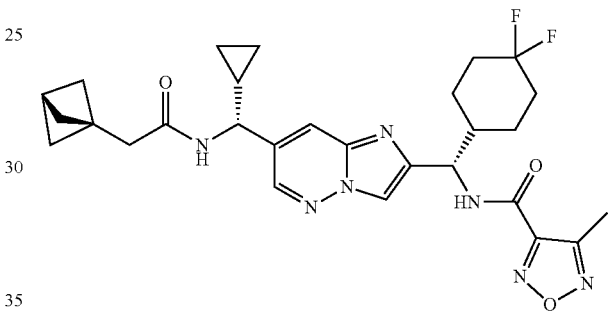

A vial was charged with a stir bar, N—((R)-(2-((S)-amino(4,4-difluorocyclohexyl)methyl)imidazo[1,2-b]pyridazin-7-yl)(cyclopropyl)methyl)-2-(bicyclo[1.1.1]pentan-1-yl)acetamide (75 mg, 0.17 mmol, Intermediate 224), 2,5-dioxopyrrolidin-1-yl 4-methyl-1,2,5-oxadiazole-3-carboxylate (38 mg, 0.17 mmol, Intermediate 223), MeCN (1 mL) and DIPEA (38 μL, 0.22 mmol). The reaction was stirred at rt for 15 min. The reaction mixture was poured over water and extracted with EtOAc (3×3 mL). The combined organic layers were washed with brine, dried over anhydrous MgSO$_4$, filtered and condensed. The crude material was purified by silica gel chromatography (0-100% EtOAc (with 10% MeOH)/hexanes). The product containing fractions were concentrated into a glassy solid which was dissolved in minimal MeCN/water and lyophilized to yield the title compound as a white powder. $^1$H NMR (400 MHz, DMSO-d$_6$) δ 9.42 (d, J=9.0 Hz, 1H), 8.52 (d, J=2.0 Hz, 1H), 8.46 (d, J=8.0 Hz, 1H), 8.28-8.19 (m, 1H), 8.01-7.92 (m, 1H), 5.18 (t, J=8.6 Hz, 1H), 4.28 (t, J=8.5 Hz, 1H), 2.48-2.42 (m, 4H), 2.35-2.27 (m, 2H), 2.25-2.12 (m, 1H), 2.12-1.95 (m, 2H), 1.95-1.87 (m, 1H), 1.87-1.57 (m, 9H), 1.46-1.16 (m, 3H), 0.65-0.44 (m, 3H), 0.42-0.33 (m, 1H). MS (ESI) m/z: [M+H]$^+$ Found 554.2.

Example 250

N—((S)-(7-((R)-Cyclopropyl(4,4-difluorobutana-mido)methyl)imidazo[1,2-b]pyridazin-2-yl)(4,4-difluorocyclohexyl)methyl)-4-methyl-1,2,5-oxadiazole-3-carboxamide

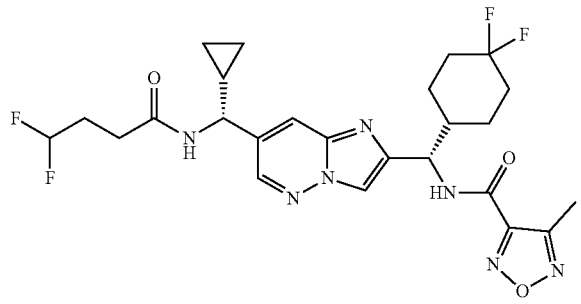 [SMILES: Cc1nonc1C(=O)N[C@H](c1cn2ncc([C@H](NC(=O)CCC(F)F)C3CC3)cc2n1)C1CCC(F)(F)CC1]

The title compound was prepared as described for the synthesis of Example 249 using 4,4-difluorobutanoic acid in place of 2-(bicyclo[1.1.1]pentan-1-yl)acetic acid. $^1$H NMR (400 MHz, DMSO-$d_6$) δ 9.40 (d, J=9.0 Hz, 1H), 8.65 (d, J=7.8 Hz, 1H), 8.52 (d, J=2.0 Hz, 1H), 8.31-8.13 (m, 1H), 8.04-7.81 (m, 1H), 6.30-5.84 (m, 1H), 5.17 (t, J=8.6 Hz, 1H), 4.29 (t, J=8.4 Hz, 1H), 2.47 (s, 3H), 2.39-2.32 (m, 2H), 2.26-2.13 (m, 1H), 2.13-1.95 (m, 4H), 1.95-1.67 (m, 3H), 1.67-1.56 (m, 1H), 1.45-1.15 (m, 3H), 0.63-0.44 (m, 3H), 0.43-0.34 (m, 1H). MS (ESI) m/z: [M+H]$^+$ Found 552.2.

Example 251

N—((S)-(7-((R)-Cyclopropyl(4-fluorobutanamido)methyl)imidazo[1,2-b]pyridazin-2-yl)(4,4-difluorocyclohexyl)methyl)-1-isopropyl-1H-pyrazole-5-carboxamide

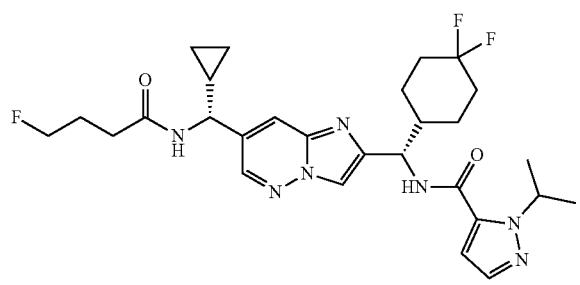 [SMILES: CC(C)n1nccc1C(=O)N[C@H](c1cn2ncc([C@H](NC(=O)CCCF)C3CC3)cc2n1)C1CCC(F)(F)CC1]

The title compound was prepared as described for the synthesis of Example 38 using 4-fluorobutanoic acid in place of 4,4,4-trifluorobutanoic acid, and 1-isopropyl-1H-pyrazole-5-carboxylic acid in place of 1-(3,3,3-trifluoropropyl)-1H-1,2,4-triazole-5-carboxylic acid. $^1$H NMR (500 MHz, DMSO-$d_6$) δ 8.71 (d, J=9.1 Hz, 1H), 8.59 (d, J=7.8 Hz, 1H), 8.51 (d, J=2.1 Hz, 1H), 8.20 (s, 1H), 7.96-7.88 (m, 1H), 7.49 (d, J=2.0 Hz, 1H), 6.92 (d, J=2.0 Hz, 1H), 5.42-5.34 (m, 1H), 5.16 (t, J=8.6 Hz, 1H), 4.54-4.33 (m, 2H), 4.29 (t, J=8.4 Hz, 1H), 2.31-2.26 (m, 2H), 2.23-2.12 (m, 1H), 2.10-1.95 (m, 2H), 1.93-1.69 (m, 5H), 1.65-1.58 (m, 1H), 1.44-1.31 (m, 7H), 1.31-1.17 (m, 2H), 0.62-0.44 (m, 3H), 0.42-0.32 (m, 1H). MS (ESI) m/z: [M+H]$^+$ Found 560.3.

Example 252

N—((S)-(7-((R)-Cyclopropyl(4-fluorobutanamido)methyl)imidazo[1,2-b]pyridazin-2-yl)(4,4-difluorocyclohexyl)methyl)-4-methyl-1,2,5-oxadiazole-3-carboxamide

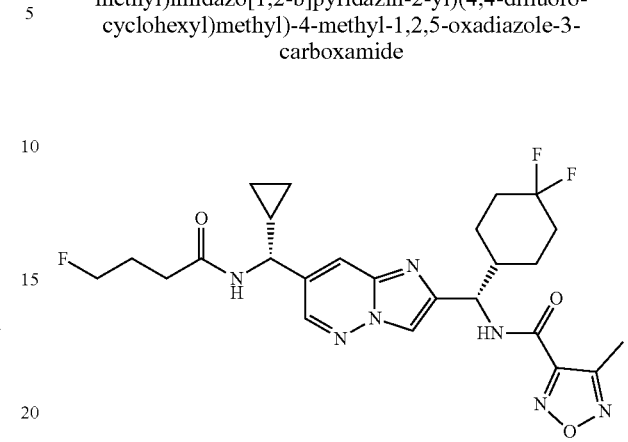

The title compound was prepared as described for the synthesis of Example 249 using 4-fluorobutanoic acid in place of 2-(bicyclo[1.1.1]pentan-1-yl)acetic acid. $^1$H NMR (500 MHz, DMSO-$d_6$) δ 9.40 (d, J=9.0 Hz, 1H), 8.59 (d, J=7.9 Hz, 1H), 8.51 (d, J=2.0 Hz, 1H), 8.23 (s, 1H), 7.94 (d, J=1.9 Hz, 1H), 5.17 (t, J=8.6 Hz, 1H), 4.53-4.33 (m, 2H), 4.29 (t, J=8.4 Hz, 1H), 2.48-2.46 (m, 3H), 2.32-2.26 (m, 2H), 2.23-2.13 (m, 1H), 2.10-1.95 (m, 2H), 1.94-1.86 (m, 2H), 1.86-1.79 (m, 2H), 1.79-1.70 (m, 1H), 1.66-1.58 (m, 1H), 1.44-1.34 (m, 1H), 1.33-1.24 (m, 1H), 1.24-1.17 (m, 1H), 0.62-0.45 (m, 3H), 0.42-0.34 (m, 1H). MS (ESI) m/z: [M+H]$^+$ Found 534.2.

Example 253

N—((S)-(7-((R)-Cyclopropyl(4,4,4-trifluoro-3,3-dimethylbutanamido)methyl)imidazo[1,2-b]pyridazin-2-yl)(4,4-difluorocyclohexyl)methyl)-4-methyl-1,2,5-oxadiazole-3-carboxamide

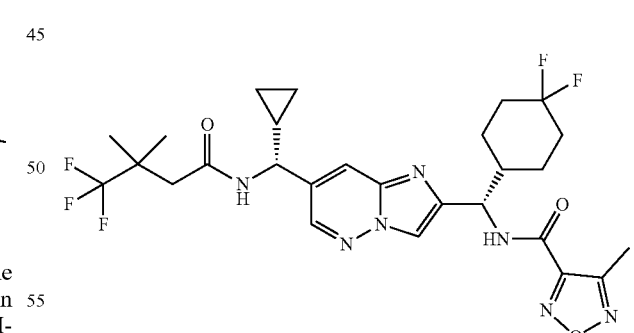

The title compound was prepared as described for the synthesis of Example 249 using 4,4,4-trifluoro-3,3-dimethylbutanoic acid in place of 2-(bicyclo[1.1.1]pentan-1-yl)acetic acid. $^1$H NMR (500 MHz, DMSO-$d_6$) δ 9.41 (d, J=9.0 Hz, 1H), 8.78 (d, J=7.8 Hz, 1H), 8.51 (d, J=2.0 Hz, 1H), 8.24 (s, 1H), 7.96 (d, J=1.9 Hz, 1H), 5.17 (t, J=8.6 Hz, 1H), 4.29 (t, J=8.5 Hz, 1H), 2.47 (s, 3H), 2.40-2.31 (m, 2H), 2.24-2.14 (m, 1H), 2.10-1.94 (m, 2H), 1.94-1.87 (m, 1H), 1.86-1.69 (m, 2H), 1.66-1.57 (m, 1H), 1.45-1.34 (m, 1H), 1.34-1.21

(m, 2H), 1.21-1.18 (m, 3H), 1.17-1.14 (m, 3H), 0.63-0.46 (m, 3H), 0.42-0.35 (m, 1H). MS (ESI) m/z: [M+H]+ Found 598.2.

Example 254

N—((S)-(7-((R)-Cyclopropyl(4,4,4-trifluoro-3,3-dimethylbutanamido)methyl)imidazo[1,2-b]pyridazin-2-yl)(4,4-difluorocyclohexyl)methyl)-1-isopropyl-1H-pyrazole-5-carboxamide

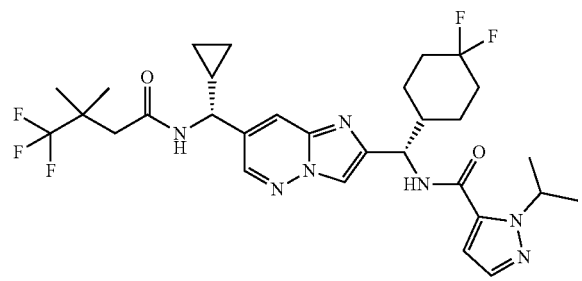 [SMILES: CC(C)n1nccc1C(=O)N[C@H](c1cn2ncc([C@H](NC(=O)CC(C)(C)C(F)(F)F)C3CC3)cc2n1)C1CCC(F)(F)CC1]

The title compound was prepared as described for the synthesis of Example 38 using 4,4,4-trifluoro-3,3-dimethylbutanoic acid in place of 4,4,4-trifluorobutanoic acid, and 1-isopropyl-1H-pyrazole-5-carboxylic acid in place of 1-(3,3,3-trifluoropropyl)-1H-1,2,4-triazole-5-carboxylic acid. 1H NMR (500 MHz, DMSO-d6) δ 8.78 (d, J=7.8 Hz, 1H), 8.72 (d, J=9.0 Hz, 1H), 8.51 (d, J=2.0 Hz, 1H), 8.21 (s, 1H), 7.95 (d, J=2.0 Hz, 1H), 7.49 (d, J=2.0 Hz, 1H), 6.91 (d, J=2.0 Hz, 1H), 5.46-5.28 (m, 1H), 5.16 (t, J=8.6 Hz, 1H), 4.29 (t, J=8.4 Hz, 1H), 2.41-2.29 (m, 2H), 2.23-2.12 (m, 1H), 2.11-1.93 (m, 2H), 1.93-1.85 (m, 1H), 1.85-1.69 (m, 2H), 1.67-1.56 (m, 1H), 1.44-1.26 (m, 8H), 1.26-1.22 (m, 1H), 1.21-1.18 (m, 3H), 1.15 (s, 3H), 0.63-0.46 (m, 3H), 0.42-0.33 (m, 1H). MS (ESI) m/z: [M+H]+ Found 624.3.

Example 255

N—((S)-(7-((R)-1-Cyclopropyl-2-((S*)-2,2-difluorocyclopropyl)ethyl)imidazo[1,2-b]pyridazin-2-yl)(4,4-difluorocyclohexyl)methyl)-4-methyl-1,2,5-oxadiazole-3-carboxamide

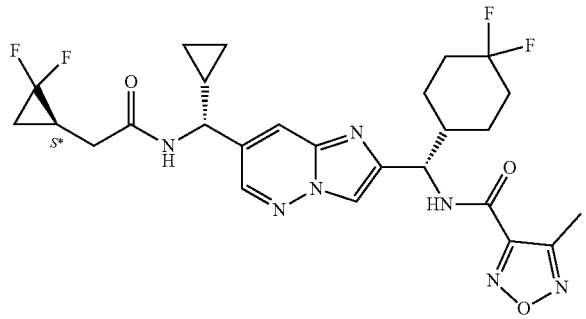 [SMILES: Cc1nonc1C(=O)N[C@H](c1cn2ncc([C@H](NC(=O)C[C@H]3CC3(F)F)C3CC3)cc2n1)C1CCC(F)(F)CC1]

A vial was charged with a stir bar, N—((R)-(2-((S)-amino(4,4-difluorocyclohexyl)methyl)imidazo[1,2-b]pyridazin-7-yl)(cyclopropyl)methyl)-2-((S*)-2,2-difluorocyclopropyl)acetamide (75 mg, 0.16 mmol, Intermediate 221), 2,5-dioxopyrrolidin-1-yl 4-methyl-1,2,5-oxadiazole-3-carboxylate (37 mg, 0.16 mmol, Intermediate 223), MeCN (1 mL), and Hünig's base (37 μL, 0.21 mmol). The reaction was stirred for 10 min at rt then poured over water. The aqueous mixture was extracted with EtOAc (3×5 mL). The combined organic layers were washed with brine, dried over anhydrous MgSO4, filtered and concentrated. The crude material was purified by silica gel chromatography (0-100% EtOAc (with 10% MeOH)/hexanes). The product containing fractions were concentrated, taken up in minimal MeCN/water and lyophilized to yield the title compound as a white powder. 1H NMR (600 MHz, DMSO-d6) δ 9.40 (d, J=9.0 Hz, 1H), 8.60 (d, J=7.8 Hz, 1H), 8.52 (d, J=2.1 Hz, 1H), 8.23 (s, 1H), 7.96 (d, J=1.9 Hz, 1H), 5.22-5.03 (m, 1H), 4.31 (t, J=8.3 Hz, 1H), 2.47 (s, 3H), 2.40-2.36 (m, 2H), 2.23-2.14 (m, 1H), 2.09-1.94 (m, 2H), 1.94-1.70 (m, 4H), 1.66-1.59 (m, 1H), 1.58-1.50 (m, 1H), 1.44-1.34 (m, 1H), 1.33-1.25 (m, 1H), 1.25-1.16 (m, 2H), 0.62-0.45 (m, 3H), 0.42-0.35 (m, 1H). MS (ESI) m/z: [M+H]+ Found 564.3.

Example 256

N—((S)-(7-((R)-1-Cyclopropyl-2-((R*)-2,2-difluorocyclopropyl)ethyl)imidazo[1,2-b]pyridazin-2-yl)(4,4-difluorocyclohexyl)methyl)-4-methyl-1,2,5-oxadiazole-3-carboxamide

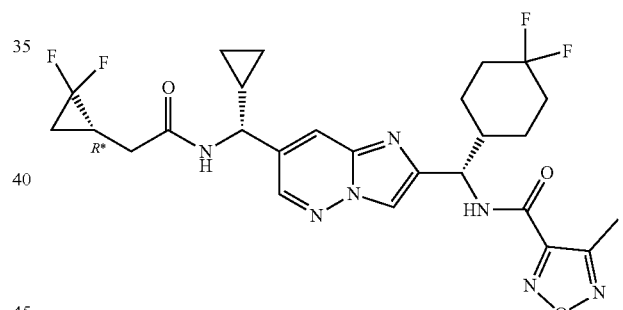

The title compound was prepared as described in Example 255 using N—((R)-(2-((S)-amino(4,4-difluorocyclohexyl)methyl)imidazo[1,2-b]pyridazin-7-yl)(cyclopropyl)methyl)-2-((R*)-2,2-difluorocyclopropyl)acetamide (Intermediate 220) in place of N—((R)-(2-((S)-amino(4,4-difluorocyclohexyl)methyl)imidazo[1,2-b]pyridazin-7-yl)(cyclopropyl)methyl)-2-((S*)-2,2-difluorocyclopropyl)acetamide to afford the title compound as a white solid. 1H NMR (500 MHz, DMSO-d6) δ 9.40 (d, J=9.0 Hz, 1H), 8.60 (d, J=7.6 Hz, 1H), 8.51 (d, J=2.0 Hz, 1H), 8.24 (s, 1H), 7.95 (d, J=2.0 Hz, 1H), 5.24-5.10 (m, 1H), 4.31 (t, J=8.3 Hz, 1H), 2.47 (s, 3H), 2.41-2.35 (m, 2H), 2.24-2.14 (m, 1H), 2.09-1.94 (m, 2H), 1.94-1.86 (m, 2H), 1.85-1.69 (m, 2H), 1.65-1.53 (m, 2H), 1.45-1.33 (m, 1H), 1.32-1.14 (m, 3H), 0.62-0.46 (m, 3H), 0.42-0.35 (m, 1H). MS (ESI) m/z: [M+H]+ Found 564.2.

Example 257

N—((S)-(7-((R)-Cyclopropyl(2-(cis-3-fluorocyclobutyl)acetamido)methyl)imidazo[1,2-b]pyridazin-2-yl)(4,4-difluorocyclohexyl)methyl)-1-isopropyl-1H-pyrazole-5-carboxamide

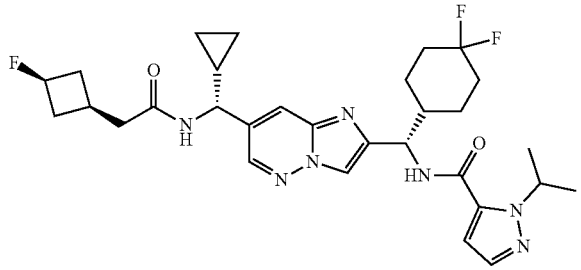 [SMILES: CC(C)n1nccc1C(=O)N[C@H](c1cn2ncc([C@H](NC(=O)C[C@H]3C[C@@H](F)C3)C3CC3)cc2n1)C1CCC(F)(F)CC1]

Example 258

N—((S)-(7-((R)-Cyclopropyl(2-(trans-3-fluorocyclobutyl)acetamido)methyl)imidazo[1,2-b]pyridazin-2-yl)(4,4-difluorocyclohexyl)methyl)-1-isopropyl-1H-pyrazole-5-carboxamide

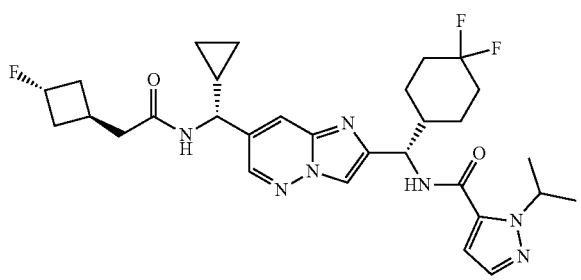 [SMILES: CC(C)n1nccc1C(=O)N[C@H](c1cn2ncc([C@H](NC(=O)C[C@H]3C[C@H](F)C3)C3CC3)cc2n1)C1CCC(F)(F)CC1]

The title compounds were prepared as described for the synthesis of Example 38 using 2-(3-fluorocyclobutyl)acetic acid in place of 4,4,4-trifluorobutanoic acid, and 1-isopropyl-1H-pyrazole-5-carboxylic acid in place of 1-(3,3,3-trifluoropropyl)-1H-1,2,4-triazole-5-carboxylic acid. The resulting mixture of diastereomers was separated by SFC using a chiral stationary phase (Stationary phase: OD-H 2×25 cm, Mobile phase: 10% MeOH (0.1% NPA)/CO$_2$). The first eluting minor isomer, Example 257, was isolated as a white powder. The second eluting major isomer, Example 258, was lyophilized into a white powder. Example 257: $^1$H NMR (600 MHz, DMSO-d$_6$) δ 8.71 (d, J=9.0 Hz, 1H), 8.53 (d, J=7.8 Hz, 1H), 8.49 (d, J=1.9 Hz, 1H), 8.20 (s, 1H), 7.91 (d, J=2.1 Hz, 1H), 7.49 (d, J=1.9 Hz, 1H), 6.91 (d, J=1.9 Hz, 1H), 5.48-5.25 (m, 1H), 5.15 (t, J=8.7 Hz, 1H), 4.98-4.76 (m, 1H), 4.27 (t, J=8.4 Hz, 1H), 2.46-2.35 (m, 2H), 2.35-2.28 (m, 2H), 2.22-2.13 (m, 1H), 2.10-2.02 (m, 1H), 2.02-1.95 (m, 2H), 1.90-1.85 (m, 2H), 1.85-1.79 (m, 2H), 1.78-1.71 (m, 1H), 1.66-1.58 (m, 1H), 1.38-1.32 (m, 7H), 1.30-1.23 (m, 1H), 1.23-1.18 (m, 1H), 0.61-0.45 (m, 3H), 0.39-0.33 (m, 1H). MS (ESI) m/z: [M+H]$^+$ Found 586.3. Example 258: $^1$H NMR (600 MHz, DMSO-d$_6$) δ 8.74-8.68 (m, 1H), 8.55-8.50 (m, 1H), 8.50-8.46 (m, 1H), 8.22-8.17 (m, 1H), 7.93-7.89 (m, 1H), 7.51-7.46 (m, 1H), 6.94-6.88 (m, 1H), 5.41-5.33 (m, 1H), 5.24-5.06 (m, 2H), 4.27 (t, J=8.4 Hz, 1H), 2.65-2.54 (m, 1H), 2.33-2.29 (m, 2H), 2.29-2.16 (m, 3H), 2.16-1.95 (m, 4H), 1.91-1.84 (m, 1H), 1.84-1.70 (m, 2H), 1.65-1.58 (m, 1H), 1.43-1.31 (m, 7H), 1.30-1.18 (m, 2H), 0.61-0.43 (m, 3H), 0.40-0.33 (m, 1H). MS (ESI) m/z: [M+H]$^+$ Found 586.3.

Example 259

N—((S)-(7-((R)-Cyclopropyl(4,4-difluoropentanamido)methyl)imidazo[1,2-b]pyridazin-2-yl)(4,4-difluorocyclohexyl)methyl)-4-methyl-1,2,5-oxadiazole-3-carboxamide

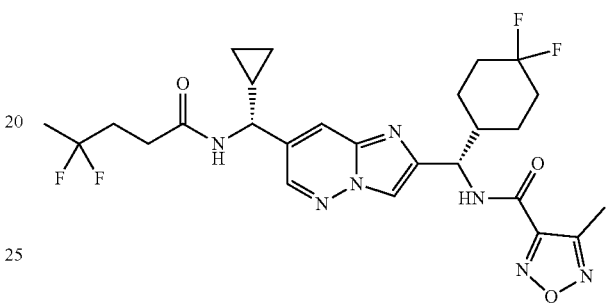

The title compound was prepared as described for the synthesis of Example 249 using 4,4-difluoropentanoic acid in place of 2-(bicyclo[1.1.1]pentan-1-yl)acetic acid to afford the title compound as a white powder. $^1$H NMR (500 MHz, DMSO-d$_6$) δ 9.32 (d, J=9.0 Hz, 1H), 8.57 (d, J=7.8 Hz, 1H), 8.43 (d, J=2.1 Hz, 1H), 8.15 (s, 1H), 7.87 (d, J=1.9 Hz, 1H), 5.17-5.01 (m, 1H), 4.22 (t, J=8.4 Hz, 1H), 2.40 (s, 3H), 2.32-2.24 (m, 2H), 2.16-2.00 (m, 3H), 1.99-1.86 (m, 2H), 1.86-1.79 (m, 1H), 1.79-1.62 (m, 2H), 1.58-1.45 (m, 4H), 1.37-1.26 (m, 1H), 1.25-1.09 (m, 2H), 0.54-0.37 (m, 3H), 0.34-0.26 (m, 1H). MS (ESI) m/z: [M+H]$^+$ Found 566.2.

Example 260

N—((S)-(7-((R)-Cyclopropyl(4,4-difluoropentanamido)methyl)imidazo[1,2-b]pyridazin-2-yl)(4,4-difluorocyclohexyl)methyl)-1-isopropyl-1H-pyrazole-5-carboxamide

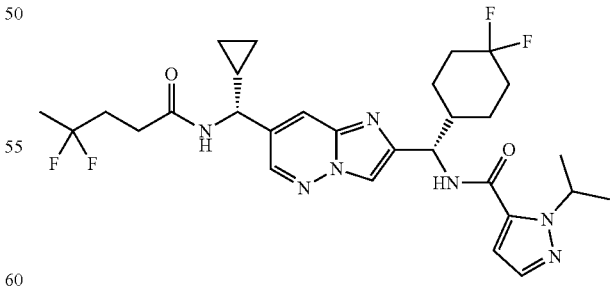

The title compounds were prepared as described for the synthesis of Example 38 using 4,4-difluoropentanoic acid in place of 4,4,4-trifluorobutanoic acid, and 1-isopropyl-1H-pyrazole-5-carboxylic acid in place of 1-(3,3,3-trifluoropropyl)-1H-1,2,4-triazole-5-carboxylic acid to afford the title compound as a white powder. $^1$H NMR (500 MHz, DMSO-d$_6$) δ 8.63 (d, J=9.0 Hz, 1H), 8.57 (d, J=7.8 Hz, 1H), 8.43 (d, J=2.0 Hz, 1H), 8.12 (s, 1H), 7.86 (d, J=1.4 Hz, 1H), 7.42 (d, J=1.9 Hz, 1H), 6.84 (d, J=1.9 Hz, 1H), 5.34-5.25 (m, 1H), 5.08 (t, J=8.6 Hz, 1H), 4.22 (t, J 8.4 Hz, 1H), 2.30-2.25 (m, 2H), 2.16-2.00 (m, 3H), 2.00-1.87 (m, 2H), 1.84-1.77 (m, 1H), 1.77-1.61 (m, 2H), 1.59-1.46 (m, 4H), 1.36-1.24 (m, 7H), 1.23-1.09 (m, 2H), 0.54-0.37 (m, 3H), 0.34-0.26 (m, 1H). MS (ESI) m/z: [M+H]$^+$ Found 592.3.

Example 261

N—((S)-(7-((R)-Cyclopropyl(3,3-difluorobutanamido)methyl)imidazo[1,2-b]pyridazin-2-yl)(4,4-difluorocyclohexyl)methyl)-1-isopropyl-1H-pyrazole-5-carboxamide

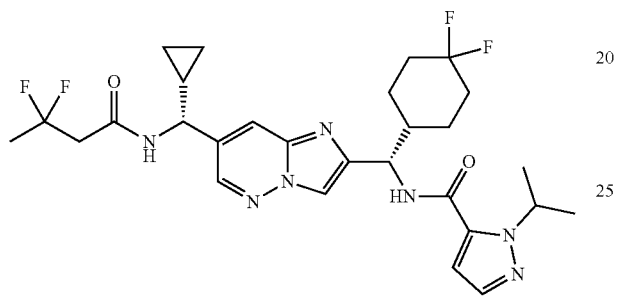

The title compound was prepared as described for the synthesis of Example 38 using 3,3-difluorobutanoic acid in place of 4,4,4-trifluorobutanoic acid, and 1-isopropyl-1H-pyrazole-5-carboxylic acid in place of 1-(3,3,3-trifluoropropyl)-1H-1,2,4-triazole-5-carboxylic acid to afford the title compound as a white powder. $^1$H NMR (500 MHz, DMSO-d$_6$) δ 8.76 (d, J=7.6 Hz, 1H), 8.64 (d, J=9.1 Hz, 1H), 8.43 (d, J=2.0 Hz, 1H), 8.13 (s, 1H), 7.85 (d, J=1.8 Hz, 1H), 7.41 (d, J=1.9 Hz, 1H), 6.84 (d, J=2.0 Hz, 1H), 5.34-5.25 (m, 1H), 5.08 (t, J=8.6 Hz, 1H), 4.23 (t, J 8.3 Hz, 1H), 2.83 (t, J=15.2 Hz, 2H), 2.15-2.05 (m, 1H), 2.02-1.86 (m, 2H), 1.84-1.77 (m, 1H), 1.77-1.66 (m, 2H), 1.61 (t, J=19.3 Hz, 3H), 1.57-1.51 (m, 1H), 1.36-1.24 (m, 7H), 1.23-1.10 (m, 2H), 0.56-0.39 (m, 3H), 0.35-0.26 (m, 1H). MS (ESI) m/z: [M+H]$^+$ Found 578.3.

Example 262

N-((1S)-(7-((1R)-Cyclopropyl(4,4-difluoro-3-methylbutanamido)methyl)imidazo[1,2-b]pyridazin-2-yl)(4,4-difluorocyclohexyl)methyl)-1-isopropyl-1H-pyrazole-5-carboxamide

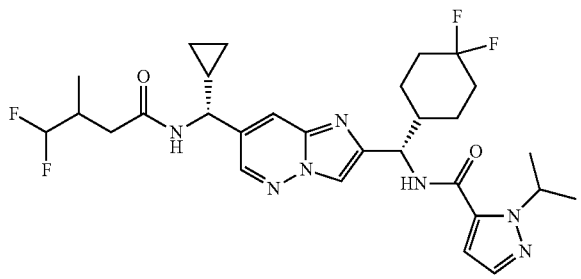 [SMILES: CC(CC(=O)N[C@@H](c1cnn2cc([C@@H](NC(=O)c3ccnn3C(C)C)C3CCC(F)(F)CC3)nc2c1)C1CC1)C(F)F]

The title compound was prepared as described for the synthesis of Example 38 using 4,4-difluoro-3-methylbutanoic acid in place of 4,4,4-trifluorobutanoic acid, and 1-isopropyl-1H-pyrazole-5-carboxylic acid in place of 1-(3,3,3-trifluoropropyl)-1H-1,2,4-triazole-5-carboxylic acid to afford the title compound as a white powder. $^1$H NMR (500 MHz, DMSO-d$_6$) δ 8.76-8.63 (m, 2H), 8.51 (d, J=1.4 Hz, 1H), 8.20 (s, 1H), 7.93 (d, J=1.6 Hz, 1H), 7.49 (d, J=1.9 Hz, 1H), 6.91 (d, J 1.5 Hz, 1H), 6.16-5.74 (m, 1H), 5.42-5.33 (m, 1H), 5.15 (t, J=8.6 Hz, 1H), 4.36-4.20 (m, 1H), 2.43-2.27 (m, 2H), 2.23-2.10 (m, 2H), 2.10-1.94 (m, 2H), 1.92-1.85 (m, 1H), 1.85-1.69 (m, 2H), 1.66-1.58 (m, 1H), 1.43-1.31 (m, 7H), 1.30-1.18 (m, 2H), 0.96-0.84 (m, 3H), 0.62-0.45 (m, 3H), 0.42-0.35 (m, 1H). MS (ESI) m/z: [M+H]$^+$ Found 592.3.

Example 263

N—((S)-(7-((R)-Cyclopropyl(3,3-difluorobutanamido)methyl)imidazo[1,2-b]pyridazin-2-yl)(4,4-difluorocyclohexyl)methyl)-4-methyl-1,2,5-oxadiazole-3-carboxamide

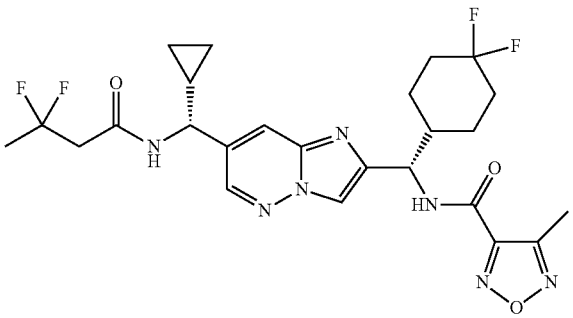 [SMILES: Cc1nonc1C(=O)N[C@H](c1cn2ncc([C@H](NC(=O)CC(C)(F)F)C3CC3)cc2n1)C1CCC(F)(F)CC1]

The title compound was prepared as described for the synthesis of Example 249 using 3,3-difluorobutanoic acid in place of 2-(bicyclo[1.1.1]pentan-1-yl)acetic acid. The reaction was further purified by basic reverse phase HPLC (Gemini® 5 μM, C18, 110 Å, 150×21.2 mm, 0-100% ACN/water (with 20 mM NH$_4$OH). $^1$H NMR (500 MHz, DMSO-d$_6$) δ 9.33 (d, J=8.9 Hz, 1H), 8.76 (d, J=7.6 Hz, 1H), 8.43 (d, J=2.0 Hz, 1H), 8.17 (s, 1H), 7.87 (d, J=2.0 Hz, 1H), 5.18-4.97 (m, 1H), 4.34-4.00 (m, 1H), 2.84 (t, J=15.1 Hz, 2H), 2.40 (s, 3H), 2.16-2.06 (m, 1H), 2.03-1.87 (m, 2H), 1.87-1.80 (m, 1H), 1.78-1.66 (m, 2H), 1.66-1.57 (m, 3H), 1.56-1.50 (m, 1H), 1.36-1.26 (m, 1H), 1.25-1.11 (m, 2H), 0.57-0.41 (m, 3H), 0.34-0.27 (m, 1H). MS (ESI) m/z: [M+H]$^+$ Found 552.2.

Example 264

N—((S)-(7-((R)-Cyclopropyl((R*)-4,4-difluoro-3-methylbutanamido)methyl)imidazo[1,2-b]pyridazin-2-yl)(4,4-difluorocyclohexyl)methyl)-4-methyl-1,2,5-oxadiazole-3-carboxamide

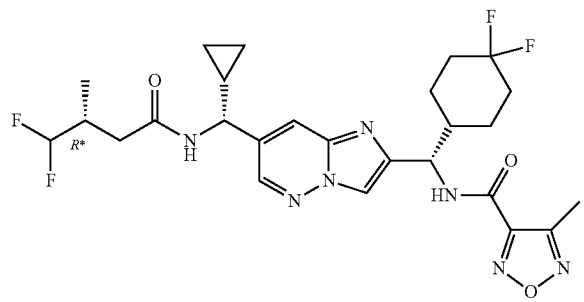 [SMILES: Cc1nonc1C(=O)N[C@H](c1cn2ncc([C@H](NC(=O)C[C@@H](C)C(F)F)C3CC3)cc2n1)C1CCC(F)(F)CC1]

Example 265

N—((S)-(7-((R)-Cyclopropyl((S*)-4,4-difluoro-3-methylbutanamido)methyl)imidazo[1,2-b]pyridazin-2-yl)(4,4-difluorocyclohexyl)methyl)-4-methyl-1,2,5-oxadiazole-3-carboxamide

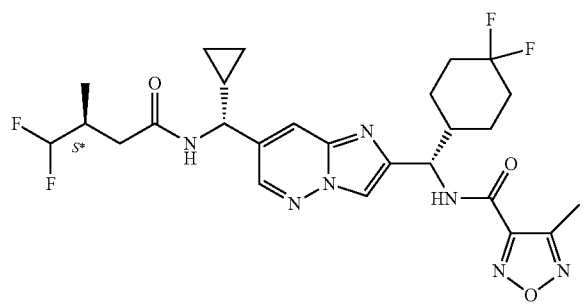 [SMILES: Cc1nonc1C(=O)N[C@H](c1cn2ncc([C@H](NC(=O)C[C@H](C)C(F)F)C3CC3)cc2n1)C1CCC(F)(F)CC1]

The title compounds were prepared as described for the synthesis of Example 249 using 4,4-difluoro-3-methylbutanoic acid in place of 2-(bicyclo[1.1.1]pentan-1-yl)acetic acid. The diastereomers were separated by SFC with a chiral stationary phase (Stationary phase: IC (2×25 cm), Mobile phase: 13% isopropanol/CO$_2$). The first eluting fraction afforded Example 264 as a white powder. The second eluting fraction afforded Example 265 as a white powder. Example 264: H NMR (500 MHz, DMSO-d$_6$) δ 9.41 (d, J=9.0 Hz, 1H), 8.70 (d, J=7.8 Hz, 1H), 8.51 (d, J 2.0 Hz, 1H), 8.24 (s, 1H), 7.95 (d, J=2.0 Hz, 1H), 6.15-5.79 (m, 1H), 5.17 (t, J=8.6 Hz, 1H), 4.30 (t, J=8.4 Hz, 1H), 2.47 (s, 3H), 2.43-2.37 (m, 1H), 2.35-2.25 (m, 1H), 2.23-2.16 (m, 1H), 2.16-2.11 (m, 1H), 2.10-1.94 (m, 2H), 1.94-1.87 (m, 1H), 1.86-1.69 (m, 2H), 1.65-1.57 (m, 1H), 1.45-1.34 (m, 1H), 1.32-1.17 (m, 2H), 0.91-0.84 (m, 3H), 0.62-0.45 (m, 3H), 0.43-0.35 (m, 1H). MS (ESI) m/z: [M+H]$^+$ Found 566.2. Example 265: $^1$H NMR (500 MHz, DMSO-d$_6$) δ 9.40 (d, J=8.9 Hz, 1H), 8.68 (d, J=7.9 Hz, 1H), 8.51 (d, J=2.0 Hz, 1H), 8.25-8.20 (m, 1H), 7.95 (d, J=1.6 Hz, 1H), 6.14-5.73 (m, 1H), 5.17 (t, J=8.5 Hz, 1H), 4.32 (t, J=8.4 Hz, 1H), 2.47 (s, 3H), 2.42-2.29 (m, 2H), 2.23-2.10 (m, 2H), 2.10-1.94 (m, 2H), 1.94-1.87 (m, 1H), 1.86-1.70 (m, 2H), 1.65-1.58 (m, 1H), 1.44-1.33 (m, 1H), 1.33-1.18 (m, 2H), 0.94 (d, J 6.9 Hz, 3H), 0.64-0.46 (m, 3H), 0.42-0.35 (m, 1H). MS (ESI) m/z: [M+H]$^+$ Found 566.2.

Example 266

N—((S)-(7-((R)-Cyclopropyl(2-(trans-3-fluorocyclobutyl)acetamido)methyl)imidazo[1,2-b]pyridazin-2-yl)(4,4-difluorocyclohexyl)methyl)-4-methyl-1,2,5-oxadiazole-3-carboxamide

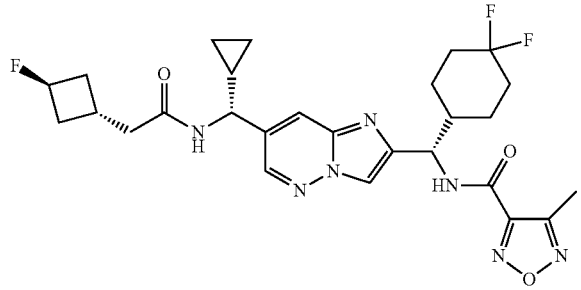 [SMILES: Cc1nonc1C(=O)N[C@H](c1cn2ncc([C@H](NC(=O)C[C@H]3C[C@H](F)C3)C3CC3)cc2n1)C1CCC(F)(F)CC1]

Example 267

N—((S)-(7-((R)-Cyclopropyl(2-(cis-3-fluorocyclobutyl)acetamido)methyl)imidazo[1,2-b]pyridazin-2-yl)(4,4-difluorocyclohexyl)methyl)-4-methyl-1,2,5-oxadiazole-3-carboxamide

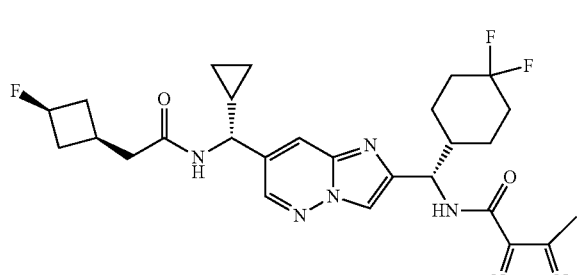

The title compounds were prepared as described for the synthesis of Example 249 using 2-(3-fluorocyclobutyl)acetic acid in place of 2-(bicyclo[1.1.1]pentan-1-yl)acetic acid. The diastereomers were separated by SFC with a chiral stationary phase (Stationary phase: IC (2×25 cm), Mobile phase: 20% ethanol/CO$_2$). The first eluting fraction afforded the minor diastereomer, Example 266, as a white powder. The second eluting fraction afforded the major diastereomer, Example 267, as a white powder. Example 266: $^1$H NMR (500 MHz, DMSO-d$_6$) δ 9.41 (d, J=9.0 Hz, 1H), 8.53 (d, J=7.9 Hz, 1H), 8.50 (d, J=2.1 Hz, 1H), 8.23 (s, 1H), 7.93 (d, J=2.0 Hz, 1H), 5.26-5.10 (m, 1H), 5.01-4.73 (m, 1H), 4.27 (t, J=8.4 Hz, 1H), 2.47 (s, 3H), 2.45-2.40 (m, 1H), 2.40-2.35 (m, 1H), 2.35-2.29 (m, 2H), 2.24-2.13 (m, 1H), 2.09-1.94 (m, 3H), 1.93-1.70 (m, 5H), 1.67-1.56 (m, 1H), 1.45-1.34 (m, 1H), 1.32-1.25 (m, 1H), 1.24-1.18 (m, 1H), 0.62-0.44 (m, 3H), 0.42-0.33 (m, 1H). MS (ESI) m/z: [M+H]$^+$ Found 560.3. Example 267: $^1$H NMR (600 MHz, DMSO-d$_6$) δ 9.40 (d, J=9.0 Hz, 1H), 8.53 (d, J=7.8 Hz, 1H), 8.50 (d, J=2.1 Hz, 1H), 8.23 (s, 1H), 7.94 (d, J=2.1 Hz, 1H), 5.23-5.07 (m, 2H), 4.27 (t, J=8.4 Hz, 1H), 2.61-2.53 (m, 1H), 2.47 (s, 3H), 2.31 (d, J=7.8 Hz, 2H), 2.29-2.15 (m, 3H), 2.15-2.03 (m, 3H), 2.03-1.94 (m, 1H), 1.94-1.87 (m, 1H), 1.85-1.71 (m, 2H), 1.65-1.58 (m, 1H), 1.44-1.35 (m, 1H), 1.32-1.18 (m, 2H), 0.61-0.43 (m, 3H), 0.40-0.31 (m, 1H). MS (ESI) m/z: [M+H]$^+$ Found 560.3.

Example 268

N—((S)-(7-((R)-Cyclopropyl(3-fluorobicyclo[1.1.1]pentane-1-carboxamido)methyl)imidazo[1,2-b]pyridazin-2-yl)(4,4-difluorocyclohexyl)methyl)-1-isopropyl-1H-pyrazole-5-carboxamide

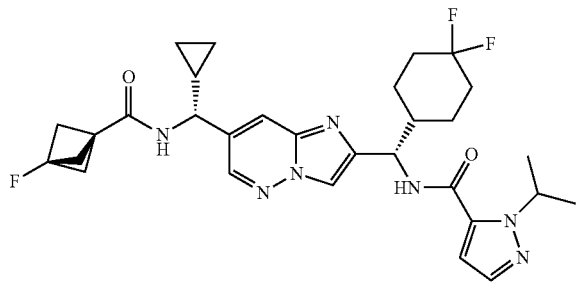 [SMILES: CC(C)n1nccc1C(=O)N[C@H](c1cn2ncc([C@H](NC(=O)[C@]34C[C@](F)(C3)C4)C3CC3)cc2n1)C1CCC(F)(F)CC1]

The title compound was prepared as described for the synthesis of Example 38 using 3-fluorobicyclo[1.1.1]pentane-1-carboxylic acid in place of 4,4,4-trifluorobutanoic acid, and 1-isopropyl-1H-pyrazole-5-carboxylic acid in place of 1-(3,3,3-trifluoropropyl)-1H-1,2,4-triazole-5-carboxylic acid to afford the title compound as a white powder. $^1$H NMR (500 MHz, DMSO-d$_6$) δ 8.71 (d, J=9.1 Hz, 1H), 8.58 (d, J=8.1 Hz, 1H), 8.52 (d, J=2.0 Hz, 1H), 8.20 (s, 1H), 7.93 (d, J=2.0 Hz, 1H), 7.49 (d, J=1.9 Hz, 1H), 6.91 (d, J=2.0 Hz, 1H), 5.42-5.33 (m, 1H), 5.15 (t, J=8.7 Hz, 1H), 4.24 (t, J=8.8 Hz, 1H), 2.30 (d, J=2.6 Hz, 6H), 2.23-2.11 (m, 1H), 2.09-1.93 (m, 2H), 1.93-1.84 (m, 1H), 1.84-1.69 (m, 2H), 1.66-1.57 (m, 1H), 1.43-1.32 (m, 7H), 1.32-1.20 (m, 2H), 0.64-0.43 (m, 3H), 0.42-0.32 (m, 1H). MS (ESI) m/z: [M+H]$^+$ Found 584.3.

Example 269

N—((S)-(7-((R)-Cyclopropyl(3-fluorobicyclo[1.1.1]pentane-1-carboxamido)methyl)imidazo[1,2-b]pyridazin-2-yl)(4,4-difluorocyclohexyl)methyl)-4-methyl-1,2,5-oxadiazole-3-carboxamide

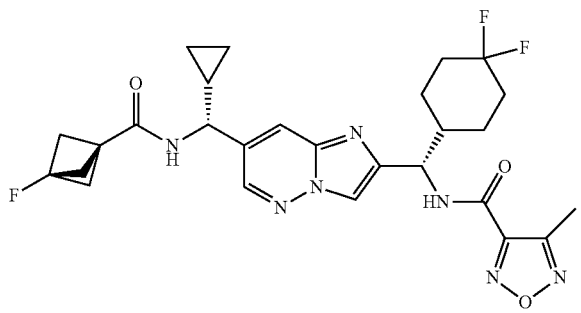 [SMILES: Cc1nonc1C(=O)N[C@H](c1cn2ncc([C@H](NC(=O)[C@]34C[C@](F)(C3)C4)C3CC3)cc2n1)C1CCC(F)(F)CC1]

The title compound was prepared as described for the synthesis of Example 249 using 3-fluorobicyclo[1.1.1]pentane-1-carboxylic acid in place of 2-(bicyclo[1.1.1]pentan-1-yl)acetic acid to afford the title compound as a white powder. $^1$H NMR (400 MHz, DMSO-d$_6$) δ 9.41 (d, J=9.0 Hz, 1H), 8.58 (d, J=8.1 Hz, 1H), 8.53 (d, J=2.1 Hz, 1H), 8.24 (s, 1H), 7.96 (d, J=2.1 Hz, 1H), 5.25-4.98 (m, 1H), 4.25 (t, J=8.6 Hz, 1H), 2.47 (s, 3H), 2.30 (d, J=2.6 Hz, 6H), 2.24-2.13 (m, 1H), 2.11-1.96 (m, 2H), 1.95-1.87 (m, 1H), 1.87-1.68 (m, 2H), 1.66-1.55 (m, 1H), 1.45-1.35 (m, 1H), 1.35-1.21 (m, 2H), 0.66-0.45 (m, 3H), 0.43-0.33 (m, 1H). MS (ESI) m/z: [M+H]$^+$ Found 558.3.

Example 270

N—((S)-(7-((R)-Cyclopropyl(3-((R*)-2,2-difluorocyclopropyl)propanamido)methyl)imidazo[1,2-b]pyridazin-2-yl)(4,4-difluorocyclohexyl)methyl)-1-isopropyl-1H-pyrazole-5-carboxamide

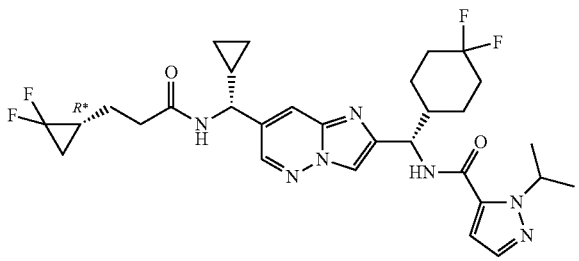 [SMILES: CC(C)n1nccc1C(=O)N[C@H](c1cn2ncc([C@H](NC(=O)CC[C@@H]3CC3(F)F)C3CC3)cc2n1)C1CCC(F)(F)CC1]

Example 271

N—((S)-(7-((R)-Cyclopropyl(3-((S*)-2,2-difluorocyclopropyl)propanamido)methyl)imidazo[1,2-b]pyridazin-2-yl)(4,4-difluorocyclohexyl)methyl)-1-isopropyl-1H-pyrazole-5-carboxamide

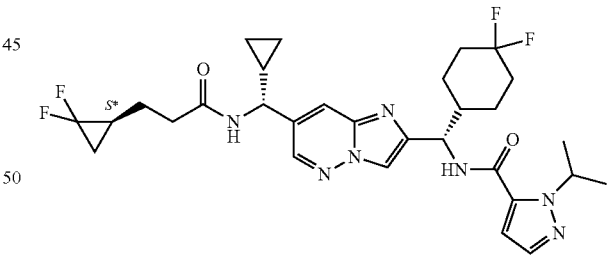

The title compounds were prepared as described for the synthesis of Example 38 using 3-(2,2-difluorocyclopropyl)propanoic acid in place of 4,4,4-trifluorobutanoic acid, and 1-isopropyl-1H-pyrazole-5-carboxylic acid in place of 1-(3,3,3-trifluoropropyl)-1H-1,2,4-triazole-5-carboxylic acid. The diastereomers were separated by SFC with achiral stationary phase (Stationary phase: AD-H (2×25 cm), Mobile phase: 15% isopropanol/CO$_2$). The first eluting fraction afforded Example 270 as a white powder. The second eluting fraction afforded Example 271 as a white powder. Example 270: $^1$H NMR (400 MHz, DMSO-d$_6$) δ 8.71 (d, J=9.0 Hz, 1H), 8.60 (d, J 7.9 Hz, 1H), 8.51 (d, J=2.1 Hz, 1H), 8.20 (s, 1H), 7.93 (d, J=1.9 Hz, 1H), 7.49 (d, J=2.0

Hz, 1H), 6.92 (d, J=2.0 Hz, 1H), 5.43-5.32 (m, 1H), 5.16 (t, J=8.6 Hz, 1H), 4.29 (t, J=8.4 Hz, 1H), 2.36-2.25 (m, 2H), 2.24-2.11 (m, 1H), 2.11-1.93 (m, 2H), 1.93-1.83 (m, 1H), 1.83-1.68 (m, 2H), 1.68-1.55 (m, 4H), 1.49-1.39 (m, 2H), 1.39-1.32 (m, 6H), 1.29-1.17 (m, 2H), 1.12-1.01 (m, 1H), 0.63-0.44 (m, 3H), 0.42-0.34 (m, 1H). MS (ESI) m/z: [M+H]$^+$ Found 604.3. Example 271: $^1$H NMR (400 MHz, DMSO-d$_6$) δ 8.71 (d, J=9.1 Hz, 1H), 8.59 (d, J=7.9 Hz, 1H), 8.51 (d, J=2.1 Hz, 1H), 8.20 (s, 1H), 7.94 (d, J=2.0 Hz, 1H), 7.49 (d, J=1.9 Hz, 1H), 6.92 (d, J=2.0 Hz, 1H), 5.45-5.26 (m, 1H), 5.16 (t, J=8.6 Hz, 1H), 4.30 (t, J=8.4 Hz, 1H), 2.37-2.23 (m, 2H), 2.23-2.11 (m, 1H), 2.10-1.93 (m, 2H), 1.93-1.84 (m, 1H), 1.83-1.67 (m, 2H), 1.67-1.55 (m, 4H), 1.53-1.42 (m, 1H), 1.42-1.26 (m, 7H), 1.26-1.16 (m, 2H), 1.15-1.02 (m, 1H), 0.63-0.43 (m, 3H), 0.43-0.33 (m, 1H). MS (ESI) m/z: [M+H]$^+$ Found 604.3.

Example 272

N—((S)-(7-((R)-Cyclopropyl(2-(3-fluorobicyclo [1.1.1]pentan-1-yl)acetamido)methyl)imidazo[1,2-b] pyridazin-2-yl)(4,4-difluorocyclohexyl)methyl)-4-methyl-1,2,5-oxadiazole-3-carboxamide

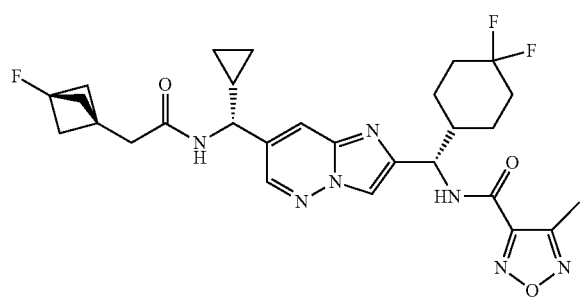 [SMILES: Cc1nonc1C(=O)N[C@H](c1cn2ncc([C@H](NC(=O)C[C@]34C[C@](F)(C3)C4)C3CC3)cc2n1)C1CCC(F)(F)CC1]

The title compound was prepared as described for the synthesis of Example 249 using N—((R)-(2-((S)-amino(4,4-difluorocyclohexyl)methyl)imidazo[1,2-b]pyridazin-7-yl)(cyclopropyl)methyl)-2-(3-fluorobicyclo[1.1.1]pentan-1-yl)acetamide (Intermediate 228) in place of N—((R)-(2-((S)-amino(4,4-difluorocyclohexyl)methyl)imidazo[1,2-b]pyridazin-7-yl)(cyclopropyl)methyl)-2-(bicyclo[1.1.1] pentan-1-yl)acetamide to afford the title compound as a white solid. $^1$H NMR (400 MHz, DMSO-d$_6$) δ 9.41 (d, J=9.0 Hz, 1H), 8.57 (d, J=7.8 Hz, 1H), 8.50 (d, J=2.1 Hz, 1H), 8.24 (s, 1H), 7.95 (d, J=2.0 Hz, 1H), 5.18 (t, J=8.6 Hz, 1H), 4.27 (t, J=8.5 Hz, 1H), 2.58-2.53 (m, 1H), 2.47 (s, 3H), 2.25-2.14 (m, 1H), 2.11-1.87 (m, 10H), 1.86-1.68 (m, 2H), 1.66-1.56 (m, 1H), 1.45-1.33 (m, 1H), 1.33-1.16 (m, 2H), 0.64-0.45 (m, 3H), 0.42-0.33 (m, 1H). MS (ESI) m/z: [M+H]$^+$ Found 572.2.

Example 273

N—((S)-(7-((R)-Cyclopropyl(2-(3-fluorobicyclo [1.1.1]pentan-1-yl)acetamido)methyl)imidazo[1,2-b] pyridazin-2-yl)(4,4-difluorocyclohexyl)methyl)-1-isopropyl-1H-pyrazole-5-carboxamide

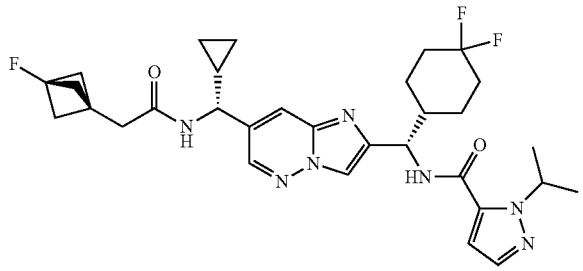 [SMILES: CC(C)n1nccc1C(=O)N[C@H](c1cn2ncc([C@H](NC(=O)C[C@]34C[C@](F)(C3)C4)C3CC3)cc2n1)C1CCC(F)(F)CC1]

The title compound was prepared as described for the synthesis of Example 38 using N—((R)-(2-((S)-amino(4,4-difluorocyclohexyl)methyl)imidazo[1,2-b]pyridazin-7-yl)(cyclopropyl)methyl)-2-(3-fluorobicyclo[1.1.1]pentan-1-yl)acetamide (Intermediate 228) in place of N—((R)-(2-((S)-amino(4,4-difluorocyclohexyl)methyl)imidazo[1,2-b]pyridazin-7-yl)(cyclopropyl)methyl)-4,4,4-trifluorobutanamide and 1-isopropyl-1H-pyrazole-5-carboxylic acid in place of 1-(3,3,3-trifluoropropyl)-1H-1,2,4-triazole-5-carboxylic acid to afford the title compound as a white solid. $^1$H NMR (400 MHz, DMSO-d$_6$) δ 8.72 (d, J=9.0 Hz, 1H), 8.57 (d, J=7.9 Hz, 1H), 8.50 (d, J 2.0 Hz, 1H), 8.21 (s, 1H), 7.93 (d, J=2.0 Hz, 1H), 7.49 (d, J=2.0 Hz, 1H), 6.91 (d, J=2.0 Hz, 1H), 5.43-5.30 (m, 1H), 5.16 (t, J=8.6 Hz, 1H), 4.26 (t, J=8.4 Hz, 1H), 2.58-2.52 (m, 2H), 2.24-2.11 (m, 1H), 2.10-1.91 (m, 8H), 1.91-1.83 (m, 1H), 1.84-1.67 (m, 2H), 1.67-1.58 (m, 1H), 1.46-1.30 (m, 7H), 1.29-1.17 (m, 2H), 0.64-0.44 (m, 3H), 0.44-0.29 (m, 1H). MS (ESI) m/z: [M+H]$^+$ Found 598.3.

Example 274

N—((S)-(7-((R)-Cyclopropyl(2-(difluoromethoxy) acetamido)methyl)imidazo[1,2-b]pyridazin-2-yl)(4, 4-difluorocyclohexyl)methyl)-1-isopropyl-1H-pyrazole-5-carboxamide

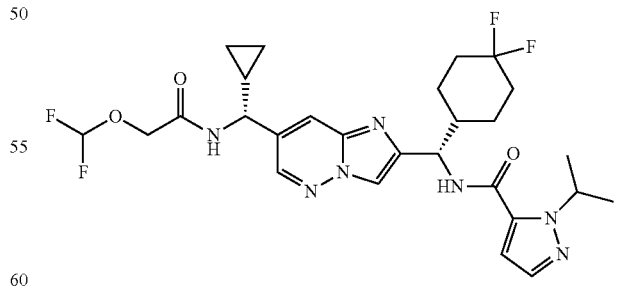

The title compound was prepare as described for the synthesis of Example 38 using 2-(difluoromethoxy)acetic acid in place of 4,4,4-trifluorobutanoic acid and 1-isopropyl-1H-pyrazole-5-carboxylic acid in place of 1-(3,3,3-trifluoropropyl)-1H-1,2,4-triazole-5-carboxylic acid to afford the title compound as a white powder. $^1$H NMR (400 MHz, DMSO-d$_6$) δ 8.83-8.65 (m, 2H), 8.55 (d, J=2.1 Hz, 1H), 8.21 (s, 1H), 7.98 (d, J=2.0 Hz, 1H), 7.50 (d, J=1.9 Hz, 1H), 7.02-6.43 (m, 2H), 5.44-5.31 (m, 1H), 5.16 (t, J=8.6 Hz, 1H), 4.38 (s, 2H), 4.30 (t, J=8.6 Hz, 1H), 2.26-2.11 (m, 1H), 2.12-1.93 (m, 2H), 1.92-1.67 (m, 3H), 1.67-1.55 (m, 1H), 1.46-1.21 (m, 9H), 0.66-0.48 (m, 3H), 0.44-0.31 (m, 1H). MS (ESI) m/z: [M+H]$^+$ Found 580.3.

Example 275

N-((1S)-(7-((1R)-Cyclopropyl(2-(2,2-difluorocyclopentyl)acetamido)methyl)imidazo[1,2-b]pyridazin-2-yl)(4,4-difluorocyclohexyl)methyl)-1-isopropyl-1H-pyrazole-5-carboxamide

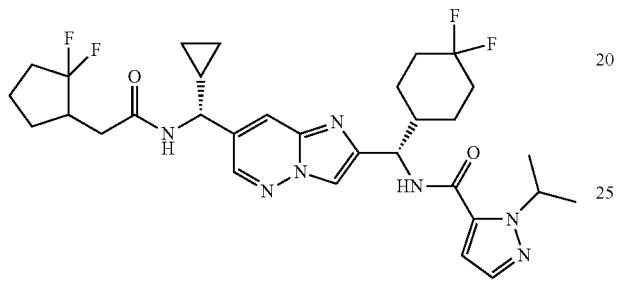

The title compound was prepared as described for the synthesis of Example 38 using 2-(2,2-difluorocyclopentyl)acetic acid in place of 4,4,4-trifluorobutanoic acid and 1-isopropyl-1H-pyrazole-5-carboxylic acid in place of 1-(3,3,3-trifluoropropyl)-1H-1,2,4-triazole-5-carboxylic acid to afford the title compound as a white powder. $^1$H NMR (500 MHz, DMSO-d$_6$) δ 8.71 (d, J 9.0 Hz, 1H), 8.58 (dd, J=4.8, 7.8 Hz, 1H), 8.52-8.44 (m, 1H), 8.20 (s, 1H), 7.93 (d, J=0.6 Hz, 1H), 7.49 (d, J=1.9 Hz, 1H), 6.91 (d, J=1.5 Hz, 1H), 5.42-5.33 (m, 1H), 5.16 (t, J=8.6 Hz, 1H), 4.29 (t, J=8.4 Hz, 1H), 2.45-2.35 (m, 1H), 2.32-2.23 (m, 2H), 2.23-2.09 (m, 3H), 2.08-1.93 (m, 3H), 1.92-1.68 (m, 5H), 1.68-1.57 (m, 1H), 1.49-1.31 (m, 8H), 1.30-1.16 (m, 2H), 0.63-0.44 (m, 3H), 0.41-0.32 (m, 1H). MS (ESI) m/z: [M+H]$^+$ Found 618.3.

Example 276

N—((S)-(7-((R)-Cyclopropyl(2-(trifluoromethoxy)acetamido)methyl)imidazo[1,2-b]pyridazin-2-yl)(4,4-difluorocyclohexyl)methyl)-1-isopropyl-1H-pyrazole-5-carboxamide

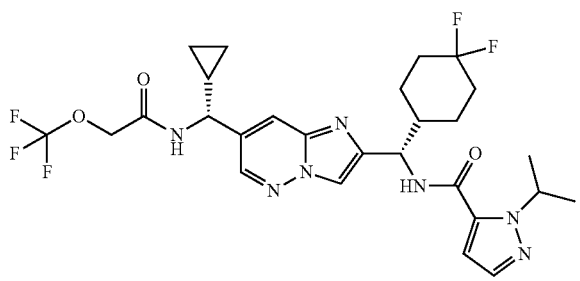 [SMILES: CC(C)n1nccc1C(=O)N[C@H](c1cn2ncc([C@H](NC(=O)COC(F)(F)F)C3CC3)cc2n1)C1CCC(F)(F)CC1]

The title compound was prepared as described for the synthesis of Example 38 using 2-(trifluoromethoxy)acetic acid in place of 4,4,4-trifluorobutanoic acid and 1-isopropyl-1H-pyrazole-5-carboxylic acid in place of 1-(3,3,3-trifluoropropyl)-1H-1,2,4-triazole-5-carboxylic acid to afford the title compound as a white powder. $^1$H NMR (500 MHz, DMSO-d$_6$) δ 8.92 (d, J 7.8 Hz, 1H), 8.71 (d, J=9.0 Hz, 1H), 8.55 (d, J=2.0 Hz, 1H), 8.21 (s, 1H), 7.99 (d, J=1.9 Hz, 1H), 7.49 (d, J=2.0 Hz, 1H), 6.92 (d, J=2.0 Hz, 1H), 5.42-5.32 (m, 1H), 5.16 (t, J=8.6 Hz, 1H), 4.65 (s, 2H), 4.31 (t, J=8.6 Hz, 1H), 2.25-2.12 (m, 1H), 2.11-1.93 (m, 2H), 1.92-1.68 (m, 3H), 1.68-1.59 (m, 1H), 1.43-1.30 (m, 8H), 1.29-1.21 (m, 1H), 0.65-0.48 (m, 3H), 0.43-0.34 (m, 1H). MS (ESI) m/z: [M+H]$^+$ Found 598.2.

Example 277

N—((S)-(7-((R)-Cyclopropyl(2-(trifluoromethoxy)acetamido)methyl)imidazo[1,2-b]pyridazin-2-yl)(4,4-difluorocyclohexyl)methyl)-4-methyl-1,2,5-oxadiazole-3-carboxamide

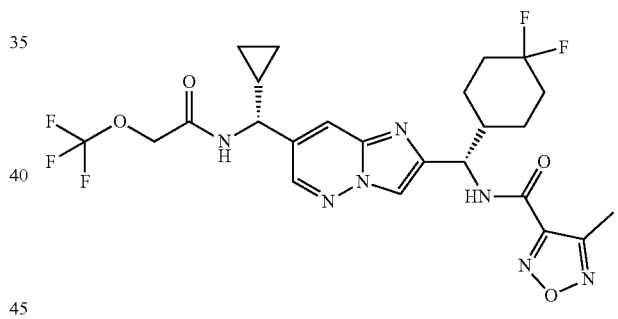

The title compound was prepared as described for the synthesis of Example 249 using 2-(trifluoromethoxy)acetic acid in place of 2-(bicyclo[1.1.1]pentan-1-yl)acetic acid to afford the title compound as a white solid. $^1$H NMR (400 MHz, DMSO-d$_6$) δ 9.41 (d, J=9.0 Hz, 1H), 8.92 (d, J 7.8 Hz, 1H), 8.56 (d, J=2.1 Hz, 1H), 8.25 (s, 1H), 8.00 (d, J=2.0 Hz, 1H), 5.18 (t, J=8.6 Hz, 1H), 4.65 (s, 2H), 4.31 (t, J=8.6 Hz, 1H), 2.49-2.45 (m, 3H), 2.26-2.13 (m, 1H), 2.12-1.95 (m, 2H), 1.95-1.87 (m, 1H), 1.87-1.68 (m, 2H), 1.68-1.56 (m, 1H), 1.46-1.35 (m, 1H), 1.35-1.21 (m, 2H), 0.67-0.49 (m, 3H), 0.47-0.34 (m, 1H). MS (ESI) m/z: [M+H]$^+$ Found 572.2.

Example 278

N—((S)-(7-((R)-Cyclopropyl(2-(difluoromethoxy)acetamido)methyl)imidazo[1,2-b]pyridazin-2-yl)(4,4-difluorocyclohexyl)methyl)-4-methyl-1,2,5-oxadiazole-3-carboxamide

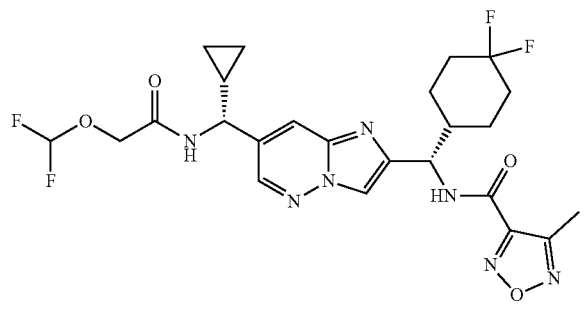 [SMILES: Cc1nonc1C(=O)N[C@H](c1cn2ncc([C@H](NC(=O)COC(F)F)C3CC3)cc2n1)C1CCC(F)(F)CC1]

The title compound was prepared as described for the synthesis of Example 249 using 2-(difluoromethoxy)acetic acid in place of 2-(bicyclo[1.1.1]pentan-1-yl)acetic acid to afford the title compound as a white solid. $^1$H NMR (400 MHz, DMSO-d$_6$) δ 9.41 (d, J=8.9 Hz, 1H), 8.77 (d, J 8.0 Hz, 1H), 8.56 (d, J=2.1 Hz, 1H), 8.24 (s, 1H), 8.00 (d, J=2.0 Hz, 1H), 7.03-6.54 (m, 1H), 5.18 (t, J=8.6 Hz, 1H), 4.39 (s, 2H), 4.30 (t, J=8.6 Hz, 1H), 2.47 (s, 3H), 2.25-2.13 (m, 1H), 2.11-1.95 (m, 2H), 1.95-1.87 (m, 1H), 1.87-1.68 (m, 2H), 1.67-1.56 (m, 1H), 1.46-1.21 (m, 3H), 0.67-0.49 (m, 3H), 0.44-0.34 (m, 1H). MS (ESI) m/z: [M+H]$^+$ Found 554.2.

Example 279

N—((S)-(7-((R)-Cyclopropyl(2-(3-fluorobicyclo[1.1.1]pentan-1-yl)acetamido)methyl)imidazo[1,2-b]pyridazin-2-yl)(4,4-difluorocyclohexyl)methyl)-4-isopropyl-1,2,5-oxadiazole-3-carboxamide

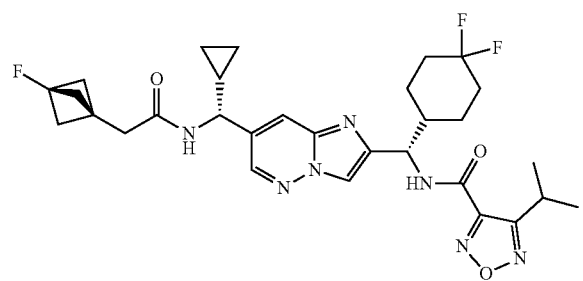 [SMILES: CC(C)c1nonc1C(=O)N[C@H](c1cn2ncc([C@H](NC(=O)C[C@]34C[C@](F)(C3)C4)C3CC3)cc2n1)C1CCC(F)(F)CC1]

The title compound was prepared as described for the synthesis of Example 38 using N—((R)-(2-((S)-amino(4,4-difluorocyclohexyl)methyl)imidazo[1,2-b]pyridazin-7-yl)(cyclopropyl)methyl)-2-(3-fluorobicyclo[1.1.1]pentan-1-yl)acetamide (Intermediate 228) in place of N—((R)-(2-((S)-amino(4,4-difluorocyclohexyl)methyl)imidazo[1,2-b]pyridazin-7-yl)(cyclopropyl)methyl)-4,4,4-trifluorobutanamide, and 4-isopropyl-1,2,5-oxadiazole-3-carboxylic acid (Intermediate 569) in place of 1-(3,3,3-trifluoropropyl)-1H-1,2,4-triazole-5-carboxylic acid to afford the title compound as a white solid. $^1$H NMR (400 MHz, DMSO-d$_6$) δ 9.51 (d, J=9.0 Hz, 1H), 8.57 (d, J=7.8 Hz, 1H), 8.51 (d, J=2.1 Hz, 1H), 8.22 (s, 1H), 7.95 (d, J=1.9 Hz, 1H), 5.19 (t, J=8.5 Hz, 1H), 4.27 (t, J=8.4 Hz, 1H), 2.54-2.52 (m, 2H), 2.25-2.12 (m, 1H), 2.10-1.97 (m, 2H), 1.96-1.93 (m, 6H), 1.93-1.68 (m, 3H), 1.68-1.57 (m, 1H), 1.46-1.32 (m, 1H), 1.32-1.16 (m, 9H), 0.66-0.45 (m, 3H), 0.44-0.34 (m, 1H). MS (ESI) m/z: [M+H]$^+$ Found 600.3.

Example 280

N—((S)-(7-((R)-Cyclopropyl(4,4-difluorobutanamido)methyl)imidazo[1,2-b]pyridazin-2-yl)(4,4-difluorocyclohexyl)methyl)-1-isopropyl-1H-pyrazole-5-carboxamide

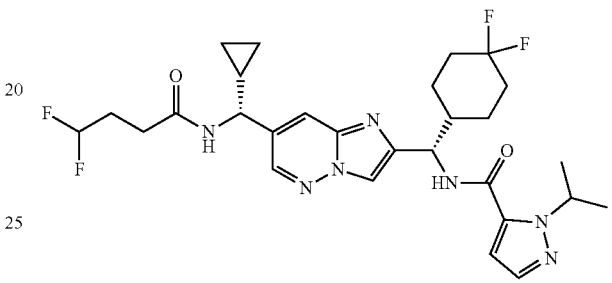

The title compound was prepared as described for the synthesis of Example 38 using 4,4-difluorobutanoic acid in place of 4,4,4-trifluorobutanoic acid, and 1-isopropyl-1H-pyrazole-5-carboxylic acid in place of 1-(3,3,3-trifluoropropyl)-1H-1,2,4-triazole-5-carboxylic acid to afford the title compound as a white powder. $^1$H NMR (500 MHz, DMSO-d$_6$) δ 9.49 (d, J=9.0 Hz, 1H), 8.65 (d, J=7.6 Hz, 1H), 8.52 (d, J=2.1 Hz, 1H), 8.21 (s, 1H), 7.95 (d, J=1.9 Hz, 1H), 6.26-5.85 (m, 1H), 5.19 (t, J=8.4 Hz, 1H), 4.29 (t, J=8.4 Hz, 1H), 3.38-3.32 (m, 1H), 2.41-2.31 (m, 2H), 2.24-2.13 (m, 1H), 2.13-1.95 (m, 4H), 1.93-1.85 (m, 1H), 1.85-1.68 (m, 2H), 1.68-1.57 (m, 1H), 1.46-1.32 (m, 1H), 1.32-1.16 (m, 8H), 0.64-0.44 (m, 3H), 0.43-0.35 (m, 1H). MS (ESI) m/z: [M+H]$^+$ Found 580.2.

Example 281

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-4-isopropyl-1,2,5-oxadiazole-3-carboxamide

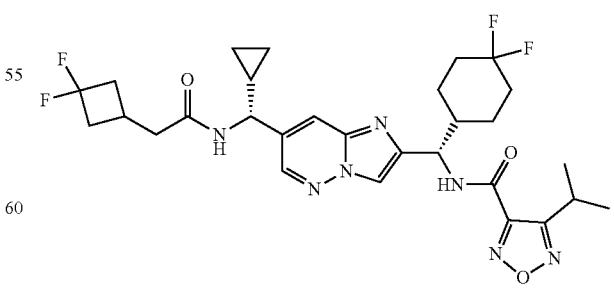

The title compound was prepared as described for the synthesis of Example 38 using 2-(3,3-difluorocyclobutyl)acetic acid in place of 4,4,4-trifluorobutanoic acid, and 4-isopropyl-1,2,5-oxadiazole-3-carboxylic acid (Intermediate 569) in place of 1-(3,3,3-trifluoropropyl)-1H-1,2,4-triazole-5-carboxylic acid to afford the title compound as a white powder. $^1$H NMR (400 MHz, DMSO-d$_6$) δ 9.50 (d, J=8.9 Hz, 1H), 8.60 (d, J=7.8 Hz, 1H), 8.51 (d, J=2.0 Hz, 1H), 8.21 (s, 1H), 7.94 (d, J=2.0 Hz, 1H), 5.19 (t, J=8.5 Hz, 1H), 4.28 (t, J=8.4 Hz, 1H), 3.38-3.33 (m, 1H), 2.74-2.57 (m, 2H), 2.44-2.37 (m, 3H), 2.36-2.25 (m, 2H), 2.22-2.13 (m, 1H), 2.11-1.95 (m, 2H), 1.93-1.69 (m, 3H), 1.68-1.59 (m, 1H), 1.46-1.33 (m, 1H), 1.32-1.18 (m, 8H), 0.64-0.44 (m, 3H), 0.43-0.31 (m, 1H). MS (ESI) m/z: [M+H]$^+$ Found 606.3.

Example 282

N—((S)-(7-((R)-Cyclopropyl(4,4-difluorobutanamido)methyl)imidazo[1,2-b]pyridazin-2-yl)(4,4-difluorocyclohexyl)methyl)-1-(ethyl-d$_5$)-1H-pyrazole-5-carboxamide

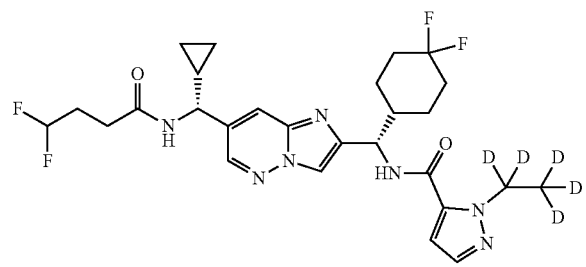 [SMILES: [2H]C([2H])([2H])C([2H])([2H])n1nccc1C(=O)N[C@H](c1cn2ncc([C@H](NC(=O)CCC(F)F)C3CC3)cc2n1)C1CCC(F)(F)CC1]

The title compound was prepared as described for the synthesis of Example 38 using 4,4-difluorobutanoic acid in place of 4,4,4-trifluorobutanoic acid, and 1-(ethyl-d$_5$)-1H-pyrazole-5-carboxylic acid (Intermediate 204) in place of 1-(3,3,3-trifluoropropyl)-1H-1,2,4-triazole-5-carboxylic acid to afford the title compound as a white powder. $^1$H NMR (400 MHz, DMSO-d$_6$) δ 8.71 (d, J=9.1 Hz, 1H), 8.65 (d, J=7.8 Hz, 1H), 8.51 (d, J=2.1 Hz, 1H), 8.21 (s, 1H), 7.93 (d, J=2.0 Hz, 1H), 7.48 (d, J=2.1 Hz, 1H), 6.99 (d, J=2.0 Hz, 1H), 6.26-5.85 (m, 1H), 5.16 (t, J 8.7 Hz, 1H), 4.29 (t, J=8.5 Hz, 1H), 2.39-2.31 (m, 2H), 2.25-2.13 (m, 1H), 2.13-1.94 (m, 4H), 1.93-1.84 (m, 1H), 1.84-1.67 (m, 2H), 1.66-1.58 (m, 1H), 1.45-1.33 (m, 1H), 1.33-1.16 (m, 2H), 0.63-0.44 (m, 3H), 0.43-0.34 (m, 1H). MS (ESI) m/z: [M+H]$^+$ Found 569.3.

Example 283

N—((S)-(7-((R)-Cyclopropyl(4,4-difluorobutanamido)methyl)imidazo[1,2-b]pyridazin-2-yl)(4,4-difluorocyclohexyl)methyl)-1-(methyl-d$_3$)-1H-pyrazole-5-carboxamide

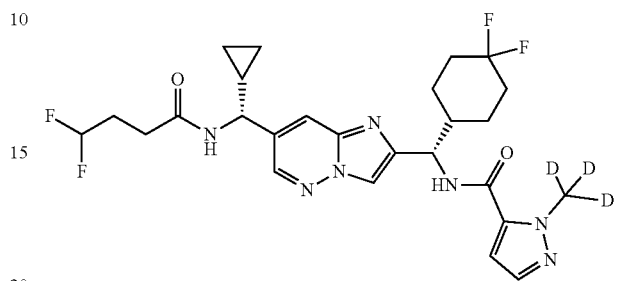

The title compound was prepared as described for the synthesis of Example 38 using 4,4-difluorobutanoic acid in place of 4,4,4-trifluorobutanoic acid, and 1-(methyl-d$_3$)-1H-pyrazole-5-carboxylic acid (Intermediate 435) in place of 1-(3,3,3-trifluoropropyl)-1H-1,2,4-triazole-5-carboxylic acid to afford the title compound as a white powder. $^1$H NMR (400 MHz, DMSO-d$_6$) δ 8.71 (d, J=9.0 Hz, 1H), 8.65 (d, J=7.8 Hz, 1H), 8.51 (d, J=2.1 Hz, 1H), 8.21 (s, 1H), 7.93 (d, J=2.0 Hz, 1H), 7.46 (d, J=2.1 Hz, 1H), 7.03 (d, J=2.0 Hz, 1H), 6.30-5.81 (m, 1H), 5.15 (t, J 8.7 Hz, 1H), 4.29 (t, J=8.4 Hz, 1H), 2.41-2.29 (m, 2H), 2.25-2.13 (m, 1H), 2.12-1.94 (m, 4H), 1.93-1.86 (m, 1H), 1.86-1.67 (m, 2H), 1.66-1.56 (m, 1H), 1.45-1.32 (m, 1H), 1.32-1.14 (m, 2H), 0.63-0.44 (m, 3H), 0.43-0.34 (m, 1H). MS (ESI) m/z: [M+H]$^+$ Found 553.3.

Example 284

N—((S)-(7-((R)-Cyclopropyl(4,4,4-trifluorobutanamido)methyl)imidazo[1,2-b]pyridazin-2-yl)(4,4-difluorocyclohexyl)methyl)-3-isopropoxyisoxazole-4-carboxamide

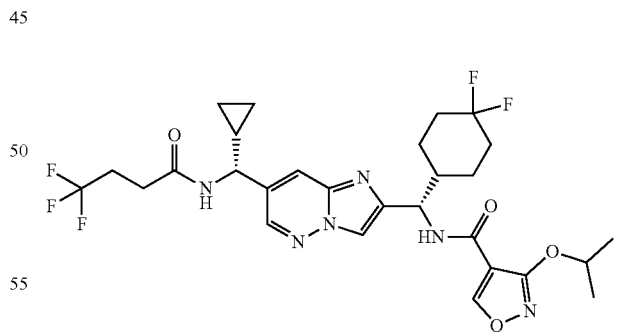

The title compound was prepared as described for the synthesis of Example 38 using 3-isopropoxyisoxazole-4-carboxylic acid (Intermediate 572) in place of 1-(3,3,3-trifluoropropyl)-1H-1,2,4-triazole-5-carboxylic acid to afford the title compound as a white powder. $^1$H NMR (400 MHz, DMSO-d$_6$) δ 9.22 (s, 1H), 8.74 (d, J=7.6 Hz, 1H), 8.53 (d, J=2.0 Hz, 1H), 8.23 (s, 1H), 7.95 (d, J=8.6 Hz, 1H), 7.91 (d, J=1.9 Hz, 1H), 5.21-5.13 (m, 1H), 4.99-4.89 (m, 1H), 4.31 (t, J=8.4 Hz, 1H), 2.49-2.45 (m, 3H), 2.13-1.93 (m, 3H), 1.88-1.76 (m, 2H), 1.76-1.60 (m, 2H), 1.49-1.44 (m, 3H), 1.44-1.40 (m, 3H), 1.40-1.27 (m, 2H), 1.27-1.16 (m, 2H), 0.65-0.48 (m, 3H), 0.43-0.34 (m, 1H). MS (ESI) m/z: [M+H]⁺ Found 613.3.

Example 285

N—((S)-(7-((R)-Cyclopropyl(4,4,4-trifluorobutanamido)methyl)imidazo[1,2-b]pyridazin-2-yl)(4,4-difluorocyclohexyl)methyl)-3-(2,2-difluoroethoxy)isoxazole-4-carboxamide

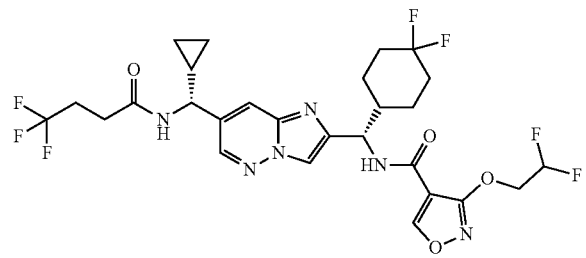 [SMILES: O=C(CCC(F)(F)F)N[C@@H](c1cnn2cc([C@@H](NC(=O)c3conc3OCC(F)F)C3CCC(F)(F)CC3)nc2c1)C1CC1]

The title compound was prepared as described for the synthesis of Example 38 using 3-(2,2-difluoroethoxy)isoxazole-4-carboxylic acid (Intermediate 573) in place of 1-(3,3,3-trifluoropropyl)-1H-1,2,4-triazole-5-carboxylic acid to afford the title compound as a white powder. ¹H NMR (400 MHz, DMSO-d₆) δ 9.29 (s, 1H), 8.76-8.70 (m, 1H), 8.52 (d, J=2.0 Hz, 1H), 8.21 (s, 1H), 8.09 (d, J=8.9 Hz, 1H), 7.93 (d, J=2.0 Hz, 1H), 6.65-6.18 (m, 1H), 5.19-5.13 (m, 1H), 4.69-4.56 (m, 2H), 4.30 (t, J=8.3 Hz, 1H), 2.59-2.53 (m, 1H), 2.49-2.44 (m, 3H), 2.15-1.93 (m, 3H), 1.88-1.79 (m, 2H), 1.79-1.60 (m, 2H), 1.43-1.31 (m, 1H), 1.30-1.16 (m, 2H), 0.64-0.46 (m, 3H), 0.43-0.34 (m, 1H). MS (ESI) m/z: [M+H]⁺ Found 635.2.

Example 286

N—((S)-(7-((R)-Cyclopropyl(4,4-difluorobutanamido)methyl)imidazo[1,2-b]pyridazin-2-yl)(4,4-difluorocyclohexyl)methyl)-3-(2,2-difluoroethoxy)isoxazole-4-carboxamide

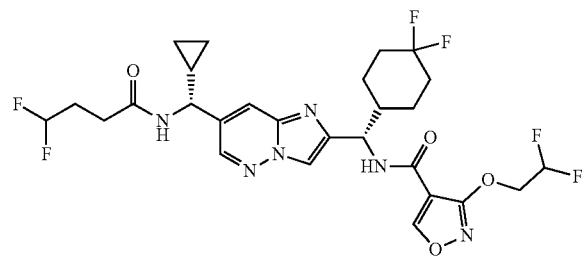 [SMILES: O=C(CCC(F)F)N[C@@H](c1cnn2cc([C@@H](NC(=O)c3conc3OCC(F)F)C3CCC(F)(F)CC3)nc2c1)C1CC1]

The title compound was prepared as described for the synthesis of Example 38 using 4,4-difluorobutanoic acid in place of 4,4,4-trifluorobutanoic acid, and 3-(2,2-difluoroethoxy)isoxazole-4-carboxylic acid (Intermediate 573) in place of 1-(3,3,3-trifluoropropyl)-1H-1,2,4-triazole-5-carboxylic acid to afford the title compound as a white powder. ¹H NMR (400 MHz, DMSO-d₆) δ 9.29 (s, 1H), 8.66 (d, J=7.6 Hz, 1H), 8.52 (d, J=2.0 Hz, 1H), 8.20 (s, 1H), 8.10 (d, J=8.9 Hz, 1H), 7.92 (d, J=1.9 Hz, 1H), 6.63-6.28 (m, 1H), 6.26-5.87 (m, 1H), 5.29-5.10 (m, 1H), 4.72-4.52 (m, 2H), 4.37-4.22 (m, 1H), 2.39-2.29 (m, 2H), 2.16-1.92 (m, 5H), 1.90-1.58 (m, 4H), 1.44-1.13 (m, 3H), 0.64-0.45 (m, 3H), 0.44-0.35 (m, 1H). MS (ESI) m/z: [M+H]⁺ Found 617.2.

Example 287

N—((S)-(7-((R)-Cyclopropyl(4,4-difluorobutanamido)methyl)imidazo[1,2-b]pyridazin-2-yl)(4,4-difluorocyclohexyl)methyl)-3-((difluoromethoxy)methyl)isoxazole-4-carboxamide

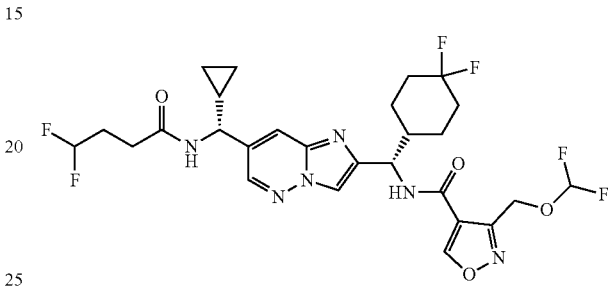

The title compound was prepared as described for the synthesis of Example 38 using 4,4-difluorobutanoic acid in place of 4,4,4-trifluorobutanoic acid, and 3-((difluoromethoxy)methyl)isoxazole-4-carboxylic acid (Intermediate 214) in place of 1-(3,3,3-trifluoropropyl)-1H-1,2,4-triazole-5-carboxylic acid to afford the title compound as a white powder. ¹H NMR (400 MHz, DMSO-d₆) δ 9.56 (s, 1H), 8.83 (d, J=9.0 Hz, 1H), 8.66 (d, J=7.6 Hz, 1H), 8.51 (d, J=2.1 Hz, 1H), 8.22 (s, 1H), 7.93 (d, J=2.1 Hz, 1H), 7.03-6.55 (m, 1H), 6.27-5.81 (m, 1H), 5.26-5.10 (m, 3H), 4.29 (t, J=8.4 Hz, 1H), 2.39-2.31 (m, 2H), 2.21-2.13 (m, 1H), 2.13-1.93 (m, 4H), 1.91-1.68 (m, 3H), 1.66-1.57 (m, 1H), 1.46-1.16 (m, 3H), 0.63-0.45 (m, 3H), 0.44-0.34 (m, 1H). MS (ESI) m/z: [M+H]⁺ Found 617.2.

Example 288

4-Cyclopropyl-N—((S)-(7-((R)-cyclopropyl(4,4-difluorobutanamido)methyl)imidazo[1,2-b]pyridazin-2-yl)(4,4-difluorocyclohexyl)methyl)-1,2,5-oxadiazole-3-carboxamide

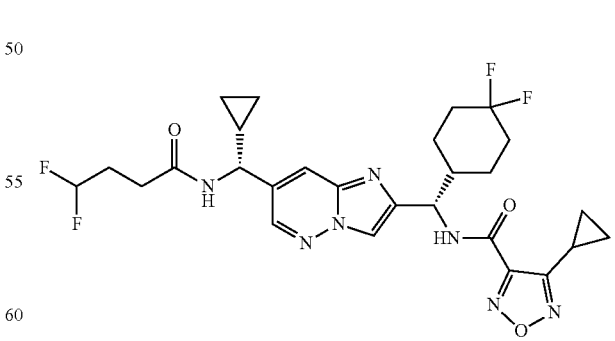

The title compound was prepared as described for the synthesis of Example 38 using 4,4-difluorobutanoic acid in place of 4,4,4-trifluorobutanoic acid, and 4-cyclopropyl-1,2,5-oxadiazole-3-carboxylic acid (Intermediate 570) in place of 1-(3,3,3-trifluoropropyl)-1H-1,2,4-triazole-5-carboxylic acid to afford the title compound as a white powder. ¹H NMR (400 MHz, DMSO-d₆) δ 9.47 (d, J=8.9 Hz, 1H), 8.65 (d, J=7.8 Hz, 1H), 8.52 (d, J=2.0 Hz, 1H), 8.23 (s, 1H), 7.95 (d, J=2.0 Hz, 1H), 6.25-5.87 (m, 1H), 5.27-4.89 (m, 1H), 4.42-4.21 (m, 1H), 2.40-2.33 (m, 2H), 2.33-2.25 (m, 1H), 2.24-2.13 (m, 1H), 2.13-1.96 (m, 4H), 1.94-1.87 (m, 1H), 1.85-1.69 (m, 2H), 1.68-1.58 (m, 1H), 1.46-1.26 (m, 2H), 1.26-1.18 (m, 1H), 1.16-1.09 (m, 2H), 0.99-0.94 (m, 2H), 0.63-0.45 (m, 3H), 0.44-0.35 (m, 1H). MS (ESI) m/z: [M+H]⁺ Found 578.2.

Example 289

4-Cyclopropyl-N—((S)-(7-((R)-cyclopropyl(2-(3,3-difluorocyclobutyl)acetamido)methyl)imidazo[1,2-b]pyridazin-2-yl)(4,4-difluorocyclohexyl)methyl)-1,2,5-oxadiazole-3-carboxamide

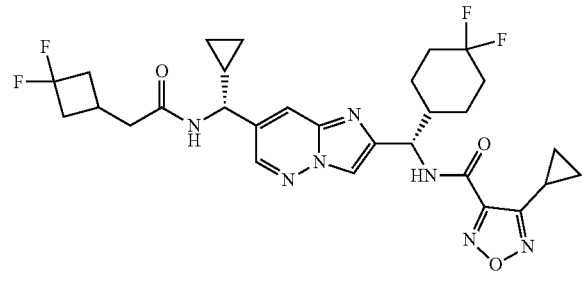 [SMILES: O=C(CC1CC(F)(F)C1)N[C@@H](c1cnn2cc([C@@H](NC(=O)c3nonc3C3CC3)C3CCC(F)(F)CC3)nc2c1)C1CC1]

The title compound was prepared as described for the synthesis of Example 38 using 2-(3,3-difluorocyclobutyl)acetic acid in place of 4,4,4-trifluorobutanoic acid, and 4-cyclopropyl-1,2,5-oxadiazole-3-carboxylic acid (Intermediate 570) in place of 1-(3,3,3-trifluoropropyl)-1H-1,2,4-triazole-5-carboxylic acid to afford the title compound as a white powder. ¹H NMR (400 MHz, DMSO-d₆) δ 9.39 (d, J=8.9 Hz, 1H), 8.52 (d, J=7.9 Hz, 1H), 8.43 (d, J=2.1 Hz, 1H), 8.15 (s, 1H), 7.87 (d, J=1.9 Hz, 1H), 5.18-5.06 (m, 1H), 4.25-4.11 (m, 1H), 2.66-2.48 (m, 2H), 2.37-2.29 (m, 3H), 2.29-2.16 (m, 3H), 2.14-2.04 (m, 1H), 2.04-1.87 (m, 2H), 1.87-1.79 (m, 1H), 1.79-1.61 (m, 2H), 1.60-1.49 (m, 1H), 1.39-1.18 (m, 2H), 1.18-1.09 (m, 1H), 1.09-1.01 (m, 2H), 0.92-0.86 (m, 2H), 0.55-0.36 (m, 3H), 0.33-0.26 (m, 1H). MS (ESI) m/z: [M+H]⁺ Found 604.3.

Example 290

N-((1S)-(7-((1R)-Cyclopropyl(3-(2,2-difluorocyclopropyl)propanamido)methyl)imidazo[1,2-b]pyridazin-2-yl)(4,4-difluorocyclohexyl)methyl)-4-methyl-1,2,5-oxadiazole-3-carboxamide

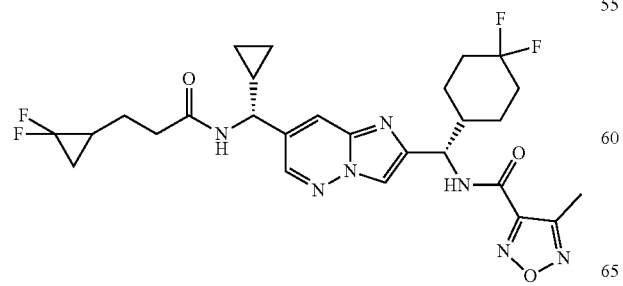

The title compound was prepared as described for the synthesis of Example 249 using 3-(2,2-difluorocyclopropyl)propanoic acid in place of 2-(bicyclo[1.1.1]pentan-1-yl)acetic acid to afford the title compound as a white solid. ¹H NMR (500 MHz, DMSO-d₆) δ 9.40 (d, J=9.0 Hz, 1H), 8.59 (d, J=7.8 Hz, 1H), 8.51 (t, J=1.6 Hz, 1H), 8.23 (s, 1H), 7.95 (s, 1H), 5.22-5.12 (m, 1H), 4.32-4.25 (m, 1H), 2.48-2.45 (m, 3H), 2.32-2.26 (m, 2H), 2.23-2.13 (m, 1H), 2.10-1.94 (m, 2H), 1.94-1.87 (m, 1H), 1.85-1.71 (m, 2H), 1.68-1.57 (m, 4H), 1.52-1.34 (m, 2H), 1.33-1.17 (m, 2H), 1.13-1.02 (m, 1H), 0.63-0.44 (m, 3H), 0.42-0.34 (m, 1H). MS (ESI) m/z: [M+H]⁺ Found 578.2.

Example 291

N-((1S)-(7-((1R)-Cyclopropyl(2-(2,2-difluorocyclopentyl)acetamido)methyl)imidazo[1,2-b]pyridazin-2-yl)(4,4-difluorocyclohexyl)methyl)-4-methyl-1,2,5-oxadiazole-3-carboxamide

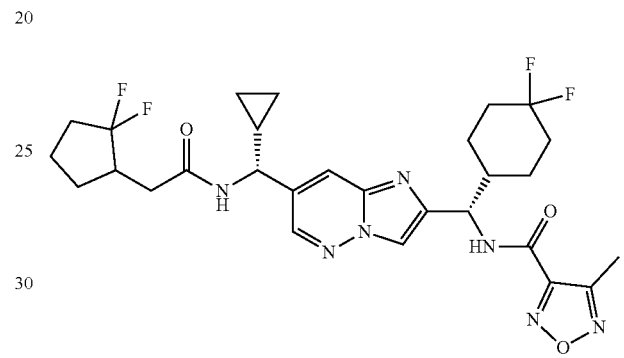

The title compound was prepare as described for the synthesis of Example 249 using 2-(2,2-difluorocyclopentyl)acetic acid in place of 2-(bicyclo[1.1.1]pentan-1-yl)acetic acid to afford the title compound as a white solid. ¹H NMR (500 MHz, DMSO-d₆) δ 9.33 (d, J=9.0 Hz, 1H), 8.53-8.47 (m, 1H), 8.45-8.39 (m, 1H), 8.16 (s, 1H), 7.90-7.84 (m, 1H), 5.10 (t, J=8.6 Hz, 1H), 4.21 (t, J=8.4 Hz, 1H), 2.40 (s, 3H), 2.37-2.28 (m, 1H), 2.21-2.18 (m, 2H), 2.18-2.02 (m, 3H), 2.01-1.87 (m, 3H), 1.87-1.79 (m, 2H), 1.78-1.62 (m, 3H), 1.58-1.50 (m, 1H), 1.40-1.26 (m, 2H), 1.25-1.10 (m, 2H), 0.54-0.36 (m, 3H), 0.34-0.27 (m, 1H). MS (ESI) m/z: [M+H]⁺ Found 592.3.

Example 292

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-3-isopropoxyisoxazole-4-carboxamide

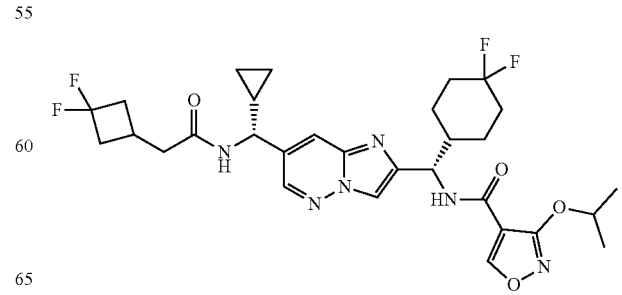

The title compound was prepared as described for the synthesis of Example 38 using 2-(3,3-difluorocyclobutyl)acetic acid in place of 4,4,4-trifluorobutanoic acid, and 3-isopropoxyisoxazole-4-carboxylic acid (Intermediate 572) in place of 1-(3,3,3-trifluoropropyl)-1H-1,2,4-triazole-5-carboxylic acid to afford the title compound as a white powder. $^1$H NMR (400 MHz, DMSO-$d_6$) δ 9.22 (s, 1H), 8.64-8.57 (m, 1H), 8.52 (d, J=2.1 Hz, 1H), 8.23 (s, 1H), 7.95 (d, J=8.6 Hz, 1H), 7.90 (d, J=1.9 Hz, 1H), 5.21-5.14 (m, 1H), 4.99-4.88 (m, 1H), 4.29 (t, J=8.4 Hz, 1H), 2.74-2.56 (m, 2H), 2.46-2.37 (m, 3H), 2.37-2.23 (m, 2H), 2.14-1.92 (m, 3H), 1.89-1.76 (m, 2H), 1.76-1.59 (m, 2H), 1.49-1.44 (m, 3H), 1.44-1.39 (m, 3H), 1.37-1.15 (m, 3H), 0.63-0.45 (m, 3H), 0.42-0.34 (m, 1H). MS (ESI) m/z: [M+H]$^+$ Found 621.3.

Example 293

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-3-(2,2-difluoroethoxy)isoxazole-4-carboxamide

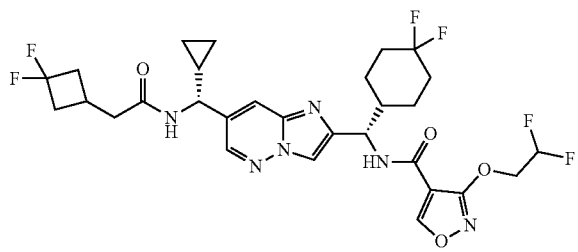 [SMILES: O=C(CC1CC(F)(F)C1)N[C@@H](c1cnn2cc([C@@H](NC(=O)c3conc3OCC(F)F)C3CCC(F)(F)CC3)nc2c1)C1CC1]

The title compound was prepared as described for the synthesis of Example 38 using 2-(3,3-difluorocyclobutyl)acetic acid in place of 4,4,4-trifluorobutanoic acid, and 3-(2,2-difluoroethoxy)isoxazole-4-carboxylic acid (Intermediate 573) in place of 1-(3,3,3-trifluoropropyl)-1H-1,2,4-triazole-5-carboxylic acid to afford the title compound as a white powder. $^1$H NMR (400 MHz, DMSO-$d_6$) δ 9.29 (s, 1H), 8.60 (d, J=7.8 Hz, 1H), 8.51 (d, J=2.1 Hz, 1H), 8.20 (s, 1H), 8.09 (d, J=8.9 Hz, 1H), 7.91 (d, J=2.0 Hz, 1H), 6.62-6.23 (m, 1H), 5.22-5.09 (m, 1H), 4.73-4.53 (m, 2H), 4.28 (t, J=8.4 Hz, 1H), 2.73-2.56 (m, 2H), 2.44-2.37 (m, 3H), 2.37-2.23 (m, 2H), 2.15-1.92 (m, 3H), 1.87-1.68 (m, 3H), 1.67-1.59 (m, 1H), 1.41-1.14 (m, 3H), 0.63-0.44 (m, 3H), 0.42-0.34 (m, 1H). MS (ESI) m/z: [M+H]$^+$ Found 643.2.

Example 294

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-3-((difluoromethoxy)methyl)isoxazole-4-carboxamide

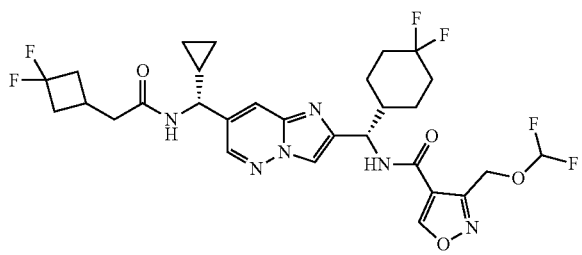 [SMILES: O=C(CC1CC(F)(F)C1)N[C@@H](c1cnn2cc([C@@H](NC(=O)c3conc3COC(F)F)C3CCC(F)(F)CC3)nc2c1)C1CC1]

The title compound was prepared as described for the synthesis of Example 38 using 2-(3,3-difluorocyclobutyl)acetic acid in place of 4,4,4-trifluorobutanoic acid, and 3-((difluoromethoxy)methyl)isoxazole-4-carboxylic acid (Intermediate 214) in place of 1-(3,3,3-trifluoropropyl)-1H-1,2,4-triazole-5-carboxylic acid to afford the title compound as a white powder. $^1$H NMR (400 MHz, DMSO-$d_6$) δ 9.56 (s, 1H), 8.83 (d, J=8.9 Hz, 1H), 8.60 (d, J=7.6 Hz, 1H), 8.50 (d, J=2.0 Hz, 1H), 8.22 (s, 1H), 7.92 (d, J=2.0 Hz, 1H), 7.01-6.53 (m, 1H), 5.27-5.07 (m, 3H), 4.34-4.21 (m, 1H), 2.72-2.57 (m, 2H), 2.47-2.22 (m, 5H), 2.21-2.10 (m, 1H), 2.10-1.92 (m, 2H), 1.91-1.68 (m, 3H), 1.66-1.57 (m, 1H), 1.46-1.14 (m, 3H), 0.63-0.42 (m, 3H), 0.42-0.28 (m, 1H). MS (ESI) m/z: [M+H]$^+$ Found 643.2.

Example 295

N—((S)-(7-((R)-Cyclopropyl(2-(3-fluorobicyclo[1.1.1]pentan-1-yl)acetamido)methyl)imidazo[1,2-b]pyridazin-2-yl)(4,4-difluorocyclohexyl)methyl)-3-(2,2-difluoroethoxy)isoxazole-4-carboxamide

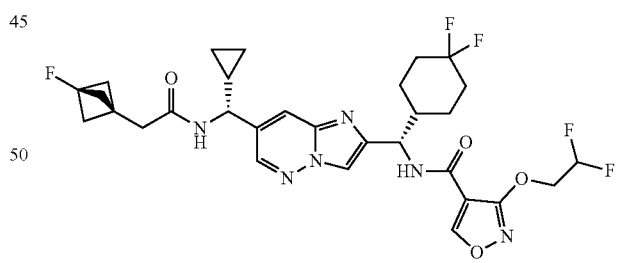

The title compound was prepared as described for the synthesis of Example 38 using N—((R)-(2-((S)-amino(4,4-difluorocyclohexyl)methyl)imidazo[1,2-b]pyridazin-7-yl)(cyclopropyl)methyl)-2-(3-fluorobicyclo[1.1.1]pentan-1-yl)acetamide (Intermediate 228) in place of N—((R)-(2-((S)-amino(4,4-difluorocyclohexyl)methyl)imidazo[1,2-b]pyridazin-7-yl)(cyclopropyl)methyl)-4,4,4-trifluorobutanamide, and 3-(2,2-difluoroethoxy)isoxazole-4-carboxylic acid (Intermediate 573) in place of 1-(3,3,3-trifluoropropyl)-1H-1,2,4-triazole-5-carboxylic acid to afford the title compound as a white solid. $^1$H NMR (400 MHz, DMSO-$d_6$) δ 9.29 (s, 1H), 8.58 (d, J=7.9 Hz, 1H), 8.51

(d, J=2.1 Hz, 1H), 8.21 (s, 1H), 8.12-8.07 (m, 1H), 7.92 (d, J=2.0 Hz, 1H), 6.62-6.27 (m, 1H), 5.26-5.08 (m, 1H), 4.71-4.47 (m, 2H), 4.33-4.15 (m, 1H), 2.58-2.55 (m, 1H), 2.48-2.43 (m, 1H), 2.14-1.91 (m, 9H), 1.88-1.59 (m, 4H), 1.43-1.15 (m, 3H), 0.65-0.44 (m, 3H), 0.43-0.32 (m, 1H). MS (ESI) m/z: [M+H]⁺ Found 637.2.

Example 296

4-Cyclopropyl-N—((S)-(7-((R)-cyclopropyl(2-(3-fluorobicyclo[1.1.1]pentan-1-yl)acetamido)methyl)imidazo[1,2-b]pyridazin-2-yl)(4,4-difluorocyclohexyl)methyl)-1,2,5-oxadiazole-3-carboxamide

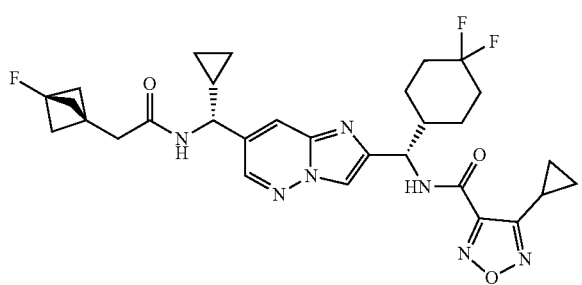 [SMILES: O=C(C[C@]12C[C@](F)(C1)C2)N[C@@H](c1cnn2cc([C@@H](NC(=O)c3nonc3C3CC3)C3CCC(F)(F)CC3)nc2c1)C1CC1]

The title compound was prepared as described for the synthesis of Example 38 using N—((R)-(2-((S)-amino(4,4-difluorocyclohexyl)methyl)imidazo[1,2-b]pyridazin-7-yl)(cyclopropyl)methyl)-2-(3-fluorobicyclo[1.1.1]pentan-1-yl)acetamide (Intermediate 228) in place of N—((R)-(2-((S)-amino(4,4-difluorocyclohexyl)methyl)imidazo[1,2-b]pyridazin-7-yl)(cyclopropyl)methyl)-4,4,4-trifluorobutanamide, and 4-cyclopropyl-1,2,5-oxadiazole-3-carboxylic acid (Intermediate 570) in place of 1-(3,3,3-trifluoropropyl)-1H-1,2,4-triazole-5-carboxylic acid to afford the title compound as a white solid. ¹H NMR (500 MHz, DMSO-d₆) δ 9.40 (d, J=9.0 Hz, 1H), 8.50 (d, J=7.8 Hz, 1H), 8.43 (d, J=2.1 Hz, 1H), 8.16 (s, 1H), 7.88 (d, J=1.9 Hz, 1H), 5.19-5.00 (m, 1H), 4.19 (t, J=8.5 Hz, 1H), 2.50-2.44 (m, 2H), 2.25-2.16 (m, 1H), 2.15-2.06 (m, 1H), 2.04-1.93 (m, 1H), 1.92-1.79 (m, 8H), 1.79-1.62 (m, 2H), 1.59-1.49 (m, 1H), 1.39-1.09 (m, 3H), 1.07-1.00 (m, 2H), 0.93-0.86 (m, 2H), 0.58-0.37 (m, 3H), 0.33-0.26 (m, 1H). MS (ESI) m/z: [M+H]⁺ Found 598.2.

Example 297

4-Cyclopropyl-N—((S)-(7-((R)-cyclopropyl(2-(1-(trifluoromethyl)cyclopropyl)acetamido)methyl)imidazo[1,2-b]pyridazin-2-yl)(4,4-difluorocyclohexyl)methyl)-1,2,5-oxadiazole-3-carboxamide

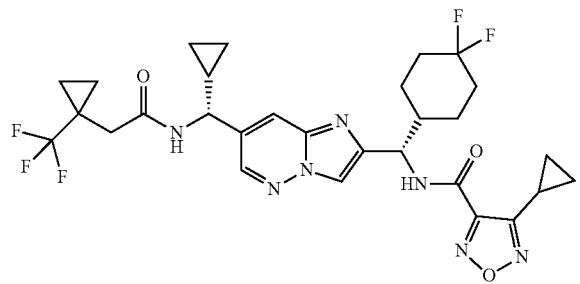 [SMILES: O=C(CC1(C(F)(F)F)CC1)N[C@@H](c1cnn2cc([C@@H](NC(=O)c3nonc3C3CC3)C3CCC(F)(F)CC3)nc2c1)C1CC1]

The title compound was prepared as described for the synthesis of Example 38 using 2-(1-(trifluoromethyl)cyclopropyl)acetic acid in place of 4,4,4-trifluorobutanoic acid, and 4-cyclopropyl-1,2,5-oxadiazole-3-carboxylic acid (Intermediate 570) in place of 1-(3,3,3-trifluoropropyl)-1H-1,2,4-triazole-5-carboxylic acid to afford the title compound as a white powder. ¹H NMR (400 MHz, DMSO-d₆) δ 9.40 (d, J=8.9 Hz, 1H), 8.63 (d, J=7.8 Hz, 1H), 8.43-8.41 (m, 1H), 8.17-8.14 (m, 1H), 7.88-7.84 (m, 1H), 5.16-5.08 (m, 1H), 4.23-4.13 (m, 1H), 2.45-2.44 (m, 2H), 2.24-2.16 (m, 1H), 2.16-2.06 (m, 1H), 2.03-1.87 (m, 2H), 1.86-1.80 (m, 1H), 1.78-1.63 (m, 2H), 1.60-1.51 (m, 1H), 1.39-1.27 (m, 1H), 1.26-1.11 (m, 2H), 1.07-1.01 (m, 2H), 0.92-0.87 (m, 2H), 0.87-0.73 (m, 4H), 0.55-0.38 (m, 3H), 0.33-0.25 (m, 1H). MS (ESI) m/z: [M+H]⁺ Found 622.2.

Example 298

N—((S)-(7-((R)-Cyclopropyl((R*)-4,4,4-trifluoro-3-methylbutanamido)methyl)imidazo[1,2-b]pyridazin-2-yl)(4,4-difluorocyclohexyl)methyl)-3-(2,2-difluoroethoxy)isoxazole-4-carboxamide

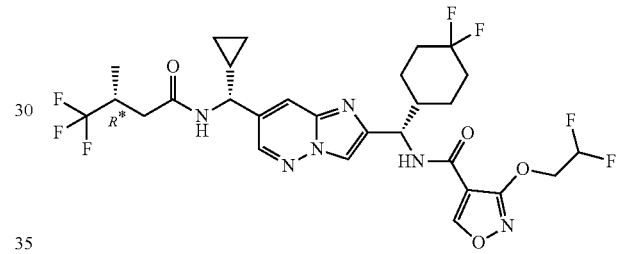

Example 299

N—((S)-(7-((R)-Cyclopropyl((S*)-4,4,4-trifluoro-3-methylbutanamido)methyl)imidazo[1,2-b]pyridazin-2-yl)(4,4-difluorocyclohexyl)methyl)-3-(2,2-difluoroethoxy)isoxazole-4-carboxamide

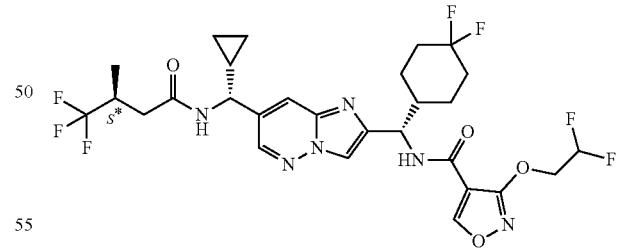

The title compounds were prepared as described for the synthesis of Example 38 using 4,4,4-trifluoro-3-methylbutanoic acid in place of 4,4,4-trifluorobutanoic acid, and 3-(2,2-difluoroethoxy)isoxazole-4-carboxylic acid (Intermediate 573) in place of 1-(3,3,3-trifluoropropyl)-1H-1,2,4-triazole-5-carboxylic acid. The diastereomers were separated by SFC with a chiral stationary phase (Stationary phase: AD-H (3×25 cm), Mobile phase: 20% isopropanol/CO₂). The first eluting fraction afforded Example 298 as a white powder. The second eluting fraction afforded Example 299 as a white powder. Example 298: $^1$H NMR (500 MHz, DMSO-d$_6$) δ 9.38-9.14 (m, 1H), 8.81-8.74 (m, 1H), 8.51 (d, J=2.1 Hz, 1H), 8.20 (s, 1H), 8.09 (d, J=8.9 Hz, 1H), 7.94-7.90 (m, 1H), 6.63-6.24 (m, 1H), 5.18-5.12 (m, 1H), 4.77-4.51 (m, 2H), 4.41-4.21 (m, 1H), 2.81-2.72 (m, 1H), 2.56-2.52 (m, 1H), 2.32-2.23 (m, 1H), 2.13-1.92 (m, 3H), 1.87-1.68 (m, 3H), 1.67-1.59 (m, 1H), 1.41-1.30 (m, 1H), 1.29-1.18 (m, 2H), 1.11-1.06 (m, 3H), 0.65-0.47 (m, 3H), 0.43-0.33 (m, 1H). MS (ESI) m/z: [M+H]$^+$ Found 649.3. Example 299: $^1$H NMR (500 MHz, DMSO-d$_6$) δ 9.29 (s, 1H), 8.80-8.75 (m, 1H), 8.52 (d, J=2.0 Hz, 1H), 8.21 (s, 1H), 8.09 (d, J=8.9 Hz, 1H), 7.95-7.89 (m, 1H), 6.59-6.24 (m, 1H), 5.23-5.09 (m, 1H), 4.72-4.52 (m, 2H), 4.40-4.21 (m, 1H), 2.85-2.70 (m, 1H), 2.56-2.52 (m, 1H), 2.31-2.22 (m, 1H), 2.12-1.93 (m, 3H), 1.87-1.69 (m, 3H), 1.68-1.59 (m, 1H), 1.42-1.30 (m, 1H), 1.28-1.17 (m, 2H), 1.03-0.97 (m, 3H), 0.64-0.45 (m, 3H), 0.43-0.36 (m, 1H). MS (ESI) m/z: [M+H]$^+$ Found 649.2.

Example 300

4-Cyclopropyl-N—((S)-(7-((R)-cyclopropyl((R*)-4,4,4-trifluoro-3-methylbutanamido)methyl)imidazo[1,2-b]pyridazin-2-yl)(4,4-difluorocyclohexyl)methyl)-1,2,5-oxadiazole-3-carboxamide

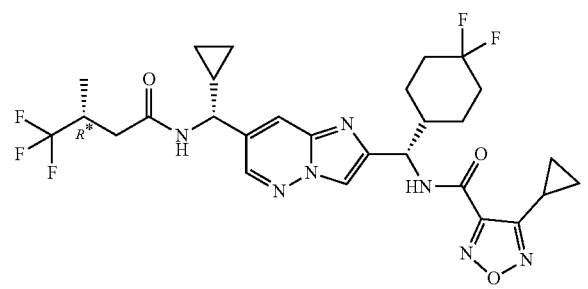 [SMILES: C[C@H](CC(=O)N[C@@H](c1cnn2cc([C@@H](NC(=O)c3nonc3C3CC3)C3CCC(F)(F)CC3)nc2c1)C1CC1)C(F)(F)F]

Example 301

4-Cyclopropyl-N—((S)-(7-((R)-cyclopropyl((S*)-4,4,4-trifluoro-3-methylbutanamido)methyl)imidazo[1,2-b]pyridazin-2-yl)(4,4-difluorocyclohexyl)methyl)-1,2,5-oxadiazole-3-carboxamide

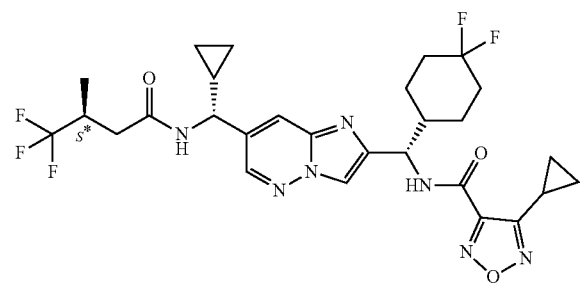 [SMILES: C[C@@H](CC(=O)N[C@@H](c1cnn2cc([C@@H](NC(=O)c3nonc3C3CC3)C3CCC(F)(F)CC3)nc2c1)C1CC1)C(F)(F)F]

The title compounds were prepared as described for the synthesis of Example 38 using 4,4,4-trifluoro-3-methylbutanoic acid in place of 4,4,4-trifluorobutanoic acid, and 4-cyclopropyl-1,2,5-oxadiazole-3-carboxylic acid (Intermediate 570) in place of 1-(3,3,3-trifluoropropyl)-1H-1,2,4-triazole-5-carboxylic acid. The diastereomers were separated by SFC with an achiral stationary phase (Stationary phase: IC (2×15 cm), Mobile phase: 12% isopropanol/CO$_2$). The first eluting fraction afforded Example 300 as a white powder. The second eluting fraction afforded Example 301 as a white powder. Example 300: $^1$H NMR (500 MHz, DMSO-d$_6$) δ 9.47 (d, J=9.0 Hz, 1H), 8.77 (d, J=7.6 Hz, 1H), 8.52 (d, J=2.0 Hz, 1H), 8.23 (s, 1H), 7.96 (d, J=1.9 Hz, 1H), 5.31-5.08 (m, 1H), 4.45-4.14 (m, 1H), 2.84-2.71 (m, 1H), 2.56-2.52 (m, 1H), 2.32-2.24 (m, 2H), 2.23-2.13 (m, 1H), 2.12-1.94 (m, 2H), 1.94-1.87 (m, 1H), 1.87-1.69 (m, 2H), 1.66-1.59 (m, 1H), 1.45-1.34 (m, 1H), 1.33-1.17 (m, 2H), 1.16-1.08 (m, 2H), 1.03-0.99 (m, 3H), 0.99-0.94 (m, 2H), 0.63-0.45 (m, 3H), 0.42-0.34 (m, 1H). MS (ESI) m/z: [M+H]$^+$ Found 610.2. Example 301: $^1$H NMR (500 MHz, DMSO-d$_6$) δ 9.47 (d, J=8.9 Hz, 1H), 8.77 (d, J=7.6 Hz, 1H), 8.51 (d, J=2.0 Hz, 1H), 8.23 (s, 1H), 7.96 (d, J=1.5 Hz, 1H), 5.24-5.15 (m, 1H), 4.38-4.27 (m, 1H), 2.84-2.70 (m, 1H), 2.57-2.52 (m, 1H), 2.32-2.24 (m, 2H), 2.23-2.13 (m, 1H), 2.11-1.94 (m, 2H), 1.94-1.87 (m, 1H), 1.86-1.71 (m, 2H), 1.66-1.58 (m, 1H), 1.47-1.35 (m, 1H), 1.34-1.18 (m, 2H), 1.15-1.10 (m, 2H), 1.09-1.06 (m, 3H), 0.99-0.93 (m, 2H), 0.63-0.45 (m, 3H), 0.43-0.34 (m, 1H). MS (ESI) m/z: [M+H]$^+$ Found 610.2.

Example 302

N—((S)-(7-((R)-Cyclopropyl(4,4-difluorobutanamido)methyl)imidazo[1,2-b]pyridazin-2-yl)(4,4-difluorocyclohexyl)methyl)-3-isopropoxyisoxazole-4-carboxamide

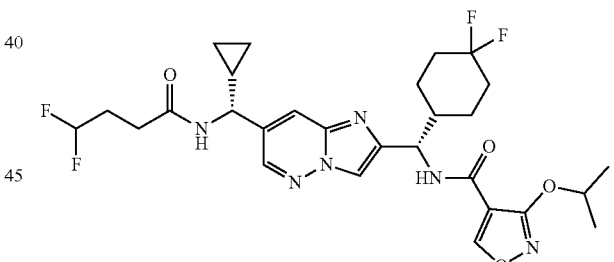

The title compound was prepared as described for the synthesis of Example 38 using 4,4-difluorobutanoic acid in place of 4,4,4-trifluorobutanoic acid, and 3-isopropoxyisoxazole-4-carboxylic acid (Intermediate 572) in place of 1-(3,3,3-trifluoropropyl)-1H-1,2,4-triazole-5-carboxylic acid to afford the title compound as a white powder. $^1$H NMR (400 MHz, DMSO-d$_6$) δ 9.22 (s, 1H), 8.67 (d, J=7.8 Hz, 1H), 8.53 (d, J=2.0 Hz, 1H), 8.23 (s, 1H), 7.96 (d, J=8.6 Hz, 1H), 7.90 (d, J=2.0 Hz, 1H), 6.30-5.88 (m, 1H), 5.24-5.11 (m, 1H), 4.99-4.88 (m, 1H), 4.39-4.24 (m, 1H), 2.40-2.31 (m, 1H), 2.14-1.94 (m, 5H), 1.88-1.76 (m, 2H), 1.76-1.60 (m, 2H), 1.49-1.44 (m, 3H), 1.44-1.40 (m, 3H), 1.39-1.25 (m, 2H), 1.24-1.16 (m, 1H), 0.64-0.46 (m, 3H), 0.44-0.36 (m, 1H). MS (ESI) m/z: [M+H]$^+$ Found 595.3.

Example 303

N—((S)-(7-((R)-Cyclopropyl(2-(2,2,2-trifluoroethoxy)acetamido)methyl)imidazo[1,2-b]pyridazin-2-yl)(4,4-difluorocyclohexyl)methyl)-1-isopropyl-1H-pyrazole-5-carboxamide

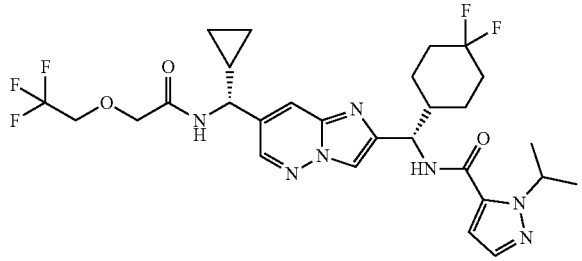 [SMILES: CC(C)n1nccc1C(=O)N[C@H](c1cn2ncc([C@H](NC(=O)COCC(F)(F)F)C3CC3)cc2n1)C1CCC(F)(F)CC1]

To a solution of 1-isopropyl-1H-pyrazole-5-carboxylic acid (72 mg, 0.47 mmol), N—((R)-(2-((S)-amino(4,4-difluorocyclohexyl)methyl)imidazo[1,2-b]pyridazin-7-yl)(cyclopropyl)methyl)-2-(2,2,2-trifluoroethoxy)acetamide hydrochloride (266 mg, 0.70 mmol, Intermediate 232), EDCI (179 mg, 0.93 mmol) and HOBt (76 mg, 0.56 mmol) in DCM (3 mL) was added Hünig's base (0.41 mL, 2.4 mmol). The mixture was stirred at rt overnight. The mixture was concentrated under reduced pressure to give a residue which was purified by silica gel chromatography (0-2% MeOH/DCM) to afford the title compound as a white solid. $^1$H NMR (400 MHz, DMSO-$d_6$) δ 8.73 (d, J 9.2 Hz, 1H), 8.62 (d, J=7.6 Hz, 1H), 8.56 (d, J=2.0 Hz, 1H), 8.20 (s, 1H), 7.98 (d, J=1.6 Hz, 1H), 7.49 (d, J=2.0 Hz, 1H), 6.91 (d, J=2.0 Hz, 1H), 5.43-5.30 (m, 1H), 5.15 (t, J=8.4 Hz, 1H), 4.27 (t, J=8.8 Hz, 1H), 4.23-4.13 (m, 4H), 2.22-1.93 (m, 3H), 1.91-1.55 (m, 4H), 1.41-1.24 (m, 9H), 0.65-0.46 (m, 3H), 0.43-0.33 (m, 1H). MS (ESI) m/z: [M+H]$^+$ Found 612.3.

Example 304

N—((S)-(7-((R)-Cyclopropyl(2-(2,2-difluoroethoxy)acetamido)methyl)imidazo[1,2-b]pyridazin-2-yl)(4,4-difluorocyclohexyl)methyl)-4-methyl-1,2,5-oxadiazole-3-carboxamide

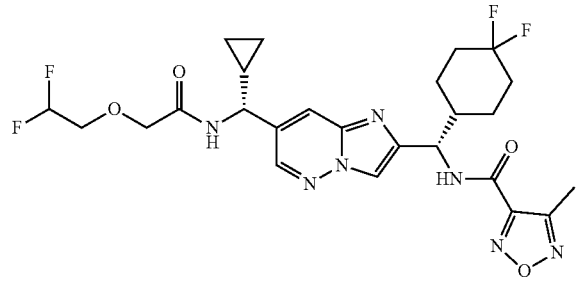 [SMILES: Cc1nonc1C(=O)N[C@H](c1cn2ncc([C@H](NC(=O)COCC(F)F)C3CC3)cc2n1)C1CCC(F)(F)CC1]

To solution of N—((R)-(2-((S)-amino(4,4-difluorocyclohexyl)methyl)imidazo[1,2-b]pyridazin-7-yl)(cyclopropyl)methyl)-2-(2,2-difluoroethoxy)acetamide (84 mg, 0.18 mmol, Intermediate 233) in DCM (3 mL) was added 4-methyl-1,2,5-oxadiazole-3-carboxylic acid (21 mg, 0.17 mmol), EDCI (64 mg, 0.33 mmol), HOBt (27 mg, 0.20 mmol), and DIPEA (108 mg, 0.84 mmol). The mixture was stirred at rt overnight and concentrated under reduced pressure to give a residue. The residue was purified by silica gel chromatography (0-5% MeOH/DCM) to afford the title compound as a white solid. $^1$H NMR (400 MHz, DMSO-$d_6$) δ 9.43 (d, J=9.2 Hz, 1H), 8.60-8.53 (m, 2H), 8.23 (s, 1H), 8.00 (d, J=2.0 Hz, 1H), 6.36-6.04 (m, 1H), 5.17 (t, J=8.8 Hz, 1H), 4.27 (t, J=8.8 Hz, 1H), 4.09 (s, 2H), 3.87-3.73 (m, 2H), 2.47 (s, 3H), 2.25-2.11 (m, 1H), 2.09-1.66 (m, 5H), 1.65-1.53 (m, 1H), 1.44-1.22 (m, 3H), 0.65-0.46 (m, 3H), 0.43-0.33 (m, 1H). MS (ESI) m/z: [M+H]$^+$ Found 568.3.

Example 305

N—((S)-(7-((R)-Cyclopropyl(2-(2,2-difluoroethoxy)acetamido)methyl)imidazo[1,2-b]pyridazin-2-yl)(4,4-difluorocyclohexyl)methyl)-1-isopropyl-1H-pyrazole-5-carboxamide

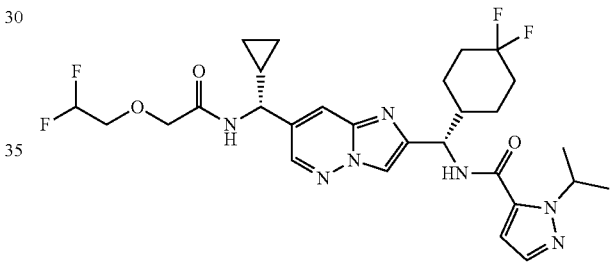

The title compound was prepared as described for Example 304, using 1-isopropyl-1H-pyrazole-5-carboxylic acid in place of 4-methyl-1,2,5-oxadiazole-3-carboxylic acid to afford a crude residue. The crude was further purified by SFC (Stationary phase: DAICEL CHIRALCEL OD-H (250×30 mm, 5 m), Mobile phase: 15% EtOH (0.1% NH$_4$OH)/CO$_2$) to afford the title compound as a white powder. $^1$H NMR (400 MHz, DMSO-$d_6$) δ 8.73 (d, J=9.2 Hz, 1H), 8.58-8.52 (m, 2H), 8.20 (s, 1H), 7.98 (s, 1H), 7.49 (d, J=1.6 Hz, 1H), 6.91 (d, J=3.2 Hz, 1H), 6.35-6.04 (m, 1H), 5.42-5.31 (m, 1H), 5.15 (t, J=8.8 Hz, 1H), 4.27 (t, J=8.8 Hz, 1H), 4.14-4.04 (m, 2H), 3.86-3.73 (m, 2H), 2.24-2.11 (m, 1H), 2.10-1.92 (m, 2H), 1.91-1.66 (m, 3H), 1.65-1.55 (m, 1H), 1.39-1.31 (m, 8H), 1.28-1.18 (m, 1H), 0.64-0.46 (m, 3H), 0.42-0.33 (m, 1H). MS (ESI) m/z: [M+H]$^+$ Found 594.2.

Example 306

N—((S)-(7-((R)-(2-Cyclopropoxyacetamido)(cyclo-propyl)methyl)imidazo[1,2-b]pyridazin-2-yl)(4,4-difluorocyclohexyl)methyl)-4-methyl-1,2,5-oxadiazole-3-carboxamide

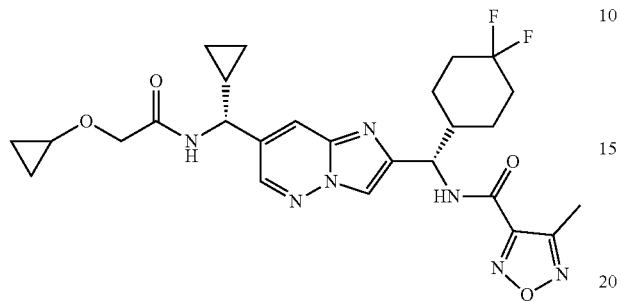

The title compound was prepared as described for Example 303, using 2-cyclopropoxyacetic acid (Intermediate 234) in place of 2-(2,2,2-trifluoroethoxy)acetic acid and 4-methyl-1,2,5-oxadiazole-3-carboxylic acid in place of 1-isopropyl-1H-pyrazole-5-carboxylic acid to afford the title compound as an off-white solid. $^1$H NMR (400 MHz, DMSO-$d_6$) δ 9.42 (d, J=9.2 Hz, 1H), 8.61-8.53 (m, 1H), 8.51 (d, J=8.0 Hz, 1H), 8.22 (s, 1H), 7.99 (d, J=1.6 Hz, 1H), 5.16 (t, J=8.4 Hz, 1H), 4.30-4.20 (m, 1H), 3.94 (s, 2H), 3.45-3.41 (m, 1H), 2.46 (s, 3H), 2.18-1.59 (m, 7H), 1.40-1.23 (m, 3H), 0.62-0.33 (m, 8H). MS (ESI) m/z: [M+H]$^+$ Found 544.2.

Example 307

N—((S)-(7-((R)-(2-Cyclopropoxyacetamido)(cyclo-propyl)methyl)imidazo[1,2-b]pyridazin-2-yl)(4,4-difluorocyclohexyl)methyl)-1-isopropyl-1H-pyrazole-5-carboxamide

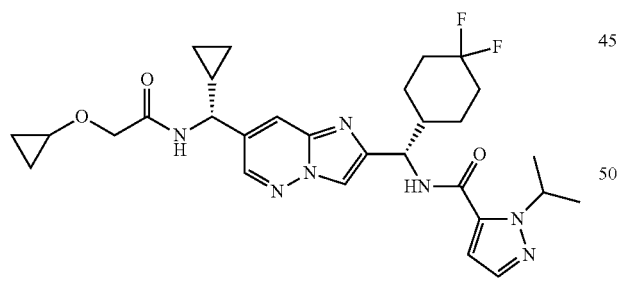

The title compound was prepared as described for Example 303, using 2-cyclopropoxyacetic acid (Intermediate 234) in place of 2-(2,2,2-trifluoroethoxy)acetic acid to afford the title compound as an off-white solid. $^1$H NMR (400 MHz, DMSO-$d_6$) δ 8.73 (d, J=8.8 Hz, 1H), 8.57 (d, J=1.6 Hz, 1H), 8.52 (d, J=8.0 Hz, 1H), 8.20 (s, 1H), 7.98 (s, 1H), 7.49 (d, J=2.0 Hz, 1H), 6.92 (d, J=2.0 Hz, 1H), 5.40-5.31 (m, 1H), 5.18-5.11 (m, 1H), 4.31-4.20 (m, 1H), 3.95 (s, 2H), 3.44-3.40 (m, 1H), 2.18-2.16 (m, 1H), 2.07-1.96 (m, 2H), 1.90-1.70 (m, 3H), 1.62-1.59 (m, 2H), 1.38-1.31 (m, 7H), 1.28-1.22 (m, 2H), 0.62-0.43 (m, 7H), 0.40-0.33 (m, 1H). MS (ESI) m/z: [M+H]$^+$ Found 570.2.

Example 308

N—((S)-(7-((R)-Cyclopropyl(2-(3,3-difluorocy-clobutoxy)acetamido)methyl)imidazo[1,2-b]pyridazin-2-yl)(4,4-difluorocyclohexyl)methyl)-4-methyl-1,2,5-oxadiazole-3-carboxamide

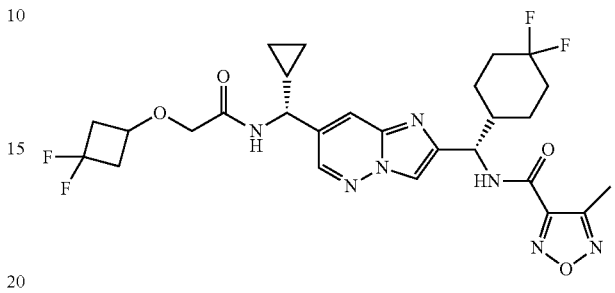

The title compound was prepared as described for Example 303 using (S)-(7-((R)-cyclopropyl(2-(3,3-difluoro-cyclobutoxy)acetamido)methyl)imidazo[1,2-b]pyridazin-2-yl)(4,4-difluorocyclohexyl)methanaminium trifluoroacetate (Intermediate 236) in place of N—((R)-(2-((S)-amino(4,4-difluorocyclohexyl)methyl)imidazo[1,2-b]pyridazin-7-yl)(cyclopropyl)methyl)-2-(2,2,2-trifluoroethoxy)acetamide hydrochloride. The crude material was purified by preparative HPLC (Stationary phase: Boston Prime C18 150×30 mm×5 m, Mobile phase: 50-80% (v/v) CH$_3$CN/H$_2$O (with 0.05% NH$_4$OH+10 mM NH$_4$HCO$_3$)) to afford the title compound as a white powder. $^1$H NMR (400 MHz, DMSO-$d_6$) δ 9.43 (d, J=8.8 Hz, 1H), 8.62-8.50 (m, 2H), 8.23 (s, 1H), 8.00 (d, J=2.0 Hz, 1H), 5.17 (t, J=8.4 Hz, 1H), 4.26 (t, J=8.8 Hz, 1H), 4.14-4.01 (m, 1H), 3.91 (s, 2H), 2.98-2.80 (m, 2H), 2.72-2.58 (m, 2H), 2.46 (s, 3H), 2.24-2.12 (m, 1H), 2.11-1.67 (m, 5H), 1.65-1.54 (m, 1H), 1.44-1.21 (m, 3H), 0.65-0.45 (m, 3H), 0.42-0.33 (m, 1H). MS (ESI) m/z: [M+H]$^+$ Found 594.2.

Example 309

N—((S)-(7-((R)-Cyclopropyl(2-(3,3-difluorocy-clobutoxy)acetamido)methyl)imidazo[1,2-b]pyridazin-2-yl)(4,4-difluorocyclohexyl)methyl)-1-isopropyl-1H-pyrazole-5-carboxamide

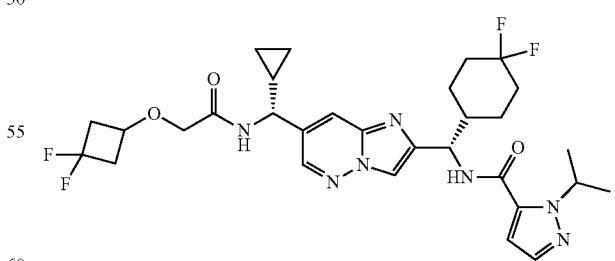

The title compound was prepared as described for Example 303 using (S)-(7-((R)-cyclopropyl(2-(3,3-difluoro-cyclobutoxy)acetamido)methyl)imidazo[1,2-b]pyridazin-2-yl)(4,4-difluorocyclohexyl)methanaminium trifluoroacetate (Intermediate 236) in place of N—((R)-(2-((S)-amino(4,4-difluorocyclohexyl)methyl)imidazo[1,2-b]pyridazin-7-yl)

(cyclopropyl)methyl)-2-(2,2,2-trifluoroethoxy)acetamide hydrochloride and 1-isopropyl-1H-pyrazole-5-carboxylic acid in place of 4-methyl-1,2,5-oxadiazole-3-carboxylic acid. The crude material was purified by preparative HPLC (Stationary phase: Phenomenex Gemini-NX 150×30 mm×5 m, Mobile phase: 42-72% (v/v) MeCN/H$_2$O (with 0.05% NH$_4$OH+10 mM NH$_4$HCO$_3$)) to afford the title compound as a white powder. $^1$H NMR (400 MHz, DMSO-d$_6$) δ 8.73 (d, J=9.6 Hz, 1H), 8.60-8.50 (m, 2H), 8.20 (s, 1H), 7.98 (d, J=1.6 Hz, 1H), 7.49 (d, J=1.6 Hz, 1H), 6.91 (d, J=2.0 Hz, 1H), 5.44-5.29 (m, 1H), 5.15 (t, J=8.4 Hz, 1H), 4.26 (t, J=8.8 Hz, 1H), 4.15-3.98 (m, 1H), 3.91 (s, 2H), 2.95-2.80 (m, 2H), 2.72-2.58 (m, 2H), 2.24-2.12 (m, 1H), 2.10-1.93 (m, 2H), 1.91-1.67 (m, 3H), 1.65-1.56 (m, 1H), 1.42-1.30 (m, 8H), 1.27-1.16 (m, 1H), 0.65-0.45 (m, 3H), 0.42-0.31 (m, 1H). MS (ESI) m/z: [M+H]$^+$ Found 620.3.

Example 310

N—((S)-(7-((R)-Cyclopropyl(2-(((S)-1,1,1-trifluoropropan-2-yl)oxy)acetamido)methyl)imidazo[1,2-b]pyridazin-2-yl)(4,4-difluorocyclohexyl)methyl)-1-isopropyl-1H-pyrazole-5-carboxamide

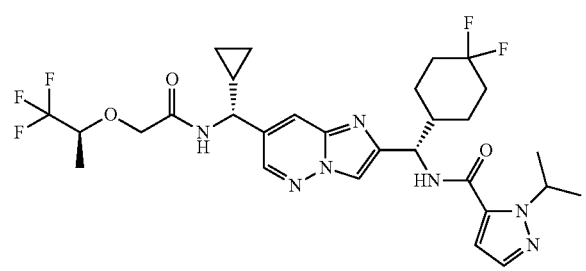 [SMILES: CC(C)n1nccc1C(=O)N[C@H](c1cn2ncc([C@H](NC(=O)CO[C@@H](C)C(F)(F)F)C3CC3)cc2n1)C1CCC(F)(F)CC1]

Example 311

N—((S)-(7-((R)-Cyclopropyl(2-(((R)-1,1,1-trifluoropropan-2-yl)oxy)acetamido)methyl)imidazo[1,2-b]pyridazin-2-yl)(4,4-difluorocyclohexyl)methyl)-1-isopropyl-1H-pyrazole-5-carboxamide

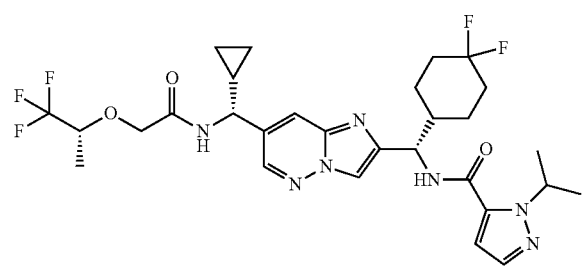 [SMILES: CC(C)n1nccc1C(=O)N[C@H](c1cn2ncc([C@H](NC(=O)CO[C@H](C)C(F)(F)F)C3CC3)cc2n1)C1CCC(F)(F)CC1]

The title compounds were prepared as described for Example 303, using 2-((1,1,1-trifluoropropan-2-yl)oxy)acetic acid in place of 2-(2,2,2-trifluoroethoxy)acetic acid to afford a mixture of diastereomers. The diastereomers were resolved by SFC using a chiral stationary phase (Stationary phase: DAICEL CHIRALPAK AS (250×30 mm×10 μm, Mobile phase: 15% EtOH (0.1% NH$_4$OH)/CO$_2$). The first eluting isomer afforded Example 310, the stereochemistry of which was confirmed by comparison to material made with enantiopure starting material. The second eluting fraction afforded Example 311 as a white powder. Example 310: $^1$H NMR (400 MHz, DMSO-d$_6$) δ 8.75 (d, J=9.2 Hz, 1H), 8.57 (d, J=2.0 Hz, 1H), 8.49 (d, J=7.6 Hz, 1H), 8.21 (s, 1H), 7.99 (d, J=1.6 Hz, 1H), 7.50 (d, J=2.0 Hz, 1H), 6.92 (d, J=2.0 Hz, 1H), 5.43-5.32 (m, 1H), 5.16 (t, J=8.4 Hz, 1H), 4.31-4.20 (m, 2H), 4.18 (s, 2H), 2.24-2.12 (m, 1H), 2.11-1.93 (m, 2H), 1.92-1.67 (m, 3H), 1.66-1.57 (m, 1H), 1.39-1.24 (m, 12H), 0.66-0.46 (m, 3H), 0.43-0.34 (m, 1H). MS (ESI) m/z: [M+H]$^+$ Found 626.2. Example 311: $^1$H NMR (400 MHz, DMSO-d$_6$) δ 8.75 (d, J=9.2 Hz, 1H), 8.56 (d, J=2.0 Hz, 1H), 8.51 (d, J=7.6 Hz, 1H), 8.22 (s, 1H), 7.99 (d, J 1.6 Hz, 1H), 7.50 (d, J=2.0 Hz, 1H), 6.92 (d, J=2.0 Hz, 1H), 5.44-5.31 (m, 1H), 5.17 (t, J 8.8 Hz, 1H), 4.32-4.22 (m, 2H), 4.21-4.13 (m, 2H), 2.25-2.12 (m, 1H), 2.10-1.94 (m, 2H), 1.92-1.68 (m, 3H), 1.67-1.57 (m, 1H), 1.42-1.23 (m, 12H), 0.65-0.47 (m, 3H), 0.44-0.35 (m, 1H). MS (ESI) m/z: [M+H]$^+$ Found 626.2.

Example 312

N—((S)-(7-((R)-Cyclopropyl(4,4-difluoro-3,3-dimethylbutanamido)methyl)imidazo[1,2-b]pyridazin-2-yl)(4,4-difluorocyclohexyl)methyl)-4-methyl-1,2,5-oxadiazole-3-carboxamide

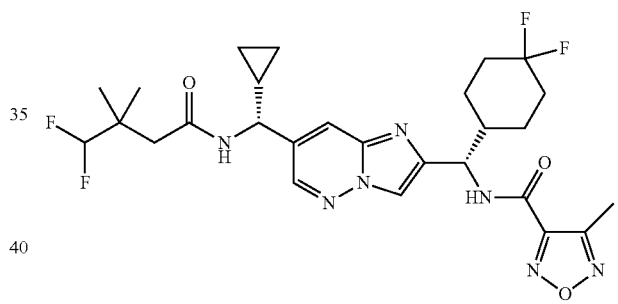

To a solution of 4,4-difluoro-3,3-dimethylbutanoic acid (100 mg, 0.66 mmol, Intermediate 239), N—((S)-(7-((R)-amino(cyclopropyl)methyl)imidazo[1,2-b]pyridazin-2-yl)(4,4-difluorocyclohexyl)methyl)-4-methyl-1,2,5-oxadiazole-3-carboxamide (117 mg, 0.26 mmol, Intermediate 287), EDCI (101 mg, 0.53 mmol) and HOBt (42.7 mg, 0.32 mmol) in DCM (5 mL) was added DIPEA (0.15 mL, 0.86 mmol). The mixture was stirred at rt overnight. The mixture was concentrated under reduced pressure to give a residue. The residue was purified by silica gel chromatography (0-4% MeOH/DCM) followed by SFC with a chiral stationary phase (Stationary phase: DAICEL CHIRALCEL OD-H (250×30 mm, 5 m, Mobile phase: 10% ethanol (0.1% NH$_4$OH)/CO$_2$) to afford the title compound as a white solid. $^1$H NMR (400 MHz, DMSO-d$_6$) δ 9.44 (d, J=9.2 Hz, 1H), 8.73 (d, J=8.0 Hz, 1H), 8.52 (d, J=2.0 Hz, 1H), 8.24 (s, 1H), 7.96 (d, J=2.0 Hz, 1H), 6.07-5.76 (m, 1H), 5.17 (t, J=8.8 Hz, 1H), 4.28 (t, J=8.4 Hz, 1H), 2.47 (s, 3H), 2.27-2.13 (m, 3H), 2.09-1.69 (m, 5H), 1.66-1.56 (m, 1H), 1.45-1.33 (m, 1H), 1.30-1.17 (m, 2H), 0.99 (s, 6H), 0.63-0.45 (m, 3H), 0.42-0.34 (m, 1H). MS (ESI) m/z: [M+H]$^+$ Found 580.2.

Example 313

N—((S)-(7-((R)-Cyclopropyl(4,4-difluoro-3,3-dimethylbutanamido)methyl)imidazo[1,2-b]pyridazin-2-yl)(4,4-difluorocyclohexyl)methyl)-1-isopropyl-1H-pyrazole-5-carboxamide

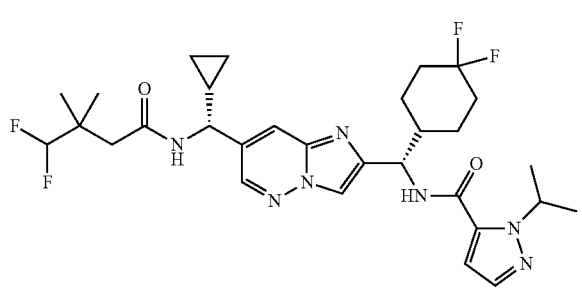 [SMILES: CC(C)n1nccc1C(=O)N[C@H](c1cn2ncc([C@H](NC(=O)CC(C)(C)C(F)F)C3CC3)cc2n1)C1CCC(F)(F)CC1]

The title compound was prepared as described for Example 303, using 4,4-difluoro-3,3-dimethylbutanoic acid (Intermediate 239) in place of 2-(2,2,2-trifluoroethoxy)acetic acid to afford the title compound as a white solid. $^1$H NMR (400 MHz, DMSO-d$_6$) δ 8.79-8.71 (m, 2H), 8.51 (d, J=2.0 Hz, 1H), 8.21 (s, 1H), 7.95 (d, J=1.2 Hz, 1H), 7.50 (d, J=2.0 Hz, 1H), 6.92 (d, J 1.6 Hz, 1H), 6.08-5.76 (m, 1H), 5.43-5.32 (m, 1H), 5.16 (t, J=8.8 Hz, 1H), 4.28 (t, J=8.4 Hz, 1H), 2.28-2.13 (m, 3H), 2.11-1.93 (m, 2H), 1.93-1.67 (m, 3H), 1.66-1.57 (m, 1H), 1.40-1.31 (m, 7H), 1.28-1.22 (m, 2H), 1.00 (s, 6H), 0.63-0.46 (m, 3H), 0.43-0.33 (m, 1H). MS (ESI) m/z: [M+H]$^+$ Found 606.2.

Example 314

N—((R)-2-(tert-Butoxy)-1-(7-((R*)-cyclopropyl(4,4,4-trifluorobutanamido)methyl)imidazo[1,2-b]pyridazin-2-yl)ethyl)-4-methyl-1,2,5-oxadiazole-3-carboxamide

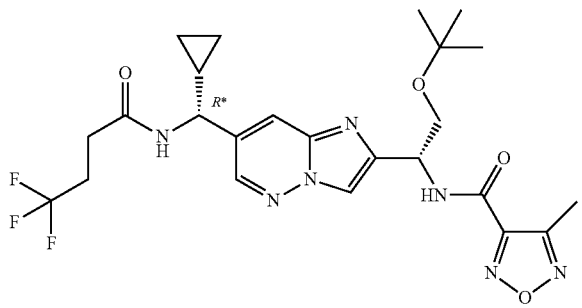 [SMILES: Cc1nonc1C(=O)N[C@@H](COC(C)(C)C)c1cn2ncc([C@H](NC(=O)CCC(F)(F)F)C3CC3)cc2n1]

Example 315

N—((R)-2-(tert-Butoxy)-1-(7-((S*)-cyclopropyl(4,4,4-trifluorobutanamido)methyl)imidazo[1,2-b]pyridazin-2-yl)ethyl)-4-methyl-1,2,5-oxadiazole-3-carboxamide

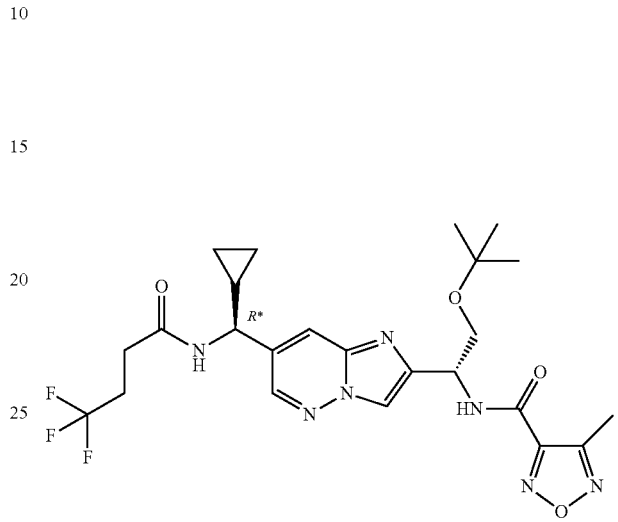

A solution of N-((2-((R)-1-amino-2-(tert-butoxy)ethyl)imidazo[1,2-b]pyridazin-7-yl)(cyclopropyl)methyl)-4,4,4-trifluorobutanamide (47 mg, 0.11 mmol, Intermediate 249), 4-methyl-1,2,5-oxadiazole-3-carboxylic acid (15 mg, 0.12 mmol), DIPEA (30 µL, 0.17 mmol), and HOBt (16 mg, 0.12 mmol) in MeCN (2 mL) was heated to 45° C. then EDCI (22 mg, 0.12 mmol) was added. The reaction was stirred at this temperature for 2 h then quenched with H$_2$O. The resulting mixture was extracted with EtOAc then the combined organics were condensed and purified by silica gel chromatography (20-100% EtOAc/hexanes). Purification by SFC using a chiral stationary phase (AD-H, 20/80 (0.1% diethylamine in iPrOH)/CO$_2$) provided the title compounds. Example 314 was the first eluting peak and Example 315 was the second eluting peak. Example 314: $^1$H NMR (400 MHz, CDCl$_3$) δ 8.31 (d, J=1.9 Hz, 1H), 8.00-7.93 (m, 1H), 7.90-7.84 (m, 1H), 7.80-7.73 (m, 1H), 6.03-5.90 (m, 1H), 5.53-5.38 (m, 1H), 4.42-4.30 (m, 1H), 3.95 (dd, J=9.2, 4.7 Hz, 1H), 3.76 (dd, J=9.1, 5.4 Hz, 1H), 2.63 (s, 3H), 2.60-2.44 (m, 4H), 1.24-1.13 (m, 10H), 0.83-0.67 (m, 2H), 0.57-0.41 (m, 2H). MS (ESI) m/z: [M+H]$^+$ Found 538.3. Example 315: $^1$H NMR (400 MHz, CDCl$_3$) δ 8.31 (d, J=2.0 Hz, 1H), 7.98-7.92 (m, 1H), 7.88-7.84 (m, 1H), 7.81-7.70 (m, 1H), 6.03-5.93 (m, 1H), 5.51-5.42 (m, 1H), 4.41-4.30 (m, 1H), 3.95 (dd, J=9.1, 4.8 Hz, 1H), 3.76 (dd, J=9.1, 5.4 Hz, 1H), 2.63 (s, 3H), 2.59-2.44 (m, 4H), 1.23-1.12 (m, 10H), 0.84-0.68 (m, 2H), 0.57-0.40 (m, 2H). MS (ESI) m/z: [M+H]$^+$ Found 538.3.

Example 316

N—((R)-2-(tert-Butoxy)-1-(7-((R*)-cyclopropyl(4,4,4-trifluorobutanamido)methyl)imidazo[1,2-b]pyridazin-2-yl)ethyl)-1-isopropyl-1H-pyrazole-5-carboxamide

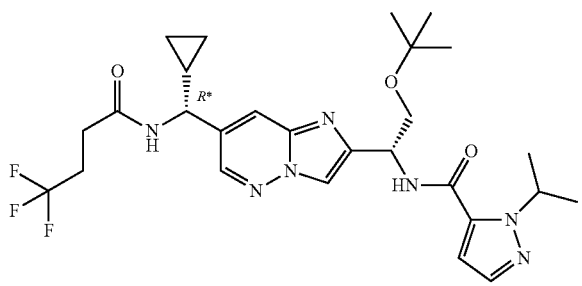 [SMILES: CC(C)n1nccc1C(=O)N[C@@H](COC(C)(C)C)c1cn2ncc([C@H](NC(=O)CCC(F)(F)F)C3CC3)cc2n1]

Example 317

N—((R)-2-(tert-Butoxy)-1-(7-((S*)-cyclopropyl(4,4,4-trifluorobutanamido)methyl)imidazo[1,2-b]pyridazin-2-yl)ethyl)-1-isopropyl-1H-pyrazole-5-carboxamide

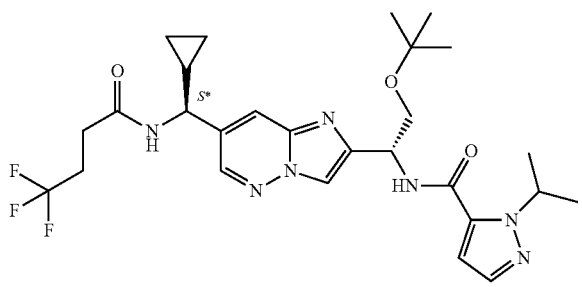 [SMILES: CC(C)n1nccc1C(=O)N[C@@H](COC(C)(C)C)c1cn2ncc([C@@H](NC(=O)CCC(F)(F)F)C3CC3)cc2n1]

The title compounds were prepared as described for Example 314 and Example 315, using 1-isopropyl-1H-pyrazole-5-carboxylic acid in place of 4-methyl-1,2,5-oxadiazole-3-carboxylic acid. Purification by SFC using a chiral stationary phase (AD-H, 20/80 (0.1% diethylamine in iPrOH)/CO$_2$) provided the title compounds. Example 316 was the first eluting peak and Example 317 was the second eluting peak. Example 316: $^1$H NMR (400 MHz, CDCl$_3$) δ 8.31 (d, J=2.1 Hz, 1H), 7.94 (s, 1H), 7.88-7.80 (m, 1H), 7.52 (d, J=2.0 Hz, 1H), 7.06-6.98 (m, 1H), 6.57 (d, J=2.0 Hz, 1H), 6.02-5.94 (m, 1H), 5.58-5.47 (m, 1H), 5.46-5.37 (m, 1H), 4.40-4.31 (m, 1H), 3.95 (dd, J=8.9, 4.6 Hz, 1H), 3.73 (dd, J=9.0, 5.6 Hz, 1H), 2.59-2.45 (m, 4H), 1.53-1.47 (m, 6H), 1.21-1.13 (m, 10H), 0.83-0.67 (m, 2H), 0.57-0.41 (m, 2H). MS (ESI) m/z: [M+H]$^+$ Found 564.3. Example 317: $^1$H NMR (400 MHz, CDCl$_3$) δ 8.31 (d, J=2.1 Hz, 1H), 7.94 (s, 1H), 7.85 (s, 1H), 7.52 (s, 1H), 7.05-6.98 (m, 1H), 6.57 (d, J=2.0 Hz, 1H), 5.99 (br d, J=6.9 Hz, 1H), 5.56-5.39 (m, 2H), 4.36 (dd, J=9.0, 7.5 Hz, 1H), 3.95 (dd, J=9.1, 4.6 Hz, 1H), 3.73 (dd, J=9.1, 5.6 Hz, 1H), 2.58-2.46 (m, 4H), 1.53-1.47 (m, 6H), 1.20-1.14 (m, 10H), 0.83-0.67 (m, 2H), 0.44-0.55 (m, 2H). MS (ESI) m/z: [M+H]$^+$ Found 564.3.

Example 318

N—((R)-2-(tert-Butoxy)-1-(7-((R)-cyclopropyl(2-(3,3-difluorocyclobutyl)acetamido)methyl)imidazo[1,2-b]pyridazin-2-yl)ethyl)-1-isopropyl-1H-pyrazole-5-carboxamide

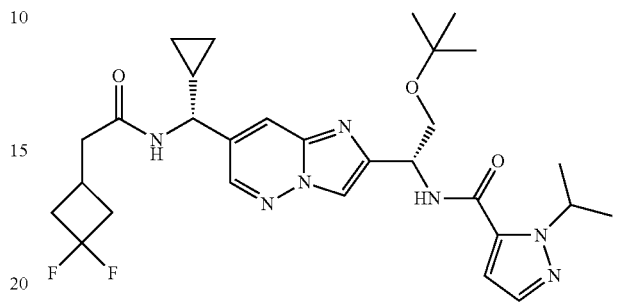

The title compound was prepared as described for Example 314, using N—((R)-(2-((R)-1-amino-2-(tert-butoxy)ethyl)imidazo[1,2-b]pyridazin-7-yl)(cyclopropyl)methyl)-2-(3,3-difluorocyclobutyl)acetamide (Intermediate 252) in place of N-((2-((R)-1-amino-2-(tert-butoxy)ethyl)imidazo[1,2-b]pyridazin-7-yl)(cyclopropyl)methyl)-4,4,4-trifluorobutanamide and 1-isopropyl-1H-pyrazole-5-carboxylic acid in place of 4-methyl-1,2,5-oxadiazole-3-carboxylic acid. $^1$H NMR (400 MHz, DMSO-d$_6$) δ 8.66-8.55 (m, 2H), 8.49 (d, J=2.0 Hz, 1H), 8.13 (s, 1H), 7.94-7.89 (m, 1H), 7.49 (d, J=1.9 Hz, 1H), 6.86 (d, J=1.9 Hz, 1H), 5.50-5.36 (m, 1H), 5.33-5.24 (m, 1H), 4.27 (t, J=8.3 Hz, 1H), 3.85-3.76 (m, 1H), 3.75-3.66 (m, 1H), 2.72-2.56 (m, 2H), 2.44-2.36 (m, 3H), 2.35-2.20 (m, 2H), 1.42-1.32 (m, 6H), 1.25-1.16 (m, 1H), 1.14 (s, 9H), 0.62-0.41 (m, 3H), 0.40-0.31 (m, 1H). MS (ESI) m/z: [M+H]$^+$ Found 572.3.

Example 319

N—((R)-2-(tert-Butoxy)-1-(7-((R)-cyclopropyl(2-(3,3-difluorocyclobutyl)acetamido)methyl)imidazo[1,2-b]pyridazin-2-yl)ethyl)-4-cyclopropyl-1,2,5-oxadiazole-3-carboxamide

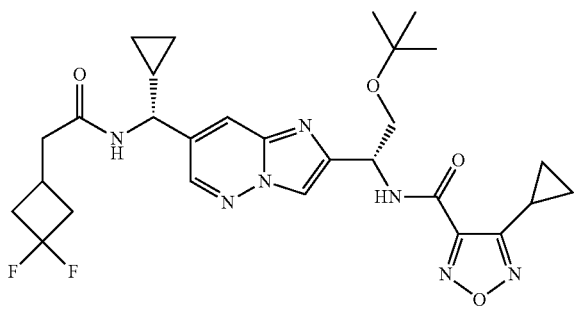 [SMILES: CC(C)(C)OC[C@H](NC(=O)c1nonc1C1CC1)c1cn2ncc([C@H](NC(=O)CC3CC(F)(F)C3)C3CC3)cc2n1]

The title compound was prepared as described for Example 314, using N—((R)-(2-((R)-1-amino-2-(tert-butoxy)ethyl)imidazo[1,2-b]pyridazin-7-yl)(cyclopropyl)methyl)-2-(3,3-difluorocyclobutyl)acetamide (Intermediate 252) in place of N-((2-((R)-1-amino-2-(tert-butoxy)ethyl)imidazo[1,2-b]pyridazin-7-yl)(cyclopropyl)methyl)-4,4,4- trifluorobutanamide and 4-cyclopropyl-1,2,5-oxadiazole-3-carboxylic acid (Intermediate 570) in place of 4-methyl-1,2,5-oxadiazole-3-carboxylic acid. $^1$H NMR (400 MHz, DMSO-d$_6$) δ 9.33 (d, J=8.6 Hz, 1H), 8.60 (d, J=7.8 Hz, 1H), 8.50 (d, J=2.0 Hz, 1H), 8.17 (s, 1H), 7.96-7.92 (m, 1H), 5.37-5.28 (m, 1H), 4.32-4.23 (m, 1H), 3.85-3.79 (m, 1H), 3.78-3.70 (m, 1H), 2.70-2.57 (m, 3H), 2.39-2.21 (m, 5H), 1.28-1.09 (m, 12H), 1.04-0.98 (m, 2H), 0.63-0.41 (m, 3H), 0.40-0.31 (m, 1H). MS (ESI) m/z: [M+H]$^+$ Found 572.3.

Example 320

N—((R)-1-(7-((R)-Cyclopropyl(2-(3,3-difluorocyclobutyl)acetamido)methyl)imidazo[1,2-b]pyridazin-2-yl)-2-((1,1,1-trifluoro-2-methylpropan-2-yl)oxy)ethyl)-1-isopropyl-1H-pyrazole-5-carboxamide

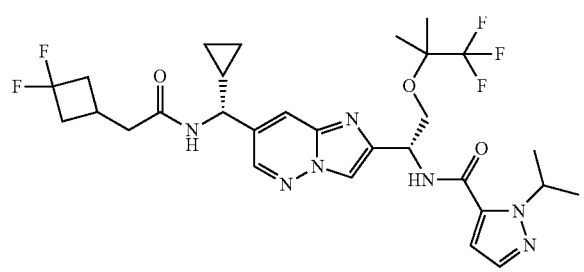 [SMILES: CC(C)n1nccc1C(=O)N[C@@H](COC(C)(C)C(F)(F)F)c1cn2ncc([C@H](NC(=O)CC3CC(F)(F)C3)C3CC3)cc2n1]

tert-Butyl ((R)-1-(7-((R)-cyclopropyl(2-(3,3-difluorocyclobutyl)acetamido)methyl)imidazo[1,2-b]pyridazin-2-yl)-2-((1,1,1-trifluoro-2-methylpropan-2-yl)oxy)ethyl)carbamate (96 mg, 0.16 mmol, Intermediate 261) was treated with HCl (0.41 mL, 1.6 mmol, 4 M in 1,4-dioxane) and the resulting mixture heated to 45° C. overnight. The reaction was diluted with saturated aqueous NaHCO$_3$ and extracted with EtOAc. The combined organic layers were dried over anhydrous Na$_2$SO$_4$, filtered and concentrated. The residue was dissolved in MeCN (1.6 mL) then 1-isopropyl-1H-pyrazole-5-carboxylic acid (38 mg, 0.24 mmol), DIPEA (84 μL, 0.49 mmol), and HOBt (39 mg, 0.24 mmol) were added. The reaction was heated to 45° C. then EDCI (62 mg, 0.33 mmol) was added. The reaction was stirred at this temperature for 40 min then diluted with H$_2$O, filtered, and purified by preparative HPLC (XBridge C18 OBD 50×100 mm, 5-95% MeCN/H$_2$O (with 20 mM NH$_4$OH)) to provide the title compound. $^1$H NMR (400 MHz, DMSO-d$_6$) δ 8.73 (d, J=8.5 Hz, 1H), 8.60 (d, J=7.8 Hz, 1H), 8.53-8.47 (m, 1H), 8.17 (s, 1H), 7.95-7.91 (m, 1H), 7.50 (d, J=1.9 Hz, 1H), 6.85 (d, J=1.9 Hz, 1H), 5.47-5.31 (m, 2H), 4.28 (t, J=8.4 Hz, 1H), 4.01 (dd, J=9.4, 5.1 Hz, 1H), 3.94-3.84 (m, 1H), 2.70-2.57 (m, 2H), 2.43-2.22 (m, 5H), 1.40-1.31 (m, 12H), 1.31-1.13 (m, 1H), 0.61-0.43 (m, 3H), 0.43-0.31 (m, 1H). MS (ESI) m/z: [M+H]$^+$ Found 626.3.

Example 321

4-Cyclopropyl-N—((R)-1-(7-((R)-cyclopropyl(2-(3,3-difluorocyclobutyl)acetamido)methyl)imidazo[1,2-b]pyridazin-2-yl)-2-((1,1,1-trifluoro-2-methylpropan-2-yl)oxy)ethyl)-1,2,5-oxadiazole-3-carboxamide

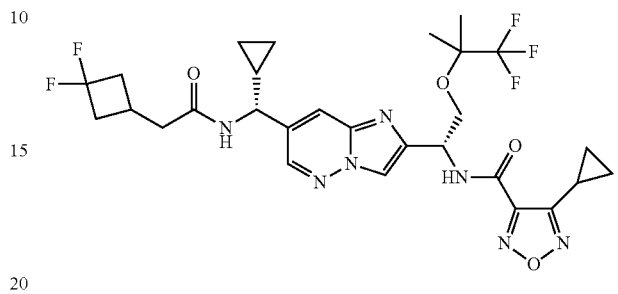

The title compound was prepared as described for Example 320, using 4-cyclopropyl-1,2,5-oxadiazole-3-carboxylic acid (Intermediate 570) in place of 1-isopropyl-1H-pyrazole-5-carboxylic acid. $^1$H NMR (400 MHz, DMSO-d$_6$) δ 9.46 (d, J=8.6 Hz, 1H), 8.60 (d, J=7.8 Hz, 1H), 8.51 (d, J=2.1 Hz, 1H), 8.20 (s, 1H), 7.96-7.92 (m, 1H), 5.46-5.35 (m, 1H), 4.32-4.23 (m, 1H), 4.06-3.88 (m, 2H), 2.72-2.54 (m, 2H), 2.42-2.22 (m, 6H), 1.36-1.32 (m, 6H), 1.25-1.11 (m, 3H), 1.03-0.96 (m, 2H), 0.62-0.43 (m, 3H), 0.40-0.31 (m, 1H). MS (ESI) m/z: [M+H]$^+$ Found 626.2.

Example 322

N—((S)-(7-((1S,2S)-1-(2-(3,3-Difluorocyclobutyl)acetamido)-2-methoxypropyl)imidazo[1,2-b]pyridazin-2-yl)(4,4-difluorocyclohexyl)methyl)-1-isopropyl-1H-pyrazole-5-carboxamide

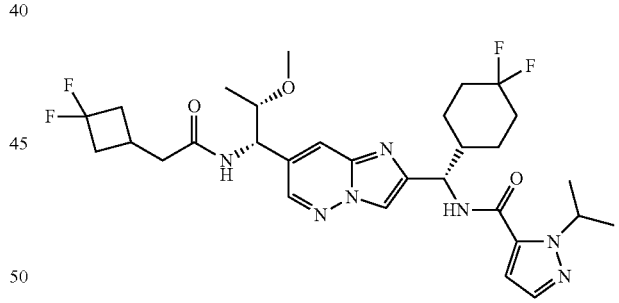

To a solution of 1-isopropyl-1H-pyrazole-5-carboxylic acid (31 mg, 0.20 mmol), N-((1S,2S)-1-(2-((S)-amino(4,4-difluorocyclohexyl)methyl)imidazo[1,2-b]pyridazin-7-yl)-2-methoxypropyl)-2-(3,3-difluorocyclobutyl)acetamide hydrochloride (107 mg, 0.2 mmol, Intermediate 274), EDCI (77.5 mg, 0.404 mmol) and HOBt (33 mg, 0.24 mmol) in anhydrous DCM (5 mL) was added DIPEA (0.18 mL, 1.03 mmol). After addition, the mixture was stirred at rt overnight then condensed. Purification by silica gel chromatography (0-2% MeOH/CH$_2$Cl$_2$) provided the title compound. $^1$H NMR (400 MHz, DMSO-d$_6$) δ 8.75 (d, J=9.2 Hz, 1H), 8.54-8.45 (m, 2H), 8.20 (s, 1H), 7.92 (s, 1H), 7.50 (d, J=2.0 Hz, 1H), 6.91 (d, J=2.0 Hz, 1H), 5.43-5.31 (m, 1H), 5.15 (t, J=8.4 Hz, 1H), 5.07-4.99 (m, 1H), 3.70-3.61 (m, 1H), 3.20 (s, 3H), 2.71-2.58 (m, 2H), 2.49-2.45 (m, 2H), 2.41-2.24 (m, 3H), 2.20-2.13 (m, 1H), 2.07-1.95 (m, 2H), 1.90-1.71 (m, 3H), 1.66-1.57 (m, 1H), 1.41-1.28 (m, 8H), 1.08 (d, J=6.4 Hz, 3H). MS (ESI) m/z: [M+H]⁺ Found 622.2.

Example 323

N—((S)-(7-(((1S,2S)-1-(2-(3,3-Difluorocyclobutyl)acetamido)-2-methoxypropyl)imidazo[1,2-b]pyridazin-2-yl)(4,4-difluorocyclohexyl)methyl)-4-methyl-1,2,5-oxadiazole-3-carboxamide

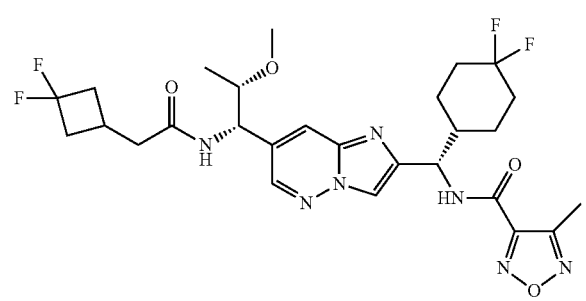 [SMILES: CO[C@@H](C)[C@@H](NC(=O)CC1CC(F)(F)C1)c1cnn2cc([C@@H](NC(=O)c3nonc3C)C3CCC(F)(F)CC3)nc2c1]

The title compound was prepared as described for Example 322, using 4-methyl-1,2,5-oxadiazole-3-carboxylic acid in place of 1-isopropyl-1H-pyrazole-5-carboxylic acid. ¹H NMR (400 MHz, DMSO-d₆) δ 9.45 (d, J=9.2 Hz, 1H), 8.55-8.46 (m, 2H), 8.23 (s, 1H), 7.93 (s, 1H), 5.17 (t, J=8.4 Hz, 1H), 5.07-5.00 (m, 1H), 3.71-3.61 (m, 1H), 3.20 (s, 3H), 2.71-2.59 (m, 2H), 2.47 (s, 3H), 2.44-2.24 (m, 4H), 2.22-2.13 (m, 1H), 2.10-1.68 (m, 6H), 1.66-1.57 (m, 1H), 1.44-1.26 (m, 2H), 1.08 (d, J=5.6 Hz, 3H). MS (ESI) m/z: [M+H]⁺ Found 596.2.

Example 324

N—((S)-(7-((R)-Cyclopropyl(2-((R*)-2,2,3,3-tetrafluorocyclobutyl)acetamido)methyl)imidazo[1,2-b]pyridazin-2-yl)(4,4-difluorocyclohexyl)methyl)-4-methyl-1,2,5-oxadiazole-3-carboxamide

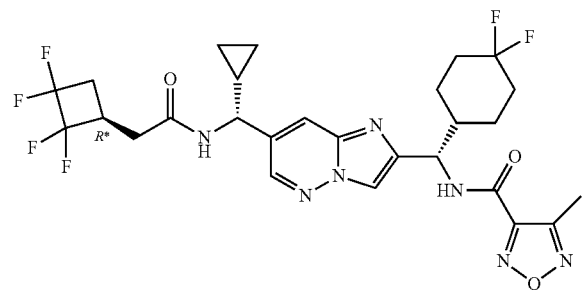 [SMILES: Cc1nonc1C(=O)N[C@H](c1cn2ncc([C@H](NC(=O)C[C@@H]3CC(F)(F)C3(F)F)C3CC3)cc2n1)C1CCC(F)(F)CC1]

Example 325

N—((S)-(7-((R)-Cyclopropyl(2-((S*)-2,2,3,3-tetrafluorocyclobutyl)acetamido)methyl)imidazo[1,2-b]pyridazin-2-yl)(4,4-difluorocyclohexyl)methyl)-4-methyl-1,2,5-oxadiazole-3-carboxamide

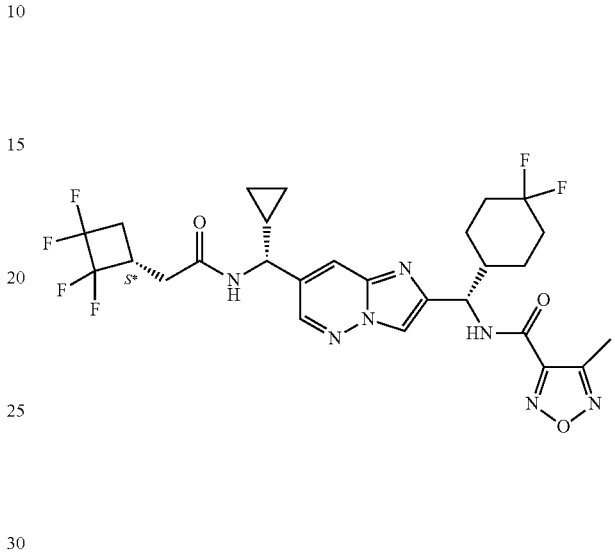

To a mixture of N—((S)-(7-((R)-amino(cyclopropyl)methyl)imidazo[1,2-b]pyridazin-2-yl)(4,4-difluorocyclohexyl)methyl)-4-methyl-1,2,5-oxadiazole-3-carboxamide (100 mg, 0.22 mmol, Intermediate 287), (2,2,3,3-tetrafluorocyclobutyl)acetic acid (46 mg, 0.25 mmol), HOBt (36 mg, 0.27 mmol) and Et₃N (156 μL, 1.12 mmol) in ACN (1 mL) was added EDCI (52 mg, 0.27 mmol). The resulting mixture was stirred at 40° C. for 2.5 h. After that time, the mixture was concentrated to dryness and purified by silica gel chromatography (0-5% MeOH/DCM) to provide a mixture of title compounds as a light yellow solid. The mixture was purified by SFC using a chiral stationary phase (Daicel Chiralpak IG, 250×30 mm, 10 μM, 35:65 (0.1% NH₄OH in IPA)/CO₂) to give a pair of diastereomers. The first-eluting isomer was Example 324, and the second-eluting isomer was Example 325. Example 324: ¹H NMR (400 MHz, CD₃OD) δ 8.45 (s, 1H), 8.12 (s, 1H), 7.87 (s, 1H), 5.25 (br d, J=8.5 Hz, 1H), 4.26 (d, J=9.5 Hz, 1H), 3.21-3.04 (m, 1H), 2.79-2.64 (m, 2H), 2.64-2.55 (m, 1H), 2.52 (s, 3H), 2.35-2.17 (m, 2H), 2.14-2.05 (m, 1H), 2.00 (br s, 2H), 1.91-1.69 (m, 2H), 1.65 (br d, J=15.5 Hz, 1H), 1.56-1.33 (m, 2H), 1.25 (ddd, J=3.9, 8.3, 12.5 Hz, 1H), 0.75-0.65 (m, 2H), 0.54-0.44 (m, 2H). MS (ESI) m/z: [M+H]⁺ Found 614.4. Example 325: ¹H NMR (400 MHz, CD₃OD) δ 8.46 (d, J=2.0 Hz, 1H), 8.11 (s, 1H), 7.86 (s, 1H), 5.25 (d, J=8.6 Hz, 1H), 4.26 (br d, J=9.4 Hz, 1H), 3.21-3.02 (m, 1H), 2.78-2.64 (m, 2H), 2.61-2.54 (m, 1H), 2.52 (s, 3H), 2.31-2.14 (m, 2H), 2.08 (dt, J=3.5, 6.9 Hz, 1H), 2.01 (br d, J 10.5 Hz, 2H), 1.91-1.69 (m, 2H), 1.64 (br d, J=15.9 Hz, 1H), 1.56-1.35 (m, 2H), 1.33-1.19 (m, 1H), 0.70 (br dd, J=5.6, 7.7 Hz, 2H), 0.50 (br d, J=2.9 Hz, 2H). MS (ESI) m/z: [M+H]⁺ Found 614.4.

Example 326

N—((S)-(7-((R)-Cyclopropyl(5,5-difluoropentanamido)methyl)imidazo[1,2-b]pyridazin-2-yl)(4,4-difluorocyclohexyl)methyl)-4-methyl-1,2,5-oxadiazole-3-carboxamide

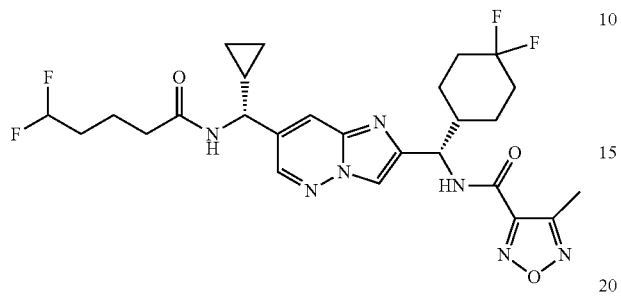

The title compound was prepared as described for the synthesis of Example 324, using 5,5-difluoropentanoic acid in place of (2,2,3,3-tetrafluorocyclobutyl)acetic acid, and running the reaction at 40° C. for 16 h instead of 2.5 h. The crude material was purified by preparative HPLC (Boston Prime C18 150×30 mm, 5 μm column; 50-80% ACN/water (0.05% NH$_4$OH+10 mM NH$_4$CO$_3$)) to afford the title compound as a white solid. $^1$H NMR (400 MHz, DMSO-d$_6$) δ 9.06 (d, J=9.0 Hz, 1H), 8.22 (d, J=7.9 Hz, 1H), 8.14 (d, J=2.0 Hz, 1H), 7.87 (s, 1H), 7.58 (d, J 1.8 Hz, 1H), 5.89-5.48 (m, 1H), 4.80 (t, J=8.5 Hz, 1H), 3.92 (t, J=8.4 Hz, 1H), 2.10 (s, 3H), 1.92-1.84 (m, 2H), 1.81 (br d, J=9.3 Hz, 1H), 1.73-1.31 (m, 7H), 1.30-1.16 (m, 3H), 1.09-0.78 (m, 3H), 0.26-0.07 (m, 3H), 0.01 (td, J=4.4, 8.8 Hz, 1H). MS (ESI) m/z: [M+H]$^+$ Found 566.2.

Example 327

N—((S)-(7-((R)-Cyclopropyl(2-(2,2,2-trifluoroethoxy)acetamido)methyl)imidazo[1,2-b]pyridazin-2-yl)(4,4-difluorocyclohexyl)methyl)-4-methyl-1,2,5-oxadiazole-3-carboxamide

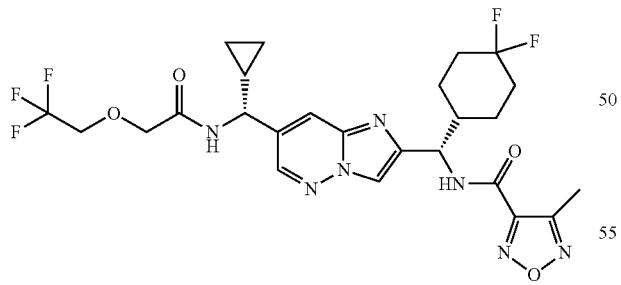

The title compound was prepared as described for the synthesis of Example 324, using 2-(2,2,2-trifluoroethoxy)acetic acid in place of (2,2,3,3-tetrafluorocyclobutyl)acetic acid, and running the reaction at 40° C. for 16 h instead of 2.5 h. The crude material was purified by preparative HPLC (Welch Xtimate C18 150×30 mm, 5 μm column; 45-75% ACN/water (0.05% NH$_4$OH)) to afford the title compound as a white solid. $^1$H NMR (400 MHz, CDCl$_3$) δ 8.33 (d, J=2.0 Hz, 1H), 7.85 (s, 2H), 7.75 (d, J=8.8 Hz, 1H), 6.92 (d, J=7.3 Hz, 1H), 5.23 (t, J=8.3 Hz, 1H), 4.36 (t, J 8.4 Hz, 1H), 4.24-4.12 (m, 2H), 4.04-3.86 (m, 2H), 2.59 (s, 3H), 2.20-1.93 (m, 4H), 1.81-1.69 (m, 2H), 1.64-1.59 (m, 1H), 1.57-1.28 (m, 2H), 1.27-1.10 (m, 1H), 0.89-0.66 (m, 2H), 0.62-0.33 (m, 2H). MS (ESI) m/z: [M+H]$^+$ Found 586.3.

Example 328

N—((S)-(7-((R)-Cyclopropyl(4,4-difluoro-2,2-dimethylbutanamido)methyl)imidazo[1,2-b]pyridazin-2-yl)(4,4-difluorocyclohexyl)methyl)-4-methyl-1,2,5-oxadiazole-3-carboxamide

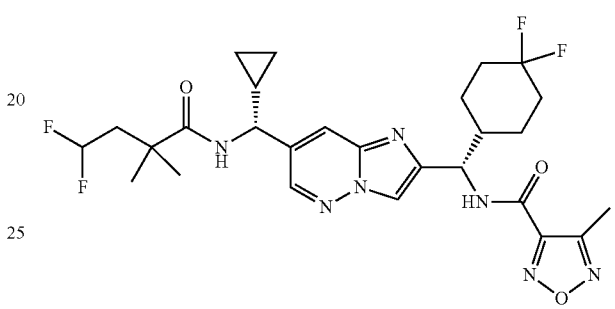

The title compound was prepare as described for the synthesis of Example 324, using 4,4-difluoro-2,2-dimethylbutanoic acid in place of (2,2,3,3-tetrafluorocyclobutyl)acetic acid, and running the reaction at 40° C. for 16 h instead of 2.5 h. The crude material was purified by preparative HPLC (Welch Xtimate C18 150×30 mm, 5 μm column; 46-76% ACN/water (0.05% NH$_4$OH)) to afford the title compound as a white solid. $^1$H NMR (400 MHz, CDCl$_3$) δ 8.29 (d, J=2.1 Hz, 1H), 7.87-7.80 (m, 2H), 7.74 (d, J=8.9 Hz, 1H), 6.13 (d, J=6.7 Hz, 1H), 6.05-5.70 (m, 1H), 5.23 (t, J=8.3 Hz, 1H), 4.27 (dd, J=9.5, 6.6 Hz, 1H), 2.59 (s, 3H), 2.20-1.90 (m, 5H), 1.83-1.10 (m, 13H), 0.81-0.66 (m, 2H), 0.51-0.43 (m, 2H). MS (ESI) m/z: [M+H]$^+$ Found 580.3.

Example 329

N—((S)-(7-((R)-Cyclopropyl((S*)-4,4-difluoro-2-methylbutanamido)methyl)imidazo[1,2-b]pyridazin-2-yl)(4,4-difluorocyclohexyl)methyl)-4-methyl-1,2,5-oxadiazole-3-carboxamide

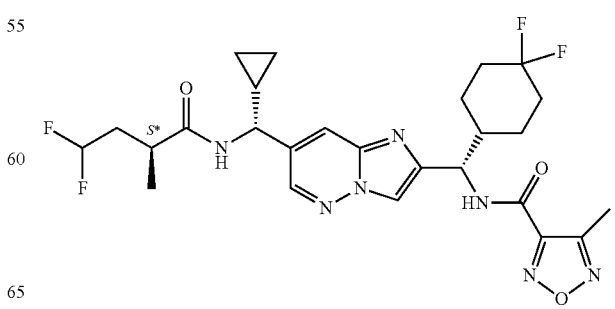

Example 330

N—((S)-(7-((R)-Cyclopropyl((R*)-4,4-difluoro-2-methylbutanamido)methyl)imidazo[1,2-b]pyridazin-2-yl)(4,4-difluorocyclohexyl)methyl)-4-methyl-1,2,5-oxadiazole-3-carboxamide

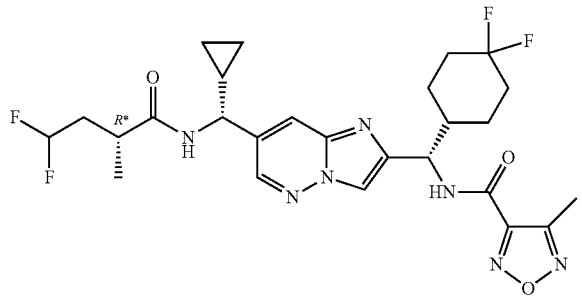 [SMILES: Cc1nonc1C(=O)N[C@H](c1cn2ncc([C@H](NC(=O)[C@H](C)CC(F)F)C3CC3)cc2n1)C1CCC(F)(F)CC1]

The title compounds were prepared as described for the synthesis of Example 324, using 4,4-difluoro-2-methylbutanoic acid in place of (2,2,3,3-tetrafluorocyclobutyl)acetic acid, and running the reaction at 40° C. for 16 h instead of 2.5 h. The crude material was purified by silica gel chromatography (0-80% EtOAc/petroleum ether) followed by SFC using a chiral stationary phase (Daicel Chiralpak AD, 250×30 mm, 10 μm, 35:65 (0.1% NH$_4$OH in EtOH)/CO$_2$) to give a pair of diastereomers. The first-eluting isomer was Example 330, and the second-eluting isomer was Example 329. Example 329: $^1$H NMR (400 MHz, CDCl$_3$) δ 8.30 (d, J=2.1 Hz, 1H), 7.93-7.78 (m, 2H), 7.74 (d, J=8.8 Hz, 1H), 7.24 (s, 1H), 6.08 (d, J=6.8 Hz, 1H), 6.05-5.66 (m, 1H), 5.22 (t, J=8.3 Hz, 1H), 4.27 (dd, J=9.5, 6.7 Hz, 1H), 2.63-2.49 (m, 4H), 2.40-2.21 (m, 1H), 2.19-1.27 (m, 9H), 1.23 (d, J=6.9 Hz, 3H), 1.18-1.05 (m, 1H), 0.84-0.66 (m, 2H), 0.56-0.40 (m, 2H). MS (ESI) m/z: [M+H]$^+$ Found 566.2. Example 330: $^1$H NMR (400 MHz, CDCl$_3$) δ 8.29 (s, 1H), 7.83 (s, 2H), 7.75 (d, J=8.8 Hz, 1H), 6.06 (d, J=6.8 Hz, 1H), 5.99-5.59 (m, 1H), 5.22 (t, J=8.4 Hz, 1H), 4.39-4.20 (m, 1H), 2.68-2.49 (m, 4H), 2.39-2.21 (m, 1H), 2.19-1.75 (m, 6H), 1.64 (br d, J=4.4 Hz, 2H), 1.57-1.43 (m, 1H), 1.42-1.31 (m, 1H), 1.26 (d, J=6.8 Hz, 3H), 1.21-1.08 (m, 1H), 0.81-0.65 (m, 2H), 0.53-0.37 (m, 2H). MS (ESI) m/z: [M+H]$^+$ Found 566.2.

Example 331

N—((S)-(7-((R)-Cyclopropyl((R*)-2-cyclopropyl-2-fluoroacetamido)methyl)imidazo[1,2-b]pyridazin-2-yl)(4,4-difluorocyclohexyl)methyl)-4-methyl-1,2,5-oxadiazole-3-carboxamide

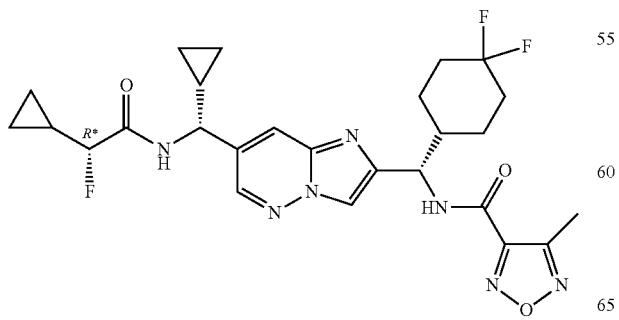

Example 332

N—((S)-(7-((R)-Cyclopropyl((S*)-2-cyclopropyl-2-fluoroacetamido)methyl)imidazo[1,2-b]pyridazin-2-yl)(4,4-difluorocyclohexyl)methyl)-4-methyl-1,2,5-oxadiazole-3-carboxamide

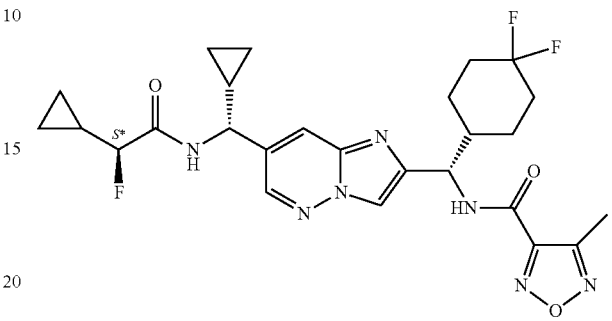

The title compounds were prepared as described for the synthesis of Example 324, using 2-cyclopropyl-2-fluoroacetic acid in place of (2,2,3,3-tetrafluorocyclobutyl)acetic acid. The crude material was purified by silica gel chromatography (0-70% EtOAc/petroleum ether) followed by SFC using a chiral stationary phase (Daicel Chiralpak AD, 250×30 mm, 10 μm, 35:65 (0.1% NH$_4$OH in IPA)/CO$_2$) to give a pair of diastereomers. The first-eluting isomer was Example 331, and the second-eluting isomer was Example 332. Example 331: $^1$H NMR (400 MHz, CDCl$_3$) δ 8.32 (d, J=2.2 Hz, 1H), 7.85 (s, 2H), 7.75 (d, J=8.8 Hz, 1H), 6.86-6.72 (m, 1H), 5.23 (t, J 8.3 Hz, 1H), 4.53-4.37 (m, 1H), 4.36-4.28 (m, 1H), 2.58 (s, 3H), 2.20-1.92 (m, 4H), 1.82-1.73 (m, 1H), 1.68-1.59 (m, 2H), 1.57-1.43 (m, 1H), 1.43-1.30 (m, 1H), 1.28-1.13 (m, 2H), 0.84-0.69 (m, 3H), 0.65-0.57 (m, 2H), 0.56-0.40 (m, 3H). MS (ESI) m/z: [M+H]$^+$ Found 546.2. Example 332: $^1$H NMR (400 MHz, CDCl$_3$) δ 8.28 (d, J=2.1 Hz, 1H), 7.88-7.77 (m, 2H), 7.72 (d, J=8.9 Hz, 1H), 6.73 (s, 1H), 5.18 (dd, J=8.9, 7.7 Hz, 1H), 4.54-4.25 (m, 2H), 2.54 (s, 3H), 2.13-1.90 (m, 4H), 1.76-1.09 (m, 9H), 0.81-0.66 (m, 2H), 0.66-0.54 (m, 2H), 0.52-0.39 (m, 2H). MS (ESI) m/z: [M+H]$^+$ Found 546.2.

Example 333

N—((S)-(7-((R)-Cyclopropyl(2-(((S)-1,1,1-trifluoropropan-2-yl)oxy)acetamido)methyl)imidazo[1,2-b]pyridazin-2-yl)(4,4-difluorocyclohexyl)methyl)-4-methyl-1,2,5-oxadiazole-3-carboxamide

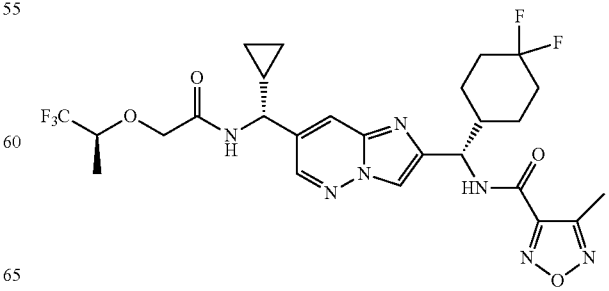

The title compound was prepared as described for the synthesis of Example 324, using (S)-2-((1,1,1-trifluoropropan-2-yl)oxy)acetic acid in place of (2,2,3,3-tetrafluorocyclobutyl)acetic acid, and running the reaction at 25° C. overnight instead of 40° C. for 2.5 h. The crude material was purified by preparative HPLC (Phenomenex Gemini-NX 150×30 mm, 5 μm column; 45-75% ACN/water (0.05% NH$_4$OH+10 mM NH$_4$CO$_3$)) to afford the title compound as a white solid. $^1$H NMR (400 MHz, CDCl$_3$) δ 8.34 (d, J=2.0 Hz, 1H), 7.87 (s, 2H), 7.78 (d, J=8.8 Hz, 1H), 6.97 (br d, J=7.4 Hz, 1H), 5.25 (t, J=8.3 Hz, 1H), 4.42-4.35 (m, 1H), 4.26-4.13 (m, 2H), 3.91 (td, J=6.4, 12.7 Hz, 1H), 2.61 (s, 3H), 2.20-2.09 (m, 2H), 2.09-1.94 (m, 2H), 1.85-1.76 (m, 1H), 1.72-1.63 (m, 2H), 1.63-1.48 (m, 1H), 1.43 (d, J=6.6 Hz, 3H), 1.41-1.33 (m, 1H), 1.24 (dt, J=4.1, 8.3 Hz, 1H), 0.78 (dt, J=4.9, 7.3 Hz, 2H), 0.58-0.45 (m, 2H). MS (ESI) m/z: [M+H]$^+$ Found 600.4.

Example 334

N—((S)-(7-((R)-Cyclopropyl((1R*,2S*)-2-fluorocyclobutane-1-carboxamido)methyl)imidazo[1,2-b]pyridazin-2-yl)(4,4-difluorocyclohexyl)methyl)-4-methyl-1,2,5-oxadiazole-3-carboxamide

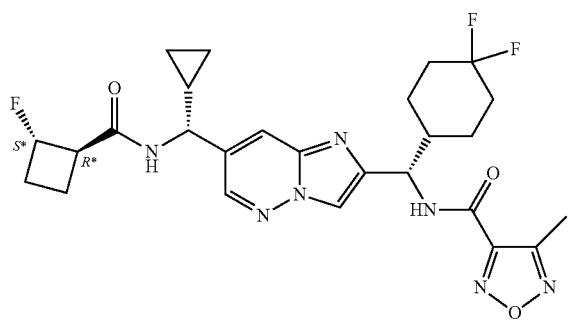 [SMILES: Cc1nonc1C(=O)N[C@H](c1cn2ncc([C@H](NC(=O)[C@H]3CC[C@@H]3F)C3CC3)cc2n1)C1CCC(F)(F)CC1]

Example 335

N—((S)-(7-((R)-Cyclopropyl((1S*,2R*)-2-fluorocyclobutane-1-carboxamido)methyl)imidazo[1,2-b]pyridazin-2-yl)(4,4-difluorocyclohexyl)methyl)-4-methyl-1,2,5-oxadiazole-3-carboxamide

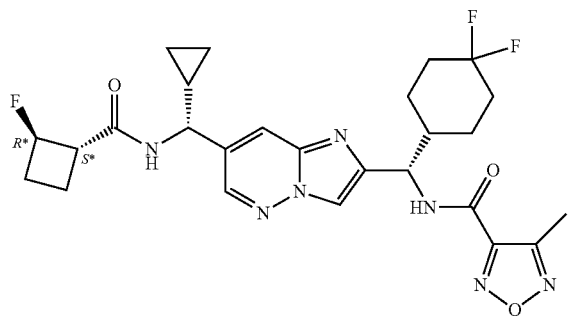 [SMILES: Cc1nonc1C(=O)N[C@H](c1cn2ncc([C@H](NC(=O)[C@@H]3CC[C@H]3F)C3CC3)cc2n1)C1CCC(F)(F)CC1]

Example 336

N—((S)-(7-((R)-Cyclopropyl((1R*,2R*)-2-fluorocyclobutane-1-carboxamido)methyl)imidazo[1,2-b]pyridazin-2-yl)(4,4-difluorocyclohexyl)methyl)-4-methyl-1,2,5-oxadiazole-3-carboxamide

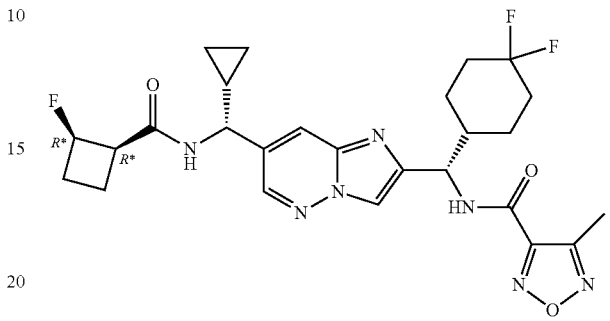

Example 337

N—((S)-(7-((R)-Cyclopropyl((1S*,2S*)-2-fluorocyclobutane-1-carboxamido)methyl)imidazo[1,2-b]pyridazin-2-yl)(4,4-difluorocyclohexyl)methyl)-4-methyl-1,2,5-oxadiazole-3-carboxamide

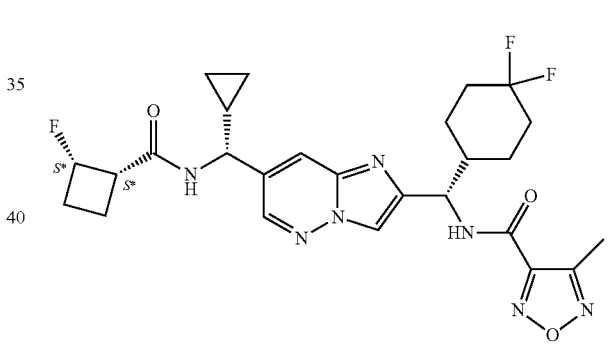

The title compounds were prepared as described for the synthesis of Example 324, using 2-fluorocyclobutane-1-carboxylic acid in place of (2,2,3,3-tetrafluorocyclobutyl)acetic acid, and running the reaction at 25° C. overnight instead of 40° C. for 2.5 h. The crude material was purified by silica gel chromatography (0-5% MeOH/DCM) followed by SFC using a chiral stationary phase (Daicel Chiralpak AD-H, 250×30 mm, 5 μm, 35:65 (0.1% NH$_4$OH in IPA)/CO$_2$) to give four diastereomers. The first-eluting isomer was Example 334, the second-eluting isomer was Example 335, the third-eluting isomer was Example 336, and the fourth-eluting isomer was Example 337. Example 334: $^1$H NMR (400 MHz, CDCl$_3$) δ 8.36 (d, J=2.0 Hz, 1H), 7.88 (s, 2H), 7.82 (d, J=8.8 Hz, 1H), 6.04 (d, J=6.9 Hz, 1H), 5.26 (t, J=8.3 Hz, 1H), 5.14-4.87 (m, 1H), 4.31 (dd, J=7.0, 9.4 Hz, 1H), 3.20-3.09 (m, 1H), 2.62 (s, 3H), 2.33-2.24 (m, 1H), 2.20-1.98 (m, 6H), 1.81-1.69 (m, 4H), 1.59-1.47 (m, 1H), 1.46-1.31 (m, 1H), 1.25-1.12 (m, 1H), 0.83-0.70 (m, 2H), 0.56-0.44 (m, 2H). MS (ESI) m/z: [M+H]$^+$ Found 546.4. Example 335: $^1$H NMR (400 MHz, CDCl$_3$) δ 8.33 (d, J=2.0 Hz, 1H), 7.87 (s, 1H), 7.84 (br s, 1H), 7.77 (d, J=8.3 Hz, 1H), 6.00 (br s, 1H), 5.34-5.21 (m, 1H), 5.17-4.92 (m, 1H), 4.32 (t, J=8.0 Hz, 1H), 3.18-3.06 (m, 1H), 2.62 (s, 3H), 2.33-2.25 (m, 1H), 2.21-1.95 (m, 6H), 1.83-1.68 (m, 4H), 1.58-1.47 (m, 1H), 1.43-1.32 (m, 1H), 1.16 (br s, 1H), 0.75 (d, J=7.5 Hz, 2H), 0.60-0.40 (m, 2H). MS (ESI) m/z: [M+H]+ Found 546.4. Example 336: $^1$H NMR (400 MHz, CDCl$_3$) δ 8.38 (d, J=2.0 Hz, 1H), 7.92-7.84 (m, 2H), 7.79 (d, J=8.8 Hz, 1H), 6.19 (dd, J=3.2, 6.7 Hz, 1H), 5.35-5.08 (m, 2H), 4.44-4.38 (m, 1H), 3.42-3.35 (m, 1H), 2.61 (s, 3H), 2.50-2.29 (m, 3H), 2.22-2.10 (m, 2H), 2.10-1.95 (m, 2H), 1.84-1.71 (m, 3H), 1.64-1.47 (m, 2H), 1.44-1.31 (m, 1H), 1.22-1.08 (m, 1H), 0.83-0.62 (m, 2H), 0.51 (q, J=4.8 Hz, 2H). MS (ESI) m/z: [M+H]+ Found 546.4. Example 337: $^1$H NMR (400 MHz, CDCl$_3$) δ 8.44-8.34 (m, 1H), 7.99-7.89 (m, 2H), 7.87 (s, 1H), 6.23 (br s, 1H), 5.34-5.07 (m, 2H), 4.39 (dd, J=6.5, 9.1 Hz, 1H), 3.48-3.24 (m, 1H), 2.61 (s, 3H), 2.51-2.27 (m, 3H), 2.21-2.09 (m, 2H), 2.09-1.96 (m, 2H), 1.85-1.68 (m, 3H), 1.64-1.46 (m, 2H), 1.44-1.34 (m, 1H), 1.24-1.14 (m, 1H), 0.75 (dq, J=5.1, 8.5 Hz, 2H), 0.62-0.45 (m, 2H). MS (ESI) m/z: [M+H]+ Found 546.4.

Example 338

N—((S)-(7-((R)-Cyclopropyl(3,3-difluoropentanamido)methyl)imidazo[1,2-b]pyridazin-2-yl)(4,4-difluorocyclohexyl)methyl)-4-methyl-1,2,5-oxadiazole-3-carboxamide

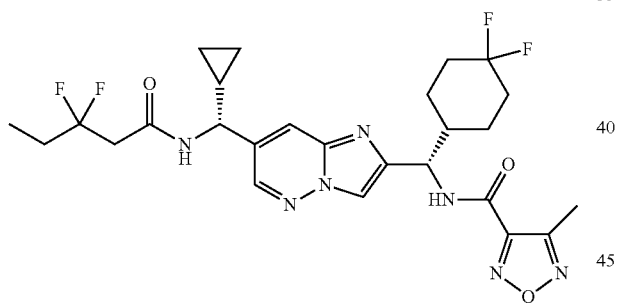

The title compound was prepared as described for the synthesis of Example 324, using 3,3-difluoropentanoic acid in place of (2,2,3,3-tetrafluorocyclobutyl)acetic acid, and running the reaction at 40° C. for 16 h instead of 2.5 h. The crude material was purified by preparative HPLC (Boston Prime C18, 150×30 mm, 5 μm column; 50-80% ACN/water (0.05% NH$_4$OH)) to provide the title compound as a white solid. $^1$H NMR (400 MHz, CDCl$_3$) δ 8.31 (d, J=1.8 Hz, 1H), 7.84 (s, 2H), 7.75 (d, J=9.0 Hz, 1H), 6.34 (d, J=6.8 Hz, 1H), 5.23 (t, J=8.4 Hz, 1H), 4.39-4.27 (m, 1H), 2.86 (t, J=16.4 Hz, 2H), 2.59 (s, 3H), 2.13 (br s, 2H), 2.04-1.88 (m, 4H), 1.82-1.65 (m, 3H), 1.54-1.44 (m, 1H), 1.43-1.29 (m, 1H), 1.21-1.10 (m, 1H), 1.04 (t, J=7.5 Hz, 3H), 0.79-0.66 (m, 2H), 0.54-0.43 (m, 2H). MS (ESI) m/z: [M+H]+ Found 566.3.

Example 339

N—((S)-(7-((R)-Cyclopropyl(3-cyclopropyl-2,2-difluoropropanamido)methyl)imidazo[1,2-b]pyridazin-2-yl)(4,4-difluorocyclohexyl)methyl)-4-methyl-1,2,5-oxadiazole-3-carboxamide

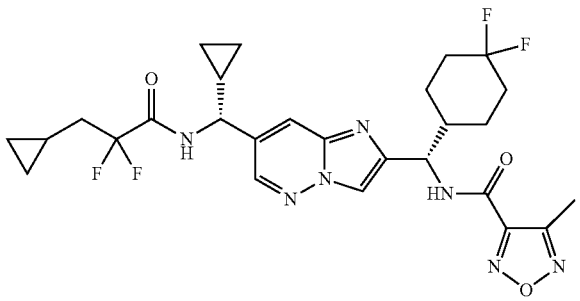 [SMILES: Cc1nonc1C(=O)N[C@H](c1cn2ncc([C@H](NC(=O)C(F)(F)CC3CC3)C3CC3)cc2n1)C1CCC(F)(F)CC1]

The title compound was prepared as described for the synthesis of Example 324, using 3-cyclopropyl-2,2-difluoropropanoic acid in place of (2,2,3,3-tetrafluorocyclobutyl)acetic acid, and running the reaction at 40° C. for 16 h instead of 2.5 h. The crude material was purified by preparative HPLC (Venusil ASB Phenyl, 150×30 mm, 5 μm column; 49-79% ACN/water (0.05% HCl)) to provide the title compound as a white solid. $^1$H NMR (400 MHz, CDCl$_3$) δ 8.20 (d, J=2.0 Hz, 1H), 7.79-7.67 (m, 2H), 7.60 (d, J=8.4 Hz, 1H), 6.75 (d, J=6.2 Hz, 1H), 5.11 (t, J=8.3 Hz, 1H), 4.21 (t, J=8.5 Hz, 1H), 2.46 (s, 3H), 2.01 (s, 2H), 1.90 (dt, J=7.1, 16.0 Hz, 4H), 1.67-1.50 (m, 3H), 1.41-1.30 (m, 1H), 1.29-1.18 (m, 1H), 1.17-1.05 (m, 1H), 0.72-0.56 (m, 3H), 0.45-0.29 (m, 4H), 0.10-0.05 (m, 2H). MS (ESI) m/z: [M+H]+ Found 578.3.

Example 340

N—((S)-(7-((R)-Cyclopropyl((1S*,3R*,4R*)-3-fluorobicyclo[2.1.0]pentane-1-carboxamido)methyl)imidazo[1,2-b]pyridazin-2-yl)(4,4-difluorocyclohexyl)methyl)-4-methyl-1,2,5-oxadiazole-3-carboxamide

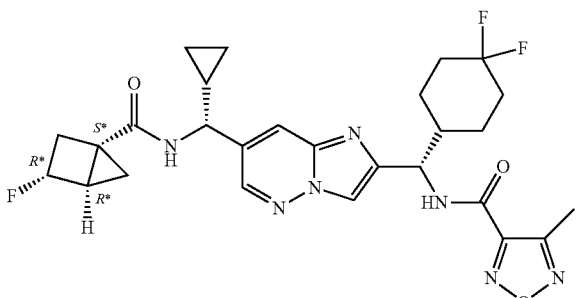

Example 341

N—((S)-(7-((R)-Cyclopropyl((1R*,3S*,4S*)-3-fluorobicyclo[2.1.0]pentane-1-carboxamido)methyl)imidazo[1,2-b]pyridazin-2-yl)(4,4-difluorocyclohexyl)methyl)-4-methyl-1,2,5-oxadiazole-3-carboxamide

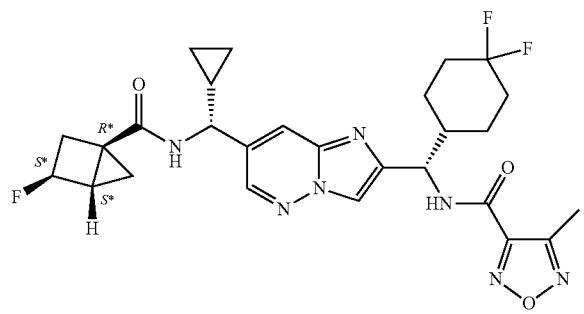 [SMILES: Cc1nonc1C(=O)N[C@H](c1cn2ncc([C@H](NC(=O)[C@@]34C[C@@H]3[C@@H](F)C4)C3CC3)cc2n1)C1CCC(F)(F)CC1]

Example 342

N—((S)-(7-((R)-Cyclopropyl((R*)-3-ethyl-5,5,5-trifluoropentanamido)methyl)imidazo[1,2-b]pyridazin-2-yl)(4,4-difluorocyclohexyl)methyl)-4-methyl-1,2,5-oxadiazole-3-carboxamide

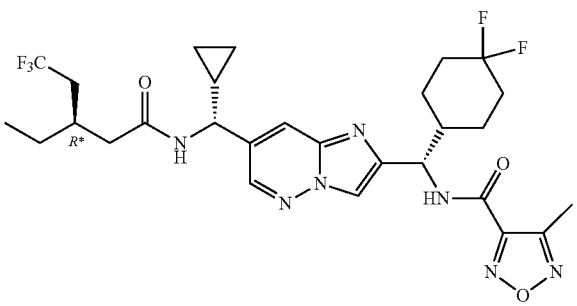 [SMILES: CC[C@H](CC(=O)N[C@@H](c1cnn2cc([C@@H](NC(=O)c3nonc3C)C3CCC(F)(F)CC3)nc2c1)C1CC1)CC(F)(F)F]

Example 343

N—((S)-(7-((R)-Cyclopropyl((S*)-3-ethyl-5,5,5-trifluoropentanamido)methyl)imidazo[1,2-b]pyridazin-2-yl)(4,4-difluorocyclohexyl)methyl)-4-methyl-1,2,5-oxadiazole-3-carboxamide

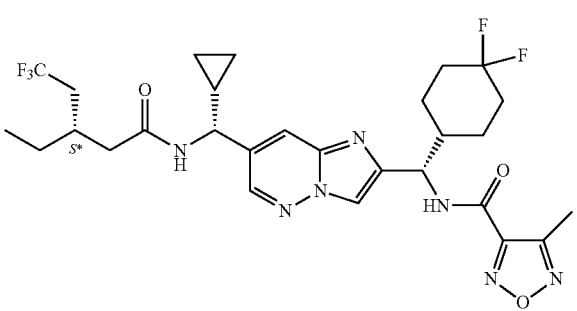 [SMILES: CC[C@@H](CC(=O)N[C@@H](c1cnn2cc([C@@H](NC(=O)c3nonc3C)C3CCC(F)(F)CC3)nc2c1)C1CC1)CC(F)(F)F]

The title compounds were prepared as described for the synthesis of Example 324, using rac-(1R,3S,4S)-3-fluorobicyclo[2.1.0]pentane-1-carboxylic acid in place of (2,2,3,3-tetrafluorocyclobutyl)acetic acid, and running the reaction at 40° C. for 16 h instead of 2.5 h. The crude material was purified by silica gel chromatography (0-80% EtOAc/petroleum ether) followed by SFC using a chiral stationary phase (Daicel Chiralpak AD, 250×30 mm, 10 µm, 60:40 (0.1% NH$_4$OH in EtOH)/CO$_2$) to give two diastereomers. The first-eluting isomer was Example 340 and the second-eluting isomer was Example 341. Example 340: $^1$H NMR (400 MHz, CDCl$_3$) δ 8.34 (d, J=2.2 Hz, 1H), 7.85 (s, 2H), 7.76 (d, J=8.6 Hz, 1H), 6.04 (d, J=6.6 Hz, 1H), 5.22 (t, J=8.4 Hz, 1H), 4.73-4.44 (m, 1H), 4.29 (dd, J=6.9, 9.4 Hz, 1H), 2.68-2.60 (m, 1H), 2.59 (s, 3H), 2.36-2.18 (m, 2H), 2.17-1.91 (m, 5H), 1.81-1.75 (m, 1H), 1.74-1.70 (m, 1H), 1.59 (br s, 1H), 1.56-1.43 (m, 1H), 1.43-1.29 (m, 1H), 1.21-1.17 (m, 1H), 1.16-1.12 (m, 1H), 0.79-0.68 (m, 2H), 0.55-0.41 (m, 2H). MS (ESI) m/z: [M+H]$^+$ Found 558.2. Example 341: $^1$H NMR (400 MHz, CDCl$_3$) δ 8.32 (d, J=2.2 Hz, 1H), 7.90-7.80 (m, 2H), 7.75 (d, J=8.8 Hz, 1H), 6.06 (d, J=6.9 Hz, 1H), 5.22 (t, J=8.3 Hz, 1H), 4.71-4.49 (m, 1H), 4.33 (dd, J=9.4, 6.8 Hz, 1H), 2.72-2.61 (m, 1H), 2.59 (s, 3H), 2.37-1.92 (m, 6H), 1.67 (s, 8H), 0.88-0.67 (m, 2H), 0.64-0.36 (m, 2H). MS (ESI) m/z: [M+H]$^+$ Found 558.3.

The title compounds were prepared as described for the synthesis of Intermediate 91, using 3-ethyl-5,5,5-trifluoropentanoic acid in place of 2-(3,3-difluorocyclobutyl)acetic acid. The crude material was purified by silica gel chromatography (0-50% EtOAc/petroleum ether) followed by SFC using a chiral stationary phase (Daicel Chiralpak IG, 250×30 mm, 10 µm, 30:70 (0.1% NH$_4$OH in IPA)/CO$_2$) to give two diastereomers. The first-eluting isomer was Example 342 and the second-eluting isomer was Example 343. Example 342: $^1$H NMR (400 MHz, DMSO-d$_6$) δ 9.43 (d, J=8.9 Hz, 1H), 8.68 (d, J=7.8 Hz, 1H), 8.50 (d, J=2.0 Hz, 1H), 8.23 (s, 1H), 7.94 (d, J=2.0 Hz, 1H), 5.17 (t, J=8.5 Hz, 1H), 4.28 (t, J=8.5 Hz, 1H), 2.47 (s, 3H), 2.36-1.55 (m, 11H), 1.46-1.17 (m, 5H), 0.83 (t, J=7.4 Hz, 3H), 0.61-0.44 (m, 4H), 0.45-0.34 (m, 1H). MS (ESI) m/z: [M+H]$^+$ Found 612.4. Example 343: $^1$H NMR (400 MHz, DMSO-d$_6$) δ 9.43 (d, J=9.0 Hz, 1H), 8.67 (d, J=7.8 Hz, 1H), 8.50 (d, J=2.0 Hz, 1H), 8.23 (s, 1H), 7.95 (d, J=1.8 Hz, 1H), 5.17 (t, J=8.5 Hz, 1H), 4.29 (t, J=8.4 Hz, 1H), 2.47 (s, 3H), 2.31-2.25 (m, 1H), 2.25-2.22 (m, 2H), 2.19 (d, J=4.3 Hz, 2H), 2.07 (dt, J=5.6, 12.5 Hz, 2H), 1.98 (d, J=8.5 Hz, 1H), 1.90 (d, J 13.1 Hz, 1H), 1.85-1.67 (m, 2H), 1.60 (d, J=11.0 Hz, 1H), 1.41-1.31 (m, 3H), 1.29-1.16 (m, 2H), 0.91-0.81 (m, 3H), 0.63-0.44 (m, 3H), 0.37 (td, J=4.2, 9.0 Hz, 1H). MS (ESI) m/z: [M+H]+ Found 612.2.

Example 344

N—((S)-(7-((R)-Cyclopropyl((R*)-3-cyclopropyl-2-fluoropropanamido)methyl)imidazo[1,2-b]pyridazin-2-yl)(4,4-difluorocyclohexyl)methyl)-4-methyl-1,2,5-oxadiazole-3-carboxamide

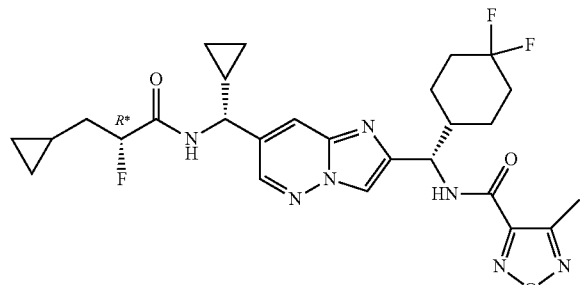

Example 345

N—(SS)-(7-((R)-Cyclopropyl-((S*)-3-cyclopropyl-2-fluoropropanamido)methyl)imidazo[1,2-h]pyridazin-2-yl)(4,4-difluorocyclohexyl)methyl)-4-methyl-1,2,5-oxadiazole-3-carboxamide

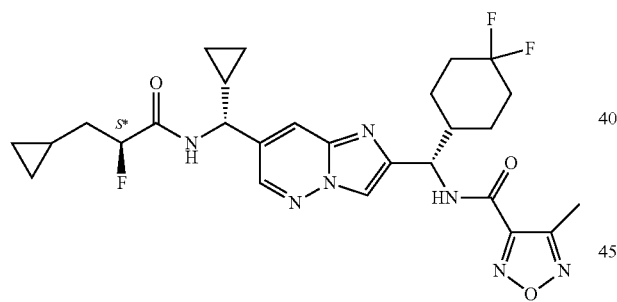

The title compounds were prepared as described for the synthesis of Intermediate 91, using 3-cyclopropyl-2-fluoropropanoic acid in place of 2-(3,3-difluorocyclobutyl)acetic acid, and running the reaction at rt for 30 min instead of 2 h. The crude material was purified by silica gel chromatography (0-50% EtOAc/petroleum ether) followed by SFC using a chiral stationary phase (Daicel Chiralpak IG, 250×30 mm, 10 μm, 35:65 (0.1% NH$_4$OH in IPA)/CO$_2$) to give two diastereomers. The first-eluting isomer was Example 344 and the second-eluting isomer was Example 345. Example 344: $^1$H NMR (400 MHz, DMSO-d$_6$) δ 9.39 (d, J=9.0 Hz, 1H), 8.91 (d, J=8.3 Hz, 1H), 8.53 (d, J=2.0 Hz, 1H), 8.19 (s, 1H), 7.96 (s, 1H), 5.12 (t, J=8.5 Hz, 1H), 5.03 (t, J=5.5 Hz, 1H), 4.20 (t, J=8.9 Hz, 1H), 2.41 (s, 3H), 2.13 (d, J=8.0 Hz, 1H), 2.05-1.89 (m, 2H), 1.88-1.71 (m, 2H), 1.71-1.62 (m, 2H), 1.62-1.50 (m, 2H), 1.41-1.26 (m, 2H), 1.21-1.18 (m, 1H), 0.73-0.61 (m, 1H), 0.60-0.52 (m, 1H), 0.51-0.40 (m, 2H), 0.38-0.28 (m, 2H), 0.27-0.16 (m, 1H), 0.11-0.07 (m, 2H). MS (ESI) m/z: [M+H]+ Found 560.2. Example 345: $^1$H NMR (400 MHz, DMSO-d$_6$) δ 9.32 (d, J=9.0 Hz, 1H), 8.83 (d, J=8.0 Hz, 1H), 8.46 (d, J=2.3 Hz, 1H), 8.12 (s, 1H), 7.89 (d, J=1.8 Hz, 1H), 5.05 (t, J=8.7 Hz, 1H), 4.98-4.79 (m, 1H), 4.16 (t, J=8.8 Hz, 1H), 2.35 (s, 3H), 2.07 (d, J=7.8 Hz, 1H), 1.99-1.83 (m, 2H), 1.82-1.68 (m, 2H), 1.67-1.60 (m, 2H), 1.60-1.55 (m, 1H), 1.54-1.42 (m, 1H), 1.33-1.22 (m, 2H), 1.17-1.11 (m, 1H), 0.77-0.60 (m, 1H), 0.54-0.36 (m, 3H), 0.35-0.22 (m, 3H), 0.08-0.07 (m, 2H). MS (ESI) m/z: [M+H]+ Found 560.2.

Example 346

N—((S)-(7-((R)-Cyclopropyl((R*)-4,4,4-trifluoro-2-methylbutanamido)methyl)imidazo[1,2-b]pyridazin-2-yl)(4,4-difluorocyclohexyl)methyl)-4-methyl-1,2,5-oxadiazole-3-carboxamide

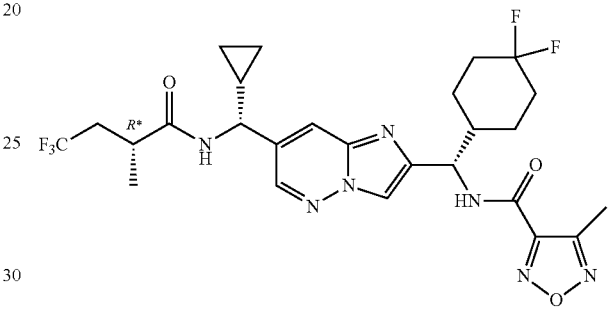

Example 347

N—((S)-(7-((R)-Cyclopropyl((S*)-4,4,4-trifluoro-2-methylbutanamido)methyl)imidazo[1,2-b]pyridazin-2-yl)(4,4-difluorocyclohexyl)methyl)-4-methyl-1,2,5-oxadiazole-3-carboxamide

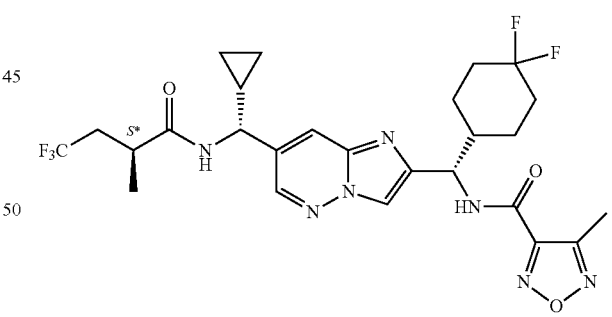

The title compounds were prepared as described for the synthesis of Example 324, using 2-methyl-4,4,4-trifluorobutyric acid in place of (2,2,3,3-tetrafluorocyclobutyl)acetic acid, and running the reaction at 30° C. for 16 h instead of 40° C. for 2.5 h. The crude material was purified by silica gel chromatography (0-100% DCM/petroleum ether) followed by SFC using a chiral stationary phase (Daicel Chiralpak AS, 250×30 mm, 10 μm, 50:50 (0.1% NH$_4$OH in EtOH)/CO$_2$) to give two diastereomers. The first-eluting isomer was Example 346 and the second-eluting isomer was Example 347. Example 346: $^1$H NMR (400 MHz, CDCl$_3$) δ 8.32 (d, J=2.3 Hz, 1H), 7.88 (s, 2H), 7.77 (d, J=9.0 Hz, 1H), 6.06 (d, J=7.0 Hz, 1H), 5.27 (t, J=8.3 Hz, 1H), 4.35 (dd, J=7.5, 9.0 Hz, 1H), 2.80-2.66 (m, 1H), 2.66-2.64 (m, 1H), 2.61 (s, 3H), 2.25-2.10 (m, 3H), 2.09-1.96 (m, 2H), 1.86-1.75 (m, 1H), 1.74-1.70 (m, 1H), 1.71-1.63 (m, 1H), 1.61-1.48 (m, 1H), 1.47-1.37 (m, 1H), 1.34 (d, J=6.8 Hz, 3H), 1.25-1.14 (m, 1H), 0.87-0.69 (m, 2H), 0.58-0.42 (m, 2H). MS (ESI) m/z: [M+H]⁺ Found 584.2. Example 347: ¹H NMR (400 MHz, CDCl₃) δ 8.34 (d, J=2.0 Hz, 1H), 7.95-7.83 (m, 2H), 7.77 (d, J=8.8 Hz, 1H), 6.09 (d, J=6.5 Hz, 1H), 5.27 (t, J 8.3 Hz, 1H), 4.31 (dd, J=7.0, 9.3 Hz, 1H), 2.81-2.70 (m, 1H), 2.70-2.65 (m, 1H), 2.63 (s, 3H), 2.25-2.11 (m, 3H), 2.11-2.06 (m, 1H), 2.05-1.97 (m, 1H), 1.87-1.75 (m, 1H), 1.72-1.77 (m, 1H), 1.61-1.48 (m, 1H), 1.47-1.34 (m, 1H), 1.30 (d, J=7.0 Hz, 3H), 1.23-1.10 (m, 1H), 0.85-0.69 (m, 2H), 0.58-0.44 (m, 2H). MS (ESI) m/z: [M+H]⁺ Found 584.2.

Example 348

N—((S)-(7-((R)-((R*)-2-Cyclobutyl-2-fluoroacetamido)(cyclopropyl)methyl)imidazo[1,2-b]pyridazin-2-yl)(4,4-difluorocyclohexyl)methyl)-4-methyl-1,2,5-oxadiazole-3-carboxamide

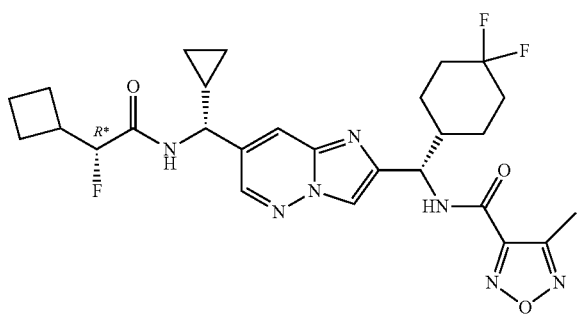 [SMILES: Cc1nonc1C(=O)N[C@H](c1cn2ncc([C@H](NC(=O)[C@H](F)C3CCC3)C3CC3)cc2n1)C1CCC(F)(F)CC1]

Example 349

N—((S)-(7-((R)-((S*)-2-Cyclobutyl-2-fluoroacetamido)(cyclopropyl)methyl)imidazo[1,2-b]pyridazin-2-yl)(4,4-difluorocyclohexyl)methyl)-4-methyl-1,2,5-oxadiazole-3-carboxamide

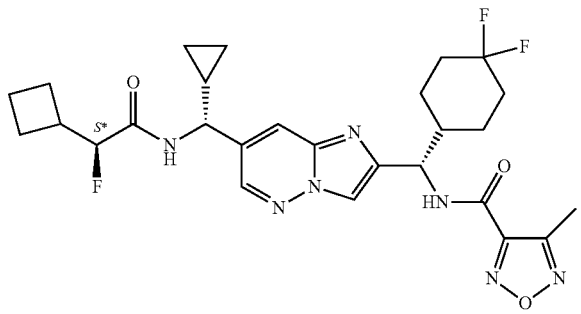 [SMILES: Cc1nonc1C(=O)N[C@H](c1cn2ncc([C@H](NC(=O)[C@@H](F)C3CCC3)C3CC3)cc2n1)C1CCC(F)(F)CC1]

The title compounds were prepared as described for the synthesis of Example 324, using 2-cyclobutyl-2-fluoroacetic acid in place of (2,2,3,3-tetrafluorocyclobutyl)acetic acid, and running the reaction at 30° C. for 16 h instead of 40° C. for 2.5 h. The crude material was purified by silica gel chromatography (0-100% DCM/petroleum ether) followed by SFC using a chiral stationary phase (Daicel Chiralpak AS, 250×30 mm, 10 µm, 50:50 (0.1% NH₄OH in EtOH)/CO₂) to give two diastereomers. The first-eluting isomer was Example 348 and the second-eluting isomer was Example 349. Example 348: ¹H NMR (400 MHz, CDCl₃) δ 8.30 (d, J=2.0 Hz, 1H), 7.88 (s, 1H), 7.87-7.83 (m, 1H), 7.78 (d, J=8.8 Hz, 1H), 6.87-6.75 (m, 1H), 5.27 (t, J=8.4 Hz, 1H), 4.97-4.76 (m, 1H), 4.44-4.14 (m, 1H), 3.07-2.79 (m, 1H), 2.63 (s, 3H), 2.24-2.11 (m, 3H), 2.11-1.99 (m, 4H), 1.98-1.88 (m, 2H), 1.87-1.78 (m, 2H), 1.69-1.61 (m, 2H), 1.60-1.49 (m, 1H), 1.46-1.32 (m, 1H), 1.30-1.16 (m, 1H), 0.85-0.72 (m, 2H), 0.61-0.44 (m, 2H). MS (ESI) m/z: [M+H]⁺ Found 560.2. Example 349: ¹H NMR (400 MHz, CDCl₃) δ 8.37 (d, J=2.3 Hz, 1H), 7.93-7.90 (m, 1H), 7.89 (s, 1H), 7.78 (d, J=9.0 Hz, 1H), 6.78-6.75 (m, 1H), 5.27 (t, J=8.2 Hz, 1H), 4.96-4.70 (m, 1H), 4.39 (t, J=8.5 Hz, 1H), 3.11-2.83 (m, 1H), 2.71-2.53 (m, 3H), 2.26-2.13 (m, 3H), 2.12-2.05 (m, 3H), 2.04-1.92 (m, 3H), 1.91-1.82 (m, 1H), 1.81-1.70 (m, 2H), 1.63 (d, J=3.5 Hz, 1H), 1.60-1.47 (m, 1H), 1.46-1.32 (m, 1H), 1.30-1.14 (m, 1H), 0.89-0.68 (m, 2H), 0.58-0.41 (m, 2H). MS (ESI) m/z: [M+H]⁺ Found 560.3.

Example 350

N—((S)-(7-((R)-Cyclopropyl((R*)-5,5,5-trifluoro-3-methylpentanamido)methyl)imidazo[1,2-b]pyridazin-2-yl)(4,4-difluorocyclohexyl)methyl)-4-methyl-1,2,5-oxadiazole-3-carboxamide

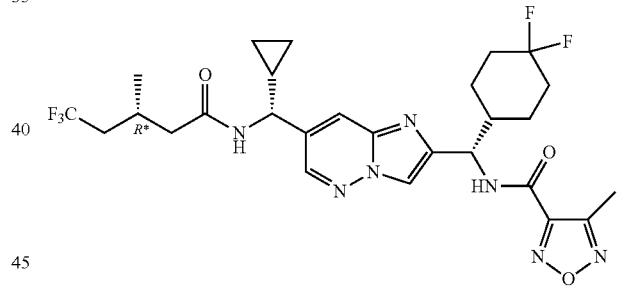

The title compound was prepared as described for the synthesis of Example 324, using 5,5,5-trifluoro-3-methylpentanoic acid in place of (2,2,3,3-tetrafluorocyclobutyl)acetic acid, and running the reaction at 40° C. overnight instead of 2.5 h. The crude material was purified by silica gel chromatography (0-50% EtOAc/petroleum ether) followed by SFC using a chiral stationary phase (Phenomenex-Cellulose-2, 250×30 mm, 5 µm, 25:75 (0.1% NH₄OH in MeOH)/CO₂) to provide the title compound as a white solid. ¹H NMR (400 MHz, CDCl₃) δ 8.34 (d, J=2.0 Hz, 1H), 7.89-7.85 (m, 2H), 7.76 (d, J=9.0 Hz, 1H), 5.96 (d, J=7.3 Hz, 1H), 5.26 (t, J=8.2 Hz, 1H), 4.37-4.31 (m, 1H), 2.62 (s, 3H), 2.47-2.35 (m, 2H), 2.27-1.96 (m, 7H), 1.77-1.67 (m, 3H), 1.55-1.50 (m, 1H), 1.45-1.35 (m, 1H), 1.23-1.06 (m, 4H), 0.82-0.70 (m, 2H), 0.55-0.45 (m, 2H). MS (ESI) m/z: [M+H]⁺ Found 598.2.

Example 351

N—((S)-(7-((R)-(4-Cyanobutanamido)(cyclopropyl)methyl)imidazo[1,2-b]pyridazin-2-yl)(4,4-difluorocyclohexyl)methyl)-4-methyl-1,2,5-oxadiazole-3-carboxamide

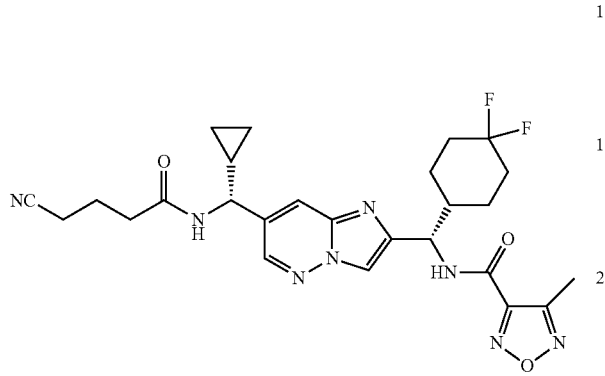

The title compound was prepared as described for the synthesis of Example 324, using 4-cyanobutanoic acid in place of (2,2,3,3-tetrafluorocyclobutyl)acetic acid, and running the reaction at 40° C. overnight instead of 2.5 h. The crude material was purified by preparative HPLC (Phenomenex Gemini-NX 150×30 mm, 5 μm column; 34-64% ACN/water (0.05% NH$_4$OH)) to afford the title compound as a white solid. $^1$H NMR (400 MHz, CD$_3$OD) δ 8.45 (d, J=2.1 Hz, 1H), 8.10 (s, 1H), 7.85 (d, J=2.0 Hz, 1H), 5.23 (d, J=8.6 Hz, 1H), 4.24 (d, J=9.4 Hz, 1H), 2.55-2.36 (m, 7H), 2.20 (d, J=10.5 Hz, 4H), 2.13-1.56 (m, 7H), 1.56-1.11 (m, 3H), 0.88-0.59 (m, 1H), 0.51-0.43 (m, 1H). MS (ESI) m/z: [M+H]$^+$ Found 541.3.

Example 352

N—((S)-(7-((R)-Cyclopropyl((2R*,3R*)-2,4,4,4-tetrafluoro-3-methylbutanamido)methyl)imidazo[1,2-b]pyridazin-2-yl)(4,4-difluorocyclohexyl)methyl)-4-methyl-1,2,5-oxadiazole-3-carboxamide

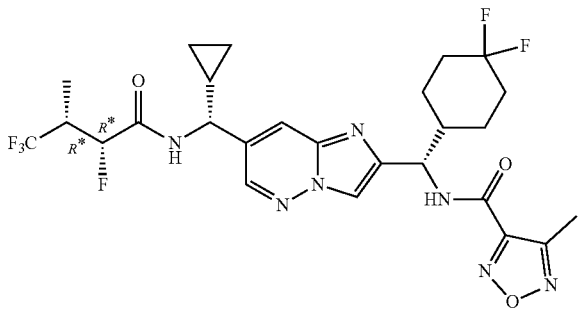 [SMILES: Cc1nonc1C(=O)N[C@H](c1cn2ncc([C@H](NC(=O)[C@H](F)[C@@H](C)C(F)(F)F)C3CC3)cc2n1)C1CCC(F)(F)CC1]

Example 353

N—((S)-(7-((R)-Cyclopropyl((2R*,3S*)-2,4,4,4-tetrafluoro-3-methylbutanamido)methyl)imidazo[1,2-b]pyridazin-2-yl)(4,4-difluorocyclohexyl)methyl)-4-methyl-1,2,5-oxadiazole-3-carboxamide

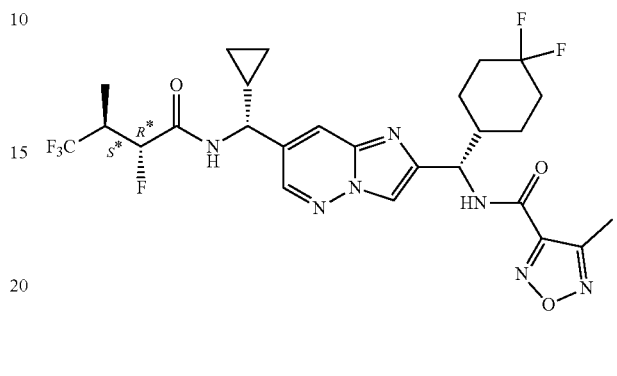

Example 354

N—((S)-(7-((R)-Cyclopropyl((2S*,3R*)-2,4,4,4-tetrafluoro-3-methylbutanamido)methyl)imidazo[1,2-b]pyridazin-2-yl)(4,4-difluorocyclohexyl)methyl)-4-methyl-1,2,5-oxadiazole-3-carboxamide

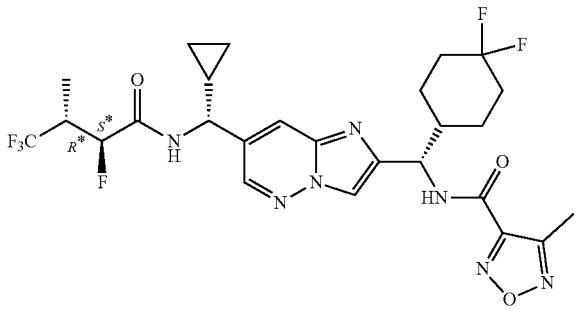 [SMILES: Cc1nonc1C(=O)N[C@H](c1cn2ncc([C@H](NC(=O)[C@@H](F)[C@@H](C)C(F)(F)F)C3CC3)cc2n1)C1CCC(F)(F)CC1]

The title compounds were prepared as described for the synthesis of Example 324, using 2,4,4,4-tetrafluoro-3-methylbutanoic acid in place of (2,2,3,3-tetrafluorocyclobutyl)acetic acid, and running the reaction at 40° C. overnight instead of 2.5 h. The crude material was purified by silica gel chromatography (0-100% EtOAc/petroleum ether) followed by SFC using a chiral stationary phase (Daicel Chiralpak AD-H, 250×30 mm, 5 μm, 30:70 (0.1% NH$_4$OH in IPA)/CO$_2$) to give three diastereomers. The first-eluting isomer was Example 352, the third-eluting isomer was Example 353, and the fourth-eluting isomer was Example 354. Example 352: $^1$H NMR (400 MHz, CD$_3$OD) δ 8.52 (d, J=2.0 Hz, 1H), 8.14 (s, 1H), 7.94 (d, J=2.0 Hz, 1H), 5.44-5.28 (m, 1H), 5.25 (d, J=8.6 Hz, 1H), 4.30 (d, J=9.9 Hz, 1H), 3.07-2.87 (m, 1H), 2.52 (s, 3H), 2.30-2.13 (m, 1H), 2.16-1.97 (m, 3H), 1.91-1.70 (m, 2H), 1.69-1.60 (m, 1H), 1.56-1.36 (m, 3H), 1.09 (d, J=7.1 Hz, 3H), 0.78-0.68 (m, 2H), 0.52 (d, J=4.9 Hz, 2H). MS (ESI) m/z: [M+H]$^+$ Found 602.2. Example 353: $^1$H NMR (400 MHz, CD$_3$OD) δ 8.50 (d, J=1.8 Hz, 1H), 8.10 (s, 1H), 7.95 (s, 1H), 5.42-5.26 (m, 1H), 5.23 (d, J=8.4 Hz, 1H), 4.33 (d, J=9.9 Hz, 1H), 3.13-2.90 (m, 1H), 2.50 (s, 3H), 2.20 (d, J=9.7 Hz, 1H), 2.13-1.94 (m, 3H), 1.88-1.57 (m, 3H), 1.54-1.32 (m, 3H), 1.20 (d, J=7.1 Hz, 3H), 0.80-0.65 (m, 2H), 0.58-0.42 (m, 2H). MS (ESI) m/z: [M+H]⁺ Found 602.3. Example 354: ¹H NMR (400 MHz, CD₃OD) δ 8.49 (d, J=2.0 Hz, 1H), 8.10 (s, 1H), 7.92 (s, 1H), 5.23 (d, J=8.6 Hz, 1H), 5.10-4.95 (m, 1H), 4.28 (d, J=9.7 Hz, 1H), 3.17-2.98 (m, 1H), 2.50 (s, 3H), 2.27-2.15 (m, 1H), 2.14-1.94 (m, 3H), 1.84-1.58 (m, 3H), 1.53-1.34 (m, 3H), 1.29 (d, J=7.3 Hz, 3H), 0.76-0.66 (m, 2H), 0.57-0.42 (m, 2H). MS (ESI) m/z: [M+H]⁺ Found 602.2.

Example 355

N—((S)-(7-((R)-Cyclopropyl((trans-3R*,4R*)-4-(trifluoromethyl)pyrrolidine-3-carboxamido)methyl)imidazo[1,2-b]pyridazin-2-yl)(4,4-difluorocyclohexyl)methyl)-4-methyl-1,2,5-oxadiazole-3-carboxamide

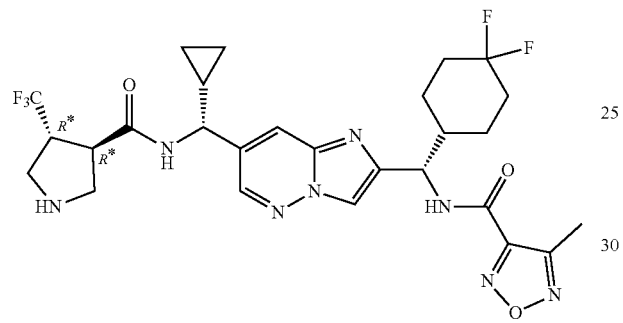

Example 356

N—((S)-(7-((R)-Cyclopropyl((trans-3S*,4S*)-4-(trifluoromethyl)pyrrolidine-3-carboxamido)methyl)imidazo[1,2-b]pyridazin-2-yl)(4,4-difluorocyclohexyl)methyl)-4-methyl-1,2,5-oxadiazole-3-carboxamide

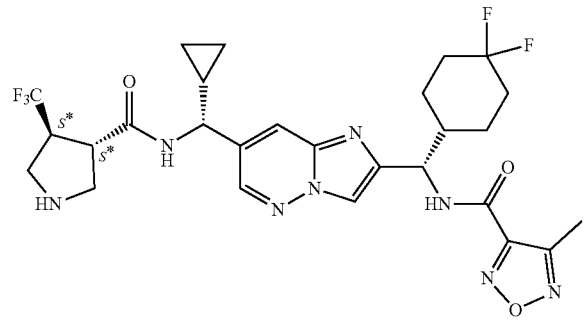 [SMILES: Cc1nonc1C(=O)N[C@H](c1cn2ncc([C@H](NC(=O)[C@@H]3CNC[C@H]3C(F)(F)F)C3CC3)cc2n1)C1CCC(F)(F)CC1]

TFA (0.5 mL, 6.53 mmol) was added to a solution of tert-butyl (trans-3,4)-3-(((R)-cyclopropyl(2-((S)-(4,4-difluorocyclohexyl)(4-methyl-1,2,5-oxadiazole-3-carboxamido)methyl)imidazo[1,2-b]pyridazin-7-yl)methyl)carbamoyl)-4-(trifluoromethyl)pyrrolidine-1-carboxylate (60 mg, 0.084 mmol, Intermediate 288) in DCM (1.5 mL) and the resulting mixture stirred at rt for 16 h. The reaction mixture was concentrated to dryness, then the residue was diluted with DCM (5 mL) and a few drops of saturated aqueous NaHCO₃ was added. The mixture was stirred at rt for 10 min then concentrated to dryness. The crude material was purified by SFC using a chiral stationary phase (Daicel Chiralpak AS, 250×30 mm, 10 μm, 25:75 (0.1% NH₄OH in IPA)/CO₂) to afford the title compounds as single trans-diastereomers. The first-eluting isomer was Example 355 and the second-eluting isomer was Example 356. Example 355: ¹H NMR (400 MHz, CDCl₃) δ 8.36-8.25 (m, 1H), 7.93-7.74 (m, 3H), 6.39 (dd, J=17.2, 6.9 Hz, 1H), 5.23 (t, J=8.3 Hz, 1H), 4.83-4.40 (m, 2H), 4.39-4.18 (m, 1H), 3.37-2.94 (m, 4H), 2.90-2.77 (m, 1H), 2.59 (s, 3H), 2.27-1.01 (m, 10H), 0.84-0.56 (m, 2H), 0.67-0.39 (m, 2H). MS (ESI) m/z: [M+H]⁺ Found 611.4. Example 356: ¹H NMR (400 MHz, CDCl₃) δ 8.23 (d, J=2.2 Hz, 1H), 7.85-7.67 (m, 3H), 6.36 (d, J=7.0 Hz, 1H), 5.18 (t, J=8.4 Hz, 1H), 4.84 (s, 2H), 4.31-4.19 (m, 1H), 3.29-2.71 (m, 5H), 2.54 (s, 3H), 2.22-1.84 (m, 5H), 1.49-1.02 (m, 5H), 0.73-0.59 (m, 2H), 0.50-0.33 (m, 2H). MS (ESI) m/z: [M+H]⁺ Found 611.4.

Example 357

N—((S)-(7-((R)-Cyclopropyl(2-(((R)-1,1,1-trifluoropropan-2-yl)oxy)acetamido)methyl)imidazo[1,2-b]pyridazin-2-yl)(4,4-difluorocyclohexyl)methyl)-4-methyl-1,2,5-oxadiazole-3-carboxamide

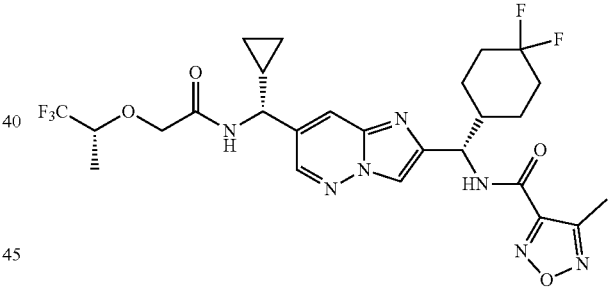

The title compound was prepared as described for the synthesis of Example 324, using (R)-2-((1,1,1-trifluoropropan-2-yl)oxy)acetic acid in place of (2,2,3,3-tetrafluorocyclobutyl)acetic acid, and running the reaction at rt for 15 h instead of 40° C. for 2.5 h. The crude material was purified by preparative HPLC (Welch Xtimate C18 150×30 mm, 5 μm column; 10-40% ACN/water (0.05% NH₄OH)) to afford the title compound. ¹H NMR (400 MHz, DMSO-d₆) δ 9.05 (d, J=9.2 Hz, 1H), 8.19 (d, J=2.0 Hz, 1H), 8.11 (d, J=7.6 Hz, 1H), 7.86 (s, 1H), 7.62 (s, 1H), 4.79 (t, J=8.4 Hz, 1H), 3.92-3.82 (m, 2H), 3.80 (s, 2H), 2.09 (s, 3H), 1.83-1.73 (m, 6H), 1.73-1.30 (m, 5H), 1.26-1.20 (m, 1H), 1.06-0.85 (m, 6H), 0.28-0.09 (m, 3H), 0.06-0.05 (m, 1H). MS (ESI) m/z: [M+H]⁺ Found 600.1.

Example 358

(1R*,2S*)—N—((S)-(7-((R*)-Cyclopropyl(4,4,4-trifluorobutanamido)methyl)imidazo[1,2-b]pyridazin-2-yl)(4,4-difluorocyclohexyl)methyl)-2-(difluoromethyl)cyclopropane-1-carboxamide

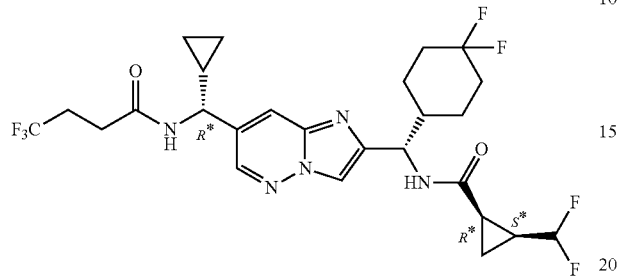

Example 359

(1S*,2R*)—N—((S)-(7-((R*)-Cyclopropyl(4,4,4-trifluorobutanamido)methyl)imidazo[1,2-b]pyridazin-2-yl)(4,4-difluorocyclohexyl)methyl)-2-(difluoromethyl)cyclopropane-1-carboxamide

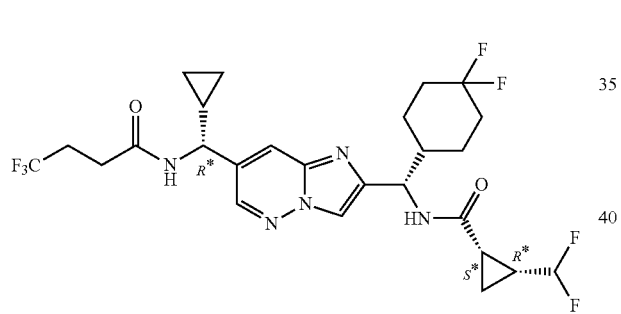

The title compounds were prepared as described for the synthesis of Example 4, using cis-2-(difluoromethyl)cyclopropane-1-carboxylic acid (Intermediate 293) in place of 2-((2,2-difluorocyclobutyl)methyl)-2H-1,2,3-triazole-4-carboxylic acid. The diastereomers were separated via SFC using a chiral stationary phase (Chiralpak® IA, 20:80 EtOH/CO$_2$). The first eluting isomer was Example 359, and the second eluting isomer was Example 358. Example 358: $^1$H NMR (500 MHz, CD$_3$OD) δ 8.45 (d, J=2.2 Hz, 1H), 7.94 (s, 1H), 7.85 (dd, J=2.1, 1.0 Hz, 1H), 5.74 (td, J=56.0, 7.7 Hz, 1H), 5.10 (d, J=7.4 Hz, 1H), 4.28 (d, J=9.5 Hz, 1H), 2.62-2.42 (m, 4H), 2.22-2.11 (m, 1H), 2.11-1.95 (m, 3H), 1.90-1.57 (m, 4H), 1.52-1.34 (m, 2H), 1.34-1.10 (m, 4H), 0.76-0.66 (m, 2H), 0.55-0.44 (m, 2H). MS (ESI) m/z: [M+H]$^+$ Found 578.2. Example 359: $^1$H NMR (500 MHz, CD$_3$OD) δ 8.45 (d, J=2.1 Hz, 1H), 8.01 (s, 1H), 7.85 (dd, J=2.0, 1.0 Hz, 1H), 5.85 (td, J=56.1, 7.7 Hz, 1H), 5.12 (d, J=7.6 Hz, 1H), 4.27 (d, J=9.5 Hz, 1H), 2.60-2.41 (m, 4H), 2.18-1.94 (m, 4H), 1.90-1.82 (m, 1H), 1.82-1.65 (m, 3H), 1.65-1.56 (m, 1H), 1.50-1.31 (m, 2H), 1.30-1.20 (m, 2H), 1.19-1.10 (m, 1H), 0.75-0.64 (m, 2H), 0.55-0.46 (m, 2H). MS (ESI) m/z: [M+H]$^+$ Found 578.3.

Example 360

(1S*,2S*)—N—((S)-(7-((R*)-Cyclopropyl(4,4,4-trifluorobutanamido)methyl)imidazo[1,2-b]pyridazin-2-yl)(4,4-difluorocyclohexyl)methyl)-2-(difluoromethyl)cyclopropane-1-carboxamide

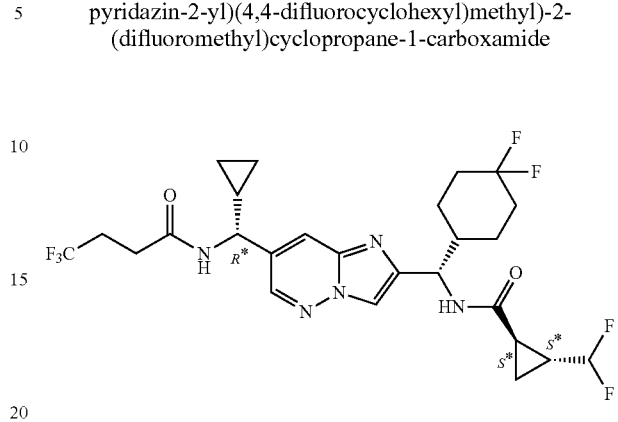

Example 361

(1R*,2R*)—N—((S)-(7-((R*)-Cyclopropyl(4,4,4-trifluorobutanamido)methyl)imidazo[1,2-b]pyridazin-2-yl)(4,4-difluorocyclohexyl)methyl)-2-(difluoromethyl)cyclopropane-1-carboxamide

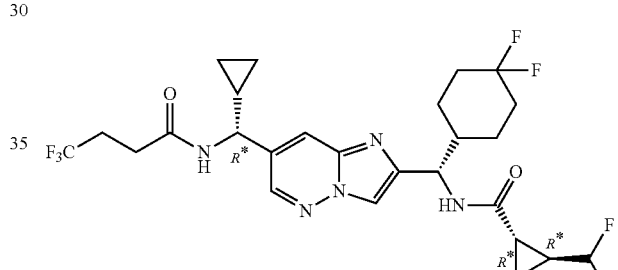

The title compounds were prepared as described for the synthesis of Example 4, using trans-2-(difluoromethyl)cyclopropane-1-carboxylic acid (Intermediate 298) in place of 2-((2,2-difluorocyclobutyl)methyl)-2H-1,2,3-triazole-4-carboxylic acid. The diastereomers were separated via SFC using a chiral stationary phase (Chiralpak® IA, 15:85 EtOH/CO$_2$). The first eluting isomer was Example 360, and the second eluting isomer was Example 361. Example 360: $^1$H NMR (600 MHz, CD$_3$OD) δ 8.45 (d, J=2.1 Hz, 1H), 7.99 (s, 1H), 7.85 (dd, J=2.0, 1.0 Hz, 1H), 5.79 (td, J=57.1, 4.2 Hz, 1H), 5.08 (d, J=7.8 Hz, 1H), 4.27 (d, J=9.5 Hz, 1H), 2.61-2.55 (m, 2H), 2.55-2.45 (m, 2H), 2.18-2.05 (m, 2H), 2.05-1.96 (m, 2H), 1.92-1.67 (m, 4H), 1.66-1.58 (m, 1H), 1.51-1.41 (m, 1H), 1.39-1.31 (m, 1H), 1.31-1.21 (m, 1H), 1.16-1.09 (m, 1H), 1.07-0.98 (m, 1H), 0.75-0.65 (m, 2H), 0.55-0.45 (m, 2H). MS (ESI) m/z: [M+H]$^+$ Found 578.3. Example 361: $^1$H NMR (600 MHz, CD$_3$OD) δ 8.45 (d, J=2.1 Hz, 1H), 7.99 (s, 1H), 7.85 (dd, J=2.0, 1.0 Hz, 1H), 5.79 (td, J=57.1, 4.2 Hz, 1H), 5.08 (d, J=7.8 Hz, 1H), 4.27 (d, J=9.5 Hz, 1H), 2.61-2.55 (m, 2H), 2.55-2.45 (m, 2H), 2.18-2.05 (m, 2H), 2.05-1.96 (m, 2H), 1.92-1.67 (m, 4H), 1.66-1.58 (m, 1H), 1.51-1.41 (m, 1H), 1.39-1.31 (m, 1H), 1.31-1.21 (m, 1H), 1.16-1.09 (m, 1H), 1.07-0.98 (m, 1H), 0.75-0.65 (m, 2H), 0.55-0.45 (m, 2H). MS (ESI) m/z: [M+H]$^+$ Found 578.3.

Example 362

(1R*,2R*)—N—((S)-(7-((R*)-Cyclopropyl(4,4,4-trifluorobutanamido)methyl)imidazo[1,2-b]pyridazin-2-yl)(4,4-difluorocyclohexyl)methyl)-2-(fluoromethyl)cyclopropane-1-carboxamide

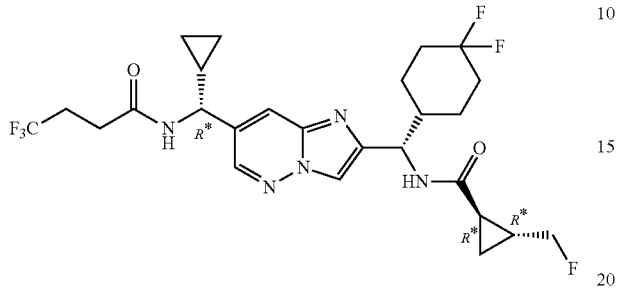

Example 363

(1S*,2S*)—N—((S)-(7-((R*)-Cyclopropyl(4,4,4-trifluorobutanamido)methyl)imidazo[1,2-b]pyridazin-2-yl)(4,4-difluorocyclohexyl)methyl)-2-(fluoromethyl)cyclopropane-1-carboxamide

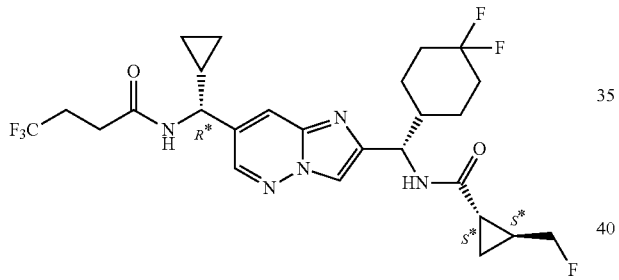

The title compounds were prepared as described for the synthesis of Example 4, using trans-2-(fluoromethyl)cyclopropane-1-carboxylic acid (Intermediate 302) in place of 2-((2,2-difluorocyclobutyl)methyl)-2H-1,2,3-triazole-4-carboxylic acid. The diastereomers were separated via SFC using a chiral stationary phase (Chiralpak® AD-H, 20:80 MeOH/CO$_2$). The first eluting isomer was Example 362, and the second eluting isomer was Example 363. Example 362: $^1$H NMR (600 MHz, CD$_3$OD) δ 8.45 (d, J=2.1 Hz, 1H), 7.99 (s, 1H), 7.85 (dd, J=2.0, 1.0 Hz, 1H), 5.08 (d, J=7.7 Hz, 1H), 4.44 (ddd, J=48.6, 9.9, 6.1 Hz, 1H), 4.32-4.26 (m, 1H), 4.19 (ddd, J=47.9, 9.9, 7.5 Hz, 1H), 2.63-2.43 (m, 4H), 2.17-1.96 (m, 3H), 1.92-1.83 (m, 1H), 1.83-1.66 (m, 4H), 1.65-1.57 (m, 1H), 1.50-1.40 (m, 1H), 1.40-1.30 (m, 1H), 1.30-1.20 (m, 1H), 1.14-1.06 (m, 1H), 0.86-0.78 (m, 1H), 0.75-0.66 (m, 2H), 0.55-0.45 (m, 2H). MS (ESI) m/z: [M+H]$^+$ Found 560.3. Example 363: $^1$H NMR (500 MHz, CD$_3$OD) δ 8.45 (d, J=2.1 Hz, 1H), 7.99 (s, 1H), 7.85 (dd, J=2.0, 1.0 Hz, 1H), 5.08 (d, J=7.8 Hz, 1H), 4.56-4.36 (m, 1H), 4.34-4.08 (m, 2H), 2.62-2.42 (m, 4H), 2.18-1.94 (m, 3H), 1.91-1.84 (m, 1H), 1.84-1.66 (m, 4H), 1.66-1.57 (m, 1H), 1.51-1.41 (m, 1H), 1.41-1.30 (m, 1H), 1.30-1.20 (m, 1H), 1.14-1.06 (m, 1H), 0.87-0.79 (m, 1H), 0.75-0.65 (m, 2H), 0.55-0.44 (m, 2H). MS (ESI) m/z: [M+H]$^+$ Found 560.3.

Example 364

(1S*,2R*)—N—((S)-(7-((R*)-Cyclopropyl(4,4,4-trifluorobutanamido)methyl)imidazo[1,2-b]pyridazin-2-yl)(4,4-difluorocyclohexyl)methyl)-2-(fluoromethyl)cyclopropane-1-carboxamide

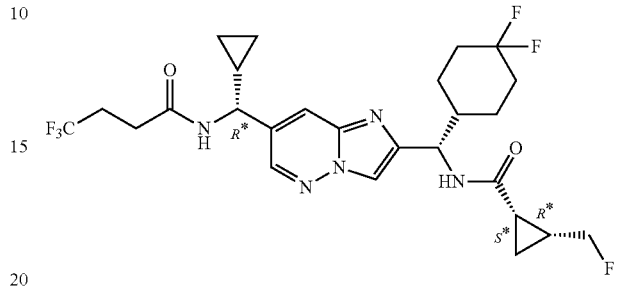

Example 365

(1R*,2S*)—N—((S)-(7-((R*)-Cyclopropyl(4,4,4-trifluorobutanamido)methyl)imidazo[1,2-b]pyridazin-2-yl)(4,4-difluorocyclohexyl)methyl)-2-(fluoromethyl)cyclopropane-1-carboxamide

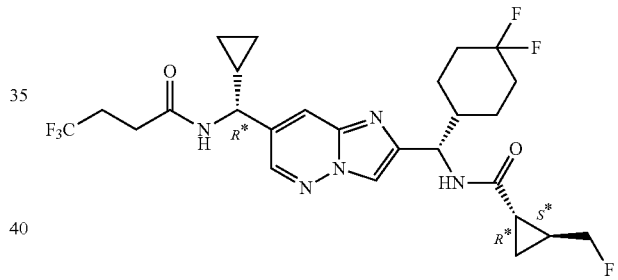

The title compounds were prepared as described for the synthesis of Example 4, using cis-2-(fluoromethyl)cyclopropane-1-carboxylic acid (Intermediate 300) in place of 2-((2,2-difluorocyclobutyl)methyl)-2H-1,2,3-triazole-4-carboxylic acid. The diastereomers were separated via SFC using a chiral stationary phase (Chiralpak® AD-H, 20:80 EtOH/CO$_2$). The first eluting isomer was Example 364, and the second eluting isomer was Example 365. Example 364: H NMR (500 MHz, CD$_3$OD) δ 8.45 (d, J=2.1 Hz, 1H), 8.01 (d, J=0.6 Hz, 1H), 7.85 (dd, J=2.0, 1.0 Hz, 1H), 5.12 (d, J=7.7 Hz, 1H), 4.79-4.60 (m, 1H), 4.53-4.35 (m, 1H), 4.27 (d, J=9.5 Hz, 1H), 2.61-2.41 (m, 4H), 2.17-1.91 (m, 4H), 1.90-1.81 (m, 1H), 1.81-1.65 (m, 3H), 1.65-1.56 (m, 1H), 1.50-1.31 (m, 2H), 1.31-1.21 (m, 1H), 1.10-1.00 (m, 2H), 0.77-0.63 (m, 2H), 0.55-0.40 (m, 2H). MS (ESI) m/z: [M+H]$^+$ Found 560.3. Example 365: $^1$H NMR (500 MHz, CD$_3$OD) δ 8.44 (d, J=2.1 Hz, 1H), 7.95 (d, J=0.7 Hz, 1H), 7.88-7.80 (m, 1H), 5.12 (d, J=7.0 Hz, 1H), 4.72-4.50 (m, 1H), 4.42-4.21 (m, 2H), 2.61-2.42 (m, 4H), 2.23-2.12 (m, 1H), 2.12-1.95 (m, 3H), 1.88-1.61 (m, 5H), 1.52-1.35 (m, 2H), 1.33-1.21 (m, 1H), 1.13-1.04 (m, 2H), 0.75-0.66 (m, 2H), 0.54-0.46 (m, 2H). MS (ESI) m/z: [M+H]$^+$ Found 560.3.

Example 366

(R*)—N—((S)-(7-((R*)-Cyclopropyl(4,4,4-trifluorobutanamido)methyl)imidazo[1,2-b]pyridazin-2-yl)(4,4-difluorocyclohexyl)methyl)spiro[2.3]hexane-1-carboxamide

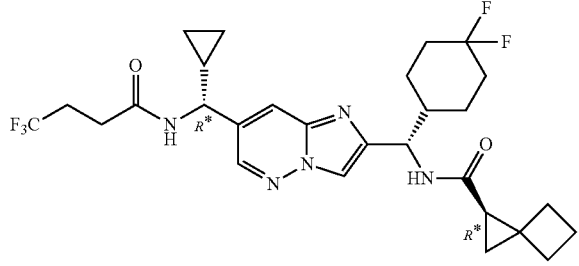 [SMILES: O=C(CCC(F)(F)F)N[C@@H](c1cnn2cc([C@@H](NC(=O)[C@@H]3CC34CCC4)C3CCC(F)(F)CC3)nc2c1)C1CC1]

Example 367

(S*)—N—((S)-(7-((R*)-Cyclopropyl(4,4,4-trifluorobutanamido)methyl)imidazo[1,2-b]pyridazin-2-yl)(4,4-difluorocyclohexyl)methyl)spiro[2.3]hexane-1-carboxamide

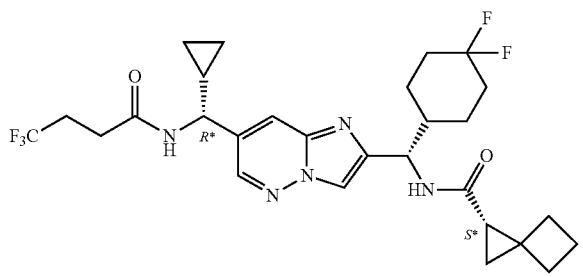 [SMILES: O=C(CCC(F)(F)F)N[C@@H](c1cnn2cc([C@@H](NC(=O)[C@H]3CC34CCC4)C3CCC(F)(F)CC3)nc2c1)C1CC1]

The title compounds were prepared as described for the synthesis of Example 4, using spiro[2.3]hexane-1-carboxylic acid in place of 2-((2,2-difluorocyclobutyl)methyl)-2H-1,2,3-triazole-4-carboxylic acid. The diastereomers were separated via SFC using a chiral stationary phase (Chiralpak® IA, 20:80 EtOH/CO$_2$). The first eluting isomer was Example 366, and the second eluting isomer was Example 367. Example 366: $^1$H NMR (600 MHz, CD$_3$OD) δ 8.45 (d, J=2.1 Hz, 1H), 7.99 (d, J=0.7 Hz, 1H), 7.90-7.80 (m, 1H), 5.13 (d, J=7.4 Hz, 1H), 4.35-4.18 (m, 1H), 2.60-2.53 (m, 2H), 2.53-2.44 (m, 2H), 2.29-2.20 (m, 1H), 2.19-1.97 (m, 8H), 1.91-1.83 (m, 1H), 1.84-1.69 (m, 2H), 1.69-1.61 (m, 2H), 1.53-1.43 (m, 1H), 1.43-1.34 (m, 1H), 1.31-1.21 (m, 1H), 1.14-1.08 (m, 1H), 0.89 (dd, J=8.3, 4.6 Hz, 1H), 0.74-0.64 (m, 2H), 0.55-0.45 (m, 2H). MS (ESI) m/z: [M+H]$^+$ Found 568.2. Example 367: $^1$H NMR (600 MHz, CD$_3$OD) δ 8.46 (d, J=2.1 Hz, 1H), 8.00 (d, J=0.6 Hz, 1H), 7.92-7.82 (m, 1H), 5.10 (d, J=7.6 Hz, 1H), 4.28 (dd, J=9.5, 0.9 Hz, 1H), 2.61-2.54 (m, 2H), 2.54-2.45 (m, 2H), 2.25-2.17 (m, 1H), 2.16-1.95 (m, 7H), 1.95-1.88 (m, 1H), 1.88-1.82 (m, 1H), 1.82-1.68 (m, 2H), 1.66 (dd, J=8.3, 5.4 Hz, 1H), 1.64-1.58 (m, 1H), 1.49-1.39 (m, 1H), 1.39-1.30 (m, 1H), 1.30-1.21 (m, 1H), 1.16-1.12 (m, 1H), 0.92 (dd, J=8.3, 4.5 Hz, 1H), 0.75-0.66 (m, 2H), 0.54-0.45 (m, 2H). MS (ESI) m/z: [M+H]$^+$ Found 568.2.

Example 368

(S*)—N—((S)-(7-((R*)-Cyclopropyl(4,4,4-trifluorobutanamido)methyl)imidazo[1,2-b]pyridazin-2-yl)(4,4-difluorocyclohexyl)methyl)-2,2-difluorospiro[2.3]hexane-1-carboxamide

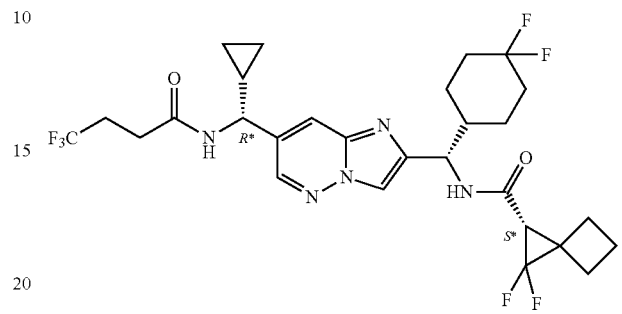

Example 369

(R*)—N—((S)-(7-((R*)-Cyclopropyl(4,4,4-trifluorobutanamido)methyl)imidazo[1,2-b]pyridazin-2-yl)(4,4-difluorocyclohexyl)methyl)-2,2-difluorospiro[2.3]hexane-1-carboxamide

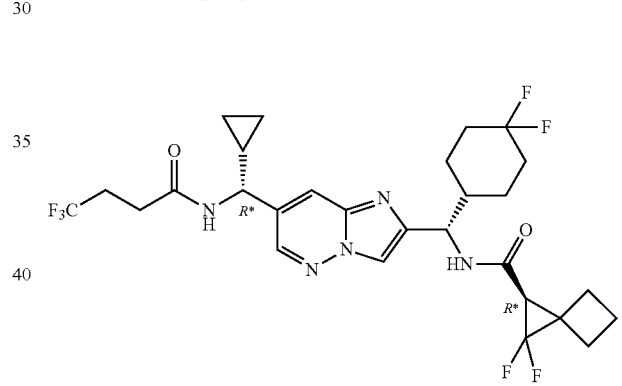

The title compounds were prepared as described for the synthesis of Example 4, using 2,2-difluorospiro[2.3]hexane-1-carboxylic acid in place of 2-((2,2-difluorocyclobutyl)methyl)-2H-1,2,3-triazole-4-carboxylic acid. The diastereomers were separated via SFC using a chiral stationary phase (Chiralpak® AD-H, 20:80 MeOH/CO$_2$). The first eluting isomer was Example 368, and the second eluting isomer was Example 369. Example 368: $^1$H NMR (500 MHz, CD$_3$OD) δ 8.45 (d, J=2.1 Hz, 1H), 7.98 (m, 1H), 7.85 (m, 1H), 5.09 (d, J=7.5 Hz, 1H), 4.33-4.22 (m, 1H), 2.61-2.40 (m, 5H), 2.37-2.24 (m, 4H), 2.17-1.95 (m, 5H), 1.90-1.68 (m, 3H), 1.68-1.58 (m, 1H), 1.52-1.31 (m, 2H), 1.31-1.21 (m, 1H), 0.74-0.66 (m, 2H), 0.53-0.47 (m, 2H). MS (ESI) m/z: [M+H]$^+$ Found 604.2. Example 369: $^1$H NMR (500 MHz, CD$_3$OD) δ 8.46 (d, J=2.1 Hz, 1H), 8.02 (s, 1H), 7.86 (dd, J=2.0, 1.0 Hz, 1H), 5.09 (d, J=7.6 Hz, 1H), 4.35-4.19 (m, 1H), 2.61-2.45 (m, 4H), 2.44-2.35 (m, 1H), 2.33-2.19 (m, 4H), 2.15-1.95 (m, 5H), 1.90-1.81 (m, 1H), 1.81-1.65 (m, 2H), 1.65-1.57 (m, 1H), 1.49-1.30 (m, 2H), 1.30-1.21 (m, 1H), 0.76-0.64 (m, 2H), 0.55-0.45 (m, 2H). MS (ESI) m/z: [M+H]$^+$ Found 604.2.

Example 370

4-Amino-N—((S)-(7-((R)-cyclopropyl(4,4,4-trifluorobutanamido)methyl)imidazo[1,2-b]pyridazin-2-yl)(4,4-difluorocyclohexyl)methyl)-1,2,5-oxadiazole-3-carboxamide

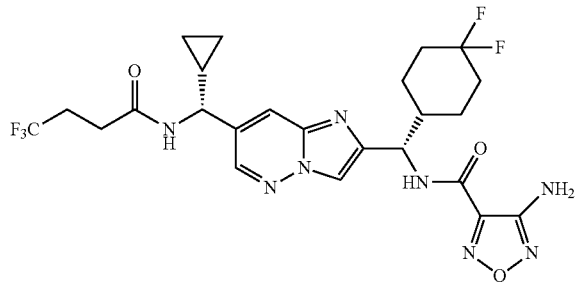 [SMILES: Nc1nonc1C(=O)N[C@H](c1cn2ncc([C@H](NC(=O)CCC(F)(F)F)C3CC3)cc2n1)C1CCC(F)(F)CC1]

A round bottom flask was charged with (E)-2-(((S)-(7-((R)-cyclopropyl(4,4,4-trifluorobutanamido)methyl)imidazo[1,2-b]pyridazin-2-yl)(4,4-difluorocyclohexyl)methyl)amino)-N-hydroxy-2-oxoacetimidoyl cyanide (290 mg, 0.53 mmol, Intermediate 323) and THF (2.1 mL). 50% Aqueous hydroxylamine (42 µL, 0.69 mmol) was added and the mixture was heated at 35° C. until complete consumption of starting material. At that time, the reaction was cooled to rt and CDI (130 mg, 0.80 mmol) was added portion-wise as a solid. Upon complete consumption of the previously formed intermediate the reaction mixture was concentrated under reduced pressure and purified directly by preparative basic HPLC (XBridge Prep OBD, 5 µm C18, 10-100% acetonitrile/water (with 20 mM $NH_4OH$). The product containing fractions were lyophilized to afford the title compound as a white powder. $^1$H NMR (500 MHz, DMSO-$d_6$) δ 9.32 (d, J=8.9 Hz, 1H), 8.71 (d, J=7.6 Hz, 1H), 8.50 (d, J=2.1 Hz, 1H), 8.23 (s, 1H), 7.95 (d, J=2.0 Hz, 1H), 6.32 (s, 2H), 5.13 (t, J=8.7 Hz, 1H), 4.29 (t, J=8.4 Hz, 1H), 2.49-2.42 (m, 4H), 2.25-2.12 (m, 1H), 2.09-1.83 (m, 3H), 1.83-1.67 (m, 2H), 1.63-1.52 (m, 1H), 1.45-1.32 (m, 1H), 1.29-1.14 (m, 2H), 0.61-0.44 (m, 3H), 0.40-0.30 (m, 1H). MS (ESI): m/z: [M+H]$^+$ Found 571.2.

Example 371

N—((S)-(7-((R)-Cyclopropyl(4,4,4-trifluorobutanamido)methyl)imidazo[1,2-b]pyridazin-2-yl)(4,4-difluorocyclohexyl)methyl)-4-(2-hydroxypropan-2-yl)-1,2,5-oxadiazole-3-carboxamide

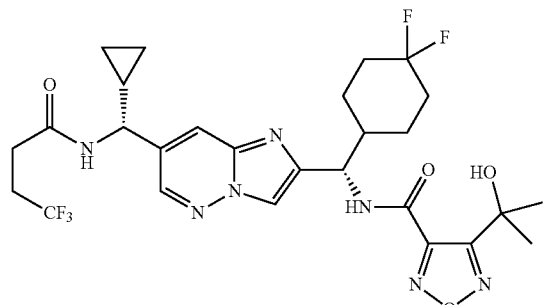

The title compound was prepared as described for the synthesis of Intermediate 359, using 6,6-dimethyl-4H,6H-furo[3,4-c][1,2,5]oxadiazol-4-one (Intermediate 350) in place of 4H,6H-furo[3,4-c][1,2,5]oxadiazol-4-one. $^1$H NMR (400 MHz, DMSO-$d_6$) δ 9.64 (d, J=9.0 Hz, 1H), 8.71 (d, J=7.7 Hz, 1H), 8.51 (d, J=2.1 Hz, 1H), 8.18 (s, 1H), 8.02-7.82 (m, 1H), 6.04 (s, 1H), 5.23 (d, J=8.9 Hz, 1H), 4.30 (d, J=8.4 Hz, 1H), 2.57-2.51 (m, 1H), 2.49-2.40 (m, 2H), 2.26-2.11 (m, 1H), 2.09-1.94 (m, 2H), 1.89-1.61 (m, 4H), 1.60-1.48 (m, 7H), 1.48-1.26 (m, 2H), 1.26-1.14 (m, 1H), 0.63-0.46 (m, 3H), 0.42-0.31 (m, 1H). MS (ESI) m/z: [M+H]$^+$ Found 614.3.

Example 372

N—((S)-(7-((R)-Cyclopropyl(4,4,4-trifluorobutanamido)methyl)imidazo[1,2-b]pyridazin-2-yl)(4,4-difluorocyclohexyl)methyl)-4-methoxyisoxazole-3-carboxamide

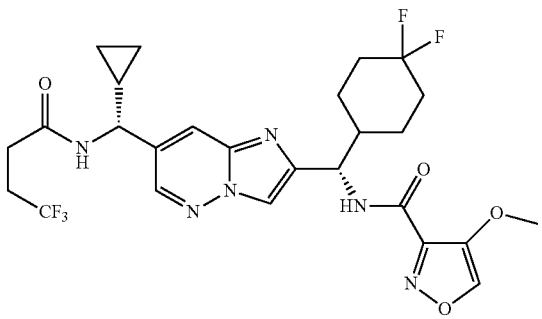 [SMILES: COc1conc1C(=O)N[C@H](c1cn2ncc([C@H](NC(=O)CCC(F)(F)F)C3CC3)cc2n1)C1CCC(F)(F)CC1]

The title compound was prepared as described for the synthesis of Example 32, using 4-methoxyisoxazole-3-carboxylic acid (Intermediate 307) in place of 2-(3,3-difluoropropyl)-2H-1,2,3-triazole-4-carboxylic acid to afford the title compound as an off-white powder. $^1$H NMR (500 MHz, DMSO-$d_6$) δ 8.93 (d, J=0.6 Hz, 1H), 8.81 (d, J=9.1 Hz, 1H), 8.71 (d, J=7.7 Hz, 1H), 8.51 (d, J=2.1 Hz, 1H), 8.19 (s, 1H), 7.97-7.93 (m, 1H), 5.16 (t, J=8.2 Hz, 1H), 4.29 (t, J=8.4 Hz, 1H), 3.79 (s, 3H), 2.55-2.52 (m, 1H), 2.48-2.42 (m, 4H), 2.17-2.07 (m, 1H), 2.07-1.94 (m, 2H), 1.89-1.67 (m, 2H), 1.67-1.54 (m, 1H), 1.41-1.30 (m, 1H), 1.31-1.23 (m, 1H), 1.23-1.18 (m, 1H), 0.64-0.46 (m, 3H), 0.43-0.31 (m, 1H). MS (ESI) m/z: [M+H]$^+$ Found 585.2.

Example 373

N—((S)-(7-((R)-Cyclopropyl(4,4,4-trifluorobutana-mido)methyl)imidazo[1,2-b]pyridazin-2-yl)(4,4-difluorocyclohexyl)methyl)-4-ethoxyisoxazole-3-carboxamide

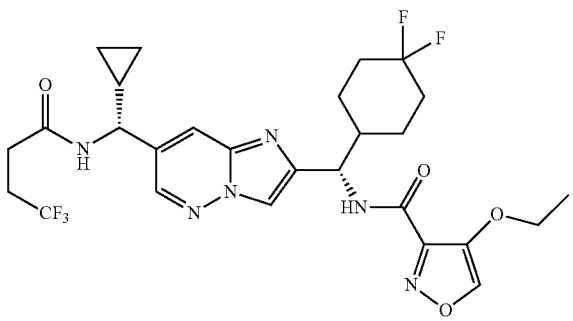 [SMILES: CCOc1conc1C(=O)N[C@H](c1cn2ncc([C@H](NC(=O)CCC(F)(F)F)C3CC3)cc2n1)C1CCC(F)(F)CC1]

The title compound was prepared as described for the synthesis of Example 32, using 4-ethoxyisoxazole-3-carboxylic acid (Intermediate 308) in place of 2-(3,3-difluoropropyl)-2H-1,2,3-triazole-4-carboxylic acid to afford the title compound as an off-white powder. $^1$H NMR (600 MHz, DMSO-$d_6$) δ 8.93 (s, 1H), 8.76 (d, J=9.0 Hz, 1H), 8.72 (d, J=7.7 Hz, 1H), 8.51 (d, J=2.1 Hz, 1H), 8.20 (s, 1H), 8.01-7.85 (m, 1H), 5.18 (dd, J=8.9, 7.3 Hz, 1H), 4.29 (t, J=8.4 Hz, 1H), 4.02 (qd, J=7.0, 2.4 Hz, 2H), 2.51 (s, 1H), 2.49-2.42 (m, 3H), 2.16-2.07 (m, 1H), 2.07-1.93 (m, 1H), 1.87-1.78 (m, 2H), 1.78-1.68 (m, 2H), 1.67-1.58 (m, 1H), 1.42-1.35 (m, 1H), 1.33 (t, J=7.0 Hz, 3H), 1.32-1.25 (m, 1H), 1.25-1.14 (m, 1H), 0.62-0.55 (m, 1H), 0.55-0.47 (m, 2H), 0.41-0.34 (m, 1H). MS (ESI) m/z: [M+H]$^+$ Found 598.6.

Example 374

N—((S)-(7-((R)-Cyclopropyl(4,4,4-trifluorobutana-mido)methyl)imidazo[1,2-b]pyridazin-2-yl)(4,4-difluorocyclohexyl)methyl)-4-isopropoxyisoxazole-3-carboxamide

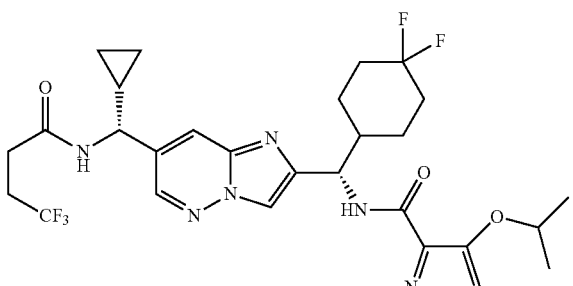

The title compound was prepared as described for the synthesis of Example 32, using 4-isopropoxyisoxazole-3-carboxylic acid (Intermediate 309) in place of 2-(3,3-difluoropropyl)-2H-1,2,3-triazole-4-carboxylic acid to afford the title compound as an off-white powder. $^1$H NMR (600 MHz, DMSO-$d_6$) δ 8.98 (s, 1H), 8.72 (dd, J=8.3, 5.5 Hz, 2H), 8.52 (d, J=2.1 Hz, 1H), 8.20 (t, J=0.6 Hz, 1H), 7.93 (dd, J=2.1, 0.8 Hz, 1H), 5.20 (dd, J=8.9, 7.1 Hz, 1H), 4.35-4.25 (m, 2H), 2.49-2.42 (m, 4H), 2.17-2.06 (m, 1H), 2.05-1.93 (m, 2H), 1.85-1.78 (m, 2H), 1.78-1.70 (m, 1H), 1.64 (d, J=13.8 Hz, 1H), 1.42-1.32 (m, 1H), 1.30 (d, J=6.1 Hz, 3H), 1.27 (d, J=6.1 Hz, 3H), 1.26-1.11 (m, 2H), 0.61-0.47 (m, 3H), 0.38 (dq, J=9.8, 4.8 Hz, 1H). MS (ESI) m/z: [M+H]$^+$ Found 613.3.

Example 375

N—((S)-(7-((R)-Cyclopropyl(4,4,4-trifluorobutana-mido)methyl)imidazo[1,2-b]pyridazin-2-yl)(4,4-difluorocyclohexyl)methyl)-4-(2,2-difluoroethoxy)isoxazole-3-carboxamide

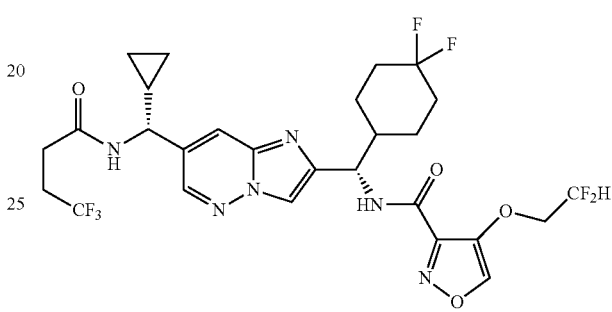

The title compound was prepared as described for the synthesis of Example 32, using 4-(2,2-difluoroethoxy)isoxazole-3-carboxylic acid (Intermediate 311) in place of 2-(3,3-difluoropropyl)-2H-1,2,3-triazole-4-carboxylic acid to afford the title compound as an off-white powder. $^1$H NMR (600 MHz, DMSO-$d_6$) δ 9.04 (s, 1H), 8.90 (d, J=9.0 Hz, 1H), 8.72 (d, J=7.7 Hz, 1H), 8.51 (d, J=2.1 Hz, 1H), 8.18 (d, J=0.6 Hz, 1H), 7.94 (dt, J=1.6, 0.7 Hz, 1H), 6.36 (tt, J=54.2, 3.5 Hz, 1H), 5.20-5.11 (m, 1H), 4.41-4.26 (m, 3H), 2.51 (s, 1H), 2.49-2.39 (m, 3H), 2.23-2.08 (m, 1H), 2.07-1.93 (m, 2H), 1.85 (d, J=13.3 Hz, 1H), 1.82-1.69 (m, 2H), 1.61 (d, J=13.7 Hz, 1H), 1.45-1.31 (m, 1H), 1.31-1.23 (m, 1H), 1.20 (tq, J=8.6, 4.6 Hz, 1H), 0.62-0.46 (m, 3H), 0.38 (dq, J=9.6, 4.8 Hz, 1H). MS (ESI) m/z: [M+H]$^+$ Found 635.2.

Example 376

N—((S)-(7-((R)-Cyclopropyl(4,4,4-trifluorobutana-mido)methyl)imidazo[1,2-b]pyridazin-2-yl)(4,4-difluorocyclohexyl)methyl)-4-(2-fluoroethoxy)isoxazole-3-carboxamide

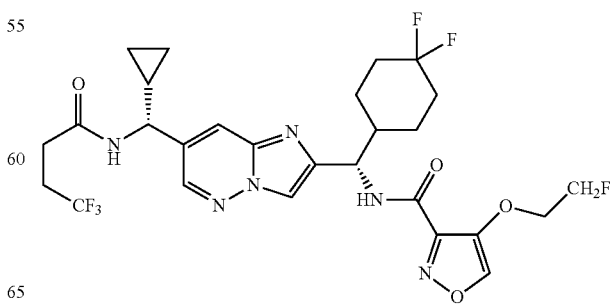

The title compound was prepared as described for the synthesis of Example 32, using 4-(2-fluoroethoxy)isoxazole-3-carboxylic acid (Intermediate 310) in place of 2-(3,3-difluoropropyl)-2H-1,2,3-triazole-4-carboxylic acid to afford the title compound as an off-white powder. $^1$H NMR (600 MHz, DMSO-$d_6$) δ 8.99 (s, 1H), 8.85 (d, J=9.0 Hz, 1H), 8.72 (d, J=7.7 Hz, 1H), 8.52 (d, J=2.1 Hz, 1H), 8.20 (d, J=0.7 Hz, 1H), 7.95 (dd, J=1.9, 1.0 Hz, 1H), 5.21-5.14 (m, 1H), 4.79-4.74 (m, 1H), 4.74-4.65 (m, 1H), 4.30 (t, J=8.4 Hz, 1H), 4.28-4.25 (m, 1H), 4.24-4.21 (m, 1H), 2.55-2.52 (m, 1H), 2.49-2.46 (m, 3H), 2.17-2.09 (m, 1H), 2.07-1.93 (m, 2H), 1.89-1.81 (m, 1H), 1.81-1.70 (m, 2H), 1.67-1.61 (m, 1H), 1.43-1.33 (m, 1H), 1.33-1.24 (m, 1H), 1.24-1.15 (m, 1H), 0.62-0.47 (m, 3H), 0.38 (dq, J=9.5, 4.8 Hz, 1H). MS (ESI) m/z: [M+H]$^+$ Found 617.2.

Example 377

N—((S)-(7-((R)-Cyclopropyl(4,4,4-trifluorobutanamido)methyl)imidazo[1,2-b]pyridazin-2-yl)(4,4-difluorocyclohexyl)methyl)-4-(2,2,2-trifluoroethyl)isoxazole-3-carboxamide

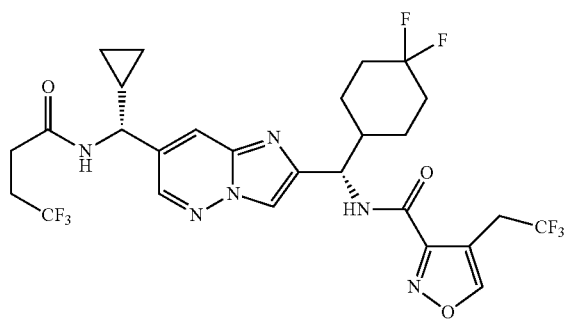 [SMILES: O=C(CCC(F)(F)F)N[C@@H](c1cnn2cc([C@@H](NC(=O)c3nocc3CC(F)(F)F)C3CCC(F)(F)CC3)nc2c1)C1CC1]

The title compound was prepared as described for the synthesis of Example 32, using 4-(2,2,2-trifluoroethyl)isoxazole-3-carboxylic acid (Intermediate 317) in place of 2-(3,3-difluoropropyl)-2H-1,2,3-triazole-4-carboxylic acid to afford the title compound as an off-white powder. $^1$H NMR (500 MHz, DMSO-$d_6$) δ 9.16 (s, 1H), 9.14 (d, J=9.1 Hz, 1H), 8.71 (d, J=7.7 Hz, 1H), 8.50 (d, J=2.1 Hz, 1H), 8.19 (s, 1H), 7.95 (dt, J=1.8, 0.8 Hz, 1H), 5.16 (t, J=8.6 Hz, 1H), 4.29 (t, J=8.4 Hz, 1H), 3.82-3.71 (m, 2H), 2.48-2.42 (m, 4H), 2.23-2.10 (m, 1H), 2.08-1.91 (m, 2H), 1.89-1.67 (m, 3H), 1.60 (d, J=13.6 Hz, 1H), 1.44-1.30 (m, 1H), 1.30-1.13 (m, 2H), 0.62-0.43 (m, 3H), 0.41-0.33 (m, 1H). MS (ESI) m/z: [M+H]$^+$ Found 637.2.

Example 378

N—((S)-(7-((R)-Cyclopropyl(4,4,4-trifluorobutanamido)methyl)imidazo[1,2-b]pyridazin-2-yl)(4,4-difluorocyclohexyl)methyl)-4-isopropylisoxazole-3-carboxamide

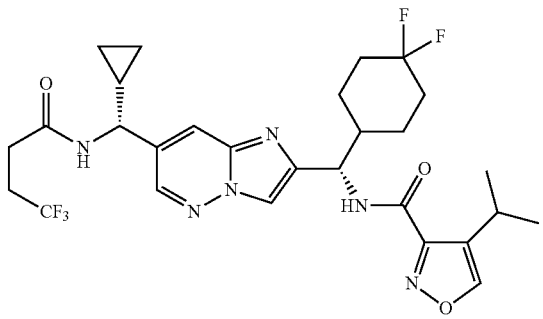 [SMILES: CC(C)c1conc1C(=O)N[C@H](c1cn2ncc([C@H](NC(=O)CCC(F)(F)F)C3CC3)cc2n1)C1CCC(F)(F)CC1]

The title compound was prepared as described for the synthesis of Example 32, using 4-isopropylisoxazole-3-carboxylic acid (Intermediate 318) in place of 2-(3,3-difluoropropyl)-2H-1,2,3-triazole-4-carboxylic acid to afford the title compound as an off-white powder. $^1$H NMR (500 MHz, DMSO-$d_6$) δ 8.91 (d, J=9.1 Hz, 1H), 8.78 (d, J=0.9 Hz, 1H), 8.65 (d, J=7.6 Hz, 1H), 8.43 (d, J=2.1 Hz, 1H), 8.12 (s, 1H), 7.88 (d, J=2.0 Hz, 1H), 5.11 (t, J=8.5 Hz, 1H), 4.23 (t, J=8.4 Hz, 1H), 3.01-2.91 (m, 1H), 2.42-2.36 (m, 4H), 2.13-2.03 (m, 1H), 1.99-1.85 (m, 2H), 1.84-1.62 (m, 3H), 1.66-1.55 (m, 1H), 1.43-1.32 (m, 1H), 1.31-1.17 (m, 1H), 1.16 (d, J=6.9 Hz, 3H), 1.13 (d, J=6.9 Hz, 3H), 0.56-0.39 (m, 3H), 0.42-0.32 (m, 1H). MS (ESI) m/z: [M+H]$^+$ Found 597.3.

Example 379

N—((S)-(7-((R)-Cyclopropyl(4,4,4-trifluorobutanamido)methyl)imidazo[1,2-b]pyridazin-2-yl)(4,4-difluorocyclohexyl)methyl)-4-isopropyl-1,2,5-oxadiazole-3-carboxamide

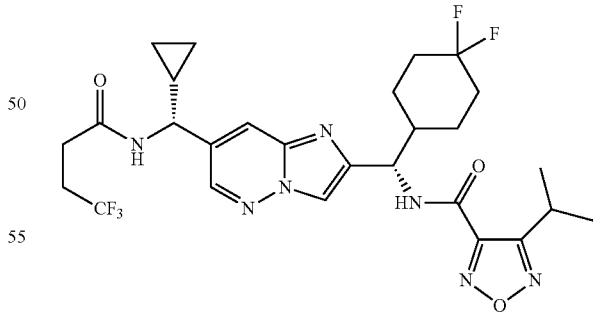

Trimethyl phosphite (0.85 mL, 7.2 mmol) was added to a solution of 4-(((S)-(7-((R)-cyclopropyl(4,4,4-trifluorobutanamido)methyl)imidazo[1,2-b]pyridazin-2-yl)(4,4-difluorocyclohexyl)methyl)carbamoyl)-3-isopropyl-1,2,5-oxadiazole 2-oxide (220 mg, 0.36 mmol, Intermediate 360) in toluene (1.8 mL). The reaction was then heated to 120° C. overnight, after which time the reaction mixture was cooled to rt and diluted with 1 M aqueous HCl (20 mL). The biphasic mixture was separated and extracted with EtOAc (3×15 mL). The combined organic layers were washed with brine, dried over anhydrous MgSO₄, filtered, and concentrated to afford the crude product. Purification by silica gel chromatography (0-100% EtOAc (10% MeOH)/hexanes) provided the title compound as an off-white solid. ¹H NMR (500 MHz, DMSO-d₆) δ 9.48 (d, J=8.9 Hz, 1H), 8.71 (d, J=7.6 Hz, 1H), 8.51 (d, J=2.0 Hz, 1H), 8.20 (s, 1H), 7.97-7.85 (m, 1H), 5.18 (t, J=8.5 Hz, 1H), 4.29 (t, J=8.4 Hz, 1H), 3.37-3.31 (m, 1H), 2.55-2.51 (m, 1H), 2.49-2.42 (m, 3H), 2.23-2.11 (m, 1H), 2.10-1.92 (m, 2H), 1.91-1.69 (m, 3H), 1.62 (d, J=13.5 Hz, 1H), 1.45-1.33 (m, 1H), 1.33-1.24 (m, 7H), 1.23-1.16 (m, 1H), 0.62-0.55 (m, 1H), 0.55-0.47 (m, 2H), 0.41-0.35 (m, 1H). MS (ESI) m/z: [M+H]⁺ Found 598.3.

Example 380

4-Cyclopropoxy-N—((S)-(7-((R)-cyclopropyl(4,4,4-trifluorobutanamido)methyl)imidazo[1,2-b]pyridazin-2-yl)(4,4-difluorocyclohexyl)methyl)-1,2,5-oxadiazole-3-carboxamide

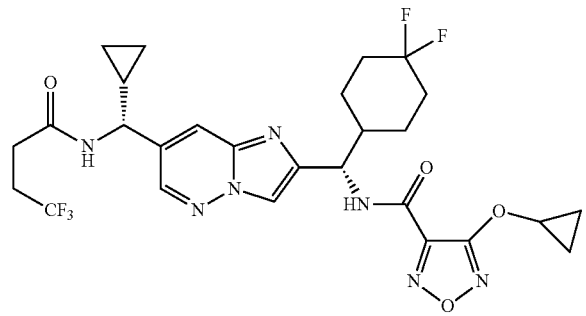 [SMILES: O=C(CCC(F)(F)F)N[C@@H](c1cnn2cc([C@@H](NC(=O)c3nonc3OC3CC3)C3CCC(F)(F)CC3)nc2c1)C1CC1]

The title compound was prepared as described for the synthesis of Intermediate 325, using cyclopropanol in place of 2,2,2-trifluoroethanol and 4-chloro-N—((S)-(7-((R)-cyclopropyl(4,4,4-trifluorobutanamido)methyl)imidazo[1,2-b]pyridazin-2-yl)(4,4-difluorocyclohexyl)methyl)-1,2,5-oxadiazole-3-carboxamide (Intermediate 324) in place of 4-chloro-N-phenyl-1,2,5-oxadiazole-3-carboxamide to afford the title compound as an off-white solid. ¹H NMR (500 MHz, DMSO-d₆) δ 9.20 (t, J=9.6 Hz, 1H), 8.72 (d, J=7.7 Hz, 1H), 8.52 (d, J=2.1 Hz, 1H), 8.24-8.13 (m, 1H), 7.96-7.92 (m, 1H), 5.21-5.12 (m, 1H), 4.44-4.38 (m, 1H), 4.38-4.34 (m, 1H), 4.33-4.26 (m, 1H), 2.48-2.42 (m, 3H), 2.18-2.10 (m, 1H), 2.07-1.93 (m, 2H), 1.88-1.67 (m, 3H), 1.65-1.57 (m, 1H), 1.40 (t, J=7.0 Hz, 1H), 1.38-1.13 (m, 3H), 0.91-0.80 (m, 3H), 0.63-0.55 (m, 1H), 0.55-0.46 (m, 2H), 0.44-0.33 (m, 1H). MS (ESI) m/z: [M+H]⁺ Found 612.2.

Example 381

4-Cyclopropyl-N—((S)-(7-((R)-cyclopropyl(4,4,4-trifluorobutanamido)methyl)imidazo[1,2-b]pyridazin-2-yl)(4,4-difluorocyclohexyl)methyl)-1,2,5-oxadiazole-3-carboxamide

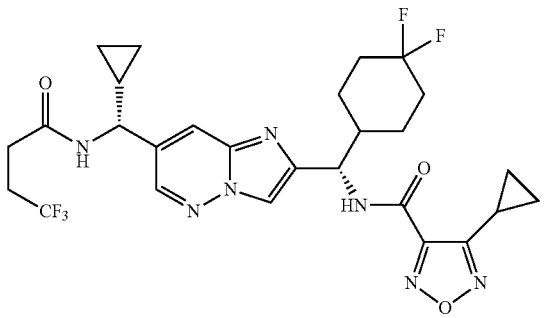 [SMILES: O=C(CCC(F)(F)F)N[C@@H](c1cnn2cc([C@@H](NC(=O)c3nonc3C3CC3)C3CCC(F)(F)CC3)nc2c1)C1CC1]

The title compound was prepared as described for the synthesis of Example 379, using 3-cyclopropyl-4-(((S)-(7-((R)-cyclopropyl(4,4,4-trifluorobutanamido)methyl)imidazo[1,2-b]pyridazin-2-yl)(4,4-difluorocyclohexyl)methyl)carbamoyl)-1,2,5-oxadiazole 2-oxide (Intermediate 361) in place of 4-(((S)-(7-((R)-Cyclopropyl(4,4,4-trifluorobutanamido)methyl)imidazo[1,2-b]pyridazin-2-yl)(4,4-difluorocyclohexyl)methyl)carbamoyl)-3-isopropyl-1,2,5-oxadiazole 2-oxide to afford the title compound as an off-white powder. ¹H NMR (400 MHz, DMSO-d₆) δ 9.46 (d, J=8.9 Hz, 1H), 8.71 (d, J=7.7 Hz, 1H), 8.51 (d, J=2.0 Hz, 1H), 8.22 (s, 1H), 8.05-7.73 (m, 1H), 5.19 (t, J=8.5 Hz, 1H), 4.29 (dd, J=9.0, 7.7 Hz, 1H), 2.56-2.51 (m, 1H), 2.49-2.42 (m, 3H), 2.33-2.24 (m, 1H), 2.23-2.12 (m, 1H), 2.11-1.94 (m, 2H), 1.94-1.69 (m, 3H), 1.66-1.57 (m, 1H), 1.46-1.25 (m, 2H), 1.24-1.16 (m, 1H), 1.15-1.09 (m, 2H), 0.99-0.93 (m, 2H), 0.62-0.45 (m, 3H), 0.43-0.32 (m, 1H). MS (ESI) m/z: [M+H]⁺ Found 596.2.

Example 382

N—((S)-(7-((R)-Cyclopropyl(4,4,4-trifluorobutanamido)methyl)imidazo[1,2-b]pyridazin-2-yl)(4,4-difluorocyclohexyl)methyl)-4-(2,2,2-trifluoroethoxy)-1,2,5-oxadiazole-3-carboxamide

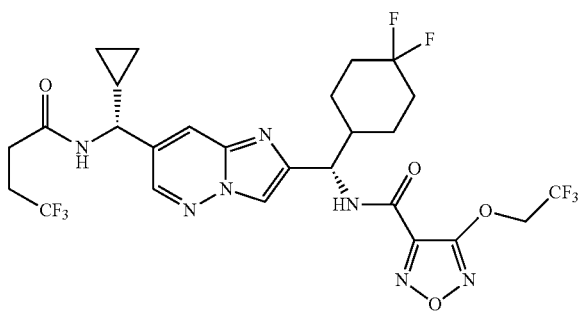 [SMILES: O=C(CCC(F)(F)F)N[C@@H](c1cnn2cc([C@@H](NC(=O)c3nonc3OCC(F)(F)F)C3CCC(F)(F)CC3)nc2c1)C1CC1]

The title compound was prepared as described for the synthesis of Intermediate 325, using 4-chloro-N—((S)-(7-((R)-cyclopropyl(4,4,4-trifluorobutanamido)methyl)imidazo[1,2-b]pyridazin-2-yl)(4,4-difluorocyclohexyl)methyl)-

1,2,5-oxadiazole-3-carboxamide (Intermediate 324) in place of 4-chloro-N-phenyl-1,2,5-oxadiazole-3-carboxamide to afford the title compound as an off-white solid. $^1$H NMR (500 MHz, DMSO-$d_6$) δ 9.38 (d, J=9.0 Hz, 1H), 8.72 (d, J=7.6 Hz, 1H), 8.52 (d, J=2.1 Hz, 1H), 8.18 (s, 1H), 8.03-7.87 (m, 1H), 5.20-5.09 (m, 3H), 4.29 (t, J=8.3 Hz, 1H), 2.48-2.44 (m, 4H), 2.21-2.11 (m, 1H), 2.07-1.93 (m, 2H), 1.90-1.68 (m, 3H), 1.66-1.56 (m, 1H), 1.42-1.26 (m, 2H), 1.26-1.16 (m, 1H), 0.61-0.55 (m, 1H), 0.55-0.45 (m, 2H), 0.41-0.34 (m, 1H). MS (ESI) m/z: [M+H]$^+$ Found 654.2.

Example 383

N—((S)-(7-((R)-Cyclopropyl(4,4,4-trifluorobutana-mido)methyl)imidazo[1,2-b]pyridazin-2-yl)(4,4-difluorocyclohexyl)methyl)-4-(2,2-difluoroethoxy)-1,2,5-oxadiazole-3-carboxamide

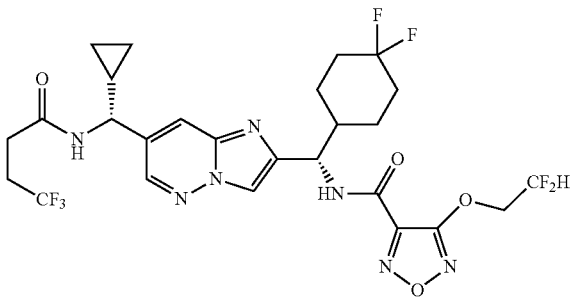 [SMILES: O=C(CCC(F)(F)F)N[C@@H](c1cnn2cc([C@@H](NC(=O)c3nonc3OCC(F)F)C3CCC(F)(F)CC3)nc2c1)C1CC1]

The title compound was prepared as described for the synthesis of Intermediate 325, using 2,2-difluoroethanol in place of 2,2,2-trifluoroethanol and 4-chloro-N—((S)-(7-((R)-cyclopropyl(4,4,4-trifluorobutanamido)methyl)imidazo[1,2-b]pyridazin-2-yl)(4,4-difluorocyclohexyl)methyl)-1,2,5-oxadiazole-3-carboxamide (Intermediate 324) in place of 4-chloro-N-phenyl-1,2,5-oxadiazole-3-carboxamide to afford the title compound as an off-white solid. $^1$H NMR (500 MHz, DMSO-$d_6$) δ 9.33 (d, J=8.9 Hz, 1H), 8.72 (d, J=7.7 Hz, 1H), 8.51 (d, J=2.1 Hz, 1H), 8.19 (s, 1H), 8.00-7.84 (m, 1H), 6.43 (tt, J=53.6, 3.1 Hz, 1H), 5.16 (dd, J=9.0, 7.8 Hz, 1H), 4.77-4.63 (m, 2H), 4.29 (t, J=8.4 Hz, 1H), 2.55-2.51 (m, 1H), 2.48-2.40 (m, 3H), 2.22-2.09 (m, 1H), 2.07-1.94 (m, 2H), 1.92-1.68 (m, 3H), 1.66-1.57 (m, 1H), 1.43-1.25 (m, 2H), 1.25-1.16 (m, 1H), 0.64-0.55 (m, 1H), 0.55-0.47 (m, 2H), 0.42-0.32 (m, 1H). MS (ESI) m/z: [M+H]$^+$ Found 635.5.

Example 384

N—((S)-(7-((R)-Cyclopropyl(4,4,4-trifluorobutana-mido)methyl)imidazo[1,2-b]pyridazin-2-yl)(4,4-difluorocyclohexyl)methyl)-4-(2-fluoroethoxy)-1,2,5-oxadiazole-3-carboxamide

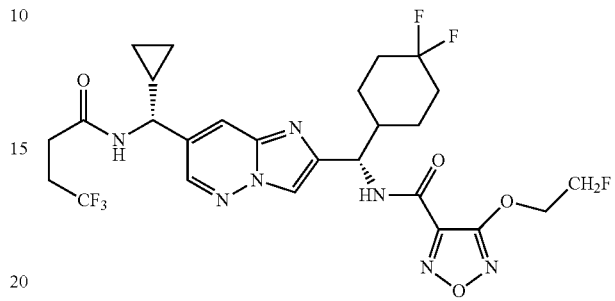

The title compound was prepared as described for the synthesis of Intermediate 325, using 2-fluoroethanol in place of 2,2,2-trifluoroethanol and 4-chloro-N—((S)-(7-((R)-cyclopropyl(4,4,4-trifluorobutanamido)methyl)imidazo[1,2-b]pyridazin-2-yl)(4,4-difluorocyclohexyl)methyl)-1,2,5-oxadiazole-3-carboxamide (Intermediate 324) in place of 4-chloro-N-phenyl-1,2,5-oxadiazole-3-carboxamide to afford the title compound as an off-white solid. $^1$H NMR (500 MHz, DMSO-$d_6$) δ 9.28 (d, J=9.0 Hz, 1H), 8.72 (d, J=7.7 Hz, 1H), 8.51 (d, J=2.1 Hz, 1H), 8.19 (s, 1H), 8.02-7.87 (m, 1H), 5.21-5.12 (m, 1H), 4.87-4.71 (m, 2H), 4.69-4.55 (m, 2H), 4.29 (t, J=8.4 Hz, 1H), 2.55-2.51 (m, 1H), 2.49-2.43 (m, 3H), 2.21-2.09 (m, 1H), 2.08-1.93 (m, 2H), 1.91-1.69 (m, 3H), 1.68-1.59 (m, 1H), 1.44-1.26 (m, 2H), 1.25-1.15 (m, 1H), 0.64-0.55 (m, 1H), 0.55-0.47 (m, 2H), 0.42-0.30 (m, 1H). MS (ESI) m/z: [M+H]$^+$ Found 618.2.

Example 385

N—((S)-(7-((R)-Cyclopropyl(2-(3,3-difluorocy-clobutyl)acetamido)methyl)imidazo[1,2-b]pyridazin-2-yl)(4,4-difluorocyclohexyl)methyl)-4-((difluo-romethoxy)methyl)-1,2,5-oxadiazole-3-carboxamide

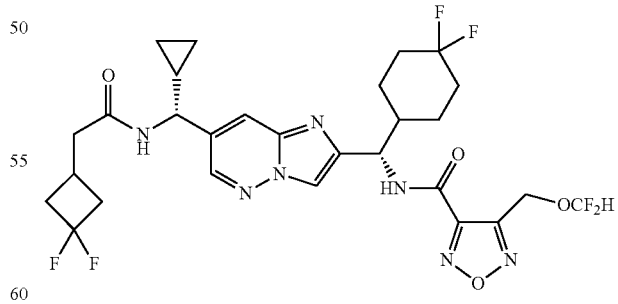

The title compound was prepared as described for the synthesis of Example 38, using 4-((difluoromethoxy)methyl)-1,2,5-oxadiazole-3-carboxylic acid (Intermediate 347) in place of 1-(3,3,3-trifluoropropyl)-1H-1,2,4-triazole-5-carboxylic acid and N—((R)-(2-((S)-amino(4,4-difluoro-cyclohexyl)methyl)imidazo[1,2-b]pyridazin-7-yl)(cyclopropyl)methyl)-2-(3,3-difluorocyclobutyl)acetamide (Intermediate 171) in place of N—((R)-(2-((S)-amino(4,4-difluorocyclohexyl)methyl)imidazo[1,2-b]pyridazin-7-yl)(cyclopropyl)methyl)-4,4,4-trifluorobutanamide to afford the title compound as an off-white solid. $^1$H NMR (500 MHz, DMSO-$d_6$) δ 9.56 (d, J=8.8 Hz, 1H), 8.59 (d, J=7.7 Hz, 1H), 8.49 (d, J=2.1 Hz, 1H), 8.22 (s, 1H), 7.93 (s, 1H), 6.83 (t, J=74.5 Hz, 1H), 5.36-5.25 (m, 2H), 5.15 (t, J=8.6 Hz, 1H), 4.26 (t, J=8.4 Hz, 1H), 2.84-2.55 (m, 2H), 2.45-2.35 (m, 3H), 2.35-2.23 (m, 1H), 2.23-2.14 (m, 1H), 2.11-1.94 (m, 2H), 1.94-1.85 (m, 1H), 1.85-1.67 (m, 2H), 1.67-1.50 (m, 1H), 1.45-1.33 (m, 1H), 1.32-1.10 (m, 3H), 0.62-0.42 (m, 3H), 0.40-0.33 (m, 1H). MS (ESI) m/z: [M+H]$^+$ Found 644.3.

Example 386

4-(Azetidin-1-yl)-N—((S)-(7-((R)-cyclopropyl(2-(3,3-difluorocyclobutyl)acetamido)methyl)imidazo[1,2-b]pyridazin-2-yl)(4,4-difluorocyclohexyl)methyl)-1,2,5-oxadiazole-3-carboxamide

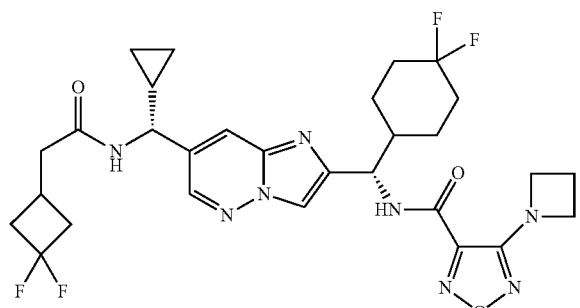

The title compound was prepared as described for the synthesis of Example 38, using 4-(azetidin-1-yl)-1,2,5-oxadiazole-3-carboxylic acid (Intermediate 333) in place of 1-(3,3,3-trifluoropropyl)-1H-1,2,4-triazole-5-carboxylic acid and N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide (Intermediate 171) in place of N—((R)-(2-((S)-amino(4,4-difluorocyclohexyl)methyl)imidazo[1,2-b]pyridazin-7-yl) (cyclopropyl)methyl)-4,4,4-trifluorobutanamide to afford the title compound as an off-white solid. $^1$H NMR (500 MHz, DMSO-$d_6$) δ 9.37 (d, J=9.1 Hz, 1H), 8.59 (d, J=7.8 Hz, 1H), 8.49 (d, J=2.1 Hz, 1H), 8.20 (s, 1H), 7.95-7.92 (m, 1H), 5.14 (t, J=8.5 Hz, 1H), 4.27 (t, J=8.4 Hz, 1H), 3.97 (t, J=7.6 Hz, 4H), 2.70-2.56 (m, 2H), 2.42-2.35 (m, 3H), 2.35-2.22 (m, 4H), 2.19-2.10 (m, 1H), 2.08-1.93 (m, 2H), 1.91-1.67 (m, 3H), 1.64-1.52 (m, 1H), 1.43-1.33 (m, 1H), 1.31-1.14 (m, 2H), 0.65-0.41 (m, 3H), 0.42-0.32 (m, 1H). MS (ESI) m/z: [M+H]$^+$ Found 619.2.

Example 387

N—((S)-(7-((R)-Cyclopropyl(4,4,4-trifluorobutanamido)methyl)imidazo[1,2-b]pyridazin-2-yl)(4,4-difluorocyclohexyl)methyl)-4-((3,3-difluoroazetidin-1-yl)methyl)-1,2,5-oxadiazole-3-carboxamide

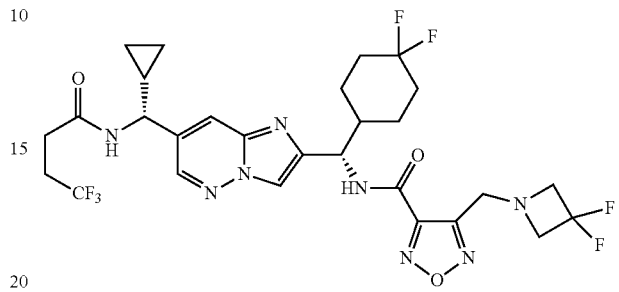

Triethylamine (0.03 mL, 0.22 mmol) and mesyl chloride (6.4 μL, 82 μmol) were sequentially added to a solution of N—((S)-(7-((R)-cyclopropyl(4,4,4-trifluorobutanamido)methyl)imidazo[1,2-b]pyridazin-2-yl)(4,4-difluorocyclohexyl)methyl)-4-(hydroxymethyl)-1,2,5-oxadiazole-3-carboxamide (32 mg, 55 μmol, Intermediate 57) in DCM (0.55 mL) at 0° C. The reaction stirred for 20 min followed by the addition of 3,3-difluoroazetidine hydrochloride (14 mg, 0.11 mmol). The reaction was stirred for 1.5 h, diluted with DMF (1.5 mL), filtered, and purified by preparative basic HPLC (XBridge Prep C18 5 μm, 50×100 mm, 10-100% acetonitrile/water (with 20 mM NH$_4$OH)). The product containing fractions were lyophilized to afford the title compound as an off-white solid. $^1$H NMR (400 MHz, DMSO-$d_6$) δ 9.85 (d, J=8.9 Hz, 1H), 8.72 (d, J=7.6 Hz, 1H), 8.51 (d, J=2.1 Hz, 1H), 8.24 (s, 1H), 7.95-7.92 (m, 1H), 5.20 (t, J=8.3 Hz, 1H), 4.29 (t, J=8.4 Hz, 1H), 4.19-4.08 (m, 2H), 3.77 (td, J=12.5, 3.7 Hz, 4H), 2.48-2.41 (m, 4H), 2.23-2.10 (m, 1H), 2.10-1.87 (m, 3H), 1.86-1.68 (m, 2H), 1.68-1.56 (m, 1H), 1.45-1.27 (m, 2H), 1.27-1.15 (m, 1H), 0.63-0.44 (m, 3H), 0.43-0.32 (m, 1H). MS (ESI) m/z: [M+H]$^+$ Found 661.2.

Example 388

N—((S)-(7-((R)-Cyclopropyl(4,4,4-trifluorobutanamido)methyl)imidazo[1,2-b]pyridazin-2-yl)(4,4-difluorocyclohexyl)methyl)-4-(2-fluoropropan-2-yl)-1,2,5-oxadiazole-3-carboxamide

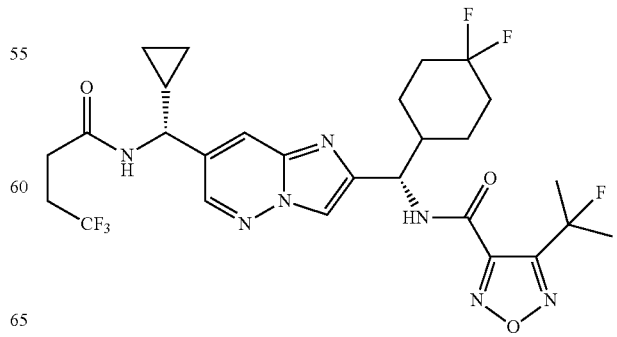

DAST (16 µL, 0.12 mmol) was added dropwise to a solution of N—((S)-(7-((R)-cyclopropyl(4,4,4-trifluorobutanamido)methyl)imidazo[1,2-b]pyridazin-2-yl)(4,4-difluorocyclohexyl)methyl)-4-(2-hydroxypropan-2-yl)-1,2,5-oxadiazole-3-carboxamide (50 mg, 82 µmol, Example 371) in DCM (4.1 mL) at −78° C. After complete addition of DAST, the reaction was warmed to 0° C. and stirred for 1 h. The reaction was quenched with a saturated aqueous solution of NaHCO₃, transferred to a separatory funnel, and extracted with DCM (3×15 mL). The combined organic layers were washed with brine, dried over anhydrous Na₂SO₄, filtered, and concentrated to dryness. The residue was purified by preparative basic HPLC (XBridge Prep C18 5 µm, 50×100 mm, 10-100% acetonitrile/water (with 20 mM NH₄OH)) followed by SFC with a chiral stationary phase (Stationary phase: Whelk 01 SS 5 µm, 21×250 mm, Mobile phase: 25% MeOH (with 0.2% i-PrNH₂)/CO₂) to afford the title compound as an off-white solid. ¹H NMR (400 MHz, DMSO-d₆) δ 9.60 (d, J=9.0 Hz, 1H), 8.72 (d, J=7.7 Hz, 1H), 8.52 (d, J=2.1 Hz, 1H), 8.14 (s, 1H), 7.95 (d, J=2.1 Hz, 1H), 5.24-5.17 (m, 1H), 4.30 (t, J=8.4 Hz, 1H), 2.49-2.43 (m, 4H), 2.24-2.10 (m, 1H), 2.10-1.94 (m, 2H), 1.89-1.68 (m, 8H), 1.68-1.59 (m, 1H), 1.46-1.28 (m, 2H), 1.26-1.13 (m, 2H), 0.67-0.45 (m, 3H), 0.43-0.34 (m, 1H). MS (ESI) m/z: [M+H]⁺ Found 616.3.

Example 389

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-4-(2,2-difluoroethoxy)-1,2,5-oxadiazole-3-carboxamide

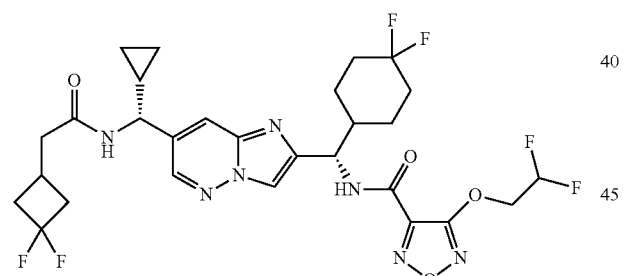

The title compound was prepared as described for the synthesis of Example 142, using 4-(2,2-difluoroethoxy)-1,2,5-oxadiazole-3-carbonyl chloride (Intermediate 362) in place of 4-methyl-1,2,5-oxadiazole-3-carbonyl chloride to afford the title compound as an off-white solid. ¹H NMR (400 MHz, DMSO-d₆) δ 9.33 (d, J=9.0 Hz, 1H), 8.59 (d, J=7.8 Hz, 1H), 8.50 (d, J=2.1 Hz, 1H), 8.19 (s, 1H), 8.03-7.80 (m, 1H), 6.43 (tt, J=53.6, 3.1 Hz, 1H), 5.16 (t, J=8.4 Hz, 1H), 4.83-4.59 (m, 2H), 4.27 (t, J=8.4 Hz, 1H), 2.72-2.55 (m, 2H), 2.43-2.22 (m, 5H), 2.20-2.10 (m, 1H), 2.08-1.94 (m, 2H), 1.85 (t, J=15.1 Hz, 2H), 1.79-1.68 (m, 1H), 1.66-1.54 (m, 1H), 1.47-1.10 (m, 3H), 0.65-0.42 (m, 3H), 0.43-0.32 (m, 1H). MS (ESI) m/z: [M+H]⁺ Found 644.3.

Example 390

N—((S)-(7-((R)-Cyclopropyl(4,4-difluorobutanamido)methyl)imidazo[1,2-b]pyridazin-2-yl)(4,4-difluorocyclohexyl)methyl)-4-(2,2-difluoroethoxy)-1,2,5-oxadiazole-3-carboxamide

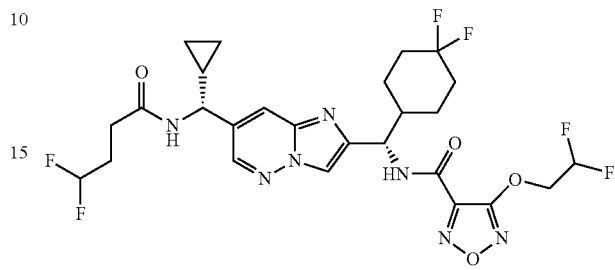

The title compound was prepared as described for the synthesis of Example 142, using 4,4-difluorobutanoic acid in place of 4,4,4-trifluorobutanoic acid, and 4-(2,2-difluoroethoxy)-1,2,5-oxadiazole-3-carbonyl chloride (Intermediate 362) in place of 1-(3,3,3-trifluoropropyl)-1H-1,2,4-triazole-5-carboxylic acid to afford the title compound as an off-white solid. ¹H NMR (400 MHz, DMSO-d₆) δ 9.33 (d, J=9.0 Hz, 1H), 8.65 (d, J=7.7 Hz, 1H), 8.51 (d, J=2.1 Hz, 1H), 8.19 (s, 1H), 7.93 (d, J=2.0 Hz, 1H), 6.43 (tt, J=53.7, 3.1 Hz, 1H), 6.07 (tt, J=56.9, 4.3 Hz, 1H), 5.16 (t, J=8.4 Hz, 1H), 4.83-4.57 (m, 2H), 4.28 (t, J=8.4 Hz, 1H), 2.40-2.24 (m, 2H), 2.21-1.93 (m, 5H), 1.91-1.67 (m, 3H), 1.67-1.54 (m, 1H), 1.46-1.10 (m, 3H), 0.64-0.45 (m, 3H), 0.44-0.33 (m, 1H). MS (ESI) m/z: [M+H]⁺ Found 618.2.

Example 391

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-4-ethoxy-1,2,5-oxadiazole-3-carboxamide

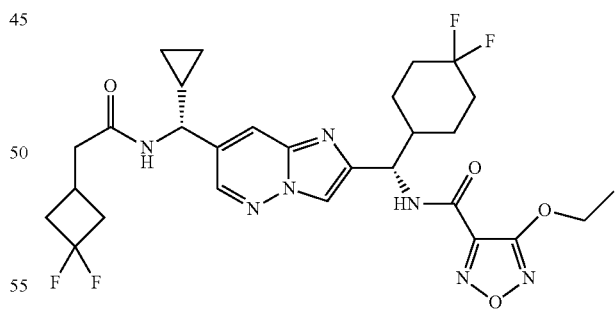

The title compound was prepared as described for the synthesis of Example 142, using 4-ethoxy-1,2,5-oxadiazole-3-carbonyl chloride (Intermediate 341) in place of 4-methyl-1,2,5-oxadiazole-3-carbonyl chloride to afford the title compound as an off-white solid. ¹H NMR (400 MHz, DMSO-d₆) δ 9.21 (d, J=9.0 Hz, 1H), 8.59 (d, J=7.8 Hz, 1H), 8.51 (d, J=2.1 Hz, 1H), 8.19 (s, 1H), 7.96-7.90 (m, 1H), 5.17 (t, J=9.0 Hz, 1H), 4.52-4.34 (m, 2H), 4.27 (t, J=8.4 Hz, 1H), 2.75-2.55 (m, 2H), 2.44-2.21 (m, 5H), 2.21-2.10 (m, 1H), 2.08-1.92 (m, 2H), 1.91-1.67 (m, 3H), 1.67-1.56 (m, 1H), 1.40 (t, J=7.0 Hz, 3H), 1.38-1.16 (m, 3H), 0.64-0.43 (m, 3H), 0.40-0.32 (m, 1H). MS (ESI) m/z: [M+H]⁺ Found 608.3.

Example 392

4-(tert-Butoxy)-N—((S)-(7-((R)-cyclopropyl(2-(3,3-difluorocyclobutyl)acetamido)methyl)imidazo[1,2-b]pyridazin-2-yl)(4,4-difluorocyclohexyl)methyl)-1,2,5-oxadiazole-3-carboxamide

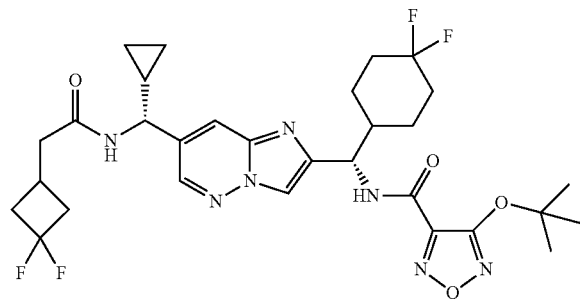 [SMILES: CC(C)(C)Oc1nonc1C(=O)N[C@H](c1cn2ncc([C@H](NC(=O)CC3CC(F)(F)C3)C3CC3)cc2n1)C1CCC(F)(F)CC1]

The title compound was prepared as described for the synthesis of Example 142, using 4-(tert-butoxy)-1,2,5-oxadiazole-3-carbonyl chloride (Intermediate 337) in place of 4-methyl-1,2,5-oxadiazole-3-carbonyl chloride to afford the title compound as an off-white solid. ¹H NMR (400 MHz, DMSO-d₆) δ 9.11 (d, J=9.0 Hz, 1H), 8.60 (d, J=7.8 Hz, 1H), 8.51 (d, J=2.1 Hz, 1H), 8.19 (s, 1H), 7.91 (d, J=2.0 Hz, 1H), 5.35-5.02 (m, 1H), 4.27 (t, J=8.4 Hz, 1H), 2.82-2.55 (m, 2H), 2.44-2.20 (m, 4H), 2.19-2.09 (m, 1H), 2.07-1.91 (m, 2H), 1.90-1.68 (m, 3H), 1.68-1.59 (m, 1H), 1.54 (s, 9H), 1.44-1.27 (m, 2H), 1.27-1.14 (m, 2H), 0.63-0.44 (m, 3H), 0.41-0.29 (m, 1H). MS (ESI) m/z: [M+H]⁺ Found 636.3.

Example 393

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-4-(1-hydroxycyclopentyl)-1,2,5-oxadiazole-3-carboxamide

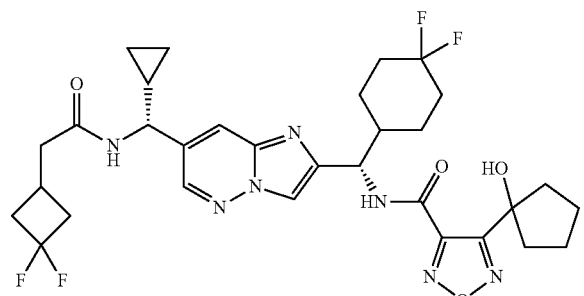

The title compound was prepared as described for the synthesis of Intermediate 359, using 6'H-spiro[cyclopentane-1,4'-furo[3,4-c][1,2,5]oxadiazol]-6'-one (Intermediate 365) in place of 4H,6H-furo[3,4-c][1,2,5]oxadiazol-4-one to afford the title compound as an off-white solid. ¹H NMR (400 MHz, DMSO-d₆) δ 9.66 (d, J=8.9 Hz, 1H), 8.59 (d, J=7.8 Hz, 1H), 8.50 (d, J=2.1 Hz, 1H), 8.19 (s, 1H), 7.94-7.87 (m, 1H), 5.93 (s, 1H), 5.30-5.14 (m, 1H), 4.27 (t, J=8.4 Hz, 1H), 2.77-2.57 (m, 2H), 2.42-2.15 (m, 6H), 2.11-1.93 (m, 6H), 1.91-1.57 (m, 8H), 1.51-1.26 (m, 2H), 1.26-1.15 (m, 1H), 0.64-0.44 (m, 3H), 0.40-0.32 (m, 1H). MS (ESI) m/z: [M+H]⁺ Found 648.2.

Example 394

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-4-(2-hydroxy-2-methylpropyl)-1,2,5-oxadiazole-3-carboxamide

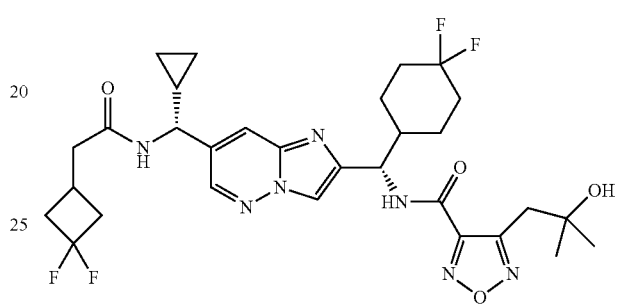

The title compound was prepared as described for the synthesis of Example 499, using 6,6-dimethyl-6,7-dihydro-4H-pyrano[3,4-c][1,2,5]oxadiazol-4-one (Intermediate 358) in place of 6,6-dimethylfuro[3,4-c][1,2,5]oxadiazol-4(6H)-one to afford the title compound as an off-white solid. ¹H NMR (400 MHz, DMSO-d₆) δ 9.56 (s, 1H), 8.59 (d, J=7.8 Hz, 1H), 8.50 (d, J=2.0 Hz, 1H), 8.18 (s, 1H), 7.92 (d, J=2.0 Hz, 1H), 5.19 (d, J=7.4 Hz, 1H), 4.97 (s, 1H), 4.27 (t, J=8.4 Hz, 1H), 3.04 (s, 2H), 2.77-2.56 (m, 2H), 2.42-2.21 (m, 4H), 2.21-1.94 (m, 3H), 1.91-1.57 (m, 5H), 1.47-1.17 (m, 3H), 1.12 (d, J=1.9 Hz, 6H), 0.63-0.43 (m, 3H), 0.34-0.25 (m, 1H). MS (ESI) m/z: [M+H]⁺ Found 636.2.

Example 395

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-4-((R*)-1-hydroxyethyl)-1,2,5-oxadiazole-3-carboxamide

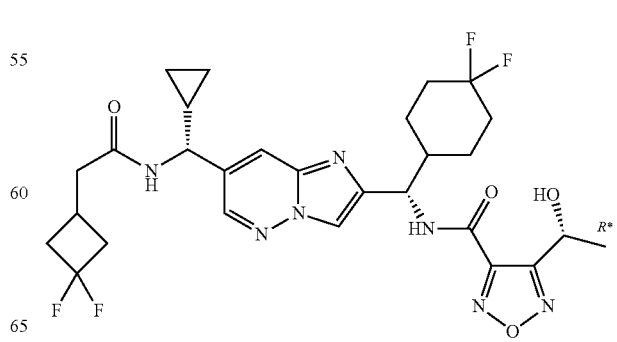

Example 396

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-4-((S*)-1-hydroxyethyl)-1,2,5-oxadiazole-3-carboxamide

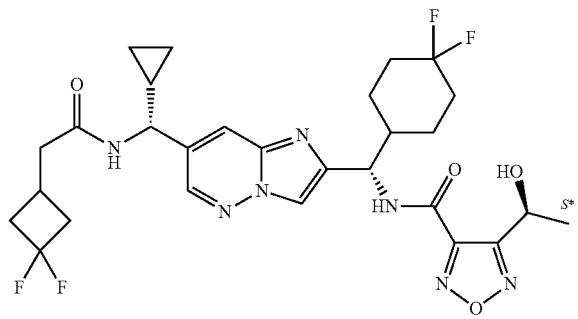 [SMILES: C[C@H](O)c1nonc1C(=O)N[C@H](c1cn2ncc([C@H](NC(=O)CC3CC(F)(F)C3)C3CC3)cc2n1)C1CCC(F)(F)CC1]

The title compound was prepared as described for the synthesis of Intermediate 359, using 6-methyl-4H,6H-furo[3,4-c][1,2,5]oxadiazol-4-one (Intermediate 353) in place of 4H,6H-furo[3,4-c][1,2,5]oxadiazol-4-one to afford the title compounds. The diastereomers were separated by SFC with a chiral stationary phase (Stationary phase: Chiralpak UT 5 μm, 250×21 mm, Mobile phase: 20% MeOH with 0.2% TEA, 80% CO$_2$). The first eluting diastereomer was Example 395 and the second eluting diastereomer was Example 396. Example 395: $^1$H NMR (500 MHz, DMSO-d$_6$) δ 9.55 (d, J=8.9 Hz, 1H), 8.60 (d, J=7.8 Hz, 1H), 8.51 (d, J=2.1 Hz, 1H), 8.22 (s, 1H), 7.93 (d, J=2.0 Hz, 1H), 6.03 (d, J=5.7 Hz, 1H), 5.25-5.13 (m, 2H), 4.28 (t, J=8.4 Hz, 1H), 3.29 (s, 1H), 2.72-2.57 (m, 2H), 2.50-2.49 (m, 2H), 2.44-2.35 (m, 3H), 2.36-2.25 (m, 2H), 2.24-2.12 (m, 1H), 2.09-1.96 (m, 1H), 1.90-1.70 (m, 1H), 1.67-1.59 (m, 1H), 1.49 (d, J=6.6 Hz, 3H), 1.46-1.25 (m, 1H), 1.25-1.14 (m, 2H), 0.64-0.44 (m, 3H), 0.41-0.32 (m, 1H). MS (ESI) m/z: [M+H]$^+$ Found 608.5. Example 396: $^1$H NMR (500 MHz, DMSO-d$_6$) δ 9.57 (d, J=8.9 Hz, 1H), 8.59 (d, J=7.8 Hz, 1H), 8.50 (d, J=2.1 Hz, 1H), 8.20 (s, 1H), 7.93 (d, J=2.1 Hz, 1H), 5.97 (d, J=5.6 Hz, 1H), 5.25-5.06 (m, 2H), 4.27 (t, J=8.4 Hz, 1H), 3.29-3.26 (m, 3H), 2.70-2.56 (m, 2H), 2.42-2.23 (m, 5H), 2.22-2.12 (m, 1H), 2.08-1.94 (m, 1H), 1.90-1.68 (m, 2H), 1.68-1.57 (m, 1H), 1.49 (d, J=7.1 Hz, 3H), 1.45-1.07 (m, 2H), 0.60-0.42 (m, 3H), 0.40-0.31 (m, 1H). MS (ESI) m/z: [M+H]$^+$ Found 608.5.

Example 397

N—((S)-(7-((S*)-2-Cyano-1-(2-(3,3-difluorocyclobutyl)acetamido)ethyl)imidazo[1,2-b]pyridazin-2-yl)(4,4-difluorocyclohexyl)methyl)-4-methyl-1,2,5-oxadiazole-3-carboxamide

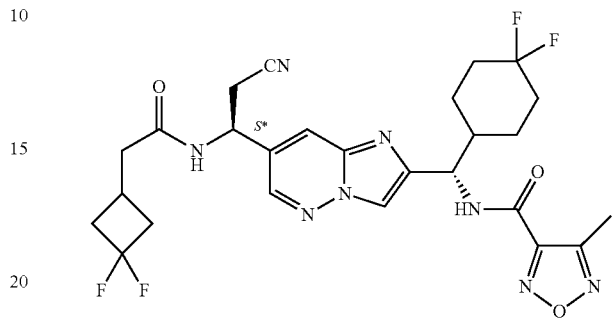

The title compound was prepared as described for the synthesis of Example 493, using N—((S*)-1-(2-((S)-amino(4,4-difluorocyclohexyl)methyl)imidazo[1,2-b]pyridazin-7-yl)-2-cyanoethyl)-2-(3,3-difluorocyclobutyl)acetamide (Intermediate 369) in place of N—((R*)-(2-((S)-amino(4,4-difluorocyclohexyl)methyl)imidazo[1,2-b]pyridazin-7-yl)(cyclobutyl)methyl)-2-(3,3-difluorocyclobutyl)acetamide. $^1$H NMR (600 MHz, DMSO-d$_6$) δ 9.42 (d, J=9.0 Hz, 1H), 8.78 (d, J=8.0 Hz, 1H), 8.54 (d, J=2.1 Hz, 1H), 8.28 (s, 1H), 8.08-8.00 (m, 1H), 5.34-5.28 (m, 1H), 5.18 (t, J=8.5 Hz, 1H), 3.16 (dd, J=16.9, 5.7 Hz, 1H), 3.09 (dd, J=16.9, 8.5 Hz, 1H), 2.75-2.58 (m, 2H), 2.46 (s, 3H), 2.45-2.40 (m, 3H), 2.36-2.25 (m, 2H), 2.22-2.13 (m, 1H), 2.10-1.93 (m, 2H), 1.93-1.85 (m, 1H), 1.84-1.70 (m, 2H), 1.63-1.56 (m, 1H), 1.43-1.33 (m, 1H), 1.31-1.19 (m, 1H). MS (ESI) m/z: [M+H]$^+$ Found 577.3.

Example 398

N—((S)-(7-((S*)-2-Cyano-1-(2-(3,3-difluorocyclobutyl)acetamido)ethyl)imidazo[1,2-b]pyridazin-2-yl)(4,4-difluorocyclohexyl)methyl)-4-cyclopropyl-1,2,5-oxadiazole-3-carboxamide

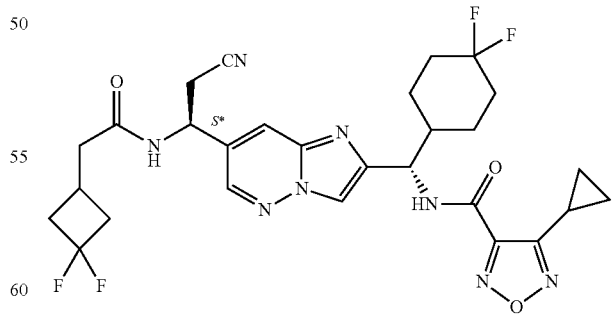

The title compound was prepared as described for the synthesis of Example 493, using N—((S*)-1-(2-((S)-amino(4,4-difluorocyclohexyl)methyl)imidazo[1,2-b]pyridazin-7-yl)-2-cyanoethyl)-2-(3,3-difluorocyclobutyl)acetamide (Intermediate 369) in place of N—((R*)-(2-((S)-amino(4,4- difluorocyclohexyl)methyl)imidazo[1,2-b]pyridazin-7-yl)(cyclobutyl)methyl)-2-(3,3-difluorocyclobutyl)acetamide and 4-cyclopropyl-1,2,5-oxadiazole-3-carboxylic acid (Intermediate 570) in place of 4-methyl-1,2,5-oxadiazole-3-carboxylic acid. $^1$H NMR (600 MHz, DMSO-d$_6$) δ 9.49 (d, J=9.0 Hz, 1H), 8.78 (d, J=8.0 Hz, 1H), 8.55 (d, J=2.1 Hz, 1H), 8.27 (t, J=0.6 Hz, 1H), 8.08-8.03 (m, 1H), 5.34-5.28 (m, 1H), 5.20 (t, J=8.5 Hz, 1H), 3.16 (dd, J=16.9, 5.7 Hz, 1H), 3.09 (dd, J=16.9, 8.5 Hz, 1H), 2.73-2.60 (m, 2H), 2.46-2.38 (m, 3H), 2.36-2.25 (m, 3H), 2.22-2.14 (m, 1H), 2.08-1.95 (m, 2H), 1.93-1.86 (m, 1H), 1.84-1.71 (m, 2H), 1.65-1.57 (m, 1H), 1.46-1.34 (m, 1H), 1.33-1.18 (m, 1H), 1.15-1.07 (m, 2H), 1.00-0.93 (m, 2H). MS (ESI) m/z: [M+H]$^+$ Found 603.3.

Example 399

N—((S)-(7-((S*)-2-Cyano-1-(2-(3,3-difluorocyclobutyl)acetamido)ethyl)imidazo[1,2-b]pyridazin-2-yl)(4,4-difluorocyclohexyl)methyl)-1-isopropyl-1H-pyrazole-5-carboxamide

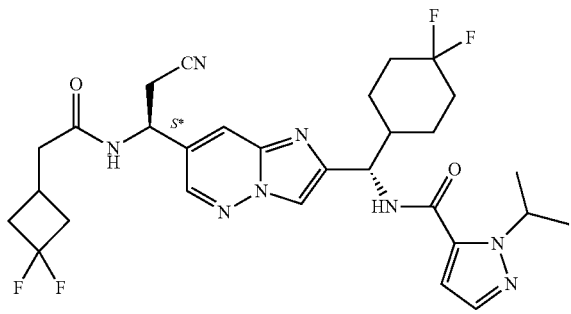 [SMILES: CC(C)n1nccc1C(=O)N[C@H](c1cn2ncc([C@H](CC#N)NC(=O)CC3CC(F)(F)C3)cc2n1)C1CCC(F)(F)CC1]

The title compound was prepared as described for the synthesis of Example 493, using N—((S*)-1-(2-((S)-amino(4,4-difluorocyclohexyl)methyl)imidazo[1,2-b]pyridazin-7-yl)-2-cyanoethyl)-2-(3,3-difluorocyclobutyl)acetamide (Intermediate 369) in place of N—((R*)-(2-((S)-amino(4,4-difluorocyclohexyl)methyl)imidazo[1,2-b]pyridazin-7-yl)(cyclobutyl)methyl)-2-(3,3-difluorocyclobutyl)acetamide and 1-isopropyl-1H-pyrazole-5-carboxylic acid in place of 4-methyl-1,2,5-oxadiazole-3-carboxylic acid. $^1$H NMR (500 MHz, DMSO-d$_6$) δ 8.78 (d, J=8.1 Hz, 1H), 8.73 (d, J=9.0 Hz, 1H), 8.54 (d, J=2.2 Hz, 1H), 8.25 (s, 1H), 8.04 (d, J=2.1 Hz, 1H), 7.48 (d, J=2.0 Hz, 1H), 6.90 (d, J=2.0 Hz, 1H), 5.40-5.27 (m, 2H), 5.16 (t, J=8.6 Hz, 1H), 3.20-3.05 (m, 2H), 2.74-2.59 (m, 2H), 2.47-2.38 (m, 3H), 2.37-2.24 (m, 2H), 2.23-2.12 (m, 1H), 2.09-1.93 (m, 2H), 1.91-1.68 (m, 3H), 1.66-1.56 (m, 1H), 1.44-1.20 (m, 8H). MS (ESI) m/z: [M+H]$^+$ Found 603.4.

Example 400

4-Cyclopropyl-N—((S)-(7-((R*)-1-(2-(3,3-difluorocyclobutyl)acetamido)-3,3-difluoropropyl)imidazo[1,2-b]pyridazin-2-yl)(4,4-difluorocyclohexyl)methyl)-1,2,5-oxadiazole-3-carboxamide

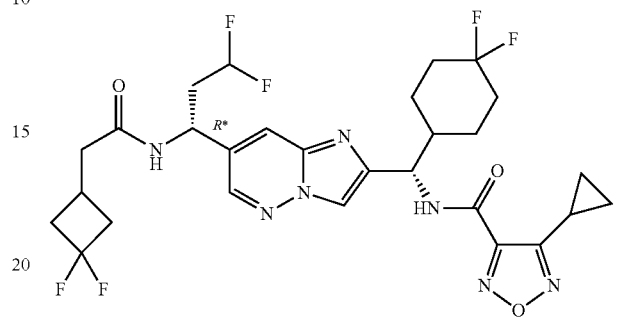

The title compound was prepared as described for the synthesis of Example 493, using N—((R*)-1-(2-((S)-amino(4,4-difluorocyclohexyl)methyl)imidazo[1,2-b]pyridazin-7-yl)-3,3-difluoropropyl)-2-(3,3-difluorocyclobutyl)acetamide (Intermediate 375) in place of N—((R*)-(2-((S)-amino(4,4-difluorocyclohexyl)methyl)imidazo[1,2-b]pyridazin-7-yl)(cyclobutyl)methyl)-2-(3,3-difluorocyclobutyl)acetamide and 4-cyclopropyl-1,2,5-oxadiazole-3-carboxylic acid (Intermediate 570) in place of 4-methyl-1,2,5-oxadiazole-3-carboxylic acid. $^1$H NMR (500 MHz, DMSO-d$_6$) δ 9.48 (d, J=9.0 Hz, 1H), 8.58 (d, J=8.0 Hz, 1H), 8.51 (d, J=2.1 Hz, 1H), 8.24 (d, J=0.6 Hz, 1H), 7.98-7.93 (m, 1H), 6.13 (tt, J=56.0, 4.6 Hz, 1H), 5.19 (t, J=8.5 Hz, 1H), 5.11 (q, J=7.6 Hz, 1H), 2.72-2.55 (m, 2H), 2.47-2.33 (m, 5H), 2.33-2.22 (m, 3H), 2.21-2.12 (m, 1H), 2.07-1.94 (m, 2H), 1.94-1.69 (m, 3H), 1.65-1.58 (m, 1H), 1.45-1.35 (m, 1H), 1.33-1.21 (m, 1H), 1.15-1.07 (m, 2H), 0.97-0.93 (m, 2H). MS (ESI) m/z: [M+H]$^+$ Found 628.2.

Example 401

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-4-((R*)-cyclopropyl(hydroxy)methyl)-1,2,5-oxadiazole-3-carboxamide

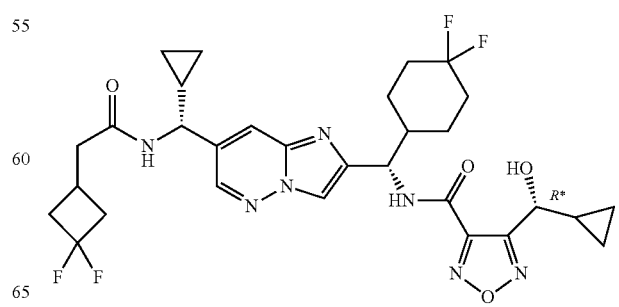

Example 402

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-4-((S*)-cyclopropyl(hydroxy)methyl)-1,2,5-oxadiazole-3-carboxamide

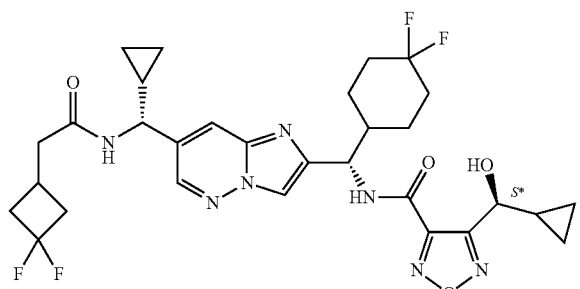

The title compound was prepared as described for the synthesis of Intermediate 359, using 6-cyclopropyl-4H,6H-furo[3,4-c][1,2,5]oxadiazol-4-one (Intermediate 356) in place of 4H,6H-furo[3,4-c][1,2,5]oxadiazol-4-one to afford the title compound as an off-white solid. The diastereomers were separated twice by SFC with a chiral stationary phase (Stationary phase: Chiralpak IH 5 μm 250×21 mm, Mobile phase: 15% MeOH, 85% CO$_2$). The first eluting diastereomer was Example 401 and the second eluting diastereomer was Example 402. Example 401: $^1$H NMR (500 MHz, DMSO-d$_6$) δ 9.58 (d, J=9.0 Hz, 1H), 8.59 (d, J=7.8 Hz, 1H), 8.50 (d, J=2.1 Hz, 1H), 8.20 (s, 1H), 8.00-7.88 (m, 1H), 6.10 (d, J=5.6 Hz, 1H), 5.22-5.15 (m, 1H), 4.43-4.36 (m, 1H), 4.27 (t, J=8.4 Hz, 1H), 2.75-2.52 (m, 2H), 2.45-2.35 (m, 3H), 2.36-2.23 (m, 2H), 2.23-2.12 (m, 1H), 2.08-1.93 (m, 2H), 1.90-1.69 (m, 3H), 1.69-1.60 (m, 1H), 1.46-1.25 (m, 3H), 1.25-1.17 (m, 1H), 0.63-0.34 (m, 7H), 0.31-0.23 (m, 1H). MS (ESI) m/z: [M+H]$^+$ Found 634.3. Example 402: $^1$H NMR (500 MHz, DMSO-d6) δ 9.61 (d, J=9.0 Hz, 1H), 8.59 (d, J=7.8 Hz, 1H), 8.50 (d, J=2.1 Hz, 1H), 8.19 (s, 1H), 7.92 (d, J=2.0 Hz, 1H), 6.05 (d, J=5.5 Hz, 1H), 5.19 (t, J=8.3 Hz, 1H), 4.44-4.37 (m, 1H), 4.27 (t, J=8.4 Hz, 1H), 2.72-2.55 (m, 2H), 2.44-2.36 (m, 3H), 2.36-2.23 (m, 2H), 2.23-2.11 (m, 1H), 2.10-1.92 (m, 2H), 1.91-1.69 (m, 3H), 1.69-1.57 (m, 1H), 1.45-1.25 (m, 3H), 1.25-1.13 (m, 1H), 0.64-0.22 (m, 8H). MS (ESI) m/z: [M+H]$^+$ Found 634.2.

Example 403

4-Cyclopropyl-N—((S)-(7-((R)-cyclopropyl(2-(3,3-difluorocyclobutyl)acetamido)methyl)imidazo[1,2-b]pyridazin-2-yl)(4,4-difluorocyclohexyl)methyl)isoxazole-3-carboxamide

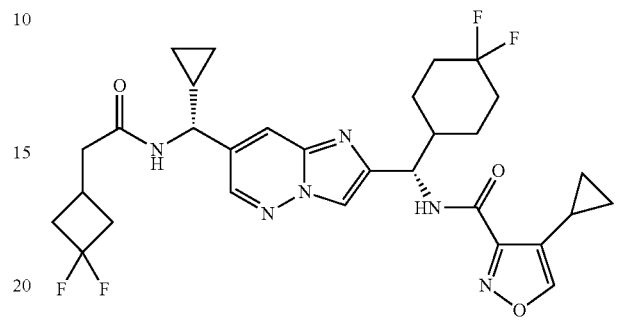

The title compound was prepared as described for the synthesis of Example 38, using 4-cyclopropylisoxazole-3-carboxylic acid (Intermediate 314) in place of 1-(3,3,3-trifluoropropyl)-1H-1,2,4-triazole-5-carboxylic acid and N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide (Intermediate 171) in place of N—((R)-(2-((S)-amino(4,4-difluorocyclohexyl)methyl)imidazo[1,2-b]pyridazin-7-yl) (cyclopropyl)methyl)-4,4,4-trifluorobutanamide to afford the title compound as an off-white solid. $^1$H NMR (500 MHz, DMSO-d$_6$) δ 8.94 (d, J=9.1 Hz, 1H), 8.74 (d, J=0.7 Hz, 1H), 8.58 (d, J=7.8 Hz, 1H), 8.49 (d, J=2.1 Hz, 1H), 8.20 (s, 1H), 7.94 (d, J=2.0 Hz, 1H), 5.19 (t, J=8.5 Hz, 1H), 4.27 (t, J=8.4 Hz, 1H), 2.74-2.56 (m, 2H), 2.45-2.21 (m, 5H), 2.21-2.10 (m, 1H), 2.10-1.93 (m, 2H), 1.93-1.67 (m, 4H), 1.67-1.54 (m, 1H), 1.45-1.16 (m, 3H), 0.92-0.78 (m, 2H), 0.64-0.32 (m, 6H). MS (ESI) m/z: [M+H]$^+$ Found 603.3.

Example 404

N—((S*)-(7-((R)-Cyclopropyl(2-(3,3-difluorocyclobutyl)acetamido)methyl)imidazo[1,2-b]pyridazin-2-yl)((1R,3s,5S)-6,6-difluorobicyclo[3.1.0]hexan-3-yl)methyl)-1-isopropyl-1H-pyrazole-5-carboxamide

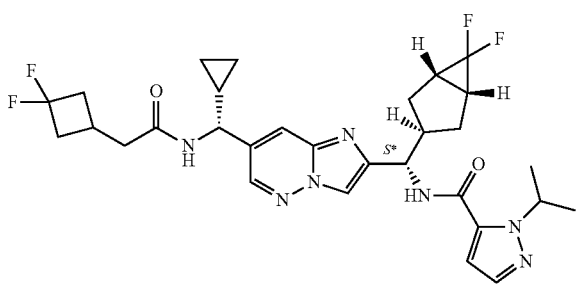 [SMILES: CC(C)n1nccc1C(=O)N[C@H](c1cn2ncc([C@H](NC(=O)CC3CC(F)(F)C3)C3CC3)cc2n1)[C@@H]1C[C@@H]2[C@H](C1)C2(F)F]

The title compound was prepared as described for the synthesis of Example 493, using N—((R)-(2-((S*)-amino((1R,3s,5S)-6,6-difluorobicyclo[3.1.0]hexan-3-yl)methyl)imidazo[1,2-b]pyridazin-7-yl)(cyclopropyl)methyl)-2-(3,3-difluorocyclobutyl)acetamide (Intermediate 386) in place of N—((R*)-(2-((S)-amino(4,4-difluorocyclohexyl)methyl)imidazo[1,2-b]pyridazin-7-yl)(cyclobutyl)methyl)-2-(3,3-difluorocyclobutyl)acetamide and 1-isopropyl-1H-pyrazole-5-carboxylic acid in place of 4-methyl-1,2,5-oxadiazole-3-carboxylic acid. ¹H NMR (500 MHz, DMSO-d₆) δ 8.79 (d, J=8.9 Hz, 1H), 8.58 (d, J=7.8 Hz, 1H), 8.48 (d, J=2.1 Hz, 1H), 8.14 (s, 1H), 7.93-7.89 (m, 1H), 7.48 (d, J=2.0 Hz, 1H), 6.90 (d, J=2.0 Hz, 1H), 5.38 (hept, J=6.6 Hz, 1H), 5.09 (t, J=9.0 Hz, 1H), 4.26 (t, J=8.4 Hz, 1H), 2.77-2.56 (m, 3H), 2.43-2.22 (m, 5H), 2.17-2.02 (m, 3H), 1.99-1.77 (m, 3H), 1.36 (d, J=6.6 Hz, 3H), 1.32 (d, J=6.6 Hz, 3H), 1.26-1.14 (m, 1H), 0.64-0.31 (m, 4H). MS (ESI) m/z: [M+H]⁺ Found 602.3.

Example 405

N—((S*)-(7-((R)-Cyclopropyl(2-(3,3-difluorocyclobutyl)acetamido)methyl)imidazo[1,2-b]pyridazin-2-yl)((1R,3s,5S)-6,6-difluorobicyclo[3.1.0]hexan-3-yl)methyl)-4-methyl-1,2,5-oxadiazole-3-carboxamide

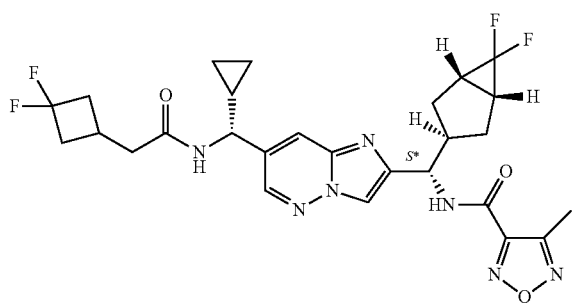 [SMILES: Cc1nonc1C(=O)N[C@H](c1cn2ncc([C@H](NC(=O)CC3CC(F)(F)C3)C3CC3)cc2n1)[C@@H]1C[C@@H]2[C@H](C1)C2(F)F]

The title compound was prepared as described for the synthesis of Example 493, using N—((R)-(2-((S*)-amino((1R,3s,5S)-6,6-difluorobicyclo[3.1.0]hexan-3-yl)methyl)imidazo[1,2-b]pyridazin-7-yl)(cyclopropyl)methyl)-2-(3,3-difluorocyclobutyl)acetamide (Intermediate 386) in place of N—((R*)-(2-((S)-amino(4,4-difluorocyclohexyl)methyl)imidazo[1,2-b]pyridazin-7-yl)(cyclobutyl)methyl)-2-(3,3-difluorocyclobutyl)acetamide. ¹H NMR (500 MHz, DMSO-d₆) δ 9.52 (d, J=8.8 Hz, 1H), 8.58 (d, J=7.8 Hz, 1H), 8.49 (d, J=2.0 Hz, 1H), 8.18 (s, 1H), 7.93 (d, J=2.0 Hz, 1H), 5.13 (t, J=8.9 Hz, 1H), 4.27 (t, J=8.4 Hz, 1H), 2.77-2.56 (m, 3H), 2.47-2.22 (m, 8H), 2.19-2.04 (m, 3H), 2.00-1.91 (m, 1H), 1.90-1.76 (m, 2H), 1.29-1.15 (m, 1H), 0.62-0.31 (m, 4H). MS (ESI) m/z: [M+H]⁺ Found 576.3.

Example 406

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-4-(dimethylamino)-1,2,5-oxadiazole-3-carboxamide

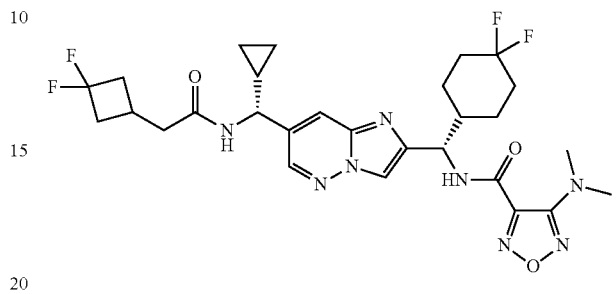

To a mixture of 4-(dimethylamino)-1,2,5-oxadiazole-3-carboxylic acid (25 mg, 0.16 mmol, Intermediate 389) and HATU (91 mg, 0.24 mmol) in DCM (5 mL) was added DIPEA (140 µL, 0.8 mmol) and the resulting mixture stirred at rt for 1 h. Then, N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide (75 mg, 0.16 mmol, Intermediate 171) was added and the mixture stirred at rt overnight. The reaction was diluted with DCM (10 mL), washed with water (15 mL) followed by brine (20 mL), dried over anhydrous Na₂SO₄, filtered and concentrated to dryness. The residue was purified by silica gel chromatography (0-2% MeOH/DCM) followed by preparative HPLC (Phenomenex Gemini-NX, 150×30 mm, 5 µm, 45-75% ACN/water (0.05% NH₄OH)) to provide the title compound as a white solid. ¹H NMR (400 MHz, DMSO-d₆) δ 9.67 (d, J=8.8 Hz, 1H), 8.69 (d, J=7.2 Hz, 1H), 8.51 (d, J=1.2 Hz, 1H), 8.18 (s, 1H), 7.93 (s, 1H), 5.18 (t, J=8.4 Hz, 1H), 4.26 (t, J=8.4 Hz, 1H), 2.87 (s, 6H), 2.73-2.58 (m, 2H), 2.43-2.25 (m, 5H), 2.20-2.10 (m, 1H), 2.08-1.94 (m, 2H), 1.89-1.69 (m, 3H), 1.67-1.57 (m, 1H), 1.43-1.19 (m, 3H), 0.64-0.44 (m, 3H), 0.42-0.33 (m, 1H). MS (ESI) m/z: [M+H]⁺ Found 607.2.

Example 407

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-4-((3-fluoroazetidin-1-yl)methyl)-1,2,5-oxadiazole-3-carboxamide

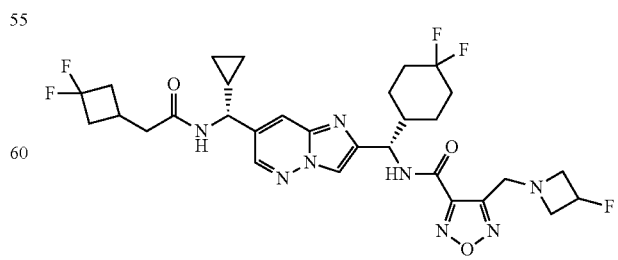

To a mixture of 4-((3-fluoroazetidin-1-yl)methyl)-1,2,5-oxadiazole-3-carboxylic acid (23 mg, 0.11 mmol, Intermediate 393), HATU (34 mg, 0.09 mmol), DIPEA (39 μL, 0.22 mmol) and DMF (1.5 mL) was added N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide (35 mg, 0.08 mmol, Intermediate 171). The resulting mixture was stirred at rt overnight, then purified by preparative HPLC (Boston Prime C18, 150×30 mm, 5 μm, 48 to 78% ACN/water (0.05% NH$_4$OH+10 mM NH$_4$HCO$_3$) to provide the title compound as a white solid. $^1$H NMR (400 MHz, DMSO-d$_6$) δ 10.28 (d, J=8.8 Hz, 1H), 8.61 (d, J=8.0 Hz, 1H), 8.51 (d, J=2.4 Hz, 1H), 8.26 (s, 1H), 7.93 (d, J=1.6 Hz, 1H), 5.37-5.10 (m, 2H), 4.29-4.24 (m, 1H), 4.04 (s, 2H), 3.71-3.63 (m, 2H), 3.31 (s, 2H), 2.70-2.60 (m, 2H), 2.40-2.39 (m, 2H), 2.34-2.27 (m, 2H), 2.20-2.14 (m, 1H), 2.03-1.97 (m, 2H), 1.92-1.75 (m, 3H), 1.66-1.58 (m, 1H), 1.38-1.29 (m, 2H), 1.24-1.20 (m, 2H), 0.59-0.46 (m, 3H), 0.39-0.35 (m, 1H). MS (ESI) m/z: [M+H]$^+$ Found 651.3.

Example 408

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-4-morpholino-1,2,5-oxadiazole-3-carboxamide

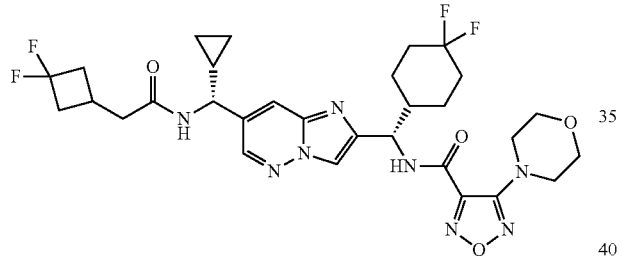

DIPEA (0.09 mL, 0.51 mmol) was added to a mixture of 4-morpholino-1,2,5-oxadiazole-3-carboxylic acid (31 mg, 0.16 mmol, Intermediate 396) and 1-propanephosphonic anhydride (245 mg, 0.38 mmol, 50% in TIF) in DCM (1 mL), and the resulting mixture was stirred at 30° C. for 30 min. Then, N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide (60 mg, 0.13 mmol, Intermediate 171) was added and the mixture stirred at 30° C. overnight. After that time, the mixture was partitioned between water (20 mL) and DCM (20 mL) and the aqueous further extracted with DCM (3×50 mL). The organic layers were combined, washed with water (20 mL) and brine (20 mL), dried over anhydrous Na$_2$SO$_4$, filtered and concentrated to dryness. The residue was purified by silica gel chromatography (0-10% MeOH/DCM) to provide the title compound as a yellow solid. $^1$H NMR (400 MHz, DMSO-d$_6$) δ 9.64 (d, J=8.8 Hz, 1H), 8.63 (d, J=7.6 Hz, 1H), 8.52 (d, J=2.0 Hz, 1H), 8.19 (s, 1H), 7.94 (s, 1H), 5.13 (t, J=8.4 Hz, 1H), 4.27 (t, J=8.4 Hz, 1H), 3.64-3.55 (m, 4H), 3.24-3.17 (m, 4H), 2.72-2.57 (m, 2H), 2.42-2.38 (m, 2H), 2.36-2.22 (m, 2H), 2.20-2.10 (m, 1H), 2.08-1.94 (m, 2H), 1.92-1.68 (m, 3H), 1.65-1.56 (m, 1H), 1.44-1.13 (m, 4H), 0.64-0.44 (m, 3H), 0.41-0.32 (m, 1H). MS (ESI) m/z: [M+H]$^+$ Found 649.3.

Example 409

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-4-methoxy-1,2,5-oxadiazole-3-carboxamide

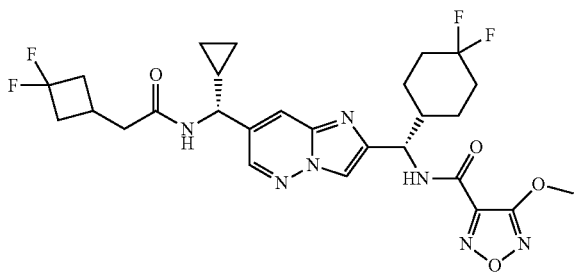 [SMILES: COc1nonc1C(=O)N[C@H](c1cn2ncc([C@H](NC(=O)CC3CC(F)(F)C3)C3CC3)cc2n1)C1CCC(F)(F)CC1]

The title compound was prepared as described for the synthesis of Example 408 using 4-methoxy-1,2,5-oxadiazole-3-carboxylic acid (Intermediate 399) in place of 4-morpholino-1,2,5-oxadiazole-3-carboxylic acid. The crude residue was purified by silica gel chromatography (0-2% MeOH/DCM) to provide the title compound as a white solid. $^1$H NMR (400 MHz, DMSO-d$_6$) δ 9.31 (d, J=8.8 Hz, 1H), 8.62 (d, J=8.0 Hz, 1H), 8.51 (d, J=2.0 Hz, 1H), 8.20 (s, 1H), 7.95 (d, J=1.6 Hz, 1H), 5.16 (t, J=8.4 Hz, 1H), 4.28 (t, J=8.4 Hz, 1H), 4.09 (s, 3H), 2.72-2.56 (m, 2H), 2.44-2.23 (m, 5H), 2.21-2.10 (m, 1H), 2.09-1.93 (m, 2H), 1.90-1.68 (m, 3H), 1.64-1.56 (m, 1H), 1.44-1.16 (m, 3H), 0.63-0.44 (m, 3H), 0.41-0.34 (m, 1H). MS (ESI) m/z: [M+H]$^+$ Found 594.2.

Example 410

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-4-(2-hydroxypropan-2-yl)-1,2,5-oxadiazole-3-carboxamide

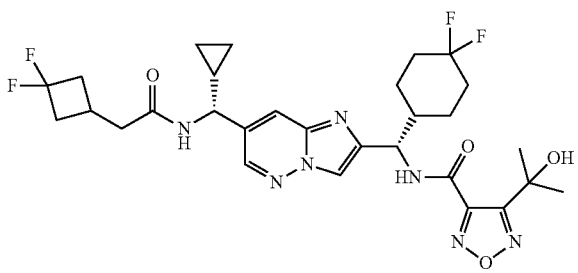 [SMILES: CC(C)(O)c1nonc1C(=O)N[C@H](c1cn2ncc([C@H](NC(=O)CC3CC(F)(F)C3)C3CC3)cc2n1)C1CCC(F)(F)CC1]

To a mixture of 6,6-dimethyl-4H,6H-furo[3,4-c][1,2,5]oxadiazol-4-one (30 mg, 0.19 mmol, Intermediate 350) and TBD (8.1 mg, 0.06 mmol) in THF (2 mL) was added N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide (109 mg, 0.23 mmol, Intermediate 171) and the resulting mixture stirred at 75° C. overnight. The reaction mixture was concentrated to dryness and the residue purified by preparative HPLC (Phenomenex Gemini-NX, 150×30 mm, 5 μm, 42-72% ACN/water (0.05% NH$_4$OH)). The pure material was suspended in water (10 mL), frozen in dry ice/EtOH and lyophilized to dryness to

Example 411

4-Cyclopropyl-N—((S)-(7-((R)-cyclopropyl(3-cyclopropyl-2,2-difluoropropanamido)methyl)imidazo[1,2-b]pyridazin-2-yl)(4,4-difluorocyclohexyl)methyl)-1,2,5-oxadiazole-3-carboxamide

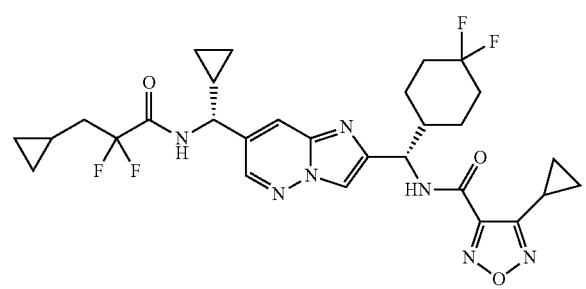 [SMILES: O=C(N[C@H](c1cn2ncc([C@H](NC(=O)C(F)(F)CC3CC3)C3CC3)cc2n1)C1CCC(F)(F)CC1)c1nonc1C1CC1]

The title compound was prepared as described for the synthesis of Example 322 using N—((R)-(2-((S)-amino(4,4-difluorocyclohexyl)methyl)imidazo[1,2-b]pyridazin-7-yl)(cyclopropyl)methyl)-3-cyclopropyl-2,2-difluoropropanamide (Intermediate 401) in place of N-((1S,2S)-1-(2-((S)-amino(4,4-difluorocyclohexyl)methyl)imidazo[1,2-b]pyridazin-7-yl)-2-methoxypropyl)-2-(3,3-difluorocyclobutyl)acetamide hydrochloride and 4-cyclopropyl-1,2,5-oxadiazole-3-carboxylic acid (Intermediate 570) in place of 1-isopropyl-1H-pyrazole-5-carboxylic acid. The residue was purified by silica gel chromatography (0-25% EtOAc/petroleum ether) to provide the title compound as a white solid. The residue was purified by preparative HPLC (Boston Prime C18, 150×30 mm, 5 μm, 50 to 80% ACN/water (0.05% aqueous $NH_3$+10 mM $NH_4HCO_3$)) to provide the title compound as a white solid. $^1$H NMR (400 MHz, DMSO-$d_6$) δ 9.55-9.47 (m, 2H), 8.59 (d, J=2.0 Hz, 1H), 8.25 (s, 1H), 8.03 (d, J=2.0 Hz, 1H), 5.25-5.14 (m, 1H), 4.32-4.20 (m, 1H), 2.32-2.24 (m, 1H), 2.22-2.13 (m, 1H), 2.05-1.71 (m, 7H), 1.66-1.56 (m, 1H), 1.51-1.36 (m, 2H), 1.30-1.23 (m, 1H), 1.15-1.09 (m, 1H), 1.15-1.09 (m, 1H), 0.99-0.94 (m, 2H), 0.70-0.50 (m, 4H), 0.46-0.37 (m, 2H), 0.36-0.29 (m, 1H), 0.14-0.02 (m, 2H). MS (ESI) m/z: [M+H]$^+$ Found 604.2.

provide the title compound as a white solid. $^1$H NMR (400 MHz, DMSO-$d_6$) δ 9.74-9.62 (m, 1H), 8.62 (d, J=7.6 Hz, 1H), 8.51 (d, J=2.0 Hz, 1H), 8.19 (s, 1H), 7.93 (d, J=1.6 Hz, 1H), 6.08 (s, 1H), 5.23 (s, 1H), 4.27 (t, J=8.6 Hz, 1H), 2.73-2.56 (m, 2H), 2.44-2.12 (m, 6H), 2.08-1.94 (m, 2H), 1.89-1.62 (m, 4H), 1.58 (s, 3H), 1.57 (s, 3H), 1.48-1.28 (m, 2H), 1.25-1.15 (m, 1H), 0.62-0.44 (m, 3H), 0.41-0.32 (m, 1H). MS (ESI) m/z: [M+H]$^+$ Found 622.2.

Example 412

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-4-hydroxy-1,2,5-oxadiazole-3-carboxamide

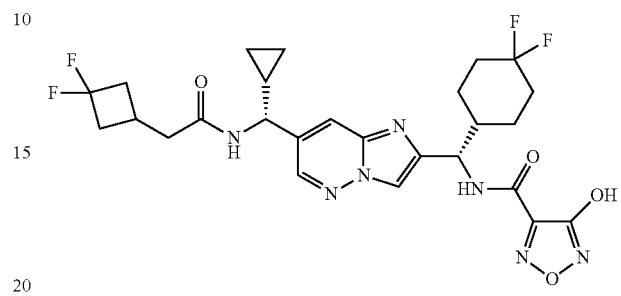

A mixture of N—((S)-(7-((R)-cyclopropyl(2-(3,3-difluorocyclobutyl)acetamido)methyl)imidazo[1,2-b]pyridazin-2-yl)(4,4-difluorocyclohexyl)methyl)-4-nitro-1,2,5-oxadiazole-3-carboxamide (50 mg, 0.08 mmol, Intermediate 405), NaOH (5 mg, 0.12 mmol) and THF/$H_2O$ (2:1, 6 mL) was stirred at 30° C. for 2 h. After that time, the mixture was diluted with water (20 mL) and extracted with EtOAc (3×10 mL). The organic layers were combined, washed with brine (10 mL), dried over anhydrous $Na_2SO_4$, filtered and concentrated to dryness. The residue was purified by preparative HPLC (Boston Prime C18, 150×30 mm, 5 μm, 20-50% ACN/water (0.05% of 25% aqueous $NH_3$+10 mM $NH_4HCO_3$)) to provide the title compound as a white solid. $^1$H NMR (400 MHz, DMSO-$d_6$) δ 9.36 (d, J=8.8 Hz, 1H), 8.67 (d, J=7.6 Hz, 1H), 8.50 (d, J=1.6 Hz, 1H), 8.20 (s, 1H), 7.94 (s, 1H), 5.19 (t, J=7.6 Hz, 1H), 4.26 (t, J=8.4 Hz, 1H), 2.73-2.59 (m, 1H), 2.44-2.35 (m, 4H), 2.34-2.25 (m, 2H), 2.18-2.10 (m, 1H), 2.05-1.96 (m, 2H), 1.87-1.72 (m, 3H), 1.65-1.57 (m, 1H), 1.43-1.24 (m, 4H), 0.65-0.51 (m, 2H), 0.51-0.41 (m, 1H), 0.41-0.29 (m, 1H). MS (ESI) m/z: [M+H]$^+$ Found 580.2.

Example 413

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-4-(difluoromethyl)-1,2,5-oxadiazole-3-carboxamide

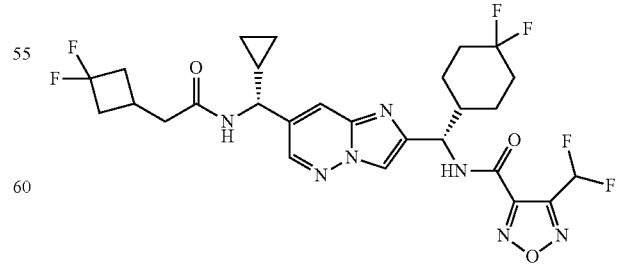

To a solution of N—((S)-(7-((R)-cyclopropyl(2-(3,3-difluorocyclobutyl)acetamido)methyl)imidazo[1,2-b]pyridazin-2-yl)(4,4-difluorocyclohexyl)methyl)-4-formyl-1, 2,5-oxadiazole-3-carboxamide (140 mg, 0.24 mmol, Intermediate 407) in anhydrous DCM (2 mL) at 0° C. was added DAST (0.06 mL, 0.5 mmol), and the resulting mixture was stirred for 2 h while warming to rt. After that time, the mixture was poured into saturated aqueous NaHCO$_3$ (50 mL) and extracted with DCM (2×30 mL). The organic layers were combined, washed with brine (50 mL), dried over anhydrous Na$_2$SO$_4$, filtered and concentrated to dryness. The residue was purified by preparative HPLC (Phenomenex Gemini-NX C18, 75×30 mm, 3 µm, 50 to 80% ACN/water (0.05% NH$_4$OH+10 mM NH$_4$HCO$_3$)) to provide the title compound as a white solid. $^1$H NMR (400 MHz, DMSO-d$_6$) δ 9.72 (d, J=8.8 Hz, 1H), 8.65 (d, J=7.6 Hz, 1H), 8.49 (d, J=2.0 Hz, 1H), 8.22 (s, 1H), 7.92 (d, J=2.0 Hz, 1H), 7.62-7.33 (m, 1H), 5.21-5.08 (m, 1H), 4.30-4.19 (m, 1H), 2.67-2.57 (m, 2H), 2.40-2.38 (m, 2H), 2.35-2.18 (m, 3H), 2.07-1.95 (m, 2H), 1.93-1.86 (m, 1H), 1.85-1.67 (m, 2H), 1.65-1.54 (m, 1H), 1.45-1.26 (m, 2H), 1.26-1.14 (m, 2H), 0.61-0.43 (m, 3H), 0.40-0.32 (m, 1H). MS (ESI) m/z: [M+H]$^+$ Found 614.2.

Example 414

5-Cyclopropyl-N—((S)-(7-((R)-cyclopropyl(4,4,4-trifluorobutanamido)methyl)imidazo[1,2-b]pyridazin-2-yl)(4,4-difluorocyclohexyl)methyl)nicotinamide

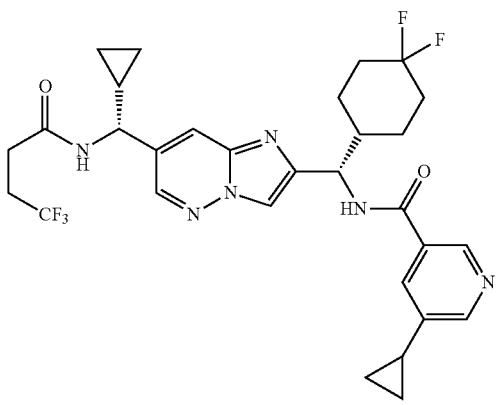 [SMILES: O=C(CCC(F)(F)F)N[C@@H](c1cnn2cc([C@@H](NC(=O)c3cncc(C4CC4)c3)C3CCC(F)(F)CC3)nc2c1)C1CC1]

The title compound was prepared as described for the synthesis of Example 48, using 5-cyclopropylnicotinic acid in place of 1-(cyclopropylmethyl)-1H-1,2,3-triazole-5-carboxylic acid to provide the title compound. $^1$H NMR (600 MHz, DMSO-d$_6$) δ 9.04 (d, J=8.7 Hz, 1H), 8.87 (d, J=2.0 Hz, 1H), 8.76 (d, J=7.6 Hz, 1H), 8.60 (dd, J=21.5, 2.1 Hz, 2H), 8.32 (s, 1H), 8.05-7.91 (m, 2H), 5.31-5.10 (m, 1H), 4.39-4.26 (m, 1H), 2.49-2.42 (m, 4H), 2.25-2.15 (m, 1H), 2.13-1.55 (m, 8H), 1.45-1.17 (m, 2H), 1.10-1.03 (m, 2H), 0.88 (dt, J=6.8, 4.5 Hz, 2H), 0.65-0.33 (m, 4H). MS (ESI) m/z: [M+H]$^+$ Found, 605.2.

Example 415

N—((S)-(7-((R)-Cyclopropyl(4,4,4-trifluorobutanamido)methyl)imidazo[1,2-b]pyridazin-2-yl)(4,4-difluorocyclohexyl)methyl)-5-isopropylnicotinamide

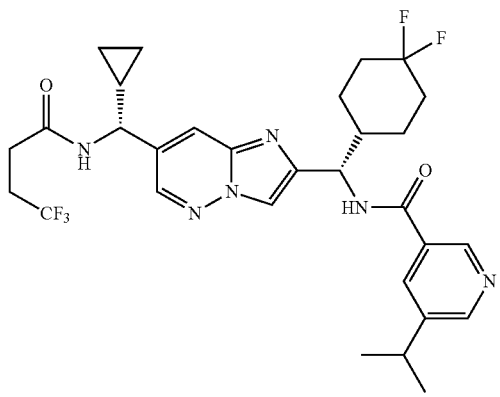 [SMILES: CC(C)c1cncc(C(=O)N[C@H](c2cn3ncc([C@H](NC(=O)CCC(F)(F)F)C4CC4)cc3n2)C2CCC(F)(F)CC2)c1]

The title compound was prepared as described for the synthesis of Example 48, using 5-isopropylnicotinic acid in place of 1-(cyclopropylmethyl)-1H-1,2,3-triazole-5-carboxylic acid to provide the title compound. $^1$H NMR (600 MHz, DMSO-d$_6$) δ 9.06 (d, J=8.7 Hz, 1H), 8.95 (d, J=2.1 Hz, 1H), 8.80-8.68 (m, 2H), 8.57 (d, J=2.1 Hz, 1H), 8.34-8.24 (m, 2H), 8.05-7.92 (m, 1H), 5.30-5.20 (m, 1H), 4.37-4.26 (m, 1H), 3.16-3.00 (m, 1H), 2.50-2.43 (m, 6H), 2.31-2.17 (m, 1H), 2.11-1.90 (m, 2H), 1.88-1.71 (m, 2H), 1.71-1.59 (m, 1H), 1.48-1.35 (m, 1H), 1.35-1.14 (m, 7H), 0.64-0.46 (m, 3H), 0.42-0.33 (m, 1H). MS (ESI) m/z: [M+H]$^+$ Found, 607.3.

Example 416

5-Cyclobutyl-N—((S)-(7-((R)-cyclopropyl(4,4,4-trifluorobutanamido)methyl)imidazo[1,2-b]pyridazin-2-yl)(4,4-difluorocyclohexyl)methyl)nicotinamide

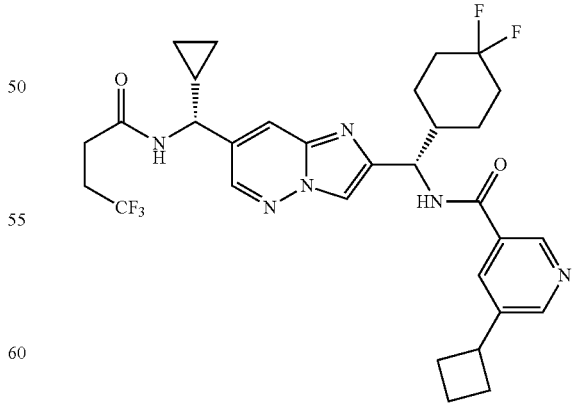

The title compound was prepared as described for the synthesis of Example 48, using 5-cyclobutylnicotinic acid in place of 1-(cyclopropylmethyl)-1H-1,2,3-triazole-5-carboxylic acid to provide the title compound. $^1$H NMR (600 MHz, DMSO-d$_6$) δ 9.06 (d, J=8.8 Hz, 1H), 8.92 (d, J=2.1 Hz, 1H), 8.75 (d, J=7.6 Hz, 1H), 8.65 (d, J=2.1 Hz, 1H), 8.57 (d, J=2.1 Hz, 1H), 8.30 (s, 1H), 8.24 (d, J=2.1 Hz, 1H), 7.98 (d, J=2.0 Hz, 1H), 5.25-5.16 (m, 1H), 4.33-4.25 (m, 1H), 3.71-3.55 (m, 1H), 2.51-2.42 (m, 6H), 2.41-2.29 (m, 2H), 2.31-2.12 (m, 3H), 2.12-1.57 (m, 6H), 1.45-1.16 (m, 3H), 0.64-0.32 (m, 4H). MS (ESI) m/z: [M+H]$^+$ Found, 619.3.

Example 417

N—((S)-(7-((R)-Cyclopropyl(4,4,4-trifluorobutanamido)methyl)imidazo[1,2-b]pyridazin-2-yl)(4,4-difluorocyclohexyl)methyl)-5-(difluoromethoxy)nicotinamide

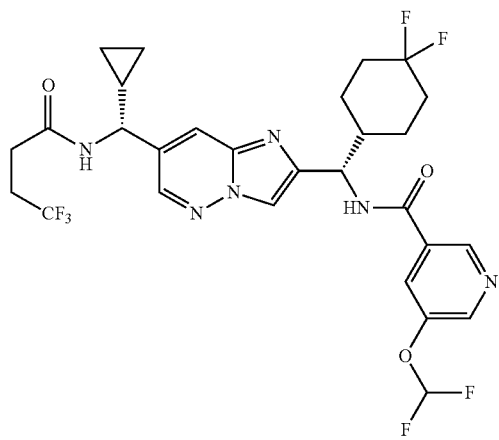 [SMILES: O=C(CCC(F)(F)F)N[C@@H](c1cnn2cc([C@@H](NC(=O)c3cncc(OC(F)F)c3)C3CCC(F)(F)CC3)nc2c1)C1CC1]

The title compound was prepared as described for the synthesis of Example 48, using 5-(difluoromethoxy)nicotinic acid in place of 1-(cyclopropylmethyl)-1H-1,2,3-triazole-5-carboxylic acid to provide the title compound. $^1$H NMR (600 MHz, DMSO-d$_6$) δ 9.12 (d, J=8.7 Hz, 1H), 8.95 (d, J=1.7 Hz, 1H), 8.78 (d, J=7.6 Hz, 1H), 8.64 (dd, J=13.6, 2.4 Hz, 2H), 8.36 (s, 1H), 8.11-8.05 (m, 1H), 8.02 (d, J=1.9 Hz, 1H), 7.54-7.21 (m, 1H), 5.26-5.17 (m, 1H), 4.34-4.23 (m, 1H), 2.50-2.42 (m, 3H), 2.28-2.14 (m, 1H), 2.13-1.61 (m, 7H), 1.46-1.14 (m, 3H), 0.66-0.33 (m, 4H). MS (ESI) m/z: [M+H]$^+$ Found, 631.2.

Example 418

N—((S)-(7-((R)-Cyclopropyl(4,4,4-trifluorobutanamido)methyl)imidazo[1,2-b]pyridazin-2-yl)(4,4-difluorocyclohexyl)methyl)-6-methylpyridazine-4-carboxamide

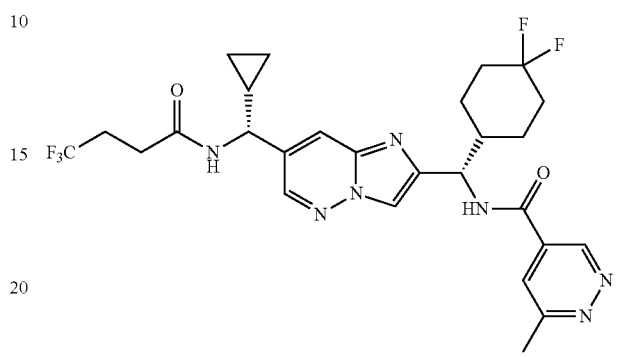

The title compound was prepared as described for the synthesis of Example 38, using 6-methylpyridazine-4-carboxylic acid in place of 1-(3,3,3-trifluoropropyl)-1H-1,2,4-triazole-5-carboxylic acid. $^1$H NMR (500 MHz, CD$_3$OD) δ 9.36 (d, J=2.2 Hz, 1H), 8.47 (d, J=2.1 Hz, 1H), 8.13 (s, 1H), 7.95 (d, J=2.1 Hz, 1H), 7.88 (s, 1H), 5.28 (d, J=8.5 Hz, 1H), 4.27 (d, J=9.5 Hz, 1H), 2.77 (s, 3H), 2.55-2.57 (m, 2H), 2.47-2.49 (m, 2H), 2.24-2.27 (m, 1H), 2.09-2.11 (m, 1H), 2.00-2.02 (m, 2H), 1.78-1.80 (m, 2H), 1.66-1.69 (m, 1H), 1.49-1.52 (m, 1H), 1.39-1.42 (m, 1H), 1.25-1.28 (m, 1H), 0.69-0.71 (m, 2H), 0.48-0.50 (m, 2H). MS (ESI) m/z: [M+H]$^+$ Found 580.2.

Example 419

N—((S)-(7-((R)-Cyclopropyl(4,4,4-trifluorobutanamido)methyl)imidazo[1,2-b]pyridazin-2-yl)(4,4-difluorocyclohexyl)methyl)-3-(2,2,2-trifluoroethoxy)picolinamide

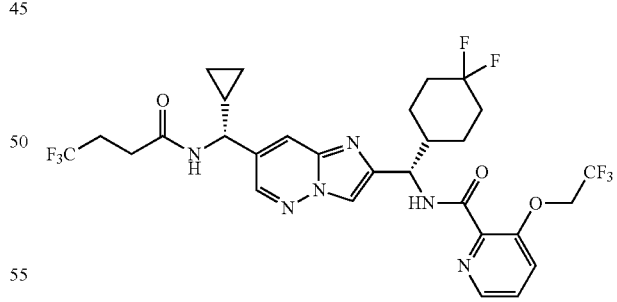

The title compound was prepared as described for the synthesis of Example 38, using 3-(2,2,2-trifluoroethoxy)picolinic acid in place of 1-(3,3,3-trifluoropropyl)-1H-1,2,4-triazole-5-carboxylic acid. $^1$H NMR (500 MHz, CD$_3$OD) δ 8.47 (d, J=2.1 Hz, 1H), 8.29 (d, J=4.7 Hz, 1H), 8.11 (s, 1H), 7.86-7.87 (m, 1H), 7.69 (d, J=8.2 Hz, 1H), 7.51-7.54 (m, 1H), 5.31 (d, J=8.1 Hz, 1H), 4.67-4.69 (m, 2H), 4.28 (d, J=9.5 Hz, 1H), 2.55-2.57 (m, 2H), 2.48-2.50 (m, 2H), 2.20-2.22 (m, 1H), 2.05-2.07 (m, 1H), 1.99-2.01 (m, 2H), 1.77-1.79 (m, 2H), 1.68-1.69 (m, 1H), 1.53-1.55 (m, 1H), 1.46-1.48 (m, 1H), 1.25-1.27 (m, 1H), 0.69-0.71 (m, 2H), 0.48-0.50 (m, 2H). MS (ESI) m/z: [M+H]+ Found 663.2.

Example 420

N—((S)-(7-((R*)-1-(2-(3,3-Difluorocyclobutyl)acetamido)-2,2-difluoroethyl)imidazo[1,2-b]pyridazin-2-yl)(4,4-difluorocyclohexyl)methyl)-1-isopropyl-1H-pyrazole-5-carboxamide

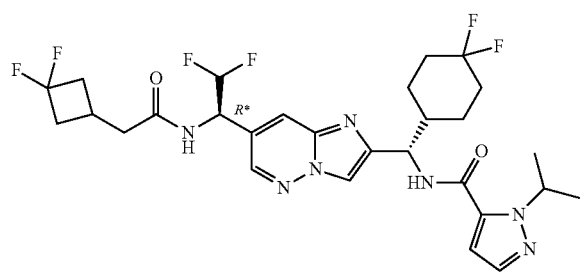 [SMILES: CC(C)n1nccc1C(=O)N[C@H](c1cn2ncc([C@@H](NC(=O)CC3CC(F)(F)C3)C(F)F)cc2n1)C1CCC(F)(F)CC1]

The title compound was prepared as described for the synthesis of Example 513 using N-(1-(2-((S)-amino(4,4-difluorocyclohexyl)methyl)imidazo[1,2-b]pyridazin-7-yl)-2,2-difluoroethyl)-2-(3,3-difluorocyclobutyl)acetamide (Intermediate 526) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide, and 1-isopropyl-1H-pyrazole-5-carboxylic acid in place of 4-methyl-1,2,5-oxadiazole-3-carboxylic acid. An additional purification step was performed by SFC using a chiral stationary phase (Regis (S,S) Whelk-O® 1, 20:80 MeOH/CO2) afforded the title compound (second-eluting isomer) as a white powder. MS (ESI) m/z: [M+H]+ Found 614.2.

Example 421

4-Cyclopropyl-N—((S)-(7-((S*)-1-(2-(3,3-difluorocyclobutyl)acetamido)-2,2,2-trifluoroethyl)imidazo[1,2-b]pyridazin-2-yl)(4,4-difluorocyclohexyl)methyl)-1,2,5-oxadiazole-3-carboxamide

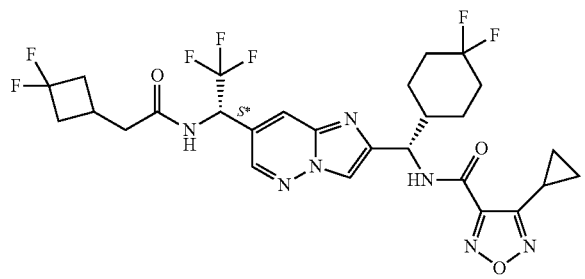 [SMILES: O=C(CC1CC(F)(F)C1)N[C@@H](c1cnn2cc([C@@H](NC(=O)c3nonc3C3CC3)C3CCC(F)(F)CC3)nc2c1)C(F)(F)F]

The title compound was prepared as described for the synthesis of Example 513 using N—((S*)-1-(2-((S)-amino(4,4-difluorocyclohexyl)methyl)imidazo[1,2-b]pyridazin-7-yl)-2,2,2-trifluoroethyl)-2-(3,3-difluorocyclobutyl)acetamide (Intermediate 530) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide, and 4-cyclopropyl-1,2,5-oxadiazole-3-carboxylic acid (Intermediate 570) in place of 4-methyl-1,2,5-oxadiazole-3-carboxylic acid. The crude product was purified by preparative HPLC (Waters XSelect CSH 5 μm C18, 19×100 mm, 45-80% MeCN/H2O (with 0.16% TFA)). The combined product-containing fractions were lyophilized to afford the title compound as a white powder. 1H NMR (500 MHz, DMSO-d6) δ 9.52 (d, J=9.0 Hz, 1H), 9.27 (d, J=9.6 Hz, 1H), 8.72 (d, J=1.9 Hz, 1H), 8.36 (d, J=1.8 Hz, 1H), 8.35 (s, 1H), 6.10 (m, 1H), 5.24-5.18 (m, 1H), 2.73-2.59 (m, 2H), 2.57-2.51 (m, 2H), 2.46-2.39 (m, 1H), 2.37-2.23 (m, 3H), 2.22-2.14 (m, 1H), 2.06-1.94 (m, 2H), 1.90 (m, 1H), 1.85-1.69 (m, 2H), 1.61 (m, 1H), 1.45-1.35 (m, 1H), 1.34-1.23 (m, 1H), 1.15-1.07 (m, 2H), 0.99-0.92 (m, 2H). MS (ESI) m/z: [M+H]+ Found 632.2.

Example 422

N—((S)-(7-((S*)-1-(2-(3,3-Difluorocyclobutyl)acetamido)-2,2,2-trifluoroethyl)imidazo[1,2-b]pyridazin-2-yl)(4,4-difluorocyclohexyl)methyl)-1-isopropyl-1H-pyrazole-5-carboxamide

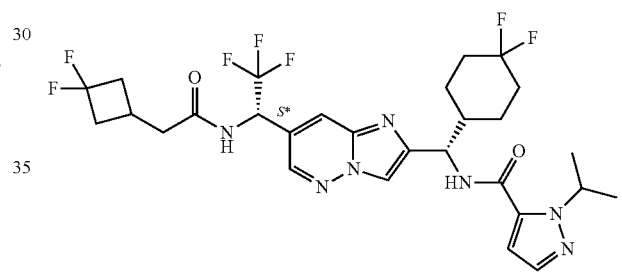

The title compound was prepared as described for the synthesis of Example 513 using N—((S*)-1-(2-((S)-amino(4,4-difluorocyclohexyl)methyl)imidazo[1,2-b]pyridazin-7-yl)-2,2,2-trifluoroethyl)-2-(3,3-difluorocyclobutyl)acetamide (Intermediate 530) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide, and 1-isopropyl-1H-pyrazole-5-carboxylic acid in place of 4-methyl-1,2,5-oxadiazole-3-carboxylic acid. The crude product was purified by preparative HPLC (Waters XSelect CSH 5 μm C18, 19×100 mm, 40-75% MeCN/H2O (with 0.16% TFA)). The combined fractions were lyophilized to afford the title compound as a white powder. 1H NMR (500 MHz, DMSO-d6) δ 9.27 (d, J=9.5 Hz, 1H), 8.75 (d, J=9.1 Hz, 1H), 8.72 (d, J=2.0 Hz, 1H), 8.35 (d, J=1.9 Hz, 1H), 8.33 (s, 1H), 7.49 (d, J=2.0 Hz, 1H), 6.91 (d, J=2.0 Hz, 1H), 6.10 (m, 1H), 5.35 (m, 1H), 5.23-5.17 (m, 1H), 2.73-2.58 (m, 2H), 2.57-2.51 (m, 2H), 2.46-2.38 (m, 1H), 2.37-2.24 (m, 2H), 2.22-2.11 (m, 1H), 2.06-1.93 (m, 2H), 1.88 (m, 1H), 1.84-1.69 (m, 2H), 1.61 (m, 1H), 1.43-1.37 (m, 1H), 1.36 (d, J=6.5 Hz, 3H), 1.32 (d, J=6.6 Hz, 3H), 1.30-1.20 (m, 1H). MS (ESI) m/z: [M+H]+ Found 632.3.

Example 423

N—((S)-(7-((S*)-(1-Cyanocyclopropyl)(2-(3,3-difluorocyclobutyl)acetamido)methyl)imidazo[1,2-b]pyridazin-2-yl)(4,4-difluorocyclohexyl)methyl)-4-methyl-1,2,5-oxadiazole-3-carboxamide

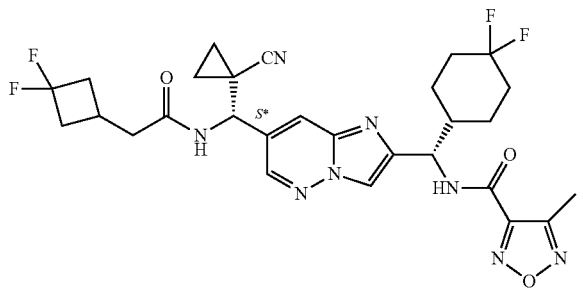 [SMILES: Cc1nonc1C(=O)N[C@H](c1cn2ncc([C@H](NC(=O)CC3CC(F)(F)C3)C3(C#N)CC3)cc2n1)C1CCC(F)(F)CC1]

The title compound was prepared as described for the synthesis of Example 513 using N—((S*)-(2-((S)-amino(4,4-difluorocyclohexyl)methyl)imidazo[1,2-b]pyridazin-7-yl)(1-cyanocyclopropyl)methyl)-2-(3,3-difluorocyclobutyl)acetamide (Intermediate 540) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide. The crude product was purified by preparative HPLC (Waters XBridge BEH 5 μm C18, 19×100 mm, 40-75% MeCN/H$_2$O (with 0.16% NH$_4$OH)). Product containing fractions were concentrated to dryness to afford the title compound as a white powder. $^1$H NMR (500 MHz, DMSO-d$_6$) δ 9.43 (d, J=9.0 Hz, 1H), 8.99 (d, J=8.0 Hz, 1H), 8.60 (d, J=2.2 Hz, 1H), 8.31 (s, 1H), 8.14 (m, 1H), 5.22-5.16 (m, 1H), 4.81 (d, J=8.0 Hz, 1H), 2.74-2.59 (m, 2H), 2.47 (m, 7H), 2.20 (m, 1H), 2.10-1.94 (m, 2H), 1.91 (m, 1H), 1.86-1.70 (m, 2H), 1.63 (m, 1H), 1.48 (m, 1H), 1.45-1.18 (m, 5H). MS (ESI) m/z: [M+H]$^+$ Found 603.2.

Example 424

N—((S)-(7-((S*)-(1-Cyanocyclopropyl)(2-(3,3-difluorocyclobutyl)acetamido)methyl)imidazo[1,2-b]pyridazin-2-yl)(4,4-difluorocyclohexyl)methyl)-4-cyclopropyl-1,2,5-oxadiazole-3-carboxamide

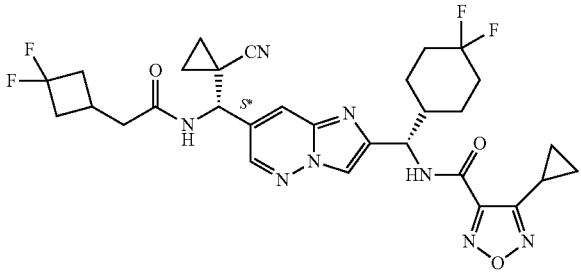 [SMILES: N#CC1([C@@H](NC(=O)CC2CC(F)(F)C2)c2cnn3cc([C@@H](NC(=O)c4nonc4C4CC4)C4CCC(F)(F)CC4)nc3c2)CC1]

The title compound was prepared as described for the synthesis of Example 513 using N—((S*)-(2-((S)-amino(4,4-difluorocyclohexyl)methyl)imidazo[1,2-b]pyridazin-7-yl)(1-cyanocyclopropyl)methyl)-2-(3,3-difluorocyclobutyl)acetamide (Intermediate 540) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide, and 4-cyclopropyl-1,2,5-oxadiazole-3-carboxylic acid (Intermediate 570) in place of 4-methyl-1,2,5-oxadiazole-3-carboxylic acid. Purification was done by preparative HPLC (Waters XBridge BEH C18, 5 μm, 19×100 mm, 40-75% MeCN/H$_2$O (with 0.16% NH$_4$OH)). Product containing fractions were concentrated to dryness to afford the title compound as a white powder. $^1$H NMR (500 MHz, DMSO-d$_6$) δ 9.50 (d, J=9.0 Hz, 1H), 8.99 (d, J=8.0 Hz, 1H), 8.61 (d, J=2.2 Hz, 1H), 8.30 (s, 1H), 8.14 (dd, J=2.1, 1.1 Hz, 1H), 5.24-5.19 (m, 1H), 4.84-4.78 (m, 1H), 2.74-2.61 (m, 2H), 2.46-2.25 (m, 5H), 2.20 (m, 1H), 2.07-1.95 (m, 2H), 1.91 (m, 1H), 1.86-1.71 (m, 2H), 1.64 (mz, 1H), 1.52-1.46 (m, 1H), 1.43-1.25 (m, 4H), 1.21 (m, 1H), 1.15-1.09 (m, 2H), 0.96 (m, 2H). MS (ESI) m/z: [M+H]$^+$ Found 629.3.

Example 425

N—((S)-(7-((S*)-(1-Cyanocyclopropyl)(2-(3,3-difluorocyclobutyl)acetamido)methyl)imidazo[1,2-b]pyridazin-2-yl)(4,4-difluorocyclohexyl)methyl)-4-(2,2-difluoroethoxy)-1,2,5-oxadiazole-3-carboxamide

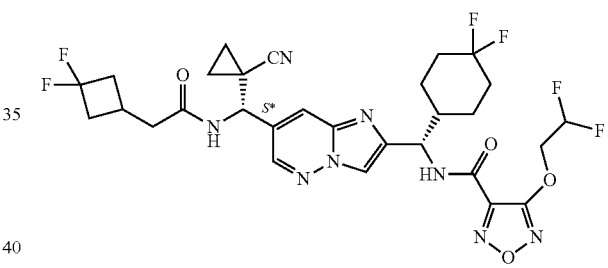

The title compound was prepared as described for the synthesis of Example 513 using N—((S*)-(2-((S)-amino(4,4-difluorocyclohexyl)methyl)imidazo[1,2-b]pyridazin-7-yl)(1-cyanocyclopropyl)methyl)-2-(3,3-difluorocyclobutyl)acetamide (Intermediate 540) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide, and 4-(2,2-difluoroethoxy)-1,2,5-oxadiazole-3-carboxylic acid (Intermediate 330) in place of 4-methyl-1,2,5-oxadiazole-3-carboxylic acid. Purification was done by preparative HPLC (Waters XBridge BEH 5 μm C18, 19×100 mm, 40-75% MeCN/H$_2$O (with 0.16% NH$_4$OH)). Product containing fractions were concentrated to dryness to afford the title compound as a white powder. $^1$H NMR (500 MHz, DMSO-d$_6$) δ 9.37 (d, J=8.9 Hz, 1H), 8.99 (d, J=8.0 Hz, 1H), 8.61 (d, J=2.2 Hz, 1H), 8.27 (s, 1H), 8.14-8.13 (m, 1H), 6.43 (m, 1H), 5.21-5.17 (m, 1H), 4.82 (m, 1H), 4.75-4.66 (m, 2H), 2.67 (m, 2H), 2.47-2.26 (m, 4H, masked by DMSO peak), 2.16 (m, 1H), 2.07-1.95 (m, 2H), 1.93-1.70 (m, 3H), 1.64 (m, 1H), 1.52-1.44 (m, 1H), 1.44-1.25 (m, 4H), 1.21 (m, 1H). MS (ESI) m/z: [M+H]$^+$ Found 669.2.

Example 426

N—((S)-(7-((S*)-(1-Cyanocyclopropyl)(2-(3,3-difluorocyclobutyl)acetamido)methyl)imidazo[1,2-b]pyridazin-2-yl)(4,4-difluorocyclohexyl)methyl)-1-isopropyl-1H-pyrazole-5-carboxamide

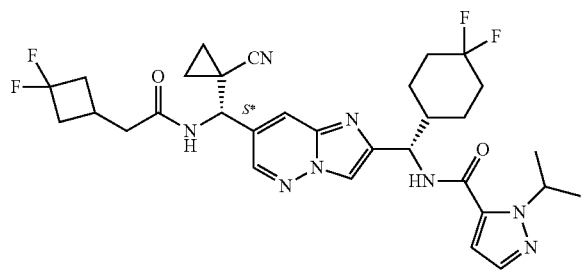 [SMILES: CC(C)n1nccc1C(=O)N[C@H](c1cn2ncc([C@H](NC(=O)CC3CC(F)(F)C3)C3(C#N)CC3)cc2n1)C1CCC(F)(F)CC1]

The title compound was prepared as described for the synthesis of Example 513 using N—((S*)-(2-((S)-amino(4,4-difluorocyclohexyl)methyl)imidazo[1,2-b]pyridazin-7-yl)(1-cyanocyclopropyl)methyl)-2-(3,3-difluorocyclobutyl)acetamide (Intermediate 540) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide, and 1-isopropyl-1H-pyrazole-5-carboxylic acid in place of 4-methyl-1,2,5-oxadiazole-3-carboxylic acid. Purification was done by preparative HPLC (Waters XSelect CSH 5 μm C18, 19×100 mm, 15-55% MeCN/H$_2$O (with 0.16% TFA)). Product containing fractions were concentrated to dryness to afford the title compound as a white powder. $^1$H NMR (500 MHz, DMSO-d$_6$) δ 9.00 (d, J=8.0 Hz, 1H), 8.74 (d, J=9.0 Hz, 1H), 8.63 (d, J=2.1 Hz, 1H), 8.31 (s, 1H), 8.14 (dd, J=2.0, 1.0 Hz, 1H), 7.49 (d, J=2.0 Hz, 1H), 6.92 (d, J=2.0 Hz, 1H), 5.37 (m, 1H), 5.23-5.21 (m, 1H), 4.82 (dd, J=8.0, 0.9 Hz, 1H), 2.73-2.60 (m, 2H), 2.46-2.27 (m, 4H), 2.18 (m, 1H), 2.10-1.93 (m, 2H), 1.92-1.69 (m, 3H), 1.64 (m, 1H), 1.52-1.45 (m, 1H), 1.44-1.25 (m, 10H), 1.20 (m, 1H). MS (ESI) m/z: [M+H]$^+$ Found 629.3.

Example 427

N—((S)-(7-((S*)-(1-Cyanocyclopropyl)(2-(1-(trifluoromethyl)cyclopropyl)acetamido)methyl)imidazo[1,2-b]pyridazin-2-yl)(4,4-difluorocyclohexyl)methyl)-4-methyl-1,2,5-oxadiazole-3-carboxamide

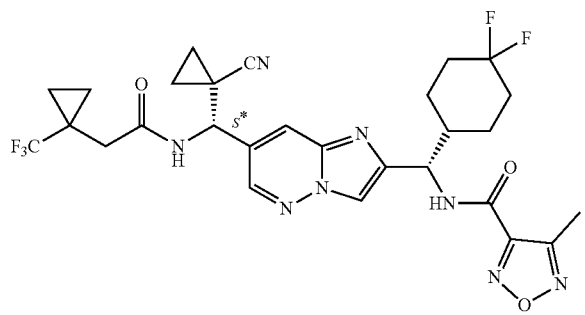 [SMILES: Cc1nonc1C(=O)N[C@H](c1cn2ncc([C@H](NC(=O)CC3(C(F)(F)F)CC3)C3(C#N)CC3)cc2n1)C1CCC(F)(F)CC1]

The title compound was prepared as described for the synthesis of Example 513 using N—((S*)-(2-((S)-amino(4,4-difluorocyclohexyl)methyl)imidazo[1,2-b]pyridazin-7-yl)(1-cyanocyclopropyl)methyl)-2-(1-(trifluoromethyl)cyclopropyl)acetamide (Intermediate 541) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide. Purification was done by preparative HPLC (Waters XSelect CSH 5 μm C18, 19×100 mm, 30-65% MeCN/H$_2$O (with 0.16% TFA)). Product containing fractions were concentrated to dryness to afford the title compound as a white powder. $^1$H NMR (500 MHz, DMSO-d6) δ 9.44 (d, J=9.0 Hz, 1H), 9.09 (d, J=8.0 Hz, 1H), 8.60 (d, J=2.1 Hz, 1H), 8.32 (s, 1H), 8.13 (m, 1H), 5.22-5.17 (m, 1H), 4.79 (d, J=8.0, 0.9 Hz, 1H), 2.67-2.55 (m, 2H), 2.47 (s, 3H), 2.20 (m, 1H), 2.10-1.87 (m, 3H), 1.78 (m, 2H), 1.63 (m, 1H), 1.53 (m, 1H), 1.44-1.16 (m, 5H), 0.99-0.90 (m, 4H). MS (ESI) m/z: [M+H]$^+$ Found 621.2.

Example 428

N—((S)-(7-((S*)-(1-Cyanocyclopropyl)(2-(1-(trifluoromethyl)cyclopropyl)acetamido)methyl)imidazo[1,2-b]pyridazin-2-yl)(4,4-difluorocyclohexyl)methyl)-1-isopropyl-1H-pyrazole-5-carboxamide

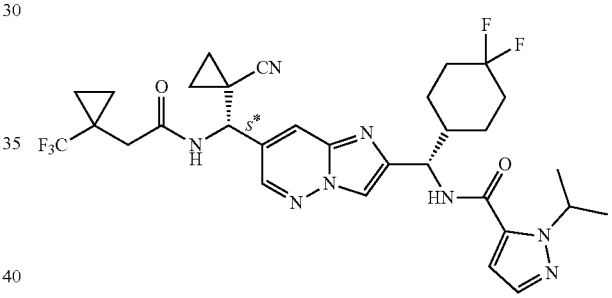

The title compound was prepared as described for the synthesis of Example 513 using N—((S*)-(2-((S)-amino(4,4-difluorocyclohexyl)methyl)imidazo[1,2-b]pyridazin-7-yl)(1-cyanocyclopropyl)methyl)-2-(1-(trifluoromethyl)cyclopropyl)acetamide (Intermediate 541) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide, and 1-isopropyl-1H-pyrazole-5-carboxylic acid in place of 4-methyl-1,2,5-oxadiazole-3-carboxylic acid. Purification was done by preparative HPLC (Waters XSelect CSH 5 μm C18, 19×100 mm, 30-65% MeCN/H$_2$O (with 0.16% TFA)). Product containing fractions were concentrated to dryness to afford the title compound as a white powder. $^1$H NMR (500 MHz, DMSO-d$_6$) δ 9.09 (d, J=8.0 Hz, 1H), 8.74 (d, J=9.0 Hz, 1H), 8.61-8.57 (m, 1H), 8.29 (s, 1H), 8.12-8.09 (m, 1H), 7.49 (d, J=1.9 Hz, 1H), 6.91 (d, J=2.0 Hz, 1H), 5.41-5.32 (m, 1H), 5.21-5.15 (m, 1H), 4.80 (d, J=8.0 Hz, 1H), 2.66-2.55 (m, 2H), 2.24-2.14 (m, 1H), 2.10-1.93 (m, 2H), 1.92-1.69 (m, 3H), 1.68-1.59 (m, 1H), 1.56-1.50 (m, 1H), 1.42-1.30 (m, 8H), 1.30-1.17 (m, 2H), 0.98-0.85 (m, 5H).). MS (ESI) m/z: [M+H]$^+$ Found 647.2.

Example 429

N—((S)-(7-((R*)-(1-Cyanocyclopropyl)(2-(3,3-difluorocyclobutyl)acetamido)methyl)imidazo[1,2-b]pyridazin-2-yl)(4,4-difluorocyclohexyl)methyl)-4-cyclopropyl-1,2,5-oxadiazole-3-carboxamide

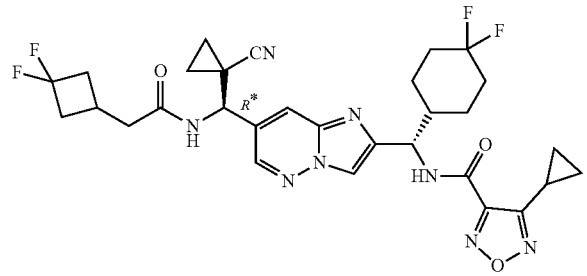 [SMILES: N#CC1([C@H](NC(=O)CC2CC(F)(F)C2)c2cnn3cc([C@@H](NC(=O)c4nonc4C4CC4)C4CCC(F)(F)CC4)nc3c2)CC1]

The title compound was prepared as described for the synthesis of Example 513 using N—((R*)-(2-((S)-amino(4,4-difluorocyclohexyl)methyl)imidazo[1,2-b]pyridazin-7-yl)(1-cyanocyclopropyl)methyl)-2-(3,3-difluorocyclobutyl)acetamide (Intermediate 542) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide, and 4-cyclopropyl-1,2,5-oxadiazole-3-carboxylic acid (Intermediate 570) in place of 4-methyl-1,2,5-oxadiazole-3-carboxylic acid. Purification was done by preparative HPLC (Waters XBridge BEH 5 μm C18, 19×100 mm, 40-75% MeCN/H₂O (with 0.16% NH₄OH)). Product containing fractions were concentrated to dryness to afford the title compound as a white powder. ¹H NMR (500 MHz, DMSO-d₆) δ 9.50 (d, J=8.8 Hz, 1H), 8.99 (d, J=8.0 Hz, 1H), 8.61 (d, J=2.1 Hz, 1H), 8.30 (s, 1H), 8.14 (d, J=2.1 Hz, 1H), 5.24-5.18 (m, 1H), 4.81 (d, J=7.9 Hz, 1H), 2.74-2.59 (m, 2H), 2.47-2.14 (m, 5H), 2.08-1.88 (m, 4H), 1.86-1.70 (m, 2H), 1.63 (m, 1H), 1.52-1.45 (m, 1H), 1.44-1.24 (m, 4H), 1.21 (m, 1H), 1.15-1.07 (m, 2H), 0.99-0.92 (m, 2H). MS (ESI) m/z: [M+H]⁺ Found 629.3.

Example 430

N—((S)-(7-((R*)-(1-Cyanocyclopropyl)(2-(3,3-difluorocyclobutyl)acetamido)methyl)imidazo[1,2-b]pyridazin-2-yl)(4,4-difluorocyclohexyl)methyl)-4-(2,2-difluoroethoxy)-1,2,5-oxadiazole-3-carboxamide

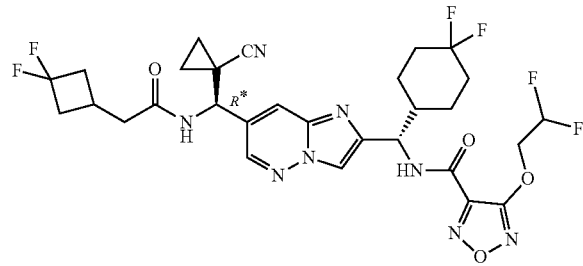 [SMILES: N#CC1([C@H](NC(=O)CC2CC(F)(F)C2)c2cnn3cc([C@@H](NC(=O)c4nonc4OCC(F)F)C4CCC(F)(F)CC4)nc3c2)CC1]

The title compound was prepared as described for the synthesis of Example 513 using N—((R*)-(2-((S)-amino(4,4-difluorocyclohexyl)methyl)imidazo[1,2-b]pyridazin-7-yl)(1-cyanocyclopropyl)methyl)-2-(3,3-difluorocyclobutyl)acetamide (Intermediate 542) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide, and 4-(2,2-difluoroethoxy)-1,2,5-oxadiazole-3-carboxylic acid (Intermediate 330) in place of 4-methyl-1,2,5-oxadiazole-3-carboxylic acid. Purification was done by preparative HPLC (Waters XBridge BEH 5 μm C18, 19×100 mm, 40-75% MeCN/H₂O (with 0.16% NH₄OH)). Product containing fractions were concentrated to dryness to afford the title compound as a white powder. ¹H NMR (500 MHz, DMSO-d₆) δ 9.37 (m, 1H), 8.98 (d, J=8.0 Hz, 1H), 8.61 (d, J=2.1 Hz, 1H), 8.27 (s, 1H), 8.13 (d, J=1.9 Hz, 1H), 6.43 (tt, J=3.1, 53.6 Hz, 1H), 5.22-5.16 (m, 1H), 4.81 (d, J=8.0 Hz, 1H), 4.70 (dt, J=2.9, 14.7 Hz, 2H), 2.74-2.58 (m, 2H), 2.49 (m, 1H), 2.47-2.26 (m, 3H), 2.21-2.12 (m, 1H), 2.07-1.94 (m, 2H), 1.89 (m, 1H), 1.85-1.70 (m, 2H), 1.62 (m, 1H), 1.50-1.44 (m, 1H), 1.43-1.25 (m, 4H), 1.24-1.18 (m, 1H). MS (ESI) m/z: [M+H]⁺ Found 669.2.

Example 431

N—((S)-(7-((R*)-(1-Cyanocyclopropyl)(2-(3,3-difluorocyclobutyl)acetamido)methyl)imidazo[1,2-b]pyridazin-2-yl)(4,4-difluorocyclohexyl)methyl)-1-isopropyl-1H-pyrazole-5-carboxamide

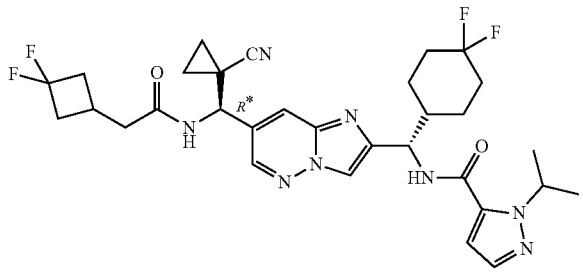 [SMILES: CC(C)n1nccc1C(=O)N[C@H](c1cn2ncc([C@@H](NC(=O)CC3CC(F)(F)C3)C3(C#N)CC3)cc2n1)C1CCC(F)(F)CC1]

The title compound was prepared as described for the synthesis of Example 513 using N—((R*)-(2-((S)-amino(4,4-difluorocyclohexyl)methyl)imidazo[1,2-b]pyridazin-7-yl)(1-cyanocyclopropyl)methyl)-2-(3,3-difluorocyclobutyl)acetamide (Intermediate 542) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide, and 1-isopropyl-1H-pyrazole-5-carboxylic acid in place of 4-methyl-1,2,5-oxadiazole-3-carboxylic acid. Purification was done by preparative HPLC (Waters XSelect CSH 5 μm C18, 19×100 mm, 15-55% MeCN/H₂O (with 0.16% TFA)). Product containing fractions were concentrated to dryness to afford the title compound as a white powder. ¹H NMR (500 MHz, DMSO-d₆) δ 8.98 (d, J=8.0 Hz, 1H), 8.73 (d, J=9.0 Hz, 1H), 8.60 (d, J=2.1 Hz, 1H), 8.28 (s, 1H), 8.12 (d, J=1.9 Hz, 1H), 7.48 (d, J=1.9 Hz, 1H), 6.91 (d, J=2.0 Hz, 1H), 5.37 (m, 1H), 5.21-5.15 (m, 1H), 4.80 (d, J=8.0 Hz, 1H), 2.75-2.59 (m, 2H), 2.49 (s, 1H), 2.46-2.26 (m, 3H), 2.24-2.14 (m, 1H), 2.07-1.95 (m, 2H), 1.88 (m, 1H), 1.85-1.70 (m, 2H), 1.63 m, 1H), 1.51-1.45 (m, 1H), 1.44-1.37 (m, 2H), 1.36 (d, J=6.6 Hz, 3H), 1.33 (d, J=6.5 Hz, 3H), 1.31-1.17 (m, 2H). MS (ESI) m/z: [M+H]⁺ Found 629.3.

Example 432

N—((S)-(7-((R*)-(1-Cyanocyclopropyl)(2-(1-(trifluoromethyl)cyclopropyl)acetamido)methyl)imidazo[1,2-b]pyridazin-2-yl)(4,4-difluorocyclohexyl)methyl)-4-methyl-1,2,5-oxadiazole-3-carboxamide

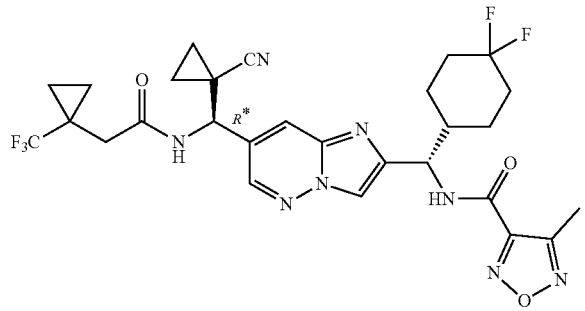 [SMILES: Cc1nonc1C(=O)N[C@H](c1cn2ncc([C@@H](NC(=O)CC3(C(F)(F)F)CC3)C3(C#N)CC3)cc2n1)C1CCC(F)(F)CC1]

The title compound was prepared as described for the synthesis of Example 513 using N—((R*)-(2-((S)-amino(4,4-difluorocyclohexyl)methyl)imidazo[1,2-b]pyridazin-7-yl)(1-cyanocyclopropyl)methyl)-2-(1-(trifluoromethyl)cyclopropyl)acetamide (Intermediate 543) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide. Purification was done by preparative HPLC (Waters XBridge BEH 5 μm C18, 19×100 mm, 40-75% MeCN/H$_2$O (with 0.16% NH$_4$OH))). Product containing fractions were concentrated to afford the title compound as a white powder. $^1$H NMR (500 MHz, DMSO-d$_6$) δ 9.44 (d, J=8.9 Hz, 1H), 9.09 (d, J=8.0 Hz, 1H), 8.59 (d, J=2.1 Hz, 1H), 8.31 (s, 1H), 8.13 (d, J=2.0 Hz, 1H), 5.22-5.16 (m, 1H), 4.79 (d, J=7.8 Hz, 1H), 2.66-2.56 (m, 2H), 2.47 (s, 3H), 2.26-2.15 (m, 1H), 2.07-1.95 (m, 2H), 1.94-1.88 (m, 1H), 1.86-1.69 (m, 2H), 1.62 (m, 1H), 1.56-1.49 (m, 1H), 1.45-1.24 (m, 4H), 1.23-1.17 (m, 1H), 0.99-0.88 (m, 4H). MS (ESI) m/z: [M+H]$^+$ Found 621.5.

Example 433

N—((S)-(7-((R*)-(1-Cyanocyclopropyl)(2-(1-(trifluoromethyl)cyclopropyl)acetamido)methyl)imidazo[1,2-b]pyridazin-2-yl)(4,4-difluorocyclohexyl)methyl)-4-cyclopropyl-1,2,5-oxadiazole-3-carboxamide

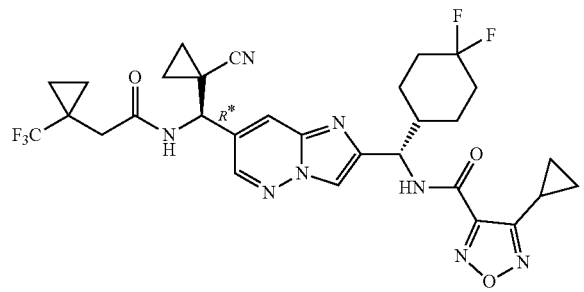 [SMILES: N#CC1([C@H](NC(=O)CC2(C(F)(F)F)CC2)c2cnn3cc([C@@H](NC(=O)c4nonc4C4CC4)C4CCC(F)(F)CC4)nc3c2)CC1]

The title compound was prepared as described for the synthesis of Example 513 using N—((R*)-(2-((S)-amino(4,4-difluorocyclohexyl)methyl)imidazo[1,2-b]pyridazin-7-yl)(1-cyanocyclopropyl)methyl)-2-(1-(trifluoromethyl)cyclopropyl)acetamide (Intermediate 543) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide, and 4-cyclopropyl-1,2,5-oxadiazole-3-carboxylic acid (Intermediate 570) in place of 4-methyl-1,2,5-oxadiazole-3-carboxylic acid. Purification was done by preparative HPLC (Waters XBridge BEH 5 μm C18, 19×100 mm, 40-75% MeCN/H$_2$O (with 0.16% NH$_4$OH))). Product containing fractions were concentrated to dryness to afford the title compound as a white powder. $^1$H NMR (500 MHz, DMSO-d$_6$) δ 9.50 (d, J=8.9 Hz, 1H), 9.09 (d, J=7.9 Hz, 1H), 8.60 (d, J=2.1 Hz, 1H), 8.31 (s, 1H), 8.13 (d, J=1.9 Hz, 1H), 5.24-5.19 (m, 1H), 4.79 (d, J=7.9 Hz, 1H), 2.67-2.55 (m, 2H), 2.28 m, 1H), 2.24-2.16 (m, 1H), 2.10-1.95 (m, 2H), 1.91 (m, 1H), 1.86-1.70 (m, 2H), 1.63 (m, 1H), 1.56-1.49 (m, 1H), 1.46-1.25 (m, 4H), 1.23-1.17 (m, 1H), 1.14-1.09 (m, 2H), 0.98-0.90 (m, 6H). MS (ESI) m/z: [M+H]$^+$ Found 647.2.

Example 434

N—((S)-(7-((R*)-(1-Cyanocyclopropyl)(2-(1-(trifluoromethyl)cyclopropyl)acetamido)methyl)imidazo[1,2-b]pyridazin-2-yl)(4,4-difluorocyclohexyl)methyl)-1-isopropyl-1H-pyrazole-5-carboxamide

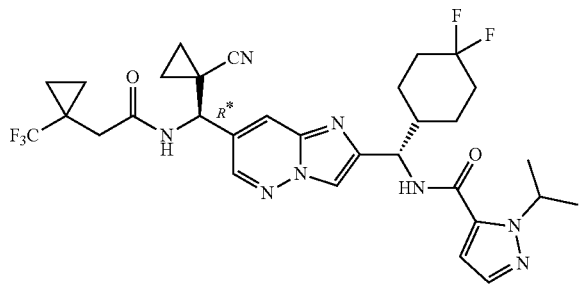 [SMILES: CC(C)n1nccc1C(=O)N[C@H](c1cn2ncc([C@@H](NC(=O)CC3(C(F)(F)F)CC3)C3(C#N)CC3)cc2n1)C1CCC(F)(F)CC1]

The title compound was prepared as described for the synthesis of Example 513 using N—((R*)-(2-((S)-amino(4,4-difluorocyclohexyl)methyl)imidazo[1,2-b]pyridazin-7-yl)(1-cyanocyclopropyl)methyl)-2-(1-(trifluoromethyl)cyclopropyl)acetamide (Intermediate 543) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide, and 1-isopropyl-1H-pyrazole-5-carboxylic acid in place of 4-methyl-1,2,5-oxadiazole-3-carboxylic acid. Purification was done by preparative HPLC (Waters XBridge BEH 5 μm C18, 19×100 mm, 40-75% MeCN/H$_2$O (with 0.16% NH$_4$OH))). Product containing fractions were concentrated to dryness to afford the title compound as a white powder $^1$H NMR (500 MHz, DMSO-d$_6$) δ 9.09 (d, J=7.9 Hz, 1H), 8.74 (d, J=9.0 Hz, 1H), 8.58 (d, J=2.1 Hz, 1H), 8.28 (s, 1H), 8.11 (d, J=1.9 Hz, 1H), 7.48 (d, J=1.9 Hz, 1H), 6.91 (d, J=2.0 Hz, 1H), 5.36 (m, 1H), 5.21-5.16 (m, 1H), 4.79 (d, J=7.8 Hz, 1H), 2.66-2.55 (m, 2H), 2.24-2.14 (m, 1H), 2.07-1.94 (m, 2H), 1.88 (m, 1H), 1.85-1.69 (m, 2H), 1.63 (m, 1H), 1.56-1.50 (m, 1H), 1.44-1.33 (m, 3H), 1.36 (d, J=6.6 Hz, 3H), 1.33 (d, J=6.6 Hz, 3H), 1.30-1.14 (m, 2H), 0.99-0.89 (m, 4H). MS (ESI) m/z: [M+H]$^+$ Found 647.2.

Example 435

N—((S)-(7-((R*)-(1-Cyanocyclopropyl)(3-cyclopropyl-2,2-difluoropropanamido)methyl)imidazo[1,2-b]pyridazin-2-yl)(4,4-difluorocyclohexyl)methyl)-4-methyl-1,2,5-oxadiazole-3-carboxamide

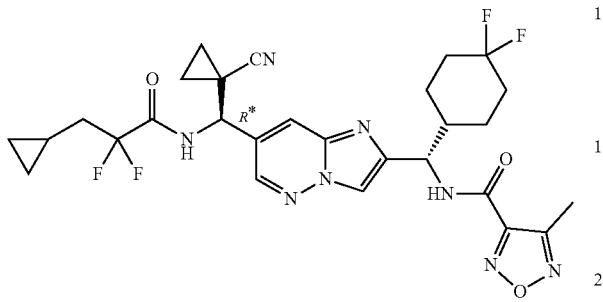

The title compound was prepared as described for the synthesis of Example 513 using N—((R*)-(2-((S)-amino(4,4-difluorocyclohexyl)methyl)imidazo[1,2-b]pyridazin-7-yl)(1-cyanocyclopropyl)methyl)-3-cyclopropyl-2,2-difluoropropanamide (Intermediate 544) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide. Purification was done by preparative HPLC (Waters XBridge BEH C18, 5 μm, 19×100 mm, 40-75% MeCN/H$_2$O (with 0.16% NH$_4$OH))). Product containing fractions were concentrated to dryness to afford the title compound as a white powder. $^1$H NMR (500 MHz, DMSO-d$_6$) δ 9.82 (m, 1H), 9.44 (d, J=8.9 Hz, 1H), 8.64 (d, J=2.0 Hz, 1H), 8.32 (s, 1H), 8.22 (s, 1H), 5.19 (t, J=8.6 Hz, 1H), 4.99 (m, 1H), 2.46 (s, 3H), 2.25-2.15 (m, 1H), 2.06-1.88 (m, 5H), 1.85-1.70 (m, 2H), 1.61 (m, 1H), 1.48-1.33 (m, 4H), 1.33-1.19 (m, 2H), 0.80-0.68 (m, 1H), 0.52-0.37 (m, 2H), 0.18-0.08 (m, 2H). MS (ESI) m/z: [M+H]$^+$ Found 603.2.

Example 436

N—((S)-(7-((R*)-(1-Cyanocyclopropyl)(3-cyclopropyl-2,2-difluoropropanamido)methyl)imidazo[1,2-b]pyridazin-2-yl)(4,4-difluorocyclohexyl)methyl)-4-cyclopropyl-1,2,5-oxadiazole-3-carboxamide

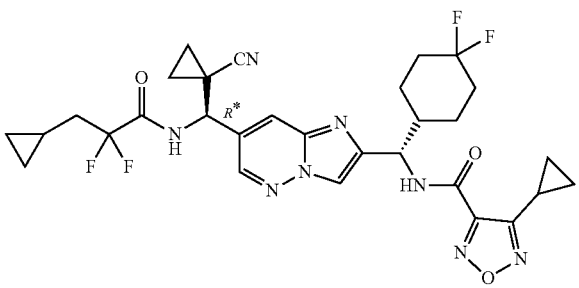 [SMILES: N#CC1([C@H](NC(=O)C(F)(F)CC2CC2)c2cnn3cc([C@@H](NC(=O)c4nonc4C4CC4)C4CCC(F)(F)CC4)nc3c2)CC1]

The title compound was prepared as described for the synthesis of Example 513 using N—((R*)-(2-((S)-amino(4,4-difluorocyclohexyl)methyl)imidazo[1,2-b]pyridazin-7-yl)(1-cyanocyclopropyl)methyl)-3-cyclopropyl-2,2-difluoropropanamide (Intermediate 544) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide and 4-cyclopropyl-1,2,5-oxadiazole-3-carboxylic acid (Intermediate 570) in place of 4-methyl-1,2,5-oxadiazole-3-carboxylic acid. Purification was done by preparative HPLC (Waters XBridge BEH C18, 5 μm, 19×100 mm, 40-75% MeCN/H$_2$O (with 0.16% NH$_4$OH)). Product containing fractions were concentrated to dryness to afford the title compound as a white powder. $^1$H NMR (500 MHz, DMSO-d$_6$) δ 9.83 (d, J=7.9 Hz, 1H), 9.50 (d, J=9.0 Hz, 1H), 8.65 (d, J=2.1 Hz, 1H), 8.32 (s, 1H), 8.22 (d, J=1.9 Hz, 1H), 5.21 (t, J=8.5 Hz, 1H), 4.99 (d, J=7.9 Hz, 1H), 2.28 (tt, J=5.0, 8.4 Hz, 1H), 2.24-2.15 (m, 1H), 2.08-1.95 (m, 4H), 1.91 (m, 1H), 1.86-1.70 (m, 2H), 1.62 (m, 1H), 1.49-1.37 (m, 4H), 1.36-1.19 (m, 2H), 1.15-1.07 (m, 2H), 0.98-0.92 (m, 2H), 0.78-0.69 (m, 1H), 0.50-0.36 (m, 2H), 0.18-0.08 (m, 2H). MS (ESI) m/z: [M+H]$^+$ Found 629.6.

Example 437

N—((S)-(7-((R*)-(1-Cyanocyclopropyl)(3-cyclopropyl-2,2-difluoropropanamido)methyl)imidazo[1,2-b]pyridazin-2-yl)(4,4-difluorocyclohexyl)methyl)-1-isopropyl-1H-pyrazole-5-carboxamide

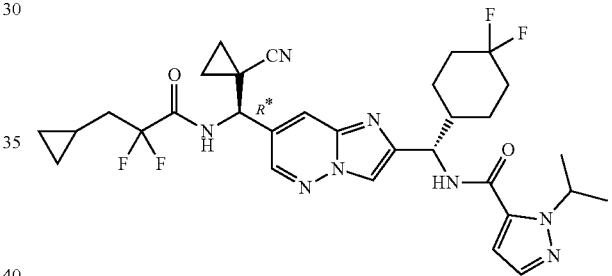

The title compound was prepared as described for the synthesis of Example 513 using N—((R*)-(2-((S)-amino(4,4-difluorocyclohexyl)methyl)imidazo[1,2-b]pyridazin-7-yl)(1-cyanocyclopropyl)methyl)-3-cyclopropyl-2,2-difluoropropanamide (Intermediate 544) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide and 1-isopropyl-1H-pyrazole-5-carboxylic acid in place of 4-methyl-1,2,5-oxadiazole-3-carboxylic acid. Purification was done by preparative HPLC (Waters XBridge BEH C18, 5 μm, 19×100 mm, 40-75% MeCN/H$_2$O (with 0.16% NH$_4$OH)). Product containing fractions were concentrated to dryness to afford the title compound as a white powder. $^1$H NMR (500 MHz, DMSO-d$_6$) δ 9.82 (m, 1H), 8.74 (d, J=9.0 Hz, 1H), 8.63 (d, J=2.1 Hz, 1H), 8.29 (s, 1H), 8.20 (s, 1H), 7.48 (d, J=2.0 Hz, 1H), 6.91 (d, J=1.9 Hz, 1H), 5.36 (m, 1H), 5.18 (t, J=8.6 Hz, 1H), 4.99 (m, 1H), 2.25-2.14 (m, 1H), 2.10-1.94 (m, 3H), 1.92-1.69 (m, 3H), 1.62 (m, 1H), 1.48-1.38 (m, 3H), 1.36 (d, J=6.6 Hz, 3H), 1.33 (d, J=6.6 Hz, 3H), 1.29-1.12 (m, 3H), 0.78-0.69 (m, 1H), 0.49-0.37 (m, 2H), 0.17-0.09 (m, 2H). MS (ESI) m/z: [M+H]$^+$ Found 629.3.

Example 438

N—((S)-(7-((R*)-2-Cyclobutyl-1-(2-(3,3-difluorocyclobutyl)acetamido)ethyl)imidazo[1,2-b]pyridazin-2-yl)(4,4-difluorocyclohexyl)methyl)-4-methyl-1,2,5-oxadiazole-3-carboxamide

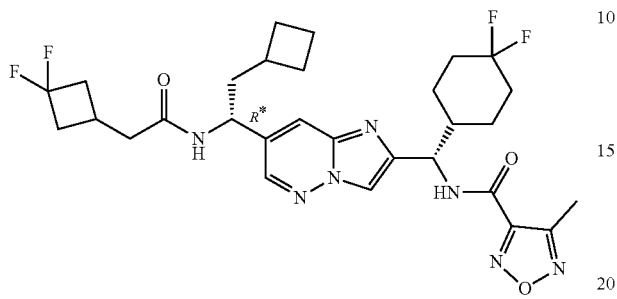

The title compound was prepared as described for the synthesis of Example 38 using N-(1-(2-((S)-amino(4,4-difluorocyclohexyl)methyl)imidazo[1,2-b]pyridazin-7-yl)-2-cyclobutylethyl)-2-(3,3-difluorocyclobutyl)acetamide (Intermediate 549) in place of N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide and 4-methyl-1,2,5-oxadiazole-3-carboxylic acid in place of 1-(3,3,3-trifluoropropyl)-1H-1,2,4-triazole-5-carboxylic acid. A second purification was performed via SFC (Daicel ChiralPak AD-H, 250×30 mm, 5 m, 30% EtOH (containing 0.1% NH$_4$OH)/CO$_2$), and the first-eluting isomer provided the title compound as a white solid. $^1$H NMR (400 MHz, DMSO-d$_6$) δ 9.44 (d, J=9.2 Hz, 1H), 8.46 (d, J=2.0 Hz, 1H), 8.42 (d, J=7.6 Hz, 1H), 8.22 (s, 1H), 7.85 (d, J=1.6 Hz, 1H), 5.16 (t, J=8.8 Hz, 1H), 4.79-4.70 (m, 1H), 2.69-2.65 (m, 1H), 2.65-2.60 (m, 1H), 2.47-2.45 (m, 3H), 2.39-2.30 (m, 4H), 2.29-2.13 (m, 3H), 2.00 (d, J=7.6 Hz, 3H), 1.94-1.56 (m, 11H), 1.32-1.26 (m, 1H), 1.23-1.18 (m, 1H). MS (ESI) m/z: [M+H]$^+$ Found 606.2.

Example 439

N—((S)-(7-((S*)-2-Cyclobutyl-1-(2-(3,3-difluorocyclobutyl)acetamido)ethyl)imidazo[1,2-b]pyridazin-2-yl)(4,4-difluorocyclohexyl)methyl)-4-methyl-1,2,5-oxadiazole-3-carboxamide

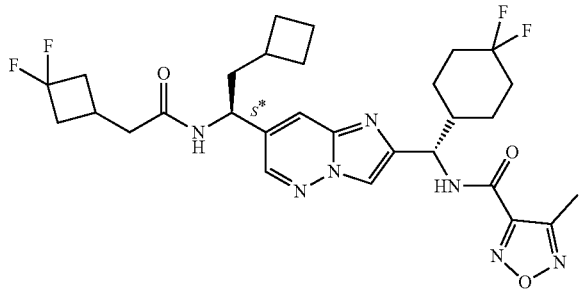 [SMILES: Cc1nonc1C(=O)N[C@H](c1cn2ncc([C@H](CC3CCC3)NC(=O)CC3CC(F)(F)C3)cc2n1)C1CCC(F)(F)CC1]

The title compound was prepared as described for the synthesis of Example 438. A second purification was performed via SFC (Daicel ChiralPak AD-H, 250×30 mm, 5 m, 30% EtOH (containing 0.1% NH$_4$OH)/CO$_2$). Product containing fractions were combined to afford the title compound, the second-eluting isomer, as a white solid. $^1$H NMR (400 MHz, DMSO-d$_6$) δ 9.44 (d, J=9.2 Hz, 1H), 8.46 (d, J=2.0 Hz, 1H), 8.42 (d, J=7.6 Hz, 1H), 8.22 (s, 1H), 7.85 (d, J=1.6 Hz, 1H), 5.16 (t, J=8.4 Hz, 1H), 4.78-4.71 (m, 1H), 2.70-2.59 (m, 2H), 2.46 (s, 3H), 2.41-2.12 (m, 7H), 2.09-1.94 (m, 3H), 1.92-1.55 (m, 11H), 1.43-1.31 (m, 1H), 1.27-1.13 (m, 1H). MS (ESI) m/z: [M+H]$^+$ Found 606.2.

Example 440

N—((S)-(7-((R*)-2-Cyclobutyl-1-(2-(3,3-difluorocyclobutyl)acetamido)ethyl)imidazo[1,2-b]pyridazin-2-yl)(4,4-difluorocyclohexyl)methyl)-1-isopropyl-1H-pyrazole-5-carboxamide

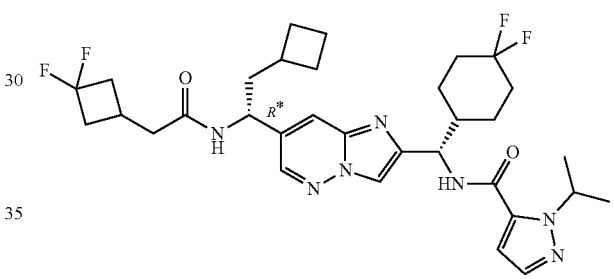

The title compound was prepared as described for the synthesis of Example 38 using N-(1-(2-((S)-amino(4,4-difluorocyclohexyl)methyl)imidazo[1,2-b]pyridazin-7-yl)-2-cyclobutylethyl)-2-(3,3-difluorocyclobutyl)acetamide (Intermediate 549) in place of N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide (Intermediate 171) and 1-isopropyl-1H-pyrazole-5-carboxylic acid in place of 1-(3,3,3-trifluoropropyl)-1H-1,2,4-triazole-5-carboxylic acid. A second purification was performed via SFC (Daicel ChiralPak AD-H, 250×30 mm, 5 m, 30% IPA (containing 0.1% NH$_4$OH)/CO$_2$). Product containing fractions were combined to afford the first-eluting isomer as a white-solid. $^1$H NMR (400 MHz, DMSO-d$_6$) δ 8.74 (d, J=9.2 Hz, 1H), 8.49-8.44 (m, 1H), 8.42 (d, J=8.0 Hz, 1H), 8.19 (s, 1H), 7.84 (s, 1H), 7.51-7.48 (m, 1H), 6.91 (d, J=2.0 Hz, 1H), 5.41-5.31 (m, 1H), 5.14 (t, J=8.4 Hz, 1H), 4.79-4.71 (m, 1H), 2.70-2.58 (m, 2H), 2.42-2.10 (m, 7H), 2.08-1.94 (m, 3H), 1.91-1.56 (m, 10H), 1.43-1.30 (m, 7H), 1.28-1.13 (m, 2H). MS (ESI) m/z: [M+H]$^+$ Found 632.3.

Example 441

N—((S)-(7-((S*)-2-Cyclobutyl-1-(2-(3,3-difluorocyclobutyl)acetamido)ethyl)imidazo[1,2-b]pyridazin-2-yl)(4,4-difluorocyclohexyl)methyl)-1-isopropyl-1H-pyrazole-5-carboxamide

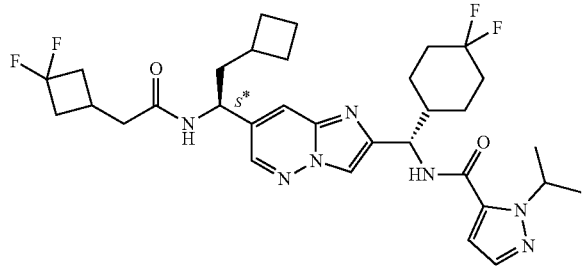 [SMILES: CC(C)n1nccc1C(=O)N[C@H](c1cn2ncc([C@H](CC3CCC3)NC(=O)CC3CC(F)(F)C3)cc2n1)C1CCC(F)(F)CC1]

The title compound was prepared as described for the synthesis of Example 440. A second purification was performed via SFC (Daicel ChiralPak AD-H, 250×30 mm, 5 m, 30% EtOH (containing 0.1% NH₄OH)/CO₂). Product containing fractions were combined to afford the second-eluting isomer as a white-solid. $^1$H NMR (400 MHz, DMSO-$d_6$) δ 8.75 (d, J=9.2 Hz, 1H), 8.48-8.42 (m, 2H), 8.20 (s, 1H), 7.84 (d, J=1.6 Hz, 1H), 7.49 (d, J=1.8 Hz, 1H), 6.91 (d, J=2.0 Hz, 1H), 5.41-5.30 (m, 1H), 5.14 (t, J=8.8 Hz, 1H), 4.81-4.68 (m, 1H), 2.72-2.56 (m, 2H), 2.40-2.13 (m, 7H), 2.08-1.94 (m, 3H), 1.91-1.57 (m, 10H), 1.40-1.30 (m, 7H), 1.30-1.15 (m, 2H). MS (ESI) m/z: [M+H]⁺ Found 632.3.

Example 442

N—((S)-(7-((S*)-1-(2-(3,3-Difluorocyclobutyl)acetamido)-2-hydroxy-2-methylpropyl)imidazo[1,2-b]pyridazin-2-yl)(4,4-difluorocyclohexyl)methyl)-1-isopropyl-1H-pyrazole-5-carboxamide

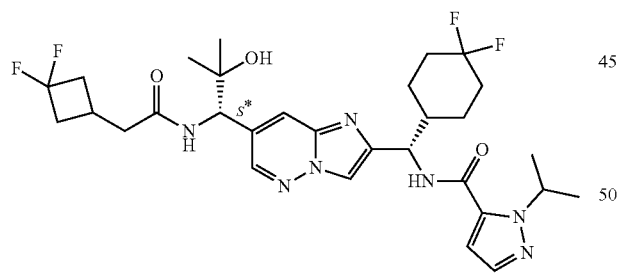

To a solution of N—((S)-(7-((R*)-1-(2-(3,3-difluorocyclobutyl)acetamido)-2-methylallyl)imidazo[1,2-b]pyridazin-2-yl)(4,4-difluorocyclohexyl)methyl)-1-isopropyl-1H-pyrazole-5-carboxamide (180 mg, 0.298 mmol, Intermediate 558) and a stir bar in anhydrous THF (3.0 mL) was added freshly distilled PhSiH₃ (80.7 mg, 0.75 mmol) and Co(acac)₂ (19.2 mg, 74.5 mol) at rt. The reaction flask was sparged with O₂ and the mixture was vigorously stirred at 25° C. under an O₂ atmosphere (15 psi) for 6 h before pouring it into H₂O (20 mL) and extracting with EtOAc (10 mL×3). The combined organic extracts were washed with brine (20 mL), dried over anhydrous Na₂SO₄, filtered, and concentrated to dryness under reduced pressure to give the crude product, which was purified by silica gel chromatography (0-9% MeOH/CH₂Cl₂). This impure material was further purified by SFC (Daicel ChiralPak AD, 250×30 mm, 10 m, (35% EtOH (containing 0.04% aqueous NH₄OH)/CO₂) followed by HPLC (Boston Prime C18 150×30 mm, m, 40-70% (v/v) MeCN/H₂O (with 0.05% aqueous NH₄OH)) to afford the title compound as a white solid. $^1$H NMR (400 MHz, DMSO-$d_6$) δ 8.74 (d, J=8.8 Hz, 1H), 8.49 (d, J=1.6 Hz, 1H), 8.43 (d, J=8.8 Hz, 1H), 8.17 (s, 1H), 7.92 (d, J=1.6 Hz, 1H), 7.49 (d, J=2.0 Hz, 1H), 6.90 (d, J=2.0 Hz, 1H), 5.41-5.31 (m, 1H), 5.14 (t, J=8.8 Hz, 1H), 4.90-4.80 (m, 2H), 2.68-2.56 (m, 2H), 2.46-2.24 (m, 5H), 2.22-1.67 (m, 7H), 1.66-1.57 (m, 1H), 1.36 (d, J=6.8 Hz, 3H), 1.33 (d, J=6.8 Hz, 3H), 1.29-1.22 (m, 1H), 1.14 (s, 3H), 1.07 (s, 3H). MS (ESI) m/z: [M+H]⁺ Found 622.3.

Example 443

N—((S)-(7-((S*)-1-(2-(3,3-Difluorocyclobutyl)acetamido)-2-hydroxy-2-methylpropyl)imidazo[1,2-b]pyridazin-2-yl)(4,4-difluorocyclohexyl)methyl)-4-methyl-1,2,5-oxadiazole-3-carboxamide

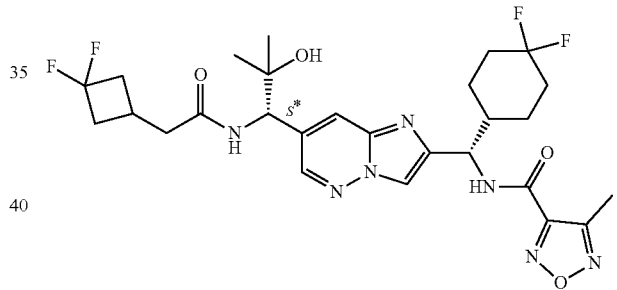

The title compound was prepared as described for the synthesis of Example 442 using N—((S)-(7-((R*)-1-(2-(3,3-difluorocyclobutyl)acetamido)-2-methylallyl)imidazo[1,2-b]pyridazin-2-yl)(4,4-difluorocyclohexyl)methyl)-4-methyl-1,2,5-oxadiazole-3-carboxamide (Intermediate 559) in place of N—((S)-(7-((R*)-1-(2-(3,3-difluorocyclobutyl)acetamido)-2-methylallyl)imidazo[1,2-b]pyridazin-2-yl)(4,4-difluorocyclohexyl)methyl)-1-isopropyl-1H-pyrazole-5-carboxamide to afford the title compound as a white solid. $^1$H NMR (400 MHz, DMSO-$d_6$) δ 9.43 (d, J=9.2 Hz, 1H), 8.50 (d, J=1.6 Hz, 1H), 8.41 (d, J=9.2 Hz, 1H), 8.21 (s, 1H), 7.94 (d, J=1.6 Hz, 1H), 5.16 (t, J=8.4 Hz, 1H), 4.87-4.80 (m, 2H), 2.69-2.56 (m, 2H), 2.46 (s, 3H), 2.39-2.14 (m, 5H), 2.07-1.67 (m, 6H), 1.64-1.55 (m, 1H), 1.40-1.23 (m, 2H), 1.14 (s, 3H), 1.07 (s, 3H). MS (ESI) m/z: [M+H]⁺ Found 596.2.

Example 444

N—((S)-(7-((R*)-1-(2-(3,3-Difluorocyclobutyl)acetamido)-2-hydroxy-2-methylpropyl)imidazo[1,2-b]pyridazin-2-yl)(4,4-difluorocyclohexyl)methyl)-1-isopropyl-1H-pyrazole-5-carboxamide

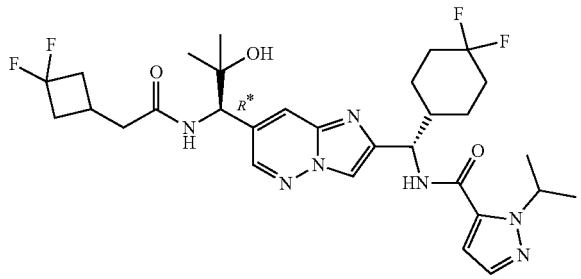 [SMILES: CC(C)n1nccc1C(=O)N[C@H](c1cn2ncc([C@@H](NC(=O)CC3CC(F)(F)C3)C(C)(C)O)cc2n1)C1CCC(F)(F)CC1]

The title compound was prepared as described for the synthesis of Example 442 using N—((S)-(7-((S*)-1-(2-(3,3-difluorocyclobutyl)acetamido)-2-methylallyl)imidazo[1,2-b]pyridazin-2-yl)(4,4-difluorocyclohexyl)methyl)-1-isopropyl-1H-pyrazole-5-carboxamide (Intermediate 560) in place of N—((S)-(7-((*R)-1-(2-(3,3-difluorocyclobutyl)acetamido)-2-methylallyl)imidazo[1,2-b]pyridazin-2-yl)(4,4-difluorocyclohexyl)methyl)-1-isopropyl-1H-pyrazole-5-carboxamide to afford the title compound as a white solid. $^1$H NMR (400 MHz, DMSO-$d_6$) δ 8.73 (d, J=8.8 Hz, 1H), 8.50 (d, J=1.6 Hz, 1H), 8.42 (d, J=8.8 Hz, 1H), 8.18 (s, 1H), 7.93 (d, J=1.2 Hz, 1H), 7.49 (d, J=1.6 Hz, 1H), 6.91 (d, J=2.0 Hz, 1H), 5.41-5.33 (m, 1H), 5.15 (t, J=8.8 Hz, 1H), 4.87-4.81 (m, 2H), 2.68-2.56 (m, 2H), 2.46-2.26 (m, 5H), 2.19-1.68 (m, 7H), 1.66-1.57 (m, 1H), 1.36 (d, J=6.4 Hz, 3H), 1.33 (d, J=6.8 Hz, 3H), 1.28-1.22 (m, 1H), 1.15 (s, 3H), 1.07 (s, 3H). MS (ESI) m/z: [M+H]$^+$ Found 622.2.

Example 445

N—((S)-(7-((R*)-1-(2-(3,3-Difluorocyclobutyl)acetamido)-2-hydroxy-2-methylpropyl)imidazo[1,2-b]pyridazin-2-yl)(4,4-difluorocyclohexyl)methyl)-4-methyl-1,2,5-oxadiazole-3-carboxamide

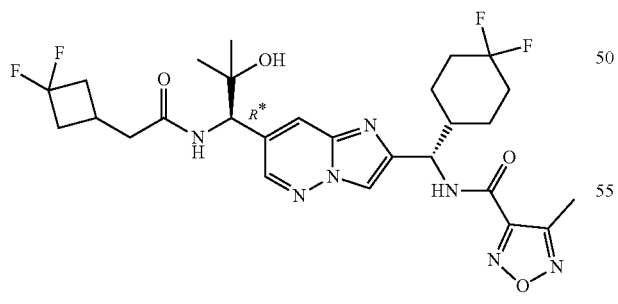

The title compound was prepared as described for the synthesis of Example 442 using N—((S)-(7-((S*)-1-(2-(3,3-difluorocyclobutyl)acetamido)-2-methylallyl)imidazo[1,2-b]pyridazin-2-yl)(4,4-difluorocyclohexyl)methyl)-4-methyl-1,2,5-oxadiazole-3-carboxamide (Intermediate 561) in place of N—((S)-(7-((*R)-1-(2-(3,3-difluorocyclobutyl)acetamido)-2-methylallyl)imidazo[1,2-b]pyridazin-2-yl)(4,4-difluorocyclohexyl)methyl)-1-isopropyl-1H-pyrazole-5-carboxamide to afford the title compound as a white solid. $^1$H NMR (400 MHz, DMSO-$d_6$) δ 9.44 (d, J=9.2 Hz, 1H), 8.51 (d, J=1.6 Hz, 1H), 8.42 (d, J=9.2 Hz, 1H), 8.21 (s, 1H), 7.94 (s, 1H), 5.16 (t, J=8.4 Hz, 1H), 4.87-4.81 (m, 2H), 2.69-2.56 (m, 2H), 2.47 (s, 3H), 2.41-2.16 (m, 5H), 2.08-1.67 (m, 6H), 1.65-1.56 (m, 1H), 1.41-1.22 (m, 2H), 1.15 (s, 3H), 1.07 (s, 3H). MS (ESI) m/z: [M+H]$^+$ Found 596.2.

Example 446

N—((S)-(7-((R*)-2-Cyano-1-(2-(3,3-difluorocyclobutyl)acetamido)ethyl)imidazo[1,2-b]pyridazin-2-yl)(4,4-difluorocyclohexyl)methyl)-4-methyl-1,2,5-oxadiazole-3-carboxamide

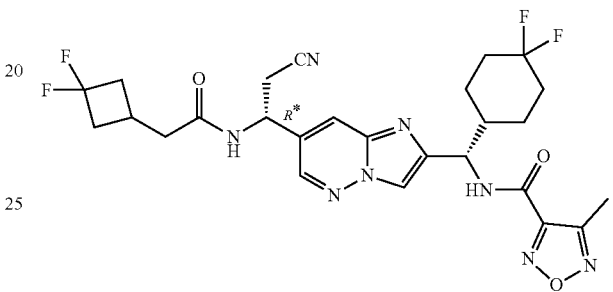

The title compound was prepared as described for the synthesis of Intermediate 439, using N—((R*)-1-(2-((S)-amino(4,4-difluorocyclohexyl)methyl)imidazo[1,2-b]pyridazin-7-yl)-2-cyanoethyl)-2-(3,3-difluorocyclobutyl)acetamide (Intermediate 565) in place of N—((R*)-(2-((S)-amino(4,4-difluorocyclohexyl)methyl)imidazo[1,2-b]pyridazin-7-yl)(cyclobutyl)methyl)-2-(3,3-difluorocyclobutyl)acetamide (Intermediate 442) to afford the title compound as a white solid. $^1$H NMR (400 MHz, DMSO-$d_6$) δ 9.46 (d, J=9.2 Hz, 1H), 8.83 (d, J=8.4 Hz, 1H), 8.55 (d, J=2.0 Hz, 1H), 8.28 (s, 1H), 8.06 (d, J=2.0 Hz, 1H), 5.35-5.28 (m, 1H), 5.18 (t, J=8.4 Hz, 1H), 3.21-3.05 (m, 2H), 2.71-2.60 (m, 2H), 2.47 (s, 3H), 2.45-2.36 (m, 3H), 2.34-2.28 (m, 1H), 2.18-2.20 (m, 1H), 2.07-1.68 (m, 5H), 1.61-1.58 (m, 1H), 1.43-1.33 (m, 1H), 1.31-1.21 (m, 2H). MS (ESI) m/z: [M+H]$^+$ Found 577.2.

Example 447

N—((S)-(7-((R*)-2-Cyano-1-(2-(3,3-difluorocyclobutyl)acetamido)ethyl)imidazo[1,2-b]pyridazin-2-yl)(4,4-difluorocyclohexyl)methyl)-1-isopropyl-1H-pyrazole-5-carboxamide

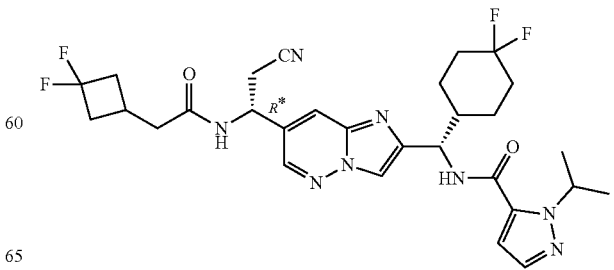

The title compound was prepared as described for the synthesis of Intermediate 439, using N—((R*)-1-(2-((S)-amino(4,4-difluorocyclohexyl)methyl)imidazo[1,2-b]pyridazin-7-yl)-2-cyanoethyl)-2-(3,3-difluorocyclobutyl)acetamide (Intermediate 565) in place of N—((R*)-(2-((S)-amino(4,4-difluorocyclohexyl)methyl)imidazo[1,2-b]pyridazin-7-yl)(cyclobutyl)methyl)-2-(3,3-difluorocyclobutyl)acetamide (Intermediate 442) and 1-isopropyl-1H-pyrazole-5-carboxylic acid in place of 4-methyl-1,2,5-oxadiazole-3-carboxylic acid to afford the title compound as a white solid. $^1$H NMR (400 MHz, DMSO-d$_6$) δ 8.82 (d, J=8.0 Hz, 1H), 8.75 (d, J=8.8 Hz, 1H), 8.54 (d, J=2.0 Hz, 1H), 8.26 (s, 1H), 8.05 (d, J=1.6 Hz, 1H), 7.49 (d, J=1.6 Hz, 1H), 6.91 (d, J=2.0 Hz, 1H), 5.40-5.27 (m, 2H), 5.16 (t, J=8.8 Hz, 1H), 3.21-3.05 (m, 2H), 2.71-2.60 (m, 2H), 2.45-2.27 (m, 5H), 2.19-2.17 (m, 1H), 2.08-1.94 (m, 2H), 1.90-1.67 (m, 3H), 1.62-1.59 (m, 1H), 1.37-1.32 (m, 6H), 1.28-1.22 (m, 2H). MS (ESI) m/z: [M+H]$^+$ Found 603.5.

Example 448

N—((S)-(7-((S*)-(1-Cyanocyclobutyl)(2-((R*)-2,2-difluorocyclopropyl)acetamido)methyl)imidazo[1,2-b]pyridazin-2-yl)(4,4-difluorocyclohexyl)methyl)-4-cyclopropyl-1,2,5-oxadiazole-3-carboxamide

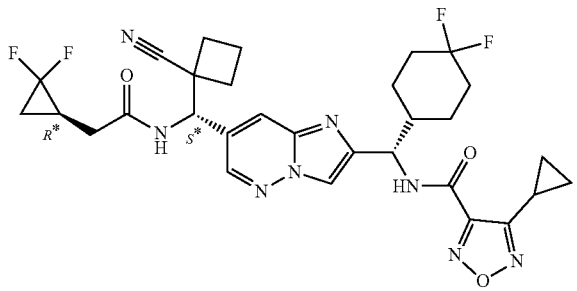 [SMILES: N#CC1([C@@H](NC(=O)C[C@H]2CC2(F)F)c2cnn3cc([C@@H](NC(=O)c4nonc4C4CC4)C4CCC(F)(F)CC4)nc3c2)CCC1]

Example 449

N—((S)-(7-((S*)-(1-Cyanocyclobutyl)(2-((S*)-2,2-difluorocyclopropyl)acetamido)methyl)imidazo[1,2-b]pyridazin-2-yl)(4,4-difluorocyclohexyl)methyl)-4-cyclopropyl-1,2,5-oxadiazole-3-carboxamide

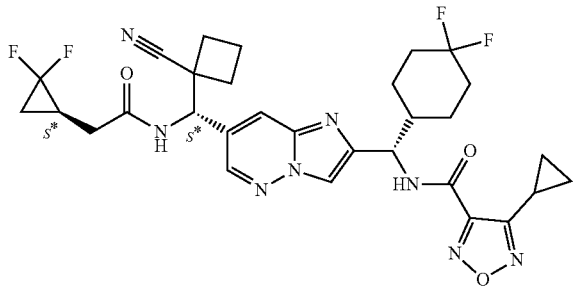 [SMILES: N#CC1([C@@H](NC(=O)C[C@H]2CC2(F)F)c2cnn3cc([C@@H](NC(=O)c4nonc4C4CC4)C4CCC(F)(F)CC4)nc3c2)CCC1]

The title compounds were prepared as described for the synthesis of Example 487, using N—((S*)-(2-((S)-amino(4,4-difluorocyclohexyl)methyl)imidazo[1,2-b]pyridazin-7-yl)(1-cyanocyclobutyl)methyl)-2-(2,2-difluorocyclopropyl)ac-etamide (Intermediate 433) in place of N—((S)-(2-((S)-amino(4,4-difluorocyclohexyl)methyl)imidazo[1,2-b]pyridazin-7-yl)(1-cyanocyclobutyl)methyl)-2-(3,3-difluorocyclobutyl)acetamide. The diastereomers were separated by SFC using a chiral stationary phase (Lux Cellulose 4 5 μm, 250×21 mm, mobile phase: 10% methanol/isopropanol (1:1) with 0.2% isopropylamine, 90% CO$_2$). The first eluting isomer was Example 448 and the second eluting isomer was Example 449. Example 448: $^1$H NMR (500 MHz, DMSO-d$_6$) δ 9.74-9.24 (m, 1H), 8.84 (br d, J=8.5 Hz, 1H), 8.65 (d, J=2.1 Hz, 1H), 8.29 (s, 1H), 8.19 (d, J=2.1 Hz, 1H), 5.47 (br d, J=8.0 Hz, 1H), 5.20 (d, J=8.1 Hz, 1H), 2.56-2.52 (m, 1H), 2.47 (br d, J=7.4 Hz, 2H), 2.44-2.33 (m, 2H), 2.31-2.24 (m, 1H), 2.24-2.15 (m, 2H), 2.13-1.94 (m, 4H), 1.90-1.69 (m, 4H), 1.66-1.50 (m, 2H), 1.43-1.34 (m, 1H), 1.34-1.25 (m, 1H), 1.24-1.16 (m, 1H), 1.13-1.10 (m, 2H), 0.98-0.93 (m, 2H). MS (ESI) m/z: [M+H]$^+$ Found 629.1. Example 449: $^1$H NMR (500 MHz, DMSO-d$_6$) δ 8.85 (br s, 1H), 8.64 (d, J=2.1 Hz, 1H), 8.29 (s, 1H), 8.18 (d, J=2.0 Hz, 1H), 5.45 (br s, 1H), 5.20 (d, J=8.1 Hz, 1H), 2.56-2.51 (m, 1H), 2.46 (d, J=7.1 Hz, 2H), 2.43-2.34 (m, 2H), 2.31-2.24 (m, 1H), 2.24-2.14 (m, 2H), 2.13-1.95 (m, 4H), 1.94-1.86 (m, 2H), 1.82-1.70 (m, 2H), 1.66-1.54 (m, 2H), 1.42-1.35 (m, 1H), 1.29 (dt, J=9.3, 12.3 Hz, 1H), 1.25-1.18 (m, 1H), 1.13-1.11 (m, 2H), 0.96-0.93 (m, 2H). MS (ESI) m/z: [M+H]$^+$ Found 629.1.

Example 450

5-Cyano-N—((S)-(7-((R)-cyclopropyl(4,4,4-trifluorobutanamido)methyl)imidazo[1,2-b]pyridazin-2-yl)(4,4-difluorocyclohexyl)methyl)nicotinamide

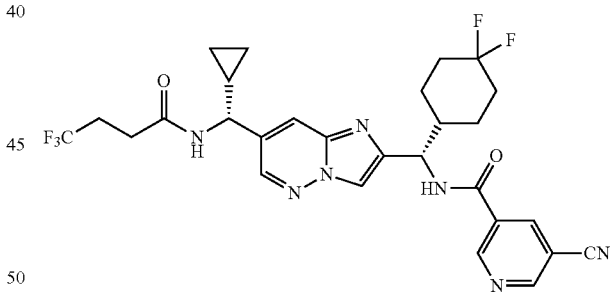

The title compound was prepared as described for the synthesis of Example 38, using 5-cyanonicotinic acid in place of 1-(3,3,3-trifluoropropyl)-1H-1,2,4-triazole-5-carboxylic acid. $^1$H NMR (500 MHz, CD$_3$OD) δ 9.22 (d, J=2.3 Hz, 1H), 9.04-9.05 (m, 1H), 8.61-8.62 (m, 1H), 8.46 (d, J=2.3 Hz, 1H), 8.13 (s, 1H), 7.88 (s, 1H), 5.28 (d, J=8.5 Hz, 1H), 4.27 (d, J=9.3 Hz, 1H), 2.55-2.57 (m, 2H), 2.49-2.50 (m, 2H), 2.25-2.26 (m, 1H), 2.11-2.13 (m, 1H), 2.00-2.03 (m, 2H), 1.77-1.80 (m, 2H), 1.67-1.68 (m, 1H), 1.49-1.51 (m, 1H), 1.38-1.40 (m, 1H), 1.25-1.27 (m, 1H), 0.69-0.71 (m, 2H), 0.48-0.50 (m, 2H). MS (ESI) m/z: [M+H]$^+$ Found 590.2.

Example 451

N—((S)-(7-((R)-Cyclopropyl(4,4,4-trifluorobutanamido)methyl)imidazo[1,2-b]pyridazin-2-yl)(4,4-difluorocyclohexyl)methyl)-5-fluoronicotinamide

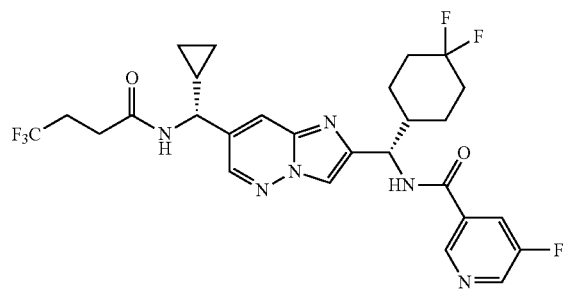 [SMILES: O=C(CCC(F)(F)F)N[C@@H](c1cnn2cc([C@@H](NC(=O)c3cncc(F)c3)C3CCC(F)(F)CC3)nc2c1)C1CC1]

The title compound was prepared as described for the synthesis of Example 38, using 5-fluoronicotinic acid in place of 1-(3,3,3-trifluoropropyl)-1H-1,2,4-triazole-5-carboxylic acid. $^1$H NMR (500 MHz, CD$_3$OD) δ 8.88 (s, 1H), 8.64 (d, J=2.8 Hz, 1H), 8.47 (d, J=2.1 Hz, 1H), 8.12 (s, 1H), 8.05-8.07 (m, 1H), 7.88 (s, 1H), 5.28 (d, J=8.6 Hz, 1H), 4.27 (d, J=9.5 Hz, 1H), 2.55-2.58 (m, 2H), 2.49-2.51 (m, 2H), 2.20-2.23 (m, 1H), 2.10-2.11 (m, 1H), 2.00-2.02 (m, 2H), 1.78-1.80 (m, 2H), 1.64-1.66 (m, 1H), 1.50-1.52 (m, 1H), 1.39-1.42 (m, 1H), 1.25-1.26 (m, 1H), 0.69-0.71 (m, 2H), 0.48-0.50 (m, 2H). MS (ESI) m/z: [M+H]$^+$ Found 583.2.

Example 452

N—((S)-(7-((R)-Cyclopropyl(4,4,4-trifluorobutanamido)methyl)imidazo[1,2-b]pyridazin-2-yl)(4,4-difluorocyclohexyl)methyl)-5-ethylnicotinamide

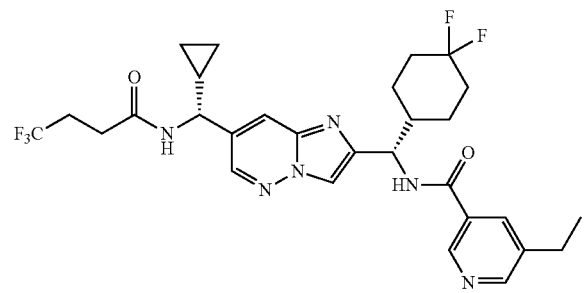 [SMILES: CCc1cncc(C(=O)N[C@H](c2cn3ncc([C@H](NC(=O)CCC(F)(F)F)C4CC4)cc3n2)C2CCC(F)(F)CC2)c1]

The title compound was prepared as described for the synthesis of Example 38, using 5-ethylnicotinic acid in place of 1-(3,3,3-trifluoropropyl)-1H-1,2,4-triazole-5-carboxylic acid. $^1$H NMR (500 MHz, CD$_3$OD) δ 8.80-8.82 (m, 1H), 8.55-8.56 (m, 1H), 8.46-8.47 (m, 1H), 8.12-8.14 (m, 2H), 7.88 (s, 1H), 5.29 (d, J=8.6 Hz, 1H), 4.28 (d, J=9.5 Hz, 1H), 2.77 (q, J=7.6 Hz, 2H), 2.55-2.57 (m, 2H), 2.48-2.50 (m, 2H), 2.25-2.27 (m, 1H), 2.08-2.11 (m, 1H), 2.02-2.03 (m, 2H), 1.79-1.80 (m, 2H), 1.64-1.66 (m, 1H), 1.52-1.53 (m, 1H), 1.40-1.42 (m, 1H), 1.30 (t, J=7.6 Hz, 3H), 1.25-1.26 (m, 1H), 0.69-0.71 (m, 2H), 0.48-0.50 (m, 2H). MS (ESI) m/z: [M+H]$^+$ Found 593.2.

Example 453

N—((S)-(7-((R)-Cyclopropyl(4,4,4-trifluorobutanamido)methyl)imidazo[1,2-b]pyridazin-2-yl)(4,4-difluorocyclohexyl)methyl)-4-ethylpicolinamide

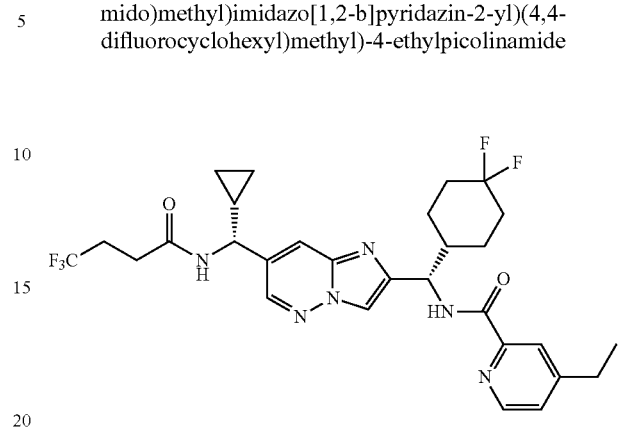

The title compound was prepared as described for the synthesis of Example 38, using 4-ethylpicolinic acid in place of 1-(3,3,3-trifluoropropyl)-1H-1,2,4-triazole-5-carboxylic acid. $^1$H NMR (500 MHz, CD$_3$OD) δ 8.52 (d, J=5.0 Hz, 1H), 8.46 (d, J=2.2 Hz, 1H), 8.12 (s, 1H), 7.97 (s, 1H), 7.90-7.89 (m, 1H), 7.42 (d, J=4.2 Hz, 1H), 5.27 (d, J=8.1 Hz, 1H), 4.28 (d, J=9.4 Hz, 1H), 2.76 (q, J=7.6 Hz, 2H), 2.56-2.58 (m, 2H), 2.49-2.50 (m, 2H), 2.23-2.24 (m, 1H), 2.04-2.06 (m, 2H), 1.97-1.99 (m, 1H), 1.78-1.79 (m, 2H), 1.66-1.68 (m, 1H), 1.49-1.50 (m, 1H), 1.39-1.40 (m, 1H), 1.27 (t, J=7.6 Hz, 3H), 1.22-1.24 (m, 1H), 0.69-0.71 (m, 2H), 0.50-0.51 (m, 2H). MS (ESI) m/z: [M+H]$^+$ Found 593.2.

Example 454

N—((S)-(7-((R)-Cyclopropyl(4,4,4-trifluorobutanamido)methyl)imidazo[1,2-b]pyridazin-2-yl)(4,4-difluorocyclohexyl)methyl)-5-methylnicotinamide

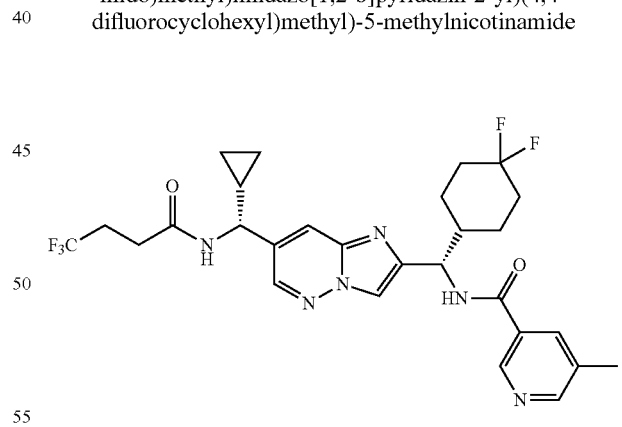

The title compound was prepared as described for the synthesis of Example 38, using 5-methylnicotinic acid in place of 1-(3,3,3-trifluoropropyl)-1H-1,2,4-triazole-5-carboxylic acid. $^1$H NMR (500 MHz, CD$_3$OD) δ 8.80 (s, 1H), 8.53 (s, 1H), 8.47 (d, J=2.0 Hz, 1H), 8.08-8.12 (m, 2H), 7.85-7.88 (m, 1H), 5.28 (d, J=8.5 Hz, 1H), 4.27 (d, J=9.5 Hz, 1H), 2.56-2.58 (m, 2H), 2.48-2.50 (m, 2H), 2.43 (s, 3H), 2.21-2.24 (m, 1H), 2.08-2.11 (m, 1H), 2.00-2.02 (m, 2H), 1.78-1.79 (m, 2H), 1.66-1.68 (m, 1H), 1.49-1.52 (m, 1H), 1.38-1.42 (m, 1H), 1.24-1.26 (m, 1H), 0.69-0.71 (m, 2H), 0.48-0.50 (m, 2H). MS (ESI) m/z: [M+H]$^+$ Found 579.2.

Example 455

N—((S)-(7-((R)-Cyclopropyl(4,4,4-trifluorobutanamido)methyl)imidazo[1,2-b]pyridazin-2-yl)(4,4-difluorocyclohexyl)methyl)-5-(difluoromethyl)nicotinamide

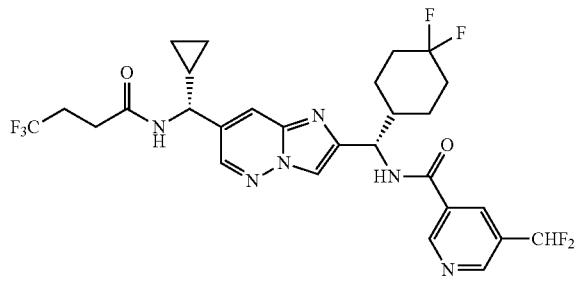 [SMILES: O=C(CCC(F)(F)F)N[C@@H](c1cnn2cc([C@@H](NC(=O)c3cncc(C(F)F)c3)C3CCC(F)(F)CC3)nc2c1)C1CC1]

The title compound was prepared as described for the synthesis of Example 38, using 5-(difluoromethyl)nicotinic acid in place of 1-(3,3,3-trifluoropropyl)-1H-1,2,4-triazole-5-carboxylic acid. $^1$H NMR (500 MHz, CD$_3$OD) δ 9.15 (s, 1H), 8.88 (s, 1H), 8.45-8.47 (m, 1H), 8.44 (s, 1H), 8.13 (s, 1H), 7.88 (s, 1H), 7.00 (t, J=55.3 Hz, 1H), 5.30 (d, J=8.6 Hz, 1H), 4.27 (d, J=9.5 Hz, 1H), 2.55-2.57 (m, 2H), 2.48-2.50 (m, 2H), 2.23-2.25 (m, 1H), 2.09-2.11 (m, 1H), 2.01-2.03 (m, 2H), 1.81-1.82 (m, 2H), 1.65-1.67 (m, 1H), 1.50-1.52 (m, 1H), 1.39-1.42 (m, 1H), 1.25-1.27 (m, 1H), 0.69-0.71 (m, 2H), 0.48-0.50 (m, 2H). MS (ESI) m/z: [M+H]$^+$ Found 615.4.

Example 456

N—((S)-(7-((R)-Cyclopropyl(4,4,4-trifluorobutanamido)methyl)imidazo[1,2-b]pyridazin-2-yl)(4,4-difluorocyclohexyl)methyl)picolinamide

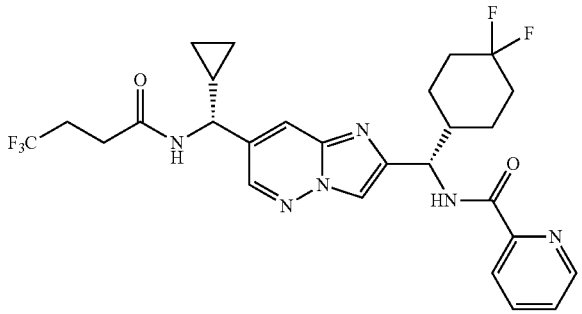 [SMILES: O=C(CCC(F)(F)F)N[C@@H](c1cnn2cc([C@@H](NC(=O)c3ccccn3)C3CCC(F)(F)CC3)nc2c1)C1CC1]

The title compound was prepare as described for the synthesis of Example 38, using picolinic acid in place of 1-(3,3,3-trifluoropropyl)-1H-1,2,4-triazole-5-carboxylic acid. $^1$H NMR (500 MHz, CD$_3$OD) δ 8.65 (d, J=4.3 Hz, 1H), 8.46 (d, J=2.1 Hz, 1H), 8.13 (s, 1H), 8.10 (d, J=7.8 Hz, 1H), 7.94-7.96 (m, 1H), 7.85-7.87 (m, 1H), 7.54-7.51 (m, 1H), 5.27 (d, J=8.2 Hz, 1H), 4.28 (d, J=9.5 Hz, 1H), 2.56-2.58 (m, 2H), 2.48-2.50 (m, 2H), 2.21-2.23 (m, 1H), 2.04-2.06 (m, 1H), 1.97-2.00 (m, 2H), 1.77-1.79 (m, 2H), 1.64-1.65 (m, 1H), 1.48-1.52 (m, 1H), 1.38-1.42 (m, 1H), 1.26-1.28 (m, 1H), 0.68-0.70 (m, 2H), 0.48-0.50 (m, 2H). MS (ESI) m/z: [M+H]$^+$ Found 565.2.

Example 457

N—((S)-(7-((R)-Cyclopropyl(4,4,4-trifluorobutanamido)methyl)imidazo[1,2-b]pyridazin-2-yl)(4,4-difluorocyclohexyl)methyl)pyridazine-4-carboxamide

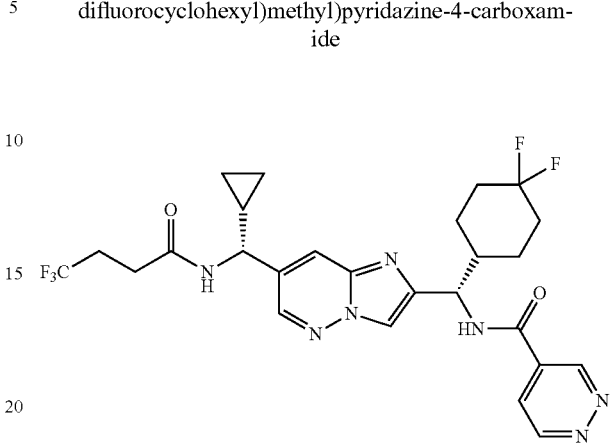

The title compound was prepared as described for the synthesis of Example 38, using pyridazine-4-carboxylic acid in place of 1-(3,3,3-trifluoropropyl)-1H-1,2,4-triazole-5-carboxylic acid. $^1$H NMR (500 MHz, CD$_3$OD) δ 9.55 (s, 1H), 9.38 (d, J=5.3 Hz, 1H), 8.47 (d, J=2.1 Hz, 1H), 8.14 (s, 1H), 8.02-8.06 (m, 1H), 7.87-7.89 (m, 1H), 5.29 (d, J=8.5 Hz, 1H), 4.27 (d, J=9.5 Hz, 1H), 2.53-2.56 (m, 2H), 2.47-2.50 (m, 2H), 2.21-2.25 (m, 1H), 2.06-2.10 (m, 1H), 2.00-2.02 (m, 2H), 1.76-1.80 (m, 2H), 1.63-1.69 (m, 1H), 1.54-1.56 (m, 1H), 1.42-1.48 (m, 1H), 1.22-1.26 (m, 1H), 0.69-0.71 (m, 2H), 0.48-0.50 (m, 2H). MS (ESI) m/z: [M+H]$^+$ Found 566.2.

Example 458

N—((S)-(7-((R)-Cyclopropyl(4,4,4-trifluorobutanamido)methyl)imidazo[1,2-b]pyridazin-2-yl)(4,4-difluorocyclohexyl)methyl)pyridazine-3-carboxamide

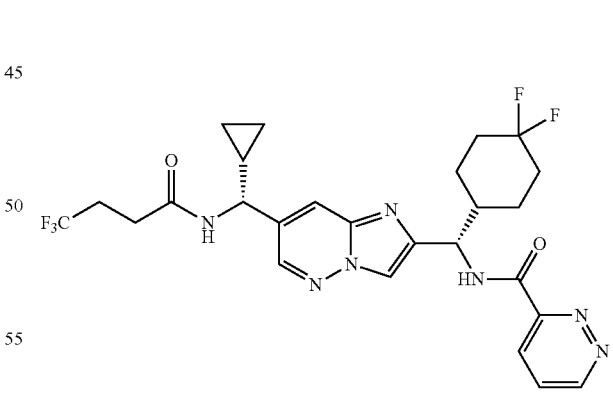

The title compound was prepared as described for the synthesis of Example 38, using pyridazine-3-carboxylic acid in place of 1-(3,3,3-trifluoropropyl)-1H-1,2,4-triazole-5-carboxylic acid. $^1$H NMR (500 MHz, CD$_3$OD) δ 9.31-9.38 (m, 1H), 8.46 (d, J=2.1 Hz, 1H), 8.26-8.31 (m, 1H), 8.16 (s, 1H), 7.88-7.92 (m, 2H), 5.33 (d, J=8.3 Hz, 1H), 4.28 (d, J=9.4 Hz, 1H), 2.56-2.59 (m, 2H), 2.44-2.49 (m, 2H), 2.23-2.26 (m, 1H), 2.03-2.09 (m, 1H), 2.00-2.02 (m, 2H), 1.74-1.79 (m, 2H), 1.63-1.67 (m, 1H), 1.48-1.51 (m, 1H), 1.38-1.42 (m, 1H), 1.22-1.26 (m, 1H), 0.68-0.71 (m, 2H), 0.48-0.50 (m, 2H). MS (ESI) m/z: [M+H]⁺ Found 566.2.

Example 459

N—((S)-(7-((R)-Cyclopropyl(4,4,4-trifluorobutanamido)methyl)imidazo[1,2-b]pyridazin-2-yl)(4,4-difluorocyclohexyl)methyl)-6-methoxypyridazine-4-carboxamide

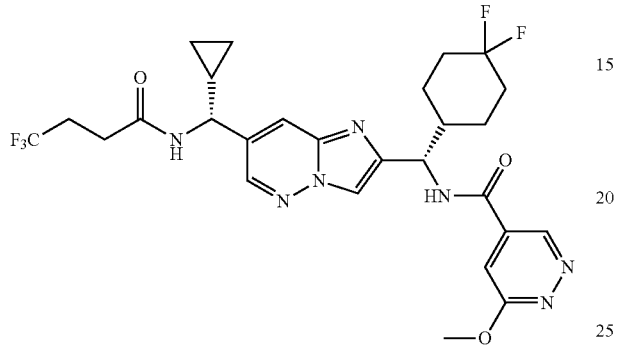

The title compound was prepared as described for the synthesis of Example 38, using 6-methoxypyridazine-4-carboxylic acid in place of 1-(3,3,3-trifluoropropyl)-1H-1,2,4-triazole-5-carboxylic acid. ¹H NMR (500 MHz, CD₃OD) δ 9.15 (d, J=1.7 Hz, 1H), 8.47 (d, J=2.1 Hz, 1H), 8.12 (s, 1H), 7.87-7.88 (m, 1H), 7.53 (d, J=1.8 Hz, 1H), 5.26 (d, J=8.5 Hz, 1H), 4.27 (d, J=9.4 Hz, 1H), 4.15 (s, 3H), 2.57-2.59 (m, 2H), 2.49-2.50 (m, 2H), 2.21-2.23 (m, 1H), 2.08-2.10 (m, 1H), 2.02-2.03 (m, 2H), 1.78-1.79 (m, 2H), 1.64-1.65 (m, 1H), 1.48-1.50 (m, 1H), 1.37-1.39 (m, 1H), 1.25-1.26 (m, 1H), 0.69-0.70 (m, 2H), 0.49-0.50 (m, 2H). MS (ESI) m/z: [M+2H]⁺ Found 597.2.

Example 460

4-Cyclopropyl-N—((S)-(7-((R)-cyclopropyl(4,4,4-trifluorobutanamido)methyl)imidazo[1,2-b]pyridazin-2-yl)(4,4-difluorocyclohexyl)methyl)picolinamide

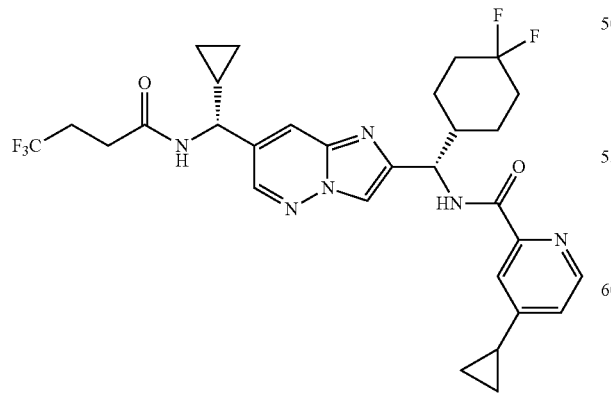

The title compound was prepared as described for the synthesis of Example 38, using 4-cyclopropylpicolinic acid in place of 1-(3,3,3-trifluoropropyl)-1H-1,2,4-triazole-5-carboxylic acid. ¹H NMR (500 MHz, CD₃OD) δ 8.46 (d, J=2.1 Hz, 1H), 8.44 (d, J=5.1 Hz, 1H), 8.12 (s, 1H), 7.88 (s, 1H), 7.77 (s, 1H), 7.25-7.26 (m, 1H), 5.26 (d, J=8.1 Hz, 1H), 4.28 (d, J=9.5 Hz, 1H), 2.54-2.56 (m, 2H), 2.51-2.53 (m, 2H), 2.20-2.22 (m, 1H), 2.08-2.09 (m, 1H), 2.02-2.04 (m, 2H), 1.96-1.98 (m, 1H), 1.76-1.78 (m, 2H), 1.63-1.64 (m, 1H), 1.48-1.50 (m, 1H), 1.39-1.41 (m, 1H), 1.23-1.25 (m, 1H), 1.15-1.17 (m, 1H), 1.12-1.14 (m, 1H), 0.86-0.87 (m, 2H), 0.69-0.71 (m, 2H), 0.48-0.50 (m, 2H). MS (ESI) m/z: [M+H]⁺ Found 605.3.

Example 461

4-Cyano-N—((S)-(7-((R)-cyclopropyl(4,4,4-trifluorobutanamido)methyl)imidazo[1,2-b]pyridazin-2-yl)(4,4-difluorocyclohexyl)methyl)picolinamide

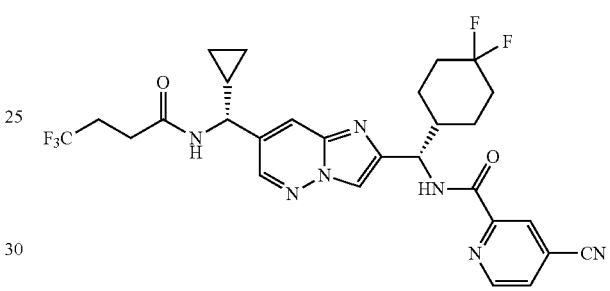

The title compound was prepared as described for the synthesis of Example 38, using 4-cyanopicolinic acid in place of 1-(3,3,3-trifluoropropyl)-1H-1,2,4-triazole-5-carboxylic acid. ¹H NMR (500 MHz, CD₃OD) δ 8.88 (d, J=5.0 Hz, 1H), 8.46 (d, J=2.1 Hz, 1H), 8.36 (s, 1H), 8.13 (s, 1H), 7.92-7.90 (m, 1H), 7.88 (s, 1H), 5.28 (d, J=8.3 Hz, 1H), 4.27 (d, J=9.4 Hz, 1H), 2.56-2.58 (m, 2H), 2.48-2.50 (m, 2H), 2.22-2.24 (m, 1H), 2.04-2.06 (m, 2H), 1.98-1.99 (m, 1H), 1.78-1.79 (m, 2H), 1.63-1.65 (m, 1H), 1.48-1.50 (m, 1H), 1.36-1.38 (m, 1H), 1.27-1.28 (m, 1H), 0.69-0.71 (m, 2H), 0.48-0.50 (m, 2H). MS (ESI) m/z: [M+H]⁺ Found 590.2.

Example 462

N—((S)-(7-((R)-Cyclopropyl(4,4,4-trifluorobutanamido)methyl)imidazo[1,2-b]pyridazin-2-yl)(4,4-difluorocyclohexyl)methyl)-5-(methoxymethyl)nicotinamide

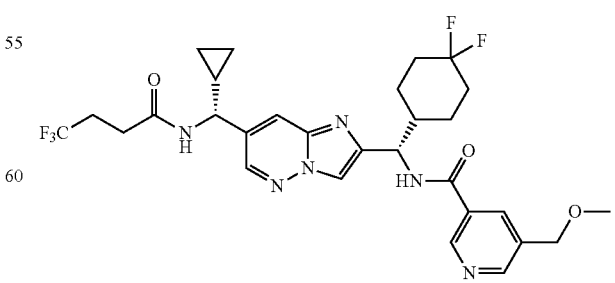

The title compound was prepared as described for the synthesis of Example 38, using 5-(methoxymethyl)nicotinic acid in place of 1-(3,3,3-trifluoropropyl)-1H-1,2,4-triazole-5-carboxylic acid. ¹H NMR (500 MHz, CD₃OD) δ 8.93 (d, J=2.2 Hz, 1H), 8.66 (d, J=2.0 Hz, 1H), 8.47 (d, J=2.1 Hz, 1H), 8.24 (t, J=2.0 Hz, 1H), 8.12 (s, 1H), 7.88-7.90 (m, 1H), 5.29 (d, J=8.6 Hz, 1H), 4.57 (s, 2H), 4.28 (d, J=9.5 Hz, 1H), 3.45 (s, 3H), 2.55-2.57 (m, 2H), 2.49-2.50 (m, 2H), 2.23-2.25 (m, 1H), 2.08-2.11 (m, 1H), 2.00-2.02 (m, 2H), 1.79-1.81 (m, 2H), 1.64-1.66 (m, 1H), 1.51-1.53 (m, 1H), 1.38-1.40 (m, 1H), 1.23-1.25 (m, 1H), 0.69-0.71 (m, 2H), 0.48-0.50 (m, 2H). MS (ESI) m/z: [M+H]⁺ Found 609.2.

Example 463

N—((S)-(7-((R)-Cyclopropyl(4,4,4-trifluorobutanamido)methyl)imidazo[1,2-b]pyridazin-2-yl)(4,4-difluorocyclohexyl)methyl)-3-isopropylthiophene-2-carboxamide

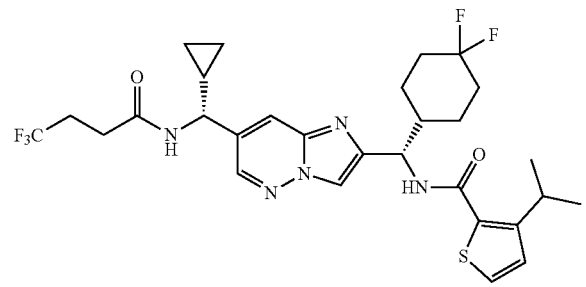 [SMILES: CC(C)c1ccsc1C(=O)N[C@H](c1cn2ncc([C@H](NC(=O)CCC(F)(F)F)C3CC3)cc2n1)C1CCC(F)(F)CC1]

The title compound was prepared as described for the synthesis of Example 38, using 3-isopropylthiophene-2-carboxylic acid in place of 1-(3,3,3-trifluoropropyl)-1H-1,2,4-triazole-5-carboxylic acid. ¹H NMR (400 MHz, DMSO-d₆) δ 8.75 (d, J=7.5 Hz, 1H), 8.50 (d, J=2.0 Hz, 1H), 8.33 (d, J=9.0 Hz, 1H), 8.16 (s, 1H), 7.94 (d, J=1.5 Hz, 1H), 7.56 (d, J=5.0 Hz, 1H), 7.12 (d, J=5.0 Hz, 1H), 5.20-5.09 (m, 1H), 4.33-4.23 (m, 1H), 3.59-3.49 (m, 1H), 2.49-2.43 (m, 4H), 2.18-1.94 (m, 3H), 1.87-1.67 (m, 3H), 1.65-1.57 (m, 1H), 1.43-1.35 (m, 1H), 1.32-1.18 (m, 2H), 1.15 (d, J=6.8 Hz, 6H), 0.62-0.46 (m, 3H), 0.41-0.33 (m, 1H). MS (ESI) m/z: [M+H]⁺ Found 612.2.

Example 464

N—((S)-(7-((R)-Cyclopropyl(4,4,4-trifluorobutanamido)methyl)imidazo[1,2-b]pyridazin-2-yl)(4,4-difluorocyclohexyl)methyl)-4-isopropylthiazole-5-carboxamide

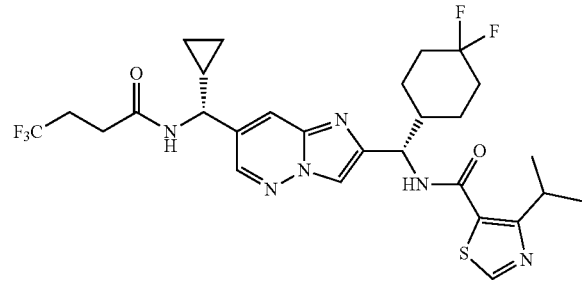

The title compound was prepared as described for the synthesis of Example 38, using 4-isopropylthiazole-5-carboxylic acid in place of 1-(3,3,3-trifluoropropyl)-1H-1,2,4-triazole-5-carboxylic acid. ¹H NMR (400 MHz, DMSO-d₆) δ 9.03 (s, 1H), 8.74 (d, J=7.6 Hz, 1H), 8.67 (d, J=8.8 Hz, 1H), 8.50 (d, J=2.0 Hz, 1H), 8.16 (s, 1H), 7.93 (s, 1H), 5.14 (t, J=8.0 Hz, 1H), 4.28 (t, J=8.0 Hz, 1H), 3.63-3.51 (m, 1H), 2.50-2.43 (m, 3H), 2.22-1.91 (m, 3H), 1.89-1.53 (m, 4H), 1.42-1.15 (m, 4H), 1.19 (d, J=6.8 Hz, 6H), 0.64-0.43 (m, 3H), 0.42-0.31 (m, 1H). MS (ESI) m/z: [M+H]⁺ Found 613.2.

Example 465

N—((S)-(7-((R)-Cyclopropyl(4,4,4-trifluorobutanamido)methyl)imidazo[1,2-b]pyridazin-2-yl)(4,4-difluorocyclohexyl)methyl)-6-methoxypyrimidine-4-carboxamide

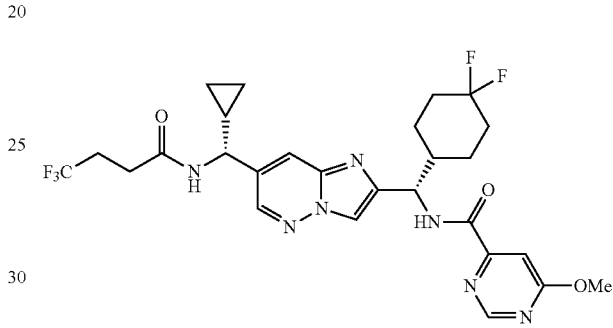

The title compound was prepared as described for the synthesis of Example 32, using 6-methoxypyrimidine-4-carboxylic acid in place of 2-(3,3-difluoropropyl)-2H-1,2,3-triazole-4-carboxylic acid. ¹H NMR (500 MHz, CD₃OD) δ 8.81 (d, J=1.0 Hz, 1H), 8.46 (d, J=2.0 Hz, 1H), 8.12 (s, 1H), 7.86-7.90 (m, 1H), 7.41 (d, J=1.0 Hz, 1H), 5.25 (d, J=8.5 Hz, 1H), 4.28 (d, J=9.5 Hz, 1H), 4.03 (s, 3H), 2.45-2.61 (m, 4H), 2.17-2.28 (m, 1H), 1.91-2.11 (m, 3H), 1.59-1.87 (m, 3H), 1.34-1.51 (m, 2H), 1.21-1.32 (m, 1H), 0.66-0.74 (m, 2H), 0.46-0.52 (m, 2H). MS (ESI) m/z: [M+H]⁺ Found 596.1.

Example 466

5-Cyclopropyl-N—((S)-(7-((R*)-cyclopropyl(4,4,4-trifluorobutanamido)methyl)imidazo[1,2-b]pyridazin-2-yl)(4,4-difluorocyclohexyl)methyl)-1,2,3-thiadiazole-4-carboxamide

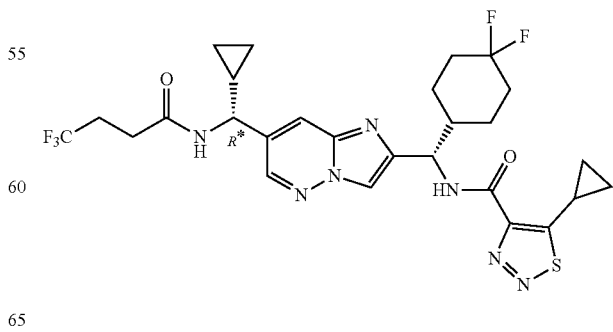

The title compound was prepared as described for the synthesis of Example 32, using 5-cyclopropyl-1,2,3-thiadiazole-4-carboxylic acid in place of 2-(3,3-difluoropropyl)-2H-1,2,3-triazole-4-carboxylic acid and N—((R*)-(2-((S)-amino(4,4-difluorocyclohexyl)methyl)imidazo[1,2-b]pyridazin-7-yl)(cyclopropyl)methyl)-4,4,4-trifluorobutanamide (Intermediate 411) in place of N—((R)-(2-((S)-amino(4,4-difluorocyclohexyl)methyl)imidazo[1,2-b]pyridazin-7-yl)(cyclopropyl)methyl)-4,4,4-trifluorobutanamide. $^1$H NMR (500 MHz, DMSO-$d_6$) δ 9.00 (d, J=9.0 Hz, 1H), 8.71 (d, J=7.5 Hz, 1H), 8.47-8.56 (m, 1H), 8.28 (s, 1H), 7.96-8.00 (m, 1H), 5.26 (t, J=8.5 Hz, 1H), 4.25-4.33 (m, 1H), 3.16-3.24 (m, 1H), 2.44-2.49 (m, 3H), 2.14-2.27 (m, 1H), 1.90-2.10 (m, 3H), 1.70-1.86 (m, 2H), 1.58-1.69 (m, 1H), 1.38-1.48 (m, 3H), 1.13-1.37 (m, 3H), 0.80-0.89 (m, 2H), 0.47-0.61 (m, 3H), 0.33-0.42 (m, 1H). MS (ESI) m/z: [M+H]$^+$ Found 612.1.

Example 467

N—((S)-(7-((R*)-Cyclopropyl(4,4,4-trifluorobutanamido)methyl)imidazo[1,2-b]pyridazin-2-yl)(4,4-difluorocyclohexyl)methyl)-4-methyl-1,2,5-thiadiazole-3-carboxamide

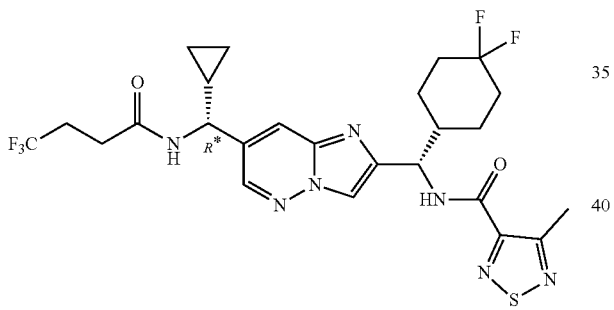

The title compound was prepared as described for the synthesis of Example 32, using 4-methyl-1,2,5-thiadiazole-3-carboxylic acid in place of 2-(3,3-difluoropropyl)-2H-1,2,3-triazole-4-carboxylic acid and N—((R*)-(2-((S)-amino(4,4-difluorocyclohexyl)methyl)imidazo[1,2-b]pyridazin-7-yl)(cyclopropyl)methyl)-4,4,4-trifluorobutanamide (Intermediate 411) in place of N—((R)-(2-((S)-amino(4,4-difluorocyclohexyl)methyl)imidazo[1,2-b]pyridazin-7-yl)(cyclopropyl)methyl)-4,4,4-trifluorobutanamide. $^1$H NMR (400 MHz, CD$_3$OD) δ 8.46 (d, J=2.3 Hz, 1H), 8.12 (s, 1H), 7.86-7.92 (m, 1H), 5.25 (d, J=8.5 Hz, 1H), 4.28 (d, J=9.5 Hz, 1H), 2.75 (s, 3H), 2.45-2.62 (m, 4H), 2.16-2.30 (m, 1H), 1.94-2.15 (m, 3H), 1.59-1.90 (m, 3H), 1.34-1.55 (m, 2H), 1.20-1.32 (m, 1H), 0.65-0.75 (m, 2H), 0.46-0.53 (m, 2H). MS (ESI) m/z: [M+H]$^+$ Found 586.1.

Example 468

N—((S)-(7-((R)-Cyclopropyl(4,4,4-trifluorobutanamido)methyl)imidazo[1,2-b]pyridazin-2-yl)(4,4-difluorocyclohexyl)methyl)-1-methyl-1H-tetrazole-5-carboxamide

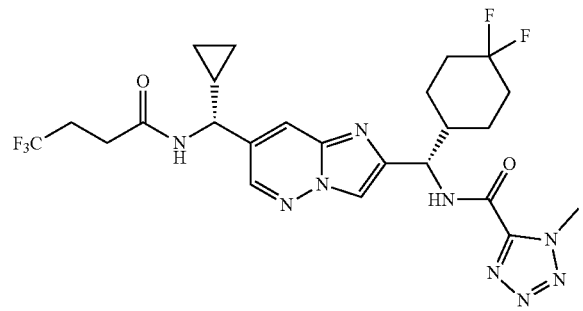 [SMILES: Cn1nnnc1C(=O)N[C@H](c1cn2ncc([C@H](NC(=O)CCC(F)(F)F)C3CC3)cc2n1)C1CCC(F)(F)CC1]

The title compound was prepared as described for the synthesis of Example 142, using potassium 1-methyl-1H-tetrazole-5-carboxylate in place of 4-methyl-1,2,5-oxadiazole-3-carboxylic acid. $^1$H NMR (500 MHz, CD$_3$OD) δ 8.44 (d, J=2.3 Hz, 1H), 8.08 (s, 1H), 7.82-7.87 (m, 1H), 5.22 (d, J=8.5 Hz, 1H), 4.33 (s, 3H), 4.26 (d, J=9.5 Hz, 1H), 2.45-2.62 (m, 4H), 2.14-2.26 (m, 1H), 1.92-2.14 (m, 3H), 1.56-1.89 (m, 3H), 1.42-1.54 (m, 1H), 1.21-1.42 (m, 2H), 0.66-0.75 (m, 2H), 0.46-0.53 (m, 2H). MS (ESI) m/z: [M+H]$^+$ Found 570.1.

Example 469

N—((S)-(7-((R)-Cyclopropyl(4,4,4-trifluorobutanamido)methyl)imidazo[1,2-b]pyridazin-2-yl)(4,4-difluorocyclohexyl)methyl)-1-methyl-1H-imidazole-2-carboxamide

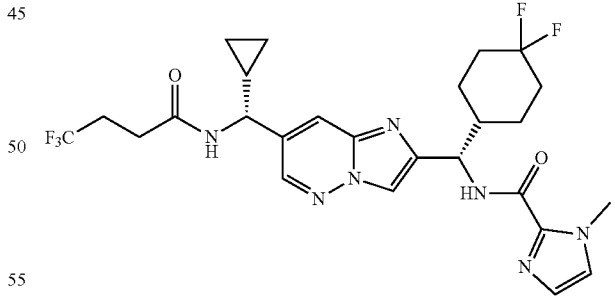

The title compound was prepared as described for the synthesis of Example 32, using 1-methyl-1H-imidazole-2-carboxylic acid in place of 2-(3,3-difluoropropyl)-2H-1,2,3-triazole-4-carboxylic acid. $^1$H NMR (500 MHz, CD$_3$OD) δ 8.45 (d, J=2.0 Hz, 1H), 8.10 (s, 1H), 7.85-7.89 (m, 1H), 7.22 (d, J=1.0 Hz, 1H), 7.02 (d, J=1.0 Hz, 1H), 5.20 (d, J=7.8 Hz, 1H), 4.28 (d, J=9.5 Hz, 1H), 4.00 (s, 3H), 2.45-2.62 (m, 4H), 2.13-2.25 (m, 1H), 1.94 (s, 3H), 1.61-1.87 (m, 3H), 1.33-1.55 (m, 2H), 1.20-1.31 (m, 1H), 0.65-0.74 (m, 2H), 0.46-0.52 (m, 2H). MS (ESI) m/z: [M+H]$^+$ Found 568.2.

Example 470

N—((S)-(7-((R)-Cyclopropyl(4,4,4-trifluorobutanamido)methyl)imidazo[1,2-b]pyridazin-2-yl)(4,4-difluorocyclohexyl)methyl)-4-ethylisoxazole-5-carboxamide

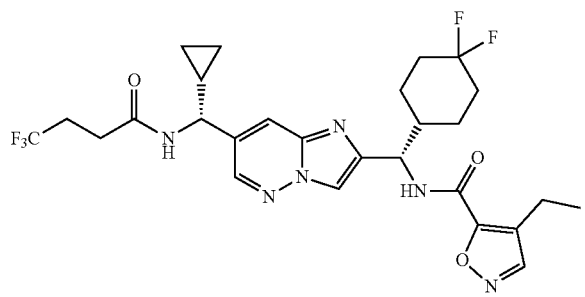 [SMILES: CCc1cnoc1C(=O)N[C@H](c1cn2ncc([C@H](NC(=O)CCC(F)(F)F)C3CC3)cc2n1)C1CCC(F)(F)CC1]

The title compound was prepared as described for the synthesis of Example 32, using 4-ethylisoxazole-5-carboxylic acid in place of 2-(3,3-difluoropropyl)-2H-1,2,3-triazole-4-carboxylic acid. $^1$H NMR (500 MHz, CD$_3$OD) δ 8.43-8.46 (m, 2H), 8.10 (s, 1H), 7.86-7.89 (m, 1H), 5.23 (d, J=8.8 Hz, 1H), 4.28 (d, J=9.5 Hz, 1H), 2.78 (q, J=7.7 Hz, 2H), 2.45-2.62 (m, 4H), 2.15-2.27 (m, 1H), 1.96-2.13 (m, 3H), 1.67-1.85 (m, 2H), 1.58-1.66 (m, 1H), 1.31-1.53 (m, 2H), 1.22-1.30 (m, 1H), 1.19 (t, J=7.5 Hz, 3H), 0.66-0.74 (m, 2H), 0.46-0.52 (m, 2H). MS (ESI) m/z: [M+H]$^+$ Found 583.2.

Example 471

N—((S)-(7-((R)-Cyclopropyl(4,4,4-trifluorobutanamido)methyl)imidazo[1,2-b]pyridazin-2-yl)(4,4-difluorocyclohexyl)methyl)-4-methyloxazole-5-carboxamide

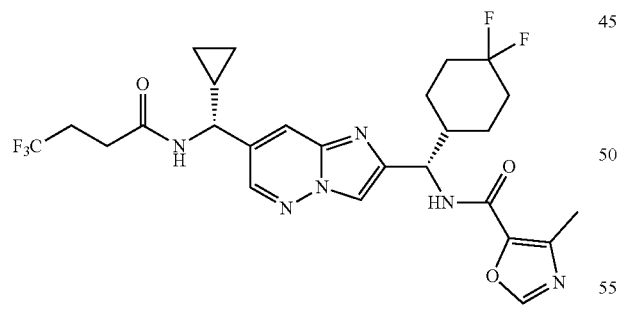

The title compound was prepared as described for the synthesis of Example 32, using 4-methyloxazole-5-carboxylic acid in place of 2-(3,3-difluoropropyl)-2H-1,2,3-triazole-4-carboxylic acid. $^1$H NMR (500 MHz, CD$_3$OD) δ 8.35 (d, J=2.0 Hz, 1H), 8.09 (s, 1H), 7.99 (s, 1H), 7.78-7.75 (m, 1H), 5.12 (d, J=8.5 Hz, 1H), 4.17 (d, J=9.5 Hz, 1H), 2.49-2.35 (m, 4H), 2.33 (s, 3H), 2.14-2.04 (m, 1H), 2.01-1.84 (m, 3H), 1.74-1.56 (m, 2H), 1.52 (br d, J=12.5 Hz, 1H), 1.41-1.21 (m, 2H), 1.19-1.11 (m, 1H), 0.64-0.54 (m, 2H), 0.44-0.35 (m, 2H). MS (ESI) m/z: [M+H]$^+$ Found 569.2.

Example 472

N—((S)-(7-((R)-Cyclopropyl(4,4,4-trifluorobutanamido)methyl)imidazo[1,2-b]pyridazin-2-yl)(4,4-difluorocyclohexyl)methyl)-2,4-dimethyloxazole-5-carboxamide

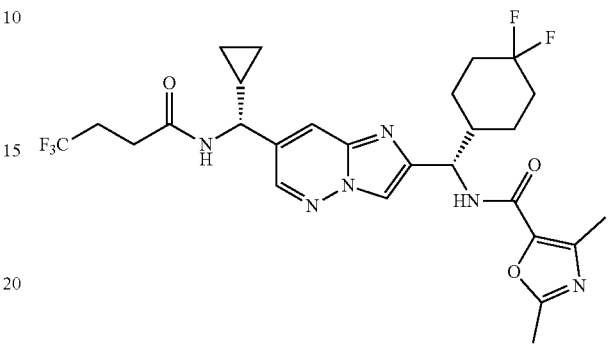

The title compound was prepared as described for the synthesis of Example 32, using 2,4-dimethyloxazole-5-carboxylic acid in place of 2-(3,3-difluoropropyl)-2H-1,2,3-triazole-4-carboxylic acid. $^1$H NMR (500 MHz, CD$_3$OD) δ 8.34 (d, J=2.0 Hz, 1H), 7.97 (s, 1H), 7.81-7.74 (m, 1H), 5.08 (d, J=8.3 Hz, 1H), 4.17 (d, J=9.3 Hz, 1H), 2.43 (s, 7H), 2.30 (s, 3H), 2.09-2.01 (m, 1H), 2.00-1.81 (m, 3H), 1.73-1.57 (m, 2H), 1.56-1.49 (m, 1H), 1.39-1.21 (m, 2H), 1.18-1.11 (m, 1H), 0.64-0.54 (m, 2H), 0.44-0.33 (m, 2H). MS (ESI) m/z: [M+H]$^+$ Found 583.2.

Example 473

N—((S)-(7-((R)-Cyclopropyl(4,4,4-trifluorobutanamido)methyl)imidazo[1,2-b]pyridazin-2-yl)(4,4-difluorocyclohexyl)methyl)-3,4-dimethylisoxazole-5-carboxamide

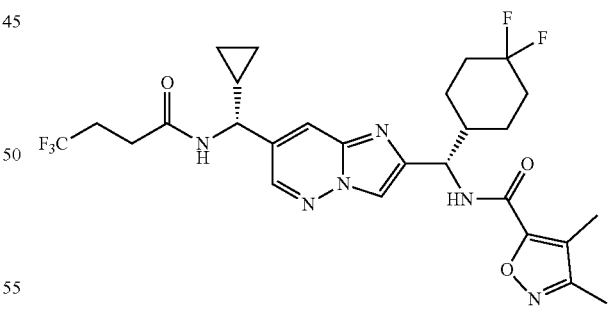

The title compound was prepared as described for the synthesis of Example 32, using 3,4-dimethylisoxazole-5-carboxylic acid in place of 2-(3,3-difluoropropyl)-2H-1,2,3-triazole-4-carboxylic acid. $^1$H NMR (400 MHz, CD$_3$OD) δ 8.48 (d, J=2.0 Hz, 1H), 8.09 (s, 1H), 7.91-7.87 (m, 1H), 5.28 (d, J=8.0 Hz, 1H), 4.29 (d, J=9.3 Hz, 1H), 2.63-2.45 (m, 7H), 2.35 (s, 3H), 2.23-2.02 (m, 3H), 2.00-1.94 (m, 1H), 1.89-1.64 (m, 3H), 1.58-1.37 (m, 2H), 1.33-1.23 (m, 1H), 0.78-0.67 (m, 2H), 0.55-0.48 (m, 2H). MS (ESI) m/z: [M+H]$^+$ Found 583.2.

Example 474

3-Cyclobutyl-N—((S)-(7-((R)-cyclopropyl(4,4,4-trifluorobutanamido)methyl)imidazo[1,2-b]pyridazin-2-yl)(4,4-difluorocyclohexyl)methyl)isoxazole-4-carboxamide

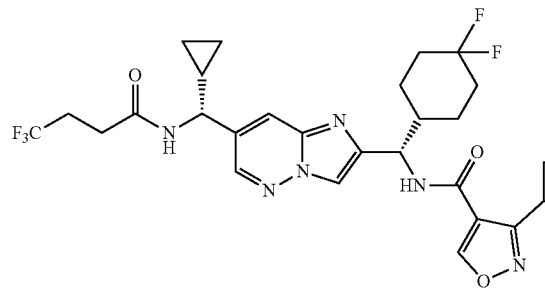

The title compound was prepared as described for the synthesis of Example 32, using 3-cyclobutylisoxazole-4-carboxylic acid in place of 2-(3,3-difluoropropyl)-2H-1,2,3-triazole-4-carboxylic acid to provide the title compound as a white powder. $^1$H NMR (600 MHz, CDCl$_3$) δ 8.74 (s, 1H), 8.34 (d, J=2.2 Hz, 1H), 7.83 (s, 1H), 7.83-7.74 (m, 1H), 6.82 (d, J=8.3 Hz, 1H), 6.01 (d, J=6.8 Hz, 1H), 5.34-5.22 (m, 1H), 4.31 (dd, J=9.3, 6.8 Hz, 1H), 3.86 (p, J=8.3 Hz, 1H), 2.59-2.48 (m, 4H), 2.45-2.39 (m, 2H), 2.17-2.01 (m, 3H), 2.01-1.91 (m, 2H), 1.79-1.65 (m, 2H), 1.53-1.46 (m, 1H), 1.37-1.14 (m, 5H), 0.91-0.81 (m, 1H), 0.81-0.73 (m, 2H), 0.51 (ddt, J=21.7, 9.3, 4.4 Hz, 2H). MS (ESI) m/z: [M+H]$^+$ Found 609.2.

Example 475

N—((R)-(7-((S)-Cyclopropyl(4,4,4-trifluorobutanamido)methyl)imidazo[1,2-b]pyridazin-2-yl)(4,4-difluorocyclohexyl)methyl)-1-((2,2-difluorocyclopropyl)methyl)-1H-1,2,4-triazole-5-carboxamide

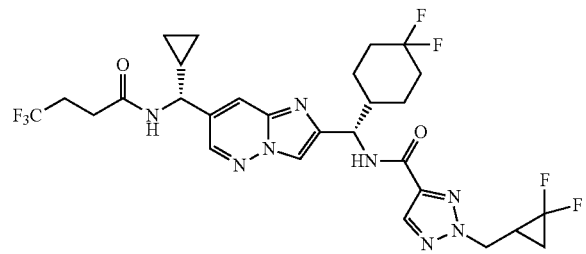 [SMILES: O=C(CCC(F)(F)F)N[C@@H](c1cnn2cc([C@@H](NC(=O)c3cnn(CC4CC4(F)F)n3)C3CCC(F)(F)CC3)nc2c1)C1CC1]

The title compound was prepared as described for the synthesis of Example 32, using lithium 1-((2,2-difluorocyclopropyl)methyl)-1H-1,2,4-triazole-5-carboxylate (Intermediate 413) in place of 2-(3,3-difluoropropyl)-2H-1,2,3-triazole-4-carboxylic acid to provide the title compound as a white powder. $^1$H NMR (500 MHz, CDCl$_3$) δ 8.31 (t, J=1.6 Hz, 1H), 8.20 (dd, J=9.1, 6.9 Hz, 1H), 7.89 (d, J=1.8 Hz, 1H), 7.86-7.84 (m, 2H), 6.08 (d, J=6.8 Hz, 1H), 5.21 (dd, J=9.5, 7.5 Hz, 1H), 4.90-4.69 (m, 2H), 4.31 (dd, J=9.5, 6.9 Hz, 1H), 2.54-2.47 (m, 3H), 2.29-1.94 (m, 5H), 1.76-1.66 (m, 2H), 1.56-1.37 (m, 4H), 1.21-1.10 (m, 2H), 0.87 (ddq, J=19.4, 15.1, 8.4, 6.9 Hz, 1H), 0.75 (ddq, J=13.2, 9.0, 4.4 Hz, 2H), 0.49 (ddq, J=18.1, 9.5, 4.6 Hz, 2H). MS (ESI) m/z: [M+H]$^+$ Found 645.2.

Example 476

N—((S)-(7-((R)-Cyclopropyl(4,4,4-trifluorobutanamido)methyl)imidazo[1,2-b]pyridazin-2-yl)(4,4-difluorocyclohexyl)methyl)-1-(3,3-difluorobutyl)-1H-1,2,4-triazole-5-carboxamide

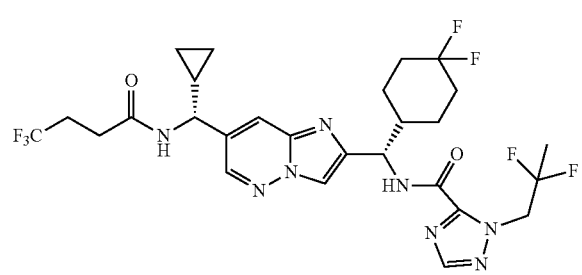 [SMILES: CC(F)(F)Cn1ncnc1C(=O)N[C@H](c1cn2ncc([C@H](NC(=O)CCC(F)(F)F)C3CC3)cc2n1)C1CCC(F)(F)CC1]

The title compound was prepared as described for the synthesis of Example 32, using methyl 1-(3,3-difluorobutyl)-1H-1,2,4-triazole-5-carboxylate (Intermediate 415) in place of 2-(3,3-difluoropropyl)-2H-1,2,3-triazole-4-carboxylic acid to provide the title compound as a white powder. $^1$H NMR (500 MHz, CDCl$_3$) δ 8.31 (d, J=2.1 Hz, 1H), 8.20 (d, J=9.2 Hz, 1H), 7.90-7.82 (m, 3H), 6.13 (d, J=6.9 Hz, 1H), 5.22 (dd, J=9.2, 7.6 Hz, 1H), 4.95-4.84 (m, 2H), 4.32 (dd, J=9.2, 6.9 Hz, 1H), 2.61-2.44 (m, 6H), 2.21-1.94 (m, 4H), 1.66 (t, J=18.5 Hz, 5H), 1.55-1.45 (m, 1H), 1.45-1.32 (m, 1H), 1.20-1.13 (m, 2H), 0.80-0.68 (m, 2H), 0.52-0.45 (m, 2H). MS (ESI) m/z: [M+H]$^+$ Found 647.2.

Example 477

N—((S)-(7-((R)-Cyclopropyl(4,4,4-trifluorobutanamido)methyl)imidazo[1,2-b]pyridazin-2-yl)(4,4-difluorocyclohexyl)methyl)-1-(2,2-difluoropropyl)-1H-1,2,4-triazole-5-carboxamide The title compound was prepared as described for the synthesis of Example 32, using lithium 1-(2,2-difluoropropyl)-1H-1,2,4-triazole-5-carboxylate (Intermediate 417) in place of 2-(3,3-difluoropropyl)-2H-1,2,3-triazole-4-carboxylic acid to provide the title compound as a white powder. $^1$H NMR (400 MHz, CDCl$_3$) δ 8.31 (d, J=2.1 Hz, 1H), 8.23 (d, J=9.1 Hz, 1H), 7.93 (s, 1H), 7.86 (d, J=1.9 Hz, 2H), 6.14 (d, J=6.9 Hz, 1H), 5.23-5.09 (m, 3H), 4.32 (dd, J=9.4, 6.9 Hz, 1H), 2.56-2.47 (m, 4H), 2.20-2.09 (m, 2H), 1.98-1.93

(m, 1H), 1.86 (s, 1H), 1.65 (t, J=18.6 Hz, 6H), 1.51 (qd, J=12.8, 3.8 Hz, 1H), 1.44-1.35 (m, 1H), 1.22-1.12 (m, 1H), 0.89-0.71 (m, 2H), 0.55-0.43 (m, 2H). MS (ESI) m/z: [M+H]+ Found 633.2.

Example 478

N—((S)-(7-((R)-Cyclopropyl(4,4,4-trifluorobutanamido)methyl)imidazo[1,2-b]pyridazin-2-yl)(4,4-difluorocyclohexyl)methyl)-1-((R)-1,1,1-trifluoropropan-2-yl)-1H-1,2,4-triazole-5-carboxamide

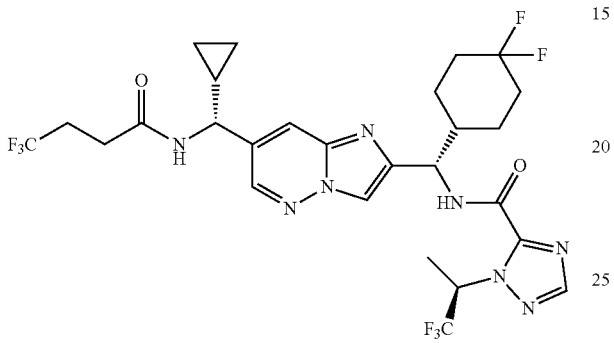

The title compound was prepared as described for the synthesis of Example 32, using lithium (R)-1-(1,1,1-trifluoropropan-2-yl)-1H-1,2,4-triazole-5-carboxylate (Intermediate 419) in place of 2-(3,3-difluoropropyl)-2H-1,2,3-triazole-4-carboxylic acid to provide the title compound as a white powder. $^1$H NMR (400 MHz, CDCl$_3$) δ 8.32 (d, J=2.1 Hz, 1H), 8.22 (d, J=9.1 Hz, 1H), 7.95 (d, J=0.6 Hz, 1H), 7.89-7.83 (m, 1H), 6.47 (p, J=7.0 Hz, 1H), 6.06 (d, J=7.0 Hz, 1H), 5.19 (dd, J=9.1, 7.8 Hz, 1H), 4.31 (dd, J=10.0, 6.4 Hz, 1H), 2.59-2.45 (m, 4H), 2.20-1.95 (m, 2H), 1.82-1.69 (m, 6H), 1.58-1.50 (m, 1H), 1.42-1.35 (m, 1H), 1.29-1.23 (m, 1H), 1.22-1.12 (m, 1H), 0.80-0.72 (m, 2H), 0.55-0.44 (m, 2H). MS (ESI) m/z: [M+H]+ Found 651.2.

Example 479

N—((S)-(7-((R)-Cyclopropyl(4,4,4-trifluorobutanamido)methyl)imidazo[1,2-b]pyridazin-2-yl)(4,4-difluorocyclohexyl)methyl)-1-(1,1-difluoropropan-2-yl)-1H-1,2,4-triazole-5-carboxamide

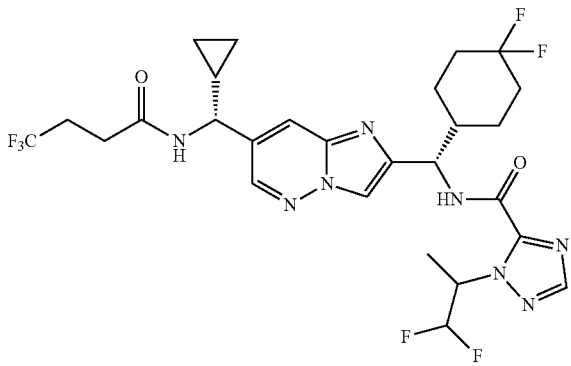 [SMILES: CC(C(F)F)n1ncnc1C(=O)N[C@H](c1cn2ncc([C@H](NC(=O)CCC(F)(F)F)C3CC3)cc2n1)C1CCC(F)(F)CC1]

The title compound was prepared as described for the synthesis of Example 32, using lithium 1-(1,1-difluoropropan-2-yl)-1H-1,2,4-triazole-5-carboxylate (Intermediate 421) in place of 2-(3,3-difluoropropyl)-2H-1,2,3-triazole-4-carboxylic acid to provide the title compound as a white powder. $^1$H NMR (400 MHz, CDCl$_3$) δ 8.31 (d, J=2.3 Hz, 1H), 8.22 (dd, J=14.1, 9.1 Hz, 1H), 7.92 (d, J=2.3 Hz, 1H), 7.89-7.80 (m, 2H), 6.22-5.83 (m, 3H), 5.21 (ddd, J=9.1, 7.6, 5.4 Hz, 1H), 4.32 (dt, J=9.5, 6.1 Hz, 1H), 2.57-2.44 (m, 4H), 2.20-2.02 (m, 2H), 2.02-1.92 (m, 1H), 1.78-1.61 (m, 7H), 1.59-1.47 (m, 1H), 1.16 (tt, J=9.1, 3.8 Hz, 1H), 0.75 (ddt, J=7.7, 6.4, 3.8 Hz, 2H), 0.55-0.43 (m, 2H). MS (ESI) m/z: [M+H]+ Found 633.2.

Example 480

N—((S)-(7-((R)-Cyclopropyl(4,4,4-trifluorobutanamido)methyl)imidazo[1,2-b]pyridazin-2-yl)(4,4-difluorocyclohexyl)methyl)-5-isopropylthiazole-4-carboxamide

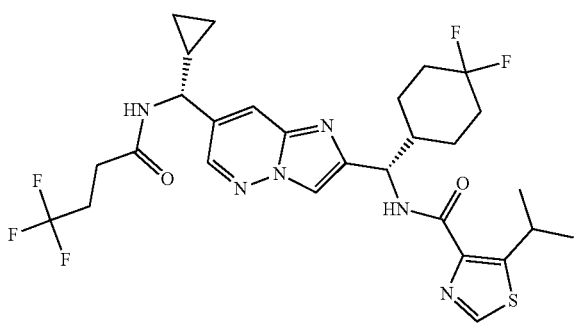 [SMILES: CC(C)c1scnc1C(=O)N[C@H](c1cn2ncc([C@H](NC(=O)CCC(F)(F)F)C3CC3)cc2n1)C1CCC(F)(F)CC1]

The title compound was prepared as described for the synthesis of Example 32, using 5-isopropylthiazole-4-carboxylic acid in place of 2-(3,3-difluoropropyl)-2H-1,2,3-triazole-4-carboxylic acid to provide the title compound as a white powder. $^1$H NMR (400 MHz, DMSO-d$_6$) δ 8.99 (s, 1H), 8.77-8.72 (m, 1H), 8.53-8.50 (m, 1H), 8.50-8.46 (m, 1H), 8.26 (s, 1H), 8.02-7.97 (m, 1H), 5.22-5.14 (m, 1H), 4.34-4.22 (m, 2H), 2.50-2.43 (m, 4H), 2.12-1.94 (m, 3H), 1.91-1.67 (m, 3H), 1.63-1.54 (m, 1H), 1.35-1.19 (m, 9H), 0.60-0.46 (m, 3H), 0.43-0.33 (m, 1H). MS (ESI) m/z: [M+H]+ Found 613.3.

Example 481

N—[(S)-[7-[(R)-Cyclopropyl-(4,4,4-trifluorobutanamido)methyl]imidazo[1,2-b]pyridazin-2-yl]-(4,4-difluorocyclohexyl)methyl]-4-isopropyl-thiadiazole-5-carboxamide

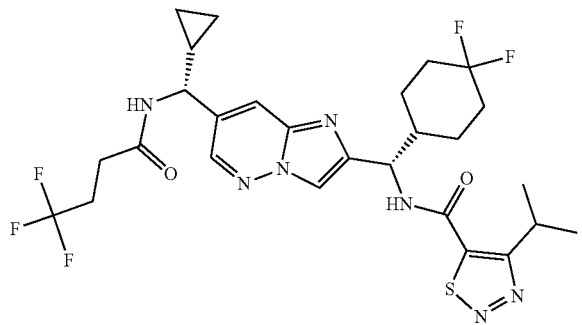 [SMILES: CC(C)c1nnsc1C(=O)N[C@H](c1cn2ncc([C@H](NC(=O)CCC(F)(F)F)C3CC3)cc2n1)C1CCC(F)(F)CC1]

The title compound was prepared as described for the synthesis of Example 32, using 4-isopropyl-1,2,3-thiadiazole-5-carboxylic acid in place of 2-(3,3-difluoropropyl)-2H-1,2,3-triazole-4-carboxylic acid to provide the title compound as a white powder. ¹H NMR (400 MHz, CDCl₃) δ 8.28 (d, J=2.0 Hz, 1H), 7.79 (s, 1H), 7.73 (s, 1H), 7.06 (d, J=8.8 Hz, 1H), 6.00 (d, J=6.8 Hz, 1H), 5.21 (t, J=8.0 Hz, 1H), 4.23 (dd, J=9.2, 6.8 Hz, 1H), 3.68-3.59 (m, 1H), 2.50-2.41 (m, 4H), 2.16-1.90 (m, 3H), 1.89 (d, J=12.8 Hz, 1H), 1.78-1.60 (m, 3H), 1.42 (dd, J=6.8, 5.2 Hz, 6H), 1.35-1.16 (m, 2H), 1.16-1.05 (m, 1H), 0.76-0.64 (m, 2H), 0.50-0.37 (m, 2H). MS (ESI) m/z: [M+H]⁺ Found 614.2.

Example 482

N—[(S)-[7-[(R)-Cyclopropyl-(4,4,4-trifluorobutanamido)methyl]imidazo[1,2-b]pyridazin-2-yl]-(4,4-difluorocyclohexyl)methyl]-5-isopropyl-isoxazole-4-carboxamide

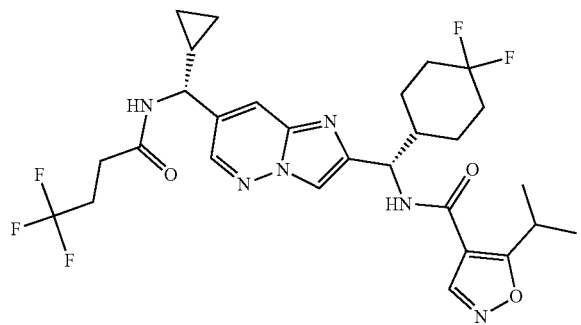 [SMILES: CC(C)c1oncc1C(=O)N[C@H](c1cn2ncc([C@H](NC(=O)CCC(F)(F)F)C3CC3)cc2n1)C1CCC(F)(F)CC1]

The title compound was prepared as described for the synthesis of Example 32, using 5-isopropylisoxazole-4-carboxylic acid in place of 2-(3,3-difluoropropyl)-2H-1,2,3-triazole-4-carboxylic acid to provide the title compound as a white powder. ¹H NMR (400 MHz, CDCl₃) δ 8.46 (s, 1H), 8.34 (d, J=2.0 Hz, 1H), 7.85 (s, 1H), 7.81 (s, 1H), 7.04 (d, J=8.4 Hz, 1H), 6.14 (d, J=6.4 Hz, 1H), 5.26 (t, J=8.0 Hz, 1H), 4.30 (dd, J=7.2, 8.8 Hz, 1H), 3.85 (td, J=7.2, 14.0 Hz, 1H), 2.61-2.43 (m, 4H), 2.23-1.94 (m, 4H), 1.76-1.58 (m, 3H), 1.56-1.43 (m, 1H), 1.35 (dd, J=6.8, 14.0 Hz, 6H), 1.32-1.12 (m, 2H), 0.82-0.68 (m, 2H), 0.58-0.42 (m, 2H). MS (ESI) m/z: [M+H]⁺ Found 597.2.

Example 483

N—[(S)-[7-[(R)-Cyclopropyl-(4,4,4-trifluorobutanamido)methyl]imidazo[1,2-b]pyridazin-2-yl]-(4,4-difluorocyclohexyl)methyl]-2-isopropyl-1,2,4-triazole-3-carboxamide

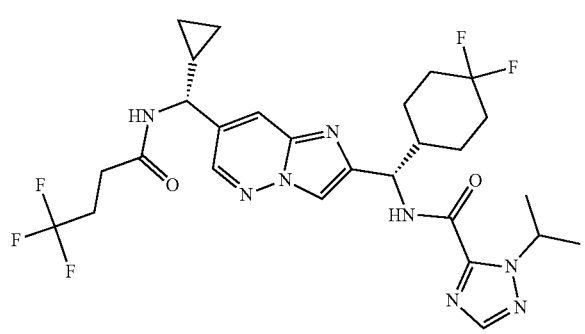 [SMILES: CC(C)n1ncnc1C(=O)N[C@H](c1cn2ncc([C@H](NC(=O)CCC(F)(F)F)C3CC3)cc2n1)C1CCC(F)(F)CC1]

The title compound was prepared as described for the synthesis of Example 32, using lithium 1-isopropyl-1H-1,2,4-triazole-5-carboxylate (Intermediate 423) in place of 2-(3,3-difluoropropyl)-2H-1,2,3-triazole-4-carboxylic acid to provide the title compound as a white powder. ¹H NMR (400 MHz, DMSO-d₆) δ 8.88 (d, J=9.2 Hz, 1H), 8.73 (d, J=8.0 Hz, 1H), 8.52 (d, J=2.0 Hz, 1H), 8.27 (s, 1H), 8.10 (s, 1H), 7.98 (d, J=1.6 Hz, 1H), 5.55 (quin, J=6.8 Hz, 1H), 5.14 (t, J=8.8 Hz, 1H), 4.29 (t, J=8.4 Hz, 1H), 2.47 (s, 4H), 2.19-1.56 (m, 7H), 1.40 (dd, J=6.8, 18.8 Hz, 6H), 1.34-1.28 (m, 1H), 1.27-1.15 (m, 2H), 0.65-0.45 (m, 3H), 0.43-0.32 (m, 1H). MS (ESI) m/z: [M+H]⁺ Found 597.2.

Example 484

N—[(S)-[7-[(R)-Cyclopropyl-(4,4,4-trifluorobutanamido)methyl]imidazo[1,2-b]pyridazin-2-yl]-(4,4-difluorocyclohexyl)methyl]-2-isopropyl-tetrazole-5-carboxamide

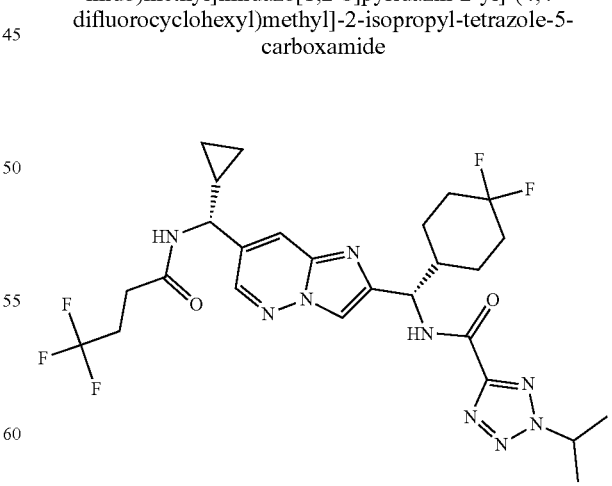

The title compound was prepared as described for the synthesis of Example 32, using lithium 1-isopropyl-1H-tetrazole-5-carboxylate (Intermediate 425) in place of 2-(3,3-difluoropropyl)-2H-1,2,3-triazole-4-carboxylic acid to provide the title compound as a white powder. $^1$H NMR (400 MHz, DMSO-$d_6$) δ 9.14 (d, J=9.04 Hz, 1H), 8.76 (d, J=7.6 Hz, 1H), 8.51 (d, J=2.0 Hz, 1H), 8.26 (s, 1H), 7.97 (d, J=2.0 Hz, 1H), 5.27-5.13 (m, 2H), 4.28 (t, J=8.4 Hz, 1H), 2.48-2.41 (m, 3H), 2.27-2.15 (m, 1H), 2.11-1.87 (m, 3H), 1.87-1.67 (m, 2H), 1.66-1.54 (m, 7H), 1.48-1.08 (m, 4H), 0.66-0.45 (m, 3H), 0.43-0.31 (m, 1H). MS (ESI) m/z: [M+H]$^+$ Found 598.2.

Example 485

N—[(S)-[7-[(R)-Cyclopropyl-(4,4,4-trifluorobutanamido)methyl]imidazo[1,2-b]pyridazin-2-yl]-(4,4-difluorocyclohexyl)methyl]-2-[2-(3,3-difluoroazetidin-1-yl)ethyl]triazole-4-carboxamide

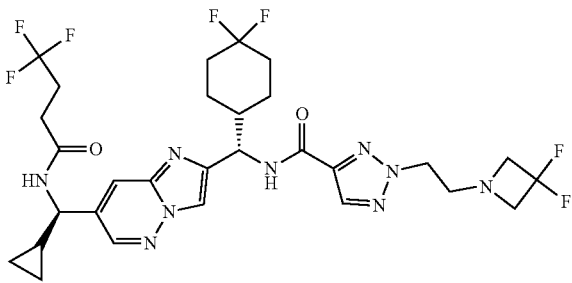 [SMILES: O=C(CCC(F)(F)F)N[C@@H](c1cnn2cc([C@@H](NC(=O)c3cnn(CCN4CC(F)(F)C4)n3)C3CCC(F)(F)CC3)nc2c1)C1CC1]

The title compound was prepared as described for the synthesis of Example 32, using lithium 2-(2-(3,3-difluoroazetidin-1-yl)ethyl)-2H-1,2,3-triazole-4-carboxylate (Intermediate 428) in place of 2-(3,3-difluoropropyl)-2H-1,2,3-triazole-4-carboxylic acid to provide the title compound as a white powder. $^1$H NMR (400 MHz, DMSO-$d_6$) δ 8.76 (d, J=7.6 Hz, 1H), 8.57-8.48 (m, 2H), 8.26-8.17 (m, 2H), 7.94 (s, 1H), 5.17 (t, J=8.6 Hz, 1H), 4.50 (t, J=6.0 Hz, 2H), 4.27 (t, J=8.4 Hz, 1H), 3.58-3.53 (m, 2H), 3.09 (t, J=5.6 Hz, 2H), 2.47 (s, 4H), 2.22-1.63 (m, 7H), 1.58 (d, J=11.6 Hz, 1H), 1.42-1.13 (m, 4H), 0.63-0.45 (m, 3H), 0.42-0.34 (m, 1H). MS (ESI) m/z: [M+H]$^+$ Found 674.2.

Example 486

2-[2-[(3-Chloro-2,2-difluoro-propyl)amino]ethyl]-N—[(S)-[7-[(R)-cyclopropyl-(4,4,4-trifluorobutanamido)methyl]imidazo[1,2-b]pyridazin-2-yl]-(4,4-difluorocyclohexyl)methyl]triazole-4-carboxamide

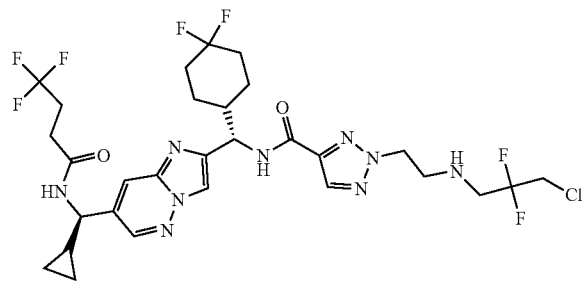 [SMILES: O=C(CCC(F)(F)F)N[C@@H](c1cnn2cc([C@@H](NC(=O)c3cnn(CCNCC(F)(F)CCl)n3)C3CCC(F)(F)CC3)nc2c1)C1CC1]

The title compound was prepared as described for the synthesis of Example 32, using lithium 2-(2-(3,3-difluoroazetidin-1-yl)ethyl)-2H-1,2,3-triazole-4-carboxylate (Intermediate 428) in place of 2-(3,3-difluoropropyl)-2H-1,2,3-triazole-4-carboxylic acid to provide the title compound as a white powder. $^1$H NMR (400 MHz, DMSO-$d_6$) δ 8.75 (d, J=7.6 Hz, 1H), 8.50 (d, J=2.0 Hz, 1H), 8.47 (d, J=9.2 Hz, 1H), 8.24 (s, 1H), 8.18 (s, 1H), 7.95 (s, 1H), 5.17 (t, J=8.6 Hz, 1H), 4.52 (t, J=6.2 Hz, 2H), 4.28 (t, J=8.6 Hz, 1H), 3.94 (t, J=14.2 Hz, 2H), 3.13 (s, 2H), 3.04 (t, J=14.2 Hz, 2H), 2.47 (s, 3H), 2.20-1.53 (m, 8H), 1.41-1.10 (m, 4H), 0.63-0.44 (m, 3H), 0.42-0.33 (m, 1H). MS (ESI) m/z: [M+H]$^+$ Found 710.2.

Example 487

N—((S)-(7-((S)-(1-Cyanocyclobutyl)(2-(3,3-difluorocyclobutyl)acetamido)methyl)imidazo[1,2-b]pyridazin-2-yl)(4,4-difluorocyclohexyl)methyl)-4-cyclopropyl-1,2,5-oxadiazole-3-carboxamide

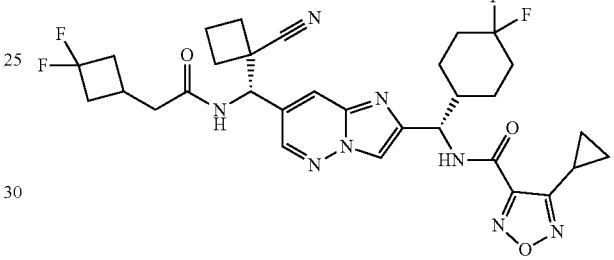

To a stirred solution of 4-cyclopropyl-1,2,5-oxadiazole-3-carboxylic acid (164 mg, 1.06 mmol, Intermediate 570) and 1-propanephosphonic anhydride (0.569 mL, 0.956 mmol, 50% in EtOAc) in EtOAc (2.66 mL) was added N,N-diisopropylethylamine (0.364 mL, 2.12 mmol). After 5 min, N—((S*)-2-((S)-amino(4,4-difluorocyclohexyl)methyl)imidazo[1,2-b]pyridazin-7-yl)(1-cyanocyclobutyl)methyl)-2-(3,3-difluorocyclobutyl)acetamide (269 mg, 0.531 mmol, Intermediate 432) in 1:1 DCM:EtOAc (4 mL) was added. After 6 h, the reaction was diluted with aqueous HCl (25 mL, 0.05 M) and the aqueous layer was extracted with EtOAc (4×15 mL). The combined organics were washed with saturated aqueous NaHCO$_3$ (10 mL), brine (10 mL), dried over anhydrous Na$_2$SO$_4$, filtered, and concentrated to dryness. The residue was purified by silica gel chromatography (15-60% acetone/hexanes) to provide the title compound as a white solid. The stereochemistry of this compound was confirmed based on the data obtained from an X-ray crystal structure of the title compound, N—((S)-(7-((S)-(1-cyanocyclobutyl)(2-(3,3-difluorocyclobutyl)acetamido)methyl)imidazo[1,2-b]pyridazin-2-yl)(4,4-difluorocyclohexyl)methyl)-4-cyclopropyl-1,2,5-oxadiazole-3-carboxamide, bound to IL-17A. $^1$H NMR (600 MHz, DMSO-$d_6$) δ 9.49 (d, J=9.0 Hz, 1H), 8.83 (d, J=8.8 Hz, 1H), 8.64 (d, J=2.1 Hz, 1H), 8.29 (s, 1H), 8.18 (d, J=2.1 Hz, 1H), 5.44 (d, J=8.6 Hz, 1H), 5.20 (t, J=8.5 Hz, 1H), 2.70-2.59 (m, 2H), 2.53-2.44 (m, 3H), 2.44-2.38 (m, 2H), 2.37-2.25 (m, 4H), 2.23-2.15 (m, 2H), 2.12-2.02 (m, 2H), 2.01-1.95 (m, 2H), 1.93-1.87 (m, 1H), 1.85-1.71 (m, 2H), 1.63 (d, J=12.2 Hz, 1H), 1.44-1.36 (m, 1H), 1.29 (dq, J=3.5, 12.5 Hz, 1H), 1.13-1.08 (m, 2H), 0.98-0.94 (m, 2H). MS (ESI) m/z: [M+H]$^+$ Found 542.8.

Example 488

N—((S)-(7-((R)-Cyclopropyl(4,4,4-trifluorobutanamido)methyl)imidazo[1,2-b]pyridazin-2-yl)(4,4-difluorocyclohexyl)methyl)-1-(methyl-d₃)-1H-pyrazole-5-carboxamide

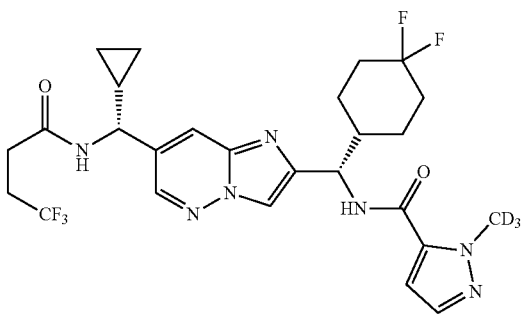 [SMILES: [2H]C([2H])([2H])n1nccc1C(=O)N[C@H](c1cn2ncc([C@H](NC(=O)CCC(F)(F)F)C3CC3)cc2n1)C1CCC(F)(F)CC1]

The title compound was prepared as described for the synthesis of Example 63, using 1-(methyl-d₃)-1H-pyrazole-5-carboxylic acid (Intermediate 435) in place of 2-((3,3-difluorocyclobutyl)methyl)-2H-1,2,3-triazole-4-carboxylic acid and acetonitrile in place of DMF to provide the title compound as a white solid. ¹H NMR (400 MHz, DMSO-d₆) δ 8.77-8.66 (m, 2H), 8.50 (d, J=2.1 Hz, 1H), 8.20 (s, 1H), 7.96-7.89 (m, 1H), 7.46 (d, J=2.1 Hz, 1H), 7.02 (d, J=2.1 Hz, 1H), 5.15 (t, J=8.7 Hz, 1H), 4.29 (t, J=8.4 Hz, 1H), 2.49-2.42 (m, 4H), 2.25-2.11 (m, 1H), 2.10-1.55 (m, 6H), 1.47-1.14 (m, 3H), 0.64-0.45 (m, 3H), 0.43-0.32 (m, 1H). MS (ESI) m/z: [M+H]⁺ Found 571.2.

Example 489

N—((S)-(7-((R)-Cyclopropyl(2-(3,3-difluorocyclobutyl)acetamido)methyl)imidazo[1,2-b]pyridazin-2-yl)(4,4-difluorocyclohexyl)methyl)-1-(methyl-d₃)-1H-pyrazole-5-carboxamide

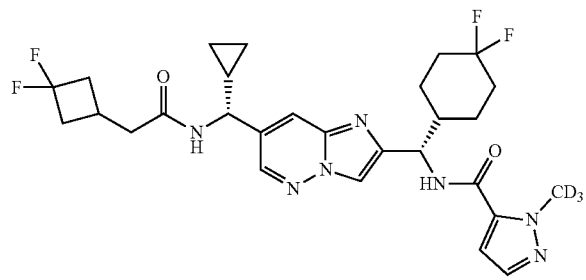 [SMILES: [2H]C([2H])([2H])n1nccc1C(=O)N[C@H](c1cn2ncc([C@H](NC(=O)CC3CC(F)(F)C3)C3CC3)cc2n1)C1CCC(F)(F)CC1]

The title compound was prepared as described for the synthesis of Example 63, using N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide (Intermediate 171) in place of N—((R)-(2-((S)-amino(4,4-difluorocyclohexyl)methyl)imidazo[1,2-b]pyridazin-7-yl)(cyclopropyl)methyl)-4,4,4-trifluorobutanamide, 1-(methyl-d₃)-1H-pyrazole-5-carboxylic acid (Intermediate 435) in place of 2-((3,3-difluorocyclobutyl)methyl)-2H-1,2,3-triazole-4-carboxylic acid, acetonitrile in place of DMF, and additional purifications by preparative basic HPLC (Gemini Prep NX-C18 5 μm, 21.5×150 mm column, 10-70% Acetonitrile/20 mM aqueous ammonium hydroxide over 20 min), preparative acidic HPLC (SunFire Prep C18 OBD 5 μm, 30×250 mm column, 10-100% Acetonitrile/0.05% aqueous TFA over 20 min) and silica gel chromatography (0-10% MeOH/DCM) provided the title compound as a white solid. ¹H NMR (400 MHz, DMSO-d₆) δ 8.71 (d, J 9.0 Hz, 1H), 8.59 (d, J=7.8 Hz, 1H), 8.50 (d, J=2.1 Hz, 1H), 8.21 (s, 1H), 7.93 (d, J=2.1 Hz, 1H), 7.46 (d, J=2.1 Hz, 1H), 7.02 (d, J=2.1 Hz, 1H), 5.15 (t, J=8.7 Hz, 1H), 4.27 (t, J 8.4 Hz, 1H), 2.72-2.56 (m, 2H), 2.45-2.23 (m, 5H), 2.23-2.13 (m, 1H), 2.12-1.93 (m, 2H), 1.93-1.85 (m, 1H), 1.86-1.69 (m, 2H), 1.65-1.56 (m, 1H), 1.44-1.32 (m, 1H), 1.32-1.14 (m, 2H), 0.63-0.43 (m, 3H), 0.41-0.31 (m, 1H). MS (ESI) m/z: [M+H]⁺ Found 579.3.

Example 490

N—((S)-(7-((R*)-Cyclobutyl(4,4,4-trifluorobutanamido)methyl)imidazo[1,2-b]pyridazin-2-yl)(4,4-difluorocyclohexyl)methyl)-1-isopropyl-1H-pyrazole-5-carboxamide

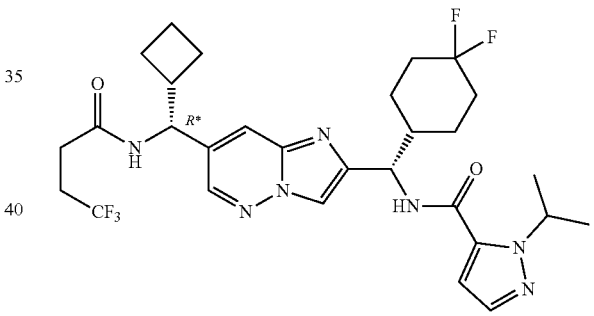

The title compound was prepared as described for the synthesis of Intermediate 173, using N—((R*)-(2-((S)-amino(4,4-difluorocyclohexyl)methyl)imidazo[1,2-b]pyridazin-7-yl) (cyclobutylyl)methyl)-4,4,4-trifluorobutanamide (Intermediate 440) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide to provide the title compound as a white solid. ¹H NMR (400 MHz, DMSO-d₆) δ 8.71 (d, J=9.0 Hz, 1H), 8.54-8.40 (m, 2H), 8.19 (s, 1H), 7.89 (d, J=2.0 Hz, 1H), 7.49 (d, J=2.0 Hz, 1H), 6.91 (d, J=2.0 Hz, 1H), 5.44-5.31 (m, 1H), 5.15 (t, J=8.6 Hz, 1H), 4.92-4.80 (m, 1H), 2.76-2.61 (m, 1H), 2.49-2.41 (m, 4H), 2.25-2.12 (m, 1H), 2.12-1.93 (m, 3H), 1.93-1.67 (m, 8H), 1.67-1.57 (m, 1H), 1.46-1.18 (m, 8H). MS (ESI) m/z: [M+H]⁺ Found 610.3.

Example 491

N—((S)-(7-((R*)-Cyclobutyl(4,4,4-trifluorobutanamido)methyl)imidazo[1,2-b]pyridazin-2-yl)(4,4-difluorocyclohexyl)methyl)-4-methyl-1,2,5-oxadiazole-3-carboxamide

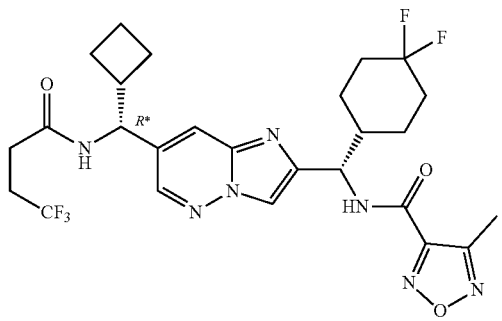 [SMILES: Cc1nonc1C(=O)N[C@H](c1cn2ncc([C@H](NC(=O)CCC(F)(F)F)C3CCC3)cc2n1)C1CCC(F)(F)CC1]

The title compound was prepared as described for the synthesis of Example 249, using N—((R*)-(2-((S)-amino(4,4-difluorocyclohexyl)methyl)imidazo[1,2-b]pyridazin-7-yl)(cyclobutylyl)methyl)-4,4,4-trifluorobutanamide (Intermediate 440) in place of N—((R)-(2-((S)-amino(4,4-difluorocyclohexyl)methyl)imidazo[1,2-b]pyridazin-7-yl)(cyclopropyl)methyl)-2-(bicyclo[1.1.1]pentan-1-yl)acetamide and the material was purified by preparative basic HPLC (X-Bridge Prep C18 5 μm, 50×100 mm column, 0-100% acetonitrile/water (with 20 mM NH₄OH). The product containing fractions were concentrated to afford the title compound as a white solid. $^1$H NMR (400 MHz, DMSO-d$_6$) δ 9.40 (d, J=8.9 Hz, 1H), 8.53-8.41 (m, 2H), 8.22 (s, 1H), 7.91 (d, J=1.9 Hz, 1H), 5.21-5.12 (m, 1H), 4.93-4.82 (m, 1H), 2.76-2.62 (m, 1H), 2.49-2.40 (m, 6H), 2.24-2.11 (m, 1H), 2.11-1.67 (m, 12H), 1.67-1.56 (m, 1H), 1.48-1.18 (m, 2H). MS (ESI) m/z: [M+H]⁺ Found 584.3.

Example 492

N—((S)-(7-((R*)-Cyclobutyl(4,4,4-trifluorobutanamido)methyl)imidazo[1,2-b]pyridazin-2-yl)(4,4-difluorocyclohexyl)methyl)-1-(methyl-d₃)-1H-pyrazole-5-carboxamide

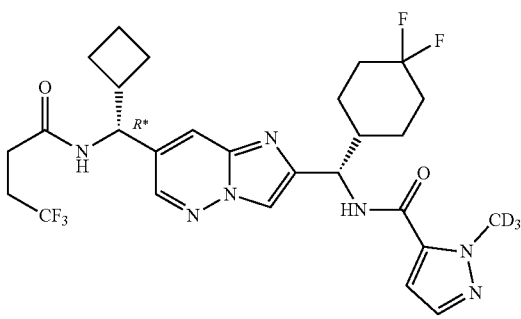 [SMILES: [2H]C([2H])([2H])n1nccc1C(=O)N[C@H](c1cn2ncc([C@H](NC(=O)CCC(F)(F)F)C3CCC3)cc2n1)C1CCC(F)(F)CC1]

The title compound was prepared as described for the synthesis of Intermediate 173, using N—((R*)-(2-((S)-amino(4,4-difluorocyclohexyl)methyl)imidazo[1,2-b]pyridazin-7-yl) (cyclobutylyl)methyl)-4,4,4-trifluorobutanamide (Intermediate 440) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide, 1-(methyl-d₃)-1H-pyrazole-5-carboxylic acid (Intermediate 435) in place of 1-isopropyl-1H-pyrazole-5-carboxylic acid and the material was purified by preparative basic HPLC (X-Bridge Prep C18 5 μm, 50×100 mm column, 0-100% acetonitrile/water (with 20 mM NH₄OH) to afford the title compound as a white solid. $^1$H NMR (400 MHz, DMSO-d$_6$) δ 8.71 (d, J=9.0 Hz, 1H), 8.48 (d, J=8.0 Hz, 1H), 8.44 (d, J=2.1 Hz, 1H), 8.19 (s, 1H), 7.89 (d, J=2.1 Hz, 1H), 7.46 (d, J=2.0 Hz, 1H), 7.02 (d, J=2.1 Hz, 1H), 5.14 (t, J=8.7 Hz, 1H), 4.91-4.82 (m, 1H), 2.76-2.63 (m, 1H), 2.49-2.40 (m, 4H), 2.24-2.12 (m, 1H), 2.12-1.66 (m, 11H), 1.66-1.54 (m, 1H), 1.44-1.18 (m, 2H). MS (ESI) m/z: [M+H]⁺ Found 585.3.

Example 493

N—((S)-(7-((R*)-Cyclobutyl(2-(3,3-difluorocyclobutyl)acetamido)methyl)imidazo[1,2-b]pyridazin-2-yl)(4,4-difluorocyclohexyl)methyl)-4-methyl-1,2,5-oxadiazole-3-carboxamide DIPEA (0.09 mL, 0.519 mmol) was added into a mixture of 4-methyl-1,2,5-oxadiazole-3-carboxylic acid (17.3 mg, 0.135 mmol), 1-propanephosphonic anhydride (198.2 mg, 0.312 mmol, 50% in EtOAc) and DCM (1.5 mL). The resulting mixture was stirred at 30° C. for 0.5 h. Next, N—((R*)-(2-((S)-amino(4,4-difluorocyclohexyl)methyl) imidazo[1,2-b]pyridazin-7-yl)(cyclobutyl)methyl)-2-(3,3-difluorocyclobutyl)acetamide (50 mg, 0.104 mmol, Intermediate 442) was added and the resulting mixture was stirred at 30° C. for 12 h. After that time, the mixture was diluted with water (5 mL) and DCM (10 mL). The organic layer was separated and dried over anhydrous Na₂SO₄, filtered, and concentrated to dryness. The crude material was purified by silica gel chromatography (0-100% ethyl acetate/petroleum ether) then the residue suspended in water (20 mL), frozen, and lyophilized to dryness to afford the title compound as a white solid. $^1$H NMR (400 MHz, DMSO-d$_6$) δ 9.43 (d, J=9.2 Hz, 1H), 8.45 (s, 1H), 8.38 (d, J=8.0 Hz, 1H), 8.22 (s, 1H), 7.89 (s, 1H), 5.15 (t, J=8.4 Hz, 1H), 4.84 (t, J=8.8 Hz, 1H), 2.70-2.61 (m, 2H), 2.46 (s, 3H), 2.42-2.26 (m, 5H), 2.25-1.91 (m, 6H), 1.84-1.61 (m, 8H), 1.41-1.25 (m, 2H). MS (ESI) m/z: [M+H]⁺ Found 592.2.

Example 494

N—((S)-(7-((S*)-Cyclobutyl(2-(3,3-difluorocyclobutyl)acetamido)methyl)imidazo[1,2-b]pyridazin-2-yl)(4,4-difluorocyclohexyl)methyl)-4-methyl-1,2,5-oxadiazole-3-carboxamide

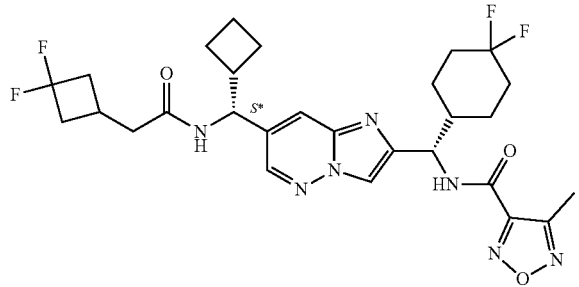 [SMILES: Cc1nonc1C(=O)N[C@H](c1cn2ncc([C@H](NC(=O)CC3CC(F)(F)C3)C3CCC3)cc2n1)C1CCC(F)(F)CC1]

The title compound was prepared as described for the synthesis of Intermediate 173, using N—((R*)-(2-((S)-amino(4,4-difluorocyclohexyl)methyl)imidazo[1,2-b]pyridazin-7-yl)(cyclobutyl)methyl)-2-(3,3-difluorocyclobutyl)acetamide (Intermediate 442) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide, 4-methyl-1,2,5-oxadiazole-3-carboxylic acid in place of 1-isopropyl-1H-pyrazole-5-carboxylic acid, and purified by silica gel preparative thin layer chromatography (50% ethyl acetate/hexanes) to afford the title compound as a white solid. $^1$H NMR (400 MHz, DMSO-d$_6$) δ 9.43 (d, J=8.8 Hz, 1H), 8.45 (s, 1H), 8.38 (d, J=7.6 Hz, 1H), 8.22 (s, 1H), 7.89 (s, 1H), 5.16 (t, J=8.0 Hz, 1H), 4.84 (t, J=8.4 Hz, 1H), 2.77-2.58 (m, 2H), 2.47 (s, 3H), 2.40-2.23 (m, 5H), 2.22-1.89 (m, 6H), 1.83-1.55 (m, 8H), 1.41-1.21 (m, 2H). MS (ESI) m/z: [M+H]$^+$ Found 592.2.

Example 495

N—((S)-(7-((R*)-Cyclobutyl(2-(3,3-difluorocyclobutyl)acetamido)methyl)imidazo[1,2-b]pyridazin-2-yl)(4,4-difluorocyclohexyl)methyl)-1-(ethyl-d$_5$)-1H-pyrazole-5-carboxamide

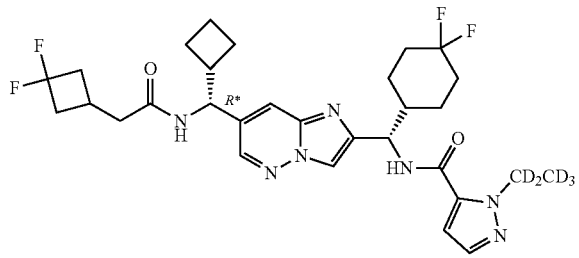

The title compound was prepared as described for the synthesis of Intermediate 173, using N—((R*)-(2-((S)-amino(4,4-difluorocyclohexyl)methyl)imidazo[1,2-b]pyridazin-7-yl)(cyclobutyl)methyl)-2-(3,3-difluorocyclobutyl)acetamide (Intermediate 442) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide, 1-(ethyl-d$_5$)-1H-pyrazole-5-carboxylic acid (Intermediate 204) in place of 1-isopropyl-1H-pyrazole-5-carboxylic acid and the material was purified by silica gel chromatography (0-100% ethyl acetate/petroleum ether) then the residue suspended in water (20 mL) frozen, and lyophilized to dryness to afford the title compound as a white solid. $^1$H NMR (400 MHz, DMSO-d$_6$) δ 8.74 (d, J=8.8 Hz, 1H), 8.44 (d, J 1.2 Hz, 1H), 8.39 (d, J=8.0 Hz, 1H), 8.20 (s, 1H), 7.88 (s, 1H), 7.47 (d, J=1.2 Hz, 1H), 6.98 (d, J=1.6 Hz, 1H), 5.15 (t, J=8.8 Hz, 1H), 4.84 (t, J=8.8 Hz, 1H), 2.72-2.63 (m, 2H), 2.41-2.23 (m, 5H), 2.21-1.85 (m, 6H), 1.83-1.58 (m, 8H), 1.41-1.22 (m, 2H). MS (ESI) m/z: [M+H]$^+$ Found 609.3.

Example 496

N—((S)-(7-((S*)-Cyclobutyl(2-(3,3-difluorocyclobutyl)acetamido)methyl)imidazo[1,2-b]pyridazin-2-yl)(4,4-difluorocyclohexyl)methyl)-1-(ethyl-d$_5$)-1H-pyrazole-5-carboxamide

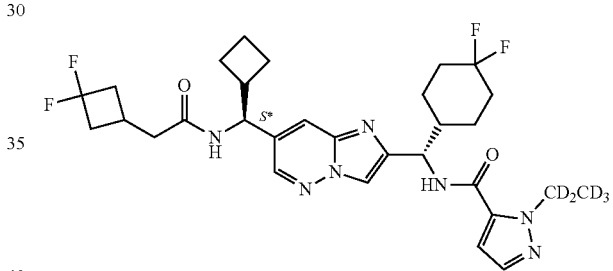

The title compound was prepared as described for the synthesis of Intermediate 173, using N—((S*)-(2-((S)-amino(4,4-difluorocyclohexyl)methyl)imidazo[1,2-b]pyridazin-7-yl)(cyclobutyl)methyl)-2-(3,3-difluorocyclobutyl)acetamide (Intermediate 443) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide, 1-(ethyl-d$_5$)-1H-pyrazole-5-carboxylic acid (Intermediate 204) in place of 1-isopropyl-1H-pyrazole-5-carboxylic acid and the material was purified by preparative HPLC (Phenomenex Gemini C18, 40-70% MeCN/aqueous NH$_4$OH (0.05%)) to provide the title compound as a white solid. $^1$H NMR (400 MHz, DMSO-d$_6$) δ 8.74 (d, J=8.8 Hz, 1H), 8.45 (d, J 2.0 Hz, 1H), 8.40 (d, J=8.0 Hz, 1H), 8.20 (s, 1H), 7.88 (s, 1H), 7.48 (d, J=2.0 Hz, 1H), 6.98 (d, J=2.0 Hz, 1H), 5.16 (t, J=8.8 Hz, 1H), 4.85 (t, J=8.8 Hz, 1H), 2.72-2.63 (m, 2H), 2.45-2.24 (m, 5H), 2.24-1.85 (m, 6H), 1.84-1.52 (m, 8H), 1.46-1.18 (m, 2H). MS (ESI) m/z: [M+H]$^+$ Found 609.3.

Example 497

N—((S)-(7-((R*)-Cyclobutyl(2-(3,3-difluorocyclobutyl)acetamido)methyl)imidazo[1,2-b]pyridazin-2-yl)(4,4-difluorocyclohexyl)methyl)-1-(methyl-d₃)-1H-pyrazole-5-carboxamide

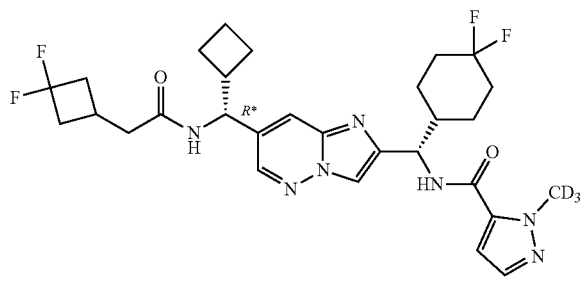 [SMILES: [2H]C([2H])([2H])n1nccc1C(=O)N[C@H](c1cn2ncc([C@H](NC(=O)CC3CC(F)(F)C3)C3CCC3)cc2n1)C1CCC(F)(F)CC1]

The title compound was prepared as described for the synthesis of Intermediate 173, using N—((R*)-(2-((S)-amino(4,4-difluorocyclohexyl)methyl)imidazo[1,2-b]pyridazin-7-yl)(cyclobutyl)methyl)-2-(3,3-difluorocyclobutyl)acetamide (Intermediate 442) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide, 1-(methyl-d₃)-1H-pyrazole-5-carboxylic acid (Intermediate 435) in place of 1-isopropyl-1H-pyrazole-5-carboxylic acid and the material was purified by silica gel chromatography (0-100% ethyl acetate/petroleum ether), suspended in water (20 mL), the mixture frozen using dry ice/ethanol, and then lyophilized to dryness to afford the title compound as a white solid. ¹H NMR (400 MHz, DMSO-d₆) δ 8.73 (d, J 9.2 Hz, 1H), 8.44 (d, J=1.6 Hz, 1H), 8.38 (d, J=8.0 Hz, 1H), 8.19 (s, 1H), 7.87 (s, 1H), 7.45 (d, J=2.0 Hz, 1H), 7.02 (d, J=2.0 Hz, 1H), 5.13 (t, J=8.8 Hz, 1H), 4.83 (t, J=8.8 Hz, 1H), 2.69-2.60 (m, 2H), 2.43-2.16 (m, 6H), 2.16-1.83 (m, 5H), 1.83-1.55 (m, 8H), 1.42-1.20 (m, 2H). MS (ESI) m/z: [M+H]⁺ Found 593.3.

Example 498

N—((S)-(7-((S*)-Cyclobutyl(2-(3,3-difluorocyclobutyl)acetamido)methyl)imidazo[1,2-b]pyridazin-2-yl)(4,4-difluorocyclohexyl)methyl)-1-(methyl-d₃)-1H-pyrazole-5-carboxamide

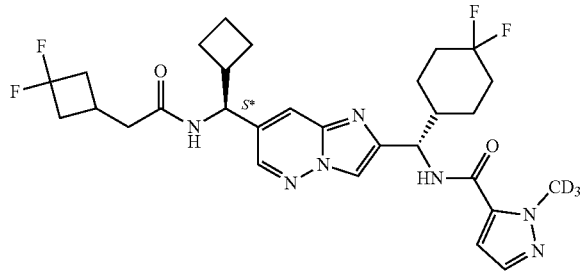 [SMILES: [2H]C([2H])([2H])n1nccc1C(=O)N[C@H](c1cn2ncc([C@@H](NC(=O)CC3CC(F)(F)C3)C3CCC3)cc2n1)C1CCC(F)(F)CC1]

The title compound was prepared as described for the synthesis of Intermediate 173, using N—((S*)-(2-((S)-amino(4,4-difluorocyclohexyl)methyl)imidazo[1,2-b]pyridazin-7-yl)(cyclobutyl)methyl)-2-(3,3-difluorocyclobutyl)acetamide (Intermediate 443) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide, 1-(methyl-d₃)-1H-pyrazole-5-carboxylic acid (Intermediate 435) in place of 1-isopropyl-1H-pyrazole-5-carboxylic acid and the material was purified by preparative HPLC (Phenomenex Gemini C18, 40-70% MeCN/aqueous NH₄OH (0.05%)) to provide the title compound as a white solid. ¹H NMR (400 MHz, DMSO-d₆) δ 8.73 (d, J=8.8 Hz, 1H), 8.44 (d, J 1.2 Hz, 1H), 8.39 (d, J=8.0 Hz, 1H), 8.19 (s, 1H), 7.88 (s, 1H), 7.46 (d, J=2.0 Hz, 1H), 7.01 (d, J=2.0 Hz, 1H), 5.14 (t, J=8.4 Hz, 1H), 4.84 (t, J=8.4 Hz, 1H), 2.68-2.65 (m, 2H), 2.43-2.18 (m, 6H), 2.16-1.88 (m, 5H), 1.84-1.57 (m, 8H), 1.45-1.17 (m, 2H). MS (ESI) m/z: [M+H]⁺ Found 593.3.

Example 499

N—((S)-(7-((R*)-Cyclobutyl(2-(3,3-difluorocyclobutyl)acetamido)methyl)imidazo[1,2-b]pyridazin-2-yl)(4,4-difluorocyclohexyl)methyl)-4-(2-hydroxypropan-2-yl)-1,2,5-oxadiazole-3-carboxamide

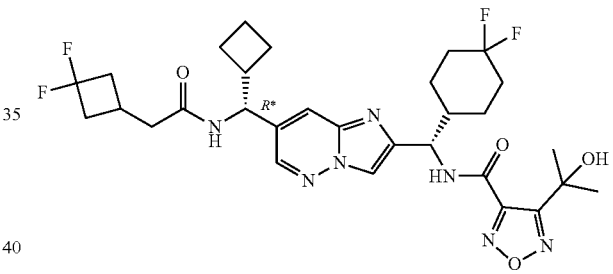

N—((*R)-(2-((S)-Amino(4,4-difluorocyclohexyl)methyl)imidazo[1,2-b]pyridazin-7-yl)(cyclobutyl)methyl)-2-(3,3-difluorocyclobutyl)acetamide (60 mg, 0.13 mmol, Intermediate 442) was added into a 10 mL single-necked round-bottomed flask containing a solution of 6,6-dimethylfuro[3,4-c][1,2,5]oxadiazol-4(6H)-one (21.1 mg, 0.14 mmol, Intermediate 350), triazabicyclodecene (5.20 mg, 0.04 mmol), a stir bar, and THF (5 mL) at 20° C. under nitrogen. The resulting mixture was heated at 75° C. for 12 h. The mixture was concentrated and the residue was purified by silica gel chromatography (0-100% ethyl acetate/petroleum ether), suspended in water (20 mL), frozen using dry ice/EtOH, then lyophilized to dryness to afford the title compound as a white solid. ¹H NMR (400 MHz, DMSO-d₆) δ 9.67 (d, J=9.2 Hz, 1H), 8.45 (s, 1H), 8.40 (d, J=7.6 Hz, 1H), 8.18 (s, 1H), 7.89 (s, 1H), 6.08 (s, 1H), 5.22 (t, J=8.0 Hz, 1H), 4.85 (t, J=8.8 Hz, 1H), 2.69-2.62 (m, 2H), 2.41-2.25 (m, 5H), 2.22-1.85 (m, 6H), 1.79-1.65 (m, 8H), 1.58 (s, 3H), 1.57 (s, 3H), 1.41-1.24 (m, 2H). MS (ESI) m/z: [M+H]⁺ Found 636.2.

Example 500

N—((S)-(7-((R*)-Cyclobutyl((S*)-4,4,4-trifluoro-3-methylbutanamido)methyl)imidazo[1,2-b]pyridazin-2-yl)(4,4-difluorocyclohexyl)methyl)-1-(ethyl-d₅)-1H-pyrazole-5-carboxamide

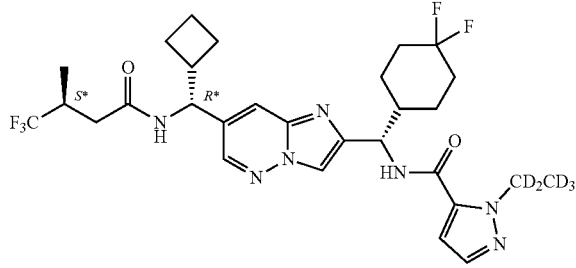

Example 501

N—((S)-(7-((R*)-Cyclobutyl((R*)-4,4,4-trifluoro-3-methylbutanamido)methyl)imidazo[1,2-b]pyridazin-2-yl)(4,4-difluorocyclohexyl)methyl)-1-(ethyl-d₅)-1H-pyrazole-5-carboxamide

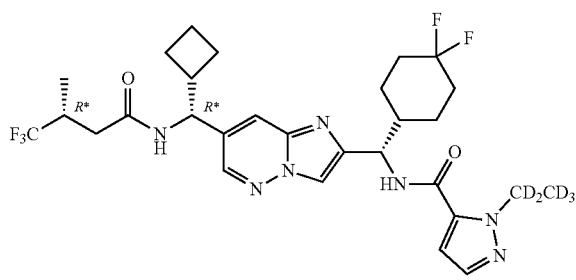

The title compounds were prepared as described for the synthesis of Intermediate 63, using N—((R*)-(2-((S)-amino(4,4-difluorocyclohexyl)methyl)imidazo[1,2-b]pyridazin-7-yl)(cyclobutyl)methyl)-4,4,4-trifluoro-3-methylbutanamide (Intermediate 445) in place of N—((R)-(2-((S)-amino(4,4-difluorocyclohexyl)methyl)imidazo[1,2-b]pyridazin-7-yl)(cyclopropyl)methyl)-4,4,4-trifluorobutanamide, 1-(ethyl-d₅)-1H-pyrazole-5-carboxylic acid (Intermediate 204) in place of 2-((3,3-difluorocyclobutyl)methyl)-2H-1,2,3-triazole-4-carboxylic acid and the material was purified by silica gel preparative thin layer chromatography (50% ethyl acetate/petroleum ether) to afford a mixture of diastereomers as a white solid. The diastereomers were separated by SFC using a chiral stationary phase (Daicel Chiralpak® IE, 20/80 EtOH (with 0.1% of 25% aqueous NH₃)/CO₂). The first-eluting isomer was Example 500, and the second-eluting isomer was Example 501. Example 500: ¹H NMR (400 MHz, DMSO-d₆) δ 8.73 (d, J=8.8 Hz, 1H), 8.55 (d, J=8.0 Hz, 1H), 8.45 (d, J=1.6 Hz, 1H), 8.19 (s, 1H), 7.90 (s, 1H), 7.47 (d, J=1.6 Hz, 1H), 6.98 (d, J=1.6 Hz, 1H), 5.14 (t, J=8.8 Hz, 1H), 4.88 (t, J=8.8 Hz, 1H), 2.82-2.62 (m, 2H), 2.28-2.14 (m, 2H), 2.10-1.87 (m, 4H), 1.85-1.59 (m, 8H), 1.43-1.33 (m, 1H), 1.32-1.13 (m, 2H), 0.97 (d, J=7.2 Hz, 3H). MS (ESI) m/z: [M+H]⁺ Found 615.3. Example 501: ¹H NMR (400 MHz, DMSO-d₆) δ 8.72 (d, J=8.8 Hz, 1H), 8.54 (d, J=8.0 Hz, 1H), 8.44 (d, J=2.0 Hz, 1H), 8.19 (s, 1H), 7.88 (s, 1H), 7.47 (d, J=2.4 Hz, 1H), 6.97 (s, 1H), 5.14 (t, J=8.8 Hz, 1H), 4.88 (t, J=8.8 Hz, 1H), 2.81-2.63 (m, 2H), 2.28-2.15 (m, 2H), 2.08-1.86 (m, 4H), 1.83-1.57 (m, 8H), 1.42-1.33 (m, 1H), 1.26-1.17 (m, 2H), 1.05 (d, J=7.2 Hz, 3H). MS (ESI) m/z: [M+H]⁺ Found 615.3.

Example 502

N—((S)-(7-((R*)-Cyclobutyl((R*)-4,4,4-trifluoro-3-methylbutanamido)methyl)imidazo[1,2-b]pyridazin-2-yl)(4,4-difluorocyclohexyl)methyl)-1-(methyl-d₃)-1H-pyrazole-5-carboxamide

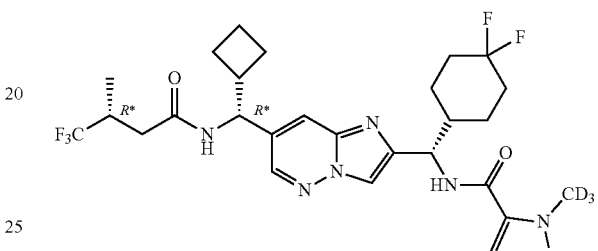

Example 503

N—((S)-(7-((R*)-Cyclobutyl((S*)-4,4,4-trifluoro-3-methylbutanamido)methyl)imidazo[1,2-b]pyridazin-2-yl)(4,4-difluorocyclohexyl)methyl)-1-(methyl-d₃)-1H-pyrazole-5-carboxamide

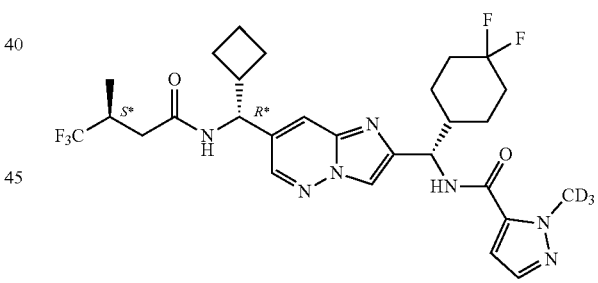

The title compounds were prepared as described for the synthesis of Intermediate 63, using N—((R*)-(2-((S)-amino(4,4-difluorocyclohexyl)methyl)imidazo[1,2-b]pyridazin-7-yl)(cyclobutyl)methyl)-4,4,4-trifluoro-3-methylbutanamide (Intermediate 445) in place of N—((R)-(2-((S)-amino(4,4-difluorocyclohexyl)methyl)imidazo[1,2-b]pyridazin-7-yl)(cyclopropyl)methyl)-4,4,4-trifluorobutanamide, 1-(methyl-d₃)-1H-pyrazole-5-carboxylic acid (Intermediate 435) in place of 2-((3,3-difluorocyclobutyl)methyl)-2H-1,2,3-triazole-4-carboxylic acid and the material was purified by silica gel preparative thin layer chromatography (50% ethyl acetate/petroleum ether) to afford a mixture of diastereomers as a white solid. The diastereomers were separated by SFC using a chiral stationary phase (Daicel Chiralpak® IE, 20/80 EtOH (with 0.1% of 25% aqueous NH₃)/CO₂). The first-eluting isomer was Example 502, and the second-eluting isomer was Example 503. Example 502: ¹H NMR (400

MHz, DMSO-d$_6$) δ 8.73 (d, J=9.2 Hz, 1H), 8.54 (d, J=8.0 Hz, 1H), 8.44 (d, J=2.0 Hz, 1H), 8.19 (s, 1H), 7.89 (d, J=1.6 Hz, 1H), 7.45 (s, 1H), 7.01 (d, J=2.0 Hz, 1H), 5.13 (t, J=8.8 Hz, 1H), 4.87 (t, J=8.8 Hz, 1H), 2.81-2.63 (m, 2H), 2.26-2.13 (m, 2H), 2.08-1.88 (m, 4H), 1.83-1.57 (m, 8H), 1.41-1.34 (m, 1H), 1.30-1.22 (m, 2H), 0.97 (d, J=7.2 Hz, 3H). MS (ESI) m/z: [M+H]$^+$ Found 599.2. Example 503: $^1$H NMR (400 MHz, DMSO-d$_6$) δ 8.71 (d, J=8.8 Hz, 1H), 8.53 (d, J=7.6 Hz, 1H), 8.43 (d, J=2.0 Hz, 1H), 8.19 (s, 1H), 7.88 (d, J=1.2 Hz, 1H), 7.45 (s, 1H), 7.01 (d, J=2.0 Hz, 1H), 5.13 (t, J=8.8 Hz, 1H), 4.88 (t, J=8.8 Hz, 1H), 2.82-2.64 (m, 2H), 2.28-2.14 (m, 2H), 2.08-1.90 (m, 4H), 1.85-1.60 (m, 8H), 1.37-1.33 (m, 1H), 1.28-1.22 (m, 2H), 1.05 (d, J=7.2 Hz, 3H)MS (ESI) m/z: [M+H]$^+$ Found 599.2.

Example 504

N—((S)-(4,4-Difluorocyclohexyl)(7-((S*)-2-methyl-1-(4,4,4-trifluorobutanamido)propyl)imidazo[1,2-b]pyridazin-2-yl)methyl)-4-methyl-1,2,5-oxadiazole-3-carboxamide

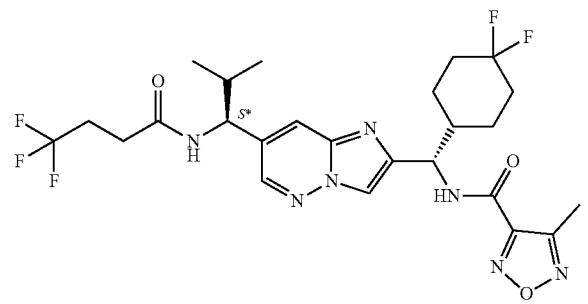 [SMILES: Cc1nonc1C(=O)N[C@H](c1cn2ncc([C@@H](NC(=O)CCC(F)(F)F)C(C)C)cc2n1)C1CCC(F)(F)CC1]

The title compound was prepared as described for the synthesis of Example 142 using N—((S*)-1-(2-((S)-amino (4,4-difluorocyclohexyl)methyl)imidazo[1,2-b]pyridazin-7-yl)-2-methylpropyl)-4,4,4-trifluorobutanamide (Intermediate 515) in place of N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide to afford the title compound as a white powder. $^1$H NMR (500 MHz, DMSO-d$_6$) δ 9.40 (d, J=8.9 Hz, 1H), 8.49 (d, J=8.4 Hz, 1H), 8.47 (d, J=2.1 Hz, 1H), 8.22 (s, 1H), 7.89 (m, 1H), 5.19-5.14 (m, 1H), 4.71-4.67 (m, 1H), 2.46 (m, 6H), 2.17 (m, 1H), 2.10-1.94 (m, 3H), 1.90 (m, 1H), 1.77 (m, 2H), 1.61 (m, 1H), 1.39 (m, 1H), 1.33-1.21 (m, 2H), 0.92 (d, J=6.7 Hz, 3H), 0.81 (d, J=6.7 Hz, 3H). MS (ESI) m/z: [M+H]$^+$ Found 572.2.

Example 505

N—((S)-(4,4-Difluorocyclohexyl)(7-((R*)-1-(4,4,4-trifluorobutanamido)ethyl)imidazo[1,2-b]pyridazin-2-yl)methyl)-4-methyl-1,2,5-oxadiazole-3-carboxamide

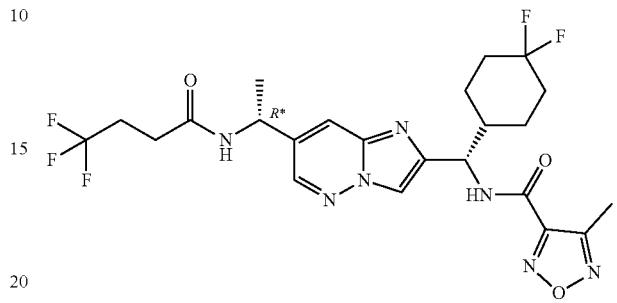

The title compound was prepared as described for the synthesis of Example 142 using N—((R*)-1-(2-((S)-amino (4,4-difluorocyclohexyl)methyl)imidazo[1,2-b]pyridazin-7-yl)ethyl)-4,4,4-trifluorobutanamide (Intermediate 519) in place of N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide to afford the title compound as a white powder. $^1$H NMR (500 MHz, DMSO-d$_6$) δ 9.39 (d, J=9.0 Hz, 1H), 8.57 (d, J=7.4 Hz, 1H), 8.48 (d, J=2.1 Hz, 1H), 8.22 (s, 1H), 7.88 (m, 1H), 5.18-5.14 (m, 1H), 5.02-4.95 (m, 1H), 2.48-2.42 (m, 6H), 2.17 (m, 1H), 2.11-1.66 (m, 5H), 1.60 (m, 1H), 1.42 (d, J=7.0 Hz, 3H), 1.26 (m, 3H). MS (ESI) m/z: [M+H]$^+$ Found 544.2.

Example 506

N—((S)-(7-((R*)-1-(2-(3,3-Difluorocyclobutyl)acetamido)propyl)imidazo[1,2-b]pyridazin-2-yl)(4,4-difluorocyclohexyl)methyl)-1-(ethyl-d$_5$)-1H-pyrazole-5-carboxamide

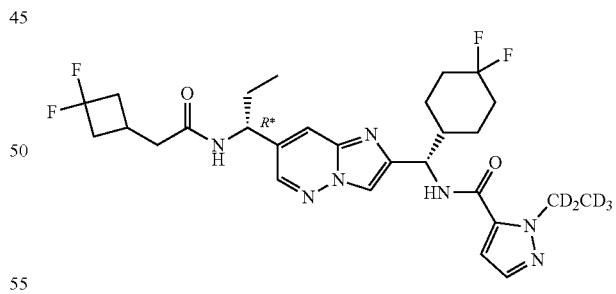

N—((R*)-1-(2-((S)-amino(4,4-difluorocyclohexyl)methyl)imidazo[1,2-b]pyridazin-7-yl)propyl)-2-(3,3-difluorocyclobutyl)acetamide (50 mg, 0.11 mmol, Intermediate 450), TEA (31 μL, 0.22 mmol), 1-(ethyl-d$_5$)-1H-pyrazole-5-carboxylic acid (24 mg, 0.17 mmol, Intermediate 204), and DCM (2.5 mL) were added to a vial with stir bar. Then slowly, 1-propanephosphonic anhydride (56 mg, 0.18 mmol) was added. The reaction was stirred for 19 hrs. The reaction was diluted with acetonitrile, filtered and purified directly by reverse phase basic HPLC (X-Bridge Prep C18 5 μm column 50×100 mm, 0-100% acetonitrile/water (with 20 mM NH₄OH). The product containing fractions were concentrated to afford the title compound as a white solid. ¹H NMR (400 MHz, DMSO-d₆) δ 8.72 (d, J=9.0 Hz, 1H), 8.46 (d, J=2.0 Hz, 1H), 8.40 (d, J=7.9 Hz, 1H), 8.20 (s, 1H), 7.85 (d, J=2.0 Hz, 1H), 7.47 (d, J=2.0 Hz, 1H), 6.98 (d, J=2.0 Hz, 1H), 5.15 (t, J=8.7 Hz, 1H), 4.82-4.71 (m, 1H), 2.72-2.55 (m, 2H), 2.44-2.13 (m, 6H), 2.12-1.56 (m, 8H), 1.45-1.19 (m, 2H), 0.89 (t, J=7.3 Hz, 3H). MS (ESI) m/z: [M+H]⁺ Found, 583.2.

Example 507

4-Cyclopropyl-N—((S)-(7-((R*)-1-(2-(3,3-difluorocyclobutyl)acetamido)propyl)imidazo[1,2-b]pyridazin-2-yl)(4,4-difluorocyclohexyl)methyl)-1,2,5-oxadiazole-3-carboxamide

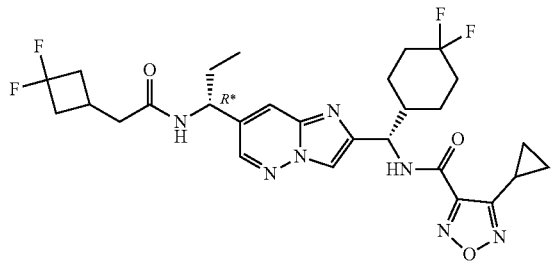 [SMILES: CC[C@@H](NC(=O)CC1CC(F)(F)C1)c1cnn2cc([C@@H](NC(=O)c3nonc3C3CC3)C3CCC(F)(F)CC3)nc2c1]

The title compound was prepared as described for the synthesis of Example 506, using 4-cyclopropyl-1,2,5-oxadiazole-3-carboxylic acid (Intermediate 570) in place of 1-(ethyl-d₅)-1H-pyrazole-5-carboxylic acid to afford the title compound as a white solid. ¹H NMR (400 MHz, DMSO-d₆) δ 9.51 (d, J=9.0 Hz, 1H), 8.51 (d, J=2.1 Hz, 1H), 8.44 (d, J=7.9 Hz, 1H), 8.25 (s, 1H), 7.90 (d, J=2.0 Hz, 1H), 5.22 (t, J=8.5 Hz, 1H), 4.86-4.75 (m, 1H), 2.77-2.59 (m, 2H), 2.48-2.15 (m, 7H), 2.14-1.71 (m, 7H), 1.71-1.58 (m, 1H), 1.51-1.23 (m, 2H), 1.19-1.10 (m, 2H), 1.04-0.96 (m, 2H), 0.92 (t, J=7.3 Hz, 3H). MS (ESI) m/z: [M+H]⁺ Found 592.1.

Example 508

N—((S)-(7-((S*)-1-(2-(3,3-Difluorocyclobutyl)acetamido)propyl)imidazo[1,2-b]pyridazin-2-yl)(4,4-difluorocyclohexyl)methyl)-1-(ethyl-d₅)-1H-pyrazole-5-carboxamide

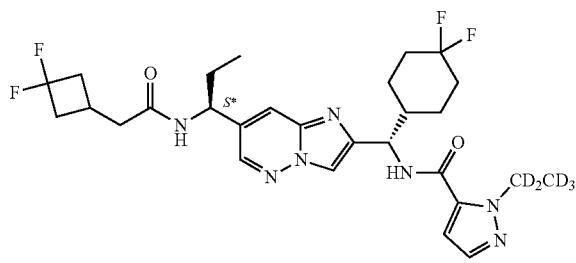

The title compound was prepared as described for the synthesis of Example 173, using N—((S*)-1-(2-((S)-amino(4,4-difluorocyclohexyl)methyl)imidazo[1,2-b]pyridazin-7-yl)propyl)-2-(3,3-difluorocyclobutyl)acetamide (Intermediate 451) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide, 1-(ethyl-d₅)-1H-pyrazole-5-carboxylic acid (Intermediate 204) in place of 1-isopropyl-1H-pyrazole-5-carboxylic and the material was purified by preparative basic HPLC (X-Bridge Prep C18 5 µm, 50×100 mm column, 0-100% acetonitrile/water (with 20 mM NH₄OH). The product containing fractions were concentrated to afford the title compound as a white solid. ¹H NMR (400 MHz, DMSO-d₆) δ 8.71 (d, J=9.0 Hz, 1H), 8.46 (d, J=2.1 Hz, 1H), 8.40 (d, J 7.9 Hz, 1H), 8.20 (s, 1H), 7.85 (d, J=2.0 Hz, 1H), 7.47 (d, J=2.0 Hz, 1H), 6.97 (d, J=2.0 Hz, 1H), 5.15 (t, J=8.7 Hz, 1H), 4.81-4.72 (m, 1H), 2.72-2.55 (m, 2H), 2.43-2.35 (m, 3H), 2.35-2.12 (m, 3H), 2.10-1.92 (m, 2H), 1.92-1.85 (m, 1H), 1.85-1.67 (m, 4H), 1.61 (d, J=13.7 Hz, 1H), 1.45-1.19 (m, 2H), 0.89 (t, J=7.3 Hz, 3H). MS (ESI) m/z: [M+H]⁺ Found 583.2.

Example 509

N—((S)-(7-((S*)-1-(2-(3,3-Difluorocyclobutyl)acetamido)propyl)imidazo[1,2-b]pyridazin-2-yl)(4,4-difluorocyclohexyl)methyl)-4-methyl-1,2,5-oxadiazole-3-carboxamide

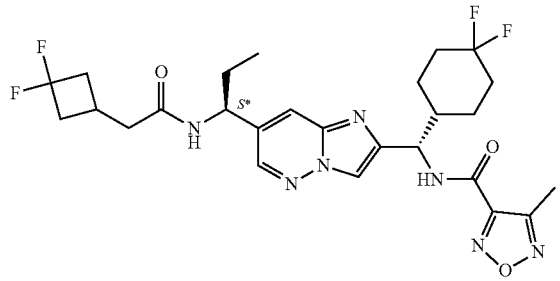 [SMILES: CC[C@H](NC(=O)CC1CC(F)(F)C1)c1cnn2cc([C@@H](NC(=O)c3nonc3C)C3CCC(F)(F)CC3)nc2c1]

The title compound was prepared as described for the synthesis of Example 249, using N—((S*)-1-(2-((S)-amino(4,4-difluorocyclohexyl)methyl)imidazo[1,2-b]pyridazin-7-yl)propyl)-2-(3,3-difluorocyclobutyl)acetamide (Intermediate 451) in place of N—((R)-(2-((S)-amino(4,4-difluorocyclohexyl)methyl)imidazo[1,2-b]pyridazin-7-yl)(cyclopropyl)methyl)-2-(bicyclo[1.1.1]pentan-1-yl)acetamide and the material was purified by preparative basic HPLC (X-Bridge Prep C18 5 µm, 50×100 mm column, 0-100% acetonitrile/water (with 20 mM NH₄OH). The product containing fractions were concentrated to afford the title compound as a white solid. ¹H NMR (400 MHz, DMSO-d₆) δ 9.40 (d, J=9.0 Hz, 1H), 8.47 (d, J=2.1 Hz, 1H), 8.40 (d, J=7.8 Hz, 1H), 8.22 (s, 1H), 7.89-7.84 (m, 1H), 5.17 (t, J=8.6 Hz, 1H), 4.81-4.72 (m, 1H), 2.71-2.56 (m, 2H), 2.47 (s, 3H), 2.45-2.35 (m, 3H), 2.34-2.23 (m, 2H), 2.22-2.13 (m, 1H), 2.09-1.94 (m, 2H), 1.94-1.86 (m, 1H), 1.85-1.69 (m, 4H), 1.65-1.56 (m, 1H), 1.45-1.34 (m, 1H), 1.33-1.22 (m, 1H), 0.89 (t, J=7.3 Hz, 3H). MS (ESI) m/z: [M+H]⁺ Found 566.2.

Example 510

N—((S)-(4,4-Difluorocyclohexyl)(7-((S*)-1-(4,4,4-trifluorobutanamido)ethyl)imidazo[1,2-b]pyridazin-2-yl)methyl)-4-methyl-1,2,5-oxadiazole-3-carboxamide

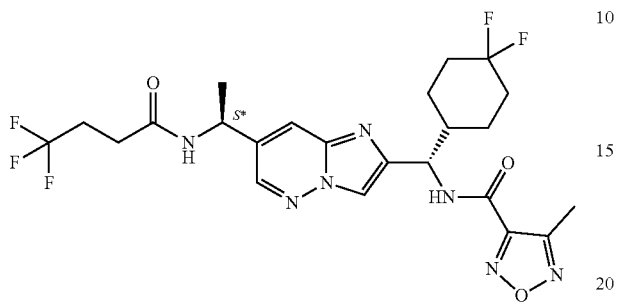

The title compound was prepared as described for the synthesis of Example 142 using N—((S*)-1-(2-((S)-amino(4,4-difluorocyclohexyl)methyl)imidazo[1,2-b]pyridazin-7-yl)ethyl)-4,4,4-trifluorobutanamide (Intermediate 520) in place of N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide to afford the title compound as a white powder. $^1$H NMR (500 MHz, DMSO-$d_6$) δ 9.40 (d, J=8.9 Hz, 1H), 8.57 (d, J=7.3 Hz, 1H), 8.48 (d, J=2.1 Hz, 1H), 8.22 (s, 1H), 7.90-7.85 (m, 1H), 5.19-5.14 (m, 1H), 5.02-4.95 (m, 1H), 2.46 (m, 7H), 2.17 (m, 1H), 2.09-1.93 (m, 2H), 1.89 (m, 1H), 1.85-1.69 (m, 2H), 1.61 (m, 1H), 1.42 (d, J=7.0 Hz, 3H), 1.41-1.33 (m, 1H), 1.27 (m, 1H). MS (ESI) m/z: [M+H]$^+$ Found 544.2.

Example 511

N—((S)-(4,4-Difluorocyclohexyl)(7-((S*)-2-methyl-1-(4,4,4-trifluorobutanamido)propyl)imidazo[1,2-b]pyridazin-2-yl)methyl)-4-isopropyl-1,2,5-oxadiazole-3-carboxamide

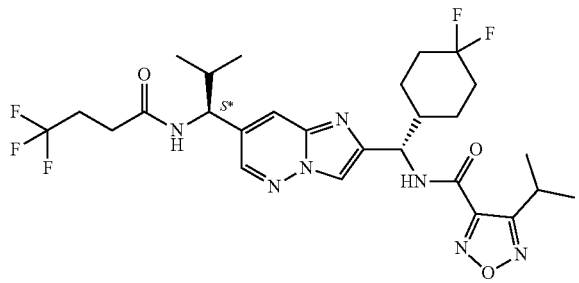 [SMILES: CC(C)c1nonc1C(=O)N[C@H](c1cn2ncc([C@@H](NC(=O)CCC(F)(F)F)C(C)C)cc2n1)C1CCC(F)(F)CC1]

A microwave vial was charged with 4-(((S)-(4,4-difluorocyclohexyl)(7-((S*)-2-methyl-1-(4,4,4-trifluorobutanamido)propyl)imidazo[1,2-b]pyridazin-2-yl)methyl)carbamoyl)-3-isopropyl-1,2,5-oxadiazole 2-oxide (302 mg, 0.491 mmol, Intermediate 516) and toluene (2.45 mL). The vial was sealed and then degassed and backfilled with N$_2$ (3 times). Trimethyl phosphite (1.15 mL, 9.82 mmol) was then added dropwise and the reaction was heated to 120° C. for 16 h. At this point, the reaction was diluted with 1 M aqueous HCl and the reaction was extracted with EtOAc (3×15 mL). The combined organic extracts were dried with anhydrous MgSO$_4$, filtered, and concentrated to dryness to give a yellow oil which was purified by preparative basic HPLC (Gemini® 5 μM, C18, 110 Å, 150×21.2 mm, 0-100% MeCN/H$_2$O (with 20 mM NH$_4$OH). The product containing fractions were lyophilized to afford the title compound as a white powder. $^1$H NMR (500 MHz, CDCl$_3$) δ 8.23 (d, J=2.1 Hz, 1H), 7.86 (s, 1H), 7.75 (d, J=8.8 Hz, 1H), 7.69 (d, J=2.1 Hz, 1H), 5.90 (d, J=7.6 Hz, 1H), 5.26 (dd, J=8.9, 7.6 Hz, 1H), 4.75 (t, J=7.5 Hz, 1H), 3.58 (hept, J=6.9 Hz, 1H), 2.58-2.38 (m, 4H), 2.20-2.01 (m, 4H), 2.02-1.95 (m, 1H), 1.82-1.67 (m, 3H), 1.59-1.48 (m, 1H), 1.40 (d, J=6.9 Hz, 3H), 1.35 (d, J=7.0 Hz, 3H), 1.04 (d, J=6.7 Hz, 3H), 0.95 (d, J=6.7 Hz, 3H). MS (ESI) m/z: [M+H]$^+$ Found 600.2.

Example 512

4-Cyclopropyl-N—((S)-(7-((S*)-1-(2-(3,3-difluorocyclobutyl)acetamido)-2-methylpropyl)imidazo[1,2-b]pyridazin-2-yl)(4,4-difluorocyclohexyl)methyl)-1,2,5-oxadiazole-3-carboxamide

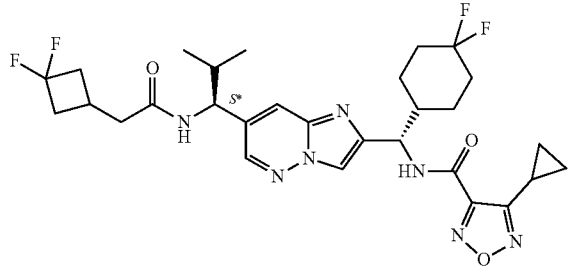 [SMILES: CC(C)[C@H](NC(=O)CC1CC(F)(F)C1)c1cnn2cc([C@@H](NC(=O)c3nonc3C3CC3)C3CCC(F)(F)CC3)nc2c1]

The title compound was prepared as described for the synthesis of Example 38, using N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide (Intermediate 517) in place of N—((R)-(2-((S)-amino(4,4-difluorocyclohexyl)methyl)imidazo[1,2-b]pyridazin-7-yl)(cyclopropyl)methyl)-4,4,4-trifluorobutanamide, and 4-cyclopropyl-1,2,5-oxadiazole-3-carboxylic acid (Intermediate 570) in place of 1-(3,3,3-trifluoropropyl)-1H-1,2,4-triazole-5-carboxylic acid to afford the title compound as white powder. $^1$H NMR (500 MHz, DMSO-$d_6$) δ 9.50 (d, J=9.0 Hz, 1H), 8.52 (d, J=2.1 Hz, 1H), 8.40 (d, J=8.5 Hz, 1H), 8.26 (s, 1H), 7.92 (d, J=2.0 Hz, 1H), 5.22-5.17 (m, 1H), 4.71-4.65 (m, 1H), 2.69-2.54 (m, 2H), 2.45-2.34 (m, 3H), 2.28 (m, 3H), 2.18 (m, 1H), 2.05 (m, 3H), 1.91 (m, 1H), 1.78 (m, 2H), 1.63 (m, 1H), 1.34 m, 2H), 1.16-1.07 (m, 2H), 0.96 m, 2H), 0.93 (d, J=6.7 Hz, 3H), 0.81 (d, J=6.7 Hz, 3H). MS (ESI) m/z: [M+H]$^+$ Found 606.2.

Example 513

N—((S)-(7-((S*)-1-(2-(3,3-Difluorocyclobutyl)acetamido)-2-methylpropyl)imidazo[1,2-b]pyridazin-2-yl)(4,4-difluorocyclohexyl)methyl)-4-methyl-1,2,5-oxadiazole-3-carboxamide

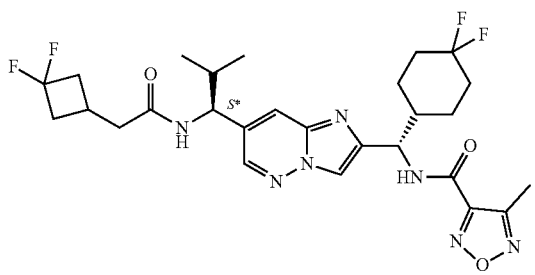 [SMILES: Cc1nonc1C(=O)N[C@H](c1cn2ncc([C@@H](NC(=O)CC3CC(F)(F)C3)C(C)C)cc2n1)C1CCC(F)(F)CC1]

A vial was charged a stir bar, 4-methyl-1,2,5-oxadiazole-3-carboxylic acid (63 mg, 0.49 mmol), EtOAc (1.23 mL), 1-propanephosphonic anhydride (50% in EtOAc, 0.262 mL, 0.441 mmol), and DIPEA (0.168 mL, 0.98 mmol). The mixture was stirred for 5 min, at which time N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide (115 mg, 0.245 mmol, Intermediate 517) was added. The reaction was stir for 24 h at which point it was diluted with 0.05 M aqueous HCl and then extracted with EtOAc (3×10 mL). The combined organic layers were washed with saturated aqueous sodium bicarbonate, dried with anhydrous sodium sulfate, filtered, and concentrated to dryness. The residue was dissolved in minimal DMSO and purified by acidic preparative HPLC (Waters XBridge CSH 5 μm C18, 19×100 mm, 10-65% MeCN/H$_2$O (with 0.16% TFA)) to afford the title compound as a white solid. $^1$H NMR (500 MHz, DMSO-d$_6$) δ 9.43 (d, J=8.9 Hz, 1H), 8.51 (d, J=2.0 Hz, 1H), 8.40 (d, J=8.5 Hz, 1H), 8.26 (s, 1H), 7.91 (d, J=2.0 Hz, 1H), 5.20-5.15 (m, 1H), 4.70-4.65 (m, 1H), 2.70-2.55 (m, 2H), 2.45-2.35 (m, 4H), 2.33-2.14 (m, 3H), 2.09-1.87 (m, 4H), 1.77 (m, 2H), 1.62 (m, 1H), 1.43-1.22 (m, 2H), 0.92 (d, J=6.7 Hz, 3H), 0.80 (d, J=6.7 Hz, 3H). MS (ESI) m/z: [M+H]$^+$ Found 580.2.

Example 514

N—((S)-(7-((S*)-1-(2-(3,3-Difluorocyclobutyl)acetamido)-2-methylpropyl)imidazo[1,2-b]pyridazin-2-yl)(4,4-difluorocyclohexyl)methyl)-4-(2,2-difluoroethoxy)-1,2,5-oxadiazole-3-carboxamide

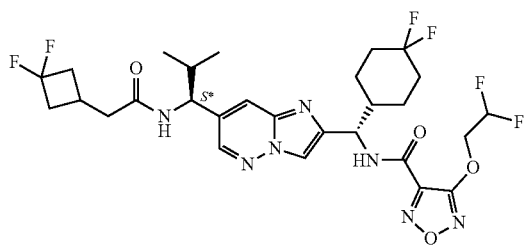 [SMILES: CC(C)[C@H](NC(=O)CC1CC(F)(F)C1)c1cnn2cc([C@@H](NC(=O)c3nonc3OCC(F)F)C3CCC(F)(F)CC3)nc2c1]

The title compound was prepared as described for the synthesis of Example 513, using 4-(2,2-difluoroethoxy)-1,2,5-oxadiazole-3-carboxylic acid (Intermediate 330) in place of 4-methyl-1,2,5-oxadiazole-3-carboxylic acid to afford the title compound as a white powder. $^1$H NMR (500 MHz, DMSO-d$_6$) δ 9.36 (d, J=9.0 Hz, 1H), 8.50 (d, J=2.1 Hz, 1H), 8.40 (d, J=8.5 Hz, 1H), 8.20 (s, 1H), 7.89 (d, J=2.0 Hz, 1H), 6.42 (tt, J=53.6, 3.1 Hz, 1H), 5.16 (t, J=8.4 Hz, 1H), 4.74-4.64 (m, 3H), 2.69-2.55 (m, 2H), 2.44-2.34 (m, 3H), 2.27 (m, 2H), 2.14 (m, 1H), 2.07-1.93 (m, 3H), 1.92-1.69 (m, 3H), 1.62 (m, 1H), 1.33 (m, 2H), 0.93 (d, J=6.7 Hz, 3H), 0.80 (d, J=6.7 Hz, 3H). MS (ESI) m/z: [M+H]$^+$ Found 646.3.

Example 515

N—((S)-(7-((S*)-2,2-Difluoro-1-(4,4,4-trifluorobutanamido)ethyl)imidazo[1,2-b]pyridazin-2-yl)(4,4-difluorocyclohexyl)methyl)-4-methyl-1,2,5-oxadiazole-3-carboxamide

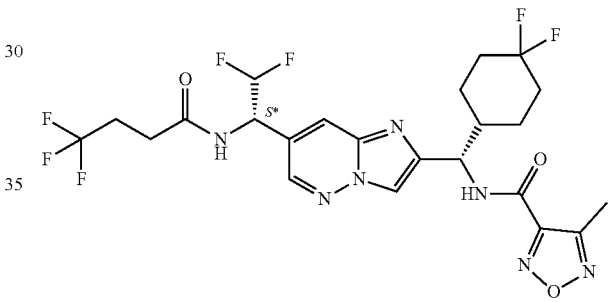

The title compound was prepare as described for the synthesis of Example 38 using N-(1-(2-((S)-amino(4,4-difluorocyclohexyl)methyl)imidazo[1,2-b]pyridazin-7-yl)-2,2-difluoroethyl)-4,4,4-trifluorobutanamide (Intermediate 525) in place of N—((R)-(2-((S)-amino(4,4-difluorocyclohexyl)methyl)imidazo[1,2-b]pyridazin-7-yl)(cyclopropyl)methyl)-4,4,4-trifluorobutanamide, and 4-methyl-1,2,5-oxadiazole-3-carboxylic acid in place of 1-(3,3,3-trifluoropropyl)-1H-1,2,4-triazole-5-carboxylic acid. An additional purification step was performed by SFC using a chiral stationary phase (Regis (S,S) Whelk-O® 1, 20:80 MeOH/CO$_2$) afforded the title compound (first-eluting isomer) as a white powder. $^1$H NMR (500 MHz, DMSO-d$_6$) δ 9.44 (d, J=9.0 Hz, 1H), 9.06 (d, J=8.8 Hz, 1H), 8.59 (d, J=2.1 Hz, 1H), 8.30 (s, 1H), 8.15 (d, J=2.0 Hz, 1H), 6.37 (m, 1H), 5.63-5.52 (m, 1H), 5.23-5.15 (m, 1H), 2.61-2.51 (m, 4H), 2.46 (s, 3H), 2.18 (d, J=9.9 Hz, 1H), 2.07-1.93 (m, 2H), 1.90 (d, J=13.0 Hz, 1H), 1.77 (m, 1H), 1.60 (d, J=13.4 Hz, 1H), 1.44-1.33 (m, 1H), 1.27 (m, 1H). MS (ESI) m/z: [M+H]$^+$ Found 580.1.

Example 516

N—((S)-(7-((R*)-2,2-Difluoro-1-(4,4,4-trifluorobutanamido)ethyl)imidazo[1,2-b]pyridazin-2-yl)(4,4-difluorocyclohexyl)methyl)-4-methyl-1,2,5-oxadiazole-3-carboxamide

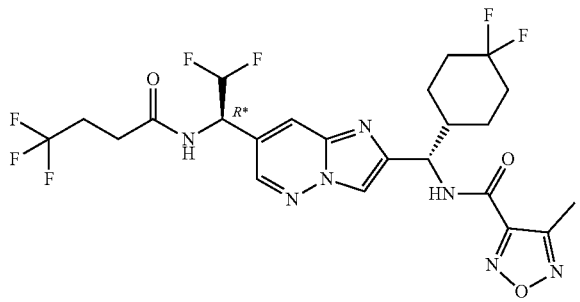

The title compound was prepared as described for the synthesis of Example 38 using N-(1-(2-((S)-amino(4,4-difluorocyclohexyl)methyl)imidazo[1,2-b]pyridazin-7-yl)-2,2-difluoroethyl)-4,4,4-trifluorobutanamide (Intermediate 525) in place of N—((R)-(2-((S)-amino(4,4-difluorocyclohexyl)methyl)imidazo[1,2-b]pyridazin-7-yl)(cyclopropyl)methyl)-4,4,4-trifluorobutanamide, and 4-methyl-1,2,5-oxadiazole-3-carboxylic acid in place of 1-(3,3,3-trifluoropropyl)-1H-1,2,4-triazole-5-carboxylic acid. An additional purification step was performed by SFC using a chiral stationary phase (Regis (S,S) Whelk-O® 1, 20:80 MeOH/CO$_2$) afforded the title compound (second-eluting isomer) as a white powder. $^1$H NMR (500 MHz, DMSO-d$_6$) δ 9.44 (d, J=8.9 Hz, 1H), 9.07 (d, J=8.7 Hz, 1H), 8.59 (d, J=2.1 Hz, 1H), 8.31 (d, J=0.6 Hz, 1H), 8.16-8.15 (m, 1H), 6.37 (td, J=54.9, 3.0 Hz, 1H), 5.62-5.50 (m, 1H), 5.21-5.13 (m, 1H), 2.61-2.51 (m, 4H), 2.46 (s, 3H), 2.24-2.15 (m, 1H), 2.06-1.87 (m, 3H), 1.86-1.69 (m, 2H), 1.60 (d, J=13.4 Hz, 1H), 1.44-1.34 (m, 1H), 1.32-1.22 (m, 1H). MS (ESI) m/z: [M+H]$^+$ Found 580.1.

Example 517

4-Cyclopropyl-N—((S)-(7-((S*)-1-(2-(3,3-difluorocyclobutyl)acetamido)-2,2-difluoroethyl)imidazo[1,2-b]pyridazin-2-yl)(4,4-difluorocyclohexyl)methyl)-1,2,5-oxadiazole-3-carboxamide

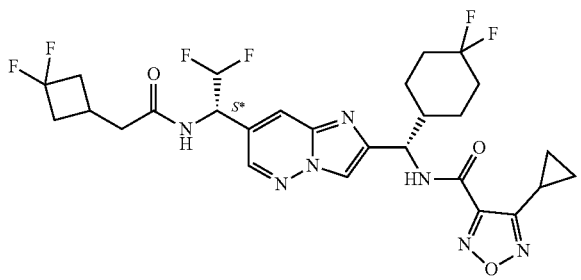 [SMILES: O=C(CC1CC(F)(F)C1)N[C@@H](c1cnn2cc([C@@H](NC(=O)c3nonc3C3CC3)C3CCC(F)(F)CC3)nc2c1)C(F)F]

The title compound was prepared as described for the synthesis of Example 513 using N-(1-(2-((S)-amino(4,4-difluorocyclohexyl)methyl)imidazo[1,2-b]pyridazin-7-yl)-2,2-difluoroethyl)-2-(3,3-difluorocyclobutyl)acetamide (Intermediate 526) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide, and 4-cyclopropyl-1,2,5-oxadiazole-3-carboxylic acid (Intermediate 570) in place of 4-methyl-1,2,5-oxadiazole-3-carboxylic acid. An additional purification step was performed by SFC using a chiral stationary phase (Regis (S,S) Whelk-O® 1, 20:80 MeOH/CO$_2$) afforded the title compound (first-eluting isomer) as a white powder. $^1$H NMR (500 MHz, DMSO-d$_6$) δ 9.50 (d, J=9.0 Hz, 1H), 8.94 (d, J=8.9 Hz, 1H), 8.59 (d, J=2.0 Hz, 1H), 8.30 (s, 1H), 8.15 (d, J=1.8 Hz, 1H), 6.35 (dt, J=2.9, 55.0 Hz, 1H), 5.60-5.47 (m, 1H), 5.23-5.17 (m, 1H), 2.72-2.57 (m, 2H), 2.46-2.37 (m, 1H), 2.34-2.24 (m, 3H), 2.22-2.13 (m, 1H), 2.10-1.94 (m, 2H), 1.89 (m, 1H), 1.85-1.69 (m, 2H), 1.61 (m, 1H), 1.44-1.34 (m, 1H), 1.33-1.22 (m, 1H), 1.15-1.07 (m, 2H), 1.00-0.91 (m, 2H). MS (ESI) m/z: [M+H]$^+$ Found 614.2.

Example 518

4-Cyclopropyl-N—((S)-(7-((R*)-1-(2-(3,3-difluorocyclobutyl)acetamido)-2,2-difluoroethyl)imidazo[1,2-b]pyridazin-2-yl)(4,4-difluorocyclohexyl)methyl)-1,2,5-oxadiazole-3-carboxamide

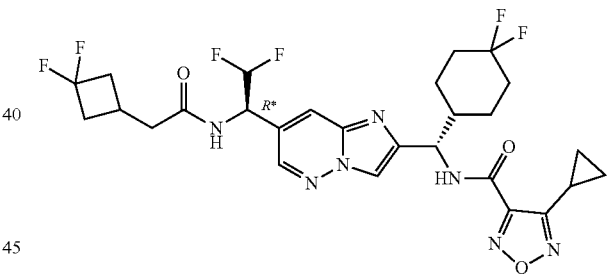

The title compound was prepared as described for the synthesis of Example 513 using N-(1-(2-((S)-amino(4,4-difluorocyclohexyl)methyl)imidazo[1,2-b]pyridazin-7-yl)-2,2-difluoroethyl)-2-(3,3-difluorocyclobutyl)acetamide (Intermediate 526) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide, and 4-cyclopropyl-1,2,5-oxadiazole-3-carboxylic acid (Intermediate 570) in place of 4-methyl-1,2,5-oxadiazole-3-carboxylic acid. An additional purification step was performed by SFC using a chiral stationary phase (Regis (S,S) Whelk-O® 1, 20:80 MeOH/CO$_2$) afforded the title compound (second-eluting isomer) as a white powder. MS (ESI) m/z: [M+H]$^+$ Found 614.2.

Example 519

N—((S)-(7-((S*)-1-(2-(3,3-Difluorocyclobutyl)acet-amido)-2,2-difluoroethyl)imidazo[1,2-b]pyridazin-2-yl)(4,4-difluorocyclohexyl)methyl)-1-isopropyl-1H-pyrazole-5-carboxamide

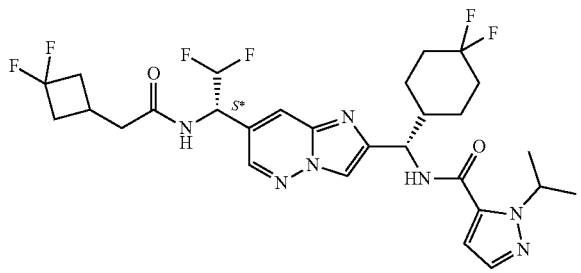 [SMILES: CC(C)n1nccc1C(=O)N[C@H](c1cn2ncc([C@H](NC(=O)CC3CC(F)(F)C3)C(F)F)cc2n1)C1CCC(F)(F)CC1]

The title compound was prepared as described for the synthesis of Example 513 using N-(1-(2-((S)-amino(4,4-difluorocyclohexyl)methyl)imidazo[1,2-b]pyridazin-7-yl)-2,2-difluoroethyl)-2-(3,3-difluorocyclobutyl)acetamide (Intermediate 526) in place of N—((S*)-1-(2-((S)-amino(4,4-difluorocyclohexyl)methyl)imidazo[1,2-b]pyridazin-7-yl)-2-methylpropyl)-2-(3,3-difluorocyclobutyl)acetamide, and 1-isopropyl-1H-pyrazole-5-carboxylic acid in place of 4-methyl-1,2,5-oxadiazole-3-carboxylic acid. An additional purification step was performed by SFC using a chiral stationary phase (Regis (S,S) Whelk-O® 1, 20:80 MeOH/CO₂) afforded the title compound (first-eluting isomer) as a white powder. $^1$H NMR (500 MHz, DMSO-d₆) δ 8.94 (d, J=8.9 Hz, 1H), 8.74 (d, J=9.0 Hz, 1H), 8.58 (d, J=2.0 Hz, 1H), 8.27 (s, 1H), 8.14 (d, J=1.8 Hz, 1H), 7.49 (d, J=2.0 Hz, 1H), 6.91 (d, J=2.0 Hz, 1H), 6.35 (dt, J=2.8, 55.0 Hz, 1H), 5.60-5.47 (m, 1H), 5.40-5.31 (m, 1H), 5.19-5.14 (m, 1H), 2.73-2.57 (m, 2H), 2.44-2.38 (m, 1H), 2.34-2.24 (m, 2H), 2.22-2.12 (m, 1H), 2.09-1.93 (m, 2H), 1.90-1.68 (m, 3H), 1.61 (m, 1H), 1.43-1.38 (m, 1H), 1.36 (d, J=6.6 Hz, 3H), 1.32 (d, J=6.6 Hz, 3H), 1.30-1.20 (m, 1H), 1.02 (m, 1H) MS (ESI) m/z: [M+H]⁺ Found 614.2.

Example 520

N—((S)-(7-((S*)-1-(2-(3,3-Difluorocyclobutyl)acet-amido)propyl)imidazo[1,2-b]pyridazin-2-yl)(4,4-difluorocyclohexyl)methyl)-1-isopropyl-1H-pyrazole-5-carboxamide

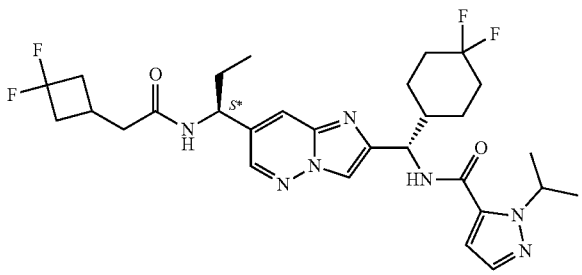 [SMILES: CC[C@H](NC(=O)CC1CC(F)(F)C1)c1cnn2cc([C@@H](NC(=O)c3ccnn3C(C)C)C3CCC(F)(F)CC3)nc2c1]

The title compound was prepared as described for the synthesis of Example 173, using N—((S*)-1-(2-((S)-amino(4,4-difluorocyclohexyl)methyl)imidazo[1,2-b]pyridazin-7-yl)propyl)-2-(3,3-difluorocyclobutyl)acetamide (Intermediate 451) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide, and the material was purified by preparative basic HPLC (X-Bridge Prep C18 5 μm, 50×100 mm column, 0-100% acetonitrile/water (with 20 mM NH₄OH). The product containing fractions were concentrated to afford the title compound as a white solid. $^1$H NMR (400 MHz, DMSO-d₆) δ 8.71 (d, J=9.1 Hz, 1H), 8.46 (d, J=2.1 Hz, 1H), 8.40 (d, J=7.9 Hz, 1H), 8.19 (s, 1H), 7.85 (d, J=2.0 Hz, 1H), 7.49 (d, J=2.0 Hz, 1H), 6.91 (d, J=2.0 Hz, 1H), 5.41-5.32 (m, 1H), 5.15 (t, J=8.6 Hz, 1H), 4.83-4.71 (m, 1H), 2.71-2.55 (m, 2H), 2.43-2.35 (m, 3H), 2.35-2.22 (m, 2H), 2.22-2.11 (m, 1H), 2.11-1.93 (m, 2H), 1.92-1.67 (m, 5H), 1.66-1.56 (m, 1H), 1.44-1.20 (m, 8H), 0.89 (t, J=7.3 Hz, 3H). MS (ESI) m/z: [M+H]⁺ Found 592.2.

Example 521

4-Cyclopropyl-N—((S*)-(7-((R)-1-(2-(3,3-difluoro-cyclobutyl)acetamido)propyl)imidazo[1,2-b]pyridazin-2-yl)(4,4-difluorocyclohexyl)methyl)-1,2,5-oxadiazole-3-carboxamide

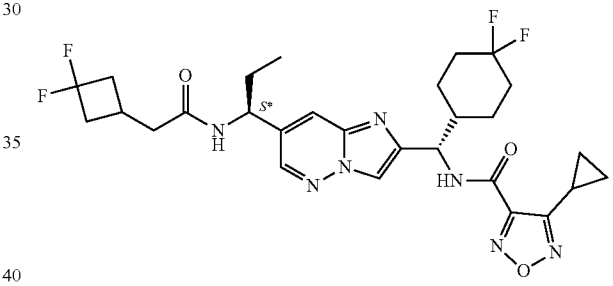

The title compound was prepared as described for the synthesis of Example 173, using N—((S*)-1-(2-((S)-amino(4,4-difluorocyclohexyl)methyl)imidazo[1,2-b]pyridazin-7-yl)propyl)-2-(3,3-difluorocyclobutyl)acetamide (Intermediate 451) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide, 4-cyclopropyl-1,2,5-oxadiazole-3-carboxylic acid (Intermediate 570) in place of 1-isopropyl-1H-pyrazole-5-carboxylic and the material was purified by preparative basic HPLC (X-Bridge Prep C18 5 μm, 50×100 mm column, 0-100% acetonitrile/water (with 20 mM NH₄OH). The product containing fractions were concentrated to afford the title compound as a white solid. $^1$H NMR (400 MHz, DMSO-d₆) δ 9.47 (d, J=9.0 Hz, 1H), 8.48 (d, J=2.1 Hz, 1H), 8.40 (d, J=7.9 Hz, 1H), 8.22 (s, 1H), 7.87 (d, J=2.0 Hz, 1H), 5.22-5.15 (m, 1H), 4.82-4.73 (m, 1H), 2.70-2.57 (m, 2H), 2.44-2.35 (m, 3H), 2.35-2.23 (m, 3H), 2.23-2.13 (m, 1H), 2.10-1.94 (m, 2H), 1.94-1.88 (m, 1H), 1.85-1.69 (m, 4H), 1.66-1.57 (m, 1H), 1.45-1.35 (m, 1H), 1.35-1.23 (m, 1H), 1.16-1.08 (m, 2H), 1.00-0.93 (m, 2H), 0.89 (t, J=7.3 Hz, 3H). MS (ESI) m/z: [M+H]⁺ Found 592.2.

Example 522

N—((S)-(7-((S*)-1-(2-(3,3-Difluorocyclobutyl)acetamido)-2-methoxyethyl)imidazo[1,2-b]pyridazin-2-yl)(4,4-difluorocyclohexyl)methyl)-1-(ethyl-d₅)-1H-pyrazole-5-carboxamide

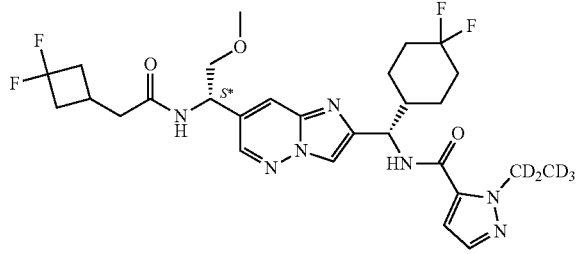

The title compound was prepared as described for the synthesis of Example 173, using N—((S*)-1-(2-((S)-amino(4,4-difluorocyclohexyl)methyl)imidazo[1,2-b]pyridazin-7-yl)-2-methoxyethyl)-2-(3,3-difluorocyclobutyl)acetamide (Intermediate 458) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide, 1-(ethyl-d₅)-1H-pyrazole-5-carboxylic acid (Intermediate 204) in place of 1-isopropyl-1H-pyrazole-5-carboxylic and the material was purified by preparative basic HPLC (X-Bridge Prep C18 5 μm, 50×100 mm column, 0-100% acetonitrile/water (with 20 mM NH₄OH). The product containing fractions were concentrated to afford the title compound as a white solid. ¹H NMR (400 MHz, DMSO-d₆) δ 8.72 (d, J=9.0 Hz, 1H), 8.57-8.44 (m, 2H), 8.21 (s, 1H), 7.91 (d, J=2.0 Hz, 1H), 7.47 (d, J=2.1 Hz, 1H), 6.98 (d, J=2.1 Hz, 1H), 5.21-5.04 (m, 2H), 3.65-3.54 (m, 2H), 3.28 (s, 3H), 2.74-2.57 (m, 2H), 2.46-2.24 (m, 5H), 2.24-2.13 (m, 1H), 2.13-1.93 (m, 2H), 1.93-1.69 (m, 3H), 1.69-1.53 (m, 1H), 1.44-1.32 (m, 1H), 1.32-1.16 (m, 1H). MS (ESI) m/z: [M+H]⁺ Found 599.3.

Example 523

N—((S)-(7-((R*)-1-(2-(3,3-Difluorocyclobutyl)acetamido)-2-methoxyethyl)imidazo[1,2-b]pyridazin-2-yl)(4,4-difluorocyclohexyl)methyl)-1-(ethyl-d₅)-1H-pyrazole-5-carboxamide

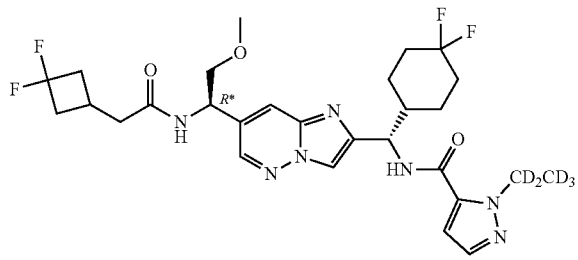

The title compound was prepared as described for the synthesis of Example 173, using N—((R*)-1-(2-((S)-amino(4,4-difluorocyclohexyl)methyl)imidazo[1,2-b]pyridazin-7-yl)-2-methoxyethyl)-2-(3,3-difluorocyclobutyl)acetamide (Intermediate 458) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide, 1-(ethyl-d₅)-1H-pyrazole-5-carboxylic acid (Intermediate 204) in place of 1-isopropyl-1H-pyrazole-5-carboxylic and the material was purified by preparative basic HPLC (X-Bridge Prep C18 5 μm, 50×100 mm column, 0-100% acetonitrile/water (with 20 mM NH₄OH). The product containing fractions were concentrated to afford the title compound as a white solid. ¹H NMR (400 MHz, DMSO-d₆) δ 8.72 (d, J=9.1 Hz, 1H), 8.56-8.46 (m, 2H), 8.21 (s, 1H), 7.92 (d, J=2.0 Hz, 1H), 7.47 (d, J=2.0 Hz, 1H), 6.98 (d, J=2.0 Hz, 1H), 5.20-5.07 (m, 2H), 3.63-3.54 (m, 2H), 3.28 (s, 3H), 2.72-2.55 (m, 2H), 2.46-2.23 (m, 5H), 2.23-2.11 (m, 1H), 2.10-1.92 (m, 2H), 1.92-1.67 (m, 3H), 1.66-1.55 (m, 1H), 1.45-1.32 (m, 1H), 1.32-1.18 (m, 1H). MS (ESI) m/z: [M+H]⁺ Found 599.3.

Example 524

4-Cyclopropyl-N—((S)-(7-((S*)-1-(2-(3,3-difluorocyclobutyl)acetamido)-2-methoxyethyl)imidazo[1,2-b]pyridazin-2-yl)(4,4-difluorocyclohexyl)methyl)-1,2,5-oxadiazole-3-carboxamide

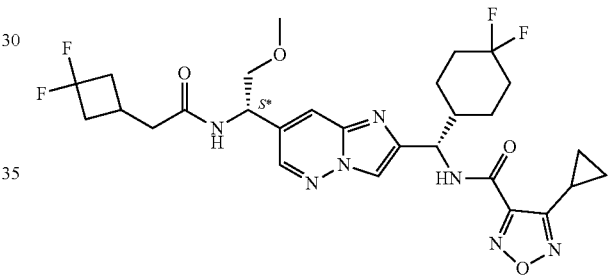

The title compound was prepared as described for the synthesis of Example 173, using N—((S*)-1-(2-((S)-amino(4,4-difluorocyclohexyl)methyl)imidazo[1,2-b]pyridazin-7-yl)-2-methoxyethyl)-2-(3,3-difluorocyclobutyl)acetamide (Intermediate 458) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide and 4-cyclopropyl-1,2,5-oxadiazole-3-carboxylic acid (Intermediate 570) in place of 1-isopropyl-1H-pyrazole-5-carboxylic. The material was purified by preparative basic HPLC (X-Bridge Prep C18 5 μm, 50×100 mm column, 0-100% acetonitrile/water (with 20 mM NH₄OH) followed by preparative acidic HPLC (SunFire® Prep C18 5 μm, 30×250 mm column, 0-100% acetonitrile (0.05% TFA)/water (0.05% TFA)). The desired fractions were concentrated and the material was purified by eluting through a silica plug (10% MeOH with 2.0 M ammonia/DCM). The product containing fractions were concentrated to afford the title compound as a white solid. ¹H NMR (400 MHz, DMSO-d₆) δ 9.48 (d, J=9.0 Hz, 1H), 8.58-8.44 (m, 2H), 8.23 (s, 1H), 7.96-7.90 (m, 1H), 5.19 (t, J=8.5 Hz, 1H), 5.16-5.07 (m, 1H), 3.65-3.53 (m, 2H), 3.28 (s, 3H), 2.75-2.56 (m, 2H), 2.45-2.12 (m, 7H), 2.12-1.67 (m, 5H), 1.67-1.55 (m, 1H), 1.47-1.22 (m, 2H), 1.19-1.07 (m, 2H), 1.01-0.89 (m, 2H). MS (ESI) m/z: [M+H]⁺ Found 608.3.

Example 525

4-Cyclopropyl-N—((S)-(7-((R*)-1-(2-(3,3-difluoro-cyclobutyl)acetamido)-2-methoxyethyl)imidazo[1,2-b]pyridazin-2-yl)(4,4-difluorocyclohexyl)methyl)-1,2,5-oxadiazole-3-carboxamide

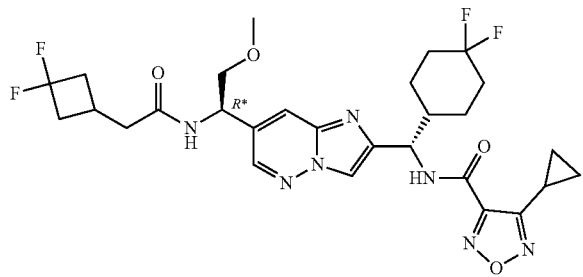 [SMILES: COC[C@H](NC(=O)CC1CC(F)(F)C1)c1cnn2cc([C@@H](NC(=O)c3nonc3C3CC3)C3CCC(F)(F)CC3)nc2c1]

The title compound was prepared as described for the synthesis of Example 173, using N—((R*)-1-(2-((S)-amino(4,4-difluorocyclohexyl)methyl)imidazo[1,2-b]pyridazin-7-yl)-2-methoxyethyl)-2-(3,3-difluorocyclobutyl)acetamide (Intermediate 457) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide and 4-cyclopropyl-1,2,5-oxadiazole-3-carboxylic acid (Intermediate 570) in place of 1-isopropyl-1H-pyrazole-5-carboxylic. The material was purified by preparative basic HPLC (X-Bridge Prep C18 5 µm, 50×100 mm column, 0-100% acetonitrile/water (with 20 mM NH$_4$OH) followed by preparative acidic HPLC (SunFire® Prep C18 5 µm, 30×250 mm column, 0-100% acetonitrile (0.05% TFA)/water (0.05% TFA)). The desired fractions were concentrated and the material was purified by eluting through a silica plug (10% MeOH with 2.0 M ammonia/DCM). The product containing fractions were concentrated to afford the title compound as a white solid. $^1$H NMR (400 MHz, DMSO-d$_6$) δ 9.48 (d, J=9.0 Hz, 1H), 8.57-8.46 (m, 2H), 8.23 (s, 1H), 7.98-7.86 (m, 1H), 5.19 (t, J=8.5 Hz, 1H), 5.16-5.07 (m, 1H), 3.65-3.53 (m, 2H), 3.28 (s, 3H), 2.73-2.56 (m, 2H), 2.47-2.12 (m, 7H), 2.12-1.68 (m, 5H), 1.68-1.54 (m, 1H), 1.50-1.21 (m, 2H), 1.17-1.08 (m, 2H), 1.00-0.89 (m, 2H). MS (ESI) m/z: [M+H]$^+$ Found 608.3.

Example 526

4-Cyclopropyl-N—((S)-(7-((S*)-1-(2-(3,3-difluoro-cyclobutyl)acetamido)-2-ethoxyethyl)imidazo[1,2-b]pyridazin-2-yl)(4,4-difluorocyclohexyl)methyl)-1,2,5-oxadiazole-3-carboxamide

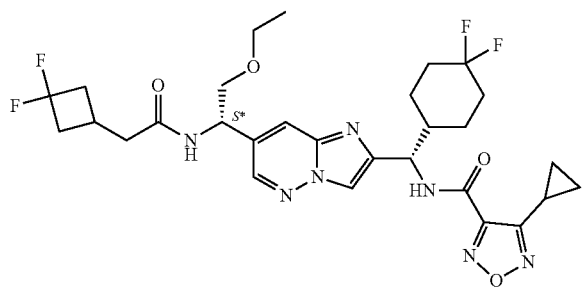 [SMILES: CCOC[C@@H](NC(=O)CC1CC(F)(F)C1)c1cnn2cc([C@@H](NC(=O)c3nonc3C3CC3)C3CCC(F)(F)CC3)nc2c1]

The title compound was prepared as described for the synthesis of Example 173, using N—((S*)-1-(2-((S)-amino(4,4-difluorocyclohexyl)methyl)imidazo[1,2-b]pyridazin-7-yl)-2-ethoxyethyl)-2-(3,3-difluorocyclobutyl)acetamide (Intermediate 465) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide, 4-cyclopropyl-1,2,5-oxadiazole-3-carboxylic acid (Intermediate 570) in place of 1-isopropyl-1H-pyrazole-5-carboxylic and the material was purified by preparative basic HPLC (X-Bridge Prep C18 5 µm, 50×100 mm column, 0-100% acetonitrile/water (with 20 mM NH$_4$OH). The product containing fractions were concentrated to afford the title compound as a white solid. $^1$H NMR (400 MHz, DMSO-d$_6$) δ 9.48 (d, J=9.0 Hz, 1H), 8.54-8.44 (m, 2H), 8.24 (s, 1H), 7.94 (d, J=2.0 Hz, 1H), 5.24-5.16 (m, 1H), 5.14-5.05 (m, 1H), 3.67-3.56 (m, 2H), 3.52-3.43 (m, 2H), 2.74-2.55 (m, 2H), 2.46-2.12 (m, 7H), 2.12-1.68 (m, 5H), 1.68-1.55 (m, 1H), 1.47-1.21 (m, 2H), 1.17-1.05 (m, 5H), 1.00-0.92 (m, 2H). MS (ESI) m/z: [M+H]$^+$ Found 622.3.

Example 527

4-Cyclopropyl-N—((S)-(7-((R*)-1-(2-(3,3-difluoro-cyclobutyl)acetamido)-2-ethoxyethyl)imidazo[1,2-b]pyridazin-2-yl)(4,4-difluorocyclohexyl)methyl)-1,2,5-oxadiazole-3-carboxamide

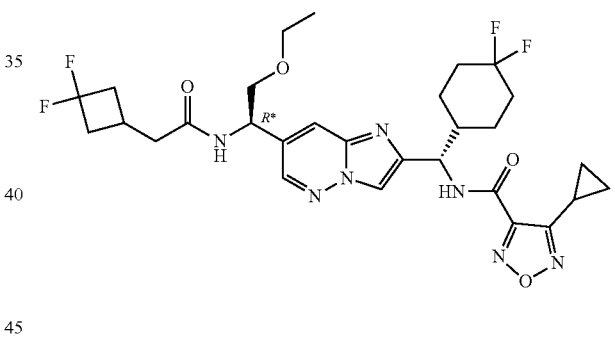

The title compound was prepared as described for the synthesis of Example 173, using N—((R*)-1-(2-((S)-amino(4,4-difluorocyclohexyl)methyl)imidazo[1,2-b]pyridazin-7-yl)-2-ethoxyethyl)-2-(3,3-difluorocyclobutyl)acetamide (Intermediate 464) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide, and 4-cyclopropyl-1,2,5-oxadiazole-3-carboxylic acid (Intermediate 570) in place of 1-isopropyl-1H-pyrazole-5-carboxylic and the material was purified by preparative basic HPLC (X-Bridge Prep 5 µm C18, 50×100 mm column, 0-100% acetonitrile/water (with 20 mM NH$_4$OH). The product containing fractions were concentrated to afford the title compound as a white solid. $^1$H NMR (400 MHz, DMSO-d$_6$) δ 9.48 (d, J=9.0 Hz, 1H), 8.54-8.44 (m, 2H), 8.23 (s, 1H), 7.94 (dd, J=2.0, 1.0 Hz, 1H), 5.23-5.16 (m, 1H), 5.13-5.06 (m, 1H), 3.66-3.59 (m, 2H), 3.53-3.42 (m, 2H), 2.71-2.56 (m, 2H), 2.45-2.25 (m, 6H), 2.24-2.13 (m, 1H), 2.11-1.70 (m, 5H), 1.67-1.57 (m, 1H), 1.44-1.22 (m, 2H), 1.16-1.05 (m, 5H), 1.04-0.91 (m, 2H). MS (ESI) m/z: [M+H]$^+$ Found 622.3.

Example 528

N—((S)-(7-((R*)-1-(2-(3,3-Difluorocyclobutyl)acetamido)-2-ethoxyethyl)imidazo[1,2-b]pyridazin-2-yl)(4,4-difluorocyclohexyl)methyl)-1-isopropyl-1H-pyrazole-5-carboxamide

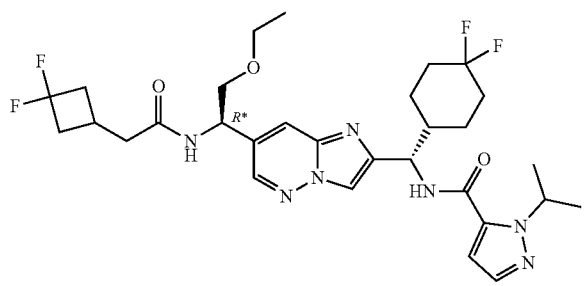 [SMILES: CCOC[C@H](NC(=O)CC1CC(F)(F)C1)c1cnn2cc([C@@H](NC(=O)c3ccnn3C(C)C)C3CCC(F)(F)CC3)nc2c1]

Example 529

N—((S)-(7-((S*)-1-(2-(3,3-Difluorocyclobutyl)acetamido)-2-ethoxyethyl)imidazo[1,2-b]pyridazin-2-yl)(4,4-difluorocyclohexyl)methyl)-1-isopropyl-1H-pyrazole-5-carboxamide

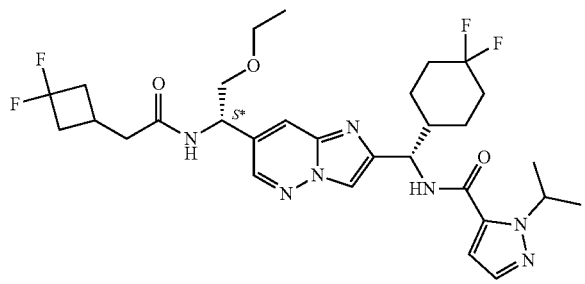 [SMILES: CCOC[C@@H](NC(=O)CC1CC(F)(F)C1)c1cnn2cc([C@@H](NC(=O)c3ccnn3C(C)C)C3CCC(F)(F)CC3)nc2c1]

The title compounds were prepared as described for the synthesis of Example 173, using a mixture of N—((R*)-1-(2-((S)-amino(4,4-difluorocyclohexyl)methyl)imidazo[1,2-b]pyridazin-7-yl)-2-ethoxyethyl)-2-(3,3-difluorocyclobutyl)acetamide (Intermediate 464) and N—((S*)-1-(2-((S)-amino(4,4-difluorocyclohexyl)methyl)imidazo[1,2-b]pyridazin-7-yl)-2-ethoxyethyl)-2-(3,3-difluorocyclobutyl)acetamide (Intermediate 465) in place of N—((R)-2-((S)-amino(4,4-difluorocyclohexyl)methyl)imidazo[1,2-b]pyridazin-7-yl)(cyclopropyl)methyl)-4,4,4-trifluoro-3-methylbutanamide. The isomers were separated by SFC using a chiral stationary phase (Chiralpak IA, 15:85 MeOH/CO$_2$) to provide the title compounds. Example 528 was the first-eluting fraction and Example 529 was the second-eluting fraction. Example 528: $^1$H NMR (400 MHz, DMSO-d$_6$) δ 8.72 (d, J=9.0 Hz, 1H), 8.53-8.45 (m, 2H), 8.21 (s, 1H), 7.94-7.89 (m, 1H), 7.49 (d, J=1.9 Hz, 1H), 6.91 (d, J=2.0 Hz, 1H), 5.37 (hept, J=6.6 Hz, 1H), 5.19-5.04 (m, 2H), 3.67-3.58 (m, 2H), 3.53-3.43 (m, 2H), 2.71-2.56 (m, 2H), 2.45-2.11 (m, 6H), 2.11-1.66 (m, 5H), 1.66-1.56 (m, 1H), 1.45-1.19 (m, 8H), 1.09 (t, J=7.0 Hz, 3H). MS (ESI) m/z: [M+H]$^+$ Found 622.3. Example 529: $^1$H NMR (400 MHz, DMSO-d$_6$) δ 8.72 (d, J=9.1 Hz, 1H), 8.53-8.46 (m, 2H), 8.21 (s, 1H), 7.92 (d, J=2.0 Hz, 1H), 7.49 (d, J=1.9 Hz, 1H), 6.91 (d, J=2.0 Hz, 1H), 5.42-5.32 (m, 1H), 5.19-5.05 (m, 2H), 3.66-3.58 (m, 2H), 3.52-3.43 (m, 2H), 2.72-2.56 (m, 2H), 2.45-2.11 (m, 6H), 2.11-1.67 (m, 5H), 1.67-1.56 (m, 1H), 1.43-1.19 (m, 8H), 1.08 (t, J=7.0 Hz, 3H). MS (ESI) m/z: [M+H]$^+$ Found 622.3.

Example 530

N—((S)-(7-((R*)-1-(2-(3,3-Difluorocyclobutyl)acetamido)-2-ethoxyethyl)imidazo[1,2-b]pyridazin-2-yl)(4,4-difluorocyclohexyl)methyl)-1-(ethyl-d$_5$)-1H-pyrazole-5-carboxamide

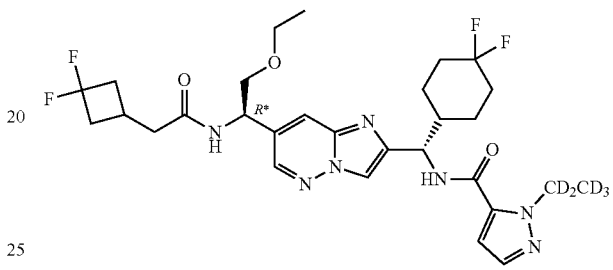

Example 531

N—((S)-(7-((S*)-1-(2-(3,3-Difluorocyclobutyl)acetamido)-2-ethoxyethyl)imidazo[1,2-b]pyridazin-2-yl)(4,4-difluorocyclohexyl)methyl)-1-(ethyl-d$_5$)-1H-pyrazole-5-carboxamide

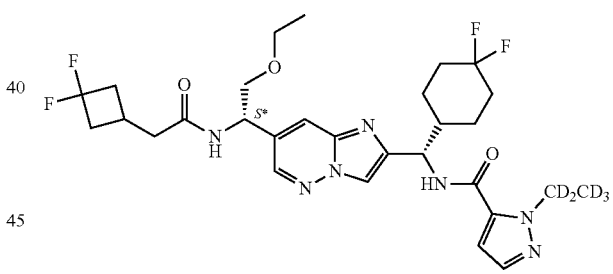

The title compounds were prepared as described for the synthesis of Example 173, using a mixture of N—((R*)-1-(2-((S)-amino(4,4-difluorocyclohexyl)methyl)imidazo[1,2-b]pyridazin-7-yl)-2-ethoxyethyl)-2-(3,3-difluorocyclobutyl)acetamide (Intermediate 464) and N—((S*)-1-(2-((S)-amino(4,4-difluorocyclohexyl)methyl)imidazo[1,2-b]pyridazin-7-yl)-2-ethoxyethyl)-2-(3,3-difluorocyclobutyl)acetamide (Intermediate 465) in place of N—((R)-2-((S)-amino(4,4-difluorocyclohexyl)methyl)imidazo[1,2-b]pyridazin-7-yl)(cyclopropyl)methyl)-4,4,4-trifluoro-3-methylbutanamide and 1-(ethyl-d$_5$)-1H-pyrazole-5-carboxylic acid (Intermediate 204) in place of 1-isopropyl-1H-pyrazole-5-carboxylic acid. The isomers were separated by SFC using a chiral stationary phase (Chiralpak IA, 15:85 MeOH/CO$_2$) to provide the title compounds. Example 530 was the first-eluting fraction and Example 531 was the second-eluting fraction. Example 530: $^1$H NMR (400 MHz, DMSO-d$_6$) δ 8.73 (d, J=9.1 Hz, 1H), 8.53-8.42 (m, 2H), 8.21 (s, 1H), 7.92 (d, J=2.0 Hz, 1H), 7.47 (d, J=2.0 Hz, 1H), 6.98

(d, J=2.1 Hz, 1H), 5.22-5.03 (m, 2H), 3.67-3.57 (m, 2H), 3.52-3.43 (m, 2H), 2.72-2.56 (m, 2H), 2.46-2.12 (m, 6H), 2.11-1.67 (m, 5H), 1.67-1.55 (m, 1H), 1.45-1.19 (m, 2H), 1.09 (t, J=7.0 Hz, 3H). MS (ESI) m/z: [M+H]$^+$ Found 613.4. Example 531: $^1$H NMR (400 MHz, DMSO-d$_6$) δ 8.73 (d, J=9.1 Hz, 1H), 8.53-8.45 (m, 2H), 8.21 (s, 1H), 7.92 (d, J=2.0 Hz, 1H), 7.47 (d, J=2.0 Hz, 1H), 6.98 (d, J=2.0 Hz, 1H), 5.20-5.05 (m, 2H), 3.66-3.57 (m, 2H), 3.53-3.42 (m, 2H), 2.72-2.56 (m, 2H), 2.46-2.11 (m, 6H), 2.10-1.67 (m, 5H), 1.66-1.56 (m, 1H), 1.45-1.19 (m, 2H), 1.08 (t, J=7.0 Hz, 3H). MS (ESI) m/z: [M+H]$^+$ Found 613.3.

Example 532

N—((S)-(7-((R*)-1-(2-(3,3-Difluorocyclobutyl)acetamido)-2-hydroxyethyl)imidazo[1,2-b]pyridazin-2-yl)(4,4-difluorocyclohexyl)methyl)-1-isopropyl-1H-pyrazole-5-carboxamide

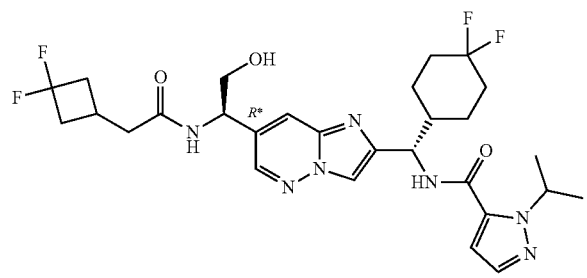 [SMILES: CC(C)n1nccc1C(=O)N[C@H](c1cn2ncc([C@H](CO)NC(=O)CC3CC(F)(F)C3)cc2n1)C1CCC(F)(F)CC1]

N—((S)-(7-((R*)-2-(benzyloxy)-1-(2-(3,3-difluorocyclobutyl)acetamido)ethyl)imidazo[1,2-b]pyridazin-2-yl)(4,4-difluorocyclohexyl)methyl)-1-isopropyl-1H-pyrazole-5-carboxamide (55 mg, 0.11 mmol, Intermediate 470) was dissolved is ethanol (15 mL) and the solution was passed in a loop through a ThalesNano H-cube using a 10% Pd/C catalyst cartridge at 1.0 mL/min, 1 bar H$_2$ at 60° C. for 4 h. The reaction mixture was concentrated to dryness and purified by silica gel chromatography (0-10% MeOH/DCM) to provide the title compound as a white foam. $^1$H NMR (600 MHz, DMSO-d$_6$) δ 8.72 (d, J=9.1 Hz, 1H), 8.46 (d, J=2.1 Hz, 1H), 8.41 (d, J=7.9 Hz, 1H), 8.19 (s, 1H), 7.88 (d, J=2.1 Hz, 1H), 7.49 (d, J=2.0 Hz, 1H), 6.91 (d, J=2.0 Hz, 1H), 5.40-5.33 (m, 1H), 5.15 (t, J=8.6 Hz, 1H), 5.01 (t, J=5.7 Hz, 1H), 4.95-4.89 (m, 1H), 3.70-3.60 (m, 2H), 2.70-2.57 (m, 2H), 2.45-2.36 (m, 3H), 2.36-2.25 (m, 2H), 2.21-2.13 (m, 1H), 2.09-1.93 (m, 2H), 1.91-1.84 (m, 1H), 1.84-1.69 (m, 2H), 1.65-1.56 (m, 1H), 1.43-1.20 (m, 8H). MS (ESI) m/z: [M+H]$^+$ Found 594.3.

Example 533

N—((S)-(7-((S*)-1-(2-(3,3-Difluorocyclobutyl)acetamido)-2-hydroxyethyl)imidazo[1,2-b]pyridazin-2-yl)(4,4-difluorocyclohexyl)methyl)-1-isopropyl-1H-pyrazole-5-carboxamide

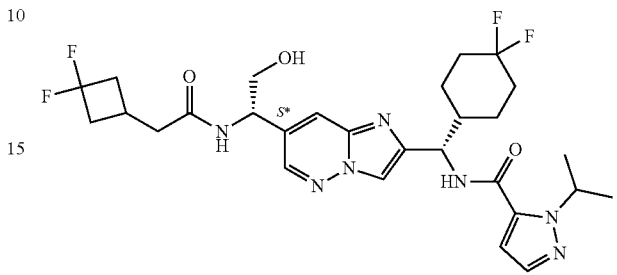

The title compound was prepared as described for the synthesis of Example 532, using N—((S)-(7-((S*)-2-(benzyloxy)-1-(2-(3,3-difluorocyclobutyl)acetamido)ethyl)imidazo[1,2-b]pyridazin-2-yl)(4,4-difluorocyclohexyl)methyl)-1-isopropyl-1H-pyrazole-5-carboxamide (Intermediate 471) in place of N—((S)-(7-((R*)-2-(benzyloxy)-1-(2-(3,3-difluorocyclobutyl)acetamido)ethyl)imidazo[1,2-b]pyridazin-2-yl)(4,4-difluorocyclohexyl)methyl)-1-isopropyl-1H-pyrazole-5-carboxamide to provide the title compound as a white foam. $^1$H NMR (600 MHz, DMSO-d$_6$) δ 8.72 (d, J=9.1 Hz, 1H), 8.46 (d, J 2.1 Hz, 1H), 8.42 (d, J=7.9 Hz, 1H), 8.19 (s, 1H), 7.88 (d, J=2.2 Hz, 1H), 7.49 (d, J=1.9 Hz, 1H), 6.91 (d, J=2.0 Hz, 1H), 5.42-5.31 (m, 1H), 5.15 (t, J=8.7 Hz, 1H), 5.03-4.99 (m, 1H), 4.95-4.88 (m, 1H), 3.71-3.58 (m, 2H), 2.71-2.57 (m, 2H), 2.47-2.36 (m, 3H), 2.36-2.24 (m, 2H), 2.22-2.13 (m, 1H), 2.09-1.93 (m, 2H), 1.92-1.84 (m, 1H), 1.84-1.70 (m, 2H), 1.65-1.57 (m, 1H), 1.44-1.19 (m, 8H). MS (ESI) m/z: [M+H]$^+$ Found 594.3.

Example 534

N—((S)-(7-((R*)-1-(2-(3,3-Difluorocyclobutyl)acetamido)(tetrahydro-2H-pyran-4-yl)methyl)imidazo[1,2-b]pyridazin-2-yl)(4,4-difluorocyclohexyl)methyl)-4-methyl-1,2,5-oxadiazole-3-carboxamide

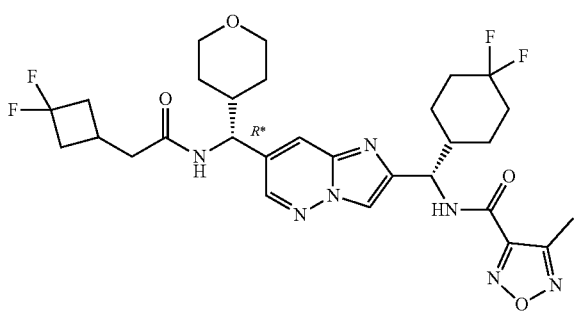 [SMILES: Cc1nonc1C(=O)N[C@H](c1cn2ncc([C@H](NC(=O)CC3CC(F)(F)C3)C3CCOCC3)cc2n1)C1CCC(F)(F)CC1]

The title compound was prepared as described for the synthesis of Example 249, using N—((R*)-2-((S)-amino(4,4-difluorocyclohexyl)methyl)imidazo[1,2-b]pyridazin-7-yl)(tetrahydro-2H-pyran-4-yl)methyl)-2-(3,3-difluorocyclobutyl)acetamide (Intermediate 475) in place of N—((R)-

(2-((S)-amino(4,4-difluorocyclohexyl)methyl)imidazo[1,2-b]pyridazin-7-yl)(cyclopropyl)methyl)-2-(bicyclo[1.1.1]pentan-1-yl)acetamide and the material was purified by preparative basic HPLC (X-Bridge Prep 5 μm C18, 50×100 mm column, 0-100% acetonitrile/water (with 20 mM NH$_4$OH). The product containing fractions were concentrated to afford the title compound as a white solid. $^1$H NMR (400 MHz, DMSO-d$_6$) δ 9.40 (d, J=9.0 Hz, 1H), 8.50-8.42 (m, 2H), 8.23 (s, 1H), 7.92 (d, J=2.0 Hz, 1H), 5.20-5.13 (m, 1H), 4.70 (t, J=8.6 Hz, 1H), 3.89 (d, J=9.9 Hz, 1H), 3.78 (d, J=9.4 Hz, 1H), 3.27-3.15 (m, 2H), 2.69-2.55 (m, 2H), 2.47 (s, 3H), 2.44-2.34 (m, 3H), 2.33-2.12 (m, 3H), 2.10-1.87 (m, 4H), 1.84-1.66 (m, 3H), 1.65-1.56 (m, 1H), 1.45-1.34 (m, 1H), 1.33-1.22 (m, 3H), 1.21-1.13 (m, 1H). MS (ESI) m/z: [M+H]$^+$ Found 622.3.

Example 535

N—((S)-(7-((R*)-1-(2-(3,3-Difluorocyclobutyl)acetamido)(tetrahydro-2H-pyran-4-yl)methyl)imidazo[1,2-b]pyridazin-2-yl)(4,4-difluorocyclohexyl)methyl)-1-isopropyl-1H-pyrazole-5-carboxamide

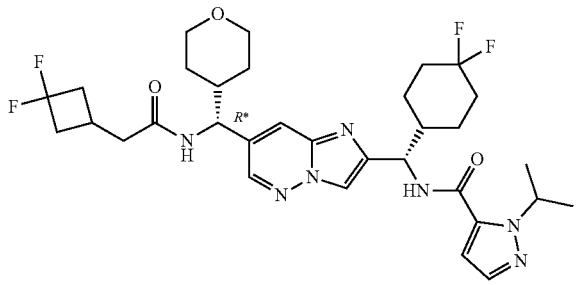 [SMILES: CC(C)n1nccc1C(=O)N[C@H](c1cn2ncc([C@H](NC(=O)CC3CC(F)(F)C3)C3CCOCC3)cc2n1)C1CCC(F)(F)CC1]

The title compound was prepared as described for the synthesis of Example 173, using N—((R*)-(2-((S)-amino(4,4-difluorocyclohexyl)methyl)imidazo[1,2-b]pyridazin-7-yl)(tetrahydro-2H-pyran-4-yl)methyl)-2-(3,3-difluorocyclobutyl)acetamide (Intermediate 475) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide and the material was purified by preparative basic HPLC (X-Bridge Prep 5 μm C18, 50×100 mm column, 0-100% acetonitrile/water (with 20 mM NH$_4$OH). The product containing fractions were concentrated to afford the title compound as a white solid. $^1$H NMR (600 MHz, DMSO-d$_6$) δ 8.71 (d, J=9.1 Hz, 1H), 8.50-8.43 (m, 2H), 8.19 (s, 1H), 7.90 (d, J=2.0 Hz, 1H), 7.49 (d, J=2.0 Hz, 1H), 6.91 (d, J=2.0 Hz, 1H), 5.39-5.33 (m, 1H), 5.15 (t, J=8.7 Hz, 1H), 4.69 (t, J=8.6 Hz, 1H), 3.92-3.74 (m, 2H), 3.27-3.15 (m, 2H), 2.70-2.55 (m, 2H), 2.44-2.32 (m, 3H), 2.33-2.12 (m, 3H), 2.09-1.84 (m, 4H), 1.84-1.66 (m, 3H), 1.65-1.55 (m, 1H), 1.44-1.31 (m, 7H), 1.31-1.21 (m, 3H), 1.20-1.13 (m, 1H). MS (ESI) m/z: [M+H]$^+$ Found 648.2.

Example 536

4-Cyclopropyl-N—((S)-(7-((R*)-1-(2-(3,3-difluorocyclobutyl)acetamido)(tetrahydro-2H-pyran-4-yl)methyl imidazo[1,2-b]pyridazin-2-yl)(4,4-difluorocyclohexyl)methyl)-1,2,5-oxadiazole-3-carboxamide

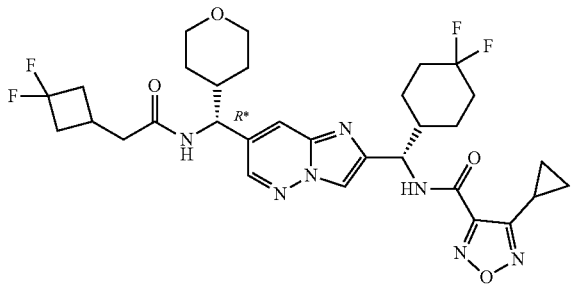 [SMILES: O=C(CC1CC(F)(F)C1)N[C@@H](c1cnn2cc([C@@H](NC(=O)c3nonc3C3CC3)C3CCC(F)(F)CC3)nc2c1)C1CCOCC1]

The title compound was prepared as described for the synthesis of Example 173, using N—((R*)-(2-((S)-amino(4,4-difluorocyclohexyl)methyl)imidazo[1,2-b]pyridazin-7-yl)(tetrahydro-2H-pyran-4-yl)methyl)-2-(3,3-difluorocyclobutyl)acetamide (Intermediate 475) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide and 4-cyclopropyl-1,2,5-oxadiazole-3-carboxylic acid (Intermediate 570) in place of 1-isopropyl-1H-pyrazole-5-carboxylic. The material was purified by preparative basic HPLC (X-Bridge Prep 5 μm C18, 50×100 mm column, 0-100% acetonitrile/water (with 20 mM NH$_4$OH) followed by preparative acidic HPLC (SunFire® Prep 5 μm C18, 30×250 mm column, 0-100% acetonitrile (0.05% TFA)/water (0.05% TFA)). The product-containing fractions were concentrated and the resulting material purified by eluting through a silica gel plug (10% MeOH with 2.0 M ammonia/DCM). The product containing fractions were concentrated to afford the title compound as a white solid. $^1$H NMR (400 MHz, DMSO-d$_6$) δ 9.47 (d, J=9.0 Hz, 1H), 8.52-8.39 (m, 2H), 8.22 (s, 1H), 7.92 (d, J=2.0 Hz, 1H), 5.19 (t, J=8.5 Hz, 1H), 4.70 (t, J=8.6 Hz, 1H), 3.89 (d, J=9.6 Hz, 1H), 3.78 (d, J=9.9 Hz, 1H), 3.29-3.12 (m, 2H), 2.73-2.55 (m, 2H), 2.45-2.12 (m, 7H), 2.11-1.55 (m, 8H), 1.46-1.07 (m, 7H), 1.03-0.89 (m, 2H). MS (ESI) m/z: [M+H]$^+$ Found 648.3.

Example 537

N—((S)-(7-((R*)-2-(3,3-Difluorocyclobutyl)acetamido)(tetrahydro-2H-pyran-4-yl)methyl)imidazo[1,2-b]pyridazin-2-yl)(4,4-difluorocyclohexyl)methyl)-1-isopropyl-1H-1,2,4-triazole-5-carboxamide

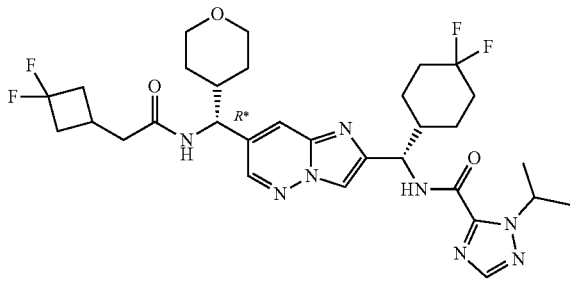 [SMILES: CC(C)n1ncnc1C(=O)N[C@H](c1cn2ncc([C@H](NC(=O)CC3CC(F)(F)C3)C3CCOCC3)cc2n1)C1CCC(F)(F)CC1]

The title compound was prepared as described for the synthesis of Example 173, using N—((R*)-2-((S)-amino(4,4-difluorocyclohexyl)methyl)imidazo[1,2-b]pyridazin-7-yl)(tetrahydro-2H-pyran-4-yl)methyl)-2-(3,3-difluorocyclobutyl)acetamide (Intermediate 475) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide and lithium 1-isopropyl-1H-1,2,4-triazole-5-carboxylate (Intermediate 423) in place of 1-isopropyl-1H-pyrazole-5-carboxylic acid. The material was purified by preparative basic HPLC (X-Bridge Prep 5 μm C18, 50×100 mm column, 0-100% acetonitrile/water (with 20 mM NH₄OH) followed by another preparative basic HPLC (XBridge Prep 5 μm C18, 19×100 mm column, 35-70% acetonitrile (0.17 NH₃)/water. The product containing fractions were concentrated to afford the title compound as a white solid. ¹H NMR (600 MHz, DMSO-d₆) δ 8.87 (d, J=9.2 Hz, 1H), 8.50-8.42 (m, 2H), 8.26 (s, 1H), 8.10 (s, 1H), 7.94 (d, J=2.2 Hz, 1H), 5.58-5.51 (m, 1H), 5.14 (t, J=8.6 Hz, 1H), 4.70 (t, J=8.7 Hz, 1H), 3.92-3.86 (m, 1H), 3.80-3.75 (m, 1H), 3.27-3.15 (m, 2H), 2.70-2.56 (m, 2H), 2.45-2.34 (m, 3H), 2.33-1.65 (m, 10H), 1.63-1.55 (m, 1H), 1.45-1.21 (m, 10H), 1.21-1.13 (m, 1H). MS (ESI) m/z: [M+H]⁺ Found 649.3.

Example 538

4-Cyclopropyl-N—((R)-1-(7-((S*)-1-(2-(3,3-difluorocyclobutyl)acetamido)-2-methoxyethyl)imidazo[1,2-b]pyridazin-2-yl)-2-((1,1,1-trifluoro-2-methylpropan-2-yl)oxy)ethyl)-1,2,5-oxadiazole-3-carboxamide

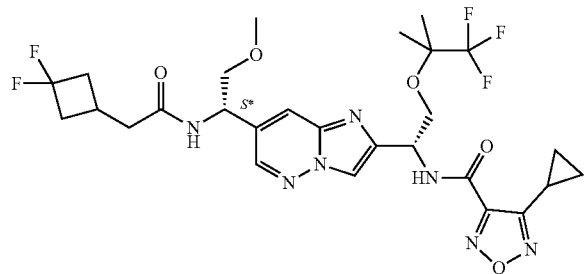 [SMILES: COC[C@@H](NC(=O)CC1CC(F)(F)C1)c1cnn2cc([C@H](COC(C)(C)C(F)(F)F)NC(=O)c3nonc3C3CC3)nc2c1]

The title compound was prepared as described for the synthesis of Example 173, using N—((S*)-1-(2-((R)-1-amino-2-((1,1,1-trifluoro-2-methylpropan-2-yl)oxy)ethyl)imidazo[1,2-b]pyridazin-7-yl)-2-methoxyethyl)-2-(3,3-difluorocyclobutyl)acetamide (Intermediate 484) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide, and 4-cyclopropyl-1,2,5-oxadiazole-3-carboxylic acid (Intermediate 570) in place of 1-isopropyl-1H-pyrazole-5-carboxylic and the material was purified by preparative basic HPLC (X-Bridge Prep 5 μm C18, 50×100 mm column, 0-100% acetonitrile/water (with 20 mM NH₄OH). Additional purifications by silica gel chromatography (0-100% ethyl acetate (with 10% MeOH)/hexanes) and SFC using a chiral stationary phase (Chiralpak IA, 15:85 MeOH/CO₂) provided the title compound. ¹H NMR (400 MHz, DMSO-d₆) δ 9.48 (d, J=8.6 Hz, 1H), 8.60-8.48 (m, 2H), 8.22 (s, 1H), 7.95 (dd, J=2.0, 1.0 Hz, 1H), 5.46-5.35 (m, 1H), 5.17-5.07 (m, 1H), 4.06-3.90 (m, 2H), 3.65-3.54 (m, 2H), 3.28 (s, 3H), 2.74-2.58 (m, 2H), 2.46-2.23 (m, 6H), 1.35 (d, J=3.2 Hz, 6H), 1.18-1.12 (m, 2H), 1.04-0.95 (m, 2H). MS (ESI) m/z: [M+H]⁺ Found 630.3.

Example 539

N—((R)-1-(7-((S*)-1-(2-(3,3-Difluorocyclobutyl)acetamido)-2-methoxyethyl)imidazo[1,2-b]pyridazin-2-yl)-2-((1,1,1-trifluoro-2-methylpropan-2-yl)oxy)ethyl)-1-isopropyl-1H-pyrazole-5-carboxamide

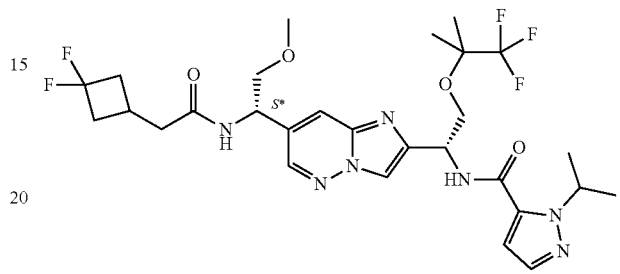

The title compound was prepared as described for the synthesis of Example 173, using N—((S*)-1-(2-((R)-1-amino-2-((1,1,1-trifluoro-2-methylpropan-2-yl)oxy)ethyl)imidazo[1,2-b]pyridazin-7-yl)-2-methoxyethyl)-2-(3,3-difluorocyclobutyl)acetamide (Intermediate 484) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide and the material was purified by preparative basic HPLC (X-Bridge Prep 5 μm C18, 50×100 mm column, 0-100% acetonitrile/water (with 20 mM NH₄OH). An additional purification step was performed by SFC using a chiral stationary phase (Chiralpak IA, 15:85 MeOH/CO₂) provided the title compound. ¹H NMR (400 MHz, DMSO-d₆) δ 8.74 (d, J=8.6 Hz, 1H), 8.54 (d, J=8.0 Hz, 1H), 8.51 (d, J=2.1 Hz, 1H), 8.18 (s, 1H), 7.93 (d, J=2.0 Hz, 1H), 7.50 (d, J=2.0 Hz, 1H), 6.86 (d, J=2.0 Hz, 1H), 5.46-5.33 (m, 2H), 5.15-5.08 (m, 1H), 4.04-3.97 (m, 1H), 3.89 (t, J=8.8 Hz, 1H), 3.64-3.54 (m, 2H), 3.28 (s, 3H), 2.71-2.57 (m, 2H), 2.45-2.23 (m, 5H), 1.46-1.29 (m, 12H). MS (ESI) m/z: [M+H]⁺ Found 630.3.

Example 540

4-Cyclopropyl-N—((R)-1-(7-((R)-(2-(3,3-difluorocyclobutyl)acetamido)(tetrahydro-2H-pyran-4-yl)methyl)imidazo[1,2-b]pyridazin-2-yl)-2-((1,1,1-trifluoro-2-methylpropan-2-yl)oxy)ethyl)-1,2,5-oxadiazole-3-carboxamide

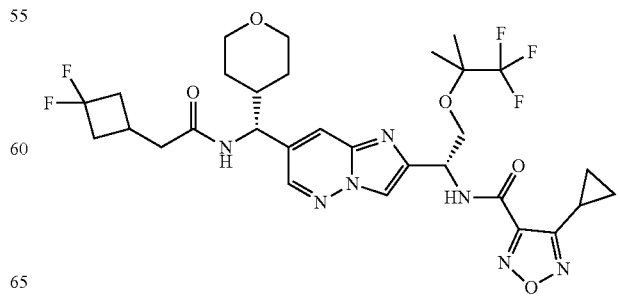

Example 541

N—((R)-1-(7-((R)-(2-(3,3-Difluorocyclobutyl)acet-amido)(tetrahydro-2H-pyran-4-yl)methyl)imidazo[1,2-b]pyridazin-2-yl)-2-((1,1,1-trifluoro-2-methylpropan-2-yl)oxy)ethyl)-1-isopropyl-1H-pyrazole-5-carboxamide

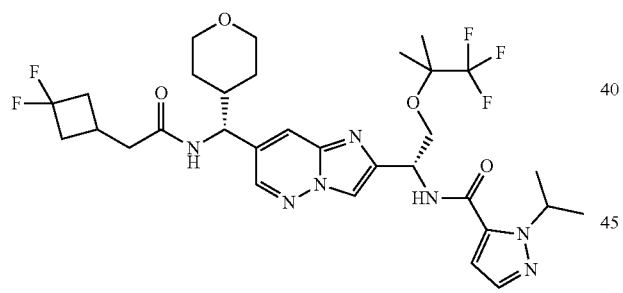

The title compound was prepared as described for the synthesis of Example 173, using N—((R)-2-((R)-1-amino-2-((1,1,1-trifluoro-2-methylpropan-2-yl)oxy)ethyl)imidazo[1,2-b]pyridazin-7-yl)(tetrahydro-2H-pyran-4-yl)methyl)-2-(3,3-difluorocyclobutyl)acetamide (Intermediate 491) in place of N—((R)-2-((S)-amino(4,4-difluorocyclohexyl)methyl)imidazo[1,2-b]pyridazin-7-yl)(cyclopropyl)methyl)-4,4,4-trifluoro-3-methylbutanamide, and 4-cyclopropyl-1,2,5-oxadiazole-3-carboxylic acid (Intermediate 570) in place of 1-isopropyl-1H-pyrazole-5-carboxylic and the material was purified by preparative basic HPLC (X-Bridge Prep 5 μm C18, 50×100 mm column, 0-100% acetonitrile/water (with 20 mM NH$_4$OH). An additional purification step was performed by SFC using a chiral stationary phase (Chiralpak IA, 15:85 MeOH/CO$_2$) provided the title compound. $^1$H NMR (400 MHz, DMSO-d$_6$) δ 9.48 (d, J=8.6 Hz, 1H), 8.53-8.42 (m, 2H), 8.20 (d, J=0.7 Hz, 1H), 7.93 (d, J=2.0 Hz, 1H), 5.45-5.35 (m, 1H), 4.71 (t, J=8.6 Hz, 1H), 4.06-3.85 (m, 3H), 3.83-3.71 (m, 1H), 3.29-3.14 (m, 2H), 2.71-2.54 (m, 2H), 2.44-2.19 (m, 6H), 2.00-1.86 (m, 1H), 1.74-1.63 (m, 1H), 1.39-1.21 (m, 8H), 1.20-1.11 (m, 3H), 1.04-0.94 (m, 2H). MS (ESI) m/z: [M+H]$^+$ Found 670.3.

Example 541

N—((R)-1-(7-((R)-(2-(3,3-Difluorocyclobutyl)acet-amido)(tetrahydro-2H-pyran-4-yl)methyl)imidazo[1,2-b]pyridazin-2-yl)-2-((1,1,1-trifluoro-2-methylpropan-2-yl)oxy)ethyl)-1-isopropyl-1H-pyrazole-5-carboxamide The title compound was prepared as described for the synthesis of Example 173, using N—((R)-2-((R)-1-amino-2-((1,1,1-trifluoro-2-methylpropan-2-yl)oxy)ethyl)imidazo[1,2-b]pyridazin-7-yl)(tetrahydro-2H-pyran-4-yl)methyl)-2-(3,3-difluorocyclobutyl)acetamide (Intermediate 491) in place of N—((R)-2-((S)-amino(4,4-difluorocyclohexyl)methyl)imidazo[1,2-b]pyridazin-7-yl)(cyclopropyl)methyl)-4,4,4-trifluoro-3-methylbutanamide. An additional purification step was performed by SFC using a chiral stationary phase (Chiralpak IA, 15:85 MeOH/CO$_2$) provided the title compound. $^1$H NMR (400 MHz, DMSO-d$_6$) δ 8.74 (d, J=8.6 Hz, 1H), 8.51-8.43 (m, 2H), 8.17 (s, 1H), 7.92 (d, J=2.0 Hz, 1H), 7.50 (d, J=2.0 Hz, 1H), 6.86 (d, J=2.0 Hz, 1H), 5.47-5.31 (m, 2H), 4.71 (t, J=8.6 Hz, 1H), 4.06-3.96 (m, 1H), 3.95-3.85 (m, 2H), 3.83-3.73 (m, 1H), 3.30-3.13 (m, 2H), 2.71-2.54 (m, 2H), 2.45-2.18 (m, 5H), 2.00-1.87 (m, 1H), 1.73-1.62 (m, 1H), 1.40-1.20 (m, 14H), 1.20-1.09 (m, 1H). MS (ESI) m/z: [M+H]$^+$ Found 670.3.

Example 542

4-Cyclopropyl-N—((S)-1-(7-((R)-cyclopropyl(2-(3,3-difluorocyclobutyl)acetamido)methyl)imidazo[1,2-b]pyridazin-2-yl)-4,4,4-trifluoro-3,3-dimethylbutyl)-1,2,5-oxadiazole-3-carboxamide

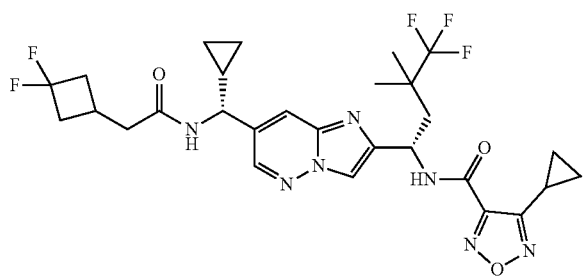 [SMILES: CC(C)(C[C@H](NC(=O)c1nonc1C1CC1)c1cn2ncc([C@H](NC(=O)CC3CC(F)(F)C3)C3CC3)cc2n1)C(F)(F)F]

The title compound was prepared as described for the synthesis of Example 173, using N—((R)-(2-((S)-1-amino-4,4,4-trifluoro-3,3-dimethylbutyl)imidazo[1,2-b]pyridazin-7-yl)(cyclopropyl)methyl)-2-(3,3-difluorocyclobutyl)acetamide (Intermediate 501) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide, and 4-cyclopropyl-1,2,5-oxadiazole-3-carboxylic acid (Intermediate 570) in place of 1-isopropyl-1H-pyrazole-5-carboxylic and the resulting material purified by preparative basic HPLC (X-Bridge Prep 5 μm C18, 50×100 mm column, 0-100% acetonitrile/water (with 20 mM NH$_4$OH) to provide the title compound. $^1$H NMR (400 MHz, DMSO-d$_6$) δ 9.73 (d, J=8.7 Hz, 1H), 8.60 (d, J=7.8 Hz, 1H), 8.50 (d, J 2.1 Hz, 1H), 8.19 (s, 1H), 8.00-7.91 (m, 1H), 5.51-5.42 (m, 1H), 4.28 (t, J=8.4 Hz, 1H), 2.71-2.57 (m, 2H), 2.45-2.22 (m, 8H), 1.27-1.10 (m, 9H), 1.05-0.93 (m, 2H), 0.62-0.43 (m, 3H), 0.41-0.32 (m, 1H). MS (ESI) m/z: [M+H]$^+$ Found 610.3.

Example 543

N—((S)-1-(7-((R)-Cyclopropyl(2-(3,3-difluorocyclobutyl)acetamido)methyl)imidazo[1,2-b]pyridazin-2-yl)-4,4,4-trifluoro-3,3-dimethylbutyl)-1-isopropyl-1H-pyrazole-5-carboxamide

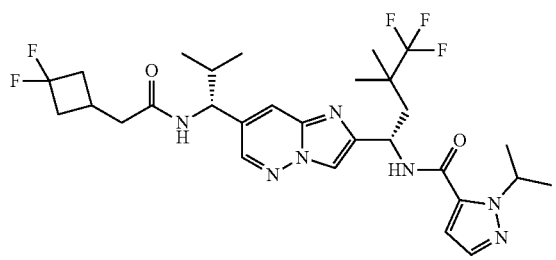 [SMILES: CC(C)[C@@H](NC(=O)CC1CC(F)(F)C1)c1cnn2cc([C@H](CC(C)(C)C(F)(F)F)NC(=O)c3ccnn3C(C)C)nc2c1]

The title compound was prepared as described for the synthesis of Example 173, using N—((R)-(2-((S)-1-amino-4,4,4-trifluoro-3,3-dimethylbutyl)imidazo[1,2-b]pyridazin-7-yl)(cyclopropyl)methyl)-2-(3,3-difluorocyclobutyl)acetamide (Intermediate 501) in place of N—((R)-(2-((S)-amino(4,4-difluorocyclohexyl)methyl)imidazo[1,2-b]pyridazin-7- yl)(cyclopropyl)methyl)-4,4,4-trifluoro-3-methylbutanamide and the resulting material purified by preparative basic HPLC (X-Bridge Prep 5 μm C18, 50×100 mm column, 0-100% acetonitrile/water (with 20 mM NH₄OH) to provide the title compound. ¹H NMR (500 MHz, DMSO-d₆) δ 8.93 (d, J=8.8 Hz, 1H), 8.59 (d, J=7.8 Hz, 1H), 8.49 (d, J=2.1 Hz, 1H), 8.10 (s, 1H), 7.95 (dd, J=2.1, 0.9 Hz, 1H), 7.51 (d, J=2.0 Hz, 1H), 6.90 (d, J=2.0 Hz, 1H), 5.50-5.39 (m, 2H), 4.28 (t, J=8.4 Hz, 1H), 2.70-2.57 (m, 2H), 2.43-2.17 (m, 7H), 1.37 (dd, J=6.6, 1.0 Hz, 6H), 1.19 (s, 7H), 0.63-0.44 (m, 3H), 0.41-0.29 (m, 1H). MS (ESI) m/z: [M+H]⁺ Found 610.3.

Example 544

N—((S)-1-(7-((R)-Cyclopropyl(2-(3,3-difluorocyclobutyl)acetamido)methyl)imidazo[1,2-b]pyridazin-2-yl)-4,4,4-trifluoro-3,3-dimethylbutyl)-4-methyl-1,2,5-oxadiazole-3-carboxamide

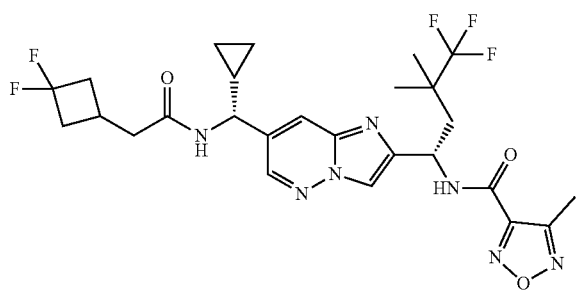 [SMILES: Cc1nonc1C(=O)N[C@@H](CC(C)(C)C(F)(F)F)c1cn2ncc([C@H](NC(=O)CC3CC(F)(F)C3)C3CC3)cc2n1]

The title compound was prepared as described for the synthesis of Example 173, using N—((R)-(2-((S)-1-amino-4,4,4-trifluoro-3,3-dimethylbutyl)imidazo[1,2-b]pyridazin-7-yl)(cyclopropyl)methyl)-2-(3,3-difluorocyclobutyl)acetamide (Intermediate 501) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide, and 4-methyl-1,2,5-oxadiazole-3-carboxylic acid in place of 1-isopropyl-1H-pyrazole-5-carboxylic and the resulting material purified by preparative basic HPLC (X-Bridge Prep 5 μm C18, 50×100 mm column, 0-100% acetonitrile/water (with 20 mM NH₄OH) to provide the title compound. ¹H NMR (400 MHz, DMSO-d₆) δ 9.69 (d, J=8.7 Hz, 1H), 8.59 (d, J=7.8 Hz, 1H), 8.50 (d, J=2.1 Hz, 1H), 8.19 (s, 1H), 7.96 (d, J=2.1 Hz, 1H), 5.50-5.38 (m, 1H), 4.28 (t, J=8.4 Hz, 1H), 2.75-2.56 (m, 2H), 2.49 (s, 3H), 2.45-2.19 (m, 7H), 1.28-1.13 (m, 7H), 0.65-0.43 (m, 3H), 0.43-0.28 (m, 1H). MS (ESI) m/z: [M+H]⁺ Found 584.2.

Example 545

N—((S)-1-(7-((R)-Cyclopropyl(2-(3,3-difluorocyclobutyl)acetamido)methyl)imidazo[1,2-b]pyridazin-2-yl)-4,4,4-trifluoro-3,3-dimethylbutyl)-1-(ethyl-d₅)-1H-pyrazole-5-carboxamide

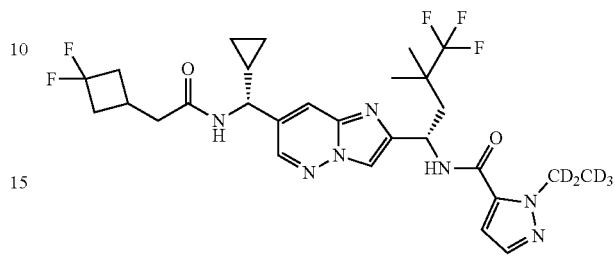

The title compound was prepared as described for the synthesis of Example 173, using N—((R)-(2-((S)-1-amino-4,4,4-trifluoro-3,3-dimethylbutyl)imidazo[1,2-b]pyridazin-7-yl)(cyclopropyl)methyl)-2-(3,3-difluorocyclobutyl)acetamide (Intermediate 501) in place of N—((R)-(2-((S)-amino(4,4-difluorocyclohexyl)methyl)imidazo[1,2-b]pyridazin-7-yl)(cyclopropyl)methyl)-4,4,4-trifluoro-3-methylbutanamide, and 1-(ethyl-d₅)-1H-pyrazole-5-carboxylic acid (Intermediate 204) in place of 1-isopropyl-1H-pyrazole-5-carboxylic and the resulting material purified by preparative basic HPLC (X-Bridge Prep 5 μm C18, 50×100 mm column, 0-100% acetonitrile/water (with 20 mM NH₄OH) to provide the title compound. ¹H NMR (500 MHz, DMSO-d₆) δ 8.93 (d, J=8.8 Hz, 1H), 8.60 (d, J=7.8 Hz, 1H), 8.49 (d, J=2.1 Hz, 1H), 8.10 (s, 1H), 7.95 (d, J=2.2 Hz, 1H), 7.49 (d, J=1.9 Hz, 1H), 7.02-6.88 (m, 1H), 5.50-5.40 (m, 1H), 4.32-4.23 (m, 1H), 2.70-2.57 (m, 2H), 2.45-2.17 (m, 7H), 1.26-1.11 (m, 7H), 0.61-0.43 (m, 3H), 0.42-0.29 (m, 1H). MS (ESI) m/z: [M+H]⁺ Found 601.3.

Example 546

N—((S)-(4,4-Difluorocyclohexyl)(7-((R*)-2-methyl-1-(4,4,4-trifluorobutanamido)propyl)imidazo[1,2-b]pyridazin-2-yl)methyl)-4-methyl-1,2,5-oxadiazole-3-carboxamide

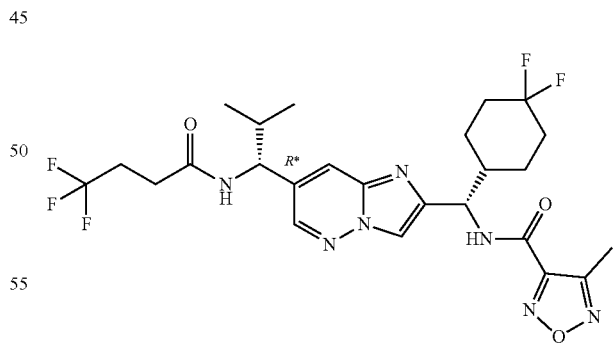

The title compound was prepared as described for the synthesis of Example 142 using N—((R*)-1-(2-((S)-amino(4,4-difluorocyclohexyl)methyl)imidazo[1,2-b]pyridazin-7-yl)-2-methylpropyl)-4,4,4-trifluorobutanamide (Intermediate 514) in place of N—((R)-(2-((S)-amino(4,4-difluorocyclohexyl)methyl)imidazo[1,2-b]pyridazin-7-yl)(cyclopropyl)methyl)-2-(3,3-difluorocyclobutyl)acetamide to afford the title compound as a white powder. ¹H NMR (500 MHz, DMSO-d₆) δ 9.41 (d, J=9.0 Hz, 1H), 8.49 (d, J=8.4 Hz, 1H), 8.47 (d, J=2.1 Hz, 1H), 8.23 (s, 1H), 7.90 (d, J=2.0 Hz, 1H), 5.19-5.14 (m, 1H), 4.71-4.67 (m, 1H), 2.47 (m, 7H), 2.18 (m, 1H), 2.10-1.86 (m, 4H), 1.78 (m, 2H), 1.61 (m, 1H), 1.39 (m, 1H), 1.33-1.21 (m, 1H), 0.93 (d, J=6.7 Hz, 3H), 0.82 (d, J=6.7 Hz, 3H). MS (ESI) m/z: [M+H]$^+$ Found 572.2.

In Vitro Biological Data

IL-17A(FLAG-Tagged): IL-17RA(His-Tagged) Binding Disruption Eu-HTRF Assay

An antibody directed against the FLAG tag of IL-17A (SEQ ID NO:1) is labeled with the HTRF donor chromophore (Europium-cryptate). IL-17A is present as a dimer that is "locked into" this quaternary structure due to the formation of loop-spanning intramolecular disulfide bridges. The construct of IL-17RA used in the assay excludes the outer-membrane portion of the receptor and is fused to a C-terminal 10×His tag (SEQ ID NO:2). An antibody directed against the His tag of the IL-17RA chimera is labeled with the HTRF acceptor chromophore ("D2"). The fluorescence-resonance energy transfer (FRET) depends on the vicinity of the donor chromophore to the acceptor, and interruption of the binding between the IL-17A and IL-17RA causes the reduction/loss of FRET. Therefore, this assay allows to evaluate the compound effect on the binding IL-17A and IL-17RA by monitoring the fluorescence intensity of donor vs acceptor. The assay is run as described below.

40 nl of 2-fold serial diluted compound solution for total 22 dilution points is added into each well of a 1536-well, white, low-volume, non-binding plate (Greiner #782904), then 2 μl of FLAG tagged IL-17A at 2× final concentration (2.5 nM) in solution of PBS+0.01% Triton-X100 is added to each well. The assay plate is briefly centrifuged then incubated for 1 h at rt. A mixed solution is prepared containing 2×5 nM 10HIS×IL-17RA, 2×2.5 nM Eu-anti-FLAG (CISBIO), 2×5 nM D2-anti-HIS (CISBIO) in PBS+0.01% Triton-X100+200 mM Potassium Fluoride (Sigma 60238) and 2 μl of mix is added to each well of the assay plate. The plate is briefly centrifuged then incubated for 2 h at rt. The HTRF intensities at the wavelength of donor (620 nm) and acceptor (665 nm) are measured using BMG Pherastar. The ratio between intensities at two wavelengths is calculated and plotted against the compound concentration and the data is fitted to a one-site competition model to yield IC$_{50}$ of the compound.

IL-17A acts directly on keratinocytes through binding to dimeric receptor IL-17RA/RC and drives the production of a number of inflammatory mediators known to be elevated in psoriasis lesional tissue. IL-17A small molecule inhibitors that block the IL-17A to interact with IL-17R would inhibit the IL-17A signaling in its targeted cells such as keratinocytes. The compound functional activity is evaluated for its impact on IL-17A-induced G-CSF production in human normal keratinocyte (NHK).

NHK Assay

Adult normal human keratinocytes are cultured in keratinocyte growth medium (Lonza) in a flask till reaching ~90% confluence, then cells are transferred to a 384-well plate at density of 3000-4000 cell/well. Recombinant human IL-17A (Gibco PHC9174) is pre-incubated with titrated compound or DMSO for 1 h at rt then added to the cell culture plate. The final concentration of IL-17A is 5 ng/mL and DMSO is 0.2%, in the culture containing 5% FBS. Cells are cultured/treated for 24 h at 37° C. Supernatants are collected and G-CSF production is measured through HTRF technology using Human G-CSF Kit (CisBio). G-CSF concentration was extrapolated from the standard curve and IC$_{50}$ is determined using GraphPad Prism. Cell viability is also evaluated using CellTiter-Glo kit (Promega) and effect of compound on cell viability is compared to DMSO control.

In cases where the compound was tested more than once, the IC$_{50}$ value shown is a simple average of the measured values.

TABLE 3

| Example | HTRF IC$_{50}$ (μM) | NHK IC$_{50}$ (μM) |
|---|---|---|
| 1 | 0.18 | 0.30 |
| 2 | 7.6 | >20 |
| 3 | 0.097 | 0.30 |
| 4 | 0.10 | 0.37 |
| 5 | 1.1 | 1.9 |
| 6 | 0.29 | 0.57 |
| 7 | 4.9 | >20 |
| 8 | 0.22 | 0.36 |
| 9 | 8.3 | >20 |
| 10 | 0.21 | 0.044 |
| 11 | 0.69 | 1.4 |
| 12 | 0.085 | 0.18 |
| 13 | 7.6 | 20 |
| 14 | 0.12 | 0.050 |
| 15 | 1.9 | 4.8 |
| 16 | 0.13 | 0.13 |
| 17 | 1.3 | 1.2 |
| 18 | 0.19 | 0.42 |
| 19 | 3.9 | 3.8 |
| 20 | 0.16 | 0.65 |
| 21 | 0.23 | 0.72 |
| 22 | 0.14 | 0.32 |
| 23 | 0.054 | 0.082 |
| 24 | 0.063 | 0.084 |
| 25 | 0.071 | 0.35 |
| 26 | 0.068 | 0.23 |
| 27 | 0.10 | 0.65 |
| 28 | 0.090 | 0.39 |
| 29 | 0.046 | 0.37 |
| 30 | 0.34 | 1.0 |
| 31 | 0.36 | 1.3 |
| 32 | 0.14 | 0.24 |
| 33 | 4.5 | >20 |
| 34 | 0.18 | 0.064 |
| 35 | 0.12 | 0.20 |
| 36 | 0.14 | 0.12 |
| 37 | 0.23 | 0.63 |
| 38 | 0.078 | 0.40 |
| 39 | 0.11 | 0.43 |
| 40 | 0.41 | 1.2 |
| 41 | 0.35 | 2.0 |
| 42 | 0.41 | 2.2 |
| 43 | 0.24 | 0.72 |
| 44 | 0.74 | 1.4 |
| 45 | 0.24 | 0.71 |
| 46 | 0.13 | 0.64 |
| 47 | 0.18 | 0.64 |
| 48 | 0.063 | 0.16 |
| 49 | 0.095 | 0.11 |
| 50 | 0.35 | 1.0 |
| 51 | 12 | ~18 |
| 52 | 0.28 | 0.67 |
| 53 | 11 | >20 |
| 54 | 0.32 | 0.71 |
| 55 | 0.10 | 0.21 |
| 56 | 0.17 | 0.73 |
| 57 | 0.22 | 0.77 |
| 58 | 0.081 | 0.27 |
| 59 | 0.42 | 3.6 |
| 60 | 0.39 | 3.5 |
| 61 | 0.19 | 1.2 |
| 62 | 0.83 | ~4.0 |
| 63 | 0.13 | 0.20 |
| 64 | 0.63 | 2.0 |
| 65 | 0.11 | 0.072 |
| 66 | 0.23 | 3.5 |
| 67 | 0.082 | 0.18 |
| 68 | 0.15 | 0.25 |
| 69 | 0.11 | 0.055 |
| 70 | 0.049 | 0.11 |

TABLE 3-continued

| Example | HTRF IC$_{50}$ (μM) | NHK IC$_{50}$ (μM) |
|---|---|---|
| 71 | 0.10 | 0.18 |
| 72 | 0.078 | 0.086 |
| 73 | 1.9 | ~15 |
| 74 | 0.12 | 0.058 |
| 75 | 0.050 | 0.092 |
| 76 | 0.067 | 0.067 |
| 77 | 0.050 | 0.060 |
| 78 | 0.26 | 0.33 |
| 79 | 0.084 | 0.15 |
| 80 | 17 | >20 |
| 81 | 5.6 | >20 |
| 82 | 3.0 | >20 |
| 83 | 0.033 | 0.060 |
| 84 | 0.080 | 0.16 |
| 85 | 0.25 | 0.34 |
| 86 | 0.21 | 0.35 |
| 87 | 0.033 | 0.095 |
| 88 | 0.056 | 0.11 |
| 89 | 0.043 | 0.065 |
| 90 | 1.5 | ~20 |
| 91 | 0.092 | 0.12 |
| 92 | 0.11 | 0.14 |
| 93 | 0.15 | 0.28 |
| 94 | 0.11 | 0.15 |
| 95 | 0.10 | 0.26 |
| 96 | 0.37 | 2.2 |
| 97 | 5.4 | >20 |
| 98 | 0.77 | 2.3 |
| 99 | 0.057 | 0.060 |
| 100 | 0.16 | 0.085 |
| 101 | 0.039 | 0.16 |
| 102 | 0.12 | 0.27 |
| 103 | 0.11 | 0.37 |
| 104 | 0.090 | 0.55 |
| 105 | 0.11 | 0.55 |
| 106 | 0.13 | 0.83 |
| 107 | 0.15 | 0.97 |
| 108 | 0.91 | >20 |
| 109 | 0.44 | 20 |
| 110 | 0.41 | >20 |
| 111 | 0.052 | 0.41 |
| 112 | 0.12 | 0.16 |
| 113 | 0.43 | 0.40 |
| 114 | 2.1 | 0.37 |
| 115 | 0.19 | 0.14 |
| 116 | 0.10 | 0.21 |
| 117 | 0.049 | 0.12 |
| 118 | 0.25 | 0.37 |
| 119 | 0.096 | 0.036 |
| 120 | 0.048 | 0.15 |
| 121 | 0.088 | 0.11 |
| 122 | 0.11 | 0.22 |
| 123 | 0.055 | 0.13 |
| 124 | 0.11 | 0.69 |
| 125 | 0.037 | 0.078 |
| 126 | 0.046 | 0.084 |
| 127 | 0.040 | 0.10 |
| 128 | 0.032 | 0.096 |
| 129 | 0.051 | 0.25 |
| 130 | 0.27 | 0.39 |
| 131 | 0.087 | 0.10 |
| 132 | 0.22 | 0.26 |
| 133 | 0.15 | 0.36 |
| 134 | 0.18 | 0.11 |
| 135 | 0.11 | 0.23 |
| 136 | 0.40 | 0.79 |
| 137 | 14 | >20 |
| 138 | 0.78 | 1.3 |
| 139 | 0.73 | 0.69 |
| 140 | 0.070 | 0.089 |
| 141 | 0.13 | 0.20 |
| 142 | 0.034 | 0.14 |
| 143 | 0.13 | 0.45 |
| 144 | 1.4 | 7.0 |
| 145 | 0.65 | 0.30 |
| 146 | 0.68 | 0.71 |
| 147 | 1.7 | >20 |
| 148 | 0.94 | 1.7 |
| 149 | 0.24 | 0.51 |
| 150 | 1.3 | >20 |
| 151 | 0.067 | 0.20 |
| 152 | 0.032 | 0.18 |
| 153 | 0.42 | 0.48 |
| 154 | 0.43 | 0.64 |
| 155 | 0.13 | 0.053 |
| 156 | 0.013 | 0.060 |
| 157 | 0.036 | 0.15 |
| 158 | 0.048 | 0.21 |
| 159 | 0.10 | 0.26 |
| 160 | 0.073 | 0.27 |
| 161 | 0.061 | 0.31 |
| 162 | 0.15 | 0.94 |
| 163 | 0.12 | 0.10 |
| 164 | 0.055 | 0.13 |
| 165 | 0.052 | 0.13 |
| 166 | 0.057 | 0.13 |
| 167 | 0.037 | 0.16 |
| 168 | 0.038 | 0.19 |
| 169 | 0.037 | 0.20 |
| 170 | 0.041 | 0.22 |
| 171 | 0.048 | 0.32 |
| 172 | 0.044 | 0.32 |
| 173 | 0.060 | 0.34 |
| 174 | 0.080 | 0.39 |
| 175 | 0.080 | 0.40 |
| 176 | 0.11 | 0.42 |
| 177 | 0.053 | 0.44 |
| 178 | 0.067 | 0.45 |
| 179 | 0.045 | 0.45 |
| 180 | 0.13 | 0.45 |
| 181 | 0.080 | 0.46 |
| 182 | 0.085 | 0.51 |
| 183 | 0.069 | 0.52 |
| 184 | 0.11 | 0.59 |
| 185 | 0.045 | 0.69 |
| 186 | 0.11 | 0.72 |
| 187 | 0.26 | 0.73 |
| 188 | 0.15 | 0.75 |
| 189 | 0.23 | 0.81 |
| 190 | 0.22 | 0.82 |
| 191 | 0.29 | 1.1 |
| 192 | 0.24 | 1.2 |
| 193 | 0.50 | 1.3 |
| 194 | 0.14 | 1.6 |
| 195 | 0.58 | 1.6 |
| 196 | 0.48 | 1.7 |
| 197 | 0.30 | 1.7 |
| 198 | 0.41 | 1.8 |
| 199 | 0.23 | 2.0 |
| 200 | 0.76 | 2.2 |
| 201 | 0.47 | 2.2 |
| 202 | 0.44 | 2.3 |
| 203 | 0.19 | 2.7 |
| 204 | 0.32 | 3.3 |
| 205 | 0.39 | 3.7 |
| 206 | 0.54 | 4.0 |
| 207 | 1.8 | 8.4 |
| 208 | 5.3 | >20 |
| 209 | 1.4 | >20 |
| 210 | 0.62 | >20 |
| 211 | 4.3 | >20 |
| 212 | 13 | >20 |
| 213 | 0.45 | 20 |
| 214 | 2.9 | >20 |
| 215 | 2.0 | >20 |
| 216 | 1.6 | >20 |
| 217 | 4.6 | >20 |
| 218 | 2.0 | >20 |
| 219 | 2.1 | >20 |
| 220 | 15 | >20 |
| 221 | 16 | >20 |
| 222 | 1.0 | >20 |
| 223 | 2.9 | >20 |
| 224 | 1.7 | >20 |
| 225 | 9.5 | >20 |
| 226 | 2.5 | >20 |

TABLE 3-continued

| Example | HTRF IC$_{50}$ (μM) | NHK IC$_{50}$ (μM) |
|---|---|---|
| 227 | 0.90 | 20 |
| 228 | 1.0 | >20 |
| 229 | 1.2 | >20 |
| 230 | 2.0 | >20 |
| 231 | 0.32 | >20 |
| 232 | 0.043 | 0.065 |
| 233 | 0.047 | 0.051 |
| 234 | 0.085 | 0.052 |
| 235 | 0.10 | 0.22 |
| 236 | 0.046 | 0.36 |
| 237 | 0.052 | 0.088 |
| 238 | 0.19 | 0.83 |
| 239 | 0.43 | 1.3 |
| 240 | 0.13 | 0.21 |
| 241 | 3.4 | >20 |
| 242 | 1.3 | 0.79 |
| 243 | 0.089 | 0.27 |
| 244 | 0.14 | 0.12 |
| 245 | 0.14 | 0.29 |
| 246 | 0.090 | 0.041 |
| 247 | 0.062 | 0.19 |
| 248 | 0.049 | 0.037 |
| 249 | 0.024 | 0.098 |
| 250 | 0.098 | 0.39 |
| 251 | 0.20 | 0.77 |
| 252 | 0.64 | 7.7 |
| 253 | 0.22 | 0.76 |
| 254 | 0.29 | 0.20 |
| 255 | 0.17 | 0.60 |
| 256 | 0.056 | 0.25 |
| 257 | 0.11 | 0.12 |
| 258 | 0.13 | 0.046 |
| 259 | 0.12 | 0.62 |
| 260 | 0.12 | 0.18 |
| 261 | 0.13 | 0.43 |
| 262 | 0.12 | 0.12 |
| 263 | 0.21 | 1.8 |
| 264 | 0.048 | 0.35 |
| 265 | 0.21 | 1.1 |
| 266 | 0.056 | 0.29 |
| 267 | 0.087 | 0.35 |
| 268 | 0.75 | 3.0 |
| 269 | 2.0 | 20 |
| 270 | 0.15 | 0.038 |
| 271 | 0.14 | 0.067 |
| 272 | 0.086 | 0.29 |
| 273 | 0.16 | 0.071 |
| 274 | 0.33 | 0.95 |
| 275 | 0.17 | 0.15 |
| 276 | 0.15 | 0.14 |
| 277 | 0.18 | 0.69 |
| 278 | 1.1 | 2.5 |
| 279 | 0.036 | 0.064 |
| 280 | 0.054 | 0.12 |
| 281 | 0.024 | 0.026 |
| 282 | 0.16 | 0.42 |
| 283 | 0.31 | 0.69 |
| 284 | 0.22 | 0.92 |
| 285 | 0.12 | 0.34 |
| 286 | 0.31 | 7.5 |
| 287 | 0.14 | 0.41 |
| 288 | 0.071 | 0.20 |
| 289 | 0.037 | 0.023 |
| 290 | 0.083 | 0.22 |
| 291 | 0.37 | 4.0 |
| 292 | 0.22 | 0.87 |
| 293 | 0.16 | 0.54 |
| 294 | 0.086 | 0.038 |
| 295 | 0.15 | 0.71 |
| 296 | 0.022 | 0.050 |
| 297 | 0.031 | 0.087 |
| 298 | 0.25 | 0.61 |
| 299 | 0.30 | 0.84 |
| 300 | 0.11 | 0.32 |
| 301 | 0.053 | 0.056 |
| 302 | 1.2 | >20 |
| 303 | 0.25 | 0.28 |
| 304 | 0.62 | 0.91 |
| 305 | 0.14 | 1.1 |
| 306 | 0.21 | 1.5 |
| 307 | 0.11 | 0.42 |
| 308 | 0.20 | 1.7 |
| 309 | 0.10 | 0.29 |
| 310 | 0.17 | 0.22 |
| 311 | 0.21 | 0.33 |
| 312 | 0.37 | 3.2 |
| 313 | 0.16 | 0.48 |
| 314 | 0.56 | 2.1 |
| 315 | 13 | >20 |
| 316 | 0.24 | 0.70 |
| 317 | 9.9 | >20 |
| 318 | 0.27 | 0.48 |
| 319 | 0.066 | 0.33 |
| 320 | 0.074 | 0.062 |
| 321 | 0.017 | 0.032 |
| 322 | 0.31 | 0.096 |
| 323 | 0.12 | 0.67 |
| 324 | 0.061 | 0.30 |
| 325 | 0.091 | 0.30 |
| 326 | 0.12 | 1.1 |
| 327 | 0.20 | 0.89 |
| 328 | 2.4 | >20 |
| 329 | 0.93 | 2.2 |
| 330 | 0.56 | 2.2 |
| 331 | 0.31 | 1.5 |
| 332 | 1.5 | 12 |
| 333 | 0.18 | 0.62 |
| 334 | 4.4 | >20 |
| 335 | 7.5 | >20 |
| 336 | 5.0 | >20 |
| 337 | 3.5 | >20 |
| 338 | 0.36 | 2.0 |
| 339 | 0.077 | 0.19 |
| 340 | 8.6 | >20 |
| 341 | 4.8 | >20 |
| 342 | 0.34 | 1.4 |
| 343 | 0.17 | 0.43 |
| 344 | 0.052 | 0.23 |
| 345 | 0.18 | 0.67 |
| 346 | 0.15 | 0.44 |
| 347 | 0.47 | 1.6 |
| 348 | 0.069 | 0.22 |
| 349 | 0.42 | 1.7 |
| 350 | 0.27 | 0.66 |
| 351 | 2.6 | — |
| 352 | 0.12 | 0.19 |
| 353 | 0.63 | 0.97 |
| 354 | 0.73 | 2.7 |
| 355 | 19 | — |
| 356 | 0.52 | 7.8 |
| 357 | 0.95 | 2.5 |
| 358 | 0.45 | 2.1 |
| 359 | 1.1 | 10 |
| 360 | 2.7 | >20 |
| 361 | 0.21 | 1.7 |
| 362 | 4.2 | >20 |
| 363 | 0.64 | 1.1 |
| 364 | 2.1 | >20 |
| 365 | 1.2 | >20 |
| 366 | 2.4 | >20 |
| 367 | 0.24 | 0.63 |
| 368 | 1.6 | 9.8 |
| 369 | 0.14 | 0.53 |
| 370 | 0.14 | 0.47 |
| 371 | 0.14 | 0.45 |
| 372 | 0.12 | 0.74 |
| 373 | 0.062 | 0.24 |
| 374 | 0.046 | 0.24 |
| 375 | 0.043 | 0.17 |
| 376 | 0.079 | 0.28 |
| 377 | 0.060 | 0.085 |
| 378 | 0.055 | 0.095 |
| 379 | 0.017 | 0.030 |
| 380 | 0.048 | 0.030 |
| 381 | 0.027 | 0.031 |
| 382 | 0.051 | 0.011 |

TABLE 3-continued

| Example | HTRF IC$_{50}$ (μM) | NHK IC$_{50}$ (μM) |
|---|---|---|
| 383 | 0.051 | 0.019 |
| 384 | 0.066 | 0.031 |
| 385 | 0.035 | 0.032 |
| 386 | 0.069 | 0.23 |
| 387 | — | 0.072 |
| 388 | 0.085 | 0.10 |
| 389 | 0.056 | 0.029 |
| 390 | 0.086 | 0.13 |
| 391 | 0.043 | 0.047 |
| 392 | — | 0.037 |
| 393 | 0.094 | 0.12 |
| 394 | 0.20 | 0.24 |
| 395 | 0.048 | 0.17 |
| 396 | 0.050 | 0.19 |
| 397 | 0.12 | 0.60 |
| 398 | 0.042 | 0.071 |
| 399 | 0.31 | 0.094 |
| 400 | 0.049 | 0.035 |
| 401 | 0.15 | 0.057 |
| 402 | 0.11 | 0.11 |
| 403 | 0.063 | 0.17 |
| 404 | 0.18 | 0.058 |
| 405 | 0.10 | 0.35 |
| 406 | 0.077 | 0.29 |
| 407 | 0.24 | 0.097 |
| 408 | 0.054 | 0.37 |
| 409 | 0.085 | 0.14 |
| 410 | 0.12 | 0.23 |
| 411 | 0.078 | 0.049 |
| 412 | >50 | >20 |
| 413 | 0.061 | 0.17 |
| 414 | 0.057 | 0.73 |
| 415 | 0.073 | 0.50 |
| 416 | 0.062 | 0.55 |
| 417 | 0.068 | 0.41 |
| 418 | 4.6 | >20 |
| 419 | 1.3 | >20 |
| 420 | — | 4.1 |
| 421 | 0.098 | 0.043 |
| 422 | 0.26 | 0.082 |
| 423 | 0.078 | 0.13 |
| 424 | 0.047 | 0.040 |
| 425 | 0.099 | 0.020 |
| 426 | 0.34 | 0.10 |
| 427 | 0.10 | 0.37 |
| 428 | 0.37 | 0.12 |
| 429 | 2.0 | >20 |
| 430 | 1.6 | 12 |
| 431 | 3.8 | >20 |
| 432 | 3.7 | >20 |
| 433 | 1.3 | >20 |
| 434 | 3.3 | >20 |
| 435 | 3.8 | >20 |
| 436 | 1.3 | >20 |
| 437 | 3.8 | >20 |
| 438 | 0.47 | 8.0 |
| 439 | 0.099 | 0.15 |
| 440 | 0.092 | 0.059 |
| 441 | — | 1.1 |
| 442 | — | 0.60 |
| 443 | — | 0.52 |
| 444 | 2.3 | 11 |
| 445 | 5.8 | >20 |
| 446 | 0.71 | 8.8 |
| 447 | 0.30 | 1.1 |
| 448 | 0.035 | 0.012 |
| 449 | 0.028 | 0.0047 |
| 450 | 0.81 | 1.7 |
| 451 | 0.12 | 0.83 |
| 452 | 0.10 | 0.57 |
| 453 | 0.15 | 3.9 |
| 454 | 0.32 | 3.4 |
| 455 | 0.13 | 0.85 |
| 456 | 0.78 | >20 |
| 457 | 1.2 | 2.9 |
| 458 | 7.8 | >20 |
| 459 | 1.3 | >20 |
| 460 | 0.11 | 1.1 |
| 461 | 1.6 | >20 |
| 462 | 0.14 | 1.1 |
| 463 | 0.094 | 0.38 |
| 464 | — | 0.63 |
| 465 | 0.92 | 1.6 |
| 466 | 0.034 | 0.21 |
| 467 | 0.058 | 0.36 |
| 468 | 0.75 | 1.7 |
| 469 | 1.2 | >20 |
| 470 | 0.054 | 0.11 |
| 471 | 0.38 | 2.3 |
| 472 | 45 | >20 |
| 473 | 8.5 | >20 |
| 474 | 0.041 | 0.13 |
| 475 | 0.13 | 0.33 |
| 476 | 0.13 | 0.39 |
| 477 | 0.29 | 1.4 |
| 478 | 0.45 | 0.85 |
| 479 | 0.19 | 0.43 |
| 480 | 0.14 | 0.47 |
| 481 | — | 0.47 |
| 482 | — | 0.076 |
| 483 | 0.075 | 0.38 |
| 484 | 0.55 | 4.6 |
| 485 | 0.92 | 0.31 |
| 486 | 0.30 | 1.1 |
| 487 | 0.045 | 0.0060 |
| 488 | 0.095 | 0.22 |
| 489 | 0.054 | 0.14 |
| 490 | 0.15 | 0.067 |
| 491 | 0.039 | 0.085 |
| 492 | 0.065 | 0.095 |
| 493 | 0.079 | 0.12 |
| 494 | 1.0 | >20 |
| 495 | 0.040 | 0.30 |
| 496 | 0.69 | 10 |
| 497 | 0.091 | 0.15 |
| 498 | 0.38 | 20 |
| 499 | 0.18 | 0.16 |
| 500 | 0.15 | 0.14 |
| 501 | 0.12 | 0.095 |
| 502 | 0.16 | 0.40 |
| 503 | 0.10 | 0.13 |
| 504 | 0.046 | 0.093 |
| 505 | 5.4 | >20 |
| 506 | 0.20 | 0.13 |
| 507 | 0.056 | 0.042 |
| 508 | 1.2 | 10 |
| 509 | 1.9 | >20 |
| 510 | 0.083 | 0.44 |
| 511 | 0.046 | 0.021 |
| 512 | 0.030 | 0.035 |
| 513 | 0.074 | 0.15 |
| 514 | 0.087 | 0.042 |
| 515 | — | 0.14 |
| 516 | 1.9 | >20 |
| 517 | 0.046 | 0.045 |
| 518 | — | 2.9 |
| 519 | 0.19 | 0.053 |
| 520 | 0.66 | 5.0 |
| 521 | 0.39 | 8.0 |
| 522 | 2.2 | 3.6 |
| 523 | 0.27 | 0.11 |
| 524 | 0.38 | 3.7 |
| 525 | 0.059 | 0.042 |
| 526 | 0.32 | 1.2 |
| 527 | 0.057 | 0.11 |
| 528 | 0.90 | 2.4 |
| 529 | 0.34 | 0.12 |
| 530 | 0.98 | 4.6 |
| 531 | 0.22 | 0.11 |
| 532 | 1.5 | 2.8 |
| 533 | 0.48 | 0.15 |
| 534 | 0.096 | 0.070 |
| 535 | 0.44 | 0.089 |
| 536 | 0.049 | 0.012 |
| 537 | 0.15 | 0.15 |
| 538 | 0.024 | 0.080 |

TABLE 3-continued

| Example | HTRF IC$_{50}$ (μM) | NHK IC$_{50}$ (μM) |
|---|---|---|
| 539 | 0.13 | 0.078 |
| 540 | 0.014 | 0.0096 |
| 541 | 0.13 | 0.029 |
| 542 | 0.052 | 0.046 |
| 543 | 0.18 | 0.072 |

SEQUENCE LISTING

```
Sequence total quantity: 2
SEQ ID NO: 1            moltype = AA  length = 182
FEATURE                 Location/Qualifiers
REGION                  1..182
                        note = Human IL17A with a FLAg tag
source                  1..182
                        mol_type = protein
                        organism = synthetic construct
SEQUENCE: 1
MATGSRTSLL LAFGLLCLPW LQEGSAGSDY KDDDDKGSGS GSLEVLFQGP GITIPRNPGC   60
PNSEDKNFPR TVMVNLNIHN RNTNTNPKRS SDYYNRSTSP WNLHRNEDPE RYPSVIWEAQ  120
CRHLGCINAD GNVDYHMNSV PIQQEILVLR REPPHCPNSF RLEKILVSVG CTCVTPIVHH  180
VQ                                                                182

SEQ ID NO: 2            moltype = AA  length = 323
FEATURE                 Location/Qualifiers
REGION                  1..323
                        note = IL17A with a His tag
source                  1..323
                        mol_type = protein
                        organism = synthetic construct
SEQUENCE: 2
MKFLVNVALV FMVVYISYIY ALRLLDHRAL VCSQPGLNCT VKNSTCLDDS WIHPRNLTPS   60
SPKDLQIQLH FAHTQQGDLF PVAHIEWTLQ TDASILYLEG AELSVLQLNT NERLCVRFEF  120
LSKLRHHHRR WRFTFSHFVV DPDQEYEVTV HHLPKPIPDG DPNHQSKNFL VPDCEHARMK  180
VTTPCMSSGS LWDPNITVET LEAHQLRVSF TLWNESTHYQ ILLTSFPPHME NHSCFEHMHH  240
IPAPRPEEFH QRSNVTLTLR NLKGCCRHQV QIQPFFSSCL NDCLRHSATV SCPEMPDTPE  300
PIPDYMPLWG SGGHHHHHHH HHH                                         323
```

HHLPKPIPDGDPNHQSKNELVPDCEHARMKVTTPCMSSGSLWDPNITVET

LEAHQLRVSFTLWNESTHYQILLTSFPHMENHSCFEHMHHIPAPRPEEFH

QRSNVTLTLRNLKGCCRHQVQIQPFFSSCLNDCLRHSATVSCPEMPDTPE

PIPDYMPLWGSGGHHHHHHHHHH*

TABLE 3-continued

| Example | HTRF IC$_{50}$ (μM) | NHK IC$_{50}$ (μM) |
|---|---|---|
| 544 | 0.12 | 0.24 |
| 545 | 0.17 | 0.15 |
| 546 | 0.64 | >20 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

Name: IL-17A-Flag
SEQ ID NO: 1
MATGSRTSLLLAFGLLCLPWLQEGSAGSDYKDDDDKGSGSGSLEVLFQGP

GITIPRNPGCPNSEDKNFPRTVMVNLNIHNRNTNTNPKRSSDYYNRSTSP

WNLHRNEDPERYPSVIWEAQCRHLGCINADGNVDYHMNSVPIQQEILVLR

REPPHCPNSFRLEKILVSVGCTCVTPIVHHVQ        60

Name: IL-17RA
SEQ ID NO: 2
MKFLVNVALVFMVVYISYIYALRLLDHRALVCSQPGLNCTVKNSTCLDDS

WIHPRNLTPSSPKDLQIQLHFAHTQQGDLEPVAHIEWTLQTDASILYLEG

AELSVLQLNTNERLCVRFEFLSKLRHHHRRWRFTESHFVVDPDQEYEVTV

We claim:
1. A compound of Formula I':

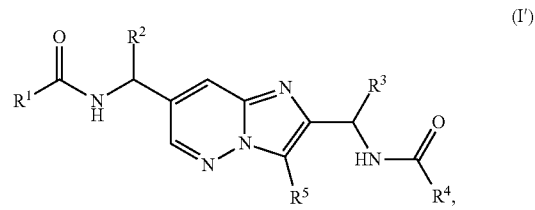

or a pharmaceutically acceptable salt thereof, wherein:
R$^1$ is —C$_{(1-6)}$alkyl, —C$_{(0-2)}$alkylC$_{(3-6)}$cycloalkyl, -C$_{(0-2)}$alkyl-cyclopropyl-C$_{(1-3)}$perfluoroalkyl, or a 5- to 6-membered heterocyclyl having 1 to 2 nitrogen atoms;
  wherein the —C$_{(1-6)}$alkyl is unsubstituted or substituted with one to six R$^{1a}$ groups;
  wherein the —C$_{(0-2)}$alkylC$_{(3-8)}$cycloalkyl is unsubstituted or substituted with one to six R$^{1b}$ groups; and
  wherein the 5- to 6-membered heterocyclyl is unsubstituted or substituted with one to three R$^{1c}$ groups;
R$^2$ is H, -C$_{(3-5)}$cycloalkyl, -C$_{(1-4)}$alkyl, or a 6-membered heterocycle having 1 to 2 oxygen atoms; wherein the —C$_{(1-4)}$alkyl is unsubstituted or substituted with one to six $R^{2a}$ groups; and wherein the —$C_{(3-5)}$cycloalkyl is unsubstituted or substituted with —CN;

$R^{1a}$, $R^{1b}$ and $R^{2a}$ are each independently fluorine, -$C_{(3-5)}$cycloalkyl, —CN, —OH, -$OC_{(1-3)}$alkyl or -$OC_{(3-4)}$cycloalkyl, wherein the —$OC_{(1-3)}$alkyl and -$OC_{(3-4)}$cycloalkyl groups are unsubstituted or substituted with one to three fluorine atoms;

each $R^{1c}$ is independently —$OCH_3$, —$OCF_3$, —$OCHF_2$, or -$C_{(1-4)}$alkyl that is unsubstituted or substituted with one to six fluorine atoms;

$R^3$ is -$C_{(0-1)}$alkyl$C_{(3-6)}$cycloalkyl, -$C_{(3-6)}$alkyl or -$C_{(1-2)}$alkyl-O—$C_{(1-3)}$alkyl, wherein the —$C_{(0-1)}$alkyl $C_{(3-6)}$cycloalkyl, -$C_{(3-6)}$alkyl and -$C_{(1-2)}$alkyl-O—$C_{(1-3)}$alkyl are unsubstituted or substituted with one to five $R^{3a}$ groups each independently selected from fluorine, —$CH_3$—$CHF_2$, —$CF_3$, OH and =O;

$R^4$ is -$C_{(3-6)}$cycloalkyl, phenyl, or a 5 to 6-membered heteroaryl having 1 to 4 heteroatoms selected from N, O, and S;

wherein the $C_{(3-6)}$ cycloalkyl is unsubstituted or substituted with one to three $R^{4a}$ groups each independently selected from halogen, -$OC_{(1-3)}$alkyl, and -$C_{(1-4)}$alkyl wherein the —$OC_{(1-3)}$alkyl, and -$C_{(1-4)}$alkyl are unsubstituted or substituted with one to three fluorine atoms;

alternatively, two $R^{4a}$ groups attached to the same ring atom can be combined with the atom to which they are attached to form a $C_{(3-6)}$cycloalkyl;

wherein the phenyl is unsubstituted or substituted with one to three $R^{4b}$ groups each independently selected from halogen, —CN, -$C_{(0-2)}$alkyl-$C_{(3-4)}$cycloalkyl, -$OC_{(0-2)}$alkyl-$C_{(3-4)}$cycloalkyl, -$OC_{(1-3)}$alkyl, -$C_{(1-4)}$alkyl and a 3 to 6-membered heterocyclyl having 1 to 2 heteroatoms selected from N and O, wherein the —$OC_{(1-3)}$alkyl, -$C_{(0-2)}$alkyl-$C_{(3-4)}$cycloalkyl and -$C_{(1-4)}$alkyl are unsubstituted or substituted with one to three fluorine atoms, and wherein the heterocyclyl is unsubstituted or substituted with 1 oxo;

wherein the 5- to 6-membered heteroaryl is unsubstituted or substituted with one or two $R^{4c}$ groups;

each $R^{4c}$ is independently halogen, —CN, —OH, -$N(R^{4c1})(R^{4c2})$, -$C_{(0-2)}$alkyl$C_{(3-6)}$cycloalkyl, -$OC_{(0-2)}$alkyl-$C_{(3-4)}$cycloalkyl, -$C_{(1-4)}$alkyl, -$OC_{(1-3)}$alkyl, or a 3 to 6-membered heterocyclyl having 1 to 2 heteroatoms selected from N and O, wherein the —$C_{(0-2)}$alkyl$C_{(3-6)}$cycloalkyl, -$C_{(1-4)}$alkyl, -$OC_{(1-3)}$alkyl and heterocyclyl groups are unsubstituted or substituted with one to six $R^{4d}$ groups;

alternatively, two $R^{4c}$ groups attached to adjacent ring atoms can be combined to form a $C_{(4-6)}$cycloalkyl;

each $R^{4d}$ is independently fluorine, —CN, —OH, oxo, -$C_{(1-3)}$alkyl, -$OC_{(1-3)}$alkyl, -$OC_{(3-4)}$cycloalkyl, —$C_{(0-2)}$alkyl-$N(R^{4d1})(R^{4d2})$, -$C_{(0-2)}$alkyl-$N(C_{(1-4)}$alkyl)$C(O)(C_{(1-4)}$alkyl) or a 3- to 6-membered heterocyclyl having 1 to 2 heteroatoms selected from N and O, wherein the —$C_{(1-3)}$alkyl, -$OC_{(1-3)}$alkyl, -$OC_{(3-4)}$cycloalkyl and heterocyclyl groups are unsubstituted or substituted with one to three fluorine atoms;

$R^{4c1}$, $R^{4c2}$, $R^{4d1}$ and $R^{4d2}$ are each independently H or -$C_{(1-3)}$alkyl, wherein the —$C_{(1-3)}$alkyl is unsubstituted or substituted with one to six groups selected from fluorine and chlorine;

alternatively $R^{4d1}$ and $R^{4d2}$ can be combined with the atom to which they are attached to form a 3- to 6-membered heterocyclyl having 1 to 3 heteroatoms selected from N, O and S, wherein the heterocyclyl is unsubstituted or substituted with 1 to 4 fluorine atoms; and $R^5$ is hydrogen or halogen;

wherein
when $R^4$ is 1,2,4-triazolyl, then $R^4$ is

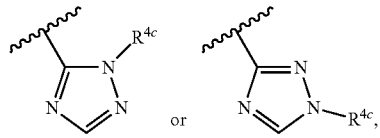

and when $R^4$ is a substituted 6-membered heteroaryl, the substituted heteroaryl is unsubstituted at the para-position.

2. The compound of claim 1, or a pharmaceutically acceptable salt thereof, wherein:

$R^1$ is-$C_{(3-5)}$alkyl,

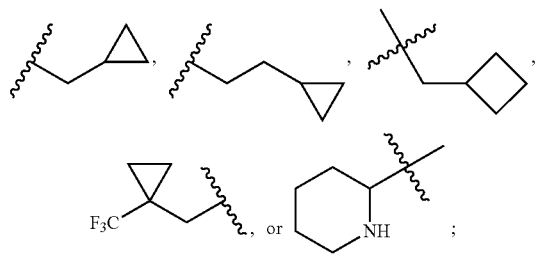

wherein the —$C_{(3-5)}$alkyl is substituted with one to six $R^{1a}$ groups;

wherein the

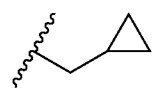 [SMILES: *CC1CC1]

is unsubstituted or substituted with one to two fluorine atoms;

wherein the

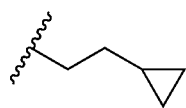

is unsubstituted or substituted with one to four fluorine atoms;

wherein the

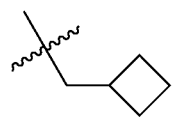 [SMILES: *CC1CCC1]

is substituted with two fluorine atoms; and
wherein the

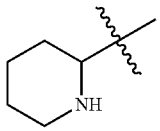 [SMILES: *C1CCCCN1]

is substituted with —CF$_3$;
each R$^{1a}$ is independently —OH or fluorine;
R$^2$ is H, methyl, isopropyl, cyclopropyl, or cyclobutyl; wherein the cyclopropyl and cyclobutyl are unsubstituted or substituted with —CN;
R$^3$ is cyclohexyl or

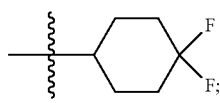

R$^4$ is cyclopropyl, spiropentanyl, spirohexanyl, phenyl, pyrazolyl, oxazolyl, isoxazolyl, 1,2,5-oxadiazolyl, triazolyl, tetrazolyl, imidazolyl, 1,2,3-thiadiazolyl or 1,2,5-thiadiazolyl;
wherein the cyclopropyl is substituted with one to two groups selected from fluorine and C$_{(1)}$alkyl that is unsubstituted or substituted with three fluorine atoms;
wherein the phenyl is unsubstituted or substituted with -chlorine, or -C$_{(1-2)}$alkyl;
wherein the 1,2,3-thiadiazolyl and 1,2,5-thiadiazolyl are substituted with C$_{(2-3)}$alkyl;
wherein the pyrazolyl, oxazolyl, isoxazolyl, 1,2,5-oxadiazolyl, triazolyl, tetrazolyl and imidazolyl are substituted with one or two R$^{4c}$ groups;
each R$^{4c}$ is independently -C$_{(0-1)}$alkylC$_{(3-4)}$cycloalkyl, or -C$_{(1-3)}$alkyl, wherein the —C$_{(0-1)}$alkylC$_{(3-4)}$cycloalkyl and -C$_{(1-3)}$alkyl groups are unsubstituted or substituted with one to four R$^{4d}$ groups;
each R$^{4d}$ is independently —OCH$_3$, —OCF$_3$, —OCHF$_2$, or fluorine; and
R$^5$ is hydrogen;
wherein
when R$^4$ is 1,2,4-triazolyl, then R$^4$ is

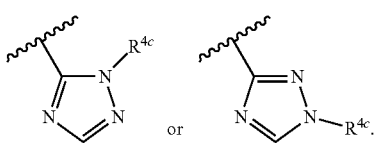

3. The compound of claim 1, or a pharmaceutically acceptable salt thereof, wherein R$^1$ is:

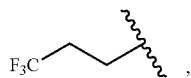, 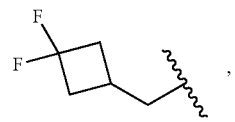,

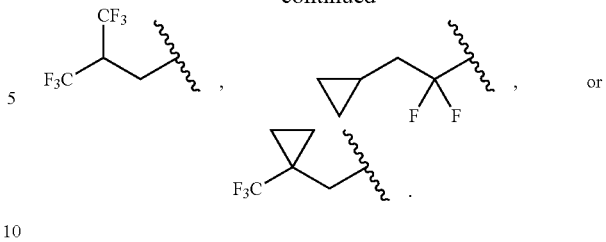

4. The compound of claim 1, or a pharmaceutically acceptable salt thereof, wherein R$^2$ is H, methyl, isopropyl, cyclopropyl, or cyclobutyl; wherein the cyclopropyl and cyclobutyl are unsubstituted or substituted with —CN.

5. The compound of claim 1, or a pharmaceutically acceptable salt thereof, wherein R$^3$ is

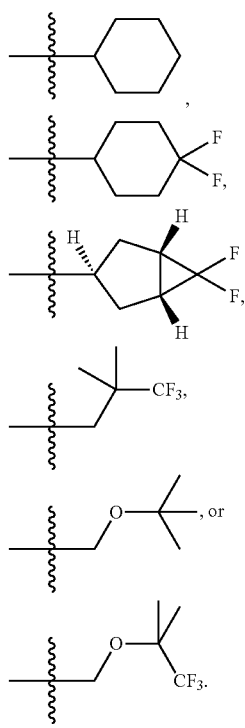

6. The compound of claim 1, or a pharmaceutically acceptable salt thereof, wherein each R$^{4c}$ is independently fluorine, —CN, —NH$_2$, N(CH$_3$)$_2$, methyl, ethyl, isopropyl,-CD$_3$,-CD$_2$CD$_3$, —OCH$_3$, —OCH$_2$CH$_3$,-OCH(CH$_3$)$_2$, —OC(CH$_3$)$_3$, CH(CH$_3$)OH, —CHF$_2$, —CF$_3$, —CH$_2$CH$_2$F, —CH$_2$CHF$_2$, —CH$_2$CF$_3$, —CF$_2$CH$_3$, —CH$_2$CH$_2$CH$_2$F, —CH$_2$CH$_2$CHF$_2$, —CH$_2$CH$_2$CF$_3$, —CH(CH$_3$)CHF$_2$, —CH(CH$_3$)CF$_3$, —CH(CH$_2$F)$_2$, —CH$_2$CF$_2$CH$_3$, —CH$_2$CH$_2$CF$_2$CH$_3$, —CH$_2$OCH$_3$, —CH$_2$CH$_2$OCH$_3$, —CH$_2$CH$_2$OCHF$_2$, —CH$_2$CH$_2$OCF$_3$, —CH$_2$OCHF$_2$, —OCHF$_2$, —OCH$_2$CHF$_2$, —OCH$_2$CH$_2$F, —OCH$_2$CF$_3$, cyclopropyl, cyclobutyl, cyclopentyl, —CH$_2$-cyclopropyl, —O-cyclopropyl, —O-cyclobutyl,

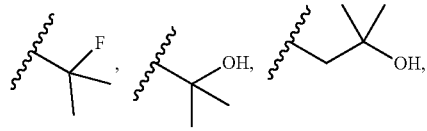

991
-continued

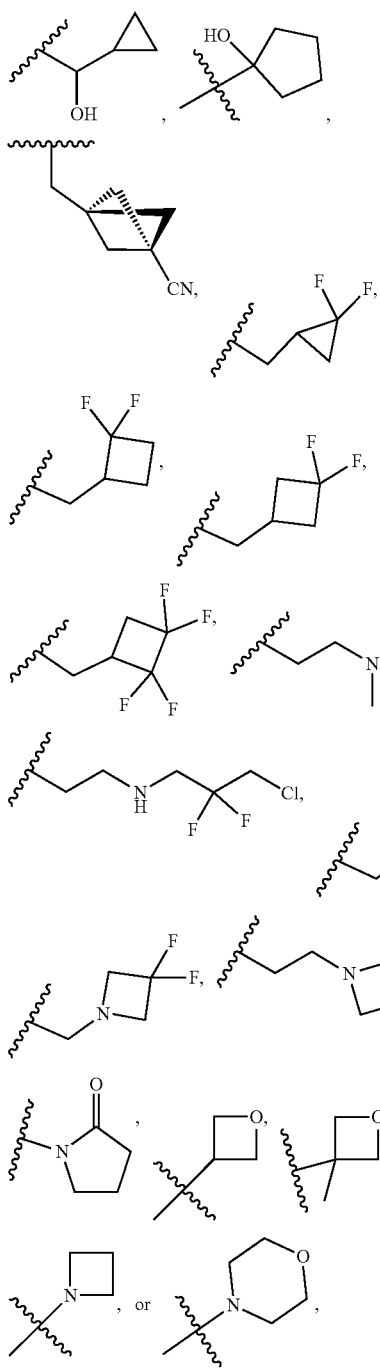

alternatively two $R^{4c}$ groups attached to adjacent ring atoms can be combined to form the group:

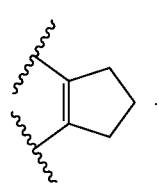 [SMILES: *C1=C(*)CCC1]

992

7. The compound of claim 1, or a pharmaceutically acceptable salt thereof, wherein $R^4$ is pyrrolyl, pyrazolyl, imidazolyl, triazolyl, tetrazolyl, furanyl, oxazolyl, isoxazolyl, oxadiazolyl, thienyl, thiazolyl, isothiazolyl or thiadiazolyl, that is substituted with one or two $R^{4c}$ groups, wherein when $R^4$ is 1,2,4-triazolyl, then $R^4$ is

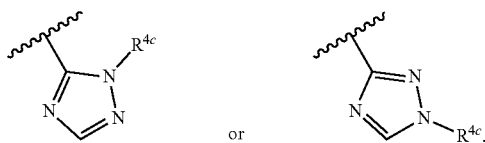

8. The compound of claim 1, or a pharmaceutically acceptable salt thereof, wherein $R^4$ is isoxazolyl substituted with one or two $R^{4c}$ groups each independently methyl, ethyl, isopropyl, —$CF_3$, —$CH_2CH_2F$, —$CH_2CH_2CF_3$, —$CH_2OCH_3$, cyclopropyl, cyclopentyl, or

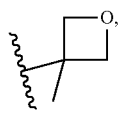

oxazolyl substituted with one isopropyl, or oxadiazolyl substituted with one methyl, ethyl, —$OCH_2CHF_2$, or cyclopropyl.

9. The compound of claim 1, or a pharmaceutically acceptable salt thereof, wherein $R^4$ is:

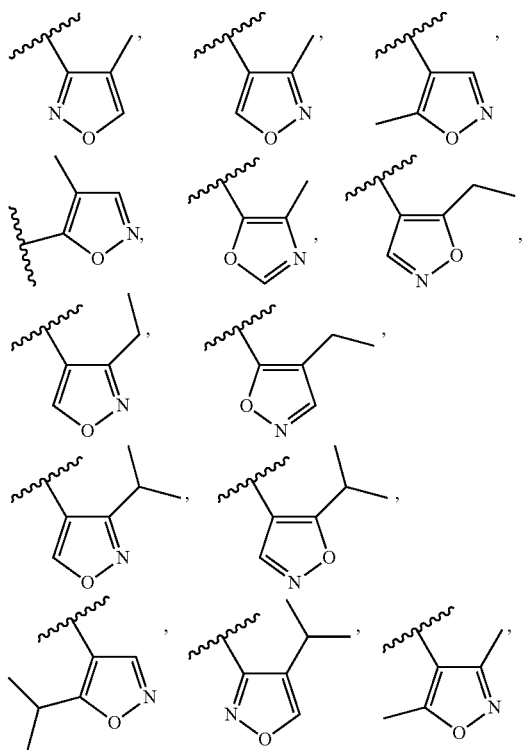

-continued
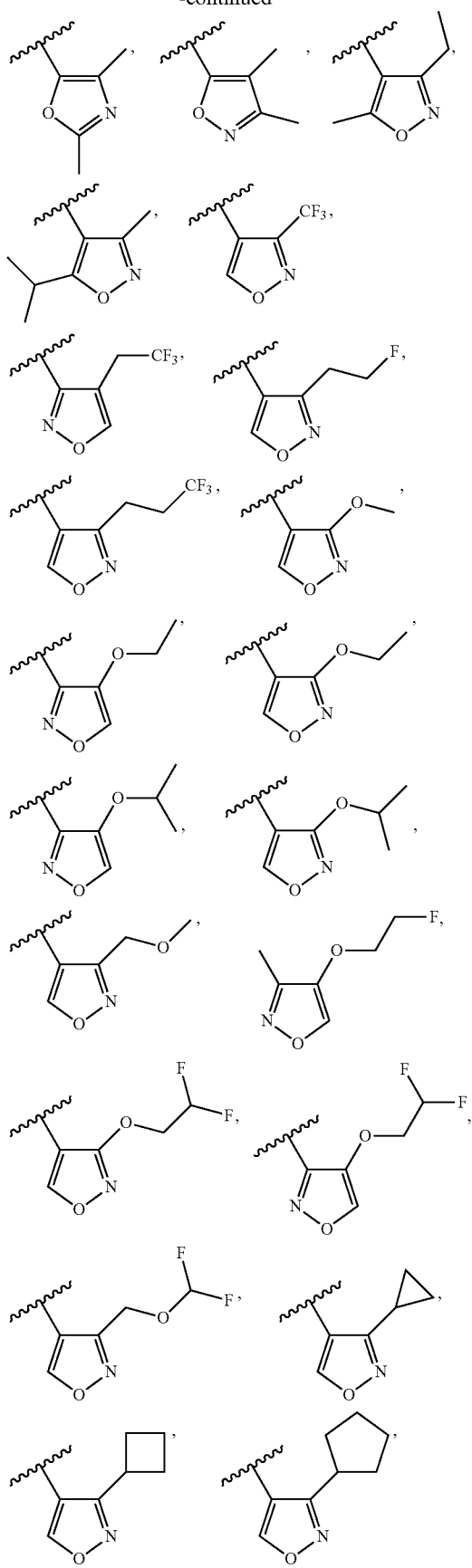
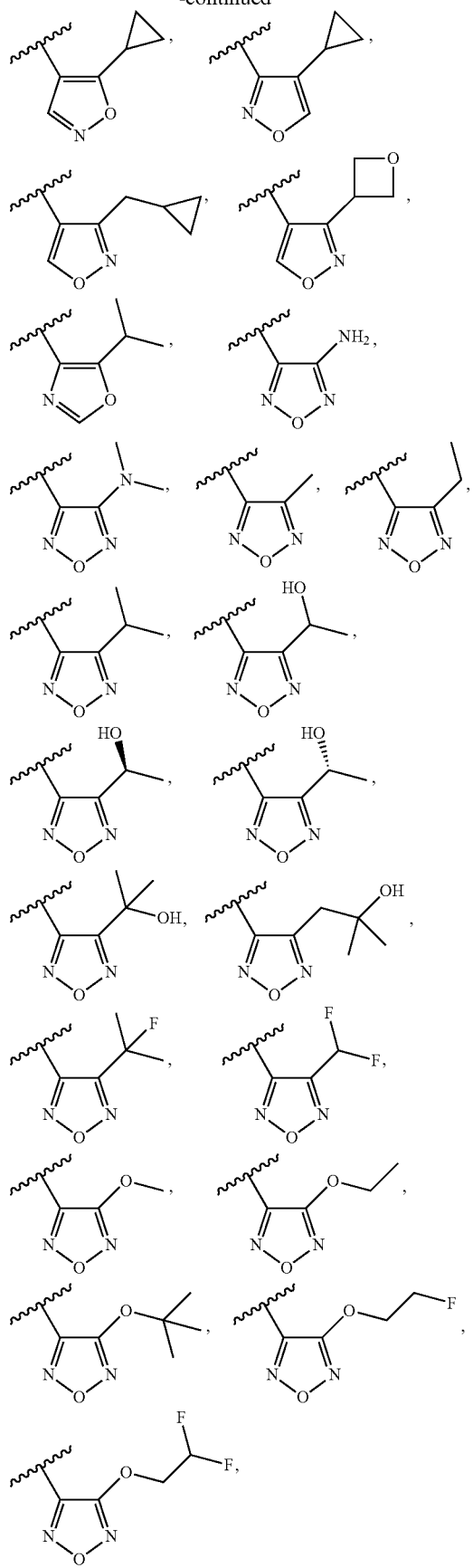

995

-continued

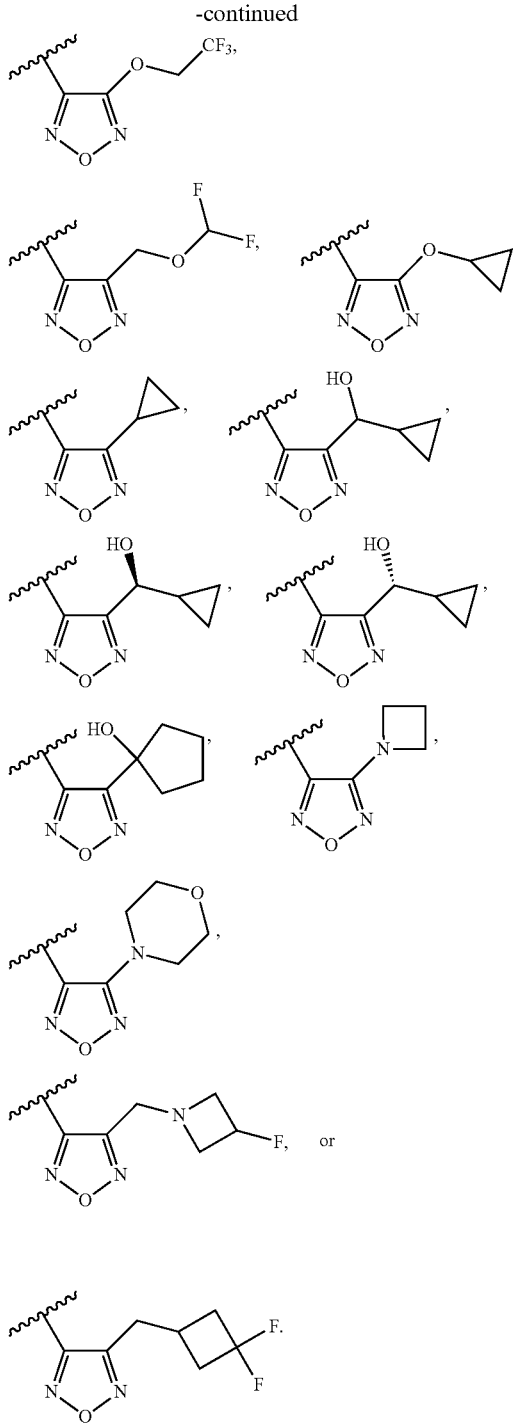

10. The compound of claim 1, or a pharmaceutically acceptable salt thereof, wherein $R^4$ is pyrazolyl substituted with one or two $R^{4c}$ groups each independently cyclopropyl, methyl, ethyl, isopropyl,-$CD_3$,-$CD_2CD_3$, fluorine, —$CHF_2$, —$CF_3$, —$CH_2CHF_2$, —$CH_2CF_3$, —$CH(CH_3)CF_3$, —$CH(CH_2F)_2$, —$CH_2CH_2OCHF_2$, or —$CH_2CH_2OCF_3$, or imidazolyl substituted with one methyl or isopropyl.

996

11. The compound of claim 1, or a pharmaceutically acceptable salt thereof, wherein $R^4$ is:

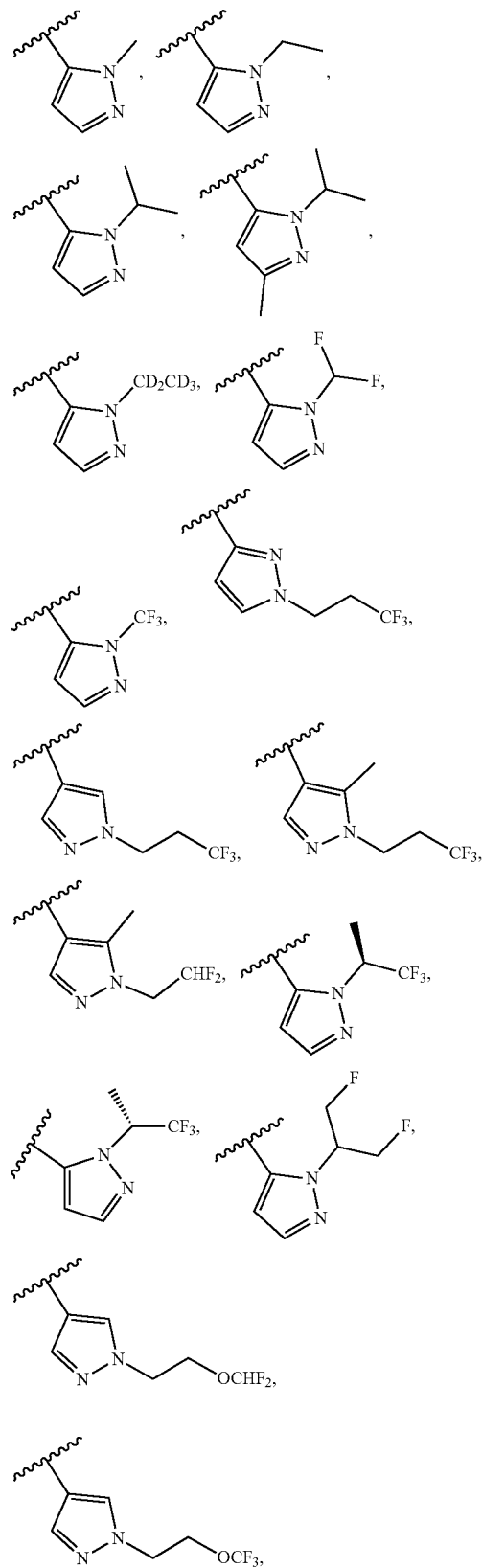

-continued

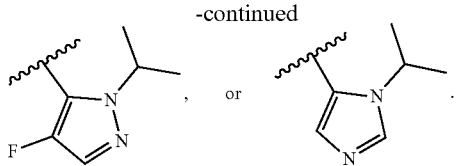

12. The compound of claim 1, or a pharmaceutically acceptable salt thereof, wherein
   $R^4$ is triazolyl that is unsubstituted or substituted with one or two $R^{4c}$ groups; and
   each $R^{4c}$ is independently methyl, ethyl, isopropyl, —CH$_2$CH$_2$OCH$_3$, —CHF$_2$, —CF$_3$, —CH$_2$CH$_2$F, —CH$_2$CHF$_2$, —CH$_2$CF$_3$, —CH$_2$CH$_2$CH$_2$F, —CH$_2$CH$_2$CHF$_2$, —CH$_2$CH$_2$CF$_3$, —CH$_2$CH$_2$OCHF$_2$, —CH$_2$CH$_2$OCF$_3$, cyclopropyl, —CH$_2$-cyclopropyl,

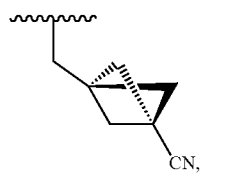

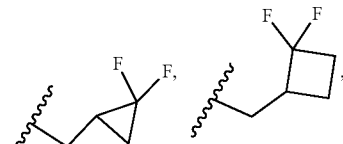

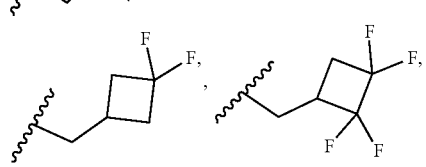

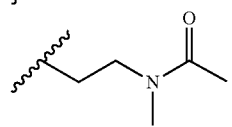

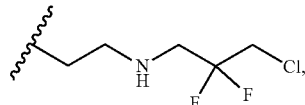

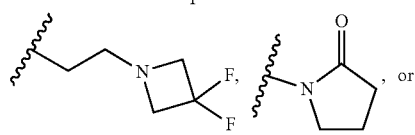

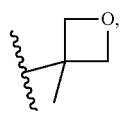

wherein when $R^4$ is 1,2,4-triazolyl, then $R^4$ is

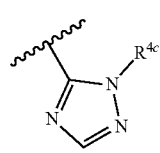 or 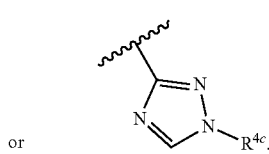

13. The compound of claim 1, or a pharmaceutically acceptable salt thereof, wherein $R^4$ is:

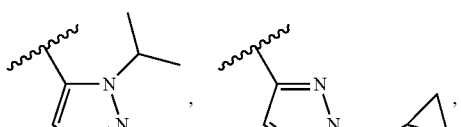

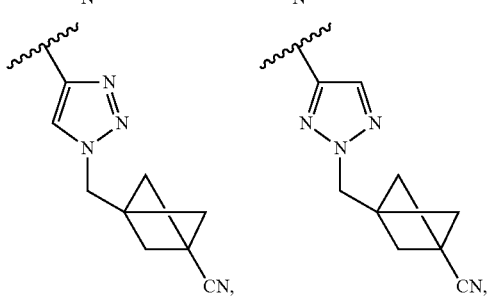

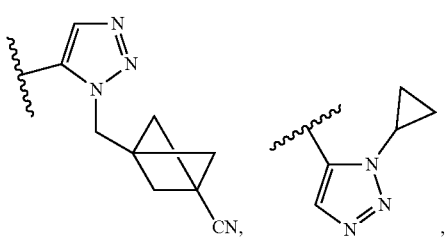

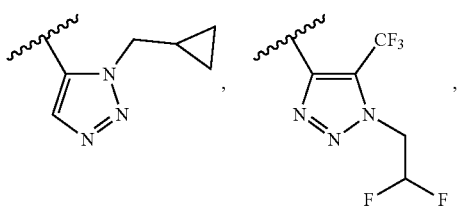

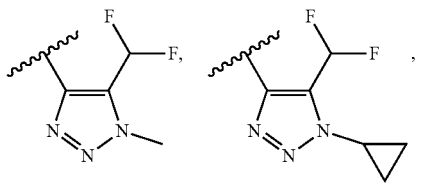

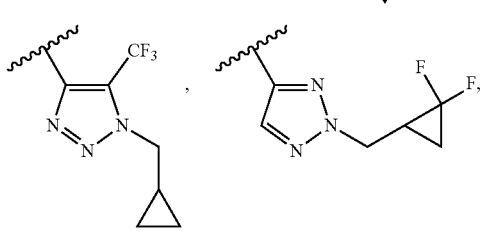

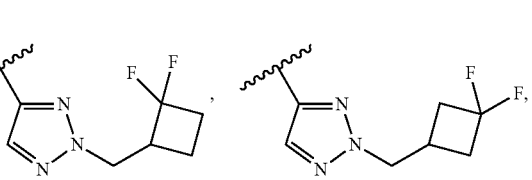

999
-continued
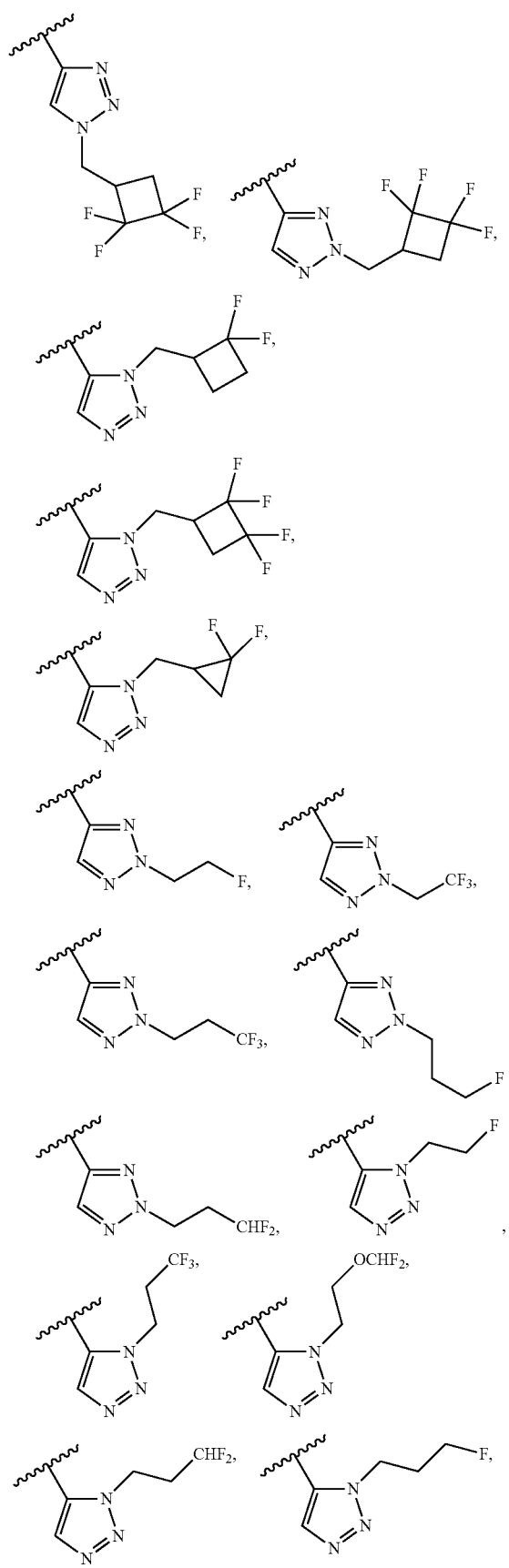
1000
-continued
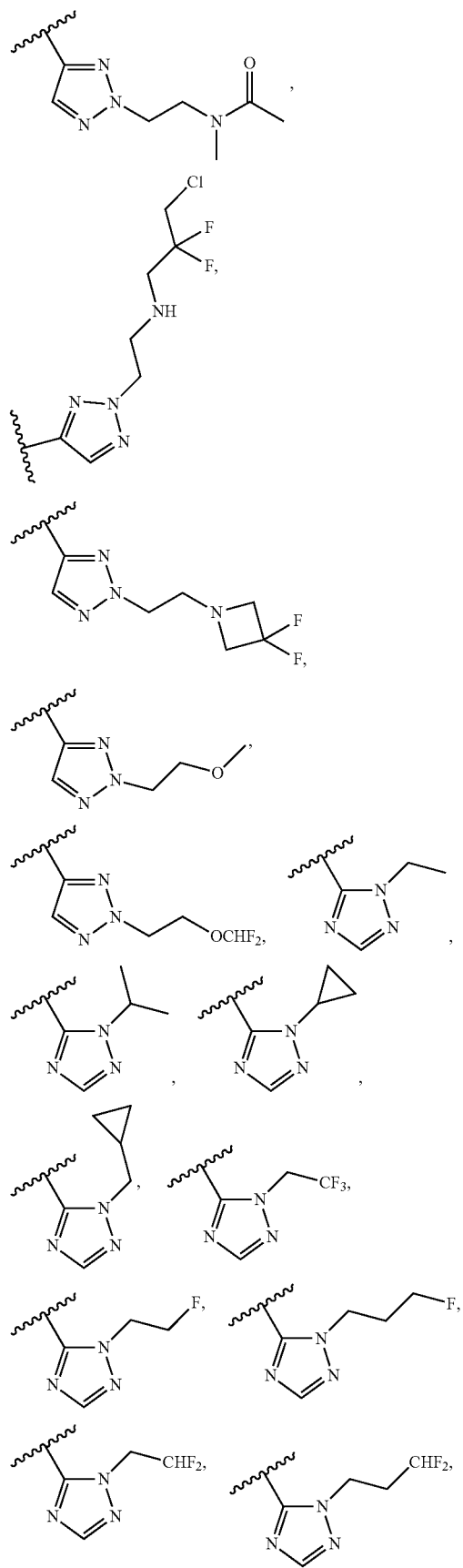

-continued

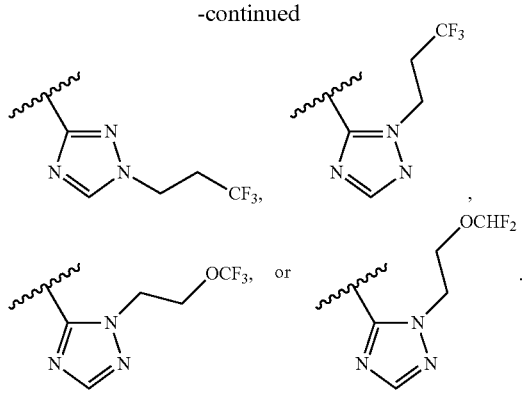

14. The compound of claim 1, or a pharmaceutically acceptable salt thereof, wherein $R^4$ is thienyl, thiazolyl, isothiazolyl or thiadiazolyl, each substituted with methyl, isopropyl or cyclopropyl.

15. The compound of claim 1, or a pharmaceutically acceptable salt thereof, wherein $R^4$ is:

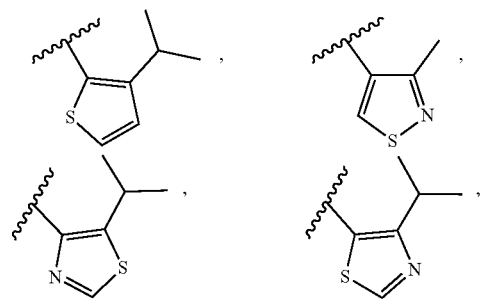

-continued

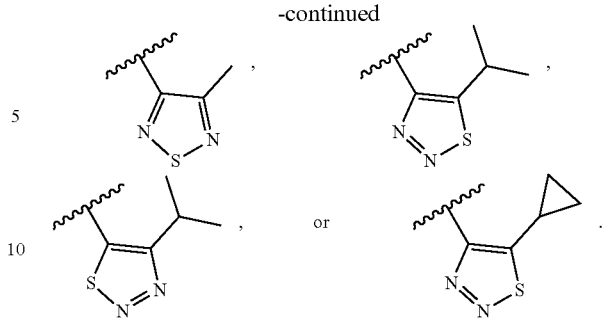

16. A pharmaceutical composition, comprising a compound of claim 1, or a pharmaceutically acceptable salt thereof, and a pharmaceutically acceptable carrier.

17. A method for treating and/or ameliorating an IL-17A mediated inflammatory syndrome, disorder, or disease comprising administering to a subject in need thereof a therapeutically effective amount of a compound of claim 1, or a pharmaceutically acceptable salt thereof.

18. The method of claim 17, wherein the IL-17A mediated inflammatory syndrome, disorder, or disease is selected from the group consisting of: psoriasis, psoriatic arthritis, rheumatoid arthritis, ankylosing spondylitis, hidradenitis suppurativa, bullous Pemphigoid, atopic dermatitis, vitiligo, multiple sclerosis, asthma, uveitis, chronic obstructive pulmonary disorder, multiple myeloma, and systemic lupus erythematosus.

19. The method of claim 18, wherein the compound, or a pharmaceutically acceptable salt thereof, is administered orally.

20. The method of claim 18, wherein the, or a pharmaceutically acceptable salt thereof, is administered as a tablet or a capsule.

* * * * *

UNITED STATES PATENT AND TRADEMARK OFFICE
CERTIFICATE OF CORRECTION

PATENT NO. : 12,024,524 B2
APPLICATION NO. : 18/297268
DATED : July 2, 2024
INVENTOR(S) : Steven Goldberg et al.

It is certified that error appears in the above-identified patent and that said Letters Patent is hereby corrected as shown below:

In the Claims

Column 986, Line 59, "C(0-2) alkyl C(3-8) cycloalkyl" should read -- C(0-2) alkyl C(3-6) cycloalkyl --.

Column 1002, Line 27, "Pemphigoid" should read -- pemphigoid --.

Column 1002, Line 33, "The method of claim 132, wherein the," should read -- The method of claim 132, wherein the compound, --.

Signed and Sealed this
Twenty-eighth Day of October, 2025

John A. Squires
*Director of the United States Patent and Trademark Office*